US009028841B2

(12) United States Patent
Henn et al.

(10) Patent No.: US 9,028,841 B2
(45) Date of Patent: May 12, 2015

(54) SYNERGISTIC BACTERIAL COMPOSITIONS AND METHODS OF PRODUCTION AND USE THEREOF

(71) Applicant: Seres Health, Inc., Cambridge, MA (US)

(72) Inventors: Matthew R. Henn, Someville, MA (US); Geoffrey von Maltzahn, Boston, MA (US); Anthony Mario D'Onofrio, Northborough, MA (US); Kevin Daniel Litcofsky, Boston, MA (US); David A. Berry, Brookline, MA (US); David N. Cook, Brooklyn, NY (US); Noubar B. Afeyan, Cambridge, MA (US); John Grant Aunins, Doylestown, PA (US)

(73) Assignee: Seres Health, Inc., Cambridge, MA (US)

( * ) Notice: Subject to any disclaimer, the term of this patent is extended or adjusted under 35 U.S.C. 154(b) by 19 days.

(21) Appl. No.: 14/221,190

(22) Filed: Mar. 20, 2014

(65) Prior Publication Data

US 2014/0199281 A1 Jul. 17, 2014

Related U.S. Application Data

(60) Division of application No. 14/091,201, filed on Nov. 26, 2013, which is a continuation-in-part of application No. PCT/US2013/071758, filed on Nov. 25, 2013.

(60) Provisional application No. 61/729,518, filed on Nov. 23, 2012, provisional application No. 61/729,519, filed on Nov. 23, 2012, provisional application No. 61/729,520, filed on Nov. 23, 2012, provisional application No. 61/729,521, filed on Nov. 23, 2012, provisional application No. 61/729,522, filed on Nov. 23, 2012, provisional application No. 61/729,524, filed on Nov. 23, 2012, provisional application No. 61/729,515, filed on Nov. 23, 2012, provisional application No. 61/729,517, filed on Nov. 23, 2012, provisional application No. 61/729,525, filed on Nov. 23, 2012, provisional application No. 61/729,526, filed on Nov. 23, 2012, provisional application No. 61/729,527, filed on Nov. 23, 2012.

(51) Int. Cl.

| | |
|---|---|
| ***A61K 39/08*** | (2006.01) |
| ***A61K 35/74*** | (2006.01) |
| ***A23L 1/30*** | (2006.01) |
| ***A61K 38/13*** | (2006.01) |

(52) U.S. Cl.

CPC ................ *A61K 35/74* (2013.01); *A23L 1/301* (2013.01); *A23L 1/3014* (2013.01); *A61K 38/13* (2013.01)

(58) Field of Classification Search

USPC ............. 424/234.1, 247.1, 203.1, 93.1, 94.1, 424/93.3, 93.41; 435/252.4, 243, 252.1, 435/252.7

See application file for complete search history.

(56) References Cited

U.S. PATENT DOCUMENTS

| | | | |
|---|---|---|---|
| 3,228,838 | A | 1/1966 | Rinfret |
| 3,608,030 | A | 9/1971 | Tint |
| 4,077,227 | A | 3/1978 | Larson |
| 4,205,132 | A | 5/1980 | Sandine et al. |
| 4,655,047 | A | 4/1987 | Temple et al. |
| 4,689,226 | A | 8/1987 | Nurmi et al. |
| 4,839,281 | A | 6/1989 | Gorbach et al. |
| 5,196,205 | A | 3/1993 | Borody |
| 5,425,951 | A | 6/1995 | Goodrich, Jr. et al. |
| 5,443,826 | A | 8/1995 | Borody |
| 5,599,795 | A | 2/1997 | McCann et al. |
| 5,648,206 | A | 7/1997 | Goodrich, Jr. et al. |
| 6,589,771 | B1 | 7/2003 | Marshall |
| 6,645,530 | B1 | 11/2003 | Borody |
| 7,628,982 | B2 | 12/2009 | Klaviniskis et al. |
| 7,708,988 | B2 | 5/2010 | Farmer |
| 7,731,976 | B2 | 6/2010 | Cobb et al. |
| 7,763,420 | B2 | 7/2010 | Stritzker et al. |
| 8,034,601 | B2 | 10/2011 | Boileau et al. |
| 8,039,006 | B2 | 10/2011 | Prato |
| 8,147,482 | B2 | 4/2012 | Shimizu et al. |
| 8,187,590 | B2 | 5/2012 | Farmer |
| 8,236,508 | B2 | 8/2012 | Mutharasan et al. |
| 8,388,996 | B2 | 3/2013 | Gehling et al. |
| 8,460,648 | B2 | 6/2013 | Borody |
| 2001/0036453 | A1 | 11/2001 | Reid |
| 2004/0028689 | A1 | 2/2004 | Borody |
| 2005/0180962 | A1 | 8/2005 | Raz |
| 2006/0046246 | A1 | 3/2006 | Zeng et al. |

(Continued)

FOREIGN PATENT DOCUMENTS

| | | | |
|---|---|---|---|
| EP | 0033584 | A3 | 1/1981 |
| EP | 0433299 | A4 | 4/1992 |

(Continued)

OTHER PUBLICATIONS

Aas, J., Gessert, C.E., and Bakken, J.S. (2003). Recurrent *Clostridium difficile* colitis: case series involving 18 patients treated with donor stool administered via a nasogastric tube. Clinical Infectious Diseases 36(5), 580-585.

(Continued)

*Primary Examiner* — Jennifer Graser

(74) *Attorney, Agent, or Firm* — Fenwick & West LLP

(57) ABSTRACT

Provided are therapeutic compositions containing Ecobiotic™ populations for prevention, treatment and reduction of symptoms associated with a dysbiosis of a mammalian subject such as a human.

9 Claims, 1 Drawing Sheet

(56) References Cited

U.S. PATENT DOCUMENTS

| | | | |
|---|---|---|---|
| 2006/0188523 A1 | 8/2006 | Pei |
| 2006/0233830 A1 | 10/2006 | Wong |
| 2007/0141139 A1 | 6/2007 | Vandenberg |
| 2011/0113863 A1 | 5/2011 | Fuhrmann et al. |
| 2011/0189132 A1 | 8/2011 | Garner et al. |
| 2011/0280840 A1 | 11/2011 | Blaser |
| 2012/0021429 A1 | 1/2012 | Rublee |
| 2012/0021921 A1 | 1/2012 | Scott |
| 2012/0058094 A1 | 3/2012 | Blaser |
| 2012/0128633 A1 | 5/2012 | Veiga et al. |
| 2012/0128634 A1 | 5/2012 | Veiga |
| 2012/0149584 A1 | 6/2012 | Olle |
| 2012/0165215 A1 | 6/2012 | Andersen |
| 2012/0177650 A1 | 7/2012 | Borody |
| 2012/0207726 A1 | 8/2012 | Lipkin |
| 2012/0238468 A1 | 9/2012 | Tuk |
| 2012/0264637 A1 | 10/2012 | Wiener-Kronish |
| 2012/0276149 A1 | 11/2012 | Littman |
| 2012/0276201 A1 | 11/2012 | Trachtman |
| 2013/0017999 A1 | 1/2013 | Fremont |
| 2013/0022575 A1 | 1/2013 | Cassity |
| 2013/0045274 A1 | 2/2013 | Hlavka |
| 2013/0045874 A1 | 2/2013 | Ehrlich |
| 2013/0149339 A1 | 6/2013 | Honda |
| 2013/0149375 A1 | 6/2013 | Geall |
| 2013/0266539 A1 | 10/2013 | Borody |
| 2014/0045744 A1 | 2/2014 | Gordon |

FOREIGN PATENT DOCUMENTS

| | | | |
|---|---|---|---|
| EP | 1107772 B1 | 4/2006 |
| EP | 1631312 B1 | 9/2008 |
| EP | 2337569 A2 | 6/2011 |
| EP | 2519108 A1 | 11/2012 |
| EP | 0479820 B1 | 7/2014 |
| WO | WO 2002/007741 A1 | 1/2002 |
| WO | WO 2006/012586 A2 | 2/2006 |
| WO | WO 2008/076696 A2 | 6/2008 |
| WO | WO 2008/083157 A2 | 7/2008 |
| WO | WO 2010/030997 A1 | 3/2010 |
| WO | WO 2010/062369 A2 | 6/2010 |
| WO | WO 2010/124387 A1 | 11/2010 |
| WO | WO 2010/151842 A2 | 12/2010 |
| WO | WO 2011/005756 A1 | 1/2011 |
| WO | WO 2011/022542 A2 | 2/2011 |
| WO | WO 2011022660 A1 | 2/2011 |
| WO | WO 2011/033310 A1 | 3/2011 |
| WO | WO 2011/043654 A1 | 4/2011 |
| WO | WO 2011/046616 A3 | 4/2011 |
| WO | WO 2011/103123 A2 | 8/2011 |
| WO | WO 2011/107482 A2 | 9/2011 |
| WO | WO 2011/113801 A1 | 9/2011 |
| WO | WO 2011107481 A2 | 9/2011 |
| WO | WO 2011/152566 A2 | 12/2011 |
| WO | WO 2012/009712 A2 | 1/2012 |
| WO | WO 2012/016287 A2 | 2/2012 |
| WO | WO 2012/045150 A1 | 4/2012 |
| WO | WO 2012/116289 A2 | 8/2012 |
| WO | WO 2012/122522 A2 | 9/2012 |
| WO | WO 2012/142605 A1 | 10/2012 |
| WO | WO 2012/148991 A1 | 11/2012 |
| WO | WO 2012/159023 A2 | 11/2012 |
| WO | WO 2013/080561 A1 | 11/2012 |
| WO | WO 2013/019896 A1 | 2/2013 |
| WO | WO 2013/032328 A1 | 3/2013 |
| WO | WO 2013/037067 A1 | 3/2013 |
| WO | WO 2013/037068 A1 | 3/2013 |
| WO | WO 2013/053836 A1 | 4/2013 |
| WO | WO 2013/166031 A1 | 11/2013 |
| WO | WO 2013/176774 A1 | 11/2013 |

OTHER PUBLICATIONS

Achtman, M., and Wagner, M. (2008). Microbial diversity and the genetic nature of microbial species. Nat. Rev. Microbiol. 6(6), 431-440.

Allen-Vercoe, E., Reid, G., Viner, N., Gloor, G.B., Hota, S., Kim, P., Lee, C., O'Doherty, K., Vanner, S.J., Weese, J.S., et al. (2012). A Canadian Working Group report on fecal microbial therapy: microbial ecosystems therapeutics. Can. J. Gastroenterol. 26(7), 457-462.

Allen-Vercoe, E., Strauss, J., and Chadee, K. (2011). *Fusobacterium nucleatum*: an emerging gut pathogen? Gut Microbes 2(5), 294-298.

Anderson, K.F., Lonsway, D.R., Rasheed, J.K., Biddle, J., Jensen, B., McDougal, L.K., Carey, R.B., Thompson, A., Stocker, S., Limbago, B., et al. (2007). Evaluation of Methods to Identify the *Klebsiella pneumoniae* Carbapenemase in Enterobacteriaceae. J. Clin. Microbiol. 45(8), 2723-2725.

Arumugam, M., Raes, J., Pelletier, E., Paslier, D.L., Yamada, T., Mende, D.R., Fernandes, G.R., Tap, J., Bruls, T., Batto, J.-M., et al. (2011). Enterotypes of the human gut microbiome. Nature 473(7346), 174-180.

Atarashi, K., Tanoue, T., Oshima, K., Suda, W., Nagano, Y., Nishikawa, H., Fukuda, S., Saito, T., Narushima, S., Hase, K., et al. (2013). Treg induction by a rationally selected mixture of Clostridia strains from the human microbiota. Nature 500(7461), 232-236.

Atarashi, K., Tanoue, T., Shima, T., Imaoka, A., Kuwahara, T., Momose, Y., Cheng, G., Yamasaki, S., Saito, T., Ohba, Y., et al. (2011). Induction of colonic regulatory T cells by indigenous *Clostridium* species. Science 331(6015), 337-341.

Backhed, F. et al., (2004). The gut microbiota as an environmental factor that regulates fat storage, PNAS, Nov. 2,2014, pp. 15718-15723, vol. 101, No. 44.

Bader, J., Albin, A., and Stahl, U. (2012). Spore-forming bacteria and their utilisation as probiotics. Benef Microbes 3(1), 67-75.

Bakken, J.S. (2009). Fecal bacteriotherapy for recurrent *Clostridium difficile* infection. Anaerobe 15(6), 285-289.

Bakken, J.S., Borody, T., Brandt, L.J., Brill, J.V., Demarco, D.C., Franzos, M.A., Kelly, C., Khoruts, A., Louie, T., Martinelli, L.P., et al.(2011). Treating *Clostridium difficile* infection with fecal microbiota transplantation. Clin. Gastroenterol. Hepatol. 9(12), 1044-1049.

Franzos, M.A., Kelly, C., Khoruts, A., Louie, T., Martinelli, L.P., et al. (2011). Treating *Clostridium difficile* infection with fecal microbiota transplantation. Clin. Gastroenterol. Hepatol. 9(12), 1044-1049.

Barreau, M., Pagnier, I., and La Scola, B. (2013). Improving the identification of anaerobes in the clinical microbiology laboratory through MALDI-TOF mass spectrometry. Anaerobe 22, 123-125.

Ben-Amor, K., Heilig, H., Smidt, H., Vaughan, E.E., Abee, T., and De Vos, W.M. (2005). Genetic diversity of viable, injured, and dead fecal bacteria assessed by fluorescence-activated cell sorting and 16S rRNA gene analysis. Applied and Environmental Microbiology 71(8), 4679-4689.

Bidawid, S., Farber, J.M., Sattar, S.A., and Hayward, S. (2000). Heat inactivation of hepatitis A virus in dairy foods. J. Food Prot. 63(4), 522-528.

Bloedt, K., Riecker, M., Poppert, S., and Wellinghausen, N. (2009). Evaluation of new selective culture media and a rapid fluorescence in situ hybridization assay for identification of *Clostridium difficile* from stool samples. J Med Microbiol 58(7), 874-877.

Bokulich, N.A., Subramanian, S., Faith, J.J., Gevers, D., Gordon, J.I., Knight, R., Mills, D.A., and Caporaso, J.G. (2013). Quality-filtering vastly.improves diversity estimates from Illumina amplicon sequencing. Nat Methods 10(1), 57-59.

Borody, T.J. et al. (2011). Fecal microbiota transplantation (FMT) in multiple sclerosis. Poster abstract at American College of Gastroenterology Annual Scientific Meeting and Postgraduate Course Oct. 28 2011.

Borody, T.J., and Khoruts, A. (2012). Fecal microbiota transplantation and emerging applications. Nat Rev Gastroenterol Hepatol 9(2), 88-96.

Borriello, S.P. (1990). The influence of the normal flora on *Clostridium difficile* colonisation of the gut. Ann. Med. 22(1), 61-67.

(56) References Cited

OTHER PUBLICATIONS

Borriello, S.P., and Barclay, F.E. (1985). Protection of hamsters against *Clostridium difficile*ileocaecitis by prior colonisation with non-pathogenic strains. J Med Microbiol 19(3), 339-350.
Borriello, S.P., and Barclay, F.E. (1986). An in-vitro model of colonisation resistance to *Clostridium difficile* infection. Journal of Medical Microbiology 21(4), 299-309.
Borriello, S.P., and Honour, P. (1981). Simplified procedure for the routine isolation of *Clostridium difficile* from faeces. J Clin Pathol 34(10), 1124-1127.
Boyles, W.A., and Lincoln, R.E. (1958). Separation and concentration of bacterial spores and vegetative cells by foam flotation. Appl Microbiol 6(5), 327-334.
Brandt, L.J. (2012). Fecal Transplantation for the Treatment of *Clostridium difficile* Infection. Gastroenterol Hepatol (N Y) 8(3), 191-194.
Brandt, L.J., Aroniadis, O.C., Mellow, M., Kanatzar, A., Kelly, C., Park, T., Stollman, N., Rohlke, F., and Surawicz, C. (2012). Long-Term Follow-Up of Colonoscopic Fecal Microbiota Transplant for Recurrent *Clostridium difficile* Infection. The American Journal of Gastroenterology 107(7), 1079-1087.
Bräuniger, S., Peters, J., Borchers, U., and Kao, M. (2000). Further studies on thermal resistance of bovine parvovirus against moist and dry heat. International Journal of Hygiene and Environmental Health 203(1), 71-75.
Broda, D.M., De Lacy, K.M., and Bell, R.G. (1998). Efficacy of heat and ethanol spore treatments for the isolation of psychrotrophic *Clostridium* spp. associated with the spoilage of chilled vacuum-packed meats. International Journal of Food Microbiology 39(1-2), 61-68.
Brosius, J., Palmer, M.L., Kennedy, P.J., and Noller, H.F. (1978). Complete nucleotide sequence of a 16S ribosomal RNA gene from *Escherichia coli.* Proc. Natl. Acad. Sci. U.S.A. 75(10), 4801-4805.
Bueche, M., Wunderlin, T., Roussel-Delif, L., Junier, T., Sauvain, L., Jeanneret, N., and Junier, P. (2013). Quantification of Endospore-Forming Firmicutes by Quantitative PCR with the Functional Gene spo0A. Applied and Environmental Microbiology 79(17), 5302-5312.
Buffie, C.G., and Pamer, E.G. (2013). Microbiota-mediated colonization resistance against intestinal pathogens. Nature Reviews Immunology 13(11), 790-801.
Burke, C.J., Hsu, T.A., and Volkin, D.B. (1999). Formulation, stability, and delivery of live attenuated vaccines for human use. Crit Rev Ther Drug Carrier Syst 16(1), 1-83.
Cani, P.D., Possemiers, S., Wiele, T.V. De, Guiot, Y., Everard, A., Rottier, O., Geurts, L., Naslain, D., Neyrinck, A., Lambert, D.M., et al. (2009). Changes in gut microbiota control inflammation in obese mice through a mechanism involving GLP-2-driven improvement of gut permeability. Gut 58(8), 1091-1103.
Carvalho, A.S., Silva, J., Ho, P., Teixeira, P., Malcata, F.X., and Gibbs, P. (2008). Effects of Various Sugars Added to Growth and Drying Media upon Thermotolerance and Survival throughout Storage of Freeze-Dried *Lactobacillus delbrueckii* ssp. *bulgaricus.* Biotechnology Progress 20(1), 248-254.
Champagne, C.P., Mondou, F., Raymond, Y., and Roy, D. (1996). Effect of polymers and storage temperature on the stability of freeze-dried lactic acid bacteria. Food Research International 29(5-6), 555-562.
Chang, J.Y., Antonopoulos, D.A., Kalra, A., Tonelli, A., Khalife, W.T., Schmidt, T.M., and Young, V.B. (2008). Decreased diversity of the fecal Microbiome in recurrent *Clostridium difficile*-associated diarrhea. J. Infect. Dis.197(3), 435-438.
Chapman, C.M.C., Gibson, G.R., and Rowland, I. (2012). In vitro evaluation of single- and multi-strain probiotics: Inter-species inhibition between probiotic strains, and inhibition of pathogens. Anaerobe 18(4), 405-413.
Chen, X., Katchar, K., Goldsmith, J.D., Nanthakumar, N., Cheknis, A., Gerding, D.N., and Kelly, C.P. (2008). A Mouse Model of *Clostridium difficile*—Associated Disease. Gastroenterology 135(6), 1984-1992.
Chow, J., Tang, H., and Mazmanian, S.K. (2011). Pathobionts of the Gastrointestinal Microbiota and Inflammatory Disease. Curr Opin Immunol 23(4), 473-480.
Claesson, M.J., Wang, Q., O'Sullivan, O., Greene-Diniz, R., Cole, J.R., Ross, R.P., and O'Toole, P.W. (2010). Comparison of two next-generation sequencing technologies for resolving highly complex microbiota composition using tandem variable 16S rRNA gene regions. Nucleic Acids Res 38(22), e200.
Clemente, J.C., Ursell, L.K., Parfrey, L.W., and Knight, R. (2012). The impact of the gut microbiota on human health: an integrative view. Cell 148(6), 1258-1270.
D'Souza, D.H., and Su, X. (2010). Efficacy of chemical treatments against murine norovirus, feline calicivirus, and MS2 bacteriophage. Foodborne Pathogens and Disease 7(3), 319-326.
David, L.A., Maurice, C.F., Carmody, R.N., Gootenberg, D.B., Button,.J.E., Wolfe, B.E., Ling, A.V., Devlin, A.S., Varma, Y., Fischbach, M.A., et al. (2013). Diet rapidly and reproducibly alters the human gut microbiome. Nature advance online publication,.
De Angelis, M., Piccolo, M., Vannini, L., Siragusa, S., De Giacomo, A., Serrazzanetti, D.I., Cristofori, F., Guerzoni, M.E., Gobbetti, M., and Francavilla, R. (2013). Fecal Microbiota and Metabolome of Children with Autism and Pervasive Developmental Disorder Not Otherwise Specified. PLoS One 8(10), e76993.
De Vos, W.M. (2013). Fame and future of faecal transplantations—developing next-generation therapies with synthetic microbiomes: Fame and future of faecal transplantations. Microbial Biotechnology 6(4), 316-325.
Defined Fecal Microbiota Transplantation for *Clostridium difficile* Diarrhea. <http://clinicaltrials.gov/ct2/show/NCT01868373> Accessed Mar. 26, 2014.
Derrien, M. (2004). *Akkermansia muciniphila* gen. nov., sp. nov., a human intestinal mucin-degrading bacterium. International Journal of Systematic and Evolutionary Microbiology 54(5), 1469-1476.
Dethlefsen, L., Huse, S., Sogin, M.L., and Relman, D.A. (2008). The Pervasive Effects of an Antibiotic on the Human Gut Microbiota, as Revealed by Deep 16S rRNA Sequencing. PLoS Biology 6(11), e280.
Detmer, a., and Glenting, J. (2006). Live bacterial vaccines—a review and identification of potential hazards. Microb Cell Fact 5,23.
Dharmani, P., De Simone, C., and Chadee, K. (2013). The Probiotic Mixture VSL#3 Accelerates Gastric Ulcer Healing by Stimulating Vascular Endothelial Growth Factor. PLoS One 8(3), e58671.
Dietrich, G., Collioud, A., and Rothen, S.A. (2008). Developing and Manufacturing Attenuated Live Bacterial Vaccines. <http://www.biopharminternational.com/biopharm/Vaccine+Manufacturing+Articles/Developing-and-Manufacturing-Attenuated-Live-Bacte/ArticleStandard/Article/detail/557306> Accessed Mar. 25, 2014.
Dragon, D.C., and Rennie, R.P. (2001). Evaluation of spore extraction and purification methods for selective recovery of viable *Bacillus anthracis* spores. Lett. Appl. Microbiol. 33(2), 100-105.
Duc, L. (2003). Germination of the spore in the gastrointestinal tract provides a novel route for heterologous antigen delivery. Vaccine 21(27-30), 4215-4224.
Duc, L.H., Hong, H.A., Fairweather, N., Ricca, E., and Cutting, S.M. (2003). Bacterial Spores as Vaccine Vehicles. Infection and Immunity 71(5), 28102818.
Dumas, M.E. et al., (2006). Metabolic profiling reveals a contribution of gut microbiota to fatty liver phenotype in insulin-resistant mice, PNAS, Aug. 15, 2006, pp. 12511-12516, vol. 103, No. 33.
Dutta, S.K., Girotra, M., Garg, S., Dutta, A., Von Rosenvinge, E.C., Maddox, C., Song, Y., Bartlett, J.G., Vinayek, R., and Fricke, W.F. (2014). Efficacy of Combined Jejunal and Colonic Fecal Microbiota Transplantation for Recurrent *Clostridium difficile* Infection. Clinical Gastroenterology and Hepatology.
Edwards, A.D., and Slater, N.K.H. (2008). Formulation of a live bacterial vaccine for stable room temperature storage results in loss of acid, bile and bile salt resistance. Vaccine 26(45), 5675-5678.
Eiseman, B., Silen, W., Bascom, G.S., and Kauvar, A.J. (1958). Fecal enema as an adjunct in the treatment of pseudomembranous enterocolitis. Surgery 44(5), 854-859.

(56) References Cited

OTHER PUBLICATIONS

Elving, J., Emmoth, E., Albihn, a., Vinneras, B., and Ottoson, J. (2012). Composting for Avian Influenza Virus Elimination. Applied and Environmental Microbiology 78(9), 3280-3285.

Emanuelsson, F., Claesson, B.E.B., Ljungström, L., Tvede, M., and Ung, K.-A. (2014). Faecal microbiota transplantation and bacteriotherapy for recurrent *Clostridium difficile* infection: A retrospective evaluation of 31 patients. Scandinavian Journal of Infectious Diseases 46(2), 89-97.

Endt, K., Stecher, B., Chaffron, S., Slack, E., Tchitchek, N., Benecke, A., Van Maele, L., Sirard, J.-C., Mueller, A.J., Heikenwalder, M., et al. (2010). The Microbiota Mediates Pathogen Clearance from the Gut Lumen after Non- Typhoidal *Salmonella* Diarrhea. PLoS Pathog 6(9), e1001097.

Everard, A., Belzer, C., Geurts, L., Ouwerkerk, J.P., Druart, C., Bindels, L.B., Guiot, Y., Derrien, M., Muccioli, G.G., Delzenne, N.M., et al. (2013). Cross-talk between *Akkermansia muciniphila* and intestinal epithelium controls diet-induced obesity. Proceedings of the National Academy of Sciences 110(22), 9066-9071.

Fairhead, H., Setlow, B., Waites, W.M., and Setlow, P. (1994). Small, acid-soluble proteins bound to DNA protect *Bacillus subtilis* spores from being killed by freeze-drying. Applied and Environmental Microbiology 60(7), 2647-2649.

Faith, J.J., Ahern, P.P., Ridaura, V.K., Cheng, J., and Gordon, J.I. (2014). Identifying Gut Microbe—Host Phenotype Relationships Using Combinatorial Communities in Gnotobiotic Mice. Sci Transl Med 6(220), 220ra11-220ra11.

Fakhry, S., Sorrentini, I., Ricca, E., De Felice, M., and Baccigalupi, L.(2008). Characterization of spore forming *Bacilli* isolated from the human gastrointestinal tract. Journal of Applied Microbiology 105(6), 2178-2186.

Fell Jr., N.F., Pellegrino, P.M., and Gillespie, J.B. (2001). Mitigating phosphate interference in bacterial endospore detection by Tb dipicolinate photoluminescence. Analytica Chimica Acta 426(1), 43-50.

Fichtel, J., Köster, J., Rullkötter, J., and Sass, H. (2007). Spore dipicolinic acid contents used for estimating the number of endospores in sediments. FEMS Microbiology Ecology 61(3), 522-532.

Fischbach, M.A., Bluestone, J.A., and Lim, W.A. (2013). Cell-Based Therapeutics: The Next Pillar of Medicine. Sci Transl Med 5(179), 179ps7.

Fonseca, F., Béal, C., and Corrieu, G. (2001). Operating Conditions That Affect the Resistance of Lactic Acid Bacteria to Freezing and Frozen Storage. Cryobiology 43(3), 189-198.

Franz, C.M.A.P., Huch, M., Abriouel, H., Holzapfel, W., and Gálvez, A. (2011). Enterococci as probiotics and their implications in food safety. International Journal of Food Microbiology 151(2), 125-140.

Friedman-Moraco, R.J., Mehta, A.K., Lyon, G.M., and Kraft, C.S. (2014). Fecal Microbiota Transplantation for Refractory *Clostridium difficile* Colitis in Solid Organ Transplant Recipients: Fecal Microbiota Transplantation in Solid Organ Transplant Recipients. American Journal of Transplantation 14(2), 477-480.

Fuentes, S., Van Nood, E., Tims, S., Heikamp-De Jong, I., Ter Braak, C.J., Keller, J.J., Zoetendal, E.G., and De Vos, W.M. (2014). Reset of a critically disturbed microbial ecosystem: faecal transplant in recurrent *Clostridium* difficile infection. The ISME Journal.

Gevers, D., Kugathasan, S., Denson, L.A., Vazquez-Baeza, Y., Van Treuren, W., Ren, B., Schwager, E., Knights, D., Song, S.J., Yassour, M., et al. (2014). The Treatment-Naive Microbiome in New-Onset Crohn's Disease. Cell Host & Microbe 15(3), 382-392.

Gilligan, P.H. (2013). Identification of Pathogens by Classical Clinical Tests. In the Prokaryotes, E. Rosenberg, E.F. DeLong, S. Lory, E. Stackebrandt, and F. Thompson, eds. (Springer Berlin Heidelberg), pp. 57-89.

Goodman, A.L., Kallstrom, G., Faith, J.J., Reyes, A., Moore, A., Dantas, G., and Gordon, J.I. (2011). From the Cover: Extensive personal human gut microbiota culture collections characterized and manipulated in gnotobiotic mice. Proceedings of the National Academy of Sciences 108(15), 6252-6257.

Goodman, N.S., Gottfried, R.J., and Rogoff, M.H. (1967). Biphasic system for separation of spores and crystals of *Bacillus thuringiensis*. Journal of Bacteriology 94(2), 485.

Gould, G.W., and Sale, A.J. (1970). Initiation of germination of bacterial spores by hydrostatic pressure. J. Gen. Microbiol. 60(3), 335-346.

Grabow, W.O., Clay, C.G., Dhaliwal, W., Vrey, M.A., and Müller, E.E. (1999). Elimination of viruses, phages, bacteria and Cryptosporidium by a new generation Aquaguard point-of-use water treatment unit. Zentralbl Hyg Umweltmed 202(5), 399-410.

Greenway, F., Wang, S., and Heiman, M. (2014). A novel cobiotic containing a prebiotic and an antioxidant augments the glucose control and gastrointestinal tolerability of metformin: a case report. Beneficial Microbes 5(1), 29-32.

Grehan, M.J., Borody, T.J., Leis, S.M., Campbell, J., Mitchell, H., and Wettstein, A. (2010). Durable alteration of the colonic microbiota by the administration of donor fecal flora. J. Clin. Gastroenterol. 44(8), 551-561.

Hamilton, M.J., Weingarden, A.R., Sadowsky, M.J., and Khoruts, A. (2012). Standardized frozen preparation for transplantation of fecal microbiota for recurrent *Clostridium difficile* infection. Am. J. Gastroenterol. 107(5), 761-767.

Hamilton, M.J., Weingarden, A.R., Unno, T., Khoruts, A., and Sadowsky, M.J. (2013). High-throughput DNA sequence analysis reveals stable engraftment of gut microbiota following transplantation of previously frozen fecal bacteria. Gut Microbes 4(2), 125-135.

Harmsen, H. J. M., Gibson, G. R., Elfferich, P., Raangs, G. C.,. Wildeboer-Veloo, A. C. M., Argaiz, A., Roberfroid, M. B., and Welling, G. W. (2000). Comparison of viable cell counts and fluorescence in situ hybridization using specific rRNA-based probes for the quantification of human fecal bacteria. FEMS Microbiology Letters 183(1), 125-129.

Hasan, J.A., Japal, K.M., Christensen, E.R., and Samalot-Freire, L.C. (2011). In vitro production of *Clostridium difficile* spores for use in the efficacy evaluation of disinfectants: a precollaborative investigation. J AOAC Int 94(1), 259-272.

Hell, M., Bernhofer, C., Stalzer, P., Kern, J.M., and Claassen, E. (2013). Probiotics in *Clostridium difficile* infection: reviewing the need for a multistrain probiotic. Beneficial Microbes 4(1), 39-51.

Hemmerling, A., Harrison, W., Schroeder, A., Park, J., Korn, A., Shiboski, S., Foster-Rosales, A., and Cohen, C.R. (2010). Phase 2a Study Assessing Colonization Efficiency, Safety, and Acceptability of *Lactobacillus crispatus* CTV-05 in Women With Bacterial Vaginosis: Sexually Transmitted Diseases 37(12), 745-750.

Herron, P.R., and Wellington, E.M.H. (1990). New Method for Extraction of *Streptomycete* Spores from Soil and Application to the Study of Lysogeny in Sterile Amended and Nonsterile Soil. Appl Environ Microbiol 56(5), 1406-1412.

Hewitt, J., Rivera-Aban, M., and Greening, G.E. (2009). Evaluation of murine norovirus as a surrogate for human norovirus and hepatitis A virus in heat inactivation studies. Journal of Applied Microbiology 107(1), 65-71.

Hindle, A.A., and Hall, E.A.H. (1999). Dipicolinic acid (DPA) assay revisited and appraised for spore detection. The Analyst 124(11), 1599-1604.

Hirsch, E.B., and Tam, V.H. (2010). Detection and treatment options for *Klebsiella pneumoniae* carbapenemases (KPCs): an emerging cause of multidrug-resistant infection. J. Antimicrob. Chemother. 65(6), 1119-1125.

Hofsten, B.V. (1966). Partition of *Escherichia coli* in an aqueous polymer two-phase system. Experimental Cell Research 41(1), 117-123.

Holmes, E., Kinross, J., Gibson, G.R., Burcelin, R., Jia, W., Pettersson, S., and Nicholson, J.K. (2012). Therapeutic Modulation of Microbiota-Host Metabolic Interactions. Science Translational Medicine 4(137), 137rv6-137rv6.

Hoppe, B., Groothoff, J.W., Hulton, S.-A., Cochat, P., Niaudet, P., Kemper, M.J., Deschênes, G., Unwin, R., and Milliner, D. (2011). Efficacy and safety of Oxalobacter formigenes to reduce urinary oxalate in primary hyperoxaluria. Nephrol. Dial. Transplant. 26(11), 3609-3615.

(56) References Cited

OTHER PUBLICATIONS

Hoyles, L., Honda, H., Logan, N.A., Halket, G., La Ragione, R.M., and McCartney, A.L. (2012). Recognition of greater diversity of *Bacillus species* and related bacteria in human faeces. Res. Microbiol. 163(1), 3-13.

Hurst, C.J., and Gerba, C.P. (1989). Fate of viruses during wastewater sludge treatment processes. Critical Reviews in Environmental Control 18(4), 317-343.

Itoh, K., and Mitsuoka, T. (1985). Characterization of clostridia isolated from faeces of limited flora mice and their effect on caecal size when associated with germ-free mice. Laboratory Animals 19(2), 111-118.

Itoh, K., Lee, W.K., Kawamura, H., Mitsuoka, T., and Magaribuchi, T. (1987). Intestinal bacteria antagonistic to *Clostridium difficile* in mice. Lab Anim 21(1), 20-25.

Itoh, K., Urano, T., and Mitsuoka, T. (1986). Colonization resistance against *Pseudomonas aeruginosa* in gnotobiotic mice. Lab Anim 20(3), 197-201.

Jalanka-Tuovinen, J., Salojarvi, J., Salonen, A., Immonen, O., Garsed, K., Kelly, F.M., Zaitoun, A., Palva, A., Spiller, R.C., and De Vos, W.M.(2013). Faecal microbiota composition and host-microbe cross-talk following gastroenteritis and in postinfectious irritable bowel syndrome. Gut 0,1-9.

Jeffs, L.B., and Khachatourians, G.G. (1997). Estimation of spore hydrophobicity for members of the genera *Beauveria, Metarhizium,* and *Tolypocladium* by salt-mediated aggregation and sedimentation. Canadian Journal of Microbiology 43(1), 23-28.

Jensen, N.S., and Canale-Parola, E. (1986). *Bacteroides pectinophilus* sp. nov. and *Bacteroides galacturonicus* sp. nov.: two pectinolytic bacteria from the human intestinal tract. Appl. Environ. Microbiol. 52(4), 880-887.

Jones, M.L., Martoni, C.J., and Prakash, S. (2012a). Cholesterol lowering and inhibition of sterol absorption by *Lactobacillus reuteri* NCIMB 30242: a randomized controlled trial. Eur J Clin Nutr 66(11), 1234-1241.

Jones, M.L., Martoni, C.J., Parent, M., and Prakash, S. (2012b). Cholesterol-lowering efficacy of a microencapsulated bile salt hydrolase-active *Lactobacillus reuteri* NCIMB 30242 yoghurt formulation in hypercholesterolaemic adults. British Journal of Nutrition 107(10), 1505-1513.

Jorgensen, J.H., and Ferraro, M.J. (2009). Antimicrobial Susceptibility Testing: A Review of General Principles and Contemporary Practices. Clin Infect Dis., Medical Microbiology, 49(11), 1749-1755.

Jorup-Rönström, C., Håkanson, A., Sandell, S., Edvinsson, O., Midtvedt, T., Persson, A.-K., and Norin, E. (2012). Fecal transplant against relapsing *Clostridium difficile*-associated diarrhea in 32 patients. Scand. J. Gastroenterol. 47(5), 548-552.

Jousimies-Somer, H., Summanen, P., Citron, D.M., Baron, E.J., Wexler,.H.M., and Finegold, S.M. (2002). Wadsworth-KLT Anaerobic Bacteriology Manual, 6th edition (California: Star), pp. 55-74, 81-132, 165-185.

Kailasapathy, K. (2002). Microencapsulation of probiotic bacteria: technology and potential applications. Curr Issues Intest Microbiol 3(2), 39-48.

Kamiya, S., Yamakawa, K., Ogura, H., and Nakamura, S. (1989). Recovery of spores of *Clostridium difficile* altered by heat or alkali. J Med Microbiol 28(3), 217-221.

Kanehisa Laboratories. KEGG: Kyoto encyclopedia of genes and genomes. <http://www.genome.jp/kegg/> Accessed 27th Match 2014.

Kelly, D., Campbell, J.I., King, T.P., Grant, G., Jansson, E.A., Coutts, A.G.P., Pettersson, S., and Conway, S. (2003). Commensal anaerobic gut bacteria attenuate inflammation by regulating nuclear-cytoplasmic shuttling of PPAR-y and ReIA. Nature Immunology 5(1), 104-112.

Khoruts, A. (2013). How Does Fecal Microbiota Transplantation Treat *Clostridium* difficile Infection.<https://www.genome.gov/Multimedia/Slides/HumanMicrobiomeScience2013/39_Khoruts.pdf> Accessed Mar. 21, 2014.

Khoruts, A., and Sadowsky, M.J. (2011). Therapeutic transplantation of the distal gut microbiota. Mucosal Immunol 4(1), 4-7.

Khoruts, A., Dicksved, J., Jansson, J.K., and Sadowsky, M.J. (2010). Changes in the composition of the human fecal microbiome after bacteriotherapy for recurrent *Clostridium difficile*-associated diarrhea. J. Clin. Gastroenterol. 44(5), 354-360.

Kim, B., Kim, n. J., Kim, M., Kim, Y.S., Woo, J., and Ryu, J. (2003). Bacteraemia Due to Tribe Proteeae: A Review of 132 Cases During a Decade (1991-2000). Scandinavian Journal of Infectious Diseases 35(2), 98-103.

Klayraung, S., Viernstein, H., and Okonogi, S. (2009). Development of tablets containing probiotics: Effects of formulation and processing parameters on bacterial viability. International Journal of Pharmaceutics 370(1-2), 54-60.

Kong, Q., He, G.-Q., Jia, J.-L., Zhu, Q.-L., and Ruan, H. (2011). Oral Administration of *Clostridium butyricum* for Modulating Gastrointestinal Microflora in Mice. Curr Microbiol 62(2), 512-517.

Konstantinidis, K.T., Ramette, A., and Tiedje, J.M. (2006). The bacterial species definition in the genomic era. Philos Trans R Soc Lond B Biol Sci 361(1475), 1929-1940.

Koonin, E.V. (2002). Chapter 22 the clusters of orthologous groups (COGS) database: Phylogenetic classification of proteins from complete genomes. <http://www.ncbi.nlm.nih.govibooks/NBK21090/pdfich22.pdf> Accessed 27th Match 2014.

Koransky, J.R., Allen, S.D., and Dowell, V.R., JR (1978). Use of ethanol for selective isolation of sporeforming microorganisms. Appl. Environ. Microbiol. 35(4), 762-765.

Kort, R., O'Brien, A.C., Stokkum, I.H.M. Van, Oomes, S.J.C.M., Crielaard, W., Hellingwerf, K.J., and Brul, S. (2005). Assessment of Heat Resistance of Bacterial Spores from Food Product Isolates by Fluorescence Monitoring of Dipicolinic Acid Release. Appl. Environ. Microbiol. 71(7), 3556-3564.

Kucerova, Z., Moura, H., Leitch, G.J., Sriram, R., Bern, C., Kawai, V., Vargas, D., Gilman, R.H., Ticona, E., and Vivar, A. (2004). Purification of *Enterocytozoon bieneusi* spores from stool specimens by gradient and cell sorting techniques. Journal of Clinical Microbiology 42(7), 3256-3261.

Kump, P.K., Gröchenig, H.-P., Lackner, S., Trajanoski, S., Reicht, G., Hoffmann, K.M., Deutschmann, A., Wenzl, H.H., Petritsch, W., Krejs, G.J., et al. (2013). Alteration of intestinal dysbiosis by fecal microbiota transplantation does not induce remission in patients with chronic active ulcerative colitis. Inflamm. Bowel Dis. 19(10), 2155-2165.

Kunde, S., Pham, A., Bonczyk, S., Crumb, T., Duba, M., Conrad, H., JR, Cloney, D., and Kugathasan, S. (2013). Safety, tolerability, and clinical response after fecal transplantation in children and young adults with ulcerative colitis. J. Pediatr. Gastroenterol. Nutr. 56(6), 597-601.

Landy, J., Al-Hassi, H.O., Mclaughlin, S.D., Walker, A.W., Ciclitira, P.J., Nicholls, R.J., Clark, S.K., and Hart, A.L. (2011). Review article: faecal transplantation therapy for gastrointestinal disease. Alimentary Pharmacology & Therapeutics 34(4), 409-415.

Lawley, T.D., Clare, S., Walker, A.W., Stares, M.D., Connor, T.R., Raisen, C., Goulding, D., Rad, R., Schreiber, F., Brandt, C., et al. (2012). Targeted Restoration of the Intestinal Microbiota with a Simple, Defined Bacteriotherapy Resolves Relapsing *Clostridium difficile* Disease in Mice. PLoS Pathog 8(10), e1002995.

Lawson, P.A., Song, Y., Liu, C., Molitoris, D.R., Vaisanen, M.-L., Collins, M.D., and Finegold, S.M. (2004). *Anaerotruncus colihominis* gen. nov., sp. nov., from human faeces. Int J Syst Evol Microbiol 54(2), 413-417.

Lee, I.-K., and Liu, J.-W. (2006). Clinical characteristics and risk factors for mortality in *Morganella morganii* bacteremia. J Microbiol Immunol Infect 39(4), 328-334.

Lee, J.S., Cha, D.S., and Park, H.J. (2004). Survival of Freeze-Dried Lactobacillus bulgaricus KFRI 673 in Chitosan-Coated Calcium Alginate Microparticles. J. Agric. Food Chem. 52(24), 7300-7305.

Lee, M., Hesek, D., Shah, I.M., Oliver, A.G., Dworkin, J., and Mobashery, S. (2010). Synthetic peptidoglycan motifs for germination of bacterial spores. Chembiochem 11(18), 2525-2529.

Lehar, J. (2007). Chemical combination effects predict connectivity in biological systems, Molecular Systems Biology, pp. 1-14, vol. 3, Article No. 80.

(56) References Cited

OTHER PUBLICATIONS

Lemon, K.P., Armitage, G.C., Relman, D.A., and Fischbach, M.A. (2012).Microbiota-Targeted Therapies: An Ecological Perspective. Science Translational Medicine 4(137), 137rv5-137rv5.

Leslie, S.B., Israeli, E., Lighthart, B., Crowe, J.H., and Crowe, L.M. (1995). Trehalose and sucrose protect both membranes and proteins in intact bacteria during drying. Applied and Environmental Microbiology 61(10), 3592-3597.

Liggins, M., Ramirez, N., Magnuson, N., and Abel-Santos, E. (2011). Progesterone analogs influence germination of *Clostridium sordellii* and *Clostridium* difficile spores in vitro. J. Bacteriol. 193(11), 2776-2783.

Lindsay, J.A., Beaman, T.C., and Gerhardt, P. (1985). Protoplast water content of bacterial spores determined by buoyant density sedimentation. J. Bacteriol. 163(2), 735-737.

Liu, K., Linder, C.R., and Warnow, T. (2011). RAxML and FastTree: Comparing Two Methods for Large-Scale Maximum Likelihood Phylogeny Estimation. PLoS One 6(11), e27731.

Livingston, S.J., Kominos, S.D., and Yee, R.B. (1978). New medium for selection and presumptive identification of the *Bacteroides fragilis* group. J. Clin. Microbiol. 7(5), 448-453.

Lopetuso, L.R., Scaldaferri, F., Petito, V., and Gasbarrini, A. (2013). Commensal Clostridia: leading players in the maintenance of gut homeostasis. Gut Pathogens 5(1), 23.

Lozupone, C., Faust, K., Raes, J., Faith, J.J., Frank, D.N., Zaneveld, J., Gordon, J.I., and Knight, R. (2012). Identifying genomic and metabolic features that can underlie early successional and opportunistic lifestyles of human gut symbionts. Genome Res 22(10), 1974-1984.

Malik, K.A. (1988). A new freeze-drying method for the preservation of nitrogen-fixing and other fragile bacteria. Journal of Microbiological Methods 8(5), 259-271.

Manichanh, C. (2006). Reduced diversity of faecal microbiota in Crohn's disease revealed by a metagenomic approach. Gut 55(2), 205-211.

Mbithi, J.N., Springthorpe, V.S., and Sattar, S.A. (1990). Chemical disinfection of hepatitis a virus on environmental surfaces. Applied and Environmental Microbiology 56(11), 3601-3604.

Mcguire, G., Denham, M.C., and Balding, D.J. (2001). Models of Sequence Evolution for DNA Sequences Containing Gaps. Mol Biol Evol 18(4), 481-490.

McNulty, N.P., Yatsunenko, T., Hsiao, A., Faith, J.J., Muegge, B.D., Goodman, A.L., Henrissat, B., Oozeer, R., Cools-Portier, S., Gobert, G., et al. (2011). The impact of a consortium of fermented milk strains on the gut microbiome of gnotobiotic mice and monozygotic twins. Sci Transl Med 3(106), 106ra106.

Mevissen-Verhage, E.A., Marcelis, J.H., Vos, M.N. DE, Amerongen, W.C.H., and Verhoef, J. (1987). Bifidobacterium, Bacteroides, and *Clostridium* spp. in fecal samples from breast-fed and bottle-fed infants with and without iron supplement. J. Clin. Microbiol. 25(2), 285-289.

Miller, R.S., and Hoskins, L.C. (1981). Mucin degradation in human colon ecosystems. Fecal population densities of mucin-degrading bacteria estimated by a "most probable number" method. Gastroenterology 81(4), 759-765.

Miyamoto-Shinohara, Y., Sukenobe, J., Imaizumi, T., Nakahara, T., and Others (2008). Survival of freeze-dried bacteria. The Journal of General and Applied Microbiology 54(1), 9.

Morgan, C.A., Herman, N., White, P.A., and Vesey, G. (2006). Preservation of micro-organisms by drying; A review. Journal of Microbiological Methods 66(2), 183-193.

Murri, M., Leiva, I., Gomez-Zumaquero, J.M., Tinahones, F.J., Cardona, F., Soriguer, F., and Queipo-Ortuño, M.I. (2013). Gut microbiota in children with type 1 diabetes differs from that in healthy children: a case-control study. BMC Med 11(1), 1-12.

Nicholson, W.L., and Law, J.F. (1999). Method for purification of bacterial endospores from soils: UV resistance of natural Sonoran desert soil populations of< i>*Bacillus*</i> spp. with reference to< i> *B. subtilis*</i> strain 168. Journal of Microbiological Methods 35(1), 13-21.

NIH human microbiome project. <http://www.hmpdacc.org/> Accessed 27th Match 2014.

Nishio, J., Atarashi, K., Tanoue, T., Baba, M., Negishi, H., Yanai, H., Honda, K., Benoist, C., Mathis, D., and Taniguchi, T. (2013). Impact of TCR repetoire on intestinal homeostasis (Taos, NM).

Nitert, M.D., Barrett, H.L., Foxcroft, K., Tremellen, A., Wilkinson, S., Lingwood, B., Tobin, J.M., McSweeney, C., O'Rourke, P., Mcintyre, H.D., et al. (2013). Spring: An Rct study of probiotics in the prevention of gestational diabetes mellitus in overweight and obese women. BMC Pregnancy and Childbirth 13(1), 50.

Noack, J., Kleessen, B., Proll, J., Dongowski, G., and Blaut, M. (1998). Dietary guar gum and pectin stimulate intestinal microbial polyamine synthesis in rats. J. Nutr. 128(8), 1385-1391.

O'Hara, C.M., Brenner, F.W., and Miller, J.M. (2000). Classification, identification, and clinical significance of Proteus, Providencia, and Morganella. Clin. Microbiol. Rev. 13(4), 534-546.

Okada, Y., Setoyama, H., Matsumoto, S., Imaoka, A., Nanno, M., Kawaguchi, M., and Umesaki, Y. (1994). Effects of fecal microorganisms and their chloroform-resistant variants derived from mice, rats, and humans on.immunological and physiological characteristics of the intestines of ex-germfree mice. Infect. Immun. 62(12), 5442-5446.

Olle, B. (2013). Medicines from microbiota. Nat. Biotechnol. 31(4), 309-315.

Openbiome. Quality metrics. <http://static.squarespace.com/static/50e0c29ae4b0a05702af7e6a/t/52e19689e4b0b.28f802c9b4e/1390517129976/OpenBiome%20Quality%20Metrics.pdf> Accessed Mar. 21, 2014.

Owens, C., Broussard, E., and Surawicz, C. (2013). Fecal microbiota transplantation and donor standardization. Trends in Microbiology 21(9), 443-445.

Paine, R.T. (1969). A note on trophic complexity and community stability. American Naturalist 103(929), 91-93.

Palmfeldt, J., and Hahn-Hagerdal, B. (2000). Influence of culture pH on survival of< i> *Lactobacillus reuteri*</i> subjected to freeze-drying. International Journal of Food Microbiology 55(1), 235-238.

Pamer, E.G. (2014). Fecal microbiota transplantation: effectiveness, complexities, and lingering concerns. Mucosal Immunology 7(2), 210-214.

Paredes-Sabja, D., Udompijitkul, P., and Sarker, M.R. (2009). Inorganic phosphate and sodium ions are cogerminants for spores of *Clostridium perfringens* type A food poisoning-related isolates. Appl. Environ. Microbiol. 75(19), 6299-6305.

Path Vaccine and Pharmaceutical Technologies Group. Summary of stability data for investigational formulations of vaccines. <http://www.path.org/publications/files/TS_vaccine_stability_table_invest.pdf> Accessed Mar. 21, 2014.

Pehkonen, K.S., Roos, Y.H., Miao, S., Ross, R.P., and Stanton, C. (2008) State transitions and physicochemical aspects of cryoprotection and stabilization in freeze-drying of *Lactobacillus rhamnosus* GG (LGG). Journal of Applied Microbiology 104(6), 1732-1743.

Peighambardoust, S.H., Golshan Tafti, A., and Hesari, J. (2011). Application of spray drying for preservation of lactic acid starter cultures: a review. Trends in Food Science & Technology 22(5), 215-224.

Pellegrino, P.M., Fell JR., N.F., and Gillespie, J.B. (2002). Enhanced spore detection using dipicolinate extraction techniques. Analytica Chimica Acta 455(2), 167-177.

Perez, F., Pultz, M.J., Endimiani, A., Bonomo, R.A., and Donskey, C.J. (2011). Effect of antibiotic treatment on establishment and elimination of intestinal colonization by KPC-producing *Klebsiella pneumoniae* in mice. Antimicrob. Agents Chemother. 55(6), 2585-2589.

Perez, J., Springthorpe, V.S., and Sattar, S.A. (2011). Clospore: a liquid medium for producing high titers of semi-purified spores of *Clostridium difficile*. J AOAC Int 94(2), 618-626.

Petrof, E.O., Claud, E.C., Gloor, G.B., and Allen-Vercoe, E. (2013a). Microbial ecosystems therapeutics: a new paradigm in medicine? Beneficial Microbes.

Petrof, E.O., Gloor, G.B., Vanner, S.J., Weese, S.J., Carter, D., Daigneault, M.C., Brown, E.M., Schroeter, K., and Allen-Vercoe, E.

(56) References Cited

OTHER PUBLICATIONS (2013b). Stool substitute transplant therapy for the eradication of *Clostridium difficile* infection: "RePOOPulating" the gut. Microbiome 1(1), 3.
Picot, A., and Lacroix, C. (2004). Encapsulation of bifidobacteria in whey protein-based microcapsules and survival in simulated gastrointestinal conditions and in yoghurt. International Dairy Journal 14(6), 505-515.
Pinn, D. et al. (2013). Follow-up Study of Fecal Microbiota Transplantation (FMT) for the Treatment of Refractory Irritable Bowel Syndrome (IBS). Abstract ACG 2013.
Postgate, J.R., and Hunter, J.R. (1961). On the Survival of Frozen Bacteria. J.Gen Microbiol 26(3), 367-378.
Pultz, N.J., Hoyen, C.K., and Donskey, C.J. (2004). Inhibition of methicillin-resistant *Staphylococcus aureus* by an in vitro continuous-flow culture containing human stool microflora. FEMS Microbiology Letters 241(2), 201-205.
Queenan, A.M., and Bush, K. (2007). Carbapenemases: the Versatile β-Lactamases. Clin. Microbiol. Rev. 20(3), 440-458.
Raibaud, P., Ducluzeau, R., Dubos, F., Hudault, S., Bewa, H., and Muller, M.C. (1980). Implantation of bacteria from the digestive tract of man and various animals into gnotobiotic mice. Am J Clin Nutr 33(11), 2440-2447.
Ramirez, N., and Abel-Santos, E. (2010). Requirements for germination of *Clostridium sordellii* spores in vitro. J. Bacteriol. 192(2), 418-425.
Rao, A.V., Shiwnarain, N., and Maharaj, I. (1989). Survival of Microencapsulated *Bifidobacterium pseudolongum* in Simulated Gastric and Intestinal Juices. Canadian Institute of Food Science and Technology Journal 22(4), 345-349.
Reeves, A.E., Koenigsknecht, M.J., Bergin, I.L., and Young, V.B. (2012). Suppression of *Clostridium* difficile in the Gastrointestinal Tracts of Germfree Mice Inoculated with a Murine Isolate from the Family Lachnospiraceae. Infection and Immunity 80(11), 3786-3794.
Rexroad, J., Wiethoff, C.M., Jones, L.S., and Middaugh, C.R. (2002). Lyophilization and the thermostability of vaccines. Cell Preservation Technology 1(2), 91-104.
Ridaura, V.K., Faith, J.J., Rey, F.E., Cheng, J., Duncan, A.E., Kau, A.L., Griffin, N.W., Lombard, V., Henrissat, B., Bain, J.R., et al. (2013). Gut Microbiota from Twins Discordant for Obesity Modulate Metabolism in Mice. Science 341(6150), 1241214-1241214.
Rode, L.J., and Foster, J.W. (1961). Germination of bacterial spores with alkyl primary amines1. J Bacteriol 81(5), 768-779.
Roffe, C. (1996). Biotherapy for antibiotic-associated and other diarrhoeas. J. Infect. 32(1), 1-10.
Rohlke, F., Surawicz, C.M., and Stollman, N. (2010). Fecal flora reconstitution for recurrent *Clostridium difficile* infection: results and methodology. J. Clin. Gastroenterol. 44(8), 567-570.
Rosen, D.L., Sharpless, C., and McGown, L.B. (1997). Bacterial Spore Detection and Determination by Use of Terbium Dipicolinate Photoluminescence. Anal. Chem. 69(6), 1082-1085.
Sack, D.A., Shimko, J., Sack, R.B., Gomes, J.G., Macleod, K., O'Sullivan,.D., and Spriggs, D. (1997). Comparison of alternative buffers for use with a new live oral cholera vaccine, Peru-15, in outpatient volunteers. Infect. Immun. 65(6), 2107-2111.
Sacks, L.E., and Alderton, G. (1961). Behavior of bacterial spores in aqueous polymer two-phase systems. J. Bacteriol. 82,331-341.
Sahlstrom, L., Bagge, E., Emmoth, E., Holmqvist, A., Danielsson-Tham, M.-L., and Albihn, A. (2008). A laboratory study of survival of selected microorganisms after heat treatment of biowaste used in biogas plants. Bioresour. Technol. 99(16), 7859-7865.
Santivarangkna, C., Kulozik, U., and Foerst, P. (2007). Alternative Drying Processes for the Industrial Preservation of Lactic Acid Starter Cultures. Biotechnology Progress 23(2), 302-315.
Sattar, S.A., Jason, T., Bidawid, S., and Farber, J. (2000). Foodborne spread of hepatitis A: recent studies on virus survival, transfer and inactivation. The Canadian Journal of Infectious Diseases 11(3), 159.
Savaiano, D.A., Ritter, A.J., Klaenhammer, T., Walker, M.R., Carlson, H.L.F., and Ruckle, J. (2012). A Novel High Purity Short-Chain Galacto-Oligosaccharide (RP-G28) Improves Lactose Digestion and Symptoms of Lactose Intolerance. Gastroenterology 142(5), S-182.
Savaiano, D.A., Ritter, A.J., Klaenhammer, T.R., Walker, W.A., James, G.M., Longcore, A.T., Chandler, J.R., and Foyt, H.L. (2013). Improving lactose digestion and symptoms of lactose intolerance with a novel galacto-oligosaccharide (RP-G28): a randomized, double-blind clinical trial. Nutrition Journal.
Seale, R.B., Flint, S.H., McQuillan, A.J., and Bremer, P.J. (2008). Recovery of Spores from Thermophilic Dairy *Bacilli* and Effects of Their Surface Characteristics on Attachment to Different Surfaces. Appl Environ Microbiol 74(3), 731-737.
Seo, M., Inoue, I., Tanaka, M., Matsuda, N., Nakano, T., Awata, T., Katayama, S., Alpers, D.H., and Komoda, T. (2013). *Clostridium butyricum* Miyairi 588 improves high-fat diet-induced non-alcoholic fatty liver disease in rats. Dig. Dis. Sci. 58(12), 3534-3544.
Setlow, B., Cowan, A. E., and Setlow, P. (2003). Germination of spores of *Bacillus subtilis* with dodecylamine. Journal of Applied Microbiology 95(3), 637-648.
Setlow, B., Yu, J., Li, Y.-Q., and Setlow, P. (2013). Analysis of the germination kinetics of individual *Bacillus subtilis* spores treated with hydrogen peroxide or sodium hypochlorite. Letters in Applied Microbiology 57(4), 259-265.
Shafaat, H.S., and Ponce, A. (2006). Applications of a Rapid Endospore Viability Assay for Monitoring UV Inactivation and Characterizing Arctic Ice Cores Appl Environ Microbiol 72(10), 6808-6814.
Shah, I.M., Laaberki, M.-H., Popham, D.L., and Dworkin, J. (2008). A eukaryotic-like Ser/Thr kinase signals bacteria to exit dormancy in response to peptidoglycan fragments. Cell 135(3), 486-496.
Shah, N.P., "Symposium: Probiotic Bacteria: Probiotic Bacteria: Selective Enumeration and Survival in Dairy Foods," Oct. 7, 1999,14 pages.
Shah, N.P. et al., "Microencapsulation of Probiotic Bacteria and Their Survival in Frozen Fermented Dairy Desserts," The Australian Journal of Dairy Technology, Oct. 2000, pp. 139-144, vol. 55, No. 3.
Shah, S. (2012). *Clostridium difficile* in inflammatory Bowel Disease: a dangerous mix (*Clostridium difficile* Symposium, Miriam Hospital, Providence, RI).
Shahinas, D., Silverman, M., Sittler, T., Chiu, C., Kim, P., Allen-Vercoe, E., Weese, S., Wong, A., Low, D.E., and Pillai, D.R. (2012). Toward an Understanding of Changes in Diversity Associated with Fecal Microbiome Transplantation Based on 16S rRNA Gene Deep Sequencing. mBio 3(5), e00338-12-e00338-12.
Sharpe, E.S., Nickerson, K.W., Bulla JR, L.A., and Aronson, J.N. (1975). Separation of spores and parasporal crystals of *Bacillus thuringiensis* in gradients of certain x-ray contrasting agents. Applied Microbiology 30(6), 1052.
Sheu, T.-Y., Marshall, R.T., and Heymann, H. (1993). Improving Survival of Culture Bacteria in Frozen Desserts by Microentrapment. Journal of Dairy Science 76(7), 1902-1907.
Siaterlis, A., Deepika, G., and Charalampopoulos, D. (2009). Effect of culture medium and cryoprotectants on the growth and survival of probiotic lactobacilli during freeze drying. Letters in Applied Microbiology 48(3), 295-301.
SIGMA-TAU. VSL#3. <http://www.vsl3.com/> Accessed Mar. 21, 2014.
Snitkin, E.S., Zelazny, A.M., Thomas, P.J., Stock, F., Henderson, D.K., Palmore, T.N., and Segre, J.A. (2012). Tracking a Hospital Outbreak of Carbapenem-Resistant *Klebsiella pneumoniae* with Whole-Genome Sequencing. Sci Transl Med 4(148), 148ra116-148ra116.
Solanki, H.K., Pawar, D.D., Shah, D.A., Prajapati, V.D., Jani, G.K., Mulla, A.M., and Thakar, P.M. (2013). Development of Microencapsulation Delivery System for Long-Term Preservation of Probiotics as Biotherapeutics Agent. BioMed Research International 2013,1-21.
SOP No. MB-28-00. <http://www.epa.gov/pesticides/methods/MB-28-00.pdf> Accessed 27th Match 2014.
Sorg, J.A., and Sonenshein, A.L. (2008). Bile Salts and Glycine as Cogerminants for *Clostridium* difficile Spores. J Bacterial 190(7), 2505-2512.

(56) References Cited

OTHER PUBLICATIONS

Sow, H., Desbiens, M., Morales-Rayas, R., Ngazoa, S.E., and Jean, J. (2011). Heat Inactivation of Hepatitis A Virus and a Norovirus Surrogate in Soft-Shell Clams (*Mya arenaria*). Foodborne Pathogens and Disease 8(3), 387-393.
Stams, A.J.M., Van Dijk, J.B., Dijkema, C., and Plugge, C.M. (1993). Growth of Syntrophic Propionate-Oxidizing Bacteria with Fumarate in the Absence of Methanogenic Bacteria. Appl Environ Microbiol 59(4), 1114-1119.
Stevens, K.A., and Jaykus, L.-A. (2004). Bacterial Separation and Concentration from Complex Sample Matrices: A Review. Critical Reviews in Microbiology 30(1), 7-24.
Su, W.J., Waechter, M.J., Bourlioux, P., Dolegeal, M., Fourniat, J., and Mahuzier, G. (1987). Role of volatile fatty acids in colonization resistance to *Clostridium difficile* in gnotobiotic mice. Infect. Immun. 55(7), 1686-1691.
Talwalkar, A., and Kailasapathy, K. (2003). Effect of microencapsulation on oxygen toxicity in probiotic bacteria. Australian Journal of Dairy Technology 58(1), 36-39.
Tamir, H., and Gilvarg, C. (1966). Density Gradient Centrifugation for the Separation of Sporulating Forms of Bacteria. J. Biol. Chem. 241(5), 1085-1090.
Taur, Y., and Pamer, E.G. (2014). Harnessing Microbiota to Kill a Pathogen: Fixing the microbiota to treat *Clostridium difficile* infections. Nature Medicine 20(3), 246-247.
Taur, Y., Xavier, J.B., Lipuma, L., Ubeda, C., Goldberg, J., Gobourne, A., Lee, Y.J., Dubin, K.A., Socci, N.D., Viale, A., et al. (2012). Intestinal Domination and the Risk of Bacteremia in Patients Undergoing Allogeneic Hematopoietic Stem Cell Transplantation. Olin Infect Dis 55(7), 905-914.
The Human Microbiome Project Consortium (2012). Structure, function and diversity of the healthy human microbiome. Nature 486(7402), 207-214.
Tisa, L.S., Koshikawa, T., and Gerhardt, P. (1982). Wet and dry bacterial spore densities determined by buoyant sedimentation. Applied and Environmental Microbiology 43(6), 1307-1310.
Tvede, M., and Rask-Madsen, J. (1989). Bacteriotherapy for chronic relapsing *Clostridium difficile* diarrhoea in six patients. Lancet 1(8648), 1156-1160.
Ubeda, C., Bucci, V., Caballero, S., Djukovic, A., Toussaint, N.C., Equinda, M., Lipuma, L., Ling, L., Gobourne, A., NO, D., et al. (2013). Intestinal Microbiota Containing *Barnesiella* Species Cures Vancomycin-Resistant *Enterococcus faecium* Colonization. Infect. Immun. 81(3), 965-973.
Ubeda, C., Taur, Y., Jenq, R.R., Equinda, M.J., Son, T., Samstein, M., Viale, A., Socci, N.D., Van Den Brink, M.R.M., Kamboj, M., et al. (2010). Vancomycin-resistant Enterococcus domination of intestinal microbiota is enabled by antibiotic treatment in mice and precedes bloodstream invasion in humans. Journal of Clinical Investigation 120(12), 4332-4341.
Van Der Woude, M.W., and Baumler, A.J. (2004). Phase and Antigenic Variation in Bacteria. Clin Microbiol Rev 17(3), 581-611.
Van Kregten, E., Westerdaal, N.A., and Willers, J.M. (1984). New, simple medium for selective recovery of *Klebsiella pneumoniae* and *Klebsiella oxytoca* from human feces. J Clin Microbiol 20(5), 936-941.
Van Nood, E., Vrieze, A., Nieuwdorp, M., Fuentes, S., Zoetendal, E.G., De Vos, W.M., Visser, C.E., Kuijper, E.J., Bartelsman, J.F.W. M., Tijssen, J.G.P., et al. (2013). Duodenal Infusion of Donor Feces for Recurrent *Clostridium difficile*. New England Journal of Medicine 368(5), 407-415.
Vandenplas, Y., Veereman, G., Van Der Werff Ten Bosch, J., Goossens, A., Pierard, D., Samsom, J.N., and Escher, J.C. (2014). Fecal Microbial Transplantation in a One-Year-Old Girl with Early Onset Colitis—Caution Advised: Journal of Pediatric Gastroenterology and Nutrition 1.
Vidal, M., Forestier, C., Charbonnel, N., Henard, S., Rabaud, C., and Lesens, O. (2010). Probiotics and Intestinal Colonization by Vancomycin-Resistant Enterococci in Mice and Humans. J Clin Microbiol 48(7), 2595-2598.
Villano, S.A., Seiberling, M., Tatarowicz, W., Monnot-Chase, E., and Gerding, D.N. (2012). Evaluation of an Oral Suspension of VP20621, Spores of Nontoxigenic *Clostridium difficile* Strain M3, in Healthy Subjects. Antimicrobial Agents and Chemotherapy 56(10), 5224-5229.
Wagman, J., and Weneck, E.J. (1963). Preservation of bacteria by circulating-gas freeze drying. Applied Microbiology 11(3), 244-248.
Waites, W.M., and Wyatt, L.R. (1971). Germination of spores of *Clostridium bifermentans* by certain amino acids, lactate and pyruvate in the presence of sodium or potassium ions. J. Gen. Microbiol. 67(2), 215-222.
Waites, W.M., and Wyatt, L.R. (1974). The effect of pH, germinants and temperature on the germination of spores of *Clostridium bifermentans*. J. Gen. Microbiol. 80(1), 253-258.
Walker, A.W., and Lawley, T.D. (2012). Therapeutic modulation of intestinal dysbiosis. Pharmacological Research 69(1), 75-86.
Wang, S., and Curtiss III, R. (2014). Development of *Streptococcus pneumoniae* Vaccines Using Live Vectors. Vaccines 2(1), 49-88.
Weingarden, A.R., Chen, C., Bobr, A., Yao, D., Lu, Y., Nelson, V.M., Sadowsky, M.J., and Khoruts, A. (2013). Microbiota transplantation restores normal fecal bile acid composition in recurrent *Clostridium* difficile infection. AJP: Gastrointestinal and Liver Physiology 306(4), G310-G319.
Wilson, K.H., and Sheagren, J.N. (1983). Antagonism of toxigenic *Clostridium difficile* by nontoxigenic C. difficile. Journal of Infectious Diseases 147(4), 733.
Wilson, K.H., Silva, J., and Fekety, F.R. (1981). Suppression of *Clostridium difficile* by Normal Hamster Cecal Flora and Prevention of Antibiotic-Associated Cecitis. Infect Immun 34(2), 626-628.
Woo, T.D.H., Oka, K., Takahashi, M., Hojo, F., Osaki, T., Hanawa, T., Kurata, S., Yonezawa, H., and Kamiya, S. (2011). Inhibition of the cytotoxic effect of Clostridium difficile in vitro by *Clostridium butyricum* Miyairi 588 strain. J. Med. Microbiol. 60(Pt 11), 1617-1625.
Wrobel, B. (2008). Statistical measures of uncertainty for branches in phylogenetic trees inferred from molecular sequences by using model-based methods. J. Appl. Genet. 49(1), 49-67.
Wroblewski, D., Hannett, G.E., Bopp, D.J., Dumyati, G.K., Halse, T.A., Dumas, N.B., and Musser, K.A. (2009). Rapid Molecular Characterization of *Clostridium* difficile and Assessment of Populations of *C. difficile* in Stool Specimens. Journal of Clinical Microbiology 47(7), 2142-2148.
Yamamura, H., Hayakawa, M., and Iimura, Y. (2003). Application of sucrose-gradient centrifugation for selective isolation of *Nocardia* spp. from soil. Journal of Applied Microbiology 95(4), 677-685.
Yang, W.-W., and Ponce, A. (2009). Rapid endospore viability assay of *Clostridium sporogenes* spores. International Journal of Food Microbiology 133(3), 213-216.
Yang, W.-W., and Ponce, A. (2011). Validation of a *Clostridium* Endospore Viability Assay and Analysis of Greenland Ices and Atacama Desert Soils. Appl. Environ. Microbiol. 77(7), 2352-2358.
Yang, W.-W., Crow-Willard, E.N., and Ponce, A. (2009). Production and characterization of pure *Clostridium* spore suspensions. J. Appl. Microbiol. 106(1), 27-33.
Yang, W.W. (2010). Fast Viability Assessment of *Clostridium* Spores Survival in Extreme Environments. PhD thesis California Institute of Technology.
Yi, X., and Setlow, P. (2010). Studies of the Commitment Step in the Germination of Spores of Bacillus Species. J. Bacteriol. 192(13), 3424-3433.
Yung, P.T., and Ponce, A. (2008). Fast Sterility Assessment by Germinable-Endospore Biodosimetry. Appl. Environ. Microbiol. 74(24), 7669-7674.
Yunoki, M., Tsujikawa, M., Urayama, T., Sasaki, Y., Morita, M., Tanaka, H., Hattori, S., Takechi, K., and Ikuta, K. (2003). Heat sensitivity of human parvovirus B19. Vox Sanguinis 84(3), 164-169.
Zeng, Y., Fan, H., Chiueh, G., Pham, B., Martin, R., Lechuga-Ballesteros, D., Truong, V.L., Josh, S.B., and Middaugh, C.R. (2009). Towards development of stable formulations of a live attenuated bacterial vaccine: a preformulation study facilitated by a biophysical approach. Hum Vaccin 5(5), 322-331.

(56) References Cited

OTHER PUBLICATIONS

Zhao, J., Krishna, V., Moudgil, B., and Koopman, B. (2008). Evaluation of endospore purification methods applied to *Bacillus cereus*. Separation and Purification Technology 61(3), 341-347.

Bolivar, I. et al., "Bacterial Diversity in Oral Samples of Children in Niger with Acute Noma, Acute Necrotizing Gingivitis and Healthy Controls," PLOS Neglected Tropical Diseases, Mar. 2012, pp. 1-11, vol. 6, No. 3, E1556; Uncultured *Catonella* sp. partial 16S rRNA Gene, Clone 402A04(oral): Nucleotide: NCBI: GenBank: AM420133.1, last accessed Mar. 12, 2014, pp. 12-13.

Kanamoto, T. et al., "Genetic Heterogeneities and Phenotypic Characteristics of Strains of the Genus *Abiotrophia* and Proposal of *Abiotrophia* para-adiacens sp. nov.," Journal of Clinical Microbiology, Feb. 2000, pp. 492-498, vol. 38, No. 2; Abiotropia para-adjacens gene for 16S rRNA, partial sequence, strain: Nucleotide: NCBI: GenBank: AB022027.1, last accessed Mar. 12, 2014, p. 8.

Myllyluoma, E. et al., "Effects of Multispecies Probiotic Combination on *Helicobacter pylori* Infection in Vitro," Clinical and Vaccine Immunology, Sep. 2008, pp. 1472-1482, vol. 15, No. 9.

PCT International Search Report and Written Opinion, PCT Application No. PCT/US13/71758, May 5, 2014, 45 pages.

Wang, M. et al., "Comparison of Bacterial Diversity Along the Human Intestinal Tract by Direct Cloning and Sequencing of 16S rRNA Genes," FEMS Microbiology Ecology, 2005, pp. 219-231, vol. 54.

United States Office Action, U.S. Appl. No. 14/091,201, Mar. 25, 2014, 19 pages.

FIGURE 1A

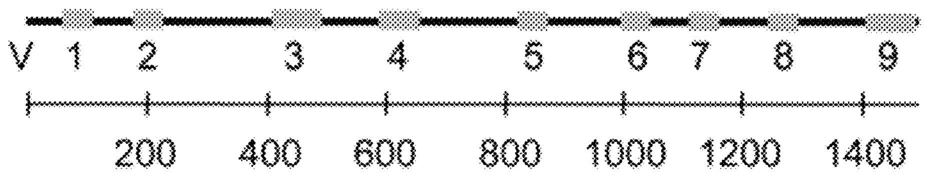

FIGURE 1B

1 AAATTGAAGAGTTTGATCATGGCTCAGATTGAACGCTGGCGGCAGGCCTA
51 ACACATGCAAGTCGAACGGTAACAGGAAGAAGCTTGCTCTTTGCTGACGA
101 GTGGCGGACGGGTGAGTAATGTCTGGGAAACTGCCTGATGGAGGGGGATA
151 ACTACTGGAAACGGTAGCTAATACCGCATAACGTCGCAAGACCAAAGAGG
201 GGGACCTTCGGGCCTCTTGCCATCGGATGTGCCCAGATGGGATTAGCTAG
251 TAGGTGGGGTAACGGCTCACCTAGGCGACGATCCCTAGCTGGTCTGAGAG
301 GATGACCAGCCACACTGGAACTGAGACACGGTCCAGACTCCTACGGGAGG
351 CAGCAGTGGGGAATATTGCACAATGGGCGCAAGCCTGATGCAGCCATGCC
401 GCGTGTATGAAGAAGGCCTTCGGGTTGTAAAGTACTTTCAGCGGGGAGGA
451 AGGGAGTAAAGTTAATACCTTTGCTCATTGACGTTACCCGCAGAAGAAGC
501 ACCGGCTAACTCGTGCCCAGGCATGCGCAGGAATACGGAGGTGCAAGCGT
551 TAATCGGAATTACTGGGCGTAAAGCGCACGCAGGCGGTTTGTTAAGTCAG
601 ATGTGAAATCCCCGGGCTCAACCTGGGAACTGCATCTGATACTGGCAAGC
651 TTGAGTCTCGTAGAGGGGGGTAGAATTCCAGGTGTAGCGGTGAAATGCGT
701 AGAGATCTGGAGGAATACCGGTGGCGAAGGCGGCCCCCTGGACGAAGACT
751 CACGCTCAGGTGCGAAAGCGTGGGGAGCAAACAGGATTAGATACCCTGGT
801 AGTCCACGCCGTAAACGATGTCGACTTGGAGGTTGTGCCCTTGAGGCGTG
851 GCTTCCGGAGCTAACGCGTTAAGTCGACCGCCTGGGGAGTACGGCCGCAA
901 GGTTAAAACTCAAATGAATTGACGGGGGCCCGCACAAGCGGTGGAGCATG
951 TGGTTTAATTCGATGCAACGCGAAGAACCTTACCTGGTCTTGACATCCAC
1001 GGAAGTTTTCAGAGATGAGAATGTGCCTTCGGGAACCGTGAGACAGGTGC
1051 TGCATGGCTGTCGTCAGCTCGTGTTGTGAAATGTTGGGTTAAGTCCCGCA
1101 ACGAGCGCAACCCTTATCCTTTGTTGCCAGCGGTCCGGCCGGGAACTCAA
1151 AGGAGACTGCCAGTGATAAACTGGAGGAAGGTGGGGATGACGTCAAGTCA
1201 TCATGGCCCTTACGACCAGGGCTACACACGTGCTACAATGGCGCATACAA
1251 AGAGAAGCGACCTCGCGAGAGCAAGCGGACCTCATAAAGTGCGTCGTAGT
1301 CCGGATTGGAGTCTGCAACTCGACTCCATGAAGTCGGAATCGCTAGTAAT
1351 CGTGGATCAGAATGCCACGGTGAATACGTTCCCGGGCCTTGTACACACCG
1401 CCCGMCACACCATGGGAGTGGGTTGCAAAAGAAGTAGGTAGCTTAACCTT
1451 CGGGAGGGCGCTTACCACTTTGTGATTCATGACTGGGGTGAAGTCGTAAC
1501 AAGGTAACCGTAGGGGAACCTGCGGTTGGATCACCTCCTTA

SYNERGISTIC BACTERIAL COMPOSITIONS AND METHODS OF PRODUCTION AND USE THEREOF

CROSS REFERENCE TO RELATED APPLICATIONS

This application is a divisional application of U.S. patent application Ser. No. 14/091,201, filed on Nov. 26, 2013, which is a continuation of International Application No. PCT/US2013/071758, filed on Nov. 25, 2013, titled "SYNERGISTIC BACTERIAL COMPOSITIONS AND METHODS OF PRODUCTION AND USE THEREOF", which claims the benefit of U.S. Provisional Patent Application Ser. No. 61/729,518, filed Nov. 23, 2012, U.S. Provisional Patent Application Ser. No. 61/729,519, filed Nov. 23, 2012, U.S. Provisional Patent Application Ser. No. 61/729,520, filed Nov. 23, 2012, U.S. Provisional Patent Application Ser. No. 61/729,521, filed Nov. 23, 2012, U.S. Provisional Patent Application Ser. No. 61/729,522, filed Nov. 23, 2012, U.S. Provisional Patent Application Ser. No. 61/729,524, filed Nov. 23, 2012, U.S. Provisional Patent Application Ser. No. 61/729,515, filed Nov. 23, 2012, U.S. Provisional Patent Application Ser. No. 61/729,517, filed Nov. 23, 2012, U.S. Provisional Patent Application Ser. No. 61/729,525, filed Nov. 23, 2012, U.S. Provisional Patent Application Ser. No. 61/729,526, filed Nov. 23, 2012, U.S. Provisional Patent Application Ser. No. 61/729,527, filed Nov. 23, 2012, all of which are incorporated herein by reference in their entirety for all purposes.

REFERENCE TO A SEQUENCE LISTING

This application includes a Sequence Listing submitted electronically as a text file named 26469_US_CRF_sequence_listing.txt, created on Mar. 20, 2014, with a size of 2,945,024 bytes. The sequence listing is incorporated by reference.

INTRODUCTION

Mammals are colonized by microbes in the gastrointestinal (GI) tract, on the skin, and in other epithelial and tissue niches such as the oral cavity, eye surface and vagina. The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population by about 3 years of age. Interactions between microbial strains in these populations and between microbes and the host, e.g. the host immune system, shape the community structure, with availability of and competition for resources affecting the distribution of microbes. Such resources may be food, location and the availability of space to grow or a physical structure to which the microbe may attach. For example, host diet is involved in shaping the GI tract flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections of the gut. For instance, patients become more susceptible to pathogenic infections when the normal intestinal microbiota has been disturbed due to use of broad-spectrum antibiotics. Many of these diseases and disorders are chronic conditions that significantly decrease a patient's quality of life and can be ultimately fatal.

Fecal transplantation has been shown to be an effective treatment for patients suffering from severe or refractory GI infections by repopulating the gut with a diverse array of microbes that control key pathogens by creating an ecological environment inimical to their proliferation and survival. Such approaches have demonstrated significant potential to decrease host susceptibility to infection. Fecal transplantation, however, is considered to be a procedure of last resort because it has the potential to transmit infectious or allergenic agents between hosts, involves the transmission of potentially hundreds of unknown strains from donor to patient, and is difficult to perform on a mass scale. Additionally, fecal transplantation is inherently nonstandardized and different desired and/or undesired material may be transmitted in any given donation. Fecal transplantation is not approved by the FDA and is unlikely to gain approval since the product cannot be standardized and characterized according to regulatory requirements for identity, potency, purity and safety. Thus, there is a need for defined compositions that can be used to decrease susceptibility to infection and/or that facilitate restoration of a healthy gut microbiota.

Thus practitioners have a need for a much safer and reproducible treatment for disorders currently treated on an experimental (non-FDA approved) basis using fecal transplantation. In order to prepare a therapeutic with commercial potential, we have designed bacterial compositions of isolated bacterial strains with a plurality of beneficial properties based on our understanding of those bacterial strains and our analysis of the properties that would enhance the utility and commercialization of a bacterial composition.

Therefore, in response to the need for durable, efficient, and effective compositions and methods for treatment of GI diseases, in particular serious pathogenic infections, by way of restoring or enhancing microbiota functions, we address these and other shortcomings of the prior art by providing compositions and methods for treating patients.

SUMMARY

In one aspect, provided are compositions comprising an effective amount of a bacterial composition comprising at least a first type of isolated bacterium capable of forming a spore and a second type of isolated bacterium capable of forming a spore, wherein the first type and the second type are not identical, and wherein at least one of the first type and the second type are capable of decreasing and/or inhibiting the growth and/or colonization of at least one type of pathogenic bacteria. In an embodiment, the bacterial composition comprises at least about 3, 4, 5, 6, 7, 8, 9, or 10 types of isolated bacteria. In an embodiment, the bacterial composition comprises at least about 3, 4, 5, 6, 7, 8, 9, or 10 types of isolated bacteria and at least 1, 2, 3, 4, 5, 6, 7, 8, 9, or 10 of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises: i) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria capable of forming spores, ii) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria not known to be capable of forming spores, or iii) any combination of i) and ii). In an embodiment, the first type and the second type are present in the composition in approximately equal concentrations. In an embodiment, the first type and the second type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of: i) between two and about twenty types of isolated bacteria, wherein at least two types of isolated bacteria are independently capable of spore formation; ii) between two and about twenty types of isolated bacteria, wherein at least two types of isolated bacteria not known to be capable of spore formation, or iii) any combination of i) and ii). In an embodiment, the first type of isolated bacterium and the second type of isolated bacterium are selected from Table 1. In an embodiment, the first type of isolated bacterium and the second type of isolated bacterium comprise an operational taxonomic unit (OTU) distinction. In an embodiment, the OTU distinction comprises 16S rRNA sequence similarity below about 95% identity. In an embodiment, the first type of isolated bacterium and the second type of isolated bacterium independently comprise bacteria that comprise 16S rRNA sequence at least 95% identical to 16S rRNA sequence present in a bacterium selected from SEQ ID NOs. 1-1,864. In an embodiment, a combination of the first type and the second type are: i) cytotoxic, ii) cytostatic, iii) capable of decreasing the growth of the pathogenic bacterium, iv) capable of inhibiting the growth of the pathogenic bacterium, v) capable of decreasing the colonization of the pathogenic bacterium, vi) capable of inhibiting the colonization of the pathogenic bacterium, or vii) any combination of i)-vi). In an embodiment, the combination is capable of inhibiting proliferation of the pathogenic bacteria present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent *Enterobacteriaceae* (CRE), extended spectrum beta-lactam resistant *Enterococci* (ESBL), and vancomycin-resistant *Enterococci* (VRE). In an embodiment, the first type and the second type synergistically interact. In an embodiment, the first type and the second type synergistically interact to inhibit the pathogenic bacterium.

In another aspect, provided are compositions comprising an effective amount of a bacterial composition comprising at least a first type of isolated bacterium and a second type of isolated bacterium, wherein only one of the first type and the second type are capable of forming a spore, and wherein at least one of the first type and the second type are capable of decreasing the growth and/or colonization of at least one type of pathogenic bacteria.

In another aspect, provided are compositions comprising an effective amount of a bacterial composition comprising at least a first type of isolated bacterium and a second type of isolated bacterium, wherein the first type and the second type are not spores or known to be capable of forming a spore, and wherein at least one of the first type and the second type are capable of decreasing the growth and/or colonization of at least one type of pathogenic bacteria.

In an embodiment, at least one of the first type and the second type are capable of reducing the growth rate of at least one type of pathogenic bacteria. In an embodiment, at least one of the first type and the second type are cytotoxic to at least one type of pathogenic bacteria. In an embodiment, at least one of the first type and the second type are cytostatic to at least one type of pathogenic bacteria. In an embodiment, the first type and the second type are selected from Table 1. In an embodiment, the first type and the second type comprise different species. In an embodiment, the first type and the second type comprise different genera. In an embodiment, the first type and the second type comprise different families. In an embodiment, the first type and the second type comprise different orders.

In another aspect, provided are compositions comprising an effective amount of a bacterial composition comprising at least a first type of isolated bacterium and a second type of isolated bacterium, wherein: i) the first type and the second type are independently capable of forming a spore; ii) only one of the first type and the second type are capable of forming a spore or iii) neither the first type nor the second type are capable of forming a spore, wherein the first type and the second type are not identical, wherein the first type and the second type are capable of functionally populating the gastrointestinal tract of a human subject to whom the composition is administered. In an embodiment, the functional populating of the gastrointestinal tract comprises preventing a dysbiosis of the gastrointestinal tract. In an embodiment, the functional populating of the gastrointestinal tract comprises treating a dysbiosis of the gastrointestinal tract. In an embodiment, the functional populating of the gastrointestinal tract comprises reducing the severity of a dysbiosis of the gastrointestinal tract. In an embodiment, the functional populating of the gastrointestinal tract comprises reducing one or more symptoms of a dysbiosis of the gastrointestinal tract. In an embodiment, the functional populating of the gastrointestinal tract comprises preventing growth and/or colonization of the gastrointestinal tract by a pathogenic bacterium. In an embodiment, the functional populating of the gastrointestinal tract comprises reducing growth and/or colonization of the gastrointestinal tract by a pathogenic bacterium. In an embodiment, the functional populating of the gastrointestinal tract comprises reducing the number of one or more types of pathogenic bacteria in the gastrointestinal tract. In an embodiment, the functional populating of the gastrointestinal tract comprises increasing the number of one or more non-pathogenic bacteria in the gastrointestinal tract. In an embodiment, the bacterial composition comprises 0, 1, 2, 3 or greater than 3 types of isolated bacteria capable of forming spores. In an embodiment, the bacterial composition comprises at least about 5 types of isolated bacteria capable of forming spores.

In an embodiment, the bacterial composition comprises at least about 7 types of isolated bacteria capable of forming spores. In an embodiment, the first type and the second type are present in the composition in not substantially equal concentrations. In an embodiment, the first type and the second type are present in the composition in approximately equal concentrations. In an embodiment, the first type is present in the composition in at least about 150% the concentration of the second type. In an embodiment, the second type is present in the composition in at least about 150% the concentration of the first type. In an embodiment, the composition consists essentially of between two and about ten types of isolated bacteria, wherein at least one type of isolated bacteria are independently capable of spore formation. In an embodiment, the first type of isolated bacterium and the second type of isolated bacterium are selected from Table 1. In an embodiment, the first type of isolated bacterium and the second type of isolated bacterium comprise an operational taxonomic unit (OTU) distinction. In an embodiment, the OTU distinction comprises 16S rRNA sequence similarity below about 95% identity. In an embodiment, the first type of isolated bacterium and the second type of isolated bacterium independently comprise bacteria that comprise 16S rRNA sequence at least 95% identical to 16S rRNA sequence present in a bacterium selected from Table 3. In an embodiment, a combination of the first type and the second type are cytotoxic or cytostatic to the pathogenic bacterium. In an embodiment, the combination is capable of inhibiting proliferation of the pathogenic bacteria present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacteria present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent *Enterobacteriaceae* (CRE), extended spectrum beta-lactam resistant *Enterococci* (ESBL), and vancomycin-resistant *Enterococci* (VRE). In an embodiment, the first type and the second type synergistically interact to be cytotoxic to the pathogenic bacterium. In an embodiment, wherein the first type and the second type synergistically interact to be cytostatic to the pathogenic bacterium.

In another aspect, provided are single dose units comprising the compositions of the present invention. In an embodiment, the dose unit comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of either spores or vegetative bacterial cells. In an embodiment, the dose unit comprises a pharmaceutically acceptable excipient, an enteric coating or a combination thereof. In an embodiment, the dose unit further comprises a drug selected from corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof. In an embodiment, the dose unit is formulated for oral administration, rectal administration, or the combination of oral and rectal administration, or is formulated for topical, nasal or inhalation administration.

In another aspect, provided are kits comprising in one or more containers: a first purified population of a first type of bacterial spores substantially free of viable vegetal bacterial cells; and a second purified population of a second type of bacterial spores substantially free of viable vegetal bacterial cells, wherein the first type and the second type of bacterial spores are not identical, and wherein the first type and the second type of bacterial spores, when co-localized in a target region of a gastrointestinal tract of a human subject in need thereof, are capable of functionally populating the gastrointestinal tract. In an embodiment, the first purified population and the second purified population are present in a single container. In an embodiment, the first purified population and the second purified population are present in two containers. In an embodiment, the first purified population and the second purified population are lyophilized or substantially dehydrated. In an embodiment, the kit further comprises in one or more containers an effective amount of an anti-bacterial agent, an effective amount of an anti-viral agent, an effective amount of an anti-fungal agent, an effective amount of an anti-parasitic agent, or a combination thereof in one or more containers. In an embodiment, the kit further comprises a pharmaceutically acceptable excipient or diluent.

Also provided are pharmaceutical formulations comprising an effective amount of the compositions of the invention, and further comprising an effective amount of an anti-bacterial agent, an effective amount of an anti-fungal agent, an effective amount of an anti-viral agent, an effective amount of an anti-parasitic agent.

Also provided are comestible products comprising a first purified population of a first type of bacterial spores and a second purified population of a second type of bacterial spores, wherein the first type and the second type of bacterial spores are not identical, wherein the comestible product is substantially free of viable vegetal bacterial cells, and wherein the first type and the second type of bacterial spores, when administered to a human subject in need thereof, are capable of functionally populating the gastrointestinal tract of the human subject. In an embodiment, the comestible product comprises a food or food additive, a beverage or beverage additive, or a medical food. In an embodiment, the comestible product comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable spores. In an embodiment, the comestible product comprises a first type of bacterial spores and a second type of bacterial spores selected from Table 1, or where the first type of bacterial spores and the second type of bacterial spores independently comprise bacterial spores that comprise 16S rRNA sequence at least 95% identical to 16S rRNA sequence present in a bacterium selected from SEQ ID NOs: 1-1,864.

Also provided are methods comprising administering to a human subject in need thereof an effective amount of a bacterial composition comprising at least a first type of isolated bacterium and a second type of isolated bacterium, wherein: the first type and the second type are independently capable of forming a spore; only one of the first type and the second type are capable of forming a spore or neither the first type nor the second type are capable of forming a spore, wherein the first type and the second type are not identical, and wherein at least one of the first type and the second type exert an inhibitory effect on a pathogenic bacterium present in the gastrointestinal tract of the human subject, such that the number of pathogenic bacteria present in the gastrointestinal tract is not detectably increased or is detectably decreased over a period of time. In an embodiment, the human subject is diagnosed as having a dysbiosis of the gastrointestinal tract. In an embodiment, wherein the human subject is diagnosed as infected with a pathogenic bacterium selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent *Enterobacteriaceae* (CRE), extended spectrum beta-lactam resistant *Enterococci* (ESBL), and vancomycin-resistant *Enterococci* (VRE). In an embodiment, the bacterial composition is administered simultaneously with i) an antibiotic, ii) a prebiotic, or iii) a combination of i) and ii). In an embodiment, the bacterial composition is administered prior to administration of i) an antibiotic, ii) a prebiotic, or iii) a combination of i) and ii). In an embodiment, the bacterial composition is administered subsequent to administration of i) an antibiotic, ii) a prebiotic, or iii) a combination of i) and ii). In an embodiment, the number of pathogenic bacterium present in or excreted from the gastrointestinal tract of the human subject is detectably reduced within one month, within two weeks, or within one week of administration of the bacterial composition. In an embodiment, the number of pathogenic bacterium present in or excreted from the gastrointestinal tract of the human subject is detectably reduced within three days, two days or one day of administration of the bacterial composition. In an embodiment, the human subject is detectably free of the pathogenic bacterium within one month, two weeks, one week, three days or one day of administration of the bacterial composition. In an embodiment, the bacterial composition comprises at least about 3, 4, 5, 6, 7, 8, 9, or 10 types of isolated bacteria. In an embodiment, the bacterial composition comprises at least about 3, 4, 5, 6, 7, 8, 9, or 10 types of isolated bacteria and at least 1, 2, 3, 4, 5, 6, 7, 8, 9, or 10 of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises: i) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria capable of forming spores, ii) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria not known to be capable of forming spores, or iii) any combination of i) and ii). In an embodiment, the bacterial composition comprises at least about 5 types of isolated bacteria and at least 1 of the isolated bacteria are capable of forming spores. In an embodiment, the bacterial composition comprises at least about 5 types of isolated bacteria and at least 1 of the isolated bacteria is not capable of forming spores. In an embodiment, the bacterial composition comprises at least about 3, 4, 5, 6, 7, 8, 9 or 10 types of isolated bacteria, wherein i) at least 1, 2, 3, 4, 5, 6, 7, 8, 9 or 10 types of isolated bacteria are capable of forming spores, ii) at least 1, 2, 3, 4, 5, 6, 7, 8, 9 or 10 types of isolated bacteria are not capable of forming spores, or iii) any combination of i) and ii). In an embodiment, the first type and the second type are present in the composition in approximately equal concentrations. In an embodiment, the first type and the second type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of between two and about ten types of isolated bacteria, wherein at least two types of isolated bacteria are independently capable of spore formation. In an embodiment, the composition consists essentially of between two and about ten types of isolated bacteria, wherein at least two types of isolated bacteria are not capable of spore formation. In an embodiment, the first type of isolated bacterium and the second type of isolated bacterium are selected from Table 1. In an embodiment, the first type of isolated bacterium and the second type of isolated bacterium comprise an operational taxonomic unit (OTU) distinction. In an embodiment, the OTU distinction comprises 16S rRNA sequence similarity below about 95% identity. In an embodiment, the first type of isolated bacterium and the second type of isolated bacterium independently comprise bacteria that comprise 16S rRNA sequence at least 95% identical to 16S rRNA sequence present in a bacterium selected from SEQ ID NOs: 1-1,864. In an embodiment, a combination of the first type and the second type are cytotoxic or cytostatic to the pathogenic bacterium. In an embodiment, the combination is capable of inhibiting proliferation of the pathogenic bacterial present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent *Enterobacteriaceae* (CRE), extended spectrum beta-lactam resistant *Enterococci* (ESBL), and vancomycin-resistant *Enterococci* (VRE). In an embodiment, the first type and the second type synergistically interact to be cytotoxic to the pathogenic bacterium. In an embodiment, the first type and the second type synergistically interact to be cytostatic to the pathogenic bacterium.

Also provided are methods of functionally populating the gastrointestinal tract of a human subject, comprising administering to the subject an effective amount of a bacterial composition comprising at least a first type of isolated bacterium and a second type of isolated bacterium, wherein i) the first type and the second type are independently capable of forming a spore; ii) only one of the first type and the second type are capable of forming a spore or iii) neither the first type nor the second type are capable of forming a spore, wherein the first type and the second type are not identical, under conditions such that the first type and the second type functionally populate the gastrointestinal tract of the human subject. In an embodiment, the bacterial composition is orally administered, rectally administered, or the combination of orally and rectally administered. In an embodiment, the bacterial composition is topically or nasally administered or inhaled. In an embodiment, the first type of isolated bacteria and the second type of isolated bacteria are selected from Table 1. In an embodiment, the bacterial composition consists essentially of spores, wherein the spores comprise spores of the first type of isolated bacteria and spores of the second type of isolated bacteria. In an embodiment, the first type of isolated bacteria and the second type of isolated bacteria independently comprise bacterial spores that comprise 16S rRNA sequence at least 95% identical to 16S rRNA sequence present in a bacterium selected from SEQ ID NOs. 1-1,864. In an embodiment, the functional populating of the gastrointestinal tract comprises preventing a dysbiosis of the gastrointestinal tract. In an embodiment, the functional populating of the gastrointestinal tract comprises treating a dysbiosis of the gastrointestinal tract. In an embodiment, the functional populating of the gastrointestinal tract comprises reducing the severity of a dysbiosis of the gastrointestinal tract. In an embodiment, the functional populating of the gastrointestinal tract comprises reducing one or more symptoms of a dysbiosis of the gastrointestinal tract. In an embodiment, the functional populating of the gastrointestinal tract comprises preventing colonization of the gastrointestinal tract by a pathogenic bacterium. In an embodiment, the functional populating of the gastrointestinal tract comprises reducing colonization of the gastrointestinal tract and/or growth by a pathogenic bacterium. In an embodiment, wherein the functional populating of the gastrointestinal tract comprises reducing the number of one or more types of pathogenic bacteria in the gastrointestinal tract. In an embodiment, the functional populating of the gastrointestinal tract comprises increasing the number of one or more non-pathogenic bacteria in the gastrointestinal tract. In an embodiment, the bacterial composition comprises at least about 3, 5, 7 or 9 types of isolated bacteria capable of forming spores. In an embodiment, the bacterial composition comprises at least about 5 types of isolated bacteria and at least 20% of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises at least about 3, 4, 5, 6, 7, 8, 9 or 10 types of isolated bacteria, wherein i) at least 1, 2, 3, 4, 5, 6, 7, 8, 9 or 10 types of isolated bacteria are capable of forming spores, ii) at least 1, 2, 3, 4, 5, 6, 7, 8, 9 or 10 types of isolated bacteria are not capable of forming spores, or iii) any combination of i) and ii). In an embodiment, the first type and the second type are present in the composition in approximately equal concentrations. In an embodiment, the first type and the second type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of between two and about ten types of isolated bacteria, wherein i) at least one type of isolated bacteria is capable of spore formation, ii) at least one type of isolated bacteria is not capable of spore formation, or iii) a combination of i) and ii). In an embodiment, a combination of the first type and the second type are inhibitory to the pathogenic bacterium. In an embodiment, the combination reduces the growth rate of the pathogenic bacterium. In an embodiment, the combination is cytostatic or cytotoxic to the pathogenic bacterium. In an embodiment, the combination is capable of inhibiting growth of the pathogenic bacterial present at a concentration at least equal to the concentration of the combination of the first type and the second type. In an embodiment, the combination is capable of inhibiting growth of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent *Enterobacteriaceae* (CRE), extended spectrum beta-lactam resistant *Enterococci* (ESBL), and vancomycin-resistant *Enterococci* (VRE). In an embodiment, the first type and the second type synergistically interact to reduce or inhibit the growth of the pathogenic bacterium. In an embodiment, the first type and the second type synergistically interact to reduce or inhibit the colonization of the pathogenic bacterium. In an embodiment, the method comprises administering to the human subject a single dose unit comprising at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable bacteria. In an embodiment, the dose unit comprises a bacterial population substantially in the form of spores. In an embodiment, the dose unit comprises a pharmaceutically acceptable excipient and/or an enteric coating. In an embodiment, the unit dose is formulated for oral administration, rectal administration, or the combination of oral and rectal administration. In an embodiment, the unit dose is formulated for topical or nasal administration or for inhalation.

In another aspect, provided are methods of reducing the number of pathogenic bacteria present in the gastrointestinal tract of a human subject, comprising administering to the subject an effective amount of a pharmaceutical formulation comprising an effective amount of the composition of any one of claim 1, 21, 22 or 31, and further comprising an effective amount of an anti-microbial agent, under conditions such that the number of pathogenic bacteria present in the gastrointestinal tract of the human subject is reduced within about one month of administration of the pharmaceutical formulation. In an embodiment, the number of pathogenic bacteria present in the gastrointestinal tract of the human subject is reduced within about two weeks of administration of the pharmaceutical formulation. In an embodiment, the number of pathogenic bacteria present in the gastrointestinal tract of the human subject is reduced within about one week of administration of the pharmaceutical formulation. In an embodiment, the number of pathogenic bacteria present in the gastrointestinal tract of the human subject is reduced within about three days of administration of the pharmaceutical formulation. In an embodiment, the number of pathogenic bacteria present in the gastrointestinal tract of the human subject is reduced within about one day of administration of the pharmaceutical formulation. In an embodiment, the anti-microbial agent comprises anti-bacterial agent. In an embodiment, the anti-microbial agent comprises anti-fungal agent. In an embodiment, the anti-microbial agent comprises anti-viral agent. In an embodiment, the anti-microbial agent comprises anti-parasitic agent.

In another aspect, provided are methods of preparing a comestible product, comprising combining with a comestible carrier a first purified population comprising at least a first type of isolated bacterium and a second purified population comprising at least a second type of isolated bacterium, wherein: i) the first type and the second type are independently capable of forming a spore; ii) only one of the first type and the second type are capable of forming a spore or iii) neither the first type nor the second type are capable of forming a spore, wherein the first type and the second type of bacteria are not identical, wherein the comestible product is substantially free of non-comestible materials. In an embodiment, at least one of the first purified population and the second purified population consist essentially of viable spores. In an embodiment, the first purified population and the second purified population consist essentially of viable spores. In an embodiment, the comestible product is substantially free of viable vegetal bacterial cells. In an embodiment, the viable spores, when the comestible product is consumed by a human subject in need thereof, are capable of functionally populating the gastrointestinal tract of the human subject. In an embodiment, the comestible product comprises a food or food additive. In an embodiment, the comestible product comprises a beverage or beverage additive. In an embodiment, the comestible product comprises a medical food. In an embodiment, the comestible product comprises at least $1\times10^4$, $1\times10^5$, $1\times10^6$, $1\times10^7$, $1\times10^8$, $1\times10^9$, $1\times10^{10}$ $1\times10^{11}$ or greater than $1\times10^{11}$ colony forming units (CFUs) of viable spores. In an embodiment, spores are of a bacterium selected from Table 1. In an embodiment, the first purified population and the second purified population independently comprise bacterial spores that comprise 16S rRNA sequence at least 95% identical to 16S rRNA sequence present in a bacterium selected from SEQ ID NOs: 1-1,864.

Also provided are methods of reducing the abundance of a pathogen in the gastrointestinal tract of a patient comprising administering the composition of the invention in a therapeutically effective amount and allowing the bacterial composition to compete with the pathogen in the gastrointestinal tract of a patient.

Further provided are methods of treating diarrhea comprising administering the composition of the invention in a therapeutically effective amount and allowing the bacterial composition to reduce the diarrheal effect of a pathogen in the gastrointestinal tract of a patient. In an embodiment, the pathogen is *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (LT or ST), *Escherichia coli* 0157:H7, *Helicobacter pylori, Lysteria monocytogenes, Plesiomonas shigelloides, Salmonella* spp., *Salmonella typhi, Shigella* spp., *Staphylococcus* spp., *Staphylococcus aureus, Vibrio* spp., *Vibrio cholerae, Vibrio parahaemolyticus, Vibrio vulnificus, Yersinia enterocolitica*, multi-drug resistant bacteria, Carbapenem-resistent *Enterobacteriaceae* (CRE), and vancomycin-resistant *Enterococci* (VRE). In an embodiment, the pathogen is *Clostridium difficile, Salmonella* spp., pathogenic *Escherichia coli*, or vancomycin-resistant *Enterococcus* spp. In an embodiment, the pathogen is *Clostridium difficile*. In an embodiment, the composition is administered orally.

Also provided are therapeutic compositions comprising a first purified bacterial population capable forming spores consisting of *Collinsella aerofaciens* and a second purified bacterial population consisting of a species selected from Table 1 or SEQ ID NOs: 1,865-1,915, wherein at least one of the first type and the second type are cytotoxic or cytostatic to a pathogenic bacterium. In an embodiment, a synergistic combination of the first bacterial spore population and the second bacterial spore population are cytotoxic or cytostatic to the pathogenic bacterium. In an embodiment, the combination is capable of inhibiting proliferation of the pathogenic bacterial present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Pseudomonas, Neisseria, Mycoplasma, Mycobacterium, Listeria, Leptospira, Legionella, Helicobacter, Haemophilus, Francisella, Escherichia, Enterococcus, Corynebacterium, Clostridium, Chlamydia, Chlamydophila, Campylobacter, Brucella, Borrelia*, and *Bordetella*. In an embodiment, the pathogenic bacterium is *Clostridium dificile*. In an embodiment, the first bacterial spore population and the second bacterial spore population synergistically interact to be cytotoxic to the pathogenic bacterium. In an embodiment, the first bacterial spore population and the second bacterial spore population synergistically interact to be cytostatic to the pathogenic bacterium. In an embodiment, the bacterial composition comprises at least about 3 types of isolated bacteria capable of forming spores. In an embodiment, the bacterial composition comprises at least about 5 types of isolated bacteria capable of forming spores. In an embodiment, the first bacterial spore population and the second bacterial spore population are present in the composition in approximately equal concentrations. In an embodiment, the composition consists essentially of between two and about ten bacterial spore populations of isolated bacteria.

In another aspect, provided are therapeutic compositions comprising a first purified bacterial spore population consisting of bacteria comprising 16S rRNA sequence at least about 97% identical to a 16S rRNA sequence present in a reference *Collinsella aerofaciens* OTU, and a second purified bacterial spore population consisting of bacteria comprising 16S rRNA sequence at least about 97% identical to a 16S rRNA sequence present in a reference bacterium listed in Table 1 or SEQ ID NOs: 1,865-1,915 wherein at least one of the first type and the second type are cytotoxic or cytostatic to a pathogenic bacterium. In an embodiment, a synergistic combination of the first type and the second type are cytotoxic or cytostatic to the pathogenic bacterium. In an embodiment, wherein the combination is capable of inhibiting proliferation of the pathogenic bacterial present at a concentration at least equal to the concentration of the combination of the first type and the second type. In an embodiment, the first type and the second type synergistically interact to be cytotoxic or cytostatic to the pathogenic bacterium. In an embodiment, the first purified bacterial spore population and the second purified bacterial spore population are capable of functionally populating the gastrointestinal tract of a human subject to whom the composition is administered. In an embodiment, the functional populating of the gastrointestinal tract comprises preventing, treating, reducing the severity of or reducing a symptom of a dysbiosis of the gastrointestinal tract. In an embodiment, the functional populating of the gastrointestinal tract comprises i) reducing the number of one or more types of pathogenic bacteria in the gastrointestinal tract; or ii) increasing the number of one or more non-pathogenic bacteria in the gastrointestinal tract. In an embodiment, the composition further comprises an effective amount of an anti-bacterial agent, an anti-fungal agent, an anti-viral agent or an anti-parasitic agent.

Also provided are methods of treating or preventing a recurrence of a *Clostridium difficile* infection, comprising administering to a human subject in need thereof an effective amount of the therapeutic composition of the invention under conditions such that the first purified bacterial spore population and the second purified bacterial spore population exert a cytotoxic or cytostatic effect on a pathogenic bacterium present in the gastrointestinal tract of the human subject, such that the number of *Clostridium difficile* bacteria present in the gastrointestinal tract is not detectably increased or is detectably decreased over a period of time. In an embodiment, the number of *Clostridium difficile* bacteria present in or excreted from the gastrointestinal tract of the human subject is detectably reduced within one month of administration of the bacterial composition. In an embodiment, the first purified bacterial spore population and the second purified bacterial spore population synergistically interact to be cytotoxic and/or cytostatic to the *Clostridium difficile* bacteria. In an embodiment, the therapeutic composition is orally administered. In an embodiment, the therapeutic composition comprises a medical food.

In another aspect, provided are kits comprising in one or more containers: a first purified population of a first type of bacteria capable of forming spores; and a second purified population of a second type of bacteria capable of forming spores, wherein the first type and the second type are not identical, and wherein the first type and the second type, when co-localized in a target region of a gastrointestinal tract of a human subject in need thereof, are capable of functionally populating the gastrointestinal tract. In an embodiment, the first purified population and the second purified population are present in a single container. In an embodiment, the kit is formulated for use as a nutritional supplement and optionally comprising a prebiotic material.

Additional objects and advantages will be set forth in part in the description which follows, and in part will be obvious from the description, or may be learned by practice of the embodiments. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to further explain the embodiments.

BRIEF DESCRIPTION OF THE DRAWINGS

FIG. 1A provides a schematic of 16S rRNA gene and denotes the coordinates of hypervariable regions 1-9 (V1-V9). Coordinates of V1-V9 are 69-99, 137-242, 433-497, 576-682, 822-879, 986-1043, 1117-1173, 1243-1294, and 1435-1465 respectively, based on numbering using *E. coli* system of nomenclature defined by Brosius et al., Complete nucleotide sequence of a 16S ribosomal RNA gene (16S rRNA) from *Escherichia coli*, PNAS 75(10):4801-4805 (1978). FIG. 1B highlights in bold the nucleotide sequences for each hypervariable region in the exemplary reference *E. coli* 16S sequence described by Brosius et al. FIG. 1B discloses SEQ ID NO: 1926.

BRIEF DESCRIPTION OF TABLES

Table 1 provides bacterial species and Operational Taxonomic Units (OTUs) of the bacterial compositions of the present invention, including taxonometric status and the ability of the OTU to form a viable spore as provided herein.

Table 2 provides representative combinations of the bacterial compositions of the present invention.

16S rRNA sequences of the bacterial species and Operational Taxonomic Units (OTUs) of the bacterial compositions of the present invention are provided in the CRF version of the Sequence Listing as SEQ ID NOS 1-1,864.

The taxonometric status, exemplary phylogenetic surrogacy and 16S rRNA sequences of exemplary bacterial compositions of the present invention are provided in the CRF version of the Sequence Listing as SEQ ID NOS 1,865-1,915.

Table 3 demonstrates the efficacy of exemplary bacterial compositions of the present invention in inhibiting a pathogenic bacterium.

Table 4 demonstrates the efficacy of exemplary bacterial compositions of the present invention in inhibiting a pathogenic bacterium.

Table 5 provides representative bacterial pathogens.

Table 6 provides representative human diseases, disorders and conditions for which the provided bacterial compositions are useful.

Table 7 provides representative human diseases, disorders and conditions for which the provided bacterial compositions are useful.

DEFINITIONS

"Microbiota" refers to the communities of microbes that live in or on the patient's body, both sustainably and transiently, including eukaryotes, archaea, bacteria, and viruses (including bacterial viruses (i.e., phage)).

"Dysbiosis" refers to a state of the microbiota or microbiome of the gut or other body area, including mucosal or skin surfaces in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis may be due to a decrease in diversity, the overgrowth of one or more pathogens or pathobionts, symbiotic organisms able to cause disease only when certain genetic and/or environmental conditions are present in a patient, or the shift to an ecological network that no longer provides a beneficial function to the host and therefore no longer promotes health.

A "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Sporeformers" or bacteria "capable of forming spores" are those bacteria containing the genes and other necessary abilities to produce spores under suitable environmental conditions.

The terms "pathogen", "pathobiont" and "pathogenic" in reference to a bacterium or any other organism or entity includes any such organism or entity that is capable of causing or affecting a disease, disorder or condition of a host organism containing the organism or entity.

The term "isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, and a purified bacterium or bacterial population may contain other materials up to about 10%, about 20%, about 30%, about 40%, about 50%, about 60%, about 70%, about 80%, about 90%, or above about 90% and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type. Bacterial compositions and the bacterial components thereof are generally purified from residual habitat products.

"Inhibition" of a pathogen encompasses the inhibition of any desired function or activity of the bacterial compositions of the present invention. Demonstrations of pathogen inhibition, such as decrease in the growth of a pathogenic bacterium or reduction in the level of colonization of a pathogenic bacterium are provided herein and otherwise recognized by one of ordinary skill in the art. Inhibition of a pathogenic bacterium's "growth" may include inhibiting the increase in size of the pathogenic bacterium and/or inhibiting the proliferation (or multiplication) of the pathogenic bacterium. Inhibition of colonization of a pathogenic bacterium may be demonstrated by measuring the amount or burden of a pathogen before and after a treatment. An "inhibition" or the act of "inhibiting" includes the total cessation and partial reduction of one or more activities of a pathogen, such as growth, proliferation, colonization, and function.

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

A "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject. Non-comestible products are often found in preparations of bacteria from the prior art.

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as micro RNA and ribosomal RNA, the epigenome, plasmids, and all other types of genetic information.

"Residual habitat products" refers to material derived from the habitat for microbiota within or on a human or animal. For example, microbiota live in feces in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, or 95% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (including bacterial viruses (i.e., phage)), fungal, mycoplasmal contaminants. In another embodiment, it means that fewer than $1\times10^{-2}$%, $1\times10^{-3}$%, $1\times10^{-4}$%, $1\times10^{-5}$%, $1\times10^{-6}$%, $1\times10^{-7}$%, $1\times10^{-8}$ of the viable cells in the bacterial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of $10^{-8}$ or $10^{-9}$), such as through multiple 10-fold serial dilutions. This can further be confirmed by showing that multiple isolated colonies have similar cell shapes and Gram staining behavior. Other methods for confirming adequate purity include genetic analysis (e.g. PCR, DNA sequencing), serology and antigen analysis, enzymatic and metabolic analysis, and methods using instrumentation such as flow cytometry with reagents that distinguish desired constituents from contaminants.

"Phylogenetic tree" refers to a graphical representation of the evolutionary relationships of one genetic sequence to another that is generated using a defined set of phylogenetic reconstruction algorithms (e.g. parsimony, maximum likelihood, or Bayesian). Nodes in the tree represent distinct ancestral sequences and the confidence of any node is provided by a bootstrap or Bayesian posterior probability, which measures branch uncertainty.

"Operational taxonomic unit (OTU, plural OTUs)" refers to a terminal leaf in a phylogenetic tree and is defined by a specific genetic sequence and all sequences that share sequence identity to this sequence at the level of species. A "type" or a plurality of "types" of bacteria includes an OTU or a plurality of different OTUs, and also encompasses a strain, species, genus, family or order of bacteria. The specific genetic sequence may be the 16S sequence or a portion of the 16S sequence or it may be a functionally conserved housekeeping gene found broadly across the eubacterial kingdom. OTUs share at least 95%, 96%, 97%, 98%, or 99% sequence identity. OTUs are frequently defined by comparing sequences between organisms. Sequences with less than 95% sequence identity are not considered to form part of the same OTU.

"Clade" refers to the set of OTUs or members of a phylogenetic tree downstream of a statistically valid node in a phylogenetic tree. The clade comprises a set of terminal leaves in the phylogenetic tree that is a distinct monophyletic evolutionary unit.

In microbiology, "16S sequencing" or "16S rRNA" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most bacteria, as well as fungi.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1,V2, and V3 regions are used to characterize an OTU. In another embodiment, the V3, V4,and V5 regions are used to characterize an OTU. In another embodiment, the V4 region is used to characterize an OTU. A person of ordinary skill in the art can identify the specific hypervariable regions of a candidate 16S rRNA (in SEQ ID NOs. 1-1,864) by comparing the candidate sequence in question to the reference sequence and identifying the hypervariable regions based on similarity to the reference hypervariable regions.

The terms "subject" or "patient" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

The term "pathobiont" refer to specific bacterial species found in healthy hosts that may trigger immune-mediated pathology and/or disease in response to certain genetic or environmental factors. Chow et al., (2011) *Curr Op Immunol*. Pathobionts of the intestinal microbiota and inflammatory disease. 23: 473-80. Thus, a pathobiont is a pathogen that is mechanistically distinct from an acquired infectious organism. Thus, the term "pathogen" includes both acquired infectious organisms and pathobionts.

DETAILED DESCRIPTION

Bacterial Compositions

Provided are bacteria and combinations of bacteria of the human gut microbiota with the capacity to meaningfully provide functions of a healthy microbiota or catalyze an augmentation to the resident microbiome when administered to mammalian hosts. In particular, provided are synergistic combinations that treat, prevent, delay or reduce the symptoms of diseases, disorders and conditions associated with a dysbiosis. Representative diseases, disorders and conditions potentially associated with a dysbiosis, which are suitable for treatment with the compositions and methods as described herein, are provided in Tables 8 and 9. Without being limited to a specific mechanism, it is thought that such compositions inhibit the growth, proliferation, and/or colonization of one or a plurality of pathogenic bacteria in the dysbiotic microbiotal niche, so that a healthy, diverse and protective microbiota colonizes and populates the intestinal lumen to establish or reestablish ecological control over pathogens or potential pathogens (e.g., some bacteria are pathogenic bacteria only when present in a dysbiotic environment). Inhibition of pathogens includes those pathogens such as *C. difficile, Salmonella* spp., enteropathogenic *E. coli*, multi-drug resistant bacteria such as *Klebsiella*, and *E. coli*, Carbapenem-resistent *Enterobacteriaceae* (CRE), extended spectrum beta-lactam resistant *Enterococci* (ESBL), and vancomycin-resistant *Enterococci* (VRE).

The bacterial compositions provided herein are produced and the efficacy thereof in inhibiting pathogenic bacteria is demonstrated as provided in further detail herein.

In particular, in order to characterize those antagonistic relationships between gut commensals that are relevant to the dynamics of the mammalian gut habitat, provided is an in vitro microplate-based screening system that demonstrates the efficacy of those bacterial compositions, including the ability to inhibit (or antagonize) the growth of a bacterial pathogen or pathobiont, typically a gastrointestinal microorganism. These methods provide novel combinations of gut microbiota species and OTUs that are able to restore or enhance ecological control over important gut pathogens or pathobionts in vivo.

Bacterial compositions may comprise two types of bacteria (termed "binary combinations" or "binary pairs") or greater than two types of bacteria. Bacterial compositions that comprise three types of bacteria are termed "ternary combinations". For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 29 30, 31, 32, 33, 34, 35, 36, 37, 38, 39, or at least 40, at least 50 or greater than 50 types of bacteria, as defined by species or operational taxonomic unit (OTU), or otherwise as provided herein. In one embodiment, the composition comprises at least two types of bacteria chosen from Table 1.

In another embodiment, the number of types of bacteria present in a bacterial composition is at or below a known value. For example, in such embodiments the bacterial composition comprises 50 or fewer types of bacteria, such as 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or fewer, or 9 or fewer types of bacteria, 8 or fewer types of bacteria, 7 or fewer types of bacteria, 6 or fewer types of bacteria, 5 or fewer types of bacteria, 4 or fewer types of bacteria, or 3 or fewer types of bacteria. In another embodiment, a bacterial composition comprises from 2 to no more than 40, from 2 to no more than 30, from 2 to no more than 20, from 2 to no more than 15, from 2 to no more than 10, or from 2 to no more than 5 types of bacteria.

In some embodiments, bacterial compositions are provided with the ability to exclude pathogenic bacteria. Exemplary bacterial compositions are demonstrated to reduce the growth rate of one pathogen, *C. difficile*, as provided in the Examples, wherein the ability of the bacterial compositions is demonstrated by assessing the antagonism activity of a combination of OTUs or strains towards a given pathogen using in vitro assays.

In some embodiments, bacterial compositions with the capacity to durably exclude *C. difficile*, are developed using a methodology for estimating an Ecological Control Factor (ECF) for constituents within the human microbiota. The ECF is determined by assessing the antagonistic activity of a given commensal strain or combination of strains towards a given pathogen using an in vitro assay, resulting in observed levels of ecological control at various concentrations of the added commensal strains. The ECF for a commensal strain or combination of strains is somewhat analogous to the longstanding minimal inhibitory concentration (MIC) assessment that is employed in the assessment of antibiotics. The ECF allows for the assessment and ranking of relative potencies of commensal strains and combinations of strains for their ability to antagonize gastrointestinal pathogens. The ECF of a commensal strain or combination of strains may be calculated by assessing the concentration of that composition that is able to mediate a given percentage of inhibition (e.g., at least 10%, 20%, 50%, 70%, 75%, 80%, 85%, 90%, 95%, or 100%) of a target pathogen in the in vitro assay. Provided herein are combinations of strains or OTUs within the human microbiota that are able to significantly reduce the rate of gastrointestinal pathogen replication within the in vitro assay. These compositions are capable of providing a safe and effective means by which to affect the growth, replication, and disease severity of such bacterial pathogens.

Bacterial compositions may be prepared comprising at least two types of isolated bacteria, wherein a first type and a second type are independently chosen from the species or OTUs listed in Table 1 and SEQ ID NOs. 1-1,864. Certain embodiments of bacterial compositions with at least two types of isolated bacteria containing binary pairs are reflected in Table 2. Additionally, a bacterial composition may be prepared comprising at least two types of isolated bacteria, wherein a first OTU and a second OTU are independently characterized by, i.e., at least 95%, 96%, 97%, 98%, 99% or including 100% sequence identity to, sequences listed in SEQ ID NOs. 1-1,864. Generally, the first bacteria and the second bacteria are not the same OTU. The sequences provided in SEQ ID NOs. 1-1,864. are full 16S sequences. Therefore, in one embodiment, the first and/or second OTUs may be characterized by the full 16S sequences listed in SEQ ID NOs. 1-1,864. In another embodiment, the first and/or second OTUs may be characterized by one or more of the variable regions of the 16S sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

Methods for Determining 16S Sequence. OTUs may be defined either by full 16S sequencing of the rRNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes. Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

Bacterial Compositions Exclusive of Certain Bacterial Species or Strains. In one embodiment, the bacterial composition does not comprise at least one of *Enterococcus faecalis* (previously known as *Streptococcus faecalis*), *Clostridium innocuum, Clostridium ramosum, Bacteroides ovatus, Bacteroides vulgatus, Bacteroides thetaoiotaomicron, Escherichia coli* (1109 and 1108-1), *Clostridum bifermentans*, and *Blautia producta* (previously known as *Peptostreptococcus productus*).

In another embodiment, the bacterial composition does not comprise at least one of *Acidaminococcus intestinalis, Bacteroides ovatus*, two species of *Bifidobacterium adolescentis*, two species of *Bifidobacterium longum, Collinsella aerofaciens*, two species of *Dorea longicatena, Escherichia coli, Eubacterium eligens, Eubacterium limosum*, four species of *Eubacterium rectale, Eubacterium ventriosumi, Faecalibacterium prausnitzii, Lactobacillus casei, Lactoba-*

*cillus paracasei, Paracateroides distasonis, Raoultella* sp., one species of *Roseburia* (chosen from *Roseburia faecalis* or *Roseburia faecis*), *Roseburia intestinalis*, two species of *Ruminococcus torques*, and *Streptococcus mitis.*

In another embodiment, the bacterial composition does not comprise at least one of *Barnesiella intestinihominis; Lactobacillus reuteri*; a species characterized as one of *Enterococcus hirae, Enterococus faecium*, or *Enterococcus durans*; a species characterized as one of *Anaerostipes caccae* or *Clostridium indolis*; a species characterized as one of *Staphylococcus wameri* or *Staphylococcus pasteuri*; and *Adlercreutzia equolifaciens.*

In another embodiment, the bacterial composition does not comprise at least one of *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum.*

In another embodiment, the bacterial composition does not comprise at least one of *Clostridium innocuum, Clostridum bifermentans, Clostridium butyricum, Bacteroides fragilis, Bacteroides thetaiotaomicron, Bacteroides uniformis*, three strains of *Escherichia coli*, and *Lactobacillus* sp.

In another embodiment, the bacterial composition does not comprise at least one of *Clostridium bifermentans, Clostridium innocuum, Clostridium butyricum*, three strains of *Escherichia coli*, three strains of *Bacteroides*, and *Blautia producta* (previously known as *Peptostreptococcus productus*).

In another embodiment, the bacterial composition does not comprise at least one of *Bacteroides* sp., *Escherichia coli*, and non pathogenic Clostridia, including *Clostridium innocuum, Clostridium bifermentans* and *Clostridium ramosum.*

In another embodiment, the bacterial composition does not comprise at least one of more than one *Bacteroides* species, *Escherichia coli* and non-pathogenic Clostridia, such as *Clostridium butyricum, Clostridium bifermentans* and *Clostridium innocuum.*

In another embodiment, the bacterial composition does not comprise at least one of *Bacteroides caccae, Bacteroides capillosus, Bacteroides coagulans, Bacteroides distasonis, Bacteroides eggerthii, Bacteroides forsythus, Bacteroides fragilis, Bacteroides fragilis-ryhm, Bacteroides gracilis, Bacteroides levii, Bacteroides macacae, Bacteroides merdae, Bacteroides ovatus, Bacteroides pneumosintes, Bacteroides putredinis, Bacteroides pyogenes, Bacteroides splanchnicus, Bacteroides stercoris, Bacteroides tectum, Bacteroides thetaiotaomicron, Bacteroides uniformis, Bacteroides ureolyticus*, and *Bacteroides vulgatus.*

In another embodiment, the bacterial composition does not comprise at least one of *Bacteroides, Eubacteria, Fusobacteria, Propionibacteria, Lactobacilli, anaerobic cocci, Ruminococcus, Escherichia coli, Gemmiger, Desulfomonas*, and *Peptostreptococcus.*

In another embodiment, the bacterial composition does not comprise at least one of *Bacteroides fragilis* ss. *Vulgatus, Eubacterium aerofaciens, Bacteroides fragilis* ss. *Thetaiotaomicron, Blautia producta* (previously known as *Peptostreptococcus productus* II), *Bacteroides fragilis* ss. *Distasonis, Fusobacterium prausnitzii, Coprococcus eutactus, Eubacterium aerofaciens* III, *Blautia producta* (previously known as *Peptostreptococcus productus* I), *Ruminococcus bromii, Bifidobacterium adolescentis, Gemmiger formicilis, Bifidobacterium longum, Eubacterium siraeum, Ruminococcus torques, Eubacterium rectale* III-H, *Eubacterium rectale* IV, *Eubacterium eligens, Bacteroides eggerthii, Clostridium leptum, Bacteroides fragilis* ss. A, *Eubacterium biforme, Bifidobacterium infantis, Eubacterium rectale* III-F, *Coprococcus comes, Bacteroides capillosus, Ruminococcus albus, Eubacterium formicigenerans, Eubacterium hallii, Eubacterium ventriosum* I, *Fusobacterium russii, Ruminococcus obeum, Eubacterium rectale* II, *Clostridium ramosum* I, *Lactobacillus leichmanii, Ruminococcus cailidus, Butyrivibrio crossotus, Acidaminococcus fermentans, Eubacterium ventriosum, Bacteroides fragilis* ss. *fragilis, Bacteroides* AR, *Coprococcus catus, Eubacterium hadrum, Eubacterium cylindroides, Eubacterium ruminantium, Eubacterium* CH-1, *Staphylococcus epidermidis, Peptostreptococcus* BL, *Eubacterium limosum, Bacteroides praeacutus, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Eubacterium* AG, -AK, -AL, -AL-1, -AN; *Bacteroides fragilis* ss. *ovatus*, -ss. d, -ss. f; *Bacteroides* L-1, L-5; *Fusobacterium nucleatum, Fusobacterium mortiferum, Escherichia coli, Streptococcus morbiliorum, Peptococcus magnus, Peptococcus* G, AU-2; *Streptococcus intermedius, Ruminococcus lactaris, Ruminococcus* CO *Gemmiger* X, *Coprococcus* BH, -CC; *Eubacterium tenue, Eubacterium ramulus, Eubacterium* AE, -AG-H, -AG-M, -AJ, -BN-1; *Bacteroides clostridiiformis* ss. *clostridliformis, Bacteroides coagulans, Bacteroides orails, Bacteroides ruminicola* ss. *brevis*, -ss. *ruminicola, Bacteroides splanchnicus, Desuifomonas pigra, Bacteroides* L-4, -N-i; *Fusobacterium* H, *Lactobacillus* G, and *Succinivibrio* A.

Inhibition of Bacterial Pathogens. The bacterial compositions offer a protective or therapeutic effect against infection by one or more GI pathogens of interest.

A list of exemplary bacterial pathogens is provided in Table 5.

In some embodiments, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, extended spectrum beta-lactam resistant *Enterococci* (ESBL), Carbapenem-resistent *Enterobacteriaceae* (CRE), and vancomycin-resistant *Enterococci* (VRE).

In some embodiments, these pathogens include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, entero hemorrhagic *Escherichia coli*, enteroinvasive *Escherichia coli*, enterotoxigenic *Escherichia coli* (such as, but not limited to, LT and/or ST), *Escherichia coli* 0157:H7, *Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, and *Yersinia enterocolitica.*

In one embodiment, the pathogen of interest is at least one pathogen chosen from *Clostridium difficile, Salmonella* spp., pathogenic *Escherichia coli*, vancomycin-resistant *Enterococcus* spp., and extended spectrum beta-lactam resistant *Enterococci* (ESBL).

In Vitro Assays Substantiating Protective Effect of Bacterial Compositions.

In one embodiment, provided is an In Vitro Assay utilizing competition between the bacterial compositions or subsets thereof and *C. difficile*. Exemplary embodiments of this Assay are provided herein and in the Examples.

In another embodiment, provided is an In Vitro Assay utilizing 10% (wt/vol) Sterile-Filtered Feces. Provided is an in vitro assay to test for the protective effect of the bacterial compositions and to screen in vitro for combinations of microbes that inhibit the growth of a pathogen. The assay can operate in automated high-throughput or manual modes. Under either system, human or animal feces may be re-suspended in an anaerobic buffer solution, such as pre-reduced PBS or other suitable buffer, the particulate removed by centrifugation, and filter sterilized. This 10% sterile-filtered feces material serves as the base media for the in vitro assay. To test a bacterial composition, an investigator may add it to the sterile-filtered feces material for a first incubation period and then may inoculate the incubated microbial solution with the pathogen of interest for a second incubation period. The resulting titer of the pathogen may be quantified by any number of methods such as those described below, and the change in the amount of pathogen is compared to standard controls including the pathogen cultivated in the absence of the bacterial composition. The assay is conducted using at least one control. Feces from a healthy subject may be used as a positive control. As a negative control, antibiotic-treated feces or heat-treated feces may be used. Various bacterial compositions may be tested in this material and the bacterial compositions optionally compared to the positive and/or negative controls. The ability to inhibit the growth of the pathogen may be measured by plating the incubated material on *C. difficile* selective media and counting colonies. After competition between the bacterial composition and *C. difficile*, each well of the in vitro assay plate is serially diluted ten-fold six times, and plated on selective media, such as but not limited to cycloserine cefoxitin mannitol agar (CCMA) or cycloserine cefoxitin fructose agar (CCFA), and incubated. Colonies of *C. difficile* are then counted to calculate the concentration of viable cells in each well at the end of the competition. Colonies of *C. difficile* are confirmed by their characteristic diffuse colony edge morphology as well as fluorescence under UV light.

In another embodiment, the in vitro assay utilizes Antibiotic-Treated Feces. In an alternative embodiment, and instead of using 10% sterile-filtered feces, human or animal feces may be resuspended in an anaerobic buffer solution, such as pre-reduced PBS or other suitable buffer. The resuspended feces is treated with an antibiotic, such as clindamycin, or a cocktail of several antibiotics in order to reduce the ability of feces from a healthy subject to inhibit the growth of *C. difficile*; this material is termed the antibiotic-treated matrix. While not being bound by any mechanism, it is believed that beneficial bacteria in healthy subjects protects them from infection by competing out *C. difficile*. Treating feces with antibiotics kills or reduces the population of those beneficial bacteria, allowing *C. difficile* to grow in this assay matrix. Antibiotics in addition to clindamycin that inhibit the normal flora include ceftriaxone and piperacillin-tazobactam and may be substituted for the clindamycin. The antibiotic-treated matrix is centrifuged, the supernatant removed, and the pelleted material resuspended in filter-sterilized, diluted feces in order to remove any residual antibiotic. This washed antibiotic-treated matrix may be used in the in vitro assay described above in lieu of the 10% sterile-filtered feces.

Alternatively, the ability to inhibit the growth of the pathogen may be measured by quantitative PCR (qPCR). Standard techniques may be followed to generate a standard curve for the pathogen of interest. Genomic DNA may be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions. The qPCR may be conducted using HotMasterMix (5PRIME, Gaithersburg, Md.) and primers specific for the pathogen of interest, and may be conducted on a MicroAmp® Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (BioRad, Hercules, Calif.), with fluorescent readings of the FAM and ROX channels. The Cq value for each well on the FAM channel is determined by the CFX Manager™ software version 2.1. The $\log_{10}$ (cfu/ml) of each experimental sample is calculated by inputting a given sample's Cq value into linear regression model generated from the standard curve comparing the Cq values of the standard curve wells to the known $\log_{10}$ (cfu/ml) of those samples. The skilled artisan may employ alternative qPCR modes.

Also provided are In Vivo Assay Establishing Protective Effect of Bacterial Compositions. Provided is an in vivo mouse model to test for the protective effect of the bacterial compositions against *C. difficile*. In this model (based on Chen, et al., A mouse model of *Clostridium difficile* associated disease, Gastroenterology 135(6):1984-1992 (2008)), mice are made susceptible to *C. difficile* by a 7 day treatment (days −12 to −5 of experiment) with 5 to 7 antibiotics (including kanamycin, colistin, gentamycin, metronidazole and vancomycin and optionally including ampicillin and ciprofloxacin) delivered via their drinking water, followed by a single dose with Clindamycin on day −3, then challenged three days later on day 0 with $10^4$ spores of *C. difficile* via oral gavage (i.e., oro-gastric lavage). Bacterial compositions may be given either before (prophylactic treatment) or after (therapeutic treatment) *C. difficile* gavage. Further, bacterial compositions may be given after (optional) vancomycin treatment (see below) to assess their ability to prevent recurrence and thus suppress the pathogen in vivo. The outcomes assessed each day from day −1 to day 6 (or beyond, for prevention of recurrence) are weight, clinical signs, mortality and shedding of *C. difficile* in the feces. Weight loss, clinical signs of disease, and *C. difficile* shedding are typically observed without treatment. Vancomycin provided by oral gavage on days −1 to 4 protects against these outcomes and serves as a positive control. Clinical signs are subjective, and scored each day by the same experienced observer. Animals that lose greater than or equal to 25% of their body weight are euthanized and counted as infection-related mortalities. Feces are gathered from mouse cages (5 mice per cage) each day, and the shedding of *C. difficile* spores is detected in the feces using a selective plating assay as described for the in vitro assay above, or via qPCR for the toxin gene as described herein. The effects of test materials including 10% suspension of human feces (as a positive control), bacterial compositions, or PBS (as a negative vehicle control), are determined by introducing the test article in a 0.2 mL volume into the mice via oral gavage on day −1, one day prior to *C. difficile* challenge, on day 1, 2 and 3 as treatment or post-vancomycin treatment on days 5, 6, 7 and 8. Vancomycin, as discussed above, is given on days 1 to 4 as another positive control. Alternative dosing schedules and routes of administration (e.g. rectal) may be employed, including multiple doses of test article, and $10^3$ to $10^{13}$ of a given organism or composition may be delivered.

Methods for Preparing a Bacterial Composition for Administration to a Subject.

Methods for producing bacterial compositions may include three main processing steps, combined with one or more mixing steps. The steps are: organism banking, organism production, and preservation.

For banking, the strains included in the bacterial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. A variety of microbiological media and variations are well known in the art (e.g. R. M. Atlas, *Handbook of Microbiological Media* (2010) CRC Press). Medium can be added to the culture at the start, may be added during the culture, or may be intermittently/continuously flowed through the culture. The strains in the bacterial composition may be cultivated alone, as a subset of the bacterial composition, or as an entire collection comprising the bacterial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions (e.g., gut microbiota), an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine•HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition may be purified by additional means such as density gradient centrifugation preserved using the techniques described above. Bacterial composition banking may be done by culturing and preserving the strains individually, or by mixing the strains together to create a combined bank. As an example of cryopreservation, a bacterial composition culture may be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production may be conducted using similar culture steps to banking, including medium composition and culture conditions. It may be conducted at larger scales of operation, especially for clinical development or commercial production. At larger scales, there may be several subcultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

Formulations. Provided are formulations for administration to humans and other subjects in need thereof. Generally the bacterial compositions are combined with additional active and/or inactive materials in order to produce a final product, which may be in single dosage unit or in a multi-dose format.

In some embodiments the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments the composition comprises at least one lipid. As used herein a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments the excipient is a buffering agent. Non-limiting examples of suitable buffering agents include sodium citrate, magnesium carbonate, magnesium bicarbonate, calcium carbonate, and calcium bicarbonate.

In some embodiments the excipient comprises a preservative. Non-limiting examples of suitable preservatives include antioxidants, such as alpha-tocopherol and ascorbate, and antimicrobials, such as parabens, chlorobutanol, and phenol.

In some embodiments the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The bacterial compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments the core material comprises at least one of a solid, a liquid, and an emulsion. In some embodiments the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In some embodiments the coating material comprises at least one of a fat and an oil. In some embodiments the at least one of a fat and an oil is high temperature melting. In some embodiments the at least one of a fat and an oil is hydrogenated or partially hydrogenated. In some embodiments the at least one of a fat and an oil is derived from a plant. In some embodiments the at least one of a fat and an oil comprises at least one of glycerides, free fatty acids, and fatty acid esters. In some embodiments the coating material comprises at least one edible wax. The edible wax can be derived from animals, insects, or plants. Non-limiting examples include beeswax, lanolin, bayberry wax, carnauba wax, and rice bran wax. Tablets and pills can additionally be prepared with enteric coatings.

Alternatively, powders or granules embodying the bacterial compositions disclosed herein can be incorporated into a food product. In some embodiments the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments the food product is a solid foodstuff. Suitable examples of a solid foodstuff include without limitation a food bar, a snack bar, a cookie, a brownie, a muffin, a cracker, an ice cream bar, a frozen yogurt bar, and the like.

In some embodiments, the compositions disclosed herein are incorporated into a therapeutic food. In some embodiments, the therapeutic food is a ready-to-use food that optionally contains some or all essential macronutrients and micronutrients. In some embodiments, the compositions disclosed herein are incorporated into a supplementary food that is designed to be blended into an existing meal. In some embodiments, the supplemental food contains some or all essential macronutrients and micronutrients. In some embodiments, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 (up to 100 mg) of lyophilized powder ($10^8$ to $10^{11}$ bacteria), 160 mg microcrystalline cellulose, 77.5 mg gelatin, and 2.5 mg magnesium stearate. In an alternative embodiment, from $10^5$ to $10^{12}$ bacteria may be used, $10^5$ to $10^7$, $10^6$ to $10^7$, or $10^8$ to $10^{10}$, with attendant adjustments of the excipients if necessary. In an alternative embodiment an enteric-coated capsule or tablet or with a buffering or protective composition may be used.

In one embodiment, the number of bacteria of each type may be present in the same amount or in different amounts. For example, in a bacterial composition with two types of bacteria, the bacteria may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three types of bacteria, the ratio of type of bacteria may be chosen pairwise from ratios for bacterial compositions with two types of bacteria. For example, in a bacterial composition comprising bacteria A, B, and C, at least one of the ratio between bacteria A and B, the ratio between bacteria B and C, and the ratio between bacteria A and C may be chosen, independently, from the pairwise combinations above.

Methods of Treating a Subject. In some embodiments the proteins and compositions disclosed herein are administered to a patient or a user (sometimes collectively referred to as a "subject"). As used herein "administer" and "administration" encompasses embodiments in which one person directs another to consume a bacterial composition in a certain manner and/or for a certain purpose, and also situations in which a user uses a bacteria composition in a certain manner and/or for a certain purpose independently of or in variance to any instructions received from a second person. Non-limiting examples of embodiments in which one person directs another to consume a bacterial composition in a certain manner and/or for a certain purpose include when a physician prescribes a course of conduct and/or treatment to a patient, when a parent commands a minor user (such as a child) to consume a bacterial composition, when a trainer advises a user (such as an athlete) to follow a particular course of conduct and/or treatment, and when a manufacturer, distributer, or marketer recommends conditions of use to an end user, for example through advertisements or labeling on packaging or on other materials provided in association with the sale or marketing of a product.

The bacterial compositions offer a protective and/or therapeutic effect against infection by one or more GI pathogens of interest and thus may be administered after an acute case of infection has been resolved in order to prevent relapse, during an acute case of infection as a complement to antibiotic therapy if the bacterial composition is not sensitive to the same antibiotics as the GI pathogen, or to prevent infection or reduce transmission from disease carriers. These pathogens include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, entero hemorrhagic *Escherichia coli*, enteroinvasive *Escherichia coli*, enterotoxigenic *Escherichia coli* (LT and/or ST), *Escherichia coli* 0157:H7, *Helicobacter pylori, Klebsiella* pneumonia, *Lysteria monocytogenes, Plesiomonas shigelloides, Salmonella* spp., *Salmonella typhi, Shigella* spp., *Staphylococcus, Staphylococcus aureus*, vancomycin-resistant *Enterococcus* spp., *Vibrio* spp., *Vibrio cholerae, Vibrio parahaemolyticus, Vibrio vulnificus*, and *Yersinia enterocolitica.*

In one embodiment, the pathogen may be *Clostridium difficile, Salmonella* spp., pathogenic *Escherichia coli*, Carbapenem-resistent *Enterobacteriaceae* (CRE), extended spectrum beta-lactam resistant *Enterococci* (ESBL) and vancomycin-resistant *Enterococci* (VRE). In yet another embodiment, the pathogen may be *Clostridium difficile.*

The present bacterial compositions may be useful in a variety of clinical situations. For example, the bacterial compositions may be administered as a complementary treatment to antibiotics when a patient is suffering from an acute infection, to reduce the risk of recurrence after an acute infection has subsided, or when a patient will be in close proximity to others with or at risk of serious gastrointestinal infections (physicians, nurses, hospital workers, family members of those who are ill or hospitalized).

The present bacterial compositions may be administered to animals, including humans, laboratory animals (e.g., primates, rats, mice), livestock (e.g., cows, sheep, goats, pigs, turkeys, chickens), and household pets (e.g., dogs, cats, rodents).

In the present method, the bacterial composition is administered enterically, in other words by a route of access to the gastrointestinal tract. This includes oral administration, rectal administration (including enema, suppository, or colonoscopy), by an oral or nasal tube (nasogastric, nasojejunal, oral gastric, or oral jejunal), as detailed more fully herein.

Pretreatment Protocols

Prior to administration of the bacterial composition, the patient may optionally have a pretreatment protocol to prepare the gastrointestinal tract to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol may enhance the ability of the bacterial composition to affect the patient's microbiome.

As one way of preparing the patient for administration of the microbial ecosystem, at least one antibiotic may be administered to alter the bacteria in the patient. As another way of preparing the patient for administration of the microbial ecosystem, a standard colon-cleansing preparation may be administered to the patient to substantially empty the contents of the colon, such as used to prepare a patient for a colonscopy. By "substantially emptying the contents of the colon," this application means removing at least 75%, at least 80%, at least 90%, at least 95%, or about 100% of the contents of the ordinary volume of colon contents. Antibiotic treatment may precede the colon-cleansing protocol.

If a patient has received an antibiotic for treatment of an infection, or if a patient has received an antibiotic as part of a specific pretreatment protocol, in one embodiment the antibiotic should be stopped in sufficient time to allow the antibiotic to be substantially reduced in concentration in the gut before the bacterial composition is administered. In one embodiment, the antibiotic may be discontinued 1, 2, or 3 days before the administration of the bacterial composition. In one embodiment, the antibiotic may be discontinued 3, 4, 5, 6, or 7 antibiotic half-lives before administration of the bacterial composition. In another embodiment, the antibiotic may be chosen so the constituents in the bacterial composition have an MIC50 that is higher than the concentration of the antibiotic in the gut.

MIC50 of a bacterial composition or the elements in the composition may be determined by methods well known in the art. Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic may be chosen so that the infection is sensitive to the antibiotic, but the constituents in the bacterial composition are not sensitive to the antibiotic.

Routes of Administration

The bacterial compositions of the invention are suitable for administration to mammals and non-mammalian animals in need thereof. In certain embodiments, the mammalian subject is a human subject who has one or more symptoms of a dysbiosis.

When the mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment(s) resulted in no improvement or a worsening of symptoms.

In some embodiments, the gastrointestinal disease, disorder or condition is diarrhea caused by *C. difficile* including recurrent *C. difficile* infection, ulcerative colitis, colitis, Crohn's disease, or irritable bowel disease. Beneficially, the therapeutic composition is administered only once prior to improvement of the disease, disorder or condition. In some embodiments the therapeutic composition is administered at intervals greater than two days, such as once every three, four, five or six days, or every week or less frequently than every week. Or the preparation may be administered intermittently according to a set schedule, e.g., once a day, once weekly, or once monthly, or when the subject relapses from the primary illness. In another embodiment, the preparation may be administered on a long-term basis to subjects who are at risk for infection with or who may be carriers of these pathogens, including subjects who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

In embodiments, the bacterial composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The bacterial composition may be administered to at least one region of the gastrointestinal tract, including the mouth, esophagus, stomach, small intestine, large intestine, and rectum. In some embodiments it is administered to all regions of the gastrointestinal tract. The bacterial compositions may be administered orally in the form of medicaments such as powders, capsules, tablets, gels or liquids. The bacterial compositions may also be administered in gel or liquid form by the oral route or through a nasogastric tube, or by the rectal route in a gel or liquid form, by enema or instillation through a colonoscope or by a suppository.

If the composition is administered colonoscopically and, optionally, if the bacterial composition is administered by other rectal routes (such as an enema or suppository) or even if the subject has an oral administration, the subject may have a colon cleansing preparation. The colon-cleansing preparation can facilitate proper use of the colonoscope or other administration devices, but even when it does not serve a mechanical purpose it can also maximize the proportion of the bacterial composition relative to the other organisms previously residing in the gastrointestinal tract of the subject. Any ordinarily acceptable colon-cleansing preparation may be used such as those typically provided when a subject undergoes a colonoscopy.

Dosages and Schedule for Administration

In some embodiments the bacteria and bacterial compositions are provided in a dosage form. In some embodiments the dosage form is designed for administration of at least one OTU or combination thereof disclosed herein, wherein the total amount of bacterial composition administered is selected from 0.1 ng to 10 g, 10 ng to 1 g, 100 ng to 0.1 g, 0.1 mg to 500 mg, 1 mg to 100 mg, or from 10-15 mg. In some embodiments the bacterial composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In some embodiments the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, from $10^5$ and $10^{12}$ microorganisms total may be administered to the patient in a given dosage form. In one mode, an effective amount may be provided in from 1 to 500 ml or from 1 to 500 grams of the bacterial composition having from $10^7$ to $10^{11}$ bacteria per ml or per gram, or a capsule, tablet or suppository having from 1 mg to 1000 mg lyophilized powder having from $10^7$ to $10^{11}$ bacteria. Those receiving acute treatment may receive higher doses than those who are receiving chronic administration (such as hospital workers or those admitted into long-term care facilities).

Any of the preparations described herein may be administered once on a single occasion or on multiple occasions, such as once a day for several days or more than once a day on the day of administration (including twice daily, three times daily, or up to five times daily). Or the preparation may be administered intermittently according to a set schedule, e.g., once weekly, once monthly, or when the patient relapses from the primary illness. In another embodiment, the preparation may be administered on a long-term basis to individuals who are at risk for infection with or who may be carriers of these pathogens, including individuals who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

Patient Selection

Particular bacterial compositions may be selected for individual patients or for patients with particular profiles. For example, 16S sequencing may be performed for a given patient to identify the bacteria present in his or her microbiota. The sequencing may either profile the patient's entire microbiome using 16S sequencing (to the family, genera, or species level), a portion of the patient's microbiome using 16S sequencing, or it may be used to detect the presence or absence of specific candidate bacteria that are biomarkers for health or a particular disease state, such as markers of multi-drug resistant organisms or specific genera of concern such as *Escherichia*. Based on the biomarker data, a particular composition may be selected for administration to a patient to supplement or complement a patient's microbiota in order to restore health or treat or prevent disease. In another embodiment, patients may be screened to determine the composition of their microbiota to determine the likelihood of successful treatment.

Combination Therapy

The bacterial compositions may be administered with other agents in a combination therapy mode, including anti-microbial agents and prebiotics. Administration may be sequential, over a period of hours or days, or simultaneous.

In one embodiment, the bacterial compositions are included in combination therapy with one or more anti-microbial agents, which include anti-bacterial agents, anti-fungal agents, anti-viral agents and anti-parasitic agents.

Anti-bacterial agents include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

A prebiotic is a selectively fermented ingredient that allows specific changes, both in the composition and/or activity in the gastrointestinal microbiota that confers benefits upon host well-being and health. Prebiotics may include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Methods for Characterization of Bacterial Compositions

In certain embodiments, provided are methods for testing certain characteristics of bacterial compositions. For example, the sensitivity of bacterial compositions to certain environmental variables is determined, e.g., in order to select for particular desirable characteristics in a given composition, formulation and/or use. For example, the constituents in the bacterial composition may be tested for pH resistance, bile acid resistance, and/or antibiotic sensitivity, either individually on a constituent-by-constituent basis or collectively as a bacterial composition comprised of multiple bacterial constituents (collectively referred to in this section as bacterial composition).

pH Sensitivity Testing. If a bacterial composition will be administered other than to the colon or rectum (i.e., through, for example, but not limited to, an oral route), optionally testing for pH resistance enhances the selection of bacterial compositions that will survive at the highest yield possible through the varying pH environments of the distinct regions of the GI tract. Understanding how the bacterial compositions react to the pH of the GI tract also assists in formulation, so that the number of bacteria in a dosage form can be increased if beneficial and/or so that the composition may be administered in an enteric-coated capsule or tablet or with a buffering or protective composition. As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This may be tested by exposing the bacterial composition to varying pH ranges for the expected gut transit times through those pH ranges. Therefore, as a nonlimiting example only, 18-hour cultures of bacterial compositions may be grown in standard media, such as gut microbiota medium ("GMM", see Goodman et al., Extensive personal human gut microbiota culture collections characterized and manipulated in gnotobiotic mice, PNAS 108 (15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in U.S. Pat. No. 4,839,281. Survival of bacteria may be determined by culturing the bacteria and counting colonies on appropriate selective or non-selective media.

Bile Acid Sensitivity Testing. Additionally, in some embodiments, testing for bile-acid resistance enhances the selection of bacterial compositions that will survive exposures to bile acid during transit through the GI tract. Bile acids are secreted into the small intestine and can, like pH, affect the survival of bacterial compositions. This may be tested by exposing the bacterial compositions to bile acids for the expected gut exposure time to bile acids. For example, bile acid solutions may be prepared at desired concentrations using 0.05 mM Tris at pH 9 as the solvent. After the bile acid is dissolved, the pH of the solution may be adjusted to 7.2 with 10% HCl. Bacterial compositions may be cultured in 2.2 ml of a bile acid composition mimicking the concentration and type of bile acids in the patient, 1.0 ml of 10% sterile-filtered feces media and 0.1 ml of an 18-hour culture of the given strain of bacteria. Incubations may be conducted for from 2.5 to 3 hours or longer. An alternative method for testing stability to bile acid is described in U.S. Pat. No. 4,839,281. Survival of bacteria may be determined by culturing the bacteria and counting colonies on appropriate selective or non-selective media.

Antibiotic Sensitivity Testing. As a further optional sensitivity test, bacterial compositions may be tested for sensitivity to antibiotics. In one embodiment, bacterial compositions may be chosen so that the bacterial constituents are sensitive to antibiotics such that if necessary they can be eliminated or substantially reduced from the patient's gastrointestinal tract by at least one antibiotic targeting the bacterial composition.

Adherence to Gastrointestinal Cells. The bacterial compositions may optionally be tested for the ability to adhere to gastrointestinal cells. A method for testing adherence to gastrointestinal cells is described in U.S. Pat. No. 4,839,281.

The specification is most thoroughly understood in light of the teachings of the references cited within the specification. The embodiments within the specification provide an illustration of embodiments and should not be construed to limit the scope. The skilled artisan readily recognizes that many other embodiments are encompassed. All publications and patents cited in this disclosure are incorporated by reference in their entirety. To the extent the material incorporated by reference contradicts or is inconsistent with this specification, the specification will supersede any such material. The citation of any references herein is not an admission that such references are prior art.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. Examples of the techniques and protocols described herein with regard to therapeutic compositions can be found in, e.g., Remington's Pharmaceutical Sciences, 16th edition, Osol, A. (ed), 1980.

Example 1

Construction of binary pairs in a high-throughput 96-well format. To allow high-throughput screening of binary pairs, vials of −80° C. glycerol stock banks were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed, plates were removed from −80° C. and thawed at room temperature under anaerobic conditions when testing in a CivSim with *Clostridium difficile.*

Example 2

Construction of ternary combinations in a high-throughput 96-well format. To allow high-throughput screening of ternary combinations, vials of −80° C. glycerol stock banks were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed for the assay, plates were removed from −80° C. and thawed at room temperature under anaerobic conditions when testing in a CivSim with *Clostridium difficile.*

Example 3

Construction of a CivSim Assay to Screen for Ecobiotic™ compositions Inhibitory to the Growth of *Clostridium difficile*. An overnight culture of *Clostridium difficile* was grown under anaerobic conditions in SweetB-Fosln or other suitable media for the growth of *C. difficile*. SweetB-Fosln is a complex media composed of brain heart infusion, yeast extract, cysteine, cellobiose, maltose, soluble starch, and fructooligosaccharides/inulin, and hemin, and is buffered with MOPs. After 24 hr of growth the culture was diluted 100,000 fold into a complex media such as SweetB-Fosln which is suitable for the growth of a wide variety of anaerobic bacterial species. The diluted *C. difficile* mixture was then aliquoted to wells of a 96-well plate (180 uL to each well). 20 uL of a unique binary pair of potential inhibitory species was then added to each well at a final concentration of 1e6 CFU/mL of each species. Alternatively the assay can be tested with binary pairs at different initial concentrations (1e9 CFU/mL, 1e8 CFU/mL, 1e7 CFU/mL, 1e5 CFU/mL, 1e4 CFU/mL, 1e3 CFU/mL, 1e2 CFU/mL). Control wells only inoculated with *C. difficile* were included for a comparison to the growth of *C. difficile* without inhibition. Additional wells were used for controls that either inhibit or do not inhibit the growth of *C. difficile*. One example of a positive control that inhibits growth was a combination of *Blautia producta, Clostridium bifermentans* and *Escherichia coli*. One example of a control that shows reduced inhibition of *C. difficile* growth as a combination of *Bacteroides thetaiotaomicron, Bacteroides ovatus* and *Bacteroides vulgatus*. Plates were wrapped with parafilm and incubated for 24 hr at 37° C. under anaerobic conditions.

After 24 hr the wells containing *C. difficile* alone were serially diluted and plated to determine titer. The 96-well plate was then frozen at −80 C before quantifying *C. difficile* by qPCR assay.

Example 4

Construction of a CivSim Assay to Screen for bacterial compositions that produce diffusible products inhibitory to the growth of *Clostridium difficile* using a filter insert. The CivSim assay described above was modified by using a 0.22 uM filter insert (Millipore™ MultiScreen™ 96-Well Assay Plates—Item MAGVS2210) in 96-well format to physically separate *C. difficile* from the bacterial compositions. The *C. difficile* was aliquoted into the 96-well plate while the bacterial compositions were aliquoted into media on the filter overlay. The nutrient media as in contact on both sides of the 0.22 uM filter, allowing exchange of nutrients, small molecules and many macromolecules (e.g., bacteriocins, cell-surface proteins, or polysaccharides) by diffusion. In this embodiment, after 24 hr incubation, the filter insert containing the bacterial compositions was removed. The plate containing *C. difficile* was then transferred to a 96-well plate reader suitable for measuring optical density (OD) at 600 nm. The growth of *C. difficile* in the presence of different bacterial compositions was compared based on the OD measurement.

Example 5

Construction of a CivSim Assay to Screen for bacterial compositions inhibitory to the growth of *Clostridium difficile* using *Clostridium difficile* selective media for quantification. The CivSim assay described above can be modified to determine final *C. difficile* titer by serially diluting and plating to *C. difficile* selective media (Bloedt et al 2009) such as CCFA (cycloserine cefoxitin fructose agar, Anaerobe Systems), CDSA (*Clostridium difficile* selective agar, which is cycloserine cefoxitin mannitol agar, Becton Dickinson).

Example 6

Quantification of *C. difficile* Using Quantitative PCR (qPCR)

A. Standard Curve Preparation

The standard curve was generated from a well on each assay plate containing only pathogenic *C. difficile* grown in SweetB+Fosln media as provided herein and quantified by selective spot plating. Serial dilutions of the culture were performed in sterile phosphate-buffered saline. Genomic DNA was extracted from the standard curve samples along with the other wells.

B. Genomic DNA Extraction

Genomic DNA was extracted from 5 μl of each sample using a dilution, freeze/thaw, and heat lysis protocol. 5 μL of thawed samples were added to 45 μL of UltraPure water (Life Technologies, Carlsbad, Calif.) and mixed by pipetting. The plates with diluted samples were frozen at −20° C. until use for qPCR which includes a heated lysis step prior to amplification. Alternatively the genomic DNA could be isolated using the Mo Bio Powersoil®-htp 96 Well Soil DNA Isolation Kit (Mo Bio Laboratories, Carlsbad, Calif.), Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

C. qPCR Composition and Conditions

The qPCR reaction mixture contained 1×SsoAdvanced Universal Probes Supermix, 900 nM of Wr-tcdB-F primer (AGCAGTTGAATATAGTGGTTTAGTTAGAGTTG (SEQ ID NO: 1916), IDT, Coralville, Iowa), 900 nM of Wr-tcdB-R primer (CATGCTTTTTTAGTTTCTGGATTGAA (SEQ ID NO: 1917), IDT, Coralville, Iowa), 250 nM of Wr-tcdB-P probe (6FAM-CATCCAGTCTCAATTGTATAT-GTTTCTCCA-MGB (SEQ ID NO: 1918), Life Technologies, Grand Island, N.Y.), and Molecular Biology Grade Water (Mo Bio Laboratories, Carlsbad, Calif.) to 18μl (Primers adapted from: Wroblewski, D. et al., Rapid Molecular Characterization of Clostridium difficile and Assessment of Populations of C. difficile in Stool Specimens, Journal of Clinical Microbiology 47:2142-2148(2009)). This reaction mixture was aliquoted to wells of a Hard-shell Low-Profile Thin Wall 96-well Skirted PCR Plate (BioRad, Hercules, Calif.). To this reaction mixture, 2 μl of diluted, frozen, and thawed samples were added and the plate sealed with a Microseal 'B' Adhesive Seal (BioRad, Hercules, Calif.). The qPCR was performed on a BioRad C1000TM Thermal Cycler equipped with a CFX96™ Real-Time System (BioRad, Hercules, Calif.). The thermocycling conditions were 95° C. for 15 minutes followed by 45 cycles of 95° C. for 5 seconds, 60° C. for 30 seconds, and fluorescent readings of the FAM channel. Alternatively, the qPCR could be performed with other standard methods known to those skilled in the art.

D. Data Analysis

The Cq value for each well on the FAM channel was determined by the CFX Manager™ 3.0 software. The $\log_{10}$ (cfu/mL) of *C. difficile* each experimental sample was calculated by inputting a given sample's Cq value into a linear regression model generated from the standard curve comparing the Cq values of the standard curve wells to the known $\log_{10}$ (cfu/mL) of those samples. The log inhibition was calculated for each sample by subtracting the $\log_{10}$ (cfu/mL) of *C. difficile* in the sample from the $\log_{10}$ (cfu/mL) of *C. difficile* in the sample on each assay plate used for the generation of the standard curve that has no additional bacteria added. The mean log inhibition was calculated for all replicates for each composition.

A histogram of the range and standard deviation of each composition was plotted. Ranges or standard deviations of the log inhibitions that were distinct from the overall distribution were examined as possible outliers. If the removal of a single log inhibition datum from one of the binary pairs that were identified in the histograms would bring the range or standard deviation in line with those from the majority of the samples, that datum was removed as an outlier, and the mean log inhibition was recalculated.

The pooled variance of all samples evaluated in the assay was estimated as the average of the sample variances weighted by the sample's degrees of freedom. The pooled standard error was then calculated as the square root of the pooled variance divided by the square root of the number of samples. Confidence intervals for the null hypothesis were determined by multiplying the pooled standard error to the z score corresponding to a given percentage threshold. Mean log inhibitions outside the confidence interval were considered to be inhibitory if positive or stimulatory if negative with the percent confidence corresponding to the interval used. Samples with mean log inhibition greater than the 99% confidence interval (C.I) of the null hypothesis are reported as ++++, those with a 95%<C.I.<99% as +++, those with a 90%<C.I.<95% as ++, those with a 80%<C.I.<90% as + while samples with mean log inhibition less than than the 99% confidence interval (C.I) of the null hypothesis are reported as −−−−, those with a 95%<C.I.<99% as −−−, those with a 90%<C.I.<95% as −−, those with a 80%<C.I.<90% as −.

Many binary pairs inhibit *C. difficile* Table 3. 622 of 989 combinations show inhibition with a confidence interval >80%; 545 of 989 with a C.I. >90%; 507 of 989 with a C.I. >95%; 430 of 989 with a C.I. of >99%. Non-limiting but exemplary binary pairs include those with mean log reduction greater than 0.366, e.g. *Allistipes shahii* paired with *Blautia producta, Clostridium hathaweyi*, or *Colinsella aerofaciens*, or *Clostidium mayombei* paired with *C. innocuum, C. tertium, Colinsella aerofaciens*, or any of the other 424 combinations shown in Table 3. Equally important, the CivSim assay describes binary pairs that do not effectively inhibit *C. difficile.* 188 of 989 combinations promote growth with >80% confidence; 52 of 989 show a lack of inhibition with >90% confidence; 22 of 989 show a lack of inhibition with >95% confidence; 3 of 989, including *B. producta* combined with *Coprococcus catus, Alistipes shahii* combined with *Dorea formicigenerans*, and *Eubacterium rectale* combined with *Roseburia intestinalis*, show a lack of inhibition with >99% confidence. 249 of 989 combinations are neutral in the assay, meaning they neither promote nor inhibit *C. difficile* growth to the limit of measurement.

Ternary combinations with mean log inhibition greater than 0.312 are reported as ++++(≥99% confidence interval (C.I.) of the null hypothesis), those with mean log inhibition between 0.221 and 0.312 as +++(95%<C.I.<99%), those with mean log inhibition between 0.171 and 0.221 as ++(90%<C.I.<95%), those with mean log inhibition between 0.113 and 0.171 as +(80%<C.I.<90%), those with mean log inhibition between −0.113 and −0.171 as −(80%<C.I.<90%), those with mean log inhibition between −0.171 and −0.221 as −−(90%<C.I.<95%), those with mean log inhibition between −0.221 and −0.312 as −−−(95%<C.I.<99%), and those with mean log inhibition less than −0.312 as −−−− (99%<C.I.).

The CivSim shows that many ternary combinations inhibit *C. difficile*. 39 of 56 combinations show inhibition with a confidence interval >80%; 36 of 56 with a C.I. >90%; 36 of 56 with a C.I. >95%; 29 of 56 with a C.I. of >99%. Non-limiting but exemplary ternary combinations include those with mean log reduction greater than 0.171, e.g. any combination shown in Table 4 with a score of ++++, such as *Colinsella aerofaciens, Coprococcus comes*, and *Blautia producta*. Equally important, the CivSim assay describes ternary combinations that do not effectively inhibit *C. difficile*. 5 of 56 combinations promote growth with >80% confidence; 2 of 56 promote growth with >90% confidence; 1 of 56, *Coprococcus comes, Clostridium symbiosum* and *Eubacterium rectale*, promote growth with >95% confidence. 12 of 56 combinations are neutral in the assay, meaning they neither promote nor inhibit *C. difficile* growth to the limit of measurement.

Example P1

Full 165 Sequencing to Determine Operational Taxonomic Unit (OTU)

A. Genomic DNA Extraction

Genomic DNA is extracted from pure microbial cultures using a hot alkaline lysis method. 2 μl of microbial culture is added to 18 μl of Lysis Buffer (25 mM NaOH, 0.2 mM EDTA) and the mixture is incubated at 95° C. for 30 minutes. Subsequently, the samples are cooled to 4° C. and neutralized by the addition of 20 μl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those skilled in the art.

B. PCR

To amplify bacterial 16S rDNA, 2 μl of extracted gDNA is added to a 20 μl A final volume PCR reaction. The PCR reaction also contains 1×HotMasterMix (5PRIME, Gaithersburg, Md.), 250 nM of 27f primer (AGRGTTTGATCMTGGCTCAG (SEQ ID NO: 1919), IDT, Coralville, Iowa), and 250 nM of 1492r primer (TACGGYTACCTTGTTAYGACTT (SEQ ID NO: 1920), IDT, Coralville, Iowa), with Molecular Biology Grade Water (Mo Bio Laboratories, Carlsbad, Calif.) for the balance of the volume. Alternatively, other universal bacterial primers or thermostable polymerases known to those skilled in the art are used.

The PCR performed on commercially available thermocyclers such as a BioRad MyCycler™ Thermal Cycler (BioRad, Hercules, Calif.). The reactions are run at 94° C. for 2 minutes followed by 30 cycles of 94° C. for 30 seconds, 51° C. for 30 seconds, and 68° C. for 1 minute 30 seconds, followed by a 7 minute extension at 72° C. and an indefinite hold at 4° C. Following PCR, gel electrophoresis of a portion of the reaction products is used to confirm successful amplification of a ~1.5 kb product.

C. PCR Cleanup

To remove nucleotides and oligonucleotides from the PCR products, 1 μl of HT ExoSap-IT (Affymetrix, Santa Clara, Calif.) is added to 2.5 μl of PCR product followed by a 15 minute incubation at 37° C. and then a 15 minute inactivation at 80° C.

D. Sanger Sequencing

For each sample, two sequencing reactions are performed, one using each primer: 27f and 1492r. 40 ng of ExoSap-IT-cleaned PCR products are mixed with 25 pmol of sequencing primer and Molecular Biology Grade Water (Mo Bio Laboratories, Carlsbad, Calif.) to 15 μl total volume. This reaction is submitted to a commercial sequencing organization such as Genewiz (South Plainfield, N.J.) for Sanger sequencing.

Example P2

V4 16S Sequencing to Determine Operational Taxonomic Unit (OTU)

E. Genomic DNA Extraction

Genomic DNA is extracted from pure microbial cultures using a hot alkaline lysis method. 2 μl of microbial culture is added to 18 μl of Lysis Buffer (25 mM NaOH, 0.2 mM EDTA) and the mixture is incubated at 95° C. for 30 minutes. Subsequently, the samples are cooled to 4° C. and neutralized by the addition of 18 μl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those in skilled in the art.

F. PCR

To amplify the V4 region of bacterial 16S rDNA, 2 μl of extracted gDNA is added to a 20 μl final volume PCR reaction. The PCR reaction also contains 1×HotMasterMix (5PRIME, Gaithersburg, Md.), 200 nM of V4_515f_adapt (AATGATACGGCGACCACCGAGATCTACACTATGGTAATTGTGTGCCAGCMGCCGCGGT AA (SEQ ID NO: 1921), IDT, Coralville, Iowa), and 200 nM of barcoded 806rbc (CAAGCAGAAGACGGCATACGAGAT (SEQ ID NO: 1922) 12bpGolayBarcode_AGTCAGTCAGCCGGACTACHVGGGTWTCTAAT (SEQ ID NO: 1923), IDT, Coralville, Iowa), with Molecular Biology Grade Water (Mo Bio Laboratories, Carlsbad, Calif.) for the balance of the volume. These primers incorporate adapters for Illumina sequencing by synthesis. Optionally, identical replicate, triplicate, or quadruplicate reactions may be performed. Alternatively other universal bacterial primers or thermostable polymerases known to those skilled in the art are used.

The PCR performed on commercially available thermocyclers such as a BioRad MyCycler™ Thermal Cycler (BioRad, Hercules, Calif.). The reactions are run at 94° C. for 3 minutes followed by 25 cycles of 94° C. for 45 seconds, 50° C. for 1 minute, and 72° C. for 1 minute 30 seconds, followed by a 10 minute extension at 72° C. and a indefinite hold at 4° C. Following PCR, gel electrophoresis of a portion of the reaction products is used to confirm successful amplification of a ~0.4 kb product.

G. PCR Cleanup

To remove nucleotides and oligonucleotides from the PCR products, the entire remaining volume of the PCR, or of the multiple PCRs, is cleaned up using the Mo Bio Ultraclean®-htp 96 Well PCR Clean-up Kit (Mo Bio Laboratories, Carlsbad, Calif.) according to the manufacturer's instructions or other commercially available kits such as the QIAquick 96 PCR Purification Kit (QIAGEN, Valencia, Calif.).

H. DNA Quantification & Pooling

The cleaned PCR products are quantified using the Quant-iT™ PicoGreen® dsDNA Assay Kit (Life Technologies, Grand Island, N.Y.) according to the manufacturer's instructions. Following quantification, the barcoded cleaned PCR products are combined such that each distinct PCR product is at an equimolar ratio to create a prepared Illumina library.

I. Illumina Sequencing

The prepared library is sequenced on Illumina HiSeq or MiSeq sequencers (Illumina, San Diego, Calif.) with cluster generation, template hybridization, iso-thermal amplification, linearization, blocking and denaturization and hybridization of the sequencing primers performed according to the manufacturer's instructions. 16SV4SeqFw (TATGGTAATTGTGTGCCAGCMGCCGCGGTAA (SEQ ID NO: 1924)), 16SV4SeqRev (AGTCAGTCAGCCGGACTACHVGGGTWTCTAAT (SEQ ID NO: 1923)), and 16SV4Index (ATTAGAWACCCBDGTAGTCCGGCTGACTGACT (SEQ ID NO: 1925)) (IDT, Coralville, Iowa) are used for sequencing. This sequencing can optionally be performed by a contract research organization such as Metanome (Houston, Tex.), Ambry Genetics (Aliso Viejo, Calif.), Edge Bio (Gaithersburg, Md.), or Covance (Princeton, N.J.).

J. Taxonomic Assignment to Sequence Read Data

Nucleic acid sequences are analyzed and taxonomic and phylogenetic assignments of specific OTUs are made using sequence similarity and phylogenetic methods that are well known to those skilled in the art, including but not limited to maximum likelihood phylogenetic reconstruction (see e.g. Liu K, Linder CR, and Warnow T. 2011. RAxML and FastTree: Comparing Two Methods for Large-Scale Maximum Likelihood Phylogeny Estimation. *PLoS ONE* 6: e27731. McGuire G, Denham MC, and Balding DJ. 2001. Models of sequence evolution for DNA sequences containing gaps. *Mol. Biol. Evol* 18: 481-490. Wróbel B. 2008. Statistical measures of uncertainty for branches in phylogenetic trees inferred from molecular sequences by using model-based methods. *J. Appl. Genet.* 49: 49-67.) From these taxonomic assignments OTUs in the dataset are defined. The certainty of the OTU call is defined based on the OTU's sequence similarity to a reference nucleic acid sequence and the proximity of the OTU sequence relative to one or more reference sequences in the phylogeny. The specificity of an OTU's taxonomic and phylogenetic assignment determines whether the match is assigned at the level of Family, Genus, Species, or Strain, and the confidence of this assignment is determined based on the position of bootstrap supported branches in the reference phylogenetic tree relative to the placement of the OTU sequence being interrogated.

Example P3

Construction of an In Vitro Assay to Screen for Combinations of Microbes Inhibitory to the Growth of Pathogenic *E. coli*

The in vitro assay is used to screen for combinations of bacteria inhibitory to the growth of *E. coli* by modifying the media used for growth of the pathogen inoculum. One of several choices of media is used for growth of the pathogen such as Reinforced Clostridial Media (RCM), Brain Heart Infusion Broth (BHI) or Luria Bertani Broth (LB) (also known as Lysogeny Broth). *E. coli* is quantified by using alternative selective media specific for *E. coli* or using qPCR probes specific for the pathogen. For example, aerobic growth on MacConkey lactose medium selects for enteric Gram negatives, including *E. coli*. qPCR is conducted using probes specific for the shiga toxin of pathogenic *E. coli*.

Example P4

Construction of an In Vitro Assay to Screen for Combinations of Microbes Inhibitory to the Growth of Vancomycin-Resistant *Enterococcus* (VRE)

The in vitro assay is used to screen for combinations of bacteria inhibitory to the growth of Vancomycin-Resistant *Enterococcus* spp. (VRE) by modifying the media used for growth of the pathogen inoculum. Several choices of media are used for growth of the pathogen such as Reinforced Clostridial Media (RCM), Brain Heart Infusion Broth (BHI) or Luria Bertani Broth (LB). VRE is quantified by using alternative selective media specific for VRE or using qPCR probes specific for the pathogen. For example, m-*Enterococcus* agar containing sodium azide is selective for *Enterococcus* spp. and a small number of other species. Probes specific to the van genes conferring vancomycin resistance are used in the qPCR.

Example P5

Testing of Bacterial Composition Against *Salmonella*

The in vitro assay is used to screen for combinations of bacteria inhibitory to the growth of *Salmonella* spp. by modifying the media used for growth of the pathogen inoculum. Several choices of media are used for growth of the pathogen such as Reinforced Clostridial Media (RCM), Brain Heart Infusion Broth (BHI) or Luria Bertani Broth (LB). *Salmonella* spp. are quantified by using alternative selective media specific for *Salmonella* spp. or using qPCR probes specific for the pathogen. For example, MacConkey agar is used to select for *Salmonella* spp. and the invA gene is targeted with qPCR probes; this gene encodes an invasion protein carried by many pathogenic *Salmonella* spp. and is used in invading eukaryotic cells.

Example P6

Method of Preparing the Bacterial Composition for Administration to a Subject

Two strains for the bacterial composition are independently cultured and mixed together before administration. Both strains are independently be grown at 37° C., pH 7, in a GMM or other animal-products-free medium, pre-reduced with 1 g/L cysteine•HCl. After each strain reaches a sufficient biomass, it is preserved for banking by adding 15% glycerol and then frozen at −80° C. in 1 ml cryotubes.

Each strain is then be cultivated to a concentration of $10^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 mg gelatin, and 2.5 mg magnesium stearate.

Example P7

Method of Treating a Subject with a Bacterial Composition

A patient has suffered from recurrent bouts of *C. difficile*. In the most recent acute phase of illness, the patient is treated with an antibiotic sufficient to ameliorate the symptoms of the illness. In order to prevent another relapse of *C. difficile*, the patient is administered one of the present bacterial compositions. Specifically, the patient is administered *Bacillus circulans* and *Roseburia* inulinivorans at a dose of $10^8$ bacteria total in a lyophilized form, specifically in a 250 mg gelatin capsule containing 10 mg of lyophilized bacteria, 160 mg microcrystalline cellulose, 77.5 mg gelatin, and 2.5 mg magnesium stearate. The patient takes the capsule by mouth and resumes a normal diet after 4, 8, 12, or 24 hours. In another embodiment, the patient may take the capsule by mouth before, during, or immediately after a meal.

Feces is collected before and at 1 day, 3 days, 1 week, and 1 month after administration. The presence of *C. difficile* is found in the feces before administration of the bacterial composition, but feces collections after administration show reducing (such as at least 50% less, 60%, 70%, 80%, 90%, or 95%) to no detectable levels of *C. difficile*, as measured by qPCR, as described above. ELISA for toxin protein or traditional microbiological identification techniques may also be used.

As another measure of patient success, a positive response may be defined as absence of diarrhea, which itself is defined as 3 or more loose or watery stools per day for at least 2 consecutive days or 8 or more loose or watery stools in 48 hours, or persisting diarrhea (due to other causes) with repeating (three times) negative stool tests for toxins of *C. difficile.*

Treatment failure is defined as persisting diarrhea with a positive *C. difficile* toxin stool test or no reduction in levels of *C. difficile*, as measured by qPCR sequencing. ELISA or traditional microbiological identification techniques may also be used.

Example P8

Method of Treating a Subject with a Bacterial Composition

A patient has suffered from recurrent bouts of *C. difficile*. In the most recent acute phase of illness, the patient is treated with an antibiotic sufficient to ameliorate the symptoms of the illness. In order to prevent another relapse of *C. difficile*, the patient is administered one of the present bacterial compositions. Specifically, the patient is administered a bacterial composition containing two bacterial types from Table 1 or SEQ ID NOs. 1-1,864, or a combination from Table 2, at a dose of $10^{8}$ bacteria total in a lyophilized form formulated in an enteric coated capsule. Example of the patient or samples derived from the patient is expected to demonstrate at least one measure of success as described herein (reducing levels of *C. difficile* as measured by qPCR, ELISA, or traditional microbiological identification; absence of diarrhea; persisting diarrhea with repeating (three times) negative stool tests for toxins of *C. difficile.*

Other embodiments will be apparent to those skilled in the art from consideration of the specification and practice of the embodiments. Consider the specification and examples as exemplary only, with a true scope and spirit being indicated by the following claims.

TABLE 1

| OTU | Domain | Phylum | Class | Order | Family | Genus |
|---|---|---|---|---|---|---|
| *Abiotrophia defectiva* | Bacteria | Firmicutes | Bacilli | Lactobacillales | Aerococcaceae | *Abiotrophia* |
| *Abiotrophia* para-adiacens | Bacteria | Firmicutes | Bacilli | Lactobacillales | Aerococcaceae | *Abiotrophia* |
| *Abiotrophia* sp. oral clone P4PA_155 P1 | Bacteria | Firmicutes | Bacilli | Lactobacillales | Aerococcaceae | *Abiotrophia* |
| *Acetanaerobacterium elongatum* | Bacteria | Firmicutes | Clostridia | Clostridiales | Ruminococcaceae | *Acetanaerobacterium* |
| *Acetivibrio cellulolyticus* | Bacteria | Firmicutes | Clostridia | Clostridiales | Ruminococcaceae | *Acetivibrio* |
| *Acetivibrio ethanolgignens* | Bacteria | Firmicutes | Clostridia | Clostridiales | Ruminococcaceae | *Acetivibrio* |
| *Acetobacter aceti* | Bacteria | Proteobacteria | Alphaproteobacteria | Rhodospirillales | Acetobacteraceae | *Acetobacter* |
| *Acetobacter fabarum* | Bacteria | Proteobacteria | Alphaproteobacteria | Rhodospirillales | Acetobacteraceae | *Acetobacter* |
| *Acetobacter lovaniensis* | Bacteria | Proteobacteria | Alphaproteobacteria | Rhodospirillales | Acetobacteraceae | *Acetobacter* |
| *Acetobacter malorum* | Bacteria | Proteobacteria | Alphaproteobacteria | Rhodospirillales | Acetobacteraceae | *Acetobacter* |
| *Acetobacter orientalis* | Bacteria | Proteobacteria | Alphaproteobacteria | Rhodospirillales | Acetobacteraceae | *Acetobacter* |
| *Acetobacter pasteurianus* | Bacteria | Proteobacteria | Alphaproteobacteria | Rhodospirillales | Acetobacteraceae | *Acetobacter* |
| *Acetobacter pomorum* | Bacteria | Proteobacteria | Alphaproteobacteria | Rhodospirillales | Acetobacteraceae | *Acetobacter* |
| *Acetobacter syzygii* | Bacteria | Proteobacteria | Alphaproteobacteria | Rhodospirillales | Acetobacteraceae | *Acetobacter* |
| *Acetobacter tropicalis* | Bacteria | Proteobacteria | Alphaproteobacteria | Rhodospirillales | Acetobacteraceae | *Acetobacter* |
| Acetobacteraceae bacterium AT-5844 | Bacteria | Proteobacteria | Alphaproteobacteria | Rhodospirillales | Acetobacteraceae | unclassified |
| *Acholeplasma laidlawii* | Bacteria | Tenericutes | Mollicutes | Acholeplasmatales | Acholeplasmataceae | *Acholeplasma* |
| *Achromobacter denitrificans* | Bacteria | Proteobacteria | Betaproteobacteria | Burkholderiales | Alcaligenaceae | *Achromobacter* |
| *Achromobacter piechaudii* | Bacteria | Proteobacteria | Betaproteobacteria | Burkholderiales | Alcaligenaceae | *Achromobacter* |
| *Achromobacter xylosoxidans* | Bacteria | Proteobacteria | Betaproteobacteria | Burkholderiales | Alcaligenaceae | *Achromobacter* |
| *Acidaminococcus fermentans* | Bacteria | Firmicutes | Negativicutes | Selenomonadales | Acidaminococcaceae | *Acidaminococcus* |
| *Acidaminococcus intestini* | Bacteria | Firmicutes | Negativicutes | Selenomonadales | Acidaminococcaceae | *Acidaminococcus* |
| *Acidaminococcus* sp. D21 | Bacteria | Firmicutes | Negativicutes | Selenomonadales | Acidaminococcaceae | *Acidaminococcus* |
| *Acidilobus saccharovorans* | Archaea | Crenarchaeota | Thermoprotei | Acidilobales | Acidilobaceae | *Acidilobus* |
| *Acidithiobacillus ferrivorans* | Bacteria | Proteobacteria | Gammaproteobacteria | Acidithiobacillales | Acidithiobacillaceae | *Acidithiobacillus* |
| *Acidovorax* sp. 98-63833 | Bacteria | Proteobacteria | Betaproteobacteria | Burkholderiales | Comamonadaceae | *Acidovorax* |
| *Acidovorax* sp. c109 | Bacteria | Actinobacteria | Actinobacteria | Actinomycetales | Actinomycetaceae | *Actinomyces* |
| *Acinetobacter baumannii* | Bacteria | Proteobacteria | Gammaproteobacteria | Pseudomonadales | Moraxellaceae | *Acinetobacter* |
| *Acinetobacter calcoaceticus* | Bacteria | Proteobacteria | Gammaproteobacteria | Pseudomonadales | Moraxellaceae | *Acinetobacter* |
| *Acinetobacter* genomosp. C1 | Bacteria | Proteobacteria | Gammaproteobacteria | Pseudomonadales | Moraxellaceae | *Acinetobacter* |
| *Acinetobacter haemolyticus* | Bacteria | Proteobacteria | Gammaproteobacteria | Pseudomonadales | Moraxellaceae | *Acinetobacter* |
| *Acinetobacter johnsonii* | Bacteria | Proteobacteria | Gammaproteobacteria | Pseudomonadales | Moraxellaceae | *Acinetobacter* |
| *Acinetobacter junii* | Bacteria | Proteobacteria | Gammaproteobacteria | Pseudomonadales | Moraxellaceae | *Acinetobacter* |
| *Acinetobacter lwoffii* | Bacteria | Proteobacteria | Gammaproteobacteria | Pseudomonadales | Moraxellaceae | *Acinetobacter* |
| *Acinetobacter parvus* | Bacteria | Proteobacteria | Gammaproteobacteria | Pseudomonadales | Moraxellaceae | *Acinetobacter* |
| *Acinetobacter radioresistens* | Bacteria | Proteobacteria | Gammaproteobacteria | Pseudomonadales | Moraxellaceae | *Acinetobacter* |
| *Acinetobacter schindleri* | Bacteria | Proteobacteria | Gammaproteobacteria | Pseudomonadales | Moraxellaceae | *Acinetobacter* |
| *Acinetobacter* sp. 56A1 | Bacteria | Proteobacteria | Gammaproteobacteria | Pseudomonadales | Moraxellaceae | *Acinetobacter* |
| *Acinetobacter* sp. CIP 101934 | Bacteria | Proteobacteria | Gammaproteobacteria | Pseudomonadales | Moraxellaceae | *Acinetobacter* |
| *Acinetobacter* sp. CIP 102143 | Bacteria | Proteobacteria | Gammaproteobacteria | Pseudomonadales | Moraxellaceae | *Acinetobacter* |
| *Acinetobacter* sp. CIP 53.82 | Bacteria | Proteobacteria | Gammaproteobacteria | Pseudomonadales | Moraxellaceae | *Acinetobacter* |
| *Acinetobacter* sp. M16-22 | Bacteria | Proteobacteria | Gammaproteobacteria | Pseudomonadales | Moraxellaceae | *Acinetobacter* |
| *Acinetobacter* sp. RUH2624 | Bacteria | Proteobacteria | Gammaproteobacteria | Pseudomonadales | Moraxellaceae | *Acinetobacter* |
| *Acinetobacter* sp. SH024 | Bacteria | Proteobacteria | Gammaproteobacteria | Pseudomonadales | Moraxellaceae | *Acinetobacter* |
| *Actinobacillus minor* | Bacteria | Proteobacteria | Gammaproteobacteria | Pasteurellales | Pasteurellaceae | *Actinobacillus* |
| *Actinobacillus pleuropneumoniae* | Bacteria | Proteobacteria | Gammaproteobacteria | Pasteurellales | Pasteurellaceae | *Actinobacillus* |

TABLE 1-continued

| OTU | Domain | Phylum | Class | Order | Family | Genus |
|---|---|---|---|---|---|---|
| *Actinobacillus succinogenes* | Bacteria | Proteobacteria | Gammaproteobacteria | Pasteurellales | Pasteurellaceae | *Aggregatibacter* |
| *Actinobacillus succinogenes* | Bacteria | Proteobacteria | Gammaproteobacteria | Pasteurellales | Pasteurellaceae | *Actinobacillus* |
| *Actinobacillus ureae* | Bacteria | Proteobacteria | Gammaproteobacteria | Pasteurellales | Pasteurellaceae | *Actinobacillus* |
| *Actinobaculum massiliae* | Bacteria | Actinobacteria | Actinobacteria | Actinomycetales | Actinomycetaceae | *Actinobaculum* |
| *Actinobaculum schaalii* | Bacteria | Actinobacteria | Actinobacteria | Actinomycetales | Actinomycetaceae | *Actinobaculum* |
| *Actinobaculum* sp. BM#101342 | Bacteria | Actinobacteria | Actinobacteria | Actinomycetales | Actinomycetaceae | *Actinobaculum* |
| *Actinobaculum* sp. P2P__19 P1 | Bacteria | Actinobacteria | Actinobacteria | Actinomycetales | Actinomycetaceae | *Actinobaculum* |
| *Actinomyces cardiffensis* | Bacteria | Actinobacteria | Actinobacteria | Actinomycetales | Actinomycetaceae | *Actinomyces* |
| *Actinomyces europaeus* | Bacteria | Actinobacteria | Actinobacteria | Actinomycetales | Actinomycetaceae | *Actinomyces* |
| *Actinomyces funkei* | Bacteria | Actinobacteria | Actinobacteria | Actinomycetales | Actinomycetaceae | *Actinomyces* |
| *Actinomyces* genomosp. C1 | Bacteria | Actinobacteria | Actinobacteria | Actinomycetales | Actinomycetaceae | *Actinomyces* |
| *Actinomyces* genomosp. C2 | Bacteria | Actinobacteria | Actinobacteria | Actinomycetales | Actinomycetaceae | *Actinomyces* |
| *Actinomyces* genomosp. P1 oral clone MB6__C03 | Bacteria | Actinobacteria | Actinobacteria | Actinomycetales | Actinomycetaceae | *Actinomyces* |
| *Actinomyces georgiae* | Bacteria | Actinobacteria | Actinobacteria | Actinomycetales | Actinomycetaceae | *Actinomyces* |
| *Actinomyces israelii* | Bacteria | Actinobacteria | Actinobacteria | Actinomycetales | Actinomycetaceae | *Actinomyces* |
| *Actinomyces massiliensis* | Bacteria | Actinobacteria | Actinobacteria | Actinomycetales | Actinomycetaceae | *Actinomyces* |
| *Actinomyces meyeri* | Bacteria | Actinobacteria | Actinobacteria | Actinomycetales | Actinomycetaceae | *Actinomyces* |
| *Actinomyces naeslundii* | Bacteria | Actinobacteria | Actinobacteria | Actinomycetales | Actinomycetaceae | *Actinomyces* |
| *Actinomyces nasicola* | Bacteria | Actinobacteria | Actinobacteria | Actinomycetales | Actinomycetaceae | *Actinomyces* |
| *Actinomyces neuii* | Bacteria | Actinobacteria | Actinobacteria | Actinomycetales | Actinomycetaceae | *Actinomyces* |
| *Actinomyces odontolyticus* | Bacteria | Actinobacteria | Actinobacteria | Actinomycetales | Actinomycetaceae | *Actinomyces* |
| *Actinomyces oricola* | Bacteria | Actinobacteria | Actinobacteria | Actinomycetales | Actinomycetaceae | *Actinomyces* |
| *Actinomyces orihominis* | Bacteria | Actinobacteria | Actinobacteria | Actinomycetales | Actinomycetaceae | *Actinomyces* |
| *Actinomyces oris* | Bacteria | Actinobacteria | Actinobacteria | Actinomycetales | Actinomycetaceae | *Actinomyces* |
| *Actinomyces* sp. 7400942 | Bacteria | Actinobacteria | Actinobacteria | Actinomycetales | Actinomycetaceae | *Actinomyces* |
| *Actinomyces* sp. c109 | Bacteria | Actinobacteria | Actinobacteria | Actinomycetales | Actinomycetaceae | *Actinomyces* |
| *Actinomyces* sp. CCUG 37290 | Bacteria | Actinobacteria | Actinobacteria | Actinomycetales | Actinomycetaceae | *Actinomyces* |
| *Actinomyces* sp. ChDC B197 | Bacteria | Actinobacteria | Actinobacteria | Actinomycetales | Actinomycetaceae | *Actinomyces* |
| *Actinomyces* sp. GEJ15 | Bacteria | Actinobacteria | Actinobacteria | Actinomycetales | Actinomycetaceae | *Actinomyces* |
| *Actinomyces* sp. HKU31 | Bacteria | Actinobacteria | Actinobacteria | Actinomycetales | Actinomycetaceae | *Actinomyces* |
| *Actinomyces* sp. ICM34 | Bacteria | Actinobacteria | Actinobacteria | Actinomycetales | Actinomycetaceae | *Actinomyces* |
| *Actinomyces* sp. ICM41 | Bacteria | Actinobacteria | Actinobacteria | Actinomycetales | Actinomycetaceae | *Actinomyces* |
| *Actinomyces* sp. ICM47 | Bacteria | Actinobacteria | Actinobacteria | Actinomycetales | Actinomycetaceae | *Actinomyces* |
| *Actinomyces* sp. ICM54 | Bacteria | Actinobacteria | Actinobacteria | Actinomycetales | Actinomycetaceae | *Actinomyces* |
| *Actinomyces* sp. M2231/94/1 | Bacteria | Actinobacteria | Actinobacteria | Actinomycetales | Actinomycetaceae | *Actinomyces* |
| *Actinomyces* sp. oral clone GU009 | Bacteria | Actinobacteria | Actinobacteria | Actinomycetales | Actinomycetaceae | *Actinomyces* |
| *Actinomyces* sp. oral clone GU067 | Bacteria | Actinobacteria | Actinobacteria | Actinomycetales | Actinomycetaceae | *Actinomyces* |
| *Actinomyces* sp. oral clone IO076 | Bacteria | Actinobacteria | Actinobacteria | Actinomycetales | Actinomycetaceae | *Actinomyces* |
| *Actinomyces* sp. oral clone IO077 | Bacteria | Actinobacteria | Actinobacteria | Actinomycetales | Actinomycetaceae | *Actinomyces* |
| *Actinomyces* sp. oral clone IP073 | Bacteria | Actinobacteria | Actinobacteria | Actinomycetales | Actinomycetaceae | *Actinomyces* |
| *Actinomyces* sp. oral clone IP081 | Bacteria | Actinobacteria | Actinobacteria | Actinomycetales | Actinomycetaceae | *Actinomyces* |
| *Actinomyces* sp. oral clone JA063 | Bacteria | Actinobacteria | Actinobacteria | Actinomycetales | Actinomycetaceae | *Actinomyces* |
| *Actinomyces* sp. oral taxon 170 | Bacteria | Actinobacteria | Actinobacteria | Actinomycetales | Actinomycetaceae | *Actinomyces* |
| *Actinomyces* sp. oral taxon 171 | Bacteria | Actinobacteria | Actinobacteria | Actinomycetales | Actinomycetaceae | *Actinomyces* |
| *Actinomyces* sp. oral taxon 178 | Bacteria | Actinobacteria | Actinobacteria | Actinomycetales | Actinomycetaceae | *Actinomyces* |
| *Actinomyces* sp. oral taxon 180 | Bacteria | Actinobacteria | Actinobacteria | Actinomycetales | Actinomycetaceae | *Actinomyces* |
| *Actinomyces* sp. oral taxon 848 | Bacteria | Actinobacteria | Actinobacteria | Actinomycetales | Actinomycetaceae | *Actinomyces* |
| *Actinomyces* sp. oral taxon C55 | Bacteria | Actinobacteria | Actinobacteria | Actinomycetales | Actinomycetaceae | *Actinomyces* |

TABLE 1-continued

| OTU | Domain | Phylum | Class | Order | Family | Genus |
|---|---|---|---|---|---|---|
| *Actinomyces* sp. TeJ5 | Bacteria | Actinobacteria | Actinobacteria | Actinomycetales | Actinomycetaceae | *Actinomyces* |
| *Actinomyces urogenitalis* | Bacteria | Actinobacteria | Actinobacteria | Actinomycetales | Actinomycetaceae | *Actinomyces* |
| *Actinomyces viscosus* | Bacteria | Actinobacteria | Actinobacteria | Actinomycetales | Actinomycetaceae | *Actinomyces* |
| *Adlercreutzia equolifaciens* | Bacteria | Actinobacteria | Actinobacteria | Coriobacteriales | Coriobacteriaceae | *Adlercreutzia* |
| *Aerococcus sanguinicola* | Bacteria | Firmicutes | Bacilli | Lactobacillales | Aerococcaceae | *Aerococcus* |
| *Aerococcus urinae* | Bacteria | Firmicutes | Bacilli | Lactobacillales | Aerococcaceae | *Aerococcus* |
| *Aerococcus urinaeequi* | Bacteria | Firmicutes | Bacilli | Lactobacillales | Aerococcaceae | *Aerococcus* |
| *Aerococcus viridans* | Bacteria | Firmicutes | Bacilli | Lactobacillales | Aerococcaceae | *Aerococcus* |
| *Aeromicrobium marinum* | Bacteria | Actinobacteria | Actinobacteria | Actinomycetales | Nocardioidaceae | *Aeromicrobium* |
| *Aeromicrobium* sp. JC14 | Bacteria | Actinobacteria | Actinobacteria | Actinomycetales | Nocardioidaceae | *Aeromicrobium* |
| *Aeromonas allosaccharophila* | Bacteria | Proteobacteria | Gammaproteobacteria | Aeromonadales | Aeromonadaceae | *Aeromonas* |
| *Aeromonas enteropelogenes* | Bacteria | Proteobacteria | Gammaproteobacteria | Aeromonadales | Aeromonadaceae | *Aeromonas* |
| *Aeromonas hydrophila* | Bacteria | Proteobacteria | Gammaproteobacteria | Aeromonadales | Aeromonadaceae | *Aeromonas* |
| *Aeromonas jandaei* | Bacteria | Proteobacteria | Gammaproteobacteria | Aeromonadales | Aeromonadaceae | *Aeromonas* |
| *Aeromonas salmonicida* | Bacteria | Proteobacteria | Gammaproteobacteria | Aeromonadales | Aeromonadaceae | *Aeromonas* |
| *Aeromonas trota* | Bacteria | Proteobacteria | Gammaproteobacteria | Aeromonadales | Aeromonadaceae | *Aeromonas* |
| *Aeromonas veronii* | Bacteria | Proteobacteria | Gammaproteobacteria | Aeromonadales | Aeromonadaceae | *Aeromonas* |
| *Afipia* genomosp. 4 | Bacteria | Proteobacteria | Alphaproteobacteria | Rhizobiales | Bradyrhizobiaceae | *Afipia* |
| *Aggregatibacter actinomycetemcomitans* | Bacteria | Proteobacteria | Gammaproteobacteria | Pasteurellales | Pasteurellaceae | *Aggregatibacter* |
| *Aggregatibacter aphrophilus* | Bacteria | Proteobacteria | Gammaproteobacteria | Pasteurellales | Pasteurellaceae | *Aggregatibacter* |
| *Aggregatibacter segnis* | Bacteria | Proteobacteria | Gammaproteobacteria | Pasteurellales | Pasteurellaceae | *Aggregatibacter* |
| *Agrobacterium radiobacter* | Bacteria | Proteobacteria | Alphaproteobacteria | Rhizobiales | Rhizobiaceae | *Agrobacterium* |
| *Agrobacterium tumefaciens* | Bacteria | Proteobacteria | Alphaproteobacteria | Rhizobiales | Rhizobiaceae | *Agrobacterium* |
| *Agrococcus jenensis* | Bacteria | Actinobacteria | Actinobacteria | Actinomycetales | Microbacteriaceae | *Agrococcus* |
| *Akkermansia muciniphila* | Bacteria | Verrucomicrobia | Verrucomicrobiae | Verrucomicrobiales | Verrucomicrobiaceae | *Akkermansia* |
| *Alcaligenes faecalis* | Bacteria | Proteobacteria | Betaproteobacteria | Burkholderiales | Alcaligenaceae | *Alcaligenes* |
| *Alcaligenes* sp. CO14 | Bacteria | Proteobacteria | Betaproteobacteria | Burkholderiales | Alcaligenaceae | *Alcaligenes* |
| *Alcaligenes* sp. S3 | Bacteria | Proteobacteria | Betaproteobacteria | Burkholderiales | Alcaligenaceae | *Alcaligenes* |
| *Alicyclobacillus acidocaldarius* | Bacteria | Firmicutes | Bacilli | Bacillales | Alicyclobacillaceae | *Alicyclobacillus* |
| *Alicyclobacillus acidoterrestris* | Bacteria | Firmicutes | Bacilli | Bacillales | Alicyclobacillaceae | *Alicyclobacillus* |
| *Alicyclobacillus contaminans* | Bacteria | Firmicutes | Bacilli | Bacillales | Alicyclobacillaceae | *Alicyclobacillus* |
| *Alicyclobacillus cycloheptanicus* | Bacteria | Firmicutes | Bacilli | Bacillales | Alicyclobacillaceae | *Alicyclobacillus* |
| *Alicyclobacillus herbarius* | Bacteria | Firmicutes | Bacilli | Bacillales | Alicyclobacillaceae | *Alicyclobacillus* |
| *Alicyclobacillus pomorum* | Bacteria | Firmicutes | Bacilli | Bacillales | Alicyclobacillaceae | *Alicyclobacillus* |
| *Alicyclobacillus* sp. CCUG 53762 | Bacteria | Firmicutes | Bacilli | Bacillales | Alicyclobacillaceae | *Alicyclobacillus* |
| *Alistipes finegoldii* | Bacteria | Bacteroidetes | Bacteroidia | Bacteroidales | Rikenellaceae | *Alistipes* |
| *Alistipes indistinctus* | Bacteria | Bacteroidetes | Bacteroidia | Bacteroidales | Rikenellaceae | *Alistipes* |
| *Alistipes onderdonkii* | Bacteria | Bacteroidetes | Bacteroidia | Bacteroidales | Rikenellaceae | *Alistipes* |
| *Alistipes putredinis* | Bacteria | Bacteroidetes | Bacteroidia | Bacteroidales | Rikenellaceae | *Alistipes* |
| *Alistipes shahii* | Bacteria | Bacteroidetes | Bacteroidia | Bacteroidales | Rikenellaceae | *Alistipes* |
| *Alistipes* sp. HGB5 | Bacteria | Bacteroidetes | Bacteroidia | Bacteroidales | Rikenellaceae | *Alistipes* |
| *Alistipes* sp. JC50 | Bacteria | Bacteroidetes | Bacteroidia | Bacteroidales | Rikenellaceae | *Alistipes* |
| *Alistipes* sp. RMA 9912 | Bacteria | Bacteroidetes | Bacteroidia | Bacteroidales | Rikenellaceae | *Alistipes* |
| *Alkaliphilus metalliredigenes* | Bacteria | Firmicutes | Clostridia | Clostridiales | Clostridiaceae | *Alkaliphilus* |
| *Alkaliphilus oremlandii* | Bacteria | Firmicutes | Clostridia | Clostridiales | Clostridiaceae | *Alkaliphilus* |
| *Alloscardovia omnicolens* | Bacteria | Actinobacteria | Actinobacteria | Bifidobacteriales | Bifidobacteriaceae | *Alloscardovia* |
| *Alloscardovia* sp. OB7196 | Bacteria | Actinobacteria | Actinobacteria | Bifidobacteriales | Bifidobacteriaceae | *Alloscardovia* |

TABLE 1-continued

| OTU | Domain | Phylum | Class | Order | Family | Genus |
|---|---|---|---|---|---|---|
| *Anaerobaculum hydrogeniformans* | Bacteria | Synergistetes | Synergistia | Synergistales | Synergistaceae | *Anaerobaculum* |
| *Anaerobiospirillum succiniciproducens* | Bacteria | Proteobacteria | Gammaproteobacteria | Aeromonadales | Succinivibrionaceae | *Anaerobiospirillum* |
| *Anaerobiospirillum thomasii* | Bacteria | Proteobacteria | Gammaproteobacteria | Aeromonadales | Succinivibrionaceae | *Anaerobiospirillum* |
| *Anaerococcus hydrogenalis* | Bacteria | Firmicutes | Clostridia | Clostridiales | Clostridiales Family XI. Incertae Sedis | *Anaerococcus* |
| *Anaerococcus lactolyticus* | Bacteria | Firmicutes | Clostridia | Clostridiales | Clostridiales Family XI. Incertae Sedis | *Anaerococcus* |
| *Anaerococcus octavius* | Bacteria | Firmicutes | Clostridia | Clostridiales | Clostridiales Family XI. Incertae Sedis | *Anaerococcus* |
| *Anaerococcus prevotii* | Bacteria | Firmicutes | Clostridia | Clostridiales | Clostridiales Family XI. Incertae Sedis | *Anaerococcus* |
| *Anaerococcus* sp. 8404299 | Bacteria | Firmicutes | Clostridia | Clostridiales | Clostridiales Family XI. Incertae Sedis | *Anaerococcus* |
| *Anaerococcus* sp. 8405254 | Bacteria | Firmicutes | Clostridia | Clostridiales | Clostridiales Family XI. Incertae Sedis | *Anaerococcus* |
| *Anaerococcus* sp. 9401487 | Bacteria | Firmicutes | Clostridia | Clostridiales | Clostridiales Family XI. Incertae Sedis | *Anaerococcus* |
| *Anaerococcus* sp. 9403502 | Bacteria | Firmicutes | Clostridia | Clostridiales | Clostridiales Family XI. Incertae Sedis | *Anaerococcus* |
| *Anaerococcus* sp. gpac104 | Bacteria | Firmicutes | Clostridia | Clostridiales | Clostridiales Family XI. Incertae Sedis | *Anaerococcus* |
| *Anaerococcus* sp. gpac126 | Bacteria | Firmicutes | Clostridia | Clostridiales | Clostridiales Family XI. Incertae Sedis | *Anaerococcus* |
| *Anaerococcus* sp. gpac155 | Bacteria | Firmicutes | Clostridia | Clostridiales | Clostridiales Family XI. Incertae Sedis | *Anaerococcus* |
| *Anaerococcus* sp. gpac199 | Bacteria | Firmicutes | Clostridia | Clostridiales | Clostridiales Family XI. Incertae Sedis | *Anaerococcus* |
| *Anaerococcus* sp. gpac215 | Bacteria | Firmicutes | Clostridia | Clostridiales | Clostridiales Family XI. Incertae Sedis | *Anaerococcus* |
| *Anaerococcus tetradius* | Bacteria | Firmicutes | Clostridia | Clostridiales | Clostridiales Family XI. Incertae Sedis | *Anaerococcus* |
| *Anaerococcus vaginalis* | Bacteria | Firmicutes | Clostridia | Clostridiales | Clostridiales Family XI. Incertae Sedis | *Anaerococcus* |
| *Anaerofustis stercorihominis* | Bacteria | Firmicutes | Clostridia | Clostridiales | Eubacteriaceae | *Anaerofustis* |
| *Anaeroglobus geminatus* | Bacteria | Firmicutes | Negativicutes | Selenomonadales | Veillonellaceae | *Anaeroglobus* |
| *Anaerosporobacter mobilis* | Bacteria | Firmicutes | Clostridia | Clostridiales | Clostridiaceae | *Anaerosporobacter* |
| *Anaerostipes caccae* | Bacteria | Firmicutes | Clostridia | Clostridiales | Lachnospiraceae | *Anaerostipes* |
| *Anaerostipes* sp. 3_2_56FAA | Bacteria | Firmicutes | Clostridia | Clostridiales | Lachnospiraceae | *Anaerostipes* |
| *Anaerotruncus colihominis* | Bacteria | Firmicutes | Clostridia | Clostridiales | Ruminococcaceae | *Anaerotruncus* |
| *Anaplasma marginale* | Bacteria | Proteobacteria | Alphaproteobacteria | Rickettsiales | Anaplasmataceae | *Anaplasma* |
| *Anaplasma phagocytophilum* | Bacteria | Proteobacteria | Alphaproteobacteria | Rickettsiales | Anaplasmataceae | *Anaplasma* |
| *Aneurinibacillus aneurinilyticus* | Bacteria | Firmicutes | Bacilli | Bacillales | Paenibacillaceae | *Aneurinibacillus* |
| *Aneurinibacillus danicus* | Bacteria | Firmicutes | Bacilli | Bacillales | Paenibacillaceae | *Aneurinibacillus* |
| *Aneurinibacillus migulanus* | Bacteria | Firmicutes | Bacilli | Bacillales | Paenibacillaceae | *Aneurinibacillus* |
| *Aneurinibacillus terranovensis* | Bacteria | Firmicutes | Bacilli | Bacillales | Paenibacillaceae | *Aneurinibacillus* |
| *Aneurinibacillus thermoaerophilus* | Bacteria | Firmicutes | Bacilli | Bacillales | Paenibacillaceae | *Aneurinibacillus* |
| *Anoxybacillus contaminans* | Bacteria | Firmicutes | Bacilli | Bacillales | Bacillaceae | *Anoxybacillus* |
| *Anoxybacillus flavithermus* | Bacteria | Firmicutes | Bacilli | Bacillales | Bacillaceae | *Anoxybacillus* |
| *Arcanobacterium haemolyticum* | Bacteria | Actinobacteria | Actinobacteria | Actinomycetales | Actinomycetaceae | *Arcanobacterium* |
| *Arcanobacterium pyogenes* | Bacteria | Actinobacteria | Actinobacteria | Actinomycetales | Actinomycetaceae | *Trueperella* |
| *Arcobacter butzleri* | Bacteria | Proteobacteria | Epsilonproteobacteria | Campylobacterales | Campylobacteraceae | *Arcobacter* |
| *Arcobacter cryaerophilus* | Bacteria | Proteobacteria | Epsilonproteobacteria | Campylobacterales | Campylobacteraceae | *Arcobacter* |
| *Arthrobacter agilis* | Bacteria | Actinobacteria | Actinobacteria | Actinomycetales | Micrococcaceae | *Arthrobacter* |
| *Arthrobacter arilaitensis* | Bacteria | Actinobacteria | Actinobacteria | Actinomycetales | Micrococcaceae | *Arthrobacter* |
| *Arthrobacter bergerei* | Bacteria | Actinobacteria | Actinobacteria | Actinomycetales | Micrococcaceae | *Arthrobacter* |
| *Arthrobacter globiformis* | Bacteria | Actinobacteria | Actinobacteria | Actinomycetales | Micrococcaceae | *Arthrobacter* |
| *Arthrobacter nicotianae* | Bacteria | Actinobacteria | Actinobacteria | Actinomycetales | Micrococcaceae | *Arthrobacter* |
| *Atopobium minutum* | Bacteria | Actinobacteria | Actinobacteria | Coriobacteriales | Coriobacteriaceae | *Atopobium* |
| *Atopobium parvulum* | Bacteria | Actinobacteria | Actinobacteria | Coriobacteriales | Coriobacteriaceae | *Atopobium* |
| *Atopobium rimae* | Bacteria | Actinobacteria | Actinobacteria | Coriobacteriales | Coriobacteriaceae | *Atopobium* |
| *Atopobium* sp. BS2 | Bacteria | Actinobacteria | Actinobacteria | Coriobacteriales | Coriobacteriaceae | *Atopobium* |
| *Atopobium* sp. F0209 | Bacteria | Actinobacteria | Actinobacteria | Coriobacteriales | Coriobacteriaceae | *Atopobium* |
| *Atopobium* sp. ICM42b10 | Bacteria | Actinobacteria | Actinobacteria | Coriobacteriales | Coriobacteriaceae | *Atopobium* |
| *Atopobium* sp. ICM57 | Bacteria | Actinobacteria | Actinobacteria | Coriobacteriales | Coriobacteriaceae | *Atopobium* |
| *Atopobium vaginae* | Bacteria | Actinobacteria | Actinobacteria | Coriobacteriales | Coriobacteriaceae | *Atopobium* |
| *Aurantimonas coralicida* | Bacteria | Proteobacteria | Alphaproteobacteria | Rhizobiales | Aurantimonadaceae | *Aurantimonas* |

TABLE 1-continued

| OTU | Domain | Phylum | Class | Order | Family | Genus |
|---|---|---|---|---|---|---|
| *Aureimonas altamirensis* | Bacteria | Proteobacteria | Alphaproteobacteria | Rhizobiales | Aurantimonadaceae | *Aurantimonas* |
| *Auritibacter ignavus* | Bacteria | Actinobacteria | Actinobacteria | Actinomycetales | Micrococcaceae | *Auritidibacter* |
| *Averyella dalhousiensis* | Bacteria | Proteobacteria | Gammaproteobacteria | Enterobacteriales | Enterobacteriaceae | *Averyella* |
| *Bacillus aeolius* | Bacteria | Firmicutes | Bacilli | Bacillales | Bacillaceae | *Bacillus* |
| *Bacillus aerophilus* | Bacteria | Firmicutes | Bacilli | Bacillales | Bacillaceae | *Bacillus* |
| *Bacillus aestuarii* | Bacteria | Firmicutes | Bacilli | Bacillales | Bacillaceae | *Bacillus* |
| *Bacillus alcalophilus* | Bacteria | Firmicutes | Bacilli | Bacillales | Bacillaceae | *Bacillus* |
| *Bacillus amyloliquefaciens* | Bacteria | Firmicutes | Bacilli | Bacillales | Bacillaceae | *Bacillus* |
| *Bacillus atrophaeus* | Bacteria | Firmicutes | Bacilli | Bacillales | Bacillaceae | *Bacillus* |
| *Bacillus badius* | Bacteria | Firmicutes | Bacilli | Bacillales | Bacillaceae | *Bacillus* |
| *Bacillus cereus* | Bacteria | Firmicutes | Bacilli | Bacillales | Bacillaceae | *Bacillus* |
| *Bacillus circulans* | Bacteria | Firmicutes | Bacilli | Bacillales | Bacillaceae | *Bacillus* |
| *Bacillus clausii* | Bacteria | Firmicutes | Bacilli | Bacillales | Bacillaceae | *Bacillus* |
| *Bacillus coagulans* | Bacteria | Firmicutes | Bacilli | Bacillales | Bacillaceae | *Bacillus* |
| *Bacillus firmus* | Bacteria | Firmicutes | Bacilli | Bacillales | Bacillaceae | *Bacillus* |
| *Bacillus flexus* | Bacteria | Firmicutes | Bacilli | Bacillales | Bacillaceae | *Bacillus* |
| *Bacillus fordii* | Bacteria | Firmicutes | Bacilli | Bacillales | Bacillaceae | *Bacillus* |
| *Bacillus gelatini* | Bacteria | Firmicutes | Bacilli | Bacillales | Bacillaceae | *Bacillus* |
| *Bacillus halmapalus* | Bacteria | Firmicutes | Bacilli | Bacillales | Bacillaceae | *Bacillus* |
| *Bacillus halodurans* | Bacteria | Firmicutes | Bacilli | Bacillales | Bacillaceae | *Bacillus* |
| *Bacillus herbersteinensis* | Bacteria | Firmicutes | Bacilli | Bacillales | Bacillaceae | *Bacillus* |
| *Bacillus horti* | Bacteria | Firmicutes | Bacilli | Bacillales | Bacillaceae | *Bacillus* |
| *Bacillus idriensis* | Bacteria | Firmicutes | Bacilli | Bacillales | Bacillaceae | *Bacillus* |
| *Bacillus lentus* | Bacteria | Firmicutes | Bacilli | Bacillales | Bacillaceae | *Bacillus* |
| *Bacillus licheniformis* | Bacteria | Firmicutes | Bacilli | Bacillales | Bacillaceae | *Bacillus* |
| *Bacillus megaterium* | Bacteria | Firmicutes | Bacilli | Bacillales | Bacillaceae | *Bacillus* |
| *Bacillus nealsonii* | Bacteria | Firmicutes | Bacilli | Bacillales | Bacillaceae | *Bacillus* |
| *Bacillus niabensis* | Bacteria | Firmicutes | Bacilli | Bacillales | Bacillaceae | *Bacillus* |
| *Bacillus niacini* | Bacteria | Firmicutes | Bacilli | Bacillales | Bacillaceae | *Bacillus* |
| *Bacillus pocheonensis* | Bacteria | Firmicutes | Bacilli | Bacillales | Bacillaceae | *Bacillus* |
| *Bacillus pumilus* | Bacteria | Firmicutes | Bacilli | Bacillales | Bacillaceae | *Bacillus* |
| *Bacillus safensis* | Bacteria | Firmicutes | Bacilli | Bacillales | Bacillaceae | *Bacillus* |
| *Bacillus simplex* | Bacteria | Firmicutes | Bacilli | Bacillales | Bacillaceae | *Bacillus* |
| *Bacillus sonorensis* | Bacteria | Firmicutes | Bacilli | Bacillales | Bacillaceae | *Bacillus* |
| *Bacillus* sp. 10403023 MM10403188 | Bacteria | Firmicutes | Bacilli | Bacillales | Bacillaceae | *Bacillus* |
| *Bacillus* sp. 2_A_57_CT2 | Bacteria | Firmicutes | Bacilli | Bacillales | Bacillaceae | *Bacillus* |
| *Bacillus* sp. 2008724126 | Bacteria | Firmicutes | Bacilli | Bacillales | Bacillaceae | *Bacillus* |
| *Bacillus* sp. 2008724139 | Bacteria | Firmicutes | Bacilli | Bacillales | Bacillaceae | *Bacillus* |
| *Bacillus* sp. 7-16AIA | Bacteria | Firmicutes | Bacilli | Bacillales | Bacillaceae | *Bacillus* |
| *Bacillus* sp. 9-3AIA | Bacteria | Firmicutes | Bacilli | Bacillales | Bacillaceae | *Bacillus* |
| *Bacillus* sp. AP8 | Bacteria | Firmicutes | Bacilli | Bacillales | Bacillaceae | *Bacillus* |
| *Bacillus* sp. B27(2008) | Bacteria | Firmicutes | Bacilli | Bacillales | Bacillaceae | *Bacillus* |
| *Bacillus* sp. BT1B_CT2 | Bacteria | Firmicutes | Bacilli | Bacillales | Bacillaceae | *Bacillus* |
| *Bacillus* sp. GB1.1 | Bacteria | Firmicutes | Bacilli | Bacillales | Bacillaceae | *Bacillus* |
| *Bacillus* sp. GB9 | Bacteria | Firmicutes | Bacilli | Bacillales | Bacillaceae | *Bacillus* |
| *Bacillus* sp. HU19.1 | Bacteria | Firmicutes | Bacilli | Bacillales | Bacillaceae | *Bacillus* |
| *Bacillus* sp. HU29 | Bacteria | Firmicutes | Bacilli | Bacillales | Bacillaceae | *Bacillus* |
| *Bacillus* sp. HU33.1 | Bacteria | Firmicutes | Bacilli | Bacillales | Bacillaceae | *Bacillus* |
| *Bacillus* sp. JC6 | Bacteria | Firmicutes | Bacilli | Bacillales | Bacillaceae | *Bacillus* |
| *Bacillus* sp. oral taxon F26 | Bacteria | Firmicutes | Bacilli | Bacillales | Bacillaceae | *Bacillus* |
| *Bacillus* sp. oral taxon F28 | Bacteria | Firmicutes | Bacilli | Bacillales | Bacillaceae | *Bacillus* |

TABLE 1-continued

| OTU | Domain | Phylum | Class | Order | Family | Genus |
|---|---|---|---|---|---|---|
| *Bacillus* sp. oral taxon F79 | Bacteria | Firmicutes | Bacilli | Bacillales | Bacillaceae | *Bacillus* |
| *Bacillus* sp. SRC_DSF1 | Bacteria | Firmicutes | Bacilli | Bacillales | Bacillaceae | *Bacillus* |
| *Bacillus* sp. SRC_DSF10 | Bacteria | Firmicutes | Bacilli | Bacillales | Bacillaceae | *Bacillus* |
| *Bacillus* sp. SRC_DSF2 | Bacteria | Firmicutes | Bacilli | Bacillales | Bacillaceae | *Bacillus* |
| *Bacillus* sp. SRC_DSF6 | Bacteria | Firmicutes | Bacilli | Bacillales | Bacillaceae | *Bacillus* |
| *Bacillus* sp. tc09 | Bacteria | Firmicutes | Bacilli | Bacillales | Bacillaceae | *Bacillus* |
| *Bacillus* sp. zh168 | Bacteria | Firmicutes | Bacilli | Bacillales | Bacillaceae | *Bacillus* |
| *Bacillus sphaericus* | Bacteria | Firmicutes | Bacilli | Bacillales | Bacillaceae | *Lysinibacillus* |
| *Bacillus sporothermodurans* | Bacteria | Firmicutes | Bacilli | Bacillales | Bacillaceae | *Bacillus* |
| *Bacillus subtilis* | Bacteria | Firmicutes | Bacilli | Bacillales | Bacillaceae | *Bacillus* |
| *Bacillus thermoamylovorans* | Bacteria | Firmicutes | Bacilli | Bacillales | Bacillaceae | *Bacillus* |
| *Bacillus thuringiensis* | Bacteria | Firmicutes | Bacilli | Bacillales | Bacillaceae | *Bacillus* |
| *Bacillus weihenstephanensis* | Bacteria | Firmicutes | Bacilli | Bacillales | Bacillaceae | *Bacillus* |
| Bacteroidales bacterium ph8 | Bacteria | Bacteroidetes | Bacteroidia | Bacteroidales | unclassified | unclassified |
| Bacteroidales genomosp. P1 | Bacteria | Bacteroidetes | Bacteroidia | Bacteroidales | unclassified | unclassified |
| Bacteroidales genomosp. P2 oral clone MB1_G13 | Bacteria | Bacteroidetes | Bacteroidia | Bacteroidales | unclassified | unclassified |
| Bacteroidales genomosp. P3 oral clone MB1_G34 | Bacteria | Bacteroidetes | Bacteroidia | Bacteroidales | unclassified | unclassified |
| Bacteroidales genomosp. P4 oral clone MB2_G17 | Bacteria | Bacteroidetes | Bacteroidia | Bacteroidales | unclassified | unclassified |
| Bacteroidales genomosp. P5 oral clone MB2_P04 | Bacteria | Bacteroidetes | Bacteroidia | Bacteroidales | unclassified | unclassified |
| Bacteroidales genomosp. P6 oral clone MB3_C19 | Bacteria | Bacteroidetes | Bacteroidia | Bacteroidales | unclassified | unclassified |
| Bacteroidales genomosp. P7 oral clone MB3_P19 | Bacteria | Bacteroidetes | Bacteroidia | Bacteroidales | unclassified | unclassified |
| Bacteroidales genomosp. P8 oral clone MB4_G15 | Bacteria | Bacteroidetes | Bacteroidia | Bacteroidales | unclassified | unclassified |
| *Bacteroides acidifaciens* | Bacteria | Bacteroidetes | Bacteroidia | Bacteroidales | Bacteroidaceae | *Bacteroides* |
| *Bacteroides barnesiae* | Bacteria | Bacteroidetes | Bacteroidia | Bacteroidales | Bacteroidaceae | *Bacteroides* |
| *Bacteroides caccae* | Bacteria | Bacteroidetes | Bacteroidia | Bacteroidales | Bacteroidaceae | *Bacteroides* |
| *Bacteroides cellulosilyticus* | Bacteria | Bacteroidetes | Bacteroidia | Bacteroidales | Bacteroidaceae | *Bacteroides* |
| *Bacteroides clarus* | Bacteria | Bacteroidetes | Bacteroidia | Bacteroidales | Bacteroidaceae | *Bacteroides* |
| *Bacteroides coagulans* | Bacteria | Firmicutes | Clostridia | Clostridiales | Clostridiales Family XI. Incertae Sedis | unclassified |
| *Bacteroides coprocola* | Bacteria | Bacteroidetes | Bacteroidia | Bacteroidales | Bacteroidaceae | *Bacteroides* |
| *Bacteroides coprophilus* | Bacteria | Bacteroidetes | Bacteroidia | Bacteroidales | Bacteroidaceae | *Bacteroides* |
| *Bacteroides dorei* | Bacteria | Bacteroidetes | Bacteroidia | Bacteroidales | Bacteroidaceae | *Bacteroides* |
| *Bacteroides eggerthii* | Bacteria | Bacteroidetes | Bacteroidia | Bacteroidales | Bacteroidaceae | *Bacteroides* |
| *Bacteroides faecis* | Bacteria | Bacteroidetes | Bacteroidia | Bacteroidales | Bacteroidaceae | *Bacteroides* |
| *Bacteroides finegoldii* | Bacteria | Bacteroidetes | Bacteroidia | Bacteroidales | Bacteroidaceae | *Bacteroides* |
| *Bacteroides fluxus* | Bacteria | Bacteroidetes | Bacteroidia | Bacteroidales | Bacteroidaceae | *Bacteroides* |
| *Bacteroides fragilis* | Bacteria | Bacteroidetes | Bacteroidia | Bacteroidales | Bacteroidaceae | *Bacteroides* |
| *Bacteroides galacturonicus* | Bacteria | Bacteroidetes | Bacteroidia | Bacteroidales | Bacteroidaceae | *Bacteroides* |
| *Bacteroides helcogenes* | Bacteria | Bacteroidetes | Bacteroidia | Bacteroidales | Bacteroidaceae | *Bacteroides* |
| *Bacteroides heparinolyticus* | Bacteria | Bacteroidetes | Bacteroidia | Bacteroidales | Bacteroidaceae | *Bacteroides* |
| *Bacteroides intestinalis* | Bacteria | Bacteroidetes | Bacteroidia | Bacteroidales | Bacteroidaceae | *Bacteroides* |
| *Bacteroides massiliensis* | Bacteria | Bacteroidetes | Bacteroidia | Bacteroidales | Bacteroidaceae | *Bacteroides* |
| *Bacteroides nordii* | Bacteria | Bacteroidetes | Bacteroidia | Bacteroidales | Bacteroidaceae | *Bacteroides* |
| *Bacteroides oleiciplenus* | Bacteria | Bacteroidetes | Bacteroidia | Bacteroidales | Bacteroidaceae | *Bacteroides* |
| *Bacteroides ovatus* | Bacteria | Bacteroidetes | Bacteroidia | Bacteroidales | Bacteroidaceae | *Bacteroides* |
| *Bacteroides pectinophilus* | Bacteria | Firmicutes | Clostridia | Clostridiales | unclassified | unclassified |
| *Bacteroides plebeius* | Bacteria | Bacteroidetes | Bacteroidia | Bacteroidales | Bacteroidaceae | *Bacteroides* |
| *Bacteroides pyogenes* | Bacteria | Bacteroidetes | Bacteroidia | Bacteroidales | Bacteroidaceae | *Bacteroides* |
| *Bacteroides salanitronis* | Bacteria | Bacteroidetes | Bacteroidia | Bacteroidales | Bacteroidaceae | *Bacteroides* |
| *Bacteroides salyersiae* | Bacteria | Bacteroidetes | Bacteroidia | Bacteroidales | Bacteroidaceae | *Bacteroides* |
| *Bacteroides* sp. 1_1_14 | Bacteria | Bacteroidetes | Bacteroidia | Bacteroidales | Bacteroidaceae | *Bacteroides* |
| *Bacteroides* sp. 1_1_30 | Bacteria | Bacteroidetes | Bacteroidia | Bacteroidales | Bacteroidaceae | *Bacteroides* |

TABLE 1-continued

| OTU | Domain | Phylum | Class | Order | Family | Genus |
|---|---|---|---|---|---|---|
| *Bacteroides* sp. 1_1_6 | Bacteria | Bacteroidetes | Bacteroidia | Bacteroidales | Bacteroidaceae | *Bacteroides* |
| *Bacteroides* sp. 1_1_6 | Bacteria | Bacteroidetes | Bacteroidia | Bacteroidales | Bacteroidaceae | *Bacteroides* |
| *Bacteroides* sp. 2_1_22 | Bacteria | Bacteroidetes | Bacteroidia | Bacteroidales | Bacteroidaceae | *Bacteroides* |
| *Bacteroides* sp. 2_1_56FAA | Bacteria | Bacteroidetes | Bacteroidia | Bacteroidales | Bacteroidaceae | *Bacteroides* |
| *Bacteroides* sp. 2_2_4 | Bacteria | Bacteroidetes | Bacteroidia | Bacteroidales | Bacteroidaceae | *Bacteroides* |
| *Bacteroides* sp. 20_3 | Bacteria | Bacteroidetes | Bacteroidia | Bacteroidales | Bacteroidaceae | *Bacteroides* |
| *Bacteroides* sp. 3_1_19 | Bacteria | Bacteroidetes | Bacteroidia | Bacteroidales | Bacteroidaceae | *Bacteroides* |
| *Bacteroides* sp. 3_1_23 | Bacteria | Bacteroidetes | Bacteroidia | Bacteroidales | Bacteroidaceae | *Bacteroides* |
| *Bacteroides* sp. 3_1_33FAA | Bacteria | Bacteroidetes | Bacteroidia | Bacteroidales | Bacteroidaceae | *Bacteroides* |
| *Bacteroides* sp. 3_1_40A | Bacteria | Bacteroidetes | Bacteroidia | Bacteroidales | Bacteroidaceae | *Bacteroides* |
| *Bacteroides* sp. 3_2_5 | Bacteria | Bacteroidetes | Bacteroidia | Bacteroidales | Bacteroidaceae | *Bacteroides* |
| *Bacteroides* sp. 315-5 | Bacteria | Bacteroidetes | Bacteroidia | Bacteroidales | Bacteroidaceae | *Bacteroides* |
| *Bacteroides* sp. 31SF15 | Bacteria | Bacteroidetes | Bacteroidia | Bacteroidales | Bacteroidaceae | *Bacteroides* |
| *Bacteroides* sp. 31SF18 | Bacteria | Bacteroidetes | Bacteroidia | Bacteroidales | Bacteroidaceae | *Bacteroides* |
| *Bacteroides* sp. 35AE31 | Bacteria | Bacteroidetes | Bacteroidia | Bacteroidales | Bacteroidaceae | *Bacteroides* |
| *Bacteroides* sp. 35AE37 | Bacteria | Bacteroidetes | Bacteroidia | Bacteroidales | Bacteroidaceae | *Bacteroides* |
| *Bacteroides* sp. 35BE34 | Bacteria | Bacteroidetes | Bacteroidia | Bacteroidales | Bacteroidaceae | *Bacteroides* |
| *Bacteroides* sp. 35BE35 | Bacteria | Bacteroidetes | Bacteroidia | Bacteroidales | Bacteroidaceae | *Bacteroides* |
| *Bacteroides* sp. 4_1_36 | Bacteria | Bacteroidetes | Bacteroidia | Bacteroidales | Bacteroidaceae | *Bacteroides* |
| *Bacteroides* sp. 4_3_47FAA | Bacteria | Bacteroidetes | Bacteroidia | Bacteroidales | Bacteroidaceae | *Bacteroides* |
| *Bacteroides* sp. 9_1_42FAA | Bacteria | Bacteroidetes | Bacteroidia | Bacteroidales | Bacteroidaceae | *Bacteroides* |
| *Bacteroides* sp. AR20 | Bacteria | Bacteroidetes | Bacteroidia | Bacteroidales | Bacteroidaceae | *Bacteroides* |
| *Bacteroides* sp. AR29 | Bacteria | Bacteroidetes | Bacteroidia | Bacteroidales | Bacteroidaceae | *Bacteroides* |
| *Bacteroides* sp. B2 | Bacteria | Bacteroidetes | Bacteroidia | Bacteroidales | Bacteroidaceae | *Bacteroides* |
| *Bacteroides* sp. D1 | Bacteria | Bacteroidetes | Bacteroidia | Bacteroidales | Bacteroidaceae | *Bacteroides* |
| *Bacteroides* sp. D2 | Bacteria | Bacteroidetes | Bacteroidia | Bacteroidales | Bacteroidaceae | *Bacteroides* |
| *Bacteroides* sp. D20 | Bacteria | Bacteroidetes | Bacteroidia | Bacteroidales | Bacteroidaceae | *Bacteroides* |
| *Bacteroides* sp. D22 | Bacteria | Bacteroidetes | Bacteroidia | Bacteroidales | Bacteroidaceae | *Bacteroides* |
| *Bacteroides* sp. F-4 | Bacteria | Bacteroidetes | Bacteroidia | Bacteroidales | Bacteroidaceae | *Bacteroides* |
| *Bacteroides* sp. NB-8 | Bacteria | Bacteroidetes | Bacteroidia | Bacteroidales | Bacteroidaceae | *Bacteroides* |
| *Bacteroides* sp. WH2 | Bacteria | Bacteroidetes | Bacteroidia | Bacteroidales | Bacteroidaceae | *Bacteroides* |
| *Bacteroides* sp. XB12B | Bacteria | Bacteroidetes | Bacteroidia | Bacteroidales | Bacteroidaceae | *Bacteroides* |
| *Bacteroides* sp. XB44A | Bacteria | Bacteroidetes | Bacteroidia | Bacteroidales | Bacteroidaceae | *Bacteroides* |
| *Bacteroides stercoris* | Bacteria | Bacteroidetes | Bacteroidia | Bacteroidales | Bacteroidaceae | *Bacteroides* |
| *Bacteroides thetaiotaomicron* | Bacteria | Bacteroidetes | Bacteroidia | Bacteroidales | Bacteroidaceae | *Bacteroides* |
| *Bacteroides uniformis* | Bacteria | Bacteroidetes | Bacteroidia | Bacteroidales | Bacteroidaceae | *Bacteroides* |
| *Bacteroides ureolyticus* | Bacteria | Proteobacteria | Epsilonproteobacteria | Campylobacterales | Campylobacteraceae | *Campylobacter* |
| *Bacteroides vulgatus* | Bacteria | Bacteroidetes | Bacteroidia | Bacteroidales | Bacteroidaceae | *Bacteroides* |
| *Bacteroides xylanisolvens* | Bacteria | Bacteroidetes | Bacteroidia | Bacteroidales | Bacteroidaceae | *Bacteroides* |
| Bacteroidetes bacterium oral taxon D27 | Bacteria | Bacteroidetes | unclassified | unclassified | unclassified | unclassified |
| Bacteroidetes bacterium oral taxon F31 | Bacteria | Bacteroidetes | unclassified | unclassified | unclassified | unclassified |
| Bacteroidetes bacterium oral taxon F44 | Bacteria | Bacteroidetes | unclassified | unclassified | unclassified | unclassified |
| *Barnesiella intestinihominis* | Bacteria | Bacteroidetes | Bacteroidia | Bacteroidales | Porphyromonadaceae | *Barnesiella* |
| *Barnesiella viscericola* | Bacteria | Bacteroidetes | Bacteroidia | Bacteroidales | Porphyromonadaceae | *Barnesiella* |
| *Bartonella bacilliformis* | Bacteria | Proteobacteria | Alphaproteobacteria | Rhizobiales | Bartonellaceae | *Bartonella* |
| *Bartonella grahamii* | Bacteria | Proteobacteria | Alphaproteobacteria | Rhizobiales | Bartonellaceae | *Bartonella* |
| *Bartonella henselae* | Bacteria | Proteobacteria | Alphaproteobacteria | Rhizobiales | Bartonellaceae | *Bartonella* |
| *Bartonella quintana* | Bacteria | Proteobacteria | Alphaproteobacteria | Rhizobiales | Bartonellaceae | *Bartonella* |
| *Bartonella tamiae* | Bacteria | Proteobacteria | Alphaproteobacteria | Rhizobiales | Bartonellaceae | *Bartonella* |
| *Bartonella washoensis* | Bacteria | Proteobacteria | Alphaproteobacteria | Rhizobiales | Bartonellaceae | *Bartonella* |
| *Bdellovibrio* sp. MPA | Bacteria | Proteobacteria | Deltaproteobacteria | Bdellovibrionales | Bdellovibrionaceae | *Bdellovibrio* |

TABLE 1-continued

| OTU | Domain | Phylum | Class | Order | Family | Genus |
|---|---|---|---|---|---|---|
| Bifidobacteriaceae genomosp. C1 | Bacteria | Actinobacteria | Actinobacteria | Bifidobacteriales | unclassified | unclassified |
| *Bifidobacterium adolescentis* | Bacteria | Actinobacteria | Actinobacteria | Bifidobacteriales | Bifidobacteriaceae | *Bifidobacterium* |
| *Bifidobacterium angulatum* | Bacteria | Actinobacteria | Actinobacteria | Bifidobacteriales | Bifidobacteriaceae | *Bifidobacterium* |
| *Bifidobacterium animalis* | Bacteria | Actinobacteria | Actinobacteria | Bifidobacteriales | Bifidobacteriaceae | *Bifidobacterium* |
| *Bifidobacterium bifidum* | Bacteria | Actinobacteria | Actinobacteria | Bifidobacteriales | Bifidobacteriaceae | *Bifidobacterium* |
| *Bifidobacterium breve* | Bacteria | Actinobacteria | Actinobacteria | Bifidobacteriales | Bifidobacteriaceae | *Bifidobacterium* |
| *Bifidobacterium catenulatum* | Bacteria | Actinobacteria | Actinobacteria | Bifidobacteriales | Bifidobacteriaceae | *Bifidobacterium* |
| *Bifidobacterium gallicum* | Bacteria | Actinobacteria | Actinobacteria | Bifidobacteriales | Bifidobacteriaceae | *Bifidobacterium* |
| *Bifidobacterium infantis* | Bacteria | Actinobacteria | Actinobacteria | Bifidobacteriales | Bifidobacteriaceae | *Bifidobacterium* |
| *Bifidobacterium kashiwanohense* | Bacteria | Actinobacteria | Actinobacteria | Bifidobacteriales | Bifidobacteriaceae | *Bifidobacterium* |
| *Bifidobacterium longum* | Bacteria | Actinobacteria | Actinobacteria | Bifidobacteriales | Bifidobacteriaceae | *Bifidobacterium* |
| *Bifidobacterium pseudocatenulatum* | Bacteria | Actinobacteria | Actinobacteria | Bifidobacteriales | Bifidobacteriaceae | *Bifidobacterium* |
| *Bifidobacterium pseudolongum* | Bacteria | Actinobacteria | Actinobacteria | Bifidobacteriales | Bifidobacteriaceae | *Bifidobacterium* |
| *Bifidobacterium scardovii* | Bacteria | Actinobacteria | Actinobacteria | Bifidobacteriales | Bifidobacteriaceae | *Bifidobacterium* |
| *Bifidobacterium* sp. HM2 | Bacteria | Actinobacteria | Actinobacteria | Bifidobacteriales | Bifidobacteriaceae | *Bifidobacterium* |
| *Bifidobacterium* sp. HMLN12 | Bacteria | Actinobacteria | Actinobacteria | Bifidobacteriales | Bifidobacteriaceae | *Bifidobacterium* |
| *Bifidobacterium* sp. M45 | Bacteria | Actinobacteria | Actinobacteria | Bifidobacteriales | Bifidobacteriaceae | *Bifidobacterium* |
| *Bifidobacterium* sp. MSX5B | Bacteria | Actinobacteria | Actinobacteria | Bifidobacteriales | Bifidobacteriaceae | *Bifidobacterium* |
| *Bifidobacterium* sp. TM-7 | Bacteria | Actinobacteria | Actinobacteria | Bifidobacteriales | Bifidobacteriaceae | *Bifidobacterium* |
| *Bifidobacterium thermophilum* | Bacteria | Actinobacteria | Actinobacteria | Bifidobacteriales | Bifidobacteriaceae | *Bifidobacterium* |
| *Bifidobacterium urinalis* | Bacteria | Actinobacteria | Actinobacteria | Bifidobacteriales | Bifidobacteriaceae | *Alloscardovia* |
| *Bilophila wadsworthia* | Bacteria | Proteobacteria | Deltaproteobacteria | Desulfovibrionales | Desulfovibrionaceae | *Bilophila* |
| Bisgaard Taxon | Bacteria | Proteobacteria | Gammaproteobacteria | Pasteurellales | Pasteurellaceae | *Pasteurella* |
| *Blastomonas natatoria* | Bacteria | Proteobacteria | Alphaproteobacteria | Sphingomonadales | Sphingomonadaceae | *Blastomonas* |
| *Blautia coccoides* | Bacteria | Firmicutes | Clostridia | Clostridiales | Lachnospiraceae | *Blautia* |
| *Blautia glucerasea* | Bacteria | Firmicutes | Clostridia | Clostridiales | Lachnospiraceae | *Blautia* |
| *Blautia glucerasei* | Bacteria | Firmicutes | Clostridia | Clostridiales | Lachnospiraceae | *Blautia* |
| *Blautia hansenii* | Bacteria | Firmicutes | Clostridia | Clostridiales | Lachnospiraceae | *Blautia* |
| *Blautia hydrogenotrophica* | Bacteria | Firmicutes | Clostridia | Clostridiales | Lachnospiraceae | *Blautia* |
| *Blautia luti* | Bacteria | Firmicutes | Clostridia | Clostridiales | Lachnospiraceae | *Blautia* |
| *Blautia producta* | Bacteria | Firmicutes | Clostridia | Clostridiales | Lachnospiraceae | *Blautia* |
| *Blautia schinkii* | Bacteria | Firmicutes | Clostridia | Clostridiales | Lachnospiraceae | *Blautia* |
| *Blautia* sp. M25 | Bacteria | Firmicutes | Clostridia | Clostridiales | Lachnospiraceae | *Blautia* |
| *Blautia stercoris* | Bacteria | Firmicutes | Clostridia | Clostridiales | Lachnospiraceae | *Blautia* |
| *Blautia wexlerae* | Bacteria | Firmicutes | Clostridia | Clostridiales | Lachnospiraceae | *Blautia* |
| *Brachybacterium alimentarium* | Bacteria | Actinobacteria | Actinobacteria | Actinomycetales | Dermabacteraceae | *Brachybacterium* |
| *Brachybacterium conglomeratum* | Bacteria | Actinobacteria | Actinobacteria | Actinomycetales | Dermabacteraceae | *Brachybacterium* |
| *Brachybacterium tyrofermentans* | Bacteria | Actinobacteria | Actinobacteria | Actinomycetales | Dermabacteraceae | *Brachybacterium* |
| *Brachyspira aalborgi* | Bacteria | Spirochaetes | Spirochaetia | Spirochaetales | Brachyspiraceae | *Brachyspira* |
| *Brachyspira pilosicoli* | Bacteria | Spirochaetes | Spirochaetia | Spirochaetales | Brachyspiraceae | *Brachyspira* |
| *Brachyspira* sp. HIS3 | Bacteria | Spirochaetes | Spirochaetia | Spirochaetales | Brachyspiraceae | *Brachyspira* |
| *Brachyspira* sp. HIS4 | Bacteria | Spirochaetes | Spirochaetia | Spirochaetales | Brachyspiraceae | *Brachyspira* |
| *Brachyspira* sp. HIS5 | Bacteria | Spirochaetes | Spirochaetia | Spirochaetales | Brachyspiraceae | *Brachyspira* |
| *Brevibacillus agri* | Bacteria | Firmicutes | Bacilli | Bacillales | Paenibacillaceae | *Brevibacillus* |
| *Brevibacillus brevis* | Bacteria | Firmicutes | Bacilli | Bacillales | Paenibacillaceae | *Brevibacillus* |
| *Brevibacillus centrosporus* | Bacteria | Firmicutes | Bacilli | Bacillales | Paenibacillaceae | *Brevibacillus* |
| *Brevibacillus choshinensis* | Bacteria | Firmicutes | Bacilli | Bacillales | Paenibacillaceae | *Brevibacillus* |
| *Brevibacillus invocatus* | Bacteria | Firmicutes | Bacilli | Bacillales | Paenibacillaceae | *Brevibacillus* |
| *Brevibacillus laterosporus* | Bacteria | Firmicutes | Bacilli | Bacillales | Paenibacillaceae | *Brevibacillus* |
| *Brevibacillus parabrevis* | Bacteria | Firmicutes | Bacilli | Bacillales | Paenibacillaceae | *Brevibacillus* |
| *Brevibacillus reuszeri* | Bacteria | Firmicutes | Bacilli | Bacillales | Paenibacillaceae | *Brevibacillus* |

TABLE 1-continued

| OTU | Domain | Phylum | Class | Order | Family | Genus |
|---|---|---|---|---|---|---|
| *Brevibacillus* sp. phR | Bacteria | Firmicutes | Bacilli | Bacillales | Paenibacillaceae | *Brevibacillus* |
| *Brevibacillus thermoruber* | Bacteria | Firmicutes | Bacilli | Bacillales | Paenibacillaceae | *Brevibacillus* |
| *Brevibacterium aurantiacum* | Bacteria | Actinobacteria | Actinobacteria | Actinomycetales | Brevibacteriaceae | *Brevibacterium* |
| *Brevibacterium casei* | Bacteria | Actinobacteria | Actinobacteria | Actinomycetales | Brevibacteriaceae | *Brevibacterium* |
| *Brevibacterium epidermidis* | Bacteria | Actinobacteria | Actinobacteria | Actinomycetales | Brevibacteriaceae | *Brevibacterium* |
| *Brevibacterium frigoritolerans* | Bacteria | Firmicutes | Bacilli | Bacillales | Bacillaceae | *Bacillus* |
| *Brevibacterium linens* | Bacteria | Actinobacteria | Actinobacteria | Actinomycetales | Brevibacteriaceae | *Brevibacterium* |
| *Brevibacterium mcbrellneri* | Bacteria | Actinobacteria | Actinobacteria | Actinomycetales | Brevibacteriaceae | *Brevibacterium* |
| *Brevibacterium paucivorans* | Bacteria | Actinobacteria | Actinobacteria | Actinomycetales | Brevibacteriaceae | *Brevibacterium* |
| *Brevibacterium sanguinis* | Bacteria | Actinobacteria | Actinobacteria | Actinomycetales | Brevibacteriaceae | *Brevibacterium* |
| *Brevibacterium* sp. H15 | Bacteria | Actinobacteria | Actinobacteria | Actinomycetales | Brevibacteriaceae | *Brevibacterium* |
| *Brevibacterium* sp. JC43 | Bacteria | Actinobacteria | Actinobacteria | Actinomycetales | Brevibacteriaceae | *Brevibacterium* |
| *Brevundimonas subvibrioides* | Bacteria | Proteobacteria | Alphaproteobacteria | Caulobacterales | Caulobacteraceae | *Brevundimonas* |
| *Bryantella formatexigens* | Bacteria | Firmicutes | Clostridia | Clostridiales | Lachnospiraceae | *Bryantella* |
| *Buchnera aphidicola* | Bacteria | Proteobacteria | Gammaproteobacteria | Enterobacteriales | Enterobacteriaceae | *Buchnera* |
| *Bulleidia extructa* | Bacteria | Firmicutes | Erysipelotrichi | Erysipelotrichales | Erysipelotrichaceae | *Bulleidia* |
| *Butyricicoccus pullicaecorum* | Bacteria | Firmicutes | Clostridia | Clostridiales | Clostridiaceae | *Butyricicoccus* |
| *Butyricimonas virosa* | Bacteria | Bacteroidetes | Bacteroidia | Bacteroidales | Porphyromonadaceae | *Butyricimonas* |
| *Butyrivibrio crossotus* | Bacteria | Firmicutes | Clostridia | Clostridiales | Lachnospiraceae | *Butyrivibrio* |
| *Butyrivibrio fibrisolvens* | Bacteria | Firmicutes | Clostridia | Clostridiales | Lachnospiraceae | *Butyrivibrio* |
| *Caldimonas manganoxidans* | Bacteria | Proteobacteria | Betaproteobacteria | Burkholderiales | Comamonadaceae | *Caldimonas* |
| *Caminicella sporogenes* | Bacteria | Firmicutes | Clostridia | Clostridiales | Clostridiaceae | *Caminicella* |
| *Candidatus Arthromitus* sp. SFB-mouse-Yit | Bacteria | Firmicutes | Clostridia | Clostridiales | Clostridiaceae | *Candidatus Arthromitus* |
| *Candidatus Sulcia muelleri* | Bacteria | Bacteroidetes | Flavobacteriia | Flavobacteriales | Flavobacteriaceae | *Candidatus Sulcia* |
| *Capnocytophaga canimorsus* | Bacteria | Bacteroidetes | Flavobacteriia | Flavobacteriales | Flavobacteriaceae | *Capnocytophaga* |
| *Capnocytophaga* genomosp. C1 | Bacteria | Bacteroidetes | Flavobacteriia | Flavobacteriales | Flavobacteriaceae | *Capnocytophaga* |
| *Capnocytophaga gingivalis* | Bacteria | Bacteroidetes | Flavobacteriia | Flavobacteriales | Flavobacteriaceae | *Capnocytophaga* |
| *Capnocytophaga granulosa* | Bacteria | Bacteroidetes | Flavobacteriia | Flavobacteriales | Flavobacteriaceae | *Capnocytophaga* |
| *Capnocytophaga ochracea* | Bacteria | Bacteroidetes | Flavobacteriia | Flavobacteriales | Flavobacteriaceae | *Capnocytophaga* |
| *Capnocytophaga* sp. GEJ8 | Bacteria | Bacteroidetes | Flavobacteriia | Flavobacteriales | Flavobacteriaceae | *Capnocytophaga* |
| *Capnocytophaga* sp. oral clone AH015 | Bacteria | Bacteroidetes | Flavobacteriia | Flavobacteriales | Flavobacteriaceae | *Capnocytophaga* |
| *Capnocytophaga* sp. oral clone ASCH05 | Bacteria | Bacteroidetes | Flavobacteriia | Flavobacteriales | Flavobacteriaceae | *Capnocytophaga* |
| *Capnocytophaga* sp. oral clone ID062 | Bacteria | Bacteroidetes | Flavobacteriia | Flavobacteriales | Flavobacteriaceae | *Capnocytophaga* |
| *Capnocytophaga* sp. oral strain A47ROY | Bacteria | Bacteroidetes | Flavobacteriia | Flavobacteriales | Flavobacteriaceae | *Capnocytophaga* |
| *Capnocytophaga* sp. oral strain S3 | Bacteria | Bacteroidetes | Flavobacteriia | Flavobacteriales | Flavobacteriaceae | *Capnocytophaga* |
| *Capnocytophaga* sp. oral taxon 338 | Bacteria | Bacteroidetes | Flavobacteriia | Flavobacteriales | Flavobacteriaceae | *Capnocytophaga* |
| *Capnocytophaga* sp. S1b | Bacteria | Bacteroidetes | Flavobacteria | Flavobacteriales | Flavobacteriaceae | *Capnocytophaga* |
| *Capnocytophaga sputigena* | Bacteria | Bacteroidetes | Flavobacteriia | Flavobacteriales | Flavobacteriaceae | *Capnocytophaga* |
| *Cardiobacterium hominis* | Bacteria | Proteobacteria | Gammaproteobacteria | Cardiobacteriales | Cardiobacteriaceae | *Cardiobacterium* |
| *Cardiobacterium valvarum* | Bacteria | Proteobacteria | Gammaproteobacteria | Cardiobacteriales | Cardiobacteriaceae | *Cardiobacterium* |
| *Carnobacterium divergens* | Bacteria | Firmicutes | Bacilli | Lactobacillales | Carnobacteriaceae | *Carnobacterium* |
| *Carnobacterium maltaromaticum* | Bacteria | Firmicutes | Bacilli | Lactobacillales | Carnobacteriaceae | *Carnobacterium* |
| *Catabacter hongkongensis* | Bacteria | Firmicutes | Clostridia | Clostridiales | Catabacteriaceae | *Catabacter* |
| *Catenibacterium mitsuokai* | Bacteria | Firmicutes | Erysipelotrichi | Erysipelotrichales | Erysipelotrichaceae | *Catenibacterium* |
| *Catonella* genomosp. P1 oral clone MB5__P12 | Bacteria | Firmicutes | Clostridia | Clostridiales | Lachnospiraceae | *Catonella* |
| *Catonella morbi* | Bacteria | Firmicutes | Clostridia | Clostridiales | Lachnospiraceae | *Catonella* |
| *Catonella* sp. oral clone FL037 | Bacteria | Firmicutes | Clostridia | Clostridiales | Lachnospiraceae | *Catonella* |
| *Cedecea davisae* | Bacteria | Proteobacteria | Gammaproteobacteria | Enterobacteriales | Enterobacteriaceae | *Cedecea* |
| *Cellulosimicrobium funkei* | Bacteria | Actinobacteria | Actinobacteria | Actinomycetales | Promicromonosporaceae | *Cellulosimicrobium* |
| *Cetobacterium somerae* | Bacteria | Fusobacteria | Fusobacteriia | Fusobacteriales | Fusobacteriaceae | *Cetobacterium* |
| Chlamydiales bacterium NS11 | Bacteria | Chlamydiae | Chlamydiia | Chlamydiales | unclassified | unclassified |

TABLE 1-continued

| OTU | Domain | Phylum | Class | Order | Family | Genus |
|---|---|---|---|---|---|---|
| Chlamydiales bacterium NS13 | Bacteria | Chlamydiae | Chlamydiia | Chlamydiales | unclassified | unclassified |
| Chlamydiales bacterium NS16 | Bacteria | Chlamydiae | Chlamydiia | Chlamydiales | unclassified | unclassified |
| Chloroflexi genomosp. P1 | Bacteria | Chloroflexi | unclassified | unclassified | unclassified | unclassified |
| *Christensenella minuta* | Bacteria | Firmicutes | Clostridia | Clostridiales | Christensenellaceae | *Christensenella* |
| *Chromobacterium violaceum* | Bacteria | Proteobacteria | Betaproteobacteria | Neisseriales | Neisseriaceae | *Chromobacterium* |
| *Chryseobacterium anthropi* | Bacteria | Bacteroidetes | Flavobacteriia | Flavobacteriales | Flavobacteriaceae | *Chryseobacterium* |
| *Chryseobacterium gleum* | Bacteria | Bacteroidetes | Flavobacteriia | Flavobacteriales | Flavobacteriaceae | *Chryseobacterium* |
| *Chryseobacterium hominis* | Bacteria | Bacteroidetes | Flavobacteriia | Flavobacteriales | Flavobacteriaceae | *Chryseobacterium* |
| *Citrobacter amalonaticus* | Bacteria | Proteobacteria | Gammaproteobacteria | Enterobacteriales | Enterobacteriaceae | *Citrobacter* |
| *Citrobacter braakii* | Bacteria | Proteobacteria | Gammaproteobacteria | Enterobacteriales | Enterobacteriaceae | *Citrobacter* |
| *Citrobacter farmeri* | Bacteria | Proteobacteria | Gammaproteobacteria | Enterobacteriales | Enterobacteriaceae | *Citrobacter* |
| *Citrobacter freundii* | Bacteria | Proteobacteria | Gammaproteobacteria | Enterobacteriales | Enterobacteriaceae | *Citrobacter* |
| *Citrobacter gillenii* | Bacteria | Proteobacteria | Gammaproteobacteria | Enterobacteriales | Enterobacteriaceae | *Citrobacter* |
| *Citrobacter koseri* | Bacteria | Proteobacteria | Gammaproteobacteria | Enterobacteriales | Enterobacteriaceae | *Citrobacter* |
| *Citrobacter murliniae* | Bacteria | Proteobacteria | Gammaproteobacteria | Enterobacteriales | Enterobacteriaceae | *Citrobacter* |
| *Citrobacter rodentium* | Bacteria | Proteobacteria | Gammaproteobacteria | Enterobacteriales | Enterobacteriaceae | *Citrobacter* |
| *Citrobacter sedlakii* | Bacteria | Proteobacteria | Gammaproteobacteria | Enterobacteriales | Enterobacteriaceae | *Citrobacter* |
| *Citrobacter* sp. 30_2 | Bacteria | Proteobacteria | Gammaproteobacteria | Enterobacteriales | Enterobacteriaceae | *Citrobacter* |
| *Citrobacter* sp. KMSI-3 | Bacteria | Proteobacteria | Gammaproteobacteria | Enterobacteriales | Enterobacteriaceae | *Citrobacter* |
| *Citrobacter werkmanii* | Bacteria | Proteobacteria | Gammaproteobacteria | Enterobacteriales | Enterobacteriaceae | *Citrobacter* |
| *Citrobacter youngae* | Bacteria | Proteobacteria | Gammaproteobacteria | Enterobacteriales | Enterobacteriaceae | *Citrobacter* |
| *Cloacibacillus evryensis* | Bacteria | Synergistetes | Synergistia | Synergistales | Synergistaceae | *Cloacibacillus* |
| Clostridiaceae bacterium END-2 | Bacteria | Firmicutes | Clostridia | Clostridiales | Clostridiaceae | unclassified |
| Clostridiaceae bacterium JC13 | Bacteria | Firmicutes | Clostridia | Clostridiales | Clostridiaceae | unclassified |
| Clostridiales bacterium 1_7_47FAA | Bacteria | Firmicutes | Clostridia | Clostridiales | unclassified | unclassified |
| Clostridiales bacterium 9400853 | Bacteria | Firmicutes | Clostridia | Clostridiales | unclassified | unclassified |
| Clostridiales bacterium 9403326 | Bacteria | Firmicutes | Clostridia | Clostridiales | unclassified | unclassified |
| Clostridiales bacterium oral clone P4PA_66 P1 | Bacteria | Firmicutes | Clostridia | Clostridiales | unclassified | unclassified |
| Clostridiales bacterium oral taxon 093 | Bacteria | Firmicutes | Clostridia | Clostridiales | unclassified | unclassified |
| Clostridiales bacterium oral taxon F32 | Bacteria | Firmicutes | Clostridia | Clostridiales | unclassified | unclassified |
| Clostridiales bacterium ph2 | Bacteria | Firmicutes | Clostridia | Clostridiales | unclassified | unclassified |
| Clostridiales bacterium SY8519 | Bacteria | Firmicutes | Clostridia | Clostridiales | unclassified | unclassified |
| Clostridiales genomosp. BVAB3 | Bacteria | Firmicutes | Clostridia | Clostridiales | unclassified | unclassified |
| Clostridiales sp. SM4/1 | Bacteria | Firmicutes | Clostridia | Clostridiales | unclassified | unclassified |
| Clostridiales sp. SS3/4 | Bacteria | Firmicutes | Clostridia | Clostridiales | unclassified | *Clostridiales* |
| Clostridiales sp. SSC/2 | Bacteria | Firmicutes | Clostridia | Clostridiales | unclassified | unclassified |
| *Clostridium acetobutylicum* | Bacteria | Firmicutes | Clostridia | Clostridiales | Clostridiaceae | *Clostridium* |
| *Clostridium aerotolerans* | Bacteria | Firmicutes | Clostridia | Clostridiales | Clostridiaceae | *Clostridium* |
| *Clostridium aldenense* | Bacteria | Firmicutes | Clostridia | Clostridiales | Clostridiaceae | *Clostridium* |
| *Clostridium aldrichii* | Bacteria | Firmicutes | Clostridia | Clostridiales | Clostridiaceae | *Clostridium* |
| *Clostridium algidicarnis* | Bacteria | Firmicutes | Clostridia | Clostridiales | Clostridiaceae | *Clostridium* |
| *Clostridium algidixylanolyticum* | Bacteria | Firmicutes | Clostridia | Clostridiales | Clostridiaceae | *Clostridium* |
| *Clostridium aminovalericum* | Bacteria | Firmicutes | Clostridia | Clostridiales | Clostridiaceae | *Clostridium* |
| *Clostridium amygdalinum* | Bacteria | Firmicutes | Clostridia | Clostridiales | Clostridiaceae | *Clostridium* |
| *Clostridium argentinense* | Bacteria | Firmicutes | Clostridia | Clostridiales | Clostridiaceae | *Clostridium* |
| *Clostridium asparagiforme* | Bacteria | Firmicutes | Clostridia | Clostridiales | Clostridiaceae | *Clostridium* |
| *Clostridium baratii* | Bacteria | Firmicutes | Clostridia | Clostridiales | Clostridiaceae | *Clostridium* |
| *Clostridium bartlettii* | Bacteria | Firmicutes | Clostridia | Clostridiales | Peptostreptococcaceae | unclassified |
| *Clostridium beijerinckii* | Bacteria | Firmicutes | Clostridia | Clostridiales | Clostridiaceae | *Clostridium* |
| *Clostridium bifermentans* | Bacteria | Firmicutes | Clostridia | Clostridiales | Peptostreptococcaceae | unclassified |
| *Clostridium bolteae* | Bacteria | Firmicutes | Clostridia | Clostridiales | Clostridiaceae | *Clostridium* |

TABLE 1-continued

| OTU | Domain | Phylum | Class | Order | Family | Genus |
|---|---|---|---|---|---|---|
| *Clostridium butyricum* | Bacteria | Firmicutes | Clostridia | Clostridiales | Clostridiaceae | *Clostridium* |
| *Clostridium cadaveris* | Bacteria | Firmicutes | Clostridia | Clostridiales | Clostridiaceae | *Clostridium* |
| *Clostridium carboxidivorans* | Bacteria | Firmicutes | Clostridia | Clostridiales | Clostridiaceae | *Clostridium* |
| *Clostridium carnis* | Bacteria | Firmicutes | Clostridia | Clostridiales | Clostridiaceae | *Clostridium* |
| *Clostridium celatum* | Bacteria | Firmicutes | Clostridia | Clostridiales | Clostridiaceae | *Clostridium* |
| *Clostridium celerecrescens* | Bacteria | Firmicutes | Clostridia | Clostridiales | Clostridiaceae | *Clostridium* |
| *Clostridium cellulosi* | Bacteria | Firmicutes | Clostridia | Clostridiales | Clostridiaceae | *Clostridium* |
| *Clostridium chauvoei* | Bacteria | Firmicutes | Clostridia | Clostridiales | Clostridiaceae | *Clostridium* |
| *Clostridium citroniae* | Bacteria | Firmicutes | Clostridia | Clostridiales | Clostridiaceae | *Clostridium* |
| *Clostridium clariflavum* | Bacteria | Firmicutes | Clostridia | Clostridiales | Clostridiaceae | *Clostridium* |
| *Clostridium clostridioforme* | Bacteria | Firmicutes | Clostridia | Clostridiales | Clostridiaceae | *Clostridium* |
| *Clostridium coccoides* | Bacteria | Firmicutes | Clostridia | Clostridiales | Lachnospiraceae | *Blautia* |
| *Clostridium cochlearium* | Bacteria | Firmicutes | Clostridia | Clostridiales | Clostridiaceae | *Clostridium* |
| *Clostridium cocleatum* | Bacteria | Firmicutes | Erysipelotrichi | Erysipelotrichales | Erysipelotrichaceae | unclassified |
| *Clostridium colicanis* | Bacteria | Firmicutes | Clostridia | Clostridiales | Clostridiaceae | *Clostridium* |
| *Clostridium colinum* | Bacteria | Firmicutes | Clostridia | Clostridiales | Clostridiaceae | *Clostridium* |
| *Clostridium disporicum* | Bacteria | Firmicutes | Clostridia | Clostridiales | Clostridiaceae | *Clostridium* |
| *Clostridium estertheticum* | Bacteria | Firmicutes | Clostridia | Clostridiales | Clostridiaceae | *Clostridium* |
| *Clostridium fallax* | Bacteria | Firmicutes | Clostridia | Clostridiales | Clostridiaceae | *Clostridium* |
| *Clostridium favososporum* | Bacteria | Firmicutes | Clostridia | Clostridiales | Clostridiaceae | *Clostridium* |
| *Clostridium felsineum* | Bacteria | Firmicutes | Clostridia | Clostridiales | Clostridiaceae | *Clostridium* |
| *Clostridium frigidicarnis* | Bacteria | Firmicutes | Clostridia | Clostridiales | Clostridiaceae | *Clostridium* |
| *Clostridium gasigenes* | Bacteria | Firmicutes | Clostridia | Clostridiales | Clostridiaceae | *Clostridium* |
| *Clostridium ghonii* | Bacteria | Firmicutes | Clostridia | Clostridiales | Peptostreptococcaceae | unclassified |
| *Clostridium glycolicum* | Bacteria | Firmicutes | Clostridia | Clostridiales | Peptostreptococcaceae | unclassified |
| *Clostridium glycyrrhizinilyticum* | Bacteria | Firmicutes | Clostridia | Clostridiales | Clostridiaceae | *Clostridium* |
| *Clostridium haemolyticum* | Bacteria | Firmicutes | Clostridia | Clostridiales | Clostridiaceae | *Clostridium* |
| *Clostridium hathewayi* | Bacteria | Firmicutes | Clostridia | Clostridiales | Clostridiaceae | *Clostridium* |
| *Clostridium hiranonis* | Bacteria | Firmicutes | Clostridia | Clostridiales | Peptostreptococcaceae | unclassified |
| *Clostridium histolyticum* | Bacteria | Firmicutes | Clostridia | Clostridiales | Clostridiaceae | *Clostridium* |
| *Clostridium hylemonae* | Bacteria | Firmicutes | Clostridia | Clostridiales | Clostridiaceae | *Clostridium* |
| *Clostridium indolis* | Bacteria | Firmicutes | Clostridia | Clostridiales | Clostridiaceae | *Clostridium* |
| *Clostridium innocuum* | Bacteria | Firmicutes | Erysipelotrichi | Erysipelotrichales | Erysipelotrichaceae | unclassified |
| *Clostridium irregulare* | Bacteria | Firmicutes | Clostridia | Clostridiales | Peptostreptococcaceae | unclassified |
| *Clostridium isatidis* | Bacteria | Firmicutes | Clostridia | Clostridiales | Clostridiaceae | *Clostridium* |
| *Clostridium kluyveri* | Bacteria | Firmicutes | Clostridia | Clostridiales | Clostridiaceae | *Clostridium* |
| *Clostridium lactatifermentans* | Bacteria | Firmicutes | Clostridia | Clostridiales | Clostridiaceae | *Clostridium* |
| *Clostridium lavalense* | Bacteria | Firmicutes | Clostridia | Clostridiales | Clostridiaceae | *Clostridium* |
| *Clostridium leptum* | Bacteria | Firmicutes | Clostridia | Clostridiales | Clostridiaceae | *Clostridium* |
| *Clostridium limosum* | Bacteria | Firmicutes | Clostridia | Clostridiales | Clostridiaceae | *Clostridium* |
| *Clostridium magnum* | Bacteria | Firmicutes | Clostridia | Clostridiales | Clostridiaceae | *Clostridium* |
| *Clostridium malenominatum* | Bacteria | Firmicutes | Clostridia | Clostridiales | Clostridiaceae | *Clostridium* |
| *Clostridium mayombei* | Bacteria | Firmicutes | Clostridia | Clostridiales | Clostridiaceae | *Clostridium* |
| *Clostridium methylpentosum* | Bacteria | Firmicutes | Clostridia | Clostridiales | Clostridiaceae | *Clostridium* |
| *Clostridium nexile* | Bacteria | Firmicutes | Clostridia | Clostridiales | Clostridiaceae | *Clostridium* |
| *Clostridium novyi* | Bacteria | Firmicutes | Clostridia | Clostridiales | Clostridiaceae | *Clostridium* |
| *Clostridium orbiscindens* | Bacteria | Firmicutes | Clostridia | Clostridiales | unclassified | *Flavonifractor* |
| *Clostridium oroticum* | Bacteria | Firmicutes | Clostridia | Clostridiales | Clostridiaceae | *Clostridium* |
| *Clostridium paraputrificum* | Bacteria | Firmicutes | Clostridia | Clostridiales | Clostridiaceae | *Clostridium* |
| *Clostridium phytofermentans* | Bacteria | Firmicutes | Clostridia | Clostridiales | Clostridiaceae | *Clostridium* |
| *Clostridium piliforme* | Bacteria | Firmicutes | Clostridia | Clostridiales | Clostridiaceae | *Clostridium* |

TABLE 1-continued

| OTU | Domain | Phylum | Class | Order | Family | Genus |
|---|---|---|---|---|---|---|
| *Clostridium putrefaciens* | Bacteria | Firmicutes | Clostridia | Clostridiales | Clostridiaceae | *Clostridium* |
| *Clostridium quinii* | Bacteria | Firmicutes | Clostridia | Clostridiales | Clostridiaceae | *Clostridium* |
| *Clostridium ramosum* | Bacteria | Firmicutes | Erysipelotrichi | Erysipelotrichales | Erysipelotrichaceae | unclassified |
| *Clostridium rectum* | Bacteria | Fusobacteria | unclassified | unclassified | unclassified | unclassified |
| *Clostridium saccharogumia* | Bacteria | Firmicutes | Clostridia | Clostridiales | Clostridiaceae | *Clostridium* |
| *Clostridium saccharolyticum* | Bacteria | Firmicutes | Clostridia | Clostridiales | Clostridiaceae | *Clostridium* |
| *Clostridium saccharolyticum* | Bacteria | Firmicutes | Clostridia | Clostridiales | Clostridiaceae | *Clostridium* |
| *Clostridium sardiniense* | Bacteria | Firmicutes | Clostridia | Clostridiales | Clostridiaceae | *Clostridium* |
| *Clostridium sartagoforme* | Bacteria | Firmicutes | Clostridia | Clostridiales | Clostridiaceae | *Clostridium* |
| *Clostridium scindens* | Bacteria | Firmicutes | Clostridia | Clostridiales | Clostridiaceae | *Clostridium* |
| *Clostridium septicum* | Bacteria | Firmicutes | Clostridia | Clostridiales | Clostridiaceae | *Clostridium* |
| *Clostridium sordellii* | Bacteria | Firmicutes | Clostridia | Clostridiales | Peptostreptococcaceae | unclassified |
| *Clostridium* sp. 7_2_43FAA | Bacteria | Firmicutes | Clostridia | Clostridiales | Clostridiaceae | *Clostridium* |
| *Clostridium* sp. D5 | Bacteria | Firmicutes | Clostridia | Clostridiales | Clostridiaceae | *Clostridium* |
| *Clostridium* sp. HGF2 | Bacteria | Firmicutes | Clostridia | Clostridiales | Clostridiaceae | *Clostridium* |
| *Clostridium* sp. HPB-46 | Bacteria | Firmicutes | Clostridia | Clostridiales | Clostridiaceae | *Clostridium* |
| *Clostridium* sp. JC122 | Bacteria | Firmicutes | Clostridia | Clostridiales | Clostridiaceae | *Clostridium* |
| *Clostridium* sp. L2-50 | Bacteria | Firmicutes | Clostridia | Clostridiales | Clostridiaceae | *Clostridium* |
| *Clostridium* sp. LMG 16094 | Bacteria | Firmicutes | Clostridia | Clostridiales | Clostridiaceae | *Clostridium* |
| *Clostridium* sp. M62/1 | Bacteria | Firmicutes | Clostridia | Clostridiales | Clostridiaceae | *Clostridium* |
| *Clostridium* sp. MLG055 | Bacteria | Firmicutes | Clostridia | Clostridiales | Clostridiaceae | *Clostridium* |
| *Clostridium* sp. MT4 E | Bacteria | Firmicutes | Clostridia | Clostridiales | Clostridiaceae | *Clostridium* |
| *Clostridium* sp. NMBHI-1 | Bacteria | Firmicutes | Clostridia | Clostridiales | Clostridiaceae | *Clostridium* |
| *Clostridium* sp. NML 04A032 | Bacteria | Firmicutes | Clostridia | Clostridiales | Clostridiaceae | *Clostridium* |
| *Clostridium* sp. SS2/1 | Bacteria | Firmicutes | Clostridia | Clostridiales | Clostridiaceae | *Clostridium* |
| *Clostridium* sp. SY8519 | Bacteria | Firmicutes | Clostridia | Clostridiales | Clostridiaceae | *Clostridium* |
| *Clostridium* sp. TM-40 | Bacteria | Firmicutes | Clostridia | Clostridiales | Clostridiaceae | *Clostridium* |
| *Clostridium* sp. YIT 12069 | Bacteria | Firmicutes | Clostridia | Clostridiales | Clostridiaceae | *Clostridium* |
| *Clostridium* sp. YIT 12070 | Bacteria | Firmicutes | Clostridia | Clostridiales | Clostridiaceae | *Clostridium* |
| *Clostridium sphenoides* | Bacteria | Firmicutes | Clostridia | Clostridiales | Clostridiaceae | *Clostridium* |
| *Clostridium spiroforme* | Bacteria | Firmicutes | Erysipelotrichi | Erysipelotrichales | Erysipelotrichaceae | unclassified |
| *Clostridium sporogenes* | Bacteria | Firmicutes | Clostridia | Clostridiales | Clostridiaceae | *Clostridium* |
| *Clostridium sporosphaeroides* | Bacteria | Firmicutes | Clostridia | Clostridiales | Clostridiaceae | *Clostridium* |
| *Clostridium stercorarium* | Bacteria | Firmicutes | Clostridia | Clostridiales | Clostridiaceae | *Clostridium* |
| *Clostridium sticklandii* | Bacteria | Firmicutes | Clostridia | Clostridiales | Peptostreptococcaceae | unclassified |
| *Clostridium straminisolvens* | Bacteria | Firmicutes | Clostridia | Clostridiales | Clostridiaceae | *Clostridium* |
| *Clostridium subterminale* | Bacteria | Firmicutes | Clostridia | Clostridiales | Clostridiaceae | *Clostridium* |
| *Clostridium sulfidigenes* | Bacteria | Firmicutes | Clostridia | Clostridiales | Clostridiaceae | *Clostridium* |
| *Clostridium symbiosum* | Bacteria | Firmicutes | Clostridia | Clostridiales | Clostridiaceae | *Clostridium* |
| *Clostridium tertium* | Bacteria | Firmicutes | Clostridia | Clostridiales | Clostridiaceae | *Clostridium* |
| *Clostridium tetani* | Bacteria | Firmicutes | Clostridia | Clostridiales | Clostridiaceae | *Clostridium* |
| *Clostridium thermocellum* | Bacteria | Firmicutes | Clostridia | Clostridiales | Clostridiaceae | *Clostridium* |
| *Clostridium tyrobutyricum* | Bacteria | Firmicutes | Clostridia | Clostridiales | Clostridiaceae | *Clostridium* |
| *Clostridium viride* | Bacteria | Firmicutes | Clostridia | Clostridiales | Clostridiaceae | *Clostridium* |
| *Clostridium xylanolyticum* | Bacteria | Firmicutes | Clostridia | Clostridiales | Clostridiaceae | *Clostridium* |
| *Collinsella aerofaciens* | Bacteria | Actinobacteria | Actinobacteria | Coriobacteriales | Coriobacteriaceae | *Collinsella* |
| *Collinsella intestinalis* | Bacteria | Actinobacteria | Actinobacteria | Coriobacteriales | Coriobacteriaceae | *Collinsella* |
| *Collinsella stercoris* | Bacteria | Actinobacteria | Actinobacteria | Coriobacteriales | Coriobacteriaceae | *Collinsella* |
| *Collinsella tanakaei* | Bacteria | Actinobacteria | Actinobacteria | Coriobacteriales | Coriobacteriaceae | *Collinsella* |
| Comamonadaceae bacterium NML000135 | Bacteria | Proteobacteria | Betaproteobacteria | Burkholderiales | Comamonadaceae | unclassified |
| Comamonadaceae bacterium NML790751 | Bacteria | Proteobacteria | Betaproteobacteria | Burkholderiales | Comamonadaceae | unclassified |

TABLE 1-continued

| OTU | Domain | Phylum | Class | Order | Family | Genus |
|---|---|---|---|---|---|---|
| Comamonadaceae bacterium NML910035 | Bacteria | Proteobacteria | Betaproteobacteria | Burkholderiales | Comamonadaceae | unclassified |
| Comamonadaceae bacterium NML910036 | Bacteria | Proteobacteria | Betaproteobacteria | Burkholderiales | Comamonadaceae | unclassified |
| Comamonadaceae bacterium oral taxon F47 | Bacteria | Proteobacteria | Betaproteobacteria | Burkholderiales | Comamonadaceae | unclassified |
| *Comamonas* sp. NSP5 | Bacteria | Proteobacteria | Betaproteobacteria | Burkholderiales | Comamonadaceae | *Comamonas* |
| *Conchiformibius kuhniae* | Bacteria | Proteobacteria | Betaproteobacteria | Neisseriales | Neisseriaceae | *Conchiformibius* |
| *Coprobacillus cateniformis* | Bacteria | Firmicutes | Erysipelotrichi | Erysipelotrichales | Erysipelotrichaceae | *Coprobacillus* |
| *Coprobacillus* sp. 29_1 | Bacteria | Firmicutes | Erysipelotrichi | Erysipelotrichales | Erysipelotrichaceae | *Coprobacillus* |
| *Coprobacillus* sp. D7 | Bacteria | Firmicutes | Erysipelotrichi | Erysipelotrichales | Erysipelotrichaceae | *Coprobacillus* |
| *Coprococcus catus* | Bacteria | Firmicutes | Clostridia | Clostridiales | Lachnospiraceae | *Coprococcus* |
| *Coprococcus comes* | Bacteria | Firmicutes | Clostridia | Clostridiales | Lachnospiraceae | *Coprococcus* |
| *Coprococcus eutactus* | Bacteria | Firmicutes | Clostridia | Clostridiales | Lachnospiraceae | *Coprococcus* |
| *Coprococcus* sp. ART55/1 | Bacteria | Firmicutes | Clostridia | Clostridiales | Lachnospiraceae | *Coprococcus* |
| Coriobacteriaceae bacterium BV3Ac1 | Bacteria | Actinobacteria | Actinobacteria | Coriobacteriales | Coriobacteriaceae | unclassified |
| Coriobacteriaceae bacterium JC110 | Bacteria | Actinobacteria | Actinobacteria | Coriobacteriales | Coriobacteriaceae | unclassified |
| Coriobacteriaceae bacterium phI | Bacteria | Actinobacteria | Actinobacteria | Coriobacteriales | Coriobacteriaceae | unclassified |
| *Corynebacterium accolens* | Bacteria | Actinobacteria | Actinobacteria | Actinomycetales | Corynebacteriaceae | *Corynebacterium* |
| *Corynebacterium ammoniagenes* | Bacteria | Actinobacteria | Actinobacteria | Actinomycetales | Corynebacteriaceae | *Corynebacterium* |
| *Corynebacterium appendicis* | Bacteria | Actinobacteria | Actinobacteria | Actinomycetales | Corynebacteriaceae | *Corynebacterium* |
| *Corynebacterium argentoratense* | Bacteria | Actinobacteria | Actinobacteria | Actinomycetales | Corynebacteriaceae | *Corynebacterium* |
| *Corynebacterium atypicum* | Bacteria | Actinobacteria | Actinobacteria | Actinomycetales | Corynebacteriaceae | *Corynebacterium* |
| *Corynebacterium aurimucosum* | Bacteria | Actinobacteria | Actinobacteria | Actinomycetales | Corynebacteriaceae | *Corynebacterium* |
| *Corynebacterium bovis* | Bacteria | Actinobacteria | Actinobacteria | Actinomycetales | Corynebacteriaceae | *Corynebacterium* |
| *Corynebacterium canis* | Bacteria | Actinobacteria | Actinobacteria | Actinomycetales | Corynebacteriaceae | *Corynebacterium* |
| *Corynebacterium casei* | Bacteria | Actinobacteria | Actinobacteria | Actinomycetales | Corynebacteriaceae | *Corynebacterium* |
| *Corynebacterium confusum* | Bacteria | Actinobacteria | Actinobacteria | Actinomycetales | Corynebacteriaceae | *Corynebacterium* |
| *Corynebacterium coyleae* | Bacteria | Actinobacteria | Actinobacteria | Actinomycetales | Corynebacteriaceae | *Corynebacterium* |
| *Corynebacterium durum* | Bacteria | Actinobacteria | Actinobacteria | Actinomycetales | Corynebacteriaceae | *Corynebacterium* |
| *Corynebacterium efficiens* | Bacteria | Actinobacteria | Actinobacteria | Actinomycetales | Corynebacteriaceae | *Corynebacterium* |
| *Corynebacterium falsenii* | Bacteria | Actinobacteria | Actinobacteria | Actinomycetales | Corynebacteriaceae | *Corynebacterium* |
| *Corynebacterium flavescens* | Bacteria | Actinobacteria | Actinobacteria | Actinomycetales | Corynebacteriaceae | *Corynebacterium* |
| *Corynebacterium genitalium* | Bacteria | Actinobacteria | Actinobacteria | Actinomycetales | Corynebacteriaceae | *Corynebacterium* |
| *Corynebacterium glaucum* | Bacteria | Actinobacteria | Actinobacteria | Actinomycetales | Corynebacteriaceae | *Corynebacterium* |
| *Corynebacterium glucuronolyticum* | Bacteria | Actinobacteria | Actinobacteria | Actinomycetales | Corynebacteriaceae | *Corynebacterium* |
| *Corynebacterium glutamicum* | Bacteria | Actinobacteria | Actinobacteria | Actinomycetales | Corynebacteriaceae | *Corynebacterium* |
| *Corynebacterium hansenii* | Bacteria | Actinobacteria | Actinobacteria | Actinomycetales | Corynebacteriaceae | *Corynebacterium* |
| *Corynebacterium imitans* | Bacteria | Actinobacteria | Actinobacteria | Actinomycetales | Corynebacteriaceae | *Corynebacterium* |
| *Corynebacterium kroppenstedtii* | Bacteria | Actinobacteria | Actinobacteria | Actinomycetales | Corynebacteriaceae | *Corynebacterium* |
| *Corynebacterium lipophiloflavum* | Bacteria | Actinobacteria | Actinobacteria | Actinomycetales | Corynebacteriaceae | *Corynebacterium* |
| *Corynebacterium macginleyi* | Bacteria | Actinobacteria | Actinobacteria | Actinomycetales | Corynebacteriaceae | *Corynebacterium* |
| *Corynebacterium mastitidis* | Bacteria | Actinobacteria | Actinobacteria | Actinomycetales | Corynebacteriaceae | *Corynebacterium* |
| *Corynebacterium matruchotii* | Bacteria | Actinobacteria | Actinobacteria | Actinomycetales | Corynebacteriaceae | *Corynebacterium* |
| *Corynebacterium minutissimum* | Bacteria | Actinobacteria | Actinobacteria | Actinomycetales | Corynebacteriaceae | *Corynebacterium* |
| *Corynebacterium mucifaciens* | Bacteria | Actinobacteria | Actinobacteria | Actinomycetales | Corynebacteriaceae | *Corynebacterium* |
| *Corynebacterium propinquum* | Bacteria | Actinobacteria | Actinobacteria | Actinomycetales | Corynebacteriaceae | *Corynebacterium* |
| *Corynebacterium pseudodiphtheriticum* | Bacteria | Actinobacteria | Actinobacteria | Actinomycetales | Corynebacteriaceae | *Corynebacterium* |
| *Corynebacterium pseudogenitalium* | Bacteria | Actinobacteria | Actinobacteria | Actinomycetales | Corynebacteriaceae | *Corynebacterium* |
| *Corynebacterium pseudotuberculosis* | Bacteria | Actinobacteria | Actinobacteria | Actinomycetales | Corynebacteriaceae | *Corynebacterium* |
| *Corynebacterium pyruviciproducens* | Bacteria | Actinobacteria | Actinobacteria | Actinomycetales | Corynebacteriaceae | *Corynebacterium* |
| *Corynebacterium renale* | Bacteria | Actinobacteria | Actinobacteria | Actinomycetales | Corynebacteriaceae | *Corynebacterium* |
| *Corynebacterium resistens* | Bacteria | Actinobacteria | Actinobacteria | Actinomycetales | Corynebacteriaceae | *Corynebacterium* |
| *Corynebacterium riegelii* | Bacteria | Actinobacteria | Actinobacteria | Actinomycetales | Corynebacteriaceae | *Corynebacterium* |

TABLE 1-continued

| OTU | Domain | Phylum | Class | Order | Family | Genus |
|---|---|---|---|---|---|---|
| *Corynebacterium simulans* | Bacteria | Actinobacteria | Actinobacteria | Actinomycetales | Corynebacteriaceae | *Corynebacterium* |
| *Corynebacterium singulare* | Bacteria | Actinobacteria | Actinobacteria | Actinomycetales | Corynebacteriaceae | *Corynebacterium* |
| *Corynebacterium* sp. 1 ex sheep | Bacteria | Actinobacteria | Actinobacteria | Actinomycetales | Corynebacteriaceae | *Corynebacterium* |
| *Corynebacterium* sp. L-2012475 | Bacteria | Actinobacteria | Actinobacteria | Actinomycetales | Corynebacteriaceae | *Corynebacterium* |
| *Corynebacterium* sp. NML 93-0481 | Bacteria | Actinobacteria | Actinobacteria | Actinomycetales | Corynebacteriaceae | *Corynebacterium* |
| *Corynebacterium* sp. NML 97-0186 | Bacteria | Actinobacteria | Actinobacteria | Actinomycetales | Corynebacteriaceae | *Corynebacterium* |
| *Corynebacterium* sp. NML 99-0018 | Bacteria | Actinobacteria | Actinobacteria | Actinomycetales | Corynebacteriaceae | *Corynebacterium* |
| *Corynebacterium sundsvallense* | Bacteria | Actinobacteria | Actinobacteria | Actinomycetales | Corynebacteriaceae | *Corynebacterium* |
| *Corynebacterium tuberculostearicum* | Bacteria | Actinobacteria | Actinobacteria | Actinomycetales | Corynebacteriaceae | *Corynebacterium* |
| *Corynebacterium tuscaniae* | Bacteria | Actinobacteria | Actinobacteria | Actinomycetales | Corynebacteriaceae | *Corynebacterium* |
| *Corynebacterium ulcerans* | Bacteria | Actinobacteria | Actinobacteria | Actinomycetales | Corynebacteriaceae | *Corynebacterium* |
| *Corynebacterium ureicelerivorans* | Bacteria | Actinobacteria | Actinobacteria | Actinomycetales | Corynebacteriaceae | *Corynebacterium* |
| *Corynebacterium variabile* | Bacteria | Actinobacteria | Actinobacteria | Actinomycetales | Corynebacteriaceae | *Corynebacterium* |
| *Cronobacter malonaticus* | Bacteria | Proteobacteria | Gammaproteobacteria | Enterobacteriales | Enterobacteriaceae | *Cronobacter* |
| *Cronobacter sakazakii* | Bacteria | Proteobacteria | Gammaproteobacteria | Enterobacteriales | Enterobacteriaceae | *Cronobacter* |
| *Cronobacter turicensis* | Bacteria | Proteobacteria | Gammaproteobacteria | Enterobacteriales | Enterobacteriaceae | *Cronobacter* |
| *Cryptobacterium curtum* | Bacteria | Actinobacteria | Actinobacteria | Coriobacteriales | Coriobacteriaceae | *Cryptobacterium* |
| *Cupriavidus metallidurans* | Bacteria | Proteobacteria | Betaproteobacteria | Burkholderiales | Burkholderiaceae | *Cupriavidus* |
| *Cytophaga xylanolytica* | Bacteria | Bacteroidetes | Cytophagia | Cytophagales | Cytophagaceae | *Cytophaga* |
| *Deferribacteres* sp. oral clone JV001 | Bacteria | Deferribacteres | Deferribacteres | unclassified | unclassified | unclassified |
| *Deferribacteres* sp. oral clone JV006 | Bacteria | Deferribacteres | Deferribacteres | unclassified | unclassified | unclassified |
| *Deferribacteres* sp. oral clone JV023 | Bacteria | Deferribacteres | Deferribacteres | unclassified | unclassified | unclassified |
| *Deinococcus radiodurans* | Bacteria | Deinococcus-Thermus | Deinococci | Deinococcales | Deinococcaceae | *Deinococcus* |
| *Deinococcus* sp. R-43890 | Bacteria | Deinococcus-Thermus | Deinococci | Deinococcales | Deinococcaceae | *Deinococcus* |
| *Delftia acidovorans* | Bacteria | Proteobacteria | Betaproteobacteria | Burkholderiales | Comamonadaceae | *Delftia* |
| *Dermabacter hominis* | Bacteria | Actinobacteria | Actinobacteria | Actinomycetales | Dermabacteraceae | *Dermabacter* |
| *Dermacoccus* sp. Ellin185 | Bacteria | Actinobacteria | Actinobacteria | Actinomycetales | Dermacoccaceae | *Dermacoccus* |
| *Desmospora activa* | Bacteria | Firmicutes | Bacilli | Bacillales | Thermoactinomycetaceae | *Desmospora* |
| *Desmospora* sp. 8437 | Bacteria | Firmicutes | Bacilli | Bacillales | Thermoactinomycetaceae | *Desmospora* |
| *Desulfitobacterium frappieri* | Bacteria | Firmicutes | Clostridia | Clostridiales | Peptococcaceae | *Desulfitobacterium* |
| *Desulfitobacterium hafniense* | Bacteria | Firmicutes | Clostridia | Clostridiales | Peptococcaceae | *Desulfitobacterium* |
| *Desulfobulbus* sp. oral clone CH031 | Bacteria | Proteobacteria | Deltaproteobacteria | Desulfobacterales | Desulfobulbaceae | *Desulfobulbus* |
| *Desulfotomaculum nigrificans* | Bacteria | Firmicutes | Clostridia | Clostridiales | Peptococcaceae | *Desulfotomaculum* |
| *Desulfovibrio desulfuricans* | Bacteria | Proteobacteria | Deltaproteobacteria | Desulfovibrionales | Desulfovibrionaceae | *Desulfovibrio* |
| *Desulfovibrio fairfieldensis* | Bacteria | Proteobacteria | Deltaproteobacteria | Desulfovibrionales | Desulfovibrionaceae | *Desulfovibrio* |
| *Desulfovibrio piger* | Bacteria | Proteobacteria | Deltaproteobacteria | Desulfovibrionales | Desulfovibrionaceae | *Desulfovibrio* |
| *Desulfovibrio* sp. 3_1_syn3 | Bacteria | Proteobacteria | Deltaproteobacteria | Desulfovibrionales | Desulfovibrionaceae | *Desulfovibrio* |
| *Desulfovibrio vulgaris* | Bacteria | Proteobacteria | Deltaproteobacteria | Desulfovibrionales | Desulfovibrionaceae | *Desulfovibrio* |
| *Dialister invisus* | Bacteria | Firmicutes | Negativicutes | Selenomonadales | Veillonellaceae | *Dialister* |
| *Dialister micraerophilus* | Bacteria | Firmicutes | Negativicutes | Selenomonadales | Veillonellaceae | *Dialister* |
| *Dialister microaerophilus* | Bacteria | Firmicutes | Negativicutes | Selenomonadales | Veillonellaceae | *Dialister* |
| *Dialister pneumosintes* | Bacteria | Firmicutes | Negativicutes | Selenomonadales | Veillonellaceae | *Dialister* |
| *Dialister propionicifaciens* | Bacteria | Firmicutes | Negativicutes | Selenomonadales | Veillonellaceae | *Dialister* |
| *Dialister* sp. oral taxon 502 | Bacteria | Firmicutes | Negativicutes | Selenomonadales | Veillonellaceae | *Dialister* |
| *Dialister succinatiphilus* | Bacteria | Firmicutes | Negativicutes | Selenomonadales | Veillonellaceae | *Dialister* |
| *Dietzia natronolimnaea* | Bacteria | Actinobacteria | Actinobacteria | Actinomycetales | Dietziaceae | *Dietzia* |
| *Dietzia* sp. BBDP51 | Bacteria | Actinobacteria | Actinobacteria | Actinomycetales | Dietziaceae | *Dietzia* |
| *Dietzia* sp. CA149 | Bacteria | Actinobacteria | Actinobacteria | Actinomycetales | Dietziaceae | *Dietzia* |
| *Dietzia timorensis* | Bacteria | Actinobacteria | Actinobacteria | Actinomycetales | Dietziaceae | *Dietzia* |
| *Dorea formicigenerans* | Bacteria | Firmicutes | Clostridia | Clostridiales | Lachnospiraceae | *Dorea* |
| *Dorea longicatena* | Bacteria | Firmicutes | Clostridia | Clostridiales | Lachnospiraceae | *Dorea* |

TABLE 1-continued

| OTU | Domain | Phylum | Class | Order | Family | Genus |
|---|---|---|---|---|---|---|
| *Dysgonomonas gadei* | Bacteria | Bacteroidetes | Bacteroidia | Bacteroidales | Porphyromonadaceae | *Dysgonomonas* |
| *Dysgonomonas mossii* | Bacteria | Bacteroidetes | Bacteroidia | Bacteroidales | Porphyromonadaceae | *Dysgonomonas* |
| *Edwardsiella tarda* | Bacteria | Proteobacteria | Gammaproteobacteria | Enterobacteriales | Enterobacteriaceae | *Edwardsiella* |
| *Eggerthella lenta* | Bacteria | Actinobacteria | Actinobacteria | Coriobacteriales | Coriobacteriaceae | *Eggerthella* |
| *Eggerthella sinensis* | Bacteria | Actinobacteria | Actinobacteria | Coriobacteriales | Coriobacteriaceae | *Eggerthella* |
| *Eggerthella* sp. 1__3__56FAA | Bacteria | Actinobacteria | Actinobacteria | Coriobacteriales | Coriobacteriaceae | *Eggerthella* |
| *Eggerthella* sp. HGA1 | Bacteria | Actinobacteria | Actinobacteria | Coriobacteriales | Coriobacteriaceae | *Eggerthella* |
| *Eggerthella* sp. YY7918 | Bacteria | Actinobacteria | Actinobacteria | Coriobacteriales | Coriobacteriaceae | *Eggerthella* |
| *Eikenella corrodens* | Bacteria | Proteobacteria | Betaproteobacteria | Neisseriales | Neisseriaceae | *Eikenella* |
| *Enhydrobacter aerosaccus* | Bacteria | Proteobacteria | Gammaproteobacteria | Pseudomonadales | Moraxellaceae | *Enhydrobacter* |
| *Enterobacter aerogenes* | Bacteria | Proteobacteria | Gammaproteobacteria | Enterobacteriales | Enterobacteriaceae | *Enterobacter* |
| *Enterobacter asburiae* | Bacteria | Proteobacteria | Gammaproteobacteria | Enterobacteriales | Enterobacteriaceae | *Enterobacter* |
| *Enterobacter cancerogenus* | Bacteria | Proteobacteria | Gammaproteobacteria | Enterobacteriales | Enterobacteriaceae | *Enterobacter* |
| *Enterobacter cloacae* | Bacteria | Proteobacteria | Gammaproteobacteria | Enterobacteriales | Enterobacteriaceae | *Enterobacter* |
| *Enterobacter cowanii* | Bacteria | Proteobacteria | Gammaproteobacteria | Enterobacteriales | Enterobacteriaceae | *Enterobacter* |
| *Enterobacter hormaechei* | Bacteria | Proteobacteria | Gammaproteobacteria | Enterobacteriales | Enterobacteriaceae | *Enterobacter* |
| *Enterobacter* sp. 247BMC | Bacteria | Proteobacteria | Gammaproteobacteria | Enterobacteriales | Enterobacteriaceae | *Enterobacter* |
| *Enterobacter* sp. 638 | Bacteria | Proteobacteria | Gammaproteobacteria | Enterobacteriales | Enterobacteriaceae | *Enterobacter* |
| *Enterobacter* sp. JC163 | Bacteria | Proteobacteria | Gammaproteobacteria | Enterobacteriales | Enterobacteriaceae | *Enterobacter* |
| *Enterobacter* sp. SCSS | Bacteria | Proteobacteria | Gammaproteobacteria | Enterobacteriales | Enterobacteriaceae | *Enterobacter* |
| *Enterobacter* sp. TSE38 | Bacteria | Proteobacteria | Gammaproteobacteria | Enterobacteriales | Enterobacteriaceae | *Enterobacter* |
| Enterobacteriaceae bacterium 9__2__54FAA | Bacteria | Proteobacteria | Gammaproteobacteria | Enterobacteriales | Enterobacteriaceae | unclassified |
| Enterobacteriaceae bacterium CF01Ent-1 | Bacteria | Proteobacteria | Gammaproteobacteria | Enterobacteriales | Enterobacteriaceae | unclassified |
| Enterobacteriaceae bacterium Smarlab 3302238 | Bacteria | Proteobacteria | Gammaproteobacteria | Enterobacteriales | Enterobacteriaceae | unclassified |
| *Enterococcus avium* | Bacteria | Firmicutes | Bacilli | Lactobacillales | Enterococcaceae | *Enterococcus* |
| *Enterococcus caccae* | Bacteria | Firmicutes | Bacilli | Lactobacillales | Enterococcaceae | *Enterococcus* |
| *Enterococcus casseliflavus* | Bacteria | Firmicutes | Bacilli | Lactobacillales | Enterococcaceae | *Enterococcus* |
| *Enterococcus durans* | Bacteria | Firmicutes | Bacilli | Lactobacillales | Enterococcaceae | *Enterococcus* |
| *Enterococcus faecalis* | Bacteria | Firmicutes | Bacilli | Lactobacillales | Enterococcaceae | *Enterococcus* |
| *Enterococcus faecium* | Bacteria | Firmicutes | Bacilli | Lactobacillales | Enterococcaceae | *Enterococcus* |
| *Enterococcus gallinarum* | Bacteria | Firmicutes | Bacilli | Lactobacillales | Enterococcaceae | *Enterococcus* |
| *Enterococcus gilvus* | Bacteria | Firmicutes | Bacilli | Lactobacillales | Enterococcaceae | *Enterococcus* |
| *Enterococcus hawaiiensis* | Bacteria | Firmicutes | Bacilli | Lactobacillales | Enterococcaceae | *Enterococcus* |
| *Enterococcus hirae* | Bacteria | Firmicutes | Bacilli | Lactobacillales | Enterococcaceae | *Enterococcus* |
| *Enterococcus italicus* | Bacteria | Firmicutes | Bacilli | Lactobacillales | Enterococcaceae | *Enterococcus* |
| *Enterococcus mundtii* | Bacteria | Firmicutes | Bacilli | Lactobacillales | Enterococcaceae | *Enterococcus* |
| *Enterococcus raffinosus* | Bacteria | Firmicutes | Bacilli | Lactobacillales | Enterococcaceae | *Enterococcus* |
| *Enterococcus* sp. BV2CASA2 | Bacteria | Firmicutes | Bacilli | Lactobacillales | Enterococcaceae | *Enterococcus* |
| *Enterococcus* sp. CCRI-16620 | Bacteria | Firmicutes | Bacilli | Lactobacillales | Enterococcaceae | *Enterococcus* |
| *Enterococcus* sp. F95 | Bacteria | Firmicutes | Bacilli | Lactobacillales | Enterococcaceae | *Enterococcus* |
| *Enterococcus* sp. RfL6 | Bacteria | Firmicutes | Bacilli | Lactobacillales | Enterococcaceae | *Enterococcus* |
| *Enterococcus thailandicus* | Bacteria | Firmicutes | Bacilli | Lactobacillales | Enterococcaceae | *Enterococcus* |
| *Eremococcus coleocola* | Bacteria | Firmicutes | Bacilli | Lactobacillales | Aerococcaceae | *Eremococcus* |
| *Erysipelothrix inopinata* | Bacteria | Firmicutes | Erysipelotrichi | Erysipelotrichales | Erysipelotrichaceae | *Erysipelothrix* |
| *Erysipelothrix rhusiopathiae* | Bacteria | Firmicutes | Erysipelotrichi | Erysipelotrichales | Erysipelotrichaceae | *Erysipelothrix* |
| *Erysipelothrix tonsillarum* | Bacteria | Firmicutes | Erysipelotrichi | Erysipelotrichales | Erysipelotrichaceae | *Erysipelothrix* |
| Erysipelotrichaceae bacterium 3__1__53 | Bacteria | Firmicutes | Erysipelotrichi | Erysipelotrichales | Erysipelotrichaceae | unclassified |
| Erysipelotrichaceae bacterium 5__2__54FAA | Bacteria | Firmicutes | Erysipelotrichi | Erysipelotrichales | Erysipelotrichaceae | unclassified |
| *Escherichia albertii* | Bacteria | Proteobacteria | Gammaproteobacteria | Enterobacteriales | Enterobacteriaceae | *Escherichia* |
| *Escherichia coli* | Bacteria | Proteobacteria | Gammaproteobacteria | Enterobacteriales | Enterobacteriaceae | *Escherichia* |
| *Escherichia fergusonii* | Bacteria | Proteobacteria | Gammaproteobacteria | Enterobacteriales | Enterobacteriaceae | *Escherichia* |

TABLE 1-continued

| OTU | Domain | Phylum | Class | Order | Family | Genus |
|---|---|---|---|---|---|---|
| *Escherichia hermannii* | Bacteria | Proteobacteria | Gammaproteobacteria | Enterobacteriales | Enterobacteriaceae | *Escherichia* |
| *Escherichia* sp. 1__1__43 | Bacteria | Proteobacteria | Gammaproteobacteria | Enterobacteriales | Enterobacteriaceae | *Escherichia* |
| *Escherichia* sp. 4__1__40B | Bacteria | Proteobacteria | Gammaproteobacteria | Enterobacteriales | Enterobacteriaceae | *Escherichia* |
| *Escherichia* sp. B4 | Bacteria | Proteobacteria | Gammaproteobacteria | Enterobacteriales | Enterobacteriaceae | *Escherichia* |
| *Escherichia vulneris* | Bacteria | Proteobacteria | Gammaproteobacteria | Enterobacteriales | Enterobacteriaceae | *Escherichia* |
| *Ethanoligenens harbinense* | Bacteria | Firmicutes | Clostridia | Clostridiales | Ruminococcaceae | *Ethanoligenens* |
| Eubacteriaceae bacterium P4P__50 P4 | Bacteria | Firmicutes | Clostridia | Clostridiales | Eubacteriaceae | unclassified |
| *Eubacterium barkeri* | Bacteria | Firmicutes | Clostridia | Clostridiales | Eubacteriaceae | *Eubacterium* |
| *Eubacterium biforme* | Bacteria | Firmicutes | Erysipelotrichi | Erysipelotrichales | Erysipelotrichaceae | unclassified |
| *Eubacterium brachy* | Bacteria | Firmicutes | Clostridia | Clostridiales | Eubacteriaceae | *Eubacterium* |
| *Eubacterium budayi* | Bacteria | Firmicutes | Clostridia | Clostridiales | Eubacteriaceae | *Eubacterium* |
| *Eubacterium callanderi* | Bacteria | Firmicutes | Clostridia | Clostridiales | Eubacteriaceae | *Eubacterium* |
| *Eubacterium cellulosolvens* | Bacteria | Firmicutes | Clostridia | Clostridiales | Eubacteriaceae | *Eubacterium* |
| *Eubacterium contortum* | Bacteria | Firmicutes | Clostridia | Clostridiales | Eubacteriaceae | *Eubacterium* |
| *Eubacterium coprostanoligenes* | Bacteria | Firmicutes | Clostridia | Clostridiales | Eubacteriaceae | *Eubacterium* |
| *Eubacterium cylindroides* | Bacteria | Firmicutes | Erysipelotrichi | Erysipelotrichales | Erysipelotrichaceae | unclassified |
| *Eubacterium desmolans* | Bacteria | Firmicutes | Clostridia | Clostridiales | Eubacteriaceae | *Eubacterium* |
| *Eubacterium dolichum* | Bacteria | Firmicutes | Erysipelotrichi | Erysipelotrichales | Erysipelotrichaceae | unclassified |
| *Eubacterium eligens* | Bacteria | Firmicutes | Clostridia | Clostridiales | Eubacteriaceae | *Eubacterium* |
| *Eubacterium fissicatena* | Bacteria | Firmicutes | Clostridia | Clostridiales | Eubacteriaceae | *Eubacterium* |
| *Eubacterium hadrum* | Bacteria | Firmicutes | Clostridia | Clostridiales | Lachnospiraceae | *Anaerostipes* |
| *Eubacterium hallii* | Bacteria | Firmicutes | Clostridia | Clostridiales | Eubacteriaceae | *Eubacterium* |
| *Eubacterium infirmum* | Bacteria | Firmicutes | Clostridia | Clostridiales | Clostridiales Family XIII. Incertae Sedis | unclassified |
| *Eubacterium limosum* | Bacteria | Firmicutes | Clostridia | Clostridiales | Eubacteriaceae | *Eubacterium* |
| *Eubacterium moniliforme* | Bacteria | Firmicutes | Clostridia | Clostridiales | Eubacteriaceae | *Eubacterium* |
| *Eubacterium multiforme* | Bacteria | Firmicutes | Clostridia | Clostridiales | Eubacteriaceae | *Eubacterium* |
| *Eubacterium nitritogenes* | Bacteria | Firmicutes | Clostridia | Clostridiales | Eubacteriaceae | *Eubacterium* |
| *Eubacterium nodatum* | Bacteria | Firmicutes | Clostridia | Clostridiales | Clostridiales Family XIII. Incertae Sedis | unclassified |
| *Eubacterium ramulus* | Bacteria | Firmicutes | Clostridia | Clostridiales | Eubacteriaceae | *Eubacterium* |
| *Eubacterium rectale* | Bacteria | Firmicutes | Clostridia | Clostridiales | Eubacteriaceae | *Eubacterium* |
| *Eubacterium ruminantium* | Bacteria | Firmicutes | Clostridia | Clostridiales | Eubacteriaceae | *Eubacterium* |
| *Eubacterium saburreum* | Bacteria | Firmicutes | Clostridia | Clostridiales | Lachnospiraceae | *Lachnoanaerobaculum* |
| *Eubacterium saphenum* | Bacteria | Firmicutes | Clostridia | Clostridiales | Eubacteriaceae | *Eubacterium* |
| *Eubacterium siraeum* | Bacteria | Firmicutes | Clostridia | Clostridiales | Eubacteriaceae | *Eubacterium* |
| *Eubacterium* sp. 3__1__31 | Bacteria | Firmicutes | Clostridia | Clostridiales | Eubacteriaceae | *Eubacterium* |
| *Eubacterium* sp. AS15b | Bacteria | Firmicutes | Clostridia | Clostridiales | Eubacteriaceae | *Eubacterium* |
| *Eubacterium* sp. OBRC9 | Bacteria | Firmicutes | Clostridia | Clostridiales | Eubacteriaceae | *Eubacterium* |
| *Eubacterium* sp. oral clone GI038 | Bacteria | Firmicutes | Clostridia | Clostridiales | Eubacteriaceae | *Eubacterium* |
| *Eubacterium* sp. oral clone IR009 | Bacteria | Firmicutes | Clostridia | Clostridiales | Eubacteriaceae | *Eubacterium* |
| *Eubacterium* sp. oral clone JH012 | Bacteria | Firmicutes | Clostridia | Clostridiales | Eubacteriaceae | *Eubacterium* |
| *Eubacterium* sp. oral clone JI012 | Bacteria | Firmicutes | Clostridia | Clostridiales | Eubacteriaceae | *Eubacterium* |
| *Eubacterium* sp. oral clone JN088 | Bacteria | Firmicutes | Clostridia | Clostridiales | Eubacteriaceae | *Eubacterium* |
| *Eubacterium* sp. oral clone JS001 | Bacteria | Firmicutes | Clostridia | Clostridiales | Eubacteriaceae | *Eubacterium* |
| *Eubacterium* sp. oral clone OH3A | Bacteria | Firmicutes | Clostridia | Clostridiales | Eubacteriaceae | *Eubacterium* |
| *Eubacterium* sp. WAL 14571 | Bacteria | Firmicutes | Clostridia | Clostridiales | Eubacteriaceae | *Eubacterium* |
| *Eubacterium tenue* | Bacteria | Firmicutes | Clostridia | Clostridiales | Peptostreptococcaceae | unclassified |
| *Eubacterium tortuosum* | Bacteria | Firmicutes | Erysipelotrichi | Erysipelotrichales | Erysipelotrichaceae | unclassified |
| *Eubacterium ventriosum* | Bacteria | Firmicutes | Clostridia | Clostridiales | Eubacteriaceae | *Eubacterium* |
| *Eubacterium xylanophilum* | Bacteria | Firmicutes | Clostridia | Clostridiales | Eubacteriaceae | *Eubacterium* |
| *Eubacterium yurii* | Bacteria | Firmicutes | Clostridia | Clostridiales | Peptostreptococcaceae | unclassified |
| *Ewingella americana* | Bacteria | Proteobacteria | Gammaproteobacteria | Enterobacteriales | Enterobacteriaceae | *Ewingella* |

TABLE 1-continued

| OTU | Domain | Phylum | Class | Order | Family | Genus |
|---|---|---|---|---|---|---|
| *Exiguobacterium acetylicum* | Bacteria | Firmicutes | Bacilli | Bacillales | unclassified | *Exiguobacterium* |
| *Facklamia hominis* | Bacteria | Firmicutes | Bacilli | Lactobacillales | Aerococcaceae | *Facklamia* |
| *Faecalibacterium prausnitzii* | Bacteria | Firmicutes | Clostridia | Clostridiales | Ruminococcaceae | *Faecalibacterium* |
| *Filifactor alocis* | Bacteria | Firmicutes | Clostridia | Clostridiales | Peptostreptococcaceae | *Filifactor* |
| *Filifactor villosus* | Bacteria | Firmicutes | Clostridia | Clostridiales | Peptostreptococcaceae | *Filifactor* |
| *Finegoldia magna* | Bacteria | Firmicutes | Clostridia | Clostridiales | Clostridiales Family XI. Incertae Sedis | *Finegoldia* |
| Flavobacteriaceae genomosp. C1 | Bacteria | Bacteroidetes | Flavobacteriia | Flavobacteriales | Flavobacteriaceae | unclassified |
| *Flavobacterium* sp. NF2-1 | Bacteria | Bacteroidetes | Flavobacteriia | Flavobacteriales | Flavobacteriaceae | *Flavobacterium* |
| *Flavonifractor plautii* | Bacteria | Firmicutes | Clostridia | Clostridiales | unclassified | unclassified |
| *Flexispira rappini* | Bacteria | Proteobacteria | Epsilonproteobacteria | Campylobacterales | Helicobacteraceae | *Flexispira* |
| *Flexistipes sinusarabici* | Bacteria | Deferribacteres | Deferribacteres | Deferribacterales | Deferribacteraceae | *Flexistipes* |
| *Francisella novicida* | Bacteria | Proteobacteria | Gammaproteobacteria | Thiotrichales | Francisellaceae | *Francisella* |
| *Francisella philomiragia* | Bacteria | Proteobacteria | Gammaproteobacteria | Thiotrichales | Francisellaceae | *Francisella* |
| *Fulvimonas* sp. NML 060897 | Bacteria | Proteobacteria | Gammaproteobacteria | Xanthomonadales | Xanthomonadaceae | *Fulvimonas* |
| *Fusobacterium canifelinum* | Bacteria | Fusobacteria | Fusobacteriia | Fusobacteriales | Fusobacteriaceae | *Fusobacterium* |
| *Fusobacterium* genomosp. C1 | Bacteria | Fusobacteria | Fusobacteriia | Fusobacteriales | Fusobacteriaceae | *Fusobacterium* |
| *Fusobacterium* genomosp. C2 | Bacteria | Fusobacteria | Fusobacteriia | Fusobacteriales | Fusobacteriaceae | *Fusobacterium* |
| *Fusobacterium gonidiaformans* | Bacteria | Fusobacteria | Fusobacteriia | Fusobacteriales | Fusobacteriaceae | *Fusobacterium* |
| *Fusobacterium mortiferum* | Bacteria | Fusobacteria | Fusobacteriia | Fusobacteriales | Fusobacteriaceae | *Fusobacterium* |
| *Fusobacterium naviforme* | Bacteria | Fusobacteria | Fusobacteriia | Fusobacteriales | Fusobacteriaceae | *Fusobacterium* |
| *Fusobacterium necrogenes* | Bacteria | Fusobacteria | Fusobacteriia | Fusobacteriales | Fusobacteriaceae | *Fusobacterium* |
| *Fusobacterium necrophorum* | Bacteria | Fusobacteria | Fusobacteriia | Fusobacteriales | Fusobacteriaceae | *Fusobacterium* |
| *Fusobacterium nucleatum* | Bacteria | Fusobacteria | Fusobacteriia | Fusobacteriales | Fusobacteriaceae | *Fusobacterium* |
| *Fusobacterium periodonticum* | Bacteria | Fusobacteria | Fusobacteriia | Fusobacteriales | Fusobacteriaceae | *Fusobacterium* |
| *Fusobacterium russii* | Bacteria | Fusobacteria | Fusobacteriia | Fusobacteriales | Fusobacteriaceae | *Fusobacterium* |
| *Fusobacterium* sp. 1_1_41FAA | Bacteria | Fusobacteria | Fusobacteriia | Fusobacteriales | Fusobacteriaceae | *Fusobacterium* |
| *Fusobacterium* sp. 11_3_2 | Bacteria | Fusobacteria | Fusobacteriia | Fusobacteriales | Fusobacteriaceae | *Fusobacterium* |
| *Fusobacterium* sp. 12_1B | Bacteria | Fusobacteria | Fusobacteriia | Fusobacteriales | Fusobacteriaceae | *Fusobacterium* |
| *Fusobacterium* sp. 2_1_31 | Bacteria | Fusobacteria | Fusobacteriia | Fusobacteriales | Fusobacteriaceae | *Fusobacterium* |
| *Fusobacterium* sp. 3_1_27 | Bacteria | Fusobacteria | Fusobacteriia | Fusobacteriales | Fusobacteriaceae | *Fusobacterium* |
| *Fusobacterium* sp. 3_1_33 | Bacteria | Fusobacteria | Fusobacteriia | Fusobacteriales | Fusobacteriaceae | *Fusobacterium* |
| *Fusobacterium* sp. 3_1_36A2 | Bacteria | Fusobacteria | Fusobacteriia | Fusobacteriales | Fusobacteriaceae | *Fusobacterium* |
| *Fusobacterium* sp. 3_1_5R | Bacteria | Fusobacteria | Fusobacteriia | Fusobacteriales | Fusobacteriaceae | *Fusobacterium* |
| *Fusobacterium* sp. AC18 | Bacteria | Fusobacteria | Fusobacteriia | Fusobacteriales | Fusobacteriaceae | *Fusobacterium* |
| *Fusobacterium* sp. ACB2 | Bacteria | Fusobacteria | Fusobacteriia | Fusobacteriales | Fusobacteriaceae | *Fusobacterium* |
| *Fusobacterium* sp. AS2 | Bacteria | Fusobacteria | Fusobacteriia | Fusobacteriales | Fusobacteriaceae | *Fusobacterium* |
| *Fusobacterium* sp. CM1 | Bacteria | Fusobacteria | Fusobacteriia | Fusobacteriales | Fusobacteriaceae | *Fusobacterium* |
| *Fusobacterium* sp. CM21 | Bacteria | Fusobacteria | Fusobacteriia | Fusobacteriales | Fusobacteriaceae | *Fusobacterium* |
| *Fusobacterium* sp. CM22 | Bacteria | Fusobacteria | Fusobacteriia | Fusobacteriales | Fusobacteriaceae | *Fusobacterium* |
| *Fusobacterium* sp. D12 | Bacteria | Fusobacteria | Fusobacteriia | Fusobacteriales | Fusobacteriaceae | *Fusobacterium* |
| *Fusobacterium* sp. oral clone ASCF06 | Bacteria | Fusobacteria | Fusobacteriia | Fusobacteriales | Fusobacteriaceae | *Fusobacterium* |
| *Fusobacterium* sp. oral clone ASCF11 | Bacteria | Fusobacteria | Fusobacteriia | Fusobacteriales | Fusobacteriaceae | *Fusobacterium* |
| *Fusobacterium ulcerans* | Bacteria | Fusobacteria | Fusobacteriia | Fusobacteriales | Fusobacteriaceae | *Fusobacterium* |
| *Fusobacterium varium* | Bacteria | Fusobacteria | Fusobacteriia | Fusobacteriales | Fusobacteriaceae | *Fusobacterium* |
| *Gardnerella vaginalis* | Bacteria | Actinobacteria | Actinobacteria | Bifidobacteriales | Bifidobacteriaceae | *Gardnerella* |
| *Gemella haemolysans* | Bacteria | Firmicutes | Bacilli | Bacillales | Bacillales Family XI. Incertae Sedis | *Gemella* |
| *Gemella morbillorum* | Bacteria | Firmicutes | Bacilli | Bacillales | Bacillales Family XI. Incertae Sedis | *Gemella* |
| *Gemella sanguinis* | Bacteria | Firmicutes | Bacilli | Bacillales | Bacillales Family XI. Incertae Sedis | *Gemella* |
| *Gemella* sp. oral clone ASCE02 | Bacteria | Firmicutes | Bacilli | Bacillales | unclassified | *Gemella* |
| *Gemella* sp. oral clone ASCF04 | Bacteria | Firmicutes | Bacilli | Bacillales | unclassified | *Gemella* |
| *Gemella* sp. oral clone ASCF12 | Bacteria | Firmicutes | Bacilli | Bacillales | unclassified | *Gemella* |

TABLE 1-continued

| OTU | Domain | Phylum | Class | Order | Family | Genus |
|---|---|---|---|---|---|---|
| *Gemella* sp. WAL 1945J | Bacteria | Firmicutes | Bacilli | Bacillales | unclassified | *Gemella* |
| *Gemmiger formicilis* | Bacteria | Proteobacteria | Alphaproteobacteria | Rhizobiales | Hyphomicrobiaceae | *Gemmiger* |
| *Geobacillus kaustophilus* | Bacteria | Firmicutes | Bacilli | Bacillales | Bacillaceae | *Geobacillus* |
| *Geobacillus* sp. E263 | Bacteria | Firmicutes | Bacilli | Bacillales | Bacillaceae | *Geobacillus* |
| *Geobacillus* sp. WCH70 | Bacteria | Firmicutes | Bacilli | Bacillales | Bacillaceae | *Geobacillus* |
| *Geobacillus stearothermophilus* | Bacteria | Firmicutes | Bacilli | Bacillales | Bacillaceae | *Geobacillus* |
| *Geobacillus thermocatenulatus* | Bacteria | Firmicutes | Bacilli | Bacillales | Bacillaceae | *Geobacillus* |
| *Geobacillus thermodenitrificans* | Bacteria | Firmicutes | Bacilli | Bacillales | Bacillaceae | *Geobacillus* |
| *Geobacillus thermoglucosidasius* | Bacteria | Firmicutes | Bacilli | Bacillales | Bacillaceae | *Geobacillus* |
| *Geobacillus thermoleovorans* | Bacteria | Firmicutes | Bacilli | Bacillales | Bacillaceae | *Geobacillus* |
| *Geobacter bemidjiensis* | Bacteria | Proteobacteria | Deltaproteobacteria | Desulfuromonadales | Geobacteraceae | *Geobacter* |
| *Gloeobacter violaceus* | Bacteria | Cyanobacteria | Gloeobacteria | Gloeobacterales | unclassified | *Gloeobacter* |
| *Gluconacetobacter azotocaptans* | Bacteria | Proteobacteria | Alphaproteobacteria | Rhodospirillales | Acetobacteraceae | *Gluconacetobacter* |
| *Gluconacetobacter diazotrophicus* | Bacteria | Proteobacteria | Alphaproteobacteria | Rhodospirillales | Acetobacteraceae | *Gluconacetobacter* |
| *Gluconacetobacter entanii* | Bacteria | Proteobacteria | Alphaproteobacteria | Rhodospirillales | Acetobacteraceae | *Gluconacetobacter* |
| *Gluconacetobacter europaeus* | Bacteria | Proteobacteria | Alphaproteobacteria | Rhodospirillales | Acetobacteraceae | *Gluconacetobacter* |
| *Gluconacetobacter hansenii* | Bacteria | Proteobacteria | Alphaproteobacteria | Rhodospirillales | Acetobacteraceae | *Gluconacetobacter* |
| *Gluconacetobacter johannae* | Bacteria | Proteobacteria | Alphaproteobacteria | Rhodospirillales | Acetobacteraceae | *Gluconacetobacter* |
| *Gluconacetobacter oboediens* | Bacteria | Proteobacteria | Alphaproteobacteria | Rhodospirillales | Acetobacteraceae | *Gluconacetobacter* |
| *Gluconacetobacter xylinus* | Bacteria | Proteobacteria | Alphaproteobacteria | Rhodospirillales | Acetobacteraceae | *Gluconacetobacter* |
| *Gordonia bronchialis* | Bacteria | Actinobacteria | Actinobacteria | Actinomycetales | Gordoniaceae | *Gordonia* |
| *Gordonia polyisoprenivorans* | Bacteria | Actinobacteria | Actinobacteria | Actinomycetales | Gordoniaceae | *Gordonia* |
| *Gordonia* sp. KTR9 | Bacteria | Actinobacteria | Actinobacteria | Actinomycetales | Gordoniaceae | *Gordonia* |
| *Gordonia sputi* | Bacteria | Actinobacteria | Actinobacteria | Actinomycetales | Gordoniaceae | *Gordonia* |
| *Gordonia terrae* | Bacteria | Actinobacteria | Actinobacteria | Actinomycetales | Gordoniaceae | *Gordonia* |
| *Gordonibacter pamelaeae* | Bacteria | Actinobacteria | Actinobacteria | Coriobacteriales | Coriobacteriaceae | *Gordonibacter* |
| *Gracilibacter thermotolerans* | Bacteria | Firmicutes | Clostridia | Clostridiales | Gracilibacteraceae | *Gracilibacter* |
| *Gramella forsetii* | Bacteria | Bacteroidetes | Flavobacteriia | Flavobacteriales | Flavobacteriaceae | *Gramella* |
| *Granulicatella adiacens* | Bacteria | Firmicutes | Bacilli | Lactobacillales | Carnobacteriaceae | *Granulicatella* |
| *Granulicatella elegans* | Bacteria | Firmicutes | Bacilli | Lactobacillales | Carnobacteriaceae | *Granulicatella* |
| *Granulicatella paradiacens* | Bacteria | Firmicutes | Bacilli | Lactobacillales | Carnobacteriaceae | *Granulicatella* |
| *Granulicatella* sp. M658/99/3 | Bacteria | Firmicutes | Bacilli | Lactobacillales | Carnobacteriaceae | *Granulicatella* |
| *Granulicatella* sp. oral clone ASC02 | Bacteria | Firmicutes | Bacilli | Lactobacillales | Carnobacteriaceae | *Granulicatella* |
| *Granulicatella* sp. oral clone ASCA05 | Bacteria | Firmicutes | Bacilli | Lactobacillales | Carnobacteriaceae | *Granulicatella* |
| *Granulicatella* sp. oral clone ASCB09 | Bacteria | Firmicutes | Bacilli | Lactobacillales | Carnobacteriaceae | *Granulicatella* |
| *Granulicatella* sp. oral clone ASCG05 | Bacteria | Firmicutes | Bacilli | Lactobacillales | Carnobacteriaceae | *Granulicatella* |
| *Grimontia hollisae* | Bacteria | Proteobacteria | Gammaproteobacteria | Vibrionales | Vibrionaceae | unclassified |
| *Haematobacter* sp. BC14248 | Bacteria | Proteobacteria | Alphaproteobacteria | Rhodobacterales | Rhodobacteraceae | *Haematobacter* |
| *Haemophilus aegyptius* | Bacteria | Proteobacteria | Gammaproteobacteria | Pasteurellales | Pasteurellaceae | *Haemophilus* |
| *Haemophilus* genomosp. P2 oral clone MB3_C24 | Bacteria | Proteobacteria | Gammaproteobacteria | Pasteurellales | Pasteurellaceae | *Haemophilus* |
| *Haemophilus* genomosp. P3 oral clone MB3_C38 | Bacteria | Proteobacteria | Gammaproteobacteria | Pasteurellales | Pasteurellaceae | *Haemophilus* |
| *Haemophilus haemolyticus* | Bacteria | Proteobacteria | Gammaproteobacteria | Pasteurellales | Pasteurellaceae | *Haemophilus* |
| *Haemophilus parahaemolyticus* | Bacteria | Proteobacteria | Gammaproteobacteria | Pasteurellales | Pasteurellaceae | *Haemophilus* |
| *Haemophilus parainfluenzae* | Bacteria | Proteobacteria | Gammaproteobacteria | Pasteurellales | Pasteurellaceae | *Haemophilus* |
| *Haemophilus paraphrophaemolyticus* | Bacteria | Proteobacteria | Gammaproteobacteria | Pasteurellales | Pasteurellaceae | *Haemophilus* |
| *Haemophilus parasuis* | Bacteria | Proteobacteria | Gammaproteobacteria | Pasteurellales | Pasteurellaceae | *Haemophilus* |
| *Haemophilus somnus* | Bacteria | Proteobacteria | Gammaproteobacteria | Pasteurellales | Pasteurellaceae | *Histophilus* |
| *Haemophilus* sp. 70334 | Bacteria | Proteobacteria | Gammaproteobacteria | Pasteurellales | Pasteurellaceae | *Haemophilus* |
| *Haemophilus* sp. HK445 | Bacteria | Proteobacteria | Gammaproteobacteria | Pasteurellales | Pasteurellaceae | *Haemophilus* |
| *Haemophilus* sp. oral clone ASCA07 | Bacteria | Proteobacteria | Gammaproteobacteria | Pasteurellales | Pasteurellaceae | *Haemophilus* |
| *Haemophilus* sp. oral clone ASCG06 | Bacteria | Proteobacteria | Gammaproteobacteria | Pasteurellales | Pasteurellaceae | *Haemophilus* |

TABLE 1-continued

| OTU | Domain | Phylum | Class | Order | Family | Genus |
|---|---|---|---|---|---|---|
| *Haemophilus* sp. oral clone BJ021 | Bacteria | Proteobacteria | Gammaproteobacteria | Pasteurellales | Pasteurellaceae | *Haemophilus* |
| *Haemophilus* sp. oral clone BJ095 | Bacteria | Proteobacteria | Gammaproteobacteria | Pasteurellales | Pasteurellaceae | *Haemophilus* |
| *Haemophilus* sp. oral clone JM053 | Bacteria | Proteobacteria | Gammaproteobacteria | Pasteurellales | Pasteurellaceae | *Haemophilus* |
| *Haemophilus* sp. oral taxon 851 | Bacteria | Proteobacteria | Gammaproteobacteria | Pasteurellales | Pasteurellaceae | *Haemophilus* |
| *Haemophilus sputorum* | Bacteria | Proteobacteria | Gammaproteobacteria | Pasteurellales | Pasteurellaceae | *Haemophilus* |
| *Hafnia alvei* | Bacteria | Proteobacteria | Gammaproteobacteria | Enterobacteriales | Enterobacteriaceae | *Hafnia* |
| *Halomonas elongata* | Bacteria | Proteobacteria | Gammaproteobacteria | Oceanospirillales | Halomonadaceae | *Halomonas* |
| *Halomonas johnsoniae* | Bacteria | Proteobacteria | Gammaproteobacteria | Oceanospirillales | Halomonadaceae | *Halomonas* |
| *Halorubrum lipolyticum* | Archaea | Euryarchaeota | Halobacteria | Halobacteriales | Halobacteriaceae | *Halorubrum* |
| *Helicobacter bilis* | Bacteria | Proteobacteria | Epsilonproteobacteria | Campylobacterales | Helicobacteraceae | *Helicobacter* |
| *Helicobacter canadensis* | Bacteria | Proteobacteria | Epsilonproteobacteria | Campylobacterales | Helicobacteraceae | *Helicobacter* |
| *Helicobacter cinaedi* | Bacteria | Proteobacteria | Epsilonproteobacteria | Campylobacterales | Helicobacteraceae | *Helicobacter* |
| *Helicobacter pullorum* | Bacteria | Proteobacteria | Epsilonproteobacteria | Campylobacterales | Helicobacteraceae | *Helicobacter* |
| *Helicobacter* sp. None | Bacteria | Proteobacteria | Epsilonproteobacteria | Campylobacterales | Helicobacteraceae | *Helicobacter* |
| *Helicobacter winghamensis* | Bacteria | Proteobacteria | Epsilonproteobacteria | Campylobacterales | Helicobacteraceae | *Helicobacter* |
| *Heliobacterium modesticaldum* | Bacteria | Firmicutes | Clostridia | Clostridiales | Heliobacteriaceae | *Heliobacterium* |
| *Herbaspirillum seropedicae* | Bacteria | Proteobacteria | Betaproteobacteria | Burkholderiales | Oxalobacteraceae | *Herbaspirillum* |
| *Herbaspirillum* sp. JC206 | Bacteria | Proteobacteria | Betaproteobacteria | Burkholderiales | Oxalobacteraceae | *Herbaspirillum* |
| *Histophilus somni* | Bacteria | Proteobacteria | Gammaproteobacteria | Pasteurellales | Pasteurellaceae | *Histophilus* |
| *Holdemania filiformis* | Bacteria | Firmicutes | Erysipelotrichi | Erysipelotrichales | Erysipelotrichaceae | *Holdemania* |
| *Hydrogenoanaerobacterium saccharovorans* | Bacteria | Firmicutes | Clostridia | Clostridiales | Ruminococcaceae | *Hydrogenoanaerobacterium* |
| *Hyperthermus butylicus* | Archaea | Crenarchaeota | Thermoprotei | Desulfurococcales | Pyrodictiaceae | *Hyperthermus* |
| *Hyphomicrobium sulfonivorans* | Bacteria | Proteobacteria | Alphaproteobacteria | Rhizobiales | Hyphomicrobiaceae | *Hyphomicrobium* |
| *Hyphomonas neptunium* | Bacteria | Proteobacteria | Alphaproteobacteria | Rhodobacterales | Hyphomonadaceae | *Hyphomonas* |
| *Ignatzschineria indica* | Bacteria | Proteobacteria | Gammaproteobacteria | Xanthomonadales | Xanthomonadaceae | *Ignatzschineria* |
| *Ignatzschineria* sp. NML 95-0260 | Bacteria | Proteobacteria | Gammaproteobacteria | Xanthomonadales | Xanthomonadaceae | *Ignatzschineria* |
| *Ignicoccus islandicus* | Archaea | Crenarchaeota | Thermoprotei | Desulfurococcales | Desulfurococcaceae | *Ignicoccus* |
| *Inquilinus limosus* | Bacteria | Proteobacteria | Alphaproteobacteria | Rhodospirillales | Rhodospirillaceae | *Inquilinus* |
| *Janibacter limosus* | Bacteria | Actinobacteria | Actinobacteria | Actinomycetales | Intrasporangiaceae | *Janibacter* |
| *Janibacter melonis* | Bacteria | Actinobacteria | Actinobacteria | Actinomycetales | Intrasporangiaceae | *Janibacter* |
| *Janthinobacterium* sp. SY12 | Bacteria | Proteobacteria | Betaproteobacteria | Burkholderiales | Oxalobacteraceae | *Janthinobacterium* |
| *Johnsonella ignava* | Bacteria | Firmicutes | Clostridia | Clostridiales | Lachnospiraceae | *Johnsonella* |
| *Jonquetella anthropi* | Bacteria | Synergistetes | Synergistia | Synergistales | Synergistaceae | *Jonquetella* |
| *Kerstersia gyiorum* | Bacteria | Proteobacteria | Betaproteobacteria | Burkholderiales | Alcaligenaceae | unclassified |
| *Kingella denitrificans* | Bacteria | Proteobacteria | Betaproteobacteria | Neisseriales | Neisseriaceae | *Kingella* |
| *Kingella* genomosp. P1 oral cone MB2__C20 | Bacteria | Proteobacteria | Betaproteobacteria | Neisseriales | Neisseriaceae | *Kingella* |
| *Kingella kingae* | Bacteria | Proteobacteria | Betaproteobacteria | Neisseriales | Neisseriaceae | *Kingella* |
| *Kingella oralis* | Bacteria | Proteobacteria | Betaproteobacteria | Neisseriales | Neisseriaceae | *Kingella* |
| *Kingella* sp. oral clone ID059 | Bacteria | Proteobacteria | Betaproteobacteria | Neisseriales | Neisseriaceae | *Kingella* |
| *Klebsiella* sp. AS10 | Bacteria | Proteobacteria | Gammaproteobacteria | Enterobacteriales | Enterobacteriaceae | *Klebsiella* |
| *Klebsiella* sp. Co9935 | Bacteria | Proteobacteria | Gammaproteobacteria | Enterobacteriales | Enterobacteriaceae | *Klebsiella* |
| *Klebsiella* sp. enrichment culture clone SRC__DSD25 | Bacteria | Proteobacteria | Gammaproteobacteria | Enterobacteriales | Enterobacteriaceae | *Klebsiella* |
| *Klebsiella* sp. OBRC7 | Bacteria | Proteobacteria | Gammaproteobacteria | Enterobacteriales | Enterobacteriaceae | *Klebsiella* |
| *Klebsiella* sp. SP-BA | Bacteria | Proteobacteria | Gammaproteobacteria | Enterobacteriales | Enterobacteriaceae | *Klebsiella* |
| *Klebsiella* sp. SRC__DSD1 | Bacteria | Proteobacteria | Gammaproteobacteria | Enterobacteriales | Enterobacteriaceae | *Klebsiella* |
| *Klebsiella* sp. SRC__DSD11 | Bacteria | Proteobacteria | Gammaproteobacteria | Enterobacteriales | Enterobacteriaceae | *Klebsiella* |
| *Klebsiella* sp. SRC__DSD12 | Bacteria | Proteobacteria | Gammaproteobacteria | Enterobacteriales | Enterobacteriaceae | *Klebsiella* |
| *Klebsiella* sp. SRC__DSD15 | Bacteria | Proteobacteria | Gammaproteobacteria | Enterobacteriales | Enterobacteriaceae | *Klebsiella* |
| *Klebsiella* sp. SRC__DSD2 | Bacteria | Proteobacteria | Gammaproteobacteria | Enterobacteriales | Enterobacteriaceae | *Klebsiella* |
| *Klebsiella* sp. SRC__DSD6 | Bacteria | Proteobacteria | Gammaproteobacteria | Enterobacteriales | Enterobacteriaceae | *Klebsiella* |
| *Klebsiella variicola* | Bacteria | Proteobacteria | Gammaproteobacteria | Enterobacteriales | Enterobacteriaceae | *Klebsiella* |

TABLE 1-continued

| OTU | Domain | Phylum | Class | Order | Family | Genus |
|---|---|---|---|---|---|---|
| *Kluyvera ascorbata* | Bacteria | Proteobacteria | Gammaproteobacteria | Enterobacteriales | Enterobacteriaceae | *Kluyvera* |
| *Kluyvera cryocrescens* | Bacteria | Proteobacteria | Gammaproteobacteria | Enterobacteriales | Enterobacteriaceae | *Kluyvera* |
| *Kocuria marina* | Bacteria | Actinobacteria | Actinobacteria | Actinomycetales | Micrococcaceae | *Kocuria* |
| *Kocuria palustris* | Bacteria | Actinobacteria | Actinobacteria | Actinomycetales | Micrococcaceae | *Kocuria* |
| *Kocuria rhizophila* | Bacteria | Actinobacteria | Actinobacteria | Actinomycetales | Micrococcaceae | *Kocuria* |
| *Kocuria rosea* | Bacteria | Actinobacteria | Actinobacteria | Actinomycetales | Micrococcaceae | *Kocuria* |
| *Kocuria varians* | Bacteria | Actinobacteria | Actinobacteria | Actinomycetales | Micrococcaceae | *Kocuria* |
| *Lachnobacterium bovis* | Bacteria | Firmicutes | Clostridia | Clostridiales | Lachnospiraceae | *Lachnobacterium* |
| *Lachnospira multipara* | Bacteria | Firmicutes | Clostridia | Clostridiales | Lachnospiraceae | *Lachnospira* |
| *Lachnospira pectinoschiza* | Bacteria | Firmicutes | Clostridia | Clostridiales | Lachnospiraceae | *Lachnospira* |
| Lachnospiraceae bacterium 1_1_57FAA | Bacteria | Firmicutes | Clostridia | Clostridiales | Lachnospiraceae | unclassified |
| Lachnospiraceae bacterium 1_4_56FAA | Bacteria | Firmicutes | Clostridia | Clostridiales | Lachnospiraceae | unclassified |
| Lachnospiraceae bacterium 2_1_46FAA | Bacteria | Firmicutes | Clostridia | Clostridiales | Lachnospiraceae | unclassified |
| Lachnospiraceae bacterium 2_1_58FAA | Bacteria | Firmicutes | Clostridia | Clostridiales | Lachnospiraceae | unclassified |
| Lachnospiraceae bacterium 3_1_57FAA_CT1 | Bacteria | Firmicutes | Clostridia | Clostridiales | Lachnospiraceae | unclassified |
| Lachnospiraceae bacterium 4_1_37FAA | Bacteria | Firmicutes | Clostridia | Clostridiales | Lachnospiraceae | unclassified |
| Lachnospiraceae bacterium 5_1_57FAA | Bacteria | Firmicutes | Clostridia | Clostridiales | Lachnospiraceae | unclassified |
| Lachnospiraceae bacterium 5_1_63FAA | Bacteria | Firmicutes | Clostridia | Clostridiales | Lachnospiraceae | unclassified |
| Lachnospiraceae bacterium 6_1_63FAA | Bacteria | Firmicutes | Clostridia | Clostridiales | Lachnospiraceae | unclassified |
| Lachnospiraceae bacterium 8_1_57FAA | Bacteria | Firmicutes | Clostridia | Clostridiales | Lachnospiraceae | unclassified |
| Lachnospiraceae bacterium 9_1_43BFAA | Bacteria | Firmicutes | Clostridia | Clostridiales | Lachnospiraceae | unclassified |
| Lachnospiraceae bacterium A4 | Bacteria | Firmicutes | Clostridia | Clostridiales | Lachnospiraceae | unclassified |
| Lachnospiraceae bacterium DJF VP30 | Bacteria | Firmicutes | Clostridia | Clostridiales | Lachnospiraceae | unclassified |
| Lachnospiraceae bacterium ICM62 | Bacteria | Firmicutes | Clostridia | Clostridiales | Lachnospiraceae | unclassified |
| Lachnospiraceae bacterium MSX33 | Bacteria | Firmicutes | Clostridia | Clostridiales | Lachnospiraceae | unclassified |
| Lachnospiraceae bacterium oral taxon 107 | Bacteria | Firmicutes | Clostridia | Clostridiales | Lachnospiraceae | unclassified |
| Lachnospiraceae bacterium oral taxon F15 | Bacteria | Firmicutes | Clostridia | Clostridiales | Lachnospiraceae | unclassified |
| Lachnospiraceae genomosp. C1 | Bacteria | Firmicutes | Clostridia | Clostridiales | Lachnospiraceae | unclassified |
| *Lactobacillus acidipiscis* | Bacteria | Firmicutes | Bacilli | Lactobacillales | Lactobacillaceae | *Lactobacillus* |
| *Lactobacillus acidophilus* | Bacteria | Firmicutes | Bacilli | Lactobacillales | Lactobacillaceae | *Lactobacillus* |
| *Lactobacillus alimentarius* | Bacteria | Firmicutes | Bacilli | Lactobacillales | Lactobacillaceae | *Lactobacillus* |
| *Lactobacillus amylolyticus* | Bacteria | Firmicutes | Bacilli | Lactobacillales | Lactobacillaceae | *Lactobacillus* |
| *Lactobacillus amylovorus* | Bacteria | Firmicutes | Bacilli | Lactobacillales | Lactobacillaceae | *Lactobacillus* |
| *Lactobacillus antri* | Bacteria | Firmicutes | Bacilli | Lactobacillales | Lactobacillaceae | *Lactobacillus* |
| *Lactobacillus brevis* | Bacteria | Firmicutes | Bacilli | Lactobacillales | Lactobacillaceae | *Lactobacillus* |
| *Lactobacillus buchneri* | Bacteria | Firmicutes | Bacilli | Lactobacillales | Lactobacillaceae | *Lactobacillus* |
| *Lactobacillus casei* | Bacteria | Firmicutes | Bacilli | Lactobacillales | Lactobacillaceae | *Lactobacillus* |
| *Lactobacillus catenaformis* | Bacteria | Firmicutes | Erysipelotrichi | Erysipelotrichales | Erysipelotrichaceae | *Eggerthia* |
| *Lactobacillus coleohominis* | Bacteria | Firmicutes | Bacilli | Lactobacillales | Lactobacillaceae | *Lactobacillus* |
| *Lactobacillus coryniformis* | Bacteria | Firmicutes | Bacilli | Lactobacillales | Lactobacillaceae | *Lactobacillus* |
| *Lactobacillus crispatus* | Bacteria | Firmicutes | Bacilli | Lactobacillales | Lactobacillaceae | *Lactobacillus* |
| *Lactobacillus curvatus* | Bacteria | Firmicutes | Bacilli | Lactobacillales | Lactobacillaceae | *Lactobacillus* |
| *Lactobacillus delbrueckii* | Bacteria | Firmicutes | Bacilli | Lactobacillales | Lactobacillaceae | *Lactobacillus* |
| *Lactobacillus dextrinicus* | Bacteria | Firmicutes | Bacilli | Lactobacillales | Lactobacillaceae | *Lactobacillus* |
| *Lactobacillus farciminis* | Bacteria | Firmicutes | Bacilli | Lactobacillales | Lactobacillaceae | *Lactobacillus* |
| *Lactobacillus fermentum* | Bacteria | Firmicutes | Bacilli | Lactobacillales | Lactobacillaceae | *Lactobacillus* |
| *Lactobacillus gasseri* | Bacteria | Firmicutes | Bacilli | Lactobacillales | Lactobacillaceae | *Lactobacillus* |
| *Lactobacillus gastricus* | Bacteria | Firmicutes | Bacilli | Lactobacillales | Lactobacillaceae | *Lactobacillus* |
| *Lactobacillus* genomosp. C1 | Bacteria | Firmicutes | Bacilli | Lactobacillales | Lactobacillaceae | *Lactobacillus* |
| *Lactobacillus* genomosp. C2 | Bacteria | Firmicutes | Bacilli | Lactobacillales | Lactobacillaceae | *Lactobacillus* |
| *Lactobacillus helveticus* | Bacteria | Firmicutes | Bacilli | Lactobacillales | Lactobacillaceae | *Lactobacillus* |

TABLE 1-continued

| OTU | Domain | Phylum | Class | Order | Family | Genus |
|---|---|---|---|---|---|---|
| *Lactobacillus hilgardii* | Bacteria | Firmicutes | Bacilli | Lactobacillales | Lactobacillaceae | *Lactobacillus* |
| *Lactobacillus hominis* | Bacteria | Firmicutes | Bacilli | Lactobacillales | Lactobacillaceae | *Lactobacillus* |
| *Lactobacillus iners* | Bacteria | Firmicutes | Bacilli | Lactobacillales | Lactobacillaceae | *Lactobacillus* |
| *Lactobacillus jensenii* | Bacteria | Firmicutes | Bacilli | Lactobacillales | Lactobacillaceae | *Lactobacillus* |
| *Lactobacillus johnsonii* | Bacteria | Firmicutes | Bacilli | Lactobacillales | Lactobacillaceae | *Lactobacillus* |
| *Lactobacillus kalixensis* | Bacteria | Firmicutes | Bacilli | Lactobacillales | Lactobacillaceae | *Lactobacillus* |
| *Lactobacillus kefiranofaciens* | Bacteria | Firmicutes | Bacilli | Lactobacillales | Lactobacillaceae | *Lactobacillus* |
| *Lactobacillus kefiri* | Bacteria | Firmicutes | Bacilli | Lactobacillales | Lactobacillaceae | *Lactobacillus* |
| *Lactobacillus kimchii* | Bacteria | Firmicutes | Bacilli | Lactobacillales | Lactobacillaceae | *Lactobacillus* |
| *Lactobacillus leichmannii* | Bacteria | Firmicutes | Bacilli | Lactobacillales | Lactobacillaceae | *Lactobacillus* |
| *Lactobacillus mucosae* | Bacteria | Firmicutes | Bacilli | Lactobacillales | Lactobacillaceae | *Lactobacillus* |
| *Lactobacillus murinus* | Bacteria | Firmicutes | Bacilli | Lactobacillales | Lactobacillaceae | *Lactobacillus* |
| *Lactobacillus nodensis* | Bacteria | Firmicutes | Bacilli | Lactobacillales | Lactobacillaceae | *Lactobacillus* |
| *Lactobacillus oeni* | Bacteria | Firmicutes | Bacilli | Lactobacillales | Lactobacillaceae | *Lactobacillus* |
| *Lactobacillus oris* | Bacteria | Firmicutes | Bacilli | Lactobacillales | Lactobacillaceae | *Lactobacillus* |
| *Lactobacillus parabrevis* | Bacteria | Firmicutes | Bacilli | Lactobacillales | Lactobacillaceae | *Lactobacillus* |
| *Lactobacillus parabuchneri* | Bacteria | Firmicutes | Bacilli | Lactobacillales | Lactobacillaceae | *Lactobacillus* |
| *Lactobacillus paracasei* | Bacteria | Firmicutes | Bacilli | Lactobacillales | Lactobacillaceae | *Lactobacillus* |
| *Lactobacillus parakefiri* | Bacteria | Firmicutes | Bacilli | Lactobacillales | Lactobacillaceae | *Lactobacillus* |
| *Lactobacillus pentosus* | Bacteria | Firmicutes | Bacilli | Lactobacillales | Lactobacillaceae | *Lactobacillus* |
| *Lactobacillus perolens* | Bacteria | Firmicutes | Bacilli | Lactobacillales | Lactobacillaceae | *Lactobacillus* |
| *Lactobacillus plantarum* | Bacteria | Firmicutes | Bacilli | Lactobacillales | Lactobacillaceae | *Lactobacillus* |
| *Lactobacillus pontis* | Bacteria | Firmicutes | Bacilli | Lactobacillales | Lactobacillaceae | *Lactobacillus* |
| *Lactobacillus reuteri* | Bacteria | Firmicutes | Bacilli | Lactobacillales | Lactobacillaceae | *Lactobacillus* |
| *Lactobacillus rhamnosus* | Bacteria | Firmicutes | Bacilli | Lactobacillales | Lactobacillaceae | *Lactobacillus* |
| *Lactobacillus rogosae* | Bacteria | Firmicutes | Bacilli | Lactobacillales | Lactobacillaceae | *Lactobacillus* |
| *Lactobacillus ruminis* | Bacteria | Firmicutes | Bacilli | Lactobacillales | Lactobacillaceae | *Lactobacillus* |
| *Lactobacillus sakei* | Bacteria | Firmicutes | Bacilli | Lactobacillales | Lactobacillaceae | *Lactobacillus* |
| *Lactobacillus salivarius* | Bacteria | Firmicutes | Bacilli | Lactobacillales | Lactobacillaceae | *Lactobacillus* |
| *Lactobacillus saniviri* | Bacteria | Firmicutes | Bacilli | Lactobacillales | Lactobacillaceae | *Lactobacillus* |
| *Lactobacillus senioris* | Bacteria | Firmicutes | Bacilli | Lactobacillales | Lactobacillaceae | *Lactobacillus* |
| *Lactobacillus* sp. 66c | Bacteria | Firmicutes | Bacilli | Lactobacillales | Lactobacillaceae | *Lactobacillus* |
| *Lactobacillus* sp. BT6 | Bacteria | Firmicutes | Bacilli | Lactobacillales | Lactobacillaceae | *Lactobacillus* |
| *Lactobacillus* sp. KLDS 1.0701 | Bacteria | Firmicutes | Bacilli | Lactobacillales | Lactobacillaceae | *Lactobacillus* |
| *Lactobacillus* sp. KLDS 1.0702 | Bacteria | Firmicutes | Bacilli | Lactobacillales | Lactobacillaceae | *Lactobacillus* |
| *Lactobacillus* sp. KLDS 1.0703 | Bacteria | Firmicutes | Bacilli | Lactobacillales | Lactobacillaceae | *Lactobacillus* |
| *Lactobacillus* sp. KLDS 1.0704 | Bacteria | Firmicutes | Bacilli | Lactobacillales | Lactobacillaceae | *Lactobacillus* |
| *Lactobacillus* sp. KLDS 1.0705 | Bacteria | Firmicutes | Bacilli | Lactobacillales | Lactobacillaceae | *Lactobacillus* |
| *Lactobacillus* sp. KLDS 1.0707 | Bacteria | Firmicutes | Bacilli | Lactobacillales | Lactobacillaceae | *Lactobacillus* |
| *Lactobacillus* sp. KLDS 1.0709 | Bacteria | Firmicutes | Bacilli | Lactobacillales | Lactobacillaceae | *Lactobacillus* |
| *Lactobacillus* sp. KLDS 1.0711 | Bacteria | Firmicutes | Bacilli | Lactobacillales | Lactobacillaceae | *Lactobacillus* |
| *Lactobacillus* sp. KLDS 1.0712 | Bacteria | Firmicutes | Bacilli | Lactobacillales | Lactobacillaceae | *Lactobacillus* |
| *Lactobacillus* sp. KLDS 1.0713 | Bacteria | Firmicutes | Bacilli | Lactobacillales | Lactobacillaceae | *Lactobacillus* |
| *Lactobacillus* sp. KLDS 1.0716 | Bacteria | Firmicutes | Bacilli | Lactobacillales | Lactobacillaceae | *Lactobacillus* |
| *Lactobacillus* sp. KLDS 1.0718 | Bacteria | Firmicutes | Bacilli | Lactobacillales | Lactobacillaceae | *Lactobacillus* |
| *Lactobacillus* sp. KLDS 1.0719 | Bacteria | Firmicutes | Bacilli | Lactobacillales | Lactobacillaceae | *Lactobacillus* |
| *Lactobacillus* sp. oral clone HT002 | Bacteria | Firmicutes | Bacilli | Lactobacillales | Lactobacillaceae | *Lactobacillus* |
| *Lactobacillus* sp. oral clone HT070 | Bacteria | Firmicutes | Bacilli | Lactobacillales | Lactobacillaceae | *Lactobacillus* |
| *Lactobacillus* sp. oral taxon 052 | Bacteria | Firmicutes | Bacilli | Lactobacillales | Lactobacillaceae | *Lactobacillus* |
| *Lactobacillus tucceti* | Bacteria | Firmicutes | Bacilli | Lactobacillales | Lactobacillaceae | *Lactobacillus* |
| *Lactobacillus ultunensis* | Bacteria | Firmicutes | Bacilli | Lactobacillales | Lactobacillaceae | *Lactobacillus* |

TABLE 1-continued

| OTU | Domain | Phylum | Class | Order | Family | Genus |
|---|---|---|---|---|---|---|
| *Lactobacillus vaginalis* | Bacteria | Firmicutes | Bacilli | Lactobacillales | Lactobacillaceae | *Lactobacillus* |
| *Lactobacillus vini* | Bacteria | Firmicutes | Bacilli | Lactobacillales | Lactobacillaceae | *Lactobacillus* |
| *Lactobacillus vitulinus* | Bacteria | Firmicutes | Erysipelotrichi | Erysipelotrichales | Erysipelotrichaceae | *Kandleria* |
| *Lactobacillus zeae* | Bacteria | Firmicutes | Bacilli | Lactobacillales | Lactobacillaceae | *Lactobacillus* |
| *Lactococcus garvieae* | Bacteria | Firmicutes | Bacilli | Lactobacillales | Streptococcaceae | *Lactococcus* |
| *Lactococcus lactis* | Bacteria | Firmicutes | Bacilli | Lactobacillales | Streptococcaceae | *Lactococcus* |
| *Lactococcus raffinolactis* | Bacteria | Firmicutes | Bacilli | Lactobacillales | Streptococcaceae | *Lactococcus* |
| *Lactonifactor longoviformis* | Bacteria | Firmicutes | Clostridia | Clostridiales | Clostridiaceae | *Lactonifactor* |
| *Laribacter hongkongensis* | Bacteria | Proteobacteria | Betaproteobacteria | Neisseriales | Neisseriaceae | *Laribacter* |
| *Lautropia mirabilis* | Bacteria | Proteobacteria | Betaproteobacteria | Burkholderiales | Burkholderiaceae | *Lautropia* |
| *Lautropia* sp. oral clone AP009 | Bacteria | Proteobacteria | Betaproteobacteria | Burkholderiales | Burkholderiaceae | *Lautropia* |
| *Leminorella grimontii* | Bacteria | Proteobacteria | Gammaproteobacteria | Enterobacteriales | Enterobacteriaceae | *Leminorella* |
| *Leminorella richardii* | Bacteria | Proteobacteria | Gammaproteobacteria | Enterobacteriales | Enterobacteriaceae | *Leminorella* |
| *Leptotrichia buccalis* | Bacteria | Fusobacteria | Fusobacteriia | Fusobacteriales | Leptotrichiaceae | *Leptotrichia* |
| *Leptotrichia* genomosp. C1 | Bacteria | Fusobacteria | Fusobacteriia | Fusobacteriales | Leptotrichiaceae | *Leptotrichia* |
| *Leptotrichia goodfellowii* | Bacteria | Fusobacteria | Fusobacteriia | Fusobacteriales | Leptotrichiaceae | *Leptotrichia* |
| *Leptotrichia hofstadii* | Bacteria | Fusobacteria | Fusobacteriia | Fusobacteriales | Leptotrichiaceae | *Leptotrichia* |
| *Leptotrichia shahii* | Bacteria | Fusobacteria | Fusobacteriia | Fusobacteriales | Leptotrichiaceae | *Leptotrichia* |
| *Leptotrichia* sp. neutropenicPatient | Bacteria | Fusobacteria | Fusobacteria | Fusobacteriales | Leptotrichiaceae | *Leptotrichia* |
| *Leptotrichia* sp. oral clone GT018 | Bacteria | Fusobacteria | Fusobacteriia | Fusobacteriales | Leptotrichiaceae | *Leptotrichia* |
| *Leptotrichia* sp. oral clone GT020 | Bacteria | Fusobacteria | Fusobacteriia | Fusobacteriales | Leptotrichiaceae | *Leptotrichia* |
| *Leptotrichia* sp. oral clone HE012 | Bacteria | Fusobacteria | Fusobacteriia | Fusobacteriales | Leptotrichiaceae | *Leptotrichia* |
| *Leptotrichia* sp. oral clone IK040 | Bacteria | Fusobacteria | Fusobacteriia | Fusobacteriales | Leptotrichiaceae | *Leptotrichia* |
| *Leptotrichia* sp. oral clone P2PB_51 P1 | Bacteria | Fusobacteria | Fusobacteriia | Fusobacteriales | Leptotrichiaceae | *Leptotrichia* |
| *Leptotrichia* sp. oral taxon 223 | Bacteria | Fusobacteria | Fusobacteriia | Fusobacteriales | Leptotrichiaceae | *Leptotrichia* |
| *Leuconostoc carnosum* | Bacteria | Firmicutes | Bacilli | Lactobacillales | Leuconostocaceae | *Leuconostoc* |
| *Leuconostoc citreum* | Bacteria | Firmicutes | Bacilli | Lactobacillales | Leuconostocaceae | *Leuconostoc* |
| *Leuconostoc gasicomitatum* | Bacteria | Firmicutes | Bacilli | Lactobacillales | Leuconostocaceae | *Leuconostoc* |
| *Leuconostoc inhae* | Bacteria | Firmicutes | Bacilli | Lactobacillales | Leuconostocaceae | *Leuconostoc* |
| *Leuconostoc kimchii* | Bacteria | Firmicutes | Bacilli | Lactobacillales | Leuconostocaceae | *Leuconostoc* |
| *Leuconostoc lactis* | Bacteria | Firmicutes | Bacilli | Lactobacillales | Leuconostocaceae | *Leuconostoc* |
| *Leuconostoc mesenteroides* | Bacteria | Firmicutes | Bacilli | Lactobacillales | Leuconostocaceae | *Leuconostoc* |
| *Leuconostoc pseudomesenteroides* | Bacteria | Firmicutes | Bacilli | Lactobacillales | Leuconostocaceae | *Leuconostoc* |
| *Listeria innocua* | Bacteria | Firmicutes | Bacilli | Bacillales | Listeriaceae | *Listeria* |
| *Listeria ivanovii* | Bacteria | Firmicutes | Bacilli | Bacillales | Listeriaceae | *Listeria* |
| *Luteococcus sanguinis* | Bacteria | Actinobacteria | Actinobacteria | Actinomycetales | Propionibacteriaceae | *Luteococcus* |
| *Lutispora thermophila* | Bacteria | Firmicutes | Clostridia | Clostridiales | Clostridiaceae | *Lutispora* |
| *Lysinibacillus fusiformis* | Bacteria | Firmicutes | Bacilli | Bacillales | Bacillaceae | *Lysinibacillus* |
| *Lysinibacillus sphaericus* | Bacteria | Firmicutes | Bacilli | Bacillales | Bacillaceae | *Lysinibacillus* |
| *Macrococcus caseolyticus* | Bacteria | Firmicutes | Bacilli | Bacillales | Staphylococcaceae | *Macrococcus* |
| *Mannheimia haemolytica* | Bacteria | Proteobacteria | Gammaproteobacteria | Pasteurellales | Pasteurellaceae | *Mannheimia* |
| *Marvinbryantia formatexigens* | Bacteria | Firmicutes | Clostridia | Clostridiales | Lachnospiraceae | unclassified |
| *Massilia* sp. CCUG 43427A | Bacteria | Proteobacteria | Betaproteobacteria | Burkholderiales | Oxalobacteraceae | *Massilia* |
| *Megamonas funiformis* | Bacteria | Firmicutes | Negativicutes | Selenomonadales | Veillonellaceae | *Megamonas* |
| *Megamonas hypermegale* | Bacteria | Firmicutes | Negativicutes | Selenomonadales | Veillonellaceae | *Megamonas* |
| *Megasphaera elsdenii* | Bacteria | Firmicutes | Negativicutes | Selenomonadales | Veillonellaceae | *Megasphaera* |
| *Megasphaera* genomosp. C1 | Bacteria | Firmicutes | Negativicutes | Selenomonadales | Veillonellaceae | *Megasphaera* |
| *Megasphaera* genomosp. type_1 | Bacteria | Firmicutes | Negativicutes | Selenomonadales | Veillonellaceae | *Megasphaera* |
| *Megasphaera micronuciformis* | Bacteria | Firmicutes | Negativicutes | Selenomonadales | Veillonellaceae | *Megasphaera* |
| *Megasphaera* sp. BLPYG-07 | Bacteria | Firmicutes | Negativicutes | Selenomonadales | Veillonellaceae | *Megasphaera* |
| *Megasphaera* sp. UPII 199-6 | Bacteria | Firmicutes | Negativicutes | Selenomonadales | Veillonellaceae | *Megasphaera* |

TABLE 1-continued

| OTU | Domain | Phylum | Class | Order | Family | Genus |
|---|---|---|---|---|---|---|
| *Metallosphaera sedula* | Archaea | Crenarchaeota | Thermoprotei | Sulfolobales | Sulfolobaceae | *Metallosphaera* |
| *Methanobacterium formicicum* | Archaea | Euryarchaeota | Methanobacteria | Methanobacteriales | Methanobacteriaceae | *Methanobacterium* |
| *Methanobrevibacter acididurans* | Archaea | Euryarchaeota | Methanobacteria | Methanobacteriales | Methanobacteriaceae | *Methanobrevibacter* |
| *Methanobrevibacter arboriphilus* | Archaea | Euryarchaeota | Methanobacteria | Methanobacteriales | Methanobacteriaceae | *Methanobrevibacter* |
| *Methanobrevibacter curvatus* | Archaea | Euryarchaeota | Methanobacteria | Methanobacteriales | Methanobacteriaceae | *Methanobrevibacter* |
| *Methanobrevibacter cuticularis* | Archaea | Euryarchaeota | Methanobacteria | Methanobacteriales | Methanobacteriaceae | *Methanobrevibacter* |
| *Methanobrevibacter filiformis* | Archaea | Euryarchaeota | Methanobacteria | Methanobacteriales | Methanobacteriaceae | *Methanobrevibacter* |
| *Methanobrevibacter gottschalkii* | Archaea | Euryarchaeota | Methanobacteria | Methanobacteriales | Methanobacteriaceae | *Methanobrevibacter* |
| *Methanobrevibacter millerae* | Archaea | Euryarchaeota | Methanobacteria | Methanobacteriales | Methanobacteriaceae | *Methanobrevibacter* |
| *Methanobrevibacter olleyae* | Archaea | Euryarchaeota | Methanobacteria | Methanobacteriales | Methanobacteriaceae | *Methanobrevibacter* |
| *Methanobrevibacter oralis* | Archaea | Euryarchaeota | Methanobacteria | Methanobacteriales | Methanobacteriaceae | *Methanobrevibacter* |
| *Methanobrevibacter ruminantium* | Archaea | Euryarchaeota | Methanobacteria | Methanobacteriales | Methanobacteriaceae | *Methanobrevibacter* |
| *Methanobrevibacter smithii* | Archaea | Euryarchaeota | Methanobacteria | Methanobacteriales | Methanobacteriaceae | *Methanobrevibacter* |
| *Methanobrevibacter thaueri* | Archaea | Euryarchaeota | Methanobacteria | Methanobacteriales | Methanobacteriaceae | *Methanobrevibacter* |
| *Methanobrevibacter woesei* | Archaea | Euryarchaeota | Methanobacteria | Methanobacteriales | Methanobacteriaceae | *Methanobrevibacter* |
| *Methanobrevibacter wolinii* | Archaea | Euryarchaeota | Methanobacteria | Methanobacteriales | Methanobacteriaceae | *Methanobrevibacter* |
| *Methanosphaera stadtmanae* | Archaea | Euryarchaeota | Methanobacteria | Methanobacteriales | Methanobacteriaceae | *Methanosphaera* |
| *Methylobacterium extorquens* | Bacteria | Proteobacteria | Alphaproteobacteria | Rhizobiales | Methylobacteriaceae | *Methylobacterium* |
| *Methylobacterium podarium* | Bacteria | Proteobacteria | Alphaproteobacteria | Rhizobiales | Methylobacteriaceae | *Methylobacterium* |
| *Methylobacterium radiotolerans* | Bacteria | Proteobacteria | Alphaproteobacteria | Rhizobiales | Methylobacteriaceae | *Methylobacterium* |
| *Methylobacterium* sp. 1sub | Bacteria | Proteobacteria | Alphaproteobacteria | Rhizobiales | Methylobacteriaceae | *Methylobacterium* |
| *Methylobacterium* sp. MM4 | Bacteria | Proteobacteria | Alphaproteobacteria | Rhizobiales | Methylobacteriaceae | *Methylobacterium* |
| *Methylocella silvestris* | Bacteria | Proteobacteria | Alphaproteobacteria | Rhizobiales | Beijerinckiaceae | *Methylocella* |
| *Methylophilus* sp. ECd5 | Bacteria | Proteobacteria | Betaproteobacteria | Methylophilales | Methylophilaceae | *Methylophilus* |
| *Microbacterium chocolatum* | Bacteria | Actinobacteria | Actinobacteria | Actinomycetales | Microbacteriaceae | *Microbacterium* |
| *Microbacterium flavescens* | Bacteria | Actinobacteria | Actinobacteria | Actinomycetales | Microbacteriaceae | *Microbacterium* |
| *Microbacterium gubbeenense* | Bacteria | Actinobacteria | Actinobacteria | Actinomycetales | Microbacteriaceae | *Microbacterium* |
| *Microbacterium lacticum* | Bacteria | Actinobacteria | Actinobacteria | Actinomycetales | Microbacteriaceae | *Microbacterium* |
| *Microbacterium oleivorans* | Bacteria | Actinobacteria | Actinobacteria | Actinomycetales | Microbacteriaceae | *Microbacterium* |
| *Microbacterium oxydans* | Bacteria | Actinobacteria | Actinobacteria | Actinomycetales | Microbacteriaceae | *Microbacterium* |
| *Microbacterium paraoxydans* | Bacteria | Actinobacteria | Actinobacteria | Actinomycetales | Microbacteriaceae | *Microbacterium* |
| *Microbacterium phyllosphaerae* | Bacteria | Actinobacteria | Actinobacteria | Actinomycetales | Microbacteriaceae | *Microbacterium* |
| *Microbacterium schleiferi* | Bacteria | Actinobacteria | Actinobacteria | Actinomycetales | Microbacteriaceae | *Microbacterium* |
| *Microbacterium* sp. 768 | Bacteria | Actinobacteria | Actinobacteria | Actinomycetales | Microbacteriaceae | *Microbacterium* |
| *Microbacterium* sp. oral strain C24KA | Bacteria | Actinobacteria | Actinobacteria | Actinomycetales | Microbacteriaceae | *Microbacterium* |
| *Microbacterium testaceum* | Bacteria | Actinobacteria | Actinobacteria | Actinomycetales | Microbacteriaceae | *Microbacterium* |
| *Micrococcus antarcticus* | Bacteria | Actinobacteria | Actinobacteria | Actinomycetales | Micrococcaceae | *Micrococcus* |
| *Micrococcus luteus* | Bacteria | Actinobacteria | Actinobacteria | Actinomycetales | Micrococcaceae | *Micrococcus* |
| *Micrococcus lylae* | Bacteria | Actinobacteria | Actinobacteria | Actinomycetales | Micrococcaceae | *Micrococcus* |
| *Micrococcus* sp. 185 | Bacteria | Actinobacteria | Actinobacteria | Actinomycetales | Micrococcaceae | *Micrococcus* |
| *Microcystis aeruginosa* | Bacteria | Cyanobacteria | unclassified | Chroococcales | unclassified | *Microcystis* |
| *Mitsuokella jalaludinii* | Bacteria | Firmicutes | Negativicutes | Selenomonadales | Veillonellaceae | *Mitsuokella* |
| *Mitsuokella multacida* | Bacteria | Firmicutes | Negativicutes | Selenomonadales | Veillonellaceae | *Mitsuokella* |
| *Mitsuokella* sp. oral taxon 521 | Bacteria | Firmicutes | Negativicutes | Selenomonadales | Veillonellaceae | *Mitsuokella* |
| *Mitsuokella* sp. oral taxon G68 | Bacteria | Firmicutes | Negativicutes | Selenomonadales | Veillonellaceae | *Mitsuokella* |
| *Mobiluncus curtisii* | Bacteria | Actinobacteria | Actinobacteria | Actinomycetales | Actinomycetaceae | *Mobiluncus* |
| *Mobiluncus mulieris* | Bacteria | Actinobacteria | Actinobacteria | Actinomycetales | Actinomycetaceae | *Mobiluncus* |
| *Moellerella wisconsensis* | Bacteria | Proteobacteria | Gammaproteobacteria | Enterobacteriales | Enterobacteriaceae | *Moellerella* |
| *Mogibacterium diversum* | Bacteria | Firmicutes | Clostridia | Clostridiales | Clostridiales Family XIII. Incertae Sedis | *Mogibacterium* |
| *Mogibacterium neglectum* | Bacteria | Firmicutes | Clostridia | Clostridiales | Clostridiales Family XIII. Incertae Sedis | *Mogibacterium* |
| *Mogibacterium pumilum* | Bacteria | Firmicutes | Clostridia | Clostridiales | Clostridiales Family XIII. Incertae Sedis | *Mogibacterium* |

TABLE 1-continued

| OTU | Domain | Phylum | Class | Order | Family | Genus |
|---|---|---|---|---|---|---|
| *Mogibacterium timidum* | Bacteria | Firmicutes | Clostridia | Clostridiales | Clostridiales Family XIII. Incertae Sedis | *Mogibacterium* |
| Mollicutes bacterium pACH93 | Bacteria | Tenericutes | Mollicutes | unclassified | unclassified | unclassified |
| *Moorella thermoacetica* | Bacteria | Firmicutes | Clostridia | Thermoanaerobacterales | Thermoanaerobacteraceae | *Moorella* |
| *Moraxella catarrhalis* | Bacteria | Proteobacteria | Gammaproteobacteria | Pseudomonadales | Moraxellaceae | *Moraxella* |
| *Moraxella lincolnii* | Bacteria | Proteobacteria | Gammaproteobacteria | Pseudomonadales | Moraxellaceae | *Moraxella* |
| *Moraxella osloensis* | Bacteria | Proteobacteria | Gammaproteobacteria | Pseudomonadales | Moraxellaceae | *Moraxella* |
| *Moraxella* sp. 16285 | Bacteria | Proteobacteria | Gammaproteobacteria | Pseudomonadales | Moraxellaceae | *Moraxella* |
| *Moraxella* sp. GM2 | Bacteria | Proteobacteria | Gammaproteobacteria | Pseudomonadales | Moraxellaceae | *Moraxella* |
| *Morganella morganii* | Bacteria | Proteobacteria | Gammaproteobacteria | Enterobacteriales | Enterobacteriaceae | *Morganella* |
| *Morganella* sp. JB-T16 | Bacteria | Proteobacteria | Gammaproteobacteria | Enterobacteriales | Enterobacteriaceae | *Morganella* |
| *Morococcus cerebrosus* | Bacteria | Proteobacteria | Betaproteobacteria | Neisseriales | Neisseriaceae | *Morococcus* |
| *Moryella indoligenes* | Bacteria | Firmicutes | Clostridia | Clostridiales | Lachnospiraceae | *Moryella* |
| *Mycobacterium* sp. 1761 | Bacteria | Actinobacteria | Actinobacteria | Actinomycetales | Mycobacteriaceae | *Mycobacterium* |
| *Mycobacterium* sp. 1776 | Bacteria | Actinobacteria | Actinobacteria | Actinomycetales | Mycobacteriaceae | *Mycobacterium* |
| *Mycobacterium* sp. 1781 | Bacteria | Actinobacteria | Actinobacteria | Actinomycetales | Mycobacteriaceae | *Mycobacterium* |
| *Mycobacterium* sp. 1791 | Bacteria | Actinobacteria | Actinobacteria | Actinomycetales | Mycobacteriaceae | *Mycobacterium* |
| *Mycobacterium* sp. 1797 | Bacteria | Actinobacteria | Actinobacteria | Actinomycetales | Mycobacteriaceae | *Mycobacterium* |
| *Mycobacterium* sp. AQ1GA4 | Bacteria | Actinobacteria | Actinobacteria | Actinomycetales | Mycobacteriaceae | *Mycobacterium* |
| *Mycobacterium* sp. B10-07.09.0206 | Bacteria | Actinobacteria | Actinobacteria | Actinomycetales | Mycobacteriaceae | *Mycobacterium* |
| *Mycobacterium* sp. GN-10546 | Bacteria | Actinobacteria | Actinobacteria | Actinomycetales | Mycobacteriaceae | *Mycobacterium* |
| *Mycobacterium* sp. GN-10827 | Bacteria | Actinobacteria | Actinobacteria | Actinomycetales | Mycobacteriaceae | *Mycobacterium* |
| *Mycobacterium* sp. GN-11124 | Bacteria | Actinobacteria | Actinobacteria | Actinomycetales | Mycobacteriaceae | *Mycobacterium* |
| *Mycobacterium* sp. GN-9188 | Bacteria | Actinobacteria | Actinobacteria | Actinomycetales | Mycobacteriaceae | *Mycobacterium* |
| *Mycobacterium* sp. GR-2007-210 | Bacteria | Actinobacteria | Actinobacteria | Actinomycetales | Mycobacteriaceae | *Mycobacterium* |
| *Mycobacterium* sp. HE5 | Bacteria | Actinobacteria | Actinobacteria | Actinomycetales | Mycobacteriaceae | *Mycobacterium* |
| *Mycobacterium* sp. NLA001000736 | Bacteria | Actinobacteria | Actinobacteria | Actinomycetales | Mycobacteriaceae | *Mycobacterium* |
| *Mycobacterium* sp. W | Bacteria | Actinobacteria | Actinobacteria | Actinomycetales | Mycobacteriaceae | *Mycobacterium* |
| *Mycoplasma agalactiae* | Bacteria | Tenericutes | Mollicutes | Mycoplasmatales | Mycoplasmataceae | *Mycoplasma* |
| *Mycoplasma amphoriforme* | Bacteria | Tenericutes | Mollicutes | Mycoplasmatales | Mycoplasmataceae | *Mycoplasma* |
| *Mycoplasma arthritidis* | Bacteria | Tenericutes | Mollicutes | Mycoplasmatales | Mycoplasmataceae | *Mycoplasma* |
| *Mycoplasma bovoculi* | Bacteria | Tenericutes | Mollicutes | Mycoplasmatales | Mycoplasmataceae | *Mycoplasma* |
| *Mycoplasma faucium* | Bacteria | Tenericutes | Mollicutes | Mycoplasmatales | Mycoplasmataceae | *Mycoplasma* |
| *Mycoplasma fermentans* | Bacteria | Tenericutes | Mollicutes | Mycoplasmatales | Mycoplasmataceae | *Mycoplasma* |
| *Mycoplasma flocculare* | Bacteria | Tenericutes | Mollicutes | Mycoplasmatales | Mycoplasmataceae | *Mycoplasma* |
| *Mycoplasma genitalium* | Bacteria | Tenericutes | Mollicutes | Mycoplasmatales | Mycoplasmataceae | *Mycoplasma* |
| *Mycoplasma hominis* | Bacteria | Tenericutes | Mollicutes | Mycoplasmatales | Mycoplasmataceae | *Mycoplasma* |
| *Mycoplasma orale* | Bacteria | Tenericutes | Mollicutes | Mycoplasmatales | Mycoplasmataceae | *Mycoplasma* |
| *Mycoplasma ovipneumoniae* | Bacteria | Tenericutes | Mollicutes | Mycoplasmatales | Mycoplasmataceae | *Mycoplasma* |
| *Mycoplasma penetrans* | Bacteria | Tenericutes | Mollicutes | Mycoplasmatales | Mycoplasmataceae | *Mycoplasma* |
| *Mycoplasma pneumoniae* | Bacteria | Tenericutes | Mollicutes | Mycoplasmatales | Mycoplasmataceae | *Mycoplasma* |
| *Mycoplasma putrefaciens* | Bacteria | Tenericutes | Mollicutes | Mycoplasmatales | Mycoplasmataceae | *Mycoplasma* |
| *Mycoplasma salivarium* | Bacteria | Tenericutes | Mollicutes | Mycoplasmatales | Mycoplasmataceae | *Mycoplasma* |
| Mycoplasmataceae genomosp. P1 oral clone MB1__G23 | Bacteria | Tenericutes | Mollicutes | Mycoplasmatales | Mycoplasmataceae | unclassified |
| *Myroides odoratimimus* | Bacteria | Bacteroidetes | Flavobacteriia | Flavobacteriales | Flavobacteriaceae | *Myroides* |
| *Myroides* sp. MY15 | Bacteria | Bacteroidetes | Flavobacteriia | Flavobacteriales | Flavobacteriaceae | *Myroides* |
| *Neisseria bacilliformis* | Bacteria | Proteobacteria | Betaproteobacteria | Neisseriales | Neisseriaceae | *Neisseria* |
| *Neisseria cinerea* | Bacteria | Proteobacteria | Betaproteobacteria | Neisseriales | Neisseriaceae | *Neisseria* |
| *Neisseria elongata* | Bacteria | Proteobacteria | Betaproteobacteria | Neisseriales | Neisseriaceae | *Neisseria* |
| *Neisseria flavescens* | Bacteria | Proteobacteria | Betaproteobacteria | Neisseriales | Neisseriaceae | *Neisseria* |
| *Neisseria* genomosp. P2 oral clone MB5__P15 | Bacteria | Proteobacteria | Betaproteobacteria | Neisseriales | Neisseriaceae | *Neisseria* |
| *Neisseria lactamica* | Bacteria | Proteobacteria | Betaproteobacteria | Neisseriales | Neisseriaceae | *Neisseria* |

TABLE 1-continued

| OTU | Domain | Phylum | Class | Order | Family | Genus |
|---|---|---|---|---|---|---|
| *Neisseria macacae* | Bacteria | Proteobacteria | Betaproteobacteria | Neisseriales | Neisseriaceae | *Neisseria* |
| *Neisseria mucosa* | Bacteria | Proteobacteria | Betaproteobacteria | Neisseriales | Neisseriaceae | *Neisseria* |
| *Neisseria pharyngis* | Bacteria | Proteobacteria | Betaproteobacteria | Neisseriales | Neisseriaceae | *Neisseria* |
| *Neisseria polysaccharea* | Bacteria | Proteobacteria | Betaproteobacteria | Neisseriales | Neisseriaceae | *Neisseria* |
| *Neisseria sicca* | Bacteria | Proteobacteria | Betaproteobacteria | Neisseriales | Neisseriaceae | *Neisseria* |
| *Neisseria* sp. KEM232 | Bacteria | Proteobacteria | Betaproteobacteria | Neisseriales | Neisseriaceae | *Neisseria* |
| *Neisseria* sp. oral clone AP132 | Bacteria | Proteobacteria | Betaproteobacteria | Neisseriales | Neisseriaceae | *Neisseria* |
| *Neisseria* sp. oral clone JC012 | Bacteria | Proteobacteria | Betaproteobacteria | Neisseriales | Neisseriaceae | *Neisseria* |
| *Neisseria* sp. oral strain B33KA | Bacteria | Proteobacteria | Betaproteobacteria | Neisseriales | Neisseriaceae | *Neisseria* |
| *Neisseria* sp. oral taxon 014 | Bacteria | Proteobacteria | Betaproteobacteria | Neisseriales | Neisseriaceae | *Neisseria* |
| *Neisseria* sp. SMC-A9199 | Bacteria | Proteobacteria | Betaproteobacteria | Neisseriales | Neisseriaceae | *Neisseria* |
| *Neisseria* sp. TM10_1 | Bacteria | Proteobacteria | Betaproteobacteria | Neisseriales | Neisseriaceae | *Neisseria* |
| *Neisseria subflava* | Bacteria | Proteobacteria | Betaproteobacteria | Neisseriales | Neisseriaceae | *Neisseria* |
| *Neorickettsia risticii* | Bacteria | Proteobacteria | Alphaproteobacteria | Rickettsiales | Anaplasmataceae | *Neorickettsia* |
| *Neorickettsia sennetsu* | Bacteria | Proteobacteria | Alphaproteobacteria | Rickettsiales | Anaplasmataceae | *Neorickettsia* |
| *Nocardia brasiliensis* | Bacteria | Actinobacteria | Actinobacteria | Actinomycetales | Nocardiaceae | *Nocardia* |
| *Nocardia cyriacigeorgica* | Bacteria | Actinobacteria | Actinobacteria | Actinomycetales | Nocardiaceae | *Nocardia* |
| *Nocardia farcinica* | Bacteria | Actinobacteria | Actinobacteria | Actinomycetales | Nocardiaceae | *Nocardia* |
| *Nocardia puris* | Bacteria | Actinobacteria | Actinobacteria | Actinomycetales | Nocardiaceae | *Nocardia* |
| *Nocardia* sp. 01-Je-025 | Bacteria | Actinobacteria | Actinobacteria | Actinomycetales | Nocardiaceae | *Nocardia* |
| *Nocardiopsis dassonvillei* | Bacteria | Actinobacteria | Actinobacteria | Actinomycetales | Nocardiopsaceae | *Nocardiopsis* |
| *Novosphingobium aromaticivorans* | Bacteria | Proteobacteria | Alphaproteobacteria | Sphingomonadales | Sphingomonadaceae | *Novosphingobium* |
| *Oceanobacillus caeni* | Bacteria | Firmicutes | Bacilli | Bacillales | Bacillaceae | *Oceanobacillus* |
| *Oceanobacillus* sp. Ndiop | Bacteria | Firmicutes | Bacilli | Bacillales | Bacillaceae | *Oceanobacillus* |
| *Ochrobactrum anthropi* | Bacteria | Proteobacteria | Alphaproteobacteria | Rhizobiales | Brucellaceae | *Ochrobactrum* |
| *Ochrobactrum intermedium* | Bacteria | Proteobacteria | Alphaproteobacteria | Rhizobiales | Brucellaceae | *Ochrobactrum* |
| *Ochrobactrum pseudintermedium* | Bacteria | Proteobacteria | Alphaproteobacteria | Rhizobiales | Brucellaceae | *Ochrobactrum* |
| *Odoribacter laneus* | Bacteria | Bacteroidetes | Bacteroidia | Bacteroidales | Porphyromonadaceae | *Odoribacter* |
| *Odoribacter splanchnicus* | Bacteria | Bacteroidetes | Bacteroidia | Bacteroidales | Porphyromonadaceae | *Odoribacter* |
| *Okadaella gastrococcus* | Bacteria | Firmicutes | Bacilli | Lactobacillales | Streptococcaceae | *Okadaella* |
| *Oligella ureolytica* | Bacteria | Proteobacteria | Betaproteobacteria | Burkholderiales | Alcaligenaceae | *Oligella* |
| *Oligella urethralis* | Bacteria | Proteobacteria | Betaproteobacteria | Burkholderiales | Alcaligenaceae | *Oligella* |
| *Olsenella* genomosp. C1 | Bacteria | Actinobacteria | Actinobacteria | Coriobacteriales | Coriobacteriaceae | *Olsenella* |
| *Olsenella profusa* | Bacteria | Actinobacteria | Actinobacteria | Coriobacteriales | Coriobacteriaceae | *Olsenella* |
| *Olsenella* sp. F0004 | Bacteria | Actinobacteria | Actinobacteria | Coriobacteriales | Coriobacteriaceae | *Olsenella* |
| *Olsenella* sp. oral taxon 809 | Bacteria | Actinobacteria | Actinobacteria | Coriobacteriales | Coriobacteriaceae | *Olsenella* |
| *Olsenella uli* | Bacteria | Actinobacteria | Actinobacteria | Coriobacteriales | Coriobacteriaceae | *Olsenella* |
| *Opitutus terrae* | Bacteria | Verrucomicrobia | Opitutae | Opitutales | Opitutaceae | *Opitutus* |
| *Oribacterium sinus* | Bacteria | Firmicutes | Clostridia | Clostridiales | Lachnospiraceae | *Oribacterium* |
| *Oribacterium* sp. ACB1 | Bacteria | Firmicutes | Clostridia | Clostridiales | Lachnospiraceae | *Oribacterium* |
| *Oribacterium* sp. ACB7 | Bacteria | Firmicutes | Clostridia | Clostridiales | Lachnospiraceae | *Oribacterium* |
| *Oribacterium* sp. CM12 | Bacteria | Firmicutes | Clostridia | Clostridiales | Lachnospiraceae | *Oribacterium* |
| *Oribacterium* sp. ICM51 | Bacteria | Firmicutes | Clostridia | Clostridiales | Lachnospiraceae | *Oribacterium* |
| *Oribacterium* sp. OBRC12 | Bacteria | Firmicutes | Clostridia | Clostridiales | Lachnospiraceae | *Oribacterium* |
| *Oribacterium* sp. oral taxon 078 | Bacteria | Firmicutes | Clostridia | Clostridiales | Lachnospiraceae | *Oribacterium* |
| *Oribacterium* sp. oral taxon 102 | Bacteria | Firmicutes | Clostridia | Clostridiales | Lachnospiraceae | *Oribacterium* |
| *Oribacterium* sp. oral taxon 108 | Bacteria | Firmicutes | Clostridia | Clostridiales | Lachnospiraceae | *Oribacterium* |
| *Ornithinibacillus bavariensis* | Bacteria | Firmicutes | Bacilli | Bacillales | Bacillaceae | *Ornithinibacillus* |
| *Ornithinibacillus* sp. 7-10AIA | Bacteria | Firmicutes | Bacilli | Bacillales | Bacillaceae | *Ornithinibacillus* |
| *Oscillibacter* sp. G2 | Bacteria | Firmicutes | Clostridia | Clostridiales | Oscillospiraceae | *Oscillibacter* |
| *Oscillibacter valericigenes* | Bacteria | Firmicutes | Clostridia | Clostridiales | Oscillospiraceae | *Oscillibacter* |

TABLE 1-continued

| OTU | Domain | Phylum | Class | Order | Family | Genus |
|---|---|---|---|---|---|---|
| *Oscillospira guilliermondii* | Bacteria | Firmicutes | Clostridia | Clostridiales | Ruminococcaceae | *Oscillospira* |
| *Oxalobacter formigenes* | Bacteria | Proteobacteria | Betaproteobacteria | Burkholderiales | Oxalobacteraceae | *Oxalobacter* |
| *Paenibacillus barcinonensis* | Bacteria | Firmicutes | Bacilli | Bacillales | Paenibacillaceae | *Paenibacillus* |
| *Paenibacillus barengoltzii* | Bacteria | Firmicutes | Bacilli | Bacillales | Paenibacillaceae | *Paenibacillus* |
| *Paenibacillus chibensis* | Bacteria | Firmicutes | Bacilli | Bacillales | Paenibacillaceae | *Paenibacillus* |
| *Paenibacillus cookii* | Bacteria | Firmicutes | Bacilli | Bacillales | Paenibacillaceae | *Paenibacillus* |
| *Paenibacillus durus* | Bacteria | Firmicutes | Bacilli | Bacillales | Paenibacillaceae | *Paenibacillus* |
| *Paenibacillus glucanolyticus* | Bacteria | Firmicutes | Bacilli | Bacillales | Paenibacillaceae | *Paenibacillus* |
| *Paenibacillus lactis* | Bacteria | Firmicutes | Bacilli | Bacillales | Paenibacillaceae | *Paenibacillus* |
| *Paenibacillus lautus* | Bacteria | Firmicutes | Bacilli | Bacillales | Paenibacillaceae | *Paenibacillus* |
| *Paenibacillus pabuli* | Bacteria | Firmicutes | Bacilli | Bacillales | Paenibacillaceae | *Paenibacillus* |
| *Paenibacillus polymyxa* | Bacteria | Firmicutes | Bacilli | Bacillales | Paenibacillaceae | *Paenibacillus* |
| *Paenibacillus popilliae* | Bacteria | Firmicutes | Bacilli | Bacillales | Paenibacillaceae | *Paenibacillus* |
| *Paenibacillus* sp. CIP 101062 | Bacteria | Firmicutes | Bacilli | Bacillales | Paenibacillaceae | *Paenibacillus* |
| *Paenibacillus* sp. HGF5 | Bacteria | Firmicutes | Bacilli | Bacillales | Paenibacillaceae | *Paenibacillus* |
| *Paenibacillus* sp. HGF7 | Bacteria | Firmicutes | Bacilli | Bacillales | Paenibacillaceae | *Paenibacillus* |
| *Paenibacillus* sp. JC66 | Bacteria | Firmicutes | Bacilli | Bacillales | Paenibacillaceae | *Paenibacillus* |
| *Paenibacillus* sp. oral taxon F45 | Bacteria | Firmicutes | Bacilli | Bacillales | Paenibacillaceae | *Paenibacillus* |
| *Paenibacillus* sp. R-27413 | Bacteria | Firmicutes | Bacilli | Bacillales | Paenibacillaceae | *Paenibacillus* |
| *Paenibacillus* sp. R-27422 | Bacteria | Firmicutes | Bacilli | Bacillales | Paenibacillaceae | *Paenibacillus* |
| *Paenibacillus timonensis* | Bacteria | Firmicutes | Bacilli | Bacillales | Paenibacillaceae | *Paenibacillus* |
| *Pantoea agglomerans* | Bacteria | Proteobacteria | Gammaproteobacteria | Enterobacteriales | Enterobacteriaceae | *Pantoea* |
| *Pantoea ananatis* | Bacteria | Proteobacteria | Gammaproteobacteria | Enterobacteriales | Enterobacteriaceae | *Pantoea* |
| *Pantoea brenneri* | Bacteria | Proteobacteria | Gammaproteobacteria | Enterobacteriales | Enterobacteriaceae | *Pantoea* |
| *Pantoea citrea* | Bacteria | Proteobacteria | Gammaproteobacteria | Enterobacteriales | Enterobacteriaceae | *Tatumella* |
| *Pantoea conspicua* | Bacteria | Proteobacteria | Gammaproteobacteria | Enterobacteriales | Enterobacteriaceae | *Pantoea* |
| *Pantoea septica* | Bacteria | Proteobacteria | Gammaproteobacteria | Enterobacteriales | Enterobacteriaceae | *Pantoea* |
| *Papillibacter cinnamivorans* | Bacteria | Firmicutes | Clostridia | Clostridiales | Ruminococcaceae | *Papillibacter* |
| *Parabacteroides distasonis* | Bacteria | Bacteroidetes | Bacteroidia | Bacteroidales | Porphyromonadaceae | *Parabacteroides* |
| *Parabacteroides goldsteinii* | Bacteria | Bacteroidetes | Bacteroidia | Bacteroidales | Porphyromonadaceae | *Parabacteroides* |
| *Parabacteroides gordonii* | Bacteria | Bacteroidetes | Bacteroidia | Bacteroidales | Porphyromonadaceae | *Parabacteroides* |
| *Parabacteroides johnsonii* | Bacteria | Bacteroidetes | Bacteroidia | Bacteroidales | Porphyromonadaceae | *Parabacteroides* |
| *Parabacteroides merdae* | Bacteria | Bacteroidetes | Bacteroidia | Bacteroidales | Porphyromonadaceae | *Parabacteroides* |
| *Parabacteroides* sp. D13 | Bacteria | Bacteroidetes | Bacteroidia | Bacteroidales | Porphyromonadaceae | *Parabacteroides* |
| *Parabacteroides* sp. NS31-3 | Bacteria | Bacteroidetes | Bacteroidia | Bacteroidales | Porphyromonadaceae | *Parabacteroides* |
| *Parachlamydia* sp. UWE25 | Bacteria | Chlamydiae | Chlamydiae | Chlamydiales | Parachlamydiaceae | *Parachlamydia* |
| *Paracoccus denitrificans* | Bacteria | Proteobacteria | Alphaproteobacteria | Rhodobacterales | Rhodobacteraceae | *Paracoccus* |
| *Paracoccus marcusii* | Bacteria | Proteobacteria | Alphaproteobacteria | Rhodobacterales | Rhodobacteraceae | *Paracoccus* |
| *Paraprevotella clara* | Bacteria | Bacteroidetes | Bacteroidia | Bacteroidales | Prevotellaceae | *Paraprevotella* |
| *Paraprevotella xylaniphila* | Bacteria | Bacteroidetes | Bacteroidia | Bacteroidales | Prevotellaceae | *Paraprevotella* |
| *Parascardovia denticolens* | Bacteria | Actinobacteria | Actinobacteria | Bifidobacteriales | Bifidobacteriaceae | *Parascardovia* |
| *Parasutterella excrementihominis* | Bacteria | Proteobacteria | Betaproteobacteria | Burkholderiales | Sutterellaceae | *Parasutterella* |
| *Parasutterella secunda* | Bacteria | Proteobacteria | Betaproteobacteria | Burkholderiales | Sutterellaceae | *Parasutterella* |
| *Parvimonas micra* | Bacteria | Firmicutes | Clostridia | Clostridiales | Clostridiales Family XI. Incertae Sedis | unclassified |
| *Parvimonas* sp. oral taxon 110 | Bacteria | Firmicutes | Clostridia | Clostridiales | Clostridiales Family XI. Incertae Sedis | unclassified |
| *Pasteurella bettyae* | Bacteria | Proteobacteria | Gammaproteobacteria | Pasteurellales | Pasteurellaceae | *Pasteurella* |
| *Pasteurella dagmatis* | Bacteria | Proteobacteria | Gammaproteobacteria | Pasteurellales | Pasteurellaceae | *Pasteurella* |
| *Pasteurella multocida* | Bacteria | Proteobacteria | Gammaproteobacteria | Pasteurellales | Pasteurellaceae | *Pasteurella* |
| *Pediococcus acidilactici* | Bacteria | Firmicutes | Bacilli | Lactobacillales | Lactobacillaceae | *Pediococcus* |
| *Pediococcus pentosaceus* | Bacteria | Firmicutes | Bacilli | Lactobacillales | Lactobacillaceae | *Pediococcus* |
| *Peptococcus niger* | Bacteria | Firmicutes | Clostridia | Clostridiales | Peptococcaceae | *Peptococcus* |

TABLE 1-continued

| OTU | Domain | Phylum | Class | Order | Family | Genus |
|---|---|---|---|---|---|---|
| *Peptococcus* sp. oral clone JM048 | Bacteria | Firmicutes | Clostridia | Clostridiales | Peptococcaceae | *Peptococcus* |
| *Peptococcus* sp. oral taxon 167 | Bacteria | Firmicutes | Clostridia | Clostridiales | Peptococcaceae | *Peptococcus* |
| *Peptoniphilus asaccharolyticus* | Bacteria | Firmicutes | Clostridia | Clostridiales | Clostridiales Family XI. Incertae Sedis | *Peptoniphilus* |
| *Peptoniphilus duerdenii* | Bacteria | Firmicutes | Clostridia | Clostridiales | Clostridiales Family XI. Incertae Sedis | *Peptoniphilus* |
| *Peptoniphilus harei* | Bacteria | Firmicutes | Clostridia | Clostridiales | Clostridiales Family XI. Incertae Sedis | *Peptoniphilus* |
| *Peptoniphilus indolicus* | Bacteria | Firmicutes | Clostridia | Clostridiales | Clostridiales Family XI. Incertae Sedis | *Peptoniphilus* |
| *Peptoniphilus ivorii* | Bacteria | Firmicutes | Clostridia | Clostridiales | Clostridiales Family XI. Incertae Sedis | *Peptoniphilus* |
| *Peptoniphilus lacrimalis* | Bacteria | Firmicutes | Clostridia | Clostridiales | Clostridiales Family XI. Incertae Sedis | *Peptoniphilus* |
| *Peptoniphilus* sp. gpac007 | Bacteria | Firmicutes | Clostridia | Clostridiales | Clostridiales Family XI. Incertae Sedis | *Peptoniphilus* |
| *Peptoniphilus* sp. gpac018A | Bacteria | Firmicutes | Clostridia | Clostridiales | Clostridiales Family XI. Incertae Sedis | *Peptoniphilus* |
| *Peptoniphilus* sp. gpac077 | Bacteria | Firmicutes | Clostridia | Clostridiales | Clostridiales Family XI. Incertae Sedis | *Peptoniphilus* |
| *Peptoniphilus* sp. gpac148 | Bacteria | Firmicutes | Clostridia | Clostridiales | Clostridiales Family XI. Incertae Sedis | *Peptoniphilus* |
| *Peptoniphilus* sp. JC140 | Bacteria | Firmicutes | Clostridia | Clostridiales | Clostridiales Family XI. Incertae Sedis | *Peptoniphilus* |
| *Peptoniphilus* sp. oral taxon 386 | Bacteria | Firmicutes | Clostridia | Clostridiales | Clostridiales Family XI. Incertae Sedis | *Peptoniphilus* |
| *Peptoniphilus* sp. oral taxon 836 | Bacteria | Firmicutes | Clostridia | Clostridiales | Clostridiales Family XI. Incertae Sedis | *Peptoniphilus* |
| Peptostreptococcaceae bacterium ph1 | Bacteria | Firmicutes | Clostridia | Clostridiales | Peptostreptococcaceae | unclassified |
| *Peptostreptococcus anaerobius* | Bacteria | Firmicutes | Clostridia | Clostridiales | Peptostreptococcaceae | *Peptostreptococcus* |
| *Peptostreptococcus micros* | Bacteria | Firmicutes | Clostridia | Clostridiales | Clostridiales Family XI. Incertae Sedis | unclassified |
| *Peptostreptococcus* sp. 9succ1 | Bacteria | Firmicutes | Clostridia | Clostridiales | Incertae Sedis XI | *Peptoniphilus* |
| *Peptostreptococcus* sp. oral clone AP24 | Bacteria | Firmicutes | Clostridia | Clostridiales | Peptostreptococcaceae | *Peptostreptococcus* |
| *Peptostreptococcus* sp. oral clone FJ023 | Bacteria | Firmicutes | Clostridia | Clostridiales | Peptostreptococcaceae | *Peptostreptococcus* |
| *Peptostreptococcus* sp. P4P__31 P3 | Bacteria | Firmicutes | Clostridia | Clostridiales | Peptostreptococcaceae | *Peptostreptococcus* |
| *Peptostreptococcus stomatis* | Bacteria | Firmicutes | Clostridia | Clostridiales | Peptostreptococcaceae | *Peptostreptococcus* |
| *Phascolarctobacterium faecium* | Bacteria | Firmicutes | Negativicutes | Selenomonadales | Acidaminococcaceae | *Phascolarctobacterium* |
| *Phascolarctobacterium* sp. YIT 12068 | Bacteria | Firmicutes | Negativicutes | Selenomonadales | Acidaminococcaceae | *Phascolarctobacterium* |
| *Phascolarctobacterium succinatutens* | Bacteria | Firmicutes | Negativicutes | Selenomonadales | Acidaminococcaceae | *Phascolarctobacterium* |
| *Phenylobacterium zucineum* | Bacteria | Proteobacteria | Alphaproteobacteria | Caulobacterales | Caulobacteraceae | *Phenylobacterium* |
| *Photorhabdus asymbiotica* | Bacteria | Proteobacteria | Gammaproteobacteria | Enterobacteriales | Enterobacteriaceae | *Photorhabdus* |
| *Pigmentiphaga daeguensis* | Bacteria | Proteobacteria | Betaproteobacteria | Burkholderiales | Alcaligenaceae | *Pigmentiphaga* |
| *Planomicrobium koreense* | Bacteria | Firmicutes | Bacilli | Bacillales | Planococcaceae | *Planomicrobium* |
| *Plesiomonas shigelloides* | Bacteria | Proteobacteria | Gammaproteobacteria | Enterobacteriales | Enterobacteriaceae | *Plesiomonas* |
| Porphyromonadaceae bacterium NML 060648 | Bacteria | Bacteroidetes | Bacteroidia | Bacteroidales | Porphyromonadaceae | unclassified |
| *Porphyromonas asaccharolytica* | Bacteria | Bacteroidetes | Bacteroidia | Bacteroidales | Porphyromonadaceae | *Porphyromonas* |
| *Porphyromonas endodontalis* | Bacteria | Bacteroidetes | Bacteroidia | Bacteroidales | Porphyromonadaceae | *Porphyromonas* |
| *Porphyromonas gingivalis* | Bacteria | Bacteroidetes | Bacteroidia | Bacteroidales | Porphyromonadaceae | *Porphyromonas* |
| *Porphyromonas levii* | Bacteria | Bacteroidetes | Bacteroidia | Bacteroidales | Porphyromonadaceae | *Porphyromonas* |
| *Porphyromonas macacae* | Bacteria | Bacteroidetes | Bacteroidia | Bacteroidales | Porphyromonadaceae | *Porphyromonas* |
| *Porphyromonas somerae* | Bacteria | Bacteroidetes | Bacteroidia | Bacteroidales | Porphyromonadaceae | *Porphyromonas* |
| *Porphyromonas* sp. oral clone BB134 | Bacteria | Bacteroidetes | Bacteroidia | Bacteroidales | Porphyromonadaceae | *Porphyromonas* |
| *Porphyromonas* sp. oral clone F016 | Bacteria | Bacteroidetes | Bacteroidia | Bacteroidales | Porphyromonadaceae | *Porphyromonas* |
| *Porphyromonas* sp. oral clone P2PB__52 P1 | Bacteria | Bacteroidetes | Bacteroidia | Bacteroidales | Porphyromonadaceae | *Porphyromonas* |
| *Porphyromonas* sp. oral clone P4GB__100 P2 | Bacteria | Bacteroidetes | Bacteroidia | Bacteroidales | Porphyromonadaceae | *Porphyromonas* |
| *Porphyromonas* sp. UQD 301 | Bacteria | Bacteroidetes | Bacteroidia | Bacteroidales | Porphyromonadaceae | *Porphyromonas* |
| *Porphyromonas uenonis* | Bacteria | Bacteroidetes | Bacteroidia | Bacteroidales | Porphyromonadaceae | *Porphyromonas* |
| *Prevotella albensis* | Bacteria | Bacteroidetes | Bacteroidia | Bacteroidales | Prevotellaceae | *Prevotella* |
| *Prevotella amnii* | Bacteria | Bacteroidetes | Bacteroidia | Bacteroidales | Prevotellaceae | *Prevotella* |
| *Prevotella bergensis* | Bacteria | Bacteroidetes | Bacteroidia | Bacteroidales | Prevotellaceae | *Prevotella* |
| *Prevotella bivia* | Bacteria | Bacteroidetes | Bacteroidia | Bacteroidales | Prevotellaceae | *Prevotella* |
| *Prevotella brevis* | Bacteria | Bacteroidetes | Bacteroidia | Bacteroidales | Prevotellaceae | *Prevotella* |
| *Prevotella buccae* | Bacteria | Bacteroidetes | Bacteroidia | Bacteroidales | Prevotellaceae | *Prevotella* |
| *Prevotella buccalis* | Bacteria | Bacteroidetes | Bacteroidia | Bacteroidales | Prevotellaceae | *Prevotella* |

TABLE 1-continued

| OTU | Domain | Phylum | Class | Order | Family | Genus |
|---|---|---|---|---|---|---|
| *Prevotella copri* | Bacteria | Bacteroidetes | Bacteroidia | Bacteroidales | Prevotellaceae | *Prevotella* |
| *Prevotella corporis* | Bacteria | Bacteroidetes | Bacteroidia | Bacteroidales | Prevotellaceae | *Prevotella* |
| *Prevotella dentalis* | Bacteria | Bacteroidetes | Bacteroidia | Bacteroidales | Prevotellaceae | *Prevotella* |
| *Prevotella denticola* | Bacteria | Bacteroidetes | Bacteroidia | Bacteroidales | Prevotellaceae | *Prevotella* |
| *Prevotella disiens* | Bacteria | Bacteroidetes | Bacteroidia | Bacteroidales | Prevotellaceae | *Prevotella* |
| *Prevotella* genomosp. C1 | Bacteria | Bacteroidetes | Bacteroidia | Bacteroidales | Prevotellaceae | *Prevotella* |
| *Prevotella* genomosp. C2 | Bacteria | Bacteroidetes | Bacteroidia | Bacteroidales | Prevotellaceae | *Prevotella* |
| *Prevotella* genomosp. P7 oral clone MB2__P31 | Bacteria | Bacteroidetes | Bacteroidia | Bacteroidales | Prevotellaceae | *Prevotella* |
| *Prevotella* genomosp. P8 oral clone MB3__P13 | Bacteria | Bacteroidetes | Bacteroidia | Bacteroidales | Prevotellaceae | *Prevotella* |
| *Prevotella* genomosp. P9 oral clone MB7__G16 | Bacteria | Bacteroidetes | Bacteroidia | Bacteroidales | Prevotellaceae | *Prevotella* |
| *Prevotella heparinolytica* | Bacteria | Bacteroidetes | Bacteroidia | Bacteroidales | Bacteroidaceae | *Bacteroides* |
| *Prevotella histicola* | Bacteria | Bacteroidetes | Bacteroidia | Bacteroidales | Prevotellaceae | *Prevotella* |
| *Prevotella intermedia* | Bacteria | Bacteroidetes | Bacteroidia | Bacteroidales | Prevotellaceae | *Prevotella* |
| *Prevotella loescheii* | Bacteria | Bacteroidetes | Bacteroidia | Bacteroidales | Prevotellaceae | *Prevotella* |
| *Prevotella maculosa* | Bacteria | Bacteroidetes | Bacteroidia | Bacteroidales | Prevotellaceae | *Prevotella* |
| *Prevotella marshii* | Bacteria | Bacteroidetes | Bacteroidia | Bacteroidales | Prevotellaceae | *Prevotella* |
| *Prevotella melaninogenica* | Bacteria | Bacteroidetes | Bacteroidia | Bacteroidales | Prevotellaceae | *Prevotella* |
| *Prevotella micans* | Bacteria | Bacteroidetes | Bacteroidia | Bacteroidales | Prevotellaceae | *Prevotella* |
| *Prevotella multiformis* | Bacteria | Bacteroidetes | Bacteroidia | Bacteroidales | Prevotellaceae | *Prevotella* |
| *Prevotella multisaccharivorax* | Bacteria | Bacteroidetes | Bacteroidia | Bacteroidales | Prevotellaceae | *Prevotella* |
| *Prevotella nanceiensis* | Bacteria | Bacteroidetes | Bacteroidia | Bacteroidales | Prevotellaceae | *Prevotella* |
| *Prevotella nigrescens* | Bacteria | Bacteroidetes | Bacteroidia | Bacteroidales | Prevotellaceae | *Prevotella* |
| *Prevotella oralis* | Bacteria | Bacteroidetes | Bacteroidia | Bacteroidales | Prevotellaceae | *Prevotella* |
| *Prevotella oris* | Bacteria | Bacteroidetes | Bacteroidia | Bacteroidales | Prevotellaceae | *Prevotella* |
| *Prevotella oulorum* | Bacteria | Bacteroidetes | Bacteroidia | Bacteroidales | Prevotellaceae | *Prevotella* |
| *Prevotella pallens* | Bacteria | Bacteroidetes | Bacteroidia | Bacteroidales | Prevotellaceae | *Prevotella* |
| *Prevotella ruminicola* | Bacteria | Bacteroidetes | Bacteroidia | Bacteroidales | Prevotellaceae | *Prevotella* |
| *Prevotella salivae* | Bacteria | Bacteroidetes | Bacteroidia | Bacteroidales | Prevotellaceae | *Prevotella* |
| *Prevotella* sp. BI-42 | Bacteria | Bacteroidetes | Bacteroidia | Bacteroidales | Prevotellaceae | *Prevotella* |
| *Prevotella* sp. CM38 | Bacteria | Bacteroidetes | Bacteroidia | Bacteroidales | Prevotellaceae | *Prevotella* |
| *Prevotella* sp. ICM1 | Bacteria | Bacteroidetes | Bacteroidia | Bacteroidales | Prevotellaceae | *Prevotella* |
| *Prevotella* sp. ICM55 | Bacteria | Bacteroidetes | Bacteroidia | Bacteroidales | Prevotellaceae | *Prevotella* |
| *Prevotella* sp. JCM 6330 | Bacteria | Bacteroidetes | Bacteroidia | Bacteroidales | Prevotellaceae | *Prevotella* |
| *Prevotella* sp. oral clone AA020 | Bacteria | Bacteroidetes | Bacteroidia | Bacteroidales | Prevotellaceae | *Prevotella* |
| *Prevotella* sp. oral clone ASCG10 | Bacteria | Bacteroidetes | Bacteroidia | Bacteroidales | Prevotellaceae | *Prevotella* |
| *Prevotella* sp. oral clone ASCG12 | Bacteria | Bacteroidetes | Bacteroidia | Bacteroidales | Prevotellaceae | *Prevotella* |
| *Prevotella* sp. oral clone AU069 | Bacteria | Bacteroidetes | Bacteroidia | Bacteroidales | Prevotellaceae | *Prevotella* |
| *Prevotella* sp. oral clone CY006 | Bacteria | Bacteroidetes | Bacteroidia | Bacteroidales | Prevotellaceae | *Prevotella* |
| *Prevotella* sp. oral clone DA058 | Bacteria | Bacteroidetes | Bacteroidia | Bacteroidales | Prevotellaceae | *Prevotella* |
| *Prevotella* sp. oral clone FL019 | Bacteria | Bacteroidetes | Bacteroidia | Bacteroidales | Prevotellaceae | *Prevotella* |
| *Prevotella* sp. oral clone FU048 | Bacteria | Bacteroidetes | Bacteroidia | Bacteroidales | Prevotellaceae | *Prevotella* |
| *Prevotella* sp. oral clone FW035 | Bacteria | Bacteroidetes | Bacteroidia | Bacteroidales | Prevotellaceae | *Prevotella* |
| *Prevotella* sp. oral clone GI030 | Bacteria | Bacteroidetes | Bacteroidia | Bacteroidales | Prevotellaceae | *Prevotella* |
| *Prevotella* sp. oral clone GI032 | Bacteria | Bacteroidetes | Bacteroidia | Bacteroidales | Prevotellaceae | *Prevotella* |
| *Prevotella* sp. oral clone GI059 | Bacteria | Bacteroidetes | Bacteroidia | Bacteroidales | Prevotellaceae | *Prevotella* |
| *Prevotella* sp. oral clone GU027 | Bacteria | Bacteroidetes | Bacteroidia | Bacteroidales | Prevotellaceae | *Prevotella* |
| *Prevotella* sp. oral clone HF050 | Bacteria | Bacteroidetes | Bacteroidia | Bacteroidales | Prevotellaceae | *Prevotella* |
| *Prevotella* sp. oral clone ID019 | Bacteria | Bacteroidetes | Bacteroidia | Bacteroidales | Prevotellaceae | *Prevotella* |
| *Prevotella* sp. oral clone IDR-CEC-0024 | Bacteria | Bacteroidetes | Bacteroidia | Bacteroidales | Prevotellaceae | *Prevotella* |
| *Prevotella* sp. oral clone IDR-CEC-0032 | Bacteria | Bacteroidetes | Bacteroidia | Bacteroidales | Prevotellaceae | *Prevotella* |
| *Prevotella* sp. oral clone IDR-CEC-0055 | Bacteria | Bacteroidetes | Bacteroidia | Bacteroidales | Prevotellaceae | *Prevotella* |

TABLE 1-continued

| OTU | Domain | Phylum | Class | Order | Family | Genus |
|---|---|---|---|---|---|---|
| *Prevotella* sp. oral clone IK053 | Bacteria | Bacteroidetes | Bacteroidia | Bacteroidales | Prevotellaceae | *Prevotella* |
| *Prevotella* sp. oral clone IK062 | Bacteria | Bacteroidetes | Bacteroidia | Bacteroidales | Prevotellaceae | *Prevotella* |
| *Prevotella* sp. oral clone P4PB__83 P2 | Bacteria | Bacteroidetes | Bacteroidia | Bacteroidales | Prevotellaceae | *Prevotella* |
| *Prevotella* sp. oral taxon 292 | Bacteria | Bacteroidetes | Bacteroidia | Bacteroidales | Prevotellaceae | *Prevotella* |
| *Prevotella* sp. oral taxon 299 | Bacteria | Bacteroidetes | Bacteroidia | Bacteroidales | Prevotellaceae | *Prevotella* |
| *Prevotella* sp. oral taxon 300 | Bacteria | Bacteroidetes | Bacteroidia | Bacteroidales | Prevotellaceae | *Prevotella* |
| *Prevotella* sp. oral taxon 302 | Bacteria | Bacteroidetes | Bacteroidia | Bacteroidales | Prevotellaceae | *Alloprevotella* |
| *Prevotella* sp. oral taxon 310 | Bacteria | Bacteroidetes | Bacteroidia | Bacteroidales | Prevotellaceae | *Prevotella* |
| *Prevotella* sp. oral taxon 317 | Bacteria | Bacteroidetes | Bacteroidia | Bacteroidales | Prevotellaceae | *Prevotella* |
| *Prevotella* sp. oral taxon 472 | Bacteria | Bacteroidetes | Bacteroidia | Bacteroidales | Prevotellaceae | *Prevotella* |
| *Prevotella* sp. oral taxon 781 | Bacteria | Bacteroidetes | Bacteroidia | Bacteroidales | Prevotellaceae | *Prevotella* |
| *Prevotella* sp. oral taxon 782 | Bacteria | Bacteroidetes | Bacteroidia | Bacteroidales | Prevotellaceae | *Prevotella* |
| *Prevotella* sp. oral taxon F68 | Bacteria | Bacteroidetes | Bacteroidia | Bacteroidales | Prevotellaceae | *Prevotella* |
| *Prevotella* sp. oral taxon G60 | Bacteria | Bacteroidetes | Bacteroidia | Bacteroidales | Prevotellaceae | *Prevotella* |
| *Prevotella* sp. oral taxon G70 | Bacteria | Bacteroidetes | Bacteroidia | Bacteroidales | Prevotellaceae | *Prevotella* |
| *Prevotella* sp. oral taxon G71 | Bacteria | Bacteroidetes | Bacteroidia | Bacteroidales | Prevotellaceae | *Prevotella* |
| *Prevotella* sp. SEQ053 | Bacteria | Bacteroidetes | Bacteroidia | Bacteroidales | Prevotellaceae | *Prevotella* |
| *Prevotella* sp. SEQ065 | Bacteria | Bacteroidetes | Bacteroidia | Bacteroidales | Prevotellaceae | *Prevotella* |
| *Prevotella* sp. SEQ072 | Bacteria | Bacteroidetes | Bacteroidia | Bacteroidales | Prevotellaceae | *Prevotella* |
| *Prevotella* sp. SEQ116 | Bacteria | Bacteroidetes | Bacteroidia | Bacteroidales | Prevotellaceae | *Prevotella* |
| *Prevotella* sp. SG12 | Bacteria | Bacteroidetes | Bacteroidia | Bacteroidales | Prevotellaceae | *Prevotella* |
| *Prevotella* sp. sp24 | Bacteria | Bacteroidetes | Bacteroidia | Bacteroidales | Prevotellaceae | *Prevotella* |
| *Prevotella* sp. sp34 | Bacteria | Bacteroidetes | Bacteroidia | Bacteroidales | Prevotellaceae | *Prevotella* |
| *Prevotella stercorea* | Bacteria | Bacteroidetes | Bacteroidia | Bacteroidales | Prevotellaceae | *Prevotella* |
| *Prevotella tannerae* | Bacteria | Bacteroidetes | Bacteroidia | Bacteroidales | Prevotellaceae | *Alloprevotella* |
| *Prevotella timonensis* | Bacteria | Bacteroidetes | Bacteroidia | Bacteroidales | Prevotellaceae | *Prevotella* |
| *Prevotella veroralis* | Bacteria | Bacteroidetes | Bacteroidia | Bacteroidales | Prevotellaceae | *Prevotella* |
| Prevotellaceae bacterium P4P__62 P1 | Bacteria | Bacteroidetes | Bacteroidia | Bacteroidales | Prevotellaceae | unclassified |
| *Prochlorococcus marinus* | Bacteria | Cyanobacteria | unclassified | Prochlorales | Prochlorococcaceae | *Prochlorococcus* |
| Propionibacteriaceae bacterium NML 02-0265 | Bacteria | Actinobacteria | Actinobacteria | Actinomycetales | Propionibacteriaceae | unclassified |
| *Propionibacterium acidipropionici* | Bacteria | Actinobacteria | Actinobacteria | Actinomycetales | Propionibacteriaceae | *Propionibacterium* |
| *Propionibacterium acnes* | Bacteria | Actinobacteria | Actinobacteria | Actinomycetales | Propionibacteriaceae | *Propionibacterium* |
| *Propionibacterium avidum* | Bacteria | Actinobacteria | Actinobacteria | Actinomycetales | Propionibacteriaceae | *Propionibacterium* |
| *Propionibacterium freudenreichii* | Bacteria | Actinobacteria | Actinobacteria | Actinomycetales | Propionibacteriaceae | *Propionibacterium* |
| *Propionibacterium granulosum* | Bacteria | Actinobacteria | Actinobacteria | Actinomycetales | Propionibacteriaceae | *Propionibacterium* |
| *Propionibacterium jensenii* | Bacteria | Actinobacteria | Actinobacteria | Actinomycetales | Propionibacteriaceae | *Propionibacterium* |
| *Propionibacterium propionicum* | Bacteria | Actinobacteria | Actinobacteria | Actinomycetales | Propionibacteriaceae | *Propionibacterium* |
| *Propionibacterium* sp. 434-HC2 | Bacteria | Actinobacteria | Actinobacteria | Actinomycetales | Propionibacteriaceae | *Propionibacterium* |
| *Propionibacterium* sp. H456 | Bacteria | Actinobacteria | Actinobacteria | Actinomycetales | Propionibacteriaceae | *Propionibacterium* |
| *Propionibacterium* sp. LG | Bacteria | Actinobacteria | Actinobacteria | Actinomycetales | Propionibacteriaceae | *Propionibacterium* |
| *Propionibacterium* sp. oral taxon 192 | Bacteria | Actinobacteria | Actinobacteria | Actinomycetales | Propionibacteriaceae | *Propionibacterium* |
| *Propionibacterium* sp. S555a | Bacteria | Actinobacteria | Actinobacteria | Actinomycetales | Propionibacteriaceae | *Propionibacterium* |
| *Propionibacterium thoenii* | Bacteria | Actinobacteria | Actinobacteria | Actinomycetales | Propionibacteriaceae | *Propionibacterium* |
| *Proteus mirabilis* | Bacteria | Proteobacteria | Gammaproteobacteria | Enterobacteriales | Enterobacteriaceae | *Proteus* |
| *Proteus penneri* | Bacteria | Proteobacteria | Gammaproteobacteria | Enterobacteriales | Enterobacteriaceae | *Proteus* |
| *Proteus* sp. HS7514 | Bacteria | Proteobacteria | Gammaproteobacteria | Enterobacteriales | Enterobacteriaceae | *Proteus* |
| *Proteus vulgaris* | Bacteria | Proteobacteria | Gammaproteobacteria | Enterobacteriales | Enterobacteriaceae | *Proteus* |
| *Providencia alcalifaciens* | Bacteria | Proteobacteria | Gammaproteobacteria | Enterobacteriales | Enterobacteriaceae | *Providencia* |
| *Providencia rettgeri* | Bacteria | Proteobacteria | Gammaproteobacteria | Enterobacteriales | Enterobacteriaceae | *Providencia* |
| *Providencia rustigianii* | Bacteria | Proteobacteria | Gammaproteobacteria | Enterobacteriales | Enterobacteriaceae | *Providencia* |
| *Providencia stuartii* | Bacteria | Proteobacteria | Gammaproteobacteria | Enterobacteriales | Enterobacteriaceae | *Providencia* |

TABLE 1-continued

| OTU | Domain | Phylum | Class | Order | Family | Genus |
|---|---|---|---|---|---|---|
| *Pseudoclavibacter* sp. Timone | Bacteria | Actinobacteria | Actinobacteria | Actinomycetales | Microbacteriaceae | *Pseudoclavibacter* |
| *Pseudoflavonifractor capillosus* | Bacteria | Firmicutes | Clostridia | Clostridiales | unclassified | *Pseudoflavonifractor* |
| *Pseudomonas aeruginosa* | Bacteria | Proteobacteria | Gammaproteobacteria | Pseudomonadales | Pseudomonadaceae | *Pseudomonas* |
| *Pseudomonas fluorescens* | Bacteria | Proteobacteria | Gammaproteobacteria | Pseudomonadales | Pseudomonadaceae | *Pseudomonas* |
| *Pseudomonas gessardii* | Bacteria | Proteobacteria | Gammaproteobacteria | Pseudomonadales | Pseudomonadaceae | *Pseudomonas* |
| *Pseudomonas mendocina* | Bacteria | Proteobacteria | Gammaproteobacteria | Pseudomonadales | Pseudomonadaceae | *Pseudomonas* |
| *Pseudomonas monteilii* | Bacteria | Proteobacteria | Gammaproteobacteria | Pseudomonadales | Pseudomonadaceae | *Pseudomonas* |
| *Pseudomonas poae* | Bacteria | Proteobacteria | Gammaproteobacteria | Pseudomonadales | Pseudomonadaceae | *Pseudomonas* |
| *Pseudomonas pseudoalcaligenes* | Bacteria | Proteobacteria | Gammaproteobacteria | Pseudomonadales | Pseudomonadaceae | *Pseudomonas* |
| *Pseudomonas putida* | Bacteria | Proteobacteria | Gammaproteobacteria | Pseudomonadales | Pseudomonadaceae | *Pseudomonas* |
| *Pseudomonas* sp. 2_1_26 | Bacteria | Proteobacteria | Gammaproteobacteria | Pseudomonadales | Pseudomonadaceae | *Pseudomonas* |
| *Pseudomonas* sp. G1229 | Bacteria | Proteobacteria | Gammaproteobacteria | Pseudomonadales | Pseudomonadaceae | *Pseudomonas* |
| *Pseudomonas* sp. NP522b | Bacteria | Proteobacteria | Gammaproteobacteria | Pseudomonadales | Pseudomonadaceae | *Pseudomonas* |
| *Pseudomonas stutzeri* | Bacteria | Proteobacteria | Gammaproteobacteria | Pseudomonadales | Pseudomonadaceae | *Pseudomonas* |
| *Pseudomonas tolaasii* | Bacteria | Proteobacteria | Gammaproteobacteria | Pseudomonadales | Pseudomonadaceae | *Pseudomonas* |
| *Pseudomonas viridiflava* | Bacteria | Proteobacteria | Gammaproteobacteria | Pseudomonadales | Pseudomonadaceae | *Pseudomonas* |
| *Pseudoramibacter alactolyticus* | Bacteria | Firmicutes | Clostridia | Clostridiales | Eubacteriaceae | *Pseudoramibacter* |
| *Psychrobacter arcticus* | Bacteria | Proteobacteria | Gammaproteobacteria | Pseudomonadales | Moraxellaceae | *Psychrobacter* |
| *Psychrobacter cibarius* | Bacteria | Proteobacteria | Gammaproteobacteria | Pseudomonadales | Moraxellaceae | *Psychrobacter* |
| *Psychrobacter cryohalolentis* | Bacteria | Proteobacteria | Gammaproteobacteria | Pseudomonadales | Moraxellaceae | *Psychrobacter* |
| *Psychrobacter faecalis* | Bacteria | Proteobacteria | Gammaproteobacteria | Pseudomonadales | Moraxellaceae | *Psychrobacter* |
| *Psychrobacter nivimaris* | Bacteria | Proteobacteria | Gammaproteobacteria | Pseudomonadales | Moraxellaceae | *Psychrobacter* |
| *Psychrobacter pulmonis* | Bacteria | Proteobacteria | Gammaproteobacteria | Pseudomonadales | Moraxellaceae | *Psychrobacter* |
| *Psychrobacter* sp. 13983 | Bacteria | Proteobacteria | Gammaproteobacteria | Pseudomonadales | Moraxellaceae | *Psychrobacter* |
| *Pyramidobacter piscolens* | Bacteria | Synergistetes | Synergistia | Synergistales | Synergistaceae | *Pyramidobacter* |
| *Ralstonia pickettii* | Bacteria | Proteobacteria | Betaproteobacteria | Burkholderiales | Burkholderiaceae | *Ralstonia* |
| *Ralstonia* sp. 5_7_47FAA | Bacteria | Proteobacteria | Betaproteobacteria | Burkholderiales | Burkholderiaceae | *Ralstonia* |
| *Raoultella ornithinolytica* | Bacteria | Proteobacteria | Gammaproteobacteria | Enterobacteriales | Enterobacteriaceae | *Raoultella* |
| *Raoultella planticola* | Bacteria | Proteobacteria | Gammaproteobacteria | Enterobacteriales | Enterobacteriaceae | *Raoultella* |
| *Raoultella terrigena* | Bacteria | Proteobacteria | Gammaproteobacteria | Enterobacteriales | Enterobacteriaceae | *Raoultella* |
| *Rhodobacter* sp. oral taxon C30 | Bacteria | Proteobacteria | Alphaproteobacteria | Rhodobacterales | Rhodobacteraceae | *Rhodobacter* |
| *Rhodobacter sphaeroides* | Bacteria | Proteobacteria | Alphaproteobacteria | Rhodobacterales | Rhodobacteraceae | *Rhodobacter* |
| *Rhodococcus corynebacterioides* | Bacteria | Actinobacteria | Actinobacteria | Actinomycetales | Nocardiaceae | *Rhodococcus* |
| *Rhodococcus equi* | Bacteria | Actinobacteria | Actinobacteria | Actinomycetales | Nocardiaceae | *Rhodococcus* |
| *Rhodococcus erythropolis* | Bacteria | Actinobacteria | Actinobacteria | Actinomycetales | Nocardiaceae | *Rhodococcus* |
| *Rhodococcus fascians* | Bacteria | Actinobacteria | Actinobacteria | Actinomycetales | Nocardiaceae | *Rhodococcus* |
| *Rhodopseudomonas palustris* | Bacteria | Proteobacteria | Alphaproteobacteria | Rhizobiales | Bradyrhizobiaceae | *Rhodopseudomonas* |
| *Robinsoniella peoriensis* | Bacteria | Firmicutes | Clostridia | Clostridiales | Lachnospiraceae | *Robinsoniella* |
| *Roseburia cecicola* | Bacteria | Firmicutes | Clostridia | Clostridiales | Lachnospiraceae | *Roseburia* |
| *Roseburia faecalis* | Bacteria | Firmicutes | Clostridia | Clostridiales | Lachnospiraceae | *Roseburia* |
| *Roseburia faecis* | Bacteria | Firmicutes | Clostridia | Clostridiales | Lachnospiraceae | *Roseburia* |
| *Roseburia hominis* | Bacteria | Firmicutes | Clostridia | Clostridiales | Lachnospiraceae | *Roseburia* |
| *Roseburia intestinalis* | Bacteria | Firmicutes | Clostridia | Clostridiales | Lachnospiraceae | *Roseburia* |
| *Roseburia inulinivorans* | Bacteria | Firmicutes | Clostridia | Clostridiales | Lachnospiraceae | *Roseburia* |
| *Roseburia* sp. 11SE37 | Bacteria | Firmicutes | Clostridia | Clostridiales | Lachnospiraceae | *Roseburia* |
| *Roseburia* sp. 11SE38 | Bacteria | Firmicutes | Clostridia | Clostridiales | Lachnospiraceae | *Roseburia* |
| *Roseiflexus castenholzii* | Bacteria | Chloroflexi | Chloroflexi | Chloroflexales | Chloroflexaceae | *Roseiflexus* |
| *Roseomonas cervicalis* | Bacteria | Proteobacteria | Alphaproteobacteria | Rhodospirillales | Acetobacteraceae | *Roseomonas* |
| *Roseomonas mucosa* | Bacteria | Proteobacteria | Alphaproteobacteria | Rhodospirillales | Acetobacteraceae | *Roseomonas* |
| *Roseomonas* sp. NML94-0193 | Bacteria | Proteobacteria | Alphaproteobacteria | Rhodospirillales | Acetobacteraceae | *Roseomonas* |
| *Roseomonas* sp. NML97-0121 | Bacteria | Proteobacteria | Alphaproteobacteria | Rhodospirillales | Acetobacteraceae | *Roseomonas* |

TABLE 1-continued

| OTU | Domain | Phylum | Class | Order | Family | Genus |
|---|---|---|---|---|---|---|
| *Roseomonas* sp. NML98-0009 | Bacteria | Proteobacteria | Alphaproteobacteria | Rhodospirillales | Acetobacteraceae | *Roseomonas* |
| *Roseomonas* sp. NML98-0157 | Bacteria | Proteobacteria | Alphaproteobacteria | Rhodospirillales | Acetobacteraceae | *Roseomonas* |
| *Rothia aeria* | Bacteria | Actinobacteria | Actinobacteria | Actinomycetales | Micrococcaceae | *Rothia* |
| *Rothia dentocariosa* | Bacteria | Actinobacteria | Actinobacteria | Actinomycetales | Micrococcaceae | *Rothia* |
| *Rothia mucilaginosa* | Bacteria | Actinobacteria | Actinobacteria | Actinomycetales | Micrococcaceae | *Rothia* |
| *Rothia nasimurium* | Bacteria | Actinobacteria | Actinobacteria | Actinomycetales | Micrococcaceae | *Rothia* |
| *Rothia* sp. oral taxon 188 | Bacteria | Actinobacteria | Actinobacteria | Actinomycetales | Micrococcaceae | *Rothia* |
| *Ruminobacter amylophilus* | Bacteria | Proteobacteria | Gammaproteobacteria | Aeromonadales | Succinivibrionaceae | *Ruminobacter* |
| Ruminococcaceae bacterium D16 | Bacteria | Firmicutes | Clostridia | Clostridiales | Ruminococcaceae | unclassified |
| *Ruminococcus albus* | Bacteria | Firmicutes | Clostridia | Clostridiales | Ruminococcaceae | *Ruminococcus* |
| *Ruminococcus bromii* | Bacteria | Firmicutes | Clostridia | Clostridiales | Ruminococcaceae | *Ruminococcus* |
| *Ruminococcus callidus* | Bacteria | Firmicutes | Clostridia | Clostridiales | Ruminococcaceae | *Ruminococcus* |
| *Ruminococcus champanellensis* | Bacteria | Firmicutes | Clostridia | Clostridiales | Ruminococcaceae | *Ruminococcus* |
| *Ruminococcus flavefaciens* | Bacteria | Firmicutes | Clostridia | Clostridiales | Ruminococcaceae | *Ruminococcus* |
| *Ruminococcus gnavus* | Bacteria | Firmicutes | Clostridia | Clostridiales | Lachnospiraceae | *Blautia* |
| *Ruminococcus hansenii* | Bacteria | Firmicutes | Clostridia | Clostridiales | Lachnospiraceae | *Blautia* |
| *Ruminococcus lactaris* | Bacteria | Firmicutes | Clostridia | Clostridiales | Ruminococcaceae | *Ruminococcus* |
| *Ruminococcus obeum* | Bacteria | Firmicutes | Clostridia | Clostridiales | Lachnospiraceae | *Blautia* |
| *Ruminococcus* sp. 18P13 | Bacteria | Firmicutes | Clostridia | Clostridiales | Ruminococcaceae | *Ruminococcus* |
| *Ruminococcus* sp. 5_1_39BFAA | Bacteria | Firmicutes | Clostridia | Clostridiales | Ruminococcaceae | *Ruminococcus* |
| *Ruminococcus* sp. 9SE51 | Bacteria | Firmicutes | Clostridia | Clostridiales | Ruminococcaceae | *Ruminococcus* |
| *Ruminococcus* sp. ID8 | Bacteria | Firmicutes | Clostridia | Clostridiales | Ruminococcaceae | *Ruminococcus* |
| *Ruminococcus* sp. K-1 | Bacteria | Firmicutes | Clostridia | Clostridiales | Ruminococcaceae | *Ruminococcus* |
| *Ruminococcus torques* | Bacteria | Firmicutes | Clostridia | Clostridiales | Lachnospiraceae | *Blautia* |
| *Saccharomonospora viridis* | Bacteria | Actinobacteria | Actinobacteria | Actinomycetales | Pseudonocardiaceae | *Saccharomonospora* |
| *Sarcina ventriculi* | Bacteria | Firmicutes | Clostridia | Clostridiales | Clostridiaceae | *Sarcina* |
| *Scardovia inopinata* | Bacteria | Actinobacteria | Actinobacteria | Bifidobacteriales | Bifidobacteriaceae | *Scardovia* |
| *Scardovia wiggsiae* | Bacteria | Actinobacteria | Actinobacteria | Bifidobacteriales | Bifidobacteriaceae | *Scardovia* |
| *Segniliparus rotundus* | Bacteria | Actinobacteria | Actinobacteria | Actinomycetales | Segniliparaceae | *Segniliparus* |
| *Segniliparus rugosus* | Bacteria | Actinobacteria | Actinobacteria | Actinomycetales | Segniliparaceae | *Segniliparus* |
| *Selenomonas artemidis* | Bacteria | Firmicutes | Negativicutes | Selenomonadales | Veillonellaceae | *Selenomonas* |
| *Selenomonas dianae* | Bacteria | Firmicutes | Negativicutes | Selenomonadales | Veillonellaceae | *Selenomonas* |
| *Selenomonas flueggei* | Bacteria | Firmicutes | Negativicutes | Selenomonadales | Veillonellaceae | *Selenomonas* |
| *Selenomonas* genomosp. C1 | Bacteria | Firmicutes | Negativicutes | Selenomonadales | Veillonellaceae | *Selenomonas* |
| *Selenomonas* genomosp. C2 | Bacteria | Firmicutes | Negativicutes | Selenomonadales | Veillonellaceae | *Selenomonas* |
| *Selenomonas* genomosp. P5 | Bacteria | Firmicutes | Negativicutes | Selenomonadales | Veillonellaceae | *Selenomonas* |
| *Selenomonas* genomosp. P6 oral clone MB3_C41 | Bacteria | Firmicutes | Negativicutes | Selenomonadales | Veillonellaceae | *Selenomonas* |
| *Selenomonas* genomosp. P7 oral clone MB5_C08 | Bacteria | Firmicutes | Negativicutes | Selenomonadales | Veillonellaceae | *Selenomonas* |
| *Selenomonas* genomosp. P8 oral clone MB5_P06 | Bacteria | Firmicutes | Negativicutes | Selenomonadales | Veillonellaceae | *Selenomonas* |
| *Selenomonas infelix* | Bacteria | Firmicutes | Negativicutes | Selenomonadales | Veillonellaceae | *Selenomonas* |
| *Selenomonas noxia* | Bacteria | Firmicutes | Negativicutes | Selenomonadales | Veillonellaceae | *Selenomonas* |
| *Selenomonas ruminantium* | Bacteria | Firmicutes | Negativicutes | Selenomonadales | Veillonellaceae | *Selenomonas* |
| *Selenomonas* sp. FOBRC9 | Bacteria | Firmicutes | Negativicutes | Selenomonadales | Veillonellaceae | *Selenomonas* |
| *Selenomonas* sp. oral clone FT050 | Bacteria | Firmicutes | Negativicutes | Selenomonadales | Veillonellaceae | *Selenomonas* |
| *Selenomonas* sp. oral clone GI064 | Bacteria | Firmicutes | Negativicutes | Selenomonadales | Veillonellaceae | *Selenomonas* |
| *Selenomonas* sp. oral clone GT010 | Bacteria | Firmicutes | Negativicutes | Selenomonadales | Veillonellaceae | *Selenomonas* |
| *Selenomonas* sp. oral clone HU051 | Bacteria | Firmicutes | Negativicutes | Selenomonadales | Veillonellaceae | *Selenomonas* |
| *Selenomonas* sp. oral clone IK004 | Bacteria | Firmicutes | Negativicutes | Selenomonadales | Veillonellaceae | *Selenomonas* |
| *Selenomonas* sp. oral clone IQ048 | Bacteria | Firmicutes | Negativicutes | Selenomonadales | Veillonellaceae | *Selenomonas* |
| *Selenomonas* sp. oral clone JI021 | Bacteria | Firmicutes | Negativicutes | Selenomonadales | Veillonellaceae | *Selenomonas* |
| *Selenomonas* sp. oral clone JS031 | Bacteria | Firmicutes | Negativicutes | Selenomonadales | Veillonellaceae | *Selenomonas* |

TABLE 1-continued

| OTU | Domain | Phylum | Class | Order | Family | Genus |
|---|---|---|---|---|---|---|
| *Selenomonas* sp. oral clone OH4A | Bacteria | Firmicutes | Negativicutes | Selenomonadales | Veillonellaceae | *Selenomonas* |
| *Selenomonas* sp. oral clone P2PA__80 P4 | Bacteria | Firmicutes | Negativicutes | Selenomonadales | Veillonellaceae | *Selenomonas* |
| *Selenomonas* sp. oral taxon 137 | Bacteria | Firmicutes | Negativicutes | Selenomonadales | Veillonellaceae | *Selenomonas* |
| *Selenomonas* sp. oral taxon 149 | Bacteria | Firmicutes | Negativicutes | Selenomonadales | Veillonellaceae | *Selenomonas* |
| *Selenomonas sputigena* | Bacteria | Firmicutes | Negativicutes | Selenomonadales | Veillonellaceae | *Selenomonas* |
| *Serratia fonticola* | Bacteria | Proteobacteria | Gammaproteobacteria | Enterobacteriales | Enterobacteriaceae | *Serratia* |
| *Serratia liquefaciens* | Bacteria | Proteobacteria | Gammaproteobacteria | Enterobacteriales | Enterobacteriaceae | *Serratia* |
| *Serratia marcescens* | Bacteria | Proteobacteria | Gammaproteobacteria | Enterobacteriales | Enterobacteriaceae | *Serratia* |
| *Serratia odorifera* | Bacteria | Proteobacteria | Gammaproteobacteria | Enterobacteriales | Enterobacteriaceae | *Serratia* |
| *Serratia proteamaculans* | Bacteria | Proteobacteria | Gammaproteobacteria | Enterobacteriales | Enterobacteriaceae | *Serratia* |
| *Shewanella putrefaciens* | Bacteria | Proteobacteria | Gammaproteobacteria | Alteromonadales | Shewanellaceae | *Shewanella* |
| *Shuttleworthia satelles* | Bacteria | Firmicutes | Clostridia | Clostridiales | Lachnospiraceae | *Shuttleworthia* |
| *Shuttleworthia* sp. MSX8B | Bacteria | Firmicutes | Clostridia | Clostridiales | Lachnospiraceae | *Shuttleworthia* |
| *Shuttleworthia* sp. oral taxon G69 | Bacteria | Firmicutes | Clostridia | Clostridiales | Lachnospiraceae | *Shuttleworthia* |
| *Simonsiella muelleri* | Bacteria | Proteobacteria | Betaproteobacteria | Neisseriales | Neisseriaceae | *Simonsiella* |
| *Slackia equolifaciens* | Bacteria | Actinobacteria | Actinobacteria | Coriobacteriales | Coriobacteriaceae | *Slackia* |
| *Slackia exigua* | Bacteria | Actinobacteria | Actinobacteria | Coriobacteriales | Coriobacteriaceae | *Slackia* |
| *Slackia faecicanis* | Bacteria | Actinobacteria | Actinobacteria | Coriobacteriales | Coriobacteriaceae | *Slackia* |
| *Slackia heliotrinireducens* | Bacteria | Actinobacteria | Actinobacteria | Coriobacteriales | Coriobacteriaceae | *Slackia* |
| *Slackia isoflavoniconvertens* | Bacteria | Actinobacteria | Actinobacteria | Coriobacteriales | Coriobacteriaceae | *Slackia* |
| *Slackia piriformis* | Bacteria | Actinobacteria | Actinobacteria | Coriobacteriales | Coriobacteriaceae | *Slackia* |
| *Slackia* sp. NATTS | Bacteria | Actinobacteria | Actinobacteria | Coriobacteriales | Coriobacteriaceae | *Slackia* |
| *Solobacterium moorei* | Bacteria | Firmicutes | Erysipelotrichi | Erysipelotrichales | Erysipelotrichaceae | *Solobacterium* |
| *Sphingobacterium faecium* | Bacteria | Bacteroidetes | Sphingobacteriia | Sphingobacteriales | Sphingobacteriaceae | *Sphingobacterium* |
| *Sphingobacterium mizutaii* | Bacteria | Bacteroidetes | Sphingobacteriia | Sphingobacteriales | Sphingobacteriaceae | *Sphingobacterium* |
| *Sphingobacterium multivorum* | Bacteria | Bacteroidetes | Sphingobacteriia | Sphingobacteriales | Sphingobacteriaceae | *Sphingobacterium* |
| *Sphingobacterium spiritivorum* | Bacteria | Bacteroidetes | Sphingobacteriia | Sphingobacteriales | Sphingobacteriaceae | *Sphingobacterium* |
| *Sphingomonas echinoides* | Bacteria | Proteobacteria | Alphaproteobacteria | Sphingomonadales | Sphingomonadaceae | *Sphingomonas* |
| *Sphingomonas* sp. oral clone FI012 | Bacteria | Proteobacteria | Alphaproteobacteria | Sphingomonadales | Sphingomonadaceae | *Sphingomonas* |
| *Sphingomonas* sp. oral clone FZ016 | Bacteria | Proteobacteria | Alphaproteobacteria | Sphingomonadales | Sphingomonadaceae | *Sphingomonas* |
| *Sphingomonas* sp. oral taxon A09 | Bacteria | Proteobacteria | Alphaproteobacteria | Sphingomonadales | Sphingomonadaceae | *Sphingomonas* |
| *Sphingomonas* sp. oral taxon F71 | Bacteria | Proteobacteria | Alphaproteobacteria | Sphingomonadales | Sphingomonadaceae | *Sphingomonas* |
| *Sphingopyxis alaskensis* | Bacteria | Proteobacteria | Alphaproteobacteria | Sphingomonadales | Sphingomonadaceae | *Sphingopyxis* |
| *Spiroplasma insolitum* | Bacteria | Tenericutes | Mollicutes | Entomoplasmatales | Spiroplasmataceae | *Spiroplasma* |
| *Sporobacter termitidis* | Bacteria | Firmicutes | Clostridia | Clostridiales | Ruminococcaceae | *Sporobacter* |
| *Sporolactobacillus inulinus* | Bacteria | Firmicutes | Bacilli | Bacillales | Sporolactobacillaceae | *Sporolactobacillus* |
| *Sporolactobacillus nakayamae* | Bacteria | Firmicutes | Bacilli | Bacillales | Sporolactobacillaceae | *Sporolactobacillus* |
| *Sporosarcina newyorkensis* | Bacteria | Firmicutes | Bacilli | Bacillales | Planococcaceae | *Sporosarcina* |
| *Sporosarcina* sp. 2681 | Bacteria | Firmicutes | Bacilli | Bacillales | Planococcaceae | *Sporosarcina* |
| Staphylococcaceae bacterium NML 92-0017 | Bacteria | Firmicutes | Bacilli | Bacillales | Staphylococcaceae | unclassified |
| *Staphylococcus aureus* | Bacteria | Firmicutes | Bacilli | Bacillales | Staphylococcaceae | *Staphylococcus* |
| *Staphylococcus auricularis* | Bacteria | Firmicutes | Bacilli | Bacillales | Staphylococcaceae | *Staphylococcus* |
| *Staphylococcus capitis* | Bacteria | Firmicutes | Bacilli | Bacillales | Staphylococcaceae | *Staphylococcus* |
| *Staphylococcus caprae* | Bacteria | Firmicutes | Bacilli | Bacillales | Staphylococcaceae | *Staphylococcus* |
| *Staphylococcus carnosus* | Bacteria | Firmicutes | Bacilli | Bacillales | Staphylococcaceae | *Staphylococcus* |
| *Staphylococcus cohnii* | Bacteria | Firmicutes | Bacilli | Bacillales | Staphylococcaceae | *Staphylococcus* |
| *Staphylococcus condimenti* | Bacteria | Firmicutes | Bacilli | Bacillales | Staphylococcaceae | *Staphylococcus* |
| *Staphylococcus epidermidis* | Bacteria | Firmicutes | Bacilli | Bacillales | Staphylococcaceae | *Staphylococcus* |
| *Staphylococcus equorum* | Bacteria | Firmicutes | Bacilli | Bacillales | Staphylococcaceae | *Staphylococcus* |
| *Staphylococcus fleurettii* | Bacteria | Firmicutes | Bacilli | Bacillales | Staphylococcaceae | *Staphylococcus* |
| *Staphylococcus haemolyticus* | Bacteria | Firmicutes | Bacilli | Bacillales | Staphylococcaceae | *Staphylococcus* |

TABLE 1-continued

| OTU | Domain | Phylum | Class | Order | Family | Genus |
|---|---|---|---|---|---|---|
| *Staphylococcus hominis* | Bacteria | Firmicutes | Bacilli | Bacillales | Staphylococcaceae | *Staphylococcus* |
| *Staphylococcus lugdunensis* | Bacteria | Firmicutes | Bacilli | Bacillales | Staphylococcaceae | *Staphylococcus* |
| *Staphylococcus pasteuri* | Bacteria | Firmicutes | Bacilli | Bacillales | Staphylococcaceae | *Staphylococcus* |
| *Staphylococcus pseudintermedius* | Bacteria | Firmicutes | Bacilli | Bacillales | Staphylococcaceae | *Staphylococcus* |
| *Staphylococcus saccharolyticus* | Bacteria | Firmicutes | Bacilli | Bacillales | Staphylococcaceae | *Staphylococcus* |
| *Staphylococcus saprophyticus* | Bacteria | Firmicutes | Bacilli | Bacillales | Staphylococcaceae | *Staphylococcus* |
| *Staphylococcus sciuri* | Bacteria | Firmicutes | Bacilli | Bacillales | Staphylococcaceae | *Staphylococcus* |
| *Staphylococcus* sp. clone bottae7 | Bacteria | Firmicutes | Bacilli | Bacillales | Staphylococcaceae | *Staphylococcus* |
| *Staphylococcus* sp. H292 | Bacteria | Firmicutes | Bacilli | Bacillales | Staphylococcaceae | *Staphylococcus* |
| *Staphylococcus* sp. H780 | Bacteria | Firmicutes | Bacilli | Bacillales | Staphylococcaceae | *Staphylococcus* |
| *Staphylococcus succinus* | Bacteria | Firmicutes | Bacilli | Bacillales | Staphylococcaceae | *Staphylococcus* |
| *Staphylococcus vitulinus* | Bacteria | Firmicutes | Bacilli | Bacillales | Staphylococcaceae | *Staphylococcus* |
| *Staphylococcus warneri* | Bacteria | Firmicutes | Bacilli | Bacillales | Staphylococcaceae | *Staphylococcus* |
| *Staphylococcus xylosus* | Bacteria | Firmicutes | Bacilli | Bacillales | Staphylococcaceae | *Staphylococcus* |
| *Stenotrophomonas maltophilia* | Bacteria | Proteobacteria | Gammaproteobacteria | Xanthomonadales | Xanthomonadaceae | *Stenotrophomonas* |
| *Stenotrophomonas* sp. FG-6 | Bacteria | Proteobacteria | Gammaproteobacteria | Xanthomonadales | Xanthomonadaceae | *Stenotrophomonas* |
| *Streptobacillus moniliformis* | Bacteria | Fusobacteria | Fusobacteriia | Fusobacteriales | Leptotrichiaceae | *Streptobacillus* |
| *Streptococcus agalactiae* | Bacteria | Firmicutes | Bacilli | Lactobacillales | Streptococcaceae | *Streptococcus* |
| *Streptococcus alactolyticus* | Bacteria | Firmicutes | Bacilli | Lactobacillales | Streptococcaceae | *Streptococcus* |
| *Streptococcus anginosus* | Bacteria | Firmicutes | Bacilli | Lactobacillales | Streptococcaceae | *Streptococcus* |
| *Streptococcus austrails* | Bacteria | Firmicutes | Bacilli | Lactobacillales | Streptococcaceae | *Streptococcus* |
| *Streptococcus bovis* | Bacteria | Firmicutes | Bacilli | Lactobacillales | Streptococcaceae | *Streptococcus* |
| *Streptococcus canis* | Bacteria | Firmicutes | Bacilli | Lactobacillales | Streptococcaceae | *Streptococcus* |
| *Streptococcus constellatus* | Bacteria | Firmicutes | Bacilli | Lactobacillales | Streptococcaceae | *Streptococcus* |
| *Streptococcus cristatus* | Bacteria | Firmicutes | Bacilli | Lactobacillales | Streptococcaceae | *Streptococcus* |
| *Streptococcus downei* | Bacteria | Firmicutes | Bacilli | Lactobacillales | Streptococcaceae | *Streptococcus* |
| *Streptococcus dysgalactiae* | Bacteria | Firmicutes | Bacilli | Lactobacillales | Streptococcaceae | *Streptococcus* |
| *Streptococcus equi* | Bacteria | Firmicutes | Bacilli | Lactobacillales | Streptococcaceae | *Streptococcus* |
| *Streptococcus equinus* | Bacteria | Firmicutes | Bacilli | Lactobacillales | Streptococcaceae | *Streptococcus* |
| *Streptococcus gallolyticus* | Bacteria | Firmicutes | Bacilli | Lactobacillales | Streptococcaceae | *Streptococcus* |
| *Streptococcus* genomosp. C1 | Bacteria | Firmicutes | Bacilli | Lactobacillales | Streptococcaceae | *Streptococcus* |
| *Streptococcus* genomosp. C2 | Bacteria | Firmicutes | Bacilli | Lactobacillales | Streptococcaceae | *Streptococcus* |
| *Streptococcus* genomosp. C3 | Bacteria | Firmicutes | Bacilli | Lactobacillales | Streptococcaceae | *Streptococcus* |
| *Streptococcus* genomosp. C4 | Bacteria | Firmicutes | Bacilli | Lactobacillales | Streptococcaceae | *Streptococcus* |
| *Streptococcus* genomosp. C5 | Bacteria | Firmicutes | Bacilli | Lactobacillales | Streptococcaceae | *Streptococcus* |
| *Streptococcus* genomosp. C6 | Bacteria | Firmicutes | Bacilli | Lactobacillales | Streptococcaceae | *Streptococcus* |
| *Streptococcus* genomosp. C7 | Bacteria | Firmicutes | Bacilli | Lactobacillales | Streptococcaceae | *Streptococcus* |
| *Streptococcus* genomosp. C8 | Bacteria | Firmicutes | Bacilli | Lactobacillales | Streptococcaceae | *Streptococcus* |
| *Streptococcus gordonii* | Bacteria | Firmicutes | Bacilli | Lactobacillales | Streptococcaceae | *Streptococcus* |
| *Streptococcus infantarius* | Bacteria | Firmicutes | Bacilli | Lactobacillales | Streptococcaceae | *Streptococcus* |
| *Streptococcus infantis* | Bacteria | Firmicutes | Bacilli | Lactobacillales | Streptococcaceae | *Streptococcus* |
| *Streptococcus intermedius* | Bacteria | Firmicutes | Bacilli | Lactobacillales | Streptococcaceae | *Streptococcus* |
| *Streptococcus lutetiensis* | Bacteria | Firmicutes | Bacilli | Lactobacillales | Streptococcaceae | *Streptococcus* |
| *Streptococcus massiliensis* | Bacteria | Firmicutes | Bacilli | Lactobacillales | Streptococcaceae | *Streptococcus* |
| *Streptococcus milleri* | Bacteria | Firmicutes | Bacilli | Lactobacillales | Streptococcaceae | *Streptococcus* |
| *Streptococcus mitis* | Bacteria | Firmicutes | Bacilli | Lactobacillales | Streptococcaceae | *Streptococcus* |
| *Streptococcus mutans* | Bacteria | Firmicutes | Bacilli | Lactobacillales | Streptococcaceae | *Streptococcus* |
| *Streptococcus oligofermentans* | Bacteria | Firmicutes | Bacilli | Lactobacillales | Streptococcaceae | *Streptococcus* |
| *Streptococcus oralis* | Bacteria | Firmicutes | Bacilli | Lactobacillales | Streptococcaceae | *Streptococcus* |
| *Streptococcus parasanguinis* | Bacteria | Firmicutes | Bacilli | Lactobacillales | Streptococcaceae | *Streptococcus* |
| *Streptococcus pasteurianus* | Bacteria | Firmicutes | Bacilli | Lactobacillales | Streptococcaceae | *Streptococcus* |

TABLE 1-continued

| OTU | Domain | Phylum | Class | Order | Family | Genus |
|---|---|---|---|---|---|---|
| *Streptococcus peroris* | Bacteria | Firmicutes | Bacilli | Lactobacillales | Streptococcaceae | *Streptococcus* |
| *Streptococcus pneumoniae* | Bacteria | Firmicutes | Bacilli | Lactobacillales | Streptococcaceae | *Streptococcus* |
| *Streptococcus porcinus* | Bacteria | Firmicutes | Bacilli | Lactobacillales | Streptococcaceae | *Streptococcus* |
| *Streptococcus pseudopneumoniae* | Bacteria | Firmicutes | Bacilli | Lactobacillales | Streptococcaceae | *Streptococcus* |
| *Streptococcus pseudoporcinus* | Bacteria | Firmicutes | Bacilli | Lactobacillales | Streptococcaceae | *Streptococcus* |
| *Streptococcus ratti* | Bacteria | Firmicutes | Bacilli | Lactobacillales | Streptococcaceae | *Streptococcus* |
| *Streptococcus salivarius* | Bacteria | Firmicutes | Bacilli | Lactobacillales | Streptococcaceae | *Streptococcus* |
| *Streptococcus sanguinis* | Bacteria | Firmicutes | Bacilli | Lactobacillales | Streptococcaceae | *Streptococcus* |
| *Streptococcus sinensis* | Bacteria | Firmicutes | Bacilli | Lactobacillales | Streptococcaceae | *Streptococcus* |
| *Streptococcus* sp. 16362 | Bacteria | Firmicutes | Bacilli | Lactobacillales | Streptococcaceae | *Streptococcus* |
| *Streptococcus* sp. 2__1__36FAA | Bacteria | Firmicutes | Bacilli | Lactobacillales | Streptococcaceae | *Streptococcus* |
| *Streptococcus* sp. 2285-97 | Bacteria | Firmicutes | Bacilli | Lactobacillales | Streptococcaceae | *Streptococcus* |
| *Streptococcus* sp. 69130 | Bacteria | Firmicutes | Bacilli | Lactobacillales | Streptococcaceae | *Streptococcus* |
| *Streptococcus* sp. AC15 | Bacteria | Firmicutes | Bacilli | Lactobacillales | Streptococcaceae | *Streptococcus* |
| *Streptococcus* sp. ACS2 | Bacteria | Firmicutes | Bacilli | Lactobacillales | Streptococcaceae | *Streptococcus* |
| *Streptococcus* sp. AS20 | Bacteria | Firmicutes | Bacilli | Lactobacillales | Streptococcaceae | *Streptococcus* |
| *Streptococcus* sp. BS35a | Bacteria | Firmicutes | Bacilli | Lactobacillales | Streptococcaceae | *Streptococcus* |
| *Streptococcus* sp. C150 | Bacteria | Firmicutes | Bacilli | Lactobacillales | Streptococcaceae | *Streptococcus* |
| *Streptococcus* sp. CM6 | Bacteria | Firmicutes | Bacilli | Lactobacillales | Streptococcaceae | *Streptococcus* |
| *Streptococcus* sp. CM7 | Bacteria | Firmicutes | Bacilli | Lactobacillales | Streptococcaceae | *Streptococcus* |
| *Streptococcus* sp. ICM10 | Bacteria | Firmicutes | Bacilli | Lactobacillales | Streptococcaceae | *Streptococcus* |
| *Streptococcus* sp. ICM12 | Bacteria | Firmicutes | Bacilli | Lactobacillales | Streptococcaceae | *Streptococcus* |
| *Streptococcus* sp. ICM2 | Bacteria | Firmicutes | Bacilli | Lactobacillales | Streptococcaceae | *Streptococcus* |
| *Streptococcus* sp. ICM4 | Bacteria | Firmicutes | Bacilli | Lactobacillales | Streptococcaceae | *Streptococcus* |
| *Streptococcus* sp. ICM45 | Bacteria | Firmicutes | Bacilli | Lactobacillales | Streptococcaceae | *Streptococcus* |
| *Streptococcus* sp. M143 | Bacteria | Firmicutes | Bacilli | Lactobacillales | Streptococcaceae | *Streptococcus* |
| *Streptococcus* sp. M334 | Bacteria | Firmicutes | Bacilli | Lactobacillales | Streptococcaceae | *Streptococcus* |
| *Streptococcus* sp. OBRC6 | Bacteria | Firmicutes | Bacilli | Lactobacillales | Streptococcaceae | *Streptococcus* |
| *Streptococcus* sp. oral clone ASB02 | Bacteria | Firmicutes | Bacilli | Lactobacillales | Streptococcaceae | *Streptococcus* |
| *Streptococcus* sp. oral clone ASCA03 | Bacteria | Firmicutes | Bacilli | Lactobacillales | Streptococcaceae | *Streptococcus* |
| *Streptococcus* sp. oral clone ASCA04 | Bacteria | Firmicutes | Bacilli | Lactobacillales | Streptococcaceae | *Streptococcus* |
| *Streptococcus* sp. oral clone ASCA09 | Bacteria | Firmicutes | Bacilli | Lactobacillales | Streptococcaceae | *Streptococcus* |
| *Streptococcus* sp. oral clone ASCB04 | Bacteria | Firmicutes | Bacilli | Lactobacillales | Streptococcaceae | *Streptococcus* |
| *Streptococcus* sp. oral clone ASCB06 | Bacteria | Firmicutes | Bacilli | Lactobacillales | Streptococcaceae | *Streptococcus* |
| *Streptococcus* sp. oral clone ASCC04 | Bacteria | Firmicutes | Bacilli | Lactobacillales | Streptococcaceae | *Streptococcus* |
| *Streptococcus* sp. oral clone ASCC05 | Bacteria | Firmicutes | Bacilli | Lactobacillales | Streptococcaceae | *Streptococcus* |
| *Streptococcus* sp. oral clone ASCC12 | Bacteria | Firmicutes | Bacilli | Lactobacillales | Streptococcaceae | *Streptococcus* |
| *Streptococcus* sp. oral clone ASCD01 | Bacteria | Firmicutes | Bacilli | Lactobacillales | Streptococcaceae | *Streptococcus* |
| *Streptococcus* sp. oral clone ASCD09 | Bacteria | Firmicutes | Bacilli | Lactobacillales | Streptococcaceae | *Streptococcus* |
| *Streptococcus* sp. oral clone ASCD10 | Bacteria | Firmicutes | Bacilli | Lactobacillales | Streptococcaceae | *Streptococcus* |
| *Streptococcus* sp. oral clone ASCE03 | Bacteria | Firmicutes | Bacilli | Lactobacillales | Streptococcaceae | *Streptococcus* |
| *Streptococcus* sp. oral clone ASCE04 | Bacteria | Firmicutes | Bacilli | Lactobacillales | Streptococcaceae | *Streptococcus* |
| *Streptococcus* sp. oral clone ASCE05 | Bacteria | Firmicutes | Bacilli | Lactobacillales | Streptococcaceae | *Streptococcus* |
| *Streptococcus* sp. oral clone ASCE06 | Bacteria | Firmicutes | Bacilli | Lactobacillales | Streptococcaceae | *Streptococcus* |
| *Streptococcus* sp. oral clone ASCE09 | Bacteria | Firmicutes | Bacilli | Lactobacillales | Streptococcaceae | *Streptococcus* |
| *Streptococcus* sp. oral clone ASCE10 | Bacteria | Firmicutes | Bacilli | Lactobacillales | Streptococcaceae | *Streptococcus* |

TABLE 1-continued

| OTU | Domain | Phylum | Class | Order | Family | Genus |
|---|---|---|---|---|---|---|
| *Streptococcus* sp. oral clone ASCE12 | Bacteria | Firmicutes | Bacilli | Lactobacillales | Streptococcaceae | *Streptococcus* |
| *Streptococcus* sp. oral clone ASCF05 | Bacteria | Firmicutes | Bacilli | Lactobacillales | Streptococcaceae | *Streptococcus* |
| *Streptococcus* sp. oral clone ASCF07 | Bacteria | Firmicutes | Bacilli | Lactobacillales | Streptococcaceae | *Streptococcus* |
| *Streptococcus* sp. oral clone ASCF09 | Bacteria | Firmicutes | Bacilli | Lactobacillales | Streptococcaceae | *Streptococcus* |
| *Streptococcus* sp. oral clone ASCG04 | Bacteria | Firmicutes | Bacilli | Lactobacillales | Streptococcaceae | *Streptococcus* |
| *Streptococcus* sp. oral clone BW009 | Bacteria | Firmicutes | Bacilli | Lactobacillales | Streptococcaceae | *Streptococcus* |
| *Streptococcus* sp. oral clone CH016 | Bacteria | Firmicutes | Bacilli | Lactobacillales | Streptococcaceae | *Streptococcus* |
| *Streptococcus* sp. oral clone GK051 | Bacteria | Firmicutes | Bacilli | Lactobacillales | Streptococcaceae | *Streptococcus* |
| *Streptococcus* sp. oral clone GM006 | Bacteria | Firmicutes | Bacilli | Lactobacillales | Streptococcaceae | *Streptococcus* |
| *Streptococcus* sp. oral clone P2PA__41 P2 | Bacteria | Firmicutes | Bacilli | Lactobacillales | Streptococcaceae | *Streptococcus* |
| *Streptococcus* sp. oral clone P4PA__13 P3 | Bacteria | Firmicutes | Bacilli | Lactobacillales | Streptococcaceae | *Streptococcus* |
| *Streptococcus* sp. oral clone P4PA__30 P4 | Bacteria | Firmicutes | Bacilli | Lactobacillales | Streptococcaceae | *Streptococcus* |
| *Streptococcus* sp. oral taxon 071 | Bacteria | Firmicutes | Bacilli | Lactobacillales | Streptococcaceae | *Streptococcus* |
| *Streptococcus* sp. oral taxon G59 | Bacteria | Firmicutes | Bacilli | Lactobacillales | Streptococcaceae | *Streptococcus* |
| *Streptococcus* sp. oral taxon G62 | Bacteria | Firmicutes | Bacilli | Lactobacillales | Streptococcaceae | *Streptococcus* |
| *Streptococcus* sp. oral taxon G63 | Bacteria | Firmicutes | Bacilli | Lactobacillales | Streptococcaceae | *Streptococcus* |
| *Streptococcus* sp. SHV515 | Bacteria | Firmicutes | Bacilli | Lactobacillales | Streptococcaceae | *Streptococcus* |
| *Streptococcus suis* | Bacteria | Firmicutes | Bacilli | Lactobacillales | Streptococcaceae | *Streptococcus* |
| *Streptococcus thermophilus* | Bacteria | Firmicutes | Bacilli | Lactobacillales | Streptococcaceae | *Streptococcus* |
| *Streptococcus uberis* | Bacteria | Firmicutes | Bacilli | Lactobacillales | Streptococcaceae | *Streptococcus* |
| *Streptococcus urinalis* | Bacteria | Firmicutes | Bacilli | Lactobacillales | Streptococcaceae | *Streptococcus* |
| *Streptococcus vestibularis* | Bacteria | Firmicutes | Bacilli | Lactobacillales | Streptococcaceae | *Streptococcus* |
| *Streptococcus viridans* | Bacteria | Firmicutes | Bacilli | Lactobacillales | Streptococcaceae | *Streptococcus* |
| *Streptomyces albus* | Bacteria | Actinobacteria | Actinobacteria | Actinomycetales | Streptomycetaceae | *Streptomyces* |
| *Streptomyces griseus* | Bacteria | Actinobacteria | Actinobacteria | Actinomycetales | Streptomycetaceae | *Streptomyces* |
| *Streptomyces* sp. 1 AIP-2009 | Bacteria | Actinobacteria | Actinobacteria | Actinomycetales | Streptomycetaceae | *Streptomyces* |
| *Streptomyces* sp. SD 511 | Bacteria | Actinobacteria | Actinobacteria | Actinomycetales | Streptomycetaceae | *Streptomyces* |
| *Streptomyces* sp. SD 524 | Bacteria | Actinobacteria | Actinobacteria | Actinomycetales | Streptomycetaceae | *Streptomyces* |
| *Streptomyces* sp. SD 528 | Bacteria | Actinobacteria | Actinobacteria | Actinomycetales | Streptomycetaceae | *Streptomyces* |
| *Streptomyces* sp. SD 534 | Bacteria | Actinobacteria | Actinobacteria | Actinomycetales | Streptomycetaceae | *Streptomyces* |
| *Streptomyces thermoviolaceus* | Bacteria | Actinobacteria | Actinobacteria | Actinomycetales | Streptomycetaceae | *Streptomyces* |
| *Subdoligranulum variabile* | Bacteria | Firmicutes | Clostridia | Clostridiales | Ruminococcaceae | *Subdoligranulum* |
| *Succinatimonas hippei* | Bacteria | Proteobacteria | Gammaproteobacteria | Aeromonadales | Succinivibrionaceae | *Succinatimonas* |
| *Sutterella morbirenis* | Bacteria | Proteobacteria | Betaproteobacteria | Burkholderiales | Sutterellaceae | *Sutterella* |
| *Sutterella parvirubra* | Bacteria | Proteobacteria | Betaproteobacteria | Burkholderiales | Sutterellaceae | *Sutterella* |
| *Sutterella sanguinus* | Bacteria | Proteobacteria | Betaproteobacteria | Burkholderiales | Sutterellaceae | *Sutterella* |
| *Sutterella* sp. YIT 12072 | Bacteria | Proteobacteria | Betaproteobacteria | Burkholderiales | Sutterellaceae | *Sutterella* |
| *Sutterella stercoricanis* | Bacteria | Proteobacteria | Betaproteobacteria | Burkholderiales | Sutterellaceae | *Sutterella* |
| *Sutterella wadsworthensis* | Bacteria | Proteobacteria | Betaproteobacteria | Burkholderiales | Sutterellaceae | *Sutterella* |
| *Synergistes* genomosp. C1 | Bacteria | Synergistetes | Synergistia | Synergistales | Synergistaceae | *Synergistes* |
| *Synergistes* sp. RMA 14551 | Bacteria | Synergistetes | Synergistia | Synergistales | Synergistaceae | *Synergistes* |
| Synergistetes bacterium ADV897 | Bacteria | Synergistetes | unclassified | unclassified | unclassified | unclassified |
| Synergistetes bacterium LBVCM1157 | Bacteria | Synergistetes | unclassified | unclassified | unclassified | unclassified |
| Synergistetes bacterium oral clone 03 5 D05 | Bacteria | Synergistetes | unclassified | unclassified | unclassified | unclassified |
| Synergistetes bacterium oral taxon 362 | Bacteria | Synergistetes | unclassified | unclassified | unclassified | unclassified |
| Synergistetes bacterium oral taxon D48 | Bacteria | Synergistetes | unclassified | unclassified | unclassified | unclassified |
| *Syntrophococcus sucromutans* | Bacteria | Firmicutes | Clostridia | Clostridiales | Lachnospiraceae | *Syntrophococcus* |

TABLE 1-continued

| OTU | Domain | Phylum | Class | Order | Family | Genus |
|---|---|---|---|---|---|---|
| Syntrophomonadaceae genomosp. P1 | Bacteria | Firmicutes | Clostridia | Clostridiales | Syntrophomonadaceae | unclassified |
| *Tannerella forsythia* | Bacteria | Bacteroidetes | Bacteroidia | Bacteroidales | Porphyromonadaceae | *Tannerella* |
| *Tannerella* sp. 6_1_58FAA_CT1 | Bacteria | Bacteroidetes | Bacteroidia | Bacteroidales | Porphyromonadaceae | *Tannerella* |
| *Tatlockia micdadei* | Bacteria | Proteobacteria | Gammaproteobacteria | Legionellales | Legionellaceae | *Tatlockia* |
| *Tatumella ptyseos* | Bacteria | Proteobacteria | Gammaproteobacteria | Enterobacteriales | Enterobacteriaceae | *Tatumella* |
| *Tessaracoccus* sp. oral taxon F04 | Bacteria | Actinobacteria | Actinobacteria | Actinomycetales | Propionibacteriaceae | *Tessaracoccus* |
| *Tetragenococcus halophilus* | Bacteria | Firmicutes | Bacilli | Lactobacillales | Enterococcaceae | *Tetragenococcus* |
| *Tetragenococcus koreensis* | Bacteria | Firmicutes | Bacilli | Lactobacillales | Enterococcaceae | *Tetragenococcus* |
| *Thermoanaerobacter pseudethanolicus* | Bacteria | Firmicutes | Clostridia | Thermoanaerobacterales | Thermoanaerobacteraceae | *Thermoanaerobacter* |
| *Thermobifida fusca* | Bacteria | Actinobacteria | Actinobacteria | Actinomycetales | Nocardiopsaceae | *Thermobifida* |
| *Thermofilum pendens* | Archaea | Crenarchaeota | Thermoprotei | Thermoproteales | Thermofilaceae | *Thermofilum* |
| *Thermus aquaticus* | Bacteria | Deinococcus-Thermus | Deinococci | Thermales | Thermaceae | *Thermus* |
| *Tissierella praeacuta* | Bacteria | Firmicutes | Clostridia | Clostridiales | Clostridiales Family XI. Incertae Sedis | *Tissierella* |
| *Trabulsiella guamensis* | Bacteria | Proteobacteria | Gammaproteobacteria | Enterobacteriales | Enterobacteriaceae | *Trabulsiella* |
| *Treponema* genomosp. P1 | Bacteria | Spirochaetes | Spirochaetia | Spirochaetales | Spirochaetaceae | *Treponema* |
| *Treponema* genomosp. P4 oral clone MB2_G19 | Bacteria | Spirochaetes | Spirochaetia | Spirochaetales | Spirochaetaceae | *Treponema* |
| *Treponema* genomosp. P5 oral clone MB3_P23 | Bacteria | Spirochaetes | Spirochaetia | Spirochaetales | Spirochaetaceae | *Treponema* |
| *Treponema* genomosp. P6 oral clone MB4_G11 | Bacteria | Spirochaetes | Spirochaetia | Spirochaetales | Spirochaetaceae | *Treponema* |
| *Treponema phagedenis* | Bacteria | Spirochaetes | Spirochaetia | Spirochaetales | Spirochaetaceae | *Treponema* |
| *Treponema* sp. 6:H:D15A-4 | Bacteria | Spirochaetes | Spirochaetia | Spirochaetales | Spirochaetaceae | *Treponema* |
| *Treponema* sp. clone DDKL-4 | Bacteria | Spirochaetes | Spirochaetes | Spirochaetales | Spirochaetaceae | *Treponema* |
| *Treponema* sp. oral clone JU025 | Bacteria | Spirochaetes | Spirochaetia | Spirochaetales | Spirochaetaceae | *Treponema* |
| *Treponema* sp. oral clone JU031 | Bacteria | Spirochaetes | Spirochaetia | Spirochaetales | Spirochaetaceae | *Treponema* |
| *Treponema* sp. oral clone P2PB_53 P3 | Bacteria | Spirochaetes | Spirochaetia | Spirochaetales | Spirochaetaceae | *Treponema* |
| *Treponema* sp. oral taxon 228 | Bacteria | Spirochaetes | Spirochaetia | Spirochaetales | Spirochaetaceae | *Treponema* |
| *Treponema* sp. oral taxon 230 | Bacteria | Spirochaetes | Spirochaetia | Spirochaetales | Spirochaetaceae | *Treponema* |
| *Treponema* sp. oral taxon 231 | Bacteria | Spirochaetes | Spirochaetia | Spirochaetales | Spirochaetaceae | *Treponema* |
| *Treponema* sp. oral taxon 232 | Bacteria | Spirochaetes | Spirochaetia | Spirochaetales | Spirochaetaceae | *Treponema* |
| *Treponema* sp. oral taxon 235 | Bacteria | Spirochaetes | Spirochaetia | Spirochaetales | Spirochaetaceae | *Treponema* |
| *Treponema* sp. oral taxon 239 | Bacteria | Spirochaetes | Spirochaetia | Spirochaetales | Spirochaetaceae | *Treponema* |
| *Treponema* sp. oral taxon 247 | Bacteria | Spirochaetes | Spirochaetia | Spirochaetales | Spirochaetaceae | *Treponema* |
| *Treponema* sp. oral taxon 250 | Bacteria | Spirochaetes | Spirochaetia | Spirochaetales | Spirochaetaceae | *Treponema* |
| *Treponema* sp. oral taxon 251 | Bacteria | Spirochaetes | Spirochaetia | Spirochaetales | Spirochaetaceae | *Treponema* |
| *Treponema* sp. oral taxon 254 | Bacteria | Spirochaetes | Spirochaetia | Spirochaetales | Spirochaetaceae | *Treponema* |
| *Treponema* sp. oral taxon 265 | Bacteria | Spirochaetes | Spirochaetia | Spirochaetales | Spirochaetaceae | *Treponema* |
| *Treponema* sp. oral taxon 270 | Bacteria | Spirochaetes | Spirochaetia | Spirochaetales | Spirochaetaceae | *Treponema* |
| *Treponema* sp. oral taxon 271 | Bacteria | Spirochaetes | Spirochaetia | Spirochaetales | Spirochaetaceae | *Treponema* |
| *Treponema* sp. oral taxon 508 | Bacteria | Spirochaetes | Spirochaetia | Spirochaetales | Spirochaetaceae | *Treponema* |
| *Treponema* sp. oral taxon 518 | Bacteria | Spirochaetes | Spirochaetia | Spirochaetales | Spirochaetaceae | *Treponema* |
| *Treponema* sp. oral taxon G85 | Bacteria | Spirochaetes | Spirochaetia | Spirochaetales | Spirochaetaceae | *Treponema* |
| *Treponema* sp. ovine footrot | Bacteria | Spirochaetes | Spirochaetes | Spirochaetales | Spirochaetaceae | *Treponema* |
| *Tropheryma whipplei* | Bacteria | Actinobacteria | Actinobacteria | Actinomycetales | unclassified | *Tropheryma* |
| *Trueperella pyogenes* | Bacteria | Actinobacteria | Actinobacteria | Actinomycetales | Actinomycetaceae | *Trueperella* |
| *Tsukamurella paurometabola* | Bacteria | Actinobacteria | Actinobacteria | Actinomycetales | Tsukamurellaceae | *Tsukamurella* |
| *Tsukamurella tyrosinosolvens* | Bacteria | Actinobacteria | Actinobacteria | Actinomycetales | Tsukamurellaceae | *Tsukamurella* |
| *Turicibacter sanguinis* | Bacteria | Firmicutes | Erysipelotrichi | Erysipelotrichales | Erysipelotrichaceae | *Turicibacter* |

TABLE 1-continued

| OTU | Domain | Phylum | Class | Order | Family | Genus |
|---|---|---|---|---|---|---|
| *Ureaplasma parvum* | Bacteria | Tenericutes | Mollicutes | Mycoplasmatales | Mycoplasmataceae | *Ureaplasma* |
| *Ureaplasma urealyticum* | Bacteria | Tenericutes | Mollicutes | Mycoplasmatales | Mycoplasmataceae | *Ureaplasma* |
| *Ureibacillus composti* | Bacteria | Firmicutes | Bacilli | Bacillales | Planococcaceae | *Ureibacillus* |
| *Ureibacillus suwonensis* | Bacteria | Firmicutes | Bacilli | Bacillales | Planococcaceae | *Ureibacillus* |
| *Ureibacillus terrenus* | Bacteria | Firmicutes | Bacilli | Bacillales | Planococcaceae | *Ureibacillus* |
| *Ureibacillus thermophilus* | Bacteria | Firmicutes | Bacilli | Bacillales | Planococcaceae | *Ureibacillus* |
| *Ureibacillus thermosphaericus* | Bacteria | Firmicutes | Bacilli | Bacillales | Planococcaceae | *Ureibacillus* |
| *Vagococcus fluvialis* | Bacteria | Firmicutes | Bacilli | Lactobacillales | Enterococcaceae | *Vagococcus* |
| *Veillonella atypica* | Bacteria | Firmicutes | Negativicutes | Selenomonadales | Veillonellaceae | *Veillonella* |
| *Veillonella dispar* | Bacteria | Firmicutes | Negativicutes | Selenomonadales | Veillonellaceae | *Veillonella* |
| *Veillonella* genomosp. P1 oral clone MB5_P17 | Bacteria | Firmicutes | Negativicutes | Selenomonadales | Veillonellaceae | *Veillonella* |
| *Veillonella montpellierensis* | Bacteria | Firmicutes | Negativicutes | Selenomonadales | Veillonellaceae | *Veillonella* |
| *Veillonella parvula* | Bacteria | Firmicutes | Negativicutes | Selenomonadales | Veillonellaceae | *Veillonella* |
| *Veillonella* sp. 3_1_44 | Bacteria | Firmicutes | Negativicutes | Selenomonadales | Veillonellaceae | *Veillonella* |
| *Veillonella* sp. 6_1_27 | Bacteria | Firmicutes | Negativicutes | Selenomonadales | Veillonellaceae | *Veillonella* |
| *Veillonella* sp. ACP1 | Bacteria | Firmicutes | Negativicutes | Selenomonadales | Veillonellaceae | *Veillonella* |
| *Veillonella* sp. AS16 | Bacteria | Firmicutes | Negativicutes | Selenomonadales | Veillonellaceae | *Veillonella* |
| *Veillonella* sp. BS32b | Bacteria | Firmicutes | Negativicutes | Selenomonadales | Veillonellaceae | *Veillonella* |
| *Veillonella* sp. ICM51a | Bacteria | Firmicutes | Negativicutes | Selenomonadales | Veillonellaceae | *Veillonella* |
| *Veillonella* sp. MSA12 | Bacteria | Firmicutes | Negativicutes | Selenomonadales | Veillonellaceae | *Veillonella* |
| *Veillonella* sp. NVG 100cf | Bacteria | Firmicutes | Negativicutes | Selenomonadales | Veillonellaceae | *Veillonella* |
| *Veillonella* sp. OK11 | Bacteria | Firmicutes | Negativicutes | Selenomonadales | Veillonellaceae | *Veillonella* |
| *Veillonella* sp. oral clone ASCA08 | Bacteria | Firmicutes | Negativicutes | Selenomonadales | Veillonellaceae | *Veillonella* |
| *Veillonella* sp. oral clone ASCB03 | Bacteria | Firmicutes | Negativicutes | Selenomonadales | Veillonellaceae | *Veillonella* |
| *Veillonella* sp. oral clone ASCG01 | Bacteria | Firmicutes | Negativicutes | Selenomonadales | Veillonellaceae | *Veillonella* |
| *Veillonella* sp. oral clone ASCG02 | Bacteria | Firmicutes | Negativicutes | Selenomonadales | Veillonellaceae | *Veillonella* |
| *Veillonella* sp. oral clone OH1A | Bacteria | Firmicutes | Negativicutes | Selenomonadales | Veillonellaceae | *Veillonella* |
| *Veillonella* sp. oral taxon 158 | Bacteria | Firmicutes | Negativicutes | Selenomonadales | Veillonellaceae | *Veillonella* |
| Veillonellaceae bacterium oral taxon 131 | Bacteria | Firmicutes | Negativicutes | Selenomonadales | Veillonellaceae | unclassified |
| Veillonellaceae bacterium oral taxon 155 | Bacteria | Firmicutes | Negativicutes | Selenomonadales | Veillonellaceae | unclassified |
| Victivallaceae bacterium NML 080035 | Bacteria | Lentisphaerae | unclassified | unclassified | Victivallaceae | unclassified |
| *Victivallis vadensis* | Bacteria | Lentisphaerae | unclassified | unclassified | Victivallaceae | *Victivallis* |
| *Virgibacillus proomii* | Bacteria | Firmicutes | Bacilli | Bacillales | Bacillaceae | *Virgibacillus* |
| *Weissella beninensis* | Bacteria | Firmicutes | Bacilli | Lactobacillales | Leuconostocaceae | *Weissella* |
| *Weissella cibaria* | Bacteria | Firmicutes | Bacilli | Lactobacillales | Leuconostocaceae | *Weissella* |
| *Weissella confusa* | Bacteria | Firmicutes | Bacilli | Lactobacillales | Leuconostocaceae | *Weissella* |
| *Weissella hellenica* | Bacteria | Firmicutes | Bacilli | Lactobacillales | Leuconostocaceae | *Weissella* |
| *Weissella kandleri* | Bacteria | Firmicutes | Bacilli | Lactobacillales | Leuconostocaceae | *Weissella* |
| *Weissella koreensis* | Bacteria | Firmicutes | Bacilli | Lactobacillales | Leuconostocaceae | *Weissella* |
| *Weissella paramesenteroides* | Bacteria | Firmicutes | Bacilli | Lactobacillales | Leuconostocaceae | *Weissella* |
| *Weissella* sp. KLDS 7.0701 | Bacteria | Firmicutes | Bacilli | Lactobacillales | Leuconostocaceae | *Weissella* |
| *Wolinella succinogenes* | Bacteria | Proteobacteria | Epsilonproteobacteria | Campylobacterales | Helicobacteraceae | *Wolinella* |
| Xanthomonadaceae bacterium NML 03-0222 | Bacteria | Proteobacteria | Gammaproteobacteria | Xanthomonadales | Xanthomonadaceae | unclassified |
| *Xanthomonas campestris* | Bacteria | Proteobacteria | Gammaproteobacteria | Xanthomonadales | Xanthomonadaceae | *Xanthomonas* |
| *Xanthomonas* sp. kmd_489 | Bacteria | Proteobacteria | Gammaproteobacteria | Xanthomonadales | Xanthomonadaceae | *Xanthomonas* |
| *Xenophilus aerolatus* | Bacteria | Proteobacteria | Betaproteobacteria | Burkholderiales | Comamonadaceae | *Xenophilus* |
| *Yokenella regensburgei* | Bacteria | Proteobacteria | Gammaproteobacteria | Enterobacteriales | Enterobacteriaceae | *Yokenella* |
| *Zimmermannella bifida* | Bacteria | Actinobacteria | Actinobacteria | Actinomycetales | Microbacteriaceae | *Pseudoclavibacter* |
| *Zymomonas mobilis* | Bacteria | Proteobacteria | Alphaproteobacteria | Sphingomonadales | Sphingomonadaceae | *Zymomonas* |

TABLE 2

Table 2. Specific binary combinations of OTUs. Individual pairings are differentiated by "|" and OTUs within a combination are differentiated by ","

Abiotrophia defectiva, Abiotrophia defectiva|Abiotrophia defectiva, Acidaminococcus fermentans|Abiotrophia defectiva, Acinetobacter baumannii|Abiotrophia defectiva, Acinetobacter johnsonii|Abiotrophia defectiva, Acinetobacter lwoffii|Abiotrophia defectiva, Acinetobacter radioresistens|Abiotrophia defectiva, Actinomyces odontolyticus|Abiotrophia defectiva, Actinomyces oris|Abiotrophia defectiva, Actinomyces viscosus|Abiotrophia defectiva, Aerococcus viridans|Abiotrophia defectiva, Aggregatibacter aphrophilus|Abiotrophia defectiva, Aggregatibacter segnis|Abiotrophia defectiva, Akkermansia muciniphila|Abiotrophia defectiva, Alistipes putredinis|Abiotrophia defectiva, Alistipes shahii|Abiotrophia defectiva, Anaerococcus hydrogenalis|Abiotrophia defectiva, Anaerococcus lactolyticus|Abiotrophia defectiva, Anaerococcus vaginalis|Abiotrophia defectiva, Anaerostipes caccae|Abiotrophia defectiva, Anaerotruncus colihominis|Abiotrophia defectiva, Atopobium parvulum|Abiotrophia defectiva, Atopobium rimae|Abiotrophia defectiva, Atopobium vaginae|Abiotrophia defectiva, Bacteroides caccae|Abiotrophia defectiva, Bacteroides cellulosilyticus|Abiotrophia defectiva, Bacteroides coprocola|Abiotrophia defectiva, Bacteroides coprophilus|Abiotrophia defectiva, Bacteroides dorei|Abiotrophia defectiva, Bacteroides eggerthii|Abiotrophia defectiva, Bacteroides finegoldii|Abiotrophia defectiva, Bacteroides fragilis|Abiotrophia defectiva, Bacteroides helcogenes|Abiotrophia defectiva, Bacteroides intestinalis|Abiotrophia defectiva, Bacteroides ovatus|Abiotrophia defectiva, Bacteroides pectinophilus|Abiotrophia defectiva, Bacteroides plebeius|Abiotrophia defectiva, Bacteroides salanitronis|Abiotrophia defectiva, Bacteroides sp. 1_1_6|Abiotrophia defectiva, Bacteroides sp. 3_1_23|Abiotrophia defectiva, Bacteroides stercoris|Abiotrophia defectiva, Bacteroides thetaiotaomicron|Abiotrophia defectiva, Bacteroides uniformis|Abiotrophia defectiva, Bacteroides vulgatus|Abiotrophia defectiva, Bacteroides xylanisolvens|Abiotrophia defectiva, Bifidobacterium adolescentis|Abiotrophia defectiva, Bifidobacterium angulatum|Abiotrophia defectiva, Bifidobacterium animalis|Abiotrophia defectiva, Bifidobacterium bifidum|Abiotrophia defectiva, Bifidobacterium breve|Abiotrophia defectiva, Bifidobacterium catenulatum|Abiotrophia defectiva, Bifidobacterium dentium|Abiotrophia defectiva, Bifidobacterium infantis|Abiotrophia defectiva, Bifidobacterium longum|Abiotrophia defectiva, Bifidobacterium pseudocatenulatum|Abiotrophia defectiva, Bilophila wadsworthia|Abiotrophia defectiva, Blautia hansenii|Abiotrophia defectiva, Blautia hydrogenotrophica|Abiotrophia defectiva, Blautia producta|Abiotrophia defectiva, Blautia schinkii|Abiotrophia defectiva, Brevibacterium linens|Abiotrophia defectiva, Brucella ceti|Abiotrophia defectiva, Brucella suis|Abiotrophia defectiva, Bulleidia extructa|Abiotrophia defectiva, Butyrivibrio crossotus|Abiotrophia defectiva, Campylobacter concisus|Abiotrophia defectiva, Campylobacter curvus|Abiotrophia defectiva, Campylobacter gracilis|Abiotrophia defectiva, Campylobacter hominis|Abiotrophia defectiva, Capnocytophaga ochracea|Abiotrophia defectiva, Cardiobacterium hominis|Abiotrophia defectiva, Catenibacterium mitsuokai|Abiotrophia defectiva, Catonella morbi|Abiotrophia defectiva, Citrobacter koseri|Abiotrophia defectiva, Clostridium asparagiforme|Abiotrophia defectiva, Clostridium bartlettii|Abiotrophia defectiva, Clostridium bolteae|Abiotrophia defectiva, Clostridium botulinum|Abiotrophia defectiva, Clostridium butyricum|Abiotrophia defectiva, Clostridium difficile|Abiotrophia defectiva, Clostridium disporicum|Abiotrophia defectiva, Clostridium hathewayi|Abiotrophia defectiva, Clostridium hylemonae|Abiotrophia defectiva, Clostridium innocuum|Abiotrophia defectiva, Clostridium leptum|Abiotrophia defectiva, Clostridium mayombei|Abiotrophia defectiva, Clostridium methylpentosum|Abiotrophia defectiva, Clostridium nexile|Abiotrophia defectiva, Clostridium orbiscindens|Abiotrophia defectiva, Clostridium perfringens|Abiotrophia defectiva, Clostridium saccharolyticum|Abiotrophia defectiva, Clostridium scindens|Abiotrophia defectiva, Clostridium symbiosum|Abiotrophia defectiva, Clostridium tertium|Abiotrophia defectiva, Collinsella aerofaciens|Abiotrophia defectiva, Collinsella intestinalis|Abiotrophia defectiva, Collinsella stercoris|Abiotrophia defectiva, Coprobacillus sp. D7|Abiotrophia defectiva, Coprococcus catus|Abiotrophia defectiva, Coprococcus comes|Abiotrophia defectiva, Coprococcus eutactus|Abiotrophia defectiva, Corynebacterium aurimucosum|Abiotrophia defectiva, Corynebacterium matruchotii|Abiotrophia defectiva, Cryptobacterium curtum|Abiotrophia defectiva, Desulfovibrio desulfuricans|Abiotrophia defectiva, Desulfovibrio piger|Abiotrophia defectiva, Dialister invisus|Abiotrophia defectiva, Dialister microaerophilus|Abiotrophia defectiva, Dorea formicigenerans|Abiotrophia defectiva, Dorea longicatena|Abiotrophia defectiva, Eggerthella lenta|Abiotrophia defectiva, Eikenella corrodens|Abiotrophia defectiva, Enterobacter cancerogenus|Abiotrophia defectiva, Enterobacter cloacae|Abiotrophia defectiva, Enterococcus faecalis|Abiotrophia defectiva, Enterococcus faecium|Abiotrophia defectiva, Enterococcus gallinarum|Abiotrophia defectiva, Erysipelotrichaceae bacterium 3_1_53|Abiotrophia defectiva, Escherichia coli|Abiotrophia defectiva, Escherichia fergusonii|Abiotrophia defectiva, Ethanoligenens harbinense|Abiotrophia defectiva, Eubacterium cellulosolvens|Abiotrophia defectiva, Eubacterium eligens|Abiotrophia defectiva, Eubacterium hallii|Abiotrophia defectiva, Eubacterium limosum|Abiotrophia defectiva, Eubacterium rectale|Abiotrophia defectiva, Eubacterium siraeum|Abiotrophia defectiva, Eubacterium ventriosum|Abiotrophia defectiva, Faecalibacterium prausnitzii|Abiotrophia defectiva, Finegoldia magna|Abiotrophia defectiva, Fusobacterium gonidiaformans|Abiotrophia defectiva, Fusobacterium mortiferum|Abiotrophia defectiva, Fusobacterium nucleatum|Abiotrophia defectiva, Fusobacterium varium|Abiotrophia defectiva, Gardnerella vaginalis|Abiotrophia defectiva, Gemella haemolysans|Abiotrophia defectiva, Gemella morbillorum|Abiotrophia defectiva, Gordonibacter pamelaeae|Abiotrophia defectiva, Granulicatella adiacens|Abiotrophia defectiva, Granulicatella elegans|Abiotrophia defectiva, Haemophilus influenzae|Abiotrophia defectiva, Haemophilus parainfluenzae|Abiotrophia defectiva, Helicobacter pullorum|Abiotrophia defectiva, Helicobacter pylori|Abiotrophia defectiva, Holdemania filiformis|Abiotrophia defectiva, Kingella oralis|Abiotrophia defectiva, Klebsiella pneumoniae|Abiotrophia defectiva, Klebsiella variicola|Abiotrophia defectiva, Lachnospiraceae bacterium 5_1_57FAA|Abiotrophia defectiva, Lactobacillus acidophilus|Abiotrophia defectiva, Lactobacillus amylovorus|Abiotrophia defectiva, Lactobacillus brevis|Abiotrophia defectiva, Lactobacillus casei|Abiotrophia defectiva, Lactobacillus crispatus|Abiotrophia defectiva, Lactobacillus delbrueckii|Abiotrophia defectiva, Lactobacillus fermentum|Abiotrophia defectiva, Lactobacillus gasseri|Abiotrophia defectiva, Lactobacillus iners|Abiotrophia defectiva, Lactobacillus jensenii|Abiotrophia defectiva, Lactobacillus johnsonii|Abiotrophia defectiva, Lactobacillus paracasei|Abiotrophia defectiva, Lactobacillus plantarum|Abiotrophia defectiva, Lactobacillus reuteri|Abiotrophia defectiva, Lactobacillus rhamnosus|Abiotrophia defectiva, Lactobacillus ruminis|Abiotrophia defectiva, Lactobacillus sakei|Abiotrophia defectiva, Lactobacillus salivarius|Abiotrophia defectiva, Lactococcus lactis|Abiotrophia defectiva, Lautropia mirabilis|Abiotrophia defectiva, Leuconostoc citreum|Abiotrophia defectiva, Leuconostoc gasicomitatum|Abiotrophia defectiva, Leuconostoc mesenteroides|Abiotrophia defectiva, Listeria monocytogenes|Abiotrophia defectiva, Marvinbryantia formatexigens|Abiotrophia defectiva, Megamonas hypermegale|Abiotrophia defectiva, Megasphaera micronuciformis|Abiotrophia defectiva, Methanobrevibacter smithii|Abiotrophia defectiva, Methanosphaera stadtmanae|Abiotrophia defectiva, Methylobacterium radiotolerans|Abiotrophia defectiva, Mitsuokella multacida|Abiotrophia defectiva, Mobiluncus curtisii|Abiotrophia defectiva, Mycoplasma hominis|Abiotrophia defectiva, Neisseria mucosa|Abiotrophia defectiva, Odoribacter splanchnicus|Abiotrophia defectiva, Olsenella uli|Abiotrophia defectiva, Oribacterium sinus|Abiotrophia defectiva, Oxalobacter formigenes|Abiotrophia defectiva, Parabacteroides distasonis|Abiotrophia defectiva, Parabacteroides johnsonii|Abiotrophia defectiva, Parabacteroides merdae|Abiotrophia defectiva, Parvimonas micra|Abiotrophia defectiva, Pediococcus acidilactici|Abiotrophia defectiva, Pediococcus pentosaceus|Abiotrophia defectiva, Peptoniphilus duerdenii|Abiotrophia defectiva, Peptoniphilus harei|Abiotrophia defectiva, Peptoniphilus lacrimalis|Abiotrophia defectiva, Peptostreptococcus anaerobius|Abiotrophia defectiva, Peptostreptococcus stomatis|Abiotrophia defectiva, Porphyromonas asaccharolytica|Abiotrophia defectiva, Porphyromonas uenonis|Abiotrophia defectiva, Prevotella amnii|Abiotrophia defectiva, Prevotella bergensis|Abiotrophia defectiva, Prevotella bivia|Abiotrophia defectiva, Prevotella buccae|Abiotrophia defectiva, Prevotella buccalis|Abiotrophia defectiva, Prevotella copri|Abiotrophia defectiva, Prevotella disiens|Abiotrophia defectiva, Prevotella melaninogenica|Abiotrophia defectiva, Prevotella multiformis|Abiotrophia defectiva, Prevotella oralis|Abiotrophia defectiva, Prevotella oris|Abiotrophia defectiva, Prevotella salivae|Abiotrophia defectiva, Prevotella timonensis|Abiotrophia defectiva, Propionibacterium acnes|Abiotrophia TABLE 2-continued Table 2. Specific binary combinations of OTUs. Individual pairings are differentiated by "|" and OTUs within a combination are differentiated by ","

defectiva, Propionibacterium freudenreichii|Abiotrophia defectiva, Proteus mirabilis|Abiotrophia defectiva, Proteus penneri|Abiotrophia defectiva, Pseudoflavonifractor capillosus|Abiotrophia defectiva, Pseudomonas aeruginosa|Abiotrophia defectiva, Pseudomonas fluorescens|Abiotrophia defectiva, Pseudomonas putida|Abiotrophia defectiva, Pseudoramibacter alactolyticus|Abiotrophia defectiva, Pyramidobacter piscolens|Abiotrophia defectiva, Rhodopseudomonas palustris|Abiotrophia defectiva, Roseburia intestinalis|Abiotrophia defectiva, Roseburia inulinivorans|Abiotrophia defectiva, Rothia dentocariosa|Abiotrophia defectiva, Rothia mucilaginosa|Abiotrophia defectiva, Ruminococcus albus|Abiotrophia defectiva, Ruminococcus bromii|Abiotrophia defectiva, Ruminococcus gnavus|Abiotrophia defectiva, Ruminococcus lactaris|Abiotrophia defectiva, Ruminococcus obeum|Abiotrophia defectiva, Ruminococcus torques|Abiotrophia defectiva, Selenomonas sputigena|Abiotrophia defectiva, Shigella boydii|Abiotrophia defectiva, Shigella dysenteriae|Abiotrophia defectiva, Shigella sonnei|Abiotrophia defectiva, Slackia exigua|Abiotrophia defectiva, Solobacterium moorei|Abiotrophia defectiva, Staphylococcus aureus|Abiotrophia defectiva, Staphylococcus epidermidis|Abiotrophia defectiva, Staphylococcus hominis|Abiotrophia defectiva, Staphylococcus saprophyticus|Abiotrophia defectiva, Staphylococcus warneri|Abiotrophia defectiva, Streptococcus agalactiae|Abiotrophia defectiva, Streptococcus anginosus|Abiotrophia defectiva, Streptococcus australis|Abiotrophia defectiva, Streptococcus bovis|Abiotrophia defectiva, Streptococcus cristatus|Abiotrophia defectiva, Streptococcus dysgalactiae|Abiotrophia defectiva, Streptococcus equinus|Abiotrophia defectiva, Streptococcus gordonii|Abiotrophia defectiva, Streptococcus infantarius|Abiotrophia defectiva, Streptococcus infantis|Abiotrophia defectiva, Streptococcus mitis|Abiotrophia defectiva, Streptococcus mutans|Abiotrophia defectiva, Streptococcus oralis|Abiotrophia defectiva, Streptococcus parasanguinis|Abiotrophia defectiva, Streptococcus peroris|Abiotrophia defectiva, Streptococcus pneumoniae|Abiotrophia defectiva, Streptococcus salivarius|Abiotrophia defectiva, Streptococcus sanguinis|Abiotrophia defectiva, Streptococcus thermophilus|Abiotrophia defectiva, Streptococcus vestibularis|Abiotrophia defectiva, Subdoligranulum variabile|Abiotrophia defectiva, Succinatimonas hippei|Abiotrophia defectiva, Sutterella wadsworthensis|Abiotrophia defectiva, Tropheryma whipplei|Abiotrophia defectiva, Veillonella atypica|Abiotrophia defectiva, Veillonella dispar|Abiotrophia defectiva, Veillonella parvula|Abiotrophia defectiva, Victivallis vadensis|Acidaminococcus fermentans, Acidaminococcus fermentans|Acidaminococcus fermentans, Acinetobacter baumannii|Acidaminococcus fermentans, Acinetobacter johnsonii|Acidaminococcus fermentans, Acinetobacter lwoffii|Acidaminococcus fermentans, Acinetobacter radioresistens|Acidaminococcus fermentans, Actinomyces odontolyticus|Acidaminococcus fermentans, Actinomyces oris|Acidaminococcus fermentans, Actinomyces viscosus|Acidaminococcus fermentans, Aerococcus viridans|Acidaminococcus fermentans, Aggregatibacter aphrophilus|Acidaminococcus fermentans, Aggregatibacter segnis|Acidaminococcus fermentans, Akkermansia muciniphila|Acidaminococcus fermentans, Alistipes putredinis|Acidaminococcus fermentans, Alistipes shahii|Acidaminococcus fermentans, Anaerococcus hydrogenalis|Acidaminococcus fermentans, Anaerococcus lactolyticus|Acidaminococcus fermentans, Anaerococcus vaginalis|Acidaminococcus fermentans, Anaerostipes caccae|Acidaminococcus fermentans, Anaerotruncus colihominis|Acidaminococcus fermentans, Atopobium parvulum|Acidaminococcus fermentans, Atopobium rimae|Acidaminococcus fermentans, Atopobium vaginae|Acidaminococcus fermentans, Bacteroides caccae|Acidaminococcus fermentans, Bacteroides cellulosilyticus|Acidaminococcus fermentans, Bacteroides coprocola|Acidaminococcus fermentans, Bacteroides coprophilus|Acidaminococcus fermentans, Bacteroides dorei|Acidaminococcus fermentans, Bacteroides eggerthii|Acidaminococcus fermentans, Bacteroides finegoldii|Acidaminococcus fermentans, Bacteroides fragilis|Acidaminococcus fermentans, Bacteroides helcogenes|Acidaminococcus fermentans, Bacteroides intestinalis|Acidaminococcus fermentans, Bacteroides ovatus|Acidaminococcus fermentans, Bacteroides pectinophilus|Acidaminococcus fermentans, Bacteroides plebeius|Acidaminococcus fermentans, Bacteroides salanitronis|Acidaminococcus fermentans, Bacteroides sp. 1_1_6|Acidaminococcus fermentans, Bacteroides sp. 3_1_23|Acidaminococcus fermentans, Bacteroides stercoris|Acidaminococcus fermentans, Bacteroides thetaiotaomicron|Acidaminococcus fermentans, Bacteroides uniformis|Acidaminococcus fermentans, Bacteroides vulgatus|Acidaminococcus fermentans, Bacteroides xylanisolvens|Acidaminococcus fermentans, Bifidobacterium adolescentis|Acidaminococcus fermentans, Bifidobacterium angulatum|Acidaminococcus fermentans, Bifidobacterium animalis|Acidaminococcus fermentans, Bifidobacterium bifidum|Acidaminococcus fermentans, Bifidobacterium breve|Acidaminococcus fermentans, Bifidobacterium catenulatum|Acidaminococcus fermentans, Bifidobacterium dentium|Acidaminococcus fermentans, Bifidobacterium infantis|Acidaminococcus fermentans, Bifidobacterium longum|Acidaminococcus fermentans, Bifidobacterium pseudocatenulatum|Acidaminococcus fermentans, Bilophila wadsworthia|Acidaminococcus fermentans, Blautia hansenii|Acidaminococcus fermentans, Blautia hydrogenotrophica|Acidaminococcus fermentans, Blautia producta|Acidaminococcus fermentans, Blautia schinkii|Acidaminococcus fermentans, Brevibacterium linens|Acidaminococcus fermentans, Brucella ceti|Acidaminococcus fermentans, Brucella suis|Acidaminococcus fermentans, Bulleidia extructa|Acidaminococcus fermentans, Butyrivibrio crossotus|Acidaminococcus fermentans, Campylobacter concisus|Acidaminococcus fermentans, Campylobacter curvus|Acidaminococcus fermentans, Campylobacter gracilis|Acidaminococcus fermentans, Campylobacter hominis|Acidaminococcus fermentans, Capnocytophaga ochracea|Acidaminococcus fermentans, Cardiobacterium hominis|Acidaminococcus fermentans, Catenibacterium mitsuokai|Acidaminococcus fermentans, Catonella morbi|Acidaminococcus fermentans, Citrobacter koseri|Acidaminococcus fermentans, Clostridium asparagiforme|Acidaminococcus fermentans, Clostridium bartletti|Acidaminococcus fermentans, Clostridium bolteae|Acidaminococcus fermentans, Clostridium botulinum|Acidaminococcus fermentans, Clostridium butyricum|Acidaminococcus fermentans, Clostridium difficile|Acidaminococcus fermentans, Clostridium disporicum|Acidaminococcus fermentans, Clostridium hathewayi|Acidaminococcus fermentans, Clostridium hylemonae|Acidaminococcus fermentans, Clostridium innocuum|Acidaminococcus fermentans, Clostridium leptum|Acidaminococcus fermentans, Clostridium mayombei|Acidaminococcus fermentans, Clostridium methylpentosum|Acidaminococcus fermentans, Clostridium nexile|Acidaminococcus fermentans, Clostridium orbiscindens|Acidaminococcus fermentans, Clostridium perfringens|Acidaminococcus fermentans, Clostridium saccharolyticum|Acidaminococcus fermentans, Clostridium scindens|Acidaminococcus fermentans, Clostridium symbiosum|Acidaminococcus fermentans, Clostridium tertium|Acidaminococcus fermentans, Collinsella aerofaciens|Acidaminococcus fermentans, Collinsella intestinalis|Acidaminococcus fermentans, Collinsella stercoris|Acidaminococcus fermentans, Coprobacillus sp. D7|Acidaminococcus fermentans, Coprococcus catus|Acidaminococcus fermentans, Coprococcus comes|Acidaminococcus fermentans, Coprococcus eutactus|Acidaminococcus fermentans, Corynebacterium aurimucosum|Acidaminococcus fermentans, Corynebacterium matruchotii|Acidaminococcus fermentans, Cryptobacterium curtum|Acidaminococcus fermentans, Desulfovibrio desulfuricans|Acidaminococcus fermentans, Desulfovibrio piger|Acidaminococcus fermentans, Dialister invisus|Acidaminococcus fermentans, Dialister microaerophilus|Acidaminococcus fermentans, Dorea formicigenerans|Acidaminococcus fermentans, Dorea longicatena|Acidaminococcus fermentans, Eggerthella lenta|Acidaminococcus fermentans, Eikenella corrodens|Acidaminococcus fermentans, Enterobacter cancerogenus|Acidaminococcus fermentans, Enterobacter cloacae|Acidaminococcus fermentans, Enterococcus faecalis|Acidaminococcus fermentans, Enterococcus faecium|Acidaminococcus fermentans, Enterococcus gallinarum|Acidaminococcus fermentans, Erysipelotrichaceae bacterium 3_1_53|Acidaminococcus fermentans, Escherichia coli|Acidaminococcus fermentans, Escherichia fergusonii|Acidaminococcus fermentans, Ethanoligenens harbinense|Acidaminococcus fermentans, Eubacterium cellulosolvens|Acidaminococcus fermentans, Eubacterium eligens|Acidaminococcus fermentans, Eubacterium hallii|Acidaminococcus fermentans, Eubacterium limosum|Acidaminococcus fermentans, Eubacterium rectale|Acidaminococcus fermentans, Eubacterium siraeum|Acidaminococcus fermentans, Eubacterium ventriosum|Acidaminococcus fermentans, Faecalibacterium prausnitzii|Acidaminococcus fermentans, Finegoldia magna|Acidaminococcus fermentans, Fusobacterium gonidiaformans|Acidaminococcus fermentans, Fusobacterium mortiferum|Acidaminococcus fermentans, Fusobacterium nucleatum|Acidaminococcus fermentans, Fusobacterium varium|Acidaminococcus fermentans, Gardnerella vaginalis|Acidaminococcus fermentans, Gemella haemolysans|Acidaminococcus fermentans, Gemella morbillorum|Acidaminococcus fermentans, Gordonibacter pamelaeae|Acidaminococcus TABLE 2-continued Table 2. Specific binary combinations of OTUs. Individual pairings are differentiated by "|" and OTUs within a combination are differentiated by ","

fermentans, Granulicatella adiacens|Acidaminococcus fermentans, Granulicatella elegans|Acidaminococcus fermentans, Haemophilus influenzae|Acidaminococcus fermentans, Haemophilus parainfluenzae|Acidaminococcus fermentans, Helicobacter pullorum|Acidaminococcus fermentans, Helicobacter pylori|Acidaminococcus fermentans, Holdemania filiformis|Acidaminococcus fermentans, Kingella oralis|Acidaminococcus fermentans, Klebsiella pneumoniae|Acidaminococcus fermentans, Klebsiella variicola|Acidaminococcus fermentans, Lachnospiraceae bacterium 5_1_57FAA|Acidaminococcus fermentans, Lactobacillus acidophilus|Acidaminococcus fermentans, Lactobacillus amylovorus|Acidaminococcus fermentans, Lactobacillus brevis|Acidaminococcus fermentans, Lactobacillus casei|Acidaminococcus fermentans, Lactobacillus crispatus|Acidaminococcus fermentans, Lactobacillus delbrueckii|Acidaminococcus fermentans, Lactobacillus fermentum|Acidaminococcus fermentans, Lactobacillus gasseri|Acidaminococcus fermentans, Lactobacillus iners|Acidaminococcus fermentans, Lactobacillus jensenii|Acidaminococcus fermentans, Lactobacillus johnsonii|Acidaminococcus fermentans, Lactobacillus paracasei|Acidaminococcus fermentans, Lactobacillus plantarum|Acidaminococcus fermentans, Lactobacillus reuteri|Acidaminococcus fermentans, Lactobacillus rhamnosus|Acidaminococcus fermentans, Lactobacillus ruminis|Acidaminococcus fermentans, Lactobacillus sakei|Acidaminococcus fermentans, Lactobacillus salivarius|Acidaminococcus fermentans, Lactococcus lactis|Acidaminococcus fermentans, Lautropia mirabilis|Acidaminococcus fermentans, Leuconostoc citreum|Acidaminococcus fermentans, Leuconostoc gasicomitatum|Acidaminococcus fermentans, Leuconostoc mesenteroides|Acidaminococcus fermentans, Listeria monocytogenes|Acidaminococcus fermentans, Marvinbryantia formatexigens|Acidaminococcus fermentans, Megamonas hypermegale|Acidaminococcus fermentans, Megasphaera micronuciformis|Acidaminococcus fermentans, Methanobrevibacter smithii|Acidaminococcus fermentans, Methanosphaera stadtmanae|Acidaminococcus fermentans, Methylobacterium radiotolerans|Acidaminococcus fermentans, Mitsuokella multacida|Acidaminococcus fermentans, Mobiluncus curtisii|Acidaminococcus fermentans, Mycoplasma hominis|Acidaminococcus fermentans, Neisseria mucosa|Acidaminococcus fermentans, Odoribacter splanchnicus|Acidaminococcus fermentans, Olsenella uli|Acidaminococcus fermentans, Oribacterium sinus|Acidaminococcus fermentans, Oxalobacter formigenes|Acidaminococcus fermentans, Parabacteroides distasonis|Acidaminococcus fermentans, Parabacteroides johnsonii|Acidaminococcus fermentans, Parabacteroides merdae|Acidaminococcus fermentans, Parvimonas micra|Acidaminococcus fermentans, Pediococcus acidilactici|Acidaminococcus fermentans, Pediococcus pentosaceus|Acidaminococcus fermentans, Peptoniphilus duerdenii|Acidaminococcus fermentans, Peptoniphilus harei|Acidaminococcus fermentans, Peptoniphilus lacrimalis|Acidaminococcus fermentans, Peptostreptococcus anaerobius|Acidaminococcus fermentans, Peptostreptococcus stomatis|Acidaminococcus fermentans, Porphyromonas asaccharolytica|Acidaminococcus fermentans, Porphyromonas uenonis|Acidaminococcus fermentans, Prevotella amnii|Acidaminococcus fermentans, Prevotella bergensis|Acidaminococcus fermentans, Prevotella bivia|Acidaminococcus fermentans, Prevotella buccae|Acidaminococcus fermentans, Prevotella buccalis|Acidaminococcus fermentans, Prevotella copri|Acidaminococcus fermentans, Prevotella disiens|Acidaminococcus fermentans, Prevotella melaninogenica|Acidaminococcus fermentans, Prevotella multiformis|Acidaminococcus fermentans, Prevotella oralis|Acidaminococcus fermentans, Prevotella oris|Acidaminococcus fermentans, Prevotella salivae|Acidaminococcus fermentans, Prevotella timonensis|Acidaminococcus fermentans, Propionibacterium acnes|Acidaminococcus fermentans, Propionibacterium freudenreichii|Acidaminococcus fermentans, Proteus mirabilis|Acidaminococcus fermentans, Proteus penneri|Acidaminococcus fermentans, Pseudoflavonifractor capillosus|Acidaminococcus fermentans, Pseudomonas aeruginosa|Acidaminococcus fermentans, Pseudomonas fluorescens|Acidaminococcus fermentans, Pseudomonas putida|Acidaminococcus fermentans, Pseudoramibacter alactolyticus|Acidaminococcus fermentans, Pyramidobacter piscolens|Acidaminococcus fermentans, Rhodopseudomonas palustris|Acidaminococcus fermentans, Roseburia intestinalis|Acidaminococcus fermentans, Roseburia inulinivorans|Acidaminococcus fermentans, Rothia dentocariosa|Acidaminococcus fermentans, Rothia mucilaginosa|Acidaminococcus fermentans, Ruminococcus albus|Acidaminococcus fermentans, Ruminococcus bromii|Acidaminococcus fermentans, Ruminococcus gnavus|Acidaminococcus fermentans, Ruminococcus lactaris|Acidaminococcus fermentans, Ruminococcus obeum|Acidaminococcus fermentans, Ruminococcus torques|Acidaminococcus fermentans, Selenomonas sputigena|Acidaminococcus fermentans, Shigella boydii|Acidaminococcus fermentans, Shigella dysenteriae|Acidaminococcus fermentans, Shigella sonnei|Acidaminococcus fermentans, Slackia exigua|Acidaminococcus fermentans, Solobacterium moorei|Acidaminococcus fermentans, Staphylococcus aureus|Acidaminococcus fermentans, Staphylococcus epidermidis|Acidaminococcus fermentans, Staphylococcus hominis|Acidaminococcus fermentans, Staphylococcus saprophyticus|Acidaminococcus fermentans, Staphylococcus warneri|Acidaminococcus fermentans, Streptococcus agalactiae|Acidaminococcus fermentans, Streptococcus anginosus|Acidaminococcus fermentans, Streptococcus australis|Acidaminococcus fermentans, Streptococcus bovis|Acidaminococcus fermentans, Streptococcus cristatus|Acidaminococcus fermentans, Streptococcus dysgalactiae|Acidaminococcus fermentans, Streptococcus equinus|Acidaminococcus fermentans, Streptococcus gordonii|Acidaminococcus fermentans, Streptococcus infantarius|Acidaminococcus fermentans, Streptococcus infantis|Acidaminococcus fermentans, Streptococcus mitis|Acidaminococcus fermentans, Streptococcus mutans|Acidaminococcus fermentans, Streptococcus oralis|Acidaminococcus fermentans, Streptococcus parasanguinis|Acidaminococcus fermentans, Streptococcus peroris|Acidaminococcus fermentans, Streptococcus pneumoniae|Acidaminococcus fermentans, Streptococcus salivarius|Acidaminococcus fermentans, Streptococcus sanguinis|Acidaminococcus fermentans, Streptococcus thermophilus|Acidaminococcus fermentans, Streptococcus vestibularis|Acidaminococcus fermentans, Subdoligranulum variabile|Acidaminococcus fermentans, Succinatimonas hippei|Acidaminococcus fermentans, Sutterella wadsworthensis|Acidaminococcus fermentans, Tropheryma whipplei|Acidaminococcus fermentans, Veillonella atypica|Acidaminococcus fermentans, Veillonella dispar|Acidaminococcus fermentans, Veillonella parvula|Acidaminococcus fermentans, Victivallis vadensis|Acinetobacter baumannii, Acinetobacter baumannii|Acinetobacter baumannii, Acinetobacter johnsonii|Acinetobacter baumannii, Acinetobacter lwoffii|Acinetobacter baumannii, Acinetobacter radioresistens|Acinetobacter baumannii, Actinomyces odontolyticus|Acinetobacter baumannii, Actinomyces oris|Acinetobacter baumannii, Actinomyces viscosus|Acinetobacter baumannii, Aerococcus viridans|Acinetobacter baumannii, Aggregatibacter aphrophilus|Acinetobacter baumannii, Aggregatibacter segnis|Acinetobacter baumannii, Akkermansia muciniphila|Acinetobacter baumannii, Alistipes putredinis|Acinetobacter baumannii, Alistipes shahii|Acinetobacter baumannii, Anaerococcus hydrogenalis|Acinetobacter baumannii, Anaerococcus lactolyticus|Acinetobacter baumannii, Anaerococcus vaginalis|Acinetobacter baumannii, Anaerostipes caccae|Acinetobacter baumannii, Anaerotruncus colihominis|Acinetobacter baumannii, Atopobium parvulum|Acinetobacter baumannii, Atopobium rimae|Acinetobacter baumannii, Atopobium vaginae|Acinetobacter baumannii, Bacteroides caccae|Acinetobacter baumannii, Bacteroides cellulosilyticus|Acinetobacter baumannii, Bacteroides coprocola|Acinetobacter baumannii, Bacteroides coprophilus|Acinetobacter baumannii, Bacteroides dorei|Acinetobacter baumannii, Bacteroides eggerthii|Acinetobacter baumannii, Bacteroides finegoldii|Acinetobacter baumannii, Bacteroides fragilis|Acinetobacter baumannii, Bacteroides helcogenes|Acinetobacter baumannii, Bacteroides intestinalis|Acinetobacter baumannii, Bacteroides ovatus|Acinetobacter baumannii, Bacteroides pectinophilus|Acinetobacter baumannii, Bacteroides plebeius|Acinetobacter baumannii, Bacteroides salanitronis|Acinetobacter baumannii, Bacteroides sp. 1_1_6|Acinetobacter baumannii, Bacteroides sp. 3_1_23|Acinetobacter baumannii, Bacteroides stercoris|Acinetobacter baumannii, Bacteroides thetaiotaomicron|Acinetobacter baumannii, Bacteroides uniformis|Acinetobacter baumannii, Bacteroides vulgatus|Acinetobacter baumannii, Bacteroides xylanisolvens|Acinetobacter baumannii, Bifidobacterium adolescentis|Acinetobacter baumannii, Bifidobacterium angulatum|Acinetobacter baumannii, Bifidobacterium animalis|Acinetobacter baumannii, Bifidobacterium bifidum|Acinetobacter baumannii, Bifidobacterium breve|Acinetobacter baumannii, Bifidobacterium catenulatum|Acinetobacter baumannii, Bifidobacterium dentium|Acinetobacter baumannii, Bifidobacterium infantis|Acinetobacter baumannii, Bifidobacterium longum|Acinetobacter baumannii, Bifidobacterium pseudocatenulatum|Acinetobacter baumannii, Bilophila wadsworthia|Acinetobacter baumannii, Blautia hansenii|Acinetobacter baumannii, Blautia hydrogenotrophica|Acinetobacter baumannii, Blautia TABLE 2-continued Table 2. Specific binary combinations of OTUs. Individual pairings are differentiated by "|" and OTUs within a combination are differentiated by ","

producta|Acinetobacter baumannii, Blautia schinkii|Acinetobacter baumannii, Brevibacterium linens|Acinetobacter baumannii, Brucella ceti|Acinetobacter baumannii, Brucella suis|Acinetobacter baumannii, Bulleidia extructa|Acinetobacter baumannii, Butyrivibrio crossotus|Acinetobacter baumannii, Campylobacter concisus|Acinetobacter baumannii, Campylobacter curvus|Acinetobacter baumannii, Campylobacter gracilis|Acinetobacter baumannii, Campylobacter hominis|Acinetobacter baumannii, Capnocytophaga ochracea|Acinetobacter baumannii, Cardiobacterium hominis|Acinetobacter baumannii, Catenibacterium mitsuokai|Acinetobacter baumannii, Catonella morbi|Acinetobacter baumannii, Citrobacter koseri|Acinetobacter baumannii, Clostridium asparagiforme|Acinetobacter baumannii, Clostridium bartlettii|Acinetobacter baumannii, Clostridium bolteae|Acinetobacter baumannii, Clostridium botulinum|Acinetobacter baumannii, Clostridium butyricum|Acinetobacter baumannii, Clostridium difficile|Acinetobacter baumannii, Clostridium disporicum|Acinetobacter baumannii, Clostridium hathewayi|Acinetobacter baumannii, Clostridium hylemonae|Acinetobacter baumannii, Clostridium innocuum|Acinetobacter baumannii, Clostridium leptum|Acinetobacter baumannii, Clostridium mayombei|Acinetobacter baumannii, Clostridium methylpentosum|Acinetobacter baumannii, Clostridium nexile|Acinetobacter baumannii, Clostridium orbiscindens|Acinetobacter baumannii, Clostridium perfringens|Acinetobacter baumannii, Clostridium saccharolyticum|Acinetobacter baumannii, Clostridium scindens|Acinetobacter baumannii, Clostridium symbiosum|Acinetobacter baumannii, Clostridium tertium|Acinetobacter baumannii, Collinsella aerofaciens|Acinetobacter baumannii, Collinsella intestinalis|Acinetobacter baumannii, Collinsella stercoris|Acinetobacter baumannii, Coprobacillus sp. D7|Acinetobacter baumannii, Coprococcus catus|Acinetobacter baumannii, Coprococcus comes|Acinetobacter baumannii, Coprococcus eutactus|Acinetobacter baumannii, Corynebacterium aurimucosum|Acinetobacter baumannii, Corynebacterium matruchotii|Acinetobacter baumannii, Cryptobacterium curtum|Acinetobacter baumannii, Desulfovibrio desulfuricans|Acinetobacter baumannii, Desulfovibrio piger|Acinetobacter baumannii, Dialister invisus|Acinetobacter baumannii, Dialister microaerophilus|Acinetobacter baumannii, Dorea formicigenerans|Acinetobacter baumannii, Dorea longicatena|Acinetobacter baumannii, Eggerthella lenta|Acinetobacter baumannii, Eikenella corrodens|Acinetobacter baumannii, Enterobacter cancerogenus|Acinetobacter baumannii, Enterobacter cloacae|Acinetobacter baumannii, Enterococcus faecalis|Acinetobacter baumannii, Enterococcus faecium|Acinetobacter baumannii, Enterococcus gallinarum|Acinetobacter baumannii, Erysipelotrichaceae bacterium 3_1_53|Acinetobacter baumannii, Escherichia coli|Acinetobacter baumannii, Escherichia fergusonii|Acinetobacter baumannii, Ethanoligenens harbinense|Acinetobacter baumannii, Eubacterium cellulosolvens|Acinetobacter baumannii, Eubacterium eligens|Acinetobacter baumannii, Eubacterium hallii|Acinetobacter baumannii, Eubacterium limosum|Acinetobacter baumannii, Eubacterium rectale|Acinetobacter baumannii, Eubacterium siraeum|Acinetobacter baumannii, Eubacterium ventriosum|Acinetobacter baumannii, Faecalibacterium prausnitzii|Acinetobacter baumannii, Finegoldia magna|Acinetobacter baumannii, Fusobacterium gonidiaformans|Acinetobacter baumannii, Fusobacterium mortiferum|Acinetobacter baumannii, Fusobacterium nucleatum|Acinetobacter baumannii, Fusobacterium varium|Acinetobacter baumannii, Gardnerella vaginalis|Acinetobacter baumannii, Gemella haemolysans|Acinetobacter baumannii, Gemella morbillorum|Acinetobacter baumannii, Gordonibacter pamelaeae|Acinetobacter baumannii, Granulicatella adiacens|Acinetobacter baumannii, Granulicatella elegans|Acinetobacter baumannii, Haemophilus influenzae|Acinetobacter baumannii, Haemophilus parainfluenzae|Acinetobacter baumannii, Helicobacter pullorum|Acinetobacter baumannii, Helicobacter pylori|Acinetobacter baumannii, Holdemania filiformis|Acinetobacter baumannii, Kingella oralis|Acinetobacter baumannii, Klebsiella pneumoniae|Acinetobacter baumannii, Klebsiella variicola|Acinetobacter baumannii, Lachnospiraceae bacterium 5_1_57FAA|Acinetobacter baumannii, Lactobacillus acidophilus|Acinetobacter baumannii, Lactobacillus amylovorus|Acinetobacter baumannii, Lactobacillus brevis|Acinetobacter baumannii, Lactobacillus casei|Acinetobacter baumannii, Lactobacillus crispatus|Acinetobacter baumannii, Lactobacillus delbrueckii|Acinetobacter baumannii, Lactobacillus fermentum|Acinetobacter baumannii, Lactobacillus gasseri|Acinetobacter baumannii, Lactobacillus iners|Acinetobacter baumannii, Lactobacillus jensenii|Acinetobacter baumannii, Lactobacillus johnsonii|Acinetobacter baumannii, Lactobacillus paracasei|Acinetobacter baumannii, Lactobacillus plantarum|Acinetobacter baumannii, Lactobacillus reuteri|Acinetobacter baumannii, Lactobacillus rhamnosus|Acinetobacter baumannii, Lactobacillus ruminis|Acinetobacter baumannii, Lactobacillus sakei|Acinetobacter baumannii, Lactobacillus salivarius|Acinetobacter baumannii, Lactococcus lactis|Acinetobacter baumannii, Lautropia mirabilis|Acinetobacter baumannii, Leuconostoc citreum|Acinetobacter baumannii, Leuconostoc gasicomitatum|Acinetobacter baumannii, Leuconostoc mesenteroides|Acinetobacter baumannii, Listeria monocytogenes|Acinetobacter baumannii, Marvinbryantia formatexigens|Acinetobacter baumannii, Megamonas hypermegale|Acinetobacter baumannii, Megasphaera micronuciformis|Acinetobacter baumannii, Methanobrevibacter smithii|Acinetobacter baumannii, Methanosphaera stadtmanae|Acinetobacter baumannii, Methylobacterium radiotolerans|Acinetobacter baumannii, Mitsuokella multacida|Acinetobacter baumannii, Mobiluncus curtisii|Acinetobacter baumannii, Mycoplasma hominis|Acinetobacter baumannii, Neisseria mucosa|Acinetobacter baumannii, Odoribacter splanchnicus|Acinetobacter baumannii, Olsenella uli|Acinetobacter baumannii, Oribacterium sinus|Acinetobacter baumannii, Oxalobacter formigenes|Acinetobacter baumannii, Parabacteroides distasonis|Acinetobacter baumannii, Parabacteroides johnsonii|Acinetobacter baumannii, Parabacteroides merdae|Acinetobacter baumannii, Parvimonas micra|Acinetobacter baumannii, Pediococcus acidilactici|Acinetobacter baumannii, Pediococcus pentosaceus|Acinetobacter baumannii, Peptoniphilus duerdenii|Acinetobacter baumannii, Peptoniphilus harei|Acinetobacter baumannii, Peptoniphilus lacrimalis|Acinetobacter baumannii, Peptostreptococcus anaerobius|Acinetobacter baumannii, Peptostreptococcus stomatis|Acinetobacter baumannii, Porphyromonas asaccharolytica|Acinetobacter baumannii, Porphyromonas uenonis|Acinetobacter baumannii, Prevotella amnii|Acinetobacter baumannii, Prevotella bergensis|Acinetobacter baumannii, Prevotella bivia|Acinetobacter baumannii, Prevotella buccae|Acinetobacter baumannii, Prevotella buccalis|Acinetobacter baumannii, Prevotella copri|Acinetobacter baumannii, Prevotella disiens|Acinetobacter baumannii, Prevotella melaninogenica|Acinetobacter baumannii, Prevotella multiformis|Acinetobacter baumannii, Prevotella oralis|Acinetobacter baumannii, Prevotella oris|Acinetobacter baumannii, Prevotella salivae|Acinetobacter baumannii, Prevotella timonensis|Acinetobacter baumannii, Propionibacterium acnes|Acinetobacter baumannii, Propionibacterium freudenreichii|Acinetobacter baumannii, Proteus mirabilis|Acinetobacter baumannii, Proteus penneri|Acinetobacter baumannii, Pseudoflavonifractor capillosus|Acinetobacter baumannii, Pseudomonas aeruginosa|Acinetobacter baumannii, Pseudomonas fluorescens|Acinetobacter baumannii, Pseudomonas putida|Acinetobacter baumannii, Pseudoramibacter alactolyticus|Acinetobacter baumannii, Pyramidobacter piscolens|Acinetobacter baumannii, Rhodopseudomonas palustris|Acinetobacter baumannii, Roseburia intestinalis|Acinetobacter baumannii, Roseburia inulinivorans|Acinetobacter baumannii, Rothia dentocariosa|Acinetobacter baumannii, Rothia mucilaginosa|Acinetobacter baumannii, Ruminococcus albus|Acinetobacter baumannii, Ruminococcus bromii|Acinetobacter baumannii, Ruminococcus gnavus|Acinetobacter baumannii, Ruminococcus lactaris|Acinetobacter baumannii, Ruminococcus obeum|Acinetobacter baumannii, Ruminococcus torques|Acinetobacter baumannii, Selenomonas sputigena|Acinetobacter baumannii, Shigella boydii|Acinetobacter baumannii, Shigella dysenteriae|Acinetobacter baumannii, Shigella sonnei|Acinetobacter baumannii, Slackia exigua|Acinetobacter baumannii, Solobacterium moorei|Acinetobacter baumannii, Staphylococcus aureus|Acinetobacter baumannii, Staphylococcus epidermidis|Acinetobacter baumannii, Staphylococcus hominis|Acinetobacter baumannii, Staphylococcus saprophyticus|Acinetobacter baumannii, Staphylococcus warneri|Acinetobacter baumannii, Streptococcus agalactiae|Acinetobacter baumannii, Streptococcus anginosus|Acinetobacter baumannii, Streptococcus australis|Acinetobacter baumannii, Streptococcus bovis|Acinetobacter baumannii, Streptococcus cristatus|Acinetobacter baumannii, Streptococcus dysgalactiae|Acinetobacter baumannii, Streptococcus equinus|Acinetobacter baumannii, Streptococcus gordonii|Acinetobacter baumannii, Streptococcus infantarius|Acinetobacter baumannii, Streptococcus infantis|Acinetobacter baumannii, Streptococcus mitis|Acinetobacter baumannii, Streptococcus mutans|Acinetobacter baumannii, Streptococcus oralis|Acinetobacter baumannii, Streptococcus parasanguinis|Acinetobacter baumannii, Streptococcus peroris|Acinetobacter baumannii, Streptococcus pneumoniae|Acinetobacter baumannii, Streptococcus salivarius|Acinetobacter baumannii, Streptococcus sanguinis|Acinetobacter baumannii, Streptococcus TABLE 2-continued Table 2. Specific binary combinations of OTUs. Individual pairings are differentiated by "|" and OTUs within a combination are differentiated by ","

thermophilus|Acinetobacter baumannii, Streptococcus vestibularis|Acinetobacter baumannii, Subdoligranulum variabile|Acinetobacter baumannii, Succinatimonas hippei|Acinetobacter baumannii, Sutterella wadsworthensis|Acinetobacter baumannii, Tropheryma whipplei|Acinetobacter baumannii, Veillonella atypica|Acinetobacter baumannii, Veillonella dispar|Acinetobacter baumannii, Veillonella parvula|Acinetobacter baumannii, Victivallis vadensis|Acinetobacter johnsonii, Acinetobacter johnsonii|Acinetobacter johnsonii, Acinetobacter lwoffii|Acinetobacter johnsonii, Acinetobacter radioresistens|Acinetobacter johnsonii, Actinomyces odontolyticus|Acinetobacter johnsonii, Actinomyces oris|Acinetobacter johnsonii, Actinomyces viscosus|Acinetobacter johnsonii, Aerococcus viridans|Acinetobacter johnsonii, Aggregatibacter aphrophilus|Acinetobacter johnsonii, Aggregatibacter segnis|Acinetobacter johnsonii, Akkermansia muciniphila|Acinetobacter johnsonii, Alistipes putredinis|Acinetobacter johnsonii, Alistipes shahii|Acinetobacter johnsonii, Anaerococcus hydrogenalis|Acinetobacter johnsonii, Anaerococcus lactolyticus|Acinetobacter johnsonii, Anaerococcus vaginalis|Acinetobacter johnsonii, Anaerostipes caccae|Acinetobacter johnsonii, Anaerotruncus colihominis|Acinetobacter johnsonii, Atopobium parvulum|Acinetobacter johnsonii, Atopobium rimae|Acinetobacter johnsonii, Atopobium vaginae|Acinetobacter johnsonii, Bacteroides caccae|Acinetobacter johnsonii, Bacteroides cellulosilyticus|Acinetobacter johnsonii, Bacteroides coprocola|Acinetobacter johnsonii, Bacteroides coprophilus|Acinetobacter johnsonii, Bacteroides dorei|Acinetobacter johnsonii, Bacteroides eggerthii|Acinetobacter johnsonii, Bacteroides finegoldii|Acinetobacter johnsonii, Bacteroides fragilis|Acinetobacter johnsonii, Bacteroides helcogenes|Acinetobacter johnsonii, Bacteroides intestinalis|Acinetobacter johnsonii, Bacteroides ovatus|Acinetobacter johnsonii, Bacteroides pectinophilus|Acinetobacter johnsonii, Bacteroides plebeius|Acinetobacter johnsonii, Bacteroides salanitronis|Acinetobacter johnsonii, Bacteroides sp. 1_1_6|Acinetobacter johnsonii, Bacteroides sp. 3_1_23|Acinetobacter johnsonii, Bacteroides stercoris|Acinetobacter johnsonii, Bacteroides thetaiotaomicron|Acinetobacter johnsonii, Bacteroides uniformis|Acinetobacter johnsonii, Bacteroides vulgatus|Acinetobacter johnsonii, Bacteroides xylanisolvens|Acinetobacter johnsonii, Bifidobacterium adolescentis|Acinetobacter johnsonii, Bifidobacterium angulatum|Acinetobacter johnsonii, Bifidobacterium animalis|Acinetobacter johnsonii, Bifidobacterium bifidum|Acinetobacter johnsonii, Bifidobacterium breve|Acinetobacter johnsonii, Bifidobacterium catenulatum|Acinetobacter johnsonii, Bifidobacterium dentium|Acinetobacter johnsonii, Bifidobacterium infantis|Acinetobacter johnsonii, Bifidobacterium longum|Acinetobacter johnsonii, Bifidobacterium pseudocatenulatum|Acinetobacter johnsonii, Bilophila wadsworthia|Acinetobacter johnsonii, Blautia hansenii|Acinetobacter johnsonii, Blautia hydrogenotrophica|Acinetobacter johnsonii, Blautia producta|Acinetobacter johnsonii, Blautia schinkii|Acinetobacter johnsonii, Brevibacterium linens|Acinetobacter johnsonii, Brucella ceti|Acinetobacter johnsonii, Brucella suis|Acinetobacter johnsonii, Bulleidia extructa|Acinetobacter johnsonii, Butyrivibrio crossotus|Acinetobacter johnsonii, Campylobacter concisus|Acinetobacter johnsonii, Campylobacter curvus|Acinetobacter johnsonii, Campylobacter gracilis|Acinetobacter johnsonii, Campylobacter hominis|Acinetobacter johnsonii, Capnocytophaga ochracea|Acinetobacter johnsonii, Cardiobacterium hominis|Acinetobacter johnsonii, Catenibacterium mitsuokai|Acinetobacter johnsonii, Catonella morbi|Acinetobacter johnsonii, Citrobacter koseri|Acinetobacter johnsonii, Clostridium asparagiforme|Acinetobacter johnsonii, Clostridium bartlettii|Acinetobacter johnsonii, Clostridium bolteae|Acinetobacter johnsonii, Clostridium botulinum|Acinetobacter johnsonii, Clostridium butyricum|Acinetobacter johnsonii, Clostridium difficile|Acinetobacter johnsonii, Clostridium disporicum|Acinetobacter johnsonii, Clostridium hathewayi|Acinetobacter johnsonii, Clostridium hylemonae|Acinetobacter johnsonii, Clostridium innocuum|Acinetobacter johnsonii, Clostridium leptum|Acinetobacter johnsonii, Clostridium mayombei|Acinetobacter johnsonii, Clostridium methylpentosum|Acinetobacter johnsonii, Clostridium nexile|Acinetobacter johnsonii, Clostridium orbiscindens|Acinetobacter johnsonii, Clostridium perfringens|Acinetobacter johnsonii, Clostridium saccharolyticum|Acinetobacter johnsonii, Clostridium scindens|Acinetobacter johnsonii, Clostridium symbiosum|Acinetobacter johnsonii, Clostridium tertium|Acinetobacter johnsonii, Collinsella aerofaciens|Acinetobacter johnsonii, Collinsella intestinalis|Acinetobacter johnsonii, Collinsella stercoris|Acinetobacter johnsonii, Coprobacillus sp. D7|Acinetobacter johnsonii, Coprococcus catus|Acinetobacter johnsonii, Coprococcus comes|Acinetobacter johnsonii, Coprococcus eutactus|Acinetobacter johnsonii, Corynebacterium aurimucosum|Acinetobacter johnsonii, Corynebacterium matruchotii|Acinetobacter johnsonii, Cryptobacterium curtum|Acinetobacter johnsonii, Desulfovibrio desulfuricans|Acinetobacter johnsonii, Desulfovibrio piger|Acinetobacter johnsonii, Dialister invisus|Acinetobacter johnsonii, Dialister microaerophilus|Acinetobacter johnsonii, Dorea formicigenerans|Acinetobacter johnsonii, Dorea longicatena|Acinetobacter johnsonii, Eggerthella lenta|Acinetobacter johnsonii, Eikenella corrodens|Acinetobacter johnsonii, Enterobacter cancerogenus|Acinetobacter johnsonii, Enterobacter cloacae|Acinetobacter johnsonii, Enterococcus faecalis|Acinetobacter johnsonii, Enterococcus faecium|Acinetobacter johnsonii, Enterococcus gallinarum|Acinetobacter johnsonii, Erysipelotrichaceae bacterium 3_1_53|Acinetobacter johnsonii, Escherichia coli|Acinetobacter johnsonii, Escherichia fergusonii|Acinetobacter johnsonii, Ethanoligenens harbinense|Acinetobacter johnsonii, Eubacterium cellulosolvens|Acinetobacter johnsonii, Eubacterium eligens|Acinetobacter johnsonii, Eubacterium hallii|Acinetobacter johnsonii, Eubacterium limosum|Acinetobacter johnsonii, Eubacterium rectale|Acinetobacter johnsonii, Eubacterium siraeum|Acinetobacter johnsonii, Eubacterium ventriosum|Acinetobacter johnsonii, Faecalibacterium prausnitzii|Acinetobacter johnsonii, Finegoldia magna|Acinetobacter johnsonii, Fusobacterium gonidiaformans|Acinetobacter johnsonii, Fusobacterium mortiferum|Acinetobacter johnsonii, Fusobacterium nucleatum|Acinetobacter johnsonii, Fusobacterium varium|Acinetobacter johnsonii, Gardnerella vaginalis|Acinetobacter johnsonii, Gemella haemolysans|Acinetobacter johnsonii, Gemella morbillorum|Acinetobacter johnsonii, Gordonibacter pamelaeae|Acinetobacter johnsonii, Granulicatella adiacens|Acinetobacter johnsonii, Granulicatella elegans|Acinetobacter johnsonii, Haemophilus influenzae|Acinetobacter johnsonii, Haemophilus parainfluenzae|Acinetobacter johnsonii, Helicobacter pullorum|Acinetobacter johnsonii, Helicobacter pylori|Acinetobacter johnsonii, Holdemania filiformis|Acinetobacter johnsonii, Kingella oralis|Acinetobacter johnsonii, Klebsiella pneumoniae|Acinetobacter johnsonii, Klebsiella variicola|Acinetobacter johnsonii, Lachnospiraceae bacterium 5_1_57FAA|Acinetobacter johnsonii, Lactobacillus acidophilus|Acinetobacter johnsonii, Lactobacillus amylovorus|Acinetobacter johnsonii, Lactobacillus brevis|Acinetobacter johnsonii, Lactobacillus casei|Acinetobacter johnsonii, Lactobacillus crispatus|Acinetobacter johnsonii, Lactobacillus delbrueckii|Acinetobacter johnsonii, Lactobacillus fermentum|Acinetobacter johnsonii, Lactobacillus gasseri|Acinetobacter johnsonii, Lactobacillus iners|Acinetobacter johnsonii, Lactobacillus jensenii|Acinetobacter johnsonii, Lactobacillus johnsonii|Acinetobacter johnsonii, Lactobacillus paracasei|Acinetobacter johnsonii, Lactobacillus plantarum|Acinetobacter johnsonii, Lactobacillus reuteri|Acinetobacter johnsonii, Lactobacillus rhamnosus|Acinetobacter johnsonii, Lactobacillus ruminis|Acinetobacter johnsonii, Lactobacillus sakei|Acinetobacter johnsonii, Lactobacillus salivarius|Acinetobacter johnsonii, Lactococcus lactis|Acinetobacter johnsonii, Lautropia mirabilis|Acinetobacter johnsonii, Leuconostoc citreum|Acinetobacter johnsonii, Leuconostoc gasicomitatum|Acinetobacter johnsonii, Leuconostoc mesenteroides|Acinetobacter johnsonii, Listeria monocytogenes|Acinetobacter johnsonii, Marvinbryantia formatexigens|Acinetobacter johnsonii, Megamonas hypermegale|Acinetobacter johnsonii, Megasphaera micronuciformis|Acinetobacter johnsonii, Methanobrevibacter smithii|Acinetobacter johnsonii, Methanosphaera stadtmanae|Acinetobacter johnsonii, Methylobacterium radiotolerans|Acinetobacter johnsonii, Mitsuokella multacida|Acinetobacter johnsonii, Mobiluncus curtisii|Acinetobacter johnsonii, Mycoplasma hominis|Acinetobacter johnsonii, Neisseria mucosa|Acinetobacter johnsonii, Odoribacter splanchnicus|Acinetobacter johnsonii, Olsenella uli|Acinetobacter johnsonii, Oribacterium sinus|Acinetobacter johnsonii, Oxalobacter formigenes|Acinetobacter johnsonii, Parabacteroides distasonis|Acinetobacter johnsonii, Parabacteroides johnsonii|Acinetobacter johnsonii, Parabacteroides merdae|Acinetobacter johnsonii, Parvimonas micra|Acinetobacter johnsonii, Pediococcus acidilactici|Acinetobacter johnsonii, Pediococcus pentosaceus|Acinetobacter johnsonii, Peptoniphilus duerdenii|Acinetobacter johnsonii, Peptoniphilus harei|Acinetobacter johnsonii, Peptoniphilus lacrimalis|Acinetobacter johnsonii, Peptostreptococcus anaerobius|Acinetobacter johnsonii, Peptostreptococcus stomatis|Acinetobacter johnsonii, Porphyromonas asaccharolytica|Acinetobacter johnsonii, Porphyromonas uenonis|Acinetobacter johnsonii, Prevotella amnii|Acinetobacter johnsonii, Prevotella bergensis|Acinetobacter johnsonii, Prevotella bivia|Acinetobacter johnsonii, Prevotella buccae|Acinetobacter TABLE 2-continued Table 2. Specific binary combinations of OTUs. Individual pairings are differentiated by "|" and OTUs within a combination are differentiated by ","

johnsonii, Prevotella buccalis|Acinetobacter johnsonii, Prevotella copri|Acinetobacter johnsonii, Prevotella disiens|Acinetobacter johnsonii, Prevotella melaninogenica|Acinetobacter johnsonii, Prevotella multiformis|Acinetobacter johnsonii, Prevotella oralis|Acinetobacter johnsonii, Prevotella oris|Acinetobacter johnsonii, Prevotella salivae|Acinetobacter johnsonii, Prevotella timonensis|Acinetobacter johnsonii, Propionibacterium acnes|Acinetobacter johnsonii, Propionibacterium freudenreichii|Acinetobacter johnsonii, Proteus mirabilis|Acinetobacter johnsonii, Proteus penneri|Acinetobacter johnsonii, Pseudoflavonifractor capillosus|Acinetobacter johnsonii, Pseudomonas aeruginosa|Acinetobacter johnsonii, Pseudomonas fluorescens|Acinetobacter johnsonii, Pseudomonas putida|Acinetobacter johnsonii, Pseudoramibacter alactolyticus|Acinetobacter johnsonii, Pyramidobacter piscolens|Acinetobacter johnsonii, Rhodopseudomonas palustris|Acinetobacter johnsonii, Roseburia intestinalis|Acinetobacter johnsonii, Roseburia inulinivorans|Acinetobacter johnsonii, Rothia dentocariosa|Acinetobacter johnsonii, Rothia mucilaginosa|Acinetobacter johnsonii, Ruminococcus albus|Acinetobacter johnsonii, Ruminococcus bromii|Acinetobacter johnsonii, Ruminococcus gnavus|Acinetobacter johnsonii, Ruminococcus lactaris|Acinetobacter johnsonii, Ruminococcus obeum|Acinetobacter johnsonii, Ruminococcus torques|Acinetobacter johnsonii, Selenomonas sputigena|Acinetobacter johnsonii, Shigella boydii|Acinetobacter johnsonii, Shigella dysenteriae|Acinetobacter johnsonii, Shigella sonnei|Acinetobacter johnsonii, Slackia exigua|Acinetobacter johnsonii, Solobacterium moorei|Acinetobacter johnsonii, Staphylococcus aureus|Acinetobacter johnsonii, Staphylococcus epidermidis|Acinetobacter johnsonii, Staphylococcus hominis|Acinetobacter johnsonii, Staphylococcus saprophyticus|Acinetobacter johnsonii, Staphylococcus warneri|Acinetobacter johnsonii, Streptococcus agalactiae|Acinetobacter johnsonii, Streptococcus anginosus|Acinetobacter johnsonii, Streptococcus australis|Acinetobacter johnsonii, Streptococcus bovis|Acinetobacter johnsonii, Streptococcus cristatus|Acinetobacter johnsonii, Streptococcus dysgalactiae|Acinetobacter johnsonii, Streptococcus equinus|Acinetobacter johnsonii, Streptococcus gordonii|Acinetobacter johnsonii, Streptococcus infantarius|Acinetobacter johnsonii, Streptococcus infantis|Acinetobacter johnsonii, Streptococcus mitis|Acinetobacter johnsonii, Streptococcus mutans|Acinetobacter johnsonii, Streptococcus oralis|Acinetobacter johnsonii, Streptococcus parasanguinis|Acinetobacter johnsonii, Streptococcus peroris|Acinetobacter johnsonii, Streptococcus pneumoniae|Acinetobacter johnsonii, Streptococcus salivarius|Acinetobacter johnsonii, Streptococcus sanguinis|Acinetobacter johnsonii, Streptococcus thermophilus|Acinetobacter johnsonii, Streptococcus vestibularis|Acinetobacter johnsonii, Subdoligranulum variabile|Acinetobacter johnsonii, Succinatimonas hippei|Acinetobacter johnsonii, Sutterella wadsworthensis|Acinetobacter johnsonii, Tropheryma whipplei|Acinetobacter johnsonii, Veillonella atypica|Acinetobacter johnsonii, Veillonella dispar|Acinetobacter johnsonii, Veillonella parvula|Acinetobacter johnsonii, Victivallis vadensis|Acinetobacter lwoffii, Acinetobacter lwoffii|Acinetobacter lwoffii, Acinetobacter radioresistens|Acinetobacter lwoffii, Actinomyces odontolyticus|Acinetobacter lwoffii, Actinomyces oris|Acinetobacter lwoffii, Actinomyces viscosus|Acinetobacter lwoffii, Aerococcus viridans|Acinetobacter lwoffii, Aggregatibacter aphrophilus|Acinetobacter lwoffii, Aggregatibacter segnis|Acinetobacter lwoffii, Akkermansia muciniphila|Acinetobacter lwoffii, Alistipes putredinis|Acinetobacter lwoffii, Alistipes shahii|Acinetobacter lwoffii, Anaerococcus hydrogenalis|Acinetobacter lwoffii, Anaerococcus lactolyticus|Acinetobacter lwoffii, Anaerococcus vaginalis|Acinetobacter lwoffii, Anaerostipes caccae|Acinetobacter lwoffii, Anaerotruncus colihominis|Acinetobacter lwoffii, Atopobium parvulum|Acinetobacter lwoffii, Atopobium rimae|Acinetobacter lwoffii, Atopobium vaginae|Acinetobacter lwoffii, Bacteroides caccae|Acinetobacter lwoffii, Bacteroides cellulosilyticus|Acinetobacter lwoffii, Bacteroides coprocola|Acinetobacter lwoffii, Bacteroides coprophilus|Acinetobacter lwoffii, Bacteroides dorei|Acinetobacter lwoffii, Bacteroides eggerthii|Acinetobacter lwoffii, Bacteroides finegoldii|Acinetobacter lwoffii, Bacteroides fragilis|Acinetobacter lwoffii, Bacteroides helcogenes|Acinetobacter lwoffii, Bacteroides intestinalis|Acinetobacter lwoffii, Bacteroides ovatus|Acinetobacter lwoffii, Bacteroides pectinophilus|Acinetobacter lwoffii, Bacteroides plebeius|Acinetobacter lwoffii, Bacteroides salanitronis|Acinetobacter lwoffii, Bacteroides sp. 1_1_6|Acinetobacter lwoffii, Bacteroides sp. 3_1_23|Acinetobacter lwoffii, Bacteroides stercoris|Acinetobacter lwoffii, Bacteroides thetaiotaomicron|Acinetobacter lwoffii, Bacteroides uniformis|Acinetobacter lwoffii, Bacteroides vulgatus|Acinetobacter lwoffii, Bacteroides xylanisolvens|Acinetobacter lwoffii, Bifidobacterium adolescentis|Acinetobacter lwoffii, Bifidobacterium angulatum|Acinetobacter lwoffii, Bifidobacterium animalis|Acinetobacter lwoffii, Bifidobacterium bifidum|Acinetobacter lwoffii, Bifidobacterium breve|Acinetobacter lwoffii, Bifidobacterium catenulatum|Acinetobacter lwoffii, Bifidobacterium dentium|Acinetobacter lwoffii, Bifidobacterium infantis|Acinetobacter lwoffii, Bifidobacterium longum|Acinetobacter lwoffii, Bifidobacterium pseudocatenulatum|Acinetobacter lwoffii, Bilophila wadsworthia|Acinetobacter lwoffii, Blautia hansenii|Acinetobacter lwoffii, Blautia hydrogenotrophica|Acinetobacter lwoffii, Blautia producta|Acinetobacter lwoffii, Blautia schinkii|Acinetobacter lwoffii, Brevibacterium linens|Acinetobacter lwoffii, Brucella ceti|Acinetobacter lwoffii, Brucella suis|Acinetobacter lwoffii, Bulleidia extructa|Acinetobacter lwoffii, Butyrivibrio crossotus|Acinetobacter lwoffii, Campylobacter concisus|Acinetobacter lwoffii, Campylobacter curvus|Acinetobacter lwoffii, Campylobacter gracilis|Acinetobacter lwoffii, Campylobacter hominis|Acinetobacter lwoffii, Capnocytophaga ochracea|Acinetobacter lwoffii, Cardiobacterium hominis|Acinetobacter lwoffii, Catenibacterium mitsuokai|Acinetobacter lwoffii, Catonella morbi|Acinetobacter lwoffii, Citrobacter koseri|Acinetobacter lwoffii, Clostridium asparagiforme|Acinetobacter lwoffii, Clostridium bartlettii|Acinetobacter lwoffii, Clostridium bolteae|Acinetobacter lwoffii, Clostridium botulinum|Acinetobacter lwoffii, Clostridium butyricum|Acinetobacter lwoffii, Clostridium difficile|Acinetobacter lwoffii, Clostridium disporicum|Acinetobacter lwoffii, Clostridium hathewayi|Acinetobacter lwoffii, Clostridium hylemonae|Acinetobacter lwoffii, Clostridium innocuum|Acinetobacter lwoffii, Clostridium leptum|Acinetobacter lwoffii, Clostridium mayombei|Acinetobacter lwoffii, Clostridium methylpentosum|Acinetobacter lwoffii, Clostridium nexile|Acinetobacter lwoffii, Clostridium orbiscindens|Acinetobacter lwoffii, Clostridium perfringens|Acinetobacter lwoffii, Clostridium saccharolyticum|Acinetobacter lwoffii, Clostridium scindens|Acinetobacter lwoffii, Clostridium symbiosum|Acinetobacter lwoffii, Clostridium tertium|Acinetobacter lwoffii, Collinsella aerofaciens|Acinetobacter lwoffii, Collinsella intestinalis|Acinetobacter lwoffii, Collinsella stercoris|Acinetobacter lwoffii, Coprobacillus sp. D7|Acinetobacter lwoffii, Coprococcus catus|Acinetobacter lwoffii, Coprococcus comes|Acinetobacter lwoffii, Coprococcus eutactus|Acinetobacter lwoffii, Corynebacterium aurimucosum|Acinetobacter lwoffii, Corynebacterium matruchotii|Acinetobacter lwoffii, Cryptobacterium curtum|Acinetobacter lwoffii, Desulfovibrio desulfuricans|Acinetobacter lwoffii, Desulfovibrio piger|Acinetobacter lwoffii, Dialister invisus|Acinetobacter lwoffii, Dialister microaerophilus|Acinetobacter lwoffii, Dorea formicigenerans|Acinetobacter lwoffii, Dorea longicatena|Acinetobacter lwoffii, Eggerthella lenta|Acinetobacter lwoffii, Eikenella corrodens|Acinetobacter lwoffii, Enterobacter cancerogenus|Acinetobacter lwoffii, Enterobacter cloacae|Acinetobacter lwoffii, Enterococcus faecalis|Acinetobacter lwoffii, Enterococcus faecium|Acinetobacter lwoffii, Enterococcus gallinarum|Acinetobacter lwoffii, Erysipelotrichaceae bacterium 3_1_53|Acinetobacter lwoffii, Escherichia coli|Acinetobacter lwoffii, Escherichia fergusonii|Acinetobacter lwoffii, Ethanoligenens harbinense|Acinetobacter lwoffii, Eubacterium cellulosolvens|Acinetobacter lwoffii, Eubacterium eligens|Acinetobacter lwoffii, Eubacterium hallii|Acinetobacter lwoffii, Eubacterium limosum|Acinetobacter lwoffii, Eubacterium rectale|Acinetobacter lwoffii, Eubacterium siraeum|Acinetobacter lwoffii, Eubacterium ventriosum|Acinetobacter lwoffii, Faecalibacterium prausnitzii|Acinetobacter lwoffii, Finegoldia magna|Acinetobacter lwoffii, Fusobacterium gonidiaformans|Acinetobacter lwoffii, Fusobacterium mortiferum|Acinetobacter lwoffii, Fusobacterium nucleatum|Acinetobacter lwoffii, Fusobacterium varium|Acinetobacter lwoffii, Gardnerella vaginalis|Acinetobacter lwoffii, Gemella haemolysans|Acinetobacter lwoffii, Gemella morbillorum|Acinetobacter lwoffii, Gordonibacter pamelaeae|Acinetobacter lwoffii, Granulicatella adiacens|Acinetobacter lwoffii, Granulicatella elegans|Acinetobacter lwoffii, Haemophilus influenzae|Acinetobacter lwoffii, Haemophilus parainfluenzae|Acinetobacter lwoffii, Helicobacter pullorum|Acinetobacter lwoffii, Helicobacter pylori|Acinetobacter lwoffii, Holdemania filiformis|Acinetobacter lwoffii, Kingella oralis|Acinetobacter lwoffii, Klebsiella pneumoniae|Acinetobacter lwoffii, Klebsiella variicola|Acinetobacter lwoffii, Lachnospiraceae bacterium 5_1_57FAA|Acinetobacter lwoffii, Lactobacillus acidophilus|Acinetobacter lwoffii, Lactobacillus amylovorus|Acinetobacter lwoffii, Lactobacillus brevis|Acinetobacter lwoffii, Lactobacillus casei|Acinetobacter lwoffii, Lactobacillus crispatus|Acinetobacter lwoffii, Lactobacillus delbrueckii|Acinetobacter lwoffii, Lactobacillus TABLE 2-continued Table 2. Specific binary combinations of OTUs. Individual pairings are differentiated by "|" and OTUs within a combination are differentiated by ","

fermentum|Acinetobacter lwoffii, Lactobacillus gasseri|Acinetobacter lwoffii, Lactobacillus iners|Acinetobacter lwoffii, Lactobacillus jensenii|Acinetobacter lwoffii, Lactobacillus johnsonii|Acinetobacter lwoffii, Lactobacillus paracasei|Acinetobacter lwoffii, Lactobacillus plantarum|Acinetobacter lwoffii, Lactobacillus reuteri|Acinetobacter lwoffii, Lactobacillus rhamnosus|Acinetobacter lwoffii, Lactobacillus ruminis|Acinetobacter lwoffii, Lactobacillus sakei|Acinetobacter lwoffii, Lactobacillus salivarius|Acinetobacter lwoffii, Lactococcus lactis|Acinetobacter lwoffii, Lautropia mirabilis|Acinetobacter lwoffii, Leuconostoc citreum|Acinetobacter lwoffii, Leuconostoc gasicomitatum|Acinetobacter lwoffii, Leuconostoc mesenteroides|Acinetobacter lwoffii, Listeria monocytogenes|Acinetobacter lwoffii, Marvinbryantia formatexigens|Acinetobacter lwoffii, Megamonas hypermegale|Acinetobacter lwoffii, Megasphaera micronuciformis|Acinetobacter lwoffii, Methanobrevibacter smithii|Acinetobacter lwoffii, Methanosphaera stadtmanae|Acinetobacter lwoffii, Methylobacterium radiotolerans|Acinetobacter lwoffii, Mitsuokella multacida|Acinetobacter lwoffii, Mobiluncus curtisii|Acinetobacter lwoffii, Mycoplasma hominis|Acinetobacter lwoffii, Neisseria mucosa|Acinetobacter lwoffii, Odoribacter splanchnicus|Acinetobacter lwoffii, Olsenella uli|Acinetobacter lwoffii, Oribacterium sinus|Acinetobacter lwoffii, Oxalobacter formigenes|Acinetobacter lwoffii, Parabacteroides distasonis|Acinetobacter lwoffii, Parabacteroides johnsonii|Acinetobacter lwoffii, Parabacteroides merdae|Acinetobacter lwoffii, Parvimonas micra|Acinetobacter lwoffii, Pediococcus acidilactici|Acinetobacter lwoffii, Pediococcus pentosaceus|Acinetobacter lwoffii, Peptoniphilus duerdenii|Acinetobacter lwoffii, Peptoniphilus harei|Acinetobacter lwoffii, Peptoniphilus lacrimalis|Acinetobacter lwoffii, Peptostreptococcus anaerobius|Acinetobacter lwoffii, Peptostreptococcus stomatis|Acinetobacter lwoffii, Porphyromonas asaccharolytica|Acinetobacter lwoffii, Porphyromonas uenonis|Acinetobacter lwoffii, Prevotella amnii|Acinetobacter lwoffii, Prevotella bergensis|Acinetobacter lwoffii, Prevotella bivia|Acinetobacter lwoffii, Prevotella buccae|Acinetobacter lwoffii, Prevotella buccalis|Acinetobacter lwoffii, Prevotella copri|Acinetobacter lwoffii, Prevotella disiens|Acinetobacter lwoffii, Prevotella melaninogenica|Acinetobacter lwoffii, Prevotella multiformis|Acinetobacter lwoffii, Prevotella oralis|Acinetobacter lwoffii, Prevotella oris|Acinetobacter lwoffii, Prevotella salivae|Acinetobacter lwoffii, Prevotella timonensis|Acinetobacter lwoffii, Propionibacterium acnes|Acinetobacter lwoffii, Propionibacterium freudenreichii|Acinetobacter lwoffii, Proteus mirabilis|Acinetobacter lwoffii, Proteus penneri|Acinetobacter lwoffii, Pseudoflavonifractor capillosus|Acinetobacter lwoffii, Pseudomonas aeruginosa|Acinetobacter lwoffii, Pseudomonas fluorescens|Acinetobacter lwoffii, Pseudomonas putida|Acinetobacter lwoffii, Pseudoramibacter alactolyticus|Acinetobacter lwoffii, Pyramidobacter piscolens|Acinetobacter lwoffii, Rhodopseudomonas palustris|Acinetobacter lwoffii, Roseburia intestinalis|Acinetobacter lwoffii, Roseburia inulinivorans|Acinetobacter lwoffii, Rothia dentocariosa|Acinetobacter lwoffii, Rothia mucilaginosa|Acinetobacter lwoffii, Ruminococcus albus|Acinetobacter lwoffii, Ruminococcus bromii|Acinetobacter lwoffii, Ruminococcus gnavus|Acinetobacter lwoffii, Ruminococcus lactaris|Acinetobacter lwoffii, Ruminococcus obeum|Acinetobacter lwoffii, Ruminococcus torques|Acinetobacter lwoffii, Selenomonas sputigena|Acinetobacter lwoffii, Shigella boydii|Acinetobacter lwoffii, Shigella dysenteriae|Acinetobacter lwoffii, Shigella sonnei|Acinetobacter lwoffii, Slackia exigua|Acinetobacter lwoffii, Solobacterium moorei|Acinetobacter lwoffii, Staphylococcus aureus|Acinetobacter lwoffii, Staphylococcus epidermidis|Acinetobacter lwoffii, Staphylococcus hominis|Acinetobacter lwoffii, Staphylococcus saprophyticus|Acinetobacter lwoffii, Staphylococcus warneri|Acinetobacter lwoffii, Streptococcus agalactiae|Acinetobacter lwoffii, Streptococcus anginosus|Acinetobacter lwoffii, Streptococcus australis|Acinetobacter lwoffii, Streptococcus bovis|Acinetobacter lwoffii, Streptococcus cristatus|Acinetobacter lwoffii, Streptococcus dysgalactiae|Acinetobacter lwoffii, Streptococcus equinus|Acinetobacter lwoffii, Streptococcus gordonii|Acinetobacter lwoffii, Streptococcus infantarius|Acinetobacter lwoffii, Streptococcus infantis|Acinetobacter lwoffii, Streptococcus mitis|Acinetobacter lwoffii, Streptococcus mutans|Acinetobacter lwoffii, Streptococcus oralis|Acinetobacter lwoffii, Streptococcus parasanguinis|Acinetobacter lwoffii, Streptococcus peroris|Acinetobacter lwoffii, Streptococcus pneumoniae|Acinetobacter lwoffii, Streptococcus salivarius|Acinetobacter lwoffii, Streptococcus sanguinis|Acinetobacter lwoffii, Streptococcus thermophilus|Acinetobacter lwoffii, Streptococcus vestibularis|Acinetobacter lwoffii, Subdoligranulum variabile|Acinetobacter lwoffii, Succinatimonas hippei|Acinetobacter lwoffii, Sutterella wadsworthensis|Acinetobacter lwoffii, Tropheryma whipplei|Acinetobacter lwoffii, Veillonella atypica|Acinetobacter lwoffii, Veillonella dispar|Acinetobacter lwoffii, Veillonella parvula|Acinetobacter lwoffii, Victivallis vadensis|Acinetobacter radioresistens, Acinetobacter radioresistens|Acinetobacter radioresistens, Actinomyces odontolyticus|Acinetobacter radioresistens, Actinomyces oris|Acinetobacter radioresistens, Actinomyces viscosus|Acinetobacter radioresistens, Aerococcus viridans|Acinetobacter radioresistens, Aggregatibacter aphrophilus|Acinetobacter radioresistens, Aggregatibacter segnis|Acinetobacter radioresistens, Akkermansia muciniphila|Acinetobacter radioresistens, Alistipes putredinis|Acinetobacter radioresistens, Alistipes shahii|Acinetobacter radioresistens, Anaerococcus hydrogenalis|Acinetobacter radioresistens, Anaerococcus lactolyticus|Acinetobacter radioresistens, Anaerococcus vaginalis|Acinetobacter radioresistens, Anaerostipes caccae|Acinetobacter radioresistens, Anaerotruncus colihominis|Acinetobacter radioresistens, Atopobium parvulum|Acinetobacter radioresistens, Atopobium rimae|Acinetobacter radioresistens, Atopobium vaginae|Acinetobacter radioresistens, Bacteroides caccae|Acinetobacter radioresistens, Bacteroides cellulosilyticus|Acinetobacter radioresistens, Bacteroides coprocola|Acinetobacter radioresistens, Bacteroides coprophilus|Acinetobacter radioresistens, Bacteroides dorei|Acinetobacter radioresistens, Bacteroides eggerthii|Acinetobacter radioresistens, Bacteroides finegoldii|Acinetobacter radioresistens, Bacteroides fragilis|Acinetobacter radioresistens, Bacteroides helcogenes|Acinetobacter radioresistens, Bacteroides intestinalis|Acinetobacter radioresistens, Bacteroides ovatus|Acinetobacter radioresistens, Bacteroides pectinophilus|Acinetobacter radioresistens, Bacteroides plebeius|Acinetobacter radioresistens, Bacteroides salanitronis|Acinetobacter radioresistens, Bacteroides sp. 1_1_6|Acinetobacter radioresistens, Bacteroides sp. 3_1_23|Acinetobacter radioresistens, Bacteroides stercoris|Acinetobacter radioresistens, Bacteroides thetaiotaomicron|Acinetobacter radioresistens, Bacteroides uniformis|Acinetobacter radioresistens, Bacteroides vulgatus|Acinetobacter radioresistens, Bacteroides xylanisolvens|Acinetobacter radioresistens, Bifidobacterium adolescentis|Acinetobacter radioresistens, Bifidobacterium angulatum|Acinetobacter radioresistens, Bifidobacterium animalis|Acinetobacter radioresistens, Bifidobacterium bifidum|Acinetobacter radioresistens, Bifidobacterium breve|Acinetobacter radioresistens, Bifidobacterium catenulatum|Acinetobacter radioresistens, Bifidobacterium dentium|Acinetobacter radioresistens, Bifidobacterium infantis|Acinetobacter radioresistens, Bifidobacterium longum|Acinetobacter radioresistens, Bifidobacterium pseudocatenulatum|Acinetobacter radioresistens, Bilophila wadsworthia|Acinetobacter radioresistens, Blautia hansenii|Acinetobacter radioresistens, Blautia hydrogenotrophica|Acinetobacter radioresistens, Blautia producta|Acinetobacter radioresistens, Blautia schinkii|Acinetobacter radioresistens, Brevibacterium linens|Acinetobacter radioresistens, Brucella ceti|Acinetobacter radioresistens, Brucella suis|Acinetobacter radioresistens, Bulleidia extructa|Acinetobacter radioresistens, Butyrivibrio crossotus|Acinetobacter radioresistens, Campylobacter concisus|Acinetobacter radioresistens, Campylobacter curvus|Acinetobacter radioresistens, Campylobacter gracilis|Acinetobacter radioresistens, Campylobacter hominis|Acinetobacter radioresistens, Capnocytophaga ochracea|Acinetobacter radioresistens, Cardiobacterium hominis|Acinetobacter radioresistens, Catenibacterium mitsuokai|Acinetobacter radioresistens, Catonella morbi|Acinetobacter radioresistens, Citrobacter koseri|Acinetobacter radioresistens, Clostridium asparagiforme|Acinetobacter radioresistens, Clostridium bartlettii|Acinetobacter radioresistens, Clostridium bolteae|Acinetobacter radioresistens, Clostridium botulinum|Acinetobacter radioresistens, Clostridium butyricum|Acinetobacter radioresistens, Clostridium difficile|Acinetobacter radioresistens, Clostridium disporicum|Acinetobacter radioresistens, Clostridium hathewayi|Acinetobacter radioresistens, Clostridium hylemonae|Acinetobacter radioresistens, Clostridium innocuum|Acinetobacter radioresistens, Clostridium leptum|Acinetobacter radioresistens, Clostridium mayombei|Acinetobacter radioresistens, Clostridium methylpentosum|Acinetobacter radioresistens, Clostridium nexile|Acinetobacter radioresistens, Clostridium orbiscindens|Acinetobacter radioresistens, Clostridium perfringens|Acinetobacter radioresistens, Clostridium saccharolyticum|Acinetobacter radioresistens, Clostridium scindens|Acinetobacter radioresistens, Clostridium symbiosum|Acinetobacter radioresistens, Clostridium tertium|Acinetobacter radioresistens, Collinsella aerofaciens|Acinetobacter radioresistens, Collinsella intestinalis|Acinetobacter radioresistens, Collinsella stercoris|Acinetobacter radioresistens, Coprobacillus sp.

TABLE 2-continued

Table 2. Specific binary combinations of OTUs. Individual pairings are differentiated by "|" and OTUs within a combination are differentiated by ","

*D7|Acinetobacter radioresistens, Coprococcus catus|Acinetobacter radioresistens, Coprococcus comes|Acinetobacter radioresistens, Coprococcus eutactus|Acinetobacter radioresistens, Corynebacterium aurimucosum|Acinetobacter radioresistens, Corynebacterium matruchotii|Acinetobacter radioresistens, Cryptobacterium curtum|Acinetobacter radioresistens, Desulfovibrio desulfuricans|Acinetobacter radioresistens, Desulfovibrio piger|Acinetobacter radioresistens, Dialister invisus|Acinetobacter radioresistens, Dialister microaerophilus|Acinetobacter radioresistens, Dorea formicigenerans|Acinetobacter radioresistens, Dorea longicatena|Acinetobacter radioresistens, Eggerthella lenta|Acinetobacter radioresistens, Eikenella corrodens|Acinetobacter radioresistens, Enterobacter cancerogenus|Acinetobacter radioresistens, Enterobacter cloacae|Acinetobacter radioresistens, Enterococcus faecalis|Acinetobacter radioresistens, Enterococcus faecium|Acinetobacter radioresistens, Enterococcus gallinarum|Acinetobacter radioresistens, Erysipelotrichaceae bacterium* 3_1_53|*Acinetobacter radioresistens, Escherichia coli|Acinetobacter radioresistens, Escherichia fergusonii|Acinetobacter radioresistens, Ethanoligenens harbinense|Acinetobacter radioresistens, Eubacterium cellulosolvens|Acinetobacter radioresistens, Eubacterium eligens|Acinetobacter radioresistens, Eubacterium hallii|Acinetobacter radioresistens, Eubacterium limosum|Acinetobacter radioresistens, Eubacterium rectale|Acinetobacter radioresistens, Eubacterium siraeum|Acinetobacter radioresistens, Eubacterium ventriosum|Acinetobacter radioresistens, Faecalibacterium prausnitzii|Acinetobacter radioresistens, Finegoldia magna|Acinetobacter radioresistens, Fusobacterium gonidiaformans|Acinetobacter radioresistens, Fusobacterium mortiferum|Acinetobacter radioresistens, Fusobacterium nucleatum|Acinetobacter radioresistens, Fusobacterium varium|Acinetobacter radioresistens, Gardnerella vaginalis|Acinetobacter radioresistens, Gemella haemolysans|Acinetobacter radioresistens, Gemella morbillorum|Acinetobacter radioresistens, Gordonibacter pamelaeae|Acinetobacter radioresistens, Granulicatella adiacens|Acinetobacter radioresistens, Granulicatella elegans|Acinetobacter radioresistens, Haemophilus influenzae|Acinetobacter radioresistens, Haemophilus parainfluenzae|Acinetobacter radioresistens, Helicobacter pullorum|Acinetobacter radioresistens, Helicobacter pylori|Acinetobacter radioresistens, Holdemania filiformis|Acinetobacter radioresistens, Kingella oralis|Acinetobacter radioresistens, Klebsiella pneumoniae|Acinetobacter radioresistens, Klebsiella variicola|Acinetobacter radioresistens, Lachnospiraceae bacterium* 5_1_57FAA|*Acinetobacter radioresistens, Lactobacillus acidophilus|Acinetobacter radioresistens, Lactobacillus amylovorus|Acinetobacter radioresistens, Lactobacillus brevis|Acinetobacter radioresistens, Lactobacillus casei|Acinetobacter radioresistens, Lactobacillus crispatus|Acinetobacter radioresistens, Lactobacillus delbrueckii|Acinetobacter radioresistens, Lactobacillus fermentum|Acinetobacter radioresistens, Lactobacillus gasseri|Acinetobacter radioresistens, Lactobacillus iners|Acinetobacter radioresistens, Lactobacillus jensenii|Acinetobacter radioresistens, Lactobacillus johnsonii|Acinetobacter radioresistens, Lactobacillus paracasei|Acinetobacter radioresistens, Lactobacillus plantarum|Acinetobacter radioresistens, Lactobacillus reuteri|Acinetobacter radioresistens, Lactobacillus rhamnosus|Acinetobacter radioresistens, Lactobacillus ruminis|Acinetobacter radioresistens, Lactobacillus sakei|Acinetobacter radioresistens, Lactobacillus salivarius|Acinetobacter radioresistens, Lactococcus lactis|Acinetobacter radioresistens, Lautropia mirabilis|Acinetobacter radioresistens, Leuconostoc citreum|Acinetobacter radioresistens, Leuconostoc gasicomitatum|Acinetobacter radioresistens, Leuconostoc mesenteroides|Acinetobacter radioresistens, Listeria monocytogenes|Acinetobacter radioresistens, Marvinbryantia formatexigens|Acinetobacter radioresistens, Megamonas hypermegale|Acinetobacter radioresistens, Megasphaera micronuciformis|Acinetobacter radioresistens, Methanobrevibacter smithii|Acinetobacter radioresistens, Methanosphaera stadtmanae|Acinetobacter radioresistens, Methylobacterium radiotolerans|Acinetobacter radioresistens, Mitsuokella multacida|Acinetobacter radioresistens, Mobiluncus curtisii|Acinetobacter radioresistens, Mycoplasma hominis|Acinetobacter radioresistens, Neisseria mucosa|Acinetobacter radioresistens, Odoribacter splanchnicus|Acinetobacter radioresistens, Olsenella uli|Acinetobacter radioresistens, Oribacterium sinus|Acinetobacter radioresistens, Oxalobacter formigenes|Acinetobacter radioresistens, Parabacteroides distasonis|Acinetobacter radioresistens, Parabacteroides johnsonii|Acinetobacter radioresistens, Parabacteroides merdae|Acinetobacter radioresistens, Parvimonas micra|Acinetobacter radioresistens, Pediococcus acidilactici|Acinetobacter radioresistens, Pediococcus pentosaceus|Acinetobacter radioresistens, Peptoniphilus duerdenii|Acinetobacter radioresistens, Peptoniphilus harei|Acinetobacter radioresistens, Peptoniphilus lacrimalis|Acinetobacter radioresistens, Peptostreptococcus anaerobius|Acinetobacter radioresistens, Peptostreptococcus stomatis|Acinetobacter radioresistens, Porphyromonas asaccharolytica|Acinetobacter radioresistens, Porphyromonas uenonis|Acinetobacter radioresistens, Prevotella amnii|Acinetobacter radioresistens, Prevotella bergensis|Acinetobacter radioresistens, Prevotella bivia|Acinetobacter radioresistens, Prevotella buccae|Acinetobacter radioresistens, Prevotella buccalis|Acinetobacter radioresistens, Prevotella copri|Acinetobacter radioresistens, Prevotella disiens|Acinetobacter radioresistens, Prevotella melaninogenica|Acinetobacter radioresistens, Prevotella multiformis|Acinetobacter radioresistens, Prevotella oralis|Acinetobacter radioresistens, Prevotella oris|Acinetobacter radioresistens, Prevotella salivae|Acinetobacter radioresistens, Prevotella timonensis|Acinetobacter radioresistens, Propionibacterium acnes|Acinetobacter radioresistens, Propionibacterium freudenreichii|Acinetobacter radioresistens, Proteus mirabilis|Acinetobacter radioresistens, Proteus penneri|Acinetobacter radioresistens, Pseudoflavonifractor capillosus|Acinetobacter radioresistens, Pseudomonas aeruginosa|Acinetobacter radioresistens, Pseudomonas fluorescens|Acinetobacter radioresistens, Pseudomonas putida|Acinetobacter radioresistens, Pseudoramibacter alactolyticus|Acinetobacter radioresistens, Pyramidobacter piscolens|Acinetobacter radioresistens, Rhodopseudomonas palustris|Acinetobacter radioresistens, Roseburia intestinalis|Acinetobacter radioresistens, Roseburia inulinivorans|Acinetobacter radioresistens, Rothia dentocariosa|Acinetobacter radioresistens, Rothia mucilaginosa|Acinetobacter radioresistens, Ruminococcus albus|Acinetobacter radioresistens, Ruminococcus bromii|Acinetobacter radioresistens, Ruminococcus gnavus|Acinetobacter radioresistens, Ruminococcus lactaris|Acinetobacter radioresistens, Ruminococcus obeum|Acinetobacter radioresistens, Ruminococcus torques|Acinetobacter radioresistens, Selenomonas sputigena|Acinetobacter radioresistens, Shigella boydii|Acinetobacter radioresistens, Shigella dysenteriae|Acinetobacter radioresistens, Shigella sonnei|Acinetobacter radioresistens, Slackia exigua|Acinetobacter radioresistens, Solobacterium moorei|Acinetobacter radioresistens, Staphylococcus aureus|Acinetobacter radioresistens, Staphylococcus epidermidis|Acinetobacter radioresistens, Staphylococcus hominis|Acinetobacter radioresistens, Staphylococcus saprophyticus|Acinetobacter radioresistens, Staphylococcus warneri|Acinetobacter radioresistens, Streptococcus agalactiae|Acinetobacter radioresistens, Streptococcus anginosus|Acinetobacter radioresistens, Streptococcus australis|Acinetobacter radioresistens, Streptococcus bovis|Acinetobacter radioresistens, Streptococcus cristatus|Acinetobacter radioresistens, Streptococcus dysgalactiae|Acinetobacter radioresistens, Streptococcus equinus|Acinetobacter radioresistens, Streptococcus gordonii|Acinetobacter radioresistens, Streptococcus infantarius|Acinetobacter radioresistens, Streptococcus infantis|Acinetobacter radioresistens, Streptococcus mitis|Acinetobacter radioresistens, Streptococcus mutans|Acinetobacter radioresistens, Streptococcus oralis|Acinetobacter radioresistens, Streptococcus parasanguinis|Acinetobacter radioresistens, Streptococcus peroris|Acinetobacter radioresistens, Streptococcus pneumoniae|Acinetobacter radioresistens, Streptococcus salivarius|Acinetobacter radioresistens, Streptococcus sanguinis|Acinetobacter radioresistens, Streptococcus thermophilus|Acinetobacter radioresistens, Streptococcus vestibularis|Acinetobacter radioresistens, Subdoligranulum variabile|Acinetobacter radioresistens, Succinatimonas hippei|Acinetobacter radioresistens, Sutterella wadsworthensis|Acinetobacter radioresistens, Tropheryma whipplei|Acinetobacter radioresistens, Veillonella atypica|Acinetobacter radioresistens, Veillonella dispar|Acinetobacter radioresistens, Veillonella parvula|Acinetobacter radioresistens, Victivallis vadensis|Actinomyces odontolyticus, Actinomyces odontolyticus|Actinomyces odontolyticus, Actinomyces oris|Actinomyces odontolyticus, Actinomyces viscosus|Actinomyces odontolyticus, Aerococcus viridans|Actinomyces odontolyticus, Aggregatibacter aphrophilus|Actinomyces odontolyticus, Aggregatibacter segnis|Actinomyces odontolyticus, Akkermansia muciniphila|Actinomyces odontolyticus, Alistipes putredinis|Actinomyces odontolyticus, Alistipes shahii|Actinomyces odontolyticus, Anaerococcus hydrogenalis|Actinomyces odontolyticus, Anaerococcus lactolyticus|Actinomyces odontolyticus, Anaerococcus vaginalis|Actinomyces odontolyticus, Anaerostipes caccae|Actinomyces odontolyticus, Anaerotruncus colihominis|Actinomyces odontolyticus, Atopobium parvulum|Actinomyces odontolyticus, Atopobium rimae|Actinomyces odontolyticus, Atopobium vaginae|Actinomyces odontolyticus, Bacteroides*

TABLE 2-continued

Table 2. Specific binary combinations of OTUs. Individual pairings are differentiated by "|" and OTUs within a combination are differentiated by ","

caccae|Actinomyces odontolyticus, Bacteroides cellulosilyticus|Actinomyces odontolyticus, Bacteroides coprocola|Actinomyces odontolyticus, Bacteroides coprophilus|Actinomyces odontolyticus, Bacteroides dorei|Actinomyces odontolyticus, Bacteroides eggerthii|Actinomyces odontolyticus, Bacteroides finegoldii|Actinomyces odontolyticus, Bacteroides fragilis|Actinomyces odontolyticus, Bacteroides helcogenes|Actinomyces odontolyticus, Bacteroides intestinalis|Actinomyces odontolyticus, Bacteroides ovatus|Actinomyces odontolyticus, Bacteroides pectinophilus|Actinomyces odontolyticus, Bacteroides plebeius|Actinomyces odontolyticus, Bacteroides salanitronis|Actinomyces odontolyticus, Bacteroides sp. 1_1_6|Actinomyces odontolyticus, Bacteroides sp. 3_1_23|Actinomyces odontolyticus, Bacteroides stercoris|Actinomyces odontolyticus, Bacteroides thetaiotaomicron|Actinomyces odontolyticus, Bacteroides uniformis|Actinomyces odontolyticus, Bacteroides vulgatus|Actinomyces odontolyticus, Bacteroides xylanisolvens|Actinomyces odontolyticus, Bifidobacterium adolescentis|Actinomyces odontolyticus, Bifidobacterium angulatum|Actinomyces odontolyticus, Bifidobacterium animalis|Actinomyces odontolyticus, Bifidobacterium bifidum|Actinomyces odontolyticus, Bifidobacterium breve|Actinomyces odontolyticus, Bifidobacterium catenulatum|Actinomyces odontolyticus, Bifidobacterium dentium|Actinomyces odontolyticus, Bifidobacterium infantis|Actinomyces odontolyticus, Bifidobacterium longum|Actinomyces odontolyticus, Bifidobacterium pseudocatenulatum|Actinomyces odontolyticus, Bilophila wadsworthia|Actinomyces odontolyticus, Blautia hansenii|Actinomyces odontolyticus, Blautia hydrogenotrophica|Actinomyces odontolyticus, Blautia producta|Actinomyces odontolyticus, Blautia schinkii|Actinomyces odontolyticus, Brevibacterium linens|Actinomyces odontolyticus, Brucella ceti|Actinomyces odontolyticus, Brucella suis|Actinomyces odontolyticus, Bulleidia extructa|Actinomyces odontolyticus, Butyrivibrio crossotus|Actinomyces odontolyticus, Campylobacter concisus|Actinomyces odontolyticus, Campylobacter curvus|Actinomyces odontolyticus, Campylobacter gracilis|Actinomyces odontolyticus, Campylobacter hominis|Actinomyces odontolyticus, Capnocytophaga ochracea|Actinomyces odontolyticus, Cardiobacterium hominis|Actinomyces odontolyticus, Catenibacterium mitsuokai|Actinomyces odontolyticus, Catonella morbi|Actinomyces odontolyticus, Citrobacter koseri|Actinomyces odontolyticus, Clostridium asparagiforme|Actinomyces odontolyticus, Clostridium bartlettii|Actinomyces odontolyticus, Clostridium bolteae|Actinomyces odontolyticus, Clostridium botulinum|Actinomyces odontolyticus, Clostridium butyricum|Actinomyces odontolyticus, Clostridium difficile|Actinomyces odontolyticus, Clostridium disporicum|Actinomyces odontolyticus, Clostridium hathewayi|Actinomyces odontolyticus, Clostridium hylemonae|Actinomyces odontolyticus, Clostridium innocuum|Actinomyces odontolyticus, Clostridium leptum|Actinomyces odontolyticus, Clostridium mayombei|Actinomyces odontolyticus, Clostridium methylpentosum|Actinomyces odontolyticus, Clostridium nexile|Actinomyces odontolyticus, Clostridium orbiscindens|Actinomyces odontolyticus, Clostridium perfringens|Actinomyces odontolyticus, Clostridium saccharolyticum|Actinomyces odontolyticus, Clostridium scindens|Actinomyces odontolyticus, Clostridium symbiosum|Actinomyces odontolyticus, Clostridium tertium|Actinomyces odontolyticus, Collinsella aerofaciens|Actinomyces odontolyticus, Collinsella intestinalis|Actinomyces odontolyticus, Collinsella stercoris|Actinomyces odontolyticus, Coprobacillus sp. D7|Actinomyces odontolyticus, Coprococcus catus|Actinomyces odontolyticus, Coprococcus comes|Actinomyces odontolyticus, Coprococcus eutactus|Actinomyces odontolyticus, Corynebacterium aurimucosum|Actinomyces odontolyticus, Corynebacterium matruchotii|Actinomyces odontolyticus, Cryptobacterium curtum|Actinomyces odontolyticus, Desulfovibrio desulfuricans|Actinomyces odontolyticus, Desulfovibrio piger|Actinomyces odontolyticus, Dialister invisus|Actinomyces odontolyticus, Dialister microaerophilus|Actinomyces odontolyticus, Dorea formicigenerans|Actinomyces odontolyticus, Dorea longicatena|Actinomyces odontolyticus, Eggerthella lenta|Actinomyces odontolyticus, Eikenella corrodens|Actinomyces odontolyticus, Enterobacter cancerogenus|Actinomyces odontolyticus, Enterobacter cloacae|Actinomyces odontolyticus, Enterococcus faecalis|Actinomyces odontolyticus, Enterococcus faecium|Actinomyces odontolyticus, Enterococcus gallinarum|Actinomyces odontolyticus, Erysipelotrichaceae bacterium 3_1_53|Actinomyces odontolyticus, Escherichia coli|Actinomyces odontolyticus, Escherichia fergusonii|Actinomyces odontolyticus, Ethanoligenens harbinense|Actinomyces odontolyticus, Eubacterium cellulosolvens|Actinomyces odontolyticus, Eubacterium eligens|Actinomyces odontolyticus, Eubacterium hallii|Actinomyces odontolyticus, Eubacterium limosum|Actinomyces odontolyticus, Eubacterium rectale|Actinomyces odontolyticus, Eubacterium siraeum|Actinomyces odontolyticus, Eubacterium ventriosum|Actinomyces odontolyticus, Faecalibacterium prausnitzii|Actinomyces odontolyticus, Finegoldia magna|Actinomyces odontolyticus, Fusobacterium gonidiaformans|Actinomyces odontolyticus, Fusobacterium mortiferum|Actinomyces odontolyticus, Fusobacterium nucleatum|Actinomyces odontolyticus, Fusobacterium varium|Actinomyces odontolyticus, Gardnerella vaginalis|Actinomyces odontolyticus, Gemella haemolysans|Actinomyces odontolyticus, Gemella morbillorum|Actinomyces odontolyticus, Gordonibacter pamelaeae|Actinomyces odontolyticus, Granulicatella adiacens|Actinomyces odontolyticus, Granulicatella elegans|Actinomyces odontolyticus, Haemophilus influenzae|Actinomyces odontolyticus, Haemophilus parainfluenzae|Actinomyces odontolyticus, Helicobacter pullorum|Actinomyces odontolyticus, Helicobacter pylori|Actinomyces odontolyticus, Holdemania filiformis|Actinomyces odontolyticus, Kingella oralis|Actinomyces odontolyticus, Klebsiella pneumoniae|Actinomyces odontolyticus, Klebsiella variicola|Actinomyces odontolyticus, Lachnospiraceae bacterium 5_1_57FAA|Actinomyces odontolyticus, Lactobacillus acidophilus|Actinomyces odontolyticus, Lactobacillus amylovorus|Actinomyces odontolyticus, Lactobacillus brevis|Actinomyces odontolyticus, Lactobacillus casei|Actinomyces odontolyticus, Lactobacillus crispatus|Actinomyces odontolyticus, Lactobacillus delbrueckii|Actinomyces odontolyticus, Lactobacillus fermentum|Actinomyces odontolyticus, Lactobacillus gasseri|Actinomyces odontolyticus, Lactobacillus iners|Actinomyces odontolyticus, Lactobacillus jensenii|Actinomyces odontolyticus, Lactobacillus johnsonii|Actinomyces odontolyticus, Lactobacillus paracasei|Actinomyces odontolyticus, Lactobacillus plantarum|Actinomyces odontolyticus, Lactobacillus reuteri|Actinomyces odontolyticus, Lactobacillus rhamnosus|Actinomyces odontolyticus, Lactobacillus ruminis|Actinomyces odontolyticus, Lactobacillus sakei|Actinomyces odontolyticus, Lactobacillus salivarius|Actinomyces odontolyticus, Lactococcus lactis|Actinomyces odontolyticus, Lautropia mirabilis|Actinomyces odontolyticus, Leuconostoc citreum|Actinomyces odontolyticus, Leuconostoc gasicomitatum|Actinomyces odontolyticus, Leuconostoc mesenteroides|Actinomyces odontolyticus, Listeria monocytogenes|Actinomyces odontolyticus, Marvinbryantia formatexigens|Actinomyces odontolyticus, Megamonas hypermegale|Actinomyces odontolyticus, Megasphaera micronuciformis|Actinomyces odontolyticus, Methanobrevibacter smithii|Actinomyces odontolyticus, Methanosphaera stadtmanae|Actinomyces odontolyticus, Methylobacterium radiotolerans|Actinomyces odontolyticus, Mitsuokella multacida|Actinomyces odontolyticus, Mobiluncus curtisii|Actinomyces odontolyticus, Mycoplasma hominis|Actinomyces odontolyticus, Neisseria mucosa|Actinomyces odontolyticus, Odoribacter splanchnicus|Actinomyces odontolyticus, Olsenella uli|Actinomyces odontolyticus, Oribacterium sinus|Actinomyces odontolyticus, Oxalobacter formigenes|Actinomyces odontolyticus, Parabacteroides distasonis|Actinomyces odontolyticus, Parabacteroides johnsonii|Actinomyces odontolyticus, Parabacteroides merdae|Actinomyces odontolyticus, Parvimonas micra|Actinomyces odontolyticus, Pediococcus acidilactici|Actinomyces odontolyticus, Pediococcus pentosaceus|Actinomyces odontolyticus, Peptoniphilus duerdenii|Actinomyces odontolyticus, Peptoniphilus harei|Actinomyces odontolyticus, Peptoniphilus lacrimalis|Actinomyces odontolyticus, Peptostreptococcus anaerobius|Actinomyces odontolyticus, Peptostreptococcus stomatis|Actinomyces odontolyticus, Porphyromonas asaccharolytica|Actinomyces odontolyticus, Porphyromonas uenonis|Actinomyces odontolyticus, Prevotella amnii|Actinomyces odontolyticus, Prevotella bergensis|Actinomyces odontolyticus, Prevotella bivia|Actinomyces odontolyticus, Prevotella buccae|Actinomyces odontolyticus, Prevotella buccalis|Actinomyces odontolyticus, Prevotella copri|Actinomyces odontolyticus, Prevotella disiens|Actinomyces odontolyticus, Prevotella melaninogenica|Actinomyces odontolyticus, Prevotella multiformis|Actinomyces odontolyticus, Prevotella oralis|Actinomyces odontolyticus, Prevotella oris|Actinomyces odontolyticus, Prevotella salivae|Actinomyces odontolyticus, Prevotella timonensis|Actinomyces odontolyticus, Propionibacterium acnes|Actinomyces odontolyticus, Propionibacterium freudenreichii|Actinomyces odontolyticus, Proteus mirabilis|Actinomyces odontolyticus, Proteus penneri|Actinomyces odontolyticus, Pseudoflavonifractor capillosus|Actinomyces odontolyticus, Pseudomonas aeruginosa|Actinomyces odontolyticus, Pseudomonas fluorescens|Actinomyces odontolyticus, Pseudomonas putida|Actinomyces TABLE 2-continued Table 2. Specific binary combinations of OTUs. Individual pairings are differentiated by "|" and OTUs within a combination are differentiated by ","

odontolyticus, Pseudoramibacter alactolyticus|Actinomyces odontolyticus, Pyramidobacter piscolens|Actinomyces odontolyticus, Rhodopseudomonas palustris|Actinomyces odontolyticus, Roseburia intestinalis|Actinomyces odontolyticus, Roseburia inulinivorans|Actinomyces odontolyticus, Rothia dentocariosa|Actinomyces odontolyticus, Rothia mucilaginosa|Actinomyces odontolyticus, Ruminococcus albus|Actinomyces odontolyticus, Ruminococcus bromii|Actinomyces odontolyticus, Ruminococcus gnavus|Actinomyces odontolyticus, Ruminococcus lactaris|Actinomyces odontolyticus, Ruminococcus obeum|Actinomyces odontolyticus, Ruminococcus torques|Actinomyces odontolyticus, Selenomonas sputigena|Actinomyces odontolyticus, Shigella boydii|Actinomyces odontolyticus, Shigella dysenteriae|Actinomyces odontolyticus, Shigella sonnei|Actinomyces odontolyticus, Slackia exigua|Actinomyces odontolyticus, Solobacterium moorei|Actinomyces odontolyticus, Staphylococcus aureus|Actinomyces odontolyticus, Staphylococcus epidermidis|Actinomyces odontolyticus, Staphylococcus hominis|Actinomyces odontolyticus, Staphylococcus saprophyticus|Actinomyces odontolyticus, Staphylococcus warneri|Actinomyces odontolyticus, Streptococcus agalactiae|Actinomyces odontolyticus, Streptococcus anginosus|Actinomyces odontolyticus, Streptococcus australis|Actinomyces odontolyticus, Streptococcus bovis|Actinomyces odontolyticus, Streptococcus cristatus|Actinomyces odontolyticus, Streptococcus dysgalactiae|Actinomyces odontolyticus, Streptococcus equinus|Actinomyces odontolyticus, Streptococcus gordonii|Actinomyces odontolyticus, Streptococcus infantarius|Actinomyces odontolyticus, Streptococcus infantis|Actinomyces odontolyticus, Streptococcus mitis|Actinomyces odontolyticus, Streptococcus mutans|Actinomyces odontolyticus, Streptococcus oralis|Actinomyces odontolyticus, Streptococcus parasanguinis|Actinomyces odontolyticus, Streptococcus peroris|Actinomyces odontolyticus, Streptococcus pneumoniae|Actinomyces odontolyticus, Streptococcus salivarius|Actinomyces odontolyticus, Streptococcus sanguinis|Actinomyces odontolyticus, Streptococcus thermophilus|Actinomyces odontolyticus, Streptococcus vestibularis|Actinomyces odontolyticus, Subdoligranulum variabile|Actinomyces odontolyticus, Succinatimonas hippei|Actinomyces odontolyticus, Sutterella wadsworthensis|Actinomyces odontolyticus, Tropheryma whipplei|Actinomyces odontolyticus, Veillonella atypica|Actinomyces odontolyticus, Veillonella dispar|Actinomyces odontolyticus, Veillonella parvula|Actinomyces odontolyticus, Victivallis vadensis|Actinomyces oris, Actinomyces oris|Actinomyces oris, Actinomyces viscosus|Actinomyces oris, Aerococcus viridans|Actinomyces oris, Aggregatibacter aphrophilus|Actinomyces oris, Aggregatibacter segnis|Actinomyces oris, Akkermansia muciniphila|Actinomyces oris, Alistipes putredinis|Actinomyces oris, Alistipes shahii|Actinomyces oris, Anaerococcus hydrogenalis|Actinomyces oris, Anaerococcus lactolyticus|Actinomyces oris, Anaerococcus vaginalis|Actinomyces oris, Anaerostipes caccae|Actinomyces oris, Anaerotruncus colihominis|Actinomyces oris, Atopobium parvulum|Actinomyces oris, Atopobium rimae|Actinomyces oris, Atopobium vaginae|Actinomyces oris, Bacteroides caccae|Actinomyces oris, Bacteroides cellulosilyticus|Actinomyces oris, Bacteroides coprocola|Actinomyces oris, Bacteroides coprophilus|Actinomyces oris, Bacteroides dorei|Actinomyces oris, Bacteroides eggerthii|Actinomyces oris, Bacteroides finegoldii|Actinomyces oris, Bacteroides fragilis|Actinomyces oris, Bacteroides helcogenes|Actinomyces oris, Bacteroides intestinalis|Actinomyces oris, Bacteroides ovatus|Actinomyces oris, Bacteroides pectinophilus|Actinomyces oris, Bacteroides plebeius|Actinomyces oris, Bacteroides salanitronis|Actinomyces oris, Bacteroides sp. 1_16|Actinomyces oris, Bacteroides sp. 3_1_23|Actinomyces oris, Bacteroides stercoris|Actinomyces oris, Bacteroides thetaiotaomicron|Actinomyces oris, Bacteroides uniformis|Actinomyces oris, Bacteroides vulgatus|Actinomyces oris, Bacteroides xylanisolvens|Actinomyces oris, Bifidobacterium adolescentis|Actinomyces oris, Bifidobacterium angulatum|Actinomyces oris, Bifidobacterium animalis|Actinomyces oris, Bifidobacterium bifidum|Actinomyces oris, Bifidobacterium breve|Actinomyces oris, Bifidobacterium catenulatum|Actinomyces oris, Bifidobacterium dentium|Actinomyces oris, Bifidobacterium infantis|Actinomyces oris, Bifidobacterium longum|Actinomyces oris, Bifidobacterium pseudocatenulatum|Actinomyces oris, Bilophila wadsworthia|Actinomyces oris, Blautia hansenii|Actinomyces oris, Blautia hydrogenotrophica|Actinomyces oris, Blautia producta|Actinomyces oris, Blautia schinkii|Actinomyces oris, Brevibacterium linens|Actinomyces oris, Brucella ceti|Actinomyces oris, Brucella suis|Actinomyces oris, Bulleidia extructa|Actinomyces oris, Butyrivibrio crossotus|Actinomyces oris, Campylobacter concisus|Actinomyces oris, Campylobacter curvus|Actinomyces oris, Campylobacter gracilis|Actinomyces oris, Campylobacter hominis|Actinomyces oris, Capnocytophaga ochracea|Actinomyces oris, Cardiobacterium hominis|Actinomyces oris, Catenibacterium mitsuokai|Actinomyces oris, Catonella morbi|Actinomyces oris, Citrobacter koseri|Actinomyces oris, Clostridium asparagiforme|Actinomyces oris, Clostridium bartlettii|Actinomyces oris, Clostridium bolteae|Actinomyces oris, Clostridium botulinum|Actinomyces oris, Clostridium butyricum|Actinomyces oris, Clostridium difficile|Actinomyces oris, Clostridium disporicum|Actinomyces oris, Clostridium hathewayi|Actinomyces oris, Clostridium hylemonae|Actinomyces oris, Clostridium innocuum|Actinomyces oris, Clostridium leptum|Actinomyces oris, Clostridium mayombei|Actinomyces oris, Clostridium methylpentosum|Actinomyces oris, Clostridium nexile|Actinomyces oris, Clostridium orbiscindens|Actinomyces oris, Clostridium perfringens|Actinomyces oris, Clostridium saccharolyticum|Actinomyces oris, Clostridium scindens|Actinomyces oris, Clostridium symbiosum|Actinomyces oris, Clostridium tertium|Actinomyces oris, Collinsella aerofaciens|Actinomyces oris, Collinsella intestinalis|Actinomyces oris, Collinsella stercoris|Actinomyces oris, Coprobacillus sp. D7|Actinomyces oris, Coprococcus catus|Actinomyces oris, Coprococcus comes|Actinomyces oris, Coprococcus eutactus|Actinomyces oris, Corynebacterium aurimucosum|Actinomyces oris, Corynebacterium matruchotii|Actinomyces oris, Cryptobacterium curtum|Actinomyces oris, Desulfovibrio desulfuricans|Actinomyces oris, Desulfovibrio piger|Actinomyces oris, Dialister invisus|Actinomyces oris, Dialister microaerophilus|Actinomyces oris, Dorea formicigenerans|Actinomyces oris, Dorea longicatena|Actinomyces oris, Eggerthella lenta|Actinomyces oris, Eikenella corrodens|Actinomyces oris, Enterobacter cancerogenus|Actinomyces oris, Enterobacter cloacae|Actinomyces oris, Enterococcus faecalis|Actinomyces oris, Enterococcus faecium|Actinomyces oris, Enterococcus gallinarum|Actinomyces oris, Erysipelotrichaceae bacterium 3_1_53|Actinomyces oris, Escherichia coli|Actinomyces oris, Escherichia fergusonii|Actinomyces oris, Ethanoligenens harbinense|Actinomyces oris, Eubacterium cellulosolvens|Actinomyces oris, Eubacterium eligens|Actinomyces oris, Eubacterium hallii|Actinomyces oris, Eubacterium limosum|Actinomyces oris, Eubacterium rectale|Actinomyces oris, Eubacterium siraeum|Actinomyces oris, Eubacterium ventriosum|Actinomyces oris, Faecalibacterium prausnitzii|Actinomyces oris, Finegoldia magna|Actinomyces oris, Fusobacterium gonidiaformans|Actinomyces oris, Fusobacterium mortiferum|Actinomyces oris, Fusobacterium nucleatum|Actinomyces oris, Fusobacterium varium|Actinomyces oris, Gardnerella vaginalis|Actinomyces oris, Gemella haemolysans|Actinomyces oris, Gemella morbillorum|Actinomyces oris, Gordonibacter pamelaeae|Actinomyces oris, Granulicatella adiacens|Actinomyces oris, Granulicatella elegans|Actinomyces oris, Haemophilus influenzae|Actinomyces oris, Haemophilus parainfluenzae|Actinomyces oris, Helicobacter pullorum|Actinomyces oris, Helicobacter pylori|Actinomyces oris, Holdemania filiformis|Actinomyces oris, Kingella oralis|Actinomyces oris, Klebsiella pneumoniae|Actinomyces oris, Klebsiella variicola|Actinomyces oris, Lachnospiraceae bacterium 5_1_57FAA|Actinomyces oris, Lactobacillus acidophilus|Actinomyces oris, Lactobacillus amylovorus|Actinomyces oris, Lactobacillus brevis|Actinomyces oris, Lactobacillus casei|Actinomyces oris, Lactobacillus crispatus|Actinomyces oris, Lactobacillus delbrueckii|Actinomyces oris, Lactobacillus fermentum|Actinomyces oris, Lactobacillus gasseri|Actinomyces oris, Lactobacillus iners|Actinomyces oris, Lactobacillus jensenii|Actinomyces oris, Lactobacillus johnsonii|Actinomyces oris, Lactobacillus paracasei|Actinomyces oris, Lactobacillus plantarum|Actinomyces oris, Lactobacillus reuteri|Actinomyces oris, Lactobacillus rhamnosus|Actinomyces oris, Lactobacillus ruminis|Actinomyces oris, Lactobacillus sakei|Actinomyces oris, Lactobacillus salivarius|Actinomyces oris, Lactococcus lactis|Actinomyces oris, Lautropia mirabilis|Actinomyces oris, Leuconostoc citreum|Actinomyces oris, Leuconostoc gasicomitatum|Actinomyces oris, Leuconostoc mesenteroides|Actinomyces oris, Listeria monocytogenes|Actinomyces oris, Marvinbryantia formatexigens|Actinomyces oris, Megamonas hypermegale|Actinomyces oris, Megasphaera micronuciformis|Actinomyces oris, Methanobrevibacter smithii|Actinomyces oris, Methanosphaera stadtmanae|Actinomyces oris, Methylobacterium radiotolerans|Actinomyces oris, Mitsuokella multacida|Actinomyces oris, Mobiluncus curtisii|Actinomyces oris, Mycoplasma hominis|Actinomyces oris, Neisseria mucosa|Actinomyces oris, Odoribacter splanchnicus|Actinomyces oris, Olsenella uli|Actinomyces oris, Oribacterium sinus|Actinomyces oris, Oxalobacter formigenes|Actinomyces oris, Parabacteroides distasonis|Actinomyces oris, Parabacteroides TABLE 2-continued

| Table 2. Specific binary combinations of OTUs. Individual pairings are differentiated by "\|" and OTUs within a combination are differentiated by "," |
|---|
| johnsonii\|Actinomyces oris, Parabacteroides merdae\|Actinomyces oris, Parvimonas micra\|Actinomyces oris, Pediococcus acidilactici\|Actinomyces oris, Pediococcus pentosaceus\|Actinomyces oris, Peptoniphilus duerdenii\|Actinomyces oris, Peptoniphilus harei\|Actinomyces oris, Peptoniphilus lacrimalis\|Actinomyces oris, Peptostreptococcus anaerobius\|Actinomyces oris, Peptostreptococcus stomatis\|Actinomyces oris, Porphyromonas asaccharolytica\|Actinomyces oris, Porphyromonas uenonis\|Actinomyces oris, Prevotella amnii\|Actinomyces oris, Prevotella bergensis\|Actinomyces oris, Prevotella bivia\|Actinomyces oris, Prevotella buccae\|Actinomyces oris, Prevotella buccalis\|Actinomyces oris, Prevotella copri\|Actinomyces oris, Prevotella disiens\|Actinomyces oris, Prevotella melaninogenica\|Actinomyces oris, Prevotella multiformis\|Actinomyces oris, Prevotella oralis\|Actinomyces oris, Prevotella oris\|Actinomyces oris, Prevotella salivae\|Actinomyces oris, Prevotella timonensis\|Actinomyces oris, Propionibacterium acnes\|Actinomyces oris, Propionibacterium freudenreichii\|Actinomyces oris, Proteus mirabilis\|Actinomyces oris, Proteus penneri\|Actinomyces oris, Pseudoflavonifractor capillosus\|Actinomyces oris, Pseudomonas aeruginosa\|Actinomyces oris, Pseudomonas fluorescens\|Actinomyces oris, Pseudomonas putida\|Actinomyces oris, Pseudoramibacter alactolyticus\|Actinomyces oris, Pyramidobacter piscolens\|Actinomyces oris, Rhodopseudomonas palustris\|Actinomyces oris, Roseburia intestinalis\|Actinomyces oris, Roseburia inulinivorans\|Actinomyces oris, Rothia dentocariosa\|Actinomyces oris, Rothia mucilaginosa\|Actinomyces oris, Ruminococcus albus\|Actinomyces oris, Ruminococcus bromii\|Actinomyces oris, Ruminococcus gnavus\|Actinomyces oris, Ruminococcus lactaris\|Actinomyces oris, Ruminococcus obeum\|Actinomyces oris, Ruminococcus torques\|Actinomyces oris, Selenomonas sputigena\|Actinomyces oris, Shigella boydii\|Actinomyces oris, Shigella dysenteriae\|Actinomyces oris, Shigella sonnei\|Actinomyces oris, Slackia exigua\|Actinomyces oris, Solobacterium moorei\|Actinomyces oris, Staphylococcus aureus\|Actinomyces oris, Staphylococcus epidermidis\|Actinomyces oris, Staphylococcus hominis\|Actinomyces oris, Staphylococcus saprophyticus\|Actinomyces oris, Staphylococcus warneri\|Actinomyces oris, Streptococcus agalactiae\|Actinomyces oris, Streptococcus anginosus\|Actinomyces oris, Streptococcus australis\|Actinomyces oris, Streptococcus bovis\|Actinomyces oris, Streptococcus cristatus\|Actinomyces oris, Streptococcus dysgalactiae\|Actinomyces oris, Streptococcus equinus\|Actinomyces oris, Streptococcus gordonii\|Actinomyces oris, Streptococcus infantarius\|Actinomyces oris, Streptococcus infantis\|Actinomyces oris, Streptococcus mitis\|Actinomyces oris, Streptococcus mutans\|Actinomyces oris, Streptococcus oralis\|Actinomyces oris, Streptococcus parasanguinis\|Actinomyces oris, Streptococcus peroris\|Actinomyces oris, Streptococcus pneumoniae\|Actinomyces oris, Streptococcus salivarius\|Actinomyces oris, Streptococcus sanguinis\|Actinomyces oris, Streptococcus thermophilus\|Actinomyces oris, Streptococcus vestibularis\|Actinomyces oris, Subdoligranulum variabile\|Actinomyces oris, Succinatimonas hippei\|Actinomyces oris, Sutterella wadsworthensis\|Actinomyces oris, Tropheryma whipplei\|Actinomyces oris, Veillonella atypica\|Actinomyces oris, Veillonella dispar\|Actinomyces oris, Veillonella parvula\|Actinomyces oris, Victivallis vadensis\|Actinomyces viscosus, Actinomyces viscosus\|Actinomyces viscosus, Aerococcus viridans\|Actinomyces viscosus, Aggregatibacter aphrophilus\|Actinomyces viscosus, Aggregatibacter segnis\|Actinomyces viscosus, Akkermansia muciniphila\|Actinomyces viscosus, Alistipes putredinis\|Actinomyces viscosus, Alistipes shahii\|Actinomyces viscosus, Anaerococcus hydrogenalis\|Actinomyces viscosus, Anaerococcus lactolyticus\|Actinomyces viscosus, Anaerococcus vaginalis\|Actinomyces viscosus, Anaerostipes caccae\|Actinomyces viscosus, Anaerotruncus colihominis\|Actinomyces viscosus, Atopobium parvulum\|Actinomyces viscosus, Atopobium rimae\|Actinomyces viscosus, Atopobium vaginae\|Actinomyces viscosus, Bacteroides caccae\|Actinomyces viscosus, Bacteroides cellulosilyticus\|Actinomyces viscosus, Bacteroides coprocola\|Actinomyces viscosus, Bacteroides coprophilus\|Actinomyces viscosus, Bacteroides dorei\|Actinomyces viscosus, Bacteroides eggerthii\|Actinomyces viscosus, Bacteroides finegoldii\|Actinomyces viscosus, Bacteroides fragilis\|Actinomyces viscosus, Bacteroides helcogenes\|Actinomyces viscosus, Bacteroides intestinalis\|Actinomyces viscosus, Bacteroides ovatus\|Actinomyces viscosus, Bacteroides pectinophilus\|Actinomyces viscosus, Bacteroides plebeius\|Actinomyces viscosus, Bacteroides salanitronis\|Actinomyces viscosus, Bacteroides sp. 1_1_6\|Actinomyces viscosus, Bacteroides sp. 3_1_23\|Actinomyces viscosus, Bacteroides stercoris\|Actinomyces viscosus, Bacteroides thetaiotaomicron\|Actinomyces viscosus, Bacteroides uniformis\|Actinomyces viscosus, Bacteroides vulgatus\|Actinomyces viscosus, Bacteroides xylanisolvens\|Actinomyces viscosus, Bifidobacterium adolescentis\|Actinomyces viscosus, Bifidobacterium angulatum\|Actinomyces viscosus, Bifidobacterium animalis\|Actinomyces viscosus, Bifidobacterium bifidum\|Actinomyces viscosus, Bifidobacterium breve\|Actinomyces viscosus, Bifidobacterium catenulatum\|Actinomyces viscosus, Bifidobacterium dentium\|Actinomyces viscosus, Bifidobacterium infantis\|Actinomyces viscosus, Bifidobacterium longum\|Actinomyces viscosus, Bifidobacterium pseudocatenulatum\|Actinomyces viscosus, Bilophila wadsworthia\|Actinomyces viscosus, Blautia hansenii\|Actinomyces viscosus, Blautia hydrogenotrophica\|Actinomyces viscosus, Blautia producta\|Actinomyces viscosus, Blautia schinkii\|Actinomyces viscosus, Brevibacterium linens\|Actinomyces viscosus, Brucella ceti\|Actinomyces viscosus, Brucella suis\|Actinomyces viscosus, Bulleidia extructa\|Actinomyces viscosus, Butyrivibrio crossotus\|Actinomyces viscosus, Campylobacter concisus\|Actinomyces viscosus, Campylobacter curvus\|Actinomyces viscosus, Campylobacter gracilis\|Actinomyces viscosus, Campylobacter hominis\|Actinomyces viscosus, Capnocytophaga ochracea\|Actinomyces viscosus, Cardiobacterium hominis\|Actinomyces viscosus, Catenibacterium mitsuokai\|Actinomyces viscosus, Catonella morbi\|Actinomyces viscosus, Citrobacter koseri\|Actinomyces viscosus, Clostridium asparagiforme\|Actinomyces viscosus, Clostridium bartlettii\|Actinomyces viscosus, Clostridium bolteae\|Actinomyces viscosus, Clostridium botulinum\|Actinomyces viscosus, Clostridium butyricum\|Actinomyces viscosus, Clostridium difficile\|Actinomyces viscosus, Clostridium disporicum\|Actinomyces viscosus, Clostridium hathewayi\|Actinomyces viscosus, Clostridium hylemonae\|Actinomyces viscosus, Clostridium innocuum\|Actinomyces viscosus, Clostridium leptum\|Actinomyces viscosus, Clostridium mayombei\|Actinomyces viscosus, Clostridium methylpentosum\|Actinomyces viscosus, Clostridium nexile\|Actinomyces viscosus, Clostridium orbiscindens\|Actinomyces viscosus, Clostridium perfringens\|Actinomyces viscosus, Clostridium saccharolyticum\|Actinomyces viscosus, Clostridium scindens\|Actinomyces viscosus, Clostridium symbiosum\|Actinomyces viscosus, Clostridium tertium\|Actinomyces viscosus, Collinsella aerofaciens\|Actinomyces viscosus, Collinsella intestinalis\|Actinomyces viscosus, Collinsella stercoris\|Actinomyces viscosus, Coprobacillus sp. D7\|Actinomyces viscosus, Coprococcus catus\|Actinomyces viscosus, Coprococcus comes\|Actinomyces viscosus, Coprococcus eutactus\|Actinomyces viscosus, Corynebacterium aurimucosum\|Actinomyces viscosus, Corynebacterium matruchotii\|Actinomyces viscosus, Cryptobacterium curtum\|Actinomyces viscosus, Desulfovibrio desulfuricans\|Actinomyces viscosus, Desulfovibrio piger\|Actinomyces viscosus, Dialister invisus\|Actinomyces viscosus, Dialister microaerophilus\|Actinomyces viscosus, Dorea formicigenerans\|Actinomyces viscosus, Dorea longicatena\|Actinomyces viscosus, Eggerthella lenta\|Actinomyces viscosus, Eikenella corrodens\|Actinomyces viscosus, Enterobacter cancerogenus\|Actinomyces viscosus, Enterobacter cloacae\|Actinomyces viscosus, Enterococcus faecalis\|Actinomyces viscosus, Enterococcus faecium\|Actinomyces viscosus, Enterococcus gallinarum\|Actinomyces viscosus, Erysipelotrichaceae bacterium 3_1_53\|Actinomyces viscosus, Escherichia coli\|Actinomyces viscosus, Escherichia fergusonii\|Actinomyces viscosus, Ethanoligenens harbinense\|Actinomyces viscosus, Eubacterium cellulosolvens\|Actinomyces viscosus, Eubacterium eligens\|Actinomyces viscosus, Eubacterium hallii\|Actinomyces viscosus, Eubacterium limosum\|Actinomyces viscosus, Eubacterium rectale\|Actinomyces viscosus, Eubacterium siraeum\|Actinomyces viscosus, Eubacterium ventriosum\|Actinomyces viscosus, Faecalibacterium prausnitzii\|Actinomyces viscosus, Finegoldia magna\|Actinomyces viscosus, Fusobacterium gonidiaformans\|Actinomyces viscosus, Fusobacterium mortiferum\|Actinomyces viscosus, Fusobacterium nucleatum\|Actinomyces viscosus, Fusobacterium varium\|Actinomyces viscosus, Gardnerella vaginalis\|Actinomyces viscosus, Gemella haemolysans\|Actinomyces viscosus, Gemella morbillorum\|Actinomyces viscosus, Gordonibacter pamelaeae\|Actinomyces viscosus, Granulicatella adiacens\|Actinomyces viscosus, Granulicatella elegans\|Actinomyces viscosus, Haemophilus influenzae\|Actinomyces viscosus, Haemophilus parainfluenzae\|Actinomyces viscosus, Helicobacter pullorum\|Actinomyces viscosus, Helicobacter pylori\|Actinomyces viscosus, Holdemania filiformis\|Actinomyces viscosus, Kingella oralis\|Actinomyces viscosus, Klebsiella pneumoniae\|Actinomyces viscosus, Klebsiella variicola\|Actinomyces viscosus, Lachnospiraceae bacterium 5_1_57FAA\|Actinomyces viscosus, Lactobacillus acidophilus\|Actinomyces viscosus, Lactobacillus amylovorus\|Actinomyces viscosus, Lactobacillus brevis\|Actinomyces viscosus, Lactobacillus |

TABLE 2-continued

Table 2. Specific binary combinations of OTUs. Individual pairings are differentiated by "|" and OTUs within a combination are differentiated by ","

casei|Actinomyces viscosus, Lactobacillus crispatus|Actinomyces viscosus, Lactobacillus delbrueckii|Actinomyces viscosus, Lactobacillus fermentum|Actinomyces viscosus, Lactobacillus gasseri|Actinomyces viscosus, Lactobacillus iners|Actinomyces viscosus, Lactobacillus jensenii|Actinomyces viscosus, Lactobacillus johnsonii|Actinomyces viscosus, Lactobacillus paracasei|Actinomyces viscosus, Lactobacillus plantarum|Actinomyces viscosus, Lactobacillus reuteri|Actinomyces viscosus, Lactobacillus rhamnosus|Actinomyces viscosus, Lactobacillus ruminis|Actinomyces viscosus, Lactobacillus sakei|Actinomyces viscosus, Lactobacillus salivarius|Actinomyces viscosus, Lactococcus lactis|Actinomyces viscosus, Lautropia mirabilis|Actinomyces viscosus, Leuconostoc citreum|Actinomyces viscosus, Leuconostoc gasicomitatum|Actinomyces viscosus, Leuconostoc mesenteroides|Actinomyces viscosus, Listeria monocytogenes|Actinomyces viscosus, Marvinbryantia formatexigens|Actinomyces viscosus, Megamonas hypermegale|Actinomyces viscosus, Megasphaera micronuciformis|Actinomyces viscosus, Methanobrevibacter smithii|Actinomyces viscosus, Methanosphaera stadtmanae|Actinomyces viscosus, Methylobacterium radiotolerans|Actinomyces viscosus, Mitsuokella multacida|Actinomyces viscosus, Mobiluncus curtisii|Actinomyces viscosus, Mycoplasma hominis|Actinomyces viscosus, Neisseria mucosa|Actinomyces viscosus, Odoribacter splanchnicus|Actinomyces viscosus, Olsenella uli|Actinomyces viscosus, Oribacterium sinus|Actinomyces viscosus, Oxalobacter formigenes|Actinomyces viscosus, Parabacteroides distasonis|Actinomyces viscosus, Parabacteroides johnsonii|Actinomyces viscosus, Parabacteroides merdae|Actinomyces viscosus, Parvimonas micra|Actinomyces viscosus, Pediococcus acidilactici|Actinomyces viscosus, Pediococcus pentosaceus|Actinomyces viscosus, Peptoniphilus duerdenii|Actinomyces viscosus, Peptoniphilus harei|Actinomyces viscosus, Peptoniphilus lacrimalis|Actinomyces viscosus, Peptostreptococcus anaerobius|Actinomyces viscosus, Peptostreptococcus stomatis|Actinomyces viscosus, Porphyromonas asaccharolytica|Actinomyces viscosus, Porphyromonas uenonis|Actinomyces viscosus, Prevotella amnii|Actinomyces viscosus, Prevotella bergensis|Actinomyces viscosus, Prevotella bivia|Actinomyces viscosus, Prevotella buccae|Actinomyces viscosus, Prevotella buccalis|Actinomyces viscosus, Prevotella copri|Actinomyces viscosus, Prevotella disiens|Actinomyces viscosus, Prevotella melaninogenica|Actinomyces viscosus, Prevotella multiformis|Actinomyces viscosus, Prevotella oralis|Actinomyces viscosus, Prevotella oris|Actinomyces viscosus, Prevotella salivae|Actinomyces viscosus, Prevotella timonensis|Actinomyces viscosus, Propionibacterium acnes|Actinomyces viscosus, Propionibacterium freudenreichii|Actinomyces viscosus, Proteus mirabilis|Actinomyces viscosus, Proteus penneri|Actinomyces viscosus, Pseudoflavonifractor capillosus|Actinomyces viscosus, Pseudomonas aeruginosa|Actinomyces viscosus, Pseudomonas fluorescens|Actinomyces viscosus, Pseudomonas putida|Actinomyces viscosus, Pseudoramibacter alactolyticus|Actinomyces viscosus, Pyramidobacter piscolens|Actinomyces viscosus, Rhodopseudomonas palustris|Actinomyces viscosus, Roseburia intestinalis|Actinomyces viscosus, Roseburia inulinivorans|Actinomyces viscosus, Rothia dentocariosa|Actinomyces viscosus, Rothia mucilaginosa|Actinomyces viscosus, Ruminococcus albus|Actinomyces viscosus, Ruminococcus bromii|Actinomyces viscosus, Ruminococcus gnavus|Actinomyces viscosus, Ruminococcus lactaris|Actinomyces viscosus, Ruminococcus obeum|Actinomyces viscosus, Ruminococcus torques|Actinomyces viscosus, Selenomonas sputigena|Actinomyces viscosus, Shigella boydii|Actinomyces viscosus, Shigella dysenteriae|Actinomyces viscosus, Shigella sonnei|Actinomyces viscosus, Slackia exigua|Actinomyces viscosus, Solobacterium moorei|Actinomyces viscosus, Staphylococcus aureus|Actinomyces viscosus, Staphylococcus epidermidis|Actinomyces viscosus, Staphylococcus hominis|Actinomyces viscosus, Staphylococcus saprophyticus|Actinomyces viscosus, Staphylococcus warneri|Actinomyces viscosus, Streptococcus agalactiae|Actinomyces viscosus, Streptococcus anginosus|Actinomyces viscosus, Streptococcus australis|Actinomyces viscosus, Streptococcus bovis|Actinomyces viscosus, Streptococcus cristatus|Actinomyces viscosus, Streptococcus dysgalactiae|Actinomyces viscosus, Streptococcus equinus|Actinomyces viscosus, Streptococcus gordonii|Actinomyces viscosus, Streptococcus infantarius|Actinomyces viscosus, Streptococcus infantis|Actinomyces viscosus, Streptococcus mitis|Actinomyces viscosus, Streptococcus mutans|Actinomyces viscosus, Streptococcus oralis|Actinomyces viscosus, Streptococcus parasanguinis|Actinomyces viscosus, Streptococcus peroris|Actinomyces viscosus, Streptococcus pneumoniae|Actinomyces viscosus, Streptococcus salivarius|Actinomyces viscosus, Streptococcus sanguinis|Actinomyces viscosus, Streptococcus thermophilus|Actinomyces viscosus, Streptococcus vestibularis|Actinomyces viscosus, Subdoligranulum variabile|Actinomyces viscosus, Succinatimonas hippei|Actinomyces viscosus, Sutterella wadsworthensis|Actinomyces viscosus, Tropheryma whipplei|Actinomyces viscosus, Veillonella atypica|Actinomyces viscosus, Veillonella dispar|Actinomyces viscosus, Veillonella parvula|Actinomyces viscosus, Victivallis vadensis|Aerococcus viridans, Aerococcus viridans|Aerococcus viridans, Aggregatibacter aphrophilus|Aerococcus viridans, Aggregatibacter segnis|Aerococcus viridans, Akkermansia muciniphila|Aerococcus viridans, Alistipes putredinis|Aerococcus viridans, Alistipes shahii|Aerococcus viridans, Anaerococcus hydrogenalis|Aerococcus viridans, Anaerococcus lactolyticus|Aerococcus viridans, Anaerococcus vaginalis|Aerococcus viridans, Anaerostipes caccae|Aerococcus viridans, Anaerotruncus colihominis|Aerococcus viridans, Atopobium parvulum|Aerococcus viridans, Atopobium rimae|Aerococcus viridans, Atopobium vaginae|Aerococcus viridans, Bacteroides caccae|Aerococcus viridans, Bacteroides cellulosilyticus|Aerococcus viridans, Bacteroides coprocola|Aerococcus viridans, Bacteroides coprophilus|Aerococcus viridans, Bacteroides dorei|Aerococcus viridans, Bacteroides eggerthii|Aerococcus viridans, Bacteroides finegoldii|Aerococcus viridans, Bacteroides fragilis|Aerococcus viridans, Bacteroides helcogenes|Aerococcus viridans, Bacteroides intestinalis|Aerococcus viridans, Bacteroides ovatus|Aerococcus viridans, Bacteroides pectinophilus|Aerococcus viridans, Bacteroides plebeius|Aerococcus viridans, Bacteroides salanitronis|Aerococcus viridans, Bacteroides sp. 1_1_6|Aerococcus viridans, Bacteroides sp. 3_1_23|Aerococcus viridans, Bacteroides stercoris|Aerococcus viridans, Bacteroides thetaiotaomicron|Aerococcus viridans, Bacteroides uniformis|Aerococcus viridans, Bacteroides vulgatus|Aerococcus viridans, Bacteroides xylanisolvens|Aerococcus viridans, Bifidobacterium adolescentis|Aerococcus viridans, Bifidobacterium angulatum|Aerococcus viridans, Bifidobacterium animalis|Aerococcus viridans, Bifidobacterium bifidum|Aerococcus viridans, Bifidobacterium breve|Aerococcus viridans, Bifidobacterium catenulatum|Aerococcus viridans, Bifidobacterium dentium|Aerococcus viridans, Bifidobacterium infantis|Aerococcus viridans, Bifidobacterium longum|Aerococcus viridans, Bifidobacterium pseudocatenulatum|Aerococcus viridans, Bilophila wadsworthia|Aerococcus viridans, Blautia hansenii|Aerococcus viridans, Blautia hydrogenotrophica|Aerococcus viridans, Blautia producta|Aerococcus viridans, Blautia schinkii|Aerococcus viridans, Brevibacterium linens|Aerococcus viridans, Brucella ceti|Aerococcus viridans, Brucella suis|Aerococcus viridans, Bulleidia extructa|Aerococcus viridans, Butyrivibrio crossotus|Aerococcus viridans, Campylobacter concisus|Aerococcus viridans, Campylobacter curvus|Aerococcus viridans, Campylobacter gracilis|Aerococcus viridans, Campylobacter hominis|Aerococcus viridans, Capnocytophaga ochracea|Aerococcus viridans, Cardiobacterium hominis|Aerococcus viridans, Catenibacterium mitsuokai|Aerococcus viridans, Catonella morbi|Aerococcus viridans, Citrobacter koseri|Aerococcus viridans, Clostridium asparagiforme|Aerococcus viridans, Clostridium bartlettii|Aerococcus viridans, Clostridium bolteae|Aerococcus viridans, Clostridium botulinum|Aerococcus viridans, Clostridium butyricum|Aerococcus viridans, Clostridium difficile|Aerococcus viridans, Clostridium disporicum|Aerococcus viridans, Clostridium hathewayi|Aerococcus viridans, Clostridium hylemonae|Aerococcus viridans, Clostridium innocuum|Aerococcus viridans, Clostridium leptum|Aerococcus viridans, Clostridium mayombei|Aerococcus viridans, Clostridium methylpentosum|Aerococcus viridans, Clostridium nexile|Aerococcus viridans, Clostridium orbiscindens|Aerococcus viridans, Clostridium perfringens|Aerococcus viridans, Clostridium saccharolyticum|Aerococcus viridans, Clostridium scindens|Aerococcus viridans, Clostridium symbiosum|Aerococcus viridans, Clostridium tertium|Aerococcus viridans, Collinsella aerofaciens|Aerococcus viridans, Collinsella intestinalis|Aerococcus viridans, Collinsella stercoris|Aerococcus viridans, Coprobacillus sp. D7|Aerococcus viridans, Coprococcus catus|Aerococcus viridans, Coprococcus comes|Aerococcus viridans, Coprococcus eutactus|Aerococcus viridans, Corynebacterium aurimucosum|Aerococcus viridans, Corynebacterium matruchotii|Aerococcus viridans, Cryptobacterium curtum|Aerococcus viridans, Desulfovibrio desulfuricans|Aerococcus viridans, Desulfovibrio piger|Aerococcus viridans, Dialister invisus|Aerococcus viridans, Dialister microaerophilus|Aerococcus viridans, Dorea formicigenerans|Aerococcus viridans, Dorea longicatena|Aerococcus viridans, Eggerthella lenta|Aerococcus viridans, Eikenella corrodens|Aerococcus viridans, Enterobacter cancerogenus|Aerococcus TABLE 2-continued

| Table 2. Specific binary combinations of OTUs. Individual pairings are differentiated by "\|" and OTUs within a combination are differentiated by "," |
|---|
| viridans, Enterobacter cloacae\|Aerococcus viridans, Enterococcus faecalis\|Aerococcus viridans, Enterococcus faecium\|Aerococcus viridans, Enterococcus gallinarum\|Aerococcus viridans, Erysipelotrichaceae bacterium 3_1_53\|Aerococcus viridans, Escherichia coli\|Aerococcus viridans, Escherichia fergusonii\|Aerococcus viridans, Ethanoligenens harbinense\|Aerococcus viridans, Eubacterium cellulosolvens\|Aerococcus viridans, Eubacterium eligens\|Aerococcus viridans, Eubacterium hallii\|Aerococcus viridans, Eubacterium limosum\|Aerococcus viridans, Eubacterium rectale\|Aerococcus viridans, Eubacterium siraeum\|Aerococcus viridans, Eubacterium ventriosum\|Aerococcus viridans, Faecalibacterium prausnitzii\|Aerococcus viridans, Finegoldia magna\|Aerococcus viridans, Fusobacterium gonidiaformans\|Aerococcus viridans, Fusobacterium mortiferum\|Aerococcus viridans, Fusobacterium nucleatum\|Aerococcus viridans, Fusobacterium varium\|Aerococcus viridans, Gardnerella vaginalis\|Aerococcus viridans, Gemella haemolysans\|Aerococcus viridans, Gemella morbillorum\|Aerococcus viridans, Gordonibacter pamelaeae\|Aerococcus viridans, Granulicatella adiacens\|Aerococcus viridans, Granulicatella elegans\|Aerococcus viridans, Haemophilus influenzae\|Aerococcus viridans, Haemophilus parainfluenzae\|Aerococcus viridans, Helicobacter pullorum\|Aerococcus viridans, Helicobacter pylori\|Aerococcus viridans, Holdemania filiformis\|Aerococcus viridans, Kingella oralis\|Aerococcus viridans, Klebsiella pneumoniae\|Aerococcus viridans, Klebsiella variicola\|Aerococcus viridans, Lachnospiraceae bacterium 5_1_57FAA\|Aerococcus viridans, Lactobacillus acidophilus\|Aerococcus viridans, Lactobacillus amylovorus\|Aerococcus viridans, Lactobacillus brevis\|Aerococcus viridans, Lactobacillus casei\|Aerococcus viridans, Lactobacillus crispatus\|Aerococcus viridans, Lactobacillus delbrueckii\|Aerococcus viridans, Lactobacillus fermentum\|Aerococcus viridans, Lactobacillus gasseri\|Aerococcus viridans, Lactobacillus iners\|Aerococcus viridans, Lactobacillus jensenii\|Aerococcus viridans, Lactobacillus johnsonii\|Aerococcus viridans, Lactobacillus paracasei\|Aerococcus viridans, Lactobacillus plantarum\|Aerococcus viridans, Lactobacillus reuteri\|Aerococcus viridans, Lactobacillus rhamnosus\|Aerococcus viridans, Lactobacillus ruminis\|Aerococcus viridans, Lactobacillus sakei\|Aerococcus viridans, Lactobacillus salivarius\|Aerococcus viridans, Lactococcus lactis\|Aerococcus viridans, Lautropia mirabilis\|Aerococcus viridans, Leuconostoc citreum\|Aerococcus viridans, Leuconostoc gasicomitatum\|Aerococcus viridans, Leuconostoc mesenteroides\|Aerococcus viridans, Listeria monocytogenes\|Aerococcus viridans, Marvinbryantia formatexigens\|Aerococcus viridans, Megamonas hypermegale\|Aerococcus viridans, Megasphaera micronuciformis\|Aerococcus viridans, Methanobrevibacter smithii\|Aerococcus viridans, Methanosphaera stadtmanae\|Aerococcus viridans, Methylobacterium radiotolerans\|Aerococcus viridans, Mitsuokella multacida\|Aerococcus viridans, Mobiluncus curtisii\|Aerococcus viridans, Mycoplasma hominis\|Aerococcus viridans, Neisseria mucosa\|Aerococcus viridans, Odoribacter splanchnicus\|Aerococcus viridans, Olsenella uli\|Aerococcus viridans, Oribacterium sinus\|Aerococcus viridans, Oxalobacter formigenes\|Aerococcus viridans, Parabacteroides distasonis\|Aerococcus viridans, Parabacteroides johnsonii\|Aerococcus viridans, Parabacteroides merdae\|Aerococcus viridans, Parvimonas micra\|Aerococcus viridans, Pediococcus acidilactici\|Aerococcus viridans, Pediococcus pentosaceus\|Aerococcus viridans, Peptoniphilus duerdenii\|Aerococcus viridans, Peptoniphilus harei\|Aerococcus viridans, Peptoniphilus lacrimalis\|Aerococcus viridans, Peptostreptococcus anaerobius\|Aerococcus viridans, Peptostreptococcus stomatis\|Aerococcus viridans, Porphyromonas asaccharolytica\|Aerococcus viridans, Porphyromonas uenonis\|Aerococcus viridans, Prevotella amnii\|Aerococcus viridans, Prevotella bergensis\|Aerococcus viridans, Prevotella bivia\|Aerococcus viridans, Prevotella buccae\|Aerococcus viridans, Prevotella buccalis\|Aerococcus viridans, Prevotella copri\|Aerococcus viridans, Prevotella disiens\|Aerococcus viridans, Prevotella melaninogenica\|Aerococcus viridans, Prevotella multiformis\|Aerococcus viridans, Prevotella oralis\|Aerococcus viridans, Prevotella oris\|Aerococcus viridans, Prevotella salivae\|Aerococcus viridans, Prevotella timonensis\|Aerococcus viridans, Propionibacterium acnes\|Aerococcus viridans, Propionibacterium freudenreichii\|Aerococcus viridans, Proteus mirabilis\|Aerococcus viridans, Proteus penneri\|Aerococcus viridans, Pseudoflavonifractor capillosus\|Aerococcus viridans, Pseudomonas aeruginosa\|Aerococcus viridans, Pseudomonas fluorescens\|Aerococcus viridans, Pseudomonas putida\|Aerococcus viridans, Pseudoramibacter alactolyticus\|Aerococcus viridans, Pyramidobacter piscolens\|Aerococcus viridans, Rhodopseudomonas palustris\|Aerococcus viridans, Roseburia intestinalis\|Aerococcus viridans, Roseburia inulinivorans\|Aerococcus viridans, Rothia dentocariosa\|Aerococcus viridans, Rothia mucilaginosa\|Aerococcus viridans, Ruminococcus albus\|Aerococcus viridans, Ruminococcus bromii\|Aerococcus viridans, Ruminococcus gnavus\|Aerococcus viridans, Ruminococcus lactaris\|Aerococcus viridans, Ruminococcus obeum\|Aerococcus viridans, Ruminococcus torques\|Aerococcus viridans, Selenomonas sputigena\|Aerococcus viridans, Shigella boydii\|Aerococcus viridans, Shigella dysenteriae\|Aerococcus viridans, Shigella sonnei\|Aerococcus viridans, Slackia exigua\|Aerococcus viridans, Solobacterium moorei\|Aerococcus viridans, Staphylococcus aureus\|Aerococcus viridans, Staphylococcus epidermidis\|Aerococcus viridans, Staphylococcus hominis\|Aerococcus viridans, Staphylococcus saprophyticus\|Aerococcus viridans, Staphylococcus warneri\|Aerococcus viridans, Streptococcus agalactiae\|Aerococcus viridans, Streptococcus anginosus\|Aerococcus viridans, Streptococcus australis\|Aerococcus viridans, Streptococcus bovis\|Aerococcus viridans, Streptococcus cristatus\|Aerococcus viridans, Streptococcus dysgalactiae\|Aerococcus viridans, Streptococcus equinus\|Aerococcus viridans, Streptococcus gordonii\|Aerococcus viridans, Streptococcus infantarius\|Aerococcus viridans, Streptococcus infantis\|Aerococcus viridans, Streptococcus mitis\|Aerococcus viridans, Streptococcus mutans\|Aerococcus viridans, Streptococcus oralis\|Aerococcus viridans, Streptococcus parasanguinis\|Aerococcus viridans, Streptococcus peroris\|Aerococcus viridans, Streptococcus pneumoniae\|Aerococcus viridans, Streptococcus salivarius\|Aerococcus viridans, Streptococcus sanguinis\|Aerococcus viridans, Streptococcus thermophilus\|Aerococcus viridans, Streptococcus vestibularis\|Aerococcus viridans, Subdoligranulum variabile\|Aerococcus viridans, Succinatimonas hippei\|Aerococcus viridans, Sutterella wadsworthensis\|Aerococcus viridans, Tropheryma whipplei\|Aerococcus viridans, Veillonella atypica\|Aerococcus viridans, Veillonella dispar\|Aerococcus viridans, Veillonella parvula\|Aerococcus viridans, Victivallis vadensis\|Aggregatibacter aphrophilus, Aggregatibacter aphrophilus\|Aggregatibacter aphrophilus, Aggregatibacter segnis\|Aggregatibacter aphrophilus, Akkermansia muciniphila\|Aggregatibacter aphrophilus, Alistipes putredinis\|Aggregatibacter aphrophilus, Alistipes shahii\|Aggregatibacter aphrophilus, Anaerococcus hydrogenalis\|Aggregatibacter aphrophilus, Anaerococcus lactolyticus\|Aggregatibacter aphrophilus, Anaerococcus vaginalis\|Aggregatibacter aphrophilus, Anaerostipes caccae\|Aggregatibacter aphrophilus, Anaerotruncus colihominis\|Aggregatibacter aphrophilus, Atopobium parvulum\|Aggregatibacter aphrophilus, Atopobium rimae\|Aggregatibacter aphrophilus, Atopobium vaginae\|Aggregatibacter aphrophilus, Bacteroides caccae\|Aggregatibacter aphrophilus, Bacteroides cellulosilyticus\|Aggregatibacter aphrophilus, Bacteroides coprocola\|Aggregatibacter aphrophilus, Bacteroides coprophilus\|Aggregatibacter aphrophilus, Bacteroides dorei\|Aggregatibacter aphrophilus, Bacteroides eggerthii\|Aggregatibacter aphrophilus, Bacteroides finegoldii\|Aggregatibacter aphrophilus, Bacteroides fragilis\|Aggregatibacter aphrophilus, Bacteroides helcogenes\|Aggregatibacter aphrophilus, Bacteroides intestinalis\|Aggregatibacter aphrophilus, Bacteroides ovatus\|Aggregatibacter aphrophilus, Bacteroides pectinophilus\|Aggregatibacter aphrophilus, Bacteroides plebeius\|Aggregatibacter aphrophilus, Bacteroides salanitronis\|Aggregatibacter aphrophilus, Bacteroides sp. 1_1_6\|Aggregatibacter aphrophilus, Bacteroides sp. 3_1_23\|Aggregatibacter aphrophilus, Bacteroides stercoris\|Aggregatibacter aphrophilus, Bacteroides thetaiotaomicron\|Aggregatibacter aphrophilus, Bacteroides uniformis\|Aggregatibacter aphrophilus, Bacteroides vulgatus\|Aggregatibacter aphrophilus, Bacteroides xylanisolvens\|Aggregatibacter aphrophilus, Bifidobacterium adolescentis\|Aggregatibacter aphrophilus, Bifidobacterium angulatum\|Aggregatibacter aphrophilus, Bifidobacterium animalis\|Aggregatibacter aphrophilus, Bifidobacterium bifidum\|Aggregatibacter aphrophilus, Bifidobacterium breve\|Aggregatibacter aphrophilus, Bifidobacterium catenulatum\|Aggregatibacter aphrophilus, Bifidobacterium dentium\|Aggregatibacter aphrophilus, Bifidobacterium infantis\|Aggregatibacter aphrophilus, Bifidobacterium longum\|Aggregatibacter aphrophilus, Bifidobacterium pseudocatenulatum\|Aggregatibacter aphrophilus, Bilophila wadsworthia\|Aggregatibacter aphrophilus, Blautia hansenii\|Aggregatibacter aphrophilus, Blautia hydrogenotrophica\|Aggregatibacter aphrophilus, Blautia producta\|Aggregatibacter aphrophilus, Blautia schinkii\|Aggregatibacter aphrophilus, Brevibacterium linens\|Aggregatibacter aphrophilus, Brucella ceti\|Aggregatibacter aphrophilus, Brucella suis\|Aggregatibacter aphrophilus, Bulleidia extructa\|Aggregatibacter aphrophilus, Butyrivibrio crossotus\|Aggregatibacter aphrophilus, Campylobacter concisus\|Aggregatibacter aphrophilus, Campylobacter curvus\|Aggregatibacter aphrophilus, Campylobacter gracilis\|Aggregatibacter |

TABLE 2-continued

| Table 2. Specific binary combinations of OTUs. Individual pairings are differentiated by "\|" and OTUs within a combination are differentiated by "," |
|---|
| *aphrophilus, Campylobacter hominis\|Aggregatibacter aphrophilus, Capnocytophaga ochracea\|Aggregatibacter aphrophilus, Cardiobacterium hominis\|Aggregatibacter aphrophilus, Catenibacterium mitsuokai\|Aggregatibacter aphrophilus, Catonella morbi\|Aggregatibacter aphrophilus, Citrobacter koseri\|Aggregatibacter aphrophilus, Clostridium asparagiforme\|Aggregatibacter aphrophilus, Clostridium bartlettii\|Aggregatibacter aphrophilus, Clostridium bolteae\|Aggregatibacter aphrophilus, Clostridium botulinum\|Aggregatibacter aphrophilus, Clostridium butyricum\|Aggregatibacter aphrophilus, Clostridium difficile\|Aggregatibacter aphrophilus, Clostridium disporicum\|Aggregatibacter aphrophilus, Clostridium hathewayi\|Aggregatibacter aphrophilus, Clostridium hylemonae\|Aggregatibacter aphrophilus, Clostridium innocuum\|Aggregatibacter aphrophilus, Clostridium leptum\|Aggregatibacter aphrophilus, Clostridium mayombei\|Aggregatibacter aphrophilus, Clostridium methylpentosum\|Aggregatibacter aphrophilus, Clostridium nexile\|Aggregatibacter aphrophilus, Clostridium orbiscindens\|Aggregatibacter aphrophilus, Clostridium perfringens\|Aggregatibacter aphrophilus, Clostridium saccharolyticum\|Aggregatibacter aphrophilus, Clostridium scindens\|Aggregatibacter aphrophilus, Clostridium symbiosum\|Aggregatibacter aphrophilus, Clostridium tertium\|Aggregatibacter aphrophilus, Collinsella aerofaciens\|Aggregatibacter aphrophilus, Collinsella intestinalis\|Aggregatibacter aphrophilus, Collinsella stercoris\|Aggregatibacter aphrophilus, Coprobacillus* sp. D7\|*Aggregatibacter aphrophilus, Coprococcus catus\|Aggregatibacter aphrophilus, Coprococcus comes\|Aggregatibacter aphrophilus, Coprococcus eutactus\|Aggregatibacter aphrophilus, Corynebacterium aurimucosum\|Aggregatibacter aphrophilus, Corynebacterium matruchotii\|Aggregatibacter aphrophilus, Cryptobacterium curtum\|Aggregatibacter aphrophilus, Desulfovibrio desulfuricans\|Aggregatibacter aphrophilus, Desulfovibrio piger\|Aggregatibacter aphrophilus, Dialister invisus\|Aggregatibacter aphrophilus, Dialister microaerophilus\|Aggregatibacter aphrophilus, Dorea formicigenerans\|Aggregatibacter aphrophilus, Dorea longicatena\|Aggregatibacter aphrophilus, Eggerthella lenta\|Aggregatibacter aphrophilus, Eikenella corrodens\|Aggregatibacter aphrophilus, Enterobacter cancerogenus\|Aggregatibacter aphrophilus, Enterobacter cloacae\|Aggregatibacter aphrophilus, Enterococcus faecalis\|Aggregatibacter aphrophilus, Enterococcus faecium\|Aggregatibacter aphrophilus, Enterococcus gallinarum\|Aggregatibacter aphrophilus, Erysipelotrichaceae bacterium* 3_1_53\|*Aggregatibacter aphrophilus, Escherichia coli\|Aggregatibacter aphrophilus, Escherichia fergusonii\|Aggregatibacter aphrophilus, Ethanoligenens harbinense\|Aggregatibacter aphrophilus, Eubacterium cellulosolvens\|Aggregatibacter aphrophilus, Eubacterium eligens\|Aggregatibacter aphrophilus, Eubacterium hallii\|Aggregatibacter aphrophilus, Eubacterium limosum\|Aggregatibacter aphrophilus, Eubacterium rectale\|Aggregatibacter aphrophilus, Eubacterium siraeum\|Aggregatibacter aphrophilus, Eubacterium ventriosum\|Aggregatibacter aphrophilus, Faecalibacterium prausnitzii\|Aggregatibacter aphrophilus, Finegoldia magna\|Aggregatibacter aphrophilus, Fusobacterium gonidiaformans\|Aggregatibacter aphrophilus, Fusobacterium mortiferum\|Aggregatibacter aphrophilus, Fusobacterium nucleatum\|Aggregatibacter aphrophilus, Fusobacterium varium\|Aggregatibacter aphrophilus, Gardnerella vaginalis\|Aggregatibacter aphrophilus, Gemella haemolysans\|Aggregatibacter aphrophilus, Gemella morbillorum\|Aggregatibacter aphrophilus, Gordonibacter pamelaeae\|Aggregatibacter aphrophilus, Granulicatella adiacens\|Aggregatibacter aphrophilus, Granulicatella elegans\|Aggregatibacter aphrophilus, Haemophilus influenzae\|Aggregatibacter aphrophilus, Haemophilus parainfluenzae\|Aggregatibacter aphrophilus, Helicobacter pullorum\|Aggregatibacter aphrophilus, Helicobacter pylori\|Aggregatibacter aphrophilus, Holdemania filiformis\|Aggregatibacter aphrophilus, Kingella oralis\|Aggregatibacter aphrophilus, Klebsiella pneumoniae\|Aggregatibacter aphrophilus, Klebsiella variicola\|Aggregatibacter aphrophilus, Lachnospiraceae bacterium* 5_1_57FAA\|*Aggregatibacter aphrophilus, Lactobacillus acidophilus\|Aggregatibacter aphrophilus, Lactobacillus amylovorus\|Aggregatibacter aphrophilus, Lactobacillus brevis\|Aggregatibacter aphrophilus, Lactobacillus casei\|Aggregatibacter aphrophilus, Lactobacillus crispatus\|Aggregatibacter aphrophilus, Lactobacillus delbrueckii\|Aggregatibacter aphrophilus, Lactobacillus fermentum\|Aggregatibacter aphrophilus, Lactobacillus gasseri\|Aggregatibacter aphrophilus, Lactobacillus iners\|Aggregatibacter aphrophilus, Lactobacillus jensenii\|Aggregatibacter aphrophilus, Lactobacillus johnsonii\|Aggregatibacter aphrophilus, Lactobacillus paracasei\|Aggregatibacter aphrophilus, Lactobacillus plantarum\|Aggregatibacter aphrophilus, Lactobacillus reuteri\|Aggregatibacter aphrophilus, Lactobacillus rhamnosus\|Aggregatibacter aphrophilus, Lactobacillus ruminis\|Aggregatibacter aphrophilus, Lactobacillus sakei\|Aggregatibacter aphrophilus, Lactobacillus salivarius\|Aggregatibacter aphrophilus, Lactococcus lactis\|Aggregatibacter aphrophilus, Lautropia mirabilis\|Aggregatibacter aphrophilus, Leuconostoc citreum\|Aggregatibacter aphrophilus, Leuconostoc gas icomitatum\|Aggregatibacter aphrophilus, Leuconostoc mesenteroides\|Aggregatibacter aphrophilus, Listeria monocytogenes\|Aggregatibacter aphrophilus, Marvinbryantia formatexigens\|Aggregatibacter aphrophilus, Megamonas hypermegale\|Aggregatibacter aphrophilus, Megasphaera micronuciformis\|Aggregatibacter aphrophilus, Methanobrevibacter smithii\|Aggregatibacter aphrophilus, Methanosphaera stadtmanae\|Aggregatibacter aphrophilus, Methylobacterium radiotolerans\|Aggregatibacter aphrophilus, Mitsuokella multacida\|Aggregatibacter aphrophilus, Mobiluncus curtisii\|Aggregatibacter aphrophilus, Mycoplasma hominis\|Aggregatibacter aphrophilus, Neisseria mucosa\|Aggregatibacter aphrophilus, Odoribacter splanchnicus\|Aggregatibacter aphrophilus, Olsenella uli\|Aggregatibacter aphrophilus, Oribacterium sinus\|Aggregatibacter aphrophilus, Oxalobacter formigenes\|Aggregatibacter aphrophilus, Parabacteroides distasonis\|Aggregatibacter aphrophilus, Parabacteroides johnsonii\|Aggregatibacter aphrophilus, Parabacteroides merdae\|Aggregatibacter aphrophilus, Parvimonas micra\|Aggregatibacter aphrophilus, Pediococcus acidilactici\|Aggregatibacter aphrophilus, Pediococcus pentosaceus\|Aggregatibacter aphrophilus, Peptoniphilus duerdenii\|Aggregatibacter aphrophilus, Peptoniphilus harei\|Aggregatibacter aphrophilus, Peptoniphilus lacrimalis\|Aggregatibacter aphrophilus, Peptostreptococcus anaerobius\|Aggregatibacter aphrophilus, Peptostreptococcus stomatis\|Aggregatibacter aphrophilus, Porphyromonas asaccharolytica\|Aggregatibacter aphrophilus, Porphyromonas uenonis\|Aggregatibacter aphrophilus, Prevotella amnii\|Aggregatibacter aphrophilus, Prevotella bergensis\|Aggregatibacter aphrophilus, Prevotella bivia\|Aggregatibacter aphrophilus, Prevotella buccae\|Aggregatibacter aphrophilus, Prevotella buccalis\|Aggregatibacter aphrophilus, Prevotella copri\|Aggregatibacter aphrophilus, Prevotella disiens\|Aggregatibacter aphrophilus, Prevotella melaninogenica\|Aggregatibacter aphrophilus, Prevotella multiformis\|Aggregatibacter aphrophilus, Prevotella oralis\|Aggregatibacter aphrophilus, Prevotella oris\|Aggregatibacter aphrophilus, Prevotella salivae\|Aggregatibacter aphrophilus, Prevotella timonensis\|Aggregatibacter aphrophilus, Propionibacterium acnes\|Aggregatibacter aphrophilus, Propionibacterium freudenreichii\|Aggregatibacter aphrophilus, Proteus mirabilis\|Aggregatibacter aphrophilus, Proteus penneri\|Aggregatibacter aphrophilus, Pseudoflavonifractor capillosus\|Aggregatibacter aphrophilus, Pseudomonas aeruginosa\|Aggregatibacter aphrophilus, Pseudomonas fluorescens\|Aggregatibacter aphrophilus, Pseudomonas putida\|Aggregatibacter aphrophilus, Pseudoramibacter alactolyticus\|Aggregatibacter aphrophilus, Pyramidobacter piscolens\|Aggregatibacter aphrophilus, Rhodopseudomonas palustris\|Aggregatibacter aphrophilus, Roseburia intestinalis\|Aggregatibacter aphrophilus, Roseburia inulinivorans\|Aggregatibacter aphrophilus, Rothia dentocariosa\|Aggregatibacter aphrophilus, Rothia mucilaginosa\|Aggregatibacter aphrophilus, Ruminococcus albus\|Aggregatibacter aphrophilus, Ruminococcus bromii\|Aggregatibacter aphrophilus, Ruminococcus gnavus\|Aggregatibacter aphrophilus, Ruminococcus lactaris\|Aggregatibacter aphrophilus, Ruminococcus obeum\|Aggregatibacter aphrophilus, Ruminococcus torques\|Aggregatibacter aphrophilus, Selenomonas sputigena\|Aggregatibacter aphrophilus, Shigella boydii\|Aggregatibacter aphrophilus, Shigella dysenteriae\|Aggregatibacter aphrophilus, Shigella sonnei\|Aggregatibacter aphrophilus, Slackia exigua\|Aggregatibacter aphrophilus, Solobacterium moorei\|Aggregatibacter aphrophilus, Staphylococcus aureus\|Aggregatibacter aphrophilus, Staphylococcus epidermidis\|Aggregatibacter aphrophilus, Staphylococcus hominis\|Aggregatibacter aphrophilus, Staphylococcus saprophyticus\|Aggregatibacter aphrophilus, Staphylococcus warneri\|Aggregatibacter aphrophilus, Streptococcus agalactiae\|Aggregatibacter aphrophilus, Streptococcus anginosus\|Aggregatibacter aphrophilus, Streptococcus australis\|Aggregatibacter aphrophilus, Streptococcus bovis\|Aggregatibacter aphrophilus, Streptococcus cristatus\|Aggregatibacter aphrophilus, Streptococcus dysgalactiae\|Aggregatibacter aphrophilus, Streptococcus equinus\|Aggregatibacter aphrophilus, Streptococcus gordonii\|Aggregatibacter aphrophilus, Streptococcus infantarius\|Aggregatibacter aphrophilus, Streptococcus infantis\|Aggregatibacter aphrophilus, Streptococcus mitis\|Aggregatibacter aphrophilus, Streptococcus mutans\|Aggregatibacter aphrophilus, Streptococcus oralis\|Aggregatibacter aphrophilus, Streptococcus parasanguinis\|Aggregatibacter* |

TABLE 2-continued

| Table 2. Specific binary combinations of OTUs. Individual pairings are differentiated by "\|" and OTUs within a combination are differentiated by "," |
|---|
| aphrophilus, Streptococcus peroris\|Aggregatibacter aphrophilus, Streptococcus pneumoniae\|Aggregatibacter aphrophilus, Streptococcus salivarius\|Aggregatibacter aphrophilus, Streptococcus sanguinis\|Aggregatibacter aphrophilus, Streptococcus thermophilus\|Aggregatibacter aphrophilus, Streptococcus vestibularis\|Aggregatibacter aphrophilus, Subdoligranulum variabile\|Aggregatibacter aphrophilus, Succinatimonas hippei\|Aggregatibacter aphrophilus, Sutterella wadsworthensis\|Aggregatibacter aphrophilus, Tropheryma whipplei\|Aggregatibacter aphrophilus, Veillonella atypica\|Aggregatibacter aphrophilus, Veillonella dispar\|Aggregatibacter aphrophilus, Veillonella parvula\|Aggregatibacter aphrophilus, Victivallis vadensis\|Aggregatibacter segnis, Aggregatibacter segnis\|Aggregatibacter segnis, Akkermansia muciniphila\|Aggregatibacter segnis, Alistipes putredinis\|Aggregatibacter segnis, Alistipes shahii\|Aggregatibacter segnis, Anaerococcus hydrogenalis\|Aggregatibacter segnis, Anaerococcus lactolyticus\|Aggregatibacter segnis, Anaerococcus vaginalis\|Aggregatibacter segnis, Anaerostipes caccae\|Aggregatibacter segnis, Anaerotruncus colihominis\|Aggregatibacter segnis, Atopobium parvulum\|Aggregatibacter segnis, Atopobium rimae\|Aggregatibacter segnis, Atopobium vaginae\|Aggregatibacter segnis, Bacteroides caccae\|Aggregatibacter segnis, Bacteroides cellulosilyticus\|Aggregatibacter segnis, Bacteroides coprocola\|Aggregatibacter segnis, Bacteroides coprophilus\|Aggregatibacter segnis, Bacteroides dorei\|Aggregatibacter segnis, Bacteroides eggerthii\|Aggregatibacter segnis, Bacteroides finegoldii\|Aggregatibacter segnis, Bacteroides fragilis\|Aggregatibacter segnis, Bacteroides helcogenes\|Aggregatibacter segnis, Bacteroides intestinalis\|Aggregatibacter segnis, Bacteroides ovatus\|Aggregatibacter segnis, Bacteroides pectinophilus\|Aggregatibacter segnis, Bacteroides plebeius\|Aggregatibacter segnis, Bacteroides salanitronis\|Aggregatibacter segnis, Bacteroides sp. 1_1_6\|Aggregatibacter segnis, Bacteroides sp. 3_1_23\|Aggregatibacter segnis, Bacteroides stercoris\|Aggregatibacter segnis, Bacteroides thetaiotaomicron\|Aggregatibacter segnis, Bacteroides uniformis\|Aggregatibacter segnis, Bacteroides vulgatus\|Aggregatibacter segnis, Bacteroides xylanisolvens\|Aggregatibacter segnis, Bifidobacterium adolescentis\|Aggregatibacter segnis, Bifidobacterium angulatum\|Aggregatibacter segnis, Bifidobacterium animalis\|Aggregatibacter segnis, Bifidobacterium bifidum\|Aggregatibacter segnis, Bifidobacteriumbreve\|Aggregatibacter segnis, Bifidobacterium catenulatum\|Aggregatibacter segnis, Bifidobacterium dentium\|Aggregatibacter segnis, Bifidobacterium infantis\|Aggregatibacter segnis, Bifidobacterium longum\|Aggregatibacter segnis, Bifidobacterium pseudocatenulatum\|Aggregatibacter segnis, Bilophila wadsworthia\|Aggregatibacter segnis, Blautia hansenii\|Aggregatibacter segnis, Blautia hydrogenotrophica\|Aggregatibacter segnis, Blautia producta\|Aggregatibacter segnis, Blautia schinkii\|Aggregatibacter segnis, Brevibacterium linens\|Aggregatibacter segnis, Brucella ceti\|Aggregatibacter segnis, Brucella suis\|Aggregatibacter segnis, Bulleidia extructa\|Aggregatibacter segnis, Butyrivibrio crossotus\|Aggregatibacter segnis, Campylobacter concisus\|Aggregatibacter segnis, Campylobacter curvus\|Aggregatibacter segnis, Campylobacter gracilis\|Aggregatibacter segnis, Campylobacter hominis\|Aggregatibacter segnis, Capnocytophaga ochracea\|Aggregatibacter segnis, Cardiobacterium hominis\|Aggregatibacter segnis, Catenibacterium mitsuokai\|Aggregatibacter segnis, Catonella morbi\|Aggregatibacter segnis, Citrobacter koseri\|Aggregatibacter segnis, Clostridium asparagiforme\|Aggregatibacter segnis, Clostridium bartlettii\|Aggregatibacter segnis, Clostridium bolteae\|Aggregatibacter segnis, Clostridium botulinum\|Aggregatibacter segnis, Clostridium butyricum\|Aggregatibacter segnis, Clostridium difficile\|Aggregatibacter segnis, Clostridium disporicum\|Aggregatibacter segnis, Clostridium hathewayi\|Aggregatibacter segnis, Clostridium hylemonae\|Aggregatibacter segnis, Clostridium innocuum\|Aggregatibacter segnis, Clostridium leptum\|Aggregatibacter segnis, Clostridium mayombei\|Aggregatibacter segnis, Clostridium methylpentosum\|Aggregatibacter segnis, Clostridium nexile\|Aggregatibacter segnis, Clostridium orbiscindens\|Aggregatibacter segnis, Clostridium perfringens\|Aggregatibacter segnis, Clostridium saccharolyticum\|Aggregatibacter segnis, Clostridium scindens\|Aggregatibacter segnis, Clostridium symbiosum\|Aggregatibacter segnis, Clostridium tertium\|Aggregatibacter segnis, Collinsella aerofaciens\|Aggregatibacter segnis, Collinsella intestinalis\|Aggregatibacter segnis, Collinsella stercoris\|Aggregatibacter segnis, Coprobacillus sp. D7\|Aggregatibacter segnis, Coprococcus catus\|Aggregatibacter segnis, Coprococcus comes\|Aggregatibacter segnis, Coprococcus eutactus\|Aggregatibacter segnis, Corynebacterium aurimucosum\|Aggregatibacter segnis, Corynebacterium matruchotii\|Aggregatibacter segnis, Cryptobacterium curtum\|Aggregatibacter segnis, Desulfovibrio desulfuricans\|Aggregatibacter segnis, Desulfovibrio piger\|Aggregatibacter segnis, Dialister invisus\|Aggregatibacter segnis, Dialister microaerophilus\|Aggregatibacter segnis, Dorea formicigenerans\|Aggregatibacter segnis, Dorea longicatena\|Aggregatibacter segnis, Eggerthella lenta\|Aggregatibacter segnis, Eikenella corrodens\|Aggregatibacter segnis, Enterobacter cancerogenus\|Aggregatibacter segnis, Enterobacter cloacae\|Aggregatibacter segnis, Enterococcus faecalis\|Aggregatibacter segnis, Enterococcus faecium\|Aggregatibacter segnis, Enterococcus gallinarum\|Aggregatibacter segnis, Erysipelotrichaceae bacterium 3_1_53\|Aggregatibacter segnis, Escherichia coli\|Aggregatibacter segnis, Escherichia fergusonii\|Aggregatibacter segnis, Ethanoligenens harbinense\|Aggregatibacter segnis, Eubacterium cellulosolvens\|Aggregatibacter segnis, Eubacterium eligens\|Aggregatibacter segnis, Eubacterium hallii\|Aggregatibacter segnis, Eubacterium limosum\|Aggregatibacter segnis, Eubacteriumrectale\|Aggregatibacter segnis, Eubacterium siraeum\|Aggregatibacter segnis, Eubacterium ventriosum\|Aggregatibacter segnis, Faecalibacterium prausnitzii\|Aggregatibacter segnis, Finegoldia magna\|Aggregatibacter segnis, Fusobacterium gonidiaformans\|Aggregatibacter segnis, Fusobacterium mortiferum\|Aggregatibacter segnis, Fusobacterium nucleatum\|Aggregatibacter segnis, Fusobacterium varium\|Aggregatibacter segnis, Gardnerella vaginalis\|Aggregatibacter segnis, Gemella haemolysans\|Aggregatibacter segnis, Gemella morbillorum\|Aggregatibacter segnis, Gordonibacter pamelaeae\|Aggregatibacter segnis, Granulicatella adiacens\|Aggregatibacter segnis, Granulicatella elegans\|Aggregatibacter segnis, Haemophilus influenzae\|Aggregatibacter segnis, Haemophilus parainfluenzae\|Aggregatibacter segnis, Helicobacter pullorum\|Aggregatibacter segnis, Helicobacter pylori\|Aggregatibacter segnis, Holdemania filiformis\|Aggregatibacter segnis, Kingella oralis\|Aggregatibacter segnis, Klebsiella pneumoniae\|Aggregatibacter segnis, Klebsiella variicola\|Aggregatibacter segnis, Lachnospiraceae bacterium 5_1_57FAA\|Aggregatibacter segnis, Lactobacillus acidophilus\|Aggregatibacter segnis, Lactobacillus amylovorus\|Aggregatibacter segnis, Lactobacillus brevis\|Aggregatibacter segnis, Lactobacillus casei\|Aggregatibacter segnis, Lactobacillus crispatus\|Aggregatibacter segnis, Lactobacillus delbrueckii\|Aggregatibacter segnis, Lactobacillus fermentum\|Aggregatibacter segnis, Lactobacillus gasseri\|Aggregatibacter segnis, Lactobacillus iners\|Aggregatibacter segnis, Lactobacillus jensenii\|Aggregatibacter segnis, Lactobacillus johnsonii\|Aggregatibacter segnis, Lactobacillus paracasei\|Aggregatibacter segnis, Lactobacillus plantarum\|Aggregatibacter segnis, Lactobacillus reuteri\|Aggregatibacter segnis, Lactobacillus rhamnosus\|Aggregatibacter segnis, Lactobacillus mminis\|Aggregatibacter segnis, Lactobacillus sakei\|Aggregatibacter segnis, Lactobacillus salivarius\|Aggregatibacter segnis, Lactococcus lactis\|Aggregatibacter segnis, Lautropia mirabilis\|Aggregatibacter segnis, Leuconostoc citreum\|Aggregatibacter segnis, Leuconostoc gasicomitatum\|Aggregatibacter segnis, Leuconostoc mesenteroides\|Aggregatibacter segnis, Listeria monocytogenes\|Aggregatibacter segnis, Marvinbryantia formatexigens\|Aggregatibacter segnis, Megamonas hypermegale\|Aggregatibacter segnis, Megasphaera micronuciformis\|Aggregatibacter segnis, Methanobrevibacter smithii\|Aggregatibacter segnis, Methanosphaera stadtmanae\|Aggregatibacter segnis, Methylobacterium radiotolerans\|Aggregatibacter segnis, Mitsuokella multacida\|Aggregatibacter segnis, Mobiluncus curtisii\|Aggregatibacter segnis, Mycoplasma hominis\|Aggregatibacter segnis, Neisseria mucosa\|Aggregatibacter segnis, Odoribacter splanchnicus\|Aggregatibacter segnis, Olsenella uli\|Aggregatibacter segnis, Oribacterium sinus\|Aggregatibacter segnis, Oxalobacter formigenes\|Aggregatibacter segnis, Parabacteroides distasonis\|Aggregatibacter segnis, Parabacteroides johnsonii\|Aggregatibacter segnis, Parabacteroides merdae\|Aggregatibacter segnis, Parvimonas micra\|Aggregatibacter segnis, Pediococcus acidilactici\|Aggregatibacter segnis, Pediococcus pentosaceus\|Aggregatibacter segnis, Peptoniphilus duerdenii\|Aggregatibacter segnis, Peptoniphilus harei\|Aggregatibacter segnis, Peptoniphilus lacrimalis\|Aggregatibacter segnis, Peptostreptococcus anaerobius\|Aggregatibacter segnis, Peptostreptococcus stomatis\|Aggregatibacter segnis, Porphyromonas asaccharolytica\|Aggregatibacter segnis, Porphyromonas uenonis\|Aggregatibacter segnis, Prevotella amnii\|Aggregatibacter segnis, Prevotella bergensis\|Aggregatibacter segnis, Prevotella bivia\|Aggregatibacter segnis, Prevotella buccae\|Aggregatibacter segnis, Prevotella buccalis\|Aggregatibacter segnis, Prevotella copri\|Aggregatibacter segnis, Prevotella disiens\|Aggregatibacter segnis, Prevotella melaninogenica\|Aggregatibacter segnis, Prevotella multiformis\|Aggregatibacter segnis, Prevotella oralis\|Aggregatibacter segnis, Prevotella oris\|Aggregatibacter segnis, Prevotella salivae\|Aggregatibacter segnis, Prevotella |

TABLE 2-continued

Table 2. Specific binary combinations of OTUs. Individual pairings are differentiated by "|" and OTUs within a combination are differentiated by ","

timonensis|Aggregatibacter segnis, Propionibacterium acnes|Aggregatibacter segnis, Propionibacterium freudenreichii|Aggregatibacter segnis, Proteus mirabilis|Aggregatibacter segnis, Proteus penneri|Aggregatibacter segnis, Pseudoflavonifractor capillosus|Aggregatibacter segnis, Pseudomonas aeruginosa|Aggregatibacter segnis, Pseudomonas fluorescens|Aggregatibacter segnis, Pseudomonas putida|Aggregatibacter segnis, Pseudoramibacter alactolyticus|Aggregatibacter segnis, Pyramidobacter piscolens|Aggregatibacter segnis, Rhodopseudomonas palustris|Aggregatibacter segnis, Roseburia intestinalis|Aggregatibacter segnis, Roseburia inulinivorans|Aggregatibacter segnis, Rothia dentocariosa|Aggregatibacter segnis, Rothia mucilaginosa|Aggregatibacter segnis, Ruminococcus albus|Aggregatibacter segnis, Ruminococcus bromii|Aggregatibacter segnis, Ruminococcus gnavus|Aggregatibacter segnis, Ruminococcus lactaris|Aggregatibacter segnis, Ruminococcus obeum|Aggregatibacter segnis, Ruminococcus torques|Aggregatibacter segnis, Selenomonas sputigena|Aggregatibacter segnis, Shigella boydii|Aggregatibacter segnis, Shigella dysenteriae|Aggregatibacter segnis, Shigella sonnei|Aggregatibacter segnis, Slackia exigua|Aggregatibacter segnis, Solobacterium moorei|Aggregatibacter segnis, Staphylococcus aureus|Aggregatibacter segnis, Staphylococcus epidermidis|Aggregatibacter segnis, Staphylococcus hominis|Aggregatibacter segnis, Staphylococcus saprophyticus|Aggregatibacter segnis, Staphylococcus warneri|Aggregatibacter segnis, Streptococcus agalactiae|Aggregatibacter segnis, Streptococcus anginosus|Aggregatibacter segnis, Streptococcus australis|Aggregatibacter segnis, Streptococcus bovis|Aggregatibacter segnis, Streptococcus cristatus|Aggregatibacter segnis, Streptococcus dysgalactiae|Aggregatibacter segnis, Streptococcus equinus|Aggregatibacter segnis, Streptococcus gordonii|Aggregatibacter segnis, Streptococcus infantarius|Aggregatibacter segnis, Streptococcus infantis|Aggregatibacter segnis, Streptococcus mitis|Aggregatibacter segnis, Streptococcus mutans|Aggregatibacter segnis, Streptococcus oralis|Aggregatibacter segnis, Streptococcus parasanguinis|Aggregatibacter segnis, Streptococcus peroris|Aggregatibacter segnis, Streptococcus pneumoniae|Aggregatibacter segnis, Streptococcus salivarius|Aggregatibacter segnis, Streptococcus sanguinis|Aggregatibacter segnis, Streptococcus thermophilus|Aggregatibacter segnis, Streptococcus vestibularis|Aggregatibacter segnis, Subdoligranulum variabile|Aggregatibacter segnis, Succinatimonas hippei|Aggregatibacter segnis, Sutterella wadsworthensis|Aggregatibacter segnis, Tropheryma whipplei|Aggregatibacter segnis, Veillonella atypica|Aggregatibacter segnis, Veillonella dispar|Aggregatibacter segnis, Veillonella parvula|Aggregatibacter segnis, Victivallis vadensis|Akkermansia muciniphila, Akkermansia muciniphila|Akkermansia muciniphila, Alistipes putredinis|Akkermansia muciniphila, Alistipes shahii|Akkermansia muciniphila, Anaerococcus hydrogenalis|Akkermansia muciniphila, Anaerococcus lactolyticus|Akkermansia muciniphila, Anaerococcus vaginalis|Akkermansia muciniphila, Anaerostipes caccae|Akkermansia muciniphila, Anaerotruncus colihominis|Akkermansia muciniphila, Atopobium parvulum|Akkermansia muciniphila, Atopobium rimae|Akkermansia muciniphila, Atopobium vaginae|Akkermansia muciniphila, Bacteroides caccae|Akkermansia muciniphila, Bacteroides cellulosilyticus|Akkermansia muciniphila, Bacteroides coprocola|Akkermansia muciniphila, Bacteroides coprophilus|Akkermansia muciniphila, Bacteroides dorei|Akkermansia muciniphila, Bacteroides eggerthii|Akkermansia muciniphila, Bacteroides finegoldii|Akkermansia muciniphila, Bacteroides fragilis|Akkermansia muciniphila, Bacteroides helcogenes|Akkermansia muciniphila, Bacteroides intestinalis|Akkermansia muciniphila, Bacteroides ovatus|Akkermansia muciniphila, Bacteroides pectinophilus|Akkermansia muciniphila, Bacteroides plebeius|Akkermansia muciniphila, Bacteroides salanitronis|Akkermansia muciniphila, Bacteroides sp. 1_1_6|Akkermansia muciniphila, Bacteroides sp. 3_1_23|Akkermansia muciniphila, Bacteroides stercoris|Akkermansia muciniphila, Bacteroides thetaiotaomicron|Akkermansia muciniphila, Bacteroides uniformis|Akkermansia muciniphila, Bacteroides vulgatus|Akkermansia muciniphila, Bacteroides xylanisolvens|Akkermansia muciniphila, Bifidobacterium adolescentis|Akkermansia muciniphila, Bifidobacterium angulatum|Akkermansia muciniphila, Bifidobacterium animalis|Akkermansia muciniphila, Bifidobacteriumbifidum|Akkermansia muciniphila, Bifidobacterium breve|Akkermansia muciniphila, Bifidobacterium catenulatum|Akkermansia muciniphila, Bifidobacterium dentium|Akkermansia muciniphila, Bifidobacterium infantis|Akkermansia muciniphila, Bifidobacterium longum|Akkermansia muciniphila, Bifidobacterium pseudocatenulatum|Akkermansia muciniphila, Bilophila wadsworthia|Aldcermansia muciniphila, Blautia hansenii|Akkermansia muciniphila, Blautia hydrogenotrophica|Akkermansia muciniphila, Blautia producta|Akkermansia muciniphila, Blautia schinkii|Akkermansia muciniphila, Brevibacterium linens|Akkermansia muciniphila, Brucella ceti|Akkermansia muciniphila, Brucella suis|Akkermansia muciniphila, Bulleidia extructa|Akkermansia muciniphila, Butyrivibrio crossotus|Akkermansia muciniphila, Campylobacter concisus|Akkermansia muciniphila, Campylobacter curvus|Akkermansia muciniphila, Campylobacter gracilis|Akkermansia muciniphila, Campylobacter hominis|Akkermansia muciniphila, Capnocytophaga ochracea|Akkermansia muciniphila, Cardiobacterium hominis|Akkermansia muciniphila, Catenibacterium mitsuokai|Akkermansia muciniphila, Catonella morbi|Akkermansia muciniphila, Citrobacter koseri|Akkermansia muciniphila, Clostridium asparagiforme|Akkermansia muciniphila, Clostridium bartlettii|Akkermansia muciniphila, Clostridium bolteae|Akkermansia muciniphila, Clostridium botulinum|Akkermansia muciniphila, Clostridium butyricum|Akkermansia muciniphila, Clostridium difficile|Akkermansia muciniphila, Clostridium disporicum|Akkermansia muciniphila, Clostridium hathewayi|Akkermansia muciniphila, Clostridium hylemonae|Akkermansia muciniphila, Clostridium innocuum|Akkermansia muciniphila, Clostridium leptum|Akkermansia muciniphila, Clostridium mayombei|Akkermansia muciniphila, Clostridium methylpentosum|Akkermansia muciniphila, Clostridium nexile|Akkermansia muciniphila, Clostridium orbiscindens|Akkermansia muciniphila, Clostridium perfringens|Akkermansia muciniphila, Clostridium saccharolyticum|Akkermansia muciniphila, Clostridium scindens|Akkermansia muciniphila, Clostridium symbiosum|Akkermansia muciniphila, Clostridium tertium|Akkermansia muciniphila, Collinsella aerofaciens|Akkermansia muciniphila, Collinsella intestinalis|Akkermansia muciniphila, Collinsella stercoris|Akkermansia muciniphila, Coprobacillus sp. D7|Akkermansia muciniphila, Coprococcus catus|Akkermansia muciniphila, Coprococcus comes|Akkermansia muciniphila, Coprococcus eutactus|Akkermansia muciniphila, Corynebacterium aurimucosum|Akkermansia muciniphila, Corynebacterium matruchotii|Akkermansia muciniphila, Cryptobacterium curtum|Akkermansia muciniphila, Desulfovibrio desulfuricans|Akkermansia muciniphila, Desulfovibrio piger|Akkermansia muciniphila, Dialister invisus|Akkermansia muciniphila, Dialister microaerophilus|Akkermansia muciniphila, Dorea formicigenerans|Akkermansia muciniphila, Dorea longicatena|Akkermansia muciniphila, Eggerthella lenta|Akkermansia muciniphila, Eikenella corrodens|Akkermansia muciniphila, Enterobacter cancerogenus|Akkermansia muciniphila, Enterobacter cloacae|Akkermansia muciniphila, Enterococcus faecalis|Akkermansia muciniphila, Enterococcus faecium|Akkermansia muciniphila, Enterococcus gallinarum|Akkermansia muciniphila, Erysipelotrichaceae bacterium 3_1_53|Akkermansia muciniphila, Escherichia coli|Akkermansia muciniphila, Escherichia fergusonii|Akkermansia muciniphila, Ethanoligenens harbinense|Akkermansia muciniphila, Eubacterium cellulosolvens|Akkermansia muciniphila, Eubacterium eligens|Akkermansia muciniphila, Eubacterium hallii|Akkermansia muciniphila, Eubacterium limosum|Akkermansia muciniphila, Eubacterium rectale|Akkermansia muciniphila, Eubacterium siraeum|Akkermansia muciniphila, Eubacterium ventriosum|Akkermansia muciniphila, Faecalibacterium prausnitzii|Akkermansia muciniphila, Finegoldia magna|Akkermansia muciniphila, Fusobacterium gonidiaformans|Akkermansia muciniphila, Fusobacterium mortiferum|Akkermansia muciniphila, Fusobacterium nucleatum|Akkermansia muciniphila, Fusobacterium varium|Akkermansia muciniphila, Gardnerella vaginalis|Akkermansia muciniphila, Gemella haemolysans|Akkermansia muciniphila, Gemella morbillorum|Akkermansia muciniphila, Gordonibacter pamelaeae|Akkermansia muciniphila, Granulicatella adiacens|Akkermansia muciniphila, Granulicatella elegans|Akkermansia muciniphila, Haemophilus influenzae|Akkermansia muciniphila, Haemophilus parainfluenzae|Akkermansia muciniphila, Helicobacter pullorum|Akkermansia muciniphila, Helicobacter pylori|Akkermansia muciniphila, Holdemania filiformis|Akkermansia muciniphila, Kingella oralis|Akkermansia muciniphila, Klebsiella pneumoniae|Akkermansia muciniphila, Klebsiella variicola|Akkermansia muciniphila, Lachnospiraceae bacterium 5_1_57FAA|Akkermansia muciniphila, Lactobacillus acidophilus|Akkermansia muciniphila, Lactobacillus amylovorus|Akkermansia muciniphila, Lactobacillus brevis|Akkermansia muciniphila, Lactobacillus casei|Akkermansia muciniphila, Lactobacillus crispatus|Akkermansia muciniphila, Lactobacillus delbrueckii|Akkermansia muciniphila, Lactobacillus fermentum|Akkermansia muciniphila, Lactobacillus gasseri|Akkermansia TABLE 2-continued Table 2. Specific binary combinations of OTUs. Individual pairings are differentiated by "|" and OTUs within a combination are differentiated by ","

*muciniphila, Lactobacillus iners|Akkermansia muciniphila, Lactobacillus jensenii|Akkermansia muciniphila, Lactobacillus johnsonii|Akkermansia muciniphila, Lactobacillus paracasei|Akkermansia muciniphila, Lactobacillus plantarum|Akkermansia muciniphila, Lactobacillus reuteri|Akkermansia muciniphila, Lactobacillus rhamnosus|Akkermansia muciniphila, Lactobacillus ruminis|Akkermansia muciniphila, Lactobacillus sakei|Akkermansia muciniphila, Lactobacillus salivarius|Akkermansia muciniphila, Lactococcus lactis|Akkermansia muciniphila, Lautropia mirabilis|Akkermansia muciniphila, Leuconostoc citreum|Akkermansia muciniphila, Leuconostoc gasicomitatum|Akkermansia muciniphila, Leuconostoc mesenteroides|Akkermansia muciniphila, Listeria monocytogenes|Akkermansia muciniphila, Marvinbryantia formatexigens|Akkermansia muciniphila, Megamonas hypermegale|Akkermansia muciniphila, Megasphaera micronuciformis|Akkermansia muciniphila, Methanobrevibacter smithii|Akkermansia muciniphila, Methanosphaera stadtmanae|Akkermansia muciniphila, Methylobacterium radiotolerans|Akkermansia muciniphila, Mitsuokella multacida|Akkermansia muciniphila, Mobiluncus curtisii|Akkermansia muciniphila, Mycoplasma hominis|Akkermansia muciniphila, Neisseria mucosa|Akkermansia muciniphila, Odoribacter splanchnicus|Akkermansia muciniphila, Olsenella uli|Akkermansia muciniphila, Oribacterium sinus|Akkermansia muciniphila, Oxalobacter formigenes|Akkermansia muciniphila, Parabacteroides distasonis|Akkermansia muciniphila, Parabacteroides johnsonii|Akkermansia muciniphila, Parabacteroides merdae|Akkermansia muciniphila, Parvimonas micra|Akkermansia muciniphila, Pediococcus acidilactici|Akkermansia muciniphila, Pediococcus pentosaceus|Akkermansia muciniphila, Peptoniphilus duerdenii|Akkermansia muciniphila, Peptoniphilus harei|Akkermansia muciniphila, Peptoniphilus lacrimalis|Akkermansia muciniphila, Peptostreptococcus anaerobius|Akkermansia muciniphila, Peptostreptococcus stomatis|Akkermansia muciniphila, Porphyromonas asaccharolytica|Akkermansia muciniphila, Porphyromonas uenonis|Akkermansia muciniphila, Prevotella amnii|Akkermansia muciniphila, Prevotella bergensis|Akkermansia muciniphila, Prevotella bivia|Akkermansia muciniphila, Prevotella buccae|Akkermansia muciniphila, Prevotella buccalis|Akkermansia muciniphila, Prevotella copri|Akkermansia muciniphila, Prevotella disiens|Akkermansia muciniphila, Prevotella melaninogenica|Akkermansia muciniphila, Prevotella multiformis|Akkermansia muciniphila, Prevotella oralis|Akkermansia muciniphila, Prevotella oris|Akkermansia muciniphila, Prevotella salivae|Akkermansia muciniphila, Prevotella timonensis|Akkermansia muciniphila, Propionibacterium acnes|Akkermansia muciniphila, Propionibacterium freudenreichii|Akkermansia muciniphila, Proteus mirabilis|Akkermansia muciniphila, Proteus penneri|Akkermansia muciniphila, Pseudoflavonifractor capillosus|Akkermansia muciniphila, Pseudomonas aeruginosa|Akkermansia muciniphila, Pseudomonas fluorescens|Akkermansia muciniphila, Pseudomonas putida|Akkermansia muciniphila, Pseudoramibacter alactolyticus|Akkermansia muciniphila, Pyramidobacter piscolens|Akkermansia muciniphila, Rhodopseudomonas palustris|Akkermansia muciniphila, Roseburia intestinalis|Akkermansia muciniphila, Roseburia inulinivorans|Akkermansia muciniphila, Rothia dentocariosa|Akkermansia muciniphila, Rothia mucilaginosa|Akkermansia muciniphila, Ruminococcus albus|Akkermansia muciniphila, Ruminococcus bromii|Akkermansia muciniphila, Ruminococcus gnavus|Akkermansia muciniphila, Ruminococcus lactaris|Akkermansia muciniphila, Ruminococcus obeum|Akkermansia muciniphila, Ruminococcus torques|Akkermansia muciniphila, Selenomonas sputigena|Akkermansia muciniphila, Shigella boydii|Akkermansia muciniphila, Shigella dysenteriae|Akkermansia muciniphila, Shigella sonnei|Akkermansia muciniphila, Slackia exigua|Akkermansia muciniphila, Solobacterium moorei|Akkermansia muciniphila, Staphylococcus aureus|Akkermansia muciniphila, Staphylococcus epidermidis|Akkermansia muciniphila, Staphylococcus hominis|Akkermansia muciniphila, Staphylococcus saprophyticus|Akkermansia muciniphila, Staphylococcus warneri|Akkermansia muciniphila, Streptococcus agalactiae|Akkermansia muciniphila, Streptococcus anginosus|Akkermansia muciniphila, Streptococcus australis|Akkermansia muciniphila, Streptococcus bovis|Akkermansia muciniphila, Streptococcus cristatus|Akkermansia muciniphila, Streptococcus dysgalactiae|Akkermansia muciniphila, Streptococcus equinus|Akkermansia muciniphila, Streptococcus gordonii|Akkermansia muciniphila, Streptococcus infantarius|Akkermansia muciniphila, Streptococcus infantis|Akkermansia muciniphila, Streptococcus mitis|Akkermansia muciniphila, Streptococcus mutans|Akkermansia muciniphila, Streptococcus oralis|Akkermansia muciniphila, Streptococcus parasanguinis|Akkermansia muciniphila, Streptococcus peroris|Akkermansia muciniphila, Streptococcus pneumoniae|Akkermansia muciniphila, Streptococcus salivarius|Akkermansia muciniphila, Streptococcus sanguinis|Akkermansia muciniphila, Streptococcus thermophilus|Akkermansia muciniphila, Streptococcus vestibularis|Akkermansia muciniphila, Subdoligranulum variabile|Akkermansia muciniphila, Succinatimonas hippei|Akkermansia muciniphila, Sutterella wadsworthensis|Akkermansia muciniphila, Tropheryma whipplei|Akkermansia muciniphila, Veillonella atypica|Akkermansia muciniphila, Veillonella dispar|Akkermansia muciniphila, Veillonella parvula|Akkermansia muciniphila, Victivallis vadensis|Alistipes putredinis, Alistipes putredinis|Alistipes putredinis, Alistipes shahii|Alistipes putredinis, Anaerococcus hydrogenalis|Alistipes putredinis, Anaerococcus lactolyticus|Alistipes putredinis, Anaerococcus vaginalis|Alistipes putredinis, Anaerostipes caccae|Alistipes putredinis, Anaerotruncus colihominis|Alistipes putredinis, Atopobium parvulum|Alistipes putredinis, Atopobium rimae|Alistipes putredinis, Atopobium vaginae|Alistipes putredinis, Bacteroides caccae|Alistipes putredinis, Bacteroides cellulosilyticus|Alistipes putredinis, Bacteroides coprocola|Alistipes putredinis, Bacteroides coprophilus|Alistipes putredinis, Bacteroides dorei|Alistipes putredinis, Bacteroides eggerthii|Alistipes putredinis, Bacteroides finegoldii|Alistipes putredinis, Bacteroides fragilis|Alistipes putredinis, Bacteroides helcogenes|Alistipes putredinis, Bacteroides intestinalis|Alistipes putredinis, Bacteroides ovatus|Alistipes putredinis, Bacteroides pectinophilus|Alistipes putredinis, Bacteroides plebeius|Alistipes putredinis, Bacteroides salanitronis|Alistipes putredinis, Bacteroides* sp. 1_1_6|*Alistipes putredinis, Bacteroides* sp. 3_1_23|*Alistipes putredinis, Bacteroides stercoris|Alistipes putredinis, Bacteroides thetaiotaomicron|Alistipes putredinis, Bacteroides uniformis|Alistipes putredinis, Bacteroides vulgatus|Alistipes putredinis, Bacteroides xylanisolvens|Alistipes putredinis, Bifidobacterium adolescentis|Alistipes putredinis, Bifidobacterium angulatum|Alistipes putredinis, Bifidobacterium animalis|Alistipes putredinis, Bifidobacterium bifidum|Alistipes putredinis, Bifidobacterium breve|Alistipes putredinis, Bifidobacterium catenulatum|Alistipes putredinis, Bifidobacterium dentium|Alistipes putredinis, Bifidobacterium infantis|Alistipes putredinis, Bifidobacterium longum|Alistipes putredinis, Bifidobacterium pseudocatenulatum|Alistipes putredinis, Bilophila wadsworthia|Alistipes putredinis, Blautia hansenii|Alistipes putredinis, Blautia hydrogenotrophica|Alistipes putredinis, Blautia producta|Alistipes putredinis, Blautia schinkii|Alistipes putredinis, Brevibacterium linens|Alistipes putredinis, Brucella ceti|Alistipes putredinis, Brucella suis|Alistipes putredinis, Bulleidia extructa|Alistipes putredinis, Butyrivibrio crossotus|Alistipes putredinis, Campylobacter concisus|Alistipes putredinis, Campylobacter curvus|Alistipes putredinis, Campylobacter gracilis|Alistipes putredinis, Campylobacter hominis|Alistipes putredinis, Capnocytophaga ochracea|Alistipes putredinis, Cardiobacterium hominis|Alistipes putredinis, Catenibacterium mitsuokai|Alistipes putredinis, Catonella morbi|Alistipes putredinis, Citrobacter koseri|Alistipes putredinis, Clostridium asparagiforme|Alistipes putredinis, Clostridium bartlettii|Alistipes putredinis, Clostridium bolteae|Alistipes putredinis, Clostridium botulinum|Alistipes putredinis, Clostridium butyricum|Alistipes putredinis, Clostridium difficile|Alistipes putredinis, Clostridium disporicum|Alistipes putredinis, Clostridium hathewayi|Alistipes putredinis, Clostridium hylemonae|Alistipes putredinis, Clostridium innocuum|Alistipes putredinis, Clostridium leptum|Alistipes putredinis, Clostridium mayombei|Alistipes putredinis, Clostridium methylpentosum|Alistipes putredinis, Clostridium nexile|Alistipes putredinis, Clostridium orbiscindens|Alistipes putredinis, Clostridium perfringens|Alistipes putredinis, Clostridium saccharolyticum|Alistipes putredinis, Clostridium scindens|Alistipes putredinis, Clostridium symbiosum|Alistipes putredinis, Clostridium tertium|Alistipes putredinis, Collinsella aerofaciens|Alistipes putredinis, Collinsella intestinalis|Alistipes putredinis, Collinsella stercoris|Alistipes putredinis, Coprobacillus* sp. D7|*Alistipes putredinis, Coprococcus catus|Alistipes putredinis, Coprococcus comes|Alistipes putredinis, Coprococcus eutactus|Alistipes putredinis, Corynebacterium aurimucosum|Alistipes putredinis, Corynebacterium matruchotii|Alistipes putredinis, Cryptobacterium curtum|Alistipes putredinis, Desulfovibrio desulfuricans|Alistipes putredinis, Desulfovibrio piger|Alistipes putredinis, Dialister invisus|Alistipes putredinis, Dialister microaerophilus|Alistipes putredinis, Dorea formicigenerans|Alistipes putredinis, Dorea longicatena|Alistipes putredinis, Eggerthella lenta|Alistipes putredinis, Eikenella corrodens|Alistipes putredinis, Enterobacter cancerogenus|Alistipes putredinis, Enterobacter cloacae|Alistipes putredinis, Enterococcus faecalis|Alistipes*

TABLE 2-continued

Table 2. Specific binary combinations of OTUs. Individual pairings are differentiated by "|" and OTUs within a combination are differentiated by ","

putredinis, Enterococcus faecium|Alistipes putredinis, Enterococcus gallinarum|Alistipes putredinis, Erysipelotrichaceae bacterium 3_1_53|Alistipes putredinis, Escherichia coli|Alistipes putredinis, Escherichia fergusonii|Alistipes putredinis, Ethanoligenens harbinense|Alistipes putredinis, Eubacterium cellulosolvens|Alistipes putredinis, Eubacterium eligens|Alistipes putredinis, Eubacterium hallii|Alistipes putredinis, Eubacterium limosum|Alistipes putredinis, Eubacterium rectale|Alistipes putredinis, Eubacterium siraeum|Alistipes putredinis, Eubacterium ventriosum|Alistipes putredinis, Faecalibacterium prausnitzii|Alistipes putredinis, Finegoldia magna|Alistipes putredinis, Fusobacterium gonidiaformans|Alistipes putredinis, Fusobacterium mortiferum|Alistipes putredinis, Fusobacterium nucleatum|Alistipes putredinis, Fusobacterium varium|Alistipes putredinis, Gardnerella vaginalis|Alistipes putredinis, Gemella haemolysans|Alistipes putredinis, Gemella morbillorum|Alistipes putredinis, Gordonibacter pamelaeae|Alistipes putredinis, Granulicatella adiacens|Alistipes putredinis, Granulicatella elegans|Alistipes putredinis, Haemophilus influenzae|Alistipes putredinis, Haemophilus parainfluenzae|Alistipes putredinis, Helicobacter pullorum|Alistipes putredinis, Helicobacter pylori|Alistipes putredinis, Holdemania filiformis|Alistipes putredinis, Kingella oralis|Alistipes putredinis, Klebsiella pneumoniae|Alistipes putredinis, Klebsiella variicola|Alistipes putredinis, Lachnospiraceae bacterium 5_1_57FAA|Alistipes putredinis, Lactobacillus acidophilus|Alistipes putredinis, Lactobacillus amylovorus|Alistipes putredinis, Lactobacillus brevis|Alistipes putredinis, Lactobacillus casei|Alistipes putredinis, Lactobacillus crispatus|Alistipes putredinis, Lactobacillus delbrueckii|Alistipes putredinis, Lactobacillus fermentum|Alistipes putredinis, Lactobacillus gasseri|Alistipes putredinis, Lactobacillus iners|Alistipes putredinis, Lactobacillus jensenii|Alistipes putredinis, Lactobacillus johnsonii|Alistipes putredinis, Lactobacillus paracasei|Alistipes putredinis, Lactobacillus plantarum|Alistipes putredinis, Lactobacillus reuteri|Alistipes putredinis, Lactobacillus rhamnosus|Alistipes putredinis, Lactobacillus ruminis|Alistipes putredinis, Lactobacillus sakei|Alistipes putredinis, Lactobacillus salivarius|Alistipes putredinis, Lactococcus lactis|Alistipes putredinis, Lautropia mirabilis|Alistipes putredinis, Leuconostoc citreum|Alistipes putredinis, Leuconostoc gasicomitatum|Alistipes putredinis, Leuconostoc mesenteroides|Alistipes putredinis, Listeria monocytogenes|Alistipes putredinis, Marvinbryantia formatexigens|Alistipes putredinis, Megamonas hypermegale|Alistipes putredinis, Megasphaera micronuciformis|Alistipes putredinis, Methanobrevibacter smithii|Alistipes putredinis, Methanosphaera stadtmanae|Alistipes putredinis, Methylobacterium radiotolerans|Alistipes putredinis, Mitsuokella multacida|Alistipes putredinis, Mobiluncus curtisii|Alistipes putredinis, Mycoplasma hominis|Alistipes putredinis, Neisseria mucosa|Alistipes putredinis, Odoribacter splanchnicus|Alistipes putredinis, Olsenella uli|Alistipes putredinis, Oribacterium sinus|Alistipes putredinis, Oxalobacter formigenes|Alistipes putredinis, Parabacteroides distasonis|Alistipes putredinis, Parabacteroides johnsonii|Alistipes putredinis, Parabacteroides merdae|Alistipes putredinis, Parvimonas micra|Alistipes putredinis, Pediococcus acidilactici|Alistipes putredinis, Pediococcus pentosaceus|Alistipes putredinis, Peptoniphilus duerdenii|Alistipes putredinis, Peptoniphilus harei|Alistipes putredinis, Peptoniphilus lacrimalis|Alistipes putredinis, Peptostreptococcus anaerobius|Alistipes putredinis, Peptostreptococcus stomatis|Alistipes putredinis, Porphyromonas asaccharolytica|Alistipes putredinis, Porphyromonas uenonis|Alistipes putredinis, Prevotella amnii|Alistipes putredinis, Prevotella bergensis|Alistipes putredinis, Prevotella bivia|Alistipes putredinis, Prevotella buccae|Alistipes putredinis, Prevotella buccalis|Alistipes putredinis, Prevotella copri|Alistipes putredinis, Prevotella disiens|Alistipes putredinis, Prevotella melaninogenica|Alistipes putredinis, Prevotella multiformis|Alistipes putredinis, Prevotella oralis|Alistipes putredinis, Prevotella oris|Alistipes putredinis, Prevotella salivae|Alistipes putredinis, Prevotella timonensis|Alistipes putredinis, Propionibacterium acnes|Alistipes putredinis, Propionibacterium freudenreichii|Alistipes putredinis, Proteus mirabilis|Alistipes putredinis, Proteus penneri|Alistipes putredinis, Pseudoflavonifractor capillosus|Alistipes putredinis, Pseudomonas aeruginosa|Alistipes putredinis, Pseudomonas fluorescens|Alistipes putredinis, Pseudomonas putida|Alistipes putredinis, Pseudoramibacter alactolyticus|Alistipes putredinis, Pyramidobacter piscolens|Alistipes putredinis, Rhodopseudomonas palustris|Alistipes putredinis, Roseburia intestinalis|Alistipes putredinis, Roseburia inulinivorans|Alistipes putredinis, Rothia dentocariosa|Alistipes putredinis, Rothia mucilaginosa|Alistipes putredinis, Ruminococcus albus|Alistipes putredinis, Ruminococcus bromii|Alistipes putredinis, Ruminococcus gnavus|Alistipes putredinis, Ruminococcus lactaris|Alistipes putredinis, Ruminococcus obeum|Alistipes putredinis, Ruminococcus torques|Alistipes putredinis, Selenomonas sputigena|Alistipes putredinis, Shigella boydii|Alistipes putredinis, Shigella dysenteriae|Alistipes putredinis, Shigella sonnei|Alistipes putredinis, Slackia exigua|Alistipes putredinis, Solobacterium moorei|Alistipes putredinis, Staphylococcus aureus|Alistipes putredinis, Staphylococcus epidermidis|Alistipes putredinis, Staphylococcus hominis|Alistipes putredinis, Staphylococcus saprophyticus|Alistipes putredinis, Staphylococcus warneri|Alistipes putredinis, Streptococcus agalactiae|Alistipes putredinis, Streptococcus anginosus|Alistipes putredinis, Streptococcus australis|Alistipes putredinis, Streptococcus bovis|Alistipes putredinis, Streptococcus cristatus|Alistipes putredinis, Streptococcus dysgalactiae|Alistipes putredinis, Streptococcus equinus|Alistipes putredinis, Streptococcus gordonii|Alistipes putredinis, Streptococcus infantarius|Alistipes putredinis, Streptococcus infantis|Alistipes putredinis, Streptococcus mitis|Alistipes putredinis, Streptococcus mutans|Alistipes putredinis, Streptococcus oralis|Alistipes putredinis, Streptococcus parasanguinis|Alistipes putredinis, Streptococcus peroris|Alistipes putredinis, Streptococcus pneumoniae|Alistipes putredinis, Streptococcus salivarius|Alistipes putredinis, Streptococcus sanguinis|Alistipes putredinis, Streptococcus thermophilus|Alistipes putredinis, Streptococcus vestibularis|Alistipes putredinis, Subdoligranulum variabile|Alistipes putredinis, Succinatimonas hippei|Alistipes putredinis, Sutterella wadsworthensis|Alistipes putredinis, Tropheryma whipplei|Alistipes putredinis, Veillonella atypica|Alistipes putredinis, Veillonella dispar|Alistipes putredinis, Veillonella parvula|Alistipes putredinis, Victivallis vadensis|Alistipes shahii, Alistipes shahii|Alistipes shahii, Anaerococcus hydrogenalis|Alistipes shahii, Anaerococcus lactolyticus|Alistipes shahii, Anaerococcus vaginalis|Alistipes shahii, Anaerostipes caccae|Alistipes shahii, Anaerotruncus colihominis|Alistipes shahii, Atopobium parvulum|Alistipes shahii, Atopobium rimae|Alistipes shahii, Atopobium vaginae|Alistipes shahii, Bacteroides caccae|Alistipes shahii, Bacteroides cellulosilyticus|Alistipes shahii, Bacteroides coprocola|Alistipes shahii, Bacteroides coprophilus|Alistipes shahii, Bacteroides dorei|Alistipes shahii, Bacteroides eggerthii|Alistipes shahii, Bacteroides finegoldii|Alistipes shahii, Bacteroides fragilis|Alistipes shahii, Bacteroides helcogenes|Alistipes shahii, Bacteroides intestinalis|Alistipes shahii, Bacteroides ovatus|Alistipes shahii, Bacteroides pectinophilus|Alistipes shahii, Bacteroides plebeius|Alistipes shahii, Bacteroides salanitronis|Alistipes shahii, Bacteroides sp. 1_1_6|Alistipes shahii, Bacteroides sp. 3_1_23|Alistipes shahii, Bacteroides stercoris|Alistipes shahii, Bacteroides thetaiotaomicron|Alistipes shahii, Bacteroides uniformis|Alistipes shahii, Bacteroides vulgatus|Alistipes shahii, Bacteroides xylanisolvens|Alistipes shahii, Bifidobacterium adolescentis|Alistipes shahii, Bifidobacterium angulatum|Alistipes shahii, Bifidobacterium animalis|Alistipes shahii, Bifidobacterium bifidum|Alistipes shahii, Bifidobacterium breve|Alistipes shahii, Bifidobacterium catenulatum|Alistipes shahii, Bifidobacterium dentium|Alistipes shahii, Bifidobacterium infantis|Alistipes shahii, Bifidobacterium longum|Alistipes shahii, Bifidobacterium pseudocatenulatum|Alistipes shahii, Bilophila wadsworthia|Alistipes shahii, Blautia hansenii|Alistipes shahii, Blautia hydrogenotrophica|Alistipes shahii, Blautia producta|Alistipes shahii, Blautia schinkii|Alistipes shahii, Brevibacterium linens|Alistipes shahii, Brucella ceti|Alistipes shahii, Brucella suis|Alistipes shahii, Bulleidia extructa|Alistipes shahii, Butyrivibrio crossotus|Alistipes shahii, Campylobacter concisus|Alistipes shahii, Campylobacter curvus|Alistipes shahii, Campylobacter gracilis|Alistipes shahii, Campylobacter hominis|Alistipes shahii, Capnocytophaga ochracea|Alistipes shahii, Cardiobacterium hominis|Alistipes shahii, Catenibacterium mitsuokai|Alistipes shahii, Catonella morbi|Alistipes shahii, Citrobacter koseri|Alistipes shahii, Clostridium asparagiforme|Alistipes shahii, Clostridium bartlettii|Alistipes shahii, Clostridium bolteae|Alistipes shahii, Clostridium botulinum|Alistipes shahii, Clostridium butyricum|Alistipes shahii, Clostridium difficile|Alistipes shahii, Clostridium disporicum|Alistipes shahii, Clostridium hathewayi|Alistipes shahii, Clostridium hylemonae|Alistipes shahii, Clostridium innocuum|Alistipes shahii, Clostridium leptum|Alistipes shahii, Clostridium mayombei|Alistipes shahii, Clostridium methylpentosum|Alistipes shahii, Clostridium nexile|Alistipes shahii, Clostridium orbiscindens|Alistipes shahii, Clostridium perfringens|Alistipes shahii, Clostridium saccharolyticum|Alistipes shahii, Clostridium scindens|Alistipes shahii, Clostridium symbiosum|Alistipes shahii, Clostridium tertium|Alistipes shahii, Collinsella aerofaciens|Alistipes shahii, Collinsella intestinalis|Alistipes shahii, Collinsella stercoris|Alistipes shahii, Coprobacillus sp. D7|Alistipes shahii, Coprococcus catus|Alistipes shahii, Coprococcus TABLE 2-continued

| Table 2. Specific binary combinations of OTUs. Individual pairings are differentiated by "\|" and OTUs within a combination are differentiated by "," |
|---|
| *comes\|Alistipes shahii, Coprococcus eutactus\|Alistipes shahii, Corynebacterium aurimucosum\|Alistipes shahii, Corynebacterium matruchotii\|Alistipes shahii, Cryptobacterium curtum\|Alistipes shahii, Desulfovibrio desulfuricans\|Alistipes shahii, Desulfovibrio piger\|Alistipes shahii, Dialister invisus\|Alistipes shahii, Dialister microaerophilus\|Alistipes shahii, Dorea formicigenerans\|Alistipes shahii, Dorea longicatena\|Alistipes shahii, Eggerthella lenta\|Alistipes shahii, Eikenella corrodens\|Alistipes shahii, Enterobacter cancerogenus\|Alistipes shahii, Enterobacter cloacae\|Alistipes shahii, Enterococcus faecalis\|Alistipes shahii, Enterococcus faecium\|Alistipes shahii, Enterococcus gallinarum\|Alistipes shahii, Erysipelotrichaceae bacterium* 3_1_53\|*Alistipes shahii, Escherichia coli\|Alistipes shahii, Escherichia fergusonii\|Alistipes shahii, Ethanoligenens harbinense\|Alistipes shahii, Eubacterium cellulosolvens\|Alistipes shahii, Eubacterium eligens\|Alistipes shahii, Eubacterium hallii\|Alistipes shahii, Eubacterium limosum\|Alistipes shahii, Eubacterium rectale\|Alistipes shahii, Eubacterium siraeum\|Alistipes shahii, Eubacterium ventriosum\|Alistipes shahii, Faecalibacterium prausnitzii\|Alistipes shahii, Finegoldia magna\|Alistipes shahii, Fusobacterium gonidiaformans\|Alistipes shahii, Fusobacterium mortiferum\|Alistipes shahii, Fusobacterium nucleatum\|Alistipes shahii, Fusobacterium varium\|Alistipes shahii, Gardnerella vaginalis\|Alistipes shahii, Gemella haemolysans\|Alistipes shahii, Gemella morbillorum\|Alistipes shahii, Gordonibacter pamelaeae\|Alistipes shahii, Granulicatella adiacens\|Alistipes shahii, Granulicatella elegans\|Alistipes shahii, Haemophilus influenzae\|Alistipes shahii, Haemophilus parainfluenzae\|Alistipes shahii, Helicobacter pullorum\|Alistipes shahii, Helicobacter pylori\|Alistipes shahii, Holdemania filiformis\|Alistipes shahii, Kingella oralis\|Alistipes shahii, Klebsiella pneumoniae\|Alistipes shahii, Klebsiella variicola\|Alistipes shahii, Lachnospiraceae bacterium* 5_1_57FAA\|*Alistipes shahii, Lactobacillus acidophilus\|Alistipes shahii, Lactobacillus amylovorus\|Alistipes shahii, Lactobacillus brevis\|Alistipes shahii, Lactobacillus casei\|Alistipes shahii, Lactobacillus crispatus\|Alistipes shahii, Lactobacillus delbrueckii\|Alistipes shahii, Lactobacillus fermentum\|Alistipes shahii, Lactobacillus gasseri\|Alistipes shahii, Lactobacillus iners\|Alistipes shahii, Lactobacillus jensenii\|Alistipes shahii, Lactobacillus johnsonii\|Alistipes shahii, Lactobacillus paracasei\|Alistipes shahii, Lactobacillus plantarum\|Alistipes shahii, Lactobacillus reuteri\|Alistipes shahii, Lactobacillus rhamnosus\|Alistipes shahii, Lactobacillus ruminis\|Alistipes shahii, Lactobacillus sakei\|Alistipes shahii, Lactobacillus salivarius\|Alistipes shahii, Lactococcus lactis\|Alistipes shahii, Lautropia mirabilis\|Alistipes shahii, Leuconostoc citreum\|Alistipes shahii, Leuconostoc gasicomitatum\|Alistipes shahii, Leuconostoc mesenteroides\|Alistipes shahii, Listeria monocytogenes\|Alistipes shahii, Marvinbryantia formatexigens\|Alistipes shahii, Megamonas hypermegale\|Alistipes shahii, Megasphaera micronuciformis\|Alistipes shahii, Methanobrevibacter smithii\|Alistipes shahii, Methanosphaera stadtmanae\|Alistipes shahii, Methylobacterium radiotolerans\|Alistipes shahii, Mitsuokella multacida\|Alistipes shahii, Mobiluncus curtisii\|Alistipes shahii, Mycoplasma hominis\|Alistipes shahii, Neisseria mucosa\|Alistipes shahii, Odoribacter splanchnicus\|Alistipes shahii, Olsenella uli\|Alistipes shahii, Oribacterium sinus\|Alistipes shahii, Oxalobacter formigenes\|Alistipes shahii, Parabacteroides distasonis\|Alistipes shahii, Parabacteroides johnsonii\|Alistipes shahii, Parabacteroides merdae\|Alistipes shahii, Parvimonas micra\|Alistipes shahii, Pediococcus acidilactici\|Alistipes shahii, Pediococcus pentosaceus\|Alistipes shahii, Peptoniphilus duerdenii\|Alistipes shahii, Peptoniphilus harei\|Alistipes shahii, Peptoniphilus lacrimalis\|Alistipes shahii, Peptostreptococcus anaerobius\|Alistipes shahii, Peptostreptococcus stomatis\|Alistipes shahii, Porphyromonas asaccharolytica\|Alistipes shahii, Porphyromonas uenonis\|Alistipes shahii, Prevotella amnii\|Alistipes shahii, Prevotella bergensis\|Alistipes shahii, Prevotella bivia\|Alistipes shahii, Prevotella buccae\|Alistipes shahii, Prevotella buccalis\|Alistipes shahii, Prevotella copri\|Alistipes shahii, Prevotella disiens\|Alistipes shahii, Prevotella melaninogenica\|Alistipes shahii, Prevotella multiformis\|Alistipes shahii, Prevotella oralis\|Alistipes shahii, Prevotella oris\|Alistipes shahii, Prevotella salivae\|Alistipes shahii, Prevotella timonensis\|Alistipes shahii, Propionibacterium acnes\|Alistipes shahii, Propionibacterium freudenreichii\|Alistipes shahii, Proteus mirabilis\|Alistipes shahii, Proteus penneri\|Alistipes shahii, Pseudoflavonifractor capillosus\|Alistipes shahii, Pseudomonas aeruginosa\|Alistipes shahii, Pseudomonas fluorescens\|Alistipes shahii, Pseudomonas putida\|Alistipes shahii, Pseudoramibacter alactolyticus\|Alistipes shahii, Pyramidobacter piscolens\|Alistipes shahii, Rhodopseudomonas palustris\|Alistipes shahii, Roseburia intestinalis\|Alistipes shahii, Roseburia inulinivorans\|Alistipes shahii, Rothia dentocariosa\|Alistipes shahii, Rothia mucilaginosa\|Alistipes shahii, Ruminococcus albus\|Alistipes shahii, Ruminococcus bromii\|Alistipes shahii, Ruminococcus gnavus\|Alistipes shahii, Ruminococcus lactaris\|Alistipes shahii, Ruminococcus obeum\|Alistipes shahii, Ruminococcus torques\|Alistipes shahii, Selenomonas sputigena\|Alistipes shahii, Shigella boydii\|Alistipes shahii, Shigella dysenteriae\|Alistipes shahii, Shigella sonnei\|Alistipes shahii, Slackia exigua\|Alistipes shahii, Solobacterium moorei\|Alistipes shahii, Staphylococcus aureus\|Alistipes shahii, Staphylococcus epidermidis\|Alistipes shahii, Staphylococcus hominis\|Alistipes shahii, Staphylococcus saprophyticus\|Alistipes shahii, Staphylococcus warneri\|Alistipes shahii, Streptococcus agalactiae\|Alistipes shahii, Streptococcus anginosus\|Alistipes shahii, Streptococcus australis\|Alistipes shahii, Streptococcus bovis\|Alistipes shahii, Streptococcus cristatus\|Alistipes shahii, Streptococcus dysgalactiae\|Alistipes shahii, Streptococcus equinus\|Alistipes shahii, Streptococcus gordonii\|Alistipes shahii, Streptococcus infantarius\|Alistipes shahii, Streptococcus infantis\|Alistipes shahii, Streptococcus mitis\|Alistipes shahii, Streptococcus mutans\|Alistipes shahii, Streptococcus oralis\|Alistipes shahii, Streptococcus parasanguinis\|Alistipes shahii, Streptococcus peroris\|Alistipes shahii, Streptococcus pneumoniae\|Alistipes shahii, Streptococcus salivarius\|Alistipes shahii, Streptococcus sanguinis\|Alistipes shahii, Streptococcus thermophilus\|Alistipes shahii, Streptococcus vestibularis\|Alistipes shahii, Subdoligranulum variabile\|Alistipes shahii, Succinatimonas hippei\|Alistipes shahii, Sutterella wadsworthensis\|Alistipes shahii, Tropheryma whipplei\|Alistipes shahii, Veillonella atypica\|Alistipes shahii, Veillonella dispar\|Alistipes shahii, Veillonella parvula\|Alistipes shahii, Victivallis vadensis\|Anaerococcus hydrogenalis, Anaerococcus hydrogenalis\|Anaerococcus hydrogenalis, Anaerococcus lactolyticus\|Anaerococcus hydrogenalis, Anaerococcus vaginalis\|Anaerococcus hydrogenalis, Anaerostipes caccae\|Anaerococcus hydrogenalis, Anaerotruncus colihominis\|Anaerococcus hydrogenalis, Atopobium parvulum\|Anaerococcus hydrogenalis, Atopobium rimae\|Anaerococcus hydrogenalis, Atopobium vaginae\|Anaerococcus hydrogenalis, Bacteroides caccae\|Anaerococcus hydrogenalis, Bacteroides cellulosilyticus\|Anaerococcus hydrogenalis, Bacteroides coprocola\|Anaerococcus hydrogenalis, Bacteroides coprophilus\|Anaerococcus hydrogenalis, Bacteroides dorei\|Anaerococcus hydrogenalis, Bacteroides eggerthii\|Anaerococcus hydrogenalis, Bacteroides finegoldii\|Anaerococcus hydrogenalis, Bacteroides fragilis\|Anaerococcus hydrogenalis, Bacteroides helcogenes\|Anaerococcus hydrogenalis, Bacteroides intestinalis\|Anaerococcus hydrogenalis, Bacteroides ovatus\|Anaerococcus hydrogenalis, Bacteroides pectinophilus\|Anaerococcus hydrogenalis, Bacteroides plebeius\|Anaerococcus hydrogenalis, Bacteroides salanitronis\|Anaerococcus hydrogenalis, Bacteroides* sp. 1_1_6\|*Anaerococcus hydrogenalis, Bacteroides* sp. 3_1_23\|*Anaerococcus hydrogenalis, Bacteroides stercoris\|Anaerococcus hydrogenalis, Bacteroides thetaiotaomicron\|Anaerococcus hydrogenalis, Bacteroides uniformis\|Anaerococcus hydrogenalis, Bacteroides vulgatus\|Anaerococcus hydrogenalis, Bacteroides xylanisolvens\|Anaerococcus hydrogenalis, Bifidobacterium adolescentis\|Anaerococcus hydrogenalis, Bifidobacterium angulatum\|Anaerococcus hydrogenalis, Bifidobacterium animalis\|Anaerococcus hydrogenalis, Bifidobacterium bifidum\|Anaerococcus hydrogenalis, Bifidobacterium breve\|Anaerococcus hydrogenalis, Bifidobacterium catenulatum\|Anaerococcus hydrogenalis, Bifidobacterium dentium\|Anaerococcus hydrogenalis, Bifidobacterium infantis\|Anaerococcus hydrogenalis, Bifidobacterium longum\|Anaerococcus hydrogenalis, Bifidobacterium pseudocatenulatum\|Anaerococcus hydrogenalis, Bilophila wadsworthia\|Anaerococcus hydrogenalis, Blautia hansenii\|Anaerococcus hydrogenalis, Blautia hydrogenotrophica\|Anaerococcus hydrogenalis, Blautia producta\|Anaerococcus hydrogenalis, Blautia schinkii\|Anaerococcus hydrogenalis, Brevibacterium linens\|Anaerococcus hydrogenalis, Brucella ceti\|Anaerococcus hydrogenalis, Brucella suis\|Anaerococcus hydrogenalis, Bulleidia extructa\|Anaerococcus hydrogenalis, Butyrivibrio crossotus\|Anaerococcus hydrogenalis, Campylobacter concisus\|Anaerococcus hydrogenalis, Campylobacter curvus\|Anaerococcus hydrogenalis, Campylobacter gracilis\|Anaerococcus hydrogenalis, Campylobacter hominis\|Anaerococcus hydrogenalis, Capnocytophaga ochracea\|Anaerococcus hydrogenalis, Cardiobacterium hominis\|Anaerococcus hydrogenalis, Catenibacterium mitsuokai\|Anaerococcus hydrogenalis, Catonella morbi\|Anaerococcus hydrogenalis, Citrobacter koseri\|Anaerococcus hydrogenalis, Clostridium asparagiforme\|Anaerococcus hydrogenalis, Clostridium bartlettii\|Anaerococcus hydrogenalis, Clostridium bolteae\|Anaerococcus hydrogenalis, Clostridium botulinum\|Anaerococcus hydrogenalis, Clostridium butyricum\|Anaerococcus hydrogenalis, Clostridium* |

TABLE 2-continued

| Table 2. Specific binary combinations of OTUs. Individual pairings are differentiated by "\|" and OTUs within a combination are differentiated by "," |
| --- |
| *difficile*\|*Anaerococcus hydrogenalis, Clostridium disporicum*\|*Anaerococcus hydrogenalis, Clostridium hathewayi*\|*Anaerococcus hydrogenalis, Clostridium hylemonae*\|*Anaerococcus hydrogenalis, Clostridium innocuum*\|*Anaerococcus hydrogenalis, Clostridium leptum*\|*Anaerococcus hydrogenalis, Clostridium mayombei*\|*Anaerococcus hydrogenalis, Clostridium methylpentosum*\|*Anaerococcus hydrogenalis, Clostridium nexile*\|*Anaerococcus hydrogenalis, Clostridium orbiscindens*\|*Anaerococcus hydrogenalis, Clostridium perfringens*\|*Anaerococcus hydrogenalis, Clostridium saccharolyticum*\|*Anaerococcus hydrogenalis, Clostridium scindens*\|*Anaerococcus hydrogenalis, Clostridium symbiosum*\|*Anaerococcus hydrogenalis, Clostridium tertium*\|*Anaerococcus hydrogenalis, Collinsella aerofaciens*\|*Anaerococcus hydrogenalis, Collinsella intestinalis*\|*Anaerococcus hydrogenalis, Collinsella stercoris*\|*Anaerococcus hydrogenalis, Coprobacillus* sp. D7\|*Anaerococcus hydrogenalis, Coprococcus catus*\|*Anaerococcus hydrogenalis, Coprococcus comes*\|*Anaerococcus hydrogenalis, Coprococcus eutactus*\|*Anaerococcus hydrogenalis, Corynebacterium aurimucosum*\|*Anaerococcus hydrogenalis, Corynebacterium matruchotii*\|*Anaerococcus hydrogenalis, Cryptobacterium curtum*\|*Anaerococcus hydrogenalis, Desulfovibrio desulfuricans*\|*Anaerococcus hydrogenalis, Desulfovibrio piger*\|*Anaerococcus hydrogenalis, Dialister invisus*\|*Anaerococcus hydrogenalis, Dialister microaerophilus*\|*Anaerococcus hydrogenalis, Dorea formicigenerans*\|*Anaerococcus hydrogenalis, Dorea longicatena*\|*Anaerococcus hydrogenalis, Eggerthella lenta*\|*Anaerococcus hydrogenalis, Eikenella corrodens*\|*Anaerococcus hydrogenalis, Enterobacter cancerogenus*\|*Anaerococcus hydrogenalis, Enterobacter cloacae*\|*Anaerococcus hydrogenalis, Enterococcus faecalis*\|*Anaerococcus hydrogenalis, Enterococcus faecium*\|*Anaerococcus hydrogenalis, Enterococcus gallinarum*\|*Anaerococcus hydrogenalis, Erysipelotrichaceae bacterium* 3_1_53\|*Anaerococcus hydrogenalis, Escherichia coli*\|*Anaerococcus hydrogenalis, Escherichia fergusonii*\|*Anaerococcus hydrogenalis, Ethanoligenens harbinense*\|*Anaerococcus hydrogenalis, Eubacterium cellulosolvens*\|*Anaerococcus hydrogenalis, Eubacterium eligens*\|*Anaerococcus hydrogenalis, Eubacterium hallii*\|*Anaerococcus hydrogenalis, Eubacterium limosum*\|*Anaerococcus hydrogenalis, Eubacterium rectale*\|*Anaerococcus hydrogenalis, Eubacterium siraeum*\|*Anaerococcus hydrogenalis, Eubacterium ventriosum*\|*Anaerococcus hydrogenalis, Faecalibacterium prausnitzii*\|*Anaerococcus hydrogenalis, Finegoldia magna*\|*Anaerococcus hydrogenalis, Fusobacterium gonidiaformans*\|*Anaerococcus hydrogenalis, Fusobacterium mortiferum*\|*Anaerococcus hydrogenalis, Fusobacterium nucleatum*\|*Anaerococcus hydrogenalis, Fusobacterium varium*\|*Anaerococcus hydrogenalis, Gardnerella vaginalis*\|*Anaerococcus hydrogenalis, Gemella haemolysans*\|*Anaerococcus hydrogenalis, Gemella morbillorum*\|*Anaerococcus hydrogenalis, Gordonibacter pamelaeae*\|*Anaerococcus hydrogenalis, Granulicatella adiacens*\|*Anaerococcus hydrogenalis, Granulicatella elegans*\|*Anaerococcus hydrogenalis, Haemophilus influenzae*\|*Anaerococcus hydrogenalis, Haemophilus parainfluenzae*\|*Anaerococcus hydrogenalis, Helicobacter pullorum*\|*Anaerococcus hydrogenalis, Helicobacter pylori*\|*Anaerococcus hydrogenalis, Holdemania filiformis*\|*Anaerococcus hydrogenalis, Kingella oralis*\|*Anaerococcus hydrogenalis, Klebsiella pneumoniae*\|*Anaerococcus hydrogenalis, Klebsiella variicola*\|*Anaerococcus hydrogenalis, Lachnospiraceae bacterium* 5_1_57FAA\|*Anaerococcus hydrogenalis, Lactobacillus acidophilus*\|*Anaerococcus hydrogenalis, Lactobacillus amylovorus*\|*Anaerococcus hydrogenalis, Lactobacillus brevis*\|*Anaerococcus hydrogenalis, Lactobacillus casei*\|*Anaerococcus hydrogenalis, Lactobacillus crispatus*\|*Anaerococcus hydrogenalis, Lactobacillus delbrueckii*\|*Anaerococcus hydrogenalis, Lactobacillus fermentum*\|*Anaerococcus hydrogenalis, Lactobacillus gasseri*\|*Anaerococcus hydrogenalis, Lactobacillus iners*\|*Anaerococcus hydrogenalis, Lactobacillus jensenii*\|*Anaerococcus hydrogenalis, Lactobacillus johnsonii*\|*Anaerococcus hydrogenalis, Lactobacillus paracasei*\|*Anaerococcus hydrogenalis, Lactobacillus plantarum*\|*Anaerococcus hydrogenalis, Lactobacillus reuteri*\|*Anaerococcus hydrogenalis, Lactobacillus rhamnosus*\|*Anaerococcus hydrogenalis, Lactobacillus ruminis*\|*Anaerococcus hydrogenalis, Lactobacillus sakei*\|*Anaerococcus hydrogenalis, Lactobacillus salivarius*\|*Anaerococcus hydrogenalis, Lactococcus lactis*\|*Anaerococcus hydrogenalis, Lautropia mirabilis*\|*Anaerococcus hydrogenalis, Leuconostoc citreum*\|*Anaerococcus hydrogenalis, Leuconostoc gasicomitatum*\|*Anaerococcus hydrogenalis, Leuconostoc mesenteroides*\|*Anaerococcus hydrogenalis, Listeria monocytogenes*\|*Anaerococcus hydrogenalis, Marvinbryantia formatexigens*\|*Anaerococcus hydrogenalis, Megamonas hypermegale*\|*Anaerococcus hydrogenalis, Megasphaera micronuciformis*\|*Anaerococcus hydrogenalis, Methanobrevibacter smithii*\|*Anaerococcus hydrogenalis, Methanosphaera stadtmanae*\|*Anaerococcus hydrogenalis, Methylobacterium radiotolerans*\|*Anaerococcus hydrogenalis, Mitsuokella multacida*\|*Anaerococcus hydrogenalis, Mobiluncus curtisii*\|*Anaerococcus hydrogenalis, Mycoplasma hominis*\|*Anaerococcus hydrogenalis, Neisseria mucosa*\|*Anaerococcus hydrogenalis, Odoribacter splanchnicus*\|*Anaerococcus hydrogenalis, Olsenella uli*\|*Anaerococcus hydrogenalis, Oribacterium sinus*\|*Anaerococcus hydrogenalis, Oxalobacter formigenes*\|*Anaerococcus hydrogenalis, Parabacteroides distasonis*\|*Anaerococcus hydrogenalis, Parabacteroides johnsonii*\|*Anaerococcus hydrogenalis, Parabacteroides merdae*\|*Anaerococcus hydrogenalis, Parvimonas micra*\|*Anaerococcus hydrogenalis, Pediococcus acidilactici*\|*Anaerococcus hydrogenalis, Pediococcus pentosaceus*\|*Anaerococcus hydrogenalis, Peptoniphilus duerdenii*\|*Anaerococcus hydrogenalis, Peptoniphilus harei*\|*Anaerococcus hydrogenalis, Peptoniphilus lacrimalis*\|*Anaerococcus hydrogenalis, Peptostreptococcus anaerobius*\|*Anaerococcus hydrogenalis, Peptostreptococcus stomatis*\|*Anaerococcus hydrogenalis, Porphyromonas asaccharolytica*\|*Anaerococcus hydrogenalis, Porphyromonas uenonis*\|*Anaerococcus hydrogenalis, Prevotella amnii*\|*Anaerococcus hydrogenalis, Prevotella bergensis*\|*Anaerococcus hydrogenalis, Prevotella bivia*\|*Anaerococcus hydrogenalis, Prevotella buccae*\|*Anaerococcus hydrogenalis, Prevotella buccalis*\|*Anaerococcus hydrogenalis, Prevotella copri*\|*Anaerococcus hydrogenalis, Prevotella disiens*\|*Anaerococcus hydrogenalis, Prevotella melaninogenica*\|*Anaerococcus hydrogenalis, Prevotella multiformis*\|*Anaerococcus hydrogenalis, Prevotella oralis*\|*Anaerococcus hydrogenalis, Prevotella oris*\|*Anaerococcus hydrogenalis, Prevotella salivae*\|*Anaerococcus hydrogenalis, Prevotella timonensis*\|*Anaerococcus hydrogenalis, Propionibacterium acnes*\|*Anaerococcus hydrogenalis, Propionibacterium freudenreichii*\|*Anaerococcus hydrogenalis, Proteus mirabilis*\|*Anaerococcus hydrogenalis, Proteus penneri*\|*Anaerococcus hydrogenalis, Pseudoflavonifractor capillosus*\|*Anaerococcus hydrogenalis, Pseudomonas aeruginosa*\|*Anaerococcus hydrogenalis, Pseudomonas fluorescens*\|*Anaerococcus hydrogenalis, Pseudomonas putida*\|*Anaerococcus hydrogenalis, Pseudoramibacter alactolyticus*\|*Anaerococcus hydrogenalis, Pyramidobacter piscolens*\|*Anaerococcus hydrogenalis, Rhodopseudomonas palustris*\|*Anaerococcus hydrogenalis, Roseburia intestinalis*\|*Anaerococcus hydrogenalis, Roseburia inulinivorans*\|*Anaerococcus hydrogenalis, Rothia dentocariosa*\|*Anaerococcus hydrogenalis, Rothia mucilaginosa*\|*Anaerococcus hydrogenalis, Ruminococcus albus*\|*Anaerococcus hydrogenalis, Ruminococcus bromii*\|*Anaerococcus hydrogenalis, Ruminococcus gnavus*\|*Anaerococcus hydrogenalis, Ruminococcus lactaris*\|*Anaerococcus hydrogenalis, Ruminococcus obeum*\|*Anaerococcus hydrogenalis, Ruminococcus torques*\|*Anaerococcus hydrogenalis, Selenomonas sputigena*\|*Anaerococcus hydrogenalis, Shigella boydii*\|*Anaerococcus hydrogenalis, Shigella dysenteriae*\|*Anaerococcus hydrogenalis, Shigella sonnei*\|*Anaerococcus hydrogenalis, Slackia exigua*\|*Anaerococcus hydrogenalis, Solobacterium moorei*\|*Anaerococcus hydrogenalis, Staphylococcus aureus*\|*Anaerococcus hydrogenalis, Staphylococcus epidermidis*\|*Anaerococcus hydrogenalis, Staphylococcus hominis*\|*Anaerococcus hydrogenalis, Staphylococcus saprophyticus*\|*Anaerococcus hydrogenalis, Staphylococcus warneri*\|*Anaerococcus hydrogenalis, Streptococcus agalactiae*\|*Anaerococcus hydrogenalis, Streptococcus anginosus*\|*Anaerococcus hydrogenalis, Streptococcus australis*\|*Anaerococcus hydrogenalis, Streptococcus bovis*\|*Anaerococcus hydrogenalis, Streptococcus cristatus*\|*Anaerococcus hydrogenalis, Streptococcus dysgalactiae*\|*Anaerococcus hydrogenalis, Streptococcus equinus*\|*Anaerococcus hydrogenalis, Streptococcus gordonii*\|*Anaerococcus hydrogenalis, Streptococcus infantarius*\|*Anaerococcus hydrogenalis, Streptococcus infantis*\|*Anaerococcus hydrogenalis, Streptococcus mitis*\|*Anaerococcus hydrogenalis, Streptococcus mutans*\|*Anaerococcus hydrogenalis, Streptococcus oralis*\|*Anaerococcus hydrogenalis, Streptococcus parasanguinis*\|*Anaerococcus hydrogenalis, Streptococcus peroris*\|*Anaerococcus hydrogenalis, Streptococcus pneumoniae*\|*Anaerococcus hydrogenalis, Streptococcus salivarius*\|*Anaerococcus hydrogenalis, Streptococcus sanguinis*\|*Anaerococcus hydrogenalis, Streptococcus thermophilus*\|*Anaerococcus hydrogenalis, Streptococcus vestibularis*\|*Anaerococcus hydrogenalis, Subdoligranulum variabile*\|*Anaerococcus hydrogenalis, Succinatimonas hippei*\|*Anaerococcus hydrogenalis, Sutterella wadsworthensis*\|*Anaerococcus hydrogenalis, Tropheryma whipplei*\|*Anaerococcus hydrogenalis, Veillonella atypica*\|*Anaerococcus hydrogenalis, Veillonella dispar*\|*Anaerococcus hydrogenalis, Veillonella parvula*\|*Anaerococcus hydrogenalis, Victivallis vadensis*\|*Anaerococcus lactolyticus, Anaerococcus lactolyticus*\|*Anaerococcus lactolyticus, Anaerococcus vaginalis*\|*Anaerococcus lactolyticus, Anaerostipes caccae*\|*Anaerococcus* |

TABLE 2-continued

Table 2. Specific binary combinations of OTUs. Individual pairings are differentiated by "|" and OTUs within a combination are differentiated by ","

lactolyticus, Anaerotruncus colihominis|Anaerococcus lactolyticus, Atopobium parvulum|Anaerococcus lactolyticus, Atopobium rimae|Anaerococcus lactolyticus, Atopobium vaginae|Anaerococcus lactolyticus, Bacteroides caccae|Anaerococcus lactolyticus, Bacteroides cellulosilyticus|Anaerococcus lactolyticus, Bacteroides coprocola|Anaerococcus lactolyticus, Bacteroides coprophilus|Anaerococcus lactolyticus, Bacteroides dorei|Anaerococcus lactolyticus, Bacteroides eggerthii|Anaerococcus lactolyticus, Bacteroides finegoldii|Anaerococcus lactolyticus, Bacteroides fragilis|Anaerococcus lactolyticus, Bacteroides helcogenes|Anaerococcus lactolyticus, Bacteroides intestinalis|Anaerococcus lactolyticus, Bacteroides ovatus|Anaerococcus lactolyticus, Bacteroides pectinophilus|Anaerococcus lactolyticus, Bacteroides plebeius|Anaerococcus lactolyticus, Bacteroides salanitronis|Anaerococcus lactolyticus, Bacteroides sp. 1_1_6|Anaerococcus lactolyticus, Bacteroides sp. 3_1_23|Anaerococcus lactolyticus, Bacteroides stercoris|Anaerococcus lactolyticus, Bacteroides thetaiotaomicron|Anaerococcus lactolyticus, Bacteroides uniformis|Anaerococcus lactolyticus, Bacteroides vulgatus|Anaerococcus lactolyticus, Bacteroides xylanisolvens|Anaerococcus lactolyticus, Bifidobacterium adolescentis|Anaerococcus lactolyticus, Bifidobacterium angulatum|Anaerococcus lactolyticus, Bifidobacterium animalis|Anaerococcus lactolyticus, Bifidobacterium bifidum|Anaerococcus lactolyticus, Bifidobacterium breve|Anaerococcus lactolyticus, Bifidobacterium catenulatum|Anaerococcus lactolyticus, Bifidobacterium dentium|Anaerococcus lactolyticus, Bifidobacterium infantis|Anaerococcus lactolyticus, Bifidobacterium longum|Anaerococcus lactolyticus, Bifidobacterium pseudocatenulatum|Anaerococcus lactolyticus, Bilophila wadsworthia|Anaerococcus lactolyticus, Blautia hansenii|Anaerococcus lactolyticus, Blautia hydrogenotrophica|Anaerococcus lactolyticus, Blautia producta|Anaerococcus lactolyticus, Blautia schinkii|Anaerococcus lactolyticus, Brevibacterium linens|Anaerococcus lactolyticus, Brucella ceti|Anaerococcus lactolyticus, Brucella suis|Anaerococcus lactolyticus, Bulleidia extructa|Anaerococcus lactolyticus, Butyrivibrio crossotus|Anaerococcus lactolyticus, Campylobacter concisus|Anaerococcus lactolyticus, Campylobacter curvus|Anaerococcus lactolyticus, Campylobacter gracilis|Anaerococcus lactolyticus, Campylobacter hominis|Anaerococcus lactolyticus, Capnocytophaga ochracea|Anaerococcus lactolyticus, Cardiobacterium hominis|Anaerococcus lactolyticus, Catenibacterium mitsuokai|Anaerococcus lactolyticus, Catonella morbi|Anaerococcus lactolyticus, Citrobacter koseri|Anaerococcus lactolyticus, Clostridium asparagiforme|Anaerococcus lactolyticus, Clostridium bartlettii|Anaerococcus lactolyticus, Clostridium bolteae|Anaerococcus lactolyticus, Clostridium botulinum|Anaerococcus lactolyticus, Clostridium butyricum|Anaerococcus lactolyticus, Clostridium difficile|Anaerococcus lactolyticus, Clostridium disporicum|Anaerococcus lactolyticus, Clostridium hathewayi|Anaerococcus lactolyticus, Clostridium hylemonae|Anaerococcus lactolyticus, Clostridium innocuum|Anaerococcus lactolyticus, Clostridium leptum|Anaerococcus lactolyticus, Clostridium mayombei|Anaerococcus lactolyticus, Clostridium methylpentosum|Anaerococcus lactolyticus, Clostridium nexile|Anaerococcus lactolyticus, Clostridium orbiscindens|Anaerococcus lactolyticus, Clostridium perfringens|Anaerococcus lactolyticus, Clostridium saccharolyticum|Anaerococcus lactolyticus, Clostridium scindens|Anaerococcus lactolyticus, Clostridium symbiosum|Anaerococcus lactolyticus, Clostridium tertium|Anaerococcus lactolyticus, Collinsella aerofaciens|Anaerococcus lactolyticus, Collinsella intestinalis|Anaerococcus lactolyticus, Collinsella stercoris|Anaerococcus lactolyticus, Coprobacillus sp. D7|Anaerococcus lactolyticus, Coprococcus catus|Anaerococcus lactolyticus, Coprococcus comes|Anaerococcus lactolyticus, Coprococcus eutactus|Anaerococcus lactolyticus, Corynebacterium aurimucosum|Anaerococcus lactolyticus, Corynebacterium matruchotii|Anaerococcus lactolyticus, Cryptobacterium curtum|Anaerococcus lactolyticus, Desulfovibrio desulfuricans|Anaerococcus lactolyticus, Desulfovibrio piger|Anaerococcus lactolyticus, Dialister invisus|Anaerococcus lactolyticus, Dialister microaerophilus|Anaerococcus lactolyticus, Dorea formicigenerans|Anaerococcus lactolyticus, Dorea longicatena|Anaerococcus lactolyticus, Eggerthella lenta|Anaerococcus lactolyticus, Eikenella corrodens|Anaerococcus lactolyticus, Enterobacter cancerogenus|Anaerococcus lactolyticus, Enterobacter cloacae|Anaerococcus lactolyticus, Enterococcus faecalis|Anaerococcus lactolyticus, Enterococcus faecium|Anaerococcus lactolyticus, Enterococcus gallinarum|Anaerococcus lactolyticus, Erysipelotrichaceae bacterium 3_1_53|Anaerococcus lactolyticus, Escherichia coli|Anaerococcus lactolyticus, Escherichia fergusonii|Anaerococcus lactolyticus, Ethanoligenens harbinense|Anaerococcus lactolyticus, Eubacterium cellulosolvens|Anaerococcus lactolyticus, Eubacterium eligens|Anaerococcus lactolyticus, Eubacterium hallii|Anaerococcus lactolyticus, Eubacterium limosum|Anaerococcus lactolyticus, Eubacterium rectale|Anaerococcus lactolyticus, Eubacterium siraeum|Anaerococcus lactolyticus, Eubacterium ventriosum|Anaerococcus lactolyticus, Faecalibacterium prausnitzii|Anaerococcus lactolyticus, Finegoldia magna|Anaerococcus lactolyticus, Fusobacterium gonidiaformans|Anaerococcus lactolyticus, Fusobacterium mortiferum|Anaerococcus lactolyticus, Fusobacterium nucleatum|Anaerococcus lactolyticus, Fusobacterium varium|Anaerococcus lactolyticus, Gardnerella vaginalis|Anaerococcus lactolyticus, Gemella haemolysans|Anaerococcus lactolyticus, Gemella morbillorum|Anaerococcus lactolyticus, Gordonibacter pamelaeae|Anaerococcus lactolyticus, Granulicatella adiacens|Anaerococcus lactolyticus, Granulicatella elegans|Anaerococcus lactolyticus, Haemophilus influenzae|Anaerococcus lactolyticus, Haemophilus parainfluenzae|Anaerococcus lactolyticus, Helicobacter pullorum|Anaerococcus lactolyticus, Helicobacter pylori|Anaerococcus lactolyticus, Holdemania filiformis|Anaerococcus lactolyticus, Kingella oralis|Anaerococcus lactolyticus, Klebsiella pneumoniae|Anaerococcus lactolyticus, Klebsiella variicola|Anaerococcus lactolyticus, Lachnospiraceae bacterium 5_1_57FAA|Anaerococcus lactolyticus, Lactobacillus acidophilus|Anaerococcus lactolyticus, Lactobacillus amylovorus|Anaerococcus lactolyticus, Lactobacillus brevis|Anaerococcus lactolyticus, Lactobacillus casei|Anaerococcus lactolyticus, Lactobacillus crispatus|Anaerococcus lactolyticus, Lactobacillus delbrueckii|Anaerococcus lactolyticus, Lactobacillus fermentum|Anaerococcus lactolyticus, Lactobacillus gasseri|Anaerococcus lactolyticus, Lactobacillus iners|Anaerococcus lactolyticus, Lactobacillus jensenii|Anaerococcus lactolyticus, Lactobacillus johnsonii|Anaerococcus lactolyticus, Lactobacillus paracasei|Anaerococcus lactolyticus, Lactobacillus plantarum|Anaerococcus lactolyticus, Lactobacillus reuteri|Anaerococcus lactolyticus, Lactobacillus rhamnosus|Anaerococcus lactolyticus, Lactobacillus ruminis|Anaerococcus lactolyticus, Lactobacillus sakei|Anaerococcus lactolyticus, Lactobacillus salivarius|Anaerococcus lactolyticus, Lactococcus lactis|Anaerococcus lactolyticus, Lautropia mirabilis|Anaerococcus lactolyticus, Leuconostoc citreum|Anaerococcus lactolyticus, Leuconostoc gasicomitatum|Anaerococcus lactolyticus, Leuconostoc mesenteroides|Anaerococcus lactolyticus, Listeria monocytogenes|Anaerococcus lactolyticus, Marvinbryantia formatexigens|Anaerococcus lactolyticus, Megamonas hypermegale|Anaerococcus lactolyticus, Megasphaera micronuciformis|Anaerococcus lactolyticus, Methanobrevibacter smithii|Anaerococcus lactolyticus, Methanosphaera stadtmanae|Anaerococcus lactolyticus, Methylobacterium radiotolerans|Anaerococcus lactolyticus, Mitsuokella multacida|Anaerococcus lactolyticus, Mobiluncus curtisii|Anaerococcus lactolyticus, Mycoplasma hominis|Anaerococcus lactolyticus, Neisseria mucosa|Anaerococcus lactolyticus, Odoribacter splanchnicus|Anaerococcus lactolyticus, Olsenella uli|Anaerococcus lactolyticus, Oribacterium sinus|Anaerococcus lactolyticus, Oxalobacter formigenes|Anaerococcus lactolyticus, Parabacteroides distasonis|Anaerococcus lactolyticus, Parabacteroides johnsonii|Anaerococcus lactolyticus, Parabacteroides merdae|Anaerococcus lactolyticus, Parvimonas micra|Anaerococcus lactolyticus, Pediococcus acidilactici|Anaerococcus lactolyticus, Pediococcus pentosaceus|Anaerococcus lactolyticus, Peptoniphilus duerdenii|Anaerococcus lactolyticus, Peptoniphilus harei|Anaerococcus lactolyticus, Peptoniphilus lacrimalis|Anaerococcus lactolyticus, Peptostreptococcus anaerobius|Anaerococcus lactolyticus, Peptostreptococcus stomatis|Anaerococcus lactolyticus, Porphyromonas asaccharolytica|Anaerococcus lactolyticus, Porphyromonas uenonis|Anaerococcus lactolyticus, Prevotella amnii|Anaerococcus lactolyticus, Prevotella bergensis|Anaerococcus lactolyticus, Prevotella bivia|Anaerococcus lactolyticus, Prevotella buccae|Anaerococcus lactolyticus, Prevotella buccalis|Anaerococcus lactolyticus, Prevotella copri|Anaerococcus lactolyticus, Prevotella disiens|Anaerococcus lactolyticus, Prevotella melaninogenica|Anaerococcus lactolyticus, Prevotella multiformis|Anaerococcus lactolyticus, Prevotella oralis|Anaerococcus lactolyticus, Prevotella oris|Anaerococcus lactolyticus, Prevotella salivae|Anaerococcus lactolyticus, Prevotella timonensis|Anaerococcus lactolyticus, Propionibacterium acnes|Anaerococcus lactolyticus, Propionibacterium freudenreichii|Anaerococcus lactolyticus, Proteus mirabilis|Anaerococcus lactolyticus, Proteus penneri|Anaerococcus lactolyticus, Pseudoflavonifractor capillosus|Anaerococcus lactolyticus, Pseudomonas aeruginosa|Anaerococcus lactolyticus, Pseudomonas fluorescens|Anaerococcus TABLE 2-continued

| Table 2. Specific binary combinations of OTUs. Individual pairings are differentiated by "\|" and OTUs within a combination are differentiated by "," |
|---|
| *lactolyticus, Pseudomonas putida\|Anaerococcus lactolyticus, Pseudoramibacter alactolyticus\|Anaerococcus lactolyticus, Pyramidobacter piscolens\|Anaerococcus lactolyticus, Rhodopseudomonas palustris\|Anaerococcus lactolyticus, Roseburia intestinalis\|Anaerococcus lactolyticus, Roseburia inulinivorans\|Anaerococcus lactolyticus, Rothia dentocariosa\|Anaerococcus lactolyticus, Rothia mucilaginosa\|Anaerococcus lactolyticus, Ruminococcus albus\|Anaerococcus lactolyticus, Ruminococcus bromii\|Anaerococcus lactolyticus, Ruminococcus gnavus\|Anaerococcus lactolyticus, Ruminococcus lactaris\|Anaerococcus lactolyticus, Ruminococcus obeum\|Anaerococcus lactolyticus, Ruminococcus torques\|Anaerococcus lactolyticus, Selenomonas sputigena\|Anaerococcus lactolyticus, Shigella boydii\|Anaerococcus lactolyticus, Shigella dysenteriae\|Anaerococcus lactolyticus, Shigella sonnei\|Anaerococcus lactolyticus, Slackia exigua\|Anaerococcus lactolyticus, Solobacterium moorei\|Anaerococcus lactolyticus, Staphylococcus aureus\|Anaerococcus lactolyticus, Staphylococcus epidermidis\|Anaerococcus lactolyticus, Staphylococcus hominis\|Anaerococcus lactolyticus, Staphylococcus saprophyticus\|Anaerococcus lactolyticus, Staphylococcus warneri\|Anaerococcus lactolyticus, Streptococcus agalactiae\|Anaerococcus lactolyticus, Streptococcus anginosus\|Anaerococcus lactolyticus, Streptococcus australis\|Anaerococcus lactolyticus, Streptococcus bovis\|Anaerococcus lactolyticus, Streptococcus cristatus\|Anaerococcus lactolyticus, Streptococcus dysgalactiae\|Anaerococcus lactolyticus, Streptococcus equinus\|Anaerococcus lactolyticus, Streptococcus gordonii\|Anaerococcus lactolyticus, Streptococcus infantarius\|Anaerococcus lactolyticus, Streptococcus infantis\|Anaerococcus lactolyticus, Streptococcus mitis\|Anaerococcus lactolyticus, Streptococcus mutans\|Anaerococcus lactolyticus, Streptococcus oralis\|Anaerococcus lactolyticus, Streptococcus parasanguinis\|Anaerococcus lactolyticus, Streptococcus peroris\|Anaerococcus lactolyticus, Streptococcus pneumoniae\|Anaerococcus lactolyticus, Streptococcus salivarius\|Anaerococcus lactolyticus, Streptococcus sanguinis\|Anaerococcus lactolyticus, Streptococcus thermophilus\|Anaerococcus lactolyticus, Streptococcus vestibularis\|Anaerococcus lactolyticus, Subdoligranulum variabile\|Anaerococcus lactolyticus, Succinatimonas hippei\|Anaerococcus lactolyticus, Sutterella wadsworthensis\|Anaerococcus lactolyticus, Tropheryma whipplei\|Anaerococcus lactolyticus, Veillonella atypica\|Anaerococcus lactolyticus, Veillonella dispar\|Anaerococcus lactolyticus, Veillonella parvula\|Anaerococcus lactolyticus, Victivallis vadensis\|Anaerococcus vaginalis, Anaerococcus vaginalis\|Anaerococcus vaginalis, Anaerostipes caccae\|Anaerococcus vaginalis, Anaerotruncus colihominis\|Anaerococcus vaginalis, Atopobium parvulum\|Anaerococcus vaginalis, Atopobium rimae\|Anaerococcus vaginalis, Atopobium vaginae\|Anaerococcus vaginalis, Bacteroides caccae\|Anaerococcus vaginalis, Bacteroides cellulosilyticus\|Anaerococcus vaginalis, Bacteroides coprocola\|Anaerococcus vaginalis, Bacteroides coprophilus\|Anaerococcus vaginalis, Bacteroides dorei\|Anaerococcus vaginalis, Bacteroides eggerthii\|Anaerococcus vaginalis, Bacteroides finegoldii\|Anaerococcus vaginalis, Bacteroides fragilis\|Anaerococcus vaginalis, Bacteroides helcogenes\|Anaerococcus vaginalis, Bacteroides intestinalis\|Anaerococcus vaginalis, Bacteroides ovatus\|Anaerococcus vaginalis, Bacteroides pectinophilus\|Anaerococcus vaginalis, Bacteroides plebeius\|Anaerococcus vaginalis, Bacteroides salanitronis\|Anaerococcus vaginalis, Bacteroides* sp. 1_1_6*\|Anaerococcus vaginalis, Bacteroides* sp. 3_1_23*\|Anaerococcus vaginalis, Bacteroides stercoris\|Anaerococcus vaginalis, Bacteroides thetaiotaomicron\|Anaerococcus vaginalis, Bacteroides uniformis\|Anaerococcus vaginalis, Bacteroides vulgatus\|Anaerococcus vaginalis, Bacteroides xylanisolvens\|Anaerococcus vaginalis, Bifidobacterium adolescentis\|Anaerococcus vaginalis, Bifidobacterium angulatum\|Anaerococcus vaginalis, Bifidobacterium animalis\|Anaerococcus vaginalis, Bifidobacterium bifidum\|Anaerococcus vaginalis, Bifidobacterium breve\|Anaerococcus vaginalis, Bifidobacterium catenulatum\|Anaerococcus vaginalis, Bifidobacterium dentium\|Anaerococcus vaginalis, Bifidobacterium infantis\|Anaerococcus vaginalis, Bifidobacterium longum\|Anaerococcus vaginalis, Bifidobacterium pseudocatenulatum\|Anaerococcus vaginalis, Bilophila wadsworthia\|Anaerococcus vaginalis, Blautia hansenii\|Anaerococcus vaginalis, Blautia hydrogenotrophica\|Anaerococcus vaginalis, Blautia producta\|Anaerococcus vaginalis, Blautia schinkii\|Anaerococcus vaginalis, Brevibacterium linens\|Anaerococcus vaginalis, Brucella ceti\|Anaerococcus vaginalis, Brucella suis\|Anaerococcus vaginalis, Bulleidia extructa\|Anaerococcus vaginalis, Butyrivibrio crossotus\|Anaerococcus vaginalis, Campylobacter concisus\|Anaerococcus vaginalis, Campylobacter curvus\|Anaerococcus vaginalis, Campylobacter gracilis\|Anaerococcus vaginalis, Campylobacter hominis\|Anaerococcus vaginalis, Capnocytophaga ochracea\|Anaerococcus vaginalis, Cardiobacterium hominis\|Anaerococcus vaginalis, Catenibacterium mitsuokai\|Anaerococcus vaginalis, Catonella morbi\|Anaerococcus vaginalis, Citrobacter koseri\|Anaerococcus vaginalis, Clostridium asparagiforme\|Anaerococcus vaginalis, Clostridium bartlettii\|Anaerococcus vaginalis, Clostridium bolteae\|Anaerococcus vaginalis, Clostridium botulinum\|Anaerococcus vaginalis, Clostridium butyricum\|Anaerococcus vaginalis, Clostridium difficile\|Anaerococcus vaginalis, Clostridium disporicum\|Anaerococcus vaginalis, Clostridium hathewayi\|Anaerococcus vaginalis, Clostridium hylemonae\|Anaerococcus vaginalis, Clostridium innocuum\|Anaerococcus vaginalis, Clostridium leptum\|Anaerococcus vaginalis, Clostridium mayombei\|Anaerococcus vaginalis, Clostridium methylpentosum\|Anaerococcus vaginalis, Clostridium nexile\|Anaerococcus vaginalis, Clostridium orbiscindens\|Anaerococcus vaginalis, Clostridium perfringens\|Anaerococcus vaginalis, Clostridium saccharolyticum\|Anaerococcus vaginalis, Clostridium scindens\|Anaerococcus vaginalis, Clostridium symbiosum\|Anaerococcus vaginalis, Clostridium tertium\|Anaerococcus vaginalis, Collinsella aerofaciens\|Anaerococcus vaginalis, Collinsella intestinalis\|Anaerococcus vaginalis, Collinsella stercoris\|Anaerococcus vaginalis, Coprobacillus* sp. D7*\|Anaerococcus vaginalis, Coprococcus catus\|Anaerococcus vaginalis, Coprococcus comes\|Anaerococcus vaginalis, Coprococcus eutactus\|Anaerococcus vaginalis, Corynebacterium aurimucosum\|Anaerococcus vaginalis, Corynebacterium matruchotii\|Anaerococcus vaginalis, Cryptobacterium curtum\|Anaerococcus vaginalis, Desulfovibrio desulfuricans\|Anaerococcus vaginalis, Desulfovibrio piger\|Anaerococcus vaginalis, Dialister invisus\|Anaerococcus vaginalis, Dialister microaerophilus\|Anaerococcus vaginalis, Dorea formicigenerans\|Anaerococcus vaginalis, Dorea longicatena\|Anaerococcus vaginalis, Eggerthella lenta\|Anaerococcus vaginalis, Eikenella corrodens\|Anaerococcus vaginalis, Enterobacter cancerogenus\|Anaerococcus vaginalis, Enterobacter cloacae\|Anaerococcus vaginalis, Enterococcus faecalis\|Anaerococcus vaginalis, Enterococcus faecium\|Anaerococcus vaginalis, Enterococcus gallinarum\|Anaerococcus vaginalis, Erysipelotrichaceae bacterium* 3_1_53*\|Anaerococcus vaginalis, Escherichia coli\|Anaerococcus vaginalis, Escherichia fergusonii\|Anaerococcus vaginalis, Ethanoligenens harbinense\|Anaerococcus vaginalis, Eubacterium cellulosolvens\|Anaerococcus vaginalis, Eubacterium eligens\|Anaerococcus vaginalis, Eubacterium hallii\|Anaerococcus vaginalis, Eubacterium limosum\|Anaerococcus vaginalis, Eubacterium rectale\|Anaerococcus vaginalis, Eubacterium siraeum\|Anaerococcus vaginalis, Eubacterium ventriosum\|Anaerococcus vaginalis, Faecalibacterium prausnitzii\|Anaerococcus vaginalis, Finegoldia magna\|Anaerococcus vaginalis, Fusobacterium gonidiaformans\|Anaerococcus vaginalis, Fusobacterium mortiferum\|Anaerococcus vaginalis, Fusobacterium nucleatum\|Anaerococcus vaginalis, Fusobacterium varium\|Anaerococcus vaginalis, Gardnerella vaginalis\|Anaerococcus vaginalis, Gemella haemolysans\|Anaerococcus vaginalis, Gemella morbillorum\|Anaerococcus vaginalis, Gordonibacter pamelaeae\|Anaerococcus vaginalis, Granulicatella adiacens\|Anaerococcus vaginalis, Granulicatella elegans\|Anaerococcus vaginalis, Haemophilus influenzae\|Anaerococcus vaginalis, Haemophilus parainfluenzae\|Anaerococcus vaginalis, Helicobacter pullorum\|Anaerococcus vaginalis, Helicobacter pylori\|Anaerococcus vaginalis, Holdemania filiformis\|Anaerococcus vaginalis, Kingella oralis\|Anaerococcus vaginalis, Klebsiella pneumoniae\|Anaerococcus vaginalis, Klebsiella variicola\|Anaerococcus vaginalis, Lachnospiraceae bacterium* 5_1_57FAA*\|Anaerococcus vaginalis, Lactobacillus acidophilus\|Anaerococcus vaginalis, Lactobacillus amylovorus\|Anaerococcus vaginalis, Lactobacillus brevis\|Anaerococcus vaginalis, Lactobacillus casei\|Anaerococcus vaginalis, Lactobacillus crispatus\|Anaerococcus vaginalis, Lactobacillus delbrueckii\|Anaerococcus vaginalis, Lactobacillus fermentum\|Anaerococcus vaginalis, Lactobacillus gasseri\|Anaerococcus vaginalis, Lactobacillus iners\|Anaerococcus vaginalis, Lactobacillus jensenii\|Anaerococcus vaginalis, Lactobacillus johnsonii\|Anaerococcus vaginalis, Lactobacillus paracasei\|Anaerococcus vaginalis, Lactobacillus plantarum\|Anaerococcus vaginalis, Lactobacillus reuteri\|Anaerococcus vaginalis, Lactobacillus rhamnosus\|Anaerococcus vaginalis, Lactobacillus ruminis\|Anaerococcus vaginalis, Lactobacillus sakei\|Anaerococcus vaginalis, Lactobacillus salivarius\|Anaerococcus vaginalis, Lactococcus lactis\|Anaerococcus vaginalis, Lautropia mirabilis\|Anaerococcus vaginalis, Leuconostoc citreum\|Anaerococcus vaginalis, Leuconostoc gasicomitatum\|Anaerococcus vaginalis, Leuconostoc mesenteroides\|Anaerococcus vaginalis, Listeria monocytogenes\|Anaerococcus vaginalis, Marvinbryantia* |

TABLE 2-continued

| Table 2. Specific binary combinations of OTUs. Individual pairings are differentiated by "\|" and OTUs within a combination are differentiated by "," |
|---|
| formatexigens\|Anaerococcus vaginalis, Megamonas hypermegale\|Anaerococcus vaginalis, Megasphaera micronuciformis\|Anaerococcus vaginalis, Methanobrevibacter smithii\|Anaerococcus vaginalis, Methanosphaera stadtmanae\|Anaerococcus vaginalis, Methylobacterium radiotolerans\|Anaerococcus vaginalis, Mitsuokella multacida\|Anaerococcus vaginalis, Mobiluncus curtisii\|Anaerococcus vaginalis, Mycoplasma hominis\|Anaerococcus vaginalis, Neisseria mucosa\|Anaerococcus vaginalis, Odoribacter splanchnicus\|Anaerococcus vaginalis, Olsenella uli\|Anaerococcus vaginalis, Oribacterium sinus\|Anaerococcus vaginalis, Oxalobacter formigenes\|Anaerococcus vaginalis, Parabacteroides distasonis\|Anaerococcus vaginalis, Parabacteroides johnsonii\|Anaerococcus vaginalis, Parabacteroides merdae\|Anaerococcus vaginalis, Parvimonas micra\|Anaerococcus vaginalis, Pediococcus acidilactici\|Anaerococcus vaginalis, Pediococcus pentosaceus\|Anaerococcus vaginalis, Peptoniphilus duerdenii\|Anaerococcus vaginalis, Peptoniphilus harei\|Anaerococcus vaginalis, Peptoniphilus lacrimalis\|Anaerococcus vaginalis, Peptostreptococcus anaerobius\|Anaerococcus vaginalis, Peptostreptococcus stomatis\|Anaerococcus vaginalis, Porphyromonas asaccharolytica\|Anaerococcus vaginalis, Porphyromonas uenonis\|Anaerococcus vaginalis, Prevotella amnii\|Anaerococcus vaginalis, Prevotella bergensis\|Anaerococcus vaginalis, Prevotella bivia\|Anaerococcus vaginalis, Prevotella buccae\|Anaerococcus vaginalis, Prevotella buccalis\|Anaerococcus vaginalis, Prevotella copri\|Anaerococcus vaginalis, Prevotella disiens\|Anaerococcus vaginalis, Prevotella melaninogenica\|Anaerococcus vaginalis, Prevotella multiformis\|Anaerococcus vaginalis, Prevotella oralis\|Anaerococcus vaginalis, Prevotella oris\|Anaerococcus vaginalis, Prevotella salivae\|Anaerococcus vaginalis, Prevotella timonensis\|Anaerococcus vaginalis, Propionibacterium acnes\|Anaerococcus vaginalis, Propionibacterium freudenreichii\|Anaerococcus vaginalis, Proteus mirabilis\|Anaerococcus vaginalis, Proteus penneri\|Anaerococcus vaginalis, Pseudoflavonifractor capillosus\|Anaerococcus vaginalis, Pseudomonas aeruginosa\|Anaerococcus vaginalis, Pseudomonas fluorescens\|Anaerococcus vaginalis, Pseudomonas putida\|Anaerococcus vaginalis, Pseudoramibacter alactolyticus\|Anaerococcus vaginalis, Pyramidobacter piscolens\|Anaerococcus vaginalis, Rhodopseudomonas palustris\|Anaerococcus vaginalis, Roseburia intestinalis\|Anaerococcus vaginalis, Roseburia inulinivorans\|Anaerococcus vaginalis, Rothia dentocariosa\|Anaerococcus vaginalis, Rothia mucilaginosa\|Anaerococcus vaginalis, Ruminococcus albus\|Anaerococcus vaginalis, Ruminococcus bromii\|Anaerococcus vaginalis, Ruminococcus gnavus\|Anaerococcus vaginalis, Ruminococcus lactaris\|Anaerococcus vaginalis, Ruminococcus obeum\|Anaerococcus vaginalis, Ruminococcus torques\|Anaerococcus vaginalis, Selenomonas sputigena\|Anaerococcus vaginalis, Shigella boydii\|Anaerococcus vaginalis, Shigella dysenteriae\|Anaerococcus vaginalis, Shigella sonnei\|Anaerococcus vaginalis, Slackia exigua\|Anaerococcus vaginalis, Solobacterium moorei\|Anaerococcus vaginalis, Staphylococcus aureus\|Anaerococcus vaginalis, Staphylococcus epidermidis\|Anaerococcus vaginalis, Staphylococcus hominis\|Anaerococcus vaginalis, Staphylococcus saprophyticus\|Anaerococcus vaginalis, Staphylococcus warneri\|Anaerococcus vaginalis, Streptococcus agalactiae\|Anaerococcus vaginalis, Streptococcus anginosus\|Anaerococcus vaginalis, Streptococcus australis\|Anaerococcus vaginalis, Streptococcus bovis\|Anaerococcus vaginalis, Streptococcus cristatus\|Anaerococcus vaginalis, Streptococcus dysgalactiae\|Anaerococcus vaginalis, Streptococcus equinus\|Anaerococcus vaginalis, Streptococcus gordonii\|Anaerococcus vaginalis, Streptococcus infantarius\|Anaerococcus vaginalis, Streptococcus infantis\|Anaerococcus vaginalis, Streptococcus mitis\|Anaerococcus vaginalis, Streptococcus mutans\|Anaerococcus vaginalis, Streptococcus oralis\|Anaerococcus vaginalis, Streptococcus parasanguinis\|Anaerococcus vaginalis, Streptococcus peroris\|Anaerococcus vaginalis, Streptococcus pneumoniae\|Anaerococcus vaginalis, Streptococcus salivarius\|Anaerococcus vaginalis, Streptococcus sanguinis\|Anaerococcus vaginalis, Streptococcus thermophilus\|Anaerococcus vaginalis, Streptococcus vestibularis\|Anaerococcus vaginalis, Subdoligranulum variabile\|Anaerococcus vaginalis, Succinatimonas hippei\|Anaerococcus vaginalis, Sutterella wadsworthensis\|Anaerococcus vaginalis, Tropheryma whipplei\|Anaerococcus vaginalis, Veillonella atypica\|Anaerococcus vaginalis, Veillonella dispar\|Anaerococcus vaginalis, Veillonella parvula\|Anaerococcus vaginalis, Victivallis vadensis\|Anaerostipes caccae, Anaerostipes caccae\|Anaerostipes caccae, Anaerotruncus colihominis\|Anaerostipes caccae, Atopobium parvulum\|Anaerostipes caccae, Atopobium rimae\|Anaerostipes caccae, Atopobium vaginae\|Anaerostipes caccae, Bacteroides caccae\|Anaerostipes caccae, Bacteroides cellulosilyticus\|Anaerostipes caccae, Bacteroides coprocola\|Anaerostipes caccae, Bacteroides coprophilus\|Anaerostipes caccae, Bacteroides dorei\|Anaerostipes caccae, Bacteroides eggerthii\|Anaerostipes caccae, Bacteroides finegoldii\|Anaerostipes caccae, Bacteroides fragilis\|Anaerostipes caccae, Bacteroides helcogenes\|Anaerostipes caccae, Bacteroides intestinalis\|Anaerostipes caccae, Bacteroides ovatus\|Anaerostipes caccae, Bacteroides pectinophilus\|Anaerostipes caccae, Bacteroides plebeius\|Anaerostipes caccae, Bacteroides salanitronis\|Anaerostipes caccae, Bacteroides sp. 1_1_6\|Anaerostipes caccae, Bacteroides sp. 3_1_23\|Anaerostipes caccae, Bacteroides stercoris\|Anaerostipes caccae, Bacteroides thetaiotaomicron\|Anaerostipes caccae, Bacteroides uniformis\|Anaerostipes caccae, Bacteroides vulgatus\|Anaerostipes caccae, Bacteroides xylanisolvens\|Anaerostipes caccae, Bifidobacterium adolescentis\|Anaerostipes caccae, Bifidobacterium angulatum\|Anaerostipes caccae, Bifidobacterium animalis\|Anaerostipes caccae, Bifidobacterium bifidum\|Anaerostipes caccae, Bifidobacterium breve\|Anaerostipes caccae, Bifidobacterium catenulatum\|Anaerostipes caccae, Bifidobacterium dentium\|Anaerostipes caccae, Bifidobacterium infantis\|Anaerostipes caccae, Bifidobacterium longum\|Anaerostipes caccae, Bifidobacterium pseudocatenulatum\|Anaerostipes caccae, Bilophila wadsworthia\|Anaerostipes caccae, Blautia hansenii\|Anaerostipes caccae, Blautia hydrogenotrophica\|Anaerostipes caccae, Blautia producta\|Anaerostipes caccae, Blautia schinkii\|Anaerostipes caccae, Brevibacterium linens\|Anaerostipes caccae, Brucella ceti\|Anaerostipes caccae, Brucella suis\|Anaerostipes caccae, Bulleidia extructa\|Anaerostipes caccae, Butyrivibrio crossotus\|Anaerostipes caccae, Campylobacter concisus\|Anaerostipes caccae, Campylobacter curvus\|Anaerostipes caccae, Campylobacter gracilis\|Anaerostipes caccae, Campylobacter hominis\|Anaerostipes caccae, Capnocytophaga ochracea\|Anaerostipes caccae, Cardiobacterium hominis\|Anaerostipes caccae, Catenibacterium mitsuokai\|Anaerostipes caccae, Catonella morbi\|Anaerostipes caccae, Citrobacter koseri\|Anaerostipes caccae, Clostridium asparagiforme\|Anaerostipes caccae, Clostridium bartlettii\|Anaerostipes caccae, Clostridium bolteae\|Anaerostipes caccae, Clostridium botulinum\|Anaerostipes caccae, Clostridium butyricum\|Anaerostipes caccae, Clostridium difficile\|Anaerostipes caccae, Clostridium disporicum\|Anaerostipes caccae, Clostridium hathewayi\|Anaerostipes caccae, Clostridium hylemonae\|Anaerostipes caccae, Clostridium innocuum\|Anaerostipes caccae, Clostridium leptum\|Anaerostipes caccae, Clostridium mayombei\|Anaerostipes caccae, Clostridium methylpentosum\|Anaerostipes caccae, Clostridium nexile\|Anaerostipes caccae, Clostridium orbiscindens\|Anaerostipes caccae, Clostridium perfringens\|Anaerostipes caccae, Clostridium saccharolyticum\|Anaerostipes caccae, Clostridium scindens\|Anaerostipes caccae, Clostridium symbiosum\|Anaerostipes caccae, Clostridium tertium\|Anaerostipes caccae, Collinsella aerofaciens\|Anaerostipes caccae, Collinsella intestinalis\|Anaerostipes caccae, Collinsella stercoris\|Anaerostipes caccae, Coprobacillus sp. D7\|Anaerostipes caccae, Coprococcus catus\|Anaerostipes caccae, Coprococcus comes\|Anaerostipes caccae, Coprococcus eutactus\|Anaerostipes caccae, Corynebacterium aurimucosum\|Anaerostipes caccae, Corynebacterium matruchotii\|Anaerostipes caccae, Cryptobacterium curtum\|Anaerostipes caccae, Desulfovibrio desulfuricans\|Anaerostipes caccae, Desulfovibrio piger\|Anaerostipes caccae, Dialister invisus\|Anaerostipes caccae, Dialister microaerophilus\|Anaerostipes caccae, Dorea formicigenerans\|Anaerostipes caccae, Dorea longicatena\|Anaerostipes caccae, Eggerthella lenta\|Anaerostipes caccae, Eikenella corrodens\|Anaerostipes caccae, Enterobacter cancerogenus\|Anaerostipes caccae, Enterobacter cloacae\|Anaerostipes caccae, Enterococcus faecalis\|Anaerostipes caccae, Enterococcus faecium\|Anaerostipes caccae, Enterococcus gallinarum\|Anaerostipes caccae, Erysipelotrichaceae bacterium 3_1_53\|Anaerostipes caccae, Escherichia coli\|Anaerostipes caccae, Escherichia fergusonii\|Anaerostipes caccae, Ethanoligenens harbinense\|Anaerostipes caccae, Eubacterium cellulosolvens\|Anaerostipes caccae, Eubacterium eligens\|Anaerostipes caccae, Eubacterium hallii\|Anaerostipes caccae, Eubacterium limosum\|Anaerostipes caccae, Eubacterium rectale\|Anaerostipes caccae, Eubacterium siraeum\|Anaerostipes caccae, Eubacterium ventriosum\|Anaerostipes caccae, Faecalibacterium prausnitzii\|Anaerostipes caccae, Finegoldia magna\|Anaerostipes caccae, Fusobacterium gonidiaformans\|Anaerostipes caccae, Fusobacterium mortiferum\|Anaerostipes caccae, Fusobacterium nucleatum\|Anaerostipes caccae, Fusobacterium varium\|Anaerostipes caccae, Gardnerella vaginalis\|Anaerostipes caccae, Gemella haemolysans\|Anaerostipes caccae, Gemella morbillorum\|Anaerostipes caccae, Gordonibacter pamelaeae\|Anaerostipes |

TABLE 2-continued

Table 2. Specific binary combinations of OTUs. Individual pairings are differentiated by "|" and OTUs within a combination are differentiated by ","

caccae, Granulicatella adiacens|Anaerostipes caccae, Granulicatella elegans|Anaerostipes caccae, Haemophilus influenzae|Anaerostipes caccae, Haemophilus parainfluenzae|Anaerostipes caccae, Helicobacter pullorum|Anaerostipes caccae, Helicobacter pylori|Anaerostipes caccae, Holdemania filiformis|Anaerostipes caccae, Kingella oralis|Anaerostipes caccae, Klebsiella pneumoniae|Anaerostipes caccae, Klebsiella variicola|Anaerostipes caccae, Lachnospiraceae bacterium 5_1_57FAA|Anaerostipes caccae, Lactobacillus acidophilus|Anaerostipes caccae, Lactobacillus amylovorus|Anaerostipes caccae, Lactobacillus brevis|Anaerostipes caccae, Lactobacillus casei|Anaerostipes caccae, Lactobacillus crispatus|Anaerostipes caccae, Lactobacillus delbrueckii|Anaerostipes caccae, Lactobacillus fermentum|Anaerostipes caccae, Lactobacillus gasseri|Anaerostipes caccae, Lactobacillus iners|Anaerostipes caccae, Lactobacillus jensenii|Anaerostipes caccae, Lactobacillus johnsonii|Anaerostipes caccae, Lactobacillus paracasei|Anaerostipes caccae, Lactobacillus plantarum|Anaerostipes caccae, Lactobacillus reuteri|Anaerostipes caccae, Lactobacillus rhamnosus|Anaerostipes caccae, Lactobacillus ruminis|Anaerostipes caccae, Lactobacillus sakei|Anaerostipes caccae, Lactobacillus salivarius|Anaerostipes caccae, Lactococcus lactis|Anaerostipes caccae, Lautropia mirabilis|Anaerostipes caccae, Leuconostoc citreum|Anaerostipes caccae, Leuconostoc gasicomitatum|Anaerostipes caccae, Leuconostoc mesenteroides|Anaerostipes caccae, Listeria monocytogenes|Anaerostipes caccae, Marvinbryantia formatexigens|Anaerostipes caccae, Megamonas hypermegale|Anaerostipes caccae, Megasphaera micronuciformis|Anaerostipes caccae, Methanobrevibacter smithii|Anaerostipes caccae, Methanosphaera stadtmanae|Anaerostipes caccae, Methylobacterium radiotolerans|Anaerostipes caccae, Mitsuokella multacida|Anaerostipes caccae, Mobiluncus curtisii|Anaerostipes caccae, Mycoplasma hominis|Anaerostipes caccae, Neisseria mucosa|Anaerostipes caccae, Odoribacter splanchnicus|Anaerostipes caccae, Olsenella uli|Anaerostipes caccae, Oribacterium sinus|Anaerostipes caccae, Oxalobacter formigenes|Anaerostipes caccae, Parabacteroides distasonis|Anaerostipes caccae, Parabacteroides johnsonii|Anaerostipes caccae, Parabacteroides merdae|Anaerostipes caccae, Parvimonas micra|Anaerostipes caccae, Pediococcus acidilactici|Anaerostipes caccae, Pediococcus pentosaceus|Anaerostipes caccae, Peptoniphilus duerdenii|Anaerostipes caccae, Peptoniphilus harei|Anaerostipes caccae, Peptoniphilus lacrimalis|Anaerostipes caccae, Peptostreptococcus anaerobius|Anaerostipes caccae, Peptostreptococcus stomatis|Anaerostipes caccae, Porphyromonas asaccharolytica|Anaerostipes caccae, Porphyromonas uenonis|Anaerostipes caccae, Prevotella amnii|Anaerostipes caccae, Prevotella bergensis|Anaerostipes caccae, Prevotella bivia|Anaerostipes caccae, Prevotella buccae|Anaerostipes caccae, Prevotella buccalis|Anaerostipes caccae, Prevotella copri|Anaerostipes caccae, Prevotella disiens|Anaerostipes caccae, Prevotella melaninogenica|Anaerostipes caccae, Prevotella multiformis|Anaerostipes caccae, Prevotella oralis|Anaerostipes caccae, Prevotella oris|Anaerostipes caccae, Prevotella salivae|Anaerostipes caccae, Prevotella timonensis|Anaerostipes caccae, Propionibacterium acnes|Anaerostipes caccae, Propionibacterium freudenreichii|Anaerostipes caccae, Proteus mirabilis|Anaerostipes caccae, Proteus penneri|Anaerostipes caccae, Pseudoflavonifractor capillosus|Anaerostipes caccae, Pseudomonas aeruginosa|Anaerostipes caccae, Pseudomonas fluorescens|Anaerostipes caccae, Pseudomonas putida|Anaerostipes caccae, Pseudoramibacter alactolyticus|Anaerostipes caccae, Pyramidobacter piscolens|Anaerostipes caccae, Rhodopseudomonas palustris|Anaerostipes caccae, Roseburia intestinalis|Anaerostipes caccae, Roseburia inulinivorans|Anaerostipes caccae, Rothia dentocariosa|Anaerostipes caccae, Rothia mucilaginosa|Anaerostipes caccae, Ruminococcus albus|Anaerostipes caccae, Ruminococcus bromii|Anaerostipes caccae, Ruminococcus gnavus|Anaerostipes caccae, Ruminococcus lactaris|Anaerostipes caccae, Ruminococcus obeum|Anaerostipes caccae, Ruminococcus torques|Anaerostipes caccae, Selenomonas sputigena|Anaerostipes caccae, Shigella boydii|Anaerostipes caccae, Shigella dysenteriae|Anaerostipes caccae, Shigella sonnei|Anaerostipes caccae, Slackia exigua|Anaerostipes caccae, Solobacterium moorei|Anaerostipes caccae, Staphylococcus aureus|Anaerostipes caccae, Staphylococcus epidermidis|Anaerostipes caccae, Staphylococcus hominis|Anaerostipes caccae, Staphylococcus saprophyticus|Anaerostipes caccae, Staphylococcus warneri|Anaerostipes caccae, Streptococcus agalactiae|Anaerostipes caccae, Streptococcus anginosus|Anaerostipes caccae, Streptococcus australis|Anaerostipes caccae, Streptococcus bovis|Anaerostipes caccae, Streptococcus cristatus|Anaerostipes caccae, Streptococcus dysgalactiae|Anaerostipes caccae, Streptococcus equinus|Anaerostipes caccae, Streptococcus gordonii|Anaerostipes caccae, Streptococcus infantarius|Anaerostipes caccae, Streptococcus infantis|Anaerostipes caccae, Streptococcus mitis|Anaerostipes caccae, Streptococcus mutans|Anaerostipes caccae, Streptococcus oralis|Anaerostipes caccae, Streptococcus parasanguinis|Anaerostipes caccae, Streptococcus peroris|Anaerostipes caccae, Streptococcus pneumoniae|Anaerostipes caccae, Streptococcus salivarius|Anaerostipes caccae, Streptococcus sanguinis|Anaerostipes caccae, Streptococcus thermophilus|Anaerostipes caccae, Streptococcus vestibularis|Anaerostipes caccae, Subdoligranulum variabile|Anaerostipes caccae, Succinatimonas hippei|Anaerostipes caccae, Sutterella wadsworthensis|Anaerostipes caccae, Tropheryma whipplei|Anaerostipes caccae, Veillonella atypica|Anaerostipes caccae, Veillonella dispar|Anaerostipes caccae, Veillonella parvula|Anaerostipes caccae, Victivallis vadensis|Anaerotruncus colihominis, Anaerotruncus colihominis|Anaerotruncus colihominis, Atopobium parvulum|Anaerotruncus colihominis, Atopobium rimae|Anaerotruncus colihominis, Atopobium vaginae|Anaerotruncus colihominis, Bacteroides caccae|Anaerotruncus colihominis, Bacteroides cellulosilyticus|Anaerotruncus colihominis, Bacteroides coprocola|Anaerotruncus colihominis, Bacteroides coprophilus|Anaerotruncus colihominis, Bacteroides dorei|Anaerotruncus colihominis, Bacteroides eggerthii|Anaerotruncus colihominis, Bacteroides finegoldii|Anaerotruncus colihominis, Bacteroides fragilis|Anaerotruncus colihominis, Bacteroides helcogenes|Anaerotruncus colihominis, Bacteroides intestinalis|Anaerotruncus colihominis, Bacteroides ovatus|Anaerotruncus colihominis, Bacteroides pectinophilus|Anaerotruncus colihominis, Bacteroides plebeius|Anaerotruncus colihominis, Bacteroides salanitronis|Anaerotruncus colihominis, Bacteroides sp. 1_1_6|Anaerotruncus colihominis, Bacteroides sp. 3_1_23|Anaerotruncus colihominis, Bacteroides stercoris|Anaerotruncus colihominis, Bacteroides thetaiotaomicron|Anaerotruncus colihominis, Bacteroides uniformis|Anaerotruncus colihominis, Bacteroides vulgatus|Anaerotruncus colihominis, Bacteroides xylanisolvens|Anaerotruncus colihominis, Bifidobacterium adolescentis|Anaerotruncus colihominis, Bifidobacterium angulatum|Anaerotruncus colihominis, Bifidobacterium animalis|Anaerotruncus colihominis, Bifidobacterium bifidum|Anaerotruncus colihominis, Bifidobacterium breve|Anaerotruncus colihominis, Bifidobacterium catenulatum|Anaerotruncus colihominis, Bifidobacterium dentium|Anaerotruncus colihominis, Bifidobacterium infantis|Anaerotruncus colihominis, Bifidobacterium longum|Anaerotruncus colihominis, Bifidobacterium pseudocatenulatum|Anaerotruncus colihominis, Bilophila wadsworthia|Anaerotruncus colihominis, Blautia hansenii|Anaerotruncus colihominis, Blautia hydrogenotrophica|Anaerotruncus colihominis, Blautia producta|Anaerotruncus colihominis, Blautia schinkii|Anaerotruncus colihominis, Brevibacterium linens|Anaerotruncus colihominis, Brucella ceti|Anaerotruncus colihominis, Brucella suis|Anaerotruncus colihominis, Bulleidia extructa|Anaerotruncus colihominis, Butyrivibrio crossotus|Anaerotruncus colihominis, Campylobacter concisus|Anaerotruncus colihominis, Campylobacter curvus|Anaerotruncus colihominis, Campylobacter gracilis|Anaerotruncus colihominis, Campylobacter hominis|Anaerotruncus colihominis, Capnocytophaga ochracea|Anaerotruncus colihominis, Cardiobacterium hominis|Anaerotruncus colihominis, Catenibacterium mitsuokai|Anaerotruncus colihominis, Catonella morbi|Anaerotruncus colihominis, Citrobacter koseri|Anaerotruncus colihominis, Clostridium asparagiforme|Anaerotruncus colihominis, Clostridium bartlettii|Anaerotruncus colihominis, Clostridium bolteae|Anaerotruncus colihominis, Clostridium botulinum|Anaerotruncus colihominis, Clostridium butyricum|Anaerotruncus colihominis, Clostridium difficile|Anaerotruncus colihominis, Clostridium disporicum|Anaerotruncus colihominis, Clostridium hathewayi|Anaerotruncus colihominis, Clostridium hylemonae|Anaerotruncus colihominis, Clostridium innocuum|Anaerotruncus colihominis, Clostridium leptum|Anaerotruncus colihominis, Clostridium mayombei|Anaerotruncus colihominis, Clostridium methylpentosum|Anaerotruncus colihominis, Clostridium nexile|Anaerotruncus colihominis, Clostridium orbiscindens|Anaerotruncus colihominis, Clostridium perfringens|Anaerotruncus colihominis, Clostridium saccharolyticum|Anaerotruncus colihominis, Clostridium scindens|Anaerotruncus colihominis, Clostridium symbiosum|Anaerotruncus colihominis, Clostridium tertium|Anaerotruncus colihominis, Collinsella aerofaciens|Anaerotruncus colihominis, Collinsella intestinalis|Anaerotruncus colihominis, Collinsella stercoris|Anaerotruncus colihominis, Coprobacillus sp. D7|Anaerotruncus colihominis, Coprococcus catus|Anaerotruncus colihominis, Coprococcus comes|Anaerotruncus colihominis, Coprococcus eutactus|Anaerotruncus colihominis, Corynebacterium aurimucosum|Anaerotruncus TABLE 2-continued Table 2. Specific binary combinations of OTUs. Individual pairings are differentiated by "|" and OTUs within a combination are differentiated by ","

colihominis, Corynebacterium matruchotii|Anaerotruncus colihominis, Cryptobacterium curtum|Anaerotruncus colihominis, Desulfovibrio desulfuricans|Anaerotruncus colihominis, Desulfovibrio piger|Anaerotruncus colihominis, Dialister invisus|Anaerotruncus colihominis, Dialister microaerophilus|Anaerotruncus colihominis, Dorea formicigenerans|Anaerotruncus colihominis, Dorea longicatena|Anaerotruncus colihominis, Eggerthella lenta|Anaerotruncus colihominis, Eikenella corrodens|Anaerotruncus colihominis, Enterobacter cancerogenus|Anaerotruncus colihominis, Enterobacter cloacae|Anaerotruncus colihominis, Enterococcus faecalis|Anaerotruncus colihominis, Enterococcus faecium|Anaerotruncus colihominis, Enterococcus gallinarum|Anaerotruncus colihominis, Erysipelotrichaceae bacterium 3_1_53|Anaerotruncus colihominis, Escherichia coli|Anaerotruncus colihominis, Escherichia fergusonii|Anaerotruncus colihominis, Ethanoligenens harbinense|Anaerotruncus colihominis, Eubacterium cellulosolvens|Anaerotruncus colihominis, Eubacterium eligens|Anaerotruncus colihominis, Eubacterium hallii|Anaerotruncus colihominis, Eubacterium limosum|Anaerotruncus colihominis, Eubacterium rectale|Anaerotruncus colihominis, Eubacterium siraeum|Anaerotruncus colihominis, Eubacterium ventriosum|Anaerotruncus colihominis, Faecalibacterium prausnitzii|Anaerotruncus colihominis, Finegoldia magna|Anaerotruncus colihominis, Fusobacterium gonidiaformans|Anaerotruncus colihominis, Fusobacterium mortiferum|Anaerotruncus colihominis, Fusobacterium nucleatum|Anaerotruncus colihominis, Fusobacterium varium|Anaerotruncus colihominis, Gardnerella vaginalis|Anaerotruncus colihominis, Gemella haemolysans|Anaerotruncus colihominis, Gemella morbillorum|Anaerotruncus colihominis, Gordonibacter pamelaeae|Anaerotruncus colihominis, Granulicatella adiacens|Anaerotruncus colihominis, Granulicatella elegans|Anaerotruncus colihominis, Haemophilus influenzae|Anaerotruncus colihominis, Haemophilus parainfluenzae|Anaerotruncus colihominis, Helicobacter pullorum|Anaerotruncus colihominis, Helicobacter pylori|Anaerotruncus colihominis, Holdemania filiformis|Anaerotruncus colihominis, Kingella oralis|Anaerotruncus colihominis, Klebsiella pneumoniae|Anaerotruncus colihominis, Klebsiella variicola|Anaerotruncus colihominis, Lachnospiraceae bacterium 5_1_57FAA|Anaerotruncus colihominis, Lactobacillus acidophilus|Anaerotruncus colihominis, Lactobacillus amylovorus|Anaerotruncus colihominis, Lactobacillus brevis|Anaerotruncus colihominis, Lactobacillus casei|Anaerotruncus colihominis, Lactobacillus crispatus|Anaerotruncus colihominis, Lactobacillus delbrueckii|Anaerotruncus colihominis, Lactobacillus fermentum|Anaerotruncus colihominis, Lactobacillus gasseri|Anaerotruncus colihominis, Lactobacillus iners|Anaerotruncus colihominis, Lactobacillus jensenii|Anaerotruncus colihominis, Lactobacillus johnsonii|Anaerotruncus colihominis, Lactobacillus paracasei|Anaerotruncus colihominis, Lactobacillus plantarum|Anaerotruncus colihominis, Lactobacillus reuteri|Anaerotruncus colihominis, Lactobacillus rhamnosus|Anaerotruncus colihominis, Lactobacillus ruminis|Anaerotruncus colihominis, Lactobacillus sakei|Anaerotruncus colihominis, Lactobacillus salivarius|Anaerotruncus colihominis, Lactococcus lactis|Anaerotruncus colihominis, Lautropia mirabilis|Anaerotruncus colihominis, Leuconostoc citreum|Anaerotruncus colihominis, Leuconostoc gasicomitatum|Anaerotruncus colihominis, Leuconostoc mesenteroides|Anaerotruncus colihominis, Listeria monocytogenes|Anaerotruncus colihominis, Marvinbryantia formatexigens|Anaerotruncus colihominis, Megamonas hypermegale|Anaerotruncus colihominis, Megasphaera micronuciformis|Anaerotruncus colihominis, Methanobrevibacter smithii|Anaerotruncus colihominis, Methanosphaera stadtmanae|Anaerotruncus colihominis, Methylobacterium radiotolerans|Anaerotruncus colihominis, Mitsuokella multacida|Anaerotruncus colihominis, Mobiluncus curtisii|Anaerotruncus colihominis, Mycoplasma hominis|Anaerotruncus colihominis, Neisseria mucosa|Anaerotruncus colihominis, Odoribacter splanchnicus|Anaerotruncus colihominis, Olsenella uli|Anaerotruncus colihominis, Oribacterium sinus|Anaerotruncus colihominis, Oxalobacter formigenes|Anaerotruncus colihominis, Parabacteroides distasonis|Anaerotruncus colihominis, Parabacteroides johnsonii|Anaerotruncus colihominis, Parabacteroides merdae|Anaerotruncus colihominis, Parvimonas micra|Anaerotruncus colihominis, Pediococcus acidilactici|Anaerotruncus colihominis, Pediococcus pentosaceus|Anaerotruncus colihominis, Peptoniphilus duerdenii|Anaerotruncus colihominis, Peptoniphilus harei|Anaerotruncus colihominis, Peptoniphilus lacrimalis|Anaerotruncus colihominis, Peptostreptococcus anaerobius|Anaerotruncus colihominis, Peptostreptococcus stomatis|Anaerotruncus colihominis, Porphyromonas asaccharolytica|Anaerotruncus colihominis, Porphyromonas uenonis|Anaerotruncus colihominis, Prevotella amnii|Anaerotruncus colihominis, Prevotella bergensis|Anaerotruncus colihominis, Prevotella bivia|Anaerotruncus colihominis, Prevotella buccae|Anaerotruncus colihominis, Prevotella buccalis|Anaerotruncus colihominis, Prevotella copri|Anaerotruncus colihominis, Prevotella disiens|Anaerotruncus colihominis, Prevotella melaninogenica|Anaerotruncus colihominis, Prevotella multiformis|Anaerotruncus colihominis, Prevotella oralis|Anaerotruncus colihominis, Prevotella oris|Anaerotruncus colihominis, Prevotella salivae|Anaerotruncus colihominis, Prevotella timonensis|Anaerotruncus colihominis, Propionibacterium acnes|Anaerotruncus colihominis, Propionibacterium freudenreichii|Anaerotruncus colihominis, Proteus mirabilis|Anaerotruncus colihominis, Proteus penneri|Anaerotruncus colihominis, Pseudoflavonifractor capillosus|Anaerotruncus colihominis, Pseudomonas aeruginosa|Anaerotruncus colihominis, Pseudomonas fluorescens|Anaerotruncus colihominis, Pseudomonas putida|Anaerotruncus colihominis, Pseudoramibacter alactolyticus|Anaerotruncus colihominis, Pyramidobacter piscolens|Anaerotruncus colihominis, Rhodopseudomonas palustris|Anaerotruncus colihominis, Roseburia intestinalis|Anaerotruncus colihominis, Roseburia inulinivorans|Anaerotruncus colihominis, Rothia dentocariosa|Anaerotruncus colihominis, Rothia mucilaginosa|Anaerotruncus colihominis, Ruminococcus albus|Anaerotruncus colihominis, Ruminococcus bromii|Anaerotruncus colihominis, Ruminococcus gnavus|Anaerotruncus colihominis, Ruminococcus lactaris|Anaerotruncus colihominis, Ruminococcus obeum|Anaerotruncus colihominis, Ruminococcus torques|Anaerotruncus colihominis, Selenomonas sputigena|Anaerotruncus colihominis, Shigella boydii|Anaerotruncus colihominis, Shigella dysenteriae|Anaerotruncus colihominis, Shigella sonnei|Anaerotruncus colihominis, Slackia exigua|Anaerotruncus colihominis, Solobacterium moorei|Anaerotruncus colihominis, Staphylococcus aureus|Anaerotruncus colihominis, Staphylococcus epidermidis|Anaerotruncus colihominis, Staphylococcus hominis|Anaerotruncus colihominis, Staphylococcus saprophyticus|Anaerotruncus colihominis, Staphylococcus warneri|Anaerotruncus colihominis, Streptococcus agalactiae|Anaerotruncus colihominis, Streptococcus anginosus|Anaerotruncus colihominis, Streptococcus australis|Anaerotruncus colihominis, Streptococcus bovis|Anaerotruncus colihominis, Streptococcus cristatus|Anaerotruncus colihominis, Streptococcus dysgalactiae|Anaerotruncus colihominis, Streptococcus equinus|Anaerotruncus colihominis, Streptococcus gordonii|Anaerotruncus colihominis, Streptococcus infantarius|Anaerotruncus colihominis, Streptococcus infantis|Anaerotruncus colihominis, Streptococcus mitis|Anaerotruncus colihominis, Streptococcus mutans|Anaerotruncus colihominis, Streptococcus oralis|Anaerotruncus colihominis, Streptococcus parasanguinis|Anaerotruncus colihominis, Streptococcus peroris|Anaerotruncus colihominis, Streptococcus pneumoniae|Anaerotruncus colihominis, Streptococcus salivarius|Anaerotruncus colihominis, Streptococcus sanguinis|Anaerotruncus colihominis, Streptococcus thermophilus|Anaerotruncus colihominis, Streptococcus vestibularis|Anaerotruncus colihominis, Subdoligranulum variabile|Anaerotruncus colihominis, Succinatimonas hippei|Anaerotruncus colihominis, Sutterella wadsworthensis|Anaerotruncus colihominis, Tropheryma whipplei|Anaerotruncus colihominis, Veillonella atypica|Anaerotruncus colihominis, Veillonella dispar|Anaerotruncus colihominis, Veillonella parvula|Anaerotruncus colihominis, Victivallis vadensis|Atopobium parvulum, Atopobium parvulum|Atopobium parvulum, Atopobium rimae|Atopobium parvulum, Atopobium vaginae|Atopobium parvulum, Bacteroides caccae|Atopobium parvulum, Bacteroides cellulosilyticus|Atopobium parvulum, Bacteroides coprocola|Atopobium parvulum, Bacteroides coprophilus|Atopobium parvulum, Bacteroides dorei|Atopobium parvulum, Bacteroides eggerthii|Atopobium parvulum, Bacteroides finegoldii|Atopobium parvulum, Bacteroides fragilis|Atopobium parvulum, Bacteroides helcogenes|Atopobium parvulum, Bacteroides intestinalis|Atopobium parvulum, Bacteroides ovatus|Atopobium parvulum, Bacteroides pectinophilus|Atopobium parvulum, Bacteroides plebeius|Atopobium parvulum, Bacteroides salanitronis|Atopobium parvulum, Bacteroides sp. 1_1_6|Atopobium parvulum, Bacteroides sp. 3_1_23|Atopobium parvulum, Bacteroides stercoris|Atopobium parvulum, Bacteroides thetaiotaomicron|Atopobium parvulum, Bacteroides uniformis|Atopobium parvulum, Bacteroides vulgatus|Atopobium parvulum, Bacteroides xylanisolvens|Atopobium parvulum, Bifidobacterium adolescentis|Atopobium parvulum, Bifidobacterium angulatum|Atopobium parvulum, Bifidobacterium animalis|Atopobium parvulum, Bifidobacterium bifidum|Atopobium parvulum, Bifidobacterium breve|Atopobium parvulum, Bifidobacterium catenulatum|Atopobium parvulum, Bifidobacterium dentium|Atopobium TABLE 2-continued

| Table 2. Specific binary combinations of OTUs. Individual pairings are differentiated by "\|" and OTUs within a combination are differentiated by "," |
|---|
| parvulum, Bifidobacterium infantis\|Atopobium parvulum, Bifidobacterium longum\|Atopobium parvulum, Bifidobacterium pseudocatenulatum\|Atopobium parvulum, Bilophila wadsworthia\|Atopobium parvulum, Blautia hansenii\|Atopobium parvulum, Blautia hydrogenotrophica\|Atopobium parvulum, Blautia producta\|Atopobium parvulum, Blautia schinkii\|Atopobium parvulum, Brevibacterium linens\|Atopobium parvulum, Brucella ceti\|Atopobium parvulum, Brucella suis\|Atopobium parvulum, Bulleidia extructa\|Atopobium parvulum, Butyrivibrio crossotus\|Atopobium parvulum, Campylobacter concisus\|Atopobium parvulum, Campylobacter curvus\|Atopobium parvulum, Campylobacter gracilis\|Atopobium parvulum, Campylobacter hominis\|Atopobium parvulum, Capnocytophaga ochracea\|Atopobium parvulum, Cardiobacterium hominis\|Atopobium parvulum, Catenibacterium mitsuokai\|Atopobium parvulum, Catonella morbi\|Atopobium parvulum, Citrobacter koseri\|Atopobium parvulum, Clostridium asparagiforme\|Atopobium parvulum, Clostridium bartlettii\|Atopobium parvulum, Clostridium bolteae\|Atopobium parvulum, Clostridium botulinum\|Atopobium parvulum, Clostridium butyricum\|Atopobium parvulum, Clostridium difficile\|Atopobium parvulum, Clostridium disporicum\|Atopobium parvulum, Clostridium hathewayi\|Atopobium parvulum, Clostridium hylemonae\|Atopobium parvulum, Clostridium innocuum\|Atopobium parvulum, Clostridium leptum\|Atopobium parvulum, Clostridium mayombei\|Atopobium parvulum, Clostridium methylpentosum\|Atopobium parvulum, Clostridium nexile\|Atopobium parvulum, Clostridium orbiscindens\|Atopobium parvulum, Clostridium perfringens\|Atopobium parvulum, Clostridium saccharolyticum\|Atopobium parvulum, Clostridium scindens\|Atopobium parvulum, Clostridium symbiosuna\|Atopobium parvulum, Clostridium tertium\|Atopobium parvulum, Collinsella aerofaciens\|Atopobium parvulum, Collinsella intestinalis\|Atopobium parvulum, Collinsella stercoris\|Atopobium parvulum, Coprobacillus sp. D7\|Atopobium parvulum, Coprococcus catus\|Atopobium parvulum, Coprococcus comes\|Atopobium parvulum, Coprococcus eutactus\|Atopobium parvulum, Corynebacterium aurimucosum\|Atopobium parvulum, Corynebacterium matruchotii\|Atopobium parvulum, Cryptobacterium curtum\|Atopobium parvulum, Desulfovibrio desulfuricans\|Atopobium parvulum, Desulfovibrio piger\|Atopobium parvulum, Dialister invisus\|Atopobium parvulum, Dialister microaerophilus\|Atopobium parvulum, Dorea formicigenerans\|Atopobium parvulum, Dorea longicatena\|Atopobium parvulum, Eggerthella lenta\|Atopobium parvulum, Eikenella corrodens\|Atopobium parvulum, Enterobacter cancerogenus\|Atopobium parvulum, Enterobacter cloacae\|Atopobium parvulum, Enterococcus faecalis\|Atopobium parvulum, Enterococcus faecium\|Atopobium parvulum, Enterococcus gallinarum\|Atopobium parvulum, Erysipelotrichaceae bacterium 31_53\|Atopobium parvulum, Escherichia coli\|Atopobium parvulum, Escherichia fergusonii\|Atopobium parvulum, Ethanoligenens harbinense\|Atopobium parvulum, Eubacterium cellulosolvens\|Atopobium parvulum, Eubacterium eligens\|Atopobium parvulum, Eubacterium hallii\|Atopobium parvulum, Eubacterium limosum\|Atopobium parvulum, Eubacterium rectale\|Atopobium parvulum, Eubacterium siraeum\|Atopobium parvulum, Eubacterium ventriosum\|Atopobium parvulum, Faecalibacterium prausnitzii\|Atopobium parvulum, Finegoldia magna\|Atopobium parvulum, Fusobacterium gonidiaformans\|Atopobium parvulum, Fusobacterium mortiferum\|Atopobium parvulum, Fusobacterium nucleatum\|Atopobium parvulum, Fusobacterium varium\|Atopobium parvulum, Gardnerella vaginalis\|Atopobium parvulum, Gemella haemolysans\|Atopobium parvulum, Gemella morbillorum\|Atopobium parvulum, Gordonibacter pamelaeae\|Atopobium parvulum, Granulicatella adiacens\|Atopobium parvulum, Granulicatella elegans\|Atopobium parvulum, Haemophilus influenzae\|Atopobium parvulum, Haemophilus parainfluenzae\|Atopobium parvulum, Helicobacter pullorum\|Atopobium parvulum, Helicobacter pylori\|Atopobium parvulum, Holdemania filiformis\|Atopobium parvulum, Kingella oralis\|Atopobium parvulum, Klebsiella pneumoniae\|Atopobium parvulum, Klebsiella variicola\|Atopobium parvulum, Lachnospiraceae bacterium 5_1_57FAA\|Atopobium parvulum, Lactobacillus acidophilus\|Atopobium parvulum, Lactobacillus amylovorus\|Atopobium parvulum, Lactobacillus brevis\|Atopobium parvulum, Lactobacillus casei\|Atopobium parvulum, Lactobacillus crispatus\|Atopobium parvulum, Lactobacillus delbrueckii\|Atopobium parvulum, Lactobacillus fermentum\|Atopobium parvulum, Lactobacillus gasseri\|Atopobium parvulum, Lactobacillus iners\|Atopobium parvulum, Lactobacillus jensenii\|Atopobium parvulum, Lactobacillus johnsonii\|Atopobium parvulum, Lactobacillus paracasei\|Atopobium parvulum, Lactobacillus plantarum\|Atopobium parvulum, Lactobacillus reuteri\|Atopobium parvulum, Lactobacillus rhamnosus\|Atopobium parvulum, Lactobacillus ruminis\|Atopobium parvulum, Lactobacillus sakei\|Atopobium parvulum, Lactobacillus salivarius\|Atopobium parvulum, Lactococcus lactis\|Atopobium parvulum, Lautropia mirabilis\|Atopobium parvulum, Leuconostoc citreum\|Atopobium parvulum, Leuconostoc gasicomitatum\|Atopobium parvulum, Leuconostoc mesenteroides\|Atopobium parvulum, Listeria monocytogenes\|Atopobium parvulum, Marvinbryantia formatexigens\|Atopobium parvulum, Megamonas hypermegale\|Atopobium parvulum, Megasphaera micronuciformis\|Atopobium parvulum, Methanobrevibacter smithii\|Atopobium parvulum, Methanosphaera stadtmanae\|Atopobium parvulum, Methylobacterium radiotolerans\|Atopobium parvulum, Mitsuokella multacida\|Atopobium parvulum, Mobiluncus curtisii\|Atopobium parvulum, Mycoplasma hominis\|Atopobium parvulum, Neisseria mucosa\|Atopobium parvulum, Odoribacter splanchnicus\|Atopobium parvulum, Olsenella uli\|Atopobium parvulum, Oribacterium sinus\|Atopobium parvulum, Oxalobacter formigenes\|Atopobium parvulum, Parabacteroides distasonis\|Atopobium parvulum, Parabacteroides johnsonii\|Atopobium parvulum, Parabacteroides merdae\|Atopobium parvulum, Parvimonas micra\|Atopobium parvulum, Pediococcus acidilactici\|Atopobium parvulum, Pediococcus pentosaceus\|Atopobium parvulum, Peptoniphilus duerdenii\|Atopobium parvulum, Peptoniphilus harei\|Atopobium parvulum, Peptoniphilus lacrimalis\|Atopobium parvulum, Peptostreptococcus anaerobius\|Atopobium parvulum, Peptostreptococcus stomatis\|Atopobium parvulum, Porphyromonas asaccharolytica\|Atopobium parvulum, Porphyromonas uenonis\|Atopobium parvulum, Prevotella amnii\|Atopobium parvulum, Prevotella bergensis\|Atopobium parvulum, Prevotella bivia\|Atopobium parvulum, Prevotella buccae\|Atopobium parvulum, Prevotella buccalis\|Atopobium parvulum, Prevotella copri\|Atopobium parvulum, Prevotella disiens\|Atopobium parvulum, Prevotella melaninogenica\|Atopobium parvulum, Prevotella multiformis\|Atopobium parvulum, Prevotella oralis\|Atopobium parvulum, Prevotella oris\|Atopobium parvulum, Prevotella salivae\|Atopobium parvulum, Prevotella timonensis\|Atopobium parvulum, Propionibacterium acnes\|Atopobium parvulum, Propionibacterium freudenreichii\|Atopobium parvulum, Proteus mirabilis\|Atopobium parvulum, Proteus penneri\|Atopobium parvulum, Pseudoflavonifractor capillosus\|Atopobium parvulum, Pseudomonas aeruginosa\|Atopobium parvulum, Pseudomonas fluorescens\|Atopobium parvulum, Pseudomonas putida\|Atopobium parvulum, Pseudoramibacter alactolyticus\|Atopobium parvulum, Pyramidobacter piscolens\|Atopobium parvulum, Rhodopseudomonas palustris\|Atopobium parvulum, Roseburia intestinalis\|Atopobium parvulum, Roseburia inulinivorans\|Atopobium parvulum, Rothia dentocariosa\|Atopobium parvulum, Rothia mucilaginosa\|Atopobium parvulum, Ruminococcus albus\|Atopobium parvulum, Ruminococcus bromii\|Atopobium parvulum, Ruminococcus gnavus\|Atopobium parvulum, Ruminococcus lactaris\|Atopobium parvulum, Ruminococcus obeum\|Atopobium parvulum, Ruminococcus torques\|Atopobium parvulum, Selenomonas sputigena\|Atopobium parvulum, Shigella boydii\|Atopobium parvulum, Shigella dysenteriae\|Atopobium parvulum, Shigella sonnei\|Atopobium parvulum, Slackia exigua\|Atopobium parvulum, Solobacterium moorei\|Atopobium parvulum, Staphylococcus aureus\|Atopobium parvulum, Staphylococcus epidermidis\|Atopobium parvulum, Staphylococcus hominis\|Atopobium parvulum, Staphylococcus saprophyticus\|Atopobium parvulum, Staphylococcus warneri\|Atopobium parvulum, Streptococcus agalactiae\|Atopobium parvulum, Streptococcus anginosus\|Atopobium parvulum, Streptococcus australis\|Atopobium parvulum, Streptococcus bovis\|Atopobium parvulum, Streptococcus cristatus\|Atopobium parvulum, Streptococcus dysgalactiae\|Atopobium parvulum, Streptococcus equinus\|Atopobium parvulum, Streptococcus gordonii\|Atopobium parvulum, Streptococcus infantarius\|Atopobium parvulum, Streptococcus infantis\|Atopobium parvulum, Streptococcus mitis\|Atopobium parvulum, Streptococcus mutans\|Atopobium parvulum, Streptococcus oralis\|Atopobium parvulum, Streptococcus parasanguinis\|Atopobium parvulum, Streptococcus peroris\|Atopobium parvulum, Streptococcus pneumoniae\|Atopobium parvulum, Streptococcus salivarius\|Atopobium parvulum, Streptococcus sanguinis\|Atopobium parvulum, Streptococcus thermophilus\|Atopobium parvulum, Streptococcus vestibularis\|Atopobium parvulum, Subdoligranulum variabile\|Atopobium parvulum, Succinatimonas hippei\|Atopobium parvulum, Sutterella wadsworthensis\|Atopobium parvulum, Tropheryma whipplei\|Atopobium parvulum, Veillonella atypica\|Atopobium parvulum, Veillonella dispar\|Atopobium parvulum, Veillonella parvula\|Atopobium parvulum, Victivallis vadensis\|Atopobium rimae, Atopobium rimae, Atopobium rimae, Atopobium vaginae\|Atopobium rimae, Bacteroides caccae\|Atopobium |

TABLE 2-continued

| Table 2. Specific binary combinations of OTUs. Individual pairings are differentiated by "\|" and OTUs within a combination are differentiated by "," |
|---|
| *rimae, Bacteroides cellulosilyticus\|Atopobium rimae, Bacteroides coprocola\|Atopobium rimae, Bacteroides coprophilus\|Atopobium rimae, Bacteroides dorei\|Atopobium rimae, Bacteroides eggerthii\|Atopobium rimae, Bacteroides finegoldii\|Atopobium rimae, Bacteroides fragilis\|Atopobium rimae, Bacteroides helcogenes\|Atopobium rimae, Bacteroides intestinalis\|Atopobium rimae, Bacteroides ovatus\|Atopobium rimae, Bacteroides pectinophilus\|Atopobium rimae, Bacteroides plebeius\|Atopobium rimae, Bacteroides salanitronis\|Atopobium rimae, Bacteroides* sp. 1_1_6\|*Atopobium rimae, Bacteroides* sp. 3_1_23\|*Atopobium rimae, Bacteroides stercoris\|Atopobium rimae, Bacteroides thetaiotaomicron\|Atopobium rimae, Bacteroides uniformis\|Atopobium rimae, Bacteroides vulgatus\|Atopobium rimae, Bacteroides xylanisolvens\|Atopobium rimae, Bifidobacterium adolescentis\|Atopobium rimae, Bifidobacterium angulatum\|Atopobium rimae, Bifidobacterium animalis\|Atopobium rimae, Bifidobacterium bifidum\|Atopobium rimae, Bifidobacterium breve\|Atopobium rimae, Bifidobacterium catenulatum\|Atopobium rimae, Bifidobacterium dentium\|Atopobium rimae, Bifidobacterium infantis\|Atopobium rimae, Bifidobacterium longum\|Atopobium rimae, Bifidobacterium pseudocatenulatum\|Atopobium rimae, Bilophila wadsworthia\|Atopobium rimae, Blautia hansenii\|Atopobium rimae, Blautia hydrogenotrophica\|Atopobium rimae, Blautia producta\|Atopobium rimae, Blautia schinkii\|Atopobium rimae, Brevibacterium linens\|Atopobium rimae, Brucella ceti\|Atopobium rimae, Brucella suis\|Atopobium rimae, Bulleidia extructa\|Atopobium rimae, Butyrivibrio crossotus\|Atopobium rimae, Campylobacter concisus\|Atopobium rimae, Campylobacter curvus\|Atopobium rimae, Campylobacter gracilis\|Atopobium rimae, Campylobacter hominis\|Atopobium rimae, Capnocytophaga ochracea\|Atopobium rimae, Cardiobacterium hominis\|Atopobium rimae, Catenibacterium mitsuokai\|Atopobium rimae, Catonella morbi\|Atopobium rimae, Citrobacter koseri\|Atopobium rimae, Clostridium asparagiforme\|Atopobium rimae, Clostridium bartlettii\|Atopobium rimae, Clostridium bolteae\|Atopobium rimae, Clostridium botulinum\|Atopobium rimae, Clostridium butyricum\|Atopobium rimae, Clostridium difficile\|Atopobium rimae, Clostridium disporicum\|Atopobium rimae, Clostridium hathewayi\|Atopobium rimae, Clostridium hylemonae\|Atopobium rimae, Clostridium innocuum\|Atopobium rimae, Clostridium leptum\|Atopobium rimae, Clostridium mayombei\|Atopobium rimae, Clostridium methylpentosum\|Atopobium rimae, Clostridium nexile\|Atopobium rimae, Clostridium orbiscindens\|Atopobium rimae, Clostridium perfringens\|Atopobium rimae, Clostridium saccharolyticum\|Atopobium rimae, Clostridium scindens\|Atopobium rimae, Clostridium symbiosum\|Atopobium rimae, Clostridium tertium\|Atopobium rimae, Collinsella aerofaciens\|Atopobium rimae, Collinsella intestinalis\|Atopobium rimae, Collinsella stercoris\|Atopobium rimae, Coprobacillus* sp. D7\|*Atopobium rimae, Coprococcus catus\|Atopobium rimae, Coprococcus comes\|Atopobium rimae, Coprococcus eutactus\|Atopobium rimae, Corynebacterium aurimucosum\|Atopobium rimae, Corynebacterium matruchotii\|Atopobium rimae, Cryptobacterium curtum\|Atopobium rimae, Desulfovibrio desulfuricans\|Atopobium rimae, Desulfovibrio piger\|Atopobium rimae, Dialister invisus\|Atopobium rimae, Dialister microaerophilus\|Atopobium rimae, Dorea formicigenerans\|Atopobium rimae, Dorea longicatena\|Atopobium rimae, Eggerthella lenta\|Atopobium rimae, Eikenella corrodens\|Atopobium rimae, Enterobacter cancerogenus\|Atopobium rimae, Enterobacter cloacae\|Atopobium rimae, Enterococcus faecalis\|Atopobium rimae, Enterococcus faecium\|Atopobium rimae, Enterococcus gallinarum\|Atopobium rimae, Erysipelotrichaceae bacterium* 3_1_53\|*Atopobium rimae, Escherichia coli\|Atopobium rimae, Escherichia fergusonii\|Atopobium rimae, Ethanoligenens harbinense\|Atopobium rimae, Eubacterium cellulosolvens\|Atopobium rimae, Eubacterium eligens\|Atopobium rimae, Eubacterium hallii\|Atopobium rimae, Eubacterium limosum\|Atopobium rimae, Eubacterium rectale\|Atopobium rimae, Eubacterium siraeum\|Atopobium rimae, Eubacterium ventriosum\|Atopobium rimae, Faecalibacterium prausnitzii\|Atopobium rimae, Finegoldia magna\|Atopobium rimae, Fusobacterium gonidiaformans\|Atopobium rimae, Fusobacterium mortiferum\|Atopobium rimae, Fusobacterium nucleatum\|Atopobium rimae, Fusobacterium varium\|Atopobium rimae, Gardnerella vaginalis\|Atopobium rimae, Gemella haemolysans\|Atopobium rimae, Gemella morbillorum\|Atopobium rimae, Gordonibacter pamelaeae\|Atopobium rimae, Granulicatella adiacens\|Atopobium rimae, Granulicatella elegans\|Atopobium rimae, Haemophilus influenzae\|Atopobium rimae, Haemophilus parainfluenzae\|Atopobium rimae, Helicobacter pullorum\|Atopobium rimae, Helicobacter pylori\|Atopobium rimae, Holdemania filiformis\|Atopobium rimae, Kingella oralis\|Atopobium rimae, Klebsiella pneumoniae\|Atopobium rimae, Klebsiella variicola\|Atopobium rimae, Lachnospiraceae bacterium* 5_1_57FAA\|*Atopobium rimae, Lactobacillus acidophilus\|Atopobium rimae, Lactobacillus amylovorus\|Atopobium rimae, Lactobacillus brevis\|Atopobium rimae, Lactobacillus casei\|Atopobium rimae, Lactobacillus crispatus\|Atopobium rimae, Lactobacillus delbrueckii\|Atopobium rimae, Lactobacillus fermentum\|Atopobium rimae, Lactobacillus gasseri\|Atopobium rimae, Lactobacillus iners\|Atopobium rimae, Lactobacillus jensenii\|Atopobium rimae, Lactobacillus johnsonii\|Atopobium rimae, Lactobacillus paracasei\|Atopobium rimae, Lactobacillus plantarum\|Atopobium rimae, Lactobacillus reuteri\|Atopobium rimae, Lactobacillus rhamnosus\|Atopobium rimae, Lactobacillus ruminis\|Atopobium rimae, Lactobacillus sakei\|Atopobium rimae, Lactobacillus salivarius\|Atopobium rimae, Lactococcus lactis\|Atopobium rimae, Lautropia mirabilis\|Atopobium rimae, Leuconostoc citreum\|Atopobium rimae, Leuconostoc gasicomitatum\|Atopobium rimae, Leuconostoc mesenteroides\|Atopobium rimae, Listeria monocytogenes\|Atopobium rimae, Marvinbryantia formatexigens\|Atopobium rimae, Megamonas hypermegale\|Atopobium rimae, Megasphaera micronuciformis\|Atopobium rimae, Methanobrevibacter smithii\|Atopobium rimae, Methanosphaera stadtmanae\|Atopobium rimae, Methylobacterium radiotolerans\|Atopobium rimae, Mitsuokella multacida\|Atopobium rimae, Mobiluncus curtisii\|Atopobium rimae, Mycoplasma hominis\|Atopobium rimae, Neisseria mucosa\|Atopobium rimae, Odoribacter splanchnicus\|Atopobium rimae, Olsenella uli\|Atopobium rimae, Oribacterium sinus\|Atopobium rimae, Oxalobacter formigenes\|Atopobium rimae, Parabacteroides distasonis\|Atopobium rimae, Parabacteroides johnsonii\|Atopobium rimae, Parabacteroides merdae\|Atopobium rimae, Parvimonas micra\|Atopobium rimae, Pediococcus acidilactici\|Atopobium rimae, Pediococcus pentosaceus\|Atopobium rimae, Peptoniphilus duerdenii\|Atopobium rimae, Peptoniphilus harei\|Atopobium rimae, Peptoniphilus lacrimalis\|Atopobium rimae, Peptostreptococcus anaerobius\|Atopobium rimae, Peptostreptococcus stomatis\|Atopobium rimae, Porphyromonas asaccharolytica\|Atopobium rimae, Porphyromonas uenonis\|Atopobium rimae, Prevotella amnii\|Atopobium rimae, Prevotella bergensis\|Atopobium rimae, Prevotella bivia\|Atopobium rimae, Prevotella buccae\|Atopobium rimae, Prevotella buccalis\|Atopobium rimae, Prevotella copri\|Atopobium rimae, Prevotella disiens\|Atopobium rimae, Prevotella melaninogenica\|Atopobium rimae, Prevotella multiformis\|Atopobium rimae, Prevotella oralis\|Atopobium rimae, Prevotella oris\|Atopobium rimae, Prevotella salivae\|Atopobium rimae, Prevotella timonensis\|Atopobium rimae, Propionibacterium acnes\|Atopobium rimae, Propionibacterium freudenreichii\|Atopobium rimae, Proteus mirabilis\|Atopobium rimae, Proteus penneri\|Atopobium rimae, Pseudoflavonifractor capillosus\|Atopobium rimae, Pseudomonas aeruginosa\|Atopobium rimae, Pseudomonas fluorescens\|Atopobium rimae, Pseudomonas putida\|Atopobium rimae, Pseudoramibacter alactolyticus\|Atopobium rimae, Pyramidobacter piscolens\|Atopobium rimae, Rhodopseudomonas palustris\|Atopobium rimae, Roseburia intestinalis\|Atopobium rimae, Roseburia inulinivorans\|Atopobium rimae, Rothia dentocariosa\|Atopobium rimae, Rothia mucilaginosa\|Atopobium rimae, Ruminococcus albus\|Atopobium rimae, Ruminococcus bromii\|Atopobium rimae, Ruminococcus gnavus\|Atopobium rimae, Ruminococcus lactaris\|Atopobium rimae, Ruminococcus obeum\|Atopobium rimae, Ruminococcus torques\|Atopobium rimae, Selenomonas sputigena\|Atopobium rimae, Shigella boydii\|Atopobium rimae, Shigella dysenteriae\|Atopobium rimae, Shigella sonnei\|Atopobium rimae, Slackia exigua\|Atopobium rimae, Solobacterium moorei\|Atopobium rimae, Staphylococcus aureus\|Atopobium rimae, Staphylococcus epidermidis\|Atopobium rimae, Staphylococcus hominis\|Atopobium rimae, Staphylococcus saprophyticus\|Atopobium rimae, Staphylococcus warneri\|Atopobium rimae, Streptococcus agalactiae\|Atopobium rimae, Streptococcus anginosus\|Atopobium rimae, Streptococcus australis\|Atopobium rimae, Streptococcus bovis\|Atopobium rimae, Streptococcus cristatus\|Atopobium rimae, Streptococcus dysgalactiae\|Atopobium rimae, Streptococcus equinus\|Atopobium rimae, Streptococcus gordonii\|Atopobium rimae, Streptococcus infantarius\|Atopobium rimae, Streptococcus infantis\|Atopobium rimae, Streptococcus mitis\|Atopobium rimae, Streptococcus mutans\|Atopobium rimae, Streptococcus oralis\|Atopobium rimae, Streptococcus parasanguinis\|Atopobium rimae, Streptococcus peroris\|Atopobium rimae, Streptococcus pneumoniae\|Atopobium rimae, Streptococcus salivarius\|Atopobium rimae, Streptococcus sanguinis\|Atopobium rimae, Streptococcus thermophilus\|Atopobium rimae, Streptococcus vestibularis\|Atopobium rimae, Subdoligranulum variabile\|Atopobium rimae, Succinatimonas hippei\|Atopobium rimae, Sutterella wadsworthensis\|Atopobium* |

TABLE 2-continued

Table 2. Specific binary combinations of OTUs. Individual pairings are differentiated by "|" and OTUs within a combination are differentiated by ","

rimae, Tropheryma whipplei|Atopobium rimae, Veillonella atypica|Atopobium rimae, Veillonella dispar|Atopobium rimae, Veillonella parvula|Atopobium rimae, Victivallis vadensis|Atopobium vaginae, Atopobium vaginae|Atopobium vaginae, Bacteroides caccae|Atopobium vaginae, Bacteroides cellulosilyticus|Atopobium vaginae, Bacteroides coprocola|Atopobium vaginae, Bacteroides coprophilus|Atopobium vaginae, Bacteroides dorei|Atopobium vaginae, Bacteroides eggerthii|Atopobium vaginae, Bacteroides finegoldii|Atopobium vaginae, Bacteroides fragilis|Atopobium vaginae, Bacteroides helcogenes|Atopobium vaginae, Bacteroides intestinalis|Atopobium vaginae, Bacteroides ovatus|Atopobium vaginae, Bacteroides pectinophilus|Atopobium vaginae, Bacteroides plebeius|Atopobium vaginae, Bacteroides salanitronis|Atopobium vaginae, Bacteroides sp. 1_1_6|Atopobium vaginae, Bacteroides sp. 3_1_23|Atopobium vaginae, Bacteroides stercoris|Atopobium vaginae, Bacteroides thetaiotaomicron|Atopobium vaginae, Bacteroides uniformis|Atopobium vaginae, Bacteroides vulgatus|Atopobium vaginae, Bacteroides xylanisolvens|Atopobium vaginae, Bifidobacterium adolescentis|Atopobium vaginae, Bifidobacterium angulatum|Atopobium vaginae, Bifidobacterium animalis|Atopobium vaginae, Bifidobacterium bifidum|Atopobium vaginae, Bifidobacterium breve|Atopobium vaginae, Bifidobacterium catenulatum|Atopobium vaginae, Bifidobacterium dentium|Atopobium vaginae, Bifidobacterium infantis|Atopobium vaginae, Bifidobacterium longum|Atopobium vaginae, Bifidobacterium pseudocatenulatum|Atopobium vaginae, Bilophila wadsworthia|Atopobium vaginae, Blautia hansenii|Atopobium vaginae, Blautia hydrogenotrophica|Atopobium vaginae, Blautia producta|Atopobium vaginae, Blautia schinkii|Atopobium vaginae, Brevibacterium linens|Atopobium vaginae, Brucella ceti|Atopobium vaginae, Brucella suis|Atopobium vaginae, Bulleidia extructa|Atopobium vaginae, Butyrivibrio crossotus|Atopobium vaginae, Campylobacter concisus|Atopobium vaginae, Campylobacter curvus|Atopobium vaginae, Campylobacter gracilis|Atopobium vaginae, Campylobacter hominis|Atopobium vaginae, Capnocytophaga ochracea|Atopobium vaginae, Cardiobacterium hominis|Atopobium vaginae, Catenibacterium mitsuokai|Atopobium vaginae, Catonella morbi|Atopobium vaginae, Citrobacter koseri|Atopobium vaginae, Clostridium asparagiforme|Atopobium vaginae, Clostridium bartlettii|Atopobium vaginae, Clostridium bolteae|Atopobium vaginae, Clostridium botulinum|Atopobium vaginae, Clostridium butyricum|Atopobium vaginae, Clostridium difficile|Atopobium vaginae, Clostridium disporicum|Atopobium vaginae, Clostridium hathewayi|Atopobium vaginae, Clostridium hylemonae|Atopobium vaginae, Clostridium innocuum|Atopobium vaginae, Clostridium leptum|Atopobium vaginae, Clostridium mayombei|Atopobium vaginae, Clostridium methylpentosum|Atopobium vaginae, Clostridium nexile|Atopobium vaginae, Clostridium orbiscindens|Atopobium vaginae, Clostridium perfringens|Atopobium vaginae, Clostridium saccharolyticum|Atopobium vaginae, Clostridium scindens|Atopobium vaginae, Clostridium symbiosum|Atopobium vaginae, Clostridium tertium|Atopobium vaginae, Collinsella aerofaciens|Atopobium vaginae, Collinsella intestinalis|Atopobium vaginae, Collinsella stercoris|Atopobium vaginae, Coprobacillus sp. D7|Atopobium vaginae, Coprococcus catus|Atopobium vaginae, Coprococcus comes|Atopobium vaginae, Coprococcus eutactus|Atopobium vaginae, Corynebacterium aurimucosum|Atopobium vaginae, Corynebacterium matruchotii|Atopobium vaginae, Cryptobacterium curtum|Atopobium vaginae, Desulfovibrio desulfuricans|Atopobium vaginae, Desulfovibrio piger|Atopobium vaginae, Dialister invisus|Atopobium vaginae, Dialister microaerophilus|Atopobium vaginae, Dorea formicigenerans|Atopobium vaginae, Dorea longicatena|Atopobium vaginae, Eggerthella lenta|Atopobium vaginae, Eikenella corrodens|Atopobium vaginae, Enterobacter cancerogenus|Atopobium vaginae, Enterobacter cloacae|Atopobium vaginae, Enterococcus faecalis|Atopobium vaginae, Enterococcus faecium|Atopobium vaginae, Enterococcus gallinarum|Atopobium vaginae, Erysipelotrichaceae bacterium 3_1_53|Atopobium vaginae, Escherichia coli|Atopobium vaginae, Escherichia fergusonii|Atopobium vaginae, Ethanoligenens harbinense|Atopobium vaginae, Eubacterium cellulosolvens|Atopobium vaginae, Eubacterium eligens|Atopobium vaginae, Eubacterium hallii|Atopobium vaginae, Eubacterium limosum|Atopobium vaginae, Eubacterium rectale|Atopobium vaginae, Eubacterium siraeum|Atopobium vaginae, Eubacterium ventriosum|Atopobium vaginae, Faecalibacterium prausnitzii|Atopobium vaginae, Finegoldia magna|Atopobium vaginae, Fusobacterium gonidiaformans|Atopobium vaginae, Fusobacterium mortiferum|Atopobium vaginae, Fusobacterium nucleatum|Atopobium vaginae, Fusobacterium varium|Atopobium vaginae, Gardnerella vaginalis|Atopobium vaginae, Gemella haemolysans|Atopobium vaginae, Gemella morbillorum|Atopobium vaginae, Gordonibacter pamelaeae|Atopobium vaginae, Granulicatella adiacens|Atopobium vaginae, Granulicatella elegans|Atopobium vaginae, Haemophilus influenzae|Atopobium vaginae, Haemophilus parainfluenzae|Atopobium vaginae, Helicobacter pullorum|Atopobium vaginae, Helicobacter pylori|Atopobium vaginae, Holdemania filiformis|Atopobium vaginae, Kingella oralis|Atopobium vaginae, Klebsiella pneumoniae|Atopobium vaginae, Klebsiella variicola|Atopobium vaginae, Lachnospiraceae bacterium 5_1_57FAA|Atopobium vaginae, Lactobacillus acidophilus|Atopobium vaginae, Lactobacillus amylovorus|Atopobium vaginae, Lactobacillus brevis|Atopobium vaginae, Lactobacillus casei|Atopobium vaginae, Lactobacillus crispatus|Atopobium vaginae, Lactobacillus delbrueckii|Atopobium vaginae, Lactobacillus fermentum|Atopobium vaginae, Lactobacillus gasseri|Atopobium vaginae, Lactobacillus iners|Atopobium vaginae, Lactobacillus jensenii|Atopobium vaginae, Lactobacillus johnsonii|Atopobium vaginae, Lactobacillus paracasei|Atopobium vaginae, Lactobacillus plantarum|Atopobium vaginae, Lactobacillus reuteri|Atopobium vaginae, Lactobacillus rhamnosus|Atopobium vaginae, Lactobacillus ruminis|Atopobium vaginae, Lactobacillus sakei|Atopobium vaginae, Lactobacillus salivarius|Atopobium vaginae, Lactococcus lactis|Atopobium vaginae, Lautropia mirabilis|Atopobium vaginae, Leuconostoc citreum|Atopobium vaginae, Leuconostoc gasicomitatum|Atopobium vaginae, Leuconostoc mesenteroides|Atopobium vaginae, Listeria monocytogenes|Atopobium vaginae, Marvinbryantia formatexigens|Atopobium vaginae, Megamonas hypermegale|Atopobium vaginae, Megasphaera micronuciformis|Atopobium vaginae, Methanobrevibacter smithii|Atopobium vaginae, Methanosphaera stadtmanae|Atopobium vaginae, Methylobacterium radiotolerans|Atopobium vaginae, Mitsuokella multacida|Atopobium vaginae, Mobiluncus curtisii|Atopobium vaginae, Mycoplasma hominis|Atopobium vaginae, Neisseria mucosa|Atopobium vaginae, Odoribacter splanchnicus|Atopobium vaginae, Olsenella uli|Atopobium vaginae, Oribacterium sinus|Atopobium vaginae, Oxalobacter formigenes|Atopobium vaginae, Parabacteroides distasonis|Atopobium vaginae, Parabacteroides johnsonii|Atopobium vaginae, Parabacteroides merdae|Atopobium vaginae, Parvimonas micra|Atopobium vaginae, Pediococcus acidilactici|Atopobium vaginae, Pediococcus pentosaceus|Atopobium vaginae, Peptoniphilus duerdenii|Atopobium vaginae, Peptoniphilus harei|Atopobium vaginae, Peptoniphilus lacrimalis|Atopobium vaginae, Peptostreptococcus anaerobius|Atopobium vaginae, Peptostreptococcus stomatis|Atopobium vaginae, Porphyromonas asaccharolytica|Atopobium vaginae, Porphyromonas uenonis|Atopobium vaginae, Prevotella amnii|Atopobium vaginae, Prevotella bergensis|Atopobium vaginae, Prevotella bivia|Atopobium vaginae, Prevotella buccae|Atopobium vaginae, Prevotella buccalis|Atopobium vaginae, Prevotella copri|Atopobium vaginae, Prevotella disiens|Atopobium vaginae, Prevotella melaninogenica|Atopobium vaginae, Prevotella multiformis|Atopobium vaginae, Prevotella oralis|Atopobium vaginae, Prevotella oris|Atopobium vaginae, Prevotella salivae|Atopobium vaginae, Prevotella timonensis|Atopobium vaginae, Propionibacterium acnes|Atopobium vaginae, Propionibacterium freudenreichii|Atopobium vaginae, Proteus mirabilis|Atopobium vaginae, Proteus penneri|Atopobium vaginae, Pseudoflavonifractor capillosus|Atopobium vaginae, Pseudomonas aeruginosa|Atopobium vaginae, Pseudomonas fluorescens|Atopobium vaginae, Pseudomonas putida|Atopobium vaginae, Pseudoramibacter alactolyticus|Atopobium vaginae, Pyramidobacter piscolens|Atopobium vaginae, Rhodopseudomonas palustris|Atopobium vaginae, Roseburia intestinalis|Atopobium vaginae, Roseburia inulinivorans|Atopobium vaginae, Rothia dentocariosa|Atopobium vaginae, Rothia mucilaginosa|Atopobium vaginae, Ruminococcus albus|Atopobium vaginae, Ruminococcus bromii|Atopobium vaginae, Ruminococcus gnavus|Atopobium vaginae, Ruminococcus lactaris|Atopobium vaginae, Ruminococcus obeum|Atopobium vaginae, Ruminococcus torques|Atopobium vaginae, Selenomonas sputigena|Atopobium vaginae, Shigella boydii|Atopobium vaginae, Shigella dysenteriae|Atopobium vaginae, Shigella sonnei|Atopobium vaginae, Slackia exigua|Atopobium vaginae, Solobacterium moorei|Atopobium vaginae, Staphylococcus aureus|Atopobium vaginae, Staphylococcus epidermidis|Atopobium vaginae, Staphylococcus hominis|Atopobium vaginae, Staphylococcus saprophyticus|Atopobium vaginae, Staphylococcus warneri|Atopobium vaginae, Streptococcus agalactiae|Atopobium vaginae, Streptococcus anginosus|Atopobium vaginae, Streptococcus australis|Atopobium TABLE 2-continued

| Table 2. Specific binary combinations of OTUs. Individual pairings are differentiated by "\|" and OTUs within a combination are differentiated by "," |
|---|
| vaginae, Streptococcus bovis\|Atopobium vaginae, Streptococcus cristatus\|Atopobium vaginae, Streptococcus dysgalactiae\|Atopobium vaginae, Streptococcus equinus\|Atopobium vaginae, Streptococcus gordonii\|Atopobium vaginae, Streptococcus infantarius\|Atopobium vaginae, Streptococcus infantis\|Atopobium vaginae, Streptococcus mitis\|Atopobium vaginae, Streptococcus mutans\|Atopobium vaginae, Streptococcus oralis\|Atopobium vaginae, Streptococcus parasanguinis\|Atopobium vaginae, Streptococcus peroris\|Atopobium vaginae, Streptococcus pneumoniae\|Atopobium vaginae, Streptococcus salivarius\|Atopobium vaginae, Streptococcus sanguinis\|Atopobium vaginae, Streptococcus thermophilus\|Atopobium vaginae, Streptococcus vestibularis\|Atopobium vaginae, Subdoligranulum variabile\|Atopobium vaginae, Succinatimonas hippei\|Atopobium vaginae, Sutterella wadsworthensis\|Atopobium vaginae, Tropheryma whipplei\|Atopobium vaginae, Veillonella atypica\|Atopobium vaginae, Veillonella dispar\|Atopobium vaginae, Veillonella parvula\|Atopobium vaginae, Victivallis vadensis\|Bacteroides caccae, Bacteroides caccae, Bacteroides caccae, Bacteroides cellulosilyticus\|Bacteroides caccae, Bacteroides coprocola\|Bacteroides caccae, Bacteroides coprophilus\|Bacteroides caccae, Bacteroides dorei\|Bacteroides caccae, Bacteroides eggerthii\|Bacteroides caccae, Bacteroides finegoldii\|Bacteroides caccae, Bacteroides fragilis\|Bacteroides caccae, Bacteroides helcogene\|Bacteroides caccae, Bacteroides intestinalis\|Bacteroides caccae, Bacteroides ovatus\|Bacteroides caccae, Bacteroides pectinophilus\|Bacteroides caccae, Bacteroides plebeius\|Bacteroides caccae, Bacteroides salanitronis\|Bacteroides caccae, Bacteroides sp. 1_1_6\|Bacteroides caccae, Bacteroides sp. 3_1_23\|Bacteroides caccae, Bacteroides stercoris\|Bacteroides caccae, Bacteroides thetaiotaomicron\|Bacteroides caccae, Bacteroides uniformis\|Bacteroides caccae, Bacteroides vulgatus\|Bacteroides caccae, Bacteroides xylanisolvens\|Bacteroides caccae, Bifidobacterium adolescentis\|Bacteroides caccae, Bifidobacterium angulatum\|Bacteroides caccae, Bifidobacterium animalis\|Bacteroides caccae, Bifidobacterium bifidum\|Bacteroides caccae, Bifidobacterium breve\|Bacteroides caccae, Bifidobacterium catenulatum\|Bacteroides caccae, Bifidobacterium dentium\|Bacteroides caccae, Bifidobacterium infantis\|Bacteroides caccae, Bifidobacterium longum\|Bacteroides caccae, Bifidobacterium pseudocatenulatum\|Bacteroides caccae, Bilophila wadsworthia\|Bacteroides caccae, Blautia hansenii\|Bacteroides caccae, Blautia hydrogenotrophica\|Bacteroides caccae, Blautia producta\|Bacteroides caccae, Blautia schinkii\|Bacteroides caccae, Brevibacterium linens\|Bacteroides caccae, Brucella ceti\|Bacteroides caccae, Brucella suis\|Bacteroides caccae, Bulleidia extructa\|Bacteroides caccae, Butyrivibrio crossotus\|Bacteroides caccae, Campylobacter concisus\|Bacteroides caccae, Campylobacter curvus\|Bacteroides caccae, Campylobacter gracilis\|Bacteroides caccae, Campylobacter hominis\|Bacteroides caccae, Capnocytophaga ochracea\|Bacteroides caccae, Cardiobacterium hominis\|Bacteroides caccae, Catenibacterium mitsuokai\|Bacteroides caccae, Catonella morbi\|Bacteroides caccae, Citrobacter koseri\|Bacteroides caccae, Clostridium asparagiforme\|Bacteroides caccae, Clostridium bartlettii\|Bacteroides caccae, Clostridium bolteae\|Bacteroides caccae, Clostridium botulinum\|Bacteroides caccae, Clostridium butyricum\|Bacteroides caccae, Clostridium difficile\|Bacteroides caccae, Clostridium disporicum\|Bacteroides caccae, Clostridium hathewayi\|Bacteroides caccae, Clostridium hylemonae\|Bacteroides caccae, Clostridium innocuum\|Bacteroides caccae, Clostridium leptum\|Bacteroides caccae, Clostridium mayombei\|Bacteroides caccae, Clostridium methylpentosum\|Bacteroides caccae, Clostridium nexile\|Bacteroides caccae, Clostridium orbiscindens\|Bacteroides caccae, Clostridium perfringens\|Bacteroides caccae, Clostridium saccharolyticum\|Bacteroides caccae, Clostridium scindens\|Bacteroides caccae, Clostridium symbiosum\|Bacteroides caccae, Clostridium tertium\|Bacteroides caccae, Collinsella aerofaciens\|Bacteroides caccae, Collinsella intestinalis\|Bacteroides caccae, Collinsella stercoris\|Bacteroides caccae, Coprobacillus sp. D7\|Bacteroides caccae, Coprococcus catus\|Bacteroides caccae, Coprococcus comes\|Bacteroides caccae, Coprococcus eutactus\|Bacteroides caccae, Corynebacterium aurimucosum\|Bacteroides caccae, Corynebacterium matruchotii\|Bacteroides caccae, Cryptobacterium curtum\|Bacteroides caccae, Desulfovibrio desulfuricans\|Bacteroides caccae, Desulfovibrio piger\|Bacteroides caccae, Dialister invisus\|Bacteroides caccae, Dialister microaerophilus\|Bacteroides caccae, Dorea formicigenerans\|Bacteroides caccae, Dorea longicatena\|Bacteroides caccae, Eggerthella lenta\|Bacteroides caccae, Eikenella corrodens\|Bacteroides caccae, Enterobacter cancerogenus\|Bacteroides caccae, Enterobacter cloacae\|Bacteroides caccae, Enterococcus faecalis\|Bacteroides caccae, Enterococcus faecium\|Bacteroides caccae, Enterococcus gallinarum\|Bacteroides caccae, Erysipelotrichaceae bacterium 3_1_53\|Bacteroides caccae, Escherichia coli\|Bacteroides caccae, Escherichia fergusonii\|Bacteroides caccae, Ethanoligenens harbinense\|Bacteroides caccae, Eubacterium cellulosolvens\|Bacteroides caccae, Eubacterium eligens\|Bacteroides caccae, Eubacterium hallii\|Bacteroides caccae, Eubacterium limosum\|Bacteroides caccae, Eubacterium rectale\|Bacteroides caccae, Eubacterium siraeum\|Bacteroides caccae, Eubacterium ventriosum\|Bacteroides caccae, Faecalibacterium prausnitzii\|Bacteroides caccae, Finegoldia magna\|Bacteroides caccae, Fusobacterium gonidiaformans\|Bacteroides caccae, Fusobacterium mortiferum\|Bacteroides caccae, Fusobacterium nucleatum\|Bacteroides caccae, Fusobacterium varium\|Bacteroides caccae, Gardnerella vaginalis\|Bacteroides caccae, Gemella haemolysans\|Bacteroides caccae, Gemella morbillorum\|Bacteroides caccae, Gordonibacter pamelaeae\|Bacteroides caccae, Granulicatella adiacens\|Bacteroides caccae, Granulicatella elegans\|Bacteroides caccae, Haemophilus influenzae\|Bacteroides caccae, Haemophilus parainfluenzae\|Bacteroides caccae, Helicobacter pullorum\|Bacteroides caccae, Helicobacter pylori\|Bacteroides caccae, Holdemania filiformis\|Bacteroides caccae, Kingella oralis\|Bacteroides caccae, Klebsiella pneumoniae\|Bacteroides caccae, Klebsiella variicola\|Bacteroides caccae, Lachnospiraceae bacterium 5_1_57FAA\|Bacteroides caccae, Lactobacillus acidophilus\|Bacteroides caccae, Lactobacillus amylovorus\|Bacteroides caccae, Lactobacillus brevis\|Bacteroides caccae, Lactobacillus casei\|Bacteroides caccae, Lactobacillus crispatus\|Bacteroides caccae, Lactobacillus delbrueckii\|Bacteroides caccae, Lactobacillus fermentum\|Bacteroides caccae, Lactobacillus gasseri\|Bacteroides caccae, Lactobacillus iners\|Bacteroides caccae, Lactobacillus jensenii\|Bacteroides caccae, Lactobacillus johnsonii\|Bacteroides caccae, Lactobacillus paracasei\|Bacteroides caccae, Lactobacillus plantarum\|Bacteroides caccae, Lactobacillus reuteri\|Bacteroides caccae, Lactobacillus rhamnosus\|Bacteroides caccae, Lactobacillus ruminis\|Bacteroides caccae, Lactobacillus sakei\|Bacteroides caccae, Lactobacillus salivarius\|Bacteroides caccae, Lactococcus lactis\|Bacteroides caccae, Lautropia mirabilis\|Bacteroides caccae, Leuconostoc citreum\|Bacteroides caccae, Leuconostoc gasicomitatum\|Bacteroides caccae, Leuconostoc mesenteroides\|Bacteroides caccae, Listeria monocytogenes\|Bacteroides caccae, Marvinbryantia formatexigens\|Bacteroides caccae, Megamonas hypermegale\|Bacteroides caccae, Megasphaera micronuciformis\|Bacteroides caccae, Methanobrevibacter smithii\|Bacteroides caccae, Methanosphaera stadtmanae\|Bacteroides caccae, Methylobacterium radiotolerans\|Bacteroides caccae, Mitsuokella multacida\|Bacteroides caccae, Mobiluncus curtisii\|Bacteroides caccae, Mycoplasma hominis\|Bacteroides caccae, Neisseria mucosa\|Bacteroides caccae, Odoribacter splanchnicus\|Bacteroides caccae, Olsenella uli\|Bacteroides caccae, Oribacterium sinus\|Bacteroides caccae, Oxalobacter formigenes\|Bacteroides caccae, Parabacteroides distasonis\|Bacteroides caccae, Parabacteroides johnsonii\|Bacteroides caccae, Parabacteroides merdae\|Bacteroides caccae, Parvimonas micra\|Bacteroides caccae, Pediococcus acidilactici\|Bacteroides caccae, Pediococcus pentosaceus\|Bacteroides caccae, Peptoniphilus duerdenii\|Bacteroides caccae, Peptoniphilus harei\|Bacteroides caccae, Peptoniphilus lacrimalis\|Bacteroides caccae, Peptostreptococcus anaerobius\|Bacteroides caccae, Peptostreptococcus stomatis\|Bacteroides caccae, Porphyromonas asaccharolytica\|Bacteroides caccae, Porphyromonas uenonis\|Bacteroides caccae, Prevotella amnii\|Bacteroides caccae, Prevotella bergensis\|Bacteroides caccae, Prevotella bivia\|Bacteroides caccae, Prevotella buccae\|Bacteroides caccae, Prevotella buccalis\|Bacteroides caccae, Prevotella copri\|Bacteroides caccae, Prevotella disiens\|Bacteroides caccae, Prevotella melaninogenica\|Bacteroides caccae, Prevotella multifonnis\|Bacteroides caccae, Prevotella oralis\|Bacteroides caccae, Prevotella oris\|Bacteroides caccae, Prevotella salivae\|Bacteroides caccae, Prevotella timonensis\|Bacteroides caccae, Propionibacterium acnes\|Bacteroides caccae, Propionibacterium freudenreichii\|Bacteroides caccae, Proteus mirabilis\|Bacteroides caccae, Proteus penneri\|Bacteroides caccae, Pseudoflavonifractor capillosus\|Bacteroides caccae, Pseudomonas aeruginosa\|Bacteroides caccae, Pseudomonas fluorescens\|Bacteroides caccae, Pseudomonas putida\|Bacteroides caccae, Pseudoramibacter alactolyticus\|Bacteroides caccae, Pyramidobacter piscolens\|Bacteroides caccae, Rhodopseudomonas palustris\|Bacteroides caccae, Roseburia intestinalis\|Bacteroides caccae, Roseburia inulinivorans\|Bacteroides caccae, Rothia dentocariosa\|Bacteroides caccae, Rothia mucilaginosa\|Bacteroides caccae, Ruminococcus albus\|Bacteroides caccae, Ruminococcus bromii\|Bacteroides caccae, Ruminococcus gnavus\|Bacteroides caccae, Ruminococcus lactaris\|Bacteroides caccae, Ruminococcus obeum\|Bacteroides caccae, Ruminococcus |

TABLE 2-continued

Table 2. Specific binary combinations of OTUs. Individual pairings are differentiated by "|" and OTUs within a combination are differentiated by ","

torques|Bacteroides caccae, Selenomonas sputigena|Bacteroides caccae, Shigella boydii|Bacteroides caccae, Shigella dysenteriae|Bacteroides caccae, Shigella sonnei|Bacteroides caccae, Slackia exigua|Bacteroides caccae, Solobacterium moorei|Bacteroides caccae, Staphylococcus aureus|Bacteroides caccae, Staphylococcus epidermidis|Bacteroides caccae, Staphylococcus hominis|Bacteroides caccae, Staphylococcus saprophyticus|Bacteroides caccae, Staphylococcus warneri|Bacteroides caccae, Streptococcus agalactiae|Bacteroides caccae, Streptococcus anginosus|Bacteroides caccae, Streptococcus australis|Bacteroides caccae, Streptococcus bovis|Bacteroides caccae, Streptococcus cristatus|Bacteroides caccae, Streptococcus dysgalactiae|Bacteroides caccae, Streptococcus equinus|Bacteroides caccae, Streptococcus gordonii|Bacteroides caccae, Streptococcus infantarius|Bacteroides caccae, Streptococcus infantis|Bacteroides caccae, Streptococcus mitis|Bacteroides caccae, Streptococcus mutans|Bacteroides caccae, Streptococcus oralis|Bacteroides caccae, Streptococcus parasanguinis|Bacteroides caccae, Streptococcus peroris|Bacteroides caccae, Streptococcus pneumoniae|Bacteroides caccae, Streptococcus salivarius|Bacteroides caccae, Streptococcus sanguinis|Bacteroides caccae, Streptococcus thermophilus|Bacteroides caccae, Streptococcus vestibularis|Bacteroides caccae, Subdoligranulum variabile|Bacteroides caccae, Succinatimonas hippei|Bacteroides caccae, Sutterella wadsworthensis|Bacteroides caccae, Tropheryma whipplei|Bacteroides caccae, Veillonella atypica|Bacteroides caccae, Veillonella dispar|Bacteroides caccae, Veillonella parvula|Bacteroides caccae, Victivallis vadensis|Bacteroides cellulosilyticus, Bacteroides cellulosilyticus|Bacteroides cellulosilyticus, Bacteroides coprocola|Bacteroides cellulosilyticus, Bacteroides coprophilus|Bacteroides cellulosilyticus, Bacteroides dorei|Bacteroides cellulosilyticus, Bacteroides eggerthii|Bacteroides cellulosilyticus, Bacteroides finegoldii|Bacteroides cellulosilyticus, Bacteroides fragilis|Bacteroides cellulosilyticus, Bacteroides helcogenes|Bacteroides cellulosilyticus, Bacteroides intestinalis|Bacteroides cellulosilyticus, Bacteroides ovatus|Bacteroides cellulosilyticus, Bacteroides pectinophilus|Bacteroides cellulosilyticus, Bacteroides plebeius|Bacteroides cellulosilyticus, Bacteroides salanitronis|Bacteroides cellulosilyticus, Bacteroides sp. 1_1_6|Bacteroides cellulosilyticus, Bacteroides sp. 3_1_23|Bacteroides cellulosilyticus, Bacteroides stercoris|Bacteroides cellulosilyticus, Bacteroides thetaiotaomicron|Bacteroides cellulosilyticus, Bacteroides uniformis|Bacteroides cellulosilyticus, Bacteroides vulgatus|Bacteroides cellulosilyticus, Bacteroides xylanisolvens|Bacteroides cellulosilyticus, Bifidobacterium adolescentis|Bacteroides cellulosilyticus, Bifidobacterium angulatum|Bacteroides cellulosilyticus, Bifidobacterium animalis|Bacteroides cellulosilyticus, Bifidobacterium bifidum|Bacteroides cellulosilyticus, Bifidobacterium breve|Bacteroides cellulosilyticus, Bifidobacterium catenulatum|Bacteroides cellulosilyticus, Bifidobacterium dentium|Bacteroides cellulosilyticus, Bifidobacterium infantis|Bacteroides cellulosilyticus, Bifidobacterium longum|Bacteroides cellulosilyticus, Bifidobacterium pseudocatenulatum|Bacteroides cellulosilyticus, Bilophila wadsworthia|Bacteroides cellulosilyticus, Blautia hansenii|Bacteroides cellulosilyticus, Blautia hydrogenotrophica|Bacteroides cellulosilyticus, Blautia producta|Bacteroides cellulosilyticus, Blautia schinkii|Bacteroides cellulosilyticus, Brevibacterium linens|Bacteroides cellulosilyticus, Brucella ceti|Bacteroides cellulosilyticus, Brucella suis|Bacteroides cellulosilyticus, Bulleidia extructa|Bacteroides cellulosilyticus, Butyrivibrio crossotus|Bacteroides cellulosilyticus, Campylobacter concisus|Bacteroides cellulosilyticus, Campylobacter curvus|Bacteroides cellulosilyticus, Campylobacter gracilis|Bacteroides cellulosilyticus, Campylobacter hominis|Bacteroides cellulosilyticus, Capnocytophaga ochracea|Bacteroides cellulosilyticus, Cardiobacterium hominis|Bacteroides cellulosilyticus, Catenibacterium mitsuokai|Bacteroides cellulosilyticus, Catonella morbi|Bacteroides cellulosilyticus, Citrobacter koseri|Bacteroides cellulosilyticus, Clostridium asparagiforme|Bacteroides cellulosilyticus, Clostridium bartlettii|Bacteroides cellulosilyticus, Clostridium bolteae|Bacteroides cellulosilyticus, Clostridium botulinum|Bacteroides cellulosilyticus, Clostridium butyricum|Bacteroides cellulosilyticus, Clostridium difficile|Bacteroides cellulosilyticus, Clostridium disporicum|Bacteroides cellulosilyticus, Clostridium hathewayi|Bacteroides cellulosilyticus, Clostridium hylemonae|Bacteroides cellulosilyticus, Clostridium innocuum|Bacteroides cellulosilyticus, Clostridium leptum|Bacteroides cellulosilyticus, Clostridium mayombei|Bacteroides cellulosilyticus, Clostridium methylpentosum|Bacteroides cellulosilyticus, Clostridium nexile|Bacteroides cellulosilyticus, Clostridium orbiscindens|Bacteroides cellulosilyticus, Clostridium perfringens|Bacteroides cellulosilyticus, Clostridium saccharolyticum|Bacteroides cellulosilyticus, Clostridium scindens|Bacteroides cellulosilyticus, Clostridium symbiosum|Bacteroides cellulosilyticus, Clostridium tertium|Bacteroides cellulosilyticus, Collinsella aerofaciens|Bacteroides cellulosilyticus, Collinsella intestinalis|Bacteroides cellulosilyticus, Collinsella stercoris|Bacteroides cellulosilyticus, Coprobacillus sp. D7|Bacteroides cellulosilyticus, Coprococcus catus|Bacteroides cellulosilyticus, Coprococcus comes|Bacteroides cellulosilyticus, Coprococcus eutactus|Bacteroides cellulosilyticus, Corynebacterium aurimucosum|Bacteroides cellulosilyticus, Corynebacterium matruchotii|Bacteroides cellulosilyticus, Cryptobacterium curtum|Bacteroides cellulosilyticus, Desulfovibrio desulfuricans|Bacteroides cellulosilyticus, Desulfovibrio piger|Bacteroides cellulosilyticus, Dialister invisus|Bacteroides cellulosilyticus, Dialister microaerophilus|Bacteroides cellulosilyticus, Dorea formicigenerans|Bacteroides cellulosilyticus, Dorea longicatena|Bacteroides cellulosilyticus, Eggerthella lenta|Bacteroides cellulosilyticus, Eikenella corrodens|Bacteroides cellulosilyticus, Enterobacter cancerogenus|Bacteroides cellulosilyticus, Enterobacter cloacae|Bacteroides cellulosilyticus, Enterococcus faecalis|Bacteroides cellulosilyticus, Enterococcus faecium|Bacteroides cellulosilyticus, Enterococcus gallinarum|Bacteroides cellulosilyticus, Erysipelotrichaceae bacterium 3_1_53|Bacteroides cellulosilyticus, Escherichia coli|Bacteroides cellulosilyticus, Escherichia fergusonii|Bacteroides cellulosilyticus, Ethanoligenens harbinense|Bacteroides cellulosilyticus, Eubacterium cellulosolvens|Bacteroides cellulosilyticus, Eubacterium eligens|Bacteroides cellulosilyticus, Eubacterium hallii|Bacteroides cellulosilyticus, Eubacterium limosum|Bacteroides cellulosilyticus, Eubacterium rectale|Bacteroides cellulosilyticus, Eubacterium siraeum|Bacteroides cellulosilyticus, Eubacterium ventriosum|Bacteroides cellulosilyticus, Faecalibacterium prausnitzii|Bacteroides cellulosilyticus, Finegoldia magna|Bacteroides cellulosilyticus, Fusobacterium gonidiaformans|Bacteroides cellulosilyticus, Fusobacterium mortiferum|Bacteroides cellulosilyticus, Fusobacterium nucleatum|Bacteroides cellulosilyticus, Fusobacterium varium|Bacteroides cellulosilyticus, Gardnerella vaginalis|Bacteroides cellulosilyticus, Gemella haemolysans|Bacteroides cellulosilyticus, Gemella morbillorum|Bacteroides cellulosilyticus, Gordonibacter pamelaeae|Bacteroides cellulosilyticus, Granulicatella adiacens|Bacteroides cellulosilyticus, Granulicatella elegans|Bacteroides cellulosilyticus, Haemophilus influenzae|Bacteroides cellulosilyticus, Haemophilus parainfluenzae|Bacteroides cellulosilyticus, Helicobacter pullorum|Bacteroides cellulosilyticus, Helicobacter pylori|Bacteroides cellulosilyticus, Holdemania filiformis|Bacteroides cellulosilyticus, Kingella oralis|Bacteroides cellulosilyticus, Klebsiella pneumoniae|Bacteroides cellulosilyticus, Klebsiella variicola|Bacteroides cellulosilyticus, Lachnospiraceae bacterium 5_1_57FAA|Bacteroides cellulosilyticus, Lactobacillus acidophilus|Bacteroides cellulosilyticus, Lactobacillus amylovorus|Bacteroides cellulosilyticus, Lactobacillus brevis|Bacteroides cellulosilyticus, Lactobacillus casei|Bacteroides cellulosilyticus, Lactobacillus crispatus|Bacteroides cellulosilyticus, Lactobacillus delbrueckii|Bacteroides cellulosilyticus, Lactobacillus fermentum|Bacteroides cellulosilyticus, Lactobacillus gasseri|Bacteroides cellulosilyticus, Lactobacillus iners|Bacteroides cellulosilyticus, Lactobacillus jensenii|Bacteroides cellulosilyticus, Lactobacillus johnsonii|Bacteroides cellulosilyticus, Lactobacillus paracasei|Bacteroides cellulosilyticus, Lactobacillus plantarum|Bacteroides cellulosilyticus, Lactobacillus reuteri|Bacteroides cellulosilyticus, Lactobacillus rhamnosus|Bacteroides cellulosilyticus, Lactobacillus ruminis|Bacteroides cellulosilyticus, Lactobacillus sakei|Bacteroides cellulosilyticus, Lactobacillus salivarius|Bacteroides cellulosilyticus, Lactococcus lactis|Bacteroides cellulosilyticus, Lautropia mirabilis|Bacteroides cellulosilyticus, Leuconostoc citreum|Bacteroides cellulosilyticus, Leuconostoc gasicomitatum|Bacteroides cellulosilyticus, Leuconostoc mesenteroides|Bacteroides cellulosilyticus, Listeria monocytogenes|Bacteroides cellulosilyticus, Marvinbryantia formatexigens|Bacteroides cellulosilyticus, Megamonas hypermegale|Bacteroides cellulosilyticus, Megasphaera micronuciformis|Bacteroides cellulosilyticus, Methanobrevibacter smithii|Bacteroides cellulosilyticus, Methanosphaera stadtmanae|Bacteroides cellulosilyticus, Methylobacterium radiotolerans|Bacteroides cellulosilyticus, Mitsuokella multacida|Bacteroides cellulosilyticus, Mobiluncus curtisii|Bacteroides cellulosilyticus, Mycoplasma hominis|Bacteroides cellulosilyticus, Neisseria mucosa|Bacteroides cellulosilyticus, Odoribacter splanchnicus|Bacteroides cellulosilyticus, Olsenella uli|Bacteroides cellulosilyticus, Oribacterium sinus|Bacteroides cellulosilyticus, Oxalobacter formigenes|Bacteroides cellulosilyticus, Parabacteroides TABLE 2-continued

| Table 2. Specific binary combinations of OTUs. Individual pairings are differentiated by "\|" and OTUs within a combination are differentiated by "," |
|---|
| distasonis\|Bacteroides cellulosilyticus, Parabacteroides johnsonii\|Bacteroides cellulosilyticus, Parabacteroides merdae\|Bacteroides cellulosilyticus, Parvimonas micra\|Bacteroides cellulosilyticus, Pediococcus acidilactici\|Bacteroides cellulosilyticus, Pediococcus pentosaceus\|Bacteroides cellulosilyticus, Peptoniphilus duerdenii\|Bacteroides cellulosilyticus, Peptoniphilus harei\|Bacteroides cellulosilyticus, Peptoniphilus lacrimalis\|Bacteroides cellulosilyticus, Peptostreptococcus anaerobius\|Bacteroides cellulosilyticus, Peptostreptococcus stomatis\|Bacteroides cellulosilyticus, Porphyromonas asaccharolytica\|Bacteroides cellulosilyticus, Porphyromonas uenonis\|Bacteroides cellulosilyticus, Prevotella amnii\|Bacteroides cellulosilyticus, Prevotella bergensis\|Bacteroides cellulosilyticus, Prevotella bivia\|Bacteroides cellulosilyticus, Prevotella buccae\|Bacteroides cellulosilyticus, Prevotella buccalis\|Bacteroides cellulosilyticus, Prevotella copri\|Bacteroides cellulosilyticus, Prevotella disiens\|Bacteroides cellulosilyticus, Prevotella melaninogenica\|Bacteroides cellulosilyticus, Prevotella multiformis\|Bacteroides cellulosilyticus, Prevotella oralis\|Bacteroides cellulosilyticus, Prevotella oris\|Bacteroides cellulosilyticus, Prevotella salivae\|Bacteroides cellulosilyticus, Prevotella timonensis\|Bacteroides cellulosilyticus, Propionibacterium acnes\|Bacteroides cellulosilyticus, Propionibacterium freudenreichii\|Bacteroides cellulosilyticus, Proteus mirabilis\|Bacteroides cellulosilyticus, Proteus penneri\|Bacteroides cellulosilyticus, Pseudoflavonifractor capillosus\|Bacteroides cellulosilyticus, Pseudomonas aeruginosa\|Bacteroides cellulosilyticus, Pseudomonas fluorescens\|Bacteroides cellulosilyticus, Pseudomonas putida\|Bacteroides cellulosilyticus, Pseudoramibacter alactolyticus\|Bacteroides cellulosilyticus, Pyramidobacter piscolens\|Bacteroides cellulosilyticus, Rhodopseudomonas palustris\|Bacteroides cellulosilyticus, Roseburia intestinalis\|Bacteroides cellulosilyticus, Roseburia inulinivorans\|Bacteroides cellulosilyticus, Rothia dentocariosa\|Bacteroides cellulosilyticus, Rothia mucilaginosa\|Bacteroides cellulosilyticus, Ruminococcus albus\|Bacteroides cellulosilyticus, Ruminococcus bromii\|Bacteroides cellulosilyticus, Ruminococcus gnavus\|Bacteroides cellulosilyticus, Ruminococcus lactaris\|Bacteroides cellulosilyticus, Ruminococcus obeum\|Bacteroides cellulosilyticus, Ruminococcus torques\|Bacteroides cellulosilyticus, Selenomonas sputigena\|Bacteroides cellulosilyticus, Shigella boydii\|Bacteroides cellulosilyticus, Shigella dysenteriae\|Bacteroides cellulosilyticus, Shigella sonnei\|Bacteroides cellulosilyticus, Slackia exigua\|Bacteroides cellulosilyticus, Solobacterium moorei\|Bacteroides cellulosilyticus, Staphylococcus aureus\|Bacteroides cellulosilyticus, Staphylococcus epidermidis\|Bacteroides cellulosilyticus, Staphylococcus hominis\|Bacteroides cellulosilyticus, Staphylococcus saprophyticus\|Bacteroides cellulosilyticus, Staphylococcus warneri\|Bacteroides cellulosilyticus, Streptococcus agalactiae\|Bacteroides cellulosilyticus, Streptococcus anginosus\|Bacteroides cellulosilyticus, Streptococcus australis\|Bacteroides cellulosilyticus, Streptococcus bovis\|Bacteroides cellulosilyticus, Streptococcus cristatus\|Bacteroides cellulosilyticus, Streptococcus dysgalactiae\|Bacteroides cellulosilyticus, Streptococcus equinus\|Bacteroides cellulosilyticus, Streptococcus gordonii\|Bacteroides cellulosilyticus, Streptococcus infantarius\|Bacteroides cellulosilyticus, Streptococcus infantis\|Bacteroides cellulosilyticus, Streptococcus mitis\|Bacteroides cellulosilyticus, Streptococcus mutans\|Bacteroides cellulosilyticus, Streptococcus oralis\|Bacteroides cellulosilyticus, Streptococcus parasanguinis\|Bacteroides cellulosilyticus, Streptococcus peroris\|Bacteroides cellulosilyticus, Streptococcus pneumoniae\|Bacteroides cellulosilyticus, Streptococcus salivarius\|Bacteroides cellulosilyticus, Streptococcus sanguinis\|Bacteroides cellulosilyticus, Streptococcus thermophilus\|Bacteroides cellulosilyticus, Streptococcus vestibularis\|Bacteroides cellulosilyticus, Subdoligranulum variabile\|Bacteroides cellulosilyticus, Succinatimonas hippei\|Bacteroides cellulosilyticus, Sutterella wadsworthensis\|Bacteroides cellulosilyticus, Tropheryma whipplei\|Bacteroides cellulosilyticus, Veillonella atypica\|Bacteroides cellulosilyticus, Veillonella dispar\|Bacteroides cellulosilyticus, Veillonella parvula\|Bacteroides cellulosilyticus, Victivallis vadensis\|Bacteroides coprocola, Bacteroides coprocola\|Bacteroides coprocola, Bacteroides coprophilus\|Bacteroides coprocola, Bacteroides dorei\|Bacteroides coprocola, Bacteroides eggerthii\|Bacteroides coprocola, Bacteroides finegoldii\|Bacteroides coprocola, Bacteroides fragilis\|Bacteroides coprocola, Bacteroides helcogenes\|Bacteroides coprocola, Bacteroides intestinalis\|Bacteroides coprocola, Bacteroides ovatus\|Bacteroides coprocola, Bacteroides pectinophilus\|Bacteroides coprocola, Bacteroides plebeius\|Bacteroides coprocola, Bacteroides salanitronis\|Bacteroides coprocola, Bacteroides sp. 1_1_6\|Bacteroides coprocola, Bacteroides sp. 3_1_23\|Bacteroides coprocola, Bacteroides stercoris\|Bacteroides coprocola, Bacteroides thetaiotaomicron\|Bacteroides coprocola, Bacteroides uniformis\|Bacteroides coprocola, Bacteroides vulgatus\|Bacteroides coprocola, Bacteroides xylanisolvens\|Bacteroides coprocola, Bifidobacterium adolescentis\|Bacteroides coprocola, Bifidobacterium angulatum\|Bacteroides coprocola, Bifidobacterium animalis\|Bacteroides coprocola, Bifidobacterium bifidum\|Bacteroides coprocola, Bifidobacterium breve\|Bacteroides coprocola, Bifidobacterium catenulatum\|Bacteroides coprocola, Bifidobacterium dentium\|Bacteroides coprocola, Bifidobacterium infantis\|Bacteroides coprocola, Bifidobacterium longum\|Bacteroides coprocola, Bifidobacterium pseudocatenulatum\|Bacteroides coprocola, Bilophila wadsworthia\|Bacteroides coprocola, Blautia hansenii\|Bacteroides coprocola, Blautia hydrogenotrophica\|Bacteroides coprocola, Blautia producta\|Bacteroides coprocola, Blautia schinkii\|Bacteroides coprocola, Brevibacterium linens\|Bacteroides coprocola, Brucella ceti\|Bacteroides coprocola, Brucella suis\|Bacteroides coprocola, Bulleidia extructa\|Bacteroides coprocola, Butyrivibrio crossotus\|Bacteroides coprocola, Campylobacter concisus\|Bacteroides coprocola, Campylobacter curvus\|Bacteroides coprocola, Campylobacter gracilis\|Bacteroides coprocola, Campylobacter hominis\|Bacteroides coprocola, Capnocytophaga ochracea\|Bacteroides coprocola, Cardiobacterium hominis\|Bacteroides coprocola, Catenibacterium mitsuokai\|Bacteroides coprocola, Catonella morbi\|Bacteroides coprocola, Citrobacter koseri\|Bacteroides coprocola, Clostridium asparagiforme\|Bacteroides coprocola, Clostridium bartlettii\|Bacteroides coprocola, Clostridium bolteae\|Bacteroides coprocola, Clostridium botulinum\|Bacteroides coprocola, Clostridium butyricum\|Bacteroides coprocola, Clostridium difficile\|Bacteroides coprocola, Clostridium disporicum\|Bacteroides coprocola, Clostridium hathewayi\|Bacteroides coprocola, Clostridium hylemonae\|Bacteroides coprocola, Clostridium innocuum\|Bacteroides coprocola, Clostridium leptum\|Bacteroides coprocola, Clostridium mayombei\|Bacteroides coprocola, Clostridium methylpentosum\|Bacteroides coprocola, Clostridium nexile\|Bacteroides coprocola, Clostridium orbiscindens\|Bacteroides coprocola, Clostridium perfringens\|Bacteroides coprocola, Clostridium saccharolyticum\|Bacteroides coprocola, Clostridium scindens\|Bacteroides coprocola, Clostridium symbiosum\|Bacteroides coprocola, Clostridium tertium\|Bacteroides coprocola, Collinsella aerofaciens\|Bacteroides coprocola, Collinsella intestinalis\|Bacteroides coprocola, Collinsella stercoris\|Bacteroides coprocola, Coprobacillus sp. D7\|Bacteroides coprocola, Coprococcus catus\|Bacteroides coprocola, Coprococcus comes\|Bacteroides coprocola, Coprococcus eutactus\|Bacteroides coprocola, Corynebacterium aurimucosum\|Bacteroides coprocola, Corynebacterium matruchotii\|Bacteroides coprocola, Cryptobacterium curtum\|Bacteroides coprocola, Desulfovibrio desulfuricans\|Bacteroides coprocola, Desulfovibrio piger\|Bacteroides coprocola, Dialister invisus\|Bacteroides coprocola, Dialister microaerophilus\|Bacteroides coprocola, Dorea formicigenerans\|Bacteroides coprocola, Dorea longicatena\|Bacteroides coprocola, Eggerthella lenta\|Bacteroides coprocola, Eikenella corrodens\|Bacteroides coprocola, Enterobacter cancerogenus\|Bacteroides coprocola, Enterobacter cloacae\|Bacteroides coprocola, Enterococcus faecalis\|Bacteroides coprocola, Enterococcus faecium\|Bacteroides coprocola, Enterococcus gallinarum\|Bacteroides coprocola, Erysipelotrichaceae bacterium 3_1_53\|Bacteroides coprocola, Escherichia coli\|Bacteroides coprocola, Escherichia fergusonii\|Bacteroides coprocola, Ethanoligenens harbinense\|Bacteroides coprocola, Eubacterium cellulosolvens\|Bacteroides coprocola, Eubacterium eligens\|Bacteroides coprocola, Eubacterium hallii\|Bacteroides coprocola, Eubacterium limosum\|Bacteroides coprocola, Eubacterium rectale\|Bacteroides coprocola, Eubacterium siraeum\|Bacteroides coprocola, Eubacterium ventriosum\|Bacteroides coprocola, Faecalibacterium prausnitzii\|Bacteroides coprocola, Finegoldia magna\|Bacteroides coprocola, Fusobacterium gonidiaformans\|Bacteroides coprocola, Fusobacterium mortiferum\|Bacteroides coprocola, Fusobacterium nucleatum\|Bacteroides coprocola, Fusobacterium varium\|Bacteroides coprocola, Gardnerella vaginalis\|Bacteroides coprocola, Gemella haemolysans\|Bacteroides coprocola, Gemella morbillorum\|Bacteroides coprocola, Gordonibacter pamelaeae\|Bacteroides coprocola, Granulicatella adiacens\|Bacteroides coprocola, Granulicatella elegans\|Bacteroides coprocola, Haemophilus influenzae\|Bacteroides coprocola, Haemophilus parainfluenzae\|Bacteroides coprocola, Helicobacter pullorum\|Bacteroides coprocola, Helicobacter pylori\|Bacteroides coprocola, Holdemania filiformis\|Bacteroides coprocola, Kingella oralis\|Bacteroides coprocola, Klebsiella pneumoniae\|Bacteroides coprocola, Klebsiella variicola\|Bacteroides coprocola, Lachnospiraceae bacterium 5_1_57FAA\|Bacteroides coprocola, Lactobacillus acidophilus\|Bacteroides coprocola, Lactobacillus |

TABLE 2-continued

| Table 2. Specific binary combinations of OTUs. Individual pairings are differentiated by "\|" and OTUs within a combination are differentiated by "," |
| --- |
| *amylovorus\|Bacteroides coprocola, Lactobacillus brevis\|Bacteroides coprocola, Lactobacillus casei\|Bacteroides coprocola, Lactobacillus crispatus\|Bacteroides coprocola, Lactobacillus delbrueckii\|Bacteroides coprocola, Lactobacillus fermentum\|Bacteroides coprocola, Lactobacillus gasseri\|Bacteroides coprocola, Lactobacillus iners\|Bacteroides coprocola, Lactobacillus jensenii\|Bacteroides coprocola, Lactobacillus johnsonii\|Bacteroides coprocola, Lactobacillus paracasei\|Bacteroides coprocola, Lactobacillus plantarum\|Bacteroides coprocola, Lactobacillus reuteri\|Bacteroides coprocola, Lactobacillus rhamnosus\|Bacteroides coprocola, Lactobacillus ruminis\|Bacteroides coprocola, Lactobacillus sakei\|Bacteroides coprocola, Lactobacillus salivarius\|Bacteroides coprocola, Lactococcus lactis\|Bacteroides coprocola, Lautropia mirabilis\|Bacteroides coprocola, Leuconostoc citreum\|Bacteroides coprocola, Leuconostoc gasicomitatum\|Bacteroides coprocola, Leuconostoc mesenteroides\|Bacteroides coprocola, Listeria monocytogenes\|Bacteroides coprocola, Marvinbryantia formatexigens\|Bacteroides coprocola, Megamonas hypermegale\|Bacteroides coprocola, Megasphaera micronuciformis\|Bacteroides coprocola, Methanobrevibacter smithii\|Bacteroides coprocola, Methanosphaera stadtmanae\|Bacteroides coprocola, Methylobacterium radiotolerans\|Bacteroides coprocola, Mitsuokella multacida\|Bacteroides coprocola, Mobiluncus curtisii\|Bacteroides coprocola, Mycoplasma hominis\|Bacteroides coprocola, Neisseria mucosa\|Bacteroides coprocola, Odoribacter splanchnicus\|Bacteroides coprocola, Olsenella uli\|Bacteroides coprocola, Oribacterium sinus\|Bacteroides coprocola, Oxalobacter formigenes\|Bacteroides coprocola, Parabacteroides distasonis\|Bacteroides coprocola, Parabacteroides johnsonii\|Bacteroides coprocola, Parabacteroides merdae\|Bacteroides coprocola, Parvimonas micra\|Bacteroides coprocola, Pediococcus acidilactici\|Bacteroides coprocola, Pediococcus pentosaceus\|Bacteroides coprocola, Peptoniphilus duerdenii\|Bacteroides coprocola, Peptoniphilus harei\|Bacteroides coprocola, Peptoniphilus lacrimalis\|Bacteroides coprocola, Peptostreptococcus anaerobius\|Bacteroides coprocola, Peptostreptococcus stomatis\|Bacteroides coprocola, Porphyromonas asaccharolytica\|Bacteroides coprocola, Porphyromonas uenonis\|Bacteroides coprocola, Prevotella amnii\|Bacteroides coprocola, Prevotella bergensis\|Bacteroides coprocola, Prevotella bivia\|Bacteroides coprocola, Prevotella buccae\|Bacteroides coprocola, Prevotella buccalis\|Bacteroides coprocola, Prevotella copri\|Bacteroides coprocola, Prevotella disiens\|Bacteroides coprocola, Prevotella melaninogenica\|Bacteroides coprocola, Prevotella multiformis\|Bacteroides coprocola, Prevotella oralis\|Bacteroides coprocola, Prevotella oris\|Bacteroides coprocola, Prevotella salivae\|Bacteroides coprocola, Prevotella timonensis\|Bacteroides coprocola, Propionibacterium acnes\|Bacteroides coprocola, Propionibacterium freudenreichii\|Bacteroides coprocola, Proteus mirabilis\|Bacteroides coprocola, Proteus penneri\|Bacteroides coprocola, Pseudoflavonifractor capillosus\|Bacteroides coprocola, Pseudomonas aeruginosa\|Bacteroides coprocola, Pseudomonas fluorescens\|Bacteroides coprocola, Pseudomonas putida\|Bacteroides coprocola, Pseudoramibacter alactolyticus\|Bacteroides coprocola, Pyramidobacter piscolens\|Bacteroides coprocola, Rhodopseudomonas palustris\|Bacteroides coprocola, Roseburia intestinalis\|Bacteroides coprocola, Roseburia inulinivorans\|Bacteroides coprocola, Rothia dentocariosa\|Bacteroides coprocola, Rothia mucilaginosa\|Bacteroides coprocola, Ruminococcus albus\|Bacteroides coprocola, Ruminococcus bromii\|Bacteroides coprocola, Ruminococcus gnavus\|Bacteroides coprocola, Ruminococcus lactaris\|Bacteroides coprocola, Ruminococcus obeum\|Bacteroides coprocola, Ruminococcus torques\|Bacteroides coprocola, Selenomonas sputigena\|Bacteroides coprocola, Shigella boydii\|Bacteroides coprocola, Shigella dysenteriae\|Bacteroides coprocola, Shigella sonnei\|Bacteroides coprocola, Slackia exigua\|Bacteroides coprocola, Solobacterium moorei\|Bacteroides coprocola, Staphylococcus aureus\|Bacteroides coprocola, Staphylococcus epidermidis\|Bacteroides coprocola, Staphylococcus hominis\|Bacteroides coprocola, Staphylococcus saprophyticus\|Bacteroides coprocola, Staphylococcus warneri\|Bacteroides coprocola, Streptococcus agalactiae\|Bacteroides coprocola, Streptococcus anginosus\|Bacteroides coprocola, Streptococcus australis\|Bacteroides coprocola, Streptococcus bovis\|Bacteroides coprocola, Streptococcus cristatus\|Bacteroides coprocola, Streptococcus dysgalactiae\|Bacteroides coprocola, Streptococcus equinus\|Bacteroides coprocola, Streptococcus gordonii\|Bacteroides coprocola, Streptococcus infantarius\|Bacteroides coprocola, Streptococcus infantis\|Bacteroides coprocola, Streptococcus mitis\|Bacteroides coprocola, Streptococcus mutans\|Bacteroides coprocola, Streptococcus oralis\|Bacteroides coprocola, Streptococcus parasanguinis\|Bacteroides coprocola, Streptococcus peroris\|Bacteroides coprocola, Streptococcus pneumoniae\|Bacteroides coprocola, Streptococcus salivarius\|Bacteroides coprocola, Streptococcus sanguinis\|Bacteroides coprocola, Streptococcus thermophilus\|Bacteroides coprocola, Streptococcus vestibularis\|Bacteroides coprocola, Subdoligranulum variabile\|Bacteroides coprocola, Succinatimonas hippei\|Bacteroides coprocola, Sutterella wadsworthensis\|Bacteroides coprocola, Tropheryma whipplei\|Bacteroides coprocola, Veillonella atypica\|Bacteroides coprocola, Veillonella dispar\|Bacteroides coprocola, Veillonella parvula\|Bacteroides coprocola, Victivallis vadensis\|Bacteroides coprophilus, Bacteroides coprophilus\|Bacteroides coprophilus, Bacteroides dorei\|Bacteroides coprophilus, Bacteroides eggerthii\|Bacteroides coprophilus, Bacteroides finegoldii\|Bacteroides coprophilus, Bacteroides fragilis\|Bacteroides coprophilus, Bacteroides helcogenes\|Bacteroides coprophilus, Bacteroides intestinalis\|Bacteroides coprophilus, Bacteroides ovatus\|Bacteroides coprophilus, Bacteroides pectinophilus\|Bacteroides coprophilus, Bacteroides plebeius\|Bacteroides coprophilus, Bacteroides salanitronis\|Bacteroides coprophilus, Bacteroides* sp. 1_1_6*\|Bacteroides coprophilus, Bacteroides* sp. 3_1_23*\|Bacteroides coprophilus, Bacteroides stercoris\|Bacteroides coprophilus, Bacteroides thetaiotaomicron\|Bacteroides coprophilus, Bacteroides uniformis\|Bacteroides coprophilus, Bacteroides vulgatus\|Bacteroides coprophilus, Bacteroides xylanisolvens\|Bacteroides coprophilus, Bifidobacterium adolescentis\|Bacteroides coprophilus, Bifidobacterium angulatum\|Bacteroides coprophilus, Bifidobacterium animalis\|Bacteroides coprophilus, Bifidobacterium bifidum\|Bacteroides coprophilus, Bifidobacterium breve\|Bacteroides coprophilus, Bifidobacterium catenulatum\|Bacteroides coprophilus, Bifidobacterium dentium\|Bacteroides coprophilus, Bifidobacterium infantis\|Bacteroides coprophilus, Bifidobacterium longum\|Bacteroides coprophilus, Bifidobacterium pseudocatenulatum\|Bacteroides coprophilus, Bilophila wadsworthia\|Bacteroides coprophilus, Blautia hansenii\|Bacteroides coprophilus, Blautia hydrogenotrophica\|Bacteroides coprophilus, Blautia producta\|Bacteroides coprophilus, Blautia schinkii\|Bacteroides coprophilus, Brevibacterium linens\|Bacteroides coprophilus, Brucella ceti\|Bacteroides coprophilus, Brucella suis\|Bacteroides coprophilus, Bulleidia extructa\|Bacteroides coprophilus, Butyrivibrio crossotus\|Bacteroides coprophilus, Campylobacter concisus\|Bacteroides coprophilus, Campylobacter curvus\|Bacteroides coprophilus, Campylobacter gracilis\|Bacteroides coprophilus, Campylobacter hominis\|Bacteroides coprophilus, Capnocytophaga ochracea\|Bacteroides coprophilus, Cardiobacterium hominis\|Bacteroides coprophilus, Catenibacterium mitsuokai\|Bacteroides coprophilus, Catonella morbi\|Bacteroides coprophilus, Citrobacter koseri\|Bacteroides coprophilus, Clostridium asparagiforme\|Bacteroides coprophilus, Clostridium bartlettii\|Bacteroides coprophilus, Clostridium bolteae\|Bacteroides coprophilus, Clostridium botulinum\|Bacteroides coprophilus, Clostridium butyricum\|Bacteroides coprophilus, Clostridium difficile\|Bacteroides coprophilus, Clostridium disporicum\|Bacteroides coprophilus, Clostridium hathewayi\|Bacteroides coprophilus, Clostridium hylemonae\|Bacteroides coprophilus, Clostridium innocuum\|Bacteroides coprophilus, Clostridium leptum\|Bacteroides coprophilus, Clostridium mayombei\|Bacteroides coprophilus, Clostridium methylpentosum\|Bacteroides coprophilus, Clostridium nexile\|Bacteroides coprophilus, Clostridium orbiscindens\|Bacteroides coprophilus, Clostridium perfringens\|Bacteroides coprophilus, Clostridium saccharolyticum\|Bacteroides coprophilus, Clostridium scindens\|Bacteroides coprophilus, Clostridium symbiosum\|Bacteroides coprophilus, Clostridium tertium\|Bacteroides coprophilus, Collinsella aerofaciens\|Bacteroides coprophilus, Collinsella intestinalis\|Bacteroides coprophilus, Collinsella stercoris\|Bacteroides coprophilus, Coprobacillus* sp. D7*\|Bacteroides coprophilus, Coprococcus catus\|Bacteroides coprophilus, Coprococcus comes\|Bacteroides coprophilus, Coprococcus eutactus\|Bacteroides coprophilus, Corynebacterium aurimucosum\|Bacteroides coprophilus, Corynebacterium matruchotii\|Bacteroides coprophilus, Cryptobacterium curtum\|Bacteroides coprophilus, Desulfovibrio desulfuricans\|Bacteroides coprophilus, Desulfovibrio piger\|Bacteroides coprophilus, Dialister invisus\|Bacteroides coprophilus, Dialister microaerophilus\|Bacteroides coprophilus, Dorea formicigenerans\|Bacteroides coprophilus, Dorea longicatena\|Bacteroides coprophilus, Eggerthella lenta\|Bacteroides coprophilus, Eikenella corrodens\|Bacteroides coprophilus, Enterobacter cancerogenus\|Bacteroides coprophilus, Enterobacter cloacae\|Bacteroides coprophilus, Enterococcus faecalis\|Bacteroides coprophilus, Enterococcus faecium\|Bacteroides coprophilus, Enterococcus gallinarum\|Bacteroides coprophilus, Erysipelotrichaceae bacterium* 3_1_53*\|Bacteroides coprophilus, Escherichia coli\|Bacteroides coprophilus, Escherichia fergusonii\|Bacteroides* |

TABLE 2-continued

Table 2. Specific binary combinations of OTUs. Individual pairings are differentiated by "|" and OTUs within a combination are differentiated by ","

*coprophilus, Ethanoligenens harbinense|Bacteroides coprophilus, Eubacterium cellulosolvens|Bacteroides coprophilus, Eubacterium eligens|Bacteroides coprophilus, Eubacterium hallii|Bacteroides coprophilus, Eubacterium limosum|Bacteroides coprophilus, Eubacterium rectale|Bacteroides coprophilus, Eubacterium siraeum|Bacteroides coprophilus, Eubacterium ventriosum|Bacteroides coprophilus, Faecalibacterium prausnitzii|Bacteroides coprophilus, Finegoldia magna|Bacteroides coprophilus, Fusobacterium gonidiaformans|Bacteroides coprophilus, Fusobacterium mortiferum|Bacteroides coprophilus, Fusobacterium nucleatum|Bacteroides coprophilus, Fusobacterium varium|Bacteroides coprophilus, Gardnerella vaginalis|Bacteroides coprophilus, Gemella haemolysans|Bacteroides coprophilus, Gemella morbillorum|Bacteroides coprophilus, Gordonibacter pamelaeae|Bacteroides coprophilus, Granulicatella adiacens|Bacteroides coprophilus, Granulicatella elegans|Bacteroides coprophilus, Haemophilus influenzae|Bacteroides coprophilus, Haemophilus parainfluenzae|Bacteroides coprophilus, Helicobacter pullorum|Bacteroides coprophilus, Helicobacter pylori|Bacteroides coprophilus, Holdemania filiformis|Bacteroides coprophilus, Kingella oralis|Bacteroides coprophilus, Klebsiella pneumoniae|Bacteroides coprophilus, Klebsiella variicola|Bacteroides coprophilus, Lachnospiraceae bacterium* 5_1_57FAA|*Bacteroides coprophilus, Lactobacillus acidophilus|Bacteroides coprophilus, Lactobacillus amylovorus|Bacteroides coprophilus, Lactobacillus brevis|Bacteroides coprophilus, Lactobacillus casei|Bacteroides coprophilus, Lactobacillus crispatus|Bacteroides coprophilus, Lactobacillus delbrueckii|Bacteroides coprophilus, Lactobacillus fermentum|Bacteroides coprophilus, Lactobacillus gasseri|Bacteroides coprophilus, Lactobacillus iners|Bacteroides coprophilus, Lactobacillus jensenii|Bacteroides coprophilus, Lactobacillus johnsonii|Bacteroides coprophilus, Lactobacillus paracasei|Bacteroides coprophilus, Lactobacillus plantarum|Bacteroides coprophilus, Lactobacillus reuteri|Bacteroides coprophilus, Lactobacillus rhamnosus|Bacteroides coprophilus, Lactobacillus ruminis|Bacteroides coprophilus, Lactobacillus sakei|Bacteroides coprophilus, Lactobacillus salivarius|Bacteroides coprophilus, Lactococcus lactis|Bacteroides coprophilus, Lautropia mirabilis|Bacteroides coprophilus, Leuconostoc citreum|Bacteroides coprophilus, Leuconostoc gasicomitatum|Bacteroides coprophilus, Leuconostoc mesenteroides|Bacteroides coprophilus, Listeria monocytogenes|Bacteroides coprophilus, Marvinbryantia formatexigens|Bacteroides coprophilus, Megamonas hypermegale|Bacteroides coprophilus, Megasphaera micronuciformis|Bacteroides coprophilus, Methanobrevibacter smithii|Bacteroides coprophilus, Methanosphaera stadtmanae|Bacteroides coprophilus, Methylobacterium radiotolerans|Bacteroides coprophilus, Mitsuokella multacida|Bacteroides coprophilus, Mobiluncus curtisii|Bacteroides coprophilus, Mycoplasma hominis|Bacteroides coprophilus, Neisseria mucosa|Bacteroides coprophilus, Odoribacter splanchnicus|Bacteroides coprophilus, Olsenella uli|Bacteroides coprophilus, Oribacterium sinus|Bacteroides coprophilus, Oxalobacter formigenes|Bacteroides coprophilus, Parabacteroides distasonis|Bacteroides coprophilus, Parabacteroides johnsonii|Bacteroides coprophilus, Parabacteroides merdae|Bacteroides coprophilus, Parvimonas micra|Bacteroides coprophilus, Pediococcus acidilactici|Bacteroides coprophilus, Pediococcus pentosaceus|Bacteroides coprophilus, Peptoniphilus duerdenii|Bacteroides coprophilus, Peptoniphilus harei|Bacteroides coprophilus, Peptoniphilus lacrimalis|Bacteroides coprophilus, Peptostreptococcus anaerobius|Bacteroides coprophilus, Peptostreptococcus stomatis|Bacteroides coprophilus, Porphyromonas asaccharolytica|Bacteroides coprophilus, Porphyromonas uenonis|Bacteroides coprophilus, Prevotella amnii|Bacteroides coprophilus, Prevotella bergensis|Bacteroides coprophilus, Prevotella bivia|Bacteroides coprophilus, Prevotella buccae|Bacteroides coprophilus, Prevotella buccalis|Bacteroides coprophilus, Prevotella copri|Bacteroides coprophilus, Prevotella disiens|Bacteroides coprophilus, Prevotella melaninogenica|Bacteroides coprophilus, Prevotella multiformis|Bacteroides coprophilus, Prevotella oralis|Bacteroides coprophilus, Prevotella oris|Bacteroides coprophilus, Prevotella salivae|Bacteroides coprophilus, Prevotella timonensis|Bacteroides coprophilus, Propionibacterium acnes|Bacteroides coprophilus, Propionibacterium freudenreichii|Bacteroides coprophilus, Proteus mirabilis|Bacteroides coprophilus, Proteus penneri|Bacteroides coprophilus, Pseudoflavonifractor capillosus|Bacteroides coprophilus, Pseudomonas aeruginosa|Bacteroides coprophilus, Pseudomonas fluorescens|Bacteroides coprophilus, Pseudomonas putida|Bacteroides coprophilus, Pseudoramibacter alactolyticus|Bacteroides coprophilus, Pyramidobacter piscolens|Bacteroides coprophilus, Rhodopseudomonas palustris|Bacteroides coprophilus, Roseburia intestinalis|Bacteroides coprophilus, Roseburia inulinivorans|Bacteroides coprophilus, Rothia dentocariosa|Bacteroides coprophilus, Rothia mucilaginosa|Bacteroides coprophilus, Ruminococcus albus|Bacteroides coprophilus, Ruminococcus bromii|Bacteroides coprophilus, Ruminococcus gnavus|Bacteroides coprophilus, Ruminococcus lactaris|Bacteroides coprophilus, Ruminococcus obeum|Bacteroides coprophilus, Ruminococcus torques|Bacteroides coprophilus, Selenomonas sputigena|Bacteroides coprophilus, Shigella boydii|Bacteroides coprophilus, Shigella dysenteriae|Bacteroides coprophilus, Shigella sonnei|Bacteroides coprophilus, Slackia exigua|Bacteroides coprophilus, Solobacterium moorei|Bacteroides coprophilus, Staphylococcus aureus|Bacteroides coprophilus, Staphylococcus epidermidis|Bacteroides coprophilus, Staphylococcus hominis|Bacteroides coprophilus, Staphylococcus saprophyticus|Bacteroides coprophilus, Staphylococcus warneri|Bacteroides coprophilus, Streptococcus agalactiae|Bacteroides coprophilus, Streptococcus anginosus|Bacteroides coprophilus, Streptococcus australis|Bacteroides coprophilus, Streptococcus bovis|Bacteroides coprophilus, Streptococcus cristatus|Bacteroides coprophilus, Streptococcus dysgalactiae|Bacteroides coprophilus, Streptococcus equinus|Bacteroides coprophilus, Streptococcus gordonii|Bacteroides coprophilus, Streptococcus infantarius|Bacteroides coprophilus, Streptococcus infantis|Bacteroides coprophilus, Streptococcus mitis|Bacteroides coprophilus, Streptococcus mutans|Bacteroides coprophilus, Streptococcus oralis|Bacteroides coprophilus, Streptococcus parasanguinis|Bacteroides coprophilus, Streptococcus peroris|Bacteroides coprophilus, Streptococcus pneumoniae|Bacteroides coprophilus, Streptococcus salivarius|Bacteroides coprophilus, Streptococcus sanguinis|Bacteroides coprophilus, Streptococcus thermophilus|Bacteroides coprophilus, Streptococcus vestibularis|Bacteroides coprophilus, Subdoligranulum variabile|Bacteroides coprophilus, Succinatimonas hippei|Bacteroides coprophilus, Sutterella wadsworthensis|Bacteroides coprophilus, Tropheryma whipplei|Bacteroides coprophilus, Veillonella atypica|Bacteroides coprophilus, Veillonella dispar|Bacteroides coprophilus, Veillonella parvula|Bacteroides coprophilus, Victivallis vadensis|Bacteroides dorei, Bacteroides dorei|Bacteroides dorei, Bacteroides eggerthii|Bacteroides dorei, Bacteroides finegoldii|Bacteroides dorei, Bacteroides fragilis|Bacteroides dorei, Bacteroides helcogenes|Bacteroides dorei, Bacteroides intestinalis|Bacteroides dorei, Bacteroides ovatus|Bacteroides dorei, Bacteroides pectinophilus|Bacteroides dorei, Bacteroides plebeius|Bacteroides dorei, Bacteroides salanitronis|Bacteroides dorei, Bacteroides* sp. 1_1_6|*Bacteroides dorei, Bacteroides* sp. 3_1_23|*Bacteroides dorei, Bacteroides stercoris|Bacteroides dorei, Bacteroides thetaiotaomicron|Bacteroides dorei, Bacteroides uniformis|Bacteroides dorei, Bacteroides vulgatus|Bacteroides dorei, Bacteroides xylanisolvens|Bacteroides dorei, Bifidobacterium adolescentis|Bacteroides dorei, Bifidobacterium angulatum|Bacteroides dorei, Bifidobacterium animalis|Bacteroides dorei, Bifidobacterium bifidum|Bacteroides dorei, Bifidobacterium breve|Bacteroides dorei, Bifidobacterium catenulatum|Bacteroides dorei, Bifidobacterium dentium|Bacteroides dorei, Bifidobacterium infantis|Bacteroides dorei, Bifidobacterium longum|Bacteroides dorei, Bifidobacterium pseudocatenulatum|Bacteroides dorei, Bilophila wadsworthia|Bacteroides dorei, Blautia hansenii|Bacteroides dorei, Blautia hydrogenotrophica|Bacteroides dorei, Blautia producta|Bacteroides dorei, Blautia schinkii|Bacteroides dorei, Brevibacterium linens|Bacteroides dorei, Brucella ceti|Bacteroides dorei, Brucella suis|Bacteroides dorei, Bulleidia extructa|Bacteroides dorei, Butyrivibrio crossotus|Bacteroides dorei, Campylobacter concisus|Bacteroides dorei, Campylobacter curvus|Bacteroides dorei, Campylobacter gracilis|Bacteroides dorei, Campylobacter hominis|Bacteroides dorei, Capnocytophaga ochracea|Bacteroides dorei, Cardiobacterium hominis|Bacteroides dorei, Catenibacterium mitsuokai|Bacteroides dorei, Catonella morbi|Bacteroides dorei, Citrobacter koseri|Bacteroides dorei, Clostridium asparagiforme|Bacteroides dorei, Clostridium bartlettii|Bacteroides dorei, Clostridium bolteae|Bacteroides dorei, Clostridium botulinum|Bacteroides dorei, Clostridium butyricum|Bacteroides dorei, Clostridium difficile|Bacteroides dorei, Clostridium disporicum|Bacteroides dorei, Clostridium hathewayi|Bacteroides dorei, Clostridium hylemonae|Bacteroides dorei, Clostridium innocuum|Bacteroides dorei, Clostridium leptum|Bacteroides dorei, Clostridium mayombei|Bacteroides dorei, Clostridium methylpentosum|Bacteroides dorei, Clostridium nexile|Bacteroides dorei, Clostridium orbiscindens|Bacteroides dorei, Clostridium perfringens|Bacteroides dorei, Clostridium saccharolyticum|Bacteroides dorei, Clostridium scindens|Bacteroides dorei, Clostridium symbiosum|Bacteroides dorei, Clostridium*

TABLE 2-continued

| Table 2. Specific binary combinations of OTUs. Individual pairings are differentiated by "\|" and OTUs within a combination are differentiated by "," |
|---|
| *tertium\|Bacteroides dorei, Collinsella aerofaciens\|Bacteroides dorei, Collinsella intestinalis\|Bacteroides dorei, Collinsella stercoris\|Bacteroides dorei, Coprobacillus* sp. D7\|*Bacteroides dorei, Coprococcus catus\|Bacteroides dorei, Coprococcus comes\|Bacteroides dorei, Coprococcus eutactus\|Bacteroides dorei, Corynebacterium aurimucosum\|Bacteroides dorei, Corynebacterium matruchotii\|Bacteroides dorei, Cryptobacterium curtum\|Bacteroides dorei, Desulfovibrio desulfuricans\|Bacteroides dorei, Desulfovibrio piger\|Bacteroides dorei, Dialister invisus\|Bacteroides dorei, Dialister microaerophilus\|Bacteroides dorei, Dorea formicigenerans\|Bacteroides dorei, Dorea longicatena\|Bacteroides dorei, Eggerthella lenta\|Bacteroides dorei, Eikenella corrodens\|Bacteroides dorei, Enterobacter cancerogenus\|Bacteroides dorei, Enterobacter cloacae\|Bacteroides dorei, Enterococcus faecalis\|Bacteroides dorei, Enterococcus faecium\|Bacteroides dorei, Enterococcus gallinarum\|Bacteroides dorei, Erysipelotrichaceae bacterium* 3_1_53\|*Bacteroides dorei, Escherichia coli\|Bacteroides dorei, Escherichia fergusonii\|Bacteroides dorei, Ethanoligenens harbinense\|Bacteroides dorei, Eubacterium cellulosolvens\|Bacteroides dorei, Eubacterium eligens\|Bacteroides dorei, Eubacterium hallii\|Bacteroides dorei, Eubacterium limosum\|Bacteroides dorei, Eubacterium rectale\|Bacteroides dorei, Eubacterium siraeum\|Bacteroides dorei, Eubacterium ventriosum\|Bacteroides dorei, Faecalibacterium prausnitzii\|Bacteroides dorei, Finegoldia magna\|Bacteroides dorei, Fusobacterium gonidiaformans\|Bacteroides dorei, Fusobacterium mortiferum\|Bacteroides dorei, Fusobacterium nucleatum\|Bacteroides dorei, Fusobacterium varium\|Bacteroides dorei, Gardnerella vaginalis\|Bacteroides dorei, Gemella haemolysans\|Bacteroides dorei, Gemella morbillorum\|Bacteroides dorei, Gordonibacter pamelaeae\|Bacteroides dorei, Granulicatella adiacens\|Bacteroides dorei, Granulicatella elegans\|Bacteroides dorei, Haemophilus influenzae\|Bacteroides dorei, Haemophilus parainfluenzae\|Bacteroides dorei, Helicobacter pullorum\|Bacteroides dorei, Helicobacter pylori\|Bacteroides dorei, Holdemania filiformis\|Bacteroides dorei, Kingella oralis\|Bacteroides dorei, Klebsiella pneumoniae\|Bacteroides dorei, Klebsiella variicola\|Bacteroides dorei, Lachnospiraceae bacterium* 5_1_57FAA\|*Bacteroides dorei, Lactobacillus acidophilus\|Bacteroides dorei, Lactobacillus amylovorus\|Bacteroides dorei, Lactobacillus brevis\|Bacteroides dorei, Lactobacillus casei\|Bacteroides dorei, Lactobacillus crispatus\|Bacteroides dorei, Lactobacillus delbrueckii\|Bacteroides dorei, Lactobacillus fermentum\|Bacteroides dorei, Lactobacillus gasseri\|Bacteroides dorei, Lactobacillus iners\|Bacteroides dorei, Lactobacillus jensenii\|Bacteroides dorei, Lactobacillus johnsonii\|Bacteroides dorei, Lactobacillus paracasei\|Bacteroides dorei, Lactobacillus plantarum\|Bacteroides dorei, Lactobacillus reuteri\|Bacteroides dorei, Lactobacillus rhamnosus\|Bacteroides dorei, Lactobacillus ruminis\|Bacteroides dorei, Lactobacillus sakei\|Bacteroides dorei, Lactobacillus salivarius\|Bacteroides dorei, Lactococcus lactis\|Bacteroides dorei, Lautropia mirabilis\|Bacteroides dorei, Leuconostoc citreum\|Bacteroides dorei, Leuconostoc gasicomitatum\|Bacteroides dorei, Leuconostoc mesenteroides\|Bacteroides dorei, Listeria monocytogenes\|Bacteroides dorei, Marvinbryantia formatexigens\|Bacteroides dorei, Megamonas hypermegale\|Bacteroides dorei, Megasphaera micronuciformis\|Bacteroides dorei, Methanobrevibacter smithii\|Bacteroides dorei, Methanosphaera stadtmanae\|Bacteroides dorei, Methylobacterium radiotolerans\|Bacteroides dorei, Mitsuokella multacida\|Bacteroides dorei, Mobiluncus curtisii\|Bacteroides dorei, Mycoplasma hominis\|Bacteroides dorei, Neisseria mucosa\|Bacteroides dorei, Odoribacter splanchnicus\|Bacteroides dorei, Olsenella uli\|Bacteroides dorei, Oribacterium sinus\|Bacteroides dorei, Oxalobacter formigenes\|Bacteroides dorei, Parabacteroides distasonis\|Bacteroides dorei, Parabacteroides johnsonii\|Bacteroides dorei, Parabacteroides merdae\|Bacteroides dorei, Parvimonas micra\|Bacteroides dorei, Pediococcus acidilactici\|Bacteroides dorei, Pediococcus pentosaceus\|Bacteroides dorei, Peptoniphilus duerdenii\|Bacteroides dorei, Peptoniphilus harei\|Bacteroides dorei, Peptoniphilus lacrimalis\|Bacteroides dorei, Peptostreptococcus anaerobius\|Bacteroides dorei, Peptostreptococcus stomatis\|Bacteroides dorei, Porphyromonas asaccharolytica\|Bacteroides dorei, Porphyromonas uenonis\|Bacteroides dorei, Prevotella amnii\|Bacteroides dorei, Prevotella bergensis\|Bacteroides dorei, Prevotella bivia\|Bacteroides dorei, Prevotella buccae\|Bacteroides dorei, Prevotella buccalis\|Bacteroides dorei, Prevotella copri\|Bacteroides dorei, Prevotella disiens\|Bacteroides dorei, Prevotella melaninogenica\|Bacteroides dorei, Prevotella multiformis\|Bacteroides dorei, Prevotella oralis\|Bacteroides dorei, Prevotella oris\|Bacteroides dorei, Prevotella salivae\|Bacteroides dorei, Prevotella timonensis\|Bacteroides dorei, Propionibacterium acnes\|Bacteroides dorei, Propionibacterium freudenreichii\|Bacteroides dorei, Proteus mirabilis\|Bacteroides dorei, Proteus penneri\|Bacteroides dorei, Pseudoflavonifractor capillosus\|Bacteroides dorei, Pseudomonas aeruginosa\|Bacteroides dorei, Pseudomonas fluorescens\|Bacteroides dorei, Pseudomonas putida\|Bacteroides dorei, Pseudoramibacter alactolyticus\|Bacteroides dorei, Pyramidobacter piscolens\|Bacteroides dorei, Rhodopseudomonas palustris\|Bacteroides dorei, Roseburia intestinalis\|Bacteroides dorei, Roseburia inulinivorans\|Bacteroides dorei, Rothia dentocariosa\|Bacteroides dorei, Rothia mucilaginosa\|Bacteroides dorei, Ruminococcus albus\|Bacteroides dorei, Ruminococcus bromii\|Bacteroides dorei, Ruminococcus gnavus\|Bacteroides dorei, Ruminococcus lactaris\|Bacteroides dorei, Ruminococcus obeum\|Bacteroides dorei, Ruminococcus torques\|Bacteroides dorei, Selenomonas sputigena\|Bacteroides dorei, Shigella boydii\|Bacteroides dorei, Shigella dysenteriae\|Bacteroides dorei, Shigella sonnei\|Bacteroides dorei, Slackia exigua\|Bacteroides dorei, Solobacterium moorei\|Bacteroides dorei, Staphylococcus aureus\|Bacteroides dorei, Staphylococcus epidermidis\|Bacteroides dorei, Staphylococcus hominis\|Bacteroides dorei, Staphylococcus saprophyticus\|Bacteroides dorei, Staphylococcus warneri\|Bacteroides dorei, Streptococcus agalactiae\|Bacteroides dorei, Streptococcus anginosus\|Bacteroides dorei, Streptococcus australis\|Bacteroides dorei, Streptococcus bovis\|Bacteroides dorei, Streptococcus cristatus\|Bacteroides dorei, Streptococcus dysgalactiae\|Bacteroides dorei, Streptococcus equinus\|Bacteroides dorei, Streptococcus gordonii\|Bacteroides dorei, Streptococcus infantarius\|Bacteroides dorei, Streptococcus infantis\|Bacteroides dorei, Streptococcus mitis\|Bacteroides dorei, Streptococcus mutans\|Bacteroides dorei, Streptococcus oralis\|Bacteroides dorei, Streptococcus parasanguinis\|Bacteroides dorei, Streptococcus peroris\|Bacteroides dorei, Streptococcus pneumoniae\|Bacteroides dorei, Streptococcus salivarius\|Bacteroides dorei, Streptococcus sanguinis\|Bacteroides dorei, Streptococcus thermophilus\|Bacteroides dorei, Streptococcus vestibularis\|Bacteroides dorei, Subdoligranulum variabile\|Bacteroides dorei, Succinatimonas hippei\|Bacteroides dorei, Sutterella wadsworthensis\|Bacteroides dorei, Tropheryma whipplei\|Bacteroides dorei, Veillonella atypica\|Bacteroides dorei, Veillonella dispar\|Bacteroides dorei, Veillonella parvula\|Bacteroides dorei, Victivallis vadensis\|Bacteroides eggerthii, Bacteroides eggerthii\|Bacteroides eggerthii, Bacteroides finegoldii\|Bacteroides eggerthii, Bacteroides fragilis\|Bacteroides eggerthii, Bacteroides helcogenes\|Bacteroides eggerthii, Bacteroides intestinalis\|Bacteroides eggerthii, Bacteroides ovatus\|Bacteroides eggerthii, Bacteroides pectinophilus\|Bacteroides eggerthii, Bacteroides plebeius\|Bacteroides eggerthii, Bacteroides salanitronis\|Bacteroides eggerthii, Bacteroides* sp. 1_1_6\|*Bacteroides eggerthii, Bacteroides* sp. 3_1_23\|*Bacteroides eggerthii, Bacteroides stercoris\|Bacteroides eggerthii, Bacteroides thetaiotaomicron\|Bacteroides eggerthii, Bacteroides uniformis\|Bacteroides eggerthii, Bacteroides vulgatus\|Bacteroides eggerthii, Bacteroides xylanisolvens\|Bacteroides eggerthii, Bifidobacterium adolescentis\|Bacteroides eggerthii, Bifidobacterium angulatum\|Bacteroides eggerthii, Bifidobacterium animalis\|Bacteroides eggerthii, Bifidobacterium bifidum\|Bacteroides eggerthii, Bifidobacterium breve\|Bacteroides eggerthii, Bifidobacterium catenulatum\|Bacteroides eggerthii, Bifidobacterium dentium\|Bacteroides eggerthii, Bifidobacterium infantis\|Bacteroides eggerthii, Bifidobacterium longum\|Bacteroides eggerthii, Bifidobacterium pseudocatenulatum\|Bacteroides eggerthii, Bilophila wadsworthia\|Bacteroides eggerthii, Blautia hansenii\|Bacteroides eggerthii, Blautia hydrogenotrophica\|Bacteroides eggerthii, Blautia producta\|Bacteroides eggerthii, Blautia schinkii\|Bacteroides eggerthii, Brevibacterium linens\|Bacteroides eggerthii, Brucella ceti\|Bacteroides eggerthii, Brucella suis\|Bacteroides eggerthii, Bulleidia extructa\|Bacteroides eggerthii, Butyrivibrio crossotus\|Bacteroides eggerthii, Campylobacter concisus\|Bacteroides eggerthii, Campylobacter curvus\|Bacteroides eggerthii, Campylobacter gracilis\|Bacteroides eggerthii, Campylobacter hominis\|Bacteroides eggerthii, Capnocytophaga ochracea\|Bacteroides eggerthii, Cardiobacterium hominis\|Bacteroides eggerthii, Catenibacterium mitsuokai\|Bacteroides eggerthii, Catonella morbi\|Bacteroides eggerthii, Citrobacter koseri\|Bacteroides eggerthii, Clostridium asparagiforme\|Bacteroides eggerthii, Clostridium bartlettii\|Bacteroides eggerthii, Clostridium bolteae\|Bacteroides eggerthii, Clostridium botulinum\|Bacteroides eggerthii, Clostridium butyricum\|Bacteroides eggerthii, Clostridium difficile\|Bacteroides eggerthii, Clostridium disporicum\|Bacteroides eggerthii, Clostridium hathewayi\|Bacteroides eggerthii, Clostridium hylemonae\|Bacteroides eggerthii, Clostridium innocuum\|Bacteroides eggerthii, Clostridium leptum\|Bacteroides eggerthii, Clostridium mayombei\|Bacteroides eggerthii, Clostridium methylpentosum\|Bacteroides eggerthii, Clostridium nexile\|Bacteroides eggerthii, Clostridium orbiscindens\|Bacteroides* |

TABLE 2-continued

Table 2. Specific binary combinations of OTUs. Individual pairings are differentiated by "|" and OTUs within a combination are differentiated by ","

*eggerthii, Clostridium perfringens*|*Bacteroides eggerthii, Clostridium saccharolyticum*|*Bacteroides eggerthii, Clostridium scindens*|*Bacteroides eggerthii, Clostridium symbiosum*|*Bacteroides eggerthii, Clostridium tertium*|*Bacteroides eggerthii, Collinsella aerofaciens*|*Bacteroides eggerthii, Collinsella intestinalis*|*Bacteroides eggerthii, Collinsella stercoris*|*Bacteroides eggerthii, Coprobacillus* sp. D7|*Bacteroides eggerthii, Coprococcus catus*|*Bacteroides eggerthii, Coprococcus comes*|*Bacteroides eggerthii, Coprococcus eutactus*|*Bacteroides eggerthii, Corynebacterium aurimucosum*|*Bacteroides eggerthii, Corynebacterium matruchotii*|*Bacteroides eggerthii, Cryptobacterium curtum*|*Bacteroides eggerthii, Desulfovibrio desulfuricans*|*Bacteroides eggerthii, Desulfovibrio piger*|*Bacteroides eggerthii, Dialister invisus*|*Bacteroides eggerthii, Dialister microaerophilus*|*Bacteroides eggerthii, Dorea formicigenerans*|*Bacteroides eggerthii, Dorea longicatena*|*Bacteroides eggerthii, Eggerthella lenta*|*Bacteroides eggerthii, Eikenella corrodens*|*Bacteroides eggerthii, Enterobacter cancerogenus*|*Bacteroides eggerthii, Enterobacter cloacae*|*Bacteroides eggerthii, Enterococcus faecalis*|*Bacteroides eggerthii, Enterococcus faecium*|*Bacteroides eggerthii, Enterococcus gallinarum*|*Bacteroides eggerthii, Erysipelotrichaceae bacterium* 3_1_53|*Bacteroides eggerthii, Escherichia coli*|*Bacteroides eggerthii, Escherichia fergusonii*|*Bacteroides eggerthii, Ethanoligenens harbinense*|*Bacteroides eggerthii, Eubacterium cellulosolvens*|*Bacteroides eggerthii, Eubacterium eligens*|*Bacteroides eggerthii, Eubacterium hallii*|*Bacteroides eggerthii, Eubacterium limosum*|*Bacteroides eggerthii, Eubacterium rectale*|*Bacteroides eggerthii, Eubacterium siraeum*|*Bacteroides eggerthii, Eubacterium ventriosum*|*Bacteroides eggerthii, Faecalibacterium prausnitzii*|*Bacteroides eggerthii, Finegoldia magna*|*Bacteroides eggerthii, Fusobacterium gonidiaformans*|*Bacteroides eggerthii, Fusobacterium mortiferum*|*Bacteroides eggerthii, Fusobacterium nucleatum*|*Bacteroides eggerthii, Fusobacterium varium*|*Bacteroides eggerthii, Gardnerella vaginalis*|*Bacteroides eggerthii, Gemella haemolysans*|*Bacteroides eggerthii, Gemella morbillorum*|*Bacteroides eggerthii, Gordonibacter pamelaeae*|*Bacteroides eggerthii, Granulicatella adiacens*|*Bacteroides eggerthii, Granulicatella elegans*|*Bacteroides eggerthii, Haemophilus influenzae*|*Bacteroides eggerthii, Haemophilus parainfluenzae*|*Bacteroides eggerthii, Helicobacter pullorum*|*Bacteroides eggerthii, Helicobacter pylori*|*Bacteroides eggerthii, Holdemania filiformis*|*Bacteroides eggerthii, Kingella oralis*|*Bacteroides eggerthii, Klebsiella pneumoniae*|*Bacteroides eggerthii, Klebsiella variicola*|*Bacteroides eggerthii, Lachnospiraceae bacterium* 5_1_57FAA|*Bacteroides eggerthii, Lactobacillus acidophilus*|*Bacteroides eggerthii, Lactobacillus amylovorus*|*Bacteroides eggerthii, Lactobacillus brevis*|*Bacteroides eggerthii, Lactobacillus casei*|*Bacteroides eggerthii, Lactobacillus crispatus*|*Bacteroides eggerthii, Lactobacillus delbrueckii*|*Bacteroides eggerthii, Lactobacillus fermentum*|*Bacteroides eggerthii, Lactobacillus gasseri*|*Bacteroides eggerthii, Lactobacillus iners*|*Bacteroides eggerthii, Lactobacillus jensenii*|*Bacteroides eggerthii, Lactobacillus johnsonii*|*Bacteroides eggerthii, Lactobacillus paracasei*|*Bacteroides eggerthii, Lactobacillus plantarum*|*Bacteroides eggerthii, Lactobacillus reuteri*|*Bacteroides eggerthii, Lactobacillus rhamnosus*|*Bacteroides eggerthii, Lactobacillus ruminis*|*Bacteroides eggerthii, Lactobacillus sakei*|*Bacteroides eggerthii, Lactobacillus salivarius*|*Bacteroides eggerthii, Lactococcus lactis*|*Bacteroides eggerthii, Lautropia mirabilis*|*Bacteroides eggerthii, Leuconostoc citreum*|*Bacteroides eggerthii, Leuconostoc gasicomitatum*|*Bacteroides eggerthii, Leuconostoc mesenteroides*|*Bacteroides eggerthii, Listeria monocytogenes*|*Bacteroides eggerthii, Marvinbryantia formatexigens*|*Bacteroides eggerthii, Megamonas hypermegale*|*Bacteroides eggerthii, Megasphaera micronuciformis*|*Bacteroides eggerthii, Methanobrevibacter smithii*|*Bacteroides eggerthii, Methanosphaera stadtmanae*|*Bacteroides eggerthii, Methylobacterium radiotolerans*|*Bacteroides eggerthii, Mitsuokella multacida*|*Bacteroides eggerthii, Mobiluncus curtisii*|*Bacteroides eggerthii, Mycoplasma hominis*|*Bacteroides eggerthii, Neisseria mucosa*|*Bacteroides eggerthii, Odoribacter splanchnicus*|*Bacteroides eggerthii, Olsenella uli*|*Bacteroides eggerthii, Oribacterium sinus*|*Bacteroides eggerthii, Oxalobacter formigenes*|*Bacteroides eggerthii, Parabacteroides distasonis*|*Bacteroides eggerthii, Parabacteroides johnsonii*|*Bacteroides eggerthii, Parabacteroides merdae*|*Bacteroides eggerthii, Parvimonas micra*|*Bacteroides eggerthii, Pediococcus acidilactici*|*Bacteroides eggerthii, Pediococcus pentosaceus*|*Bacteroides eggerthii, Peptoniphilus duerdenii*|*Bacteroides eggerthii, Peptoniphilus harei*|*Bacteroides eggerthii, Peptoniphilus lacrimalis*|*Bacteroides eggerthii, Peptostreptococcus anaerobius*|*Bacteroides eggerthii, Peptostreptococcus stomatis*|*Bacteroides eggerthii, Porphyromonas asaccharolytica*|*Bacteroides eggerthii, Porphyromonas uenonis*|*Bacteroides eggerthii, Prevotella amnii*|*Bacteroides eggerthii, Prevotella bergensis*|*Bacteroides eggerthii, Prevotella bivia*|*Bacteroides eggerthii, Prevotella buccae*|*Bacteroides eggerthii, Prevotella buccalis*|*Bacteroides eggerthii, Prevotella copri*|*Bacteroides eggerthii, Prevotella disiens*|*Bacteroides eggerthii, Prevotella melaninogenica*|*Bacteroides eggerthii, Prevotella multiformis*|*Bacteroides eggerthii, Prevotella oralis*|*Bacteroides eggerthii, Prevotella oris*|*Bacteroides eggerthii, Prevotella salivae*|*Bacteroides eggerthii, Prevotella timonensis*|*Bacteroides eggerthii, Propionibacterium acnes*|*Bacteroides eggerthii, Propionibacterium freudenreichii*|*Bacteroides eggerthii, Proteus mirabilis*|*Bacteroides eggerthii, Proteus penneri*|*Bacteroides eggerthii, Pseudoflavonifractor capillosus*|*Bacteroides eggerthii, Pseudomonas aeruginosa*|*Bacteroides eggerthii, Pseudomonas fluorescens*|*Bacteroides eggerthii, Pseudomonas putida*|*Bacteroides eggerthii, Pseudoramibacter alactolyticus*|*Bacteroides eggerthii, Pyramidobacter piscolens*|*Bacteroides eggerthii, Rhodopseudomonas palustris*|*Bacteroides eggerthii, Roseburia intestinalis*|*Bacteroides eggerthii, Roseburia inulinivorans*|*Bacteroides eggerthii, Rothia dentocariosa*|*Bacteroides eggerthii, Rothia mucilaginosa*|*Bacteroides eggerthii, Ruminococcus albus*|*Bacteroides eggerthii, Ruminococcus bromii*|*Bacteroides eggerthii, Ruminococcus gnavus*|*Bacteroides eggerthii, Ruminococcus lactaris*|*Bacteroides eggerthii, Ruminococcus obeum*|*Bacteroides eggerthii, Ruminococcus torques*|*Bacteroides eggerthii, Selenomonas sputigena*|*Bacteroides eggerthii, Shigella boydii*|*Bacteroides eggerthii, Shigella dysenteriae*|*Bacteroides eggerthii, Shigella sonnei*|*Bacteroides eggerthii, Slackia exigua*|*Bacteroides eggerthii, Solobacterium moorei*|*Bacteroides eggerthii, Staphylococcus aureus*|*Bacteroides eggerthii, Staphylococcus epidermidis*|*Bacteroides eggerthii, Staphylococcus hominis*|*Bacteroides eggerthii, Staphylococcus saprophyticus*|*Bacteroides eggerthii, Staphylococcus warneri*|*Bacteroides eggerthii, Streptococcus agalactiae*|*Bacteroides eggerthii, Streptococcus anginosus*|*Bacteroides eggerthii, Streptococcus australis*|*Bacteroides eggerthii, Streptococcus bovis*|*Bacteroides eggerthii, Streptococcus cristatus*|*Bacteroides eggerthii, Streptococcus dysgalactiae*|*Bacteroides eggerthii, Streptococcus equinus*|*Bacteroides eggerthii, Streptococcus gordonii*|*Bacteroides eggerthii, Streptococcus infantarius*|*Bacteroides eggerthii, Streptococcus infantis*|*Bacteroides eggerthii, Streptococcus mitis*|*Bacteroides eggerthii, Streptococcus mutans*|*Bacteroides eggerthii, Streptococcus oralis*|*Bacteroides eggerthii, Streptococcus parasanguinis*|*Bacteroides eggerthii, Streptococcus peroris*|*Bacteroides eggerthii, Streptococcus pneumoniae*|*Bacteroides eggerthii, Streptococcus salivarius*|*Bacteroides eggerthii, Streptococcus sanguinis*|*Bacteroides eggerthii, Streptococcus thermophilus*|*Bacteroides eggerthii, Streptococcus vestibularis*|*Bacteroides eggerthii, Subdoligranulum variabile*|*Bacteroides eggerthii, Succinatimonas hippei*|*Bacteroides eggerthii, Sutterella wadsworthensis*|*Bacteroides eggerthii, Tropheryma whipplei*|*Bacteroides eggerthii, Veillonella atypica*|*Bacteroides eggerthii, Veillonella dispar*|*Bacteroides eggerthii, Veillonella parvula*|*Bacteroides eggerthii, Victivallis vadensis*|*Bacteroides finegoldii, Bacteroides finegoldii*|*Bacteroides finegoldii, Bacteroides fragilis*|*Bacteroides finegoldii, Bacteroides helcogenes*|*Bacteroides finegoldii, Bacteroides intestinalis*|*Bacteroides finegoldii, Bacteroides ovatus*|*Bacteroides finegoldii, Bacteroides pectinophilus*|*Bacteroides finegoldii, Bacteroides plebeius*|*Bacteroides finegoldii, Bacteroides salanitronis*|*Bacteroides finegoldii, Bacteroides* sp. 1_1_6|*Bacteroides finegoldii, Bacteroides* sp. 3_1_23|*Bacteroides finegoldii, Bacteroides stercoris*|*Bacteroides finegoldii, Bacteroides thetaiotaomicron*|*Bacteroides finegoldii, Bacteroides uniformis*|*Bacteroides finegoldii, Bacteroides vulgatus*|*Bacteroides finegoldii, Bacteroides xylanisolvens*|*Bacteroides finegoldii, Bifidobacterium adolescentis*|*Bacteroides finegoldii, Bifidobacterium angulatum*|*Bacteroides finegoldii, Bifidobacterium animalis*|*Bacteroides finegoldii, Bifidobacterium bifidum*|*Bacteroides finegoldii, Bifidobacterium breve*|*Bacteroides finegoldii, Bifidobacterium catenulatum*|*Bacteroides finegoldii, Bifidobacterium dentium*|*Bacteroides finegoldii, Bifidobacterium infantis*|*Bacteroides finegoldii, Bifidobacterium longum*|*Bacteroides finegoldii, Bifidobacterium pseudocatenulatum*|*Bacteroides finegoldii, Bilophila wadsworthia*|*Bacteroides finegoldii, Blautia hansenii*|*Bacteroides finegoldii, Blautia hydrogenotrophica*|*Bacteroides finegoldii, Blautia producta*|*Bacteroides finegoldii, Blautia schinkii*|*Bacteroides finegoldii, Brevibacterium linens*|*Bacteroides finegoldii, Brucella ceti*|*Bacteroides finegoldii, Brucella suis*|*Bacteroides finegoldii, Bulleidia extructa*|*Bacteroides finegoldii, Butyrivibrio crossotus*|*Bacteroides finegoldii, Campylobacter concisus*|*Bacteroides finegoldii, Campylobacter curvus*|*Bacteroides finegoldii, Campylobacter gracilis*|*Bacteroides finegoldii, Campylobacter hominis*|*Bacteroides finegoldii, Capnocytophaga*

TABLE 2-continued

| Table 2. Specific binary combinations of OTUs. Individual pairings are differentiated by "\|" and OTUs within a combination are differentiated by "," |
| --- |
| ochracea\|Bacteroides finegoldii, Cardiobacterium hominis\|Bacteroides finegoldii, Catenibacterium mitsuokai\|Bacteroides finegoldii, Catonella morbi\|Bacteroides finegoldii, Citrobacter koseri\|Bacteroides finegoldii, Clostridium asparagiforme\|Bacteroides finegoldii, Clostridium bartlettii\|Bacteroides finegoldii, Clostridium bolteae\|Bacteroides finegoldii, Clostridium botulinum\|Bacteroides finegoldii, Clostridium butyricum\|Bacteroides finegoldii, Clostridium difficile\|Bacteroides finegoldii, Clostridium disporicum\|Bacteroides finegoldii, Clostridium hathewayi\|Bacteroides finegoldii, Clostridium hylemonae\|Bacteroides finegoldii, Clostridium innocuum\|Bacteroides finegoldii, Clostridium leptum\|Bacteroides finegoldii, Clostridium mayombei\|Bacteroides finegoldii, Clostridium methylpentosum\|Bacteroides finegoldii, Clostridium nexile\|Bacteroides finegoldii, Clostridium orbiscindens\|Bacteroides finegoldii, Clostridium perfringens\|Bacteroides finegoldii, Clostridium saccharolyticum\|Bacteroides finegoldii, Clostridium scindens\|Bacteroides finegoldii, Clostridium symbiosum\|Bacteroides finegoldii, Clostridium tertium\|Bacteroides finegoldii, Collinsella aerofaciens\|Bacteroides finegoldii, Collinsella intestinalis\|Bacteroides finegoldii, Collinsella stercoris\|Bacteroides finegoldii, Coprobacillus sp. D7\|Bacteroides finegoldii, Coprococcus catus\|Bacteroides finegoldii, Coprococcus comes\|Bacteroides finegoldii, Coprococcus eutactus\|Bacteroides finegoldii, Corynebacterium aurimucosum\|Bacteroides finegoldii, Corynebacterium matruchotii\|Bacteroides finegoldii, Cryptobacterium curtum\|Bacteroides finegoldii, Desulfovibrio desulfuricans\|Bacteroides finegoldii, Desulfovibrio piger\|Bacteroides finegoldii, Dialister invisus\|Bacteroides finegoldii, Dialister microaerophilus\|Bacteroides finegoldii, Dorea formicigenerans\|Bacteroides finegoldii, Dorea longicatena\|Bacteroides finegoldii, Eggerthella lenta\|Bacteroides finegoldii, Eikenella corrodens\|Bacteroides finegoldii, Enterobacter cancerogenus\|Bacteroides finegoldii, Enterobacter cloacae\|Bacteroides finegoldii, Enterococcus faecalis\|Bacteroides finegoldii, Enterococcus faecium\|Bacteroides finegoldii, Enterococcus gallinarum\|Bacteroides finegoldii, Erysipelotrichaceae bacterium 3_1_53\|Bacteroides finegoldii, Escherichia coli\|Bacteroides finegoldii, Escherichia fergusonii\|Bacteroides finegoldii, Ethanoligenens harbinense\|Bacteroides finegoldii, Eubacterium cellulosolvens\|Bacteroides finegoldii, Eubacterium eligens\|Bacteroides finegoldii, Eubacterium hallii\|Bacteroides finegoldii, Eubacterium limosum\|Bacteroides finegoldii, Eubacterium rectale\|Bacteroides finegoldii, Eubacterium siraeum\|Bacteroides finegoldii, Eubacterium ventriosum\|Bacteroides finegoldii, Faecalibacterium prausnitzii\|Bacteroides finegoldii, Finegoldia magna\|Bacteroides finegoldii, Fusobacterium gonidiaformans\|Bacteroides finegoldii, Fusobacterium mortiferum\|Bacteroides finegoldii, Fusobacterium nucleatum\|Bacteroides finegoldii, Fusobacterium varium\|Bacteroides finegoldii, Gardnerella vaginalis\|Bacteroides finegoldii, Gemella haemolysans\|Bacteroides finegoldii, Gemella morbillorum\|Bacteroides finegoldii, Gordonibacter pamelaeae\|Bacteroides finegoldii, Granulicatella adiacens\|Bacteroides finegoldii, Granulicatella elegans\|Bacteroides finegoldii, Haemophilus influenzae\|Bacteroides finegoldii, Haemophilus parainfluenzae\|Bacteroides finegoldii, Helicobacter pullorum\|Bacteroides finegoldii, Helicobacter pylori\|Bacteroides finegoldii, Holdemania filiformis\|Bacteroides finegoldii, Kingella oralis\|Bacteroides finegoldii, Klebsiella pneumoniae\|Bacteroides finegoldii, Klebsiella variicola\|Bacteroides finegoldii, Lachnospiraceae bacterium 5_1_57FAA\|Bacteroides finegoldii, Lactobacillus acidophilus\|Bacteroides finegoldii, Lactobacillus amylovorus\|Bacteroides finegoldii, Lactobacillus brevis\|Bacteroides finegoldii, Lactobacillus casei\|Bacteroides finegoldii, Lactobacillus crispatus\|Bacteroides finegoldii, Lactobacillus delbrueckii\|Bacteroides finegoldii, Lactobacillus fermentum\|Bacteroides finegoldii, Lactobacillus gasseri\|Bacteroides finegoldii, Lactobacillus iners\|Bacteroides finegoldii, Lactobacillus jensenii\|Bacteroides finegoldii, Lactobacillus johnsonii\|Bacteroides finegoldii, Lactobacillus paracasei\|Bacteroides finegoldii, Lactobacillus plantarum\|Bacteroides finegoldii, Lactobacillus reuteri\|Bacteroides finegoldii, Lactobacillus rhamnosus\|Bacteroides finegoldii, Lactobacillus ruminis\|Bacteroides finegoldii, Lactobacillus sakei\|Bacteroides finegoldii, Lactobacillus salivarius\|Bacteroides finegoldii, Lactococcus lactis\|Bacteroides finegoldii, Lautropia mirabilis\|Bacteroides finegoldii, Leuconostoc citreum\|Bacteroides finegoldii, Leuconostoc gasicomitatum\|Bacteroides finegoldii, Leuconostoc mesenteroides\|Bacteroides finegoldii, Listeria monocytogenes\|Bacteroides finegoldii, Marvinbryantia formatexigens\|Bacteroides finegoldii, Megamonas hypermegale\|Bacteroides finegoldii, Megasphaera micronuciformis\|Bacteroides finegoldii, Methanobrevibacter smithii\|Bacteroides finegoldii, Methanosphaera stadtmanae\|Bacteroides finegoldii, Methylobacterium radiotolerans\|Bacteroides finegoldii, Mitsuokella multacida\|Bacteroides finegoldii, Mobiluncus curtisii\|Bacteroides finegoldii, Mycoplasma hominis\|Bacteroides finegoldii, Neisseria mucosa\|Bacteroides finegoldii, Odoribacter splanchnicus\|Bacteroides finegoldii, Olsenella uli\|Bacteroides finegoldii, Oribacterium sinus\|Bacteroides finegoldii, Oxalobacter formigenes\|Bacteroides finegoldii, Parabacteroides distasonis\|Bacteroides finegoldii, Parabacteroides johnsonii\|Bacteroides finegoldii, Parabacteroides merdae\|Bacteroides finegoldii, Parvimonas micra\|Bacteroides finegoldii, Pediococcus acidilactici\|Bacteroides finegoldii, Pediococcus pentosaceus\|Bacteroides finegoldii, Peptoniphilus duerdenii\|Bacteroides finegoldii, Peptoniphilus harei\|Bacteroides finegoldii, Peptoniphilus lacrimalis\|Bacteroides finegoldii, Peptostreptococcus anaerobius\|Bacteroides finegoldii, Peptostreptococcus stomatis\|Bacteroides finegoldii, Porphyromonas asaccharolytica\|Bacteroides finegoldii, Porphyromonas uenonis\|Bacteroides finegoldii, Prevotella amnii\|Bacteroides finegoldii, Prevotella bergensis\|Bacteroides finegoldii, Prevotella bivia\|Bacteroides finegoldii, Prevotella buccae\|Bacteroides finegoldii, Prevotella buccalis\|Bacteroides finegoldii, Prevotella copri\|Bacteroides finegoldii, Prevotella disiens\|Bacteroides finegoldii, Prevotella melaninogenica\|Bacteroides finegoldii, Prevotella multiformis\|Bacteroides finegoldii, Prevotella oralis\|Bacteroides finegoldii, Prevotella oris\|Bacteroides finegoldii, Prevotella salivae\|Bacteroides finegoldii, Prevotella timonensis\|Bacteroides finegoldii, Propionibacterium acnes\|Bacteroides finegoldii, Propionibacterium freudenreichii\|Bacteroides finegoldii, Proteus mirabilis\|Bacteroides finegoldii, Proteus penneri\|Bacteroides finegoldii, Pseudoflavonifractor capillosus\|Bacteroides finegoldii, Pseudomonas aeruginosa\|Bacteroides finegoldii, Pseudomonas fluorescens\|Bacteroides finegoldii, Pseudomonas putida\|Bacteroides finegoldii, Pseudoramibacter alactolyticus\|Bacteroides finegoldii, Pyramidobacter piscolens\|Bacteroides finegoldii, Rhodopseudomonas palustris\|Bacteroides finegoldii, Roseburia intestinalis\|Bacteroides finegoldii, Roseburia inulinivorans\|Bacteroides finegoldii, Rothia dentocariosa\|Bacteroides finegoldii, Rothia mucilaginosa\|Bacteroides finegoldii, Ruminococcus albus\|Bacteroides finegoldii, Ruminococcus bromii\|Bacteroides finegoldii, Ruminococcus gnavus\|Bacteroides finegoldii, Ruminococcus lactaris\|Bacteroides finegoldii, Ruminococcus obeum\|Bacteroides finegoldii, Ruminococcus torques\|Bacteroides finegoldii, Selenomonas sputigena\|Bacteroides finegoldii, Shigella boydii\|Bacteroides finegoldii, Shigella dysenteriae\|Bacteroides finegoldii, Shigella sonnei\|Bacteroides finegoldii, Slackia exigua\|Bacteroides finegoldii, Solobacterium moorei\|Bacteroides finegoldii, Staphylococcus aureus\|Bacteroides finegoldii, Staphylococcus epidermidis\|Bacteroides finegoldii, Staphylococcus hominis\|Bacteroides finegoldii, Staphylococcus saprophyticus\|Bacteroides finegoldii, Staphylococcus warneri\|Bacteroides finegoldii, Streptococcus agalactiae\|Bacteroides finegoldii, Streptococcus anginosus\|Bacteroides finegoldii, Streptococcus australis\|Bacteroides finegoldii, Streptococcus bovis\|Bacteroides finegoldii, Streptococcus cristatus\|Bacteroides finegoldii, Streptococcus dysgalactiae\|Bacteroides finegoldii, Streptococcus equinus\|Bacteroides finegoldii, Streptococcus gordonii\|Bacteroides finegoldii, Streptococcus infantarius\|Bacteroides finegoldii, Streptococcus infantis\|Bacteroides finegoldii, Streptococcus mitis\|Bacteroides finegoldii, Streptococcus mutans\|Bacteroides finegoldii, Streptococcus oralis\|Bacteroides finegoldii, Streptococcus parasanguinis\|Bacteroides finegoldii, Streptococcus peroris\|Bacteroides finegoldii, Streptococcus pneumoniae\|Bacteroides finegoldii, Streptococcus salivarius\|Bacteroides finegoldii, Streptococcus sanguinis\|Bacteroides finegoldii, Streptococcus thermophilus\|Bacteroides finegoldii, Streptococcus vestibularis\|Bacteroides finegoldii, Subdoligranulum variabile\|Bacteroides finegoldii, Succinatimonas hippei\|Bacteroides finegoldii, Sutterella wadsworthensis\|Bacteroides finegoldii, Tropheryma whipplei\|Bacteroides finegoldii, Veillonella atypica\|Bacteroides finegoldii, Veillonella dispar\|Bacteroides finegoldii, Veillonella parvula\|Bacteroides finegoldii, Victivallis vadensis\|Bacteroides fragilis, Bacteroides fragilis\|Bacteroides fragilis, Bacteroides helcogenes\|Bacteroides fragilis, Bacteroides intestinalis\|Bacteroides fragilis, Bacteroides ovatus\|Bacteroides fragilis, Bacteroides pectinophilus\|Bacteroides fragilis, Bacteroides plebeius\|Bacteroides fragilis, Bacteroides salanitronis\|Bacteroides fragilis, Bacteroides sp. 1_1_61\|Bacteroides fragilis, Bacteroides sp. 3_1_23\|Bacteroides fragilis, Bacteroides stercoris\|Bacteroides fragilis, Bacteroides thetaiotaomicron\|Bacteroides fragilis, Bacteroides uniformis\|Bacteroides fragilis, Bacteroides vulgatus\|Bacteroides fragilis, Bacteroides xylanisolvens\|Bacteroides fragilis, Bifidobacterium adolescentis\|Bacteroides fragilis, Bifidobacterium angulatum\|Bacteroides fragilis, Bifidobacterium |

TABLE 2-continued

Table 2. Specific binary combinations of OTUs. Individual pairings are differentiated by "|" and OTUs within a combination are differentiated by ","

animalis|Bacteroides fragilis, Bifidobacterium bifidum|Bacteroides fragilis, Bifidobacterium breve|Bacteroides fragilis, Bifidobacterium catenulatum|Bacteroides fragilis, Bifidobacterium dentium|Bacteroides fragilis, Bifidobacterium infantis|Bacteroides fragilis, Bifidobacterium longum|Bacteroides fragilis, Bifidobacterium pseudocatenulatum|Bacteroides fragilis, Bilophila wadsworthia|Bacteroides fragilis, Blautia hansenii|Bacteroides fragilis, Blautia hydrogenotrophica|Bacteroides fragilis, Blautia producta|Bacteroides fragilis, Blautia schinkii|Bacteroides fragilis, Brevibacterium linens|Bacteroides fragilis, Brucella ceti|Bacteroides fragilis, Brucella suis|Bacteroides fragilis, Bulleidia extructa|Bacteroides fragilis, Butyrivibrio crossotus|Bacteroides fragilis, Campylobacter concisus|Bacteroides fragilis, Campylobacter curvus|Bacteroides fragilis, Campylobacter gracilis|Bacteroides fragilis, Campylobacter hominis|Bacteroides fragilis, Capnocytophaga ochracea|Bacteroides fragilis, Cardiobacterium hominis|Bacteroides fragilis, Catenibacterium mitsuokai|Bacteroides fragilis, Catonella morbi|Bacteroides fragilis, Citrobacter koseri|Bacteroides fragilis, Clostridium asparagiforme|Bacteroides fragilis, Clostridium bartlettii|Bacteroides fragilis, Clostridium bolteae|Bacteroides fragilis, Clostridium botulinum|Bacteroides fragilis, Clostridium butyricum|Bacteroides fragilis, Clostridium difficile|Bacteroides fragilis, Clostridium disporicum|Bacteroides fragilis, Clostridium hathewayi|Bacteroides fragilis, Clostridium hylemonae|Bacteroides fragilis, Clostridium innocuum|Bacteroides fragilis, Clostridium leptum|Bacteroides fragilis, Clostridium mayombei|Bacteroides fragilis, Clostridium methylpentosum|Bacteroides fragilis, Clostridium nexile|Bacteroides fragilis, Clostridium orbiscindens|Bacteroides fragilis, Clostridium perfringens|Bacteroides fragilis, Clostridium saccharolyticum|Bacteroides fragilis, Clostridium scindens|Bacteroides fragilis, Clostridium symbiosum|Bacteroides fragilis, Clostridium tertium|Bacteroides fragilis, Collinsella aerofaciens|Bacteroides fragilis, Collinsella intestinalis|Bacteroides fragilis, Collinsella stercoris|Bacteroides fragilis, Coprobacillus sp. D7|Bacteroides fragilis, Coprococcus catus|Bacteroides fragilis, Coprococcus comes|Bacteroides fragilis, Coprococcus eutactus|Bacteroides fragilis, Corynebacterium aurimucosum|Bacteroides fragilis, Corynebacterium matruchotii|Bacteroides fragilis, Cryptobacterium curtum|Bacteroides fragilis, Desulfovibrio desulfuricans|Bacteroides fragilis, Desulfovibrio piger|Bacteroides fragilis, Dialister invisus|Bacteroides fragilis, Dialister microaerophilus|Bacteroides fragilis, Dorea formicigenerans|Bacteroides fragilis, Dorea longicatena|Bacteroides fragilis, Eggerthella lenta|Bacteroides fragilis, Eikenella corrodens|Bacteroides fragilis, Enterobacter cancerogenus|Bacteroides fragilis, Enterobacter cloacae|Bacteroides fragilis, Enterococcus faecalis|Bacteroides fragilis, Enterococcus faecium|Bacteroides fragilis, Enterococcus gallinarum|Bacteroides fragilis, Erysipelotrichaceae bacterium 3_1_53|Bacteroides fragilis, Escherichia coli|Bacteroides fragilis, Escherichia fergusonii|Bacteroides fragilis, Ethanoligenens harbinense|Bacteroides fragilis, Eubacterium cellulosolvens|Bacteroides fragilis, Eubacterium eligens|Bacteroides fragilis, Eubacterium hallii|Bacteroides fragilis, Eubacterium limosum|Bacteroides fragilis, Eubacterium rectale|Bacteroides fragilis, Eubacterium siraeum|Bacteroides fragilis, Eubacterium ventriosum|Bacteroides fragilis, Faecalibacterium prausnitzii|Bacteroides fragilis, Finegoldia magna|Bacteroides fragilis, Fusobacterium gonidiaformans|Bacteroides fragilis, Fusobacterium mortiferum|Bacteroides fragilis, Fusobacterium nucleatum|Bacteroides fragilis, Fusobacterium varium|Bacteroides fragilis, Gardnerella vaginalis|Bacteroides fragilis, Gemella haemolysans|Bacteroides fragilis, Gemella morbillorum|Bacteroides fragilis, Gordonibacter pamelaeae|Bacteroides fragilis, Granulicatella adiacens|Bacteroides fragilis, Granulicatella elegans|Bacteroides fragilis, Haemophilus influenzae|Bacteroides fragilis, Haemophilus parainfluenzae|Bacteroides fragilis, Helicobacter pullorum|Bacteroides fragilis, Helicobacter pylori|Bacteroides fragilis, Holdemania filiformis|Bacteroides fragilis, Kingella oralis|Bacteroides fragilis, Klebsiella pneumoniae|Bacteroides fragilis, Klebsiella variicola|Bacteroides fragilis, Lachnospiraceae bacterium 5_1_57FAA|Bacteroides fragilis, Lactobacillus acidophilus|Bacteroides fragilis, Lactobacillus amylovorus|Bacteroides fragilis, Lactobacillus brevis|Bacteroides fragilis, Lactobacillus casei|Bacteroides fragilis, Lactobacillus crispatus|Bacteroides fragilis, Lactobacillus delbrueckii|Bacteroides fragilis, Lactobacillus fermentum|Bacteroides fragilis, Lactobacillus gasseri|Bacteroides fragilis, Lactobacillus iners|Bacteroides fragilis, Lactobacillus jensenii|Bacteroides fragilis, Lactobacillus johnsonii|Bacteroides fragilis, Lactobacillus paracasei|Bacteroides fragilis, Lactobacillus plantarum|Bacteroides fragilis, Lactobacillus reuteri|Bacteroides fragilis, Lactobacillus rhamnosus|Bacteroides fragilis, Lactobacillus ruminis|Bacteroides fragilis, Lactobacillus sakei|Bacteroides fragilis, Lactobacillus salivarius|Bacteroides fragilis, Lactococcus lactis|Bacteroides fragilis, Lautropia mirabilis|Bacteroides fragilis, Leuconostoc citreum|Bacteroides fragilis, Leuconostoc gasicomitatum|Bacteroides fragilis, Leuconostoc mesenteroides|Bacteroides fragilis, Listeria monocytogenes|Bacteroides fragilis, Marvinbryantia formatexigens|Bacteroides fragilis, Megamonas hypermegale|Bacteroides fragilis, Megasphaera micronuciformis|Bacteroides fragilis, Methanobrevibacter smithii|Bacteroides fragilis, Methanosphaera stadtmanae|Bacteroides fragilis, Methylobacterium radiotolerans|Bacteroides fragilis, Mitsuokella multacida|Bacteroides fragilis, Mobiluncus curtisii|Bacteroides fragilis, Mycoplasma hominis|Bacteroides fragilis, Neisseria mucosa|Bacteroides fragilis, Odoribacter splanchnicus|Bacteroides fragilis, Olsenella uli|Bacteroides fragilis, Oribacterium sinus|Bacteroides fragilis, Oxalobacter formigenes|Bacteroides fragilis, Parabacteroides distasonis|Bacteroides fragilis, Parabacteroides johnsonii|Bacteroides fragilis, Parabacteroides merdae|Bacteroides fragilis, Parvimonas micra|Bacteroides fragilis, Pediococcus acidilactici|Bacteroides fragilis, Pediococcus pentosaceus|Bacteroides fragilis, Peptoniphilus duerdenii|Bacteroides fragilis, Peptoniphilus harei|Bacteroides fragilis, Peptoniphilus lacrimalis|Bacteroides fragilis, Peptostreptococcus anaerobius|Bacteroides fragilis, Peptostreptococcus stomatis|Bacteroides fragilis, Porphyromonas asaccharolytica|Bacteroides fragilis, Porphyromonas uenonis|Bacteroides fragilis, Prevotella amnii|Bacteroides fragilis, Prevotella bergensis|Bacteroides fragilis, Prevotella bivia|Bacteroides fragilis, Prevotella buccae|Bacteroides fragilis, Prevotella buccalis|Bacteroides fragilis, Prevotella copri|Bacteroides fragilis, Prevotella disiens|Bacteroides fragilis, Prevotella melaninogenica|Bacteroides fragilis, Prevotella multiformis|Bacteroides fragilis, Prevotella oralis|Bacteroides fragilis, Prevotella oris|Bacteroides fragilis, Prevotella salivae|Bacteroides fragilis, Prevotella timonensis|Bacteroides fragilis, Propionibacterium acnes|Bacteroides fragilis, Propionibacterium freudenreichii|Bacteroides fragilis, Proteus mirabilis|Bacteroides fragilis, Proteus penneri|Bacteroides fragilis, Pseudoflavonifractor capillosus|Bacteroides fragilis, Pseudomonas aeruginosa|Bacteroides fragilis, Pseudomonas fluorescens|Bacteroides fragilis, Pseudomonas putida|Bacteroides fragilis, Pseudoramibacter alactolyticus|Bacteroides fragilis, Pyramidobacter piscolens|Bacteroides fragilis, Rhodopseudomonas palustris|Bacteroides fragilis, Roseburia intestinalis|Bacteroides fragilis, Roseburia inulinivorans|Bacteroides fragilis, Rothia dentocariosa|Bacteroides fragilis, Rothia mucilaginosa|Bacteroides fragilis, Ruminococcus albus|Bacteroides fragilis, Ruminococcus bromii|Bacteroides fragilis, Ruminococcus gnavus|Bacteroides fragilis, Ruminococcus lactaris|Bacteroides fragilis, Ruminococcus obeum|Bacteroides fragilis, Ruminococcus torques|Bacteroides fragilis, Selenomonas sputigena|Bacteroides fragilis, Shigella boydii|Bacteroides fragilis, Shigella dysenteriae|Bacteroides fragilis, Shigella sonnei|Bacteroides fragilis, Slackia exigua|Bacteroides fragilis, Solobacterium moorei|Bacteroides fragilis, Staphylococcus aureus|Bacteroides fragilis, Staphylococcus epidermidis|Bacteroides fragilis, Staphylococcus hominis|Bacteroides fragilis, Staphylococcus saprophyticus|Bacteroides fragilis, Staphylococcus warneri|Bacteroides fragilis, Streptococcus agalactiae|Bacteroides fragilis, Streptococcus anginosus|Bacteroides fragilis, Streptococcus australis|Bacteroides fragilis, Streptococcus bovis|Bacteroides fragilis, Streptococcus cristatus|Bacteroides fragilis, Streptococcus dysgalactiae|Bacteroides fragilis, Streptococcus equinus|Bacteroides fragilis, Streptococcus gordonii|Bacteroides fragilis, Streptococcus infantarius|Bacteroides fragilis, Streptococcus infantis|Bacteroides fragilis, Streptococcus mitis|Bacteroides fragilis, Streptococcus mutans|Bacteroides fragilis, Streptococcus oralis|Bacteroides fragilis, Streptococcus parasanguinis|Bacteroides fragilis, Streptococcus peroris|Bacteroides fragilis, Streptococcus pneumoniae|Bacteroides fragilis, Streptococcus salivarius|Bacteroides fragilis, Streptococcus sanguinis|Bacteroides fragilis, Streptococcus thermophilus|Bacteroides fragilis, Streptococcus vestibularis|Bacteroides fragilis, Subdoligranulum variabile|Bacteroides fragilis, Succinatimonas hippei|Bacteroides fragilis, Sutterella wadsworthensis|Bacteroides fragilis, Tropheryma whipplei|Bacteroides fragilis, Veillonella atypica|Bacteroides fragilis, Veillonella dispar|Bacteroides fragilis, Veillonella parvula|Bacteroides fragilis, Victivallis vadensis|Bacteroides helcogenes, Bacteroides helcogenes|Bacteroides helcogenes, Bacteroides intestinalis|Bacteroides helcogenes, Bacteroides ovatus|Bacteroides helcogenes, Bacteroides pectinophilus|Bacteroides helcogenes, Bacteroides plebeius|Bacteroides helcogenes, Bacteroides salanitronis|Bacteroides helcogenes, Bacteroides sp.

TABLE 2-continued

| Table 2. Specific binary combinations of OTUs. Individual pairings are differentiated by "\|" and OTUs within a combination are differentiated by "," |
| --- |
| 1_1_6\|Bacteroides helcogenes, Bacteroides sp. 3_1_23\|Bacteroides helcogenes, Bacteroides stercoris\|Bacteroides helcogenes, Bacteroides thetaiotaomicron\|Bacteroides helcogenes, Bacteroides uniformis\|Bacteroides helcogenes, Bacteroides vulgatus\|Bacteroides helcogenes, Bacteroides xylanisolvens\|Bacteroides helcogenes, Bifidobacterium adolescentis\|Bacteroides helcogenes, Bifidobacterium angulatum\|Bacteroides helcogenes, Bifidobacterium animalis\|Bacteroides helcogenes, Bifidobacterium bifidum\|Bacteroides helcogenes, Bifidobacterium breve\|Bacteroides helcogenes, Bifidobacterium catenulatum\|Bacteroides helcogenes, Bifidobacterium dentium\|Bacteroides helcogenes, Bifidobacterium infantis\|Bacteroides helcogenes, Bifidobacterium longum\|Bacteroides helcogenes, Bifidobacterium pseudocatenulatum\|Bacteroides helcogenes, Bilophila wadsworthia\|Bacteroides helcogenes, Blautia hansenii\|Bacteroides helcogenes, Blautia hydrogenotrophica\|Bacteroides helcogenes, Blautia producta\|Bacteroides helcogenes, Blautia schinkii\|Bacteroides helcogenes, Brevibacterium linens\|Bacteroides helcogenes, Brucella ceti\|Bacteroides helcogenes, Brucella suis\|Bacteroides helcogenes, Bulleidia extructa\|Bacteroides helcogenes, Butyrivibrio crossotus\|Bacteroides helcogenes, Campylobacter concisus\|Bacteroides helcogenes, Campylobacter curvus\|Bacteroides helcogenes, Campylobacter gracilis\|Bacteroides helcogenes, Campylobacter hominis\|Bacteroides helcogenes, Capnocytophaga ochracea\|Bacteroides helcogenes, Cardiobacterium hominis\|Bacteroides helcogenes, Catenibacterium mitsuokai\|Bacteroides helcogenes, Catonella morbi\|Bacteroides helcogenes, Citrobacter koseri\|Bacteroides helcogenes, Clostridium asparagiforme\|Bacteroides helcogenes, Clostridium bartlettii\|Bacteroides helcogenes, Clostridium bolteae\|Bacteroides helcogenes, Clostridium botulinum\|Bacteroides helcogenes, Clostridium butyricum\|Bacteroides helcogenes, Clostridium difficile\|Bacteroides helcogenes, Clostridium disporicum\|Bacteroides helcogenes, Clostridium hathewayi\|Bacteroides helcogenes, Clostridium hylemonae\|Bacteroides helcogenes, Clostridium innocuum\|Bacteroides helcogenes, Clostridium leptum\|Bacteroides helcogenes, Clostridium mayombei\|Bacteroides helcogenes, Clostridium methylpentosum\|Bacteroides helcogenes, Clostridium nexile\|Bacteroides helcogenes, Clostridium orbiscindens\|Bacteroides helcogenes, Clostridium perfringens\|Bacteroides helcogenes, Clostridium saccharolyticum\|Bacteroides helcogenes, Clostridium scindens\|Bacteroides helcogenes, Clostridium symbiosum\|Bacteroides helcogenes, Clostridium tertium\|Bacteroides helcogenes, Collinsella aerofaciens\|Bacteroides helcogenes, Collinsella intestinalis\|Bacteroides helcogenes, Collinsella stercoris\|Bacteroides helcogenes, Coprobacillus sp. D7\|Bacteroides helcogenes, Coprococcus catus\|Bacteroides helcogenes, Coprococcus comes\|Bacteroides helcogenes, Coprococcus eutactus\|Bacteroides helcogenes, Corynebacterium aurimucosum\|Bacteroides helcogenes, Corynebacterium matruchotii\|Bacteroides helcogenes, Cryptobacterium curtum\|Bacteroides helcogenes, Desulfovibrio desulfuricans\|Bacteroides helcogenes, Desulfovibrio piger\|Bacteroides helcogenes, Dialister invisus\|Bacteroides helcogenes, Dialister microaerophilus\|Bacteroides helcogenes, Dorea formicigenerans\|Bacteroides helcogenes, Dorea longicatena\|Bacteroides helcogenes, Eggerthella lenta\|Bacteroides helcogenes, Eikenella corrodens\|Bacteroides helcogenes, Enterobacter cancerogenus\|Bacteroides helcogenes, Enterobacter cloacae\|Bacteroides helcogenes, Enterococcus faecalis\|Bacteroides helcogenes, Enterococcus faecium\|Bacteroides helcogenes, Enterococcus gallinarum\|Bacteroides helcogenes, Erysipelotrichaceae bacterium 3_1_53\|Bacteroides helcogenes, Escherichia coli\|Bacteroides helcogenes, Escherichia fergusonii\|Bacteroides helcogenes, Ethanoligenens harbinense\|Bacteroides helcogenes, Eubacterium cellulosolvens\|Bacteroides helcogenes, Eubacterium eligens\|Bacteroides helcogenes, Eubacterium hallii\|Bacteroides helcogenes, Eubacterium limosum\|Bacteroides helcogenes, Eubacterium rectale\|Bacteroides helcogenes, Eubacterium siraeum\|Bacteroides helcogenes, Eubacterium ventriosum\|Bacteroides helcogenes, Faecalibacterium prausnitzii\|Bacteroides helcogenes, Finegoldia magna\|Bacteroides helcogenes, Fusobacterium gonidiaformans\|Bacteroides helcogenes, Fusobacterium mortiferum\|Bacteroides helcogenes, Fusobacterium nucleatum\|Bacteroides helcogenes, Fusobacterium varium\|Bacteroides helcogenes, Gardnerella vaginalis\|Bacteroides helcogenes, Gemella haemolysans\|Bacteroides helcogenes, Gemella morbillorum\|Bacteroides helcogenes, Gordonibacter pamelaeae\|Bacteroides helcogenes, Granulicatella adiacens\|Bacteroides helcogenes, Granulicatella elegans\|Bacteroides helcogenes, Haemophilus influenzae\|Bacteroides helcogenes, Haemophilus parainfluenzae\|Bacteroides helcogenes, Helicobacter pullorum\|Bacteroides helcogenes, Helicobacter pylori\|Bacteroides helcogenes, Holdemania filiformis\|Bacteroides helcogenes, Kingella oralis\|Bacteroides helcogenes, Klebsiella pneumoniae\|Bacteroides helcogenes, Klebsiella variicola\|Bacteroides helcogenes, Lachnospiraceae bacterium 5_1_57FAA\|Bacteroides helcogenes, Lactobacillus acidophilus\|Bacteroides helcogenes, Lactobacillus amylovorus\|Bacteroides helcogenes, Lactobacillus brevis\|Bacteroides helcogenes, Lactobacillus casei\|Bacteroides helcogenes, Lactobacillus crispatus\|Bacteroides helcogenes, Lactobacillus delbrueckii\|Bacteroides helcogenes, Lactobacillus fermentum\|Bacteroides helcogenes, Lactobacillus gasseri\|Bacteroides helcogenes, Lactobacillus iners\|Bacteroides helcogenes, Lactobacillus jensenii\|Bacteroides helcogenes, Lactobacillus johnsonii\|Bacteroides helcogenes, Lactobacillus paracasei\|Bacteroides helcogenes, Lactobacillus plantarum\|Bacteroides helcogenes, Lactobacillus reuteri\|Bacteroides helcogenes, Lactobacillus rhamnosus\|Bacteroides helcogenes, Lactobacillus ruminis\|Bacteroides helcogenes, Lactobacillus sakei\|Bacteroides helcogenes, Lactobacillus salivarius\|Bacteroides helcogenes, Lactococcus lactis\|Bacteroides helcogenes, Lautropia mirabilis\|Bacteroides helcogenes, Leuconostoc citreum\|Bacteroides helcogenes, Leuconostoc gasicomitatum\|Bacteroides helcogenes, Leuconostoc mesenteroides\|Bacteroides helcogenes, Listeria monocytogenes\|Bacteroides helcogenes, Marvinbryantia formatexigens\|Bacteroides helcogenes, Megamonas hypermegale\|Bacteroides helcogenes, Megasphaera micronuciformis\|Bacteroides helcogenes, Methanobrevibacter smithii\|Bacteroides helcogenes, Methanosphaera stadtmanae\|Bacteroides helcogenes, Methylobacterium radiotolerans\|Bacteroides helcogenes, Mitsuokella multacida\|Bacteroides helcogenes, Mobiluncus curtisii\|Bacteroides helcogenes, Mycoplasma hominis\|Bacteroides helcogenes, Neisseria mucosa\|Bacteroides helcogenes, Odoribacter splanchnicus\|Bacteroides helcogenes, Olsenella uli\|Bacteroides helcogenes, Oribacterium sinus\|Bacteroides helcogenes, Oxalobacter formigenes\|Bacteroides helcogenes, Parabacteroides distasonis\|Bacteroides helcogenes, Parabacteroides johnsonii\|Bacteroides helcogenes, Parabacteroides merdae\|Bacteroides helcogenes, Parvimonas micra\|Bacteroides helcogenes, Pediococcus acidilactici\|Bacteroides helcogenes, Pediococcus pentosaceus\|Bacteroides helcogenes, Peptoniphilus duerdenii\|Bacteroides helcogenes, Peptoniphilus harei\|Bacteroides helcogenes, Peptoniphilus lacrimalis\|Bacteroides helcogenes, Peptostreptococcus anaerobius\|Bacteroides helcogenes, Peptostreptococcus stomatis\|Bacteroides helcogenes, Porphyromonas asaccharolytica\|Bacteroides helcogenes, Porphyromonas uenonis\|Bacteroides helcogenes, Prevotella amnii\|Bacteroides helcogenes, Prevotella bergensis\|Bacteroides helcogenes, Prevotella bivia\|Bacteroides helcogenes, Prevotella buccae\|Bacteroides helcogenes, Prevotella buccalis\|Bacteroides helcogenes, Prevotella copri\|Bacteroides helcogenes, Prevotella disiens\|Bacteroides helcogenes, Prevotella melaninogenica\|Bacteroides helcogenes, Prevotella multiformis\|Bacteroides helcogenes, Prevotella oralis\|Bacteroides helcogenes, Prevotella oris\|Bacteroides helcogenes, Prevotella salivae\|Bacteroides helcogenes, Prevotella timonensis\|Bacteroides helcogenes, Propionibacterium acnes\|Bacteroides helcogenes, Propionibacterium freudenreichii\|Bacteroides helcogenes, Proteus mirabilis\|Bacteroides helcogenes, Proteus penneri\|Bacteroides helcogenes, Pseudoflavonifractor capillosus\|Bacteroides helcogenes, Pseudomonas aeruginosa\|Bacteroides helcogenes, Pseudomonas fluorescens\|Bacteroides helcogenes, Pseudomonas putida\|Bacteroides helcogenes, Pseudoramibacter alactolyticus\|Bacteroides helcogenes, Pyramidobacter piscolens\|Bacteroides helcogenes, Rhodopseudomonas palustris\|Bacteroides helcogenes, Roseburia intestinalis, Bacteroides helcogenes, Roseburia inulinivorans\|Bacteroides helcogenes, Rothia dentocariosa\|Bacteroides helcogenes, Rothia mucilaginosa\|Bacteroides helcogenes, Ruminococcus albus\|Bacteroides helcogenes, Ruminococcus bromii\|Bacteroides helcogenes, Ruminococcus gnavus\|Bacteroides helcogenes, Ruminococcus lactaris\|Bacteroides helcogenes, Ruminococcus obeum\|Bacteroides helcogenes, Ruminococcus torques\|Bacteroides helcogenes, Selenomonas sputigena\|Bacteroides helcogenes, Shigella boydii\|Bacteroides helcogenes, Shigella dysenteriae\|Bacteroides helcogenes, Shigella sonnei\|Bacteroides helcogenes, Slackia exigua\|Bacteroides helcogenes, Solobacterium moorei\|Bacteroides helcogenes, Staphylococcus aureus\|Bacteroides helcogenes, Staphylococcus epidermidis\|Bacteroides helcogenes, Staphylococcus hominis\|Bacteroides helcogenes, Staphylococcus saprophyticus\|Bacteroides helcogenes, Staphylococcus warneri\|Bacteroides helcogenes, Streptococcus agalactiae\|Bacteroides helcogenes, Streptococcus anginosus\|Bacteroides helcogenes, Streptococcus australis\|Bacteroides helcogenes, Streptococcus bovis\|Bacteroides helcogenes, Streptococcus cristatus\|Bacteroides |

TABLE 2-continued

Table 2. Specific binary combinations of OTUs. Individual pairings are differentiated by "|" and OTUs within a combination are differentiated by ","

*helcogenes, Streptococcus dysgalactiae|Bacteroides helcogenes, Streptococcus equinus|Bacteroides helcogenes, Streptococcus gordonii|Bacteroides helcogenes, Streptococcus infantarius|Bacteroides helcogenes, Streptococcus infantis|Bacteroides helcogenes, Streptococcus mitis|Bacteroides helcogenes, Streptococcus mutans|Bacteroides helcogenes, Streptococcus oralis|Bacteroides helcogenes, Streptococcus parasanguinis|Bacteroides helcogenes, Streptococcus peroris|Bacteroides helcogenes, Streptococcus pneumoniae|Bacteroides helcogenes, Streptococcus salivarius|Bacteroides helcogenes, Streptococcus sanguinis|Bacteroides helcogenes, Streptococcus thermophilus|Bacteroides helcogenes, Streptococcus vestibularis|Bacteroides helcogenes, Subdoligranulum variabile|Bacteroides helcogenes, Succinatimonas hippei|Bacteroides helcogenes, Sutterella wadsworthensis|Bacteroides helcogenes, Tropheryma whipplei|Bacteroides helcogenes, Veillonella atypica|Bacteroides helcogenes, Veillonella dispar|Bacteroides helcogenes, Veillonella parvula|Bacteroides helcogenes, Victivallis vadensis|Bacteroides intestinalis, Bacteroides intestinalis|Bacteroides intestinalis, Bacteroides ovatus|Bacteroides intestinalis, Bacteroides pectinophilus|Bacteroides intestinalis, Bacteroides plebeius|Bacteroides intestinalis, Bacteroides salanitronis|Bacteroides intestinalis, Bacteroides* sp. 1_1_6|*Bacteroides intestinalis, Bacteroides* sp. 3_1_23|*Bacteroides intestinalis, Bacteroides stercoris|Bacteroides intestinalis, Bacteroides thetaiotaomicron|Bacteroides intestinalis, Bacteroides uniformis|Bacteroides intestinalis, Bacteroides vulgatus|Bacteroides intestinalis, Bacteroides xylanisolvens|Bacteroides intestinalis, Bifidobacterium adolescentis|Bacteroides intestinalis, Bifidobacterium angulatum|Bacteroides intestinalis, Bifidobacterium animalis|Bacteroides intestinalis, Bifidobacterium bifidum|Bacteroides intestinalis, Bifidobacterium breve|Bacteroides intestinalis, Bifidobacterium catenulatum|Bacteroides intestinalis, Bifidobacterium dentium|Bacteroides intestinalis, Bifidobacterium infantis|Bacteroides intestinalis, Bifidobacterium longum|Bacteroides intestinalis, Bifidobacterium pseudocatenulatum|Bacteroides intestinalis, Bilophila wadsworthia|Bacteroides intestinalis, Blautia hansenii|Bacteroides intestinalis, Blautia hydrogenotrophica|Bacteroides intestinalis, Blautia producta|Bacteroides intestinalis, Blautia schinkii|Bacteroides intestinalis, Brevibacterium linens|Bacteroides intestinalis, Brucella ceti|Bacteroides intestinalis, Brucella suis|Bacteroides intestinalis, Bulleidia extructa|Bacteroides intestinalis, Butyrivibrio crossotus|Bacteroides intestinalis, Campylobacter concisus|Bacteroides intestinalis, Campylobacter curvus|Bacteroides intestinalis, Campylobacter gracilis|Bacteroides intestinalis, Campylobacter hominis|Bacteroides intestinalis, Capnocytophaga ochracea|Bacteroides intestinalis, Cardiobacterium hominis|Bacteroides intestinalis, Catenibacterium mitsuokai|Bacteroides intestinalis, Catonella morbi|Bacteroides intestinalis, Citrobacter koseri|Bacteroides intestinalis, Clostridium asparagiforme|Bacteroides intestinalis, Clostridium bartlettii|Bacteroides intestinalis, Clostridium bolteae|Bacteroides intestinalis, Clostridium botulinum|Bacteroides intestinalis, Clostridium butyricum|Bacteroides intestinalis, Clostridium difficile|Bacteroides intestinalis, Clostridium disporicum|Bacteroides intestinalis, Clostridium hathewayi|Bacteroides intestinalis, Clostridium hylemonae|Bacteroides intestinalis, Clostridium innocuum|Bacteroides intestinalis, Clostridium leptum|Bacteroides intestinalis, Clostridium mayombei|Bacteroides intestinalis, Clostridium methylpentosum|Bacteroides intestinalis, Clostridium nexile|Bacteroides intestinalis, Clostridium orbiscindens|Bacteroides intestinalis, Clostridium perfringens|Bacteroides intestinalis, Clostridium saccharolyticum|Bacteroides intestinalis, Clostridium scindens|Bacteroides intestinalis, Clostridium symbiosum|Bacteroides intestinalis, Clostridium tertium|Bacteroides intestinalis, Collinsella aerofaciens|Bacteroides intestinalis, Collinsella intestinalis|Bacteroides intestinalis, Collinsella stercoris|Bacteroides intestinalis, Coprobacillus* sp. D7|*Bacteroides intestinalis, Coprococcus catus|Bacteroides intestinalis, Coprococcus comes|Bacteroides intestinalis, Coprococcus eutactus|Bacteroides intestinalis, Corynebacterium aurimucosum|Bacteroides intestinalis, Corynebacterium matruchotii|Bacteroides intestinalis, Cryptobacterium curtum|Bacteroides intestinalis, Desulfovibrio desulfuricans|Bacteroides intestinalis, Desulfovibrio piger|Bacteroides intestinalis, Dialister invisus|Bacteroides intestinalis, Dialister microaerophilus|Bacteroides intestinalis, Dorea formicigenerans|Bacteroides intestinalis, Dorea longicatena|Bacteroides intestinalis, Eggerthella lenta|Bacteroides intestinalis, Eikenella corrodens|Bacteroides intestinalis, Enterobacter cancerogenus|Bacteroides intestinalis, Enterobacter cloacae|Bacteroides intestinalis, Enterococcus faecalis|Bacteroides intestinalis, Enterococcus faecium|Bacteroides intestinalis, Enterococcus gallinarum|Bacteroides intestinalis, Erysipelotrichaceae bacterium* 3_1_53|*Bacteroides intestinalis, Escherichia coli|Bacteroides intestinalis, Escherichia fergusonii|Bacteroides intestinalis, Ethanoligenens harbinense|Bacteroides intestinalis, Eubacterium cellulosolvens|Bacteroides intestinalis, Eubacterium eligens|Bacteroides intestinalis, Eubacterium hallii|Bacteroides intestinalis, Eubacterium limosum|Bacteroides intestinalis, Eubacterium rectale|Bacteroides intestinalis, Eubacterium siraeum|Bacteroides intestinalis, Eubacterium ventriosum|Bacteroides intestinalis, Faecalibacterium prausnitzii|Bacteroides intestinalis, Finegoldia magna|Bacteroides intestinalis, Fusobacterium gonidiaformans|Bacteroides intestinalis, Fusobacterium mortiferum|Bacteroides intestinalis, Fusobacterium nucleatum|Bacteroides intestinalis, Fusobacterium varium|Bacteroides intestinalis, Gardnerella vaginalis|Bacteroides intestinalis, Gemella haemolysans|Bacteroides intestinalis, Gemella morbillorum|Bacteroides intestinalis, Gordonibacter pamelaeae|Bacteroides intestinalis, Granulicatella adiacens|Bacteroides intestinalis, Granulicatella elegans|Bacteroides intestinalis, Haemophilus influenzae|Bacteroides intestinalis, Haemophilus parainfluenzae|Bacteroides intestinalis, Helicobacter pullorum|Bacteroides intestinalis, Helicobacter pylori|Bacteroides intestinalis, Holdemania filiformis|Bacteroides intestinalis, Kingella oralis|Bacteroides intestinalis, Klebsiella pneumoniae|Bacteroides intestinalis, Klebsiella variicola|Bacteroides intestinalis, Lachnospiraceae bacterium* 5_1_57FAA|*Bacteroides intestinalis, Lactobacillus acidophilus|Bacteroides intestinalis, Lactobacillus amylovorus|Bacteroides intestinalis, Lactobacillus brevis|Bacteroides intestinalis, Lactobacillus casei|Bacteroides intestinalis, Lactobacillus crispatus|Bacteroides intestinalis, Lactobacillus delbrueckii|Bacteroides intestinalis, Lactobacillus fermentum|Bacteroides intestinalis, Lactobacillus gasseri|Bacteroides intestinalis, Lactobacillus iners|Bacteroides intestinalis, Lactobacillus jensenii|Bacteroides intestinalis, Lactobacillus johnsonii|Bacteroides intestinalis, Lactobacillus paracasei|Bacteroides intestinalis, Lactobacillus plantarum|Bacteroides intestinalis, Lactobacillus reuteri|Bacteroides intestinalis, Lactobacillus rhamnosus|Bacteroides intestinalis, Lactobacillus ruminis|Bacteroides intestinalis, Lactobacillus sakei|Bacteroides intestinalis, Lactobacillus salivarius|Bacteroides intestinalis, Lactococcus lactis|Bacteroides intestinalis, Lautropia mirabilis|Bacteroides intestinalis, Leuconostoc citreum|Bacteroides intestinalis, Leuconostoc gasicomitatum|Bacteroides intestinalis, Leuconostoc mesenteroides|Bacteroides intestinalis, Listeria monocytogenes|Bacteroides intestinalis, Marvinbryantia formatexigens|Bacteroides intestinalis, Megamonas hypermegale|Bacteroides intestinalis, Megasphaera micronuciformis|Bacteroides intestinalis, Methanobrevibacter smithii|Bacteroides intestinalis, Methanosphaera stadtmanae|Bacteroides intestinalis, Methylobacterium radiotolerans|Bacteroides intestinalis, Mitsuokella multacida|Bacteroides intestinalis, Mobiluncus curtisii|Bacteroides intestinalis, Mycoplasma hominis|Bacteroides intestinalis, Neisseria mucosa|Bacteroides intestinalis, Odoribacter splanchnicus|Bacteroides intestinalis, Olsenella uli|Bacteroides intestinalis, Oribacterium sinus|Bacteroides intestinalis, Oxalobacter formigenes|Bacteroides intestinalis, Parabacteroides distasonis|Bacteroides intestinalis, Parabacteroides johnsonii|Bacteroides intestinalis, Parabacteroides merdae|Bacteroides intestinalis, Parvimonas micra|Bacteroides intestinalis, Pediococcus acidilactici|Bacteroides intestinalis, Pediococcus pentosaceus|Bacteroides intestinalis, Peptoniphilus duerdenii|Bacteroides intestinalis, Peptoniphilus harei|Bacteroides intestinalis, Peptoniphilus lacrimalis|Bacteroides intestinalis, Peptostreptococcus anaerobius|Bacteroides intestinalis, Peptostreptococcus stomatis|Bacteroides intestinalis, Porphyromonas asaccharolytica|Bacteroides intestinalis, Porphyromonas uenonis|Bacteroides intestinalis, Prevotella amnii|Bacteroides intestinalis, Prevotella bergensis|Bacteroides intestinalis, Prevotella bivia|Bacteroides intestinalis, Prevotella buccae|Bacteroides intestinalis, Prevotella buccalis|Bacteroides intestinalis, Prevotella copri|Bacteroides intestinalis, Prevotella disiens|Bacteroides intestinalis, Prevotella melaninogenica|Bacteroides intestinalis, Prevotella multiformis|Bacteroides intestinalis, Prevotella oralis|Bacteroides intestinalis, Prevotella oris|Bacteroides intestinalis, Prevotella salivae|Bacteroides intestinalis, Prevotella timonensis|Bacteroides intestinalis, Propionibacterium acnes|Bacteroides intestinalis, Propionibacterium freudenreichii|Bacteroides intestinalis, Proteus mirabilis|Bacteroides intestinalis, Proteus penneri|Bacteroides intestinalis, Pseudoflavonifractor capillosus|Bacteroides intestinalis, Pseudomonas aeruginosa|Bacteroides intestinalis, Pseudomonas fluorescens|Bacteroides intestinalis, Pseudomonas putida|Bacteroides intestinalis, Pseudoramibacter alactolyticus|Bacteroides intestinalis, Pyramidobacter piscolens|Bacteroides intestinalis, Rhodopseudomonas*

TABLE 2-continued

Table 2. Specific binary combinations of OTUs. Individual pairings are differentiated by "|" and OTUs within a combination are differentiated by ","

*palustris|Bacteroides intestinalis, Roseburia intestinalis|Bacteroides intestinalis, Roseburia inulinivorans|Bacteroides intestinalis, Rothia dentocariosa|Bacteroides intestinalis, Rothia mucilaginosa|Bacteroides intestinalis, Ruminococcus albus|Bacteroides intestinalis, Ruminococcus bromii|Bacteroides intestinalis, Ruminococcus gnavus|Bacteroides intestinalis, Ruminococcus lactaris|Bacteroides intestinalis, Ruminococcus obeum|Bacteroides intestinalis, Ruminococcus torques|Bacteroides intestinalis, Selenomonas sputigena|Bacteroides intestinalis, Shigella boydii|Bacteroides intestinalis, Shigella dysenteriae|Bacteroides intestinalis, Shigella sonnei|Bacteroides intestinalis, Slackia exigua|Bacteroides intestinalis, Solobacterium moorei|Bacteroides intestinalis, Staphylococcus aureus|Bacteroides intestinalis, Staphylococcus epidermidis|Bacteroides intestinalis, Staphylococcus hominis|Bacteroides intestinalis, Staphylococcus saprophyticus|Bacteroides intestinalis, Staphylococcus warneri|Bacteroides intestinalis, Streptococcus agalactiae|Bacteroides intestinalis, Streptococcus anginosus|Bacteroides intestinalis, Streptococcus australis|Bacteroides intestinalis, Streptococcus bovis|Bacteroides intestinalis, Streptococcus cristatus|Bacteroides intestinalis, Streptococcus dysgalactiae|Bacteroides intestinalis, Streptococcus equinus|Bacteroides intestinalis, Streptococcus gordonii|Bacteroides intestinalis, Streptococcus infantarius|Bacteroides intestinalis, Streptococcus infantis|Bacteroides intestinalis, Streptococcus mitis|Bacteroides intestinalis, Streptococcus mutans|Bacteroides intestinalis, Streptococcus oralis|Bacteroides intestinalis, Streptococcus parasanguinis|Bacteroides intestinalis, Streptococcus peroris|Bacteroides intestinalis, Streptococcus pneumoniae|Bacteroides intestinalis, Streptococcus salivarius|Bacteroides intestinalis, Streptococcus sanguinis|Bacteroides intestinalis, Streptococcus thermophilus|Bacteroides intestinalis, Streptococcus vestibularis|Bacteroides intestinalis, Subdoligranulum variabile|Bacteroides intestinalis, Succinatimonas hippei|Bacteroides intestinalis, Sutterella wadsworthensis|Bacteroides intestinalis, Tropheryma whipplei|Bacteroides intestinalis, Veillonella atypica|Bacteroides intestinalis, Veillonella dispar|Bacteroides intestinalis, Veillonella parvula|Bacteroides intestinalis, Victivallis vadensis|Bacteroides ovatus, Bacteroides ovatus|Bacteroides ovatus, Bacteroides pectinophilus|Bacteroides ovatus, Bacteroides plebeius|Bacteroides ovatus, Bacteroides salanitronis|Bacteroides ovatus, Bacteroides* sp. 1_1_6|*Bacteroides ovatus, Bacteroides* sp. 3_1_23|*Bacteroides ovatus, Bacteroides stercoris|Bacteroides ovatus, Bacteroides thetaiotaomicron|Bacteroides ovatus, Bacteroides uniformis|Bacteroides ovatus, Bacteroides vulgatus|Bacteroides ovatus, Bacteroides xylanisolvens|Bacteroides ovatus, Bifidobacterium adolescentis|Bacteroides ovatus, Bifidobacterium angulatum|Bacteroides ovatus, Bifidobacterium animalis|Bacteroides ovatus, Bifidobacterium bifidum|Bacteroides ovatus, Bifidobacterium breve|Bacteroides ovatus, Bifidobacterium catenulatum|Bacteroides ovatus, Bifidobacterium dentium|Bacteroides ovatus, Bifidobacterium infantis|Bacteroides ovatus, Bifidobacterium longum|Bacteroides ovatus, Bifidobacterium pseudocatenulatum|Bacteroides ovatus, Bilophila wadsworthia|Bacteroides ovatus, Blautia hansenii|Bacteroides ovatus, Blautia hydrogenotrophica|Bacteroides ovatus, Blautia producta|Bacteroides ovatus, Blautia schinkii|Bacteroides ovatus, Brevibacterium linens|Bacteroides ovatus, Brucella ceti|Bacteroides ovatus, Brucella suis|Bacteroides ovatus, Bulleidia extructa|Bacteroides ovatus, Butyrivibrio crossotus|Bacteroides ovatus, Campylobacter concisus|Bacteroides ovatus, Campylobacter curvus|Bacteroides ovatus, Campylobacter gracilis|Bacteroides ovatus, Campylobacter hominis|Bacteroides ovatus, Capnocytophaga ochracea|Bacteroides ovatus, Cardiobacterium hominis|Bacteroides ovatus, Catenibacterium mitsuokai|Bacteroides ovatus, Catonella morbi|Bacteroides ovatus, Citrobacter koseri|Bacteroides ovatus, Clostridium asparagiforme|Bacteroides ovatus, Clostridium bartlettii|Bacteroides ovatus, Clostridium bolteae|Bacteroides ovatus, Clostridium botulinum|Bacteroides ovatus, Clostridium butyricum|Bacteroides ovatus, Clostridium difficile|Bacteroides ovatus, Clostridium disporicum|Bacteroides ovatus, Clostridium hathewayi|Bacteroides ovatus, Clostridium hylemonae|Bacteroides ovatus, Clostridium innocuum|Bacteroides ovatus, Clostridium leptum|Bacteroides ovatus, Clostridium mayombei|Bacteroides ovatus, Clostridium methylpentosum|Bacteroides ovatus, Clostridium nexile|Bacteroides ovatus, Clostridium orbiscindens|Bacteroides ovatus, Clostridium perfringens|Bacteroides ovatus, Clostridium saccharolyticum|Bacteroides ovatus, Clostridium scindens|Bacteroides ovatus, Clostridium symbiosum|Bacteroides ovatus, Clostridium tertium|Bacteroides ovatus, Collinsella aerofaciens|Bacteroides ovatus, Collinsella intestinalis|Bacteroides ovatus, Collinsella stercoris|Bacteroides ovatus, Coprobacillus* sp. D7|*Bacteroides ovatus, Coprococcus catus|Bacteroides ovatus, Coprococcus comes|Bacteroides ovatus, Coprococcus eutactus|Bacteroides ovatus, Corynebacterium aurimucosum|Bacteroides ovatus, Corynebacterium matruchotii|Bacteroides ovatus, Cryptobacterium curtum|Bacteroides ovatus, Desulfovibrio desulfuricans|Bacteroides ovatus, Desulfovibrio piger|Bacteroides ovatus, Dialister invisus|Bacteroides ovatus, Dialister microaerophilus|Bacteroides ovatus, Dorea formicigenerans|Bacteroides ovatus, Dorea longicatena|Bacteroides ovatus, Eggerthella lenta|Bacteroides ovatus, Eikenella corrodens|Bacteroides ovatus, Enterobacter cancerogenus|Bacteroides ovatus, Enterobacter cloacae|Bacteroides ovatus, Enterococcus faecalis|Bacteroides ovatus, Enterococcus faecium|Bacteroides ovatus, Enterococcus gallinarum|Bacteroides ovatus, Erysipelotrichaceae bacterium* 3_1_53|*Bacteroides ovatus, Escherichia coli|Bacteroides ovatus, Escherichia fergusonii|Bacteroides ovatus, Ethanoligenens harbinense|Bacteroides ovatus, Eubacterium cellulosolvens|Bacteroides ovatus, Eubacterium eligens|Bacteroides ovatus, Eubacterium hallii|Bacteroides ovatus, Eubacterium limosum|Bacteroides ovatus, Eubacterium rectale|Bacteroides ovatus, Eubacterium siraeum|Bacteroides ovatus, Eubacterium ventriosum|Bacteroides ovatus, Faecalibacterium prausnitzii|Bacteroides ovatus, Finegoldia magna|Bacteroides ovatus, Fusobacterium gonidiaformans|Bacteroides ovatus, Fusobacterium mortiferum|Bacteroides ovatus, Fusobacterium nucleatum|Bacteroides ovatus, Fusobacterium varium|Bacteroides ovatus, Gardnerella vaginalis|Bacteroides ovatus, Gemella haemolysans|Bacteroides ovatus, Gemella morbillorum|Bacteroides ovatus, Gordonibacter pamelaeae|Bacteroides ovatus, Granulicatella adiacens|Bacteroides ovatus, Granulicatella elegans|Bacteroides ovatus, Haemophilus influenzae|Bacteroides ovatus, Haemophilus parainfluenzae|Bacteroides ovatus, Helicobacter pullorum|Bacteroides ovatus, Helicobacter pylori|Bacteroides ovatus, Holdemania filiformis|Bacteroides ovatus, Kingella oralis|Bacteroides ovatus, Klebsiella pneumoniae|Bacteroides ovatus, Klebsiella variicola|Bacteroides ovatus, Lachnospiraceae bacterium* 5_1_57FAA|*Bacteroides ovatus, Lactobacillus acidophilus|Bacteroides ovatus, Lactobacillus amylovorus|Bacteroides ovatus, Lactobacillus brevis|Bacteroides ovatus, Lactobacillus casei|Bacteroides ovatus, Lactobacillus crispatus|Bacteroides ovatus, Lactobacillus delbrueckii|Bacteroides ovatus, Lactobacillus fermentum|Bacteroides ovatus, Lactobacillus gasseri|Bacteroides ovatus, Lactobacillus iners|Bacteroides ovatus, Lactobacillus jensenii|Bacteroides ovatus, Lactobacillus johnsonii|Bacteroides ovatus, Lactobacillus paracasei|Bacteroides ovatus, Lactobacillus plantarum|Bacteroides ovatus, Lactobacillus reuteri|Bacteroides ovatus, Lactobacillus rhamnosus|Bacteroides ovatus, Lactobacillus ruminis|Bacteroides ovatus, Lactobacillus sakei|Bacteroides ovatus, Lactobacillus salivarius|Bacteroides ovatus, Lactococcus lactis|Bacteroides ovatus, Lautropia mirabilis|Bacteroides ovatus, Leuconostoc citreum|Bacteroides ovatus, Leuconostoc gasicomitatum|Bacteroides ovatus, Leuconostoc mesenteroides|Bacteroides ovatus, Listeria monocytogenes|Bacteroides ovatus, Marvinbryantia formatexigens|Bacteroides ovatus, Megamonas hypermegale|Bacteroides ovatus, Megasphaera micronuciformis|Bacteroides ovatus, Methanobrevibacter smithii|Bacteroides ovatus, Methanosphaera stadtmanae|Bacteroides ovatus, Methylobacterium radiotolerans|Bacteroides ovatus, Mitsuokella multacida|Bacteroides ovatus, Mobiluncus curtisii|Bacteroides ovatus, Mycoplasma hominis|Bacteroides ovatus, Neisseria mucosa|Bacteroides ovatus, Odoribacter splanchnicus|Bacteroides ovatus, Olsenella uli|Bacteroides ovatus, Oribacterium sinus|Bacteroides ovatus, Oxalobacter formigenes|Bacteroides ovatus, Parabacteroides distasonis|Bacteroides ovatus, Parabacteroides johnsonii|Bacteroides ovatus, Parabacteroides merdae|Bacteroides ovatus, Parvimonas micra|Bacteroides ovatus, Pediococcus acidilactici|Bacteroides ovatus, Pediococcus pentosaceus|Bacteroides ovatus, Peptoniphilus duerdenii|Bacteroides ovatus, Peptoniphilus harei|Bacteroides ovatus, Peptoniphilus lacrimalis|Bacteroides ovatus, Peptostreptococcus anaerobius|Bacteroides ovatus, Peptostreptococcus stomatis|Bacteroides ovatus, Porphyromonas asaccharolytica|Bacteroides ovatus, Porphyromonas uenonis|Bacteroides ovatus, Prevotella amnii|Bacteroides ovatus, Prevotella bergensis|Bacteroides ovatus, Prevotella bivia|Bacteroides ovatus, Prevotella buccae|Bacteroides ovatus, Prevotella buccalis|Bacteroides ovatus, Prevotella copri|Bacteroides ovatus, Prevotella disiens|Bacteroides ovatus, Prevotella melaninogenica|Bacteroides ovatus, Prevotella multiformis|Bacteroides ovatus, Prevotella oralis|Bacteroides ovatus, Prevotella oris|Bacteroides ovatus, Prevotella salivae|Bacteroides ovatus, Prevotella timonensis|Bacteroides ovatus, Propionibacterium acnes|Bacteroides ovatus, Propionibacterium freudenreichii|Bacteroides ovatus, Proteus*

TABLE 2-continued

| Table 2. Specific binary combinations of OTUs. Individual pairings are differentiated by "\|" and OTUs within a combination are differentiated by "," |
| --- |
| mirabilis\|Bacteroides ovatus, Proteus penneri\|Bacteroides ovatus, Pseudoflavonifractor capillosus\|Bacteroides ovatus, Pseudomonas aeruginosa\|Bacteroides ovatus, Pseudomonas fluorescens\|Bacteroides ovatus, Pseudomonas putida\|Bacteroides ovatus, Pseudoramibacter alactolyticus\|Bacteroides ovatus, Pyramidobacter piscolens\|Bacteroides ovatus, Rhodopseudomonas palustris\|Bacteroides ovatus, Roseburia intestinalis\|Bacteroides ovatus, Roseburia inulinivorans\|Bacteroides ovatus, Rothia dentocariosa\|Bacteroides ovatus, Rothia mucilaginosa\|Bacteroides ovatus, Ruminococcus albus\|Bacteroides ovatus, Ruminococcus bromii\|Bacteroides ovatus, Ruminococcus gnavus\|Bacteroides ovatus, Ruminococcus lactaris\|Bacteroides ovatus, Ruminococcus obeum\|Bacteroides ovatus, Ruminococcus torques\|Bacteroides ovatus, Selenomonas sputigena\|Bacteroides ovatus, Shigella boydii\|Bacteroides ovatus, Shigella dysenteriae\|Bacteroides ovatus, Shigella sonnei\|Bacteroides ovatus, Slackia exigua\|Bacteroides ovatus, Solobacterium moorei\|Bacteroides ovatus, Staphylococcus aureus\|Bacteroides ovatus, Staphylococcus epidermidis\|Bacteroides ovatus, Staphylococcus hominis\|Bacteroides ovatus, Staphylococcus saprophyticus\|Bacteroides ovatus, Staphylococcus warneri\|Bacteroides ovatus, Streptococcus agalactiae\|Bacteroides ovatus, Streptococcus anginosus\|Bacteroides ovatus, Streptococcus australis\|Bacteroides ovatus, Streptococcus bovis\|Bacteroides ovatus, Streptococcus cristatus\|Bacteroides ovatus, Streptococcus dysgalactiae\|Bacteroides ovatus, Streptococcus equinus\|Bacteroides ovatus, Streptococcus gordonii\|Bacteroides ovatus, Streptococcus infantarius\|Bacteroides ovatus, Streptococcus infantis\|Bacteroides ovatus, Streptococcus mitis\|Bacteroides ovatus, Streptococcus mutans\|Bacteroides ovatus, Streptococcus oralis\|Bacteroides ovatus, Streptococcus parasanguinis\|Bacteroides ovatus, Streptococcus peroris\|Bacteroides ovatus, Streptococcus pneumoniae\|Bacteroides ovatus, Streptococcus salivarius\|Bacteroides ovatus, Streptococcus sanguinis\|Bacteroides ovatus, Streptococcus thermophilus\|Bacteroides ovatus, Streptococcus vestibularis\|Bacteroides ovatus, Subdoligranulum variabile\|Bacteroides ovatus, Succinatimonas hippei\|Bacteroides ovatus, Sutterella wadsworthensis\|Bacteroides ovatus, Tropheryma whipplei\|Bacteroides ovatus, Veillonella atypica\|Bacteroides ovatus, Veillonella dispar\|Bacteroides ovatus, Veillonella parvula\|Bacteroides ovatus, Victivallis vadensis\|Bacteroides pectinophilus, Bacteroides pectinophilus\|Bacteroides pectinophilus, Bacteroides plebeius\|Bacteroides pectinophilus, Bacteroides salanitronis\|Bacteroides pectinophilus, Bacteroides sp. 1_1_6\|Bacteroides pectinophilus, Bacteroides sp. 3_1_23\|Bacteroides pectinophilus, Bacteroides stercoris\|Bacteroides pectinophilus, Bacteroides thetaiotaomicron\|Bacteroides pectinophilus, Bacteroides uniformis\|Bacteroides pectinophilus, Bacteroides vulgatus\|Bacteroides pectinophilus, Bacteroides xylanisolvens\|Bacteroides pectinophilus, Bifidobacterium adolescentis\|Bacteroides pectinophilus, Bifidobacterium angulatum\|Bacteroides pectinophilus, Bifidobacterium animalis\|Bacteroides pectinophilus, Bifidobacterium bifidum\|Bacteroides pectinophilus, Bifidobacterium breve\|Bacteroides pectinophilus, Bifidobacterium catenulatum\|Bacteroides pectinophilus, Bifidobacterium dentium\|Bacteroides pectinophilus, Bifidobacterium infantis\|Bacteroides pectinophilus, Bifidobacterium longum\|Bacteroides pectinophilus, Bifidobacterium pseudocatenulatum\|Bacteroides pectinophilus, Bilophila wadsworthia\|Bacteroides pectinophilus, Blautia hansenii\|Bacteroides pectinophilus, Blautia hydrogenotrophica\|Bacteroides pectinophilus, Blautia producta\|Bacteroides pectinophilus, Blautia schinkii\|Bacteroides pectinophilus, Brevibacterium linens\|Bacteroides pectinophilus, Brucella ceti\|Bacteroides pectinophilus, Brucella suis\|Bacteroides pectinophilus, Bulleidia extructa\|Bacteroides pectinophilus, Butyrivibrio crossotus\|Bacteroides pectinophilus, Campylobacter concisus\|Bacteroides pectinophilus, Campylobacter curvus\|Bacteroides pectinophilus, Campylobacter gracilis\|Bacteroides pectinophilus, Campylobacter hominis\|Bacteroides pectinophilus, Capnocytophaga ochracea\|Bacteroides pectinophilus, Cardiobacterium hominis\|Bacteroides pectinophilus, Catenibacterium mitsuokai\|Bacteroides pectinophilus, Catonella morbi\|Bacteroides pectinophilus, Citrobacter koseri\|Bacteroides pectinophilus, Clostridium asparagiforme\|Bacteroides pectinophilus, Clostridium bartlettii\|Bacteroides pectinophilus, Clostridium bolteae\|Bacteroides pectinophilus, Clostridium botulinum\|Bacteroides pectinophilus, Clostridium butyricum\|Bacteroides pectinophilus, Clostridium difficile\|Bacteroides pectinophilus, Clostridium disporicum\|Bacteroides pectinophilus, Clostridium hathewayi\|Bacteroides pectinophilus, Clostridium hylemonae\|Bacteroides pectinophilus, Clostridium innocuum\|Bacteroides pectinophilus, Clostridium leptum\|Bacteroides pectinophilus, Clostridium mayombei\|Bacteroides pectinophilus, Clostridium methylpentosum\|Bacteroides pectinophilus, Clostridium nexile\|Bacteroides pectinophilus, Clostridium orbiscindens\|Bacteroides pectinophilus, Clostridium perfringens\|Bacteroides pectinophilus, Clostridium saccharolyticum\|Bacteroides pectinophilus, Clostridium scindens\|Bacteroides pectinophilus, Clostridium symbiosum\|Bacteroides pectinophilus, Clostridium tertium\|Bacteroides pectinophilus, Collinsella aerofaciens\|Bacteroides pectinophilus, Collinsella intestinalis\|Bacteroides pectinophilus, Collinsella stercoris\|Bacteroides pectinophilus, Coprobacillus sp. D7\|Bacteroides pectinophilus, Coprococcus catus\|Bacteroides pectinophilus, Coprococcus comes\|Bacteroides pectinophilus, Coprococcus eutactus\|Bacteroides pectinophilus, Corynebacterium aurimucosum\|Bacteroides pectinophilus, Corynebacterium matruchotii\|Bacteroides pectinophilus, Cryptobacterium curtum\|Bacteroides pectinophilus, Desulfovibrio desulfuricans\|Bacteroides pectinophilus, Desulfovibrio piger\|Bacteroides pectinophilus, Dialister invisus\|Bacteroides pectinophilus, Dialister microaerophilus\|Bacteroides pectinophilus, Dorea formicigenerans\|Bacteroides pectinophilus, Dorea longicatena\|Bacteroides pectinophilus, Eggerthella lenta\|Bacteroides pectinophilus, Eikenella corrodens\|Bacteroides pectinophilus, Enterobacter cancerogenus\|Bacteroides pectinophilus, Enterobacter cloacae\|Bacteroides pectinophilus, Enterococcus faecalis\|Bacteroides pectinophilus, Enterococcus faecium\|Bacteroides pectinophilus, Enterococcus gallinarum\|Bacteroides pectinophilus, Erysipelotrichaceae bacterium 3_1_53\|Bacteroides pectinophilus, Escherichia coli\|Bacteroides pectinophilus, Escherichia fergusonii\|Bacteroides pectinophilus, Ethanoligenens harbinense\|Bacteroides pectinophilus, Eubacterium cellulosolvens\|Bacteroides pectinophilus, Eubacterium eligens\|Bacteroides pectinophilus, Eubacterium hallii\|Bacteroides pectinophilus, Eubacterium limosum\|Bacteroides pectinophilus, Eubacterium rectale\|Bacteroides pectinophilus, Eubacterium siraeum\|Bacteroides pectinophilus, Eubacterium ventriosum\|Bacteroides pectinophilus, Faecalibacterium prausnitzii\|Bacteroides pectinophilus, Finegoldia magna\|Bacteroides pectinophilus, Fusobacterium gonidiaformans\|Bacteroides pectinophilus, Fusobacterium mortiferum\|Bacteroides pectinophilus, Fusobacterium nucleatum\|Bacteroides pectinophilus, Fusobacterium varium\|Bacteroides pectinophilus, Gardnerella vaginalis\|Bacteroides pectinophilus, Gemella haemolysans\|Bacteroides pectinophilus, Gemella morbillorum\|Bacteroides pectinophilus, Gordonibacter pamelaeae\|Bacteroides pectinophilus, Granulicatella adiacens\|Bacteroides pectinophilus, Granulicatella elegans\|Bacteroides pectinophilus, Haemophilus influenzae\|Bacteroides pectinophilus, Haemophilus parainfluenzae\|Bacteroides pectinophilus, Helicobacter pullorum\|Bacteroides pectinophilus, Helicobacter pylori\|Bacteroides pectinophilus, Holdemania filiformis\|Bacteroides pectinophilus, Kingella oralis\|Bacteroides pectinophilus, Klebsiella pneumoniae\|Bacteroides pectinophilus, Klebsiella variicola\|Bacteroides pectinophilus, Lachnospiraceae bacterium 5_1_57FAA\|Bacteroides pectinophilus, Lactobacillus acidophilus\|Bacteroides pectinophilus, Lactobacillus amylovorus\|Bacteroides pectinophilus, Lactobacillus brevis\|Bacteroides pectinophilus, Lactobacillus casei\|Bacteroides pectinophilus, Lactobacillus crispatus\|Bacteroides pectinophilus, Lactobacillus delbrueckii\|Bacteroides pectinophilus, Lactobacillus fermentum\|Bacteroides pectinophilus, Lactobacillus gasseri\|Bacteroides pectinophilus, Lactobacillus iners\|Bacteroides pectinophilus, Lactobacillus jensenii\|Bacteroides pectinophilus, Lactobacillus johnsonii\|Bacteroides pectinophilus, Lactobacillus paracasei\|Bacteroides pectinophilus, Lactobacillus plantarum\|Bacteroides pectinophilus, Lactobacillus reuteri\|Bacteroides pectinophilus, Lactobacillus rhamnosus\|Bacteroides pectinophilus, Lactobacillus ruminis\|Bacteroides pectinophilus, Lactobacillus sakei\|Bacteroides pectinophilus, Lactobacillus salivarius\|Bacteroides pectinophilus, Lactococcus lactis\|Bacteroides pectinophilus, Lautropia mirabilis\|Bacteroides pectinophilus, Leuconostoc citreum\|Bacteroides pectinophilus, Leuconostoc gasicomitatum\|Bacteroides pectinophilus, Leuconostoc mesenteroides\|Bacteroides pectinophilus, Listeria monocytogenes\|Bacteroides pectinophilus, Marvinbryantia formatexigens\|Bacteroides pectinophilus, Megamonas hypermegale\|Bacteroides pectinophilus, Megasphaera micronuciformis\|Bacteroides pectinophilus, Methanobrevibacter smithii\|Bacteroides pectinophilus, Methanosphaera stadtmanae\|Bacteroides pectinophilus, Methylobacterium radiotolerans\|Bacteroides pectinophilus, Mitsuokella multacida\|Bacteroides pectinophilus, Mobiluncus curtisii\|Bacteroides pectinophilus, Mycoplasma hominis\|Bacteroides pectinophilus, Neisseria mucosa\|Bacteroides pectinophilus, Odoribacter splanchnicus\|Bacteroides pectinophilus, Olsenella uli\|Bacteroides pectinophilus, Oribacterium sinus\|Bacteroides pectinophilus, Oxalobacter formigenes\|Bacteroides pectinophilus, Parabacteroides distasonis\|Bacteroides pectinophilus, Parabacteroides johnsonii\|Bacteroides |

TABLE 2-continued

<table>
<tr><th>Table 2. Specific binary combinations of OTUs. Individual pairings are differentiated by “|” and OTUs within a combination are differentiated by “,”</th></tr>
<tr><td>pectinophilus, Parabacteroides merdae|Bacteroides pectinophilus, Parvimonas micra|Bacteroides pectinophilus, Pediococcus acidilactici|Bacteroides pectinophilus, Pediococcus pentosaceus|Bacteroides pectinophilus, Peptoniphilus duerdenii|Bacteroides pectinophilus, Peptoniphilus harei|Bacteroides pectinophilus, Peptoniphilus lacrimalis|Bacteroides pectinophilus, Peptostreptococcus anaerobius|Bacteroides pectinophilus, Peptostreptococcus stomatis|Bacteroides pectinophilus, Porphyromonas asaccharolytica|Bacteroides pectinophilus, Porphyromonas uenonis|Bacteroides pectinophilus, Prevotella amnii|Bacteroides pectinophilus, Prevotella bergensis|Bacteroides pectinophilus, Prevotella bivia|Bacteroides pectinophilus, Prevotella buccae|Bacteroides pectinophilus, Prevotella buccalis|Bacteroides pectinophilus, Prevotella copri|Bacteroides pectinophilus, Prevotella disiens|Bacteroides pectinophilus, Prevotella melaninogenica|Bacteroides pectinophilus, Prevotella multiformis|Bacteroides pectinophilus, Prevotella oralis|Bacteroides pectinophilus, Prevotella oris|Bacteroides pectinophilus, Prevotella salivae|Bacteroides pectinophilus, Prevotella timonensis|Bacteroides pectinophilus, Propionibacterium acnes|Bacteroides pectinophilus, Propionibacterium freudenreichii|Bacteroides pectinophilus, Proteus mirabilis|Bacteroides pectinophilus, Proteus penneri|Bacteroides pectinophilus, Pseudoflavonifractor capillosus|Bacteroides pectinophilus, Pseudomonas aeruginosa|Bacteroides pectinophilus, Pseudomonas fluorescens|Bacteroides pectinophilus, Pseudomonas putida|Bacteroides pectinophilus, Pseudoramibacter alactolyticus|Bacteroides pectinophilus, Pyramidobacter piscolens|Bacteroides pectinophilus, Rhodopseudomonas palustris|Bacteroides pectinophilus, Roseburia intestinalis|Bacteroides pectinophilus, Roseburia inulinivorans|Bacteroides pectinophilus, Rothia dentocariosa|Bacteroides pectinophilus, Rothia mucilaginosa|Bacteroides pectinophilus, Ruminococcus albus|Bacteroides pectinophilus, Ruminococcus bromii|Bacteroides pectinophilus, Ruminococcus gnavus|Bacteroides pectinophilus, Ruminococcus lactaris|Bacteroides pectinophilus, Ruminococcus obeum|Bacteroides pectinophilus, Ruminococcus torques|Bacteroides pectinophilus, Selenomonas sputigena|Bacteroides pectinophilus, Shigella boydii|Bacteroides pectinophilus, Shigella dysenteriae|Bacteroides pectinophilus, Shigella sonnei|Bacteroides pectinophilus, Slackia exigua|Bacteroides pectinophilus, Solobacterium moorei|Bacteroides pectinophilus, Staphylococcus aureus|Bacteroides pectinophilus, Staphylococcus epidermidis|Bacteroides pectinophilus, Staphylococcus hominis|Bacteroides pectinophilus, Staphylococcus saprophyticus|Bacteroides pectinophilus, Staphylococcus warneri|Bacteroides pectinophilus, Streptococcus agalactiae|Bacteroides pectinophilus, Streptococcus anginosus|Bacteroides pectinophilus, Streptococcus australis|Bacteroides pectinophilus, Streptococcus bovis|Bacteroides pectinophilus, Streptococcus cristatus|Bacteroides pectinophilus, Streptococcus dysgalactiae|Bacteroides pectinophilus, Streptococcus equinus|Bacteroides pectinophilus, Streptococcus gordonii|Bacteroides pectinophilus, Streptococcus infantarius|Bacteroides pectinophilus, Streptococcus infantis|Bacteroides pectinophilus, Streptococcus mitis|Bacteroides pectinophilus, Streptococcus mutans|Bacteroides pectinophilus, Streptococcus oralis|Bacteroides pectinophilus, Streptococcus parasanguinis|Bacteroides pectinophilus, Streptococcus peroris|Bacteroides pectinophilus, Streptococcus pneumoniae|Bacteroides pectinophilus, Streptococcus salivarius|Bacteroides pectinophilus, Streptococcus sanguinis|Bacteroides pectinophilus, Streptococcus thermophilus|Bacteroides pectinophilus, Streptococcus vestibularis|Bacteroides pectinophilus, Subdoligranulum variabile|Bacteroides pectinophilus, Succinatimonas hippei|Bacteroides pectinophilus, Sutterella wadsworthensis|Bacteroides pectinophilus, Tropheryma whipplei|Bacteroides pectinophilus, Veillonella atypica|Bacteroides pectinophilus, Veillonella dispar|Bacteroides pectinophilus, Veillonella parvula|Bacteroides pectinophilus, Victivallis vadensis|Bacteroides plebeius, Bacteroides plebeius|Bacteroides plebeius, Bacteroides salanitronis|Bacteroides plebeius, Bacteroides sp. 1_1_6|Bacteroides plebeius, Bacteroides sp. 3_1_23|Bacteroides plebeius, Bacteroides stercoris|Bacteroides plebeius, Bacteroides thetaiotaomicron|Bacteroides plebeius, Bacteroides uniformis|Bacteroides plebeius, Bacteroides vulgatus|Bacteroides plebeius, Bacteroides xylanisolvens|Bacteroides plebeius, Bifidobacterium adolescentis|Bacteroides plebeius, Bifidobacterium angulatum|Bacteroides plebeius, Bifidobacterium animalis|Bacteroides plebeius, Bifidobacterium bifidum|Bacteroides plebeius, Bifidobacterium breve|Bacteroides plebeius, Bifidobacterium catenulatum|Bacteroides plebeius, Bifidobacterium dentium|Bacteroides plebeius, Bifidobacterium infantis|Bacteroides plebeius, Bifidobacterium longum|Bacteroides plebeius, Bifidobacterium pseudocatenulatum|Bacteroides plebeius, Bilophila wadsworthia|Bacteroides plebeius, Blautia hansenii|Bacteroides plebeius, Blautia hydrogenotrophica|Bacteroides plebeius, Blautia producta|Bacteroides plebeius, Blautia schinkii|Bacteroides plebeius, Brevibacterium linens|Bacteroidesplebeius, Brucella ceti|Bacteroides plebeius, Brucella suis|Bacteroides plebeius, Bulleidia extructa|Bacteroides plebeius, Butyrivibrio crossotus|Bacteroides plebeius, Campylobacter concisus|Bacteroides plebeius, Campylobacter curvus|Bacteroides plebeius, Campylobacter gracilis|Bacteroides plebeius, Campylobacter hominis|Bacteroides plebeius, Capnocytophaga ochracea|Bacteroides plebeius, Cardiobacterium hominis|Bacteroides plebeius, Catenibacterium mitsuokai|Bacteroides plebeius, Catonella morbi|Bacteroides plebeius, Citrobacter koseri|Bacteroides plebeius, Clostridium asparagiforme|Bacteroides plebeius, Clostridium bartlettii|Bacteroides plebeius, Clostridium bolteae|Bacteroides plebeius, Clostridium botulinum|Bacteroides plebeius, Clostridium butyricum|Bacteroides plebeius, Clostridium difficile|Bacteroides plebeius, Clostridium disporicum|Bacteroides plebeius, Clostridium hathewayi|Bacteroides plebeius, Clostridium hylemonae|Bacteroides plebeius, Clostridium innocuum|Bacteroides plebeius, Clostridium leptum|Bacteroides plebeius, Clostridium mayombei|Bacteroides plebeius, Clostridium methylpentosum|Bacteroides plebeius, Clostridium nexile|Bacteroides plebeius, Clostridium orbiscindens|Bacteroides plebeius, Clostridium perfringens|Bacteroides plebeius, Clostridium saccharolyticum|Bacteroides plebeius, Clostridium scindens|Bacteroides plebeius, Clostridium symbiosum|Bacteroides plebeius, Clostridium tertium|Bacteroides plebeius, Collinsella aerofaciens|Bacteroides plebeius, Collinsella intestinalis|Bacteroides plebeius, Collinsella stercoris|Bacteroides plebeius, Coprobacillus sp. D7|Bacteroides plebeius, Coprococcus catus|Bacteroides plebeius, Coprococcus comes|Bacteroides plebeius, Coprococcus eutactus|Bacteroides plebeius, Corynebacterium aurimucosum|Bacteroides plebeius, Corynebacterium matruchotii|Bacteroides plebeius, Cryptobacterium curtum|Bacteroides plebeius, Desulfovibrio desulfuricans|Bacteroides plebeius, Desulfovibrio piger|Bacteroides plebeius, Dialister invisus|Bacteroides plebeius, Dialister microaerophilus|Bacteroides plebeius, Dorea formicigenerans|Bacteroides plebeius, Dorea longicatena|Bacteroides plebeius, Eggerthella lenta|Bacteroides plebeius, Eikenella corrodens|Bacteroides plebeius, Enterobacter cancerogenus|Bacteroides plebeius, Enterobacter cloacae|Bacteroides plebeius, Enterococcus faecalis|Bacteroides plebeius, Enterococcus faecium|Bacteroides plebeius, Enterococcus gallinarum|Bacteroides plebeius, Erysipelotrichaceae bacterium 3_1_53|Bacteroides plebeius, Escherichia coli|Bacteroides plebeius, Escherichia fergusonii|Bacteroides plebeius, Ethanoligenens harbinense|Bacteroides plebeius, Eubacterium cellulosolvens|Bacteroides plebeius, Eubacterium eligens|Bacteroides plebeius, Eubacterium hallii|Bacteroides plebeius, Eubacterium limosum|Bacteroides plebeius, Eubacterium rectale|Bacteroides plebeius, Eubacterium siraeum|Bacteroides plebeius, Eubacterium ventriosum|Bacteroides plebeius, Faecalibacterium prausnitzii|Bacteroides plebeius, Finegoldia magna|Bacteroides plebeius, Fusobacterium gonidiaformans|Bacteroides plebeius, Fusobacterium mortiferum|Bacteroides plebeius, Fusobacterium nucleatum|Bacteroides plebeius, Fusobacterium varium|Bacteroides plebeius, Gardnerella vaginalis|Bacteroides plebeius, Gemella haemolysans|Bacteroides plebeius, Gemella morbillorum|Bacteroides plebeius, Gordonibacter pamelaeae|Bacteroides plebeius, Granulicatella adiacens|Bacteroides plebeius, Granulicatella elegans|Bacteroides plebeius, Haemophilus influenzae|Bacteroides plebeius, Haemophilus parainfluenzae|Bacteroides plebeius, Helicobacter pullorum|Bacteroides plebeius, Helicobacter pylori|Bacteroides plebeius, Holdemania filiformis|Bacteroides plebeius, Kingella oralis|Bacteroides plebeius, Klebsiella pneumoniae|Bacteroides plebeius, Klebsiella variicola|Bacteroides plebeius, Lachnospiraceae bacterium 5_1_57FAA|Bacteroides plebeius, Lactobacillus acidophilus|Bacteroides plebeius, Lactobacillus amylovorus|Bacteroides plebeius, Lactobacillus brevis|Bacteroides plebeius, Lactobacillus casei|Bacteroides plebeius, Lactobacillus crispatus|Bacteroides plebeius, Lactobacillus delbrueckii|Bacteroides plebeius, Lactobacillus fermentum|Bacteroides plebeius, Lactobacillus gasseri|Bacteroides plebeius, Lactobacillus iners|Bacteroides plebeius, Lactobacillus jensenii|Bacteroides plebeius, Lactobacillus johnsonii|Bacteroides plebeius, Lactobacillus paracasei|Bacteroides plebeius, Lactobacillus plantarum|Bacteroides plebeius, Lactobacillus reuteri|Bacteroides plebeius, Lactobacillus rhamnosus|Bacteroides plebeius, Lactobacillus ruminis|Bacteroides plebeius, Lactobacillus sakei|Bacteroides plebeius, Lactobacillus salivarius|Bacteroides plebeius, Lactococcus lactis|Bacteroides plebeius, Lautropia</td></tr>
</table>

TABLE 2-continued

| Table 2. Specific binary combinations of OTUs. Individual pairings are differentiated by "\|" and OTUs within a combination are differentiated by "," |
| --- |
| mirabilis\|Bacteroides plebeius, Leuconostoc citreum\|Bacteroides plebeius, Leuconostoc gasicomitatum\|Bacteroides plebeius, Leuconostoc mesenteroides\|Bacteroides plebeius, Listeria monocytogenes\|Bacteroides plebeius, Marvinbryantia formatexigens\|Bacteroides plebeius, Megamonas hypermegale\|Bacteroides plebeius, Megasphaera micronuciformis\|Bacteroides plebeius, Methanobrevibacter smithii\|Bacteroides plebeius, Methanosphaera stadtmanae\|Bacteroides plebeius, Methylobacterium radiotolerans\|Bacteroides plebeius, Mitsuokella multacida\|Bacteroides plebeius, Mobiluncus curtisii\|Bacteroides plebeius, Mycoplasma hominis\|Bacteroides plebeius, Neisseria mucosa\|Bacteroides plebeius, Odoribacter splanchnicus\|Bacteroides plebeius, Olsenella uli\|Bacteroides plebeius, Oribacterium sinus\|Bacteroides plebeius, Oxalobacter formigenes\|Bacteroides plebeius, Parabacteroides distasonis\|Bacteroides plebeius, Parabacteroides johnsonii\|Bacteroides plebeius, Parabacteroides merdae\|Bacteroides plebeius, Parvimonas micra\|Bacteroides plebeius, Pediococcus acidilactici\|Bacteroides plebeius, Pediococcus pentosaceus\|Bacteroides plebeius, Peptoniphilus duerdenii\|Bacteroides plebeius, Peptoniphilus harei\|Bacteroides plebeius, Peptoniphilus lacrimalis\|Bacteroides plebeius, Peptostreptococcus anaerobius\|Bacteroides plebeius, Peptostreptococcus stomatis\|Bacteroides plebeius, Porphyromonas asaccharolytica\|Bacteroides plebeius, Porphyromonas uenonis\|Bacteroides plebeius, Prevotella amnii\|Bacteroides plebeius, Prevotella bergensis\|Bacteroides plebeius, Prevotella bivia\|Bacteroides plebeius, Prevotella buccae\|Bacteroides plebeius, Prevotella buccalis\|Bacteroides plebeius, Prevotella copri\|Bacteroides plebeius, Prevotella disiens\|Bacteroides plebeius, Prevotella melaninogenica\|Bacteroides plebeius, Prevotella multiformis\|Bacteroides plebeius, Prevotella oralis\|Bacteroides plebeius, Prevotella oris\|Bacteroides plebeius, Prevotella salivae\|Bacteroides plebeius, Prevotella timonensis\|Bacteroides plebeius, Propionibacterium acnes\|Bacteroides plebeius, Propionibacterium freudenreichii\|Bacteroides plebeius, Proteus mirabilis\|Bacteroides plebeius, Proteus penneri\|Bacteroides plebeius, Pseudoflavonifractor capillosus\|Bacteroides plebeius, Pseudomonas aeruginosa\|Bacteroides plebeius, Pseudomonas fluorescens\|Bacteroides plebeius, Pseudomonas putida\|Bacteroides plebeius, Pseudoramibacter alactolyticus\|Bacteroides plebeius, Pyramidobacter piscolens\|Bacteroides plebeius, Rhodopseudomonas palustris\|Bacteroides plebeius, Roseburia intestinalis\|Bacteroides plebeius, Roseburia inulinivorans\|Bacteroides plebeius, Rothia dentocariosa\|Bacteroides plebeius, Rothia mucilaginosa\|Bacteroides plebeius, Ruminococcus albus\|Bacteroides plebeius, Ruminococcus bromii\|Bacteroides plebeius, Ruminococcus gnavus\|Bacteroides plebeius, Ruminococcus lactaris\|Bacteroides plebeius, Ruminococcus obeum\|Bacteroides plebeius, Ruminococcus torques\|Bacteroides plebeius, Selenomonas sputigena\|Bacteroides plebeius, Shigella boydii\|Bacteroides plebeius, Shigella dysenteriae\|Bacteroides plebeius, Shigella sonnei\|Bacteroides plebeius, Slackia exigua\|Bacteroides plebeius, Solobacterium moorei\|Bacteroides plebeius, Staphylococcus aureus\|Bacteroides plebeius, Staphylococcus epidermidis\|Bacteroides plebeius, Staphylococcus hominis\|Bacteroides plebeius, Staphylococcus saprophyticus\|Bacteroides plebeius, Staphylococcus warneri\|Bacteroides plebeius, Streptococcus agalactiae\|Bacteroides plebeius, Streptococcus anginosus\|Bacteroides plebeius, Streptococcus australis\|Bacteroides plebeius, Streptococcus bovis\|Bacteroides plebeius, Streptococcus cristatus\|Bacteroides plebeius, Streptococcus dysgalactiae\|Bacteroides plebeius, Streptococcus equinus\|Bacteroides plebeius, Streptococcus gordonii\|Bacteroides plebeius, Streptococcus infantarius\|Bacteroides plebeius, Streptococcus infantis\|Bacteroides plebeius, Streptococcus mitis\|Bacteroides plebeius, Streptococcus mutans\|Bacteroides plebeius, Streptococcus oralis\|Bacteroides plebeius, Streptococcus parasanguinis\|Bacteroides plebeius, Streptococcus peroris\|Bacteroides plebeius, Streptococcus pneumoniae\|Bacteroides plebeius, Streptococcus salivarius\|Bacteroides plebeius, Streptococcus sanguinis\|Bacteroides plebeius, Streptococcus thermophilus\|Bacteroides plebeius, Streptococcus vestibularis\|Bacteroides plebeius, Subdoligranulum variabile\|Bacteroides plebeius, Succinatimonas hippei\|Bacteroides plebeius, Sutterella wadsworthensis\|Bacteroides plebeius, Tropheryma whipplei\|Bacteroides plebeius, Veillonella atypica\|Bacteroides plebeius, Veillonella dispar\|Bacteroides plebeius, Veillonella parvula\|Bacteroides plebeius, Victivallis vadensis\|Bacteroides salanitronis, Bacteroides salanitronis\|Bacteroides salanitronis, Bacteroides sp. 1_1_6\|Bacteroides salanitronis, Bacteroides sp. 3_1_23\|Bacteroides salanitronis, Bacteroides stercoris\|Bacteroides salanitronis, Bacteroides thetaiotaomicron\|Bacteroides salanitronis, Bacteroides uniformis\|Bacteroides salanitronis, Bacteroides vulgatus\|Bacteroides salanitronis, Bacteroides xylanisolvens\|Bacteroides salanitronis, Bifidobacterium adolescentis\|Bacteroides salanitronis, Bifidobacterium angulatum\|Bacteroides salanitronis, Bifidobacterium animalis\|Bacteroides salanitronis, Bifidobacterium bifidum\|Bacteroides salanitronis, Bifidobacterium breve\|Bacteroides salanitronis, Bifidobacterium catenulatum\|Bacteroides salanitronis, Bifidobacterium dentium\|Bacteroides salanitronis, Bifidobacterium infantis\|Bacteroides salanitronis, Bifidobacterium longum\|Bacteroides salanitronis, Bifidobacterium pseudocatenulatum\|Bacteroides salanitronis, Bilophila wadsworthia\|Bacteroides salanitronis, Blautia hansenii\|Bacteroides salanitronis, Blautia hydrogenotrophica\|Bacteroides salanitronis, Blautia producta\|Bacteroides salanitronis, Blautia schinkii\|Bacteroides salanitronis, Brevibacterium linens\|Bacteroides salanitronis, Brucella ceti\|Bacteroides salanitronis, Brucella suis\|Bacteroides salanitronis, Bulleidia extructa\|Bacteroides salanitronis, Butyrivibrio crossotus\|Bacteroides salanitronis, Campylobacter concisus\|Bacteroides salanitronis, Campylobacter curvus\|Bacteroides salanitronis, Campylobacter gracilis\|Bacteroides salanitronis, Campylobacter hominis\|Bacteroides salanitronis, Capnocytophaga ochracea\|Bacteroides salanitronis, Cardiobacterium hominis\|Bacteroides salanitronis, Catenibacterium mitsuokai\|Bacteroides salanitronis, Catonella morbi\|Bacteroides salanitronis, Citrobacter koseri\|Bacteroides salanitronis, Clostridium asparagiforme\|Bacteroides salanitronis, Clostridium bartlettii\|Bacteroides salanitronis, Clostridium bolteae\|Bacteroides salanitronis, Clostridium botulinum\|Bacteroides salanitronis, Clostridium butyricum\|Bacteroides salanitronis, Clostridium difficile\|Bacteroides salanitronis, Clostridium disporicum\|Bacteroides salanitronis, Clostridium hathewayi\|Bacteroides salanitronis, Clostridium hylemonae\|Bacteroides salanitronis, Clostridium innocuum\|Bacteroides salanitronis, Clostridium leptum\|Bacteroides salanitronis, Clostridium mayombei\|Bacteroides salanitronis, Clostridium methylpentosum\|Bacteroides salanitronis, Clostridium nexile\|Bacteroides salanitronis, Clostridium orbiscindens\|Bacteroides salanitronis, Clostridium perfringens\|Bacteroides salanitronis, Clostridium saccharolyticum\|Bacteroides salanitronis, Clostridium scindens\|Bacteroides salanitronis, Clostridium symbiosum\|Bacteroides salanitronis, Clostridium tertium\|Bacteroides salanitronis, Collinsella aerofaciens\|Bacteroides salanitronis, Collinsella intestinalis\|Bacteroides salanitronis, Collinsella stercoris\|Bacteroides salanitronis, Coprobacillus sp. D7\|Bacteroides salanitronis, Coprococcus catus\|Bacteroides salanitronis, Coprococcus comes\|Bacteroides salanitronis, Coprococcus eutactus\|Bacteroides salanitronis, Corynebacterium aurimucosum\|Bacteroides salanitronis, Corynebacterium matruchotii\|Bacteroides salanitronis, Cryptobacterium curtum\|Bacteroides salanitronis, Desulfovibrio desulfuricans\|Bacteroides salanitronis, Desulfovibrio piger\|Bacteroides salanitronis, Dialister invisus\|Bacteroides salanitronis, Dialister microaerophilus\|Bacteroides salanitronis, Dorea formicigenerans\|Bacteroides salanitronis, Dorea longicatena\|Bacteroides salanitronis, Eggerthella lenta\|Bacteroides salanitronis, Eikenella corrodens\|Bacteroides salanitronis, Enterobacter cancerogenus\|Bacteroides salanitronis, Enterobacter cloacae\|Bacteroides salanitronis, Enterococcus faecalis\|Bacteroides salanitronis, Enterococcus faecium\|Bacteroides salanitronis, Enterococcus gallinarum\|Bacteroides salanitronis, Erysipelotrichaceae bacterium 3_1_53\|Bacteroides salanitronis, Escherichia coli\|Bacteroides salanitronis, Escherichia fergusonii\|Bacteroides salanitronis, Ethanoligenens harbinense\|Bacteroides salanitronis, Eubacterium cellulosolvens\|Bacteroides salanitronis, Eubacterium eligens\|Bacteroides salanitronis, Eubacterium hallii\|Bacteroides salanitronis, Eubacterium limosum\|Bacteroides salanitronis, Eubacterium rectale\|Bacteroides salanitronis, Eubacterium siraeum\|Bacteroides salanitronis, Eubacterium ventriosum\|Bacteroides salanitronis, Faecalibacterium prausnitzii\|Bacteroides salanitronis, Finegoldia magna\|Bacteroides salanitronis, Fusobacterium gonidiaformans\|Bacteroides salanitronis, Fusobacterium mortiferum\|Bacteroides salanitronis, Fusobacterium nucleatum\|Bacteroides salanitronis, Fusobacterium varium\|Bacteroides salanitronis, Gardnerella vaginalis\|Bacteroides salanitronis, Gemella haemolysans\|Bacteroides salanitronis, Gemella morbillorum\|Bacteroides salanitronis, Gordonibacter pamelaeae\|Bacteroides salanitronis, Granulicatella adiacens\|Bacteroides salanitronis, Granulicatella elegans\|Bacteroides salanitronis, Haemophilus influenzae\|Bacteroides salanitronis, Haemophilus parainfluenzae\|Bacteroides salanitronis, Helicobacter pullorum\|Bacteroides salanitronis, Helicobacter pylori\|Bacteroides salanitronis, Holdemania filiformis\|Bacteroides salanitronis, Kingella oralis\|Bacteroides salanitronis, Klebsiella pneumoniae\|Bacteroides salanitronis, Klebsiella variicola\|Bacteroides salanitronis, Lachnospiraceae bacterium |

TABLE 2-continued

Table 2. Specific binary combinations of OTUs. Individual pairings are differentiated by "|" and OTUs within a combination are differentiated by ","

5_1_57FAA|Bacteroides salanitronis, Lactobacillus acidophilus|Bacteroides salanitronis, Lactobacillus amylovorus|Bacteroides salanitronis, Lactobacillus brevis|Bacteroides salanitronis, Lactobacillus casei|Bacteroides salanitronis, Lactobacillus crispatus|Bacteroides salanitronis, Lactobacillus delbrueckii|Bacteroides salanitronis, Lactobacillus fermentum|Bacteroides salanitronis, Lactobacillus gasseri|Bacteroides salanitronis, Lactobacillus iners|Bacteroides salanitronis, Lactobacillus jensenii|Bacteroides salanitronis, Lactobacillus johnsonii|Bacteroides salanitronis, Lactobacillus paracasei|Bacteroides salanitronis, Lactobacillus plantarum|Bacteroides salanitronis, Lactobacillus reuteri|Bacteroides salanitronis, Lactobacillus rhamnosus|Bacteroides salanitronis, Lactobacillus ruminis|Bacteroides salanitronis, Lactobacillus sakei|Bacteroides salanitronis, Lactobacillus salivarius|Bacteroides salanitronis, Lactococcus lactis|Bacteroides salanitronis, Lautropia mirabilis|Bacteroides salanitronis, Leuconostoc citreum|Bacteroides salanitronis, Leuconostoc gasicomitatum|Bacteroides salanitronis, Leuconostoc mesenteroides|Bacteroides salanitronis, Listeria monocytogenes|Bacteroides salanitronis, Marvinbryantia formatexigens|Bacteroides salanitronis, Megamonas hypermegale|Bacteroides salanitronis, Megasphaera micronuciformis|Bacteroides salanitronis, Methanobrevibacter smithii|Bacteroides salanitronis, Methanosphaera stadtmanae|Bacteroides salanitronis, Methylobacterium radiotolerans|Bacteroides salanitronis, Mitsuokella multacida|Bacteroides salanitronis, Mobiluncus curtisii|Bacteroides salanitronis, Mycoplasma hominis|Bacteroides salanitronis, Neisseria mucosa|Bacteroides salanitronis, Odoribacter splanchnicus|Bacteroides salanitronis, Olsenella uli|Bacteroides salanitronis, Oribacterium sinus|Bacteroides salanitronis, Oxalobacter formigenes|Bacteroides salanitronis, Parabacteroides distasonis|Bacteroides salanitronis, Parabacteroides johnsonii|Bacteroides salanitronis, Parabacteroides merdae|Bacteroides salanitronis, Parvimonas micra|Bacteroides salanitronis, Pediococcus acidilactici|Bacteroides salanitronis, Pediococcus pentosaceus|Bacteroides salanitronis, Peptoniphilus duerdenii|Bacteroides salanitronis, Peptoniphilus harei|Bacteroides salanitronis, Peptoniphilus lacrimalis|Bacteroides salanitronis, Peptostreptococcus anaerobius|Bacteroides salanitronis, Peptostreptococcus stomatis|Bacteroides salanitronis, Porphyromonas asaccharolytica|Bacteroides salanitronis, Porphyromonas uenonis|Bacteroides salanitronis, Prevotella amnii|Bacteroides salanitronis, Prevotella bergensis|Bacteroides salanitronis, Prevotella bivia|Bacteroides salanitronis, Prevotella buccae|Bacteroides salanitronis, Prevotella buccalis|Bacteroides salanitronis, Prevotella copri|Bacteroides salanitronis, Prevotella disiens|Bacteroides salanitronis, Prevotella melaninogenica|Bacteroides salanitronis, Prevotella multiformis|Bacteroides salanitronis, Prevotella oralis|Bacteroides salanitronis, Prevotella oris|Bacteroides salanitronis, Prevotella salivae|Bacteroides salanitronis, Prevotella timonensis|Bacteroides salanitronis, Propionibacterium acnes|Bacteroides salanitronis, Propionibacterium freudenreichii|Bacteroides salanitronis, Proteus mirabilis|Bacteroides salanitronis, Proteus penneri|Bacteroides salanitronis, Pseudoflavonifractor capillosus|Bacteroides salanitronis, Pseudomonas aeruginosa|Bacteroides salanitronis, Pseudomonas fluorescens|Bacteroides salanitronis, Pseudomonas putida|Bacteroides salanitronis, Pseudoramibacter alactolyticus|Bacteroides salanitronis, Pyramidobacter piscolens|Bacteroides salanitronis, Rhodopseudomonas palustris|Bacteroides salanitronis, Roseburia intestinalis|Bacteroides salanitronis, Roseburia inulinivorans|Bacteroides salanitronis, Rothia dentocariosa|Bacteroides salanitronis, Rothia mucilaginosa|Bacteroides salanitronis, Ruminococcus albus|Bacteroides salanitronis, Ruminococcus bromii|Bacteroides salanitronis, Ruminococcus gnavus|Bacteroides salanitronis, Ruminococcus lactaris|Bacteroides salanitronis, Ruminococcus obeum|Bacteroides salanitronis, Ruminococcus torques|Bacteroidessalanitronis, Selenomonas sputigena|Bacteroides salanitronis, Shigella boydii|Bacteroides salanitronis, Shigella dysenteriae|Bacteroides salanitronis, Shigella sonnei|Bacteroides salanitronis, Slackia exigua|Bacteroides salanitronis, Solobacterium moorei|Bacteroides salanitronis, Staphylococcus aureus|Bacteroides salanitronis, Staphylococcus epidermidis|Bacteroides salanitronis, Staphylococcus hominis|Bacteroides salanitronis, Staphylococcus saprophyticus|Bacteroides salanitronis, Staphylococcus warneri|Bacteroides salanitronis, Streptococcus agalactiae|Bacteroides salanitronis, Streptococcus anginosus|Bacteroides salanitronis, Streptococcus australis|Bacteroides salanitronis, Streptococcus bovis|Bacteroides salanitronis, Streptococcus cristatus|Bacteroides salanitronis, Streptococcus dysgalactiae|Bacteroides salanitronis, Streptococcus equinus|Bacteroides salanitronis, Streptococcus gordonii|Bacteroides salanitronis, Streptococcus infantarius|Bacteroides salanitronis, Streptococcus infantis|Bacteroides salanitronis, Streptococcus mitis|Bacteroides salanitronis, Streptococcus mutans|Bacteroides salanitronis, Streptococcus oralis|Bacteroides salanitronis, Streptococcus parasanguinis|Bacteroides salanitronis, Streptococcus peroris|Bacteroides salanitronis, Streptococcus pneumoniae|Bacteroides salanitronis, Streptococcus salivarius|Bacteroides salanitronis, Streptococcus sanguinis|Bacteroides salanitronis, Streptococcus thermophilus|Bacteroides salanitronis, Streptococcus vestibularis|Bacteroides salanitronis, Subdoligranulum variabile|Bacteroides salanitronis, Succinatimonas hippei|Bacteroides salanitronis, Sutterella wadsworthensis|Bacteroides salanitronis, Tropheryma whipplei|Bacteroides salanitronis, Veillonella atypica|Bacteroides salanitronis, Veillonella dispar|Bacteroides salanitronis, Veillonella parvula|Bacteroides salanitronis, Victivallis vadensis|Bacteroides sp. 1_1_6, Bacteroides sp. 1_1_6|Bacteroides sp. 1_1_6, Bacteroides sp. 3_1_23|Bacteroides sp. 1_1_6, Bacteroides stercoris|Bacteroides sp. 1_1_6, Bacteroides thetaiotaomicron|Bacteroides sp. 1_1_6, Bacteroides uniformis|Bacteroides sp. 1_1_6, Bacteroides vulgatus|Bacteroides sp. 1_1_6, Bacteroides xylanisolvens|Bacteroides sp. 1_1_6, Bifidobacterium adolescentis|Bacteroides sp. 1_1_6, Bifidobacterium angulatum|Bacteroides sp. 1_1_6, Bifidobacterium animalis|Bacteroides sp. 1_1_6, Bifidobacterium bifidum|Bacteroides sp. 1_1_6, Bifidobacterium breve|Bacteroides sp. 1_1_6, Bifidobacterium catenulatum|Bacteroides sp. 1_1_6, Bifidobacterium dentium|Bacteroides sp. 1_1_6, Bifidobacterium infantis|Bacteroides sp. 1_1_6, Bifidobacterium longum|Bacteroides sp. 1_1_6, Bifidobacterium pseudocatenulatum|Bacteroides sp. 1_1_6, Bilophila wadsworthia|Bacteroides sp. 1_1_6, Blautia hansenii|Bacteroides sp. 1_1_6, Blautia hydrogenotrophica|Bacteroides sp. 1_1_6, Blautia producta|Bacteroides sp. 1_1_6, Blautia schinkii|Bacteroides sp. 1_1_6, Brevibacterium linens|Bacteroides sp. 1_1_6, Brucella ceti|Bacteroides sp. 1_1_6, Brucella suis|Bacteroides sp. 1_1_6, Bulleidia extructa|Bacteroides sp. 1_1_6, Butyrivibrio crossotus|Bacteroides sp. 1_1_6, Campylobacter concisus|Bacteroides sp. 1_1_6, Campylobacter curvus|Bacteroides sp. 1_1_6, Campylobacter gracilis|Bacteroides sp. 1_1_6, Campylobacter hominis|Bacteroides sp. 1_1_6, Capnocytophaga ochracea|Bacteroides sp. 1_1_6, Cardiobacterium hominis|Bacteroides sp. 1_1_6, Catenibacterium mitsuokai|Bacteroides sp. 1_1_6, Catonella morbi|Bacteroides sp. 1_1_6, Citrobacter koseri|Bacteroides sp. 1_1_6, Clostridium asparagiforme|Bacteroides sp. 1_1_6, Clostridium bartlettii|Bacteroides sp. 1_1_6, Clostridium bolteae|Bacteroides sp. 1_1_6, Clostridium botulinum|Bacteroides sp. 1_1_6, Clostridium butyricum|Bacteroides sp. 1_1_6, Clostridium difficile|Bacteroides sp. 1_1_6, Clostridium disporicum|Bacteroides sp. 1_1_6, Clostridium hathewayi|Bacteroides sp. 1_1_6, Clostridium hylemonae|Bacteroides sp. 1_1_6, Clostridium innocuum|Bacteroides sp. 1_1_6, Clostridium leptum|Bacteroides sp. 1_1_6, Clostridium mayombei|Bacteroides sp. 1_1_6, Clostridium methylpentosum|Bacteroides sp. 1_1_6, Clostridium nexile|Bacteroides sp. 1_1_6, Clostridium orbiscindens|Bacteroides sp. 1_1_6, Clostridium perfringens|Bacteroides sp. 1_1_6, Clostridium saccharolyticum|Bacteroides sp. 1_1_6, Clostridium scindens|Bacteroides sp. 1_1_6, Clostridium symbiosum|Bacteroides sp. 1_1_6, Clostridium tertium|Bacteroides sp. 1_1_6, Collinsella aerofaciens|Bacteroides sp. 1_1_6, Collinsella intestinalis|Bacteroides sp. 1_1_6, Collinsella stercoris|Bacteroides sp. 1_1_6, Coprobacillus sp. D7|Bacteroides sp. 1_1_6, Coprococcus catus|Bacteroides sp. 1_1_6, Coprococcus comes|Bacteroides sp. 1_1_6, Coprococcus eutactus|Bacteroides sp. 1_1_6, Corynebacterium aurimucosum|Bacteroides sp. 1_1_6, Corynebacterium matruchotii|Bacteroides sp. 1_1_6, Cryptobacterium curtum|Bacteroides sp. 1_1_6, Desulfovibrio desulfuricans|Bacteroides sp. 1_1_6, Desulfovibrio piger|Bacteroides sp. 1_1_6, Dialister invisus|Bacteroides sp. 1_1_6, Dialister microaerophilus|Bacteroides sp. 1_1_6, Dorea formicigenerans|Bacteroides sp. 1_1_6, Dorea longicatena|Bacteroides sp. 1_1_6, Eggerthella lenta|Bacteroides sp. 1_1_6, Eikenella corrodens|Bacteroides sp. 1_1_6, Enterobacter cancerogenus|Bacteroides sp. 1_1_6, Enterobacter cloacae|Bacteroides sp. 1_1_6, Enterococcus faecalis|Bacteroides sp. 1_1_6, Enterococcus faecium|Bacteroides sp. 1_1_6, Enterococcus gallinarum|Bacteroides sp. 1_1_6, Erysipelotrichaceae bacterium 3_1_53|Bacteroides sp. 1_1_6, Escherichia coli|Bacteroides sp. 1_1_6, Escherichia fergusonii|Bacteroides sp. 1_1_6, Ethanoligenens harbinense|Bacteroides sp. 1_1_6, Eubacterium cellulosolvens|Bacteroides sp. 1_1_6, Eubacterium eligens|Bacteroides sp. 1_1_6, Eubacterium hallii|Bacteroides sp. 1_1_6, Eubacterium limosum|Bacteroides sp. 1_1_6, Eubacterium rectale|Bacteroides sp. 1_1_6, Eubacterium siraeum|Bacteroides sp. 1_1_6, Eubacterium TABLE 2-continued Table 2. Specific binary combinations of OTUs. Individual pairings are differentiated by "|" and OTUs within a combination are differentiated by ","

ventriosum|Bacteroides sp. 1_1_6, Faecalibacterium prausnitzii|Bacteroides sp. 1_1_6, Finegoldia magna|Bacteroides sp. 1_1_6, Fusobacterium gonidiaformans|Bacteroides sp. 1_1_6, Fusobacterium mortiferum|Bacteroides sp. 1_1_6, Fusobacterium nucleatum|Bacteroides sp. 1_1_6, Fusobacterium varium|Bacteroides sp. 1_1_6, Gardnerella vaginalis|Bacteroides sp. 1_1_6, Gemella haemolysans|Bacteroides sp. 1_1_6, Gemella morbillorum|Bacteroides sp. 1_1_6, Gordonibacter pamelaeae|Bacteroides sp. 1_1_6, Granulicatella adiacens|Bacteroides sp. 1_1_6, Granulicatella elegans|Bacteroides sp. 1_1_6, Haemophilus influenzae|Bacteroides sp. 1_1_6, Haemophilus parainfluenzae|Bacteroides sp. 1_1_6, Helicobacter pullorum|Bacteroides sp. 1_1_6, Helicobacter pylori|Bacteroides sp. 1_1_6, Holdemania filiformis|Bacteroides sp. 1_1_6, Kingella oralis|Bacteroides sp. 1_1_6, Klebsiella pneumoniae|Bacteroides sp. 1_1_6, Klebsiella variicola|Bacteroides sp. 1_1_6, Lachnospiraceae bacterium 5_1_57FAA|Bacteroides sp. 1_1_6, Lactobacillus acidophilus|Bacteroides sp. 1_1_6, Lactobacillus amylovorus|Bacteroides sp. 1_1_6, Lactobacillus brevis|Bacteroides sp. 1_1_6, Lactobacillus casei|Bacteroides sp. 1_1_6, Lactobacillus crispatus|Bacteroides sp. 1_1_6, Lactobacillus delbrueckii|Bacteroides sp. 1_1_6, Lactobacillus fermentum|Bacteroides sp. 1_1_6, Lactobacillus gasseri|Bacteroides sp. 1_1_6, Lactobacillus iners|Bacteroides sp. 1_1_6, Lactobacillus jensenii|Bacteroides sp. 1_1_6, Lactobacillus johnsonii|Bacteroides sp. 1_1_6, Lactobacillus paracasei|Bacteroides sp. 1_1_6, Lactobacillus plantarum|Bacteroides sp. 1_1_6, Lactobacillus reuteri|Bacteroides sp. 1_1_6, Lactobacillus rhamnosus|Bacteroides sp. 1_1_6, Lactobacillus ruminis|Bacteroides sp. 1_1_6, Lactobacillus sakei|Bacteroides sp. 1_1_6, Lactobacillus salivarius|Bacteroides sp. 1_1_6, Lactococcus lactis|Bacteroides sp. 1_1_6, Lautropia mirabilis|Bacteroides sp. 1_1_6, Leuconostoc citreum|Bacteroides sp. 1_1_6, Leuconostoc gasicomitatum|Bacteroides sp. 1_1_6, Leuconostoc mesenteroides|Bacteroides sp. 1_1_6, Listeria monocytogenes|Bacteroides sp. 1_1_6, Marvinbryantia formatexigens|Bacteroides sp. 1_1_6, Megamonas hypermegale|Bacteroides sp. 1_1_6, Megasphaera micronuciformis|Bacteroides sp. 1_1_6, Methanobrevibacter smithii|Bacteroides sp. 1_1_6, Methanosphaera stadtmanae|Bacteroides sp. 1_1_6, Methylobacterium radiotolerans|Bacteroides sp. 1_1_6, Mitsuokella multacida|Bacteroides sp. 1_1_6, Mobiluncus curtisii|Bacteroides sp. 1_1_6, Mycoplasma hominis|Bacteroides sp. 1_1_6, Neisseria mucosa|Bacteroides sp. 1_1_6, Odoribacter splanchnicus|Bacteroides sp. 1_1_6, Olsenella uli|Bacteroides sp. 1_1_6, Oribacterium sinus|Bacteroides sp. 1_1_6, Oxalobacter formigenes|Bacteroides sp. 1_1_6, Parabacteroides distasonis|Bacteroides sp. 1_1_6, Parabacteroides johnsonii|Bacteroides sp. 1_1_6, Parabacteroides merdae|Bacteroides sp. 1_1_6, Parvimonas micra|Bacteroides sp. 1_1_6, Pediococcus acidilactici|Bacteroides sp. 1_1_6, Pediococcus pentosaceus|Bacteroides sp. 1_1_6, Peptoniphilus duerdenii|Bacteroides sp. 1_1_6, Peptoniphilus harei|Bacteroides sp. 1_1_6, Peptoniphilus lacrimalis|Bacteroides sp. 1_1_6, Peptostreptococcus anaerobius|Bacteroides sp. 1_1_6, Peptostreptococcus stomatis|Bacteroides sp. 1_1_6, Porphyromonas asaccharolytica|Bacteroides sp. 1_1_6, Porphyromonas uenonis|Bacteroides sp. 1_1_6, Prevotella amnii|Bacteroides sp. 1_1_6, Prevotella bergensis|Bacteroides sp. 1_1_6, Prevotella bivia|Bacteroides sp. 1_1_6, Prevotella buccae|Bacteroides sp. 1_1_6, Prevotella buccalis|Bacteroides sp. 1_1_6, Prevotella copri|Bacteroides sp. 1_1_6, Prevotella disiens|Bacteroides sp. 1_1_6, Prevotella melaninogenica|Bacteroides sp. 1_1_6, Prevotella multiformis|Bacteroides sp. 1_1_6, Prevotella oralis|Bacteroides sp. 1_1_6, Prevotella oris|Bacteroides sp. 1_1_6, Prevotella salivae|Bacteroides sp. 1_1_6, Prevotella timonensis|Bacteroides sp. 1_1_6, Propionibacterium acnes|Bacteroides sp. 1_1_6, Propionibacterium freudenreichii|Bacteroides sp. 1_1_6, Proteus mirabilis|Bacteroides sp. 1_1_6, Proteus penneri|Bacteroides sp. 1_1_6, Pseudoflavonifractor capillosus|Bacteroides sp. 1_1_6, Pseudomonas aeruginosa|Bacteroides sp. 1_1_6, Pseudomonas fluorescens|Bacteroides sp. 1_1_6, Pseudomonas putida|Bacteroides sp. 1_1_6, Pseudoramibacter alactolyticus|Bacteroides sp. 1_1_6, Pyramidobacter piscolens|Bacteroides sp. 1_1_6, Rhodopseudomonas palustris|Bacteroides sp. 1_1_6, Roseburia intestinalis|Bacteroides sp. 1_1_6, Roseburia inulinivorans|Bacteroides sp. 1_1_6, Rothia dentocariosa|Bacteroides sp. 1_1_6, Rothia mucilaginosa|Bacteroides sp. 1_1_6, Ruminococcus albus|Bacteroides sp. 1_1_6, Ruminococcus bromii|Bacteroides sp. 1_1_6, Ruminococcus gnavus|Bacteroides sp. 1_1_6, Ruminococcus lactaris|Bacteroides sp. 1_1_6, Ruminococcus obeum|Bacteroides sp. 1_1_6, Ruminococcus torques|Bacteroides sp. 1_1_6, Selenomonas sputigena|Bacteroides sp. 1_1_6, Shigella boydii|Bacteroides sp. 1_1_6, Shigella dysenteriae|Bacteroides sp. 1_1_6, Shigella sonnei|Bacteroides sp. 1_1_6, Slackia exigua|Bacteroides sp. 1_1_6, Solobacterium moorei|Bacteroides sp. 1_1_6, Staphylococcus aureus|Bacteroides sp. 1_1_6, Staphylococcus epidermidis|Bacteroides sp. 1_1_6, Staphylococcus hominis|Bacteroides sp. 1_1_6, Staphylococcus saprophyticus|Bacteroides sp. 1_1_6, Staphylococcus warneri|Bacteroides sp. 1_1_6, Streptococcus agalactiae|Bacteroides sp. 1_1_6, Streptococcus anginosus|Bacteroides sp. 1_1_6, Streptococcus australis|Bacteroides sp. 1_1_6, Streptococcus bovis|Bacteroides sp. 1_1_6, Streptococcus cristatus|Bacteroides sp. 1_1_6, Streptococcus dysgalactiae|Bacteroides sp. 1_1_6, Streptococcus equinus|Bacteroides sp. 1_1_6, Streptococcus gordonii|Bacteroides sp. 1_1_6, Streptococcus infantarius|Bacteroides sp. 1_1_6, Streptococcus infantis|Bacteroides sp. 1_1_6, Streptococcus mitis|Bacteroides sp. 1_1_6, Streptococcus mutans|Bacteroides sp. 1_1_6, Streptococcus oralis|Bacteroides sp. 1_1_6, Streptococcus parasanguinis|Bacteroides sp. 1_1_6, Streptococcus peroris|Bacteroides sp. 1_1_6, Streptococcus pneumoniae|Bacteroides sp. 1_1_6, Streptococcus salivarius|Bacteroides sp. 1_1_6, Streptococcus sanguinis|Bacteroides sp. 1_1_6, Streptococcus thermophilus|Bacteroides sp. 1_1_6, Streptococcus vestibularis|Bacteroides sp. 1_1_6, Subdoligranulum variabile|Bacteroides sp. 1_1_6, Succinatimonas hippei|Bacteroides sp. 1_1_6, Sutterella wadsworthensis|Bacteroides sp. 1_1_6, Tropheryma whipplei|Bacteroides sp. 1_1_6, Veillonella atypica|Bacteroides sp. 1_1_6, Veillonella dispar|Bacteroides sp. 1_1_6, Veillonella parvula|Bacteroides sp. 1_1_6, Victivallis vadensis|Bacteroides sp. 3_1_23, Bacteroides sp. 3_1_23|Bacteroides sp. 3_1_23, Bacteroides stercoris|Bacteroides sp. 3_1_23, Bacteroides thetaiotaomicron|Bacteroides sp. 3_1_23, Bacteroides uniformis|Bacteroides sp. 3_1_23, Bacteroides vulgatus|Bacteroides sp. 3_1_23, Bacteroides xylanisolvens|Bacteroides sp. 3_1_23, Bifidobacterium adolescentis|Bacteroides sp. 3_1_23, Bifidobacterium angulatum|Bacteroides sp. 3_1_23, Bifidobacterium animalis|Bacteroides sp. 3_1_23, Bifidobacterium bifidum|Bacteroides sp. 3_1_23, Bifidobacterium breve|Bacteroides sp. 3_1_23, Bifidobacterium catenulatum|Bacteroides sp. 3_1_23, Bifidobacterium dentium|Bacteroides sp. 3_1_23, Bifidobacterium infantis|Bacteroides sp. 3_1_23, Bifidobacterium longum|Bacteroides sp. 3_1_23, Bifidobacterium pseudocatenulatum|Bacteroides sp. 3_1_23, Bilophila wadsworthia|Bacteroides sp. 3_1_23, Blautia hansenii|Bacteroides sp. 3_1_23, Blautia hydrogenotrophica|Bacteroides sp. 3_1_23, Blautia producta|Bacteroides sp. 3_1_23, Blautia schinkii|Bacteroides sp. 3_1_23, Brevibacterium linens|Bacteroides sp. 3_1_23, Brucella ceti|Bacteroides sp. 3_1_23, Brucella suis|Bacteroides sp. 3_1_23, Bulleidia extructa|Bacteroides sp. 3_1_23, Butyrivibrio crossotus|Bacteroides sp. 3_1_23, Campylobacter concisus|Bacteroides sp. 3_1_23, Campylobacter curvus|Bacteroides sp. 3_1_23, Campylobacter gracilis|Bacteroides sp. 3_1_23, Campylobacter hominis|Bacteroides sp. 3_1_23, Capnocytophaga ochracea|Bacteroides sp. 3_1_23, Cardiobacterium hominis|Bacteroides sp. 3_1_23, Catenibacterium mitsuokai|Bacteroides sp. 3_1_23, Catonella morbi|Bacteroides sp. 3_1_23, Citrobacter koseri|Bacteroides sp. 3_1_23, Clostridium asparagiforme|Bacteroides sp. 3_1_23, Clostridium bartlettii|Bacteroides sp. 3_1_23, Clostridium bolteae|Bacteroides sp. 3_1_23, Clostridium botulinum|Bacteroides sp. 3_1_23, Clostridium butyricum|Bacteroides sp. 3_1_23, Clostridium difficile|Bacteroides sp. 3_1_23, Clostridium disporicum|Bacteroides sp. 3_1_23, Clostridium hathewayi|Bacteroides sp. 3_1_23, Clostridium hylemonae|Bacteroides sp. 3_1_23, Clostridium innocuum|Bacteroides sp. 3_1_23, Clostridium leptum|Bacteroides sp. 3_1_23, Clostridium mayombei|Bacteroides sp. 3_1_23, Clostridium methylpentosum|Bacteroides sp. 3_1_23, Clostridium nexile|Bacteroides sp. 3_1_23, Clostridium orbiscindens|Bacteroides sp. 3_1_23, Clostridium perfringens|Bacteroides sp. 3_1_23, Clostridium saccharolyticum|Bacteroides sp. 3_1_23, Clostridium scindens|Bacteroides sp. 3_1_23, Clostridium symbiosum|Bacteroides sp. 3_1_23, Clostridium tertium|Bacteroides sp. 3_1_23, Collinsella aerofaciens|Bacteroides sp. 3_1_23, Collinsella intestinalis|Bacteroides sp. 3_1_23, Collinsella stercoris|Bacteroides sp. 3_1_23, Coprobacillus sp. D7|Bacteroides sp. 3_1_23, Coprococcus catus|Bacteroides sp. 3_1_23, Coprococcus comes|Bacteroides sp. 3_1_23, Coprococcus eutactus|Bacteroides sp. 3_1_23, Corynebacterium aurimucosum|Bacteroides sp. 3_1_23, Corynebacterium matruchotii|Bacteroides sp. 3_1_23, Cryptobacterium curtum|Bacteroides sp. 3_1_23, Desulfovibrio desulfuricans|Bacteroides sp. 3_1_23, Desulfovibrio piger|Bacteroides sp. 3_1_23, Dialister invisus|Bacteroides sp. 3_1_23, Dialister microaerophilus|Bacteroides sp. 3_1_23, Dorea formicigenerans|Bacteroides sp. 3_1_23, Dorea longicatena|Bacteroides sp. 3_1_23, Eggerthella lenta|Bacteroides sp. 3_1_23, Eikenella corrodens|Bacteroides sp. 3_1_23, Enterobacter cancerogenus|Bacteroides sp. 3_1_23, Enterobacter TABLE 2-continued Table 2. Specific binary combinations of OTUs. Individual pairings are differentiated by "|" and OTUs within a combination are differentiated by ","

cloacae|Bacteroides sp. 3_1_23, Enterococcus faecalis|Bacteroides sp. 3_1_23, Enterococcus faecium|Bacteroides sp. 3_1_23, Enterococcus gallinarum|Bacteroides sp. 3_1_23, Erysipelotrichaceae bacterium 3_1_53|Bacteroides sp. 3_1_23, Escherichia coli|Bacteroides sp. 3_1_23, Escherichia fergusonii|Bacteroides sp. 3_1_23, Ethanoligenens harbinense|Bacteroides sp. 3_1_23, Eubacterium cellulosolvens|Bacteroides sp. 3_1_23, Eubacterium eligens|Bacteroides sp. 3_1_23, Eubacterium hallii|Bacteroides sp. 3_1_23, Eubacterium limosum|Bacteroides sp. 3_1_23, Eubacterium rectale|Bacteroides sp. 3_1_23, Eubacterium siraeum|Bacteroides sp. 3_1_23, Eubacterium ventriosum|Bacteroides sp. 3_1_23, Faecalibacterium prausnitzii|Bacteroides sp. 3_1_23, Finegoldia magna|Bacteroides sp. 3_1_23, Fusobacterium gonidiaformans|Bacteroides sp. 3_1_23, Fusobacterium mortiferum|Bacteroides sp. 3_1_23, Fusobacterium nucleatum|Bacteroides sp. 3_1_23, Fusobacterium varium|Bacteroides sp. 3_1_23, Gardnerella vaginalis|Bacteroides sp. 3_1_23, Gemella haemolysans|Bacteroides sp. 3_1_23, Gemella morbillorum|Bacteroides sp. 3_1_23, Gordonibacter pamelaeae|Bacteroides sp. 3_1_23, Granulicatella adiacens|Bacteroides sp. 3_1_23, Granulicatella elegans|Bacteroides sp. 3_1_23, Haemophilus influenzae|Bacteroides sp. 3_1_23, Haemophilus parainfluenzae|Bacteroides sp. 3_1_23, Helicobacter pullorum|Bacteroides sp. 3_1_23, Helicobacter pylori|Bacteroides sp. 3_1_23, Holdemania filiformis|Bacteroides sp. 3_1_23, Kingella oralis|Bacteroides sp. 3_1_23, Klebsiella pneumoniae|Bacteroides sp. 3_1_23, Klebsiella variicola|Bacteroides sp. 3_1_23, Lachnospiraceae bacterium 5_1_57FAA|Bacteroides sp. 3_1_23, Lactobacillus acidophilus|Bacteroides sp. 3_1_23, Lactobacillus amylovorus|Bacteroides sp. 3_1_23, Lactobacillus brevis|Bacteroides sp. 3_1_23, Lactobacillus casei|Bacteroides sp. 3_1_23, Lactobacillus crispatus|Bacteroides sp. 3_1_23, Lactobacillus delbrueckii|Bacteroides sp. 3_1_23, Lactobacillus fermentum|Bacteroides sp. 3_1_23, Lactobacillus gasseri|Bacteroides sp. 3_1_23, Lactobacillus iners|Bacteroides sp. 3_1_23, Lactobacillus jensenii|Bacteroides sp. 3_1_23, Lactobacillus johnsonii|Bacteroides sp. 3_1_23, Lactobacillus paracasei|Bacteroides sp. 3_1_23, Lactobacillus plantarum|Bacteroides sp. 3_1_23, Lactobacillus reuteri|Bacteroides sp. 3_1_23, Lactobacillus rhamnosus|Bacteroides sp. 3_1_23, Lactobacillus ruminis|Bacteroides sp. 3_1_23, Lactobacillus sakei|Bacteroides sp. 3_1_23, Lactobacillus salivarius|Bacteroides sp. 3_1_23, Lactococcus lactis|Bacteroides sp. 3_1_23, Lautropia mirabilis|Bacteroides sp. 3_1_23, Leuconostoc citreum|Bacteroides sp. 3_1_23, Leuconostoc gasicomitatum|Bacteroides sp. 3_1_23, Leuconostoc mesenteroides|Bacteroides sp. 3_1_23, Listeria monocytogenes|Bacteroides sp. 3_1_23, Marvinbryantia formatexigens|Bacteroides sp. 3_1_23, Megamonas hypermegale|Bacteroides sp. 3_1_23, Megasphaera micronuciformis|Bacteroides sp. 3_1_23, Methanobrevibacter smithii|Bacteroides sp. 3_1_23, Methanosphaera stadtmanae|Bacteroides sp. 3_1_23, Methylobacterium radiotolerans|Bacteroides sp. 3_1_23, Mitsuokella multacida|Bacteroides sp. 3_1_23, Mobiluncus curtisii|Bacteroides sp. 3_1_23, Mycoplasma hominis|Bacteroides sp. 3_1_23, Neisseria mucosa|Bacteroides sp. 3_1_23, Odoribacter splanchnicus|Bacteroides sp. 3_1_23, Olsenella uli|Bacteroides sp. 3_1_23, Oribacterium sinus|Bacteroides sp. 3_1_23, Oxalobacter formigenes|Bacteroides sp. 3_1_23, Parabacteroides distasonis|Bacteroides sp. 3_1_23, Parabacteroides johnsonii|Bacteroides sp. 3_1_23, Parabacteroides merdae|Bacteroides sp. 3_1_23, Parvimonas micra|Bacteroides sp. 3_1_23, Pediococcus acidilactici|Bacteroides sp. 3_1_23, Pediococcus pentosaceus|Bacteroides sp. 3_1_23, Peptoniphilus duerdenii|Bacteroides sp. 3_1_23, Peptoniphilus harei|Bacteroides sp. 3_1_23, Peptoniphilus lacrimalis|Bacteroides sp. 3_1_23, Peptostreptococcus anaerobius|Bacteroides sp. 3_1_23, Peptostreptococcus stomatis|Bacteroides sp. 3_1_23, Porphyromonas asaccharolytica|Bacteroides sp. 3_1_23, Porphyromonas uenonis|Bacteroides sp. 3_1_23, Prevotella amnii|Bacteroides sp. 3_1_23, Prevotella bergensis|Bacteroides sp. 3_1_23, Prevotella bivia|Bacteroides sp. 3_1_23, Prevotella buccae|Bacteroides sp. 3_1_23, Prevotella buccalis|Bacteroides sp. 3_1_23, Prevotella copri|Bacteroides sp. 3_1_23, Prevotella disiens|Bacteroides sp. 3_1_23, Prevotella melaninogenica|Bacteroides sp. 3_1_23, Prevotella multiformis|Bacteroides sp. 3_1_23, Prevotella oralis|Bacteroides sp. 3_1_23, Prevotella oris|Bacteroides sp. 3_1_23, Prevotella salivae|Bacteroides sp. 3_1_23, Prevotella timonensis|Bacteroides sp. 3_1_23, Propionibacterium acnes|Bacteroides sp. 3_1_23, Propionibacterium freudenreichii|Bacteroides sp. 3_1_23, Proteus mirabilis|Bacteroides sp. 3_1_23, Proteus penneri|Bacteroides sp. 3_1_23, Pseudoflavonifractor capillosus|Bacteroides sp. 3_1_23, Pseudomonas aeruginosa|Bacteroides sp. 3_1_23, Pseudomonas fluorescens|Bacteroides sp. 3_1_23, Pseudomonas putida|Bacteroides sp. 3_1_23, Pseudoramibacter alactolyticus|Bacteroides sp. 3_1_23, Pyramidobacter piscolens|Bacteroides sp. 3_1_23, Rhodopseudomonas palustris|Bacteroides sp. 3_1_23, Roseburia intestinalis|Bacteroides sp. 3_1_23, Roseburia inulinivorans|Bacteroides sp. 3_1_23, Rothia dentocariosa|Bacteroides sp. 3_1_23, Rothia mucilaginosa|Bacteroides sp. 3_1_23, Ruminococcus albus|Bacteroides sp. 3_1_23, Ruminococcus bromii|Bacteroides sp. 3_1_23, Ruminococcus gnavus|Bacteroides sp. 3_1_23, Ruminococcus lactaris|Bacteroides sp. 3_1_23, Ruminococcus obeum|Bacteroides sp. 3_1_23, Ruminococcus torques|Bacteroides sp. 3_1_23, Selenomonas sputigena|Bacteroides sp. 3_1_23, Shigella boydii|Bacteroides sp. 3_1_23, Shigella dysenteriae|Bacteroides sp. 3_1_23, Shigella sonnei|Bacteroides sp. 3_1_23, Slackia exigua|Bacteroides sp. 3_1_23, Solobacterium moorei|Bacteroides sp. 3_1_23, Staphylococcus aureus|Bacteroides sp. 3_1_23, Staphylococcus epidermidis|Bacteroides sp. 3_1_23, Staphylococcus hominis|Bacteroides sp. 3_1_23, Staphylococcus saprophyticus|Bacteroides sp. 3_1_23, Staphylococcus warneri|Bacteroides sp. 3_1_23, Streptococcus agalactiae|Bacteroides sp. 3_1_23, Streptococcus anginosus|Bacteroides sp. 3_1_23, Streptococcus australis|Bacteroides sp. 3_1_23, Streptococcus bovis|Bacteroides sp. 3_1_23, Streptococcus cristatus|Bacteroides sp. 3_1_23, Streptococcus dysgalactiae|Bacteroides sp. 3_1_23, Streptococcus equinus|Bacteroides sp. 3_1_23, Streptococcus gordonii|Bacteroides sp. 3_1_23, Streptococcus infantarius|Bacteroides sp. 3_1_23, Streptococcus infantis|Bacteroides sp. 3_1_23, Streptococcus mitis|Bacteroides sp. 3_1_23, Streptococcus mutans|Bacteroides sp. 3_1_23, Streptococcus oralis|Bacteroides sp. 3_1_23, Streptococcus parasanguinis|Bacteroides sp. 3_1_23, Streptococcus peroris|Bacteroides sp. 3_1_23, Streptococcus pneumoniae|Bacteroides sp. 3_1_23, Streptococcus salivarius|Bacteroides sp. 3_1_23, Streptococcus sanguinis|Bacteroides sp. 3_1_23, Streptococcus thermophilus|Bacteroides sp. 3_1_23, Streptococcus vestibularis|Bacteroides sp. 3_1_23, Subdoligranulum variabile|Bacteroides sp. 3_1_23, Succinatimonas hippei|Bacteroides sp. 3_1_23, Sutterella wadsworthensis|Bacteroides sp. 3_1_23, Tropheryma whipplei|Bacteroides sp. 3_1_23, Veillonella atypica|Bacteroides sp. 3_1_23, Veillonella dispar|Bacteroides sp. 3_1_23, Veillonella parvula|Bacteroides sp. 3_1_23, Victivallis vadensis|Bacteroides stercoris, Bacteroides stercoris|Bacteroides stercoris, Bacteroides thetaiotaomicron|Bacteroides stercoris, Bacteroides uniformis|Bacteroides stercoris, Bacteroides vulgatus|Bacteroides stercoris, Bacteroides xylanisolvens|Bacteroides stercoris, Bifidobacterium adolescentis|Bacteroides stercoris, Bifidobacterium angulatum|Bacteroides stercoris, Bifidobacterium animalis|Bacteroides stercoris, Bifidobacterium bifidum|Bacteroides stercoris, Bifidobacterium breve|Bacteroides stercoris, Bifidobacterium catenulatum|Bacteroides stercoris, Bifidobacterium dentium|Bacteroides stercoris, Bifidobacterium infantis|Bacteroides stercoris, Bifidobacterium longum|Bacteroides stercoris, Bifidobacterium pseudocatenulatum|Bacteroides stercoris, Bilophila wadsworthia|Bacteroides stercoris, Blautia hansenii|Bacteroides stercoris, Blautia hydrogenotrophica|Bacteroides stercoris, Blautia producta|Bacteroides stercoris, Blautia schinkii|Bacteroides stercoris, Brevibacterium linens|Bacteroides stercoris, Brucella ceti|Bacteroides stercoris, Brucella suis|Bacteroides stercoris, Bulleidia extructa|Bacteroides stercoris, Butyrivibrio crossotus|Bacteroides stercoris, Campylobacter concisus|Bacteroides stercoris, Campylobacter curvus|Bacteroides stercoris, Campylobacter gracilis|Bacteroides stercoris, Campylobacter hominis|Bacteroides stercoris, Capnocytophaga ochracea|Bacteroides stercoris, Cardiobacterium hominis|Bacteroides stercoris, Catenibacterium mitsuokai|Bacteroides stercoris, Catonella morbi|Bacteroides stercoris, Citrobacter koseri|Bacteroides stercoris, Clostridium asparagiforme|Bacteroides stercoris, Clostridium bartlettii|Bacteroides stercoris, Clostridium bolteae|Bacteroides stercoris, Clostridium botulinum|Bacteroides stercoris, Clostridium butyricum|Bacteroides stercoris, Clostridium difficile|Bacteroides stercoris, Clostridium disporicum|Bacteroides stercoris, Clostridium hathewayi|Bacteroides stercoris, Clostridium hylemonae|Bacteroides stercoris, Clostridium innocuum|Bacteroides stercoris, Clostridium leptum|Bacteroides stercoris, Clostridium mayombei|Bacteroides stercoris, Clostridium methylpentosum|Bacteroides stercoris, Clostridium nexile|Bacteroides stercoris, Clostridium orbiscindens|Bacteroides stercoris, Clostridium perfringens|Bacteroides stercoris, Clostridium saccharolyticum|Bacteroides stercoris, Clostridium scindens|Bacteroides stercoris, Clostridium symbiosum|Bacteroides stercoris, Clostridium tertium|Bacteroides stercoris, Collinsella aerofaciens|Bacteroides stercoris, Collinsella intestinalis|Bacteroides stercoris, Collinsella TABLE 2-continued

| Table 2. Specific binary combinations of OTUs. Individual pairings are differentiated by "\|" and OTUs within a combination are differentiated by "," |
|---|
| stercoris\|Bacteroides stercoris, Coprobacillus sp. D7\|Bacteroides stercoris, Coprococcus catus\|Bacteroides stercoris, Coprococcus comes\|Bacteroides stercoris, Coprococcus eutactus\|Bacteroides stercoris, Corynebacterium aurimucosum\|Bacteroides stercoris, Corynebacterium matruchotii\|Bacteroides stercoris, Cryptobacterium curtum\|Bacteroides stercoris, Desulfovibrio desulfuricans\|Bacteroides stercoris, Desulfovibrio piger\|Bacteroides stercoris, Dialister invisus\|Bacteroides stercoris, Dialister microaerophilus\|Bacteroides stercoris, Dorea formicigenerans\|Bacteroides stercoris, Dorea longicatena\|Bacteroides stercoris, Eggerthella lenta\|Bacteroides stercoris, Eikenella corrodens\|Bacteroides stercoris, Enterobacter cancerogenus\|Bacteroides stercoris, Enterobacter cloacae\|Bacteroides stercoris, Enterococcus faecalis\|Bacteroides stercoris, Enterococcus faecium\|Bacteroides stercoris, Enterococcus gallinarum\|Bacteroides stercoris, Erysipelotrichaceae bacterium 3_1_53\|Bacteroides stercoris, Escherichia coli\|Bacteroides stercoris, Escherichia fergusonii\|Bacteroides stercoris, Ethanoligenens harbinense\|Bacteroides stercoris, Eubacterium cellulosolvens\|Bacteroides stercoris, Eubacterium eligens\|Bacteroides stercoris, Eubacterium hallii\|Bacteroides stercoris, Eubacterium limosum\|Bacteroides stercoris, Eubacterium rectale\|Bacteroides stercoris, Eubacterium siraeum\|Bacteroides stercoris, Eubacterium ventriosum\|Bacteroides stercoris, Faecalibacterium prausnitzii\|Bacteroides stercoris, Finegoldia magna\|Bacteroides stercoris, Fusobacterium gonidiaformans\|Bacteroides stercoris, Fusobacterium mortiferum\|Bacteroides stercoris, Fusobacterium nucleatum\|Bacteroides stercoris, Fusobacterium varium\|Bacteroides stercoris, Gardnerella vaginalis\|Bacteroides stercoris, Gemella haemolysans\|Bacteroides stercoris, Gemella morbillorum\|Bacteroides stercoris, Gordonibacter pamelaeae\|Bacteroides stercoris, Granulicatella adiacens\|Bacteroides stercoris, Granulicatella elegans\|Bacteroides stercoris, Haemophilus influenzae\|Bacteroides stercoris, Haemophilus parainfluenzae\|Bacteroides stercoris, Helicobacter pullorum\|Bacteroides stercoris, Helicobacter pylori\|Bacteroides stercoris, Holdemania filiformis\|Bacteroides stercoris, Kingella oralis\|Bacteroides stercoris, Klebsiella pneumoniae\|Bacteroides stercoris, Klebsiella variicola\|Bacteroides stercoris, Lachnospiraceae bacterium 5_1_57FAA\|Bacteroides stercoris, Lactobacillus acidophilus\|Bacteroides stercoris, Lactobacillus amylovorus\|Bacteroides stercoris, Lactobacillus brevis\|Bacteroides stercoris, Lactobacillus casei\|Bacteroides stercoris, Lactobacillus crispatus\|Bacteroides stercoris, Lactobacillus delbrueckii\|Bacteroides stercoris, Lactobacillus fermentum\|Bacteroides stercoris, Lactobacillus gasseri\|Bacteroides stercoris, Lactobacillus iners\|Bacteroides stercoris, Lactobacillus jensenii\|Bacteroides stercoris, Lactobacillus johnsonii\|Bacteroides stercoris, Lactobacillus paracasei\|Bacteroides stercoris, Lactobacillus plantarum\|Bacteroides stercoris, Lactobacillus reuteri\|Bacteroides stercoris, Lactobacillus rhamnosus\|Bacteroides stercoris, Lactobacillus ruminis\|Bacteroides stercoris, Lactobacillus sakei\|Bacteroides stercoris, Lactobacillus salivarius\|Bacteroides stercoris, Lactococcus lactis\|Bacteroides stercoris, Lautropia mirabilis\|Bacteroides stercoris, Leuconostoc citreum\|Bacteroides stercoris, Leuconostoc gasicomitatum\|Bacteroides stercoris, Leuconostoc mesenteroides\|Bacteroides stercoris, Listeria monocytogenes\|Bacteroides stercoris, Marvinbryantia formatexigens\|Bacteroides stercoris, Megamonas hypermegale\|Bacteroides stercoris, Megasphaera micronuciformis\|Bacteroides stercoris, Methanobrevibacter smithii\|Bacteroides stercoris, Methanosphaera stadtmanae\|Bacteroides stercoris, Methylobacterium radiotolerans\|Bacteroides stercoris, Mitsuokella multacida\|Bacteroides stercoris, Mobiluncus curtisii\|Bacteroides stercoris, Mycoplasma hominis\|Bacteroides stercoris, Neisseria mucosa\|Bacteroides stercoris, Odoribacter splanchnicus\|Bacteroides stercoris, Olsenella uli\|Bacteroides stercoris, Oribacterium sinus\|Bacteroides stercoris, Oxalobacter formigenes\|Bacteroides stercoris, Parabacteroides distasonis\|Bacteroides stercoris, Parabacteroides johnsonii\|Bacteroides stercoris, Parabacteroides merdae\|Bacteroides stercoris, Parvimonas micra\|Bacteroides stercoris, Pediococcus acidilactici\|Bacteroides stercoris, Pediococcus pentosaceus\|Bacteroides stercoris, Peptoniphilus duerdenii\|Bacteroides stercoris, Peptoniphilus harei\|Bacteroides stercoris, Peptoniphilus lacrimalis\|Bacteroides stercoris, Peptostreptococcus anaerobius\|Bacteroides stercoris, Peptostreptococcus stomatis\|Bacteroides stercoris, Porphyromonas asaccharolytica\|Bacteroides stercoris, Porphyromonas uenonis\|Bacteroides stercoris, Prevotella amnii\|Bacteroides stercoris, Prevotella bergensis\|Bacteroides stercoris, Prevotella bivia\|Bacteroides stercoris, Prevotella buccae\|Bacteroides stercoris, Prevotella buccalis\|Bacteroides stercoris, Prevotella copri\|Bacteroides stercoris, Prevotella disiens\|Bacteroides stercoris, Prevotella melaninogenica\|Bacteroides stercoris, Prevotella multiformis\|Bacteroides stercoris, Prevotella oralis\|Bacteroides stercoris, Prevotella oris\|Bacteroides stercoris, Prevotella salivae\|Bacteroides stercoris, Prevotella timonensis\|Bacteroides stercoris, Propionibacterium acnes\|Bacteroides stercoris, Propionibacterium freudenreichii\|Bacteroides stercoris, Proteus mirabilis\|Bacteroides stercoris, Proteus penneri\|Bacteroides stercoris, Pseudoflavonifractor capillosus\|Bacteroides stercoris, Pseudomonas aeruginosa\|Bacteroides stercoris, Pseudomonas fluorescens\|Bacteroides stercoris, Pseudomonas putida\|Bacteroides stercoris, Pseudoramibacter alactolyticus\|Bacteroides stercoris, Pyramidobacter piscolens\|Bacteroides stercoris, Rhodopseudomonas palustris\|Bacteroides stercoris, Roseburia intestinalis\|Bacteroides stercoris, Roseburia inulinivorans\|Bacteroides stercoris, Rothia dentocariosa\|Bacteroides stercoris, Rothia mucilaginosa\|Bacteroides stercoris, Ruminococcus albus\|Bacteroides stercoris, Ruminococcus bromii\|Bacteroides stercoris, Ruminococcus gnavus\|Bacteroides stercoris, Ruminococcus lactaris\|Bacteroides stercoris, Ruminococcus obeum\|Bacteroides stercoris, Ruminococcus torques\|Bacteroides stercoris, Selenomonas sputigena\|Bacteroides stercoris, Shigella boydii\|Bacteroides stercoris, Shigella dysenteriae\|Bacteroides stercoris, Shigella sonnei\|Bacteroides stercoris, Slackia exigua\|Bacteroides stercoris, Solobacterium moorei\|Bacteroides stercoris, Staphylococcus aureus\|Bacteroides stercoris, Staphylococcus epidermidis\|Bacteroides stercoris, Staphylococcus hominis\|Bacteroides stercoris, Staphylococcus saprophyticus\|Bacteroides stercoris, Staphylococcus warneri\|Bacteroides stercoris, Streptococcus agalactiae\|Bacteroides stercoris, Streptococcus anginosus\|Bacteroides stercoris, Streptococcus australis\|Bacteroides stercoris, Streptococcus bovis\|Bacteroides stercoris, Streptococcus cristatus\|Bacteroides stercoris, Streptococcus dysgalactiae\|Bacteroides stercoris, Streptococcus equinus\|Bacteroides stercoris, Streptococcus gordonii\|Bacteroides stercoris, Streptococcus infantarius\|Bacteroides stercoris, Streptococcus infantis\|Bacteroides stercoris, Streptococcus mitis\|Bacteroides stercoris, Streptococcus mutans\|Bacteroides stercoris, Streptococcus oralis\|Bacteroides stercoris, Streptococcus parasanguinis\|Bacteroides stercoris, Streptococcus peroris\|Bacteroides stercoris, Streptococcus pneumoniae\|Bacteroides stercoris, Streptococcus salivarius\|Bacteroides stercoris, Streptococcus sanguinis\|Bacteroides stercoris, Streptococcus thermophilus\|Bacteroides stercoris, Streptococcus vestibularis\|Bacteroides stercoris, Subdoligranulum variabile\|Bacteroides stercoris, Succinatimonas hippei\|Bacteroides stercoris, Sutterella wadsworthensis\|Bacteroides stercoris, Tropheryma whipplei\|Bacteroides stercoris, Veillonella atypica\|Bacteroides stercoris, Veillonella dispar\|Bacteroides stercoris, Veillonella parvula\|Bacteroides stercoris, Victivallis vadensis\|Bacteroides thetaiotaomicron, Bacteroides thetaiotaomicron\|Bacteroides thetaiotaomicron, Bacteroides uniformis\|Bacteroides thetaiotaomicron, Bacteroides vulgatus\|Bacteroides thetaiotaomicron, Bacteroides xylanisolvens\|Bacteroides thetaiotaomicron, Bifidobacterium adolescentis\|Bacteroides thetaiotaomicron, Bifidobacterium angulatum\|Bacteroides thetaiotaomicron, Bifidobacterium animalis\|Bacteroides thetaiotaomicron, Bifidobacterium bifidum\|Bacteroides thetaiotaomicron, Bifidobacterium breve\|Bacteroides thetaiotaomicron, Bifidobacterium catenulatum\|Bacteroides thetaiotaomicron, Bifidobacterium dentium\|Bacteroides thetaiotaomicron, Bifidobacterium infantis\|Bacteroides thetaiotaomicron, Bifidobacterium longum\|Bacteroides thetaiotaomicron, Bifidobacterium pseudocatenulatum\|Bacteroides thetaiotaomicron, Bilophila wadsworthia\|Bacteroides thetaiotaomicron, Blautia hansenii\|Bacteroides thetaiotaomicron, Blautia hydrogenotrophica\|Bacteroides thetaiotaomicron, Blautia producta\|Bacteroides thetaiotaomicron, Blautia schinkii\|Bacteroides thetaiotaomicron, Brevibacterium linens\|Bacteroides thetaiotaomicron, Brucella ceti\|Bacteroides thetaiotaomicron, Brucella suis\|Bacteroides thetaiotaomicron, Bulleidia extructa\|Bacteroides thetaiotaomicron, Butyrivibrio crossotus\|Bacteroides thetaiotaomicron, Campylobacter concisus\|Bacteroides thetaiotaomicron, Campylobacter curvus\|Bacteroides thetaiotaomicron, Campylobacter gracilis\|Bacteroides thetaiotaomicron, Campylobacter hominis\|Bacteroides thetaiotaomicron, Capnocytophaga ochracea\|Bacteroides thetaiotaomicron, Cardiobacterium hominis\|Bacteroides thetaiotaomicron, Catenibacterium mitsuokai\|Bacteroides thetaiotaomicron, Catonella morbi\|Bacteroides thetaiotaomicron, Citrobacter koseri\|Bacteroides thetaiotaomicron, Clostridium asparagiforme\|Bacteroides thetaiotaomicron, Clostridium bartlettii\|Bacteroides thetaiotaomicron, Clostridium bolteae\|Bacteroides thetaiotaomicron, Clostridium botulinum\|Bacteroides thetaiotaomicron, Clostridium butyricum\|Bacteroides thetaiotaomicron, Clostridium difficile\|Bacteroides thetaiotaomicron, Clostridium disporicum\|Bacteroides thetaiotaomicron, Clostridium hathewayi\|Bacteroides thetaiotaomicron, Clostridium |

TABLE 2-continued

Table 2. Specific binary combinations of OTUs. Individual pairings are differentiated by "|" and OTUs within a combination are differentiated by ","

hylemonae|Bacteroides thetaiotaomicron, Clostridium innocuum|Bacteroides thetaiotaomicron, Clostridium leptum|Bacteroides thetaiotaomicron, Clostridium mayombei|Bacteroides thetaiotaomicron, Clostridium methylpentosum|Bacteroides thetaiotaomicron, Clostridium nexile|Bacteroides thetaiotaomicron, Clostridium orbiscindens|Bacteroides thetaiotaomicron, Clostridium perfringens|Bacteroides thetaiotaomicron, Clostridium saccharolyticum|Bacteroides thetaiotaomicron, Clostridium scindens|Bacteroides thetaiotaomicron, Clostridium symbiosum|Bacteroides thetaiotaomicron, Clostridium tertium|Bacteroides thetaiotaomicron, Collinsella aerofaciens|Bacteroides thetaiotaomicron, Collinsella intestinalis|Bacteroides thetaiotaomicron, Collinsella stercoris|Bacteroides thetaiotaomicron, Coprobacillus sp. D7|Bacteroides thetaiotaomicron, Coprococcus catus|Bacteroides thetaiotaomicron, Coprococcus comes|Bacteroides thetaiotaomicron, Coprococcus eutactus|Bacteroides thetaiotaomicron, Corynebacterium aurimucosum|Bacteroides thetaiotaomicron, Corynebacterium matruchotii|Bacteroides thetaiotaomicron, Cryptobacterium curtum|Bacteroides thetaiotaomicron, Desulfovibrio desulfuricans|Bacteroides thetaiotaomicron, Desulfovibrio piger|Bacteroides thetaiotaomicron, Dialister invisus|Bacteroides thetaiotaomicron, Dialister microaerophilus|Bacteroides thetaiotaomicron, Dorea formicigenerans|Bacteroides thetaiotaomicron, Dorea longicatena|Bacteroides thetaiotaomicron, Eggerthella lenta|Bacteroides thetaiotaomicron, Eikenella corrodens|Bacteroides thetaiotaomicron, Enterobacter cancerogenus|Bacteroides thetaiotaomicron, Enterobacter cloacae|Bacteroides thetaiotaomicron, Enterococcus faecalis|Bacteroides thetaiotaomicron, Enterococcus faecium|Bacteroides thetaiotaomicron, Enterococcus gallinarum|Bacteroides thetaiotaomicron, Erysipelotrichaceae bacterium 3_1_53|Bacteroides thetaiotaomicron, Escherichia coli|Bacteroides thetaiotaomicron, Escherichia fergusonii|Bacteroides thetaiotaomicron, Ethanoligenens harbinense|Bacteroides thetaiotaomicron, Eubacterium cellulosolvens|Bacteroides thetaiotaomicron, Eubacterium eligens|Bacteroides thetaiotaomicron, Eubacterium hallii|Bacteroides thetaiotaomicron, Eubacterium limosum|Bacteroides thetaiotaomicron, Eubacterium rectale|Bacteroides thetaiotaomicron, Eubacterium siraeum|Bacteroides thetaiotaomicron, Eubacterium ventriosum|Bacteroides thetaiotaomicron, Faecalibacterium prausnitzii|Bacteroides thetaiotaomicron, Finegoldia magna|Bacteroides thetaiotaomicron, Fusobacterium gonidiaformans|Bacteroides thetaiotaomicron, Fusobacterium mortiferum|Bacteroides thetaiotaomicron, Fusobacterium nucleatum|Bacteroides thetaiotaomicron, Fusobacterium varium|Bacteroides thetaiotaomicron, Gardnerella vaginalis|Bacteroides thetaiotaomicron, Gemella haemolysans|Bacteroides thetaiotaomicron, Gemella morbillorum|Bacteroides thetaiotaomicron, Gordonibacter pamelaeae|Bacteroides thetaiotaomicron, Granulicatella adiacens|Bacteroides thetaiotaomicron, Granulicatella elegans|Bacteroides thetaiotaomicron, Haemophilus influenzae|Bacteroides thetaiotaomicron, Haemophilus parainfluenzae|Bacteroides thetaiotaomicron, Helicobacter pullorum|Bacteroides thetaiotaomicron, Helicobacter pylori|Bacteroides thetaiotaomicron, Holdemania filiformis|Bacteroides thetaiotaomicron, Kingella oralis|Bacteroides thetaiotaomicron, Klebsiella pneumoniae|Bacteroides thetaiotaomicron, Klebsiella variicola|Bacteroides thetaiotaomicron, Lachnospiraceae bacterium 5_1_57FAA|Bacteroides thetaiotaomicron, Lactobacillus acidophilus|Bacteroides thetaiotaomicron, Lactobacillus amylovorus|Bacteroides thetaiotaomicron, Lactobacillus brevis|Bacteroides thetaiotaomicron, Lactobacillus casei|Bacteroides thetaiotaomicron, Lactobacillus crispatus|Bacteroides thetaiotaomicron, Lactobacillus delbrueckii|Bacteroides thetaiotaomicron, Lactobacillus fermentum|Bacteroides thetaiotaomicron, Lactobacillus gasseri|Bacteroides thetaiotaomicron, Lactobacillus iners|Bacteroides thetaiotaomicron, Lactobacillus jensenii|Bacteroides thetaiotaomicron, Lactobacillus johnsonii|Bacteroides thetaiotaomicron, Lactobacillus paracasei|Bacteroides thetaiotaomicron, Lactobacillus plantarum|Bacteroides thetaiotaomicron, Lactobacillus reuteri|Bacteroides thetaiotaomicron, Lactobacillus rhamnosus|Bacteroides thetaiotaomicron, Lactobacillus ruminis|Bacteroides thetaiotaomicron, Lactobacillus sakei|Bacteroides thetaiotaomicron, Lactobacillus salivarius|Bacteroides thetaiotaomicron, Lactococcus lactis|Bacteroides thetaiotaomicron, Lautropia mirabilis|Bacteroides thetaiotaomicron, Leuconostoc citreum|Bacteroides thetaiotaomicron, Leuconostoc gasicomitatum|Bacteroides thetaiotaomicron, Leuconostoc mesenteroides|Bacteroides thetaiotaomicron, Listeria monocytogenes|Bacteroides thetaiotaomicron, Marvinbryantia formatexigens|Bacteroides thetaiotaomicron, Megamonas hypermegale|Bacteroides thetaiotaomicron, Megasphaera micronuciformis|Bacteroides thetaiotaomicron, Methanobrevibacter smithii|Bacteroides thetaiotaomicron, Methanosphaera stadtmanae|Bacteroides thetaiotaomicron, Methylobacterium radiotolerans|Bacteroides thetaiotaomicron, Mitsuokella multacida|Bacteroides thetaiotaomicron, Mobiluncus curtisii|Bacteroides thetaiotaomicron, Mycoplasma hominis|Bacteroides thetaiotaomicron, Neisseria mucosa|Bacteroides thetaiotaomicron, Odoribacter splanchnicus|Bacteroides thetaiotaomicron, Olsenella uli|Bacteroides thetaiotaomicron, Oribacterium sinus|Bacteroides thetaiotaomicron, Oxalobacter formigenes|Bacteroides thetaiotaomicron, Parabacteroides distasonis|Bacteroides thetaiotaomicron, Parabacteroides johnsonii|Bacteroides thetaiotaomicron, Parabacteroides merdae|Bacteroides thetaiotaomicron, Parvimonas micra|Bacteroides thetaiotaomicron, Pediococcus acidilactici|Bacteroides thetaiotaomicron, Pediococcus pentosaceus|Bacteroides thetaiotaomicron, Peptoniphilus duerdenii|Bacteroides thetaiotaomicron, Peptoniphilus harei|Bacteroides thetaiotaomicron, Peptoniphilus lacrimalis|Bacteroides thetaiotaomicron, Peptostreptococcus anaerobius|Bacteroides thetaiotaomicron, Peptostreptococcus stomatis|Bacteroides thetaiotaomicron, Porphyromonas asaccharolytica|Bacteroides thetaiotaomicron, Porphyromonas uenonis|Bacteroides thetaiotaomicron, Prevotella amnii|Bacteroides thetaiotaomicron, Prevotella bergensis|Bacteroides thetaiotaomicron, Prevotella bivia|Bacteroides thetaiotaomicron, Prevotella buccae|Bacteroides thetaiotaomicron, Prevotella buccalis|Bacteroides thetaiotaomicron, Prevotella copri|Bacteroides thetaiotaomicron, Prevotella disiens|Bacteroides thetaiotaomicron, Prevotella melaninogenica|Bacteroides thetaiotaomicron, Prevotella multiformis|Bacteroides thetaiotaomicron, Prevotella oralis|Bacteroides thetaiotaomicron, Prevotella oris|Bacteroides thetaiotaomicron, Prevotella salivae|Bacteroides thetaiotaomicron, Prevotella timonensis|Bacteroides thetaiotaomicron, Propionibacterium acnes|Bacteroides thetaiotaomicron, Propionibacterium freudenreichii|Bacteroides thetaiotaomicron, Proteus mirabilis|Bacteroides thetaiotaomicron, Proteus penneri|Bacteroides thetaiotaomicron, Pseudoflavonifractor capillosus|Bacteroides thetaiotaomicron, Pseudomonas aeruginosa|Bacteroides thetaiotaomicron, Pseudomonas fluorescens|Bacteroides thetaiotaomicron, Pseudomonas putida|Bacteroides thetaiotaomicron, Pseudoramibacter alactolyticus|Bacteroides thetaiotaomicron, Pyramidobacter piscolens|Bacteroides thetaiotaomicron, Rhodopseudomonas palustris|Bacteroides thetaiotaomicron, Roseburia intestinalis|Bacteroides thetaiotaomicron, Roseburia inulinivorans|Bacteroides thetaiotaomicron, Rothia dentocariosa|Bacteroides thetaiotaomicron, Rothia mucilaginosa|Bacteroides thetaiotaomicron, Ruminococcus albus|Bacteroides thetaiotaomicron, Ruminococcus bromii|Bacteroides thetaiotaomicron, Ruminococcus gnavus|Bacteroides thetaiotaomicron, Ruminococcus lactaris|Bacteroides thetaiotaomicron, Ruminococcus obeum|Bacteroides thetaiotaomicron, Ruminococcus torques|Bacteroides thetaiotaomicron, Selenomonas sputigena|Bacteroides thetaiotaomicron, Shigella boydii|Bacteroides thetaiotaomicron, Shigella dysenteriae|Bacteroides thetaiotaomicron, Shigella sonnei|Bacteroides thetaiotaomicron, Slackia exigua|Bacteroides thetaiotaomicron, Solobacterium moorei|Bacteroides thetaiotaomicron, Staphylococcus aureus|Bacteroides thetaiotaomicron, Staphylococcus epidermidis|Bacteroides thetaiotaomicron, Staphylococcus hominis|Bacteroides thetaiotaomicron, Staphylococcus saprophyticus|Bacteroides thetaiotaomicron, Staphylococcus warneri|Bacteroides thetaiotaomicron, Streptococcus agalactiae|Bacteroides thetaiotaomicron, Streptococcus anginosus|Bacteroides thetaiotaomicron, Streptococcus australis|Bacteroides thetaiotaomicron, Streptococcus bovis|Bacteroides thetaiotaomicron, Streptococcus cristatus|Bacteroides thetaiotaomicron, Streptococcus dysgalactiae|Bacteroides thetaiotaomicron, Streptococcus equinus|Bacteroides thetaiotaomicron, Streptococcus gordonii|Bacteroides thetaiotaomicron, Streptococcus infantarius|Bacteroides thetaiotaomicron, Streptococcus infantis|Bacteroides thetaiotaomicron, Streptococcus mitis|Bacteroides thetaiotaomicron, Streptococcus mutans|Bacteroides thetaiotaomicron, Streptococcus oralis|Bacteroides thetaiotaomicron, Streptococcus parasanguinis|Bacteroides thetaiotaomicron, Streptococcus peroris|Bacteroides thetaiotaomicron, Streptococcus pneumoniae|Bacteroides thetaiotaomicron, Streptococcus salivarius|Bacteroides thetaiotaomicron, Streptococcus sanguinis|Bacteroides thetaiotaomicron, Streptococcus thermophilus|Bacteroides thetaiotaomicron, Streptococcus vestibularis|Bacteroides thetaiotaomicron, Subdoligranulum variabile|Bacteroides thetaiotaomicron, Succinatimonas hippei|Bacteroides thetaiotaomicron, Sutterella wadsworthensis|Bacteroides thetaiotaomicron, Tropheryma whipplei|Bacteroides TABLE 2-continued Table 2. Specific binary combinations of OTUs. Individual pairings are differentiated by "|" and OTUs within a combination are differentiated by ","

thetaiotaomicron, Veillonella atypica|Bacteroides thetaiotaomicron, Veillonella dispar|Bacteroides thetaiotaomicron, Veillonella parvula|Bacteroides thetaiotaomicron, Victivallis vadensis|Bacteroides uniformis, Bacteroides uniformis|Bacteroides uniformis, Bacteroides vulgatus|Bacteroides uniformis, Bacteroides xylanisolvens|Bacteroides uniformis, Bifidobacterium adolescentis|Bacteroides uniformis, Bifidobacterium angulatum|Bacteroides uniformis, Bifidobacterium animalis|Bacteroides uniformis, Bifidobacterium bifidum|Bacteroides uniformis, Bifidobacterium breve|Bacteroides uniformis, Bifidobacterium catenulatum|Bacteroides uniformis, Bifidobacterium dentium|Bacteroides uniformis, Bifidobacterium infantis|Bacteroides uniformis, Bifidobacterium longum|Bacteroides uniformis, Bifidobacterium pseudocatenulatum|Bacteroides uniformis, Bilophila wadsworthia|Bacteroides uniformis, Blautia hansenii|Bacteroides uniformis, Blautia hydrogenotrophica|Bacteroides uniformis, Blautia producta|Bacteroides uniformis, Blautia schinkii|Bacteroides uniformis, Brevibacterium linens|Bacteroides uniformis, Brucella ceti|Bacteroides uniformis, Brucella suis|Bacteroides uniformis, Bulleidia extructa|Bacteroides uniformis, Butyrivibrio crossotus|Bacteroides uniformis, Campylobacter concisus|Bacteroides uniformis, Campylobacter curvus|Bacteroides uniformis, Campylobacter gracilis|Bacteroides uniformis, Campylobacter hominis|Bacteroides uniformis, Capnocytophaga ochracea|Bacteroides uniformis, Cardiobacterium hominis|Bacteroides uniformis, Catenibacterium mitsuokai|Bacteroides uniformis, Catonella morbi|Bacteroides uniformis, Citrobacter koseri|Bacteroides uniformis, Clostridium asparagiforme|Bacteroides uniformis, Clostridium bartlettii|Bacteroides uniformis, Clostridium bolteae|Bacteroides uniformis, Clostridium botulinum|Bacteroides uniformis, Clostridium butyricum|Bacteroides uniformis, Clostridium difficile|Bacteroides uniformis, Clostridium disporicum|Bacteroides uniformis, Clostridium hathewayi|Bacteroides uniformis, Clostridium hylemonae|Bacteroides uniformis, Clostridium innocuum|Bacteroides uniformis, Clostridium leptum|Bacteroides uniformis, Clostridium mayombei|Bacteroides uniformis, Clostridium methylpentosum|Bacteroides uniformis, Clostridium nexile|Bacteroides uniformis, Clostridium orbiscindens|Bacteroides uniformis, Clostridium perfringens|Bacteroides uniformis, Clostridium saccharolyticum|Bacteroides uniformis, Clostridium scindens|Bacteroides uniformis, Clostridium symbiosum|Bacteroides uniformis, Clostridium tertium|Bacteroides uniformis, Collinsella aerofaciens|Bacteroides uniformis, Collinsella intestinalis|Bacteroides uniformis, Collinsella stercoris|Bacteroides uniformis, Coprobacillus sp. D7|Bacteroides uniformis, Coprococcus catus|Bacteroides uniformis, Coprococcus comes|Bacteroides uniformis, Coprococcus eutactus|Bacteroides uniformis, Corynebacterium aurimucosum|Bacteroides uniformis, Corynebacterium matruchotii|Bacteroides uniformis, Cryptobacterium curtum|Bacteroides uniformis, Desulfovibrio desulfuricans|Bacteroides uniformis, Desulfovibrio piger|Bacteroides uniformis, Dialister invisus|Bacteroides uniformis, Dialister microaerophilus|Bacteroides uniformis, Dorea formicigenerans|Bacteroides uniformis, Dorea longicatena|Bacteroides uniformis, Eggerthella lenta|Bacteroides uniformis, Eikenella corrodens|Bacteroides uniformis, Enterobacter cancerogenus|Bacteroides uniformis, Enterobacter cloacae|Bacteroides uniformis, Enterococcus faecalis|Bacteroides uniformis, Enterococcus faecium|Bacteroides uniformis, Enterococcus gallinarum|Bacteroides uniformis, Erysipelotrichaceae bacterium 3_1_53|Bacteroides uniformis, Escherichia coli|Bacteroides uniformis, Escherichia fergusonii|Bacteroides uniformis, Ethanoligenens harbinense|Bacteroides uniformis, Eubacterium cellulosolvens|Bacteroides uniformis, Eubacterium eligens|Bacteroides uniformis, Eubacterium hallii|Bacteroides uniformis, Eubacterium limosum|Bacteroides uniformis, Eubacterium rectale|Bacteroides uniformis, Eubacterium siraeum|Bacteroides uniformis, Eubacterium ventriosum|Bacteroides uniformis, Faecalibacterium prausnitzii|Bacteroides uniformis, Finegoldia magna|Bacteroides uniformis, Fusobacterium gonidiaformans|Bacteroides uniformis, Fusobacterium mortiferum|Bacteroides uniformis, Fusobacterium nucleatum|Bacteroides uniformis, Fusobacterium varium|Bacteroides uniformis, Gardnerella vaginalis|Bacteroides uniformis, Gemella haemolysans|Bacteroides uniformis, Gemella morbillorum|Bacteroides uniformis, Gordonibacter pamelaeae|Bacteroides uniformis, Granulicatella adiacens|Bacteroides uniformis, Granulicatella elegans|Bacteroides uniformis, Haemophilus influenzae|Bacteroides uniformis, Haemophilus parainfluenzae|Bacteroides uniformis, Helicobacter pullorum|Bacteroides uniformis, Helicobacter pylori|Bacteroides uniformis, Holdemania filiformis|Bacteroides uniformis, Kingella oralis|Bacteroides uniformis, Klebsiella pneumoniae|Bacteroides uniformis, Klebsiella variicola|Bacteroides uniformis, Lachnospiraceae bacterium 5_1_57FAA|Bacteroides uniformis, Lactobacillus acidophilus|Bacteroides uniformis, Lactobacillus amylovorus|Bacteroides uniformis, Lactobacillus brevis|Bacteroides uniformis, Lactobacillus casei|Bacteroides uniformis, Lactobacillus crispatus|Bacteroides uniformis, Lactobacillus delbrueckii|Bacteroides uniformis, Lactobacillus fermentum|Bacteroides uniformis, Lactobacillus gasseri|Bacteroides uniformis, Lactobacillus iners|Bacteroides uniformis, Lactobacillus jensenii|Bacteroides uniformis, Lactobacillus johnsonii|Bacteroides uniformis, Lactobacillus paracasei|Bacteroides uniformis, Lactobacillus plantarum|Bacteroides uniformis, Lactobacillus reuteri|Bacteroides uniformis, Lactobacillus rhamnosus|Bacteroides uniformis, Lactobacillus ruminis|Bacteroides uniformis, Lactobacillus sakei|Bacteroides uniformis, Lactobacillus salivarius|Bacteroides uniformis, Lactococcus lactis|Bacteroides uniformis, Lautropia mirabilis|Bacteroides uniformis, Leuconostoc citreum|Bacteroides uniformis, Leuconostoc gasicomitatum|Bacteroides uniformis, Leuconostoc mesenteroides|Bacteroides uniformis, Listeria monocytogenes|Bacteroides uniformis, Marvinbryantia formatexigens|Bacteroides uniformis, Megamonas hypermegale|Bacteroides uniformis, Megasphaera micronuciformis|Bacteroides uniformis, Methanobrevibacter smithii|Bacteroides uniformis, Methanosphaera stadtmanae|Bacteroides uniformis, Methylobacterium radiotolerans|Bacteroides uniformis, Mitsuokella multacida|Bacteroides uniformis, Mobiluncus curtisii|Bacteroides uniformis, Mycoplasma hominis|Bacteroides uniformis, Neisseria mucosa|Bacteroides uniformis, Odoribacter splanchnicus|Bacteroides uniformis, Olsenella uli|Bacteroides uniformis, Oribacterium sinus|Bacteroides uniformis, Oxalobacter formigenes|Bacteroides uniformis, Parabacteroides distasonis|Bacteroides uniformis, Parabacteroides johnsonii|Bacteroides uniformis, Parabacteroides merdae|Bacteroides uniformis, Parvimonas micra|Bacteroides uniformis, Pediococcus acidilactici|Bacteroides uniformis, Pediococcus pentosaceus|Bacteroides uniformis, Peptoniphilus duerdenii|Bacteroides uniformis, Peptoniphilus harei|Bacteroides uniformis, Peptoniphilus lacrimalis|Bacteroides uniformis, Peptostreptococcus anaerobius|Bacteroides uniformis, Peptostreptococcus stomatis|Bacteroides uniformis, Porphyromonas asaccharolytica|Bacteroides uniformis, Porphyromonas uenonis|Bacteroides uniformis, Prevotella amnii|Bacteroides uniformis, Prevotella bergensis|Bacteroides uniformis, Prevotella bivia|Bacteroides uniformis, Prevotella buccae|Bacteroides uniformis, Prevotella buccalis|Bacteroides uniformis, Prevotella copri|Bacteroides uniformis, Prevotella disiens|Bacteroides uniformis, Prevotella melaninogenica|Bacteroides uniformis, Prevotella multiformis|Bacteroides uniformis, Prevotella oralis|Bacteroides uniformis, Prevotella oris|Bacteroides uniformis, Prevotella salivae|Bacteroides uniformis, Prevotella timonensis|Bacteroides uniformis, Propionibacterium acnes|Bacteroides uniformis, Propionibacterium freudenreichii|Bacteroides uniformis, Proteus mirabilis|Bacteroides uniformis, Proteus penneri|Bacteroides uniformis, Pseudoflavonifractor capillosus|Bacteroides uniformis, Pseudomonas aeruginosa|Bacteroides uniformis, Pseudomonas fluorescens|Bacteroides uniformis, Pseudomonas putida|Bacteroides uniformis, Pseudoramibacter alactolyticus|Bacteroides uniformis, Pyramidobacter piscolens|Bacteroides uniformis, Rhodopseudomonas palustris|Bacteroides uniformis, Roseburia intestinalis|Bacteroides uniformis, Roseburia inulinivorans|Bacteroides uniformis, Rothia dentocariosa|Bacteroides uniformis, Rothia mucilaginosa|Bacteroides uniformis, Ruminococcus albus|Bacteroides uniformis, Ruminococcus bromii|Bacteroides uniformis, Ruminococcus gnavus|Bacteroides uniformis, Ruminococcus lactaris|Bacteroides uniformis, Ruminococcus obeum|Bacteroides uniformis, Ruminococcus torques|Bacteroides uniformis, Selenomonas sputigena|Bacteroides uniformis, Shigella boydii|Bacteroides uniformis, Shigella dysenteriae|Bacteroides uniformis, Shigella sonnei|Bacteroides uniformis, Slackia exigua|Bacteroides uniformis, Solobacterium moorei|Bacteroides uniformis, Staphylococcus aureus|Bacteroides uniformis, Staphylococcus epidermidis|Bacteroides uniformis, Staphylococcus hominis|Bacteroides uniformis, Staphylococcus saprophyticus|Bacteroides uniformis, Staphylococcus warneri|Bacteroides uniformis, Streptococcus agalactiae|Bacteroides uniformis, Streptococcus anginosus|Bacteroides uniformis, Streptococcus australis|Bacteroides uniformis, Streptococcus bovis|Bacteroides uniformis, Streptococcus cristatus|Bacteroides uniformis, Streptococcus dysgalactiae|Bacteroides uniformis, Streptococcus equinus|Bacteroides uniformis, Streptococcus gordonii|Bacteroides uniformis, Streptococcus infantarius|Bacteroides uniformis, Streptococcus infantis|Bacteroides uniformis, Streptococcus mitis|Bacteroides uniformis, Streptococcus mutans|Bacteroides uniformis, Streptococcus oralis|Bacteroides uniformis, Streptococcus TABLE 2-continued Table 2. Specific binary combinations of OTUs. Individual pairings are differentiated by "|" and OTUs within a combination are differentiated by ","

parasanguinis|Bacteroides uniformis, Streptococcus peroris|Bacteroides uniformis, Streptococcus pneumoniae|Bacteroides uniformis, Streptococcus salivarius|Bacteroides uniformis, Streptococcus sanguinis|Bacteroides uniformis, Streptococcus thermophilus|Bacteroides uniformis, Streptococcus vestibularis|Bacteroides uniformis, Subdoligranulum variabile|Bacteroides uniformis, Succinatimonas hippei|Bacteroides uniformis, Sutterella wadsworthensis|Bacteroides uniformis, Tropheryma whipplei|Bacteroides uniformis, Veillonella atypica|Bacteroides uniformis, Veillonella dispar|Bacteroides uniformis, Veillonella parvula|Bacteroides uniformis, Victivallis vadensis|Bacteroides vulgatus, Bacteroides vulgatus|Bacteroides vulgatus, Bacteroides xylanisolvens|Bacteroides vulgatus, Bifidobacterium adolescentis|Bacteroides vulgatus, Bifidobacterium angulatum|Bacteroides vulgatus, Bifidobacterium animalis|Bacteroides vulgatus, Bifidobacterium bifidum|Bacteroides vulgatus, Bifidobacterium breve|Bacteroides vulgatus, Bifidobacterium catenulatum|Bacteroides vulgatus, Bifidobacterium dentium|Bacteroides vulgatus, Bifidobacterium infantis|Bacteroides vulgatus, Bifidobacterium longum|Bacteroides vulgatus, Bifidobacterium pseudocatenulatum|Bacteroides vulgatus, Bilophila wadsworthia|Bacteroides vulgatus, Blautia hansenii|Bacteroides vulgatus, Blautia hydrogenotrophica|Bacteroides vulgatus, Blautia producta|Bacteroides vulgatus, Blautia schinkii|Bacteroides vulgatus, Brevibacterium linens|Bacteroides vulgatus, Brucella ceti|Bacteroides vulgatus, Brucella suis|Bacteroides vulgatus, Bulleidia extructa|Bacteroides vulgatus, Butyrivibrio crossotus|Bacteroides vulgatus, Campylobacter concisus|Bacteroides vulgatus, Campylobacter curvus|Bacteroides vulgatus, Campylobacter gracilis|Bacteroides vulgatus, Campylobacter hominis|Bacteroides vulgatus, Capnocytophaga ochracea|Bacteroides vulgatus, Cardiobacterium hominis|Bacteroides vulgatus, Catenibacterium mitsuokai|Bacteroides vulgatus, Catonella morbi|Bacteroides vulgatus, Citrobacter koseri|Bacteroides vulgatus, Clostridium asparagiforme|Bacteroides vulgatus, Clostridium bartlettii|Bacteroides vulgatus, Clostridium bolteae|Bacteroides vulgatus, Clostridium botulinum|Bacteroides vulgatus, Clostridium butyricum|Bacteroides vulgatus, Clostridium difficile|Bacteroides vulgatus, Clostridium disporicum|Bacteroides vulgatus, Clostridium hathewayi|Bacteroides vulgatus, Clostridium hylemonae|Bacteroides vulgatus, Clostridium innocuum|Bacteroides vulgatus, Clostridium leptum|Bacteroides vulgatus, Clostridium mayombei|Bacteroides vulgatus, Clostridium methylpentosum|Bacteroides vulgatus, Clostridium nexile|Bacteroides vulgatus, Clostridium orbiscindens|Bacteroides vulgatus, Clostridium perfringens|Bacteroides vulgatus, Clostridium saccharolyticum|Bacteroides vulgatus, Clostridium scindens|Bacteroides vulgatus, Clostridium symbiosum|Bacteroides vulgatus, Clostridium tertium|Bacteroides vulgatus, Collinsella aerofaciens|Bacteroides vulgatus, Collinsella intestinalis|Bacteroides vulgatus, Collinsella stercoris|Bacteroides vulgatus, Coprobacillus sp. D7|Bacteroides vulgatus, Coprococcus catus|Bacteroides vulgatus, Coprococcus comes|Bacteroides vulgatus, Coprococcus eutactus|Bacteroides vulgatus, Corynebacterium aurimucosum|Bacteroides vulgatus, Corynebacterium matruchotii|Bacteroides vulgatus, Cryptobacterium curtum|Bacteroides vulgatus, Desulfovibrio desulfuricans|Bacteroides vulgatus, Desulfovibrio piger|Bacteroides vulgatus, Dialister invisus|Bacteroides vulgatus, Dialister microaerophilus|Bacteroides vulgatus, Dorea formicigenerans|Bacteroides vulgatus, Dorea longicatena|Bacteroides vulgatus, Eggerthella lenta|Bacteroides vulgatus, Eikenella corrodens|Bacteroides vulgatus, Enterobacter cancerogenus|Bacteroides vulgatus, Enterobacter cloacae|Bacteroides vulgatus, Enterococcus faecalis|Bacteroides vulgatus, Enterococcus faecium|Bacteroides vulgatus, Enterococcus gallinarum|Bacteroides vulgatus, Erysipelotrichaceae bacterium 3_1_53|Bacteroides vulgatus, Escherichia coli|Bacteroides vulgatus, Escherichia fergusonii|Bacteroides vulgatus, Ethanoligenens harbinense|Bacteroides vulgatus, Eubacterium cellulosolvens|Bacteroides vulgatus, Eubacterium eligens|Bacteroides vulgatus, Eubacterium hallii|Bacteroides vulgatus, Eubacterium limosum|Bacteroides vulgatus, Eubacterium rectale|Bacteroides vulgatus, Eubacterium siraeum|Bacteroides vulgatus, Eubacterium ventriosum|Bacteroides vulgatus, Faecalibacterium prausnitzii|Bacteroides vulgatus, Finegoldia magna|Bacteroides vulgatus, Fusobacterium gonidiaformans|Bacteroides vulgatus, Fusobacterium mortiferum|Bacteroides vulgatus, Fusobacterium nucleatum|Bacteroides vulgatus, Fusobacterium varium|Bacteroides vulgatus, Gardnerella vaginalis|Bacteroides vulgatus, Gemella haemolysans|Bacteroides vulgatus, Gemella morbillorum|Bacteroides vulgatus, Gordonibacter pamelaeae|Bacteroides vulgatus, Granulicatella adiacens|Bacteroides vulgatus, Granulicatella elegans|Bacteroides vulgatus, Haemophilus influenzae|Bacteroides vulgatus, Haemophilus parainfluenzae|Bacteroides vulgatus, Helicobacter pullorum|Bacteroides vulgatus, Helicobacter pylori|Bacteroides vulgatus, Holdemania filiformis|Bacteroides vulgatus, Kingella oralis|Bacteroides vulgatus, Klebsiella pneumoniae|Bacteroides vulgatus, Klebsiella variicola|Bacteroides vulgatus, Lachnospiraceae bacterium 5_1_57FAA|Bacteroides vulgatus, Lactobacillus acidophilus|Bacteroides vulgatus, Lactobacillus amylovorus|Bacteroides vulgatus, Lactobacillus brevis|Bacteroides vulgatus, Lactobacillus casei|Bacteroides vulgatus, Lactobacillus crispatus|Bacteroides vulgatus, Lactobacillus delbrueckii|Bacteroides vulgatus, Lactobacillus fermentum|Bacteroides vulgatus, Lactobacillus gasseri|Bacteroides vulgatus, Lactobacillus iners|Bacteroides vulgatus, Lactobacillus jensenii|Bacteroides vulgatus, Lactobacillus johnsonii|Bacteroides vulgatus, Lactobacillus paracasei|Bacteroides vulgatus, Lactobacillus plantarum|Bacteroides vulgatus, Lactobacillus reuteri|Bacteroides vulgatus, Lactobacillus rhamnosus|Bacteroides vulgatus, Lactobacillus ruminis|Bacteroides vulgatus, Lactobacillus sakei|Bacteroides vulgatus, Lactobacillus salivarius|Bacteroides vulgatus, Lactococcus lactis|Bacteroides vulgatus, Lautropia mirabilis|Bacteroides vulgatus, Leuconostoc citreum|Bacteroides vulgatus, Leuconostoc gasicomitatum|Bacteroides vulgatus, Leuconostoc mesenteroides|Bacteroides vulgatus, Listeria monocytogenes|Bacteroides vulgatus, Marvinbryantia formatexigens|Bacteroides vulgatus, Megamonas hypermegale|Bacteroides vulgatus, Megasphaera micronuciformis|Bacteroides vulgatus, Methanobrevibacter smithii|Bacteroides vulgatus, Methanosphaera stadtmanae|Bacteroides vulgatus, Methylobacterium radiotolerans|Bacteroides vulgatus, Mitsuokella multacida|Bacteroides vulgatus, Mobiluncus curtisii|Bacteroides vulgatus, Mycoplasma hominis|Bacteroides vulgatus, Neisseria mucosa|Bacteroides vulgatus, Odoribacter splanchnicus|Bacteroides vulgatus, Olsenella uli|Bacteroides vulgatus, Oribacterium sinus|Bacteroides vulgatus, Oxalobacter formigenes|Bacteroides vulgatus, Parabacteroides distasonis|Bacteroides vulgatus, Parabacteroides johnsonii|Bacteroides vulgatus, Parabacteroides merdae|Bacteroides vulgatus, Parvimonas micra|Bacteroides vulgatus, Pediococcus acidilactici|Bacteroides vulgatus, Pediococcus pentosaceus|Bacteroides vulgatus, Peptoniphilus duerdenii|Bacteroides vulgatus, Peptoniphilus harei|Bacteroides vulgatus, Peptoniphilus lacrimalis|Bacteroides vulgatus, Peptostreptococcus anaerobius|Bacteroides vulgatus, Peptostreptococcus stomatis|Bacteroides vulgatus, Porphyromonas asaccharolytica|Bacteroides vulgatus, Porphyromonas uenonis|Bacteroides vulgatus, Prevotella amnii|Bacteroides vulgatus, Prevotella bergensis|Bacteroides vulgatus, Prevotella bivia|Bacteroides vulgatus, Prevotella buccae|Bacteroides vulgatus, Prevotella buccalis|Bacteroides vulgatus, Prevotella copri|Bacteroides vulgatus, Prevotella disiens|Bacteroides vulgatus, Prevotella melaninogenica|Bacteroides vulgatus, Prevotella multiformis|Bacteroides vulgatus, Prevotella oralis|Bacteroides vulgatus, Prevotella oris|Bacteroides vulgatus, Prevotella salivae|Bacteroides vulgatus, Prevotella timonensis|Bacteroides vulgatus, Propionibacterium acnes|Bacteroides vulgatus, Propionibacterium freudenreichii|Bacteroides vulgatus, Proteus mirabilis|Bacteroides vulgatus, Proteus penneri|Bacteroides vulgatus, Pseudoflavonifractor capillosus|Bacteroides vulgatus, Pseudomonas aeruginosa|Bacteroides vulgatus, Pseudomonas fluorescens|Bacteroides vulgatus, Pseudomonas putida|Bacteroides vulgatus, Pseudoramibacter alactolyticus|Bacteroides vulgatus, Pyramidobacter piscolens|Bacteroides vulgatus, Rhodopseudomonas palustris|Bacteroides vulgatus, Roseburia intestinalis|Bacteroides vulgatus, Roseburia inulinivorans|Bacteroides vulgatus, Rothia dentocariosa|Bacteroides vulgatus, Rothia mucilaginosa|Bacteroides vulgatus, Ruminococcus albus|Bacteroides vulgatus, Ruminococcus bromii|Bacteroides vulgatus, Ruminococcus gnavus|Bacteroides vulgatus, Ruminococcus lactaris|Bacteroides vulgatus, Ruminococcus obeum|Bacteroides vulgatus, Ruminococcus torques|Bacteroides vulgatus, Selenomonas sputigena|Bacteroides vulgatus, Shigella boydii|Bacteroides vulgatus, Shigella dysenteriae|Bacteroides vulgatus, Shigella sonnei|Bacteroides vulgatus, Slackia exigua|Bacteroides vulgatus, Solobacterium moorei|Bacteroides vulgatus, Staphylococcus aureus|Bacteroides vulgatus, Staphylococcus epidermidis|Bacteroides vulgatus, Staphylococcus hominis|Bacteroides vulgatus, Staphylococcus saprophyticus|Bacteroides vulgatus, Staphylococcus warneri|Bacteroides vulgatus, Streptococcus agalactiae|Bacteroides vulgatus, Streptococcus anginosus|Bacteroides vulgatus, Streptococcus australis|Bacteroides vulgatus, Streptococcus bovis|Bacteroides vulgatus, Streptococcus cristatus|Bacteroides vulgatus, Streptococcus dysgalactiae|Bacteroides vulgatus, Streptococcus equinus|Bacteroides vulgatus, Streptococcus gordonii|Bacteroides vulgatus, Streptococcus infantarius|Bacteroides TABLE 2-continued Table 2. Specific binary combinations of OTUs. Individual pairings are differentiated by "|" and OTUs within a combination are differentiated by ","

*vulgatus, Streptococcus infantis|Bacteroides vulgatus, Streptococcus mitis|Bacteroides vulgatus, Streptococcus mutans|Bacteroides vulgatus, Streptococcus oralis|Bacteroides vulgatus, Streptococcus parasanguinis|Bacteroides vulgatus, Streptococcus peroris|Bacteroides vulgatus, Streptococcus pneumoniae|Bacteroides vulgatus, Streptococcus salivarius|Bacteroides vulgatus, Streptococcus sanguinis|Bacteroides vulgatus, Streptococcus thermophilus|Bacteroides vulgatus, Streptococcus vestibularis|Bacteroides vulgatus, Subdoligranulum variabile|Bacteroides vulgatus, Succinatimonas hippei|Bacteroides vulgatus, Sutterella wadsworthensis|Bacteroides vulgatus, Tropheryma whipplei|Bacteroides vulgatus, Veillonella atypica|Bacteroides vulgatus, Veillonella dispar|Bacteroides vulgatus, Veillonella parvula|Bacteroides vulgatus, Victivallis vadensis|Bacteroides xylanisolvens, Bacteroides xylanisolvens|Bacteroides xylanisolvens, Bifidobacterium adolescentis|Bacteroides xylanisolvens, Bifidobacterium angulatum|Bacteroides xylanisolvens, Bifidobacterium animalis|Bacteroides xylanisolvens, Bifidobacterium bifidum|Bacteroides xylanisolvens, Bifidobacterium breve|Bacteroides xylanisolvens, Bifidobacterium catenulatum|Bacteroides xylanisolvens, Bifidobacterium dentium|Bacteroides xylanisolvens, Bifidobacterium infantis|Bacteroides xylanisolvens, Bifidobacterium longum|Bacteroides xylanisolvens, Bifidobacterium pseudocatenulatum|Bacteroides xylanisolvens, Bilophila wadsworthia|Bacteroides xylanisolvens, Blautia hansenii|Bacteroides xylanisolvens, Blautia hydrogenotrophica|Bacteroides xylanisolvens, Blautia producta|Bacteroides xylanisolvens, Blautia schinkii|Bacteroides xylanisolvens, Brevibacterium linens|Bacteroides xylanisolvens, Brucella ceti|Bacteroides xylanisolvens, Brucella suis|Bacteroides xylanisolvens, Bulleidia extructa|Bacteroides xylanisolvens, Butyrivibrio crossotus|Bacteroides xylanisolvens, Campylobacter concisus|Bacteroides xylanisolvens, Campylobacter curvus|Bacteroides xylanisolvens, Campylobacter gracilis|Bacteroides xylanisolvens, Campylobacter hominis|Bacteroides xylanisolvens, Capnocytophaga ochracea|Bacteroides xylanisolvens, Cardiobacterium hominis|Bacteroides xylanisolvens, Catenibacterium mitsuokai|Bacteroides xylanisolvens, Catonella morbi|Bacteroides xylanisolvens, Citrobacter koseri|Bacteroides xylanisolvens, Clostridium asparagiforme|Bacteroides xylanisolvens, Clostridium bartlettii|Bacteroides xylanisolvens, Clostridium bolteae|Bacteroides xylanisolvens, Clostridium botulinum|Bacteroides xylanisolvens, Clostridium butyricum|Bacteroides xylanisolvens, Clostridium difficile|Bacteroides xylanisolvens, Clostridium disporicum|Bacteroides xylanisolvens, Clostridium hathewayi|Bacteroides xylanisolvens, Clostridium hylemonae|Bacteroides xylanisolvens, Clostridium innocuum|Bacteroides xylanisolvens, Clostridium leptum|Bacteroides xylanisolvens, Clostridium mayombei|Bacteroides xylanisolvens, Clostridium methylpentosum|Bacteroides xylanisolvens, Clostridium nexile|Bacteroides xylanisolvens, Clostridium orbiscindens|Bacteroides xylanisolvens, Clostridium perfringens|Bacteroides xylanisolvens, Clostridium saccharolyticum|Bacteroides xylanisolvens, Clostridium scindens|Bacteroides xylanisolvens, Clostridium symbiosum|Bacteroides xylanisolvens, Clostridium tertium|Bacteroides xylanisolvens, Collinsella aerofaciens|Bacteroides xylanisolvens, Collinsella intestinalis|Bacteroides xylanisolvens, Collinsella stercoris|Bacteroides xylanisolvens, Coprobacillus* sp. D7|*Bacteroides xylanisolvens, Coprococcus catus|Bacteroides xylanisolvens, Coprococcus comes|Bacteroides xylanisolvens, Coprococcus eutactus|Bacteroides xylanisolvens, Corynebacterium aurimucosum|Bacteroides xylanisolvens, Corynebacterium matruchotii|Bacteroides xylanisolvens, Cryptobacterium curtum|Bacteroides xylanisolvens, Desulfovibrio desulfuricans|Bacteroides xylanisolvens, Desulfovibrio piger|Bacteroides xylanisolvens, Dialister invisus|Bacteroides xylanisolvens, Dialister microaerophilus|Bacteroides xylanisolvens, Dorea formicigenerans|Bacteroides xylanisolvens, Dorea longicatena|Bacteroides xylanisolvens, Eggerthella lenta|Bacteroides xylanisolvens, Eikenella corrodens|Bacteroides xylanisolvens, Enterobacter cancerogenus|Bacteroides xylanisolvens, Enterobacter cloacae|Bacteroides xylanisolvens, Enterococcus faecalis|Bacteroides xylanisolvens, Enterococcus faecium|Bacteroides xylanisolvens, Enterococcus gallinarum|Bacteroides xylanisolvens, Erysipelotrichaceae bacterium* 3_1_53|*Bacteroides xylanisolvens, Escherichia coli|Bacteroides xylanisolvens, Escherichia fergusonii|Bacteroides xylanisolvens, Ethanoligenens harbinense|Bacteroides xylanisolvens, Eubacterium cellulosolvens|Bacteroides xylanisolvens, Eubacterium eligens|Bacteroides xylanisolvens, Eubacterium hallii|Bacteroides xylanisolvens, Eubacterium limosum|Bacteroides xylanisolvens, Eubacterium rectale|Bacteroides xylanisolvens, Eubacterium siraeum|Bacteroides xylanisolvens, Eubacterium ventriosum|Bacteroides xylanisolvens, Faecalibacterium prausnitzii|Bacteroides xylanisolvens, Finegoldia magna|Bacteroides xylanisolvens, Fusobacterium gonidiaformans|Bacteroides xylanisolvens, Fusobacterium mortiferum|Bacteroides xylanisolvens, Fusobacterium nucleatum|Bacteroides xylanisolvens, Fusobacterium varium|Bacteroides xylanisolvens, Gardnerella vaginalis|Bacteroides xylanisolvens, Gemella haemolysans|Bacteroides xylanisolvens, Gemella morbillorum|Bacteroides xylanisolvens, Gordonibacter pamelaeae|Bacteroides xylanisolvens, Granulicatella adiacens|Bacteroides xylanisolvens, Granulicatella elegans|Bacteroides xylanisolvens, Haemophilus influenzae|Bacteroides xylanisolvens, Haemophilus parainfluenzae|Bacteroides xylanisolvens, Helicobacter pullorum|Bacteroides xylanisolvens, Helicobacter pylori|Bacteroides xylanisolvens, Holdemania filiformis|Bacteroides xylanisolvens, Kingella oralis|Bacteroides xylanisolvens, Klebsiella pneumoniae|Bacteroides xylanisolvens, Klebsiella variicola|Bacteroides xylanisolvens, Lachnospiraceae bacterium* 5_1_57FAA|*Bacteroides xylanisolvens, Lactobacillus acidophilus|Bacteroides xylanisolvens, Lactobacillus amylovorus|Bacteroides xylanisolvens, Lactobacillus brevis|Bacteroides xylanisolvens, Lactobacillus casei|Bacteroides xylanisolvens, Lactobacillus crispatus|Bacteroides xylanisolvens, Lactobacillus delbrueckii|Bacteroides xylanisolvens, Lactobacillus fermentum|Bacteroides xylanisolvens, Lactobacillus gasseri|Bacteroides xylanisolvens, Lactobacillus iners|Bacteroides xylanisolvens, Lactobacillus jensenii|Bacteroides xylanisolvens, Lactobacillus johnsonii|Bacteroides xylanisolvens, Lactobacillus paracasei|Bacteroides xylanisolvens, Lactobacillus plantarum|Bacteroides xylanisolvens, Lactobacillus reuteri|Bacteroides xylanisolvens, Lactobacillus rhamnosus|Bacteroides xylanisolvens, Lactobacillus ruminis|Bacteroides xylanisolvens, Lactobacillus sakei|Bacteroides xylanisolvens, Lactobacillus salivarius|Bacteroides xylanisolvens, Lactococcus lactis|Bacteroides xylanisolvens, Lautropia mirabilis|Bacteroides xylanisolvens, Leuconostoc citreum|Bacteroides xylanisolvens, Leuconostoc gasicomitatum|Bacteroides xylanisolvens, Leuconostoc mesenteroides|Bacteroides xylanisolvens, Listeria monocytogenes|Bacteroides xylanisolvens, Marvinbryantia formatexigens|Bacteroides xylanisolvens, Megamonas hypermegale|Bacteroides xylanisolvens, Megasphaera micronuciformis|Bacteroides xylanisolvens, Methanobrevibacter smithii|Bacteroides xylanisolvens, Methanosphaera stadtmanae|Bacteroides xylanisolvens, Methylobacterium radiotolerans|Bacteroides xylanisolvens, Mitsuokella multacida|Bacteroides xylanisolvens, Mobiluncus curtisii|Bacteroides xylanisolvens, Mycoplasma hominis|Bacteroides xylanisolvens, Neisseria mucosa|Bacteroides xylanisolvens, Odoribacter splanchnicus|Bacteroides xylanisolvens, Olsenella uli|Bacteroides xylanisolvens, Oribacterium sinus|Bacteroides xylanisolvens, Oxalobacter formigenes|Bacteroides xylanisolvens, Parabacteroides distasonis|Bacteroides xylanisolvens, Parabacteroides johnsonii|Bacteroides xylanisolvens, Parabacteroides merdae|Bacteroides xylanisolvens, Parvimonas micra|Bacteroides xylanisolvens, Pediococcus acidilactici|Bacteroides xylanisolvens, Pediococcus pentosaceus|Bacteroides xylanisolvens, Peptoniphilus duerdenii|Bacteroides xylanisolvens, Peptoniphilus harei|Bacteroides xylanisolvens, Peptoniphilus lacrimalis|Bacteroides xylanisolvens, Peptostreptococcus anaerobius|Bacteroides xylanisolvens, Peptostreptococcus stomatis|Bacteroides xylanisolvens, Porphyromonas asaccharolytica|Bacteroides xylanisolvens, Porphyromonas uenonis|Bacteroides xylanisolvens, Prevotella amnii|Bacteroides xylanisolvens, Prevotella bergensis|Bacteroides xylanisolvens, Prevotella bivia|Bacteroides xylanisolvens, Prevotella buccae|Bacteroides xylanisolvens, Prevotella buccalis|Bacteroides xylanisolvens, Prevotella copri|Bacteroides xylanisolvens, Prevotella disiens|Bacteroides xylanisolvens, Prevotella melaninogenica|Bacteroides xylanisolvens, Prevotella multiformis|Bacteroides xylanisolvens, Prevotella oralis|Bacteroides xylanisolvens, Prevotella oris|Bacteroides xylanisolvens, Prevotella salivae|Bacteroides xylanisolvens, Prevotella timonensis|Bacteroides xylanisolvens, Propionibacterium acnes|Bacteroides xylanisolvens, Propionibacterium freudenreichii|Bacteroides xylanisolvens, Proteus mirabilis|Bacteroides xylanisolvens, Proteus penneri|Bacteroides xylanisolvens, Pseudoflavonifractor capillosus|Bacteroides xylanisolvens, Pseudomonas aeruginosa|Bacteroides xylanisolvens, Pseudomonas fluorescens|Bacteroides xylanisolvens, Pseudomonas putida|Bacteroides xylanisolvens, Pseudoramibacter alactolyticus|Bacteroides xylanisolvens, Pyramidobacter piscolens|Bacteroides xylanisolvens, Rhodopseudomonas palustris|Bacteroides xylanisolvens, Roseburia intestinalis|Bacteroides xylanisolvens, Roseburia inulinivorans|Bacteroides xylanisolvens, Rothia dentocariosa|Bacteroides xylanisolvens, Rothia*

TABLE 2-continued

Table 2. Specific binary combinations of OTUs. Individual pairings are differentiated by "|" and OTUs within a combination are differentiated by ","

mucilaginosa|Bacteroides xylanisolvens, Ruminococcus albus|Bacteroides xylanisolvens, Ruminococcus bromii|Bacteroides xylanisolvens, Ruminococcus gnavus|Bacteroides xylanisolvens, Ruminococcus lactaris|Bacteroides xylanisolvens, Ruminococcus obeum|Bacteroides xylanisolvens, Ruminococcus torques|Bacteroides xylanisolvens, Selenomonas sputigena|Bacteroides xylanisolvens, Shigella boydii|Bacteroides xylanisolvens, Shigella dysenteriae|Bacteroides xylanisolvens, Shigella sonnei|Bacteroides xylanisolvens, Slackia exigua|Bacteroides xylanisolvens, Solobacterium moorei|Bacteroides xylanisolvens, Staphylococcus aureus|Bacteroides xylanisolvens, Staphylococcus epidermidis|Bacteroides xylanisolvens, Staphylococcus hominis|Bacteroides xylanisolvens, Staphylococcus saprophyticus|Bacteroides xylanisolvens, Staphylococcus warneri|Bacteroides xylanisolvens, Streptococcus agalactiae|Bacteroides xylanisolvens, Streptococcus anginosus|Bacteroides xylanisolvens, Streptococcus australis|Bacteroides xylanisolvens, Streptococcus bovis|Bacteroides xylanisolvens, Streptococcus cristatus|Bacteroides xylanisolvens, Streptococcus dysgalactiae|Bacteroides xylanisolvens, Streptococcus equinus|Bacteroides xylanisolvens, Streptococcus gordonii|Bacteroides xylanisolvens, Streptococcus infantarius|Bacteroides xylanisolvens, Streptococcus infantis|Bacteroides xylanisolvens, Streptococcus mitis|Bacteroides xylanisolvens, Streptococcus mutans|Bacteroides xylanisolvens, Streptococcus oralis|Bacteroides xylanisolvens, Streptococcus parasanguinis|Bacteroides xylanisolvens, Streptococcus peroris|Bacteroides xylanisolvens, Streptococcus pneumoniae|Bacteroides xylanisolvens, Streptococcus salivarius|Bacteroides xylanisolvens, Streptococcus sanguinis|Bacteroides xylanisolvens, Streptococcus thermophilus|Bacteroides xylanisolvens, Streptococcus vestibularis|Bacteroides xylanisolvens, Subdoligranulum variabile|Bacteroides xylanisolvens, Succinatimonas hippei|Bacteroides xylanisolvens, Sutterella wadsworthensis|Bacteroides xylanisolvens, Tropheryma whipplei|Bacteroides xylanisolvens, Veillonella atypica|Bacteroides xylanisolvens, Veillonella dispar|Bacteroides xylanisolvens, Veillonella parvula|Bacteroides xylanisolvens, Victivallis vadensis|Bifidobacterium adolescentis, Bifidobacterium adolescentis|Bifidobacterium adolescentis, Bifidobacterium angulatum|Bifidobacterium adolescentis, Bifidobacterium animalis|Bifidobacterium adolescentis, Bifidobacterium bifidum|Bifidobacterium adolescentis, Bifidobacterium breve|Bifidobacterium adolescentis, Bifidobacterium catenulatum|Bifidobacterium adolescentis, Bifidobacterium dentium|Bifidobacterium adolescentis, Bifidobacterium infantis|Bifidobacterium adolescentis, Bifidobacterium longum|Bifidobacterium adolescentis, Bifidobacterium pseudocatenulatum|Bifidobacterium adolescentis, Bilophila wadsworthia|Bifidobacterium adolescentis, Blautia hansenii|Bifidobacterium adolescentis, Blautia hydrogenotrophica|Bifidobacterium adolescentis, Blautia producta|Bifidobacterium adolescentis, Blautia schinkii|Bifidobacterium adolescentis, Brevibacterium linens|Bifidobacterium adolescentis, Brucella ceti|Bifidobacterium adolescentis, Brucella suis|Bifidobacterium adolescentis, Bulleidia extructa|Bifidobacterium adolescentis, Butyrivibrio crossotus|Bifidobacterium adolescentis, Campylobacter concisus|Bifidobacterium adolescentis, Campylobacter curvus|Bifidobacterium adolescentis, Campylobacter gracilis|Bifidobacterium adolescentis, Campylobacter hominis|Bifidobacterium adolescentis, Capnocytophaga ochracea|Bifidobacterium adolescentis, Cardiobacterium hominis|Bifidobacterium adolescentis, Catenibacterium mitsuokai|Bifidobacterium adolescentis, Catonella morbi|Bifidobacterium adolescentis, Citrobacter koseri|Bifidobacterium adolescentis, Clostridium asparagiforme|Bifidobacterium adolescentis, Clostridium bartlettii|Bifidobacterium adolescentis, Clostridium bolteae|Bifidobacterium adolescentis, Clostridium botulinum|Bifidobacterium adolescentis, Clostridium butyricum|Bifidobacterium adolescentis, Clostridium difficile|Bifidobacterium adolescentis, Clostridium disporicum|Bifidobacterium adolescentis, Clostridium hathewayi|Bifidobacterium adolescentis, Clostridium hylemonae|Bifidobacterium adolescentis, Clostridium innocuum|Bifidobacterium adolescentis, Clostridium leptum|Bifidobacterium adolescentis, Clostridium mayombei|Bifidobacterium adolescentis, Clostridium methylpentosum|Bifidobacterium adolescentis, Clostridium nexile|Bifidobacterium adolescentis, Clostridium orbiscindens|Bifidobacterium adolescentis, Clostridium perfringens|Bifidobacterium adolescentis, Clostridium saccharolyticum|Bifidobacterium adolescentis, Clostridium scindens|Bifidobacterium adolescentis, Clostridium symbiosum|Bifidobacterium adolescentis, Clostridium tertium|Bifidobacterium adolescentis, Collinsella aerofaciens|Bifidobacterium adolescentis, Collinsella intestinalis|Bifidobacterium adolescentis, Collinsella stercoris|Bifidobacterium adolescentis, Coprobacillus sp. D7|Bifidobacterium adolescentis, Coprococcus catus|Bifidobacterium adolescentis, Coprococcus comes|Bifidobacterium adolescentis, Coprococcus eutactus|Bifidobacterium adolescentis, Corynebacterium aurimucosum|Bifidobacterium adolescentis, Corynebacterium matruchotii|Bifidobacterium adolescentis, Cryptobacterium curtum|Bifidobacterium adolescentis, Desulfovibrio desulfuricans|Bifidobacterium adolescentis, Desulfovibrio piger|Bifidobacterium adolescentis, Dialister invisus|Bifidobacterium adolescentis, Dialister microaerophilus|Bifidobacterium adolescentis, Dorea formicigenerans|Bifidobacterium adolescentis, Dorea longicatena|Bifidobacterium adolescentis, Eggerthella lenta|Bifidobacterium adolescentis, Eikenella corrodens|Bifidobacterium adolescentis, Enterobacter cancerogenus|Bifidobacterium adolescentis, Enterobacter cloacae|Bifidobacterium adolescentis, Enterococcus faecalis|Bifidobacterium adolescentis, Enterococcus faecium|Bifidobacterium adolescentis, Enterococcus gallinarum|Bifidobacterium adolescentis, Erysipelotrichaceae bacterium 3_1_53|Bifidobacterium adolescentis, Escherichia coli|Bifidobacterium adolescentis, Escherichia fergusonii|Bifidobacterium adolescentis, Ethanoligenens harbinense|Bifidobacterium adolescentis, Eubacterium cellulosolvens|Bifidobacterium adolescentis, Eubacterium eligens|Bifidobacterium adolescentis, Eubacterium hallii|Bifidobacterium adolescentis, Eubacterium limosum|Bifidobacterium adolescentis, Eubacterium rectale|Bifidobacterium adolescentis, Eubacterium siraeum|Bifidobacterium adolescentis, Eubacterium ventriosum|Bifidobacterium adolescentis, Faecalibacterium prausnitzii|Bifidobacterium adolescentis, Finegoldia magna|Bifidobacterium adolescentis, Fusobacterium gonidiaformans|Bifidobacterium adolescentis, Fusobacterium mortiferum|Bifidobacterium adolescentis, Fusobacterium nucleatum|Bifidobacterium adolescentis, Fusobacterium varium|Bifidobacterium adolescentis, Gardnerella vaginalis|Bifidobacterium adolescentis, Gemella haemolysans|Bifidobacterium adolescentis, Gemella morbillorum|Bifidobacterium adolescentis, Gordonibacter pamelaeae|Bifidobacterium adolescentis, Granulicatella adiacens|Bifidobacterium adolescentis, Granulicatella elegans|Bifidobacterium adolescentis, Haemophilus influenzae|Bifidobacterium adolescentis, Haemophilus parainfluenzae|Bifidobacterium adolescentis, Helicobacter pullorum|Bifidobacterium adolescentis, Helicobacter pylori|Bifidobacterium adolescentis, Holdemania filiformis|Bifidobacterium adolescentis, Kingella oralis|Bifidobacterium adolescentis, Klebsiella pneumoniae|Bifidobacterium adolescentis, Klebsiella variicola|Bifidobacterium adolescentis, Lachnospiraceae bacterium 5_1_57FAA|Bifidobacterium adolescentis, Lactobacillus acidophilus|Bifidobacterium adolescentis, Lactobacillus amylovorus|Bifidobacterium adolescentis, Lactobacillus brevis|Bifidobacterium adolescentis, Lactobacillus casei|Bifidobacterium adolescentis, Lactobacillus crispatus|Bifidobacterium adolescentis, Lactobacillus delbrueckii|Bifidobacterium adolescentis, Lactobacillus fermentum|Bifidobacterium adolescentis, Lactobacillus gasseri|Bifidobacterium adolescentis, Lactobacillus iners|Bifidobacterium adolescentis, Lactobacillus jensenii|Bifidobacterium adolescentis, Lactobacillus johnsonii|Bifidobacterium adolescentis, Lactobacillus paracasei|Bifidobacterium adolescentis, Lactobacillus plantarum|Bifidobacterium adolescentis, Lactobacillus reuteri|Bifidobacterium adolescentis, Lactobacillus rhamnosus|Bifidobacterium adolescentis, Lactobacillus ruminis|Bifidobacterium adolescentis, Lactobacillus sakei|Bifidobacterium adolescentis, Lactobacillus salivarius|Bifidobacterium adolescentis, Lactococcus lactis|Bifidobacterium adolescentis, Lautropia mirabilis|Bifidobacterium adolescentis, Leuconostoc citreum|Bifidobacterium adolescentis, Leuconostoc gasicomitatum|Bifidobacterium adolescentis, Leuconostoc mesenteroides|Bifidobacterium adolescentis, Listeria monocytogenes|Bifidobacterium adolescentis, Marvinbryantia formatexigens|Bifidobacterium adolescentis, Megamonas hypermegale|Bifidobacterium adolescentis, Megasphaera micronuciformis|Bifidobacterium adolescentis, Methanobrevibacter smithii|Bifidobacterium adolescentis, Methanosphaera stadtmanae|Bifidobacterium adolescentis, Methylobacterium radiotolerans|Bifidobacterium adolescentis, Mitsuokella multacida|Bifidobacterium adolescentis, Mobiluncus curtisii|Bifidobacterium adolescentis, Mycoplasma hominis|Bifidobacterium adolescentis, Neisseria mucosa|Bifidobacterium adolescentis, Odoribacter splanchnicus|Bifidobacterium adolescentis, Olsenella uli|Bifidobacterium adolescentis, Oribacterium sinus|Bifidobacterium adolescentis, Oxalobacter formigenes|Bifidobacterium adolescentis, Parabacteroides distasonis|Bifidobacterium adolescentis, Parabacteroides johnsonii|Bifidobacterium adolescentis, Parabacteroides merdae|Bifidobacterium TABLE 2-continued Table 2. Specific binary combinations of OTUs. Individual pairings are differentiated by "|" and OTUs within a combination are differentiated by ","

adolescentis, Parvimonas micra|Bifidobacterium adolescentis, Pediococcus acidilactici|Bifidobacterium adolescentis, Pediococcus pentosaceus|Bifidobacterium adolescentis, Peptoniphilus duerdenii|Bifidobacterium adolescentis, Peptoniphilus harei|Bifidobacterium adolescentis, Peptoniphilus lacrimalis|Bifidobacterium adolescentis, Peptostreptococcus anaerobius|Bifidobacterium adolescentis, Peptostreptococcus stomatis|Bifidobacterium adolescentis, Porphyromonas asaccharolytica|Bifidobacterium adolescentis, Porphyromonas uenonis|Bifidobacterium adolescentis, Prevotella amnii|Bifidobacterium adolescentis, Prevotella bergensis|Bifidobacterium adolescentis, Prevotella bivia|Bifidobacterium adolescentis, Prevotella buccae|Bifidobacterium adolescentis, Prevotella buccalis|Bifidobacterium adolescentis, Prevotella copri|Bifidobacterium adolescentis, Prevotella disiens|Bifidobacterium adolescentis, Prevotella melaninogenica|Bifidobacterium adolescentis, Prevotella multiformis|Bifidobacterium adolescentis, Prevotella oralis|Bifidobacterium adolescentis, Prevotella oris|Bifidobacterium adolescentis, Prevotella salivae|Bifidobacterium adolescentis, Prevotella timonensis|Bifidobacterium adolescentis, Propionibacterium acnes|Bifidobacterium adolescentis, Propionibacterium freudenreichii|Bifidobacterium adolescentis, Proteus mirabilis|Bifidobacterium adolescentis, Proteus penneri|Bifidobacterium adolescentis, Pseudoflavonifractor capillosus|Bifidobacterium adolescentis, Pseudomonas aeruginosa|Bifidobacterium adolescentis, Pseudomonas fluorescens|Bifidobacterium adolescentis, Pseudomonas putida|Bifidobacterium adolescentis, Pseudoramibacter alactolyticus|Bifidobacterium adolescentis, Pyramidobacter piscolens|Bifidobacterium adolescentis, Rhodopseudomonas palustris|Bifidobacterium adolescentis, Roseburia intestinalis|Bifidobacterium adolescentis, Roseburia inulinivorans|Bifidobacterium adolescentis, Rothia dentocariosa|Bifidobacterium adolescentis, Rothia mucilaginosa|Bifidobacterium adolescentis, Ruminococcus albus|Bifidobacterium adolescentis, Ruminococcus bromii|Bifidobacterium adolescentis, Ruminococcus gnavus|Bifidobacterium adolescentis, Ruminococcus lactaris|Bifidobacterium adolescentis, Ruminococcus obeum|Bifidobacterium adolescentis, Ruminococcus torques|Bifidobacterium adolescentis, Selenomonas sputigena|Bifidobacterium adolescentis, Shigella boydii|Bifidobacterium adolescentis, Shigella dysenteriae|Bifidobacterium adolescentis, Shigella sonnei|Bifidobacterium adolescentis, Slackia exigua|Bifidobacterium adolescentis, Solobacterium moorei|Bifidobacterium adolescentis, Staphylococcus aureus|Bifidobacterium adolescentis, Staphylococcus epidermidis|Bifidobacterium adolescentis, Staphylococcus hominis|Bifidobacterium adolescentis, Staphylococcus saprophyticus|Bifidobacterium adolescentis, Staphylococcus warneri|Bifidobacterium adolescentis, Streptococcus agalactiae|Bifidobacterium adolescentis, Streptococcus anginosus|Bifidobacterium adolescentis, Streptococcus australis|Bifidobacterium adolescentis, Streptococcus bovis|Bifidobacterium adolescentis, Streptococcus cristatus|Bifidobacterium adolescentis, Streptococcus dysgalactiae|Bifidobacterium adolescentis, Streptococcus equinus|Bifidobacterium adolescentis, Streptococcus gordonii|Bifidobacterium adolescentis, Streptococcus infantarius|Bifidobacterium adolescentis, Streptococcus infantis|Bifidobacterium adolescentis, Streptococcus mitis|Bifidobacterium adolescentis, Streptococcus mutans|Bifidobacterium adolescentis, Streptococcus oralis|Bifidobacterium adolescentis, Streptococcus parasanguinis|Bifidobacterium adolescentis, Streptococcus peroris|Bifidobacterium adolescentis, Streptococcus pneumoniae|Bifidobacterium adolescentis, Streptococcus salivarius|Bifidobacterium adolescentis, Streptococcus sanguinis|Bifidobacterium adolescentis, Streptococcus thermophilus|Bifidobacterium adolescentis, Streptococcus vestibularis|Bifidobacterium adolescentis, Subdoligranulum variabile|Bifidobacterium adolescentis, Succinatimonas hippei|Bifidobacterium adolescentis, Sutterella wadsworthensis|Bifidobacterium adolescentis, Tropheryma whipplei|Bifidobacterium adolescentis, Veillonella atypica|Bifidobacterium adolescentis, Veillonella dispar|Bifidobacterium adolescentis, Veillonella parvula|Bifidobacterium adolescentis, Victivallis vadensis|Bifidobacterium angulatum, Bifidobacterium angulatum|Bifidobacterium angulatum, Bifidobacterium animalis|Bifidobacterium angulatum, Bifidobacterium bifidum|Bifidobacterium angulatum, Bifidobacterium breve|Bifidobacterium angulatum, Bifidobacterium catenulatum|Bifidobacterium angulatum, Bifidobacterium dentium|Bifidobacterium angulatum, Bifidobacterium infantis|Bifidobacterium angulatum, Bifidobacterium longum|Bifidobacterium angulatum, Bifidobacterium pseudocatenulatum|Bifidobacterium angulatum, Bilophila wadsworthia|Bifidobacterium angulatum, Blautia hansenii|Bifidobacterium angulatum, Blautia hydrogenotrophica|Bifidobacterium angulatum, Blautia producta|Bifidobacterium angulatum, Blautia schinkii|Bifidobacterium angulatum, Brevibacterium linens|Bifidobacterium angulatum, Brucella ceti|Bifidobacterium angulatum, Brucella suis|Bifidobacterium angulatum, Bulleidia extructa|Bifidobacterium angulatum, Butyrivibrio crossotus|Bifidobacterium angulatum, Campylobacter concisus|Bifidobacterium angulatum, Campylobacter curvus|Bifidobacterium angulatum, Campylobacter gracilis|Bifidobacterium angulatum, Campylobacter hominis|Bifidobacterium angulatum, Capnocytophaga ochracea|Bifidobacterium angulatum, Cardiobacterium hominis|Bifidobacterium angulatum, Catenibacterium mitsuokai|Bifidobacterium angulatum, Catonella morbi|Bifidobacterium angulatum, Citrobacter koseri|Bifidobacterium angulatum, Clostridium asparagiforme|Bifidobacterium angulatum, Clostridium bartlettii|Bifidobacterium angulatum, Clostridium bolteae|Bifidobacterium angulatum, Clostridium botulinum|Bifidobacterium angulatum, Clostridium butyricum|Bifidobacterium angulatum, Clostridium difficile|Bifidobacterium angulatum, Clostridium disporicum|Bifidobacterium angulatum, Clostridium hathewayi|Bifidobacterium angulatum, Clostridium hylemonae|Bifidobacterium angulatum, Clostridium innocuum|Bifidobacterium angulatum, Clostridium leptum|Bifidobacterium angulatum, Clostridium mayombei|Bifidobacterium angulatum, Clostridium methylpentosum|Bifidobacterium angulatum, Clostridium nexile|Bifidobacterium angulatum, Clostridium orbiscindens|Bifidobacterium angulatum, Clostridium perfringens|Bifidobacterium angulatum, Clostridium saccharolyticum|Bifidobacterium angulatum, Clostridium scindens|Bifidobacterium angulatum, Clostridium symbiosum|Bifidobacterium angulatum, Clostridium tertium|Bifidobacterium angulatum, Collinsella aerofaciens|Bifidobacterium angulatum, Collinsella intestinalis|Bifidobacterium angulatum, Collinsella stercoris|Bifidobacterium angulatum, Coprobacillus sp. D7|Bifidobacterium angulatum, Coprococcus catus|Bifidobacterium angulatum, Coprococcus comes|Bifidobacterium angulatum, Coprococcus eutactus|Bifidobacterium angulatum, Corynebacterium aurimucosum|Bifidobacterium angulatum, Corynebacterium matruchotii|Bifidobacterium angulatum, Cryptobacterium curtum|Bifidobacterium angulatum, Desulfovibrio desulfuricans|Bifidobacterium angulatum, Desulfovibrio piger|Bifidobacterium angulatum, Dialister invisus|Bifidobacterium angulatum, Dialister microaerophilus|Bifidobacterium angulatum, Dorea formicigenerans|Bifidobacterium angulatum, Dorea longicatena|Bifidobacterium angulatum, Eggerthella lenta|Bifidobacterium angulatum, Eikenella corrodens|Bifidobacterium angulatum, Enterobacter cancerogenus|Bifidobacterium angulatum, Enterobacter cloacae|Bifidobacterium angulatum, Enterococcus faecalis|Bifidobacterium angulatum, Enterococcus faecium|Bifidobacterium angulatum, Enterococcus gallinarum|Bifidobacterium angulatum, Erysipelotrichaceae bacterium 3_1_53|Bifidobacterium angulatum, Escherichia coli|Bifidobacterium angulatum, Escherichia fergusonii|Bifidobacterium angulatum, Ethanoligenens harbinense|Bifidobacterium angulatum, Eubacterium cellulosolvens|Bifidobacterium angulatum, Eubacterium eligens|Bifidobacterium angulatum, Eubacterium hallii|Bifidobacterium angulatum, Eubacterium limosum|Bifidobacterium angulatum, Eubacterium rectale|Bifidobacterium angulatum, Eubacterium siraeum|Bifidobacterium angulatum, Eubacterium ventriosum|Bifidobacterium angulatum, Faecalibacterium prausnitzii|Bifidobacterium angulatum, Finegoldia magna|Bifidobacterium angulatum, Fusobacterium gonidiaformans|Bifidobacterium angulatum, Fusobacterium mortiferum|Bifidobacterium angulatum, Fusobacterium nucleatum|Bifidobacterium angulatum, Fusobacterium varium|Bifidobacterium angulatum, Gardnerella vaginalis|Bifidobacterium angulatum, Gemella haemolysans|Bifidobacterium angulatum, Gemella morbillorum|Bifidobacterium angulatum, Gordonibacter pamelaeae|Bifidobacterium angulatum, Granulicatella adiacens|Bifidobacterium angulatum, Granulicatella elegans|Bifidobacterium angulatum, Haemophilus influenzae|Bifidobacterium angulatum, Haemophilus parainfluenzae|Bifidobacterium angulatum, Helicobacter pullorum|Bifidobacterium angulatum, Helicobacter pylori|Bifidobacterium angulatum, Holdemania filiformis|Bifidobacterium angulatum, Kingella oralis|Bifidobacterium angulatum, Klebsiella pneumoniae|Bifidobacterium angulatum, Klebsiella variicola|Bifidobacterium angulatum, Lachnospiraceae bacterium 5_1_57FAA|Bifidobacterium angulatum, Lactobacillus acidophilus|Bifidobacterium angulatum, Lactobacillus amylovorus|Bifidobacterium angulatum, Lactobacillus brevis|Bifidobacterium angulatum, Lactobacillus casei|Bifidobacterium TABLE 2-continued Table 2. Specific binary combinations of OTUs. Individual pairings are differentiated by "|" and OTUs within a combination are differentiated by ","

*angulatum, Lactobacillus crispatus|Bifidobacterium angulatum, Lactobacillus delbrueckii|Bifidobacterium angulatum, Lactobacillus fermentum|Bifidobacterium angulatum, Lactobacillus gasseri|Bifidobacterium angulatum, Lactobacillus iners|Bifidobacterium angulatum, Lactobacillus jensenii|Bifidobacterium angulatum, Lactobacillus johnsonii|Bifidobacterium angulatum, Lactobacillus paracasei|Bifidobacterium angulatum, Lactobacillus plantarum|Bifidobacterium angulatum, Lactobacillus reuteri|Bifidobacterium angulatum, Lactobacillus rhamnosus|Bifidobacterium angulatum, Lactobacillus ruminis|Bifidobacterium angulatum, Lactobacillus sakei|Bifidobacterium angulatum, Lactobacillus salivarius|Bifidobacterium angulatum, Lactococcus lactis|Bifidobacterium angulatum, Lautropia mirabilis|Bifidobacterium angulatum, Leuconostoc citreum|Bifidobacterium angulatum, Leuconostoc gasicomitatum|Bifidobacterium angulatum, Leuconostoc mesenteroides|Bifidobacterium angulatum, Listeria monocytogenes|Bifidobacterium angulatum, Marvinbryantia formatexigens|Bifidobacterium angulatum, Megamonas hypermegale|Bifidobacterium angulatum, Megasphaera micronuciformis|Bifidobacterium angulatum, Methanobrevibacter smithii|Bifidobacterium angulatum, Methanosphaera stadtmanae|Bifidobacterium angulatum, Methylobacterium radiotolerans|Bifidobacterium angulatum, Mitsuokella multacida|Bifidobacterium angulatum, Mobiluncus curtisii|Bifidobacterium angulatum, Mycoplasma hominis|Bifidobacterium angulatum, Neisseria mucosa|Bifidobacterium angulatum, Odoribacter splanchnicus|Bifidobacterium angulatum, Olsenella uli|Bifidobacterium angulatum, Oribacterium sinus|Bifidobacterium angulatum, Oxalobacter formigenes|Bifidobacterium angulatum, Parabacteroides distasonis|Bifidobacterium angulatum, Parabacteroides johnsonii|Bifidobacterium angulatum, Parabacteroides merdae|Bifidobacterium angulatum, Parvimonas micra|Bifidobacterium angulatum, Pediococcus acidilactici|Bifidobacterium angulatum, Pediococcus pentosaceus|Bifidobacterium angulatum, Peptoniphilus duerdenii|Bifidobacterium angulatum, Peptoniphilus harei|Bifidobacterium angulatum, Peptoniphilus lacrimalis|Bifidobacterium angulatum, Peptostreptococcus anaerobius|Bifidobacterium angulatum, Peptostreptococcus stomatis|Bifidobacterium angulatum, Porphyromonas asaccharolytica|Bifidobacterium angulatum, Porphyromonas uenonis|Bifidobacterium angulatum, Prevotella amnii|Bifidobacterium angulatum, Prevotella bergensis|Bifidobacterium angulatum, Prevotella bivia|Bifidobacterium angulatum, Prevotella buccae|Bifidobacterium angulatum, Prevotella buccalis|Bifidobacterium angulatum, Prevotella copri|Bifidobacterium angulatum, Prevotella disiens|Bifidobacterium angulatum, Prevotella melaninogenica|Bifidobacterium angulatum, Prevotella multiformis|Bifidobacterium angulatum, Prevotella oralis|Bifidobacterium angulatum, Prevotella oris|Bifidobacterium angulatum, Prevotella salivae|Bifidobacterium angulatum, Prevotella timonensis|Bifidobacterium angulatum, Propionibacterium acnes|Bifidobacterium angulatum, Propionibacterium freudenreichii|Bifidobacterium angulatum, Proteus mirabilis|Bifidobacterium angulatum, Proteus penneri|Bifidobacterium angulatum, Pseudoflavonifractor capillosus|Bifidobacterium angulatum, Pseudomonas aeruginosa|Bifidobacterium angulatum, Pseudomonas fluorescens|Bifidobacterium angulatum, Pseudomonas putida|Bifidobacterium angulatum, Pseudoramibacter alactolyticus|Bifidobacterium angulatum, Pyramidobacter piscolens|Bifidobacterium angulatum, Rhodopseudomonas palustris|Bifidobacterium angulatum, Roseburia intestinalis|Bifidobacterium angulatum, Roseburia inulinivorans|Bifidobacterium angulatum, Rothia dentocariosa|Bifidobacterium angulatum, Rothia mucilaginosa|Bifidobacterium angulatum, Ruminococcus albus|Bifidobacterium angulatum, Ruminococcus bromii|Bifidobacterium angulatum, Ruminococcus gnavus|Bifidobacterium angulatum, Ruminococcus lactaris|Bifidobacterium angulatum, Ruminococcus obeum|Bifidobacterium angulatum, Ruminococcus torques|Bifidobacterium angulatum, Selenomonas sputigena|Bifidobacterium angulatum, Shigella boydii|Bifidobacterium angulatum, Shigella dysenteriae|Bifidobacterium angulatum, Shigella sonnei|Bifidobacterium angulatum, Slackia exigua|Bifidobacterium angulatum, Solobacterium moorei|Bifidobacterium angulatum, Staphylococcus aureus|Bifidobacterium angulatum, Staphylococcus epidermidis|Bifidobacterium angulatum, Staphylococcus hominis|Bifidobacterium angulatum, Staphylococcus saprophyticus|Bifidobacterium angulatum, Staphylococcus warneri|Bifidobacterium angulatum, Streptococcus agalactiae|Bifidobacterium angulatum, Streptococcus anginosus|Bifidobacterium angulatum, Streptococcus australis|Bifidobacterium angulatum, Streptococcus bovis|Bifidobacterium angulatum, Streptococcus cristatus|Bifidobacterium angulatum, Streptococcus dysgalactiae|Bifidobacterium angulatum, Streptococcus equinus|Bifidobacterium angulatum, Streptococcus gordonii|Bifidobacterium angulatum, Streptococcus infantarius|Bifidobacterium angulatum, Streptococcus infantis|Bifidobacterium angulatum, Streptococcus mitis|Bifidobacterium angulatum, Streptococcus mutans|Bifidobacterium angulatum, Streptococcus oralis|Bifidobacterium angulatum, Streptococcus parasanguinis|Bifidobacterium angulatum, Streptococcus peroris|Bifidobacterium angulatum, Streptococcus pneumoniae|Bifidobacterium angulatum, Streptococcus salivarius|Bifidobacterium angulatum, Streptococcus sanguinis|Bifidobacterium angulatum, Streptococcus thermophilus|Bifidobacterium angulatum, Streptococcus vestibularis|Bifidobacterium angulatum, Subdoligranulum variabile|Bifidobacterium angulatum, Succinatimonas hippei|Bifidobacterium angulatum, Sutterella wadsworthensis|Bifidobacterium angulatum, Tropheryma whipplei|Bifidobacterium angulatum, Veillonella atypica|Bifidobacterium angulatum, Veillonella dispar|Bifidobacterium angulatum, Veillonella parvula|Bifidobacterium angulatum, Victivallis vadensis|Bifidobacterium animalis, Bifidobacterium animalis|Bifidobacterium animalis, Bifidobacterium bifidum|Bifidobacterium animalis, Bifidobacterium breve|Bifidobacterium animalis, Bifidobacterium catenulatum|Bifidobacterium animalis, Bifidobacterium dentium|Bifidobacterium animalis, Bifidobacterium infantis|Bifidobacterium animalis, Bifidobacterium longum|Bifidobacterium animalis, Bifidobacterium pseudocatenulatum|Bifidobacterium animalis, Bilophila wadsworthia|Bifidobacterium animalis, Blautia hansenii|Bifidobacterium animalis, Blautia hydrogenotrophica|Bifidobacterium animalis, Blautia producta|Bifidobacterium animalis, Blautia schinkii|Bifidobacterium animalis, Brevibacterium linens|Bifidobacterium animalis, Brucella ceti|Bifidobacterium animalis, Brucella suis|Bifidobacterium animalis, Bulleidia extructa|Bifidobacterium animalis, Butyrivibrio crossotus|Bifidobacterium animalis, Campylobacter concisus|Bifidobacterium animalis, Campylobacter curvus|Bifidobacterium animalis, Campylobacter gracilis|Bifidobacterium animalis, Campylobacter hominis|Bifidobacterium animalis, Capnocytophaga ochracea|Bifidobacterium animalis, Cardiobacterium hominis|Bifidobacterium animalis, Catenibacterium mitsuokai|Bifidobacterium animalis, Catonella morbi|Bifidobacterium animalis, Citrobacter koseri|Bifidobacterium animalis, Clostridium asparagiforme|Bifidobacterium animalis, Clostridium bartlettii|Bifidobacterium animalis, Clostridium bolteae|Bifidobacterium animalis, Clostridium botulinum|Bifidobacterium animalis, Clostridium butyricum|Bifidobacterium animalis, Clostridium difficile|Bifidobacterium animalis, Clostridium disporicum|Bifidobacterium animalis, Clostridium hathewayi|Bifidobacterium animalis, Clostridium hylemonae|Bifidobacterium animalis, Clostridium innocuum|Bifidobacterium animalis, Clostridium leptum|Bifidobacterium animalis, Clostridium mayombei|Bifidobacterium animalis, Clostridium methylpentosum|Bifidobacterium animalis, Clostridium nexile|Bifidobacterium animalis, Clostridium orbiscindens|Bifidobacterium animalis, Clostridium perfringens|Bifidobacterium animalis, Clostridium saccharolyticum|Bifidobacterium animalis, Clostridium scindens|Bifidobacterium animalis, Clostridium symbiosum|Bifidobacterium animalis, Clostridium tertium|Bifidobacterium animalis, Collinsella aerofaciens|Bifidobacterium animalis, Collinsella intestinalis|Bifidobacterium animalis, Collinsella stercoris|Bifidobacterium animalis, Coprobacillus* sp. D7|*Bifidobacterium animalis, Coprococcus catus|Bifidobacterium animalis, Coprococcus comes|Bifidobacterium animalis, Coprococcus eutactus|Bifidobacterium animalis, Corynebacterium aurimucosum|Bifidobacterium animalis, Corynebacterium matruchotii|Bifidobacterium animalis, Cryptobacterium curtum|Bifidobacterium animalis, Desulfovibrio desulfuricans|Bifidobacterium animalis, Desulfovibrio piger|Bifidobacterium animalis, Dialister invisus|Bifidobacterium animalis, Dialister microaerophilus|Bifidobacterium animalis, Dorea formicigenerans|Bifidobacterium animalis, Dorea longicatena|Bifidobacterium animalis, Eggerthella lenta|Bifidobacterium animalis, Eikenella corrodens|Bifidobacterium animalis, Enterobacter cancerogenus|Bifidobacterium animalis, Enterobacter cloacae|Bifidobacterium animalis, Enterococcus faecalis|Bifidobacterium animalis, Enterococcus faecium|Bifidobacterium animalis, Enterococcus gallinarum|Bifidobacterium animalis, Erysipelotrichaceae bacterium* 3_1_53|*Bifidobacterium animalis, Escherichia coli|Bifidobacterium animalis, Escherichia fergusonii|Bifidobacterium animalis, Ethanoligenens harbinense|Bifidobacterium animalis, Eubacterium cellulosolvens|Bifidobacterium animalis, Eubacterium eligens|Bifidobacterium animalis, Eubacterium hallii|Bifidobacterium animalis, Eubacterium limosum|Bifidobacterium animalis, Eubacterium rectale|Bifidobacterium animalis, Eubacterium siraeum|Bifidobacterium animalis, Eubacterium*

TABLE 2-continued

Table 2. Specific binary combinations of OTUs. Individual pairings are differentiated by "|" and OTUs within a combination are differentiated by ","

*ventriosum|Bifidobacterium animalis, Faecalibacterium prausnitzii|Bifidobacterium animalis, Finegoldia magna|Bifidobacterium animalis, Fusobacterium gonidiaformans|Bifidobacterium animalis, Fusobacterium mortiferum|Bifidobacterium animalis, Fusobacterium nucleatum|Bifidobacterium animalis, Fusobacterium varium|Bifidobacterium animalis, Gardnerella vaginalis|Bifidobacterium animalis, Gemella haemolysans|Bifidobacterium animalis, Gemella morbillorum|Bifidobacterium animalis, Gordonibacter pamelaeae|Bifidobacterium animalis, Granulicatella adiacens|Bifidobacterium animalis, Granulicatella elegans|Bifidobacterium animalis, Haemophilus influenzae|Bifidobacterium animalis, Haemophilus parainfluenzae|Bifidobacterium animalis, Helicobacter pullorum|Bifidobacterium animalis, Helicobacter pylori|Bifidobacterium animalis, Holdemania filiformis|Bifidobacterium animalis, Kingella oralis|Bifidobacterium animalis, Klebsiella pneumoniae|Bifidobacterium animalis, Klebsiella variicola|Bifidobacterium animalis, Lachnospiraceae bacterium* 5_1_57FAA|*Bifidobacterium animalis, Lactobacillus acidophilus|Bifidobacterium animalis, Lactobacillus amylovorus|Bifidobacterium animalis, Lactobacillus brevis|Bifidobacterium animalis, Lactobacillus casei|Bifidobacterium animalis, Lactobacillus crispatus|Bifidobacterium animalis, Lactobacillus delbrueckii|Bifidobacterium animalis, Lactobacillus fermentum|Bifidobacterium animalis, Lactobacillus gasseri|Bifidobacterium animalis, Lactobacillus iners|Bifidobacterium animalis, Lactobacillus jensenii|Bifidobacterium animalis, Lactobacillus johnsonii|Bifidobacterium animalis, Lactobacillus paracasei|Bifidobacterium animalis, Lactobacillus plantarum|Bifidobacterium animalis, Lactobacillus reuteri|Bifidobacterium animalis, Lactobacillus rhamnosus|Bifidobacterium animalis, Lactobacillus ruminis|Bifidobacterium animalis, Lactobacillus sakei|Bifidobacterium animalis, Lactobacillus salivarius|Bifidobacterium animalis, Lactococcus lactis|Bifidobacterium animalis, Lautropia mirabilis|Bifidobacterium animalis, Leuconostoc citreum|Bifidobacterium animalis, Leuconostoc gasicomitatum|Bifidobacterium animalis, Leuconostoc mesenteroides|Bifidobacterium animalis, Listeria monocytogenes|Bifidobacterium animalis, Marvinbryantia formatexigens|Bifidobacterium animalis, Megamonas hypermegale|Bifidobacterium animalis, Megasphaera micronuciformis|Bifidobacterium animalis, Methanobrevibacter smithii|Bifidobacterium animalis, Methanosphaera stadtmanae|Bifidobacterium animalis, Methylobacterium radiotolerans|Bifidobacterium animalis, Mitsuokella multacida|Bifidobacterium animalis, Mobiluncus curtisii|Bifidobacterium animalis, Mycoplasma hominis|Bifidobacterium animalis, Neisseria mucosa|Bifidobacterium animalis, Odoribacter splanchnicus|Bifidobacterium animalis, Olsenella uli|Bifidobacterium animalis, Oribacterium sinus|Bifidobacterium animalis, Oxalobacter formigenes|Bifidobacterium animalis, Parabacteroides distasonis|Bifidobacterium animalis, Parabacteroides johnsonii|Bifidobacterium animalis, Parabacteroides merdae|Bifidobacterium animalis, Parvimonas micra|Bifidobacterium animalis, Pediococcus acidilactici|Bifidobacterium animalis, Pediococcus pentosaceus|Bifidobacterium animalis, Peptoniphilus duerdenii|Bifidobacterium animalis, Peptoniphilus harei|Bifidobacterium animalis, Peptoniphilus lacrimalis|Bifidobacterium animalis, Peptostreptococcus anaerobius|Bifidobacterium animalis, Peptostreptococcus stomatis|Bifidobacterium animalis, Porphyromonas asaccharolytica|Bifidobacterium animalis, Porphyromonas uenonis|Bifidobacterium animalis, Prevotella amnii|Bifidobacterium animalis, Prevotella bergensis|Bifidobacterium animalis, Prevotella bivia|Bifidobacterium animalis, Prevotella buccae|Bifidobacterium animalis, Prevotella buccalis|Bifidobacterium animalis, Prevotella copri|Bifidobacterium animalis, Prevotella disiens|Bifidobacterium animalis, Prevotella melaninogenica|Bifidobacterium animalis, Prevotella multiformis|Bifidobacterium animalis, Prevotella oralis|Bifidobacterium animalis, Prevotella oris|Bifidobacterium animalis, Prevotella salivae|Bifidobacterium animalis, Prevotella timonensis|Bifidobacterium animalis, Propionibacterium acnes|Bifidobacterium animalis, Propionibacterium freudenreichii|Bifidobacterium animalis, Proteus mirabilis|Bifidobacterium animalis, Proteus penneri|Bifidobacterium animalis, Pseudoflavonifractor capillosus|Bifidobacterium animalis, Pseudomonas aeruginosa|Bifidobacterium animalis, Pseudomonas fluorescens|Bifidobacterium animalis, Pseudomonas putida|Bifidobacterium animalis, Pseudoramibacter alactolyticus|Bifidobacterium animalis, Pyramidobacter piscolens|Bifidobacterium animalis, Rhodopseudomonas palustris|Bifidobacterium animalis, Roseburia intestinalis|Bifidobacterium animalis, Roseburia inulinivorans|Bifidobacterium animalis, Rothia dentocariosa|Bifidobacterium animalis, Rothia mucilaginosa|Bifidobacterium animalis, Ruminococcus albus|Bifidobacterium animalis, Ruminococcus bromii|Bifidobacterium animalis, Ruminococcus gnavus|Bifidobacterium animalis, Ruminococcus lactaris|Bifidobacterium animalis, Ruminococcus obeum|Bifidobacterium animalis, Ruminococcus torques|Bifidobacterium animalis, Selenomonas sputigena|Bifidobacterium animalis, Shigella boydii|Bifidobacterium animalis, Shigella dysenteriae|Bifidobacterium animalis, Shigella sonnei|Bifidobacterium animalis, Slackia exigua|Bifidobacterium animalis, Solobacterium moorei|Bifidobacterium animalis, Staphylococcus aureus|Bifidobacterium animalis, Staphylococcus epidermidis|Bifidobacterium animalis, Staphylococcus hominis|Bifidobacterium animalis, Staphylococcus saprophyticus|Bifidobacterium animalis, Staphylococcus warneri|Bifidobacterium animalis, Streptococcus agalactiae|Bifidobacterium animalis, Streptococcus anginosus|Bifidobacterium animalis, Streptococcus australis|Bifidobacterium animalis, Streptococcus bovis|Bifidobacterium animalis, Streptococcus cristatus|Bifidobacterium animalis, Streptococcus dysgalactiae|Bifidobacterium animalis, Streptococcus equinus|Bifidobacterium animalis, Streptococcus gordonii|Bifidobacterium animalis, Streptococcus infantarius|Bifidobacterium animalis, Streptococcus infantis|Bifidobacterium animalis, Streptococcus mitis|Bifidobacterium animalis, Streptococcus mutans|Bifidobacterium animalis, Streptococcus oralis|Bifidobacterium animalis, Streptococcus parasanguinis|Bifidobacterium animalis, Streptococcus peroris|Bifidobacterium animalis, Streptococcus pneumoniae|Bifidobacterium animalis, Streptococcus salivarius|Bifidobacterium animalis, Streptococcus sanguinis|Bifidobacterium animalis, Streptococcus thermophilus|Bifidobacterium animalis, Streptococcus vestibularis|Bifidobacterium animalis, Subdoligranulum variabile|Bifidobacterium animalis, Succinatimonas hippei|Bifidobacterium animalis, Sutterella wadsworthensis|Bifidobacterium animalis, Tropheryma whipplei|Bifidobacterium animalis, Veillonella atypica|Bifidobacterium animalis, Veillonella dispar|Bifidobacterium animalis, Veillonella parvula|Bifidobacterium animalis, Victivallis vadensis|Bifidobacterium bifidum, Bifidobacterium bifidum|Bifidobacterium bifidum, Bifidobacterium breve|Bifidobacterium bifidum, Bifidobacterium catenulatum|Bifidobacterium bifidum, Bifidobacterium dentium|Bifidobacterium bifidum, Bifidobacterium infantis|Bifidobacterium bifidum, Bifidobacterium longum|Bifidobacterium bifidum, Bifidobacterium pseudocatenulatum|Bifidobacterium bifidum, Bilophila wadsworthia|Bifidobacterium bifidum, Blautia hansenii|Bifidobacterium bifidum, Blautia hydrogenotrophica|Bifidobacterium bifidum, Blautia producta|Bifidobacterium bifidum, Blautia schinkii|Bifidobacterium bifidum, Brevibacterium linens|Bifidobacterium bifidum, Brucella ceti|Bifidobacterium bifidum, Brucella suis|Bifidobacterium bifidum, Bulleidia extructa|Bifidobacterium bifidum, Butyrivibrio crossotus|Bifidobacterium bifidum, Campylobacter concisus|Bifidobacterium bifidum, Campylobacter curvus|Bifidobacterium bifidum, Campylobacter gracilis|Bifidobacterium bifidum, Campylobacter hominis|Bifidobacterium bifidum, Capnocytophaga ochracea|Bifidobacterium bifidum, Cardiobacterium hominis|Bifidobacterium bifidum, Catenibacterium mitsuokai|Bifidobacterium bifidum, Catonella morbi|Bifidobacterium bifidum, Citrobacter koseri|Bifidobacterium bifidum, Clostridium asparagiforme|Bifidobacterium bifidum, Clostridium bartlettii|Bifidobacterium bifidum, Clostridium bolteae|Bifidobacterium bifidum, Clostridium botulinum|Bifidobacterium bifidum, Clostridium butyricum|Bifidobacterium bifidum, Clostridium difficile|Bifidobacterium bifidum, Clostridium disporicum|Bifidobacterium bifidum, Clostridium hathewayi|Bifidobacterium bifidum, Clostridium hylemonae|Bifidobacterium bifidum, Clostridium innocuum|Bifidobacterium bifidum, Clostridium leptum|Bifidobacterium bifidum, Clostridium mayombei|Bifidobacterium bifidum, Clostridium methylpentosum|Bifidobacterium bifidum, Clostridium nexile|Bifidobacterium bifidum, Clostridium orbiscindens|Bifidobacterium bifidum, Clostridium perfringens|Bifidobacterium bifidum, Clostridium saccharolyticum|Bifidobacterium bifidum, Clostridium scindens|Bifidobacterium bifidum, Clostridium symbiosum|Bifidobacterium bifidum, Clostridium tertium|Bifidobacterium bifidum, Collinsella aerofaciens|Bifidobacterium bifidum, Collinsella intestinalis|Bifidobacterium bifidum, Collinsella stercoris|Bifidobacterium bifidum, Coprobacillus* sp. D7|*Bifidobacterium bifidum, Coprococcus catus|Bifidobacterium bifidum, Coprococcus comes|Bifidobacterium bifidum, Coprococcus eutactus|Bifidobacterium bifidum, Corynebacterium aurimucosum|Bifidobacterium bifidum, Corynebacterium matruchotii|Bifidobacterium bifidum, Cryptobacterium curtum|Bifidobacterium bifidum, Desulfovibrio desulfuricans|Bifidobacterium bifidum, Desulfovibrio piger|Bifidobacterium*

TABLE 2-continued

Table 2. Specific binary combinations of OTUs. Individual pairings are differentiated by "|" and OTUs within a combination are differentiated by ","

*bifidum, Dialister invisus|Bifidobacterium bifidum, Dialister microaerophilus|Bifidobacterium bifidum, Dorea formicigenerans|Bifidobacterium bifidum, Dorea longicatena|Bifidobacterium bifidum, Eggerthella lenta|Bifidobacterium bifidum, Eikenella corrodens|Bifidobacterium bifidum, Enterobacter cancerogenus|Bifidobacterium bifidum, Enterobacter cloacae|Bifidobacterium bifidum, Enterococcus faecalis|Bifidobacterium bifidum, Enterococcus faecium|Bifidobacterium bifidum, Enterococcus gallinarum|Bifidobacterium bifidum, Erysipelotrichaceae bacterium* 3_1_53|*Bifidobacterium bifidum, Escherichia coli|Bifidobacterium bifidum, Escherichia fergusonii|Bifidobacterium bifidum, Ethanoligenens harbinense|Bifidobacterium bifidum, Eubacterium cellulosolvens|Bifidobacterium bifidum, Eubacterium eligens|Bifidobacterium bifidum, Eubacterium hallii|Bifidobacterium bifidum, Eubacterium limosum|Bifidobacterium bifidum, Eubacterium rectale|Bifidobacterium bifidum, Eubacterium siraeum|Bifidobacterium bifidum, Eubacterium ventriosum|Bifidobacterium bifidum, Faecalibacterium prausnitzii|Bifidobacterium bifidum, Finegoldia magna|Bifidobacterium bifidum, Fusobacterium gonidiaformans|Bifidobacterium bifidum, Fusobacterium mortiferum|Bifidobacterium bifidum, Fusobacterium nucleatum|Bifidobacterium bifidum, Fusobacterium varium|Bifidobacterium bifidum, Gardnerella vaginalis|Bifidobacterium bifidum, Gemella haemolysans|Bifidobacterium bifidum, Gemella morbillorum|Bifidobacterium bifidum, Gordonibacter pamelaeae|Bifidobacterium bifidum, Granulicatella adiacens|Bifidobacterium bifidum, Granulicatella elegans|Bifidobacterium bifidum, Haemophilus influenzae|Bifidobacterium bifidum, Haemophilus parainfluenzae|Bifidobacterium bifidum, Helicobacter pullorum|Bifidobacterium bifidum, Helicobacter pylori|Bifidobacterium bifidum, Holdemania filiformis|Bifidobacterium bifidum, Kingella oralis|Bifidobacterium bifidum, Klebsiella pneumoniae|Bifidobacterium bifidum, Klebsiella variicola|Bifidobacterium bifidum, Lachnospiraceae bacterium* 5_1_57FAA|*Bifidobacterium bifidum, Lactobacillus acidophilus|Bifidobacterium bifidum, Lactobacillus amylovorus|Bifidobacterium bifidum, Lactobacillus brevis|Bifidobacterium bifidum, Lactobacillus casei|Bifidobacterium bifidum, Lactobacillus crispatus|Bifidobacterium bifidum, Lactobacillus delbrueckii|Bifidobacterium bifidum, Lactobacillus fermentum|Bifidobacterium bifidum, Lactobacillus gasseri|Bifidobacterium bifidum, Lactobacillus iners|Bifidobacterium bifidum, Lactobacillus jensenii|Bifidobacterium bifidum, Lactobacillus johnsonii|Bifidobacterium bifidum, Lactobacillus paracasei|Bifidobacterium bifidum, Lactobacillus plantarum|Bifidobacterium bifidum, Lactobacillus reuteri|Bifidobacterium bifidum, Lactobacillus rhamnosus|Bifidobacterium bifidum, Lactobacillus ruminis|Bifidobacterium bifidum, Lactobacillus sakei|Bifidobacterium bifidum, Lactobacillus salivarius|Bifidobacterium bifidum, Lactococcus lactis|Bifidobacterium bifidum, Lautropia mirabilis|Bifidobacterium bifidum, Leuconostoc citreum|Bifidobacterium bifidum, Leuconostoc gasicomitatum|Bifidobacterium bifidum, Leuconostoc mesenteroides|Bifidobacterium bifidum, Listeria monocytogenes|Bifidobacterium bifidum, Marvinbryantia formatexigens|Bifidobacterium bifidum, Megamonas hypermegale|Bifidobacterium bifidum, Megasphaera micronuciformis|Bifidobacterium bifidum, Methanobrevibacter smithii|Bifidobacterium bifidum, Methanosphaera stadtmanae|Bifidobacterium bifidum, Methylobacterium radiotolerans|Bifidobacterium bifidum, Mitsuokella multacida|Bifidobacterium bifidum, Mobiluncus curtisii|Bifidobacterium bifidum, Mycoplasma hominis|Bifidobacterium bifidum, Neisseria mucosa|Bifidobacterium bifidum, Odoribacter splanchnicus|Bifidobacterium bifidum, Olsenella uli|Bifidobacterium bifidum, Oribacterium sinus|Bifidobacterium bifidum, Oxalobacter formigenes|Bifidobacterium bifidum, Parabacteroides distasonis|Bifidobacterium bifidum, Parabacteroides johnsonii|Bifidobacterium bifidum, Parabacteroides merdae|Bifidobacterium bifidum, Parvimonas micra|Bifidobacterium bifidum, Pediococcus acidilactici|Bifidobacterium bifidum, Pediococcus pentosaceus|Bifidobacterium bifidum, Peptoniphilus duerdenii|Bifidobacterium bifidum, Peptoniphilus harei|Bifidobacterium bifidum, Peptoniphilus lacrimalis|Bifidobacterium bifidum, Peptostreptococcus anaerobius|Bifidobacterium bifidum, Peptostreptococcus stomatis|Bifidobacterium bifidum, Porphyromonas asaccharolytica|Bifidobacterium bifidum, Porphyromonas uenonis|Bifidobacterium bifidum, Prevotella amnii|Bifidobacterium bifidum, Prevotella bergensis|Bifidobacterium bifidum, Prevotella bivia|Bifidobacterium bifidum, Prevotella buccae|Bifidobacterium bifidum, Prevotella buccalis|Bifidobacterium bifidum, Prevotella copri|Bifidobacterium bifidum, Prevotella disiens|Bifidobacterium bifidum, Prevotella melaninogenica|Bifidobacterium bifidum, Prevotella multiformis|Bifidobacterium bifidum, Prevotella oralis|Bifidobacterium bifidum, Prevotella oris|Bifidobacterium bifidum, Prevotella salivae|Bifidobacterium bifidum, Prevotella timonensis|Bifidobacterium bifidum, Propionibacterium acnes|Bifidobacterium bifidum, Propionibacterium freudenreichii|Bifidobacterium bifidum, Proteus mirabilis|Bifidobacterium bifidum, Proteus penneri|Bifidobacterium bifidum, Pseudoflavonifractor capillosus|Bifidobacterium bifidum, Pseudomonas aeruginosa|Bifidobacterium bifidum, Pseudomonas fluorescens|Bifidobacterium bifidum, Pseudomonas putida|Bifidobacterium bifidum, Pseudoramibacter alactolyticus|Bifidobacterium bifidum, Pyramidobacter piscolens|Bifidobacterium bifidum, Rhodopseudomonas palustris|Bifidobacterium bifidum, Roseburia intestinalis|Bifidobacterium bifidum, Roseburia inulinivorans|Bifidobacterium bifidum, Rothia dentocariosa|Bifidobacterium bifidum, Rothia mucilaginosa|Bifidobacterium bifidum, Ruminococcus albus|Bifidobacterium bifidum, Ruminococcus bromii|Bifidobacterium bifidum, Ruminococcus gnavus|Bifidobacterium bifidum, Ruminococcus lactaris|Bifidobacterium bifidum, Ruminococcus obeum|Bifidobacterium bifidum, Ruminococcus torques|Bifidobacterium bifidum, Selenomonas sputigena|Bifidobacterium bifidum, Shigella boydii|Bifidobacterium bifidum, Shigella dysenteriae|Bifidobacterium bifidum, Shigella sonnei|Bifidobacterium bifidum, Slackia exigua|Bifidobacterium bifidum, Solobacterium moorei|Bifidobacterium bifidum, Staphylococcus aureus|Bifidobacterium bifidum, Staphylococcus epidermidis|Bifidobacterium bifidum, Staphylococcus hominis|Bifidobacterium bifidum, Staphylococcus saprophyticus|Bifidobacterium bifidum, Staphylococcus warneri|Bifidobacterium bifidum, Streptococcus agalactiae|Bifidobacterium bifidum, Streptococcus anginosus|Bifidobacterium bifidum, Streptococcus australis|Bifidobacterium bifidum, Streptococcus bovis|Bifidobacterium bifidum, Streptococcus cristatus|Bifidobacterium bifidum, Streptococcus dysgalactiae|Bifidobacterium bifidum, Streptococcus equinus|Bifidobacterium bifidum, Streptococcus gordonii|Bifidobacterium bifidum, Streptococcus infantarius|Bifidobacterium bifidum, Streptococcus infantis|Bifidobacterium bifidum, Streptococcus mitis|Bifidobacterium bifidum, Streptococcus mutans|Bifidobacterium bifidum, Streptococcus oralis|Bifidobacterium bifidum, Streptococcus parasanguinis|Bifidobacterium bifidum, Streptococcus peroris|Bifidobacterium bifidum, Streptococcus pneumoniae|Bifidobacterium bifidum, Streptococcus salivarius|Bifidobacterium bifidum, Streptococcus sanguinis|Bifidobacterium bifidum, Streptococcus thermophilus|Bifidobacterium bifidum, Streptococcus vestibularis|Bifidobacterium bifidum, Subdoligranulum variabile|Bifidobacterium bifidum, Succinatimonas hippei|Bifidobacterium bifidum, Sutterella wadsworthensis|Bifidobacterium bifidum, Tropheryma whipplei|Bifidobacterium bifidum, Veillonella atypica|Bifidobacterium bifidum, Veillonella dispar|Bifidobacterium bifidum, Veillonella parvula|Bifidobacterium bifidum, Victivallis vadensis|Bifidobacterium breve, Bifidobacterium breve|Bifidobacterium breve, Bifidobacterium catenulatum|Bifidobacterium breve, Bifidobacterium dentium|Bifidobacterium breve, Bifidobacterium infantis|Bifidobacterium breve, Bifidobacterium longum|Bifidobacterium breve, Bifidobacterium pseudocatenulatum|Bifidobacterium breve, Bilophila wadsworthia|Bifidobacterium breve, Blautia hansenii|Bifidobacterium breve, Blautia hydrogenotrophica|Bifidobacterium breve, Blautia producta|Bifidobacterium breve, Blautia schinkii|Bifidobacterium breve, Brevibacterium linens|Bifidobacterium breve, Brucella ceti|Bifidobacterium breve, Brucella suis|Bifidobacterium breve, Bulleidia extructa|Bifidobacterium breve, Butyrivibrio crossotus|Bifidobacterium breve, Campylobacter concisus|Bifidobacterium breve, Campylobacter curvus|Bifidobacterium breve, Campylobacter gracilis|Bifidobacterium breve, Campylobacter hominis|Bifidobacterium breve, Capnocytophaga ochracea|Bifidobacterium breve, Cardiobacterium hominis|Bifidobacterium breve, Catenibacterium mitsuokai|Bifidobacterium breve, Catonella morbi|Bifidobacterium breve, Citrobacter koseri|Bifidobacterium breve, Clostridium asparagiforme|Bifidobacterium breve, Clostridium bartlettii|Bifidobacterium breve, Clostridium bolteae|Bifidobacterium breve, Clostridium botulinum|Bifidobacterium breve, Clostridium butyricum|Bifidobacterium breve, Clostridium difficile|Bifidobacterium breve, Clostridium disporicum|Bifidobacterium breve, Clostridium hathewayi|Bifidobacterium breve, Clostridium hylemonae|Bifidobacterium breve, Clostridium innocuum|Bifidobacterium breve, Clostridium leptum|Bifidobacterium breve, Clostridium mayombei|Bifidobacterium breve, Clostridium methylpentosum|Bifidobacterium breve, Clostridium nexile|Bifidobacterium breve, Clostridium orbiscindens|Bifidobacterium breve, Clostridium perfringens|Bifidobacterium breve, Clostridium*

TABLE 2-continued

| Table 2. Specific binary combinations of OTUs. Individual pairings are differentiated by "\|" and OTUs within a combination are differentiated by "," |
|---|
| saccharolyticum\|Bifidobacterium breve, Clostridium scindens\|Bifidobacterium breve, Clostridium symbiosum\|Bifidobacterium breve, Clostridium tertium\|Bifidobacterium breve, Collinsella aerofaciens\|Bifidobacterium breve, Collinsella intestinalis\|Bifidobacterium breve, Collinsella stercoris\|Bifidobacterium breve, Coprobacillus sp. D7\|Bifidobacterium breve, Coprococcus catus\|Bifidobacterium breve, Coprococcus comes\|Bifidobacterium breve, Coprococcus eutactus\|Bifidobacterium breve, Corynebacterium aurimucosum\|Bifidobacterium breve, Corynebacterium matruchotii\|Bifidobacterium breve, Cryptobacterium curtum\|Bifidobacterium breve, Desulfovibrio desulfuricans\|Bifidobacterium breve, Desulfovibrio piger\|Bifidobacterium breve, Dialister invisus\|Bifidobacterium breve, Dialister microaerophilus\|Bifidobacterium breve, Dorea formicigenerans\|Bifidobacterium breve, Dorea longicatena\|Bifidobacterium breve, Eggerthella lenta\|Bifidobacterium breve, Eikenella corrodens\|Bifidobacterium breve, Enterobacter cancerogenus\|Bifidobacterium breve, Enterobacter cloacae\|Bifidobacterium breve, Enterococcus faecalis\|Bifidobacterium breve, Enterococcus faecium\|Bifidobacterium breve, Enterococcus gallinarum\|Bifidobacterium breve, Erysipelotrichaceae bacterium 3_1_53\|Bifidobacterium breve, Escherichia coli\|Bifidobacterium breve, Escherichia fergusonii\|Bifidobacterium breve, Ethanoligenens harbinense\|Bifidobacterium breve, Eubacterium cellulosolvens\|Bifidobacterium breve, Eubacterium eligens\|Bifidobacterium breve, Eubacterium hallii\|Bifidobacterium breve, Eubacterium limosum\|Bifidobacterium breve, Eubacterium rectale\|Bifidobacterium breve, Eubacterium siraeum\|Bifidobacterium breve, Eubacterium ventriosum\|Bifidobacterium breve, Faecalibacterium prausnitzii\|Bifidobacterium breve, Finegoldia magna\|Bifidobacterium breve, Fusobacterium gonidiaformans\|Bifidobacterium breve, Fusobacterium mortiferum\|Bifidobacterium breve, Fusobacterium nucleatum\|Bifidobacterium breve, Fusobacterium varium\|Bifidobacterium breve, Gardnerella vaginalis\|Bifidobacterium breve, Gemella haemolysans\|Bifidobacterium breve, Gemella morbillorum\|Bifidobacterium breve, Gordonibacter pamelaeae\|Bifidobacterium breve, Granulicatella adiacens\|Bifidobacterium breve, Granulicatella elegans\|Bifidobacterium breve, Haemophilus influenzae\|Bifidobacterium breve, Haemophilus parainfluenzae\|Bifidobacterium breve, Helicobacter pullorum\|Bifidobacterium breve, Helicobacter pylori\|Bifidobacterium breve, Holdemania filiformis\|Bifidobacterium breve, Kingella oralis\|Bifidobacterium breve, Klebsiella pneumoniae\|Bifidobacterium breve, Klebsiella variicola\|Bifidobacterium breve, Lachnospiraceae bacterium 5_1_57FAA\|Bifidobacterium breve, Lactobacillus acidophilus\|Bifidobacterium breve, Lactobacillus amylovorus\|Bifidobacterium breve, Lactobacillus brevis\|Bifidobacterium breve, Lactobacillus casei\|Bifidobacterium breve, Lactobacillus crispatus\|Bifidobacterium breve, Lactobacillus delbrueckii\|Bifidobacterium breve, Lactobacillus fermentum\|Bifidobacterium breve, Lactobacillus gasseri\|Bifidobacterium breve, Lactobacillus iners\|Bifidobacterium breve, Lactobacillus jensenii\|Bifidobacterium breve, Lactobacillus johnsonii\|Bifidobacterium breve, Lactobacillus paracasei\|Bifidobacterium breve, Lactobacillus plantarum\|Bifidobacterium breve, Lactobacillus reuteri\|Bifidobacterium breve, Lactobacillus rhamnosus\|Bifidobacterium breve, Lactobacillus ruminis\|Bifidobacterium breve, Lactobacillus sakei\|Bifidobacterium breve, Lactobacillus salivarius\|Bifidobacterium breve, Lactococcus lactis\|Bifidobacterium breve, Lautropia mirabilis\|Bifidobacterium breve, Leuconostoc citreum\|Bifidobacterium breve, Leuconostoc gasicomitatum\|Bifidobacterium breve, Leuconostoc mesenteroides\|Bifidobacterium breve, Listeria monocytogenes\|Bifidobacterium breve, Marvinbryantia formatexigens\|Bifidobacterium breve, Megamonas hypermegale\|Bifidobacterium breve, Megasphaera micronuciformis\|Bifidobacterium breve, Methanobrevibacter smithii\|Bifidobacterium breve, Methanosphaera stadtmanae\|Bifidobacterium breve, Methylobacterium radiotolerans\|Bifidobacterium breve, Mitsuokella multacida\|Bifidobacterium breve, Mobiluncus curtisii\|Bifidobacterium breve, Mycoplasma hominis\|Bifidobacterium breve, Neisseria mucosa\|Bifidobacterium breve, Odoribacter splanchnicus\|Bifidobacterium breve, Olsenella uli\|Bifidobacterium breve, Oribacterium sinus\|Bifidobacterium breve, Oxalobacter formigenes\|Bifidobacterium breve, Parabacteroides distasonis\|Bifidobacterium breve, Parabacteroides johnsonii\|Bifidobacterium breve, Parabacteroides merdae\|Bifidobacterium breve, Parvimonas micra\|Bifidobacterium breve, Pediococcus acidilactici\|Bifidobacterium breve, Pediococcus pentosaceus\|Bifidobacterium breve, Peptoniphilus duerdenii\|Bifidobacterium breve, Peptoniphilus harei\|Bifidobacterium breve, Peptoniphilus lacrimalis\|Bifidobacterium breve, Peptostreptococcus anaerobius\|Bifidobacterium breve, Peptostreptococcus stomatis\|Bifidobacterium breve, Porphyromonas asaccharolytica\|Bifidobacterium breve, Porphyromonas uenonis\|Bifidobacterium breve, Prevotella amnii\|Bifidobacterium breve, Prevotella bergensis\|Bifidobacterium breve, Prevotella bivia\|Bifidobacterium breve, Prevotella buccae\|Bifidobacterium breve, Prevotella buccalis\|Bifidobacterium breve, Prevotella copri\|Bifidobacterium breve, Prevotella disiens\|Bifidobacterium breve, Prevotella melaninogenica\|Bifidobacterium breve, Prevotella multiformis\|Bifidobacterium breve, Prevotella oralis\|Bifidobacterium breve, Prevotella oris\|Bifidobacterium breve, Prevotella salivae\|Bifidobacterium breve, Prevotella timonensis\|Bifidobacterium breve, Propionibacterium acnes\|Bifidobacterium breve, Propionibacterium freudenreichii\|Bifidobacterium breve, Proteus mirabilis\|Bifidobacterium breve, Proteus penneri\|Bifidobacterium breve, Pseudoflavonifractor capillosus\|Bifidobacterium breve, Pseudomonas aeruginosa\|Bifidobacterium breve, Pseudomonas fluorescens\|Bifidobacterium breve, Pseudomonas putida\|Bifidobacterium breve, Pseudoramibacter alactolyticus\|Bifidobacterium breve, Pyramidobacter piscolens\|Bifidobacterium breve, Rhodopseudomonas palustris\|Bifidobacterium breve, Roseburia intestinalis\|Bifidobacterium breve, Roseburia inulinivorans\|Bifidobacterium breve, Rothia dentocariosa\|Bifidobacterium breve, Rothia mucilaginosa\|Bifidobacterium breve, Ruminococcus albus\|Bifidobacterium breve, Ruminococcus bromii\|Bifidobacterium breve, Ruminococcus gnavus\|Bifidobacterium breve, Ruminococcus lactaris\|Bifidobacterium breve, Ruminococcus obeum\|Bifidobacterium breve, Ruminococcus torques\|Bifidobacterium breve, Selenomonas sputigena\|Bifidobacterium breve, Shigella boydii\|Bifidobacterium breve, Shigella dysenteriae\|Bifidobacterium breve, Shigella sonnei\|Bifidobacterium breve, Slackia exigua\|Bifidobacterium breve, Solobacterium moorei\|Bifidobacterium breve, Staphylococcus aureus\|Bifidobacterium breve, Staphylococcus epidermidis\|Bifidobacterium breve, Staphylococcus hominis\|Bifidobacterium breve, Staphylococcus saprophyticus\|Bifidobacterium breve, Staphylococcus warneri\|Bifidobacterium breve, Streptococcus agalactiae\|Bifidobacterium breve, Streptococcus anginosus\|Bifidobacterium breve, Streptococcus australis\|Bifidobacterium breve, Streptococcus bovis\|Bifidobacterium breve, Streptococcus cristatus\|Bifidobacterium breve, Streptococcus dysgalactiae\|Bifidobacterium breve, Streptococcus equinus\|Bifidobacterium breve, Streptococcus gordonii\|Bifidobacterium breve, Streptococcus infantarius\|Bifidobacterium breve, Streptococcus infantis\|Bifidobacterium breve, Streptococcus mitis\|Bifidobacterium breve, Streptococcus mutans\|Bifidobacterium breve, Streptococcus oralis\|Bifidobacterium breve, Streptococcus parasanguinis\|Bifidobacterium breve, Streptococcus peroris\|Bifidobacterium breve, Streptococcus pneumoniae\|Bifidobacterium breve, Streptococcus salivarius\|Bifidobacterium breve, Streptococcus sanguinis\|Bifidobacterium breve, Streptococcus thermophilus\|Bifidobacterium breve, Streptococcus vestibularis\|Bifidobacterium breve, Subdoligranulum variabile\|Bifidobacterium breve, Succinatimonas hippei\|Bifidobacterium breve, Sutterella wadsworthensis\|Bifidobacterium breve, Tropheryma whipplei\|Bifidobacterium breve, Veillonella atypica\|Bifidobacterium breve, Veillonella dispar\|Bifidobacterium breve, Veillonella parvula\|Bifidobacterium breve, Victivallis vadensis\|Bifidobacterium catenulatum, Bifidobacterium catenulatum\|Bifidobacterium catenulatum, Bifidobacterium dentium\|Bifidobacterium catenulatum, Bifidobacterium infantis\|Bifidobacterium catenulatum, Bifidobacterium longum\|Bifidobacterium catenulatum, Bifidobacterium pseudocatenulatum\|Bifidobacterium catenulatum, Bilophila wadsworthia\|Bifidobacterium catenulatum, Blautia hansenii\|Bifidobacterium catenulatum, Blautia hydrogenotrophica\|Bifidobacterium catenulatum, Blautia producta\|Bifidobacterium catenulatum, Blautia schinkii\|Bifidobacterium catenulatum, Brevibacterium linens\|Bifidobacterium catenulatum, Brucella ceti\|Bifidobacterium catenulatum, Brucella suis\|Bifidobacterium catenulatum, Bulleidia extructa\|Bifidobacterium catenulatum, Butyrivibrio crossotus\|Bifidobacterium catenulatum, Campylobacter concisus\|Bifidobacterium catenulatum, Campylobacter curvus\|Bifidobacterium catenulatum, Campylobacter gracilis\|Bifidobacterium catenulatum, Campylobacter hominis\|Bifidobacterium catenulatum, Capnocytophaga ochracea\|Bifidobacterium catenulatum, Cardiobacterium hominis\|Bifidobacterium catenulatum, Catenibacterium mitsuokai\|Bifidobacterium catenulatum, Catonella morbi\|Bifidobacterium catenulatum, Citrobacter koseri\|Bifidobacterium catenulatum, Clostridium asparagiforme\|Bifidobacterium catenulatum, Clostridium bartlettii\|Bifidobacterium catenulatum, Clostridium bolteae\|Bifidobacterium catenulatum, Clostridium botulinum\|Bifidobacterium catenulatum, Clostridium butyricum\|Bifidobacterium catenulatum, Clostridium difficile\|Bifidobacterium catenulatum, Clostridium disporicum\|Bifidobacterium catenulatum, Clostridium |

TABLE 2-continued

Table 2. Specific binary combinations of OTUs. Individual pairings are differentiated by "|" and OTUs within a combination are differentiated by ","

hathewayi|Bifidobacterium catenulatum, Clostridium hylemonae|Bifidobacterium catenulatum, Clostridium innocuum|Bifidobacterium catenulatum, Clostridium leptum|Bifidobacterium catenulatum, Clostridium mayombei|Bifidobacterium catenulatum, Clostridium methylpentosum|Bifidobacterium catenulatum, Clostridium nexile|Bifidobacterium catenulatum, Clostridium orbiscindens|Bifidobacterium catenulatum, Clostridium perfringens|Bifidobacterium catenulatum, Clostridium saccharolyticum|Bifidobacterium catenulatum, Clostridium scindens|Bifidobacterium catenulatum, Clostridium symbiosum|Bifidobacterium catenulatum, Clostridium tertium|Bifidobacterium catenulatum, Collinsella aerofaciens|Bifidobacterium catenulatum, Collinsella intestinalis|Bifidobacterium catenulatum, Collinsella stercoris|Bifidobacterium catenulatum, Coprobacillus sp. D7|Bifidobacterium catenulatum, Coprococcus catus|Bifidobacterium catenulatum, Coprococcus comes|Bifidobacterium catenulatum, Coprococcus eutactus|Bifidobacterium catenulatum, Corynebacterium aurimucosum|Bifidobacterium catenulatum, Corynebacterium matruchotii|Bifidobacterium catenulatum, Cryptobacterium curtum|Bifidobacterium catenulatum, Desulfovibrio desulfuricans|Bifidobacterium catenulatum, Desulfovibrio piger|Bifidobacterium catenulatum, Dialister invisus|Bifidobacterium catenulatum, Dialister microaerophilus|Bifidobacterium catenulatum, Dorea formicigenerans|Bifidobacterium catenulatum, Dorea longicatena|Bifidobacterium catenulatum, Eggerthella lenta|Bifidobacterium catenulatum, Eikenella corrodens|Bifidobacterium catenulatum, Enterobacter cancerogenus|Bifidobacterium catenulatum, Enterobacter cloacae|Bifidobacterium catenulatum, Enterococcus faecalis|Bifidobacterium catenulatum, Enterococcus faecium|Bifidobacterium catenulatum, Enterococcus gallinarum|Bifidobacterium catenulatum, Erysipelotrichaceae bacterium 3_1_53|Bifidobacterium catenulatum, Escherichia coli|Bifidobacterium catenulatum, Escherichia fergusonii|Bifidobacterium catenulatum, Ethanoligenens harbinense|Bifidobacterium catenulatum, Eubacterium cellulosolvens|Bifidobacterium catenulatum, Eubacterium eligens|Bifidobacterium catenulatum, Eubacterium hallii|Bifidobacterium catenulatum, Eubacterium limosum|Bifidobacterium catenulatum, Eubacterium rectale|Bifidobacterium catenulatum, Eubacterium siraeum|Bifidobacterium catenulatum, Eubacterium ventriosum|Bifidobacterium catenulatum, Faecalibacterium prausnitzii|Bifidobacterium catenulatum, Finegoldia magna|Bifidobacterium catenulatum, Fusobacterium gonidiaformans|Bifidobacterium catenulatum, Fusobacterium mortiferum|Bifidobacterium catenulatum, Fusobacterium nucleatum|Bifidobacterium catenulatum, Fusobacterium varium|Bifidobacterium catenulatum, Gardnerella vaginalis|Bifidobacterium catenulatum, Gemella haemolysans|Bifidobacterium catenulatum, Gemella morbillorum|Bifidobacterium catenulatum, Gordonibacter pamelaeae|Bifidobacterium catenulatum, Granulicatella adiacens|Bifidobacterium catenulatum, Granulicatella elegans|Bifidobacterium catenulatum, Haemophilus influenzae|Bifidobacterium catenulatum, Haemophilus parainfluenzae|Bifidobacterium catenulatum, Helicobacter pullorum|Bifidobacterium catenulatum, Helicobacter pylori|Bifidobacterium catenulatum, Holdemania filiformis|Bifidobacterium catenulatum, Kingella oralis|Bifidobacterium catenulatum, Klebsiella pneumoniae|Bifidobacterium catenulatum, Klebsiella variicola|Bifidobacterium catenulatum, Lachnospiraceae bacterium 5_1_57FAA|Bifidobacterium catenulatum, Lactobacillus acidophilus|Bifidobacterium catenulatum, Lactobacillus amylovorus|Bifidobacterium catenulatum, Lactobacillus brevis|Bifidobacterium catenulatum, Lactobacillus casei|Bifidobacterium catenulatum, Lactobacillus crispatus|Bifidobacterium catenulatum, Lactobacillus delbrueckii|Bifidobacterium catenulatum, Lactobacillus fermentum|Bifidobacterium catenulatum, Lactobacillus gasseri|Bifidobacterium catenulatum, Lactobacillus iners|Bifidobacterium catenulatum, Lactobacillus jensenii|Bifidobacterium catenulatum, Lactobacillus johnsonii|Bifidobacterium catenulatum, Lactobacillus paracasei|Bifidobacterium catenulatum, Lactobacillus plantarum|Bifidobacterium catenulatum, Lactobacillus reuteri|Bifidobacterium catenulatum, Lactobacillus rhamnosus|Bifidobacterium catenulatum, Lactobacillus ruminis|Bifidobacterium catenulatum, Lactobacillus sakei|Bifidobacterium catenulatum, Lactobacillus salivarius|Bifidobacterium catenulatum, Lactococcus lactis|Bifidobacterium catenulatum, Lautropia mirabilis|Bifidobacterium catenulatum, Leuconostoc citreum|Bifidobacterium catenulatum, Leuconostoc gasicomitatum|Bifidobacterium catenulatum, Leuconostoc mesenteroides|Bifidobacterium catenulatum, Listeria monocytogenes|Bifidobacterium catenulatum, Marvinbryantia formatexigens|Bifidobacterium catenulatum, Megamonas hypermegale|Bifidobacterium catenulatum, Megasphaera micronuciformis|Bifidobacterium catenulatum, Methanobrevibacter smithii|Bifidobacterium catenulatum, Methanosphaera stadtmanae|Bifidobacterium catenulatum, Methylobacterium radiotolerans|Bifidobacterium catenulatum, Mitsuokella multacida|Bifidobacterium catenulatum, Mobiluncus curtisii|Bifidobacterium catenulatum, Mycoplasma hominis|Bifidobacterium catenulatum, Neisseria mucosa|Bifidobacterium catenulatum, Odoribacter splanchnicus|Bifidobacterium catenulatum, Olsenella uli|Bifidobacterium catenulatum, Oribacterium sinus|Bifidobacterium catenulatum, Oxalobacter formigenes|Bifidobacterium catenulatum, Parabacteroides distasonis|Bifidobacterium catenulatum, Parabacteroides johnsonii|Bifidobacterium catenulatum, Parabacteroides merdae|Bifidobacterium catenulatum, Parvimonas micra|Bifidobacterium catenulatum, Pediococcus acidilactici|Bifidobacterium catenulatum, Pediococcus pentosaceus|Bifidobacterium catenulatum, Peptoniphilus duerdenii|Bifidobacterium catenulatum, Peptoniphilus harei|Bifidobacterium catenulatum, Peptoniphilus lacrimalis|Bifidobacterium catenulatum, Peptostreptococcus anaerobius|Bifidobacterium catenulatum, Peptostreptococcus stomatis|Bifidobacterium catenulatum, Porphyromonas asaccharolytica|Bifidobacterium catenulatum, Porphyromonas uenonis|Bifidobacterium catenulatum, Prevotella amnii|Bifidobacterium catenulatum, Prevotella bergensis|Bifidobacterium catenulatum, Prevotella bivia|Bifidobacterium catenulatum, Prevotella buccae|Bifidobacterium catenulatum, Prevotella buccalis|Bifidobacterium catenulatum, Prevotella copri|Bifidobacterium catenulatum, Prevotella disiens|Bifidobacterium catenulatum, Prevotella melaninogenica|Bifidobacterium catenulatum, Prevotella multiformis|Bifidobacterium catenulatum, Prevotella oralis|Bifidobacterium catenulatum, Prevotella oris|Bifidobacterium catenulatum, Prevotella salivae|Bifidobacterium catenulatum, Prevotella timonensis|Bifidobacterium catenulatum, Propionibacterium acnes|Bifidobacterium catenulatum, Propionibacterium freudenreichii|Bifidobacterium catenulatum, Proteus mirabilis|Bifidobacterium catenulatum, Proteus penneri|Bifidobacterium catenulatum, Pseudoflavonifractor capillosus|Bifidobacterium catenulatum, Pseudomonas aeruginosa|Bifidobacterium catenulatum, Pseudomonas fluorescens|Bifidobacterium catenulatum, Pseudomonas putida|Bifidobacterium catenulatum, Pseudoramibacter alactolyticus|Bifidobacterium catenulatum, Pyramidobacter piscolens|Bifidobacterium catenulatum, Rhodopseudomonas palustris|Bifidobacterium catenulatum, Roseburia intestinalis|Bifidobacterium catenulatum, Roseburia inulinivorans|Bifidobacterium catenulatum, Rothia dentocariosa|Bifidobacterium catenulatum, Rothia mucilaginosa|Bifidobacterium catenulatum, Ruminococcus albus|Bifidobacterium catenulatum, Ruminococcus bromii|Bifidobacterium catenulatum, Ruminococcus gnavus|Bifidobacterium catenulatum, Ruminococcus lactaris|Bifidobacterium catenulatum, Ruminococcus obeum|Bifidobacterium catenulatum, Ruminococcus torques|Bifidobacterium catenulatum, Selenomonas sputigena|Bifidobacterium catenulatum, Shigella boydii|Bifidobacterium catenulatum, Shigella dysenteriae|Bifidobacterium catenulatum, Shigella sonnei|Bifidobacterium catenulatum, Slackia exigua|Bifidobacterium catenulatum, Solobacterium moorei|Bifidobacterium catenulatum, Staphylococcus aureus|Bifidobacterium catenulatum, Staphylococcus epidermidis|Bifidobacterium catenulatum, Staphylococcus hominis|Bifidobacterium catenulatum, Staphylococcus saprophyticus|Bifidobacterium catenulatum, Staphylococcus warneri|Bifidobacterium catenulatum, Streptococcus agalactiae|Bifidobacterium catenulatum, Streptococcus anginosus|Bifidobacterium catenulatum, Streptococcus australis|Bifidobacterium catenulatum, Streptococcus bovis|Bifidobacterium catenulatum, Streptococcus cristatus|Bifidobacterium catenulatum, Streptococcus dysgalactiae|Bifidobacterium catenulatum, Streptococcus equinus|Bifidobacterium catenulatum, Streptococcus gordonii|Bifidobacterium catenulatum, Streptococcus infantarius|Bifidobacterium catenulatum, Streptococcus infantis|Bifidobacterium catenulatum, Streptococcus mitis|Bifidobacterium catenulatum, Streptococcus mutans|Bifidobacterium catenulatum, Streptococcus oralis|Bifidobacterium catenulatum, Streptococcus parasanguinis|Bifidobacterium catenulatum, Streptococcus peroris|Bifidobacterium catenulatum, Streptococcus pneumoniae|Bifidobacterium catenulatum, Streptococcus salivarius|Bifidobacterium catenulatum, Streptococcus sanguinis|Bifidobacterium catenulatum, Streptococcus thermophilus|Bifidobacterium catenulatum, Streptococcus vestibularis|Bifidobacterium catenulatum, Subdoligranulum variabile|Bifidobacterium catenulatum, Succinatimonas hippei|Bifidobacterium catenulatum, Sutterella wadsworthensis|Bifidobacterium catenulatum, Tropheryma whipplei|Bifidobacterium TABLE 2-continued Table 2. Specific binary combinations of OTUs. Individual pairings are differentiated by "|" and OTUs within a combination are differentiated by ","

catenulatum, Veillonella atypica|Bifidobacterium catenulatum, Veillonella dispar|Bifidobacterium catenulatum, Veillonella parvula|Bifidobacterium catenulatum, Victivallis vadensis|Bifidobacterium dentium, Bifidobacterium dentium|Bifidobacterium dentium, Bifidobacterium infantis|Bifidobacterium dentium, Bifidobacterium longum|Bifidobacterium dentium, Bifidobacterium pseudocatenulatum|Bifidobacterium dentium, Bilophila wadsworthia|Bifidobacterium dentium, Blautia hansenii|Bifidobacterium dentium, Blautia hydrogenotrophica|Bifidobacterium dentium, Blautia producta|Bifidobacterium dentium, Blautia schinkii|Bifidobacterium dentium, Brevibacterium linens|Bifidobacterium dentium, Brucella ceti|Bifidobacterium dentium, Brucella suis|Bifidobacterium dentium, Bulleidia extructa|Bifidobacterium dentium, Butyrivibrio crossotus|Bifidobacterium dentium, Campylobacter concisus|Bifidobacterium dentium, Campylobacter curvus|Bifidobacterium dentium, Campylobacter gracilis|Bifidobacterium dentium, Campylobacter hominis|Bifidobacterium dentium, Capnocytophaga ochracea|Bifidobacterium dentium, Cardiobacterium hominis|Bifidobacterium dentium, Catenibacterium mitsuokai|Bifidobacterium dentium, Catonella morbi|Bifidobacterium dentium, Citrobacter koseri|Bifidobacterium dentium, Clostridium asparagiforme|Bifidobacterium dentium, Clostridium bartlettii|Bifidobacterium dentium, Clostridium bolteae|Bifidobacterium dentium, Clostridium botulinum|Bifidobacterium dentium, Clostridium butyricum|Bifidobacterium dentium, Clostridium difficile|Bifidobacterium dentium, Clostridium disporicum|Bifidobacterium dentium, Clostridium hathewayi|Bifidobacterium dentium, Clostridium hylemonae|Bifidobacterium dentium, Clostridium innocuum|Bifidobacterium dentium, Clostridium leptum|Bifidobacterium dentium, Clostridium mayombei|Bifidobacterium dentium, Clostridium methylpentosuna|Bifidobacterium dentium, Clostridium nexile|Bifidobacterium dentium, Clostridium orbiscindens|Bifidobacterium dentium, Clostridium perfringens|Bifidobacterium dentium, Clostridium saccharolyticum|Bifidobacterium dentium, Clostridium scindens|Bifidobacterium dentium, Clostridium symbiosum|Bifidobacterium dentium, Clostridium tertium|Bifidobacterium dentium, Collinsella aerofaciens|Bifidobacterium dentium, Collinsella intestinalis|Bifidobacterium dentium, Collinsella stercoris|Bifidobacterium dentium, Coprobacillus sp. D7|Bifidobacterium dentium, Coprococcus catus|Bifidobacterium dentium, Coprococcus comes|Bifidobacterium dentium, Coprococcus eutactus|Bifidobacterium dentium, Corynebacterium aurimucosum|Bifidobacterium dentium, Corynebacterium matruchotii|Bifidobacterium dentium, Cryptobacterium curtum|Bifidobacterium dentium, Desulfovibrio desulfuricans|Bifidobacterium dentium, Desulfovibrio piger|Bifidobacterium dentium, Dialister invisus|Bifidobacterium dentium, Dialister microaerophilus|Bifidobacterium dentium, Dorea formicigenerans|Bifidobacterium dentium, Dorea longicatena|Bifidobacterium dentium, Eggerthella lenta|Bifidobacterium dentium, Eikenella corrodens|Bifidobacterium dentium, Enterobacter cancerogenus|Bifidobacterium dentium, Enterobacter cloacae|Bifidobacterium dentium, Enterococcus faecalis|Bifidobacterium dentium, Enterococcus faecium|Bifidobacterium dentium, Enterococcus gallinarum|Bifidobacterium dentium, Erysipelotrichaceae bacterium 3_1_53|Bifidobacterium dentium, Escherichia coli|Bifidobacterium dentium, Escherichia fergusonii|Bifidobacterium dentium, Ethanoligenens harbinense|Bifidobacterium dentium, Eubacterium cellulosolvens|Bifidobacterium dentium, Eubacterium eligens|Bifidobacterium dentium, Eubacterium hallii|Bifidobacterium dentium, Eubacterium limosum|Bifidobacterium dentium, Eubacterium rectale|Bifidobacterium dentium, Eubacterium siraeum|Bifidobacterium dentium, Eubacterium ventriosum|Bifidobacterium dentium, Faecalibacterium prausnitzii|Bifidobacterium dentium, Finegoldia magna|Bifidobacterium dentium, Fusobacterium gonidiaformans|Bifidobacterium dentium, Fusobacterium mortiferum|Bifidobacterium dentium, Fusobacterium nucleatum|Bifidobacterium dentium, Fusobacterium varium|Bifidobacterium dentium, Gardnerella vaginalis|Bifidobacterium dentium, Gemella haemolysans|Bifidobacterium dentium, Gemella morbillorum|Bifidobacterium dentium, Gordonibacter pamelaeae|Bifidobacterium dentium, Granulicatella adiacens|Bifidobacterium dentium, Granulicatella elegans|Bifidobacterium dentium, Haemophilus influenzae|Bifidobacterium dentium, Haemophilus parainfluenzae|Bifidobacterium dentium, Helicobacter pullorum|Bifidobacterium dentium, Helicobacter pylori|Bifidobacterium dentium, Holdemania filiformis|Bifidobacterium dentium, Kingella oralis|Bifidobacterium dentium, Klebsiella pneumoniae|Bifidobacterium dentium, Klebsiella variicola|Bifidobacterium dentium, Lachnospiraceae bacterium 5_1_57FAA|Bifidobacterium dentium, Lactobacillus acidophilus|Bifidobacterium dentium, Lactobacillus amylovorus|Bifidobacterium dentium, Lactobacillus brevis|Bifidobacterium dentium, Lactobacillus casei|Bifidobacterium dentium, Lactobacillus crispatus|Bifidobacterium dentium, Lactobacillus delbrueckii|Bifidobacterium dentium, Lactobacillus fermentum|Bifidobacterium dentium, Lactobacillus gasseri|Bifidobacterium dentium, Lactobacillus iners|Bifidobacterium dentium, Lactobacillus jensenii|Bifidobacterium dentium, Lactobacillus johnsonii|Bifidobacterium dentium, Lactobacillus paracasei|Bifidobacterium dentium, Lactobacillus plantarum|Bifidobacterium dentium, Lactobacillus reuteri|Bifidobacterium dentium, Lactobacillus rhamnosus|Bifidobacterium dentium, Lactobacillus ruminis|Bifidobacterium dentium, Lactobacillus sakei|Bifidobacterium dentium, Lactobacillus salivarius|Bifidobacterium dentium, Lactococcus lactis|Bifidobacterium dentium, Lautropia mirabilis|Bifidobacterium dentium, Leuconostoc citreum|Bifidobacterium dentium, Leuconostoc gasicomitatum|Bifidobacterium dentium, Leuconostoc mesenteroides|Bifidobacterium dentium, Listeria monocytogenes|Bifidobacterium dentium, Marvinbryantia formatexigens|Bifidobacterium dentium, Megamonas hypermegale|Bifidobacterium dentium, Megasphaera micronuciformis|Bifidobacterium dentium, Methanobrevibacter smithii|Bifidobacterium dentium, Methanosphaera stadtmanae|Bifidobacterium dentium, Methylobacterium radiotolerans|Bifidobacterium dentium, Mitsuokella multacida|Bifidobacterium dentium, Mobiluncus curtisii|Bifidobacterium dentium, Mycoplasma hominis|Bifidobacterium dentium, Neisseria mucosa|Bifidobacterium dentium, Odoribacter splanchnicus|Bifidobacterium dentium, Olsenella uli|Bifidobacterium dentium, Oribacterium sinus|Bifidobacterium dentium, Oxalobacter formigenes|Bifidobacterium dentium, Parabacteroides distasonis|Bifidobacterium dentium, Parabacteroides johnsonii|Bifidobacterium dentium, Parabacteroides merdae|Bifidobacterium dentium, Parvimonas micra|Bifidobacterium dentium, Pediococcus acidilactici|Bifidobacterium dentium, Pediococcus pentosaceus|Bifidobacterium dentium, Peptoniphilus duerdenii|Bifidobacterium dentium, Peptoniphilus harei|Bifidobacterium dentium, Peptoniphilus lacrimalis|Bifidobacterium dentium, Peptostreptococcus anaerobius|Bifidobacterium dentium, Peptostreptococcus stomatis|Bifidobacterium dentium, Porphyromonas asaccharolytica|Bifidobacterium dentium, Porphyromonas uenonis|Bifidobacterium dentium, Prevotella amnii|Bifidobacterium dentium, Prevotella bergensis|Bifidobacterium dentium, Prevotella bivia|Bifidobacterium dentium, Prevotella buccae|Bifidobacterium dentium, Prevotella buccalis|Bifidobacterium dentium, Prevotella copri|Bifidobacterium dentium, Prevotella disiens|Bifidobacterium dentium, Prevotella melaninogenica|Bifidobacterium dentium, Prevotella multiformis|Bifidobacterium dentium, Prevotella oralis|Bifidobacterium dentium, Prevotella oris|Bifidobacterium dentium, Prevotella salivae|Bifidobacterium dentium, Prevotella timonensis|Bifidobacterium dentium, Propionibacterium acnes|Bifidobacterium dentium, Propionibacterium freudenreichii|Bifidobacterium dentium, Proteus mirabilis|Bifidobacterium dentium, Proteus penneri|Bifidobacterium dentium, Pseudoflavonifractor capillosus|Bifidobacterium dentium, Pseudomonas aeruginosa|Bifidobacterium dentium, Pseudomonas fluorescens|Bifidobacterium dentium, Pseudomonas putida|Bifidobacterium dentium, Pseudoramibacter alactolyticus|Bifidobacterium dentium, Pyramidobacter piscolens|Bifidobacterium dentium, Rhodopseudomonas palustris|Bifidobacterium dentium, Roseburia intestinalis|Bifidobacterium dentium, Roseburia inulinivorans|Bifidobacterium dentium, Rothia dentocariosa|Bifidobacterium dentium, Rothia mucilaginosa|Bifidobacterium dentium, Ruminococcus albus|Bifidobacterium dentium, Ruminococcus bromii|Bifidobacterium dentium, Ruminococcus gnavus|Bifidobacterium dentium, Ruminococcus lactaris|Bifidobacterium dentium, Ruminococcus obeum|Bifidobacterium dentium, Ruminococcus torques|Bifidobacterium dentium, Selenomonas sputigena|Bifidobacterium dentium, Shigella boydii|Bifidobacterium dentium, Shigella dysenteriae|Bifidobacterium dentium, Shigella sonnei|Bifidobacterium dentium, Slackia exigua|Bifidobacterium dentium, Solobacterium moorei|Bifidobacterium dentium, Staphylococcus aureus|Bifidobacterium dentium, Staphylococcus epidermidis|Bifidobacterium dentium, Staphylococcus hominis|Bifidobacterium dentium, Staphylococcus saprophyticus|Bifidobacterium dentium, Staphylococcus warneri|Bifidobacterium dentium, Streptococcus agalactiae|Bifidobacterium dentium, Streptococcus anginosus|Bifidobacterium dentium, Streptococcus australis|Bifidobacterium dentium, Streptococcus bovis|Bifidobacterium dentium, Streptococcus cristatus|Bifidobacterium dentium, Streptococcus dysgalactiae|Bifidobacterium dentium, Streptococcus TABLE 2-continued

| Table 2. Specific binary combinations of OTUs. Individual pairings are differentiated by "\|" and OTUs within a combination are differentiated by "," |
|---|
| *equinus\|Bifidobacterium dentium, Streptococcus gordonii\|Bifidobacterium dentium, Streptococcus infantarius\|Bifidobacterium dentium, Streptococcus infantis\|Bifidobacterium dentium, Streptococcus mitis\|Bifidobacterium dentium, Streptococcus mutans\|Bifidobacterium dentium, Streptococcus oralis\|Bifidobacterium dentium, Streptococcus parasanguinis\|Bifidobacterium dentium, Streptococcus peroris\|Bifidobacterium dentium, Streptococcus pneumoniae\|Bifidobacterium dentium, Streptococcus salivarius\|Bifidobacterium dentium, Streptococcus sanguinis\|Bifidobacterium dentium, Streptococcus thermophilus\|Bifidobacterium dentium, Streptococcus vestibularis\|Bifidobacterium dentium, Subdoligranulum variabile\|Bifidobacterium dentium, Succinatimonas hippei\|Bifidobacterium dentium, Sutterella wadsworthensis\|Bifidobacterium dentium, Tropheryma whipplei\|Bifidobacterium dentium, Veillonella atypica\|Bifidobacterium dentium, Veillonella dispar\|Bifidobacterium dentium, Veillonella parvula\|Bifidobacterium dentium, Victivallis vadensis\|Bifidobacterium infantis, Bifidobacterium infantis\|Bifidobacterium infantis, Bifidobacterium longum\|Bifidobacterium infantis, Bifidobacterium pseudocatenulatum\|Bifidobacterium infantis, Bilophila wadsworthia\|Bifidobacterium infantis, Blautia hansenii\|Bifidobacterium infantis, Blautia hydrogenotrophica\|Bifidobacterium infantis, Blautia producta\|Bifidobacterium infantis, Blautia schinkii\|Bifidobacterium infantis, Brevibacterium linens\|Bifidobacterium infantis, Brucella ceti\|Bifidobacterium infantis, Brucella suis\|Bifidobacterium infantis, Bulleidia extructa\|Bifidobacterium infantis, Butyrivibrio crossotus\|Bifidobacterium infantis, Campylobacter concisus\|Bifidobacterium infantis, Campylobacter curvus\|Bifidobacterium infantis, Campylobacter gracilis\|Bifidobacterium infantis, Campylobacter hominis\|Bifidobacterium infantis, Capnocytophaga ochracea\|Bifidobacterium infantis, Cardiobacterium hominis\|Bifidobacterium infantis, Catenibacterium mitsuokai\|Bifidobacterium infantis, Catonella morbi\|Bifidobacterium infantis, Citrobacter koseri\|Bifidobacterium infantis, Clostridium asparagiforme\|Bifidobacterium infantis, Clostridium bartlettii\|Bifidobacterium infantis, Clostridium bolteae\|Bifidobacterium infantis, Clostridium botulinum\|Bifidobacterium infantis, Clostridium butyricum\|Bifidobacterium infantis, Clostridium difficile\|Bifidobacterium infantis, Clostridium disporicum\|Bifidobacterium infantis, Clostridium hathewayi\|Bifidobacterium infantis, Clostridium hylemonae\|Bifidobacterium infantis, Clostridium innocuum\|Bifidobacterium infantis, Clostridium leptum\|Bifidobacterium infantis, Clostridium mayombei\|Bifidobacterium infantis, Clostridium methylpentosum\|Bifidobacterium infantis, Clostridium nexile\|Bifidobacterium infantis, Clostridium orbiscindens\|Bifidobacterium infantis, Clostridium perfringens\|Bifidobacterium infantis, Clostridium saccharolyticum\|Bifidobacterium infantis, Clostridium scindens\|Bifidobacterium infantis, Clostridium symbiosum\|Bifidobacterium infantis, Clostridium tertium\|Bifidobacterium infantis, Collinsella aerofaciens\|Bifidobacterium infantis, Collinsella intestinalis\|Bifidobacterium infantis, Collinsella stercoris\|Bifidobacterium infantis, Coprobacillus* sp. D7\|*Bifidobacterium infantis, Coprococcus catus\|Bifidobacterium infantis, Coprococcus comes\|Bifidobacterium infantis, Coprococcus eutactus\|Bifidobacterium infantis, Corynebacterium aurimucosum\|Bifidobacterium infantis, Corynebacterium matruchotii\|Bifidobacterium infantis, Cryptobacterium curtum\|Bifidobacterium infantis, Desulfovibrio desulfuricans\|Bifidobacterium infantis, Desulfovibrio piger\|Bifidobacterium infantis, Dialister invisus\|Bifidobacterium infantis, Dialister microaerophilus\|Bifidobacterium infantis, Dorea formicigenerans\|Bifidobacterium infantis, Dorea longicatena\|Bifidobacterium infantis, Eggerthella lenta\|Bifidobacterium infantis, Eikenella corrodens\|Bifidobacterium infantis, Enterobacter cancerogenus\|Bifidobacterium infantis, Enterobacter cloacae\|Bifidobacterium infantis, Enterococcus faecalis\|Bifidobacterium infantis, Enterococcus faecium\|Bifidobacterium infantis, Enterococcus gallinarum\|Bifidobacterium infantis, Erysipelotrichaceae bacterium* 3_1_53\|*Bifidobacterium infantis, Escherichia coli\|Bifidobacterium infantis, Escherichia fergusonii\|Bifidobacterium infantis, Ethanoligenens harbinense\|Bifidobacterium infantis, Eubacterium cellulosolvens\|Bifidobacterium infantis, Eubacterium eligens\|Bifidobacterium infantis, Eubacterium hallii\|Bifidobacterium infantis, Eubacterium limosum\|Bifidobacterium infantis, Eubacterium rectale\|Bifidobacterium infantis, Eubacterium siraeum\|Bifidobacterium infantis, Eubacterium ventriosum\|Bifidobacterium infantis, Faecalibacterium prausnitzii\|Bifidobacterium infantis, Finegoldia magna\|Bifidobacterium infantis, Fusobacterium gonidiaformans\|Bifidobacterium infantis, Fusobacterium mortiferum\|Bifidobacterium infantis, Fusobacterium nucleatum\|Bifidobacterium infantis, Fusobacterium varium\|Bifidobacterium infantis, Gardnerella vaginalis\|Bifidobacterium infantis, Gemella haemolysans\|Bifidobacterium infantis, Gemella morbillorum\|Bifidobacterium infantis, Gordonibacter pamelaeae\|Bifidobacterium infantis, Granulicatella adiacens\|Bifidobacterium infantis, Granulicatella elegans\|Bifidobacterium infantis, Haemophilus influenzae\|Bifidobacterium infantis, Haemophilus parainfluenzae\|Bifidobacterium infantis, Helicobacter pullorum\|Bifidobacterium infantis, Helicobacter pylori\|Bifidobacterium infantis, Holdemania filiformis\|Bifidobacterium infantis, Kingella oralis\|Bifidobacterium infantis, Klebsiella pneumoniae\|Bifidobacterium infantis, Klebsiella variicola\|Bifidobacterium infantis, Lachnospiraceae bacterium* 5_1_57FAA\|*Bifidobacterium infantis, Lactobacillus acidophilus\|Bifidobacterium infantis, Lactobacillus amylovorus\|Bifidobacterium infantis, Lactobacillus brevis\|Bifidobacterium infantis, Lactobacillus casei\|Bifidobacterium infantis, Lactobacillus crispatus\|Bifidobacterium infantis, Lactobacillus delbrueckii\|Bifidobacterium infantis, Lactobacillus fermentum\|Bifidobacterium infantis, Lactobacillus gasseri\|Bifidobacterium infantis, Lactobacillus iners\|Bifidobacterium infantis, Lactobacillus jensenii\|Bifidobacterium infantis, Lactobacillus johnsonii\|Bifidobacterium infantis, Lactobacillus paracasei\|Bifidobacterium infantis, Lactobacillus plantarum\|Bifidobacterium infantis, Lactobacillus reuteri\|Bifidobacterium infantis, Lactobacillus rhamnosus\|Bifidobacterium infantis, Lactobacillus ruminis\|Bifidobacterium infantis, Lactobacillus sakei\|Bifidobacterium infantis, Lactobacillus salivarius\|Bifidobacterium infantis, Lactococcus lactis\|Bifidobacterium infantis, Lautropia mirabilis\|Bifidobacterium infantis, Leuconostoc citreum\|Bifidobacterium infantis, Leuconostoc gasicomitatum\|Bifidobacterium infantis, Leuconostoc mesenteroides\|Bifidobacterium infantis, Listeria monocytogenes\|Bifidobacterium infantis, Marvinbryantia formatexigens\|Bifidobacterium infantis, Megamonas hypermegale\|Bifidobacterium infantis, Megasphaera micronuciformis\|Bifidobacterium infantis, Methanobrevibacter smithii\|Bifidobacterium infantis, Methanosphaera stadtmanae\|Bifidobacterium infantis, Methylobacterium radiotolerans\|Bifidobacterium infantis, Mitsuokella multacida\|Bifidobacterium infantis, Mobiluncus curtisii\|Bifidobacterium infantis, Mycoplasma hominis\|Bifidobacterium infantis, Neisseria mucosa\|Bifidobacterium infantis, Odoribacter splanchnicus\|Bifidobacterium infantis, Olsenella uli\|Bifidobacterium infantis, Oribacterium sinus\|Bifidobacterium infantis, Oxalobacter formigenes\|Bifidobacterium infantis, Parabacteroides distasonis\|Bifidobacterium infantis, Parabacteroides johnsonii\|Bifidobacterium infantis, Parabacteroides merdae\|Bifidobacterium infantis, Parvimonas micra\|Bifidobacterium infantis, Pediococcus acidilactici\|Bifidobacterium infantis, Pediococcus pentosaceus\|Bifidobacterium infantis, Peptoniphilus duerdenii\|Bifidobacterium infantis, Peptoniphilus harei\|Bifidobacterium infantis, Peptoniphilus lacrimalis\|Bifidobacterium infantis, Peptostreptococcus anaerobius\|Bifidobacterium infantis, Peptostreptococcus stomatis\|Bifidobacterium infantis, Porphyromonas asaccharolytica\|Bifidobacterium infantis, Porphyromonas uenonis\|Bifidobacterium infantis, Prevotella amnii\|Bifidobacterium infantis, Prevotella bergensis\|Bifidobacterium infantis, Prevotella bivia\|Bifidobacterium infantis, Prevotella buccae\|Bifidobacterium infantis, Prevotella buccalis\|Bifidobacterium infantis, Prevotella copri\|Bifidobacterium infantis, Prevotella disiens\|Bifidobacterium infantis, Prevotella melaninogenica\|Bifidobacterium infantis, Prevotella multiformis\|Bifidobacterium infantis, Prevotella oralis\|Bifidobacterium infantis, Prevotella oris\|Bifidobacterium infantis, Prevotella salivae\|Bifidobacterium infantis, Prevotella timonensis\|Bifidobacterium infantis, Propionibacterium acnes\|Bifidobacterium infantis, Propionibacterium freudenreichii\|Bifidobacterium infantis, Proteus mirabilis\|Bifidobacterium infantis, Proteus penneri\|Bifidobacterium infantis, Pseudoflavonifractor capillosus\|Bifidobacterium infantis, Pseudomonas aeruginosa\|Bifidobacterium infantis, Pseudomonas fluorescens\|Bifidobacterium infantis, Pseudomonas putida\|Bifidobacterium infantis, Pseudoramibacter alactolyticus\|Bifidobacterium infantis, Pyramidobacter piscolens\|Bifidobacterium infantis, Rhodopseudomonas palustris\|Bifidobacterium infantis, Roseburia intestinalis\|Bifidobacterium infantis, Roseburia inulinivorans\|Bifidobacterium infantis, Rothia dentocariosa\|Bifidobacterium infantis, Rothia mucilaginosa\|Bifidobacterium infantis, Ruminococcus albus\|Bifidobacterium infantis, Ruminococcus bromii\|Bifidobacterium infantis, Ruminococcus gnavus\|Bifidobacterium infantis, Ruminococcus lactaris\|Bifidobacterium infantis, Ruminococcus obeum\|Bifidobacterium infantis, Ruminococcus torques\|Bifidobacterium infantis, Selenomonas sputigena\|Bifidobacterium* |

TABLE 2-continued

| Table 2. Specific binary combinations of OTUs. Individual pairings are differentiated by "\|" and OTUs within a combination are differentiated by "," |
|---|
| *infantis, Shigella boydii\|Bifidobacterium infantis, Shigella dysenteriae\|Bifidobacterium infantis, Shigella sonnei\|Bifidobacterium infantis, Slackia exigua\|Bifidobacterium infantis, Solobacterium moorei\|Bifidobacterium infantis, Staphylococcus aureus\|Bifidobacterium infantis, Staphylococcus epidermidis\|Bifidobacterium infantis, Staphylococcus hominis\|Bifidobacterium infantis, Staphylococcus saprophyticus\|Bifidobacterium infantis, Staphylococcus warneri\|Bifidobacterium infantis, Streptococcus agalactiae\|Bifidobacterium infantis, Streptococcus anginosus\|Bifidobacterium infantis, Streptococcus australis\|Bifidobacterium infantis, Streptococcus bovis\|Bifidobacterium infantis, Streptococcus cristatus\|Bifidobacterium infantis, Streptococcus dysgalactiae\|Bifidobacterium infantis, Streptococcus equinus\|Bifidobacterium infantis, Streptococcus gordonii\|Bifidobacterium infantis, Streptococcus infantarius\|Bifidobacterium infantis, Streptococcus infantis\|Bifidobacterium infantis, Streptococcus mitis\|Bifidobacterium infantis, Streptococcus mutans\|Bifidobacterium infantis, Streptococcus oralis\|Bifidobacterium infantis, Streptococcus parasanguinis\|Bifidobacterium infantis, Streptococcus peroris\|Bifidobacterium infantis, Streptococcus pneumoniae\|Bifidobacterium infantis, Streptococcus salivarius\|Bifidobacterium infantis, Streptococcus sanguinis\|Bifidobacterium infantis, Streptococcus thermophilus\|Bifidobacterium infantis, Streptococcus vestibularis\|Bifidobacterium infantis, Subdoligranulum variabile\|Bifidobacterium infantis, Succinatimonas hippei\|Bifidobacterium infantis, Sutterella wadsworthensis\|Bifidobacterium infantis, Tropheryma whipplei\|Bifidobacterium infantis, Veillonella atypica\|Bifidobacterium infantis, Veillonella dispar\|Bifidobacterium infantis, Veillonella parvula\|Bifidobacterium infantis, Victivallis vadensis\|Bifidobacterium longum, Bifidobacterium longum\|Bifidobacterium longum, Bifidobacterium pseudocatenulatum\|Bifidobacterium longum, Bilophila wadsworthia\|Bifidobacterium longum, Blautia hansenii\|Bifidobacterium longum, Blautia hydrogenotrophica\|Bifidobacterium longum, Blautia producta\|Bifidobacterium longum, Blautia schinkii\|Bifidobacterium longum, Brevibacterium linens\|Bifidobacterium longum, Brucella ceti\|Bifidobacterium longum, Brucella suis\|Bifidobacterium longum, Bulleidia extructa\|Bifidobacterium longum, Butyrivibrio crossotus\|Bifidobacterium longum, Campylobacter concisus\|Bifidobacterium longum, Campylobacter curvus\|Bifidobacterium longum, Campylobacter gracilis\|Bifidobacterium longum, Campylobacter hominis\|Bifidobacterium longum, Capnocytophaga ochracea\|Bifidobacterium longum, Cardiobacterium hominis\|Bifidobacterium longum, Catenibacterium mitsuokai\|Bifidobacterium longum, Catonella morbi\|Bifidobacterium longum, Citrobacter koseri\|Bifidobacterium longum, Clostridium asparagiforme\|Bifidobacterium longum, Clostridium bartlettii\|Bifidobacterium longum, Clostridium bolteae\|Bifidobacterium longum, Clostridium botulinum\|Bifidobacterium longum, Clostridium butyricum\|Bifidobacterium longum, Clostridium difficile\|Bifidobacterium longum, Clostridium disporicum\|Bifidobacterium longum, Clostridium hathewayi\|Bifidobacterium longum, Clostridium hylemonae\|Bifidobacterium longum, Clostridium innocuum\|Bifidobacterium longum, Clostridium leptum\|Bifidobacterium longum, Clostridium mayombei\|Bifidobacterium longum, Clostridium methylpentosum\|Bifidobacterium longum, Clostridium nexile\|Bifidobacterium longum, Clostridium orbiscindens\|Bifidobacterium longum, Clostridium perfringens\|Bifidobacterium longum, Clostridium saccharolyticum\|Bifidobacterium longum, Clostridium scindens\|Bifidobacterium longum, Clostridium symbiosum\|Bifidobacterium longum, Clostridium tertium\|Bifidobacterium longum, Collinsella aerofaciens\|Bifidobacterium longum, Collinsella intestinalis\|Bifidobacterium longum, Collinsella stercoris\|Bifidobacterium longum, Coprobacillus* sp. D7\|*Bifidobacterium longum, Coprococcus catus\|Bifidobacterium longum, Coprococcus comes\|Bifidobacterium longum, Coprococcus eutactus\|Bifidobacterium longum, Corynebacterium aurimucosum\|Bifidobacterium longum, Corynebacterium matruchotii\|Bifidobacterium longum, Cryptobacterium curtum\|Bifidobacterium longum, Desulfovibrio desulfuricans\|Bifidobacterium longum, Desulfovibrio piger\|Bifidobacterium longum, Dialister invisus\|Bifidobacterium longum, Dialister microaerophilus\|Bifidobacterium longum, Dorea formicigenerans\|Bifidobacterium longum, Dorea longicatena\|Bifidobacterium longum, Eggerthella lenta\|Bifidobacterium longum, Eikenella corrodens\|Bifidobacterium longum, Enterobacter cancerogenus\|Bifidobacterium longum, Enterobacter cloacae\|Bifidobacterium longum, Enterococcus faecalis\|Bifidobacterium longum, Enterococcus faecium\|Bifidobacterium longum, Enterococcus gallinarum\|Bifidobacterium longum, Erysipelotrichaceae bacterium* 3_1_53\|*Bifidobacterium longum, Escherichia coli\|Bifidobacterium longum, Escherichia fergusonii\|Bifidobacterium longum, Ethanoligenens harbinense\|Bifidobacterium longum, Eubacterium cellulosolvens\|Bifidobacterium longum, Eubacterium eligens\|Bifidobacterium longum, Eubacterium hallii\|Bifidobacterium longum, Eubacterium limosum\|Bifidobacterium longum, Eubacterium rectale\|Bifidobacterium longum, Eubacterium siraeum\|Bifidobacterium longum, Eubacterium ventriosum\|Bifidobacterium longum, Faecalibacterium prausnitzii\|Bifidobacterium longum, Finegoldia magna\|Bifidobacterium longum, Fusobacterium gonidiaformans\|Bifidobacterium longum, Fusobacterium mortiferum\|Bifidobacterium longum, Fusobacterium nucleatum\|Bifidobacterium longum, Fusobacterium varium\|Bifidobacterium longum, Gardnerella vaginalis\|Bifidobacterium longum, Gemella haemolysans\|Bifidobacterium longum, Gemella morbillorum\|Bifidobacterium longum, Gordonibacter pamelaeae\|Bifidobacterium longum, Granulicatella adiacens\|Bifidobacterium longum, Granulicatella elegans\|Bifidobacterium longum, Haemophilus influenzae\|Bifidobacterium longum, Haemophilus parainfluenzae\|Bifidobacterium longum, Helicobacter pullorum\|Bifidobacterium longum, Helicobacter pylori\|Bifidobacterium longum, Holdemania filiformis\|Bifidobacterium longum, Kingella oralis\|Bifidobacterium longum, Klebsiella pneumoniae\|Bifidobacterium longum, Klebsiella variicola\|Bifidobacterium longum, Lachnospiraceae bacterium* 5_1_57FAA\|*Bifidobacterium longum, Lactobacillus acidophilus\|Bifidobacterium longum, Lactobacillus amylovorus\|Bifidobacterium longum, Lactobacillus brevis\|Bifidobacterium longum, Lactobacillus casei\|Bifidobacterium longum, Lactobacillus crispatus\|Bifidobacterium longum, Lactobacillus delbrueckii\|Bifidobacterium longum, Lactobacillus fermentum\|Bifidobacterium longum, Lactobacillus gasseri\|Bifidobacterium longum, Lactobacillus iners\|Bifidobacterium longum, Lactobacillus jensenii\|Bifidobacterium longum, Lactobacillus johnsonii\|Bifidobacterium longum, Lactobacillus paracasei\|Bifidobacterium longum, Lactobacillus plantarum\|Bifidobacterium longum, Lactobacillus reuteri\|Bifidobacterium longum, Lactobacillus rhamnosus\|Bifidobacterium longum, Lactobacillus ruminis\|Bifidobacterium longum, Lactobacillus sakei\|Bifidobacterium longum, Lactobacillus salivarius\|Bifidobacterium longum, Lactococcus lactis\|Bifidobacterium longum, Lautropia mirabilis\|Bifidobacterium longum, Leuconostoc citreum\|Bifidobacterium longum, Leuconostoc gasicomitatum\|Bifidobacterium longum, Leuconostoc mesenteroides\|Bifidobacterium longum, Listeria monocytogenes\|Bifidobacterium longum, Marvinbryantia formatexigens\|Bifidobacterium longum, Megamonas hypermegale\|Bifidobacterium longum, Megasphaera micronuciformis\|Bifidobacterium longum, Methanobrevibacter smithii\|Bifidobacterium longum, Methanosphaera stadtmanae\|Bifidobacterium longum, Methylobacterium radiotolerans\|Bifidobacterium longum, Mitsuokella multacida\|Bifidobacterium longum, Mobiluncus curtisii\|Bifidobacterium longum, Mycoplasma hominis\|Bifidobacterium longum, Neisseria mucosa\|Bifidobacterium longum, Odoribacter splanchnicus\|Bifidobacterium longum, Olsenella uli\|Bifidobacterium longum, Oribacterium sinus\|Bifidobacterium longum, Oxalobacter formigenes\|Bifidobacterium longum, Parabacteroides distasonis\|Bifidobacterium longum, Parabacteroides johnsonii\|Bifidobacterium longum, Parabacteroides merdae\|Bifidobacterium longum, Parvimonas micra\|Bifidobacterium longum, Pediococcus acidilactici\|Bifidobacterium longum, Pediococcus pentosaceus\|Bifidobacterium longum, Peptoniphilus duerdenii\|Bifidobacterium longum, Peptoniphilus harei\|Bifidobacterium longum, Peptoniphilus lacrimalis\|Bifidobacterium longum, Peptostreptococcus anaerobius\|Bifidobacterium longum, Peptostreptococcus stomatis\|Bifidobacterium longum, Porphyromonas asaccharolytica\|Bifidobacterium longum, Porphyromonas uenonis\|Bifidobacterium longum, Prevotella amnii\|Bifidobacterium longum, Prevotella bergensis\|Bifidobacterium longum, Prevotella bivia\|Bifidobacterium longum, Prevotella buccae\|Bifidobacterium longum, Prevotella buccalis\|Bifidobacterium longum, Prevotella copri\|Bifidobacterium longum, Prevotella disiens\|Bifidobacterium longum, Prevotella melaninogenica\|Bifidobacterium longum, Prevotella multiformis\|Bifidobacterium longum, Prevotella oralis\|Bifidobacterium longum, Prevotella oris\|Bifidobacterium longum, Prevotella salivae\|Bifidobacterium longum, Prevotella timonensis\|Bifidobacterium longum, Propionibacterium acnes\|Bifidobacterium longum, Propionibacterium freudenreichii\|Bifidobacterium longum, Proteus mirabilis\|Bifidobacterium longum, Proteus penneri\|Bifidobacterium longum, Pseudoflavonifractor capillosus\|Bifidobacterium longum, Pseudomonas aeruginosa\|Bifidobacterium longum, Pseudomonas fluorescens\|Bifidobacterium longum, Pseudomonas putida\|Bifidobacterium longum, Pseudoramibacter alactolyticus\|Bifidobacterium longum, Pyramidobacter* |

TABLE 2-continued

| Table 2. Specific binary combinations of OTUs. Individual pairings are differentiated by "\|" and OTUs within a combination are differentiated by "," |
|---|
| piscolens\|Bifidobacterium longum, Rhodopseudomonas palustris\|Bifidobacterium longum, Roseburia intestinalis\|Bifidobacterium longum, Roseburia inulinivorans\|Bifidobacterium longum, Rothia dentocariosa\|Bifidobacterium longum, Rothia mucilaginosa\|Bifidobacterium longum, Ruminococcus albus\|Bifidobacterium longum, Ruminococcus bromii\|Bifidobacterium longum, Ruminococcus gnavus\|Bifidobacterium longum, Ruminococcus lactaris\|Bifidobacterium longum, Ruminococcus obeum\|Bifidobacterium longum, Ruminococcus torques\|Bifidobacterium longum, Selenomonas sputigena\|Bifidobacterium longum, Shigella boydii\|Bifidobacterium longum, Shigella dysenteriae\|Bifidobacterium longum, Shigella sonnei\|Bifidobacterium longum, Slackia exigua\|Bifidobacterium longum, Solobacterium moorei\|Bifidobacterium longum, Staphylococcus aureus\|Bifidobacterium longum, Staphylococcus epidermidis\|Bifidobacterium longum, Staphylococcus hominis\|Bifidobacterium longum, Staphylococcus saprophyticus\|Bifidobacterium longum, Staphylococcus warneri\|Bifidobacterium longum, Streptococcus agalactiae\|Bifidobacterium longum, Streptococcus anginosus\|Bifidobacterium longum, Streptococcus australis\|Bifidobacterium longum, Streptococcus bovis\|Bifidobacterium longum, Streptococcus cristatus\|Bifidobacterium longum, Streptococcus dysgalactiae\|Bifidobacterium longum, Streptococcus equinus\|Bifidobacterium longum, Streptococcus gordonii\|Bifidobacterium longum, Streptococcus infantarius\|Bifidobacterium longum, Streptococcus infantis\|Bifidobacterium longum, Streptococcus mitis\|Bifidobacterium longum, Streptococcus mutans\|Bifidobacterium longum, Streptococcus oralis\|Bifidobacterium longum, Streptococcus parasanguinis\|Bifidobacterium longum, Streptococcus peroris\|Bifidobacterium longum, Streptococcus pneumoniae\|Bifidobacterium longum, Streptococcus salivarius\|Bifidobacterium longum, Streptococcus sanguinis\|Bifidobacterium longum, Streptococcus thermophilus\|Bifidobacterium longum, Streptococcus vestibularis\|Bifidobacterium longum, Subdoligranulum variabile\|Bifidobacterium longum, Succinatimonas hippei\|Bifidobacterium longum, Sutterella wadsworthensis\|Bifidobacterium longum, Tropheryma whipplei\|Bifidobacterium longum, Veillonella atypica\|Bifidobacterium longum, Veillonella dispar\|Bifidobacterium longum, Veillonella parvula\|Bifidobacterium longum, Victivallis vadensis\|Bifidobacterium pseudocatenulatum, Bifidobacterium pseudocatenulatum\|Bifidobacterium pseudocatenulatum, Bilophila wadsworthia\|Bifidobacterium pseudocatenulatum, Blautia hansenii\|Bifidobacterium pseudocatenulatum, Blautia hydrogenotrophica\|Bifidobacterium pseudocatenulatum, Blautia producta\|Bifidobacterium pseudocatenulatum, Blautia schinkii\|Bifidobacterium pseudocatenulatum, Brevibacterium linens\|Bifidobacterium pseudocatenulatum, Brucella ceti\|Bifidobacterium pseudocatenulatum, Brucella suis\|Bifidobacterium pseudocatenulatum, Bulleidia extructa\|Bifidobacterium pseudocatenulatum, Butyrivibrio crossotus\|Bifidobacterium pseudocatenulatum, Campylobacter concisus\|Bifidobacterium pseudocatenulatum, Campylobacter curvus\|Bifidobacterium pseudocatenulatum, Campylobacter gracilis\|Bifidobacterium pseudocatenulatum, Campylobacter hominis\|Bifidobacterium pseudocatenulatum, Capnocytophaga ochracea\|Bifidobacterium pseudocatenulatum, Cardiobacterium hominis\|Bifidobacterium pseudocatenulatum, Catenibacterium mitsuokai\|Bifidobacterium pseudocatenulatum, Catonella morbi\|Bifidobacterium pseudocatenulatum, Citrobacter koseri\|Bifidobacterium pseudocatenulatum, Clostridium asparagiforme\|Bifidobacterium pseudocatenulatum, Clostridium bartlettii\|Bifidobacterium pseudocatenulatum, Clostridium bolteae\|Bifidobacterium pseudocatenulatum, Clostridium botulinum\|Bifidobacterium pseudocatenulatum, Clostridium butyricum\|Bifidobacterium pseudocatenulatum, Clostridium difficile\|Bifidobacterium pseudocatenulatum, Clostridium disporicum\|Bifidobacterium pseudocatenulatum, Clostridium hathewayi\|Bifidobacterium pseudocatenulatum, Clostridium hylemonae\|Bifidobacterium pseudocatenulatum, Clostridium innocuum\|Bifidobacterium pseudocatenulatum, Clostridium leptum\|Bifidobacterium pseudocatenulatum, Clostridium mayombei\|Bifidobacterium pseudocatenulatum, Clostridium methylpentosum\|Bifidobacterium pseudocatenulatum, Clostridium nexile\|Bifidobacterium pseudocatenulatum, Clostridium orbiscindens\|Bifidobacterium pseudocatenulatum, Clostridium perfringens\|Bifidobacterium pseudocatenulatum, Clostridium saccharolyticum\|Bifidobacterium pseudocatenulatum, Clostridium scindens\|Bifidobacterium pseudocatenulatum, Clostridium symbiosum\|Bifidobacterium pseudocatenulatum, Clostridium tertium\|Bifidobacterium pseudocatenulatum, Collinsella aerofaciens\|Bifidobacterium pseudocatenulatum, Collinsella intestinalis\|Bifidobacterium pseudocatenulatum, Collinsella stercoris\|Bifidobacterium pseudocatenulatum, Coprobacillus sp. D7\|Bifidobacterium pseudocatenulatum, Coprococcus catus\|Bifidobacterium pseudocatenulatum, Coprococcus comes\|Bifidobacterium pseudocatenulatum, Coprococcus eutactus\|Bifidobacterium pseudocatenulatum, Corynebacterium aurimucosum\|Bifidobacterium pseudocatenulatum, Corynebacterium matruchotii\|Bifidobacterium pseudocatenulatum, Cryptobacterium curtum\|Bifidobacterium pseudocatenulatum, Desulfovibrio desulfuricans\|Bifidobacterium pseudocatenulatum, Desulfovibrio piger\|Bifidobacterium pseudocatenulatum, Dialister invisus\|Bifidobacterium pseudocatenulatum, Dialister microaerophilus\|Bifidobacterium pseudocatenulatum, Dorea formicigenerans\|Bifidobacterium pseudocatenulatum, Dorea longicatena\|Bifidobacterium pseudocatenulatum, Eggerthella lenta\|Bifidobacterium pseudocatenulatum, Eikenella corrodens\|Bifidobacterium pseudocatenulatum, Enterobacter cancerogenus\|Bifidobacterium pseudocatenulatum, Enterobacter cloacae\|Bifidobacterium pseudocatenulatum, Enterococcus faecalis\|Bifidobacterium pseudocatenulatum, Enterococcus faecium\|Bifidobacterium pseudocatenulatum, Enterococcus gallinarum\|Bifidobacterium pseudocatenulatum, Erysipelotrichaceae bacterium 3_1_53\|Bifidobacterium pseudocatenulatum, Escherichia coli\|Bifidobacterium pseudocatenulatum, Escherichia fergusonii\|Bifidobacterium pseudocatenulatum, Ethanoligenens harbinense\|Bifidobacterium pseudocatenulatum, Eubacterium cellulosolvens\|Bifidobacterium pseudocatenulatum, Eubacterium eligens\|Bifidobacterium pseudocatenulatum, Eubacterium hallii\|Bifidobacterium pseudocatenulatum, Eubacterium limosum\|Bifidobacterium pseudocatenulatum, Eubacterium rectale\|Bifidobacterium pseudocatenulatum, Eubacterium siraeum\|Bifidobacterium pseudocatenulatum, Eubacterium ventriosum\|Bifidobacterium pseudocatenulatum, Faecalibacterium prausnitzii\|Bifidobacterium pseudocatenulatum, Finegoldia magna\|Bifidobacterium pseudocatenulatum, Fusobacterium gonidiaformans\|Bifidobacterium pseudocatenulatum, Fusobacterium mortiferum\|Bifidobacterium pseudocatenulatum, Fusobacterium nucleatum\|Bifidobacterium pseudocatenulatum, Fusobacterium varium\|Bifidobacterium pseudocatenulatum, Gardnerella vaginalis\|Bifidobacterium pseudocatenulatum, Gemella haemolysans\|Bifidobacterium pseudocatenulatum, Gemella morbillorum\|Bifidobacterium pseudocatenulatum, Gordonibacter pamelaeae\|Bifidobacterium pseudocatenulatum, Granulicatella adiacens\|Bifidobacterium pseudocatenulatum, Granulicatella elegans\|Bifidobacterium pseudocatenulatum, Haemophilus influenzae\|Bifidobacterium pseudocatenulatum, Haemophilus parainfluenzae\|Bifidobacterium pseudocatenulatum, Helicobacter pullorum\|Bifidobacterium pseudocatenulatum, Helicobacter pylori\|Bifidobacterium pseudocatenulatum, Holdemania filiformis\|Bifidobacterium pseudocatenulatum, Kingella oralis\|Bifidobacterium pseudocatenulatum, Klebsiella pneumoniae\|Bifidobacterium pseudocatenulatum, Klebsiella variicola\|Bifidobacterium pseudocatenulatum, Lachnospiraceae bacterium 5_1_57FAA\|Bifidobacterium pseudocatenulatum, Lactobacillus acidophilus\|Bifidobacterium pseudocatenulatum, Lactobacillus amylovorus\|Bifidobacterium pseudocatenulatum, Lactobacillus brevis\|Bifidobacterium pseudocatenulatum, Lactobacillus casei\|Bifidobacterium pseudocatenulatum, Lactobacillus crispatus\|Bifidobacterium pseudocatenulatum, Lactobacillus delbrueckii\|Bifidobacterium pseudocatenulatum, Lactobacillus fermentum\|Bifidobacterium pseudocatenulatum, Lactobacillus gasseri\|Bifidobacterium pseudocatenulatum, Lactobacillus iners\|Bifidobacterium pseudocatenulatum, Lactobacillus jensenii\|Bifidobacterium pseudocatenulatum, Lactobacillus johnsonii\|Bifidobacterium pseudocatenulatum, Lactobacillus paracasei\|Bifidobacterium pseudocatenulatum, Lactobacillus plantarum\|Bifidobacterium pseudocatenulatum, Lactobacillus reuteri\|Bifidobacterium pseudocatenulatum, Lactobacillus rhamnosus\|Bifidobacterium pseudocatenulatum, Lactobacillus ruminis\|Bifidobacterium pseudocatenulatum, Lactobacillus sakei\|Bifidobacterium pseudocatenulatum, Lactobacillus salivarius\|Bifidobacterium pseudocatenulatum, Lactococcus lactis\|Bifidobacterium pseudocatenulatum, Lautropia mirabilis\|Bifidobacterium pseudocatenulatum, Leuconostoc citreum\|Bifidobacterium pseudocatenulatum, Leuconostoc gasicomitatum\|Bifidobacterium pseudocatenulatum, Leuconostoc mesenteroides\|Bifidobacterium pseudocatenulatum, Listeria monocytogenes\|Bifidobacterium pseudocatenulatum, Marvinbryantia formatexigens\|Bifidobacterium pseudocatenulatum, Megamonas hypermegale\|Bifidobacterium pseudocatenulatum, Megasphaera micronuciformis\|Bifidobacterium pseudocatenulatum, Methanobrevibacter smithii\|Bifidobacterium pseudocatenulatum, Methanosphaera stadtmanae\|Bifidobacterium pseudocatenulatum, Methylobacterium |

TABLE 2-continued

Table 2. Specific binary combinations of OTUs. Individual pairings are differentiated by "|" and OTUs within a combination are differentiated by ","

radiotolerans|Bifidobacterium pseudocatenulatum, Mitsuokella multacida|Bifidobacterium pseudocatenulatum, Mobiluncus curtisii|Bifidobacterium pseudocatenulatum, Mycoplasma hominis|Bifidobacterium pseudocatenulatum, Neisseria mucosa|Bifidobacterium pseudocatenulatum, Odoribacter splanchnicus|Bifidobacterium pseudocatenulatum, Olsenella uli|Bifidobacterium pseudocatenulatum, Oribacterium sinus|Bifidobacterium pseudocatenulatum, Oxalobacter formigenes|Bifidobacterium pseudocatenulatum, Parabacteroides distasonis|Bifidobacterium pseudocatenulatum, Parabacteroides johnsonii|Bifidobacterium pseudocatenulatum, Parabacteroides merdae|Bifidobacterium pseudocatenulatum, Parvimonas micra|Bifidobacterium pseudocatenulatum, Pediococcus acidilactic|Bifidobacterium pseudocatenulatum, Pediococcus pentosaceus|Bifidobacterium pseudocatenulatum, Peptoniphilus duerdenii|Bifidobacterium pseudocatenulatum, Peptoniphilus harei|Bifidobacterium pseudocatenulatum, Peptoniphilus lacrimalis|Bifidobacterium pseudocatenulatum, Peptostreptococcus anaerobius|Bifidobacterium pseudocatenulatum, Peptostreptococcus stomatis|Bifidobacterium pseudocatenulatum, Porphyromonas asaccharolytica|Bifidobacterium pseudocatenulatum, Porphyromonas uenonis|Bifidobacterium pseudocatenulatum, Prevotella amnii|Bifidobacterium pseudocatenulatum, Prevotella bergensis|Bifidobacterium pseudocatenulatum, Prevotella bivia|Bifidobacterium pseudocatenulatum, Prevotella buccae|Bifidobacterium pseudocatenulatum, Prevotella buccalis|Bifidobacterium pseudocatenulatum, Prevotella copri|Bifidobacterium pseudocatenulatum, Prevotella disiens|Bifidobacterium pseudocatenulatum, Prevotella melaninogenica|Bifidobacterium pseudocatenulatum, Prevotella multiformis|Bifidobacterium pseudocatenulatum, Prevotella oralis|Bifidobacterium pseudocatenulatum, Prevotella oris|Bifidobacterium pseudocatenulatum, Prevotella salivae|Bifidobacterium pseudocatenulatum, Prevotella timonensis|Bifidobacterium pseudocatenulatum, Propionibacterium acnes|Bifidobacterium pseudocatenulatum, Propionibacterium freudenreichii|Bifidobacterium pseudocatenulatum, Proteus mirabilis|Bifidobacterium pseudocatenulatum, Proteus penneri|Bifidobacterium pseudocatenulatum, Pseudoflavonifractor capillosus|Bifidobacterium pseudocatenulatum, Pseudomonas aeruginosa|Bifidobacterium pseudocatenulatum, Pseudomonas fluorescens|Bifidobacterium pseudocatenulatum, Pseudomonas putida|Bifidobacterium pseudocatenulatum, Pseudoramibacter alactolyticus|Bifidobacterium pseudocatenulatum, Pyramidobacter piscolens|Bifidobacterium pseudocatenulatum, Rhodopseudomonas palustris|Bifidobacterium pseudocatenulatum, Roseburia intestinalis|Bifidobacterium pseudocatenulatum, Roseburia inulinivorans|Bifidobacterium pseudocatenulatum, Rothia dentocariosa|Bifidobacterium pseudocatenulatum, Rothia mucilaginosa|Bifidobacterium pseudocatenulatum, Ruminococcus albus|Bifidobacterium pseudocatenulatum, Ruminococcus bromii|Bifidobacterium pseudocatenulatum, Ruminococcus gnavus|Bifidobacterium pseudocatenulatum, Ruminococcus lactaris|Bifidobacterium pseudocatenulatum, Ruminococcus obeum|Bifidobacterium pseudocatenulatum, Ruminococcus torques|Bifidobacterium pseudocatenulatum, Selenomonas sputigena|Bifidobacterium pseudocatenulatum, Shigella boydii|Bifidobacterium pseudocatenulatum, Shigella dysenteriae|Bifidobacterium pseudocatenulatum, Shigella sonnei|Bifidobacterium pseudocatenulatum, Slackia exigua|Bifidobacterium pseudocatenulatum, Solobacterium moorei|Bifidobacterium pseudocatenulatum, Staphylococcus aureus|Bifidobacterium pseudocatenulatum, Staphylococcus epidermidis|Bifidobacterium pseudocatenulatum, Staphylococcus hominis|Bifidobacterium pseudocatenulatum, Staphylococcus saprophyticus|Bifidobacterium pseudocatenulatum, Staphylococcus warneri|Bifidobacterium pseudocatenulatum, Streptococcus agalactiae|Bifidobacterium pseudocatenulatum, Streptococcus anginosus|Bifidobacterium pseudocatenulatum, Streptococcus australis|Bifidobacterium pseudocatenulatum, Streptococcus bovis|Bifidobacterium pseudocatenulatum, Streptococcus cristatus|Bifidobacterium pseudocatenulatum, Streptococcus dysgalactiae|Bifidobacterium pseudocatenulatum, Streptococcus equinus|Bifidobacterium pseudocatenulatum, Streptococcus gordonii|Bifidobacterium pseudocatenulatum, Streptococcus infantarius|Bifidobacterium pseudocatenulatum, Streptococcus infantis|Bifidobacterium pseudocatenulatum, Streptococcus mitis|Bifidobacterium pseudocatenulatum, Streptococcus mutans|Bifidobacterium pseudocatenulatum, Streptococcus oralis|Bifidobacterium pseudocatenulatum, Streptococcus parasanguinis|Bifidobacterium pseudocatenulatum, Streptococcus peroris|Bifidobacterium pseudocatenulatum, Streptococcus pneumoniae|Bifidobacterium pseudocatenulatum, Streptococcus salivarius|Bifidobacterium pseudocatenulatum, Streptococcus sanguinis|Bifidobacterium pseudocatenulatum, Streptococcus thermophilus|Bifidobacterium pseudocatenulatum, Streptococcus vestibularis|Bifidobacterium pseudocatenulatum, Subdoligranulum variabile|Bifidobacterium pseudocatenulatum, Succinatimonas hippei|Bifidobacterium pseudocatenulatum, Sutterella wadsworthensis|Bifidobacterium pseudocatenulatum, Tropheryma whipplei|Bifidobacterium pseudocatenulatum, Veillonella atypica|Bifidobacterium pseudocatenulatum, Veillonella dispar|Bifidobacterium pseudocatenulatum, Veillonella parvula|Bifidobacterium pseudocatenulatum, Victivallis vadensis|Bilophila wadsworthia, Bilophila wadsworthia|Bilophila wadsworthia, Blautia hansenii|Bilophila wadsworthia, Blautia hydrogenotrophica|Bilophila wadsworthia, Blautia producta|Bilophila wadsworthia, Blautia schinkii|Bilophila wadsworthia, Brevibacterium linens|Bilophila wadsworthia, Brucella ceti|Bilophila wadsworthia, Brucella suis|Bilophila wadsworthia, Bulleidia extructa|Bilophila wadsworthia, Butyrivibrio crossotus|Bilophila wadsworthia, Campylobacter concisus|Bilophila wadsworthia, Campylobacter curvus|Bilophila wadsworthia, Campylobacter gracilis|Bilophila wadsworthia, Campylobacter hominis|Bilophila wadsworthia, Capnocytophaga ochracea|Bilophila wadsworthia, Cardiobacterium hominis|Bilophila wadsworthia, Catenibacterium mitsuokai|Bilophila wadsworthia, Catonella morbi|Bilophila wadsworthia, Citrobacter koseri|Bilophila wadsworthia, Clostridium asparagiforme|Bilophila wadsworthia, Clostridium bartlettii|Bilophila wadsworthia, Clostridium bolteae|Bilophila wadsworthia, Clostridium botulinum|Bilophila wadsworthia, Clostridium butyricum|Bilophila wadsworthia, Clostridium difficile|Bilophila wadsworthia, Clostridium disporicum|Bilophila wadsworthia, Clostridium hathewayi|Bilophila wadsworthia, Clostridium hylemonae|Bilophila wadsworthia, Clostridium innocuum|Bilophila wadsworthia, Clostridium leptum|Bilophila wadsworthia, Clostridium mayombei|Bilophila wadsworthia, Clostridium methylpentosum|Bilophila wadsworthia, Clostridium nexile|Bilophila wadsworthia, Clostridium orbiscindens|Bilophila wadsworthia, Clostridium perfringens|Bilophila wadsworthia, Clostridium saccharolyticum|Bilophila wadsworthia, Clostridium scindens|Bilophila wadsworthia, Clostridium symbiosum|Bilophila wadsworthia, Clostridium tertium|Bilophila wadsworthia, Collinsella aerofaciens|Bilophila wadsworthia, Collinsella intestinalis|Bilophila wadsworthia, Collinsella stercoris|Bilophila wadsworthia, Coprobacillus sp. D7|Bilophila wadsworthia, Coprococcus catus|Bilophila wadsworthia, Coprococcus comes|Bilophila wadsworthia, Coprococcus eutactus|Bilophila wadsworthia, Corynebacterium aurimucosum|Bilophila wadsworthia, Corynebacterium matruchotii|Bilophila wadsworthia, Cryptobacterium curtum|Bilophila wadsworthia, Desulfovibrio desulfuricans|Bilophila wadsworthia, Desulfovibrio piger|Bilophila wadsworthia, Dialister invisus|Bilophila wadsworthia, Dialister microaerophilus|Bilophila wadsworthia, Dorea formicigenerans|Bilophila wadsworthia, Dorea longicatena|Bilophila wadsworthia, Eggerthella lenta|Bilophila wadsworthia, Eikenella corrodens|Bilophila wadsworthia, Enterobacter cancerogenus|Bilophila wadsworthia, Enterobacter cloacae|Bilophila wadsworthia, Enterococcus faecalis|Bilophila wadsworthia, Enterococcus faecium|Bilophila wadsworthia, Enterococcus gallinarum|Bilophila wadsworthia, Erysipelotrichaceae bacterium 3_1_53|Bilophila wadsworthia, Escherichia coli|Bilophila wadsworthia, Escherichia fergusonii|Bilophila wadsworthia, Ethanoligenens harbinense|Bilophila wadsworthia, Eubacterium cellulosolvens|Bilophila wadsworthia, Eubacterium eligens|Bilophila wadsworthia, Eubacterium hallii|Bilophila wadsworthia, Eubacterium limosum|Bilophila wadsworthia, Eubacterium rectale|Bilophila wadsworthia, Eubacterium siraeum|Bilophila wadsworthia, Eubacterium ventriosum|Bilophila wadsworthia, Faecalibacterium prausnitzii|Bilophila wadsworthia, Finegoldia magna|Bilophila wadsworthia, Fusobacterium gonidiaformans|Bilophila wadsworthia, Fusobacterium mortiferum|Bilophila wadsworthia, Fusobacterium nucleatum|Bilophila wadsworthia, Fusobacterium varium|Bilophila wadsworthia, Gardnerella vaginalis|Bilophila wadsworthia, Gemella haemolysans|Bilophila wadsworthia, Gemella morbillorum|Bilophila wadsworthia, Gordonibacter pamelaeae|Bilophila wadsworthia, Granulicatella adiacens|Bilophila wadsworthia, Granulicatella elegans|Bilophila wadsworthia, Haemophilus influenzae|Bilophila wadsworthia, Haemophilus parainfluenzae|Bilophila wadsworthia, Helicobacter pullorum|Bilophila wadsworthia, Helicobacter pylori|Bilophila wadsworthia, Holdemania filiformis|Bilophila wadsworthia, Kingella oralis|Bilophila wadsworthia, Klebsiella pneumoniae|Bilophila wadsworthia, Klebsiella TABLE 2-continued

| Table 2. Specific binary combinations of OTUs. Individual pairings are differentiated by "\|" and OTUs within a combination are differentiated by "," |
|---|
| variicola\|Bilophila wadsworthia, Lachnospiraceae bacterium 5_1_57FAA\|Bilophila wadsworthia, Lactobacillus acidophilus\|Bilophila wadsworthia, Lactobacillus amylovorus\|Bilophila wadsworthia, Lactobacillus brevis\|Bilophila wadsworthia, Lactobacillus casei\|Bilophila wadsworthia, Lactobacillus crispatus\|Bilophila wadsworthia, Lactobacillus delbrueckii\|Bilophila wadsworthia, Lactobacillus fermentum\|Bilophila wadsworthia, Lactobacillus gasseri\|Bilophila wadsworthia, Lactobacillus iners\|Bilophila wadsworthia, Lactobacillus jensenii\|Bilophila wadsworthia, Lactobacillus johnsonii\|Bilophila wadsworthia, Lactobacillus paracasei\|Bilophila wadsworthia, Lactobacillus plantarum\|Bilophila wadsworthia, Lactobacillus reuteri\|Bilophila wadsworthia, Lactobacillus rhamnosus\|Bilophila wadsworthia, Lactobacillus ruminis\|Bilophila wadsworthia, Lactobacillus sakei\|Bilophila wadsworthia, Lactobacillus salivarius\|Bilophila wadsworthia, Lactococcus lactis\|Bilophila wadsworthia, Lautropia mirabilis\|Bilophila wadsworthia, Leuconostoc citreum\|Bilophila wadsworthia, Leuconostoc gasicomitatum\|Bilophila wadsworthia, Leuconostoc mesenteroides\|Bilophila wadsworthia, Listeria monocytogenes\|Bilophila wadsworthia, Marvinbryantia formatexigens\|Bilophila wadsworthia, Megamonas hypermegale\|Bilophila wadsworthia, Megasphaera micronuciformis\|Bilophila wadsworthia, Methanobrevibacter smithii\|Bilophila wadsworthia, Methanosphaera stadtmanae\|Bilophila wadsworthia, Methylobacterium radiotolerans\|Bilophila wadsworthia, Mitsuokella multacida\|Bilophila wadsworthia, Mobiluncus curtisii\|Bilophila wadsworthia, Mycoplasma hominis\|Bilophila wadsworthia, Neisseria mucosa\|Bilophila wadsworthia, Odoribacter splanchnicus\|Bilophila wadsworthia, Olsenella uli\|Bilophila wadsworthia, Oribacterium sinus\|Bilophila wadsworthia, Oxalobacter formigenes\|Bilophila wadsworthia, Parabacteroides distasonis\|Bilophila wadsworthia, Parabacteroides johnsonii\|Bilophila wadsworthia, Parabacteroides merdae\|Bilophila wadsworthia, Parvimonas micra\|Bilophila wadsworthia, Pediococcus acidilactici\|Bilophila wadsworthia, Pediococcus pentosaceus\|Bilophila wadsworthia, Peptoniphilus duerdenii\|Bilophila wadsworthia, Peptoniphilus harei\|Bilophila wadsworthia, Peptoniphilus lacrimalis\|Bilophila wadsworthia, Peptostreptococcus anaerobius\|Bilophila wadsworthia, Peptostreptococcus stomatis\|Bilophila wadsworthia, Porphyromonas asaccharolytica\|Bilophila wadsworthia, Porphyromonas uenonis\|Bilophila wadsworthia, Prevotella amnii\|Bilophila wadsworthia, Prevotella bergensis\|Bilophila wadsworthia, Prevotella bivia\|Bilophila wadsworthia, Prevotella buccae\|Bilophila wadsworthia, Prevotella buccalis\|Bilophila wadsworthia, Prevotella copri\|Bilophila wadsworthia, Prevotella disiens\|Bilophila wadsworthia, Prevotella melaninogenica\|Bilophila wadsworthia, Prevotella multiformis\|Bilophila wadsworthia, Prevotella oralis\|Bilophila wadsworthia, Prevotella oris\|Bilophila wadsworthia, Prevotella salivae\|Bilophila wadsworthia, Prevotella timonensis\|Bilophila wadsworthia, Propionibacterium acnes\|Bilophila wadsworthia, Propionibacterium freudenreichii\|Bilophila wadsworthia, Proteus mirabilis\|Bilophila wadsworthia, Proteus penneri\|Bilophila wadsworthia, Pseudoflavonifractor capillosus\|Bilophila wadsworthia, Pseudomonas aeruginosa\|Bilophila wadsworthia, Pseudomonas fluorescens\|Bilophila wadsworthia, Pseudomonas putida\|Bilophila wadsworthia, Pseudoramibacter alactolyticus\|Bilophila wadsworthia, Pyramidobacter piscolens\|Bilophila wadsworthia, Rhodopseudomonas palustris\|Bilophila wadsworthia, Roseburia intestinalis\|Bilophila wadsworthia, Roseburia inulinivorans\|Bilophila wadsworthia, Rothia dentocariosa\|Bilophila wadsworthia, Rothia mucilaginosa\|Bilophila wadsworthia, Ruminococcus albus\|Bilophila wadsworthia, Ruminococcus bromii\|Bilophila wadsworthia, Ruminococcus gnavus\|Bilophila wadsworthia, Ruminococcus lactaris\|Bilophila wadsworthia, Ruminococcus obeum\|Bilophila wadsworthia, Ruminococcus torques\|Bilophila wadsworthia, Selenomonas sputigena\|Bilophila wadsworthia, Shigella boydii\|Bilophila wadsworthia, Shigella dysenteriae\|Bilophila wadsworthia, Shigella sonnei\|Bilophila wadsworthia, Slackia exigua\|Bilophila wadsworthia, Solobacterium moorei\|Bilophila wadsworthia, Staphylococcus aureus\|Bilophila wadsworthia, Staphylococcus epidermidis\|Bilophila wadsworthia, Staphylococcus hominis\|Bilophila wadsworthia, Staphylococcus saprophyticus\|Bilophila wadsworthia, Staphylococcus warneri\|Bilophila wadsworthia, Streptococcus agalactiae\|Bilophila wadsworthia, Streptococcus anginosus\|Bilophila wadsworthia, Streptococcus australis\|Bilophila wadsworthia, Streptococcus bovis\|Bilophila wadsworthia, Streptococcus cristatus\|Bilophila wadsworthia, Streptococcus dysgalactiae\|Bilophila wadsworthia, Streptococcus equinus\|Bilophila wadsworthia, Streptococcus gordonii\|Bilophila wadsworthia, Streptococcus infantarius\|Bilophila wadsworthia, Streptococcus infantis\|Bilophila wadsworthia, Streptococcus mitis\|Bilophila wadsworthia, Streptococcus mutans\|Bilophila wadsworthia, Streptococcus oralis\|Bilophila wadsworthia, Streptococcus parasanguinis\|Bilophila wadsworthia, Streptococcus peroris\|Bilophila wadsworthia, Streptococcus pneumoniae\|Bilophila wadsworthia, Streptococcus salivarius\|Bilophila wadsworthia, Streptococcus sanguinis\|Bilophila wadsworthia, Streptococcus thermophilus\|Bilophila wadsworthia, Streptococcus vestibularis\|Bilophila wadsworthia, Subdoligranulum variabile\|Bilophila wadsworthia, Succinatimonas hippei\|Bilophila wadsworthia, Sutterella wadsworthensis\|Bilophila wadsworthia, Tropheryma whipplei\|Bilophila wadsworthia, Veillonella atypica\|Bilophila wadsworthia, Veillonella dispar\|Bilophila wadsworthia, Veillonella parvula\|Bilophila wadsworthia, Victivallis vadensis\|Blautia hansenii, Blautia hansenii\|Blautia hansenii, Blautia hydrogenotrophica\|Blautia hansenii, Blautia producta\|Blautia hansenii, Blautia schinkii\|Blautia hansenii, Brevibacterium linens\|Blautia hansenii, Brucella ceti\|Blautia hansenii, Brucella suis\|Blautia hansenii, Bulleidia extructa\|Blautia hansenii, Butyrivibrio crossotus\|Blautia hansenii, Campylobacter concisus\|Blautia hansenii, Campylobacter curvus\|Blautia hansenii, Campylobacter gracilis\|Blautia hansenii, Campylobacter hominis\|Blautia hansenii, Capnocytophaga ochracea\|Blautia hansenii, Cardiobacterium hominis\|Blautia hansenii, Catenibacterium mitsuokai\|Blautia hansenii, Catonella morbi\|Blautia hansenii, Citrobacter koseri\|Blautia hansenii, Clostridium asparagiforme\|Blautia hansenii, Clostridium bartlettii\|Blautia hansenii, Clostridium bolteae\|Blautia hansenii, Clostridium botulinum\|Blautia hansenii, Clostridium butyricum\|Blautia hansenii, Clostridium difficile\|Blautia hansenii, Clostridium disporicum\|Blautia hansenii, Clostridium hathewayi\|Blautia hansenii, Clostridium hylemonae\|Blautia hansenii, Clostridium innocuum\|Blautia hansenii, Clostridium leptum\|Blautia hansenii, Clostridium mayombei\|Blautia hansenii, Clostridium methylpentosum\|Blautia hansenii, Clostridium nexile\|Blautia hansenii, Clostridium orbiscindens\|Blautia hansenii, Clostridium perfringens\|Blautia hansenii, Clostridium saccharolyticum\|Blautia hansenii, Clostridium scindens\|Blautia hansenii, Clostridium symbiosum\|Blautia hansenii, Clostridium tertium\|Blautia hansenii, Collinsella aerofaciens\|Blautia hansenii, Collinsella intestinalis\|Blautia hansenii, Collinsella stercoris\|Blautia hansenii, Coprobacillus sp. D7\|Blautia hansenii, Coprococcus catus\|Blautia hansenii, Coprococcus comes\|Blautia hansenii, Coprococcus eutactus\|Blautia hansenii, Corynebacterium aurimucosum\|Blautia hansenii, Corynebacterium matruchotii\|Blautia hansenii, Cryptobacterium curtum\|Blautia hansenii, Desulfovibrio desulfuricans\|Blautia hansenii, Desulfovibrio piger\|Blautia hansenii, Dialister invisus\|Blautia hansenii, Dialister microaerophilus\|Blautia hansenii, Dorea formicigenerans\|Blautia hansenii, Dorea longicatena\|Blautia hansenii, Eggerthella lenta\|Blautia hansenii, Eikenella corrodens\|Blautia hansenii, Enterobacter cancerogenus\|Blautia hansenii, Enterobacter cloacae\|Blautia hansenii, Enterococcus faecalis\|Blautia hansenii, Enterococcus faecium\|Blautia hansenii, Enterococcus gallinarum\|Blautia hansenii, Erysipelotrichaceae bacterium 3_1_53\|Blautia hansenii, Escherichia coli\|Blautia hansenii, Escherichia fergusonii\|Blautia hansenii, Ethanoligenens harbinense\|Blautia hansenii, Eubacterium cellulosolvens\|Blautia hansenii, Eubacterium eligens\|Blautia hansenii, Eubacterium hallii\|Blautia hansenii, Eubacterium limosum\|Blautia hansenii, Eubacterium rectale\|Blautia hansenii, Eubacterium siraeum\|Blautia hansenii, Eubacterium ventriosum\|Blautia hansenii, Faecalibacterium prausnitzii\|Blautia hansenii, Finegoldia magna\|Blautia hansenii, Fusobacterium gonidiaformans\|Blautia hansenii, Fusobacterium mortiferum\|Blautia hansenii, Fusobacterium nucleatum\|Blautia hansenii, Fusobacterium varium\|Blautia hansenii, Gardnerella vaginalis\|Blautia hansenii, Gemella haemolysans\|Blautia hansenii, Gemella morbillorum\|Blautia hansenii, Gordonibacter pamelaeae\|Blautia hansenii, Granulicatella adiacens\|Blautia hansenii, Granulicatella elegans\|Blautia hansenii, Haemophilus influenzae\|Blautia hansenii, Haemophilus parainfluenzae\|Blautia hansenii, Helicobacter pullorum\|Blautia hansenii, Helicobacter pylori\|Blautia hansenii, Holdemania filiformis\|Blautia hansenii, Kingella oralis\|Blautia hansenii, Klebsiella pneumoniae\|Blautia hansenii, Klebsiella variicola\|Blautia hansenii, Lachnospiraceae bacterium 5_1_57FAA\|Blautia hansenii, Lactobacillus acidophilus\|Blautia hansenii, Lactobacillus amylovorus\|Blautia hansenii, Lactobacillus brevis\|Blautia hansenii, Lactobacillus casei\|Blautia hansenii, Lactobacillus crispatus\|Blautia hansenii, Lactobacillus delbrueckii\|Blautia hansenii, Lactobacillus fermentum\|Blautia hansenii, Lactobacillus gasseri\|Blautia hansenii, Lactobacillus iners\|Blautia hansenii, Lactobacillus jensenii\|Blautia hansenii, Lactobacillus johnsonii\|Blautia hansenii, Lactobacillus paracasei\|Blautia hansenii, Lactobacillus plantantm\|Blautia hansenii, Lactobacillus reuteri\|Blautia hansenii, Lactobacillus rhamnosus\|Blautia |

TABLE 2-continued

Table 2. Specific binary combinations of OTUs. Individual pairings are differentiated by "|" and OTUs within a combination are differentiated by ","

hansenii, Lactobacillus ruminis|Blautia hansenii, Lactobacillus sakei|Blautia hansenii, Lactobacillus salivarius|Blautia hansenii, Lactococcus lactis|Blautia hansenii, Lautropia mirabilis|Blautia hansenii, Leuconostoc citreum|Blautia hansenii, Leuconostoc gasicomitatum|Blautia hansenii, Leuconostoc mesenteroides|Blautia hansenii, Listeria monocytogenes|Blautia hansenii, Marvinbryantia formatexigens|Blautia hansenii, Megamonas hypermegale|Blautia hansenii, Megasphaera micronuciformis|Blautia hansenii, Methanobrevibacter smithii|Blautia hansenii, Methanosphaera stadtmanae|Blautia hansenii, Methylobacterium radiotolerans|Blautia hansenii, Mitsuokella multacida|Blautia hansenii, Mobiluncus curtisii|Blautia hansenii, Mycoplasma hominis|Blautia hansenii, Neisseria mucosa|Blautia hansenii, Odoribacter splanchnicus|Blautia hansenii, Olsenella uli|Blautia hansenii, Oribacterium sinus|Blautia hansenii, Oxalobacter formigenes|Blautia hansenii, Parabacteroides distasonis|Blautia hansenii, Parabacteroides johnsonii|Blautia hansenii, Parabacteroides merdae|Blautia hansenii, Parvimonas micra|Blautia hansenii, Pediococcus acidilactici|Blautia hansenii, Pediococcus pentosaceus|Blautia hansenii, Peptoniphilus duerdenii|Blautia hansenii, Peptoniphilus harei|Blautia hansenii, Peptoniphilus lacrimalis|Blautia hansenii, Peptostreptococcus anaerobius|Blautia hansenii, Peptostreptococcus stomatis|Blautia hansenii, Porphyromonas asaccharolytica|Blautia hansenii, Porphyromonas uenonis|Blautia hansenii, Prevotella amnii|Blautia hansenii, Prevotella bergensis|Blautia hansenii, Prevotella bivia|Blautia hansenii, Prevotella buccae|Blautia hansenii, Prevotella buccalis|Blautia hansenii, Prevotella copri|Blautia hansenii, Prevotella disiens|Blautia hansenii, Prevotella melaninogenica|Blautia hansenii, Prevotella multiformis|Blautia hansenii, Prevotella oralis|Blautia hansenii, Prevotella oris|Blautia hansenii, Prevotella salivae|Blautia hansenii, Prevotella timonensis|Blautia hansenii, Propionibacterium acnes|Blautia hansenii, Propionibacterium freudenreichii|Blautia hansenii, Proteus mirabilis|Blautia hansenii, Proteus penneri|Blautia hansenii, Pseudoflavonifractor capillosus|Blautia hansenii, Pseudomonas aeruginosa|Blautia hansenii, Pseudomonas fluorescens|Blautia hansenii, Pseudomonas putida|Blautia hansenii, Pseudoramibacter alactolyticus|Blautia hansenii, Pyramidobacter piscolens|Blautia hansenii, Rhodopseudomonas palustris|Blautia hansenii, Roseburia intestinalis|Blautia hansenii, Roseburia inulinivorans|Blautia hansenii, Rothia dentocariosa|Blautia hansenii, Rothia mucilaginosa|Blautia hansenii, Ruminococcus albus|Blautia hansenii, Ruminococcus bromii|Blautia hansenii, Ruminococcus gnavus|Blautia hansenii, Ruminococcus lactaris|Blautia hansenii, Ruminococcus obeum|Blautia hansenii, Ruminococcus torques|Blautia hansenii, Selenomonas sputigena|Blautia hansenii, Shigella boydii|Blautia hansenii, Shigella dysenteriae|Blautia hansenii, Shigella sonnei|Blautia hansenii, Slackia exigua|Blautia hansenii, Solobacterium moorei|Blautia hansenii, Staphylococcus aureus|Blautia hansenii, Staphylococcus epidermidis|Blautia hansenii, Staphylococcus hominis|Blautia hansenii, Staphylococcus saprophyticus|Blautia hansenii, Staphylococcus warneri|Blautia hansenii, Streptococcus agalactiae|Blautia hansenii, Streptococcus anginosus|Blautia hansenii, Streptococcus australis|Blautia hansenii, Streptococcus bovis|Blautia hansenii, Streptococcus cristatus|Blautia hansenii, Streptococcus dysgalactiae|Blautia hansenii, Streptococcus equinus|Blautia hansenii, Streptococcus gordonii|Blautia hansenii, Streptococcus infantarius|Blautia hansenii, Streptococcus infantis|Blautia hansenii, Streptococcus mitis|Blautia hansenii, Streptococcus mutans|Blautia hansenii, Streptococcus oralis|Blautia hansenii, Streptococcus parasanguinis|Blautia hansenii, Streptococcus peroris|Blautia hansenii, Streptococcus pneumoniae|Blautia hansenii, Streptococcus salivarius|Blautia hansenii, Streptococcus sanguinis|Blautia hansenii, Streptococcus thermophilus|Blautia hansenii, Streptococcus vestibularis|Blautia hansenii, Subdoligranulum variabile|Blautia hansenii, Succinatimonas hippei|Blautia hansenii, Sutterella wadsworthensis|Blautia hansenii, Tropheryma whipplei|Blautia hansenii, Veillonella atypica|Blautia hansenii, Veillonella dispar|Blautia hansenii, Veillonella parvula|Blautia hansenii, Victivallis vadensis|Blautia hydrogenotrophica, Blautia hydrogenotrophica|Blautia hydrogenotrophica, Blautia producta|Blautia hydrogenotrophica, Blautia schinkii|Blautia hydrogenotrophica, Brevibacterium linens|Blautia hydrogenotrophica, Brucella ceti|Blautia hydrogenotrophica, Brucella suis|Blautia hydrogenotrophica, Bulleidia extructa|Blautia hydrogenotrophica, Butyrivibrio crossotus|Blautia hydrogenotrophica, Campylobacter concisus|Blautia hydrogenotrophica, Campylobacter curvus|Blautia hydrogenotrophica, Campylobacter gracilis|Blautia hydrogenotrophica, Campylobacter hominis|Blautia hydrogenotrophica, Capnocytophaga ochracea|Blautia hydrogenotrophica, Cardiobacterium hominis|Blautia hydrogenotrophica, Catenibacterium mitsuokai|Blautia hydrogenotrophica, Catonella morbi|Blautia hydrogenotrophica, Citrobacter koseri|Blautia hydrogenotrophica, Clostridium asparagiforme|Blautia hydrogenotrophica, Clostridium bartlettii|Blautia hydrogenotrophica, Clostridium bolteae|Blautia hydrogenotrophica, Clostridium botulinum|Blautia hydrogenotrophica, Clostridium butyricum|Blautia hydrogenotrophica, Clostridium difficile|Blautia hydrogenotrophica, Clostridium disporicum|Blautia hydrogenotrophica, Clostridium hathewayi|Blautia hydrogenotrophica, Clostridium hylemonae|Blautia hydrogenotrophica, Clostridium innocuum|Blautia hydrogenotrophica, Clostridium leptum|Blautia hydrogenotrophica, Clostridium mayombei|Blautia hydrogenotrophica, Clostridium methylpentosum|Blautia hydrogenotrophica, Clostridium nexile|Blautia hydrogenotrophica, Clostridium orbiscindens|Blautia hydrogenotrophica, Clostridium perfringens|Blautia hydrogenotrophica, Clostridium saccharolyticum|Blautia hydrogenotrophica, Clostridium scindens|Blautia hydrogenotrophica, Clostridium symbiosum|Blautia hydrogenotrophica, Clostridium tertium|Blautia hydrogenotrophica, Collinsella aerofaciens|Blautia hydrogenotrophica, Collinsella intestinalis|Blautia hydrogenotrophica, Collinsella stercoris|Blautia hydrogenotrophica, Coprobacillus sp. D7|Blautia hydrogenotrophica, Coprococcus catus|Blautia hydrogenotrophica, Coprococcus comes|Blautia hydrogenotrophica, Coprococcus eutactus|Blautia hydrogenotrophica, Corynebacterium aurimucosum|Blautia hydrogenotrophica, Corynebacterium matruchotii|Blautia hydrogenotrophica, Cryptobacterium curtum|Blautia hydrogenotrophica, Desulfovibrio desulfuricans|Blautia hydrogenotrophica, Desulfovibrio piger|Blautia hydrogenotrophica, Dialister invisus|Blautia hydrogenotrophica, Dialister microaerophilus|Blautia hydrogenotrophica, Dorea formicigenerans|Blautia hydrogenotrophica, Dorea longicatena|Blautia hydrogenotrophica, Eggerthella lenta|Blautia hydrogenotrophica, Eikenella corrodens|Blautia hydrogenotrophica, Enterobacter cancerogenus|Blautia hydrogenotrophica, Enterobacter cloacae|Blautia hydrogenotrophica, Enterococcus faecalis|Blautia hydrogenotrophica, Enterococcus faecium|Blautia hydrogenotrophica, Enterococcus gallinarum|Blautia hydrogenotrophica, Erysipelotrichaceae bacterium 3_1_53|Blautia hydrogenotrophica, Escherichia coli|Blautia hydrogenotrophica, Escherichia fergusonii|Blautia hydrogenotrophica, Ethanoligenens harbinense|Blautia hydrogenotrophica, Eubacterium cellulosolvens|Blautia hydrogenotrophica, Eubacterium eligens|Blautia hydrogenotrophica, Eubacterium hallii|Blautia hydrogenotrophica, Eubacterium limosum|Blautia hydrogenotrophica, Eubacterium rectale|Blautia hydrogenotrophica, Eubacterium siraeum|Blautia hydrogenotrophica, Eubacterium ventriosum|Blautia hydrogenotrophica, Faecalibacterium prausnitzii|Blautia hydrogenotrophica, Finegoldia magna|Blautia hydrogenotrophica, Fusobacterium gonidiaformans|Blautia hydrogenotrophica, Fusobacterium mortiferum|Blautia hydrogenotrophica, Fusobacterium nucleatum|Blautia hydrogenotrophica, Fusobacterium varium|Blautia hydrogenotrophica, Gardnerella vaginalis|Blautia hydrogenotrophica, Gemella haemolysans|Blautia hydrogenotrophica, Gemella morbillorum|Blautia hydrogenotrophica, Gordonibacter pamelaeae|Blautia hydrogenotrophica, Granulicatella adiacens|Blautia hydrogenotrophica, Granulicatella elegans|Blautia hydrogenotrophica, Haemophilus influenzae|Blautia hydrogenotrophica, Haemophilus parainfluenzae|Blautia hydrogenotrophica, Helicobacter pullorum|Blautia hydrogenotrophica, Helicobacter pylori|Blautia hydrogenotrophica, Holdemania filiformis|Blautia hydrogenotrophica, Kingella oralis|Blautia hydrogenotrophica, Klebsiella pneumoniae|Blautia hydrogenotrophica, Klebsiella variicola|Blautia hydrogenotrophica, Lachnospiraceae bacterium 5_1_57FAA|Blautia hydrogenotrophica, Lactobacillus acidophilus|Blautia hydrogenotrophica, Lactobacillus amylovorus|Blautia hydrogenotrophica, Lactobacillus brevis|Blautia hydrogenotrophica, Lactobacillus casei|Blautia hydrogenotrophica, Lactobacillus crispatus|Blautia hydrogenotrophica, Lactobacillus delbrueckii|Blautia hydrogenotrophica, Lactobacillus fermentum|Blautia hydrogenotrophica, Lactobacillus gasseri|Blautia hydrogenotrophica, Lactobacillus iners|Blautia hydrogenotrophica, Lactobacillus jensenii|Blautia hydrogenotrophica, Lactobacillus johnsonii|Blautia hydrogenotrophica, Lactobacillus paracasei|Blautia hydrogenotrophica, Lactobacillus plantarum|Blautia hydrogenotrophica, Lactobacillus reuteri|Blautia hydrogenotrophica, Lactobacillus rhamnosus|Blautia hydrogenotrophica, Lactobacillus ruminis|Blautia hydrogenotrophica, Lactobacillus sakei|Blautia hydrogenotrophica, Lactobacillus salivarius|Blautia hydrogenotrophica, Lactococcus lactis|Blautia hydrogenotrophica, Lautropia mirabilis|Blautia hydrogenotrophica, Leuconostoc citreum|Blautia hydrogenotrophica, Leuconostoc gasicomitatum|Blautia hydrogenotrophica, Leuconostoc TABLE 2-continued Table 2. Specific binary combinations of OTUs. Individual pairings are differentiated by "|" and OTUs within a combination are differentiated by ","

mesenteroides|Blautia hydrogenotrophica, Listeria monocytogenes|Blautia hydrogenotrophica, Marvinbryantia formatexigens|Blautia hydrogenotrophica, Megamonas hypermegale|Blautia hydrogenotrophica, Megasphaera micronuciformis|Blautia hydrogenotrophica, Methanobrevibacter smithii|Blautia hydrogenotrophica, Methanosphaera stadtmanae|Blautia hydrogenotrophica, Methylobacterium radiotolerans|Blautia hydrogenotrophica, Mitsuokella multacida|Blautia hydrogenotrophica, Mobiluncus curtisii|Blautia hydrogenotrophica, Mycoplasma hominis|Blautia hydrogenotrophica, Neisseria mucosa|Blautia hydrogenotrophica, Odoribacter splanchnicus|Blautia hydrogenotrophica, Olsenella uli|Blautia hydrogenotrophica, Oribacterium sinus|Blautia hydrogenotrophica, Oxalobacter formigenes|Blautia hydrogenotrophica, Parabacteroides distasonis|Blautia hydrogenotrophica, Parabacteroides johnsonii|Blautia hydrogenotrophica, Parabacteroides merdae|Blautia hydrogenotrophica, Parvimonas micra|Blautia hydrogenotrophica, Pediococcus acidilactici|Blautia hydrogenotrophica, Pediococcus pentosaceus|Blautia hydrogenotrophica, Peptoniphilus duerdenii|Blautia hydrogenotrophica, Peptoniphilus harei|Blautia hydrogenotrophica, Peptoniphilus lacrimalis|Blautia hydrogenotrophica, Peptostreptococcus anaerobius|Blautia hydrogenotrophica, Peptostreptococcus stomatis|Blautia hydrogenotrophica, Porphyromonas asaccharolytica|Blautia hydrogenotrophica, Porphyromonas uenonis|Blautia hydrogenotrophica, Prevotella amnii|Blautia hydrogenotrophica, Prevotella bergensis|Blautia hydrogenotrophica, Prevotella bivia|Blautia hydrogenotrophica, Prevotella buccae|Blautia hydrogenotrophica, Prevotella buccalis|Blautia hydrogenotrophica, Prevotella copri|Blautia hydrogenotrophica, Prevotella disiens|Blautia hydrogenotrophica, Prevotella melaninogenica|Blautia hydrogenotrophica, Prevotella multiformis|Blautia hydrogenotrophica, Prevotella oralis|Blautia hydrogenotrophica, Prevotella oris|Blautia hydrogenotrophica, Prevotella salivae|Blautia hydrogenotrophica, Prevotella timonensis|Blautia hydrogenotrophica, Propionibacterium acnes|Blautia hydrogenotrophica, Propionibacterium freudenreichii|Blautia hydrogenotrophica, Proteus mirabilis|Blautia hydrogenotrophica, Proteus penneri|Blautia hydrogenotrophica, Pseudoflavonifractor capillosus|Blautia hydrogenotrophica, Pseudomonas aeruginosa|Blautia hydrogenotrophica, Pseudomonas fluorescens|Blautia hydrogenotrophica, Pseudomonas putida|Blautia hydrogenotrophica, Pseudoramibacter alactolyticus|Blautia hydrogenotrophica, Pyramidobacter piscolens|Blautia hydrogenotrophica, Rhodopseudomonas palustris|Blautia hydrogenotrophica, Roseburia intestinalis|Blautia hydrogenotrophica, Roseburia inulinivorans|Blautia hydrogenotrophica, Rothia dentocariosa|Blautia hydrogenotrophica, Rothia mucilaginosa|Blautia hydrogenotrophica, Ruminococcus albus|Blautia hydrogenotrophica, Ruminococcus bromii|Blautia hydrogenotrophica, Ruminococcus gnavus|Blautia hydrogenotrophica, Ruminococcus lactaris|Blautia hydrogenotrophica, Ruminococcus obeum|Blautia hydrogenotrophica, Ruminococcus torques|Blautia hydrogenotrophica, Selenomonas sputigena|Blautia hydrogenotrophica, Shigella boydii|Blautia hydrogenotrophica, Shigella dysenteriae|Blautia hydrogenotrophica, Shigella sonnei|Blautia hydrogenotrophica, Slackia exigua|Blautia hydrogenotrophica, Solobacterium moorei|Blautia hydrogenotrophica, Staphylococcus aureus|Blautia hydrogenotrophica, Staphylococcus epidermidis|Blautia hydrogenotrophica, Staphylococcus hominis|Blautia hydrogenotrophica, Staphylococcus saprophyticus|Blautia hydrogenotrophica, Staphylococcus warneri|Blautia hydrogenotrophica, Streptococcus agalactiae|Blautia hydrogenotrophica, Streptococcus anginosus|Blautia hydrogenotrophica, Streptococcus australis|Blautia hydrogenotrophica, Streptococcus bovis|Blautia hydrogenotrophica, Streptococcus cristatus|Blautia hydrogenotrophica, Streptococcus dysgalactiae|Blautia hydrogenotrophica, Streptococcus equinus|Blautia hydrogenotrophica, Streptococcus gordonii|Blautia hydrogenotrophica, Streptococcus infantarius|Blautia hydrogenotrophica, Streptococcus infantis|Blautia hydrogenotrophica, Streptococcus mitis|Blautia hydrogenotrophica, Streptococcus mutans|Blautia hydrogenotrophica, Streptococcus oralis|Blautia hydrogenotrophica, Streptococcus parasanguinis|Blautia hydrogenotrophica, Streptococcus peroris|Blautia hydrogenotrophica, Streptococcus pneumoniae|Blautia hydrogenotrophica, Streptococcus salivarius|Blautia hydrogenotrophica, Streptococcus sanguinis|Blautia hydrogenotrophica, Streptococcus thermophilus|Blautia hydrogenotrophica, Streptococcus vestibularis|Blautia hydrogenotrophica, Subdoligranulum variabile|Blautia hydrogenotrophica, Succinatimonas hippei|Blautia hydrogenotrophica, Sutterella wadsworthensis|Blautia hydrogenotrophica, Tropheryma whipplei|Blautia hydrogenotrophica, Veillonella atypica|Blautia hydrogenotrophica, Veillonella dispar|Blautia hydrogenotrophica, Veillonella parvula|Blautia hydrogenotrophica, Victivallis vadensis|Blautia producta, Blautia producta|Blautia producta, Blautia schinkii|Blautia producta, Brevibacterium linens|Blautia producta, Brucella ceti|Blautia producta, Brucella suis|Blautia producta, Bulleidia extructa|Blautia producta, Butyrivibrio crossotus|Blautia producta, Campylobacter concisus|Blautia producta, Campylobacter curvus|Blautia producta, Campylobacter gracilis|Blautia producta, Campylobacter hominis|Blautia producta, Capnocytophaga ochracea|Blautia producta, Cardiobacterium hominis|Blautia producta, Catenibacterium mitsuokai|Blautia producta, Catonella morbi|Blautia producta, Citrobacter koseri|Blautia producta, Clostridium asparagiforme|Blautia producta, Clostridium bartlettii|Blautia producta, Clostridium bolteae|Blautia producta, Clostridium botulinum|Blautia producta, Clostridium butyricum|Blautia producta, Clostridium difficile|Blautia producta, Clostridium disporicum|Blautia producta, Clostridium hathewayi|Blautia producta, Clostridium hylemonae|Blautia producta, Clostridium innocuum|Blautia producta, Clostridium leptum|Blautia producta, Clostridium mayombei|Blautia producta, Clostridium methylpentosum|Blautia producta, Clostridium nexile|Blautia producta, Clostridium orbiscindens|Blautia producta, Clostridium perfringens|Blautia producta, Clostridium saccharolyticum|Blautia producta, Clostridium scindens|Blautia producta, Clostridium symbiosum|Blautia producta, Clostridium tertium|Blautia producta, Collinsella aerofaciens|Blautia producta, Collinsella intestinalis|Blautia producta, Collinsella stercoris|Blautia producta, Coprobacillus sp. D7|Blautia producta, Coprococcus catus|Blautia producta, Coprococcus comes|Blautia producta, Coprococcus eutactus|Blautia producta, Corynebacterium aurimucosum|Blautia producta, Corynebacterium matruchotii|Blautia producta, Cryptobacterium curtum|Blautia producta, Desulfovibrio desulfuricans|Blautia producta, Desulfovibrio piger|Blautia producta, Dialister invisus|Blautia producta, Dialister microaerophilus|Blautia producta, Dorea formicigenerans|Blautia producta, Dorea longicatena|Blautia producta, Eggerthella lenta|Blautia producta, Eikenella corrodens|Blautia producta, Enterobacter cancerogenus|Blautia producta, Enterobacter cloacae|Blautia producta, Enterococcus faecalis|Blautia producta, Enterococcus faecium|Blautia producta, Enterococcus gallinarum|Blautia producta, Erysipelotrichaceae bacterium 3_1_53|Blautia producta, Escherichia coli|Blautia producta, Escherichia fergusonii|Blautia producta, Ethanoligenens harbinense|Blautia producta, Eubacterium cellulosolvens|Blautia producta, Eubacterium eligens|Blautia producta, Eubacterium hallii|Blautia producta, Eubacterium limosum|Blautia producta, Eubacterium rectale|Blautia producta, Eubacterium siraeum|Blautia producta, Eubacterium ventriosum|Blautia producta, Faecalibacterium prausnitzii|Blautia producta, Finegoldia magna|Blautia producta, Fusobacterium gonidiaformans|Blautia producta, Fusobacterium mortiferum|Blautia producta, Fusobacterium nucleatum|Blautia producta, Fusobacterium varium|Blautia producta, Gardnerella vaginalis|Blautia producta, Gemella haemolysans|Blautia producta, Gemella morbillorum|Blautia producta, Gordonibacter pamelaeae|Blautia producta, Granulicatella adiacens|Blautia producta, Granulicatella elegans|Blautia producta, Haemophilus influenzae|Blautia producta, Haemophilus parainfluenzae|Blautia producta, Helicobacter pullorum|Blautia producta, Helicobacter pylori|Blautia producta, Holdemania filiformis|Blautia producta, Kingella oralis|Blautia producta, Klebsiella pneumoniae|Blautia producta, Klebsiella variicola|Blautia producta, Lachnospiraceae bacterium 5_1_57FAA|Blautia producta, Lactobacillus acidophilus|Blautia producta, Lactobacillus amylovorus|Blautia producta, Lactobacillus brevis|Blautia producta, Lactobacillus casei|Blautia producta, Lactobacillus crispatus|Blautia producta, Lactobacillus delbrueckii|Blautia producta, Lactobacillus fermentum|Blautia producta, Lactobacillus gasseri|Blautia producta, Lactobacillus iners|Blautia producta, Lactobacillus jensenii|Blautia producta, Lactobacillus johnsonii|Blautia producta, Lactobacillus paracasei|Blautia producta, Lactobacillus plantarum|Blautia producta, Lactobacillus reuteri|Blautia producta, Lactobacillus rhamnosus|Blautia producta, Lactobacillus ruminis|Blautia producta, Lactobacillus sakei|Blautia producta, Lactobacillus salivarius|Blautia producta, Lactococcus lactis|Blautia producta, Lautropia mirabilis|Blautia producta, Leuconostoc citreum|Blautia producta, Leuconostoc gasicomitatum|Blautia producta, Leuconostoc mesenteroides|Blautia producta, Listeria monocytogenes|Blautia producta, Marvinbryantia formatexigens|Blautia producta, Megamonas hypermegale|Blautia producta, Megasphaera micronuciformis|Blautia producta, Methanobrevibacter smithii|Blautia producta, Methanosphaera stadtmanae|Blautia producta, Methylobacterium radiotolerans|Blautia producta, Mitsuokella multacida|Blautia producta, Mobiluncus curtisii|Blautia producta, Mycoplasma hominis|Blautia producta, Neisseria mucosa|Blautia TABLE 2-continued

| Table 2. Specific binary combinations of OTUs. Individual pairings are differentiated by "\|" and OTUs within a combination are differentiated by "," |
|---|
| *producta, Odoribacter splanchnicus\|Blautia producta, Olsenella uli\|Blautia producta, Oribacterium sinus\|Blautia producta, Oxalobacter formigenes\|Blautia producta, Parabacteroides distasonis\|Blautia producta, Parabacteroides johnsonii\|Blautia producta, Parabacteroides merdae\|Blautia producta, Parvimonas micra\|Blautia producta, Pediococcus acidilactici\|Blautia producta, Pediococcus pentosaceus\|Blautia producta, Peptoniphilus duerdenii\|Blautia producta, Peptoniphilus harei\|Blautia producta, Peptoniphilus lacrimalis\|Blautia producta, Peptostreptococcus anaerobius\|Blautia producta, Peptostreptococcus stomatis\|Blautia producta, Porphyromonas asaccharolytica\|Blautia producta, Porphyromonas uenonis\|Blautia producta, Prevotella amnii\|Blautia producta, Prevotella bergensis\|Blautia producta, Prevotella bivia\|Blautia producta, Prevotella buccae\|Blautia producta, Prevotella buccalis\|Blautia producta, Prevotella copri\|Blautia producta, Prevotella disiens\|Blautia producta, Prevotella melaninogenica\|Blautia producta, Prevotella multiformis\|Blautia producta, Prevotella oralis\|Blautia producta, Prevotella oris\|Blautia producta, Prevotella salivae\|Blautia producta, Prevotella timonensis\|Blautia producta, Propionibacterium acnes\|Blautia producta, Propionibacterium freudenreichii\|Blautia producta, Proteus mirabilis\|Blautia producta, Proteus penneri\|Blautia producta, Pseudoflavonifractor capillosus\|Blautia producta, Pseudomonas aeruginosa\|Blautia producta, Pseudomonas fluorescens\|Blautia producta, Pseudomonas putida\|Blautia producta, Pseudoramibacter alactolyticus\|Blautia producta, Pyramidobacter piscolens\|Blautia producta, Rhodopseudomonas palustris\|Blautia producta, Roseburia intestinalis\|Blautia producta, Roseburia inulinivorans\|Blautia producta, Rothia dentocariosa\|Blautia producta, Rothia mucilaginosa\|Blautia producta, Ruminococcus albus\|Blautia producta, Ruminococcus bromii\|Blautia producta, Ruminococcus gnavus\|Blautia producta, Ruminococcus lactaris\|Blautia producta, Ruminococcus obeum\|Blautia producta, Ruminococcus torques\|Blautia producta, Selenomonas sputigena\|Blautia producta, Shigella boydii\|Blautia producta, Shigella dysenteriae\|Blautia producta, Shigella sonnei\|Blautia producta, Slackia exigua\|Blautia producta, Solobacterium moorei\|Blautia producta, Staphylococcus aureus\|Blautia producta, Staphylococcus epidermidis\|Blautia producta, Staphylococcus hominis\|Blautia producta, Staphylococcus saprophyticus\|Blautia producta, Staphylococcus warneri\|Blautia producta, Streptococcus agalactiae\|Blautia producta, Streptococcus anginosus\|Blautia producta, Streptococcus australis\|Blautia producta, Streptococcus bovis\|Blautia producta, Streptococcus cristatus\|Blautia producta, Streptococcus dysgalactiae\|Blautia producta, Streptococcus equinus\|Blautia producta, Streptococcus gordonii\|Blautia producta, Streptococcus infantarius\|Blautia producta, Streptococcus infantis\|Blautia producta, Streptococcus mitis\|Blautia producta, Streptococcus mutans\|Blautia producta, Streptococcus oralis\|Blautia producta, Streptococcus parasanguinis\|Blautia producta, Streptococcus peroris\|Blautia producta, Streptococcus pneumoniae\|Blautia producta, Streptococcus salivarius\|Blautia producta, Streptococcus sanguinis\|Blautia producta, Streptococcus thermophilus\|Blautia producta, Streptococcus vestibularis\|Blautia producta, Subdoligranulum variabile\|Blautia producta, Succinatimonas hippei\|Blautia producta, Sutterella wadsworthensis\|Blautia producta, Tropheryma whipplei\|Blautia producta, Veillonella atypica\|Blautia producta, Veillonella dispar\|Blautia producta, Veillonella parvula\|Blautia producta, Victivallis vadensis\|Blautia schinkii, Blautia schinkii\|Blautia schinkii, Brevibacterium linens\|Blautia schinkii, Brucella ceti\|Blautia schinkii, Brucella suis\|Blautia schinkii, Bulleidia extructa\|Blautia schinkii, Butyrivibrio crossotus\|Blautia schinkii, Campylobacter concisus\|Blautia schinkii, Campylobacter curvus\|Blautia schinkii, Campylobacter gracilis\|Blautia schinkii, Campylobacter hominis\|Blautia schinkii, Capnocytophaga ochracea\|Blautia schinkii, Cardiobacterium hominis\|Blautia schinkii, Catenibacterium mitsuokai\|Blautia schinkii, Catonella morbi\|Blautia schinkii, Citrobacter koseri\|Blautia schinkii, Clostridium asparagiforme\|Blautia schinkii, Clostridium bartlettii\|Blautia schinkii, Clostridium bolteae\|Blautia schinkii, Clostridium botulinum\|Blautia schinkii, Clostridium butyricum\|Blautia schinkii, Clostridium difficile\|Blautia schinkii, Clostridium disporicum\|Blautia schinkii, Clostridium hathewayi\|Blautia schinkii, Clostridium hylemonae\|Blautia schinkii, Clostridium innocuum\|Blautia schinkii, Clostridium leptum\|Blautia schinkii, Clostridium mayombei\|Blautia schinkii, Clostridium methylpentosum\|Blautia schinkii, Clostridium nexile\|Blautia schinkii, Clostridium orbiscindens\|Blautia schinkii, Clostridium perfringens\|Blautia schinkii, Clostridium saccharolyticum\|Blautia schinkii, Clostridium scindens\|Blautia schinkii, Clostridium symbiosum\|Blautia schinkii, Clostridium tertium\|Blautia schinkii, Collinsella aerofaciens\|Blautia schinkii, Collinsella intestinalis\|Blautia schinkii, Collinsella stercoris\|Blautia schinkii, Coprobacillus* sp. D7\|*Blautia schinkii, Coprococcus catus\|Blautia schinkii, Coprococcus comes\|Blautia schinkii, Coprococcus eutactus\|Blautia schinkii, Corynebacterium aurimucosum\|Blautia schinkii, Corynebacterium matruchotii\|Blautia schinkii, Cryptobacterium curtum\|Blautia schinkii, Desulfovibrio desulfuricans\|Blautia schinkii, Desulfovibrio piger\|Blautia schinkii, Dialister invisus\|Blautia schinkii, Dialister microaerophilus\|Blautia schinkii, Dorea formicigenerans\|Blautia schinkii, Dorea longicatena\|Blautia schinkii, Eggerthella lenta\|Blautia schinkii, Eikenella corrodens\|Blautia schinkii, Enterobacter cancerogenus\|Blautia schinkii, Enterobacter cloacae\|Blautia schinkii, Enterococcus faecalis\|Blautia schinkii, Enterococcus faecium\|Blautia schinkii, Enterococcus gallinarum\|Blautia schinkii, Erysipelotrichaceae bacterium* 3_1_53\|*Blautia schinkii, Escherichia coli\|Blautia schinkii, Escherichia fergusonii\|Blautia schinkii, Ethanoligenens harbinense\|Blautia schinkii, Eubacterium cellulosolvens\|Blautia schinkii, Eubacterium eligens\|Blautia schinkii, Eubacterium hallii\|Blautia schinkii, Eubacterium limosum\|Blautia schinkii, Eubacterium rectale\|Blautia schinkii, Eubacterium siraeum\|Blautia schinkii, Eubacterium ventriosum\|Blautia schinkii, Faecalibacterium prausnitzii\|Blautia schinkii, Finegoldia magna\|Blautia schinkii, Fusobacterium gonidiaformans\|Blautia schinkii, Fusobacterium mortiferum\|Blautia schinkii, Fusobacterium nucleatum\|Blautia schinkii, Fusobacterium varium\|Blautia schinkii, Gardnerella vaginalis\|Blautia schinkii, Gemella haemolysans\|Blautia schinkii, Gemella morbillorum\|Blautia schinkii, Gordonibacter pamelaeae\|Blautia schinkii, Granulicatella adiacens\|Blautia schinkii, Granulicatella elegans\|Blautia schinkii, Haemophilus influenzae\|Blautia schinkii, Haemophilus parainfluenzae\|Blautia schinkii, Helicobacter pullorum\|Blautia schinkii, Helicobacter pylori\|Blautia schinkii, Holdemania filiformis\|Blautia schinkii, Kingella oralis\|Blautia schinkii, Klebsiella pneumoniae\|Blautia schinkii, Klebsiella variicola\|Blautia schinkii, Lachnospiraceae bacterium* 5_1_57FAA\|*Blautia schinkii, Lactobacillus acidophilus\|Blautia schinkii, Lactobacillus amylovorus\|Blautia schinkii, Lactobacillus brevis\|Blautia schinkii, Lactobacillus casei\|Blautia schinkii, Lactobacillus crispatus\|Blautia schinkii, Lactobacillus delbrueckii\|Blautia schinkii, Lactobacillus fermentum\|Blautia schinkii, Lactobacillus gasseri\|Blautia schinkii, Lactobacillus iners\|Blautia schinkii, Lactobacillus jensenii\|Blautia schinkii, Lactobacillus johnsonii\|Blautia schinkii, Lactobacillus paracasei\|Blautia schinkii, Lactobacillus plantarum\|Blautia schinkii, Lactobacillus reuteri\|Blautia schinkii, Lactobacillus rhamnosus\|Blautia schinkii, Lactobacillus ruminis\|Blautia schinkii, Lactobacillus sakei\|Blautia schinkii, Lactobacillus salivarius\|Blautia schinkii, Lactococcus lactis\|Blautia schinkii, Lautropia mirabilis\|Blautia schinkii, Leuconostoc citreum\|Blautia schinkii, Leuconostoc gasicomitatum\|Blautia schinkii, Leuconostoc mesenteroides\|Blautia schinkii, Listeria monocytogenes\|Blautia schinkii, Marvinbryantia formatexigens\|Blautia schinkii, Megamonas hypermegale\|Blautia schinkii, Megasphaera micronuciformis\|Blautia schinkii, Methanobrevibacter smithii\|Blautia schinkii, Methanosphaera stadtmanae\|Blautia schinkii, Methylobacterium radiotolerans\|Blautia schinkii, Mitsuokella multacida\|Blautia schinkii, Mobiluncus curtisii\|Blautia schinkii, Mycoplasma hominis\|Blautia schinkii, Neisseria mucosa\|Blautia schinkii, Odoribacter splanchnicus\|Blautia schinkii, Olsenella uli\|Blautia schinkii, Oribacterium sinus\|Blautia schinkii, Oxalobacter formigenes\|Blautia schinkii, Parabacteroides distasonis\|Blautia schinkii, Parabacteroides johnsonii\|Blautia schinkii, Parabacteroides merdae\|Blautia schinkii, Parvimonas micra\|Blautia schinkii, Pediococcus acidilactici\|Blautia schinkii, Pediococcus pentosaceus\|Blautia schinkii, Peptoniphilus duerdenii\|Blautia schinkii, Peptoniphilus harei\|Blautia schinkii, Peptoniphilus lacrimalis\|Blautia schinkii, Peptostreptococcus anaerobius\|Blautia schinkii, Peptostreptococcus stomatis\|Blautia schinkii, Porphyromonas asaccharolytica\|Blautia schinkii, Porphyromonas uenonis\|Blautia schinkii, Prevotella amnii\|Blautia schinkii, Prevotella bergensis\|Blautia schinkii, Prevotella bivia\|Blautia schinkii, Prevotella buccae\|Blautia schinkii, Prevotella buccalis\|Blautia schinkii, Prevotella copri\|Blautia schinkii, Prevotella disiens\|Blautia schinkii, Prevotella melaninogenica\|Blautia schinkii, Prevotella multiformis\|Blautia schinkii, Prevotella oralis\|Blautia schinkii, Prevotella oris\|Blautia schinkii, Prevotella salivae\|Blautia schinkii, Prevotella timonensis\|Blautia schinkii, Propionibacterium acnes\|Blautia schinkii, Propionibacterium freudenreichii\|Blautia schinkii, Proteus mirabilis\|Blautia schinkii, Proteus penneri\|Blautia schinkii, Pseudoflavonifractor capillosus\|Blautia schinkii, Pseudomonas aeruginosa\|Blautia schinkii, Pseudomonas fluorescens\|Blautia schinkii, Pseudomonas putida\|Blautia schinkii, Pseudoramibacter alactolyticus\|Blautia schinkii, Pyramidobacter piscolens\|Blautia schinkii, Rhodopseudomonas* |

TABLE 2-continued

| Table 2. Specific binary combinations of OTUs. Individual pairings are differentiated by "\|" and OTUs within a combination are differentiated by "," |
|---|
| palustris\|Blautia schinkii, Roseburia intestinalis\|Blautia schinkii, Roseburia inulinivorans\|Blautia schinkii, Rothia dentocariosa\|Blautia schinkii, Rothia mucilaginosa\|Blautia schinkii, Ruminococcus albus\|Blautia schinkii, Ruminococcus bromii\|Blautia schinkii, Ruminococcus gnavus\|Blautia schinkii, Ruminococcus lactaris\|Blautia schinkii, Ruminococcus obeum\|Blautia schinkii, Ruminococcus torques\|Blautia schinkii, Selenomonas sputigena\|Blautia schinkii, Shigella boydii\|Blautia schinkii, Shigella dysenteriae\|Blautia schinkii, Shigella sonnei\|Blautia schinkii, Slackia exigua\|Blautia schinkii, Solobacterium moorei\|Blautia schinkii, Staphylococcus aureus\|Blautia schinkii, Staphylococcus epidermidis\|Blautia schinkii, Staphylococcus hominis\|Blautia schinkii, Staphylococcus saprophyticus\|Blautia schinkii, Staphylococcus warneri\|Blautia schinkii, Streptococcus agalactiae\|Blautia schinkii, Streptococcus anginosus\|Blautia schinkii, Streptococcus australis\|Blautia schinkii, Streptococcus bovis\|Blautia schinkii, Streptococcus cristatus\|Blautia schinkii, Streptococcus dysgalactiae\|Blautia schinkii, Streptococcus equinus\|Blautia schinkii, Streptococcus gordonii\|Blautia schinkii, Streptococcus infantarius\|Blautia schinkii, Streptococcus infantis\|Blautia schinkii, Streptococcus mitis\|Blautia schinkii, Streptococcus mutans\|Blautia schinkii, Streptococcus oralis\|Blautia schinkii, Streptococcus parasanguinis\|Blautia schinkii, Streptococcus peroris\|Blautia schinkii, Streptococcus pneumoniae\|Blautia schinkii, Streptococcus salivarius\|Blautia schinkii, Streptococcus sanguinis\|Blautia schinkii, Streptococcus thermophilus\|Blautia schinkii, Streptococcus vestibularis\|Blautia schinkii, Subdoligranulum variabile\|Blautia schinkii, Succinatimonas hippei\|Blautia schinkii, Sutterella wadsworthensis\|Blautia schinkii, Tropheryma whipplei\|Blautia schinkii, Veillonella atypica\|Blautia schinkii, Veillonella dispar\|Blautia schinkii, Veillonella parvula\|Blautia schinkii, Victivallis vadensis\|Brevibacterium linens, Brevibacterium linens\|Brevibacterium linens, Brucella ceti\|Brevibacterium linens, Brucella suis\|Brevibacterium linens, Bulleidia extructa\|Brevibacterium linens, Butyrivibrio crossotus\|Brevibacterium linens, Campylobacter concisus\|Brevibacterium linens, Campylobacter curvus\|Brevibacterium linens, Campylobacter gracilis\|Brevibacterium linens, Campylobacter hominis\|Brevibacterium linens, Capnocytophaga ochracea\|Brevibacterium linens, Cardiobacterium hominis\|Brevibacterium linens, Catenibacterium mitsuokai\|Brevibacterium linens, Catonella morbi\|Brevibacterium linens, Citrobacter koseri\|Brevibacterium linens, Clostridium asparagiforme\|Brevibacterium linens, Clostridium bartlettii\|Brevibacterium linens, Clostridium bolteae\|Brevibacterium linens, Clostridium botulinum\|Brevibacterium linens, Clostridium butyricum\|Brevibacterium linens, Clostridium difficile\|Brevibacterium linens, Clostridium disporicum\|Brevibacterium linens, Clostridium hathewayi\|Brevibacterium linens, Clostridium hylemonae\|Brevibacterium linens, Clostridium innocuum\|Brevibacterium linens, Clostridium leptum\|Brevibacterium linens, Clostridium mayombei\|Brevibacterium linens, Clostridium methylpentosum\|Brevibacterium linens, Clostridium nexile\|Brevibacterium linens, Clostridium orbiscindens\|Brevibacterium linens, Clostridium perfringens\|Brevibacterium linens, Clostridium saccharolyticum\|Brevibacterium linens, Clostridium scindens\|Brevibacterium linens, Clostridium symbiosum\|Brevibacterium linens, Clostridium tertium\|Brevibacterium linens, Collinsella aerofaciens\|Brevibacterium linens, Collinsella intestinalis\|Brevibacterium linens, Collinsella stercoris\|Brevibacterium linens, Coprobacillus sp. D7\|Brevibacterium linens, Coprococcus catus\|Brevibacterium linens, Coprococcus comes\|Brevibacterium linens, Coprococcus eutactus\|Brevibacterium linens, Corynebacterium aurimucosum\|Brevibacterium linens, Corynebacterium matruchotii\|Brevibacterium linens, Cryptobacterium curtum\|Brevibacterium linens, Desulfovibrio desulfuricans\|Brevibacterium linens, Desulfovibrio piger\|Brevibacterium linens, Dialister invisus\|Brevibacterium linens, Dialister microaerophilus\|Brevibacterium linens, Dorea formicigenerans\|Brevibacterium linens, Dorea longicatena\|Brevibacterium linens, Eggerthella lenta\|Brevibacterium linens, Eikenella corrodens\|Brevibacterium linens, Enterobacter cancerogenus\|Brevibacterium linens, Enterobacter cloacae\|Brevibacterium linens, Enterococcus faecalis\|Brevibacterium linens, Enterococcus faecium\|Brevibacterium linens, Enterococcus gallinarum\|Brevibacterium linens, Erysipelotrichaceae bacterium 3_1_53\|Brevibacterium linens, Escherichia coli\|Brevibacterium linens, Escherichia fergusonii\|Brevibacterium linens, Ethanoligenens harbinense\|Brevibacterium linens, Eubacterium cellulosolvens\|Brevibacterium linens, Eubacterium eligens\|Brevibacterium linens, Eubacterium hallii\|Brevibacterium linens, Eubacterium limosum\|Brevibacterium linens, Eubacterium rectale\|Brevibacterium linens, Eubacterium siraeum\|Brevibacterium linens, Eubacterium ventriosum\|Brevibacterium linens, Faecalibacterium prausnitzii\|Brevibacterium linens, Finegoldia magna\|Brevibacterium linens, Fusobacterium gonidiaformans\|Brevibacterium linens, Fusobacterium mortiferum\|Brevibacterium linens, Fusobacterium nucleatum\|Brevibacterium linens, Fusobacterium varium\|Brevibacterium linens, Gardnerella vaginalis\|Brevibacterium linens, Gemella haemolysans\|Brevibacterium linens, Gemella morbillorum\|Brevibacterium linens, Gordonibacter pamelaeae\|Brevibacterium linens, Granulicatella adiacens\|Brevibacterium linens, Granulicatella elegans\|Brevibacterium linens, Haemophilus influenzae\|Brevibacterium linens, Haemophilus parainfluenzae\|Brevibacterium linens, Helicobacter pullorum\|Brevibacterium linens, Helicobacter pylori\|Brevibacterium linens, Holdemania filiformis\|Brevibacterium linens, Kingella oralis\|Brevibacterium linens, Klebsiella pneumoniae\|Brevibacterium linens, Klebsiella variicola\|Brevibacterium linens, Lachnospiraceae bacterium 5_1_57FAA\|Brevibacterium linens, Lactobacillus acidophilus\|Brevibacterium linens, Lactobacillus amylovorus\|Brevibacterium linens, Lactobacillus brevis\|Brevibacterium linens, Lactobacillus casei\|Brevibacterium linens, Lactobacillus crispatus\|Brevibacterium linens, Lactobacillus delbrueckii\|Brevibacterium linens, Lactobacillus fermentum\|Brevibacterium linens, Lactobacillus gasseri\|Brevibacterium linens, Lactobacillus iners\|Brevibacterium linens, Lactobacillus jensenii\|Brevibacterium linens, Lactobacillus johnsonii\|Brevibacterium linens, Lactobacillus paracasei\|Brevibacterium linens, Lactobacillus plantarum\|Brevibacterium linens, Lactobacillus reuteri\|Brevibacterium linens, Lactobacillus rhamnosus\|Brevibacterium linens, Lactobacillus ruminis\|Brevibacterium linens, Lactobacillus sakei\|Brevibacterium linens, Lactobacillus salivarius\|Brevibacterium linens, Lactococcus lactis\|Brevibacterium linens, Lautropia mirabilis\|Brevibacterium linens, Leuconostoc citreum\|Brevibacterium linens, Leuconostoc gasicomitatum\|Brevibacterium linens, Leuconostoc mesenteroides\|Brevibacterium linens, Listeria monocytogenes\|Brevibacterium linens, Marvinbryantia formatexigens\|Brevibacterium linens, Megamonas hypermegale\|Brevibacterium linens, Megasphaera micronuciformis\|Brevibacterium linens, Methanobrevibacter smithii\|Brevibacterium linens, Methanosphaera stadtmanae\|Brevibacterium linens, Methylobacterium radiotolerans\|Brevibacterium linens, Mitsuokella multacida\|Brevibacterium linens, Mobiluncus curtisii\|Brevibacterium linens, Mycoplasma hominis\|Brevibacterium linens, Neisseria mucosa\|Brevibacterium linens, Odoribacter splanchnicus\|Brevibacterium linens, Olsenella uli\|Brevibacterium linens, Oribacterium sinus\|Brevibacterium linens, Oxalobacter formigenes\|Brevibacterium linens, Parabacteroides distasonis\|Brevibacterium linens, Parabacteroides johnsonii\|Brevibacterium linens, Parabacteroides merdae\|Brevibacterium linens, Parvimonas micra\|Brevibacterium linens, Pediococcus acidilactici\|Brevibacterium linens, Pediococcus pentosaceus\|Brevibacterium linens, Peptoniphilus duerdenii\|Brevibacterium linens, Peptoniphilus harei\|Brevibacterium linens, Peptoniphilus lacrimalis\|Brevibacterium linens, Peptostreptococcus anaerobius\|Brevibacterium linens, Peptostreptococcus stomatis\|Brevibacterium linens, Porphyromonas asaccharolytica\|Brevibacterium linens, Porphyromonas uenonis\|Brevibacterium linens, Prevotella amnii\|Brevibacterium linens, Prevotella bergensis\|Brevibacterium linens, Prevotella bivia\|Brevibacterium linens, Prevotella buccae\|Brevibacterium linens, Prevotella buccalis\|Brevibacterium linens, Prevotella copri\|Brevibacterium linens, Prevotella disiens\|Brevibacterium linens, Prevotella melaninogenica\|Brevibacterium linens, Prevotella multiformis\|Brevibacterium linens, Prevotella oralis\|Brevibacterium linens, Prevotella oris\|Brevibacterium linens, Prevotella salivae\|Brevibacterium linens, Prevotella timonensis\|Brevibacterium linens, Propionibacterium acnes\|Brevibacterium linens, Propionibacterium freudenreichii\|Brevibacterium linens, Proteus mirabilis\|Brevibacterium linens, Proteus penneri\|Brevibacterium linens, Pseudoflavonifractor capillosus\|Brevibacterium linens, Pseudomonas aeruginosa\|Brevibacterium linens, Pseudomonas fluorescens\|Brevibacterium linens, Pseudomonas putida\|Brevibacterium linens, Pseudoramibacter alactolyticus\|Brevibacterium linens, Pyramidobacter piscolens\|Brevibacterium linens, Rhodopseudomonas palustris\|Brevibacterium linens, Roseburia intestinalis\|Brevibacterium linens, Roseburia inulinivorans\|Brevibacterium linens, Rothia dentocariosa\|Brevibacterium linens, Rothia mucilaginosa\|Brevibacterium linens, Ruminococcus albus\|Brevibacterium linens, Ruminococcus bromii\|Brevibacterium linens, Ruminococcus gnavus\|Brevibacterium linens, Ruminococcus lactaris\|Brevibacterium linens, Ruminococcus obeum\|Brevibacterium linens, Ruminococcus torques\|Brevibacterium linens, Selenomonas sputigena\|Brevibacterium linens, Shigella boydii\|Brevibacterium linens, Shigella dysenteriae\|Brevibacterium linens, Shigella sonnei\|Brevibacterium linens, Slackia exigua\|Brevibacterium linens, Solobacterium |

TABLE 2-continued

Table 2. Specific binary combinations of OTUs. Individual pairings are differentiated by "|" and OTUs within a combination are differentiated by ","

moorei|Brevibacterium linens, Staphylococcus aureus|Brevibacterium linens, Staphylococcus epidermidis|Brevibacterium linens, Staphylococcus hominis|Brevibacterium linens, Staphylococcus saprophyticus|Brevibacterium linens, Staphylococcus warneri|Brevibacterium linens, Streptococcus agalactiae|Brevibacterium linens, Streptococcus anginosus|Brevibacterium linens, Streptococcus australis|Brevibacterium linens, Streptococcus bovis|Brevibacterium linens, Streptococcus cristatus|Brevibacterium linens, Streptococcus dysgalactiae|Brevibacterium linens, Streptococcus equinus|Brevibacterium linens, Streptococcus gordonii|Brevibacterium linens, Streptococcus infantarius|Brevibacterium linens, Streptococcus infantis|Brevibacterium linens, Streptococcus mitis|Brevibacterium linens, Streptococcus mutans|Brevibacterium linens, Streptococcus oralis|Brevibacterium linens, Streptococcus parasanguinis|Brevibacterium linens, Streptococcus peroris|Brevibacterium linens, Streptococcus pneumoniae|Brevibacterium linens, Streptococcus salivarius|Brevibacterium linens, Streptococcus sanguinis|Brevibacterium linens, Streptococcus thermophilus|Brevibacterium linens, Streptococcus vestibularis|Brevibacterium linens, Subdoligranulum variabile|Brevibacterium linens, Succinatimonas hippei|Brevibacterium linens, Sutterella wadsworthensis|Brevibacterium linens, Tropheryma whipplei|Brevibacterium linens, Veillonella atypica|Brevibacterium linens, Veillonella dispar|Brevibacterium linens, Veillonella parvula|Brevibacterium linens, Victivallis vadensis|Brucella ceti, Brucella ceti|Brucella ceti, Brucella suis|Brucella ceti, Bulleidia extructa|Brucella ceti, Butyrivibrio crossotus|Brucella ceti, Campylobacter concisus|Brucella ceti, Campylobacter curvus|Brucella ceti, Campylobacter gracilis|Brucella ceti, Campylobacter hominis|Brucella ceti, Capnocytophaga ochracea|Brucella ceti, Cardiobacterium hominis|Brucella ceti, Catenibacterium mitsuokai|Brucella ceti, Catonella morbi|Brucella ceti, Citrobacter koseri|Brucella ceti, Clostridium asparagiforme|Brucella ceti, Clostridium bartlettii|Brucella ceti, Clostridium bolteae|Brucella ceti, Clostridium botulinum|Brucella ceti, Clostridium butyricum|Brucella ceti, Clostridium difficile|Brucella ceti, Clostridium disporicum|Brucella ceti, Clostridium hathewayi|Brucella ceti, Clostridium hylemonae|Brucella ceti, Clostridium innocuum|Brucella ceti, Clostridium leptum|Brucella ceti, Clostridium mayombei|Brucella ceti, Clostridium methylpentosum|Brucella ceti, Clostridium nexile|Brucella ceti, Clostridium orbiscindens|Brucella ceti, Clostridium perfringens|Brucella ceti, Clostridium saccharolyticum|Brucella ceti, Clostridium scindens|Brucella ceti, Clostridium symbiosum|Brucella ceti, Clostridium tertium|Brucella ceti, Collinsella aerofaciens|Brucella ceti, Collinsella intestinalis|Brucella ceti, Collinsella stercoris|Brucella ceti, Coprobacillus sp. D7|Brucella ceti, Coprococcus catus|Brucella ceti, Coprococcus comes|Brucella ceti, Coprococcus eutactus|Brucella ceti, Corynebacterium aurimucosum|Brucella ceti, Corynebacterium matruchotii|Brucella ceti, Cryptobacterium curtum|Brucella ceti, Desulfovibrio desulfuricans|Brucella ceti, Desulfovibrio piger|Brucella ceti, Dialister invisus|Brucella ceti, Dialister microaerophilus|Brucella ceti, Dorea formicigenerans|Brucella ceti, Dorea longicatena|Brucella ceti, Eggerthella lenta|Brucella ceti, Eikenella corrodens|Brucella ceti, Enterobacter cancerogenus|Brucella ceti, Enterobacter cloacae|Brucella ceti, Enterococcus faecalis|Brucella ceti, Enterococcus faecium|Brucella ceti, Enterococcus gallinarum|Brucella ceti, Erysipelotrichaceae bacterium 3_1_53|Brucella ceti, Escherichia coli|Brucella ceti, Escherichia fergusonii|Brucella ceti, Ethanoligenens harbinense|Brucella ceti, Eubacterium cellulosolvens|Brucella ceti, Eubacterium eligens|Brucella ceti, Eubacterium hallii|Brucella ceti, Eubacterium limosum|Brucella ceti, Eubacterium rectale|Brucella ceti, Eubacterium siraeum|Brucella ceti, Eubacterium ventriosum|Brucella ceti, Faecalibacterium prausnitzii|Brucella ceti, Finegoldia magna|Brucella ceti, Fusobacterium gonidiaformans|Brucella ceti, Fusobacterium mortiferum|Brucella ceti, Fusobacterium nucleatum|Brucella ceti, Fusobacterium varium|Brucella ceti, Gardnerella vaginalis|Brucella ceti, Gemella haemolysans|Brucella ceti, Gemella morbillorum|Brucella ceti, Gordonibacter pamelaeae|Brucella ceti, Granulicatella adiacens|Brucella ceti, Granulicatella elegans|Brucella ceti, Haemophilus influenzae|Brucella ceti, Haemophilus parainfluenzae|Brucella ceti, Helicobacter pullorum|Brucella ceti, Helicobacter pylori|Brucella ceti, Holdemania filiformis|Brucella ceti, Kingella oralis|Brucella ceti, Klebsiella pneumoniae|Brucella ceti, Klebsiella variicola|Brucella ceti, Lachnospiraceae bacterium 5_1_57FAA|Brucella ceti, Lactobacillus acidophilus|Brucella ceti, Lactobacillus amylovorus|Brucella ceti, Lactobacillus brevis|Brucella ceti, Lactobacillus casei|Brucella ceti, Lactobacillus crispatus|Brucella ceti, Lactobacillus delbrueckii|Brucella ceti, Lactobacillus fermentum|Brucella ceti, Lactobacillus gasseri|Brucella ceti, Lactobacillus iners|Brucella ceti, Lactobacillus jensenii|Brucella ceti, Lactobacillus johnsonii|Brucella ceti, Lactobacillus paracasei|Brucella ceti, Lactobacillus plantarum|Brucella ceti, Lactobacillus reuteri|Brucella ceti, Lactobacillus rhamnosus|Brucella ceti, Lactobacillus ruminis|Brucella ceti, Lactobacillus sakei|Brucella ceti, Lactobacillus salivarius|Brucella ceti, Lactococcus lactis|Brucella ceti, Lautropia mirabilis|Brucella ceti, Leuconostoc citreum|Brucella ceti, Leuconostoc gasicomitatum|Brucella ceti, Leuconostoc mesenteroides|Brucella ceti, Listeria monocytogenes|Brucella ceti, Marvinbryantia formatexigens|Brucella ceti, Megamonas hypermegale|Brucella ceti, Megasphaera micronuciformis|Brucella ceti, Methanobrevibacter smithii|Brucella ceti, Methanosphaera stadtmanae|Brucella ceti, Methylobacterium radiotolerans|Brucella ceti, Mitsuokella multacida|Brucella ceti, Mobiluncus curtisii|Brucella ceti, Mycoplasma hominis|Brucella ceti, Neisseria mucosa|Brucella ceti, Odoribacter splanchnicus|Brucella ceti, Olsenella uli|Brucella ceti, Oribacterium sinus|Brucella ceti, Oxalobacter formigenes|Brucella ceti, Parabacteroides distasonis|Brucella ceti, Parabacteroides johnsonii|Brucella ceti, Parabacteroides merdae|Brucella ceti, Parvimonas micra|Brucella ceti, Pediococcus acidilactici|Brucella ceti, Pediococcus pentosaceus|Brucella ceti, Peptoniphilus duerdenii|Brucella ceti, Peptoniphilus harei|Brucella ceti, Peptoniphilus lacrimalis|Brucella ceti, Peptostreptococcus anaerobius|Brucella ceti, Peptostreptococcus stomatis|Brucella ceti, Porphyromonas asaccharolytica|Brucella ceti, Porphyromonas uenonis|Brucella ceti, Prevotella amnii|Brucella ceti, Prevotella bergensis|Brucella ceti, Prevotella bivia|Brucella ceti, Prevotella buccae|Brucella ceti, Prevotella buccalis|Brucella ceti, Prevotella copri|Brucella ceti, Prevotella disiens|Brucella ceti, Prevotella melaninogenica|Brucella ceti, Prevotella multiformis|Brucella ceti, Prevotella oralis|Brucella ceti, Prevotella oris|Brucella ceti, Prevotella salivae|Brucella ceti, Prevotella timonensis|Brucella ceti, Propionibacterium acnes|Brucella ceti, Propionibacterium freudenreichii|Brucella ceti, Proteus mirabilis|Brucella ceti, Proteus penneri|Brucella ceti, Pseudoflavonifractor capillosus|Brucella ceti, Pseudomonas aeruginosa|Brucella ceti, Pseudomonas fluorescens|Brucella ceti, Pseudomonas putida|Brucella ceti, Pseudoramibacter alactolyticus|Brucella ceti, Pyramidobacter piscolens|Brucella ceti, Rhodopseudomonas palustris|Brucella ceti, Roseburia intestinalis|Brucella ceti, Roseburia inulinivorans|Brucella ceti, Rothia dentocariosa|Brucella ceti, Rothia mucilaginosa|Brucella ceti, Ruminococcus albus|Brucella ceti, Ruminococcus bromii|Brucella ceti, Ruminococcus gnavus|Brucella ceti, Ruminococcus lactaris|Brucella ceti, Ruminococcus obeum|Brucella ceti, Ruminococcus torques|Brucella ceti, Selenomonas sputigena|Brucella ceti, Shigella boydii|Brucella ceti, Shigella dysenteriae|Brucella ceti, Shigella sonnei|Brucella ceti, Slackia exigua|Brucella ceti, Solobacterium moorei|Brucella ceti, Staphylococcus aureus|Brucella ceti, Staphylococcus epidermidis|Brucella ceti, Staphylococcus hominis|Brucella ceti, Staphylococcus saprophyticus|Brucella ceti, Staphylococcus warneri|Brucella ceti, Streptococcus agalactiae|Brucella ceti, Streptococcus anginosus|Brucella ceti, Streptococcus australis|Brucella ceti, Streptococcus bovis|Brucella ceti, Streptococcus cristatus|Brucella ceti, Streptococcus dysgalactiae|Brucella ceti, Streptococcus equinus|Brucella ceti, Streptococcus gordonii|Brucella ceti, Streptococcus infantarius|Brucella ceti, Streptococcus infantis|Brucella ceti, Streptococcus mitis|Brucella ceti, Streptococcus mutans|Brucella ceti, Streptococcus oralis|Brucella ceti, Streptococcus parasanguinis|Brucella ceti, Streptococcus peroris|Brucella ceti, Streptococcus pneumoniae|Brucella ceti, Streptococcus salivarius|Brucella ceti, Streptococcus sanguinis|Brucella ceti, Streptococcus thermophilus|Brucella ceti, Streptococcus vestibularis|Brucella ceti, Subdoligranulum variabile|Brucella ceti, Succinatimonas hippei|Brucella ceti, Sutterella wadsworthensis|Brucella ceti, Tropheryma whipplei|Brucella ceti, Veillonella atypica|Brucella ceti, Veillonella dispar|Brucella ceti, Veillonella parvula|Brucella ceti, Victivallis vadensis|Brucella suis, Brucella suis|Brucella suis, Bulleidia extructa|Brucella suis, Butyrivibrio crossotus|Brucella suis, Campylobacter concisus|Brucella suis, Campylobacter curvus|Brucella suis, Campylobacter gracilis|Brucella suis, Campylobacter hominis|Brucella suis, Capnocytophaga ochracea|Brucella suis, Cardiobacterium hominis|Brucella suis, Catenibacterium mitsuokai|Brucella suis, Catonella morbi|Brucella suis, Citrobacter koseri|Brucella suis, Clostridium asparagiforme|Brucella suis, Clostridium bartlettii|Brucella suis, Clostridium bolteae|Brucella suis, Clostridium botulinum|Brucella suis, Clostridium butyricum|Brucella suis, Clostridium difficile|Brucella suis, Clostridium disporicum|Brucella suis, Clostridium hathewayi|Brucella suis, Clostridium hylemonae|Brucella suis, Clostridium innocuum|Brucella suis, Clostridium leptum|Brucella suis, Clostridium mayombei|Brucella suis, Clostridium TABLE 2-continued

| Table 2. Specific binary combinations of OTUs. Individual pairings are differentiated by "\|" and OTUs within a combination are differentiated by "," |
|---|
| methylpentosum\|Brucella suis, Clostridium nexile\|Brucella suis, Clostridium orbiscindens\|Brucella suis, Clostridium perfringens\|Brucella suis, Clostridium saccharolyticum\|Brucella suis, Clostridium scindens\|Brucella suis, Clostridium symbiosum\|Brucella suis, Clostridium tertium\|Brucella suis, Collinsella aerofaciens\|Brucella suis, Collinsella intestinalis\|Brucella suis, Collinsella stercoris\|Brucella suis, Coprobacillus sp. D7\|Brucella suis, Coprococcus catus\|Brucella suis, Coprococcus comes\|Brucella suis, Coprococcus eutactus\|Brucella suis, Corynebacterium aurimucosum\|Brucella suis, Corynebacterium matruchotii\|Brucella suis, Cryptobacterium curtum\|Brucella suis, Desulfovibrio desulfuricans\|Brucella suis, Desulfovibrio piger\|Brucella suis, Dialister invisus\|Brucella suis, Dialister microaerophilus\|Brucella suis, Dorea formicigenerans\|Brucella suis, Dorea longicatena\|Brucella suis, Eggerthella lenta\|Brucella suis, Eikenella corrodens\|Brucella suis, Enterobacter cancerogenus\|Brucella suis, Enterobacter cloacae\|Brucella suis, Enterococcus faecalis\|Brucella suis, Enterococcus faecium\|Brucella suis, Enterococcus gallinarum\|Brucella suis, Erysipelotrichaceae bacterium 3_1_53\|Brucella suis, Escherichia coli\|Brucella suis, Escherichia fergusonii\|Brucella suis, Ethanoligenens harbinense\|Brucella suis, Eubacterium cellulosolvens\|Brucella suis, Eubacterium eligens\|Brucella suis, Eubacterium hallii\|Brucella suis, Eubacterium limosum\|Brucella suis, Eubacterium rectale\|Brucella suis, Eubacterium siraeum\|Brucella suis, Eubacterium ventriosum\|Brucella suis, Faecalibacterium prausnitzii\|Brucella suis, Finegoldia magna\|Brucella suis, Fusobacterium gonidiaformans\|Brucella suis, Fusobacterium mortiferum\|Brucella suis, Fusobacterium nucleatum\|Brucella suis, Fusobacterium varium\|Brucella suis, Gardnerella vaginalis\|Brucella suis, Gemella haemolysans\|Brucella suis, Gemella morbillorum\|Brucella suis, Gordonibacter pamelaeae\|Brucella suis, Granulicatella adiacens\|Brucella suis, Granulicatella elegans\|Brucella suis, Haemophilus influenzae\|Brucella suis, Haemophilus parainfluenzae\|Brucella suis, Helicobacter pullorum\|Brucella suis, Helicobacter pylori\|Brucella suis, Holdemania filiformis\|Brucella suis, Kingella oralis\|Brucella suis, Klebsiella pneumoniae\|Brucella suis, Klebsiella vaniicola\|Brucella suis, Lachnospiraceae bacterium 5_1_57FAA\|Brucella suis, Lactobacillus acidophilus\|Brucella suis, Lactobacillus amylovorus\|Brucella suis, Lactobacillus brevis\|Brucella suis, Lactobacillus casei\|Brucella suis, Lactobacillus crispatus\|Brucella suis, Lactobacillus delbrueckii\|Brucella suis, Lactobacillus fermentum\|Brucella suis, Lactobacillus gasseri\|Brucella suis, Lactobacillus iners\|Brucella suis, Lactobacillus jensenii\|Brucella suis, Lactobacillus johnsonii\|Brucella suis, Lactobacillus paracasei\|Brucella suis, Lactobacillus plantarum\|Brucella suis, Lactobacillus reuteri\|Brucella suis, Lactobacillus rhamnosus\|Brucella suis, Lactobacillus ruminis\|Brucella suis, Lactobacillus sakei\|Brucella suis, Lactobacillus salivarius\|Brucella suis, Lactococcus lactis\|Brucella suis, Lautropia mirabilis\|Brucella suis, Leuconostoc citreum\|Brucella suis, Leuconostoc gasicomitatum\|Brucella suis, Leuconostoc mesenteroides\|Brucella suis, Listeria monocytogenes\|Brucella suis, Marvinbryantia formatexigens\|Brucella suis, Megamonas hypermegale\|Brucella suis, Megasphaera micronuciformis\|Brucella suis, Methanobrevibacter smithii\|Brucella suis, Methanosphaera stadtmanae\|Brucella suis, Methylobacterium radiotolerans\|Brucella suis, Mitsuokella multacida\|Brucella suis, Mobiluncus curtisii\|Brucella suis, Mycoplasma hominis\|Brucella suis, Neisseria mucosa\|Brucella suis, Odoribacter splanchnicus\|Brucella suis, Olsenella uli\|Brucella suis, Oribacterium sinus\|Brucella suis, Oxalobacter formigenes\|Brucella suis, Parabacteroides distasonis\|Brucella suis, Parabacteroides johnsonii\|Brucella suis, Parabacteroides merdae\|Brucella suis, Parvimonas micra\|Brucella suis, Pediococcus acidilactici\|Brucella suis, Pediococcus pentosaceus\|Brucella suis, Peptoniphilus duerdenii\|Brucella suis, Peptoniphilus harei\|Brucella suis, Peptoniphilus lacrimalis\|Brucella suis, Peptostreptococcus anaerobius\|Brucella suis, Peptostreptococcus stomatis\|Brucella suis, Porphyromonas asaccharolytica\|Brucella suis, Porphyromonas uenonis\|Brucella suis, Prevotella amnii\|Brucella suis, Prevotella bergensis\|Brucella suis, Prevotella bivia\|Brucella suis, Prevotella buccae\|Brucella suis, Prevotella buccalis\|Brucella suis, Prevotella copri\|Brucella suis, Prevotella disiens\|Brucella suis, Prevotella melaninogenica\|Brucella suis, Prevotella multiformis\|Brucella suis, Prevotella oralis\|Brucella suis, Prevotella oris\|Brucella suis, Prevotella salivae\|Brucella suis, Prevotella timonensis\|Brucella suis, Propionibacterium acnes\|Brucella suis, Propionibacterium freudenreichii\|Brucella suis, Proteus mirabilis\|Brucella suis, Proteus penneri\|Brucella suis, Pseudoflavonifractor capillosus\|Brucella suis, Pseudomonas aeruginosa\|Brucella suis, Pseudomonas fluorescens\|Brucella suis, Pseudomonas putida\|Brucella suis, Pseudoramibacter alactolyticus\|Brucella suis, Pyramidobacter piscolens\|Brucella suis, Rhodopseudomonas palustris\|Brucella suis, Roseburia intestinalis\|Brucella suis, Roseburia inulinivorans\|Brucella suis, Rothia dentocariosa\|Brucella suis, Rothia mucilaginosa\|Brucella suis, Ruminococcus albus\|Brucella suis, Ruminococcus bromii\|Brucella suis, Ruminococcus gnavus\|Brucella suis, Ruminococcus lactaris\|Brucella suis, Ruminococcus obeum\|Brucella suis, Ruminococcus torques\|Brucella suis, Selenomonas sputigena\|Brucella suis, Shigella boydii\|Brucella suis, Shigella dysenteriae\|Brucella suis, Shigella sonnei\|Brucella suis, Slackia exigua\|Brucella suis, Solobacterium moorei\|Brucella suis, Staphylococcus aureus\|Brucella suis, Staphylococcus epidermidis\|Brucella suis, Staphylococcus hominis\|Brucella suis, Staphylococcus saprophyticus\|Brucella suis, Staphylococcus warneri\|Brucella suis, Streptococcus agalactiae\|Brucella suis, Streptococcus anginosus\|Brucella suis, Streptococcus australis\|Brucella suis, Streptococcus bovis\|Brucella suis, Streptococcus cristatus\|Brucella suis, Streptococcus dysgalactiae\|Brucella suis, Streptococcus equinus\|Brucella suis, Streptococcus gordonii\|Brucella suis, Streptococcus infantarius\|Brucella suis, Streptococcus infantis\|Brucella suis, Streptococcus mitis\|Brucella suis, Streptococcus mutans\|Brucella suis, Streptococcus oralis\|Brucella suis, Streptococcus parasanguinis\|Brucella suis, Streptococcus peroris\|Brucella suis, Streptococcus pneumoniae\|Brucella suis, Streptococcus salivarius\|Brucella suis, Streptococcus sanguinis\|Brucella suis, Streptococcus thermophilus\|Brucella suis, Streptococcus vestibularis\|Brucella suis, Subdoligranulum variabile\|Brucella suis, Succinatimonas hippei\|Brucella suis, Sutterella wadsworthensis\|Brucella suis, Tropheryma whipplei\|Brucella suis, Veillonella atypica\|Brucella suis, Veillonella dispar\|Brucella suis, Veillonella parvula\|Brucella suis, Victivallis vadensis\|Bulleidia extructa, Bulleidia extructa\|Bulleidia extructa, Butyrivibrio crossotus\|Bulleidia extructa, Campylobacter concisus\|Bulleidia extructa, Campylobacter curvus\|Bulleidia extructa, Campylobacter gracilis\|Bulleidia extructa, Campylobacter hominis\|Bulleidia extructa, Capnocytophaga ochracea\|Bulleidia extructa, Cardiobacterium hominis\|Bulleidia extructa, Catenibacterium mitsuokai\|Bulleidia extructa, Catonella morbi\|Bulleidia extructa, Citrobacter koseri\|Bulleidia extructa, Clostridium asparagiforme\|Bulleidia extructa, Clostridium bartlettii\|Bulleidia extructa, Clostridium bolteae\|Bulleidia extructa, Clostridium botulinum\|Bulleidia extructa, Clostridium butyricum\|Bulleidia extructa, Clostridium difficile\|Bulleidia extructa, Clostridium disporicum\|Bulleidia extructa, Clostridium hathewayi\|Bulleidia extructa, Clostridium hylemonae\|Bulleidia extructa, Clostridium innocuum\|Bulleidia extructa, Clostridium leptum\|Bulleidia extructa, Clostridium mayombei\|Bulleidia extructa, Clostridium methylpentosum\|Bulleidia extructa, Clostridium nexile\|Bulleidia extructa, Clostridium orbiscindens\|Bulleidia extructa, Clostridium perfringens\|Bulleidia extructa, Clostridium saccharolyticum\|Bulleidia extructa, Clostridium scindens\|Bulleidia extructa, Clostridium symbiosum\|Bulleidia extructa, Clostridium tertium\|Bulleidia extructa, Collinsella aerofaciens\|Bulleidia extructa, Collinsella intestinalis\|Bulleidia extructa, Collinsella stercoris\|Bulleidia extructa, Coprobacillus sp. D7\|Bulleidia extructa, Coprococcus catus\|Bulleidia extructa, Coprococcus comes\|Bulleidia extructa, Coprococcus eutactus\|Bulleidia extructa, Corynebacterium aurimucosum\|Bulleidia extructa, Corynebacterium matruchotii\|Bulleidia extructa, Cryptobacterium curtum\|Bulleidia extructa, Desulfovibrio desulfuricans\|Bulleidia extructa, Desulfovibrio piger\|Bulleidia extructa, Dialister invisus\|Bulleidia extructa, Dialister microaerophilus\|Bulleidia extructa, Dorea formicigenerans\|Bulleidia extructa, Dorea longicatena\|Bulleidia extructa, Eggerthella lenta\|Bulleidia extructa, Eikenella corrodens\|Bulleidia extructa, Enterobacter cancerogenus\|Bulleidia extructa, Enterobacter cloacae\|Bulleidia extructa, Enterococcus faecalis\|Bulleidia extructa, Enterococcus faecium\|Bulleidia extructa, Enterococcus gallinarum\|Bulleidia extructa, Erysipelotrichaceae bacterium 3_1_53\|Bulleidia extructa, Escherichia coli\|Bulleidia extructa, Escherichia fergusonii\|Bulleidia extructa, Ethanoligenens harbinense\|Bulleidia extructa, Eubacterium cellulosolvens\|Bulleidia extructa, Eubacterium eligens\|Bulleidia extructa, Eubacterium hallii\|Bulleidia extructa, Eubacterium limosum\|Bulleidia extructa, Eubacterium rectale\|Bulleidia extructa, Eubacterium siraeum\|Bulleidia extructa, Eubacterium ventriosum\|Bulleidia extructa, Faecalibacterium prausnitzii\|Bulleidia extructa, Finegoldia magna\|Bulleidia extructa, Fusobacterium gonidiaformans\|Bulleidia extructa, Fusobacterium mortifentm\|Bulleidia extructa, Fusobacterium nucleatum\|Bulleidia extructa, Fusobacterium varium\|Bulleidia extructa, Gardnerella vaginalis\|Bulleidia extructa, Gemella haemolysans\|Bulleidia extructa, Gemella morbillorum\|Bulleidia extructa, Gordonibacter pamelaeae\|Bulleidia extructa, Granulicatella adiacens\|Bulleidia extructa, Granulicatella elegans\|Bulleidia extructa, Haemophilus influenzae\|Bulleidia extructa, Haemophilus parainfluenzae\|Bulleidia |

TABLE 2-continued

| Table 2. Specific binary combinations of OTUs. Individual pairings are differentiated by "\|" and OTUs within a combination are differentiated by "," |
|---|
| *extructa, Helicobacter pullorum\|Bulleidia extructa, Helicobacter pylori\|Bulleidia extructa, Holdemania filiformis\|Bulleidia extructa, Kingella oralis\|Bulleidia extructa, Klebsiella pneumoniae\|Bulleidia extructa, Klebsiella variicola\|Bulleidia extructa, Lachnospiraceae bacterium* 5_1_57FAA\|*Bulleidia extructa, Lactobacillus acidophilus\|Bulleidia extructa, Lactobacillus amylovorus\|Bulleidia extructa, Lactobacillus brevis\|Bulleidia extructa, Lactobacillus casei\|Bulleidia extructa, Lactobacillus crispatus\|Bulleidia extructa, Lactobacillus delbrueckii\|Bulleidia extructa, Lactobacillus fermentum\|Bulleidia extructa, Lactobacillus gasseri\|Bulleidia extructa, Lactobacillus iners\|Bulleidia extructa, Lactobacillus jensenii\|Bulleidia extructa, Lactobacillus johnsonii\|Bulleidia extructa, Lactobacillus paracasei\|Bulleidia extructa, Lactobacillus plantarum\|Bulleidia extructa, Lactobacillus reuteri\|Bulleidia extructa, Lactobacillus rhamnosus\|Bulleidia extructa, Lactobacillus ruminis\|Bulleidia extructa, Lactobacillus sakei\|Bulleidia extructa, Lactobacillus salivarius\|Bulleidia extructa, Lactococcus lactis\|Bulleidia extructa, Lautropia mirabilis\|Bulleidia extructa, Leuconostoc citreum\|Bulleidia extructa, Leuconostoc gasicomitatum\|Bulleidia extructa, Leuconostoc mesenteroides\|Bulleidia extructa, Listeria monocytogenes\|Bulleidia extructa, Marvinbryantia formatexigens\|Bulleidia extructa, Megamonas hypermegale\|Bulleidia extructa, Megasphaera micronuciformis\|Bulleidia extructa, Methanobrevibacter smithii\|Bulleidia extructa, Methanosphaera stadtmanae\|Bulleidia extructa, Methylobacterium radiotolerans\|Bulleidia extructa, Mitsuokella multacida\|Bulleidia extructa, Mobiluncus curtisii\|Bulleidia extructa, Mycoplasma hominis\|Bulleidia extructa, Neisseria mucosa\|Bulleidia extructa, Odoribacter splanchnicus\|Bulleidia extructa, Olsenella uli\|Bulleidia extructa, Oribacterium sinus\|Bulleidia extructa, Oxalobacter formigenes\|Bulleidia extructa, Parabacteroides distasonis\|Bulleidia extructa, Parabacteroides johnsonii\|Bulleidia extructa, Parabacteroides merdae\|Bulleidia extructa, Parvimonas micra\|Bulleidia extructa, Pediococcus acidilactici\|Bulleidia extructa, Pediococcus pentosaceus\|Bulleidia extructa, Peptoniphilus duerdenii\|Bulleidia extructa, Peptoniphilus harei\|Bulleidia extructa, Peptoniphilus lacrimalis\|Bulleidia extructa, Peptostreptococcus anaerobius\|Bulleidia extructa, Peptostreptococcus stomatis\|Bulleidia extructa, Porphyromonas asaccharolytica\|Bulleidia extructa, Porphyromonas uenonis\|Bulleidia extructa, Prevotella amnii\|Bulleidia extructa, Prevotella bergensis\|Bulleidia extructa, Prevotella bivia\|Bulleidia extructa, Prevotella buccae\|Bulleidia extructa, Prevotella buccalis\|Bulleidia extructa, Prevotella copri\|Bulleidia extructa, Prevotella disiens\|Bulleidia extructa, Prevotella melaninogenica\|Bulleidia extructa, Prevotella multiformis\|Bulleidia extructa, Prevotella oralis\|Bulleidia extructa, Prevotella oris\|Bulleidia extructa, Prevotella salivae\|Bulleidia extructa, Prevotella timonensis\|Bulleidia extructa, Propionibacterium acnes\|Bulleidia extructa, Propionibacterium freudenreichii\|Bulleidia extructa, Proteus mirabilis\|Bulleidia extructa, Proteus penneri\|Bulleidia extructa, Pseudoflavonifractor capillosus\|Bulleidia extructa, Pseudomonas aeruginosa\|Bulleidia extructa, Pseudomonas fluorescens\|Bulleidia extructa, Pseudomonas putida\|Bulleidia extructa, Pseudoramibacter alactolyticus\|Bulleidia extructa, Pyramidobacter piscolens\|Bulleidia extructa, Rhodopseudomonas palustris\|Bulleidia extructa, Roseburia intestinalis\|Bulleidia extructa, Roseburia inulinivorans\|Bulleidia extructa, Rothia dentocariosa\|Bulleidia extructa, Rothia mucilaginosa\|Bulleidia extructa, Ruminococcus albus\|Bulleidia extructa, Ruminococcus bromii\|Bulleidia extructa, Ruminococcus gnavus\|Bulleidia extructa, Ruminococcus lactaris\|Bulleidia extructa, Ruminococcus obeum\|Bulleidia extructa, Ruminococcus torques\|Bulleidia extructa, Selenomonas sputigena\|Bulleidia extructa, Shigella boydii\|Bulleidia extructa, Shigella dysenteriae\|Bulleidia extructa, Shigella sonnei\|Bulleidia extructa, Slackia exigua\|Bulleidia extructa, Solobacterium moorei\|Bulleidia extructa, Staphylococcus aureus\|Bulleidia extructa, Staphylococcus epidermidis\|Bulleidia extructa, Staphylococcus hominis\|Bulleidia extructa, Staphylococcus saprophyticus\|Bulleidia extructa, Staphylococcus warneri\|Bulleidia extructa, Streptococcus agalactiae\|Bulleidia extructa, Streptococcus anginosus\|Bulleidia extructa, Streptococcus australis\|Bulleidia extructa, Streptococcus bovis\|Bulleidia extructa, Streptococcus cristatus\|Bulleidia extructa, Streptococcus dysgalactiae\|Bulleidia extructa, Streptococcus equinus\|Bulleidia extructa, Streptococcus gordonii\|Bulleidia extructa, Streptococcus infantarius\|Bulleidia extructa, Streptococcus infantis\|Bulleidia extructa, Streptococcus mitis\|Bulleidia extructa, Streptococcus mutans\|Bulleidia extructa, Streptococcus oralis\|Bulleidia extructa, Streptococcus parasanguinis\|Bulleidia extructa, Streptococcus peroris\|Bulleidia extructa, Streptococcus pneumoniae\|Bulleidia extructa, Streptococcus salivarius\|Bulleidia extructa, Streptococcus sanguinis\|Bulleidia extructa, Streptococcus thermophilus\|Bulleidia extructa, Streptococcus vestibularis\|Bulleidia extructa, Subdoligranulum variabile\|Bulleidia extructa, Succinatimonas hippei\|Bulleidia extructa, Sutterella wadsworthensis\|Bulleidia extructa, Tropheryma whipplei\|Bulleidia extructa, Veillonella atypica\|Bulleidia extructa, Veillonella dispar\|Bulleidia extructa, Veillonella parvula\|Bulleidia extructa, Victivallis vadensis\|Butyrivibrio crossotus, Butyrivibrio crossotus\|Butyrivibrio crossotus, Campylobacter concisus\|Butyrivibrio crossotus, Campylobacter curvus\|Butyrivibrio crossotus, Campylobacter gracilis\|Butyrivibrio crossotus, Campylobacter hominis\|Butyrivibrio crossotus, Capnocytophaga ochracea\|Butyrivibrio crossotus, Cardiobacterium hominis\|Butyrivibrio crossotus, Catenibacterium mitsuokai\|Butyrivibrio crossotus, Catonella morbi\|Butyrivibrio crossotus, Citrobacter koseri\|Butyrivibrio crossotus, Clostridium asparagiforme\|Butyrivibrio crossotus, Clostridium bartlettii\|Butyrivibrio crossotus, Clostridium bolteae\|Butyrivibrio crossotus, Clostridium botulinum\|Butyrivibrio crossotus, Clostridium butyricum\|Butyrivibrio crossotus, Clostridium difficile\|Butyrivibrio crossotus, Clostridium disporicum\|Butyrivibrio crossotus, Clostridium hathewayi\|Butyrivibrio crossotus, Clostridium hylemonae\|Butyrivibrio crossotus, Clostridium innocuum\|Butyrivibrio crossotus, Clostridium leptum\|Butyrivibrio crossotus, Clostridium mayombei\|Butyrivibrio crossotus, Clostridium methylpentosum\|Butyrivibrio crossotus, Clostridium nexile\|Butyrivibrio crossotus, Clostridium orbiscindens\|Butyrivibrio crossotus, Clostridium perfringens\|Butyrivibrio crossotus, Clostridium saccharolyticum\|Butyrivibrio crossotus, Clostridium scindens\|Butyrivibrio crossotus, Clostridium symbiosum\|Butyrivibrio crossotus, Clostridium tertium\|Butyrivibrio crossotus, Collinsella aerofaciens\|Butyrivibrio crossotus, Collinsella intestinalis\|Butyrivibrio crossotus, Collinsella stercoris\|Butyrivibrio crossotus, Coprobacillus* sp. D7\|*Butyrivibrio crossotus, Coprococcus catus\|Butyrivibrio crossotus, Coprococcus comes\|Butyrivibrio crossotus, Coprococcus eutactus\|Butyrivibrio crossotus, Corynebacterium aurimucosum\|Butyrivibrio crossotus, Corynebacterium matruchotii\|Butyrivibrio crossotus, Cryptobacterium curtum\|Butyrivibrio crossotus, Desulfovibrio desulfuricans\|Butyrivibrio crossotus, Desulfovibrio piger\|Butyrivibrio crossotus, Dialister invisus\|Butyrivibrio crossotus, Dialister microaerophilus\|Butyrivibrio crossotus, Dorea formicigenerans\|Butyrivibrio crossotus, Dorea longicatena\|Butyrivibrio crossotus, Eggerthella lenta\|Butyrivibrio crossotus, Eikenella corrodens\|Butyrivibrio crossotus, Enterobacter cancerogenus\|Butyrivibrio crossotus, Enterobacter cloacae\|Butyrivibrio crossotus, Enterococcus faecalis\|Butyrivibrio crossotus, Enterococcus faecium\|Butyrivibrio crossotus, Enterococcus gallinarum\|Butyrivibrio crossotus, Erysipelotrichaceae bacterium* 3_1_53\|*Butyrivibrio crossotus, Escherichia coli\|Butyrivibrio crossotus, Escherichia fergusonii\|Butyrivibrio crossotus, Ethanoligenens harbinense\|Butyrivibrio crossotus, Eubacterium cellulosolvens\|Butyrivibrio crossotus, Eubacterium eligens\|Butyrivibrio crossotus, Eubacterium hallii\|Butyrivibrio crossotus, Eubacterium limosum\|Butyrivibrio crossotus, Eubacterium rectale\|Butyrivibrio crossotus, Eubacterium siraeum\|Butyrivibrio crossotus, Eubacterium ventriosum\|Butyrivibrio crossotus, Faecalibacterium prausnitzii\|Butyrivibrio crossotus, Finegoldia magna\|Butyrivibrio crossotus, Fusobacterium gonidiaformans\|Butyrivibrio crossotus, Fusobacterium mortiferum\|Butyrivibrio crossotus, Fusobacterium nucleatum\|Butyrivibrio crossotus, Fusobacterium varium\|Butyrivibrio crossotus, Gardnerella vaginalis\|Butyrivibrio crossotus, Gemella haemolysans\|Butyrivibrio crossotus, Gemella morbillorum\|Butyrivibrio crossotus, Gordonibacter pamelaeae\|Butyrivibrio crossotus, Granulicatella adiacens\|Butyrivibrio crossotus, Granulicatella elegans\|Butyrivibrio crossotus, Haemophilus influenzae\|Butyrivibrio crossotus, Haemophilus parainfluenzae\|Butyrivibrio crossotus, Helicobacter pullorum\|Butyrivibrio crossotus, Helicobacter pylori\|Butyrivibrio crossotus, Holdemania filiformis\|Butyrivibrio crossotus, Kingella oralis\|Butyrivibrio crossotus, Klebsiella pneumoniae\|Butyrivibrio crossotus, Klebsiella variicola\|Butyrivibrio crossotus, Lachnospiraceae bacterium* 5_1_57FAA\|*Butyrivibrio crossotus, Lactobacillus acidophilus\|Butyrivibrio crossotus, Lactobacillus amylovorus\|Butyrivibrio crossotus, Lactobacillus brevis\|Butyrivibrio crossotus, Lactobacillus casei\|Butyrivibrio crossotus, Lactobacillus crispatus\|Butyrivibrio crossotus, Lactobacillus delbrueckii\|Butyrivibrio crossotus, Lactobacillus fermentum\|Butyrivibrio crossotus, Lactobacillus gasseri\|Butyrivibrio crossotus, Lactobacillus iners\|Butyrivibrio crossotus, Lactobacillus jensenii\|Butyrivibrio crossotus, Lactobacillus johnsonii\|Butyrivibrio crossotus, Lactobacillus paracasei\|Butyrivibrio crossotus, Lactobacillus plantarum\|Butyrivibrio crossotus, Lactobacillus reuteri\|Butyrivibrio crossotus, Lactobacillus rhamnosus\|Butyrivibrio crossotus, Lactobacillus ruminis\|Butyrivibrio crossotus, Lactobacillus sakei\|Butyrivibrio crossotus, Lactobacillus salivarius\|Butyrivibrio* |

TABLE 2-continued

| Table 2. Specific binary combinations of OTUs. Individual pairings are differentiated by "\|" and OTUs within a combination are differentiated by "," |
|---|
| crossotus, Lactococcus lactis\|Butyrivibrio crossotus, Lautropia mirabilis\|Butyrivibrio crossotus, Leuconostoc citreum\|Butyrivibrio crossotus, Leuconostoc gasicomitatum\|Butyrivibrio crossotus, Leuconostoc mesenteroides\|Butyrivibrio crossotus, Listeria monocytogenes\|Butyrivibrio crossotus, Marvinbryantia formatexigens\|Butyrivibrio crossotus, Megamonas hypermegale\|Butyrivibrio crossotus, Megasphaera micronuciformis\|Butyrivibrio crossotus, Methanobrevibacter smithii\|Butyrivibrio crossotus, Methanosphaera stadtmanae\|Butyrivibrio crossotus, Methylobacterium radiotolerans\|Butyrivibrio crossotus, Mitsuokella multacida\|Butyrivibrio crossotus, Mobiluncus curtisii\|Butyrivibrio crossotus, Mycoplasma hominis\|Butyrivibrio crossotus, Neisseria mucosa\|Butyrivibrio crossotus, Odoribacter splanchnicus\|Butyrivibrio crossotus, Olsenella uli\|Butyrivibrio crossotus, Oribacterium sinus\|Butyrivibrio crossotus, Oxalobacter formigenes\|Butyrivibrio crossotus, Parabacteroides distasonis\|Butyrivibrio crossotus, Parabacteroides johnsonii\|Butyrivibrio crossotus, Parabacteroides merdae\|Butyrivibrio crossotus, Parvimonas micra\|Butyrivibrio crossotus, Pediococcus acidilactici\|Butyrivibrio crossotus, Pediococcus pentosaceus\|Butyrivibrio crossotus, Peptoniphilus duerdenii\|Butyrivibrio crossotus, Peptoniphilus harei\|Butyrivibrio crossotus, Peptoniphilus lacrimalis\|Butyrivibrio crossotus, Peptostreptococcus anaerobius\|Butyrivibrio crossotus, Peptostreptococcus stomatis\|Butyrivibrio crossotus, Porphyromonas asaccharolytica\|Butyrivibrio crossotus, Porphyromonas uenonis\|Butyrivibrio crossotus, Prevotella amnii\|Butyrivibrio crossotus, Prevotella bergensis\|Butyrivibrio crossotus, Prevotella bivia\|Butyrivibrio crossotus, Prevotella buccae\|Butyrivibrio crossotus, Prevotella buccalis\|Butyrivibrio crossotus, Prevotella copri\|Butyrivibrio crossotus, Prevotella disiens\|Butyrivibrio crossotus, Prevotella melaninogenica\|Butyrivibrio crossotus, Prevotella multiformis\|Butyrivibrio crossotus, Prevotella oralis\|Butyrivibrio crossotus, Prevotella oris\|Butyrivibrio crossotus, Prevotella salivae\|Butyrivibrio crossotus, Prevotella timonensis\|Butyrivibrio crossotus, Propionibacterium acnes\|Butyrivibrio crossotus, Propionibacterium freudenreichii\|Butyrivibrio crossotus, Proteus mirabilis\|Butyrivibrio crossotus, Proteus penneri\|Butyrivibrio crossotus, Pseudoflavonifractor capillosus\|Butyrivibrio crossotus, Pseudomonas aeruginosa\|Butyrivibrio crossotus, Pseudomonas fluorescens\|Butyrivibrio crossotus, Pseudomonas putida\|Butyrivibrio crossotus, Pseudoramibacter alactolyticus\|Butyrivibrio crossotus, Pyramidobacter piscolens\|Butyrivibrio crossotus, Rhodopseudomonas palustris\|Butyrivibrio crossotus, Roseburia intestinalis\|Butyrivibrio crossotus, Roseburia inulinivorans\|Butyrivibrio crossotus, Rothia dentocariosa\|Butyrivibrio crossotus, Rothia mucilaginosa\|Butyrivibrio crossotus, Ruminococcus albus\|Butyrivibrio crossotus, Ruminococcus bromii\|Butyrivibrio crossotus, Ruminococcus gnavus\|Butyrivibrio crossotus, Ruminococcus lactaris\|Butyrivibrio crossotus, Ruminococcus obeum\|Butyrivibrio crossotus, Ruminococcus torques\|Butyrivibrio crossotus, Selenomonas sputigena\|Butyrivibrio crossotus, Shigella boydii\|Butyrivibrio crossotus, Shigella dysenteriae\|Butyrivibrio crossotus, Shigella sonnei\|Butyrivibrio crossotus, Slackia exigua\|Butyrivibrio crossotus, Solobacterium moorei\|Butyrivibrio crossotus, Staphylococcus aureus\|Butyrivibrio crossotus, Staphylococcus epidermidis\|Butyrivibrio crossotus, Staphylococcus hominis\|Butyrivibrio crossotus, Staphylococcus saprophyticus\|Butyrivibrio crossotus, Staphylococcus warneri\|Butyrivibrio crossotus, Streptococcus agalactiae\|Butyrivibrio crossotus, Streptococcus anginosus\|Butyrivibrio crossotus, Streptococcus australis\|Butyrivibrio crossotus, Streptococcus bovis\|Butyrivibrio crossotus, Streptococcus cristatus\|Butyrivibrio crossotus, Streptococcus dysgalactiae\|Butyrivibrio crossotus, Streptococcus equinus\|Butyrivibrio crossotus, Streptococcus gordonii\|Butyrivibrio crossotus, Streptococcus infantarius\|Butyrivibrio crossotus, Streptococcus infantis\|Butyrivibrio crossotus, Streptococcus mitis\|Butyrivibrio crossotus, Streptococcus mutans\|Butyrivibrio crossotus, Streptococcus oralis\|Butyrivibrio crossotus, Streptococcus parasanguinis\|Butyrivibrio crossotus, Streptococcus peroris\|Butyrivibrio crossotus, Streptococcus pneumoniae\|Butyrivibrio crossotus, Streptococcus salivarius\|Butyrivibrio crossotus, Streptococcus sanguinis\|Butyrivibrio crossotus, Streptococcus thermophilus\|Butyrivibrio crossotus, Streptococcus vestibularis\|Butyrivibrio crossotus, Subdoligranulum variabile\|Butyrivibrio crossotus, Succinatimonas hippei\|Butyrivibrio crossotus, Sutterella wadsworthensis\|Butyrivibrio crossotus, Tropheryma whipplei\|Butyrivibrio crossotus, Veillonella atypica\|Butyrivibrio crossotus, Veillonella dispar\|Butyrivibrio crossotus, Veillonella parvula\|Butyrivibrio crossotus, Victivallis vadensis\|Campylobacter concisus, Campylobacter concisus\|Campylobacter concisus, Campylobacter curvus\|Campylobacter concisus, Campylobacter gracilis\|Campylobacter concisus, Campylobacter hominis\|Campylobacter concisus, Capnocytophaga ochracea\|Campylobacter concisus, Cardiobacterium hominis\|Campylobacter concisus, Catenibacterium mitsuokai\|Campylobacter concisus, Catonella morbi\|Campylobacter concisus, Citrobacter koseri\|Campylobacter concisus, Clostridium asparagiforme\|Campylobacter concisus, Clostridium bartlettii\|Campylobacter concisus, Clostridium bolteae\|Campylobacter concisus, Clostridium botulinum\|Campylobacter concisus, Clostridium butyricum\|Campylobacter concisus, Clostridium difficile\|Campylobacter concisus, Clostridium disporicum\|Campylobacter concisus, Clostridium hathewayi\|Campylobacter concisus, Clostridium hylemonae\|Campylobacter concisus, Clostridium innocuum\|Campylobacter concisus, Clostridium leptum\|Campylobacter concisus, Clostridium mayombei\|Campylobacter concisus, Clostridium methylpentosum\|Campylobacter concisus, Clostridium nexile\|Campylobacter concisus, Clostridium orbiscindens\|Campylobacter concisus, Clostridium perfringens\|Campylobacter concisus, Clostridium saccharolyticum\|Campylobacter concisus, Clostridium scindens\|Campylobacter concisus, Clostridium symbiosum\|Campylobacter concisus, Clostridium tertium\|Campylobacter concisus, Collinsella aerofaciens\|Campylobacter concisus, Collinsella intestinalis\|Campylobacter concisus, Collinsella stercoris\|Campylobacter concisus, Coprobacillus sp. D7\|Campylobacter concisus, Coprococcus catus\|Campylobacter concisus, Coprococcus comes\|Campylobacter concisus, Coprococcus eutactus\|Campylobacter concisus, Corynebacterium aurimucosum\|Campylobacter concisus, Corynebacterium matruchotii\|Campylobacter concisus, Cryptobacterium curtum\|Campylobacter concisus, Desulfovibrio desulfuricans\|Campylobacter concisus, Desulfovibrio piger\|Campylobacter concisus, Dialister invisus\|Campylobacter concisus, Dialister microaerophilus\|Campylobacter concisus, Dorea formicigenerans\|Campylobacter concisus, Dorea longicatena\|Campylobacter concisus, Eggerthella lenta\|Campylobacter concisus, Eikenella corrodens\|Campylobacter concisus, Enterobacter cancerogenus\|Campylobacter concisus, Enterobacter cloacae\|Campylobacter concisus, Enterococcus faecalis\|Campylobacter concisus, Enterococcus faecium\|Campylobacter concisus, Enterococcus gallinarum\|Campylobacter concisus, Erysipelotrichaceae bacterium 3_1_53\|Campylobacter concisus, Escherichia coli\|Campylobacter concisus, Escherichia fergusonii\|Campylobacter concisus, Ethanoligenens harbinense\|Campylobacter concisus, Eubacterium cellulosolvens\|Campylobacter concisus, Eubacterium eligens\|Campylobacter concisus, Eubacterium hallii\|Campylobacter concisus, Eubacterium limosum\|Campylobacter concisus, Eubacterium rectale\|Campylobacter concisus, Eubacterium siraeum\|Campylobacter concisus, Eubacterium ventriosum\|Campylobacter concisus, Faecalibacterium prausnitzii\|Campylobacter concisus, Finegoldia magna\|Campylobacter concisus, Fusobacterium gonidiaformans\|Campylobacter concisus, Fusobacterium mortiferum\|Campylobacter concisus, Fusobacterium nucleatum\|Campylobacter concisus, Fusobacterium varium\|Campylobacter concisus, Gardnerella vaginalis\|Campylobacter concisus, Gemella Chaemolysans\|Campylobacter concisus, Gemella morbillorum\|Campylobacter concisus, Gordonibacter pamelaeae\|Campylobacter concisus, Granulicatella adiacens\|Campylobacter concisus, Granulicatella elegans\|Campylobacter concisus, Haemophilus influenzae\|Campylobacter concisus, Haemophilus parainfluenzae\|Campylobacter concisus, Helicobacter pullorum\|Campylobacter concisus, Helicobacter pylori\|Campylobacter concisus, Holdemania filiformis\|Campylobacter concisus, Kingella oralis\|Campylobacter concisus, Klebsiella pneumoniae\|Campylobacter concisus, Klebsiella variicola\|Campylobacter concisus, Lachnospiraceae bacterium 5_1_57FAA\|Campylobacter concisus, Lactobacillus acidophilus\|Campylobacter concisus, Lactobacillus amylovorus\|Campylobacter concisus, Lactobacillus brevis\|Campylobacter concisus, Lactobacillus casei\|Campylobacter concisus, Lactobacillus crispatus\|Campylobacter concisus, Lactobacillus delbrueckii\|Campylobacter concisus, Lactobacillus fermentum\|Campylobacter concisus, Lactobacillus gasseri\|Campylobacter concisus, Lactobacillus iners\|Campylobacter concisus, Lactobacillus jensenii\|Campylobacter concisus, Lactobacillus johnsonii\|Campylobacter concisus, Lactobacillus paracasei\|Campylobacter concisus, Lactobacillus plantarum\|Campylobacter concisus, Lactobacillus reuteri\|Campylobacter concisus, Lactobacillus rhamnosus\|Campylobacter concisus, Lactobacillus ruminis\|Campylobacter concisus, Lactobacillus sakei\|Campylobacter concisus, Lactobacillus salivarius\|Campylobacter concisus, Lactococcus lactis\|Campylobacter concisus, Lautropia mirabilis\|Campylobacter concisus, Leuconostoc citreum\|Campylobacter concisus, Leuconostoc gasicomitatum\|Campylobacter concisus, Leuconostoc |

TABLE 2-continued

| Table 2. Specific binary combinations of OTUs. Individual pairings are differentiated by "\|" and OTUs within a combination are differentiated by "," |
|---|
| mesenteroides\|Campylobacter concisus, Listeria monocytogenes\|Campylobacter concisus, Marvinbryantia formatexigens\|Campylobacter concisus, Megamonas hypermegale\|Campylobacter concisus, Megasphaera micronuciformis\|Campylobacter concisus, Methanobrevibacter smithii\|Campylobacter concisus, Methanosphaera stadtmanae\|Campylobacter concisus, Methylobacterium radiotolerans\|Campylobacter concisus, Mitsuokella multacida\|Campylobacter concisus, Mobiluncus curtisii\|Campylobacter concisus, Mycoplasma hominis\|Campylobacter concisus, Neisseria mucosa\|Campylobacter concisus, Odoribacter splanchnicus\|Campylobacter concisus, Olsenella uli\|Campylobacter concisus, Oribacterium sinus\|Campylobacter concisus, Oxalobacter formigenes\|Campylobacter concisus, Parabacteroides distasonis\|Campylobacter concisus, Parabacteroides johnsonii\|Campylobacter concisus, Parabacteroides merdae\|Campylobacter concisus, Parvimonas micra\|Campylobacter concisus, Pediococcus acidilactici\|Campylobacter concisus, Pediococcus pentosaceus\|Campylobacter concisus, Peptoniphilus duerdenii\|Campylobacter concisus, Peptoniphilus harei\|Campylobacter concisus, Peptoniphilus lacrimalis\|Campylobacter concisus, Peptostreptococcus anaerobius\|Campylobacter concisus, Peptostreptococcus stomatis\|Campylobacter concisus, Porphyromonas asaccharolytica\|Campylobacter concisus, Porphyromonas uenonis\|Campylobacter concisus, Prevotella amnii\|Campylobacter concisus, Prevotella bergensis\|Campylobacter concisus, Prevotella bivia\|Campylobacter concisus, Prevotella buccae\|Campylobacter concisus, Prevotella buccalis\|Campylobacter concisus, Prevotella copri\|Campylobacter concisus, Prevotella disiens\|Campylobacter concisus, Prevotella melaninogenica\|Campylobacter concisus, Prevotella multiformis\|Campylobacter concisus, Prevotella oralis\|Campylobacter concisus, Prevotella oris\|Campylobacter concisus, Prevotella salivae\|Campylobacter concisus, Prevotella timonensis\|Campylobacter concisus, Propionibacterium acnes\|Campylobacter concisus, Propionibacterium freudenreichii\|Campylobacter concisus, Proteus mirabilis\|Campylobacter concisus, Proteus penneri\|Campylobacter concisus, Pseudoflavonifractor capillosus\|Campylobacter concisus, Pseudomonas aeruginosa\|Campylobacter concisus, Pseudomonas fluorescens\|Campylobacter concisus, Pseudomonas putida\|Campylobacter concisus, Pseudoramibacter alactolyticus\|Campylobacter concisus, Pyramidobacter piscolens\|Campylobacter concisus, Rhodopseudomonas palustris\|Campylobacter concisus, Roseburia intestinalis\|Campylobacter concisus, Roseburia inulinivorans\|Campylobacter concisus, Rothia dentocariosa\|Campylobacter concisus, Rothia mucilaginosa\|Campylobacter concisus, Ruminococcus albus\|Campylobacter concisus, Ruminococcus bromii\|Campylobacter concisus, Ruminococcus gnavus\|Campylobacter concisus, Ruminococcus lactaris\|Campylobacter concisus, Ruminococcus obeum\|Campylobacter concisus, Ruminococcus torques\|Campylobacter concisus, Selenomonas sputigena\|Campylobacter concisus, Shigella boydii\|Campylobacter concisus, Shigella dysenteriae\|Campylobacter concisus, Shigella sonnei\|Campylobacter concisus, Slackia exigua\|Campylobacter concisus, Solobacterium moorei\|Campylobacter concisus, Staphylococcus aureus\|Campylobacter concisus, Staphylococcus epidermidis\|Campylobacter concisus, Staphylococcus hominis\|Campylobacter concisus, Staphylococcus saprophyticus\|Campylobacter concisus, Staphylococcus warneri\|Campylobacter concisus, Streptococcus agalactiae\|Campylobacter concisus, Streptococcus anginosus\|Campylobacter concisus, Streptococcus australis\|Campylobacter concisus, Streptococcus bovis\|Campylobacter concisus, Streptococcus cristatus\|Campylobacter concisus, Streptococcus dysgalactiae\|Campylobacter concisus, Streptococcus equinus\|Campylobacter concisus, Streptococcus gordonii\|Campylobacter concisus, Streptococcus infantarius\|Campylobacter concisus, Streptococcus infantis\|Campylobacter concisus, Streptococcus mitis\|Campylobacter concisus, Streptococcus mutans\|Campylobacter concisus, Streptococcus oralis\|Campylobacter concisus, Streptococcus parasanguinis\|Campylobacter concisus, Streptococcus peroris\|Campylobacter concisus, Streptococcus pneumoniae\|Campylobacter concisus, Streptococcus salivarius\|Campylobacter concisus, Streptococcus sanguinis\|Campylobacter concisus, Streptococcus thermophilus\|Campylobacter concisus, Streptococcus vestibularis\|Campylobacter concisus, Subdoligranulum variabile\|Campylobacter concisus, Succinatimonas hippei\|Campylobacter concisus, Sutterella wadsworthensis\|Campylobacter concisus, Tropheryma whipplei\|Campylobacter concisus, Veillonella atypica\|Campylobacter concisus, Veillonella dispar\|Campylobacter concisus, Veillonella parvula\|Campylobacter concisus, Victivallis vadensis\|Campylobacter curvus, Campylobacter curvus\|Campylobacter curvus, Campylobacter gracilis\|Campylobacter curvus, Campylobacter hominis\|Campylobacter curvus, Capnocytophaga ochracea\|Campylobacter curvus, Cardiobacterium hominis\|Campylobacter curvus, Catenibacterium mitsuokai\|Campylobacter curvus, Catonella morbi\|Campylobacter curvus, Citrobacter koseri\|Campylobacter curvus, Clostridium asparagiforme\|Campylobacter curvus, Clostridium bartlettii\|Campylobacter curvus, Clostridium bolteae\|Campylobacter curvus, Clostridium botulinum\|Campylobacter curvus, Clostridium butyricum\|Campylobacter curvus, Clostridium difficile\|Campylobacter curvus, Clostridium disporicum\|Campylobacter curvus, Clostridium hathewayi\|Campylobacter curvus, Clostridium hylemonae\|Campylobacter curvus, Clostridium innocuum\|Campylobacter curvus, Clostridium leptum\|Campylobacter curvus, Clostridium mayombei\|Campylobacter curvus, Clostridium methylpentosum\|Campylobacter curvus, Clostridium nexile\|Campylobacter curvus, Clostridium orbiscindens\|Campylobacter curvus, Clostridium perfringens\|Campylobacter curvus, Clostridium saccharolyticum\|Campylobacter curvus, Clostridium scindens\|Campylobacter curvus, Clostridium symbiosum\|Campylobacter curvus, Clostridium tertium\|Campylobacter curvus, Collinsella aerofaciens\|Campylobacter curvus, Collinsella intestinalis\|Campylobacter curvus, Collinsella stercoris\|Campylobacter curvus, Coprobacillus sp. D7\|Campylobacter curvus, Coprococcus catus\|Campylobacter curvus, Coprococcus comes\|Campylobacter curvus, Coprococcus eutactus\|Campylobacter curvus, Corynebacterium aurimucosum\|Campylobacter curvus, Corynebacterium matruchotii\|Campylobacter curvus, Cryptobacterium curtum\|Campylobacter curvus, Desulfovibrio desulfuricans\|Campylobacter curvus, Desulfovibrio piger\|Campylobacter curvus, Dialister invisus\|Campylobacter curvus, Dialister microaerophilus\|Campylobacter curvus, Dorea formicigenerans\|Campylobacter curvus, Dorea longicatena\|Campylobacter curvus, Eggerthella lenta\|Campylobacter curvus, Eikenella corrodens\|Campylobacter curvus, Enterobacter cancerogenus\|Campylobacter curvus, Enterobacter cloacae\|Campylobacter curvus, Enterococcus faecalis\|Campylobacter curvus, Enterococcus faecium\|Campylobacter curvus, Enterococcus gallinarum\|Campylobacter curvus, Erysipelotrichaceae bacterium 3_1_53\|Campylobacter curvus, Escherichia coli\|Campylobacter curvus, Escherichia fergusonii\|Campylobacter curvus, Ethanoligenens harbinense\|Campylobacter curvus, Eubacterium cellulosolvens\|Campylobacter curvus, Eubacterium eligens\|Campylobacter curvus, Eubacterium hallii\|Campylobacter curvus, Eubacterium limosum\|Campylobacter curvus, Eubacterium rectale\|Campylobacter curvus, Eubacterium siraeum\|Campylobacter curvus, Eubacterium ventriosum\|Campylobacter curvus, Faecalibacterium prausnitzii\|Campylobacter curvus, Finegoldia magna\|Campylobacter curvus, Fusobacterium gonidiaformans\|Campylobacter curvus, Fusobacterium mortiferum\|Campylobacter curvus, Fusobacterium nucleatum\|Campylobacter curvus, Fusobacterium varium\|Campylobacter curvus, Gardnerella vaginalis\|Campylobacter curvus, Gemella haemolysans\|Campylobacter curvus, Gemella morbillorum\|Campylobacter curvus, Gordonibacter pamelaeae\|Campylobacter curvus, Granulicatella adiacens\|Campylobacter curvus, Granulicatella elegans\|Campylobacter curvus, Haemophilus influenzae\|Campylobacter curvus, Haemophilus parainfluenzae\|Campylobacter curvus, Helicobacter pullorum\|Campylobacter curvus, Helicobacter pylori\|Campylobacter curvus, Holdemania filiformis\|Campylobacter curvus, Kingella oralis\|Campylobacter curvus, Klebsiella pneumoniae\|Campylobacter curvus, Klebsiella variicola\|Campylobacter curvus, Lachnospiraceae bacterium 5_1_57FAA\|Campylobacter curvus, Lactobacillus acidophilus\|Campylobacter curvus, Lactobacillus amylovorus\|Campylobacter curvus, Lactobacillus brevis\|Campylobacter curvus, Lactobacillus casei\|Campylobacter curvus, Lactobacillus crispatus\|Campylobacter curvus, Lactobacillus delbrueckii\|Campylobacter curvus, Lactobacillus fermentum\|Campylobacter curvus, Lactobacillus gasseri\|Campylobacter curvus, Lactobacillus iners\|Campylobacter curvus, Lactobacillus jensenii\|Campylobacter curvus, Lactobacillus johnsonii\|Campylobacter curvus, Lactobacillus paracasei\|Campylobacter curvus, Lactobacillus plantarum\|Campylobacter curvus, Lactobacillus reuteri\|Campylobacter curvus, Lactobacillus rhamnosus\|Campylobacter curvus, Lactobacillus ruminis\|Campylobacter curvus, Lactobacillus sakei\|Campylobacter curvus, Lactobacillus salivarius\|Campylobacter curvus, Lactococcus lactis\|Campylobacter curvus, Lautropia mirabilis\|Campylobacter curvus, Leuconostoc citreum\|Campylobacter curvus, Leuconostoc gasicomitatum\|Campylobacter curvus, Leuconostoc mesenteroides\|Campylobacter curvus, Listeria monocytogenes\|Campylobacter curvus, Marvinbryantia formatexigens\|Campylobacter curvus, Megamonas hypermegale\|Campylobacter curvus, Megasphaera |

TABLE 2-continued

Table 2. Specific binary combinations of OTUs. Individual pairings are differentiated by "|" and OTUs within a combination are differentiated by ","

micronuciformis|Campylobacter curvus, Methanobrevibacter smithii|Campylobacter curvus, Methanosphaera stadtmanae|Campylobacter curvus, Methylobacterium radiotolerans|Campylobacter curvus, Mitsuokella multacida|Campylobacter curvus, Mobiluncus curtisii|Campylobacter curvus, Mycoplasma hominis|Campylobacter curvus, Neisseria mucosa|Campylobacter curvus, Odoribacter splanchnicus|Campylobacter curvus, Olsenella uli|Campylobacter curvus, Oribacterium sinus|Campylobacter curvus, Oxalobacter formigenes|Campylobacter curvus, Parabacteroides distasonis|Campylobacter curvus, Parabacteroides johnsonii|Campylobacter curvus, Parabacteroides merdae|Campylobacter curvus, Parvimonas micra|Campylobacter curvus, Pediococcus acidilactici|Campylobacter curvus, Pediococcus pentosaceus|Campylobacter curvus, Peptoniphilus duerdenii|Campylobacter curvus, Peptoniphilus harei|Campylobacter curvus, Peptoniphilus lacrimalis|Campylobacter curvus, Peptostreptococcus anaerobius|Campylobacter curvus, Peptostreptococcus stomatis|Campylobacter curvus, Porphyromonas asaccharolytica|Campylobacter curvus, Porphyromonas uenonis|Campylobacter curvus, Prevotella amnii|Campylobacter curvus, Prevotella bergensis|Campylobacter curvus, Prevotella bivia|Campylobacter curvus, Prevotella buccae|Campylobacter curvus, Prevotella buccalis|Campylobacter curvus, Prevotella copri|Campylobacter curvus, Prevotella disiens|Campylobacter curvus, Prevotella melaninogenica|Campylobacter curvus, Prevotella multiformis|Campylobacter curvus, Prevotella oralis|Campylobacter curvus, Prevotella oris|Campylobacter curvus, Prevotella salivae|Campylobacter curvus, Prevotella timonensis|Campylobacter curvus, Propionibacterium acnes|Campylobacter curvus, Propionibacterium freudenreichii|Campylobacter curvus, Proteus mirabilis|Campylobacter curvus, Proteus penneri|Campylobacter curvus, Pseudoflavonifractor capillosus|Campylobacter curvus, Pseudomonas aeruginosa|Campylobacter curvus, Pseudomonas fluorescens|Campylobacter curvus, Pseudomonas putida|Campylobacter curvus, Pseudoramibacter alactolyticus|Campylobacter curvus, Pyramidobacter piscolens|Campylobacter curvus, Rhodopseudomonas palustris|Campylobacter curvus, Roseburia intestinalis|Campylobacter curvus, Roseburia inulinivorans|Campylobacter curvus, Rothia dentocariosa|Campylobacter curvus, Rothia mucilaginosa|Campylobacter curvus, Ruminococcus albus|Campylobacter curvus, Ruminococcus bromii|Campylobacter curvus, Ruminococcus gnavus|Campylobacter curvus, Ruminococcus lactaris|Campylobacter curvus, Ruminococcus obeum|Campylobacter curvus, Ruminococcus torques|Campylobacter curvus, Selenomonas sputigena|Campylobacter curvus, Shigella boydii|Campylobacter curvus, Shigella dysenteriae|Campylobacter curvus, Shigella sonnei|Campylobacter curvus, Slackia exigua|Campylobacter curvus, Solobacterium moorei|Campylobacter curvus, Staphylococcus aureus|Campylobacter curvus, Staphylococcus epidermidis|Campylobacter curvus, Staphylococcus hominis|Campylobacter curvus, Staphylococcus saprophyticus|Campylobacter curvus, Staphylococcus warneri|Campylobacter curvus, Streptococcus agalactiae|Campylobacter curvus, Streptococcus anginosus|Campylobacter curvus, Streptococcus australis|Campylobacter curvus, Streptococcus bovis|Campylobacter curvus, Streptococcus cristatus|Campylobacter curvus, Streptococcus dysgalactiae|Campylobacter curvus, Streptococcus equinus|Campylobacter curvus, Streptococcus gordonii|Campylobacter curvus, Streptococcus infantarius|Campylobacter curvus, Streptococcus infantis|Campylobacter curvus, Streptococcus mitis|Campylobacter curvus, Streptococcus mutans|Campylobacter curvus, Streptococcus oralis|Campylobacter curvus, Streptococcus parasanguinis|Campylobacter curvus, Streptococcus peroris|Campylobacter curvus, Streptococcus pneumoniae|Campylobacter curvus, Streptococcus salivarius|Campylobacter curvus, Streptococcus sanguinis|Campylobacter curvus, Streptococcus thermophilus|Campylobacter curvus, Streptococcus vestibularis|Campylobacter curvus, Subdoligranulum variabile|Campylobacter curvus, Succinatimonas hippei|Campylobacter curvus, Sutterella wadsworthensis|Campylobacter curvus, Tropheryma whipplei|Campylobacter curvus, Veillonella atypica|Campylobacter curvus, Veillonella dispar|Campylobacter curvus, Veillonella parvula|Campylobacter curvus, Victivallis vadensis|Campylobacter gracilis, Campylobacter gracilis|Campylobacter gracilis, Campylobacter hominis|Campylobacter gracilis, Capnocytophaga ochracea|Campylobacter gracilis, Cardiobacterium hominis|Campylobacter gracilis, Catenibacterium mitsuokai|Campylobacter gracilis, Catonella morbi|Campylobacter gracilis, Citrobacter koseri|Campylobacter gracilis, Clostridium asparagiforme|Campylobacter gracilis, Clostridium bartlettii|Campylobacter gracilis, Clostridium bolteae|Campylobacter gracilis, Clostridium botulinum|Campylobacter gracilis, Clostridium butyricum|Campylobacter gracilis, Clostridium difficile|Campylobacter gracilis, Clostridium disporicum|Campylobacter gracilis, Clostridium hathewayi|Campylobacter gracilis, Clostridium hylemonae|Campylobacter gracilis, Clostridium innocuum|Campylobacter gracilis, Clostridium leptum|Campylobacter gracilis, Clostridium mayombei|Campylobacter gracilis, Clostridium methylpentosum|Campylobacter gracilis, Clostridium nexile|Campylobacter gracilis, Clostridium orbiscindens|Campylobacter gracilis, Clostridium perfringens|Campylobacter gracilis, Clostridium saccharolyticum|Campylobacter gracilis, Clostridium scindens|Campylobacter gracilis, Clostridium symbiosum|Campylobacter gracilis, Clostridium tertium|Campylobacter gracilis, Collinsella aerofaciens|Campylobacter gracilis, Collinsella intestinalis|Campylobacter gracilis, Collinsella stercoris|Campylobacter gracilis, Coprobacillus sp. D7|Campylobacter gracilis, Coprococcus catus|Campylobacter gracilis, Coprococcus comes|Campylobacter gracilis, Coprococcus eutactus|Campylobacter gracilis, Corynebacterium aurimucosum|Campylobacter gracilis, Corynebacterium matruchotii|Campylobacter gracilis, Cryptobacterium curtum|Campylobacter gracilis, Desulfovibrio desulfuricans|Campylobacter gracilis, Desulfovibrio piger|Campylobacter gracilis, Dialister invisus|Campylobacter gracilis, Dialister microaerophilus|Campylobacter gracilis, Dorea formicigenerans|Campylobacter gracilis, Dorea longicatena|Campylobacter gracilis, Eggerthella lenta|Campylobacter gracilis, Eikenella corrodens|Campylobacter gracilis, Enterobacter cancerogenus|Campylobacter gracilis, Enterobacter cloacae|Campylobacter gracilis, Enterococcus faecalis|Campylobacter gracilis, Enterococcus faecium|Campylobacter gracilis, Enterococcus gallinarum|Campylobacter gracilis, Erysipelotrichaceae bacterium 3_1_53|Campylobacter gracilis, Escherichia coli|Campylobacter gracilis, Escherichia fergusonii|Campylobacter gracilis, Ethanoligenens harbinense|Campylobacter gracilis, Eubacterium cellulosolvens|Campylobacter gracilis, Eubacterium eligens|Campylobacter gracilis, Eubacterium hallii|Campylobacter gracilis, Eubacterium limosuna|Campylobacter gracilis, Eubacterium rectale|Campylobacter gracilis, Eubacterium siraeum|Campylobacter gracilis, Eubacterium ventriosum|Campylobacter gracilis, Faecalibacterium prausnitzii|Campylobacter gracilis, Finegoldia magna|Campylobacter gracilis, Fusobacterium gonidiaformans|Campylobacter gracilis, Fusobacterium mortiferum|Campylobacter gracilis, Fusobacterium nucleatum|Campylobacter gracilis, Fusobacterium varium|Campylobacter gracilis, Gardnerella vaginalis|Campylobacter gracilis, Gemella haemolysans|Campylobacter gracilis, Gemella morbillorum|Campylobacter gracilis, Gordonibacter pamelaeae|Campylobacter gracilis, Granulicatella adiacens|Campylobacter gracilis, Granulicatella elegans|Campylobacter gracilis, Haemophilus influenzae|Campylobacter gracilis, Haemophilus parainfluenzae|Campylobacter gracilis, Helicobacter pullorum|Campylobacter gracilis, Helicobacter pylori|Campylobacter gracilis, Holdemania filiformis|Campylobacter gracilis, Kingella oralis|Campylobacter gracilis, Klebsiella pneumoniae|Campylobacter gracilis, Klebsiella variicola|Campylobacter gracilis, Lachnospiraceae bacterium 5_1_57FAA|Campylobacter gracilis, Lactobacillus acidophilus|Campylobacter gracilis, Lactobacillus amylovorus|Campylobacter gracilis, Lactobacillus brevis|Campylobacter gracilis, Lactobacillus casei|Campylobacter gracilis, Lactobacillus crispatus|Campylobacter gracilis, Lactobacillus delbrueckii|Campylobacter gracilis, Lactobacillus fermentum|Campylobacter gracilis, Lactobacillus gasseri|Campylobacter gracilis, Lactobacillus iners|Campylobacter gracilis, Lactobacillus jensenii|Campylobacter gracilis, Lactobacillus johnsonii|Campylobacter gracilis, Lactobacillus paracasei|Campylobacter gracilis, Lactobacillus plantarum|Campylobacter gracilis, Lactobacillus reuteri|Campylobacter gracilis, Lactobacillus rhamnosus|Campylobacter gracilis, Lactobacillus ruminis|Campylobacter gracilis, Lactobacillus sakei|Campylobacter gracilis, Lactobacillus salivarius|Campylobacter gracilis, Lactococcus lactis|Campylobacter gracilis, Lautropia mirabilis|Campylobacter gracilis, Leuconostoc citreum|Campylobacter gracilis, Leuconostoc gasicomitatum|Campylobacter gracilis, Leuconostoc mesenteroides|Campylobacter gracilis, Listeria monocytogenes|Campylobacter gracilis, Marvinbryantia formatexigens|Campylobacter gracilis, Megamonas hypermegale|Campylobacter gracilis, Megasphaera micronuciformis|Campylobacter gracilis, Methanobrevibacter smithii|Campylobacter gracilis, Methanosphaera stadtmanae|Campylobacter gracilis, Methylobacterium radiotolerans|Campylobacter gracilis, Mitsuokella multacida|Campylobacter gracilis, Mobiluncus curtisii|Campylobacter gracilis, Mycoplasma hominis|Campylobacter gracilis, Neisseria mucosa|Campylobacter gracilis, Odoribacter splanchnicus|Campylobacter gracilis, Olsenella TABLE 2-continued

| Table 2. Specific binary combinations of OTUs. Individual pairings are differentiated by "\|" and OTUs within a combination are differentiated by "," |
|---|
| uli\|Campylobacter gracilis, Oribacterium sinus\|Campylobacter gracilis, Oxalobacter formigenes\|Campylobacter gracilis, Parabacteroides distasonis\|Campylobacter gracilis, Parabacteroides johnsonii\|Campylobacter gracilis, Parabacteroides merdae\|Campylobacter gracilis, Parvimonas micra\|Campylobacter gracilis, Pediococcus acidilactici\|Campylobacter gracilis, Pediococcus pentosaceus\|Campylobacter gracilis, Peptoniphilus duerdenii\|Campylobacter gracilis, Peptoniphilus harei\|Campylobacter gracilis, Peptoniphilus lacrimalis\|Campylobacter gracilis, Peptostreptococcus anaerobius\|Campylobacter gracilis, Peptostreptococcus stomatis\|Campylobacter gracilis, Porphyromonas asaccharolytica\|Campylobacter gracilis, Porphyromonas uenonis\|Campylobacter gracilis, Prevotella amnii\|Campylobacter gracilis, Prevotella bergensis\|Campylobacter gracilis, Prevotella bivia\|Campylobacter gracilis, Prevotella buccae\|Campylobacter gracilis, Prevotella buccalis\|Campylobacter gracilis, Prevotella copri\|Campylobacter gracilis, Prevotella disiens\|Campylobacter gracilis, Prevotella melaninogenica\|Campylobacter gracilis, Prevotella multiformis\|Campylobacter gracilis, Prevotella oralis\|Campylobacter gracilis, Prevotella oris\|Campylobacter gracilis, Prevotella salivae\|Campylobacter gracilis, Prevotella timonensis\|Campylobacter gracilis, Propionibacterium acnes\|Campylobacter gracilis, Propionibacterium freudenreichii\|Campylobacter gracilis, Proteus mirabilis\|Campylobacter gracilis, Proteus penneri\|Campylobacter gracilis, Pseudoflavonifractor capillosus\|Campylobacter gracilis, Pseudomonas aeruginosa\|Campylobacter gracilis, Pseudomonas fluorescens\|Campylobacter gracilis, Pseudomonas putida\|Campylobacter gracilis, Pseudoramibacter alactolyticus\|Campylobacter gracilis, Pyramidobacter piscolens\|Campylobacter gracilis, Rhodopseudomonas palustris\|Campylobacter gracilis, Roseburia intestinalis\|Campylobacter gracilis, Roseburia inulinivorans\|Campylobacter gracilis, Rothia dentocariosa\|Campylobacter gracilis, Rothia mucilaginosa\|Campylobacter gracilis, Ruminococcus albus\|Campylobacter gracilis, Ruminococcus bromii\|Campylobacter gracilis, Ruminococcus gnavus\|Campylobacter gracilis, Ruminococcus lactaris\|Campylobacter gracilis, Ruminococcus obeum\|Campylobacter gracilis, Ruminococcus torques\|Campylobacter gracilis, Selenomonas sputigena\|Campylobacter gracilis, Shigella boydii\|Campylobacter gracilis, Shigella dysenteriae\|Campylobacter gracilis, Shigella sonnei\|Campylobacter gracilis, Slackia exigua\|Campylobacter gracilis, Solobacterium moorei\|Campylobacter gracilis, Staphylococcus aureus\|Campylobacter gracilis, Staphylococcus epidermidis\|Campylobacter gracilis, Staphylococcus hominis, Campylobacter gracilis, Staphylococcus saprophyticus\|Campylobacter gracilis, Staphylococcus warneri\|Campylobacter gracilis, Streptococcus agalactiae\|Campylobacter gracilis, Streptococcus anginosus\|Campylobacter gracilis, Streptococcus australis\|Campylobacter gracilis, Streptococcus bovis\|Campylobacter gracilis, Streptococcus cristatus\|Campylobacter gracilis, Streptococcus dysgalactiae\|Campylobacter gracilis, Streptococcus equinus\|Campylobacter gracilis, Streptococcus gordonii\|Campylobacter gracilis, Streptococcus infantarius\|Campylobacter gracilis, Streptococcus infantis\|Campylobacter gracilis, Streptococcus mitis\|Campylobacter gracilis, Streptococcus mutans\|Campylobacter gracilis, Streptococcus oralis\|Campylobacter gracilis, Streptococcus parasanguinis\|Campylobacter gracilis, Streptococcus peroris\|Campylobacter gracilis, Streptococcus pneumoniae\|Campylobacter gracilis, Streptococcus salivarius\|Campylobacter gracilis, Streptococcus sanguinis\|Campylobacter gracilis, Streptococcus thermophilus\|Campylobacter gracilis, Streptococcus vestibularis\|Campylobacter gracilis, Subdoligranulum variabile\|Campylobacter gracilis, Succinatimonas hippei\|Campylobacter gracilis, Sutterella wadsworthensis\|Campylobacter gracilis, Tropheryma whipplei\|Campylobacter gracilis, Veillonella atypica\|Campylobacter gracilis, Veillonella dispar\|Campylobacter gracilis, Veillonella parvula\|Campylobacter gracilis, Victivallis vadensis\|Campylobacter hominis, Campylobacter hominis\|Campylobacter hominis, Capnocytophaga ochracea\|Campylobacter hominis, Cardiobacterium hominis, Campylobacter hominis, Catenibacterium mitsuokai\|Campylobacter hominis, Catonella morbi\|Campylobacter hominis, Citrobacter koseri\|Campylobacter hominis, Clostridium asparagiforme\|Campylobacter hominis, Clostridium bartlettii\|Campylobacter hominis, Clostridium bolteae\|Campylobacter hominis, Clostridium botulinum\|Campylobacter hominis, Clostridium butyricum\|Campylobacter hominis, Clostridium difficile\|Campylobacter hominis, Clostridium disporicum\|Campylobacter hominis, Clostridium hathewayi\|Campylobacter hominis, Clostridium hylemonae\|Campylobacter hominis, Clostridium innocuum\|Campylobacter hominis, Clostridium leptum\|Campylobacter hominis, Clostridium mayombei\|Campylobacter hominis, Clostridium methylpentosum\|Campylobacter hominis, Clostridium nexile\|Campylobacter hominis, Clostridium orbiscindens\|Campylobacter hominis, Clostridium perfringens\|Campylobacter hominis, Clostridium saccharolyticum\|Campylobacter hominis, Clostridium scindens\|Campylobacter hominis, Clostridium symbiosum\|Campylobacter hominis, Clostridium tertium\|Campylobacter hominis, Collinsella aerofaciens\|Campylobacter hominis, Collinsella intestinalis\|Campylobacter hominis, Collinsella stercoris\|Campylobacter hominis, Coprobacillus sp. D7\|Campylobacter hominis, Coprococcus catus\|Campylobacter hominis, Coprococcus comes\|Campylobacter hominis, Coprococcus eutactus\|Campylobacter hominis, Corynebacterium aurimucosum\|Campylobacter hominis, Corynebacterium matruchotii\|Campylobacter hominis, Cryptobacterium curtum\|Campylobacter hominis, Desulfovibrio desulfuricans\|Campylobacter hominis, Desulfovibrio piger\|Campylobacter hominis, Dialister invisus\|Campylobacter hominis, Dialister microaerophilus\|Campylobacter hominis, Dorea formicigenerans\|Campylobacter hominis, Dorea longicatena\|Campylobacter hominis, Eggerthella lenta\|Campylobacter hominis, Eikenella corrodens\|Campylobacter hominis, Enterobacter cancerogenus\|Campylobacter hominis, Enterobacter cloacae\|Campylobacter hominis, Enterococcus faecalis\|Campylobacter hominis, Enterococcus faecium\|Campylobacter hominis, Enterococcus gallinarum\|Campylobacter hominis, Erysipelotrichaceae bacterium 3_1_53\|Campylobacter hominis, Escherichia coli\|Campylobacter hominis, Escherichia fergusonii\|Campylobacter hominis, Ethanoligenens harbinense\|Campylobacter hominis, Eubacterium cellulosolvens\|Campylobacter hominis, Eubacterium eligens\|Campylobacter hominis, Eubacterium hallii\|Campylobacter hominis, Eubacterium limosum\|Campylobacter hominis, Eubacterium rectale\|Campylobacter hominis, Eubacterium siraeum\|Campylobacter hominis, Eubacterium ventriosum\|Campylobacter hominis, Faecalibacterium prausnitzii\|Campylobacter hominis, Finegoldia magna\|Campylobacter hominis, Fusobacterium gonidiaformans\|Campylobacter hominis, Fusobacterium mortiferum\|Campylobacter hominis, Fusobacterium nucleatum\|Campylobacter hominis, Fusobacterium varium\|Campylobacter hominis, Gardnerella vaginalis\|Campylobacter hominis, Gemella haemolysans\|Campylobacter hominis, Gemella morbillorum\|Campylobacter hominis, Gordonibacter pamelaeae\|Campylobacter hominis, Granulicatella adiacens\|Campylobacter hominis, Granulicatella elegans\|Campylobacter hominis, Haemophilus influenzae\|Campylobacter hominis, Haemophilus parainfluenzae\|Campylobacter hominis, Helicobacter pullorum\|Campylobacter hominis, Helicobacter pylori\|Campylobacter hominis, Holdemania filiformis\|Campylobacter hominis, Kingella oralis\|Campylobacter hominis, Klebsiella pneumoniae\|Campylobacter hominis, Klebsiella variicola\|Campylobacter hominis, Lachnospiraceae bacterium 5_1_57FAA\|Campylobacter hominis, Lactobacillus acidophilus\|Campylobacter hominis, Lactobacillus amylovorus\|Campylobacter hominis, Lactobacillus brevis\|Campylobacter hominis, Lactobacillus casei\|Campylobacter hominis, Lactobacillus crispatus\|Campylobacter hominis, Lactobacillus delbrueckii\|Campylobacter hominis, Lactobacillus fermentum\|Campylobacter hominis, Lactobacillus gasseri\|Campylobacter hominis, Lactobacillus iners\|Campylobacter hominis, Lactobacillus jensenii\|Campylobacter hominis, Lactobacillus johnsonii\|Campylobacter hominis, Lactobacillus paracasei\|Campylobacter hominis, Lactobacillus plantarum\|Campylobacter hominis, Lactobacillus reuteri\|Campylobacter hominis, Lactobacillus rhamnosus\|Campylobacter hominis, Lactobacillus ruminis\|Campylobacter hominis, Lactobacillus sakei\|Campylobacter hominis, Lactobacillus salivarius\|Campylobacter hominis, Lactococcus lactis\|Campylobacter hominis, Lautropia mirabilis\|Campylobacter hominis, Leuconostoc citreum\|Campylobacter hominis, Leuconostoc gasicomitatum\|Campylobacter hominis, Leuconostoc mesenteroides\|Campylobacter hominis, Listeria monocytogenes\|Campylobacter hominis, Marvinbryantia formatexigens\|Campylobacter hominis, Megamonas hypermegale\|Campylobacter hominis, Megasphaera micronuciformis\|Campylobacter hominis, Methanobrevibacter smithii\|Campylobacter hominis, Methanosphaera stadtmanae\|Campylobacter hominis, Methylobacterium radiotolerans\|Campylobacter hominis, Mitsuokella multacida\|Campylobacter hominis, Mobiluncus curtisii\|Campylobacter hominis, Mycoplasma hominis\|Campylobacter hominis, Neisseria mucosa\|Campylobacter hominis, Odoribacter splanchnicus\|Campylobacter hominis, Olsenella uli\|Campylobacter hominis, Oribacterium sinus\|Campylobacter hominis, Oxalobacter formigenes\|Campylobacter hominis, Parabacteroides distasonis\|Campylobacter hominis, Parabacteroides johnsonii\|Campylobacter |

TABLE 2-continued

| Table 2. Specific binary combinations of OTUs. Individual pairings are differentiated by "\|" and OTUs within a combination are differentiated by "," |
| --- |
| hominis, Parabacteroides merdae\|Campylobacter hominis, Parvimonas micra\|Campylobacter hominis, Pediococcus acidilactici\|Campylobacter hominis, Pediococcus pentosaceus\|Campylobacter hominis, Peptoniphilus duerdenii\|Campylobacter hominis, Peptoniphilus harei\|Campylobacter hominis, Peptoniphilus lacrimalis\|Campylobacter hominis, Peptostreptococcus anaerobius\|Campylobacter hominis, Peptostreptococcus stomatis\|Campylobacter hominis, Porphyromonas asaccharolytica\|Campylobacter hominis, Porphyromonas uenonis\|Campylobacter hominis, Prevotella amnii\|Campylobacter hominis, Prevotella bergensis\|Campylobacter hominis, Prevotella bivia\|Campylobacter hominis, Prevotella buccae\|Campylobacter hominis, Prevotella buccalis\|Campylobacter hominis, Prevotella copri\|Campylobacter hominis, Prevotella disiens\|Campylobacter hominis, Prevotella melaninogenica\|Campylobacter hominis, Prevotella multiformis\|Campylobacter hominis, Prevotella oralis\|Campylobacter hominis, Prevotella oris\|Campylobacter hominis, Prevotella salivae\|Campylobacter hominis, Prevotella timonensis\|Campylobacter hominis, Propionibacterium acnes\|Campylobacter hominis, Propionibacterium freudenreichii\|Campylobacter hominis, Proteus mirabilis\|Campylobacter hominis, Proteus penneri\|Campylobacter hominis, Pseudoflavonifractor capillosus\|Campylobacter hominis, Pseudomonas aeruginosa\|Campylobacter hominis, Pseudomonas fluorescens\|Campylobacter hominis, Pseudomonas putida\|Campylobacter hominis, Pseudoramibacter alactolyticus\|Campylobacter hominis, Pyramidobacter piscolens\|Campylobacter hominis, Rhodopseudomonas palustris\|Campylobacter hominis, Roseburia intestinalis\|Campylobacter hominis, Roseburia inulinivorans\|Campylobacter hominis, Rothia dentocariosa\|Campylobacter hominis, Rothia mucilaginosa\|Campylobacter hominis, Ruminococcus albus\|Campylobacter hominis, Ruminococcus bromii\|Campylobacter hominis, Ruminococcus gnavus\|Campylobacter hominis, Ruminococcus lactaris\|Campylobacter hominis, Ruminococcus obeum\|Campylobacter hominis, Ruminococcus torques\|Campylobacter hominis, Selenomonas sputigena\|Campylobacter hominis, Shigella boydii\|Campylobacter hominis, Shigella dysenteriae\|Campylobacter hominis, Shigella sonnei\|Campylobacter hominis, Slackia exigua\|Campylobacter hominis, Solobacterium moorei\|Campylobacter hominis, Staphylococcus aureus\|Campylobacter hominis, Staphylococcus epidermidis\|Campylobacter hominis, Staphylococcus hominis\|Campylobacter hominis, Staphylococcus saprophyticus\|Campylobacter hominis, Staphylococcus warneri\|Campylobacter hominis, Streptococcus agalactiae\|Campylobacter hominis, Streptococcus anginosus\|Campylobacter hominis, Streptococcus australis\|Campylobacter hominis, Streptococcus bovis\|Campylobacter hominis, Streptococcus cristatus\|Campylobacter hominis, Streptococcus dysgalactiae\|Campylobacter hominis, Streptococcus equinus\|Campylobacter hominis, Streptococcus gordonii\|Campylobacter hominis, Streptococcus infantarius\|Campylobacter hominis, Streptococcus infantis\|Campylobacter hominis, Streptococcus mitis\|Campylobacter hominis, Streptococcus mutans\|Campylobacter hominis, Streptococcus oralis\|Campylobacter hominis, Streptococcus parasanguinis\|Campylobacter hominis, Streptococcus peroris\|Campylobacter hominis, Streptococcus pneumoniae\|Campylobacter hominis, Streptococcus salivarius\|Campylobacter hominis, Streptococcus sanguinis\|Campylobacter hominis, Streptococcus thermophilus\|Campylobacter hominis, Streptococcus vestibularis\|Campylobacter hominis, Subdoligranulum variabile\|Campylobacter hominis, Succinatimonas hippei\|Campylobacter hominis, Sutterella wadsworthensis\|Campylobacter hominis, Tropheryma whipplei\|Campylobacter hominis, Veillonella atypica\|Campylobacter hominis, Veillonella dispar\|Campylobacter hominis, Veillonella parvula\|Campylobacter hominis, Victivallis vadensis\|Capnocytophaga ochracea, Capnocytophaga ochracea\|Capnocytophaga ochracea, Cardiobacterium hominis\|Capnocytophaga ochracea, Catenibacterium mitsuokai\|Capnocytophaga ochracea, Catonella morbi\|Capnocytophaga ochracea, Citrobacter koseri\|Capnocytophaga ochracea, Clostridium asparagiforme\|Capnocytophaga ochracea, Clostridium bartlettii\|Capnocytophaga ochracea, Clostridium bolteae\|Capnocytophaga ochracea, Clostridium botulinum\|Capnocytophaga ochracea, Clostridium butyricum\|Capnocytophaga ochracea, Clostridium difficile\|Capnocytophaga ochracea, Clostridium disporicum\|Capnocytophaga ochracea, Clostridium hathewayi\|Capnocytophaga ochracea, Clostridium hylemonae\|Capnocytophaga ochracea, Clostridium innocuum\|Capnocytophaga ochracea, Clostridium leptum\|Capnocytophaga ochracea, Clostridium mayombei\|Capnocytophaga ochracea, Clostridium methylpentosum\|Capnocytophaga ochracea, Clostridium nexile\|Capnocytophaga ochracea, Clostridium orbiscindens\|Capnocytophaga ochracea, Clostridium perfringens\|Capnocytophaga ochracea, Clostridium saccharolyticum\|Capnocytophaga ochracea, Clostridium scindens\|Capnocytophaga ochracea, Clostridium symbiosum\|Capnocytophaga ochracea, Clostridium tertium\|Capnocytophaga ochracea, Collinsella aerofaciens\|Capnocytophaga ochracea, Collinsella intestinalis\|Capnocytophaga ochracea, Collinsella stercoris\|Capnocytophaga ochracea, Coprobacillus sp. D7\|Capnocytophaga ochracea, Coprococcus catus\|Capnocytophaga ochracea, Coprococcus comes\|Capnocytophaga ochracea, Coprococcus eutactus\|Capnocytophaga ochracea, Corynebacterium aurimucosum\|Capnocytophaga ochracea, Corynebacterium matruchotii\|Capnocytophaga ochracea, Cryptobacterium curtum\|Capnocytophaga ochracea, Desulfovibrio desulfuricans\|Capnocytophaga ochracea, Desulfovibrio piger\|Capnocytophaga ochracea, Dialister invisus\|Capnocytophaga ochracea, Dialister microaerophilus\|Capnocytophaga ochracea, Dorea formicigenerans\|Capnocytophaga ochracea, Dorea longicatena\|Capnocytophaga ochracea, Eggerthella lenta\|Capnocytophaga ochracea, Eikenella corrodens\|Capnocytophaga ochracea, Enterobacter cancerogenus\|Capnocytophaga ochracea, Enterobacter cloacae\|Capnocytophaga ochracea, Enterococcus faecalis\|Capnocytophaga ochracea, Enterococcus faecium\|Capnocytophaga ochracea, Enterococcus gallinarum\|Capnocytophaga ochracea, Erysipelotrichaceae bacterium 3_1_53\|Capnocytophaga ochracea, Escherichia coli\|Capnocytophaga ochracea, Escherichia fergusonii\|Capnocytophaga ochracea, Ethanoligenens harbinense\|Capnocytophaga ochracea, Eubacterium cellulosolvens\|Capnocytophaga ochracea, Eubacterium eligens\|Capnocytophaga ochracea, Eubacterium hallii\|Capnocytophaga ochracea, Eubacterium limosum\|Capnocytophaga ochracea, Eubacterium rectale\|Capnocytophaga ochracea, Eubacterium siraeum\|Capnocytophaga ochracea, Eubacterium ventriosum\|Capnocytophaga ochracea, Faecalibacterium prausnitzii\|Capnocytophaga ochracea, Finegoldia magna\|Capnocytophaga ochracea, Fusobacterium gonidiaformans\|Capnocytophaga ochracea, Fusobacterium mortiferum\|Capnocytophaga ochracea, Fusobacterium nucleatum\|Capnocytophaga ochracea, Fusobacterium varium\|Capnocytophaga ochracea, Gardnerella vaginalis\|Capnocytophaga ochracea, Gemella haemolysans\|Capnocytophaga ochracea, Gemella morbillorum\|Capnocytophaga ochracea, Gordonibacter pamelaeae\|Capnocytophaga ochracea, Granulicatella adiacens\|Capnocytophaga ochracea, Granulicatella elegans\|Capnocytophaga ochracea, Haemophilus influenzae\|Capnocytophaga ochracea, Haemophilus parainfluenzae\|Capnocytophaga ochracea, Helicobacter pullorum\|Capnocytophaga ochracea, Helicobacter pylori\|Capnocytophaga ochracea, Holdemania filiformis\|Capnocytophaga ochracea, Kingella oralis\|Capnocytophaga ochracea, Klebsiella pneumoniae\|Capnocytophaga ochracea, Klebsiella variicola\|Capnocytophaga ochracea, Lachnospiraceae bacterium 5_1_57FAA\|Capnocytophaga ochracea, Lactobacillus acidophilus\|Capnocytophaga ochracea, Lactobacillus amylovorus\|Capnocytophaga ochracea, Lactobacillus brevis\|Capnocytophaga ochracea, Lactobacillus casei\|Capnocytophaga ochracea, Lactobacillus crispatus\|Capnocytophaga ochracea, Lactobacillus delbrueckii\|Capnocytophaga ochracea, Lactobacillus fermentum\|Capnocytophaga ochracea, Lactobacillus gasseri\|Capnocytophaga ochracea, Lactobacillus iners\|Capnocytophaga ochracea, Lactobacillus jensenii\|Capnocytophaga ochracea, Lactobacillus johnsonii\|Capnocytophaga ochracea, Lactobacillus paracasei\|Capnocytophaga ochracea, Lactobacillus plantarum\|Capnocytophaga ochracea, Lactobacillus reuteri\|Capnocytophaga ochracea, Lactobacillus rhamnosus\|Capnocytophaga ochracea, Lactobacillus ruminis\|Capnocytophaga ochracea, Lactobacillus sakei\|Capnocytophaga ochracea, Lactobacillus salivarius\|Capnocytophaga ochracea, Lactococcus lactis\|Capnocytophaga ochracea, Lautropia mirabilis\|Capnocytophaga ochracea, Leuconostoc citreum\|Capnocytophaga ochracea, Leuconostoc gasicomitatum\|Capnocytophaga ochracea, Leuconostoc mesenteroides\|Capnocytophaga ochracea, Listeria monocytogenes\|Capnocytophaga ochracea, Marvinbryantia formatexigens\|Capnocytophaga ochracea, Megamonas hypermegale\|Capnocytophaga ochracea, Megasphaera micronuciformis\|Capnocytophaga ochracea, Methanobrevibacter smithii\|Capnocytophaga ochracea, Methanosphaera stadtmanae\|Capnocytophaga ochracea, Methylobacterium radiotolerans\|Capnocytophaga ochracea, Mitsuokella multacida\|Capnocytophaga ochracea, Mobiluncus curtisii\|Capnocytophaga ochracea, Mycoplasma hominis\|Capnocytophaga ochracea, Neisseria mucosa\|Capnocytophaga ochracea, Odoribacter splanchnicus\|Capnocytophaga ochracea, Olsenella uli\|Capnocytophaga ochracea, Oribacterium sinus\|Capnocytophaga ochracea, Oxalobacter formigenes\|Capnocytophaga ochracea, Parabacteroides distasonis\|Capnocytophaga ochracea, Parabacteroides |

TABLE 2-continued

| Table 2. Specific binary combinations of OTUs. Individual pairings are differentiated by "\|" and OTUs within a combination are differentiated by "," |
|---|
| *johnsonii\|Capnocytophaga ochracea, Parabacteroides merdae\|Capnocytophaga ochracea, Parvimonas micra\|Capnocytophaga ochracea, Pediococcus acidilactici\|Capnocytophaga ochracea, Pediococcus pentosaceus\|Capnocytophaga ochracea, Peptoniphilus duerdenii\|Capnocytophaga ochracea, Peptoniphilus harei\|Capnocytophaga ochracea, Peptoniphilus lacrimalis\|Capnocytophaga ochracea, Peptostreptococcus anaerobius\|Capnocytophaga ochracea, Peptostreptococcus stomatis\|Capnocytophaga ochracea, Porphyromonas asaccharolytica\|Capnocytophaga ochracea, Porphyromonas uenonis\|Capnocytophaga ochracea, Prevotella amnii\|Capnocytophaga ochracea, Prevotella bergensis\|Capnocytophaga ochracea, Prevotella bivia\|Capnocytophaga ochracea, Prevotella buccae\|Capnocytophaga ochracea, Prevotella buccalis\|Capnocytophaga ochracea, Prevotella copri\|Capnocytophaga ochracea, Prevotella disiens\|Capnocytophaga ochracea, Prevotella melaninogenica\|Capnocytophaga ochracea, Prevotella multiformis\|Capnocytophaga ochracea, Prevotella oralis\|Capnocytophaga ochracea, Prevotella oris\|Capnocytophaga ochracea, Prevotella salivae\|Capnocytophaga ochracea, Prevotella timonensis\|Capnocytophaga ochracea, Propionibacterium acnes\|Capnocytophaga ochracea, Propionibacterium freudenreichii\|Capnocytophaga ochracea, Proteus mirabilis\|Capnocytophaga ochracea, Proteus penneri\|Capnocytophaga ochracea, Pseudoflavonifractor capillosus\|Capnocytophaga ochracea, Pseudomonas aeruginosa\|Capnocytophaga ochracea, Pseudomonas fluorescens\|Capnocytophaga ochracea, Pseudomonas putida\|Capnocytophaga ochracea, Pseudoramibacter alactolyticus\|Capnocytophaga ochracea, Pyramidobacter piscolens\|Capnocytophaga ochracea, Rhodopseudomonas palustris\|Capnocytophaga ochracea, Roseburia intestinalis\|Capnocytophaga ochracea, Roseburia inulinivorans\|Capnocytophaga ochracea, Rothia dentocariosa\|Capnocytophaga ochracea, Rothia mucilaginosa\|Capnocytophaga ochracea, Ruminococcus albus\|Capnocytophaga ochracea, Ruminococcus bromii\|Capnocytophaga ochracea, Ruminococcus gnavus\|Capnocytophaga ochracea, Ruminococcus lactaris\|Capnocytophaga ochracea, Ruminococcus obeum\|Capnocytophaga ochracea, Ruminococcus torques\|Capnocytophaga ochracea, Selenomonas sputigena\|Capnocytophaga ochracea, Shigella boydii\|Capnocytophaga ochracea, Shigella dysenteriae\|Capnocytophaga ochracea, Shigella sonnei\|Capnocytophaga ochracea, Slackia exigua\|Capnocytophaga ochracea, Solobacterium moorei\|Capnocytophaga ochracea, Staphylococcus aureus\|Capnocytophaga ochracea, Staphylococcus epidermidis\|Capnocytophaga ochracea, Staphylococcus hominis\|Capnocytophaga ochracea, Staphylococcus saprophyticus\|Capnocytophaga ochracea, Staphylococcus warneri\|Capnocytophaga ochracea, Streptococcus agalactiae\|Capnocytophaga ochracea, Streptococcus anginosus\|Capnocytophaga ochracea, Streptococcus australis\|Capnocytophaga ochracea, Streptococcus bovis\|Capnocytophaga ochracea, Streptococcus cristatus\|Capnocytophaga ochracea, Streptococcus dysgalactiae\|Capnocytophaga ochracea, Streptococcus equinus\|Capnocytophaga ochracea, Streptococcus gordonii\|Capnocytophaga ochracea, Streptococcus infantarius\|Capnocytophaga ochracea, Streptococcus infantis\|Capnocytophaga ochracea, Streptococcus mitis\|Capnocytophaga ochracea, Streptococcus mutans\|Capnocytophaga ochracea, Streptococcus oralis\|Capnocytophaga ochracea, Streptococcus parasanguinis\|Capnocytophaga ochracea, Streptococcus peroris\|Capnocytophaga ochracea, Streptococcus pneumoniae\|Capnocytophaga ochracea, Streptococcus salivarius\|Capnocytophaga ochracea, Streptococcus sanguinis\|Capnocytophaga ochracea, Streptococcus thermophilus\|Capnocytophaga ochracea, Streptococcus vestibularis\|Capnocytophaga ochracea, Subdoligranulum variabile\|Capnocytophaga ochracea, Succinatimonas hippei\|Capnocytophaga ochracea, Sutterella wadsworthensis\|Capnocytophaga ochracea, Tropheryma whipplei\|Capnocytophaga ochracea, Veillonella atypica\|Capnocytophaga ochracea, Veillonella dispar\|Capnocytophaga ochracea, Veillonella parvula\|Capnocytophaga ochracea, Victivallis vadensis\|Cardiobacterium hominis, Cardiobacterium hominis\|Cardiobacterium hominis, Catenibacterium mitsuokai\|Cardiobacterium hominis, Catonella morbi\|Cardiobacterium hominis, Citrobacter koseri\|Cardiobacterium hominis, Clostridium asparagiforme\|Cardiobacterium hominis, Clostridium bartlettii\|Cardiobacterium hominis, Clostridium bolteae\|Cardiobacterium hominis, Clostridium botulinum\|Cardiobacterium hominis, Clostridium butyricum\|Cardiobacterium hominis, Clostridium difficile\|Cardiobacterium hominis, Clostridium disporicum\|Cardiobacterium hominis, Clostridium hathewayi\|Cardiobacterium hominis, Clostridium hylemonae\|Cardiobacterium hominis, Clostridium innocuum\|Cardiobacterium hominis, Clostridium leptum\|Cardiobacterium hominis, Clostridium mayombei\|Cardiobacterium hominis, Clostridium methylpentosum\|Cardiobacterium hominis, Clostridium nexile\|Cardiobacterium hominis, Clostridium orbiscindens\|Cardiobacterium hominis, Clostridium perfringens\|Cardiobacterium hominis, Clostridium saccharolyticum\|Cardiobacterium hominis, Clostridium scindens\|Cardiobacterium hominis, Clostridium symbiosum\|Cardiobacterium hominis, Clostridium tertium\|Cardiobacterium hominis, Collinsella aerofaciens\|Cardiobacterium hominis, Collinsella intestinalis\|Cardiobacterium hominis, Collinsella stercoris\|Cardiobacterium hominis, Coprobacillus* sp. D7\|*Cardiobacterium hominis, Coprococcus catus\|Cardiobacterium hominis, Coprococcus comes\|Cardiobacterium hominis, Coprococcus eutactus\|Cardiobacterium hominis, Corynebacterium aurimucosum\|Cardiobacterium hominis, Corynebacterium matruchotii\|Cardiobacterium hominis, Cryptobacterium curtum\|Cardiobacterium hominis, Desulfovibrio desulfuricans\|Cardiobacterium hominis, Desulfovibrio piger\|Cardiobacterium hominis, Dialister invisus\|Cardiobacterium hominis, Dialister microaerophilus\|Cardiobacterium hominis, Dorea formicigenerans\|Cardiobacterium hominis, Dorea longicatena\|Cardiobacterium hominis, Eggerthella lenta\|Cardiobacterium hominis, Eikenella corrodens\|Cardiobacterium hominis, Enterobacter cancerogenus\|Cardiobacterium hominis, Enterobacter cloacae\|Cardiobacterium hominis, Enterococcus faecalis\|Cardiobacterium hominis, Enterococcus faecium\|Cardiobacterium hominis, Enterococcus gallinarum\|Cardiobacterium hominis, Erysipelotrichaceae bacterium* 3_1_53\|*Cardiobacterium hominis, Escherichia coli\|Cardiobacterium hominis, Escherichia fergusonii\|Cardiobacterium hominis, Ethanoligenens harbinense\|Cardiobacterium hominis, Eubacterium cellulosolvens\|Cardiobacterium hominis, Eubacterium eligens\|Cardiobacterium hominis, Eubacterium hallii\|Cardiobacterium hominis, Eubacterium limosum\|Cardiobacterium hominis, Eubacterium rectale\|Cardiobacterium hominis, Eubacterium siraeum\|Cardiobacterium hominis, Eubacterium ventriosum\|Cardiobacterium hominis, Faecalibacterium prausnitzii\|Cardiobacterium hominis, Finegoldia magna\|Cardiobacterium hominis, Fusobacterium gonidiaformans\|Cardiobacterium hominis, Fusobacterium mortiferum\|Cardiobacterium hominis, Fusobacterium nucleatum\|Cardiobacterium hominis, Fusobacterium varium\|Cardiobacterium hominis, Gardnerella vaginalis\|Cardiobacterium hominis, Gemella haemolysans\|Cardiobacterium hominis, Gemella morbillorum\|Cardiobacterium hominis, Gordonibacter pamelaeae\|Cardiobacterium hominis, Granulicatella adiacens\|Cardiobacterium hominis, Granulicatella elegans\|Cardiobacterium hominis, Haemophilus influenzae\|Cardiobacterium hominis, Haemophilus parainfluenzae\|Cardiobacterium hominis, Helicobacter pullorum\|Cardiobacterium hominis, Helicobacter pylori\|Cardiobacterium hominis, Holdemania filiformis\|Cardiobacterium hominis, Kingella oralis\|Cardiobacterium hominis, Klebsiella pneumoniae\|Cardiobacterium hominis, Klebsiella variicola\|Cardiobacterium hominis, Lachnospiraceae bacterium* 5_1_57FAA\|*Cardiobacterium hominis, Lactobacillus acidophilus\|Cardiobacterium hominis, Lactobacillus amylovorus\|Cardiobacterium hominis, Lactobacillus brevis\|Cardiobacterium hominis, Lactobacillus casei\|Cardiobacterium hominis, Lactobacillus crispatus\|Cardiobacterium hominis, Lactobacillus delbrueckii\|Cardiobacterium hominis, Lactobacillus fermentum\|Cardiobacterium hominis, Lactobacillus gasseri\|Cardiobacterium hominis, Lactobacillus iners\|Cardiobacterium hominis, Lactobacillus jensenii\|Cardiobacterium hominis, Lactobacillus johnsonii\|Cardiobacterium hominis, Lactobacillus paracasei\|Cardiobacterium hominis, Lactobacillus plantarum\|Cardiobacterium hominis, Lactobacillus reuteri\|Cardiobacterium hominis, Lactobacillus rhamnosus\|Cardiobacterium hominis, Lactobacillus ruminis\|Cardiobacterium hominis, Lactobacillus sakei\|Cardiobacterium hominis, Lactobacillus salivarius\|Cardiobacterium hominis, Lactococcus lactis\|Cardiobacterium hominis, Lautropia mirabilis\|Cardiobacterium hominis, Leuconostoc citreum\|Cardiobacterium hominis, Leuconostoc gas icomitatum\|Cardiobacterium hominis, Leuconostoc mesenteroides\|Cardiobacterium hominis, Listeria monocytogenes\|Cardiobacterium hominis, Marvinbryantia formatexigens\|Cardiobacterium hominis, Megamonas hypermegale\|Cardiobacterium hominis, Megasphaera micronuciformis\|Cardiobacterium hominis, Methanobrevibacter smithii\|Cardiobacterium hominis, Methanosphaera stadtmanae\|Cardiobacterium hominis, Methylobacterium radiotolerans\|Cardiobacterium hominis, Mitsuokella multacida\|Cardiobacterium hominis, Mobiluncus curtisii\|Cardiobacterium hominis, Mycoplasma hominis\|Cardiobacterium hominis, Neisseria mucosa\|Cardiobacterium hominis, Odoribacter splanchnicus\|Cardiobacterium hominis, Olsenella uli\|Cardiobacterium hominis, Oribacterium sinus\|Cardiobacterium hominis, Oxalobacter formigenes\|Cardiobacterium hominis, Parabacteroides* |

TABLE 2-continued

Table 2. Specific binary combinations of OTUs. Individual pairings are differentiated by "|" and OTUs within a combination are differentiated by ","

distasonis|Cardiobacterium hominis, Parabacteroides johnsonii|Cardiobacterium hominis, Parabacteroides merdae|Cardiobacterium hominis, Parvimonas micra|Cardiobacterium hominis, Pediococcus acidilactici|Cardiobacterium hominis, Pediococcus pentosaceus|Cardiobacterium hominis, Peptoniphilus duerdenii|Cardiobacterium hominis, Peptoniphilus harei|Cardiobacterium hominis, Peptoniphilus lacrimalis|Cardiobacterium hominis, Peptostreptococcus anaerobius|Cardiobacterium hominis, Peptostreptococcus stomatis|Cardiobacterium hominis, Porphyromonas asaccharolytica|Cardiobacterium hominis, Porphyromonas uenonis|Cardiobacterium hominis, Prevotella amnii|Cardiobacterium hominis, Prevotella bergensis|Cardiobacterium hominis, Prevotella bivia|Cardiobacterium hominis, Prevotella buccae|Cardiobacterium hominis, Prevotella buccalis|Cardiobacterium hominis, Prevotella copri|Cardiobacterium hominis, Prevotella disiens|Cardiobacterium hominis, Prevotella melaninogenica|Cardiobacterium hominis, Prevotella multiformis|Cardiobacterium hominis, Prevotella oralis|Cardiobacterium hominis, Prevotella oris|Cardiobacterium hominis, Prevotella salivae|Cardiobacterium hominis, Prevotella timonensis|Cardiobacterium hominis, Propionibacterium acnes|Cardiobacterium hominis, Propionibacterium freudenreichii|Cardiobacterium hominis, Proteus mirabilis|Cardiobacterium hominis, Proteus penneri|Cardiobacterium hominis, Pseudoflavonifractor capillosus|Cardiobacterium hominis, Pseudomonas aeruginosa|Cardiobacterium hominis, Pseudomonas fluorescens|Cardiobacterium hominis, Pseudomonas putida|Cardiobacterium hominis, Pseudoramibacter alactolyticus|Cardiobacterium hominis, Pyramidobacter piscolens|Cardiobacterium hominis, Rhodopseudomonas palustris|Cardiobacterium hominis, Roseburia intestinalis|Cardiobacterium hominis, Roseburia inulinivorans|Cardiobacterium hominis, Rothia dentocariosa|Cardiobacterium hominis, Rothia mucilaginosa|Cardiobacterium hominis, Ruminococcus albus|Cardiobacterium hominis, Ruminococcus bromii|Cardiobacterium hominis, Ruminococcus gnavus|Cardiobacterium hominis, Ruminococcus lactaris|Cardiobacterium hominis, Ruminococcus obeum|Cardiobacterium hominis, Ruminococcus torques|Cardiobacterium hominis, Selenomonas sputigena|Cardiobacterium hominis, Shigella boydii|Cardiobacterium hominis, Shigella dysenteriae|Cardiobacterium hominis, Shigella sonnei|Cardiobacterium hominis, Slackia exigua|Cardiobacterium hominis, Solobacterium moorei|Cardiobacterium hominis, Staphylococcus aureus|Cardiobacterium hominis, Staphylococcus epidermidis|Cardiobacterium hominis, Staphylococcus hominis|Cardiobacterium hominis, Staphylococcus saprophyticus|Cardiobacterium hominis, Staphylococcus warneri|Cardiobacterium hominis, Streptococcus agalactiae|Cardiobacterium hominis, Streptococcus anginosus|Cardiobacterium hominis, Streptococcus australis|Cardiobacterium hominis, Streptococcus bovis|Cardiobacterium hominis, Streptococcus cristatus|Cardiobacterium hominis, Streptococcus dysgalactiae|Cardiobacterium hominis, Streptococcus equinus|Cardiobacterium hominis, Streptococcus gordonii|Cardiobacterium hominis, Streptococcus infantarius|Cardiobacterium hominis, Streptococcus infantis|Cardiobacterium hominis, Streptococcus mitis|Cardiobacterium hominis, Streptococcus mutans|Cardiobacterium hominis, Streptococcus oralis|Cardiobacterium hominis, Streptococcus parasanguinis|Cardiobacterium hominis, Streptococcus peroris|Cardiobacterium hominis, Streptococcus pneumoniae|Cardiobacterium hominis, Streptococcus salivarius|Cardiobacterium hominis, Streptococcus sanguinis|Cardiobacterium hominis, Streptococcus thermophilus|Cardiobacterium hominis, Streptococcus vestibularis|Cardiobacterium hominis, Subdoligranulum variabile|Cardiobacterium hominis, Succinatimonas hippei|Cardiobacterium hominis, Sutterella wadsworthensis|Cardiobacterium hominis, Tropheryma whipplei|Cardiobacterium hominis, Veillonella atypica|Cardiobacterium hominis, Veillonella dispar|Cardiobacterium hominis, Veillonella parvula|Cardiobacterium hominis, Victivallis vadensis|Catenibacterium mitsuokai, Catenibacterium mitsuokai|Catenibacterium mitsuokai, Catonella morbi|Catenibacterium mitsuokai, Citrobacter koseri|Catenibacterium mitsuokai, Clostridium asparagiforme|Catenibacterium mitsuokai, Clostridium bartlettii|Catenibacterium mitsuokai, Clostridium bolteae|Catenibacterium mitsuokai, Clostridium botulinum|Catenibacterium mitsuokai, Clostridium butyricum|Catenibacterium mitsuokai, Clostridium difficile|Catenibacterium mitsuokai, Clostridium disporicum|Catenibacterium mitsuokai, Clostridium hathewayi|Catenibacterium mitsuokai, Clostridium hylemonae|Catenibacterium mitsuokai, Clostridium innocuum|Catenibacterium mitsuokai, Clostridium leptum|Catenibacterium mitsuokai, Clostridium mayombei|Catenibacterium mitsuokai, Clostridium methylpentosum|Catenibacterium mitsuokai, Clostridium nexile|Catenibacterium mitsuokai, Clostridium orbiscindens|Catenibacterium mitsuokai, Clostridium perfringens|Catenibacterium mitsuokai, Clostridium saccharolyticum|Catenibacterium mitsuokai, Clostridium scindens|Catenibacterium mitsuokai, Clostridium symbiosum|Catenibacterium mitsuokai, Clostridium tertium|Catenibacterium mitsuokai, Collinsella aerofaciens|Catenibacterium mitsuokai, Collinsella intestinalis|Catenibacterium mitsuokai, Collinsella stercoris|Catenibacterium mitsuokai, Coprobacillus sp. D7|Catenibacterium mitsuokai, Coprococcus catus|Catenibacterium mitsuokai, Coprococcus comes|Catenibacterium mitsuokai, Coprococcus eutactus|Catenibacterium mitsuokai, Corynebacterium aurimucosum|Catenibacterium mitsuokai, Corynebacterium matruchotii|Catenibacterium mitsuokai, Cryptobacterium curtum|Catenibacterium mitsuokai, Desulfovibrio desulfuricans|Catenibacterium mitsuokai, Desulfovibrio piger|Catenibacterium mitsuokai, Dialister invisus|Catenibacterium mitsuokai, Dialister microaerophilus|Catenibacterium mitsuokai, Dorea formicigenerans|Catenibacterium mitsuokai, Dorea longicatena|Catenibacterium mitsuokai, Eggerthella lenta|Catenibacterium mitsuokai, Eikenella corrodens|Catenibacterium mitsuokai, Enterobacter cancerogenus|Catenibacterium mitsuokai, Enterobacter cloacae|Catenibacterium mitsuokai, Enterococcus faecalis|Catenibacterium mitsuokai, Enterococcus faecium|Catenibacterium mitsuokai, Enterococcus gallinarum|Catenibacterium mitsuokai, Erysipelotrichaceae bacterium 3_1_53|Catenibacterium mitsuokai, Escherichia coli|Catenibacterium mitsuokai, Escherichia fergusonii|Catenibacterium mitsuokai, Ethanoligenens harbinense|Catenibacterium mitsuokai, Eubacterium cellulosolvens|Catenibacterium mitsuokai, Eubacterium eligens|Catenibacterium mitsuokai, Eubacterium hallii|Catenibacterium mitsuokai, Eubacterium limosum|Catenibacterium mitsuokai, Eubacterium rectale|Catenibacterium mitsuokai, Eubacterium siraeum|Catenibacterium mitsuokai, Eubacterium ventriosum|Catenibacterium mitsuokai, Faecalibacterium prausnitzii|Catenibacterium mitsuokai, Finegoldia magna|Catenibacterium mitsuokai, Fusobacterium gonidiaformans|Catenibacterium mitsuokai, Fusobacterium mortiferum|Catenibacterium mitsuokai, Fusobacterium nucleatum|Catenibacterium mitsuokai, Fusobacterium varium|Catenibacterium mitsuokai, Gardnerella vaginalis|Catenibacterium mitsuokai, Gemella haemolysans|Catenibacterium mitsuokai, Gemella morbillorum|Catenibacterium mitsuokai, Gordonibacter pamelaeae|Catenibacterium mitsuokai, Granulicatella adiacens|Catenibacterium mitsuokai, Granulicatella elegans|Catenibacterium mitsuokai, Haemophilus influenzae|Catenibacterium mitsuokai, Haemophilus parainfluenzae|Catenibacterium mitsuokai, Helicobacter pullorum|Catenibacterium mitsuokai, Helicobacter pylori|Catenibacterium mitsuokai, Holdemania filiformis|Catenibacterium mitsuokai, Kingella oralis|Catenibacterium mitsuokai, Klebsiella pneumoniae|Catenibacterium mitsuokai, Klebsiella variicola|Catenibacterium mitsuokai, Lachnospiraceae bacterium 5_1_57FAA|Catenibacterium mitsuokai, Lactobacillus acidophilus|Catenibacterium mitsuokai, Lactobacillus amylovorus|Catenibacterium mitsuokai, Lactobacillus brevis|Catenibacterium mitsuokai, Lactobacillus casei|Catenibacterium mitsuokai, Lactobacillus crispatus|Catenibacterium mitsuokai, Lactobacillus delbrueckii|Catenibacterium mitsuokai, Lactobacillus fermentum|Catenibacterium mitsuokai, Lactobacillus gasseri|Catenibacterium mitsuokai, Lactobacillus iners|Catenibacterium mitsuokai, Lactobacillus jensenii|Catenibacterium mitsuokai, Lactobacillus johnsonii|Catenibacterium mitsuokai, Lactobacillus paracasei|Catenibacterium mitsuokai, Lactobacillus plantarum|Catenibacterium mitsuokai, Lactobacillus reuteri|Catenibacterium mitsuokai, Lactobacillus rhamnosus|Catenibacterium mitsuokai, Lactobacillus ruminis|Catenibacterium mitsuokai, Lactobacillus sakei|Catenibacterium mitsuokai, Lactobacillus salivarius|Catenibacterium mitsuokai, Lactococcus lactis|Catenibacterium mitsuokai, Lautropia mirabilis|Catenibacterium mitsuokai, Leuconostoc citreum|Catenibacterium mitsuokai, Leuconostoc gasicomitatum|Catenibacterium mitsuokai, Leuconostoc mesenteroides|Catenibacterium mitsuokai, Listeria monocytogenes|Catenibacterium mitsuokai, Marvinbryantia formatexigens|Catenibacterium mitsuokai, Megamonas hypermegale|Catenibacterium mitsuokai, Megasphaera micronuciformis|Catenibacterium mitsuokai, Methanobrevibacter smithii|Catenibacterium mitsuokai, Methanosphaera stadtmanae|Catenibacterium mitsuokai, Methylobacterium radiotolerans|Catenibacterium mitsuokai, Mitsuokella multacida|Catenibacterium mitsuokai, Mobiluncus curtisii|Catenibacterium mitsuokai, Mycoplasma hominis|Catenibacterium mitsuokai, Neisseria mucosa|Catenibacterium mitsuokai, Odoribacter splanchnicus|Catenibacterium mitsuokai, Olsenella uli|Catenibacterium TABLE 2-continued Table 2. Specific binary combinations of OTUs. Individual pairings are differentiated by "|" and OTUs within a combination are differentiated by ","

mitsuokai, Oribacterium sinus|Catenibacterium mitsuokai, Oxalobacter formigenes|Catenibacterium mitsuokai, Parabacteroides distasonis|Catenibacterium mitsuokai, Parabacteroides johnsonii|Catenibacterium mitsuokai, Parabacteroides merdae|Catenibacterium mitsuokai, Parvimonas micra|Catenibacterium mitsuokai, Pediococcus acidilactici|Catenibacterium mitsuokai, Pediococcus pentosaceus|Catenibacterium mitsuokai, Peptoniphilus duerdenii|Catenibacterium mitsuokai, Peptoniphilus harei|Catenibacterium mitsuokai, Peptoniphilus lacrimalis|Catenibacterium mitsuokai, Peptostreptococcus anaerobius|Catenibacterium mitsuokai, Peptostreptococcus stomatis|Catenibacterium mitsuokai, Porphyromonas asaccharolytica|Catenibacterium mitsuokai, Porphyromonas uenonis|Catenibacterium mitsuokai, Prevotella amnii|Catenibacterium mitsuokai, Prevotella bergensis|Catenibacterium mitsuokai, Prevotella bivia|Catenibacterium mitsuokai, Prevotella buccae|Catenibacterium mitsuokai, Prevotella buccalis|Catenibacterium mitsuokai, Prevotella copri|Catenibacterium mitsuokai, Prevotella disiens|Catenibacterium mitsuokai, Prevotella melaninogenica|Catenibacterium mitsuokai, Prevotella multiformis|Catenibacterium mitsuokai, Prevotella oralis|Catenibacterium mitsuokai, Prevotella oris|Catenibacterium mitsuokai, Prevotella salivae|Catenibacterium mitsuokai, Prevotella timonensis|Catenibacterium mitsuokai, Propionibacterium acnes|Catenibacterium mitsuokai, Propionibacterium freudenreichii|Catenibacterium mitsuokai, Proteus mirabilis|Catenibacterium mitsuokai, Proteus penneri|Catenibacterium mitsuokai, Pseudoflavonifractor capillosus|Catenibacterium mitsuokai, Pseudomonas aeruginosa|Catenibacterium mitsuokai, Pseudomonas fluorescens|Catenibacterium mitsuokai, Pseudomonas putida|Catenibacterium mitsuokai, Pseudoramibacter alactolyticus|Catenibacterium mitsuokai, Pyramidobacter piscolens|Catenibacterium mitsuokai, Rhodopseudomonas palustris|Catenibacterium mitsuokai, Roseburia intestinalis|Catenibacterium mitsuokai, Roseburia inulinivorans|Catenibacterium mitsuokai, Rothia dentocariosa|Catenibacterium mitsuokai, Rothia mucilaginosa|Catenibacterium mitsuokai, Ruminococcus albus|Catenibacterium mitsuokai, Ruminococcus bromii|Catenibacterium mitsuokai, Ruminococcus gnavus|Catenibacterium mitsuokai, Ruminococcus lactaris|Catenibacterium mitsuokai, Ruminococcus obeum|Catenibacterium mitsuokai, Ruminococcus torques|Catenibacterium mitsuokai, Selenomonas sputigena|Catenibacterium mitsuokai, Shigella boydii|Catenibacterium mitsuokai, Shigella dysenteriae|Catenibacterium mitsuokai, Shigella sonnei|Catenibacterium mitsuokai, Slackia exigua|Catenibacterium mitsuokai, Solobacterium moorei|Catenibacterium mitsuokai, Staphylococcus aureus|Catenibacterium mitsuokai, Staphylococcus epidermidis|Catenibacterium mitsuokai, Staphylococcus hominis|Catenibacterium mitsuokai, Staphylococcus saprophyticus|Catenibacterium mitsuokai, Staphylococcus warneri|Catenibacterium mitsuokai, Streptococcus agalactiae|Catenibacterium mitsuokai, Streptococcus anginosus|Catenibacterium mitsuokai, Streptococcus australis|Catenibacterium mitsuokai, Streptococcus bovis|Catenibacterium mitsuokai, Streptococcus cristatus|Catenibacterium mitsuokai, Streptococcus dysgalactiae|Catenibacterium mitsuokai, Streptococcus equinus|Catenibacterium mitsuokai, Streptococcus gordonii|Catenibacterium mitsuokai, Streptococcus infantarius|Catenibacterium mitsuokai, Streptococcus infantis|Catenibacterium mitsuokai, Streptococcus mitis|Catenibacterium mitsuokai, Streptococcus mutans|Catenibacterium mitsuokai, Streptococcus oralis|Catenibacterium mitsuokai, Streptococcus parasanguinis|Catenibacterium mitsuokai, Streptococcus peroris|Catenibacterium mitsuokai, Streptococcus pneumoniae|Catenibacterium mitsuokai, Streptococcus salivarius|Catenibacterium mitsuokai, Streptococcus sanguinis|Catenibacterium mitsuokai, Streptococcus thermophilus|Catenibacterium mitsuokai, Streptococcus vestibularis|Catenibacterium mitsuokai, Subdoligranulum variabile|Catenibacterium mitsuokai, Succinatimonas hippei|Catenibacterium mitsuokai, Sutterella wadsworthensis|Catenibacterium mitsuokai, Tropheryma whipplei|Catenibacterium mitsuokai, Veillonella atypica|Catenibacterium mitsuokai, Veillonella dispar|Catenibacterium mitsuokai, Veillonella parvula|Catenibacterium mitsuokai, Victivallis vadensis|Catonella morbi, Catonella morbi|Catonella morbi, Citrobacter koseri|Catonella morbi, Clostridium asparagiforme|Catonella morbi, Clostridium bartlettii|Catonella morbi, Clostridium bolteae|Catonella morbi, Clostridium botulinum|Catonella morbi, Clostridium butyricum|Catonella morbi, Clostridium difficile|Catonella morbi, Clostridium disporicum|Catonella morbi, Clostridium hathewayi|Catonella morbi, Clostridium hylemonae|Catonella morbi, Clostridium innocuum|Catonella morbi, Clostridium leptum|Catonella morbi, Clostridium mayombei|Catonella morbi, Clostridium methylpentosum|Catonella morbi, Clostridium nexile|Catonella morbi, Clostridium orbiscindens|Catonella morbi, Clostridium perfringens|Catonella morbi, Clostridium saccharolyticum|Catonella morbi, Clostridium scindens|Catonella morbi, Clostridium symbiosum|Catonella morbi, Clostridium tertium|Catonella morbi, Collinsella aerofaciens|Catonella morbi, Collinsella intestinalis|Catonella morbi, Collinsella stercoris|Catonella morbi, Coprobacillus sp. D7|Catonella morbi, Coprococcus catus|Catonella morbi, Coprococcus comes|Catonella morbi, Coprococcus eutactus|Catonella morbi, Corynebacterium aurimucosum|Catonella morbi, Corynebacterium matruchotii|Catonella morbi, Cryptobacterium curtum|Catonella morbi, Desulfovibrio desulfuricans|Catonella morbi, Desulfovibrio piger|Catonella morbi, Dialister invisus|Catonella morbi, Dialister microaerophilus|Catonella morbi, Dorea formicigenerans|Catonella morbi, Dorea longicatena|Catonella morbi, Eggerthella lenta|Catonella morbi, Eikenella corrodens|Cratonella morbi, Enterobacter cancerogenus|Catonella morbi, Enterobacter cloacae|Catonella morbi, Enterococcus faecalis|Cratonella morbi, Enterococcus faecium|Catonella morbi, Enterococcus gallinarum|Catonella morbi, Erysipelotrichaceae bacterium 3_1_53|Catonella morbi, Escherichia coli|Catonella morbi, Escherichia fergusonii|Catonella morbi, Ethanoligenens harbinense|Catonella morbi, Eubacterium cellulosolvens|Catonella morbi, Eubacterium eligens|Catonella morbi, Eubacterium hallii|Catonella morbi, Eubacterium limosum|Catonella morbi, Eubacterium rectale|Catonella morbi, Eubacterium siraeum|Catonella morbi, Eubacterium ventriosum|Catonella morbi, Faecalibacterium prausnitzii|Catonella morbi, Finegoldia magna|Catonella morbi, Fusobacterium gonidiaformans|Catonella morbi, Fusobacterium mortiferum|Catonella morbi, Fusobacterium nucleatum|Catonella morbi, Fusobacterium varium|Catonella morbi, Gardnerella vaginalis|Catonella morbi, Gemella haemolysans|Catonella morbi, Gemella morbillorum|Catonella morbi, Gordonibacter pamelaeae|Catonella morbi, Granulicatella adiacens|Catonella morbi, Granulicatella elegans|Catonella morbi, Haemophilus influenzae|Catonella morbi, Haemophilus parainfluenzae|Catonella morbi, Helicobacter pullorum|Catonella morbi, Helicobacter pylori|Catonella morbi, Holdemania filiformis|Catonella morbi, Kingella oralis|Catonella morbi, Klebsiella pneumoniae|Catonella morbi, Klebsiella variicola|Catonella morbi, Lachnospiraceae bacterium 5_1_57FAA|Catonella morbi, Lactobacillus acidophilus|Catonella morbi, Lactobacillus amylovorus|Catonella morbi, Lactobacillus brevis|Catonella morbi, Lactobacillus casei|Catonella morbi, Lactobacillus crispatus|Catonella morbi, Lactobacillus delbrueckii|Catonella morbi, Lactobacillus fermentum|Catonella morbi, Lactobacillus gasseri|Catonella morbi, Lactobacillus iners|Catonella morbi, Lactobacillus jensenii|Catonella morbi, Lactobacillus johnsonii|Catonella morbi, Lactobacillus paracasei|Catonella morbi, Lactobacillus plantarum|Catonella morbi, Lactobacillus reuteri|Catonella morbi, Lactobacillus rhamnosus|Catonella morbi, Lactobacillus ruminis|Catonella morbi, Lactobacillus sakei|Catonella morbi, Lactobacillus salivarius|Catonella morbi, Lactococcus lactis|Catonella morbi, Lautropia mirabilis|Catonella morbi, Leuconostoc citreum|Catonella morbi, Leuconostoc gasicomitatum|Catonella morbi, Leuconostoc mesenteroides|Catonella morbi, Listeria monocytogenes|Catonella morbi, Marvinbryantia formatexigens|Catonella morbi, Megamonas hypermegale|Catonella morbi, Megasphaera micronuciformis|Catonella morbi, Methanobrevibacter smithii|Catonella morbi, Methanosphaera stadtmanae|Catonella morbi, Methylobacterium radiotolerans|Catonella morbi, Mitsuokella multacida|Catonella morbi, Mobiluncus curtisii|Catonella morbi, Mycoplasma hominis|Catonella morbi, Neisseria mucosa|Catonella morbi, Odoribacter splanchnicus|Catonella morbi, Olsenella uli|Catonella morbi, Oribacterium sinus|Catonella morbi, Oxalobacter formigenes|Catonella morbi, Parabacteroides distasonis|Catonella morbi, Parabacteroides johnsonii|Catonella morbi, Parabacteroides merdae|Catonella morbi, Parvimonas micra|Catonella morbi, Pediococcus acidilactici|Catonella morbi, Pediococcus pentosaceus|Catonella morbi, Peptoniphilus duerdenii|Catonella morbi, Peptoniphilus harei|Catonella morbi, Peptoniphilus lacrimalis|Catonella morbi, Peptostreptococcus anaerobius|Catonella morbi, Peptostreptococcus stomatis|Catonella morbi, Porphyromonas asaccharolytica|Catonella morbi, Porphyromonas uenonis|Catonella morbi, Prevotella amnii|Catonella morbi, Prevotella bergensis|Catonella morbi, Prevotella bivia|Catonella morbi, Prevotella buccae|Catonella morbi, Prevotella buccalis|Catonella morbi, Prevotella copri|Catonella morbi, Prevotella disiens|Catonella morbi, Prevotella melaninogenica|Catonella morbi, Prevotella multiformis|Catonella morbi, Prevotella oralis|Catonella morbi, Prevotella oris|Catonella morbi, Prevotella salivae|Catonella morbi, Prevotella timonensis|Catonella morbi, Propionibacterium acnes|Catonella TABLE 2-continued Table 2. Specific binary combinations of OTUs. Individual pairings are differentiated by "|" and OTUs within a combination are differentiated by ","

*morbi, Propionibacterium freudenreichii|Catonella morbi, Proteus mirabilis|Catonella morbi, Proteus penneri|Catonella morbi, Pseudoflavonifractor capillosus|Catonella morbi, Pseudomonas aemginosa|Catonella morbi, Pseudomonas fluorescens|Catonella morbi, Pseudomonas putida|Catonella morbi, Pseudoramibacter alactolyticus|Catonella morbi, Pyramidobacter piscolens|Catonella morbi, Rhodopseudomonas palustris|Catonella morbi, Roseburia intestinalis|Catonella morbi, Roseburia inulinivorans|Catonella morbi, Rothia dentocariosa|Catonella morbi, Rothia mucilaginosa|Catonella morbi, Ruminococcus albus|Catonella morbi, Ruminococcus bromii|Catonella morbi, Ruminococcus gnvus|Catonella morbi, Ruminococcus lactaris|Catonella morbi, Ruminococcus obeum|Catonella morbi, Ruminococcus torques|Catonella morbi, Selenomonas sputigena|Catonella morbi, Shigella boydii|Catonella morbi, Shigella dysenteriae|Catonella morbi, Shigella sonnei|Catonella morbi, Slackia exigua|Catonella morbi, Solobacterium moorei|Catonella morbi, Staphylococcus aureus|Catonella morbi, Staphylococcus epidermidis|Catonella morbi, Staphylococcus hominis|Catonella morbi, Staphylococcus saprophyticus|Catonella morbi, Staphylococcus warneri|Catonella morbi, Streptococcus agalactiae|Catonella morbi, Streptococcus anginosus|Catonella morbi, Streptococcus australis|Catonella morbi, Streptococcus bovis|Catonella morbi, Streptococcus cristatus|Catonella morbi, Streptococcus dysgalactiae|Catonella morbi, Streptococcus equinus|Catonella morbi, Streptococcus gordonii|Catonella morbi, Streptococcus infantarius|Catonella morbi, Streptococcus infantis|Catonella morbi, Streptococcus mitis|Catonella morbi, Streptococcus mutans|Catonella morbi, Streptococcus oralis|Catonella morbi, Streptococcus parasanguinis|Catonella morbi, Streptococcus peroris|Catonella morbi, Streptococcus pneumoniae|Catonella morbi, Streptococcus salivarius|Catonella morbi, Streptococcus sanguinis|Catonella morbi, Streptococcus thermophilus|Catonella morbi, Streptococcus vestibularis|Catonella morbi, Subdoligranulum variabile|Catonella morbi, Succinatimonas hippei|Catonella morbi, Sutterella wadsworthensis|Catonella morbi, Tropheryma whipplei|Catonella morbi, Veillonella atypica|Catonella morbi, Veillonella dispar|Catonella morbi, Veillonella parvula|Catonella morbi, Victivallis vadensis|Citrobacter koseri, Citrobacter koseri|Citrobacter koseri, Clostridium asparagiforme|Citrobacter koseri, Clostridium bartlettii|Citrobacter koseri, Clostridium bolteae|Citrobacter koseri, Clostridium botulinum|Citrobacter koseri, Clostridium butyricum|Citrobacter koseri, Clostridium difficile|Citrobacter koseri, Clostridium disporicum|Citrobacter koseri, Clostridium hathewayi|Citrobacter koseri, Clostridium hylemonae|Citrobacter koseri, Clostridium innocuum|Citrobacter koseri, Clostridium leptum|Citrobacter koseri, Clostridium mayombei|Citrobacter koseri, Clostridium methylpentosum|Citrobacter koseri, Clostridium nexile|Citrobacter koseri, Clostridium orbiscindens|Citrobacter koseri, Clostridium perfringens|Citrobacter koseri, Clostridium saccharolyticum|Citrobacter koseri, Clostridium scindens|Citrobacter koseri, Clostridium symbiosum|Citrobacter koseri, Clostridium tertium|Citrobacter koseri, Collinsella aerofaciens|Citrobacter koseri, Collinsella intestinalis|Citrobacter koseri, Collinsella stercoris|Citrobacter koseri, Coprobacillus* sp. D7|*Citrobacter koseri, Coprococcus catus|Citrobacter koseri, Coprococcus comes|Citrobacter koseri, Coprococcus eutactus|Citrobacter koseri, Corynebacterium aurimucosum|Citrobacter koseri, Corynebacterium matruchotii|Citrobacter koseri, Cryptobacterium curtum|Citrobacter koseri, Desulfovibrio desulfuricans|Citrobacter koseri, Desulfovibrio piger|Citrobacter koseri, Dialister invisus|Citrobacter koseri, Dialister microaerophilus|Citrobacter koseri, Dorea formicigenerans|Citrobacter koseri, Dorea longicatena|Citrobacter koseri, Eggerthella lenta|Citrobacter koseri, Eikenella corrodens|Citrobacter koseri, Enterobacter cancerogenus|Citrobacter koseri, Enterobacter cloacae|Citrobacter koseri, Enterococcus faecalis|Citrobacter koseri, Enterococcus faecium|Citrobacter koseri, Enterococcus gallinarum|Citrobacter koseri, Erysipelotrichaceae bacterium* 3_1_53|*Citrobacter koseri, Escherichia coli|Citrobacter koseri, Escherichia fergusonii|Citrobacter koseri, Ethanoligenens harbinense|Citrobacter koseri, Eubacterium cellulosolvens|Citrobacter koseri, Eubacterium eligens|Citrobacter koseri, Eubacterium hallii|Citrobacter koseri, Eubacterium limosum|Citrobacter koseri, Eubacterium rectale|Citrobacter koseri, Eubacterium siraeum|Citrobacter koseri, Eubacterium ventriosum|Citrobacter koseri, Faecalibacterium prausnitzii|Citrobacter koseri, Finegoldia magna|Citrobacter koseri, Fusobacterium gonidiaformans|Citrobacter koseri, Fusobacterium mortiferum|Citrobacter koseri, Fusobacterium nucleatum|Citrobacter koseri, Fusobacterium varium|Citrobacter koseri, Gardnerella vaginalis|Citrobacter koseri, Gemella haemolysans|Citrobacter koseri, Gemella morbillorum|Citrobacter koseri, Gordonibacter pamelaeae|Citrobacter koseri, Granulicatella adiacens|Citrobacter koseri, Granulicatella elegans|Citrobacter koseri, Haemophilus influenzae|Citrobacter koseri, Haemophilus parainfluenzae|Citrobacter koseri, Helicobacter pullorum|Citrobacter koseri, Helicobacter pylori|Citrobacter koseri, Holdemania filiformis|Citrobacter koseri, Kingella oralis|Citrobacter koseri, Klebsiella pneumoniae|Citrobacter koseri, Klebsiella variicola|Citrobacter koseri, Lachnospiraceae bacterium* 5_1_57FAA|*Citrobacter koseri, Lactobacillus acidophilus|Citrobacter koseri, Lactobacillus amylovorus|Citrobacter koseri, Lactobacillus brevis|Citrobacter koseri, Lactobacillus casei|Citrobacter koseri, Lactobacillus crispatus|Citrobacter koseri, Lactobacillus delbrueckii|Citrobacter koseri, Lactobacillus fermentum|Citrobacter koseri, Lactobacillus gasseri|Citrobacter koseri, Lactobacillus iners|Citrobacter koseri, Lactobacillus jensenii|Citrobacter koseri, Lactobacillus johnsonii|Citrobacter koseri, Lactobacillus paracasei|Citrobacter koseri, Lactobacillus plantarum|Citrobacter koseri, Lactobacillus reuteri|Citrobacter koseri, Lactobacillus rhamnosus|Citrobacter koseri, Lactobacillus ruminis|Citrobacter koseri, Lactobacillus sakei|Citrobacter koseri, Lactobacillus salivarius|Citrobacter koseri, Lactococcus lactis|Citrobacter koseri, Lautropia mirabilis|Citrobacter koseri, Leuconostoc citreum|Citrobacter koseri, Leuconostoc gasicomitatum|Citrobacter koseri, Leuconostoc mesenteroides|Citrobacter koseri, Listeria monocytogenes|Citrobacter koseri, Marvinbryantia formatexigens|Citrobacter koseri, Megamonas hypermegale|Citrobacter koseri, Megasphaera micronuciformis|Citrobacter koseri, Methanobrevibacter smithii|Citrobacter koseri, Methanosphaera stadtmanae|Citrobacter koseri, Methylobacterium radiotolerans|Citrobacter koseri, Mitsuokella multacida|Citrobacter koseri, Mobiluncus curtisii|Citrobacter koseri, Mycoplasma hominis|Citrobacter koseri, Neisseria mucosa|Citrobacter koseri, Odoribacter splanchnicus|Citrobacter koseri, Olsenella uli|Citrobacter koseri, Oribacterium sinus|Citrobacter koseri, Oxalobacter formigenes|Citrobacter koseri, Parabacteroides distasonis|Citrobacter koseri, Parabacteroides johnsonii|Citrobacter koseri, Parabacteroides merdae|Citrobacter koseri, Parvimonas micra|Citrobacter koseri, Pediococcus acidilactici|Citrobacter koseri, Pediococcus pentosaceus|Citrobacter koseri, Peptoniphilus duerdenii|Citrobacter koseri, Peptoniphilus harei|Citrobacter koseri, Peptoniphilus lacrimalis|Citrobacter koseri, Peptostreptococcus anaerobius|Citrobacter koseri, Peptostreptococcus stomatis|Citrobacter koseri, Porphyromonas asaccharolytica|Citrobacter koseri, Porphyromonas uenonis|Citrobacter koseri, Prevotella amnii|Citrobacter koseri, Prevotella bergensis|Citrobacter koseri, Prevotella bivia|Citrobacter koseri, Prevotella buccae|Citrobacter koseri, Prevotella buccalis|Citrobacter koseri, Prevotella copri|Citrobacter koseri, Prevotella disiens|Citrobacter koseri, Prevotella melaninogenica|Citrobacter koseri, Prevotella multiformis|Citrobacter koseri, Prevotella oralis|Citrobacter koseri, Prevotella oris|Citrobacter koseri, Prevotella salivae|Citrobacter koseri, Prevotella timonensis|Citrobacter koseri, Propionibacterium acnes|Citrobacter koseri, Propionibacterium freudenreichii|Citrobacter koseri, Proteus mirabilis|Citrobacter koseri, Proteus penneri|Citrobacter koseri, Pseudoflavonifractor capillosus|Citrobacter koseri, Pseudomonas aeruginosa|Citrobacter koseri, Pseudomonas fluorescens|Citrobacter koseri, Pseudomonas putida|Citrobacter koseri, Pseudoramibacter alactolyticus|Citrobacter koseri, Pyramidobacter piscolens|Citrobacter koseri, Rhodopseudomonas palustris|Citrobacter koseri, Roseburia intestinalis|Citrobacter koseri, Roseburia inulinivorans|Citrobacter koseri, Rothia dentocariosa|Citrobacter koseri, Rothia mucilaginosa|Citrobacter koseri, Ruminococcus albus|Citrobacter koseri, Ruminococcus bromii|Citrobacter koseri, Ruminococcus gnavus|Citrobacter koseri, Ruminococcus lactaris|Citrobacter koseri, Ruminococcus obeum|Citrobacter koseri, Ruminococcus torques|Citrobacter koseri, Selenomonas sputigena|Citrobacter koseri, Shigella boydii|Citrobacter koseri, Shigella dysenteriae|Citrobacter koseri, Shigella sonnei|Citrobacter koseri, Slackia exigua|Citrobacter koseri, Solobacterium moorei|Citrobacter koseri, Staphylococcus aureus|Citrobacter koseri, Staphylococcus epidermidis|Citrobacter koseri, Staphylococcus hominis|Citrobacter koseri, Staphylococcus saprophyticus|Citrobacter koseri, Staphylococcus warneri|Citrobacter koseri, Streptococcus agalactiae|Citrobacter koseri, Streptococcus anginosus|Citrobacter koseri, Streptococcus australis|Citrobacter koseri, Streptococcus bovis|Citrobacter koseri, Streptococcus cristatus|Citrobacter koseri, Streptococcus dysgalactiae|Citrobacter koseri, Streptococcus equinus|Citrobacter koseri, Streptococcus gordonii|Citrobacter koseri, Streptococcus infantarius|Citrobacter koseri, Streptococcus infantis|Citrobacter koseri, Streptococcus mitis|Citrobacter koseri, Streptococcus mutans|Citrobacter koseri, Streptococcus oralis|Citrobacter*

TABLE 2-continued

Table 2. Specific binary combinations of OTUs. Individual pairings are differentiated by "|" and OTUs within a combination are differentiated by ","

*koseri, Streptococcus parasanguinis|Citrobacter koseri, Streptococcus peroris|Citrobacter koseri, Streptococcus pneumoniae|Citrobacter koseri, Streptococcus salivarius|Citrobacter koseri, Streptococcus sanguinis|Citrobacter koseri, Streptococcus thermophilus|Citrobacter koseri, Streptococcus vestibularis|Citrobacter koseri, Subdoligranulum variabile|Citrobacter koseri, Succinatimonas hippei|Citrobacter koseri, Sutterella wadsworthensis|Citrobacter koseri, Tropheryma whipplei|Citrobacter koseri, Veillonella atypica|Citrobacter koseri, Veillonella dispar|Citrobacter koseri, Veillonella parvula|Citrobacter koseri, Victivallis vadensis|Clostridium asparagiforme, Clostridium asparagiforme|Clostridium asparagiforme, Clostridium bartlettii|Clostridium asparagiforme, Clostridium bolteae|Clostridium asparagiforme, Clostridium botulinum|Clostridium asparagiforme, Clostridium butyricum|Clostridium asparagiforme, Clostridium difficile|Clostridium asparagiforme, Clostridium disporicum|Clostridium asparagiforme, Clostridium hathewayi|Clostridium asparagiforme, Clostridium hylemonae|Clostridium asparagiforme, Clostridium innocuum|Clostridium asparagiforme, Clostridium leptum|Clostridium asparagiforme, Clostridium mayombei|Clostridium asparagiforme, Clostridium methylpentosum|Clostridium asparagiforme, Clostridium nexile|Clostridium asparagiforme, Clostridium orbiscindens|Clostridium asparagiforme, Clostridium perfringens|Clostridium asparagiforme, Clostridium saccharolyticum|Clostridium asparagiforme, Clostridium scindens|Clostridium asparagiforme, Clostridium symbiosum|Clostridium asparagiforme, Clostridium tertium|Clostridium asparagiforme, Collinsella aerofaciens|Clostridium asparagiforme, Collinsella intestinalis|Clostridium asparagiforme, Collinsella stercoris|Clostridium asparagiforme, Coprobacillus* sp. D7|*Clostridium asparagiforme, Coprococcus catus|Clostridium asparagiforme, Coprococcus comes|Clostridium asparagiforme, Coprococcus eutactus|Clostridium asparagiforme, Corynebacterium aurimucosum|Clostridium asparagiforme, Corynebacterium matruchotii|Clostridium asparagiforme, Cryptobacterium curtum|Clostridium asparagiforme, Desulfovibrio desulfuricans|Clostridium asparagiforme, Desulfovibrio piger|Clostridium asparagiforme, Dialister invisus|Clostridium asparagiforme, Dialister microaerophilus|Clostridium asparagiforme, Dorea formicigenerans|Clostridium asparagiforme, Dorea longicatena|Clostridium asparagiforme, Eggerthella lenta|Clostridium asparagiforme, Eikenella corrodens|Clostridium asparagiforme, Enterobacter cancerogenus|Clostridium asparagiforme, Enterobacter cloacae|Clostridium asparagiforme, Enterococcus faecalis|Clostridium asparagiforme, Enterococcus faecium|Clostridium asparagiforme, Enterococcus gallinarum|Clostridium asparagiforme, Erysipelotrichaceae bacterium* 3_1_53|*Clostridium asparagiforme, Escherichia coli|Clostridium asparagiforme, Escherichia fergusonii|Clostridium asparagiforme, Ethanoligenens harbinense|Clostridium asparagiforme, Eubacterium cellulosolvens|Clostridium asparagiforme, Eubacterium eligens|Clostridium asparagiforme, Eubacterium hallii|Clostridium asparagiforme, Eubacterium limosum|Clostridium asparagiforme, Eubacterium rectale|Clostridium asparagiforme, Eubacterium siraeum|Clostridium asparagiforme, Eubacterium ventriosum|Clostridium asparagiforme, Faecalibacterium prausnitzii|Clostridium asparagiforme, Finegoldia magna|Clostridium asparagiforme, Fusobacterium gonidiaformans|Clostridium asparagiforme, Fusobacterium mortiferum|Clostridium asparagiforme, Fusobacterium nucleatum|Clostridium asparagiforme, Fusobacterium varium|Clostridium asparagiforme, Gardnerella vaginalis|Clostridium asparagiforme, Gemella haemolysans|Clostridium asparagiforme, Gemella morbillorum|Clostridium asparagiforme, Gordonibacter pamelaeae|Clostridium asparagiforme, Granulicatella adiacens|Clostridium asparagiforme, Granulicatella elegans|Clostridium asparagiforme, Haemophilus influenzae|Clostridium asparagiforme, Haemophilus parainfluenzae|Clostridium asparagiforme, Helicobacter pullorum|Clostridium asparagiforme, Helicobacter pylori|Clostridium asparagiforme, Holdemania filiformis|Clostridium asparagiforme, Kingella oralis|Clostridium asparagiforme, Klebsiella pneumoniae|Clostridium asparagiforme, Klebsiella variicola|Clostridium asparagiforme, Lachnospiraceae bacterium* 5_1_57FAA|*Clostridium asparagiforme, Lactobacillus acidophilus|Clostridium asparagiforme, Lactobacillus amylovorus|Clostridium asparagiforme, Lactobacillus brevis|Clostridium asparagiforme, Lactobacillus casei|Clostridium asparagiforme, Lactobacillus crispatus|Clostridium asparagiforme, Lactobacillus delbrueckii|Clostridium asparagiforme, Lactobacillus fermentum|Clostridium asparagiforme, Lactobacillus gasseri|Clostridium asparagiforme, Lactobacillus iners|Clostridium asparagiforme, Lactobacillus jensenii|Clostridium asparagiforme, Lactobacillus johnsonii|Clostridium asparagiforme, Lactobacillus paracasei|Clostridium asparagiforme, Lactobacillus plantarum|Clostridium asparagiforme, Lactobacillus reuteri|Clostridium asparagiforme, Lactobacillus rhamnosus|Clostridium asparagiforme, Lactobacillus ruminis|Clostridium asparagiforme, Lactobacillus sakei|Clostridium asparagiforme, Lactobacillus salivarius|Clostridium asparagiforme, Lactococcus lactis|Clostridium asparagiforme, Lautropia mirabilis|Clostridium asparagiforme, Leuconostoc citreum|Clostridium asparagiforme, Leuconostoc gasicomitatum|Clostridium asparagiforme, Leuconostoc mesenteroides|Clostridium asparagiforme, Listeria monocytogenes|Clostridium asparagiforme, Marvinbryantia formatexigens|Clostridium asparagiforme, Megamonas hypermegale|Clostridium asparagiforme, Megasphaera micronuciformis|Clostridium asparagiforme, Methanobrevibacter smithii|Clostridium asparagiforme, Methanosphaera stadtmanae|Clostridium asparagiforme, Methylobacterium radiotolerans|Clostridium asparagiforme, Mitsuokella multacida|Clostridium asparagiforme, Mobiluncus curtisii|Clostridium asparagiforme, Mycoplasma hominis|Clostridium asparagiforme, Neisseria mucosa|Clostridium asparagiforme, Odoribacter splanchnicus|Clostridium asparagiforme, Olsenella uli|Clostridium asparagiforme, Oribacterium sinus|Clostridium asparagiforme, Oxalobacter formigenes|Clostridium asparagiforme, Parabacteroides distasonis|Clostridium asparagiforme, Parabacteroides johnsonii|Clostridium asparagiforme, Parabacteroides merdae|Clostridium asparagiforme, Parvimonas micra|Clostridium asparagiforme, Pediococcus acidilactici|Clostridium asparagiforme, Pediococcus pentosaceus|Clostridium asparagiforme, Peptoniphilus duerdenii|Clostridium asparagiforme, Peptoniphilus harei|Clostridium asparagiforme, Peptoniphilus lacrimalis|Clostridium asparagiforme, Peptostreptococcus anaerobius|Clostridium asparagiforme, Peptostreptococcus stomatis|Clostridium asparagiforme, Porphyromonas asaccharolytica|Clostridium asparagiforme, Porphyromonas uenonis|Clostridium asparagiforme, Prevotella amnii|Clostridium asparagiforme, Prevotella bergensis|Clostridium asparagiforme, Prevotella bivia|Clostridium asparagiforme, Prevotella buccae|Clostridium asparagiforme, Prevotella buccalis|Clostridium asparagiforme, Prevotella copri|Clostridium asparagiforme, Prevotella disiens|Clostridium asparagiforme, Prevotella melaninogenica|Clostridium asparagiforme, Prevotella multiformis|Clostridium asparagiforme, Prevotella oralis|Clostridium asparagiforme, Prevotella oris|Clostridium asparagiforme, Prevotella salivae|Clostridium asparagiforme, Prevotella timonensis|Clostridium asparagiforme, Propionibacterium acnes|Clostridium asparagiforme, Propionibacterium freudenreichii|Clostridium asparagiforme, Proteus mirabilis|Clostridium asparagiforme, Proteus penneri|Clostridium asparagiforme, Pseudoflavonifractor capillosus|Clostridium asparagiforme, Pseudomonas aeruginosa|Clostridium asparagiforme, Pseudomonas fluorescens|Clostridium asparagiforme, Pseudomonas putida|Clostridium asparagiforme, Pseudoramibacter alactolyticus|Clostridium asparagiforme, Pyramidobacter piscolens|Clostridium asparagiforme, Rhodopseudomonas palustris|Clostridium asparagiforme, Roseburia intestinalis|Clostridium asparagiforme, Roseburia inulinivorans|Clostridium asparagiforme, Rothia dentocariosa|Clostridium asparagiforme, Rothia mucilaginosa|Clostridium asparagiforme, Ruminococcus albus|Clostridium asparagiforme, Ruminococcus bromii|Clostridium asparagiforme, Ruminococcus gnavus|Clostridium asparagiforme, Ruminococcus lactaris|Clostridium asparagiforme, Ruminococcus obeum|Clostridium asparagiforme, Ruminococcus torques|Clostridium asparagiforme, Selenomonas sputigena|Clostridium asparagiforme, Shigella boydii|Clostridium asparagiforme, Shigella dysenteriae|Clostridium asparagiforme, Shigella sonnei|Clostridium asparagiforme, Slackia exigua|Clostridium asparagiforme, Solobacterium moorei|Clostridium asparagiforme, Staphylococcus aureus|Clostridium asparagiforme, Staphylococcus epidermidis|Clostridium asparagiforme, Staphylococcus hominis|Clostridium asparagiforme, Staphylococcus saprophyticus|Clostridium asparagiforme, Staphylococcus warneri|Clostridium asparagiforme, Streptococcus agalactiae|Clostridium asparagiforme, Streptococcus anginosus|Clostridium asparagiforme, Streptococcus australis|Clostridium asparagiforme, Streptococcus bovis|Clostridium asparagiforme, Streptococcus cristatus|Clostridium asparagiforme, Streptococcus dysgalactiae|Clostridium asparagiforme, Streptococcus equinus|Clostridium asparagiforme, Streptococcus gordonii|Clostridium asparagiforme, Streptococcus infantarius|Clostridium asparagiforme, Streptococcus infantis|Clostridium asparagiforme, Streptococcus mitis|Clostridium asparagiforme, Streptococcus mutans|Clostridium asparagiforme, Streptococcus oralis|Clostridium asparagiforme, Streptococcus parasanguinis|Clostridium asparagiforme, Streptococcus peroris|Clostridium asparagiforme, Streptococcus*

TABLE 2-continued

| Table 2. Specific binary combinations of OTUs. Individual pairings are differentiated by "\|" and OTUs within a combination are differentiated by "," |
|---|
| *pneumoniae*\|*Clostridium asparagiforme, Streptococcus salivarius*\|*Clostridium asparagiforme, Streptococcus sanguinis*\|*Clostridium asparagiforme, Streptococcus thermophilus*\|*Clostridium asparagiforme, Streptococcus vestibularis*\|*Clostridium asparagiforme, Subdoligranulum variabile*\|*Clostridium asparagiforme, Succinatimonas hippei*\|*Clostridium asparagiforme, Sutterella wadsworthensis*\|*Clostridium asparagiforme, Tropheryma whipplei*\|*Clostridium asparagiforme, Veillonella atypica*\|*Clostridium asparagiforme, Veillonella dispar*\|*Clostridium asparagiforme, Veillonella parvula*\|*Clostridium asparagiforme, Victivallis vadensis*\|*Clostridium bartlettii, Clostridium bartlettii*\|*Clostridium bartlettii, Clostridium bolteae*\|*Clostridium bartlettii, Clostridium botulinum*\|*Clostridium bartlettii, Clostridium butyricum*\|*Clostridium bartlettii, Clostridium difficile*\|*Clostridium bartlettii, Clostridium disporicum*\|*Clostridium bartlettii, Clostridium hathewayi*\|*Clostridium bartlettii, Clostridium hylemonae*\|*Clostridium bartlettii, Clostridium innocuum*\|*Clostridium bartlettii, Clostridium leptum*\|*Clostridium bartlettii, Clostridium mayombei*\|*Clostridium bartlettii, Clostridium methylpentosum*\|*Clostridium bartlettii, Clostridium nexile*\|*Clostridium bartlettii, Clostridium orbiscindens*\|*Clostridium bartlettii, Clostridium perfringens*\|*Clostridium bartlettii, Clostridium saccharolyticum*\|*Clostridium bartlettii, Clostridium scindens*\|*Clostridium bartlettii, Clostridium symbiosum*\|*Clostridium bartlettii, Clostridium tertium*\|*Clostridium bartlettii, Collinsella aerofaciens*\|*Clostridium bartlettii, Collinsella intestinalis*\|*Clostridium bartlettii, Collinsella stercoris*\|*Clostridium bartlettii, Coprobacillus* sp. D7\|*Clostridium bartlettii, Coprococcus catus*\|*Clostridium bartlettii, Coprococcus comes*\|*Clostridium bartlettii, Coprococcus eutactus*\|*Clostridium bartlettii, Corynebacterium aurimucosum*\|*Clostridium bartlettii, Corynebacterium matruchotii*\|*Clostridium bartlettii, Cryptobacterium curtum*\|*Clostridium bartlettii, Desulfovibrio desulfuricans*\|*Clostridium bartlettii, Desulfovibrio piger*\|*Clostridium bartlettii, Dialister invisus*\|*Clostridium bartlettii, Dialister microaerophilus*\|*Clostridium bartlettii, Dorea formicigenerans*\|*Clostridium bartlettii, Dorea longicatena*\|*Clostridium bartlettii, Eggerthella lenta*\|*Clostridium bartlettii, Eikenella corrodens*\|*Clostridium bartlettii, Enterobacter cancerogenus*\|*Clostridium bartlettii, Enterobacter cloacae*\|*Clostridium bartlettii, Enterococcus faecalis*\|*Clostridium bartlettii, Enterococcus faecium*\|*Clostridium bartlettii, Enterococcus gallinarum*\|*Clostridium bartlettii, Erysipelotrichaceae bacterium* 31_53\|*Clostridium bartlettii, Escherichia coli*\|*Clostridium bartlettii, Escherichia fergusonii*\|*Clostridium bartlettii, Ethanoligenens harbinense*\|*Clostridium bartlettii, Eubacterium cellulosolvens*\|*Clostridium bartlettii, Eubacterium eligens*\|*Clostridium bartlettii, Eubacterium hallii*\|*Clostridium bartlettii, Eubacterium limosum*\|*Clostridium bartlettii, Eubacterium rectale*\|*Clostridium bartlettii, Eubacterium siraeum*\|*Clostridium bartlettii, Eubacterium ventriosum*\|*Clostridium bartlettii, Faecalibacterium prausnitzii*\|*Clostridium bartlettii, Finegoldia magna*\|*Clostridium bartlettii, Fusobacterium gonidiaformans*\|*Clostridium bartlettii, Fusobacterium mortiferum*\|*Clostridium bartlettii, Fusobacterium nucleatum*\|*Clostridium bartlettii, Fusobacterium varium*\|*Clostridium bartlettii, Gardnerella vaginalis*\|*Clostridium bartlettii, Gemella haemolysans*\|*Clostridium bartlettii, Gemella morbillorum*\|*Clostridium bartlettii, Gordonibacter pamelaeae*\|*Clostridium bartlettii, Granulicatella adiacens*\|*Clostridium bartlettii, Granulicatella elegans*\|*Clostridium bartlettii, Haemophilus influenzae*\|*Clostridium bartlettii, Haemophilus parainfluenzae*\|*Clostridium bartlettii, Helicobacter pullorum*\|*Clostridium bartlettii, Helicobacter pylori*\|*Clostridium bartlettii, Holdemania filiformis*\|*Clostridium bartlettii, Kingella oralis*\|*Clostridium bartlettii, Klebsiella pneumoniae*\|*Clostridium bartlettii, Klebsiella variicola*\|*Clostridium bartlettii, Lachnospiraceae bacterium* 5_1_57FAA\|*Clostridium bartlettii, Lactobacillus acidophilus*\|*Clostridium bartlettii, Lactobacillus amylovorus*\|*Clostridium bartlettii, Lactobacillus brevis*\|*Clostridium bartlettii, Lactobacillus casei*\|*Clostridium bartlettii, Lactobacillus crispatus*\|*Clostridium bartlettii, Lactobacillus delbrueckii*\|*Clostridium bartlettii, Lactobacillus fermentum*\|*Clostridium bartlettii, Lactobacillus gasseri*\|*Clostridium bartlettii, Lactobacillus iners*\|*Clostridium bartlettii, Lactobacillus jensenii*\|*Clostridium bartlettii, Lactobacillus johnsonii*\|*Clostridium bartlettii, Lactobacillus paracasei*\|*Clostridium bartlettii, Lactobacillus plantarum*\|*Clostridium bartlettii, Lactobacillus reuteri*\|*Clostridium bartlettii, Lactobacillus rhamnosus*\|*Clostridium bartlettii, Lactobacillus ruminis*\|*Clostridium bartlettii, Lactobacillus sakei*\|*Clostridium bartlettii, Lactobacillus salivarius*\|*Clostridium bartlettii, Lactococcus lactis*\|*Clostridium bartlettii, Lautropia mirabilis*\|*Clostridium bartlettii, Leuconostoc citreum*\|*Clostridium bartlettii, Leuconostoc gasicomitatum*\|*Clostridium bartlettii, Leuconostoc mesenteroides*\|*Clostridium bartlettii, Listeria monocytogenes*\|*Clostridium bartlettii, Marvinbryantia formatexigens*\|*Clostridium bartlettii, Megamonas hypermegale*\|*Clostridium bartlettii, Megasphaera micronuciformis*\|*Clostridium bartlettii, Methanobrevibacter smithii*\|*Clostridium bartlettii, Methanosphaera stadtmanae*\|*Clostridium bartlettii, Methylobacterium radiotolerans*\|*Clostridium bartlettii, Mitsuokella multacida*\|*Clostridium bartlettii, Mobiluncus curtisii*\|*Clostridium bartlettii, Mycoplasma hominis*\|*Clostridium bartlettii, Neisseria mucosa*\|*Clostridium bartlettii, Odoribacter splanchnicus*\|*Clostridium bartlettii, Olsenella uli*\|*Clostridium bartlettii, Oribacterium sinus*\|*Clostridium bartlettii, Oxalobacter formigenes*\|*Clostridium bartlettii, Parabacteroides distasonis*\|*Clostridium bartlettii, Parabacteroides johnsonii*\|*Clostridium bartlettii, Parabacteroides merdae*\|*Clostridium bartlettii, Parvimonas micra*\|*Clostridium bartlettii, Pediococcus acidilactici*\|*Clostridium bartlettii, Pediococcus pentosaceus*\|*Clostridium bartlettii, Peptoniphilus duerdenii*\|*Clostridium bartlettii, Peptoniphilus harei*\|*Clostridium bartlettii, Peptoniphilus lacrimalis*\|*Clostridium bartlettii, Peptostreptococcus anaerobius*\|*Clostridium bartlettii, Peptostreptococcus stomatis*\|*Clostridium bartlettii, Porphyromonas asaccharolytica*\|*Clostridium bartlettii, Porphyromonas uenonis*\|*Clostridium bartlettii, Prevotella amnii*\|*Clostridium bartlettii, Prevotella bergensis*\|*Clostridium bartlettii, Prevotella bivia*\|*Clostridium bartlettii, Prevotella buccae*\|*Clostridium bartlettii, Prevotella buccalis*\|*Clostridium bartlettii, Prevotella copri*\|*Clostridium bartlettii, Prevotella disiens*\|*Clostridium bartlettii, Prevotella melaninogenica*\|*Clostridium bartlettii, Prevotella multiformis*\|*Clostridium bartlettii, Prevotella oralis*\|*Clostridium bartlettii, Prevotella oris*\|*Clostridium bartlettii, Prevotella salivae*\|*Clostridium bartlettii, Prevotella timonensis*\|*Clostridium bartlettii, Propionibacterium acnes*\|*Clostridium bartlettii, Propionibacterium freudenreichii*\|*Clostridium bartlettii, Proteus mirabilis*\|*Clostridium bartlettii, Proteus penneri*\|*Clostridium bartlettii, Pseudoflavonifractor capillosus*\|*Clostridium bartlettii, Pseudomonas aeruginosa*\|*Clostridium bartlettii, Pseudomonas fluorescens*\|*Clostridium bartlettii, Pseudomonas putida*\|*Clostridium bartlettii, Pseudoramibacter alactolyticus*\|*Clostridium bartlettii, Pyramidobacter piscolens*\|*Clostridium bartlettii, Rhodopseudomonas palustris*\|*Clostridium bartlettii, Roseburia intestinalis*\|*Clostridium bartlettii, Roseburia inulinivorans*\|*Clostridium bartlettii, Rothia dentocariosa*\|*Clostridium bartlettii, Rothia mucilaginosa*\|*Clostridium bartlettii, Ruminococcus albus*\|*Clostridium bartlettii, Ruminococcus bromii*\|*Clostridium bartlettii, Ruminococcus gnavus*\|*Clostridium bartlettii, Ruminococcus lactaris*\|*Clostridium bartlettii, Ruminococcus obeum*\|*Clostridium bartlettii, Ruminococcus torques*\|*Clostridium bartlettii, Selenomonas sputigena*\|*Clostridium bartlettii, Shigella boydii*\|*Clostridium bartlettii, Shigella dysenteriae*\|*Clostridium bartlettii, Shigella sonnei*\|*Clostridium bartlettii, Slackia exigua*\|*Clostridium bartlettii, Solobacterium moorei*\|*Clostridium bartlettii, Staphylococcus aureus*\|*Clostridium bartlettii, Staphylococcus epidermidis*\|*Clostridium bartlettii, Staphylococcus hominis*\|*Clostridium bartlettii, Staphylococcus saprophyticus*\|*Clostridium bartlettii, Staphylococcus warneri*\|*Clostridium bartlettii, Streptococcus agalactiae*\|*Clostridium bartlettii, Streptococcus anginosus*\|*Clostridium bartlettii, Streptococcus australis*\|*Clostridium bartlettii, Streptococcus bovis*\|*Clostridium bartlettii, Streptococcus cristatus*\|*Clostridium bartlettii, Streptococcus dysgalactiae*\|*Clostridium bartlettii, Streptococcus equinus*\|*Clostridium bartlettii, Streptococcus gordonii*\|*Clostridium bartlettii, Streptococcus infantarius*\|*Clostridium bartlettii, Streptococcus infantis*\|*Clostridium bartlettii, Streptococcus mitis*\|*Clostridium bartlettii, Streptococcus mutans*\|*Clostridium bartlettii, Streptococcus oralis*\|*Clostridium bartlettii, Streptococcus parasanguinis*\|*Clostridium bartlettii, Streptococcus peroris*\|*Clostridium bartlettii, Streptococcus pneumoniae*\|*Clostridium bartlettii, Streptococcus salivarius*\|*Clostridium bartlettii, Streptococcus sanguinis*\|*Clostridium bartlettii, Streptococcus thermophilus*\|*Clostridium bartlettii, Streptococcus vestibularis*\|*Clostridium bartlettii, Subdoligranulum variabile*\|*Clostridium bartlettii, Succinatimonas hippei*\|*Clostridium bartlettii, Sutterella wadsworthensis*\|*Clostridium bartlettii, Tropheryma whipplei*\|*Clostridium bartlettii, Veillonella atypica*\|*Clostridium bartlettii, Veillonella dispar*\|*Clostridium bartlettii, Veillonella parvula*\|*Clostridium bartlettii, Victivallis vadensis*\|*Clostridium bolteae, Clostridium bolteae*\|*Clostridium bolteae, Clostridium botulinum*\|*Clostridium bolteae, Clostridium butyricum*\|*Clostridium bolteae, Clostridium difficile*\|*Clostridium bolteae, Clostridium disporicum*\|*Clostridium bolteae, Clostridium hathewayi*\|*Clostridium bolteae, Clostridium hylemonae*\|*Clostridium bolteae, Clostridium innocuum*\|*Clostridium bolteae, Clostridium leptum*\|*Clostridium bolteae, Clostridium mayombei*\|*Clostridium bolteae, Clostridium methylpentosum*\|*Clostridium bolteae, Clostridium* |

TABLE 2-continued

| Table 2. Specific binary combinations of OTUs. Individual pairings are differentiated by "\|" and OTUs within a combination are differentiated by "," |
|---|
| *nexile*\|*Clostridium bolteae, Clostridium orbiscindens*\|*Clostridium bolteae, Clostridium perfringens*\|*Clostridium bolteae, Clostridium saccharolyticum*\|*Clostridium bolteae, Clostridium scindens*\|*Clostridium bolteae, Clostridium symbiosum*\|*Clostridium bolteae, Clostridium tertium*\|*Clostridium bolteae, Collinsella aerofaciens*\|*Clostridium bolteae, Collinsella intestinalis*\|*Clostridium bolteae, Collinsella stercoris*\|*Clostridium bolteae, Coprobacillus* sp. D7\|*Clostridium bolteae, Coprococcus catus*\|*Clostridium bolteae, Coprococcus comes*\|*Clostridium bolteae, Coprococcus eutactus*\|*Clostridium bolteae, Corynebacterium aurimucosum*\|*Clostridium bolteae, Corynebacterium matruchotii*\|*Clostridium bolteae, Cryptobacterium curtum*\|*Clostridium bolteae, Desulfovibrio desulfuricans*\|*Clostridium bolteae, Desulfovibrio piger*\|*Clostridium bolteae, Dialister invisus*\|*Clostridium bolteae, Dialister microaerophilus*\|*Clostridium bolteae, Dorea formicigenerans*\|*Clostridium bolteae, Dorea longicatena*\|*Clostridium bolteae, Eggerthella lenta*\|*Clostridium bolteae, Eikenella corrodens*\|*Clostridium bolteae, Enterobacter cancerogenus*\|*Clostridium bolteae, Enterobacter cloacae*\|*Clostridium bolteae, Enterococcus faecalis*\|*Clostridium bolteae, Enterococcus faecium*\|*Clostridium bolteae, Enterococcus gallinarum*\|*Clostridium bolteae, Erysipelotrichaceae bacterium* 3_1_53\|*Clostridium bolteae, Escherichia coli*\|*Clostridium bolteae, Escherichia fergusonii*\|*Clostridium bolteae, Ethanoligenens harbinense*\|*Clostridium bolteae, Eubacterium cellulosolvens*\|*Clostridium bolteae, Eubacterium eligens*\|*Clostridium bolteae, Eubacterium hallii*\|*Clostridium bolteae, Eubacterium limosum*\|*Clostridium bolteae, Eubacterium rectale*\|*Clostridium bolteae, Eubacterium siraeum*\|*Clostridium bolteae, Eubacterium ventriosum*\|*Clostridium bolteae, Faecalibacterium prausnitzii*\|*Clostridium bolteae, Finegoldia magna*\|*Clostridium bolteae, Fusobacterium gonidiaformans*\|*Clostridium bolteae, Fusobacterium mortiferum*\|*Clostridium bolteae, Fusobacterium nucleatum*\|*Clostridium bolteae, Fusobacterium varium*\|*Clostridium bolteae, Gardnerella vaginalis*\|*Clostridium bolteae, Gemella haemolysans*\|*Clostridium bolteae, Gemella morbillorum*\|*Clostridium bolteae, Gordonibacter pamelaeae*\|*Clostridium bolteae, Granulicatella adiacens*\|*Clostridium bolteae, Granulicatella elegans*\|*Clostridium bolteae, Haemophilus influenzae*\|*Clostridium bolteae, Haemophilus parainfluenzae*\|*Clostridium bolteae, Helicobacter pullorum*\|*Clostridium bolteae, Helicobacter pylori*\|*Clostridium bolteae, Holdemania filiformis*\|*Clostridium bolteae, Kingella oralis*\|*Clostridium bolteae, Klebsiella pneumoniae*\|*Clostridium bolteae, Klebsiella variicola*\|*Clostridium bolteae, Lachnospiraceae bacterium* 5_1_57FAA\|*Clostridium bolteae, Lactobacillus acidophilus*\|*Clostridium bolteae, Lactobacillus amylovorus*\|*Clostridium bolteae, Lactobacillus brevis*\|*Clostridium bolteae, Lactobacillus casei*\|*Clostridium bolteae, Lactobacillus crispatus*\|*Clostridium bolteae, Lactobacillus delbrueckii*\|*Clostridium bolteae, Lactobacillus fermentum*\|*Clostridium bolteae, Lactobacillus gasseri*\|*Clostridium bolteae, Lactobacillus iners*\|*Clostridium bolteae, Lactobacillus jensenii*\|*Clostridium bolteae, Lactobacillus johnsonii*\|*Clostridium bolteae, Lactobacillus paracasei*\|*Clostridium bolteae, Lactobacillus plantarum*\|*Clostridium bolteae, Lactobacillus reuteri*\|*Clostridium bolteae, Lactobacillus rhamnosus*\|*Clostridium bolteae, Lactobacillus ruminis*\|*Clostridium bolteae, Lactobacillus sakei*\|*Clostridium bolteae, Lactobacillus salivarius*\|*Clostridium bolteae, Lactococcus lactis*\|*Clostridium bolteae, Lautropia mirabilis*\|*Clostridium bolteae, Leuconostoc citreum*\|*Clostridium bolteae, Leuconostoc gasicomitatum*\|*Clostridium bolteae, Leuconostoc mesenteroides*\|*Clostridium bolteae, Listeria monocytogenes*\|*Clostridium bolteae, Marvinbryantia formatexigens*\|*Clostridium bolteae, Megamonas hypermegale*\|*Clostridium bolteae, Megasphaera micronuciformis*\|*Clostridium bolteae, Methanobrevibacter smithii*\|*Clostridium bolteae, Methanosphaera stadtmanae*\|*Clostridium bolteae, Methylobacterium radiotolerans*\|*Clostridium bolteae, Mitsuokella multacida*\|*Clostridium bolteae, Mobiluncus curtisii*\|*Clostridium bolteae, Mycoplasma hominis*\|*Clostridium bolteae, Neisseria mucosa*\|*Clostridium bolteae, Odoribacter splanchnicus*\|*Clostridium bolteae, Olsenella uli*\|*Clostridium bolteae, Oribacterium sinus*\|*Clostridium bolteae, Oxalobacter formigenes*\|*Clostridium bolteae, Parabacteroides distasonis*\|*Clostridium bolteae, Parabacteroides johnsonii*\|*Clostridium bolteae, Parabacteroides merdae*\|*Clostridium bolteae, Parvimonas micra*\|*Clostridium bolteae, Pediococcus acidilactici*\|*Clostridium bolteae, Pediococcus pentosaceus*\|*Clostridium bolteae, Peptoniphilus duerdenii*\|*Clostridium bolteae, Peptoniphilus harei*\|*Clostridium bolteae, Peptoniphilus lacrimalis*\|*Clostridium bolteae, Peptostreptococcus anaerobius*\|*Clostridium bolteae, Peptostreptococcus stomatis*\|*Clostridium bolteae, Porphyromonas asaccharolytica*\|*Clostridium bolteae, Porphyromonas uenonis*\|*Clostridium bolteae, Prevotella amnii*\|*Clostridium bolteae, Prevotella bergensis*\|*Clostridium bolteae, Prevotella bivia*\|*Clostridium bolteae, Prevotella buccae*\|*Clostridium bolteae, Prevotella buccalis*\|*Clostridium bolteae, Prevotella copri*\|*Clostridium bolteae, Prevotella disiens*\|*Clostridium bolteae, Prevotella melaninogenica*\|*Clostridium bolteae, Prevotella multiformis*\|*Clostridium bolteae, Prevotella oralis*\|*Clostridium bolteae, Prevotella oris*\|*Clostridium bolteae, Prevotella salivae*\|*Clostridium bolteae, Prevotella timonensis*\|*Clostridium bolteae, Propionibacterium acnes*\|*Clostridium bolteae, Propionibacterium freudenreichii*\|*Clostridium bolteae, Proteus mirabilis*\|*Clostridium bolteae, Proteus penneri*\|*Clostridium bolteae, Pseudoflavonifractor capillosus*\|*Clostridium bolteae, Pseudomonas aeruginosa*\|*Clostridium bolteae, Pseudomonas fluorescens*\|*Clostridium bolteae, Pseudomonas putida*\|*Clostridium bolteae, Pseudoramibacter alactolyticus*\|*Clostridium bolteae, Pyramidobacter piscolens*\|*Clostridium bolteae, Rhodopseudomonas palustris*\|*Clostridium bolteae, Roseburia intestinalis*\|*Clostridium bolteae, Roseburia inulinivorans*\|*Clostridium bolteae, Rothia dentocariosa*\|*Clostridium bolteae, Rothia mucilaginosa*\|*Clostridium bolteae, Ruminococcus albus*\|*Clostridium bolteae, Ruminococcus bromii*\|*Clostridium bolteae, Ruminococcus gnavus*\|*Clostridium bolteae, Ruminococcus lactaris*\|*Clostridium bolteae, Ruminococcus obeum*\|*Clostridium bolteae, Ruminococcus torques*\|*Clostridium bolteae, Selenomonas sputigena*\|*Clostridium bolteae, Shigella boydii*\|*Clostridium bolteae, Shigella dysenteriae*\|*Clostridium bolteae, Shigella sonnei*\|*Clostridium bolteae, Slackia exigua*\|*Clostridium bolteae, Solobacterium moorei*\|*Clostridium bolteae, Staphylococcus aureus*\|*Clostridium bolteae, Staphylococcus epidermidis*\|*Clostridium bolteae, Staphylococcus hominis*\|*Clostridium bolteae, Staphylococcus saprophyticus*\|*Clostridium bolteae, Staphylococcus warneri*\|*Clostridium bolteae, Streptococcus agalactiae*\|*Clostridium bolteae, Streptococcus anginosus*\|*Clostridium bolteae, Streptococcus australis*\|*Clostridium bolteae, Streptococcus bovis*\|*Clostridium bolteae, Streptococcus cristatus*\|*Clostridium bolteae, Streptococcus dysgalactiae*\|*Clostridium bolteae, Streptococcus equinus*\|*Clostridium bolteae, Streptococcus gordonii*\|*Clostridium bolteae, Streptococcus infantarius*\|*Clostridium bolteae, Streptococcus infantis*\|*Clostridium bolteae, Streptococcus mitis*\|*Clostridium bolteae, Streptococcus mutans*\|*Clostridium bolteae, Streptococcus oralis*\|*Clostridium bolteae, Streptococcus parasanguinis*\|*Clostridium bolteae, Streptococcus peroris*\|*Clostridium bolteae, Streptococcus pneumoniae*\|*Clostridium bolteae, Streptococcus salivarius*\|*Clostridium bolteae, Streptococcus sanguinis*\|*Clostridium bolteae, Streptococcus thermophilus*\|*Clostridium bolteae, Streptococcus vestibularis*\|*Clostridium bolteae, Subdoligranulum variabile*\|*Clostridium bolteae, Succinatimonas hippei*\|*Clostridium bolteae, Sutterella wadsworthensis*\|*Clostridium bolteae, Tropheryma whipplei*\|*Clostridium bolteae, Veillonella atypica*\|*Clostridium bolteae, Veillonella dispar*\|*Clostridium bolteae, Veillonella parvula*\|*Clostridium bolteae, Victivallis vadensis*\|*Clostridium botulinum, Clostridium botulinum*\|*Clostridium botulinum, Clostridium butyricum*\|*Clostridium botulinum, Clostridium difficile*\|*Clostridium botulinum, Clostridium disporicum*\|*Clostridium botulinum, Clostridium hathewayi*\|*Clostridium botulinum, Clostridium hylemonae*\|*Clostridium botulinum, Clostridium innocuum*\|*Clostridium botulinum, Clostridium leptum*\|*Clostridium botulinum, Clostridium mayombei*\|*Clostridium botulinum, Clostridium methylpentosum*\|*Clostridium botulinum, Clostridium nexile*\|*Clostridium botulinum, Clostridium orbiscindens*\|*Clostridium botulinum, Clostridium perfringens*\|*Clostridium botulinum, Clostridium saccharolyticum*\|*Clostridium botulinum, Clostridium scindens*\|*Clostridium botulinum, Clostridium symbiosum*\|*Clostridium botulinum, Clostridium tertium*\|*Clostridium botulinum, Collinsella aerofaciens*\|*Clostridium botulinum, Collinsella intestinalis*\|*Clostridium botulinum, Collinsella stercoris*\|*Clostridium botulinum, Coprobacillus* sp. D7\|*Clostridium botulinum, Coprococcus catus*\|*Clostridium botulinum, Coprococcus comes*\|*Clostridium botulinum, Coprococcus eutactus*\|*Clostridium botulinum, Corynebacterium aurimucosum*\|*Clostridium botulinum, Corynebacterium matruchotii*\|*Clostridium botulinum, Cryptobacterium curtum*\|*Clostridium botulinum, Desulfovibrio desulfuricans*\|*Clostridium botulinum, Desulfovibrio piger*\|*Clostridium botulinum, Dialister invisus*\|*Clostridium botulinum, Dialister microaerophilus*\|*Clostridium botulinum, Dorea formicigenerans*\|*Clostridium botulinum, Dorea longicatena*\|*Clostridium botulinum, Eggerthella lenta*\|*Clostridium botulinum, Eikenella corrodens*\|*Clostridium botulinum, Enterobacter cancerogenus*\|*Clostridium botulinum, Enterobacter cloacae*\|*Clostridium botulinum, Enterococcus faecalis*\|*Clostridium botulinum, Enterococcus faecium*\|*Clostridium botulinum, Enterococcus gallinarum*\|*Clostridium botulinum, Erysipelotrichaceae bacterium* 3_1_53\|*Clostridium botulinum, Escherichia coli*\|*Clostridium* |

TABLE 2-continued

| Table 2. Specific binary combinations of OTUs. Individual pairings are differentiated by "\|" and OTUs within a combination are differentiated by "," |
| --- |
| botulinum, Escherichia fergusonii\|Clostridium botulinum, Ethanoligenens harbinense\|Clostridium botulinum, Eubacterium cellulosolvens\|Clostridium botulinum, Eubacterium eligens\|Clostridium botulinum, Eubacterium hallii\|Clostridium botulinum, Eubacterium limosum\|Clostridium botulinum, Eubacterium rectale\|Clostridium botulinum, Eubacterium siraeum\|Clostridium botulinum, Eubacterium ventriosum\|Clostridium botulinum, Faecalibacterium prausnitzii\|Clostridium botulinum, Finegoldia magna\|Clostridium botulinum, Fusobacterium gonidiaformans\|Clostridium botulinum, Fusobacterium mortiferum\|Clostridium botulinum, Fusobacterium nucleatum\|Clostridium botulinum, Fusobacterium varium\|Clostridium botulinum, Gardnerella vaginalis\|Clostridium botulinum, Gemella haemolysans\|Clostridium botulinum, Gemella morbillorum\|Clostridium botulinum, Gordonibacter pamelaeae\|Clostridium botulinum, Granulicatella adiacens\|Clostridium botulinum, Granulicatella elegans\|Clostridium botulinum, Haemophilus influenzae\|Clostridium botulinum, Haemophilus parainfluenzae\|Clostridium botulinum, Helicobacter pullorum\|Clostridium botulinum, Helicobacter pylori\|Clostridium botulinum, Holdemania filiformis\|Clostridium botulinum, Kingella oralis\|Clostridium botulinum, Klebsiella pneumoniae\|Clostridium botulinum, Klebsiella variicola\|Clostridium botulinum, Lachnospiraceae bacterium 5_1_57FAA\|Clostridium botulinum, Lactobacillus acidophilus\|Clostridium botulinum, Lactobacillus amylovorus\|Clostridium botulinum, Lactobacillus brevis\|Clostridium botulinum, Lactobacillus casei\|Clostridium botulinum, Lactobacillus crispatus\|Clostridium botulinum, Lactobacillus delbrueckii\|Clostridium botulinum, Lactobacillus fermentum\|Clostridium botulinum, Lactobacillus gasseri\|Clostridium botulinum, Lactobacillus iners\|Clostridium botulinum, Lactobacillus jensenii\|Clostridium botulinum, Lactobacillus johns onii\|Clostridium botulinum, Lactobacillus paracasei\|Clostridium botulinum, Lactobacillus plantarum\|Clostridium botulinum, Lactobacillus reuteri\|Clostridium botulinum, Lactobacillus rhamnosus\|Clostridium botulinum, Lactobacillus ruminis\|Clostridium botulinum, Lactobacillus sakei\|Clostridium botulinum, Lactobacillus salivarius\|Clostridium botulinum, Lactococcus lactis\|Clostridium botulinum, Lautropia mirabilis\|Clostridium botulinum, Leuconostoc citreum\|Clostridium botulinum, Leuconostoc gas icomitatum\|Clostridium botulinum, Leuconostoc mesenteroides\|Clostridium botulinum, Listeria monocytogenes\|Clostridium botulinum, Marvinbryantia formatexigens\|Clostridium botulinum, Megamonas hypermegale\|Clostridium botulinum, Megasphaera micronuciformis\|Clostridium botulinum, Methanobrevibacter smithii\|Clostridium botulinum, Methanosphaera stadtmanae\|Clostridium botulinum, Methylobacterium radiotolerans\|Clostridium botulinum, Mitsuokella multacida\|Clostridium botulinum, Mobiluncus curtisii\|Clostridium botulinum, Mycoplasma hominis\|Clostridium botulinum, Neisseria mucosa\|Clostridium botulinum, Odoribacter splanchnicus\|Clostridium botulinum, Olsenella uli\|Clostridium botulinum, Oribacterium sinus\|Clostridium botulinum, Oxalobacter formigenes\|Clostridium botulinum, Parabacteroides distasonis\|Clostridium botulinum, Parabacteroides johnsonii\|Clostridium botulinum, Parabacteroides merdae\|Clostridium botulinum, Parvimonas micra\|Clostridium botulinum, Pediococcus acidilactici\|Clostridium botulinum, Pediococcus pentosaceus\|Clostridium botulinum, Peptoniphilus duerdenii\|Clostridium botulinum, Peptoniphilus harei\|Clostridium botulinum, Peptoniphilus lacrimalis\|Clostridium botulinum, Peptostreptococcus anaerobius\|Clostridium botulinum, Peptostreptococcus stomatis\|Clostridium botulinum, Porphyromonas asaccharolytica\|Clostridium botulinum, Porphyromonas uenonis\|Clostridium botulinum, Prevotella amnii\|Clostridium botulinum, Prevotella bergensis\|Clostridium botulinum, Prevotella bivia\|Clostridium botulinum, Prevotella buccae\|Clostridium botulinum, Prevotella buccalis\|Clostridium botulinum, Prevotella copri\|Clostridium botulinum, Prevotella disiens\|Clostridium botulinum, Prevotella melaninogenica\|Clostridium botulinum, Prevotella multiformis\|Clostridium botulinum, Prevotella oralis\|Clostridium botulinum, Prevotella oris\|Clostridium botulinum, Prevotella salivae\|Clostridium botulinum, Prevotella timonensis\|Clostridium botulinum, Propionibacterium acnes\|Clostridium botulinum, Propionibacterium freudenreichii\|Clostridium botulinum, Proteus mirabilis\|Clostridium botulinum, Proteus penneri\|Clostridium botulinum, Pseudoflavonifractor capillosus\|Clostridium botulinum, Pseudomonas aeruginosa\|Clostridium botulinum, Pseudomonas fluorescens\|Clostridium botulinum, Pseudomonas putida\|Clostridium botulinum, Pseudoramibacter alactolyticus\|Clostridium botulinum, Pyramidobacter piscolens\|Clostridium botulinum, Rhodopseudomonas palustris\|Clostridium botulinum, Roseburia intestinalis\|Clostridium botulinum, Roseburia inulinivorans\|Clostridium botulinum, Rothia dentocariosa\|Clostridium botulinum, Rothia mucilaginosa\|Clostridium botulinum, Ruminococcus albus\|Clostridium botulinum, Ruminococcus bromii\|Clostridium botulinum, Ruminococcus gnavus\|Clostridium botulinum, Ruminococcus lactaris\|Clostridium botulinum, Ruminococcus obeum\|Clostridium botulinum, Ruminococcus torques\|Clostridium botulinum, Selenomonas sputigena\|Clostridium botulinum, Shigella boydii\|Clostridium botulinum, Shigella dysenteriae\|Clostridium botulinum, Shigella sonnei\|Clostridium botulinum, Slackia exigua\|Clostridium botulinum, Solobacterium moorei\|Clostridium botulinum, Staphylococcus aureus\|Clostridium botulinum, Staphylococcus epidermidis\|Clostridium botulinum, Staphylococcus hominis\|Clostridium botulinum, Staphylococcus saprophyticus\|Clostridium botulinum, Staphylococcus warneri\|Clostridium botulinum, Streptococcus agalactiae\|Clostridium botulinum, Streptococcus anginosus\|Clostridium botulinum, Streptococcus australis\|Clostridium botulinum, Streptococcus bovis\|Clostridium botulinum, Streptococcus cristatus\|Clostridium botulinum, Streptococcus dysgalactiae\|Clostridium botulinum, Streptococcus equinus\|Clostridium botulinum, Streptococcus gordonii\|Clostridium botulinum, Streptococcus infantarius\|Clostridium botulinum, Streptococcus infantis\|Clostridium botulinum, Streptococcus mitis\|Clostridium botulinum, Streptococcus mutans\|Clostridium botulinum, Streptococcus oralis\|Clostridium botulinum, Streptococcus parasanguinis\|Clostridium botulinum, Streptococcus peroris\|Clostridium botulinum, Streptococcus pneumoniae\|Clostridium botulinum, Streptococcus salivarius\|Clostridium botulinum, Streptococcus sanguinis\|Clostridium botulinum, Streptococcus thermophilus\|Clostridium botulinum, Streptococcus vestibularis\|Clostridium botulinum, Subdoligranulum variabile\|Clostridium botulinum, Succinatimonas hippei\|Clostridium botulinum, Sutterella wadsworthensis\|Clostridium botulinum, Tropheryma whipplei\|Clostridium botulinum, Veillonella atypica\|Clostridium botulinum, Veillonella dispar\|Clostridium botulinum, Veillonella parvula\|Clostridium botulinum, Victivallis vadensis\|Clostridium butyricum, Clostridium butyricum, Clostridium butyricum, Clostridium difficile\|Clostridium butyricum, Clostridium disporicum\|Clostridium butyricum, Clostridium hathewayi\|Clostridium butyricum, Clostridium hylemonae\|Clostridium butyricum, Clostridium innocuum\|Clostridium butyricum, Clostridium leptum\|Clostridium butyricum, Clostridium mayombei\|Clostridium butyricum, Clostridium methylpentosum\|Clostridium butyricum, Clostridium nexile\|Clostridium butyricum, Clostridium orbiscindens\|Clostridium butyricum, Clostridium perfringens\|Clostridium butyricum, Clostridium saccharolyticum\|Clostridium butyricum, Clostridium scindens\|Clostridium butyricum, Clostridium symbiosum\|Clostridium butyricum, Clostridium tertium\|Clostridium butyricum, Collinsella aerofaciens\|Clostridium butyricum, Collinsella intestinalis\|Clostridium butyricum, Collinsella stercoris\|Clostridium butyricum, Coprobacillus sp. D7\|Clostridium butyricum, Coprococcus catus\|Clostridium butyricum, Coprococcus comes\|Clostridium butyricum, Coprococcus eutactus\|Clostridium butyricum, Corynebacterium aurimucosum\|Clostridium butyricum, Corynebacterium matruchotii\|Clostridium butyricum, Cryptobacterium curtum\|Clostridium butyricum, Desulfovibrio desulfuricans\|Clostridium butyricum, Desulfovibrio piger\|Clostridium butyricum, Dialister invisus\|Clostridium butyricum, Dialister microaerophilus\|Clostridium butyricum, Dorea formicigenerans\|Clostridium butyricum, Dorea longicatena\|Clostridium butyricum, Eggerthella lenta\|Clostridium butyricum, Eikenella corrodens\|Clostridium butyricum, Enterobacter cancerogenus\|Clostridium butyricum, Enterobacter cloacae\|Clostridium butyricum, Enterococcus faecalis\|Clostridium butyricum, Enterococcus faecium\|Clostridium butyricum, Enterococcus gallinarum\|Clostridium butyricum, Erysipelotrichaceae bacterium 3_1_53\|Clostridium butyricum, Escherichia coli\|Clostridium butyricum, Escherichia fergusonii\|Clostridium butyricum, Ethanoligenens harbinense\|Clostridium butyricum, Eubacterium cellulosolvens\|Clostridium butyricum, Eubacterium eligens\|Clostridium butyricum, Eubacterium hallii\|Clostridium butyricum, Eubacterium limosum\|Clostridium butyricum, Eubacterium rectale\|Clostridium butyricum, Eubacterium siraeum\|Clostridium butyricum, Eubacterium ventriosum\|Clostridium butyricum, Faecalibacterium prausnitzii\|Clostridium butyricum, Finegoldia magna\|Clostridium butyricum, Fusobacterium gonidiaformans\|Clostridium butyricum, Fusobacterium mortiferum\|Clostridium butyricum, Fusobacterium nucleatum\|Clostridium butyricum, Fusobacterium varium\|Clostridium butyricum, Gardnerella vaginalis\|Clostridium butyricum, Gemella haemolysans\|Clostridium butyricum, Gemella morbillorum\|Clostridium butyricum, Gordonibacter pamelaeae\|Clostridium butyricum, Granulicatella adiacens\|Clostridium butyricum, Granulicatella |

TABLE 2-continued

| Table 2. Specific binary combinations of OTUs. Individual pairings are differentiated by "\|" and OTUs within a combination are differentiated by "," |
|---|
| *elegans*\|*Clostridium butyricum, Haemophilus influenzae*\|*Clostridium butyricum, Haemophilus parainfluenzae*\|*Clostridium butyricum, Helicobacter pullorum*\|*Clostridium butyricum, Helicobacter pylori*\|*Clostridium butyricum, Holdemania filiformis*\|*Clostridium butyricum, Kingella oralis*\|*Clostridium butyricum, Klebsiella pneumoniae*\|*Clostridium butyricum, Klebsiella variicola*\|*Clostridium butyricum, Lachnospiraceae bacterium* 5_1_57FAA\|*Clostridium butyricum, Lactobacillus acidophilus*\|*Clostridium butyricum, Lactobacillus amylovorus*\|*Clostridium butyricum, Lactobacillus brevis*\|*Clostridium butyricum, Lactobacillus casei*\|*Clostridium butyricum, Lactobacillus crispatus*\|*Clostridium butyricum, Lactobacillus delbrueckii*\|*Clostridium butyricum, Lactobacillus fermentum*\|*Clostridium butyricum, Lactobacillus gasseri*\|*Clostridium butyricum, Lactobacillus iners*\|*Clostridium butyricum, Lactobacillus jensenii*\|*Clostridium butyricum, Lactobacillus johnsonii*\|*Clostridium butyricum, Lactobacillus paracasei*\|*Clostridium butyricum, Lactobacillus plantarum*\|*Clostridium butyricum, Lactobacillus reuteri*\|*Clostridium butyricum, Lactobacillus rhamnosus*\|*Clostridium butyricum, Lactobacillus ruminis*\|*Clostridium butyricum, Lactobacillus sakei*\|*Clostridium butyricum, Lactobacillus salivarius*\|*Clostridium butyricum, Lactococcus lactis*\|*Clostridium butyricum, Lautropia mirabilis*\|*Clostridium butyricum, Leuconostoc citreum*\|*Clostridium butyricum, Leuconostoc gasicomitatum*\|*Clostridium butyricum, Leuconostoc mesenteroides*\|*Clostridium butyricum, Listeria monocytogenes*\|*Clostridium butyricum, Marvinbryantia formatexigens*\|*Clostridium butyricum, Megamonas hypermegale*\|*Clostridium butyricum, Megasphaera micronuciformis*\|*Clostridium butyricum, Methanobrevibacter smithii*\|*Clostridium butyricum, Methanosphaera stadtmanae*\|*Clostridium butyricum, Methylobacterium radiotolerans*\|*Clostridium butyricum, Mitsuokella multacida*\|*Clostridium butyricum, Mobiluncus curtisii*\|*Clostridium butyricum, Mycoplasma hominis*\|*Clostridium butyricum, Neisseria mucosa*\|*Clostridium butyricum, Odoribacter splanchnicus*\|*Clostridium butyricum, Olsenella uli*\|*Clostridium butyricum, Oribacterium sinus*\|*Clostridium butyricum, Oxalobacter formigenes*\|*Clostridium butyricum, Parabacteroides distasonis*\|*Clostridium butyricum, Parabacteroides johnsonii*\|*Clostridium butyricum, Parabacteroides merdae*\|*Clostridium butyricum, Parvimonas micra*\|*Clostridium butyricum, Pediococcus acidilactici*\|*Clostridium butyricum, Pediococcus pentosaceus*\|*Clostridium butyricum, Peptoniphilus duerdenii*\|*Clostridium butyricum, Peptoniphilus harei*\|*Clostridium butyricum, Peptoniphilus lacrimalis*\|*Clostridium butyricum, Peptostreptococcus anaerobius*\|*Clostridium butyricum, Peptostreptococcus stomatis*\|*Clostridium butyricum, Porphyromonas asaccharolytica*\|*Clostridium butyricum, Porphyromonas uenonis*\|*Clostridium butyricum, Prevotella amnii*\|*Clostridium butyricum, Prevotella bergensis*\|*Clostridium butyricum, Prevotella bivia*\|*Clostridium butyricum, Prevotella buccae*\|*Clostridium butyricum, Prevotella buccalis*\|*Clostridium butyricum, Prevotella copri*\|*Clostridium butyricum, Prevotella disiens*\|*Clostridium butyricum, Prevotella melaninogenica*\|*Clostridium butyricum, Prevotella multiformis*\|*Clostridium butyricum, Prevotella oralis*\|*Clostridium butyricum, Prevotella oris*\|*Clostridium butyricum, Prevotella salivae*\|*Clostridium butyricum, Prevotella timonensis*\|*Clostridium butyricum, Propionibacterium acnes*\|*Clostridium butyricum, Propionibacterium freudenreichii*\|*Clostridium butyricum, Proteus mirabilis*\|*Clostridium butyricum, Proteus penneri*\|*Clostridium butyricum, Pseudoflavonifractor capillosus*\|*Clostridium butyricum, Pseudomonas aeruginosa*\|*Clostridium butyricum, Pseudomonas fluorescens*\|*Clostridium butyricum, Pseudomonas putida*\|*Clostridium butyricum, Pseudoramibacter alactolyticus*\|*Clostridium butyricum, Pyramidobacter piscolens*\|*Clostridium butyricum, Rhodopseudomonas palustris*\|*Clostridium butyricum, Roseburia intestinalis*\|*Clostridium butyricum, Roseburia inulinivorans*\|*Clostridium butyricum, Rothia dentocariosa*\|*Clostridium butyricum, Rothia mucilaginosa*\|*Clostridium butyricum, Ruminococcus albus*\|*Clostridium butyricum, Ruminococcus bromii*\|*Clostridium butyricum, Ruminococcus gnavus*\|*Clostridium butyricum, Ruminococcus lactaris*\|*Clostridium butyricum, Ruminococcus obeum*\|*Clostridium butyricum, Ruminococcus torques*\|*Clostridium butyricum, Selenomonas sputigena*\|*Clostridium butyricum, Shigella boydii*\|*Clostridium butyricum, Shigella dysenteriae*\|*Clostridium butyricum, Shigella sonnei*\|*Clostridium butyricum, Slackia exigua*\|*Clostridium butyricum, Solobacterium moorei*\|*Clostridium butyricum, Staphylococcus aureus*\|*Clostridium butyricum, Staphylococcus epidermidis*\|*Clostridium butyricum, Staphylococcus hominis*\|*Clostridium butyricum, Staphylococcus saprophyticus*\|*Clostridium butyricum, Staphylococcus warneri*\|*Clostridium butyricum, Streptococcus agalactiae*\|*Clostridium butyricum, Streptococcus anginosus*\|*Clostridium butyricum, Streptococcus australis*\|*Clostridium butyricum, Streptococcus bovis*\|*Clostridium butyricum, Streptococcus cristatus*\|*Clostridium butyricum, Streptococcus dysgalactiae*\|*Clostridium butyricum, Streptococcus equinus*\|*Clostridium butyricum, Streptococcus gordonii*\|*Clostridium butyricum, Streptococcus infantarius*\|*Clostridium butyricum, Streptococcus infantis*\|*Clostridium butyricum, Streptococcus mitis*\|*Clostridium butyricum, Streptococcus mutans*\|*Clostridium butyricum, Streptococcus oralis*\|*Clostridium butyricum, Streptococcus parasanguinis*\|*Clostridium butyricum, Streptococcus peroris*\|*Clostridium butyricum, Streptococcus pneumoniae*\|*Clostridium butyricum, Streptococcus salivarius*\|*Clostridium butyricum, Streptococcus sanguinis*\|*Clostridium butyricum, Streptococcus thermophilus*\|*Clostridium butyricum, Streptococcus vestibularis*\|*Clostridium butyricum, Subdoligranulum variabile*\|*Clostridium butyricum, Succinatimonas hippei*\|*Clostridium butyricum, Sutterella wadsworthensis*\|*Clostridium butyricum, Tropheryma whipplei*\|*Clostridium butyricum, Veillonella atypica*\|*Clostridium butyricum, Veillonella dispar*\|*Clostridium butyricum, Veillonella parvula*\|*Clostridium butyricum, Victivallis vadensis*\|*Clostridium difficile, Clostridium difficile*\|*Clostridium difficile, Clostridium disporicum*\|*Clostridium difficile, Clostridium hathewayi*\|*Clostridium difficile, Clostridium hylemonae*\|*Clostridium difficile, Clostridium innocuum*\|*Clostridium difficile, Clostridium leptum*\|*Clostridium difficile, Clostridium mayombei*\|*Clostridium difficile, Clostridium methylpentosum*\|*Clostridium difficile, Clostridium nexile*\|*Clostridium difficile, Clostridium orbiscindens*\|*Clostridium difficile, Clostridium perfringens*\|*Clostridium difficile, Clostridium saccharolyticum*\|*Clostridium difficile, Clostridium scindens*\|*Clostridium difficile, Clostridium symbiosum*\|*Clostridium difficile, Clostridium tertium*\|*Clostridium difficile, Collinsella aerofaciens*\|*Clostridium difficile, Collinsella intestinalis*\|*Clostridium difficile, Collinsella stercoris*\|*Clostridium difficile, Coprobacillus* sp. D7\|*Clostridium difficile, Coprococcus catus*\|*Clostridium difficile, Coprococcus comes*\|*Clostridium difficile, Coprococcus eutactus*\|*Clostridium difficile, Corynebacterium aurimucosum*\|*Clostridium difficile, Corynebacterium matruchotii*\|*Clostridium difficile, Cryptobacterium curtum*\|*Clostridium difficile, Desulfovibrio desulfuricans*\|*Clostridium difficile, Desulfovibrio piger*\|*Clostridium difficile, Dialister invisus*\|*Clostridium difficile, Dialister microaerophilus*\|*Clostridium difficile, Dorea formicigenerans*\|*Clostridium difficile, Dorea longicatena*\|*Clostridium difficile, Eggerthella lenta*\|*Clostridium difficile, Eikenella corrodens*\|*Clostridium difficile, Enterobacter cancerogenus*\|*Clostridium difficile, Enterobacter cloacae*\|*Clostridium difficile, Enterococcus faecalis*\|*Clostridium difficile, Enterococcus faecium*\|*Clostridium difficile, Enterococcus gallinarum*\|*Clostridium difficile, Erysipelotrichaceae bacterium* 3_1_53\|*Clostridium difficile, Escherichia coli*\|*Clostridium difficile, Escherichia fergusonii*\|*Clostridium difficile, Ethanoligenens harbinense*\|*Clostridium difficile, Eubacterium cellulosolvens*\|*Clostridium difficile, Eubacterium eligens*\|*Clostridium difficile, Eubacterium hallii*\|*Clostridium difficile, Eubacterium limosum*\|*Clostridium difficile, Eubacterium rectale*\|*Clostridium difficile, Eubacterium siraeum*\|*Clostridium difficile, Eubacterium ventriosum*\|*Clostridium difficile, Faecalibacterium prausnitzii*\|*Clostridium difficile, Finegoldia magna*\|*Clostridium difficile, Fusobacterium gonidiaformans*\|*Clostridium difficile, Fusobacterium mortiferum*\|*Clostridium difficile, Fusobacterium nucleatum*\|*Clostridium difficile, Fusobacterium varium*\|*Clostridium difficile, Gardnerella vaginalis*\|*Clostridium difficile, Gemella haemolysans*\|*Clostridium difficile, Gemella morbillorum*\|*Clostridium difficile, Gordonibacter pamelaeae*\|*Clostridium difficile, Granulicatella adiacens*\|*Clostridium difficile, Granulicatella elegans*\|*Clostridium difficile, Haemophilus influenzae*\|*Clostridium difficile, Haemophilus parainfluenzae*\|*Clostridium difficile, Helicobacter pullorum*\|*Clostridium difficile, Helicobacter pylori*\|*Clostridium difficile, Holdemania filiformis*\|*Clostridium difficile, Kingella oralis*\|*Clostridium difficile, Klebsiella pneumoniae*\|*Clostridium difficile, Klebsiella variicola*\|*Clostridium difficile, Lachnospiraceae bacterium* 5_1_57FAA\|*Clostridium difficile, Lactobacillus acidophilus*\|*Clostridium difficile, Lactobacillus amylovorus*\|*Clostridium difficile, Lactobacillus brevis*\|*Clostridium difficile, Lactobacillus casei*\|*Clostridium difficile, Lactobacillus crispatus*\|*Clostridium difficile, Lactobacillus delbrueckii*\|*Clostridium difficile, Lactobacillus fermentum*\|*Clostridium difficile, Lactobacillus gasseri*\|*Clostridium difficile, Lactobacillus iners*\|*Clostridium difficile, Lactobacillus jensenii*\|*Clostridium difficile, Lactobacillus johnsonii*\|*Clostridium difficile, Lactobacillus paracasei*\|*Clostridium difficile, Lactobacillus plantarum*\|*Clostridium difficile, Lactobacillus reuteri*\|*Clostridium difficile, Lactobacillus rhamnosus*\|*Clostridium difficile, Lactobacillus ruminis*\|*Clostridium difficile, Lactobacillus* |

TABLE 2-continued

Table 2. Specific binary combinations of OTUs. Individual pairings are differentiated by "|" and OTUs within a combination are differentiated by ","

*sakei*|*Clostridium difficile*, *Lactobacillus salivarius*|*Clostridium difficile*, *Lactococcus lactis*|*Clostridium difficile*, *Lautropia mirabilis*|*Clostridium difficile*, *Leuconostoc citreum*|*Clostridium difficile*, *Leuconostoc gasicomitatum*|*Clostridium difficile*, *Leuconostoc mesenteroides*|*Clostridium difficile*, *Listeria monocytogenes*|*Clostridium difficile*, *Marvinbryantia formatexigens*|*Clostridium difficile*, *Megamonas hypermegale*|*Clostridium difficile*, *Megasphaera micronuciformis*|*Clostridium difficile*, *Methanobrevibacter smithii*|*Clostridium difficile*, *Methanosphaera stadtmanae*|*Clostridium difficile*, *Methylobacterium radiotolerans*|*Clostridium difficile*, *Mitsuokella multacida*|*Clostridium difficile*, *Mobiluncus curtisii*|*Clostridium difficile*, *Mycoplasma hominis*|*Clostridium difficile*, *Neisseria mucosa*|*Clostridium difficile*, *Odoribacter splanchnicus*|*Clostridium difficile*, *Olsenella uli*|*Clostridium difficile*, *Oribacterium sinus*|*Clostridium difficile*, *Oxalobacter formigenes*|*Clostridium difficile*, *Parabacteroides distasonis*|*Clostridium difficile*, *Parabacteroides johnsonii*|*Clostridium difficile*, *Parabacteroides merdae*|*Clostridium difficile*, *Parvimonas micra*|*Clostridium difficile*, *Pediococcus acidilactici*|*Clostridium difficile*, *Pediococcus pentosaceus*|*Clostridium difficile*, *Peptoniphilus duerdenii*|*Clostridium difficile*, *Peptoniphilus harei*|*Clostridium difficile*, *Peptoniphilus lacrimalis*|*Clostridium difficile*, *Peptostreptococcus anaerobius*|*Clostridium difficile*, *Peptostreptococcus stomatis*|*Clostridium difficile*, *Porphyromonas asaccharolytica*|*Clostridium difficile*, *Porphyromonas uenonis*|*Clostridium difficile*, *Prevotella amnii*|*Clostridium difficile*, *Prevotella bergensis*|*Clostridium difficile*, *Prevotella bivia*|*Clostridium difficile*, *Prevotella buccae*|*Clostridium difficile*, *Prevotella buccalis*|*Clostridium difficile*, *Prevotella copri*|*Clostridium difficile*, *Prevotella disiens*|*Clostridium difficile*, *Prevotella melaninogenica*|*Clostridium difficile*, *Prevotella multiformis*|*Clostridium difficile*, *Prevotella oralis*|*Clostridium difficile*, *Prevotella oris*|*Clostridium difficile*, *Prevotella salivae*|*Clostridium difficile*, *Prevotella timonensis*|*Clostridium difficile*, *Propionibacterium acnes*|*Clostridium difficile*, *Propionibacterium freudenreichii*|*Clostridium difficile*, *Proteus mirabilis*|*Clostridium difficile*, *Proteus penneri*|*Clostridium difficile*, *Pseudoflavonifractor capillosus*|*Clostridium difficile*, *Pseudomonas aeruginosa*|*Clostridium difficile*, *Pseudomonas fluorescens*|*Clostridium difficile*, *Pseudomonas putida*|*Clostridium difficile*, *Pseudoramibacter alactolyticus*|*Clostridium difficile*, *Pyramidobacter piscolens*|*Clostridium difficile*, *Rhodopseudomonas palustris*|*Clostridium difficile*, *Roseburia intestinalis*|*Clostridium difficile*, *Roseburia inulinivorans*|*Clostridium difficile*, *Rothia dentocariosa*|*Clostridium difficile*, *Rothia mucilaginosa*|*Clostridium difficile*, *Ruminococcus albus*|*Clostridium difficile*, *Ruminococcus bromii*|*Clostridium difficile*, *Ruminococcus gnavus*|*Clostridium difficile*, *Ruminococcus lactaris*|*Clostridium difficile*, *Ruminococcus obeum*|*Clostridium difficile*, *Ruminococcus torques*|*Clostridium difficile*, *Selenomonas sputigena*|*Clostridium difficile*, *Shigella boydii*|*Clostridium difficile*, *Shigella dysenteriae*|*Clostridium difficile*, *Shigella sonnei*|*Clostridium difficile*, *Slackia exigua*|*Clostridium difficile*, *Solobacterium moorei*|*Clostridium difficile*, *Staphylococcus aureus*|*Clostridium difficile*, *Staphylococcus epidermidis*|*Clostridium difficile*, *Staphylococcus hominis*|*Clostridium difficile*, *Staphylococcus saprophyticus*|*Clostridium difficile*, *Staphylococcus warneri*|*Clostridium difficile*, *Streptococcus agalactiae*|*Clostridium difficile*, *Streptococcus anginosus*|*Clostridium difficile*, *Streptococcus australis*|*Clostridium difficile*, *Streptococcus bovis*|*Clostridium difficile*, *Streptococcus cristatus*|*Clostridium difficile*, *Streptococcus dysgalactiae*|*Clostridium difficile*, *Streptococcus equinus*|*Clostridium difficile*, *Streptococcus gordonii*|*Clostridium difficile*, *Streptococcus infantarius*|*Clostridium difficile*, *Streptococcus infantis*|*Clostridium difficile*, *Streptococcus mitis*|*Clostridium difficile*, *Streptococcus mutans*|*Clostridium difficile*, *Streptococcus oralis*|*Clostridium difficile*, *Streptococcus parasanguinis*|*Clostridium difficile*, *Streptococcus peroris*|*Clostridium difficile*, *Streptococcus pneumoniae*|*Clostridium difficile*, *Streptococcus salivarius*|*Clostridium difficile*, *Streptococcus sanguinis*|*Clostridium difficile*, *Streptococcus thermophilus*|*Clostridium difficile*, *Streptococcus vestibularis*|*Clostridium difficile*, *Subdoligranulum variabile*|*Clostridium difficile*, *Succinatimonas hippei*|*Clostridium difficile*, *Sutterella wadsworthensis*|*Clostridium difficile*, *Tropheryma whipplei*|*Clostridium difficile*, *Veillonella atypica*|*Clostridium difficile*, *Veillonella dispar*|*Clostridium difficile*, *Veillonella parvula*|*Clostridium difficile*, *Victivallis vadensis*|*Clostridium disporicum*, *Clostridium disporicum*|*Clostridium disporicum*, *Clostridium hathewayi*|*Clostridium disporicum*, *Clostridium hylemonae*|*Clostridium disporicum*, *Clostridium innocuum*|*Clostridium disporicum*, *Clostridium leptum*|*Clostridium disporicum*, *Clostridium mayombei*|*Clostridium disporicum*, *Clostridium methylpentosum*|*Clostridium disporicum*, *Clostridium nexile*|*Clostridium disporicum*, *Clostridium orbiscindens*|*Clostridium disporicum*, *Clostridium perfringens*|*Clostridium disporicum*, *Clostridium saccharolyticum*|*Clostridium disporicum*, *Clostridium scindens*|*Clostridium disporicum*, *Clostridium symbiosum*|*Clostridium disporicum*, *Clostridium tertium*|*Clostridium disporicum*, *Collinsella aerofaciens*|*Clostridium disporicum*, *Collinsella intestinalis*|*Clostridium disporicum*, *Collinsella stercoris*|*Clostridium disporicum*, *Coprobacillus* sp. D7|*Clostridium disporicum*, *Coprococcus catus*|*Clostridium disporicum*, *Coprococcus comes*|*Clostridium disporicum*, *Coprococcus eutactus*|*Clostridium disporicum*, *Corynebacterium aurimucosum*|*Clostridium disporicum*, *Corynebacterium matruchotii*|*Clostridium disporicum*, *Cryptobacterium curtum*|*Clostridium disporicum*, *Desulfovibrio desulfuricans*|*Clostridium disporicum*, *Desulfovibrio piger*|*Clostridium disporicum*, *Dialister invisus*|*Clostridium disporicum*, *Dialister microaerophilus*|*Clostridium disporicum*, *Dorea formicigenerans*|*Clostridium disporicum*, *Dorea longicatena*|*Clostridium disporicum*, *Eggerthella lenta*|*Clostridium disporicum*, *Eikenella corrodens*|*Clostridium disporicum*, *Enterobacter cancerogenus*|*Clostridium disporicum*, *Enterobacter cloacae*|*Clostridium disporicum*, *Enterococcus faecalis*|*Clostridium disporicum*, *Enterococcus faecium*|*Clostridium disporicum*, *Enterococcus gallinarum*|*Clostridium disporicum*, *Erysipelotrichaceae bacterium* 3_1_53|*Clostridium disporicum*, *Escherichia coli*|*Clostridium disporicum*, *Escherichia fergusonii*|*Clostridium disporicum*, *Ethanoligenens harbinense*|*Clostridium disporicum*, *Eubacterium cellulosolvens*|*Clostridium disporicum*, *Eubacterium eligens*|*Clostridium disporicum*, *Eubacterium hallii*|*Clostridium disporicum*, *Eubacterium limosum*|*Clostridium disporicum*, *Eubacterium rectale*|*Clostridium disporicum*, *Eubacterium siraeum*|*Clostridium disporicum*, *Eubacterium ventriosum*|*Clostridium disporicum*, *Faecalibacterium prausnitzii*|*Clostridium disporicum*, *Finegoldia magna*|*Clostridium disporicum*, *Fusobacterium gonidiaformans*|*Clostridium disporicum*, *Fusobacterium mortiferum*|*Clostridium disporicum*, *Fusobacterium nucleatum*|*Clostridium disporicum*, *Fusobacterium varium*|*Clostridium disporicum*, *Gardnerella vaginalis*|*Clostridium disporicum*, *Gemella haemolysans*|*Clostridium disporicum*, *Gemella morbillorum*|*Clostridium disporicum*, *Gordonibacter pamelaeae*|*Clostridium disporicum*, *Granulicatella adiacens*|*Clostridium disporicum*, *Granulicatella elegans*|*Clostridium disporicum*, *Haemophilus influenzae*|*Clostridium disporicum*, *Haemophilus parainfluenzae*|*Clostridium disporicum*, *Helicobacter pullorum*|*Clostridium disporicum*, *Helicobacter pylori*|*Clostridium disporicum*, *Holdemania filiformis*|*Clostridium disporicum*, *Kingella oralis*|*Clostridium disporicum*, *Klebsiella pneumoniae*|*Clostridium disporicum*, *Klebsiella variicola*|*Clostridium disporicum*, *Lachnospiraceae bacterium* 5_1_57FAA|*Clostridium disporicum*, *Lactobacillus acidophilus*|*Clostridium disporicum*, *Lactobacillus amylovorus*|*Clostridium disporicum*, *Lactobacillus brevis*|*Clostridium disporicum*, *Lactobacillus casei*|*Clostridium disporicum*, *Lactobacillus crispatus*|*Clostridium disporicum*, *Lactobacillus delbrueckii*|*Clostridium disporicum*, *Lactobacillus fermentum*|*Clostridium disporicum*, *Lactobacillus gasseri*|*Clostridium disporicum*, *Lactobacillus iners*|*Clostridium disporicum*, *Lactobacillus jensenii*|*Clostridium disporicum*, *Lactobacillus johnsonii*|*Clostridium disporicum*, *Lactobacillus paracasei*|*Clostridium disporicum*, *Lactobacillus plantarum*|*Clostridium disporicum*, *Lactobacillus reuteri*|*Clostridium disporicum*, *Lactobacillus rhamnosus*|*Clostridium disporicum*, *Lactobacillus ruminis*|*Clostridium disporicum*, *Lactobacillus sakei*|*Clostridium disporicum*, *Lactobacillus salivarius*|*Clostridium disporicum*, *Lactococcus lactis*|*Clostridium disporicum*, *Lautropia mirabilis*|*Clostridium disporicum*, *Leuconostoc citreum*|*Clostridium disporicum*, *Leuconostoc gasicomitatum*|*Clostridium disporicum*, *Leuconostoc mesenteroides*|*Clostridium disporicum*, *Listeria monocytogenes*|*Clostridium disporicum*, *Marvinbryantia formatexigens*|*Clostridium disporicum*, *Megamonas hypermegale*|*Clostridium disporicum*, *Megasphaera micronuciformis*|*Clostridium disporicum*, *Methanobrevibacter smithii*|*Clostridium disporicum*, *Methanosphaera stadtmanae*|*Clostridium disporicum*, *Methylobacterium radiotolerans*|*Clostridium disporicum*, *Mitsuokella multacida*|*Clostridium disporicum*, *Mobiluncus curtisii*|*Clostridium disporicum*, *Mycoplasma hominis*|*Clostridium disporicum*, *Neisseria mucosa*|*Clostridium disporicum*, *Odoribacter splanchnicus*|*Clostridium disporicum*, *Olsenella uli*|*Clostridium disporicum*, *Oribacterium sinus*|*Clostridium disporicum*, *Oxalobacter formigenes*|*Clostridium disporicum*, *Parabacteroides distasonis*|*Clostridium disporicum*, *Parabacteroides johnsonii*|*Clostridium disporicum*, *Parabacteroides merdae*|*Clostridium disporicum*, *Parvimonas*

TABLE 2-continued

Table 2. Specific binary combinations of OTUs. Individual pairings are differentiated by "|" and OTUs within a combination are differentiated by ","

micra|Clostridium disporicum, Pediococcus acidilactici|Clostridium disporicum, Pediococcus pentosaceus|Clostridium disporicum, Peptoniphilus duerdenii|Clostridium disporicum, Peptoniphilus harei|Clostridium disporicum, Peptoniphilus lacrimalis|Clostridium disporicum, Peptostreptococcus anaerobius|Clostridium disporicum, Peptostreptococcus stomatis|Clostridium disporicum, Porphyromonas asaccharolytica|Clostridium disporicum, Porphyromonas uenonis|Clostridium disporicum, Prevotella amnii|Clostridium disporicum, Prevotella bergensis|Clostridium disporicum, Prevotella bivia|Clostridium disporicum, Prevotella buccae|Clostridium disporicum, Prevotella buccalis|Clostridium disporicum, Prevotella copri|Clostridium disporicum, Prevotella disiens|Clostridium disporicum, Prevotella melaninogenica|Clostridium disporicum, Prevotella multiformis|Clostridium disporicum, Prevotella oralis|Clostridium disporicum, Prevotella oris|Clostridium disporicum, Prevotella salivae|Clostridium disporicum, Prevotella timonensis|Clostridium disporicum, Propionibacterium acnes|Clostridium disporicum, Propionibacterium freudenreichii|Clostridium disporicum, Proteus mirabilis|Clostridium disporicum, Proteus penneri|Clostridium disporicum, Pseudoflavonifractor capillosus|Clostridium disporicum, Pseudomonas aeruginosa|Clostridium disporicum, Pseudomonas fluorescens|Clostridium disporicum, Pseudomonas putida|Clostridium disporicum, Pseudoramibacter alactolyticus|Clostridium disporicum, Pyramidobacter piscolens|Clostridium disporicum, Rhodopseudomonas palustris|Clostridium disporicum, Roseburia intestinalis|Clostridium disporicum, Roseburia inulinivorans|Clostridium disporicum, Rothia dentocariosa|Clostridium disporicum, Rothia mucilaginosa|Clostridium disporicum, Ruminococcus albus|Clostridium disporicum, Ruminococcus bromii|Clostridium disporicum, Ruminococcus gnavus|Clostridium disporicum, Ruminococcus lactaris|Clostridium disporicum, Ruminococcus obeum|Clostridium disporicum, Ruminococcus torques|Clostridium disporicum, Selenomonas sputigena|Clostridium disporicum, Shigella boydii|Clostridium disporicum, Shigella dysenteriae|Clostridium disporicum, Shigella sonnei|Clostridium disporicum, Slackia exigua|Clostridium disporicum, Solobacterium moorei|Clostridium disporicum, Staphylococcus aureus|Clostridium disporicum, Staphylococcus epidermidis|Clostridium disporicum, Staphylococcus hominis|Clostridium disporicum, Staphylococcus saprophyticus|Clostridium disporicum, Staphylococcus warneri|Clostridium disporicum, Streptococcus agalactiae|Clostridium disporicum, Streptococcus anginosus|Clostridium disporicum, Streptococcus australis|Clostridium disporicum, Streptococcus bovis|Clostridium disporicum, Streptococcus cristatus|Clostridium disporicum, Streptococcus dysgalactiae|Clostridium disporicum, Streptococcus equinus|Clostridium disporicum, Streptococcus gordonii|Clostridium disporicum, Streptococcus infantarius|Clostridium disporicum, Streptococcus infantis|Clostridium disporicum, Streptococcus mitis|Clostridium disporicum, Streptococcus mutans|Clostridium disporicum, Streptococcus oralis|Clostridium disporicum, Streptococcus parasanguinis|Clostridium disporicum, Streptococcus peroris|Clostridium disporicum, Streptococcus pneumoniae|Clostridium disporicum, Streptococcus salivarius|Clostridium disporicum, Streptococcus sanguinis|Clostridium disporicum, Streptococcus thermophilus|Clostridium disporicum, Streptococcus vestibularis|Clostridium disporicum, Subdoligranulum variabile|Clostridium disporicum, Succinatimonas hippei|Clostridium disporicum, Sutterella wadsworthensis|Clostridium disporicum, Tropheryma whipplei|Clostridium disporicum, Veillonella atypica|Clostridium disporicum, Veillonella dispar|Clostridium disporicum, Veillonella parvula|Clostridium disporicum, Victivallis vadensis|Clostridium hathewayi, Clostridium hathewayi|Clostridium hathewayi, Clostridium hylemonae|Clostridium hathewayi, Clostridium innocuum|Clostridium hathewayi, Clostridium leptum|Clostridium hathewayi, Clostridium mayombei|Clostridium hathewayi, Clostridium methylpentosum|Clostridium hathewayi, Clostridium nexile|Clostridium hathewayi, Clostridium orbiscindens|Clostridium hathewayi, Clostridium perfringens|Clostridium hathewayi, Clostridium saccharolyticum|Clostridium hathewayi, Clostridium scindens|Clostridium hathewayi, Clostridium symbiosum|Clostridium hathewayi, Clostridium tertium|Clostridium hathewayi, Collinsella aerofaciens|Clostridium hathewayi, Collinsella intestinalis|Clostridium hathewayi, Collinsella stercoris|Clostridium hathewayi, Coprobacillus sp. D7|Clostridium hathewayi, Coprococcus catus|Clostridium hathewayi, Coprococcus comes|Clostridium hathewayi, Coprococcus eutactus|Clostridium hathewayi, Corynebacterium aurimucosum|Clostridium hathewayi, Corynebacterium matruchotii|Clostridium hathewayi, Cryptobacterium curtum|Clostridium hathewayi, Desulfovibrio desulfuricans|Clostridium hathewayi, Desulfovibrio piger|Clostridium hathewayi, Dialister invisus|Clostridium hathewayi, Dialister microaerophilus|Clostridium hathewayi, Dorea formicigenerans|Clostridium hathewayi, Dorea longicatena|Clostridium hathewayi, Eggerthella lenta|Clostridium hathewayi, Eikenella corrodens|Clostridium hathewayi, Enterobacter cancerogenus|Clostridium hathewayi, Enterobacter cloacae|Clostridium hathewayi, Enterococcus faecalis|Clostridium hathewayi, Enterococcus faecium|Clostridium hathewayi, Enterococcus gallinarum|Clostridium hathewayi, Erysipelotrichaceae bacterium 3_1_53|Clostridium hathewayi, Escherichia coli|Clostridium hathewayi, Escherichia fergusonii|Clostridium hathewayi, Ethanoligenens harbinense|Clostridium hathewayi, Eubacterium cellulosolvens|Clostridium hathewayi, Eubacterium eligens|Clostridium hathewayi, Eubacterium hallii|Clostridium hathewayi, Eubacterium limosum|Clostridium hathewayi, Eubacterium rectale|Clostridium hathewayi, Eubacterium siraeum|Clostridium hathewayi, Eubacterium ventriosum|Clostridium hathewayi, Faecalibacterium prausnitzii|Clostridium hathewayi, Finegoldia magna|Clostridium hathewayi, Fusobacterium gonidiaformans|Clostridium hathewayi, Fusobacterium mortiferum|Clostridium hathewayi, Fusobacterium nucleatum|Clostridium hathewayi, Fusobacterium varium|Clostridium hathewayi, Gardnerella vaginalis|Clostridium hathewayi, Gemella haemolysans|Clostridium hathewayi, Gemella morbillorum|Clostridium hathewayi, Gordonibacter pamelaeae|Clostridium hathewayi, Granulicatella adiacens|Clostridium hathewayi, Granulicatella elegans|Clostridium hathewayi, Haemophilus influenzae|Clostridium hathewayi, Haemophilus parainfluenzae|Clostridium hathewayi, Helicobacter pullorum|Clostridium hathewayi, Helicobacter pylori|Clostridium hathewayi, Holdemania filiformis|Clostridium hathewayi, Kingella oralis|Clostridium hathewayi, Klebsiella pneumoniae|Clostridium hathewayi, Klebsiella variicola|Clostridium hathewayi, Lachnospiraceae bacterium 5_1_57FAA|Clostridium hathewayi, Lactobacillus acidophilus|Clostridium hathewayi, Lactobacillus amylovorus|Clostridium hathewayi, Lactobacillus brevis|Clostridium hathewayi, Lactobacillus casei|Clostridium hathewayi, Lactobacillus crispatus|Clostridium hathewayi, Lactobacillus delbrueckii|Clostridium hathewayi, Lactobacillus fermentum|Clostridium hathewayi, Lactobacillus gasseri|Clostridium hathewayi, Lactobacillus iners|Clostridium hathewayi, Lactobacillus jensenii|Clostridium hathewayi, Lactobacillus johnsonii|Clostridium hathewayi, Lactobacillus paracasei|Clostridium hathewayi, Lactobacillus plantarum|Clostridium hathewayi, Lactobacillus reuteri|Clostridium hathewayi, Lactobacillus rhamnosus|Clostridium hathewayi, Lactobacillus ruminis|Clostridium hathewayi, Lactobacillus sakei|Clostridium hathewayi, Lactobacillus salivarius|Clostridium hathewayi, Lactococcus lactis|Clostridium hathewayi, Lautropia mirabilis|Clostridium hathewayi, Leuconostoc citreum|Clostridium hathewayi, Leuconostoc gasicomitatum|Clostridium hathewayi, Leuconostoc mesenteroides|Clostridium hathewayi, Listeria monocytogenes|Clostridium hathewayi, Marvinbryantia formatexigens|Clostridium hathewayi, Megamonas hypermegale|Clostridium hathewayi, Megasphaera micronuciformis|Clostridium hathewayi, Methanobrevibacter smithii|Clostridium hathewayi, Methanosphaera stadtmanae|Clostridium hathewayi, Methylobacterium radiotolerans|Clostridium hathewayi, Mitsuokella multacida|Clostridium hathewayi, Mobiluncus curtisii|Clostridium hathewayi, Mycoplasma hominis|Clostridium hathewayi, Neisseria mucosa|Clostridium hathewayi, Odoribacter splanchnicus|Clostridium hathewayi, Olsenella uli|Clostridium hathewayi, Oribacterium sinus|Clostridium hathewayi, Oxalobacter formigenes|Clostridium hathewayi, Parabacteroides distasonis|Clostridium hathewayi, Parabacteroides johnsonii|Clostridium hathewayi, Parabacteroides merdae|Clostridium hathewayi, Parvimonas micra|Clostridium hathewayi, Pediococcus acidilactici|Clostridium hathewayi, Pediococcus pentosaceus|Clostridium hathewayi, Peptoniphilus duerdenii|Clostridium hathewayi, Peptoniphilus harei|Clostridium hathewayi, Peptoniphilus lacrimalis|Clostridium hathewayi, Peptostreptococcus anaerobius|Clostridium hathewayi, Peptostreptococcus stomatis|Clostridium hathewayi, Porphyromonas asaccharolytica|Clostridium hathewayi, Porphyromonas uenonis|Clostridium hathewayi, Prevotella amnii|Clostridium hathewayi, Prevotella bergensis|Clostridium hathewayi, Prevotella bivia|Clostridium hathewayi, Prevotella buccae|Clostridium hathewayi, Prevotella buccalis|Clostridium hathewayi, Prevotella copri|Clostridium hathewayi, Prevotella disiens|Clostridium hathewayi, Prevotella melaninogenica|Clostridium hathewayi, Prevotella multiformis|Clostridium hathewayi, Prevotella oralis|Clostridium hathewayi, Prevotella oris|Clostridium hathewayi, Prevotella salivae|Clostridium TABLE 2-continued Table 2. Specific binary combinations of OTUs. Individual pairings are differentiated by "|" and OTUs within a combination are differentiated by ","

hathewayi, Prevotella timonensis|Clostridium hathewayi, Propionibacterium acnes|Clostridium hathewayi, Propionibacterium freudenreichii|Clostridium hathewayi, Proteus mirabilis|Clostridium hathewayi, Proteus penneri|Clostridium hathewayi, Pseudoflavonifractor capillosus|Clostridium hathewayi, Pseudomonas aeruginosa|Clostridium hathewayi, Pseudomonas fluorescens|Clostridium hathewayi, Pseudomonas putida|Clostridium hathewayi, Pseudoramibacter alactolyticus|Clostridium hathewayi, Pyramidobacter piscolens|Clostridium hathewayi, Rhodopseudomonas palustris|Clostridium hathewayi, Roseburia intestinalis|Clostridium hathewayi, Roseburia inulinivorans|Clostridium hathewayi, Rothia dentocariosa|Clostridium hathewayi, Rothia mucilaginosa|Clostridium hathewayi, Ruminococcus albus|Clostridium hathewayi, Ruminococcus bromii|Clostridium hathewayi, Ruminococcus gnavus|Clostridium hathewayi, Ruminococcus lactaris|Clostridium hathewayi, Ruminococcus obeum|Clostridium hathewayi, Ruminococcus torques|Clostridium hathewayi, Selenomonas sputigena|Clostridium hathewayi, Shigella boydii|Clostridium hathewayi, Shigella dysenteriae|Clostridium hathewayi, Shigella sonnei|Clostridium hathewayi, Slackia exigua|Clostridium hathewayi, Solobacterium moorei|Clostridium hathewayi, Staphylococcus aureus|Clostridium hathewayi, Staphylococcus epidermidis|Clostridium hathewayi, Staphylococcus hominis|Clostridium hathewayi, Staphylococcus saprophyticus|Clostridium hathewayi, Staphylococcus warneri|Clostridium hathewayi, Streptococcus agalactiae|Clostridium hathewayi, Streptococcus anginosus|Clostridium hathewayi, Streptococcus australis|Clostridium hathewayi, Streptococcus bovis|Clostridium hathewayi, Streptococcus cristatus|Clostridium hathewayi, Streptococcus dysgalactiae|Clostridium hathewayi, Streptococcus equinus|Clostridium hathewayi, Streptococcus gordonii|Clostridium hathewayi, Streptococcus infantarius|Clostridium hathewayi, Streptococcus infantis|Clostridium hathewayi, Streptococcus mitis|Clostridium hathewayi, Streptococcus mutans|Clostridium hathewayi, Streptococcus oralis|Clostridium hathewayi, Streptococcus parasanguinis|Clostridium hathewayi, Streptococcus peroris|Clostridium hathewayi, Streptococcus pneumoniae|Clostridium hathewayi, Streptococcus salivarius|Clostridium hathewayi, Streptococcus sanguinis|Clostridium hathewayi, Streptococcus thermophilus|Clostridium hathewayi, Streptococcus vestibularis|Clostridium hathewayi, Subdoligranulum variabile|Clostridium hathewayi, Succinatimonas hippei|Clostridium hathewayi, Sutterella wadsworthensis|Clostridium hathewayi, Tropheryma whipplei|Clostridium hathewayi, Veillonella atypica|Clostridium hathewayi, Veillonella dispar|Clostridium hathewayi, Veillonella parvula|Clostridium hathewayi, Victivallis vadensis|Clostridium hylemonae, Clostridium hylemonae|Clostridium hylemonae, Clostridium innocuum|Clostridium hylemonae, Clostridium leptum|Clostridium hylemonae, Clostridium mayombei|Clostridium hylemonae, Clostridium methylpentosum|Clostridium hylemonae, Clostridium nexile|Clostridium hylemonae, Clostridium orbiscindens|Clostridium hylemonae, Clostridium perfringens|Clostridium hylemonae, Clostridium saccharolyticum|Clostridium hylemonae, Clostridium scindens|Clostridium hylemonae, Clostridium symbiosum|Clostridium hylemonae, Clostridium tertium|Clostridium hylemonae, Collinsella aerofaciens|Clostridium hylemonae, Collinsella intestinalis|Clostridium hylemonae, Collinsella stercoris|Clostridium hylemonae, Coprobacillus sp. D7|Clostridium hylemonae, Coprococcus catus|Clostridium hylemonae, Coprococcus comes|Clostridium hylemonae, Coprococcus eutactus|Clostridium hylemonae, Corynebacterium aurimucosum|Clostridium hylemonae, Corynebacterium matruchotii|Clostridium hylemonae, Cryptobacterium curtum|Clostridium hylemonae, Desulfovibrio desulfuricans|Clostridium hylemonae, Desulfovibrio piger|Clostridium hylemonae, Dialister invisus|Clostridium hylemonae, Dialister microaerophilus|Clostridium hylemonae, Dorea formicigenerans|Clostridium hylemonae, Dorea longicatena|Clostridium hylemonae, Eggerthella lenta|Clostridium hylemonae, Eikenella corrodens|Clostridium hylemonae, Enterobacter cancerogenus|Clostridium hylemonae, Enterobacter cloacae|Clostridium hylemonae, Enterococcus faecalis|Clostridium hylemonae, Enterococcus faecium|Clostridium hylemonae, Enterococcus gallinarum|Clostridium hylemonae, Erysipelotrichaceae bacterium 3_1_53|Clostridium hylemonae, Escherichia coli|Clostridium hylemonae, Escherichia fergusonii|Clostridium hylemonae, Ethanoligenens harbinense|Clostridium hylemonae, Eubacterium cellulosolvens|Clostridium hylemonae, Eubacterium eligens|Clostridium hylemonae, Eubacterium hallii|Clostridium hylemonae, Eubacterium limosum|Clostridium hylemonae, Eubacterium rectale|Clostridium hylemonae, Eubacterium siraeum|Clostridium hylemonae, Eubacterium ventriosum|Clostridium hylemonae, Faecalibacterium prausnitzii|Clostridium hylemonae, Finegoldia magna|Clostridium hylemonae, Fusobacterium gonidiaformans|Clostridium hylemonae, Fusobacterium mortiferum|Clostridium hylemonae, Fusobacterium nucleatum|Clostridium hylemonae, Fusobacterium varium|Clostridium hylemonae, Gardnerella vaginalis|Clostridium hylemonae, Gemella haemolysans|Clostridium hylemonae, Gemella morbillorum|Clostridium hylemonae, Gordonibacter pamelaeae|Clostridium hylemonae, Granulicatella adiacens|Clostridium hylemonae, Granulicatella elegans|Clostridium hylemonae, Haemophilus influenzae|Clostridium hylemonae, Haemophilus parainfluenzae|Clostridium hylemonae, Helicobacter pullorum|Clostridium hylemonae, Helicobacter pylori|Clostridium hylemonae, Holdemania filiformis|Clostridium hylemonae, Kingella oralis|Clostridium hylemonae, Klebsiella pneumoniae|Clostridium hylemonae, Klebsiella variicola|Clostridium hylemonae, Lachnospiraceae bacterium 5_1_57FAA|Clostridium hylemonae, Lactobacillus acidophilus|Clostridium hylemonae, Lactobacillus amylovorus|Clostridium hylemonae, Lactobacillus brevis|Clostridium hylemonae, Lactobacillus casei|Clostridium hylemonae, Lactobacillus crispatus|Clostridium hylemonae, Lactobacillus delbrueckii|Clostridium hylemonae, Lactobacillus fermentum|Clostridium hylemonae, Lactobacillus gasseri|Clostridium hylemonae, Lactobacillus iners|Clostridium hylemonae, Lactobacillus jensenii|Clostridium hylemonae, Lactobacillus johnsonii|Clostridium hylemonae, Lactobacillus paracasei|Clostridium hylemonae, Lactobacillus plantarum|Clostridium hylemonae, Lactobacillus reuteri|Clostridium hylemonae, Lactobacillus rhamnosus|Clostridium hylemonae, Lactobacillus ruminis|Clostridium hylemonae, Lactobacillus sakei|Clostridium hylemonae, Lactobacillus salivarius|Clostridium hylemonae, Lactococcus lactis|Clostridium hylemonae, Lautropia mirabilis|Clostridium hylemonae, Leuconostoc citreum|Clostridium hylemonae, Leuconostoc gasicomitatum|Clostridium hylemonae, Leuconostoc mesenteroides|Clostridium hylemonae, Listeria monocytogenes|Clostridium hylemonae, Marvinbryantia formatexigens|Clostridium hylemonae, Megamonas hypermegale|Clostridium hylemonae, Megasphaera micronuciformis|Clostridium hylemonae, Methanobrevibacter smithii|Clostridium hylemonae, Methanosphaera stadtmanae|Clostridium hylemonae, Methylobacterium radiotolerans|Clostridium hylemonae, Mitsuokella multacida|Clostridium hylemonae, Mobiluncus curtisii|Clostridium hylemonae, Mycoplasma hominis|Clostridium hylemonae, Neisseria mucosa|Clostridium hylemonae, Odoribacter splanchnicus|Clostridium hylemonae, Olsenella uli|Clostridium hylemonae, Oribacterium sinus|Clostridium hylemonae, Oxalobacter formigenes|Clostridium hylemonae, Parabacteroides distasonis|Clostridium hylemonae, Parabacteroides johnsonii|Clostridium hylemonae, Parabacteroides merdae|Clostridium hylemonae, Parvimonas micra|Clostridium hylemonae, Pediococcus acidilactici|Clostridium hylemonae, Pediococcus pentosaceus|Clostridium hylemonae, Peptoniphilus duerdenii|Clostridium hylemonae, Peptoniphilus harei|Clostridium hylemonae, Peptoniphilus lacrimalis|Clostridium hylemonae, Peptostreptococcus anaerobius|Clostridium hylemonae, Peptostreptococcus stomatis|Clostridium hylemonae, Porphyromonas asaccharolytica|Clostridium hylemonae, Porphyromonas uenonis|Clostridium hylemonae, Prevotella amnii|Clostridium hylemonae, Prevotella bergensis|Clostridium hylemonae, Prevotella bivia|Clostridium hylemonae, Prevotella buccae|Clostridium hylemonae, Prevotella buccalis|Clostridium hylemonae, Prevotella copri|Clostridium hylemonae, Prevotella disiens|Clostridium hylemonae, Prevotella melaninogenica|Clostridium hylemonae, Prevotella multiformis|Clostridium hylemonae, Prevotella oralis|Clostridium hylemonae, Prevotella oris|Clostridium hylemonae, Prevotella salivae|Clostridium hylemonae, Prevotella timonensis|Clostridium hylemonae, Propionibacterium acnes|Clostridium hylemonae, Propionibacterium freudenreichii|Clostridium hylemonae, Proteus mirabilis|Clostridium hylemonae, Proteus penneri|Clostridium hylemonae, Pseudoflavonifractor capillosus|Clostridium hylemonae, Pseudomonas aeruginosa|Clostridium hylemonae, Pseudomonas fluorescens|Clostridium hylemonae, Pseudomonas putida|Clostridium hylemonae, Pseudoramibacter alactolyticus|Clostridium hylemonae, Pyramidobacter piscolens|Clostridium hylemonae, Rhodopseudomonas palustris|Clostridium hylemonae, Roseburia intestinalis|Clostridium hylemonae, Roseburia inulinivorans|Clostridium hylemonae, Rothia dentocariosa|Clostridium hylemonae, Rothia mucilaginosa|Clostridium hylemonae, Ruminococcus albus|Clostridium hylemonae, Ruminococcus bromii|Clostridium hylemonae, Ruminococcus gnavus|Clostridium hylemonae, Ruminococcus lactaris|Clostridium hylemonae, Ruminococcus obeum|Clostridium TABLE 2-continued Table 2. Specific binary combinations of OTUs. Individual pairings are differentiated by "|" and OTUs within a combination are differentiated by ","

hylemonae, Ruminococcus torques|Clostridium hylemonae, Selenomonas sputigena|Clostridium hylemonae, Shigella boydii|Clostridium hylemonae, Shigella dysenteriae|Clostridium hylemonae, Shigella sonnei|Clostridium hylemonae, Slackia exigua|Clostridium hylemonae, Solobacterium moorei|Clostridium hylemonae, Staphylococcus aureus|Clostridium hylemonae, Staphylococcus epidermidis|Clostridium hylemonae, Staphylococcus hominis|Clostridium hylemonae, Staphylococcus saprophyticus|Clostridium hylemonae, Staphylococcus warneri|Clostridium hylemonae, Streptococcus agalactiae|Clostridium hylemonae, Streptococcus anginosus|Clostridium hylemonae, Streptococcus australis|Clostridium hylemonae, Streptococcus bovis|Clostridium hylemonae, Streptococcus cristatus|Clostridium hylemonae, Streptococcus dysgalactiae|Clostridium hylemonae, Streptococcus equinus|Clostridium hylemonae, Streptococcus gordonii|Clostridium hylemonae, Streptococcus infantarius|Clostridium hylemonae, Streptococcus infantis|Clostridium hylemonae, Streptococcus mitis|Clostridium hylemonae, Streptococcus mutans|Clostridium hylemonae, Streptococcus oralis|Clostridium hylemonae, Streptococcus parasanguinis|Clostridium hylemonae, Streptococcus peroris|Clostridium hylemonae, Streptococcus pneumoniae|Clostridium hylemonae, Streptococcus salivarius|Clostridium hylemonae, Streptococcus sanguinis|Clostridium hylemonae, Streptococcus thermophilus|Clostridium hylemonae, Streptococcus vestibularis|Clostridium hylemonae, Subdoligranulum variabile|Clostridium hylemonae, Succinatimonas hippei|Clostridium hylemonae, Sutterella wadsworthensis|Clostridium hylemonae, Tropheryma whipplei|Clostridium hylemonae, Veillonella atypica|Clostridium hylemonae, Veillonella dispar|Clostridium hylemonae, Veillonella parvula|Clostridium hylemonae, Victivallis vadensis|Clostridium innocuum, Clostridium innocuum|Clostridium innocuum, Clostridium leptum|Clostridium innocuum, Clostridium mayombei|Clostridium innocuum, Clostridium methylpentosum|Clostridium innocuum, Clostridium nexile|Clostridium innocuum, Clostridium orbiscindens|Clostridium innocuum, Clostridium perfringens|Clostridium innocuum, Clostridium saccharolyticum|Clostridium innocuum, Clostridium scindens|Clostridium innocuum, Clostridium symbiosum|Clostridium innocuum, Clostridium tertium|Clostridium innocuum, Collinsella aerofaciens|Clostridium innocuum, Collinsella intestinalis|Clostridium innocuum, Collinsella stercoris|Clostridium innocuum, Coprobacillus sp. D7|Clostridium innocuum, Coprococcus catus|Clostridium innocuum, Coprococcus comes|Clostridium innocuum, Coprococcus eutactus|Clostridium innocuum, Corynebacterium aurimucosum|Clostridium innocuum, Corynebacterium matruchotii|Clostridium innocuum, Cryptobacterium curtum|Clostridium innocuum, Desulfovibrio desulfuricans|Clostridium innocuum, Desulfovibrio piger|Clostridium innocuum, Dialister invisus|Clostridium innocuum, Dialister microaerophilus|Clostridium innocuum, Dorea formicigenerans|Clostridium innocuum, Dorea longicatena|Clostridium innocuum, Eggerthella lenta|Clostridium innocuum, Eikenella corrodens|Clostridium innocuum, Enterobacter cancerogenus|Clostridium innocuum, Enterobacter cloacae|Clostridium innocuum, Enterococcus faecalis|Clostridium innocuum, Enterococcus faecium|Clostridium innocuum, Enterococcus gallinarum|Clostridium innocuum, Erysipelotrichaceae bacterium 3_1_53|Clostridium innocuum, Escherichia coli|Clostridium innocuum, Escherichia fergusonii|Clostridium innocuum, Ethanoligenens harbinense|Clostridium innocuum, Eubacterium cellulosolvens|Clostridium innocuum, Eubacterium eligens|Clostridium innocuum, Eubacterium hallii|Clostridium innocuum, Eubacterium limosum|Clostridium innocuum, Eubacterium rectale|Clostridium innocuum, Eubacterium siraeum|Clostridium innocuum, Eubacterium ventriosum|Clostridium innocuum, Faecalibacterium prausnitzii|Clostridium innocuum, Finegoldia magna|Clostridium innocuum, Fusobacterium gonidiaformans|Clostridium innocuum, Fusobacterium mortiferum|Clostridium innocuum, Fusobacterium nucleatum|Clostridium innocuum, Fusobacterium varium|Clostridium innocuum, Gardnerella vaginalis|Clostridium innocuum, Gemella haemolysans|Clostridium innocuum, Gemella morbillorum|Clostridium innocuum, Gordonibacter pamelaeae|Clostridium innocuum, Granulicatella adiacens|Clostridium innocuum, Granulicatella elegans|Clostridium innocuum, Haemophilus influenzae|Clostridium innocuum, Haemophilus parainfluenzae|Clostridium innocuum, Helicobacter pullorum|Clostridium innocuum, Helicobacter pylori|Clostridium innocuum, Holdemania filiformis|Clostridium innocuum, Kingella oralis|Clostridium innocuum, Klebsiella pneumoniae|Clostridium innocuum, Klebsiella variicola|Clostridium innocuum, Lachnospiraceae bacterium 5_1_57FAA|Clostridium innocuum, Lactobacillus acidophilus|Clostridium innocuum, Lactobacillus amylovorus|Clostridium innocuum, Lactobacillus brevis|Clostridium innocuum, Lactobacillus casei|Clostridium innocuum, Lactobacillus crispatus|Clostridium innocuum, Lactobacillus delbrueckii|Clostridium innocuum, Lactobacillus fermentum|Clostridium innocuum, Lactobacillus gasseri|Clostridium innocuum, Lactobacillus iners|Clostridium innocuum, Lactobacillus jensenii|Clostridium innocuum, Lactobacillus johnsonii|Clostridium innocuum, Lactobacillus paracasei|Clostridium innocuum, Lactobacillus plantarum|Clostridium innocuum, Lactobacillus reuteri|Clostridium innocuum, Lactobacillus rhamnosus|Clostridium innocuum, Lactobacillus ruminis|Clostridium innocuum, Lactobacillus sakei|Clostridium innocuum, Lactobacillus salivarius|Clostridium innocuum, Lactococcus lactis|Clostridium innocuum, Lautropia mirabilis|Clostridium innocuum, Leuconostoc citreum|Clostridium innocuum, Leuconostoc gasicomitatum|Clostridium innocuum, Leuconostoc mesenteroides|Clostridium innocuum, Listeria monocytogenes|Clostridium innocuum, Marvinbryantia formatexigens|Clostridium innocuum, Megamonas hypermegale|Clostridium innocuum, Megasphaera micronuciformis|Clostridium innocuum, Methanobrevibacter smithii|Clostridium innocuum, Methanosphaera stadtmanae|Clostridium innocuum, Methylobacterium radiotolerans|Clostridium innocuum, Mitsuokella multacida|Clostridium innocuum, Mobiluncus curtisii|Clostridium innocuum, Mycoplasma hominis|Clostridium innocuum, Neisseria mucosa|Clostridium innocuum, Odoribacter splanchnicus|Clostridium innocuum, Olsenella uli|Clostridium innocuum, Oribacterium sinus|Clostridium innocuum, Oxalobacter formigenes|Clostridium innocuum, Parabacteroides distasonis|Clostridium innocuum, Parabacteroides johnsonii|Clostridium innocuum, Parabacteroides merdae|Clostridium innocuum, Parvimonas micra|Clostridium innocuum, Pediococcus acidilactici|Clostridium innocuum, Pediococcus pentosaceus|Clostridium innocuum, Peptoniphilus duerdenii|Clostridium innocuum, Peptoniphilus harei|Clostridium innocuum, Peptoniphilus lacrimalis|Clostridium innocuum, Peptostreptococcus anaerobius|Clostridium innocuum, Peptostreptococcus stomatis|Clostridium innocuum, Porphyromonas asaccharolytica|Clostridium innocuum, Porphyromonas uenonis|Clostridium innocuum, Prevotella amnii|Clostridium innocuum, Prevotella bergensis|Clostridium innocuum, Prevotella bivia|Clostridium innocuum, Prevotella buccae|Clostridium innocuum, Prevotella buccalis|Clostridium innocuum, Prevotella copri|Clostridium innocuum, Prevotella disiens|Clostridium innocuum, Prevotella melaninogenica|Clostridium innocuum, Prevotella multiformis|Clostridium innocuum, Prevotella oralis|Clostridium innocuum, Prevotella oris|Clostridium innocuum, Prevotella salivae|Clostridium innocuum, Prevotella timonensis|Clostridium innocuum, Propionibacterium acnes|Clostridium innocuum, Propionibacterium freudenreichii|Clostridium innocuum, Proteus mirabilis|Clostridium innocuum, Proteus penneri|Clostridium innocuum, Pseudoflavonifractor capillosus|Clostridium innocuum, Pseudomonas aeruginosa|Clostridium innocuum, Pseudomonas fluorescens|Clostridium innocuum, Pseudomonas putida|Clostridium innocuum, Pseudoramibacter alactolyticus|Clostridium innocuum, Pyramidobacter piscolens|Clostridium innocuum, Rhodopseudomonas palustris|Clostridium innocuum, Roseburia intestinalis|Clostridium innocuum, Roseburia inulinivorans|Clostridium innocuum, Rothia dentocariosa|Clostridium innocuum, Rothia mucilaginosa|Clostridium innocuum, Ruminococcus albus|Clostridium innocuum, Ruminococcus bromii|Clostridium innocuum, Ruminococcus gnavus|Clostridium innocuum, Ruminococcus lactaris|Clostridium innocuum, Ruminococcus obeum|Clostridium innocuum, Ruminococcus torques|Clostridium innocuum, Selenomonas sputigena|Clostridium innocuum, Shigella boydii|Clostridium innocuum, Shigella dysenteriae|Clostridium innocuum, Shigella sonnei|Clostridium innocuum, Slackia exigua|Clostridium innocuum, Solobacterium moorei|Clostridium innocuum, Staphylococcus aureus|Clostridium innocuum, Staphylococcus epidermidis|Clostridium innocuum, Staphylococcus hominis|Clostridium innocuum, Staphylococcus saprophyticus|Clostridium innocuum, Staphylococcus warneri|Clostridium innocuum, Streptococcus agalactiae|Clostridium innocuum, Streptococcus anginosus|Clostridium innocuum, Streptococcus australis|Clostridium innocuum, Streptococcus bovis|Clostridium innocuum, Streptococcus cristatus|Clostridium innocuum, Streptococcus dysgalactiae|Clostridium innocuum, Streptococcus equinus|Clostridium innocuum, Streptococcus gordonii|Clostridium innocuum, Streptococcus infantarius|Clostridium innocuum, Streptococcus infantis|Clostridium innocuum, Streptococcus mitis|Clostridium innocuum, Streptococcus mutans|Clostridium innocuum, Streptococcus oralis|Clostridium innocuum, Streptococcus parasanguinis|Clostridium innocuum, Streptococcus TABLE 2-continued

| Table 2. Specific binary combinations of OTUs. Individual pairings are differentiated by "\|" and OTUs within a combination are differentiated by "," |
|---|
| peroris\|Clostridium innocuum, Streptococcus pneumoniae\|Clostridium innocuum, Streptococcus salivarius\|Clostridium innocuum, Streptococcus sanguinis\|Clostridium innocuum, Streptococcus thermophilus\|Clostridium innocuum, Streptococcus vestibularis\|Clostridium innocuum, Subdoligranulum variabile\|Clostridium innocuum, Succinatimonas hippei\|Clostridium innocuum, Sutterella wadsworthensis\|Clostridium innocuum, Tropheryma whipplei\|Clostridium innocuum, Veillonella atypica\|Clostridium innocuum, Veillonella dispar\|Clostridium innocuum, Veillonella parvula\|Clostridium innocuum, Victivallis vadensis\|Clostridium leptum, Clostridium leptum, Clostridium leptum, Clostridium mayombei\|Clostridium leptum, Clostridium methylpentosum\|Clostridium leptum, Clostridium nexile\|Clostridium leptum, Clostridium orbiscindens\|Clostridium leptum, Clostridium perfringens\|Clostridium leptum, Clostridium saccharolyticum\|Clostridium leptum, Clostridium scindens\|Clostridium leptum, Clostridium symbiosum\|Clostridium leptum, Clostridium tertium\|Clostridium leptum, Collinsella aerofaciens\|Clostridium leptum, Collinsella intestinalis\|Clostridium leptum, Collinsella stercoris\|Clostridium leptum, Coprobacillus sp. D7\|Clostridium leptum, Coprococcus catus\|Clostridium leptum, Coprococcus comes\|Clostridium leptum, Coprococcus eutactus\|Clostridium leptum, Corynebacterium aurimucosum\|Clostridium leptum, Corynebacterium matruchotii\|Clostridium leptum, Cryptobacterium curtum\|Clostridium leptum, Desulfovibrio desulfuricans\|Clostridium leptum, Desulfovibrio piger\|Clostridium leptum, Dialister invisus\|Clostridium leptum, Dialister microaerophilus\|Clostridium leptum, Dorea formicigenerans\|Clostridium leptum, Dorea longicatena\|Clostridium leptum, Eggerthella lenta\|Clostridium leptum, Eikenella corrodens\|Clostridium leptum, Enterobacter cancerogenus\|Clostridium leptum, Enterobacter cloacae\|Clostridium leptum, Enterococcus faecalis\|Clostridium leptum, Enterococcus faecium\|Clostridium leptum, Enterococcus gallinarum\|Clostridium leptum, Erysipelotrichaceae bacterium 3_1_53\|Clostridium leptum, Escherichia coli\|Clostridium leptum, Escherichia fergusonii\|Clostridium leptum, Ethanoligenens harbinense\|Clostridium leptum, Eubacterium cellulosolvens\|Clostridium leptum, Eubacterium eligens\|Clostridium leptum, Eubacterium hallii\|Clostridium leptum, Eubacterium limosum\|Clostridium leptum, Eubacterium rectale\|Clostridium leptum, Eubacterium siraeum\|Clostridium leptum, Eubacterium ventriosum\|Clostridium leptum, Faecalibacterium prausnitzii\|Clostridium leptum, Finegoldia magna\|Clostridium leptum, Fusobacterium gonidiaformans\|Clostridium leptum, Fusobacterium mortiferum\|Clostridium leptum, Fusobacterium nucleatum\|Clostridium leptum, Fusobacterium varium\|Clostridium leptum, Gardnerella vaginalis\|Clostridium leptum, Gemella haemolysans\|Clostridium leptum, Gemella morbillorum\|Clostridium leptum, Gordonibacter pamelaeae\|Clostridium leptum, Granulicatella adiacens\|Clostridium leptum, Granulicatella elegans\|Clostridium leptum, Haemophilus influenzae\|Clostridium leptum, Haemophilus parainfluenzae\|Clostridium leptum, Helicobacter pullorum\|Clostridium leptum, Helicobacter pylori\|Clostridium leptum, Holdemania filiformis\|Clostridium leptum, Kingella oralis\|Clostridium leptum, Klebsiella pneumoniae\|Clostridium leptum, Klebsiella variicola\|Clostridium leptum, Lachnospiraceae bacterium 5_1_57FAA\|Clostridium leptum, Lactobacillus acidophilus\|Clostridium leptum, Lactobacillus amylovorus\|Clostridium leptum, Lactobacillus brevis\|Clostridium leptum, Lactobacillus casei\|Clostridium leptum, Lactobacillus crispatus\|Clostridium leptum, Lactobacillus delbrueckii\|Clostridium leptum, Lactobacillus fermentum\|Clostridium leptum, Lactobacillus gasseri\|Clostridium leptum, Lactobacillus iners\|Clostridium leptum, Lactobacillus jensenii\|Clostridium leptum, Lactobacillus johnsonii\|Clostridium leptum, Lactobacillus paracasei\|Clostridium leptum, Lactobacillus plantarum\|Clostridium leptum, Lactobacillus reuteri\|Clostridium leptum, Lactobacillus rhamnosus\|Clostridium leptum, Lactobacillus ruminis\|Clostridium leptum, Lactobacillus sakei\|Clostridium leptum, Lactobacillus salivarius\|Clostridium leptum, Lactococcus lactis\|Clostridium leptum, Lautropia mirabilis\|Clostridium leptum, Leuconostoc citreum\|Clostridium leptum, Leuconostoc gasicomitatum\|Clostridium leptum, Leuconostoc mesenteroides\|Clostridium leptum, Listeria monocytogenes\|Clostridium leptum, Marvinbryantia formatexigens\|Clostridium leptum, Megamonas hypermegale\|Clostridium leptum, Megasphaera micronuciformis\|Clostridium leptum, Methanobrevibacter smithii\|Clostridium leptum, Methanosphaera stadtmanae\|Clostridium leptum, Methylobacterium radiotolerans\|Clostridium leptum, Mitsuokella multacida\|Clostridium leptum, Mobiluncus curtisii\|Clostridium leptum, Mycoplasma hominis\|Clostridium leptum, Neisseria mucosa\|Clostridium leptum, Odoribacter splanchnicus\|Clostridium leptum, Olsenella uli\|Clostridium leptum, Oribacterium sinus\|Clostridium leptum, Oxalobacter formigenes\|Clostridium leptum, Parabacteroides distasonis\|Clostridium leptum, Parabacteroides johnsonii\|Clostridium leptum, Parabacteroides merdae\|Clostridium leptum, Parvimonas micra\|Clostridium leptum, Pediococcus acidilactici\|Clostridium leptum, Pediococcus pentosaceus\|Clostridium leptum, Peptoniphilus duerdenii\|Clostridium leptum, Peptoniphilus harei\|Clostridium leptum, Peptoniphilus lacrimalis\|Clostridium leptum, Peptostreptococcus anaerobius\|Clostridium leptum, Peptostreptococcus stomatis\|Clostridium leptum, Porphyromonas asaccharolytica\|Clostridium leptum, Porphyromonas uenonis\|Clostridium leptum, Prevotella amnii\|Clostridium leptum, Prevotella bergensis\|Clostridium leptum, Prevotella bivia\|Clostridium leptum, Prevotella buccae\|Clostridium leptum, Prevotella buccalis\|Clostridium leptum, Prevotella copri\|Clostridium leptum, Prevotella disiens\|Clostridium leptum, Prevotella melaninogenica\|Clostridium leptum, Prevotella multiformis\|Clostridium leptum, Prevotella oralis\|Clostridium leptum, Prevotella oris\|Clostridium leptum, Prevotella salivae\|Clostridium leptum, Prevotella timonensis\|Clostridium leptum, Propionibacterium acnes\|Clostridium leptum, Propionibacterium freudenreichii\|Clostridium leptum, Proteus mirabilis\|Clostridium leptum, Proteus penneri\|Clostridium leptum, Pseudoflavonifractor capillosus\|Clostridium leptum, Pseudomonas aeruginosa\|Clostridium leptum, Pseudomonas fluorescens\|Clostridium leptum, Pseudomonas putida\|Clostridium leptum, Pseudoramibacter alactolyticus\|Clostridium leptum, Pyramidobacter piscolens\|Clostridium leptum, Rhodopseudomonas palustris\|Clostridium leptum, Roseburia intestinalis\|Clostridium leptum, Roseburia inulinivorans\|Clostridium leptum, Rothia dentocariosa\|Clostridium leptum, Rothia mucilaginosa\|Clostridium leptum, Ruminococcus albus\|Clostridium leptum, Ruminococcus bromii\|Clostridium leptum, Ruminococcus gnavus\|Clostridium leptum, Ruminococcus lactaris\|Clostridium leptum, Ruminococcus obeum\|Clostridium leptum, Ruminococcus torques\|Clostridium leptum, Selenomonas sputigena\|Clostridium leptum, Shigella boydii\|Clostridium leptum, Shigella dysenteriae\|Clostridium leptum, Shigella sonnei\|Clostridium leptum, Slackia exigua\|Clostridium leptum, Solobacterium moorei\|Clostridium leptum, Staphylococcus aureus\|Clostridium leptum, Staphylococcus epidermidis\|Clostridium leptum, Staphylococcus hominis\|Clostridium leptum, Staphylococcus saprophyticus\|Clostridium leptum, Staphylococcus warneri\|Clostridium leptum, Streptococcus agalactiae\|Clostridium leptum, Streptococcus anginosus\|Clostridium leptum, Streptococcus australis\|Clostridium leptum, Streptococcus bovis\|Clostridium leptum, Streptococcus cristatus\|Clostridium leptum, Streptococcus dysgalactiae\|Clostridium leptum, Streptococcus equinus\|Clostridium leptum, Streptococcus gordonii\|Clostridium leptum, Streptococcus infantarius\|Clostridium leptum, Streptococcus infantis\|Clostridium leptum, Streptococcus mitis\|Clostridium leptum, Streptococcus mutans\|Clostridium leptum, Streptococcus oralis\|Clostridium leptum, Streptococcus parasanguinis\|Clostridium leptum, Streptococcus peroris\|Clostridium leptum, Streptococcus pneumoniae\|Clostridium leptum, Streptococcus salivarius\|Clostridium leptum, Streptococcus sanguinis\|Clostridium leptum, Streptococcus thermophilus\|Clostridium leptum, Streptococcus vestibularis\|Clostridium leptum, Subdoligranulum variabile\|Clostridium leptum, Succinatimonas hippei\|Clostridium leptum, Sutterella wadsworthensis\|Clostridium leptum, Tropheryma whipplei\|Clostridium leptum, Veillonella atypica\|Clostridium leptum, Veillonella dispar\|Clostridium leptum, Veillonella parvula\|Clostridium leptum, Victivallis vadensis\|Clostridium mayombei, Clostridium mayombei\|Clostridium mayombei, Clostridium methylpentosum\|Clostridium mayombei, Clostridium nexile\|Clostridium mayombei, Clostridium orbiscindens\|Clostridium mayombei, Clostridium perfringens\|Clostridium mayombei, Clostridium saccharolyticum\|Clostridium mayombei, Clostridium scindens\|Clostridium mayombei, Clostridium symbiosum\|Clostridium mayombei, Clostridium tertium\|Clostridium mayombei, Collinsella aerofaciens\|Clostridium mayombei, Collinsella intestinalis\|Clostridium mayombei, Collinsella stercoris\|Clostridium mayombei, Coprobacillus sp. D7\|Clostridium mayombei, Coprococcus catus\|Clostridium mayombei, Coprococcus comes\|Clostridium mayombei, Coprococcus eutactus\|Clostridium mayombei, Corynebacterium aurimucosum\|Clostridium mayombei, Corynebacterium matruchotii\|Clostridium mayombei, Cryptobacterium curtum\|Clostridium mayombei, Desulfovibrio desulfuricans\|Clostridium mayombei, Desulfovibrio piger\|Clostridium mayombei, Dialister invisus\|Clostridium mayombei, Dialister microaerophilus\|Clostridium mayombei, Dorea formicigenerans\|Clostridium mayombei, Dorea longicatena\|Clostridium mayombei, Eggerthella lenta\|Clostridium mayombei, Eikenella |

TABLE 2-continued

Table 2. Specific binary combinations of OTUs. Individual pairings are differentiated by "|" and OTUs within a combination are differentiated by ","

*corrodens*|*Clostridium mayombei*, *Enterobacter cancerogenus*|*Clostridium mayombei*, *Enterobacter cloacae*|*Clostridium mayombei*, *Enterococcus faecalis*|*Clostridium mayombei*, *Enterococcus faecium*|*Clostridium mayombei*, *Enterococcus gallinarum*|*Clostridium mayombei*, *Erysipelotrichaceae bacterium* 3_1_53|*Clostridium mayombei*, *Escherichia coli*|*Clostridium mayombei*, *Escherichia fergusonii*|*Clostridium mayombei*, *Ethanoligenens harbinense*|*Clostridium mayombei*, *Eubacterium cellulosolvens*|*Clostridium mayombei*, *Eubacterium eligens*|*Clostridium mayombei*, *Eubacterium hallii*|*Clostridium mayombei*, *Eubacterium limosum*|*Clostridium mayombei*, *Eubacterium rectale*|*Clostridium mayombei*, *Eubacterium siraeum*|*Clostridium mayombei*, *Eubacterium ventriosum*|*Clostridium mayombei*, *Faecalibacterium prausnitzii*|*Clostridium mayombei*, *Finegoldia magna*|*Clostridium mayombei*, *Fusobacterium gonidiaformans*|*Clostridium mayombei*, *Fusobacterium mortiferum*|*Clostridium mayombei*, *Fusobacterium nucleatum*|*Clostridium mayombei*, *Fusobacterium varium*|*Clostridium mayombei*, *Gardnerella vaginalis*|*Clostridium mayombei*, *Gemella haemolysans*|*Clostridium mayombei*, *Gemella morbillorum*|*Clostridium mayombei*, *Gordonibacter pamelaeae*|*Clostridium mayombei*, *Granulicatella adiacens*|*Clostridium mayombei*, *Granulicatella elegans*|*Clostridium mayombei*, *Haemophilus influenzae*|*Clostridium mayombei*, *Haemophilus parainfluenzae*|*Clostridium mayombei*, *Helicobacter pullorum*|*Clostridium mayombei*, *Helicobacter pylori*|*Clostridium mayombei*, *Holdemania filiformis*|*Clostridium mayombei*, *Kingella oralis*|*Clostridium mayombei*, *Klebsiella pneumoniae*|*Clostridium mayombei*, *Klebsiella variicola*|*Clostridium mayombei*, *Lachnospiraceae bacterium* 5_1_57FAA|*Clostridium mayombei*, *Lactobacillus acidophilus*|*Clostridium mayombei*, *Lactobacillus amylovorus*|*Clostridium mayombei*, *Lactobacillus brevis*|*Clostridium mayombei*, *Lactobacillus casei*|*Clostridium mayombei*, *Lactobacillus crispatus*|*Clostridium mayombei*, *Lactobacillus delbrueckii*|*Clostridium mayombei*, *Lactobacillus fermentum*|*Clostridium mayombei*, *Lactobacillus gasseri*|*Clostridium mayombei*, *Lactobacillus iners*|*Clostridium mayombei*, *Lactobacillus jensenii*|*Clostridium mayombei*, *Lactobacillus johnsonii*|*Clostridium mayombei*, *Lactobacillus paracasei*|*Clostridium mayombei*, *Lactobacillus plantarum*|*Clostridium mayombei*, *Lactobacillus reuteri*|*Clostridium mayombei*, *Lactobacillus rhamnosus*|*Clostridium mayombei*, *Lactobacillus ruminis*|*Clostridium mayombei*, *Lactobacillus sakei*|*Clostridium mayombei*, *Lactobacillus salivarius*|*Clostridium mayombei*, *Lactococcus lactis*|*Clostridium mayombei*, *Lautropia mirabilis*|*Clostridium mayombei*, *Leuconostoc citreum*|*Clostridium mayombei*, *Leuconostoc gas icomitatum*|*Clostridium mayombei*, *Leuconostoc mesenteroides*|*Clostridium mayombei*, *Listeria monocytogenes*|*Clostridium mayombei*, *Marvinbryantia formatexigens*|*Clostridium mayombei*, *Megamonas hypermegale*|*Clostridium mayombei*, *Megasphaera micronuciformis*|*Clostridium mayombei*, *Methanobrevibacter smithii*|*Clostridium mayombei*, *Methanosphaera stadtmanae*|*Clostridium mayombei*, *Methylobacterium radiotolerans*|*Clostridium mayombei*, *Mitsuokella multacida*|*Clostridium mayombei*, *Mobiluncus curtisii*|*Clostridium mayombei*, *Mycoplasma hominis*|*Clostridium mayombei*, *Neisseria mucosa*|*Clostridium mayombei*, *Odoribacter splanchnicus*|*Clostridium mayombei*, *Olsenella uli*|*Clostridium mayombei*, *Oribacterium sinus*|*Clostridium mayombei*, *Oxalobacter formigenes*|*Clostridium mayombei*, *Parabacteroides distasonis*|*Clostridium mayombei*, *Parabacteroides johnsonii*|*Clostridium mayombei*, *Parabacteroides merdae*|*Clostridium mayombei*, *Parvimonas micra*|*Clostridium mayombei*, *Pediococcus acidilactici*|*Clostridium mayombei*, *Pediococcus pentosaceus*|*Clostridium mayombei*, *Peptoniphilus duerdenii*|*Clostridium mayombei*, *Peptoniphilus harei*|*Clostridium mayombei*, *Peptoniphilus lacrimalis*|*Clostridium mayombei*, *Peptostreptococcus anaerobius*|*Clostridium mayombei*, *Peptostreptococcus stomatis*|*Clostridium mayombei*, *Porphyromonas asaccharolytica*|*Clostridium mayombei*, *Porphyromonas uenonis*|*Clostridium mayombei*, *Prevotella amnii*|*Clostridium mayombei*, *Prevotella bergensis*|*Clostridium mayombei*, *Prevotella bivia*|*Clostridium mayombei*, *Prevotella buccae*|*Clostridium mayombei*, *Prevotella buccalis*|*Clostridium mayombei*, *Prevotella copri*|*Clostridium mayombei*, *Prevotella disiens*|*Clostridium mayombei*, *Prevotella melaninogenica*|*Clostridium mayombei*, *Prevotella multiformis*|*Clostridium mayombei*, *Prevotella oralis*|*Clostridium mayombei*, *Prevotella oris*|*Clostridium mayombei*, *Prevotella salivae*|*Clostridium mayombei*, *Prevotella timonensis*|*Clostridium mayombei*, *Propionibacterium acnes*|*Clostridium mayombei*, *Propionibacterium freudenreichii*|*Clostridium mayombei*, *Proteus mirabilis*|*Clostridium mayombei*, *Proteus penneri*|*Clostridium mayombei*, *Pseudoflavonifractor capillosus*|*Clostridium mayombei*, *Pseudomonas aeruginosa*|*Clostridium mayombei*, *Pseudomonas fluorescens*|*Clostridium mayombei*, *Pseudomonas putida*|*Clostridium mayombei*, *Pseudoramibacter alactolyticus*|*Clostridium mayombei*, *Pyramidobacter piscolens*|*Clostridium mayombei*, *Rhodopseudomonas palustris*|*Clostridium mayombei*, *Roseburia intestinalis*|*Clostridium mayombei*, *Roseburia inulinivorans*|*Clostridium mayombei*, *Rothia dentocariosa*|*Clostridium mayombei*, *Rothia mucilaginosa*|*Clostridium mayombei*, *Ruminococcus albus*|*Clostridium mayombei*, *Ruminococcus bromii*|*Clostridium mayombei*, *Ruminococcus gnavus*|*Clostridium mayombei*, *Ruminococcus lactaris*|*Clostridium mayombei*, *Ruminococcus obeum*|*Clostridium mayombei*, *Ruminococcus torques*|*Clostridium mayombei*, *Selenomonas sputigena*|*Clostridium mayombei*, *Shigella boydii*|*Clostridium mayombei*, *Shigella dysenteriae*|*Clostridium mayombei*, *Shigella sonnei*|*Clostridium mayombei*, *Slackia exigua*|*Clostridium mayombei*, *Solobacterium moorei*|*Clostridium mayombei*, *Staphylococcus aureus*|*Clostridium mayombei*, *Staphylococcus epidermidis*|*Clostridium mayombei*, *Staphylococcus hominis*|*Clostridium mayombei*, *Staphylococcus saprophyticus*|*Clostridium mayombei*, *Staphylococcus warneri*|*Clostridium mayombei*, *Streptococcus agalactiae*|*Clostridium mayombei*, *Streptococcus anginosus*|*Clostridium mayombei*, *Streptococcus australis*|*Clostridium mayombei*, *Streptococcus bovis*|*Clostridium mayombei*, *Streptococcus cristatus*|*Clostridium mayombei*, *Streptococcus dysgalactiae*|*Clostridium mayombei*, *Streptococcus equinus*|*Clostridium mayombei*, *Streptococcus gordonii*|*Clostridium mayombei*, *Streptococcus infantarius*|*Clostridium mayombei*, *Streptococcus infantis*|*Clostridium mayombei*, *Streptococcus mitis*|*Clostridium mayombei*, *Streptococcus mutans*|*Clostridium mayombei*, *Streptococcus oralis*|*Clostridium mayombei*, *Streptococcus parasanguinis*|*Clostridium mayombei*, *Streptococcus peroris*|*Clostridium mayombei*, *Streptococcus pneumoniae*|*Clostridium mayombei*, *Streptococcus salivarius*|*Clostridium mayombei*, *Streptococcus sanguinis*|*Clostridium mayombei*, *Streptococcus thermophilus*|*Clostridium mayombei*, *Streptococcus vestibularis*|*Clostridium mayombei*, *Subdoligranulum variabile*|*Clostridium mayombei*, *Succinatimonas hippei*|*Clostridium mayombei*, *Sutterella wadsworthensis*|*Clostridium mayombei*, *Tropheryma whipplei*|*Clostridium mayombei*, *Veillonella atypica*|*Clostridium mayombei*, *Veillonella dispar*|*Clostridium mayombei*, *Veillonella parvula*|*Clostridium mayombei*, *Victivallis vadensis*|*Clostridium methylpentosum*, *Clostridium methylpentosum*|*Clostridium methylpentosum*, *Clostridium nexile*|*Clostridium methylpentosum*, *Clostridium orbiscindens*|*Clostridium methylpentosum*, *Clostridium perfringens*|*Clostridium methylpentosum*, *Clostridium saccharolyticum*|*Clostridium methylpentosum*, *Clostridium scindens*|*Clostridium methylpentosum*, *Clostridium symbiosum*|*Clostridium methylpentosum*, *Clostridium tertium*|*Clostridium methylpentosum*, *Collinsella aerofaciens*|*Clostridium methylpentosum*, *Collinsella intestinalis*|*Clostridium methylpentosum*, *Collinsella stercoris*|*Clostridium methylpentosum*, *Coprobacillus* sp. D7|*Clostridium methylpentosum*, *Coprococcus catus*|*Clostridium methylpentosum*, *Coprococcus comes*|*Clostridium methylpentosum*, *Coprococcus eutactus*|*Clostridium methylpentosum*, *Corynebacterium aurimucosum*|*Clostridium methylpentosum*, *Corynebacterium matruchotii*|*Clostridium methylpentosum*, *Cryptobacterium curtum*|*Clostridium methylpentosum*, *Desulfovibrio desulfuricans*|*Clostridium methylpentosum*, *Desulfovibrio piger*|*Clostridium methylpentosum*, *Dialister invisus*|*Clostridium methylpentosum*, *Dialister microaerophilus*|*Clostridium methylpentosum*, *Dorea formicigenerans*|*Clostridium methylpentosum*, *Dorea longicatena*|*Clostridium methylpentosum*, *Eggerthella lenta*|*Clostridium methylpentosum*, *Eikenella corrodens*|*Clostridium methylpentosum*, *Enterobacter cancerogenus*|*Clostridium methylpentosum*, *Enterobacter cloacae*|*Clostridium methylpentosum*, *Enterococcus faecalis*|*Clostridium methylpentosum*, *Enterococcus faecium*|*Clostridium methylpentosum*, *Enterococcus gallinarum*|*Clostridium methylpentosum*, *Erysipelotrichaceae bacterium* 3_1_53|*Clostridium methylpentosum*, *Escherichia coli*|*Clostridium methylpentosum*, *Escherichia fergusonii*|*Clostridium methylpentosum*, *Ethanoligenens harbinense*|*Clostridium methylpentosum*, *Eubacterium cellulosolvens*|*Clostridium methylpentosum*, *Eubacterium eligens*|*Clostridium methylpentosum*, *Eubacterium hallii*|*Clostridium methylpentosum*, *Eubacterium limosum*|*Clostridium methylpentosum*, *Eubacterium rectale*|*Clostridium methylpentosum*, *Eubacterium siraeum*|*Clostridium methylpentosum*, *Eubacterium ventriosum*|*Clostridium methylpentosum*, *Faecalibacterium prausnitzii*|*Clostridium methylpentosum*, *Finegoldia magna*|*Clostridium methylpentosum*, *Fusobacterium gonidiaformans*|*Clostridium methylpentosum*, *Fusobacterium mortiferum*|*Clostridium methylpentosum*, *Fusobacterium*

TABLE 2-continued

Table 2. Specific binary combinations of OTUs. Individual pairings are differentiated by “|” and OTUs within a combination are differentiated by “,”

*nucleatum|Clostridium methylpentosum, Fusobacterium varium|Clostridium methylpentosum, Gardnerella vaginalis|Clostridium methylpentosum, Gemella haemolysans|Clostridium methylpentosum, Gemella morbillorum|Clostridium methylpentosum, Gordonibacter pamelaeae|Clostridium methylpentosum, Granulicatella adiacens|Clostridium methylpentosum, Granulicatella elegans|Clostridium methylpentosum, Haemophilus influenzae|Clostridium methylpentosum, Haemophilus parainfluenzae|Clostridium methylpentosum, Helicobacter pullorum|Clostridium methylpentosum, Helicobacter pylori|Clostridium methylpentosum, Holdemania filiformis|Clostridium methylpentosum, Kingella oralis|Clostridium methylpentosum, Klebsiella pneumoniae|Clostridium methylpentosum, Klebsiella variicola|Clostridium methylpentosum, Lachnospiraceae bacterium* 5_1_57FAA|*Clostridium methylpentosum, Lactobacillus acidophilus|Clostridium methylpentosum, Lactobacillus amylovorus|Clostridium methylpentosum, Lactobacillus brevis|Clostridium methylpentosum, Lactobacillus casei|Clostridium methylpentosum, Lactobacillus crispatus|Clostridium methylpentosum, Lactobacillus delbrueckii|Clostridium methylpentosum, Lactobacillus fermentum|Clostridium methylpentosum, Lactobacillus gasseri|Clostridium methylpentosum, Lactobacillus iners|Clostridium methylpentosum, Lactobacillus jensenii|Clostridium methylpentosum, Lactobacillus johnsonii|Clostridium methylpentosum, Lactobacillus paracasei|Clostridium methylpentosum, Lactobacillus plantarum|Clostridium methylpentosum, Lactobacillus reuteri|Clostridium methylpentosum, Lactobacillus rhamnosus|Clostridium methylpentosum, Lactobacillus ruminis|Clostridium methylpentosum, Lactobacillus sakei|Clostridium methylpentosum, Lactobacillus salivarius|Clostridium methylpentosum, Lactococcus lactis|Clostridium methylpentosum, Lautropia mirabilis|Clostridium methylpentosum, Leuconostoc citreum|Clostridium methylpentosum, Leuconostoc gasicomitatum|Clostridium methylpentosum, Leuconostoc mesenteroides|Clostridium methylpentosum, Listeria monocytogenes|Clostridium methylpentosum, Marvinbryantia formatexigens|Clostridium methylpentosum, Megamonas hypermegale|Clostridium methylpentosum, Megasphaera micronuciformis|Clostridium methylpentosum, Methanobrevibacter smithii|Clostridium methylpentosum, Methanosphaera stadtmanae|Clostridium methylpentosum, Methylobacterium radiotolerans|Clostridium methylpentosum, Mitsuokella multacida|Clostridium methylpentosum, Mobiluncus curtisii|Clostridium methylpentosum, Mycoplasma hominis|Clostridium methylpentosum, Neisseria mucosa|Clostridium methylpentosum, Odoribacter splanchnicus|Clostridium methylpentosum, Olsenella uli|Clostridium methylpentosum, Oribacterium sinus|Clostridium methylpentosum, Oxalobacter formigenes|Clostridium methylpentosum, Parabacteroides distasonis|Clostridium methylpentosum, Parabacteroides johnsonii|Clostridium methylpentosum, Parabacteroides merdae|Clostridium methylpentosum, Parvimonas micra|Clostridium methylpentosum, Pediococcus acidilactici|Clostridium methylpentosum, Pediococcus pentosaceus|Clostridium methylpentosum, Peptoniphilus duerdenii|Clostridium methylpentosum, Peptoniphilus harei|Clostridium methylpentosum, Peptoniphilus lacrimalis|Clostridium methylpentosum, Peptostreptococcus anaerobius|Clostridium methylpentosum, Peptostreptococcus stomatis|Clostridium methylpentosum, Porphyromonas asaccharolytica|Clostridium methylpentosum, Porphyromonas uenonis|Clostridium methylpentosum, Prevotella amnii|Clostridium methylpentosum, Prevotella bergensis|Clostridium methylpentosum, Prevotella bivia|Clostridium methylpentosum, Prevotella buccae|Clostridium methylpentosum, Prevotella buccalis|Clostridium methylpentosum, Prevotella copri|Clostridium methylpentosum, Prevotella disiens|Clostridium methylpentosum, Prevotella melaninogenica|Clostridium methylpentosum, Prevotella multiformis|Clostridium methylpentosum, Prevotella oralis|Clostridium methylpentosum, Prevotella oris|Clostridium methylpentosum, Prevotella salivae|Clostridium methylpentosum, Prevotella timonensis|Clostridium methylpentosum, Propionibacterium acnes|Clostridium methylpentosum, Propionibacterium freudenreichii|Clostridium methylpentosum, Proteus mirabilis|Clostridium methylpentosum, Proteus penneri|Clostridium methylpentosum, Pseudoflavonifractor capillosus|Clostridium methylpentosum, Pseudomonas aeruginosa|Clostridium methylpentosum, Pseudomonas fluorescens|Clostridium methylpentosum, Pseudomonas putida|Clostridium methylpentosum, Pseudoramibacter alactolyticus|Clostridium methylpentosum, Pyramidobacter piscolens|Clostridium methylpentosum, Rhodopseudomonas palustris|Clostridium methylpentosum, Roseburia intestinalis|Clostridium methylpentosum, Roseburia inulinivorans|Clostridium methylpentosum, Rothia dentocariosa|Clostridium methylpentosum, Rothia mucilaginosa|Clostridium methylpentosum, Ruminococcus albus|Clostridium methylpentosum, Ruminococcus bromii|Clostridium methylpentosum, Ruminococcus gnavus|Clostridium methylpentosum, Ruminococcus lactaris|Clostridium methylpentosum, Ruminococcus obeum|Clostridium methylpentosum, Ruminococcus torques|Clostridium methylpentosum, Selenomonas sputigena|Clostridium methylpentosum, Shigella boydii|Clostridium methylpentosum, Shigella dysenteriae|Clostridium methylpentosum, Shigella sonnei|Clostridium methylpentosum, Slackia exigua|Clostridium methylpentosum, Solobacterium moorei|Clostridium methylpentosum, Staphylococcus aureus|Clostridium methylpentosum, Staphylococcus epidermidis|Clostridium methylpentosum, Staphylococcus hominis|Clostridium methylpentosum, Staphylococcus saprophyticus|Clostridium methylpentosum, Staphylococcus warneri|Clostridium methylpentosum, Streptococcus agalactiae|Clostridium methylpentosum, Streptococcus anginosus|Clostridium methylpentosum, Streptococcus australis|Clostridium methylpentosum, Streptococcus bovis|Clostridium methylpentosum, Streptococcus cristatus|Clostridium methylpentosum, Streptococcus dysgalactiae|Clostridium methylpentosum, Streptococcus equinus|Clostridium methylpentosum, Streptococcus gordonii|Clostridium methylpentosum, Streptococcus infantarius|Clostridium methylpentosum, Streptococcus infantis|Clostridium methylpentosum, Streptococcus mitis|Clostridium methylpentosum, Streptococcus mutans|Clostridium methylpentosum, Streptococcus oralis|Clostridium methylpentosum, Streptococcus parasanguinis|Clostridium methylpentosum, Streptococcus peroris|Clostridium methylpentosum, Streptococcus pneumoniae|Clostridium methylpentosum, Streptococcus salivarius|Clostridium methylpentosum, Streptococcus sanguinis|Clostridium methylpentosum, Streptococcus thermophilus|Clostridium methylpentosum, Streptococcus vestibularis|Clostridium methylpentosum, Subdoligranulum variabile|Clostridium methylpentosum, Succinatimonas hippei|Clostridium methylpentosum, Sutterella wadsworthensis|Clostridium methylpentosum, Tropheryma whipplei|Clostridium methylpentosum, Veillonella atypica|Clostridium methylpentosum, Veillonella dispar|Clostridium methylpentosum, Veillonella parvula|Clostridium methylpentosum, Victivallis vadensis|Clostridium nexile, Clostridium nexile|Clostridium nexile, Clostridium orbiscindens|Clostridium nexile, Clostridium perfringens|Clostridium nexile, Clostridium saccharolyticum|Clostridium nexile, Clostridium scindens|Clostridium nexile, Clostridium symbiosum|Clostridium nexile, Clostridium tertium|Clostridium nexile, Collinsella aerofaciens|Clostridium nexile, Collinsella intestinalis|Clostridium nexile, Collinsella stercoris|Clostridium nexile, Coprobacillus* sp. D7|*Clostridium nexile, Coprococcus catus|Clostridium nexile, Coprococcus comes|Clostridium nexile, Coprococcus eutactus|Clostridium nexile, Corynebacterium aurimucosum|Clostridium nexile, Corynebacterium matruchotii|Clostridium nexile, Cryptobacterium curtum|Clostridium nexile, Desulfovibrio desulfuricans|Clostridium nexile, Desulfovibrio piger|Clostridium nexile, Dialister invisus|Clostridium nexile, Dialister microaerophilus|Clostridium nexile, Dorea formicigenerans|Clostridium nexile, Dorea longicatena|Clostridium nexile, Eggerthella lenta|Clostridium nexile, Eikenella corrodens|Clostridium nexile, Enterobacter cancerogenus|Clostridium nexile, Enterobacter cloacae|Clostridium nexile, Enterococcus faecalis|Clostridium nexile, Enterococcus faecium|Clostridium nexile, Enterococcus gallinarum|Clostridium nexile, Erysipelotrichaceae bacterium* 3_1_53|*Clostridium nexile, Escherichia coli|Clostridium nexile, Escherichia fergusonii|Clostridium nexile, Ethanoligenens harbinense|Clostridium nexile, Eubacterium cellulosolvens|Clostridium nexile, Eubacterium eligens|Clostridium nexile, Eubacterium hallii|Clostridium nexile, Eubacterium limosum|Clostridium nexile, Eubacterium rectale|Clostridium nexile, Eubacterium siraeum|Clostridium nexile, Eubacterium ventriosum|Clostridium nexile, Faecalibacterium prausnitzii|Clostridium nexile, Finegoldia magna|Clostridium nexile, Fusobacterium gonidiaformans|Clostridium nexile, Fusobacterium mortiferum|Clostridium nexile, Fusobacterium nucleatum|Clostridium nexile, Fusobacterium varium|Clostridium nexile, Gardnerella vaginalis|Clostridium nexile, Gemella haemolysans|Clostridium nexile, Gemella morbillorum|Clostridium nexile, Gordonibacter pamelaeae|Clostridium nexile, Granulicatella adiacens|Clostridium nexile, Granulicatella elegans|Clostridium nexile, Haemophilus influenzae|Clostridium nexile, Haemophilus parainfluenzae|Clostridium nexile, Helicobacter pullorum|Clostridium nexile, Helicobacter pylori|Clostridium nexile, Holdemania filiformis|Clostridium nexile, Kingella oralis|Clostridium nexile, Klebsiella pneumoniae|Clostridium nexile, Klebsiella*

TABLE 2-continued

| Table 2. Specific binary combinations of OTUs. Individual pairings are differentiated by "\|" and OTUs within a combination are differentiated by "," |
|---|
| variicola\|Clostridium nexile, Lachnospiraceae bacterium 5_1_57FAA\|Clostridium nexile, Lactobacillus acidophilus\|Clostridium nexile, Lactobacillus amylovorus\|Clostridium nexile, Lactobacillus brevis\|Clostridium nexile, Lactobacillus casei\|Clostridium nexile, Lactobacillus crispatus\|Clostridium nexile, Lactobacillus delbrueckii\|Clostridium nexile, Lactobacillus fermentum\|Clostridium nexile, Lactobacillus gasseri\|Clostridium nexile, Lactobacillus iners\|Clostridium nexile, Lactobacillus jensenii\|Clostridium nexile, Lactobacillus johnsonii\|Clostridium nexile, Lactobacillus paracasei\|Clostridium nexile, Lactobacillus plantarum\|Clostridium nexile, Lactobacillus reuteri\|Clostridium nexile, Lactobacillus rhamnosus\|Clostridium nexile, Lactobacillus ruminis\|Clostridium nexile, Lactobacillus sakei\|Clostridium nexile, Lactobacillus salivarius\|Clostridium nexile, Lactococcus lactis\|Clostridium nexile, Lautropia mirabilis\|Clostridium nexile, Leuconostoc citreum\|Clostridium nexile, Leuconostoc gasicomitatum\|Clostridium nexile, Leuconostoc mesenteroides\|Clostridium nexile, Listeria monocytogenes\|Clostridium nexile, Marvinbryantia formatexigens\|Clostridium nexile, Megamonas hypermegale\|Clostridium nexile, Megasphaera micronuciformis\|Clostridium nexile, Methanobrevibacter smithii\|Clostridium nexile, Methanosphaera stadtmanae\|Clostridium nexile, Methylobacterium radiotolerans\|Clostridium nexile, Mitsuokella multacida\|Clostridium nexile, Mobiluncus curtisii\|Clostridium nexile, Mycoplasma hominis\|Clostridium nexile, Neisseria mucosa\|Clostridium nexile, Odoribacter splanchnicus\|Clostridium nexile, Olsenella uli\|Clostridium nexile, Oribacterium sinus\|Clostridium nexile, Oxalobacter formigenes\|Clostridium nexile, Parabacteroides distasonis\|Clostridium nexile, Parabacteroides johnsonii\|Clostridium nexile, Parabacteroides merdae\|Clostridium nexile, Parvimonas micra\|Clostridium nexile, Pediococcus acidilactici\|Clostridium nexile, Pediococcus pentosaceus\|Clostridium nexile, Peptoniphilus duerdenii\|Clostridium nexile, Peptoniphilus harei\|Clostridium nexile, Peptoniphilus lacrimalis\|Clostridium nexile, Peptostreptococcus anaerobius\|Clostridium nexile, Peptostreptococcus stomatis\|Clostridium nexile, Porphyromonas asaccharolytica\|Clostridium nexile, Porphyromonas uenonis\|Clostridium nexile, Prevotella amnii\|Clostridium nexile, Prevotella bergensis\|Clostridium nexile, Prevotella bivia\|Clostridium nexile, Prevotella buccae\|Clostridium nexile, Prevotella buccalis\|Clostridium nexile, Prevotella copri\|Clostridium nexile, Prevotella disiens\|Clostridium nexile, Prevotella melaninogenica\|Clostridium nexile, Prevotella multiformis\|Clostridium nexile, Prevotella oralis\|Clostridium nexile, Prevotella oris\|Clostridium nexile, Prevotella salivae\|Clostridium nexile, Prevotella timonensis\|Clostridium nexile, Propionibacterium acnes\|Clostridium nexile, Propionibacterium freudenreichii\|Clostridium nexile, Proteus mirabilis\|Clostridium nexile, Proteus penneri\|Clostridium nexile, Pseudoflavonifractor capillosus\|Clostridium nexile, Pseudomonas aeruginosa\|Clostridium nexile, Pseudomonas fluorescens\|Clostridium nexile, Pseudomonas putida\|Clostridium nexile, Pseudoramibacter alactolyticus\|Clostridium nexile, Pyramidobacter piscolens\|Clostridium nexile, Rhodopseudomonas palustris\|Clostridium nexile, Roseburia intestinalis\|Clostridium nexile, Roseburia inulinivorans\|Clostridium nexile, Rothia dentocariosa\|Clostridium nexile, Rothia mucilaginosa\|Clostridium nexile, Ruminococcus albus\|Clostridium nexile, Ruminococcus bromii\|Clostridium nexile, Ruminococcus gnavus\|Clostridium nexile, Ruminococcus lactaris\|Clostridium nexile, Ruminococcus obeum\|Clostridium nexile, Ruminococcus torques\|Clostridium nexile, Selenomonas sputigena\|Clostridium nexile, Shigella boydii\|Clostridium nexile, Shigella dysenteriae\|Clostridium nexile, Shigella sonnei\|Clostridium nexile, Slackia exigua\|Clostridium nexile, Solobacterium moorei\|Clostridium nexile, Staphylococcus aureus\|Clostridium nexile, Staphylococcus epidermidis\|Clostridium nexile, Staphylococcus hominis\|Clostridium nexile, Staphylococcus saprophyticus\|Clostridium nexile, Staphylococcus warneri\|Clostridium nexile, Streptococcus agalactiae\|Clostridium nexile, Streptococcus anginosus\|Clostridium nexile, Streptococcus australis\|Clostridium nexile, Streptococcus bovis\|Clostridium nexile, Streptococcus cristatus\|Clostridium nexile, Streptococcus dysgalactiae\|Clostridium nexile, Streptococcus equinus\|Clostridium nexile, Streptococcus gordonii\|Clostridium nexile, Streptococcus infantarius\|Clostridium nexile, Streptococcus infantis\|Clostridium nexile, Streptococcus mitis\|Clostridium nexile, Streptococcus mutans\|Clostridium nexile, Streptococcus oralis\|Clostridium nexile, Streptococcus parasanguinis\|Clostridium nexile, Streptococcus peroris\|Clostridium nexile, Streptococcus pneumoniae\|Clostridium nexile, Streptococcus salivarius\|Clostridium nexile, Streptococcus sanguinis\|Clostridium nexile, Streptococcus thermophilus\|Clostridium nexile, Streptococcus vestibularis\|Clostridium nexile, Subdoligranulum variabile\|Clostridium nexile, Succinatimonas hippei\|Clostridium nexile, Sutterella wadsworthensis\|Clostridium nexile, Tropheryma whipplei\|Clostridium nexile, Veillonella atypica\|Clostridium nexile, Veillonella dispar\|Clostridium nexile, Veillonella parvula\|Clostridium nexile, Victivallis vadensis\|Clostridium orbiscindens, Clostridium orbiscindens\|Clostridium orbiscindens, Clostridium perfringens\|Clostridium orbiscindens, Clostridium saccharolyticum\|Clostridium orbiscindens, Clostridium scindens\|Clostridium orbiscindens, Clostridium symbiosum\|Clostridium orbiscindens, Clostridium tertium\|Clostridium orbiscindens, Collinsella aerofaciens\|Clostridium orbiscindens, Collinsella intestinalis\|Clostridium orbiscindens, Collinsella stercoris\|Clostridium orbiscindens, Coprobacillus sp. D7\|Clostridium orbiscindens, Coprococcus catus\|Clostridium orbiscindens, Coprococcus comes\|Clostridium orbiscindens, Coprococcus eutactus\|Clostridium orbiscindens, Corynebacterium aurimucosum\|Clostridium orbiscindens, Corynebacterium matruchotii\|Clostridium orbiscindens, Cryptobacterium curtum\|Clostridium orbiscindens, Desulfovibrio desulfuricans\|Clostridium orbiscindens, Desulfovibrio piger\|Clostridium orbiscindens, Dialister invisus\|Clostridium orbiscindens, Dialister microaerophilus\|Clostridium orbiscindens, Dorea formicigenerans\|Clostridium orbiscindens, Dorea longicatena\|Clostridium orbiscindens, Eggerthella lenta\|Clostridium orbiscindens, Eikenella corrodens\|Clostridium orbiscindens, Enterobacter cancerogenus\|Clostridium orbiscindens, Enterobacter cloacae\|Clostridium orbiscindens, Enterococcus faecalis\|Clostridium orbiscindens, Enterococcus faecium\|Clostridium orbiscindens, Enterococcus gallinarum\|Clostridium orbiscindens, Erysipelotrichaceae bacterium 3_1_53\|Clostridium orbiscindens, Escherichia coli\|Clostridium orbiscindens, Escherichia fergusonii\|Clostridium orbiscindens, Ethanoligenens harbinense\|Clostridium orbiscindens, Eubacterium cellulosolvens\|Clostridium orbiscindens, Eubacterium eligens\|Clostridium orbiscindens, Eubacterium hallii\|Clostridium orbiscindens, Eubacterium limosum\|Clostridium orbiscindens, Eubacterium rectale\|Clostridium orbiscindens, Eubacterium siraeum\|Clostridium orbiscindens, Eubacterium ventriosum\|Clostridium orbiscindens, Faecalibacterium prausnitzii\|Clostridium orbiscindens, Finegoldia magna\|Clostridium orbiscindens, Fusobacterium gonidiaformans\|Clostridium orbiscindens, Fusobacterium mortiferum\|Clostridium orbiscindens, Fusobacterium nucleatum\|Clostridium orbiscindens, Fusobacterium varium\|Clostridium orbiscindens, Gardnerella vaginalis\|Clostridium orbiscindens, Gemella haemolysans\|Clostridium orbiscindens, Gemella morbillorum\|Clostridium orbiscindens, Gordonibacter pamelaeae\|Clostridium orbiscindens, Granulicatella adiacens\|Clostridium orbiscindens, Granulicatella elegans\|Clostridium orbiscindens, Haemophilus influenzae\|Clostridium orbiscindens, Haemophilus parainfluenzae\|Clostridium orbiscindens, Helicobacter pullorum\|Clostridium orbiscindens, Helicobacter pylori\|Clostridium orbiscindens, Holdemania filiformis\|Clostridium orbiscindens, Kingella oralis\|Clostridium orbiscindens, Klebsiella pneumoniae\|Clostridium orbiscindens, Klebsiella variicola\|Clostridium orbiscindens, Lachnospiraceae bacterium 5_1_57FAA\|Clostridium orbiscindens, Lactobacillus acidophilus\|Clostridium orbiscindens, Lactobacillus amylovorus\|Clostridium orbiscindens, Lactobacillus brevis\|Clostridium orbiscindens, Lactobacillus casei\|Clostridium orbiscindens, Lactobacillus crispatus\|Clostridium orbiscindens, Lactobacillus delbrueckii\|Clostridium orbiscindens, Lactobacillus fermentum\|Clostridium orbiscindens, Lactobacillus gasseri\|Clostridium orbiscindens, Lactobacillus iners\|Clostridium orbiscindens, Lactobacillus jensenii\|Clostridium orbiscindens, Lactobacillus johnsonii\|Clostridium orbiscindens, Lactobacillus paracasei\|Clostridium orbiscindens, Lactobacillus plantarum\|Clostridium orbiscindens, Lactobacillus reuteri\|Clostridium orbiscindens, Lactobacillus rhamnosus\|Clostridium orbiscindens, Lactobacillus ruminis\|Clostridium orbiscindens, Lactobacillus sakei\|Clostridium orbiscindens, Lactobacillus salivarius\|Clostridium orbiscindens, Lactococcus lactis\|Clostridium orbiscindens, Lautropia mirabilis\|Clostridium orbiscindens, Leuconostoc citreum\|Clostridium orbiscindens, Leuconostoc gasicomitatum\|Clostridium orbiscindens, Leuconostoc mesenteroides\|Clostridium orbiscindens, Listeria monocytogenes\|Clostridium orbiscindens, Marvinbryantia formatexigens\|Clostridium orbiscindens, Megamonas hypermegale\|Clostridium orbiscindens, Megasphaera micronuciformis\|Clostridium orbiscindens, Methanobrevibacter smithii\|Clostridium orbiscindens, Methanosphaera stadtmanae\|Clostridium orbiscindens, Methylobacterium radiotolerans\|Clostridium orbiscindens, Mitsuokella multacida\|Clostridium orbiscindens, Mobiluncus curtisii\|Clostridium orbiscindens, Mycoplasma hominis\|Clostridium orbiscindens, Neisseria |

TABLE 2-continued

| Table 2. Specific binary combinations of OTUs. Individual pairings are differentiated by "\|" and OTUs within a combination are differentiated by "," |
|---|
| *mucosa\|Clostridium orbiscindens, Odoribacter splanchnicus\|Clostridium orbiscindens, Olsenella uli\|Clostridium orbiscindens, Oribacterium sinus\|Clostridium orbiscindens, Oxalobacter formigenes\|Clostridium orbiscindens, Parabacteroides distasonis\|Clostridium orbiscindens, Parabacteroides johnsonii\|Clostridium orbiscindens, Parabacteroides merdae\|Clostridium orbiscindens, Parvimonas micra\|Clostridium orbiscindens, Pediococcus acidilactici\|Clostridium orbiscindens, Pediococcus pentosaceus\|Clostridium orbiscindens, Peptoniphilus duerdenii\|Clostridium orbiscindens, Peptoniphilus harei\|Clostridium orbiscindens, Peptoniphilus lacrimalis\|Clostridium orbiscindens, Peptostreptococcus anaerobius\|Clostridium orbiscindens, Peptostreptococcus stomatis\|Clostridium orbiscindens, Porphyromonas asaccharolytica\|Clostridium orbiscindens, Porphyromonas uenonis\|Clostridium orbiscindens, Prevotella amnii\|Clostridium orbiscindens, Prevotella bergensis\|Clostridium orbiscindens, Prevotella bivia\|Clostridium orbiscindens, Prevotella buccae\|Clostridium orbiscindens, Prevotella buccalis\|Clostridium orbiscindens, Prevotella copri\|Clostridium orbiscindens, Prevotella disiens\|Clostridium orbiscindens, Prevotella melaninogenica\|Clostridium orbiscindens, Prevotella multiformis\|Clostridium orbiscindens, Prevotella oralis\|Clostridium orbiscindens, Prevotella oris\|Clostridium orbiscindens, Prevotella salivae\|Clostridium orbiscindens, Prevotella timonensis\|Clostridium orbiscindens, Propionibacterium acnes\|Clostridium orbiscindens, Propionibacterium freudenreichii\|Clostridium orbiscindens, Proteus mirabilis\|Clostridium orbiscindens, Proteus penneri\|Clostridium orbiscindens, Pseudoflavonifractor capillosus\|Clostridium orbiscindens, Pseudomonas aeruginosa\|Clostridium orbiscindens, Pseudomonas fluorescens\|Clostridium orbiscindens, Pseudomonas putida\|Clostridium orbiscindens, Pseudoramibacter alactolyticus\|Clostridium orbiscindens, Pyramidobacter piscolens\|Clostridium orbiscindens, Rhodopseudomonas palustris\|Clostridium orbiscindens, Roseburia intestinalis\|Clostridium orbiscindens, Roseburia inulinivorans\|Clostridium orbiscindens, Rothia dentocariosa\|Clostridium orbiscindens, Rothia mucilaginosa\|Clostridium orbiscindens, Ruminococcus albus\|Clostridium orbiscindens, Ruminococcus bromii\|Clostridium orbiscindens, Ruminococcus gnavus\|Clostridium orbiscindens, Ruminococcus lactaris\|Clostridium orbiscindens, Ruminococcus obeum\|Clostridium orbiscindens, Ruminococcus torques\|Clostridium orbiscindens, Selenomonas sputigena\|Clostridium orbiscindens, Shigella boydii\|Clostridium orbiscindens, Shigella dysenteriae\|Clostridium orbiscindens, Shigella sonnei\|Clostridium orbiscindens, Slackia exigua\|Clostridium orbiscindens, Solobacterium moorei\|Clostridium orbiscindens, Staphylococcus aureus\|Clostridium orbiscindens, Staphylococcus epidermidis\|Clostridium orbiscindens, Staphylococcus hominis\|Clostridium orbiscindens, Staphylococcus saprophyticus\|Clostridium orbiscindens, Staphylococcus warneri\|Clostridium orbiscindens, Streptococcus agalactiae\|Clostridium orbiscindens, Streptococcus anginosus\|Clostridium orbiscindens, Streptococcus australis\|Clostridium orbiscindens, Streptococcus bovis\|Clostridium orbiscindens, Streptococcus cristatus\|Clostridium orbiscindens, Streptococcus dysgalactiae\|Clostridium orbiscindens, Streptococcus equinus\|Clostridium orbiscindens, Streptococcus gordonii\|Clostridium orbiscindens, Streptococcus infantarius\|Clostridium orbiscindens, Streptococcus infantis\|Clostridium orbiscindens, Streptococcus mitis\|Clostridium orbiscindens, Streptococcus mutans\|Clostridium orbiscindens, Streptococcus oralis\|Clostridium orbiscindens, Streptococcus parasanguinis\|Clostridium orbiscindens, Streptococcus peroris\|Clostridium orbiscindens, Streptococcus pneumoniae\|Clostridium orbiscindens, Streptococcus salivarius\|Clostridium orbiscindens, Streptococcus sanguinis\|Clostridium orbiscindens, Streptococcus thermophilus\|Clostridium orbiscindens, Streptococcus vestibularis\|Clostridium orbiscindens, Subdoligranulum variabile\|Clostridium orbiscindens, Succinatimonas hippei\|Clostridium orbiscindens, Sutterella wadsworthensis\|Clostridium orbiscindens, Tropheryma whipplei\|Clostridium orbiscindens, Veillonella atypica\|Clostridium orbiscindens, Veillonella dispar\|Clostridium orbiscindens, Veillonella parvula\|Clostridium orbiscindens, Victivallis vadensis\|Clostridium perfringens, Clostridium perfringens\|Clostridium perfringens, Clostridium saccharolyticum\|Clostridium perfringens, Clostridium scindens\|Clostridium perfringens, Clostridium symbiosum\|Clostridium perfringens, Clostridium tertium\|Clostridium perfringens, Collinsella aerofaciens\|Clostridium perfringens, Collinsella intestinalis\|Clostridium perfringens, Collinsella stercoris\|Clostridium perfringens, Coprobacillus* sp. D7\|*Clostridium perfringens, Coprococcus catus\|Clostridium perfringens, Coprococcus comes\|Clostridium perfringens, Coprococcus eutactus\|Clostridium perfringens, Corynebacterium aurimucosum\|Clostridium perfringens, Corynebacterium matruchotii\|Clostridium perfringens, Cryptobacterium curtum\|Clostridium perfringens, Desulfovibrio desulfuricans\|Clostridium perfringens, Desulfovibrio piger\|Clostridium perfringens, Dialister invisus\|Clostridium perfringens, Dialister microaerophilus\|Clostridium perfringens, Dorea formicigenerans\|Clostridium perfringens, Dorea longicatena\|Clostridium perfringens, Eggerthella lenta\|Clostridium perfringens, Eikenella corrodens\|Clostridium perfringens, Enterobacter cancerogenus\|Clostridium perfringens, Enterobacter cloacae\|Clostridium perfringens, Enterococcus faecalis\|Clostridium perfringens, Enterococcus faecium\|Clostridium perfringens, Enterococcus gallinarum\|Clostridium perfringens, Erysipelotrichaceae bacterium* 3_1_53\|*Clostridium perfringens, Escherichia coli\|Clostridium perfringens, Escherichia fergusonii\|Clostridium perfringens, Ethanoligenens harbinense\|Clostridium perfringens, Eubacterium cellulosolvens\|Clostridium perfringens, Eubacterium eligens\|Clostridium perfringens, Eubacterium hallii\|Clostridium perfringens, Eubacterium limosum\|Clostridium perfringens, Eubacterium rectale\|Clostridium perfringens, Eubacterium siraeum\|Clostridium perfringens, Eubacterium ventriosum\|Clostridium perfringens, Faecalibacterium prausnitzii\|Clostridium perfringens, Finegoldia magna\|Clostridium perfringens, Fusobacterium gonidiaformans\|Clostridium perfringens, Fusobacterium mortiferum\|Clostridium perfringens, Fusobacterium nucleatum\|Clostridium perfringens, Fusobacterium varium\|Clostridium perfringens, Gardnerella vaginalis\|Clostridium perfringens, Gemella haemolysans\|Clostridium perfringens, Gemella morbillorum\|Clostridium perfringens, Gordonibacter pamelaeae\|Clostridium perfringens, Granulicatella adiacens\|Clostridium perfringens, Granulicatella elegans\|Clostridium perfringens, Haemophilus influenzae\|Clostridium perfringens, Haemophilus parainfluenzae\|Clostridium perfringens, Helicobacter pullorum\|Clostridium perfringens, Helicobacter pylori\|Clostridium perfringens, Holdemania filiformis\|Clostridium perfringens, Kingella oralis\|Clostridium perfringens, Klebsiella pneumoniae\|Clostridium perfringens, Klebsiella variicola\|Clostridium perfringens, Lachnospiraceae bacterium* 5_1_57FAA\|*Clostridium perfringens, Lactobacillus acidophilus\|Clostridium perfringens, Lactobacillus amylovorus\|Clostridium perfringens, Lactobacillus brevis\|Clostridium perfringens, Lactobacillus casei\|Clostridium perfringens, Lactobacillus crispatus\|Clostridium perfringens, Lactobacillus delbrueckii\|Clostridium perfringens, Lactobacillus fermentum\|Clostridium perfringens, Lactobacillus gasseri\|Clostridium perfringens, Lactobacillus iners\|Clostridium perfringens, Lactobacillus jensenii\|Clostridium perfringens, Lactobacillus johnsonii\|Clostridium perfringens, Lactobacillus paracasei\|Clostridium perfringens, Lactobacillus plantarum\|Clostridium perfringens, Lactobacillus reuteri\|Clostridium perfringens, Lactobacillus rhamnosus\|Clostridium perfringens, Lactobacillus ruminis\|Clostridium perfringens, Lactobacillus sakei\|Clostridium perfringens, Lactobacillus salivarius\|Clostridium perfringens, Lactococcus lactis\|Clostridium perfringens, Lautropia mirabilis\|Clostridium perfringens, Leuconostoc citreum\|Clostridium perfringens, Leuconostoc gasicomitatum\|Clostridium perfringens, Leuconostoc mesenteroides\|Clostridium perfringens, Listeria monocytogenes\|Clostridium perfringens, Marvinbryantia formatexigens\|Clostridium perfringens, Megamonas hypermegale\|Clostridium perfringens, Megasphaera micronuciformis\|Clostridium perfringens, Methanobrevibacter smithii\|Clostridium perfringens, Methanosphaera stadtmanae\|Clostridium perfringens, Methylobacterium radiotolerans\|Clostridium perfringens, Mitsuokella multacida\|Clostridium perfringens, Mobiluncus curtisii\|Clostridium perfringens, Mycoplasma hominis\|Clostridium perfringens, Neisseria mucosa\|Clostridium perfringens, Odoribacter splanchnicus\|Clostridium perfringens, Olsenella uli\|Clostridium perfringens, Oribacterium sinus\|Clostridium perfringens, Oxalobacter formigenes\|Clostridium perfringens, Parabacteroides distasonis\|Clostridium perfringens, Parabacteroides johnsonii\|Clostridium perfringens, Parabacteroides merdae\|Clostridium perfringens, Parvimonas micra\|Clostridium perfringens, Pediococcus acidilactici\|Clostridium perfringens, Pediococcus pentosaceus\|Clostridium perfringens, Peptoniphilus duerdenii\|Clostridium perfringens, Peptoniphilus harei\|Clostridium perfringens, Peptoniphilus lacrimalis\|Clostridium perfringens, Peptostreptococcus anaerobius\|Clostridium perfringens, Peptostreptococcus stomatis\|Clostridium perfringens, Porphyromonas asaccharolytica\|Clostridium perfringens, Porphyromonas uenonis\|Clostridium perfringens, Prevotella amnii\|Clostridium perfringens, Prevotella bergensis\|Clostridium perfringens, Prevotella bivia\|Clostridium perfringens, Prevotella buccae\|Clostridium perfringens, Prevotella buccalis\|Clostridium perfringens, Prevotella copri\|Clostridium* |

TABLE 2-continued

Table 2. Specific binary combinations of OTUs. Individual pairings are differentiated by "|" and OTUs within a combination are differentiated by ","

perfringens, Prevotella disiens|Clostridium perfringens, Prevotella melaninogenica|Clostridium perfringens, Prevotella multiformis|Clostridium perfringens, Prevotella oralis|Clostridium perfringens, Prevotella oris|Clostridium perfringens, Prevotella salivae|Clostridium perfringens, Prevotella timonensis|Clostridium perfringens, Propionibacterium acnes|Clostridium perfringens, Propionibacterium freudenreichii|Clostridium perfringens, Proteus mirabilis|Clostridium perfringens, Proteus penneri|Clostridium perfringens, Pseudoflavonifractor capillosus|Clostridium perfringens, Pseudomonas aeruginosa|Clostridium perfringens, Pseudomonas fluorescens|Clostridium perfringens, Pseudomonas putida|Clostridium perfringens, Pseudoramibacter alactolyticus|Clostridium perfringens, Pyramidobacter piscolens|Clostridium perfringens, Rhodopseudomonas palustris|Clostridium perfringens, Roseburia intestinalis|Clostridium perfringens, Roseburia inulinivorans|Clostridium perfringens, Rothia dentocariosa|Clostridium perfringens, Rothia mucilaginosa|Clostridium perfringens, Ruminococcus albus|Clostridium perfringens, Ruminococcus bromii|Clostridium perfringens, Ruminococcus gnavus|Clostridium perfringens, Ruminococcus lactaris|Clostridium perfringens, Ruminococcus obeum|Clostridium perfringens, Ruminococcus torques|Clostridium perfringens, Selenomonas sputigena|Clostridium perfringens, Shigella boydii|Clostridium perfringens, Shigella dysenteriae|Clostridium perfringens, Shigella sonnei|Clostridium perfringens, Slackia exigua|Clostridium perfringens, Solobacterium moorei|Clostridium perfringens, Staphylococcus aureus|Clostridium perfringens, Staphylococcus epidermidis|Clostridium perfringens, Staphylococcus hominis|Clostridium perfringens, Staphylococcus saprophyticus|Clostridium perfringens, Staphylococcus warneri|Clostridium perfringens, Streptococcus agalactiae|Clostridium perfringens, Streptococcus anginosus|Clostridium perfringens, Streptococcus australis|Clostridium perfringens, Streptococcus bovis|Clostridium perfringens, Streptococcus cristatus|Clostridium perfringens, Streptococcus dysgalactiae|Clostridium perfringens, Streptococcus equinus|Clostridium perfringens, Streptococcus gordonii|Clostridium perfringens, Streptococcus infantarius|Clostridium perfringens, Streptococcus infantis|Clostridium perfringens, Streptococcus mitis|Clostridium perfringens, Streptococcus mutans|Clostridium perfringens, Streptococcus oralis|Clostridium perfringens, Streptococcus parasanguinis|Clostridium perfringens, Streptococcus peroris|Clostridium perfringens, Streptococcus pneumoniae|Clostridium perfringens, Streptococcus salivarius|Clostridium perfringens, Streptococcus sanguinis|Clostridium perfringens, Streptococcus thermophilus|Clostridium perfringens, Streptococcus vestibularis|Clostridium perfringens, Subdoligranulum variabile|Clostridium perfringens, Succinatimonas hippei|Clostridium perfringens, Sutterella wadsworthensis|Clostridium perfringens, Tropheryma whipplei|Clostridium perfringens, Veillonella atypica|Clostridium perfringens, Veillonella dispar|Clostridium perfringens, Veillonella parvula|Clostridium perfringens, Victivallis vadensis|Clostridium saccharolyticum, Clostridium saccharolyticum|Clostridium saccharolyticum, Clostridium scindens|Clostridium saccharolyticum, Clostridium symbiosum|Clostridium saccharolyticum, Clostridium tertium|Clostridium saccharolyticum, Collinsella aerofaciens|Clostridium saccharolyticum, Collinsella intestinalis|Clostridium saccharolyticum, Collinsella stercoris|Clostridium saccharolyticum, Coprobacillus sp. D7|Clostridium saccharolyticum, Coprococcus catus|Clostridium saccharolyticum, Coprococcus comes|Clostridium saccharolyticum, Coprococcus eutactus|Clostridium saccharolyticum, Corynebacterium aurimucosum|Clostridium saccharolyticum, Corynebacterium matruchotii|Clostridium saccharolyticum, Cryptobacterium curtum|Clostridium saccharolyticum, Desulfovibrio desulfuricans|Clostridium saccharolyticum, Desulfovibrio piger|Clostridium saccharolyticum, Dialister invisus|Clostridium saccharolyticum, Dialister microaerophilus|Clostridium saccharolyticum, Dorea formicigenerans|Clostridium saccharolyticum, Dorea longicatena|Clostridium saccharolyticum, Eggerthella lenta|Clostridium saccharolyticum, Eikenella corrodens|Clostridium saccharolyticum, Enterobacter cancerogenus|Clostridium saccharolyticum, Enterobacter cloacae|Clostridium saccharolyticum, Enterococcus faecalis|Clostridium saccharolyticum, Enterococcus faecium|Clostridium saccharolyticum, Enterococcus gallinarum|Clostridium saccharolyticum, Erysipelotrichaceae bacterium 3_1_53|Clostridium saccharolyticum, Escherichia coli|Clostridium saccharolyticum, Escherichia fergusonii|Clostridium saccharolyticum, Ethanoligenens harbinense|Clostridium saccharolyticum, Eubacterium cellulosolvens|Clostridium saccharolyticum, Eubacterium eligens|Clostridium saccharolyticum, Eubacterium hallii|Clostridium saccharolyticum, Eubacterium limosum|Clostridium saccharolyticum, Eubacterium rectale|Clostridium saccharolyticum, Eubacterium siraeum|Clostridium saccharolyticum, Eubacterium ventriosum|Clostridium saccharolyticum, Faecalibacterium prausnitzii|Clostridium saccharolyticum, Finegoldia magna|Clostridium saccharolyticum, Fusobacterium gonidiaformans|Clostridium saccharolyticum, Fusobacterium mortiferum|Clostridium saccharolyticum, Fusobacterium nucleatum|Clostridium saccharolyticum, Fusobacterium varium|Clostridium saccharolyticum, Gardnerella vaginalis|Clostridium saccharolyticum, Gemella haemolysans|Clostridium saccharolyticum, Gemella morbillorum|Clostridium saccharolyticum, Gordonibacter pamelaeae|Clostridium saccharolyticum, Granulicatella adiacens|Clostridium saccharolyticum, Granulicatella elegans|Clostridium saccharolyticum, Haemophilus influenzae|Clostridium saccharolyticum, Haemophilus parainfluenzae|Clostridium saccharolyticum, Helicobacter pullorum|Clostridium saccharolyticum, Helicobacter pylori|Clostridium saccharolyticum, Holdemania filiformis|Clostridium saccharolyticum, Kingella oralis|Clostridium saccharolyticum, Klebsiella pneumoniae|Clostridium saccharolyticum, Klebsiella variicola|Clostridium saccharolyticum, Lachnospiraceae bacterium 5_1_57FAA|Clostridium saccharolyticum, Lactobacillus acidophilus|Clostridium saccharolyticum, Lactobacillus amylovorus|Clostridium saccharolyticum, Lactobacillus brevis|Clostridium saccharolyticum, Lactobacillus casei|Clostridium saccharolyticum, Lactobacillus crispatus|Clostridium saccharolyticum, Lactobacillus delbrueckii|Clostridium saccharolyticum, Lactobacillus fermentum|Clostridium saccharolyticum, Lactobacillus gasseri|Clostridium saccharolyticum, Lactobacillus iners|Clostridium saccharolyticum, Lactobacillus jensenii|Clostridium saccharolyticum, Lactobacillus johnsonii|Clostridium saccharolyticum, Lactobacillus paracasei|Clostridium saccharolyticum, Lactobacillus plantarum|Clostridium saccharolyticum, Lactobacillus reuteri|Clostridium saccharolyticum, Lactobacillus rhamnosus|Clostridium saccharolyticum, Lactobacillus ruminis|Clostridium saccharolyticum, Lactobacillus sakei|Clostridium saccharolyticum, Lactobacillus salivarius|Clostridium saccharolyticum, Lactococcus lactis|Clostridium saccharolyticum, Lautropia mirabilis|Clostridium saccharolyticum, Leuconostoc citreum|Clostridium saccharolyticum, Leuconostoc gasicomitatum|Clostridium saccharolyticum, Leuconostoc mesenteroides|Clostridium saccharolyticum, Listeria monocytogenes|Clostridium saccharolyticum, Marvinbryantia formatexigens|Clostridium saccharolyticum, Megamonas hypermegale|Clostridium saccharolyticum, Megasphaera micronuciformis|Clostridium saccharolyticum, Methanobrevibacter smithii|Clostridium saccharolyticum, Methanosphaera stadtmanae|Clostridium saccharolyticum, Methylobacterium radiotolerans|Clostridium saccharolyticum, Mitsuokella multacida|Clostridium saccharolyticum, Mobiluncus curtisii|Clostridium saccharolyticum, Mycoplasma hominis|Clostridium saccharolyticum, Neisseria mucosa|Clostridium saccharolyticum, Odoribacter splanchnicus|Clostridium saccharolyticum, Olsenella uli|Clostridium saccharolyticum, Oribacterium sinus|Clostridium saccharolyticum, Oxalobacter formigenes|Clostridium saccharolyticum, Parabacteroides distasonis|Clostridium saccharolyticum, Parabacteroides johnsonii|Clostridium saccharolyticum, Parabacteroides merdae|Clostridium saccharolyticum, Parvimonas micra|Clostridium saccharolyticum, Pediococcus acidilactici|Clostridium saccharolyticum, Pediococcus pentosaceus|Clostridium saccharolyticum, Peptoniphilus duerdenii|Clostridium saccharolyticum, Peptoniphilus harei|Clostridium saccharolyticum, Peptoniphilus lacrimalis|Clostridium saccharolyticum, Peptostreptococcus anaerobius|Clostridium saccharolyticum, Peptostreptococcus stomatis|Clostridium saccharolyticum, Porphyromonas asaccharolytica|Clostridium saccharolyticum, Porphyromonas uenonis|Clostridium saccharolyticum, Prevotella amnii|Clostridium saccharolyticum, Prevotella bergensis|Clostridium saccharolyticum, Prevotella bivia|Clostridium saccharolyticum, Prevotella buccae|Clostridium saccharolyticum, Prevotella buccalis|Clostridium saccharolyticum, Prevotella copri|Clostridium saccharolyticum, Prevotella disiens|Clostridium saccharolyticum, Prevotella melaninogenica|Clostridium saccharolyticum, Prevotella multiformis|Clostridium saccharolyticum, Prevotella oralis|Clostridium saccharolyticum, Prevotella oris|Clostridium saccharolyticum, Prevotella salivae|Clostridium saccharolyticum, Prevotella timonensis|Clostridium saccharolyticum, Propionibacterium acnes|Clostridium saccharolyticum, Propionibacterium freudenreichii|Clostridium saccharolyticum, Proteus mirabilis|Clostridium saccharolyticum, Proteus penneri|Clostridium saccharolyticum, Pseudoflavonifractor capillosus|Clostridium TABLE 2-continued

| Table 2. Specific binary combinations of OTUs. Individual pairings are differentiated by "\|" and OTUs within a combination are differentiated by "," |
|---|
| saccharolyticum, Pseudomonas aeruginosa\|Clostridium saccharolyticum, Pseudomonas fluorescens\|Clostridium saccharolyticum, Pseudomonas putida\|Clostridium saccharolyticum, Pseudoramibacter alactolyticus\|Clostridium saccharolyticum, Pyramidobacter piscolens\|Clostridium saccharolyticum, Rhodopseudomonas palustris\|Clostridium saccharolyticum, Roseburia intestinalis\|Clostridium saccharolyticum, Roseburia inulinivorans\|Clostridium saccharolyticum, Rothia dentocariosa\|Clostridium saccharolyticum, Rothia mucilaginosa\|Clostridium saccharolyticum, Ruminococcus albus\|Clostridium saccharolyticum, Ruminococcus bromii\|Clostridium saccharolyticum, Ruminococcus gnavus\|Clostridium saccharolyticum, Ruminococcus lactaris\|Clostridium saccharolyticum, Ruminococcus obeum\|Clostridium saccharolyticum, Ruminococcus torques\|Clostridium saccharolyticum, Selenomonas sputigena\|Clostridium saccharolyticum, Shigella boydii\|Clostridium saccharolyticum, Shigella dysenteriae\|Clostridium saccharolyticum, Shigella sonnei\|Clostridium saccharolyticum, Slackia exigua\|Clostridium saccharolyticum, Solobacterium moorei\|Clostridium saccharolyticum, Staphylococcus aureus\|Clostridium saccharolyticum, Staphylococcus epidermidis\|Clostridium saccharolyticum, Staphylococcus hominis\|Clostridium saccharolyticum, Staphylococcus saprophyticus\|Clostridium saccharolyticum, Staphylococcus warneri\|Clostridium saccharolyticum, Streptococcus agalactiae\|Clostridium saccharolyticum, Streptococcus anginosus\|Clostridium saccharolyticum, Streptococcus australis\|Clostridium saccharolyticum, Streptococcus bovis\|Clostridium saccharolyticum, Streptococcus cristatus\|Clostridium saccharolyticum, Streptococcus dysgalactiae\|Clostridium saccharolyticum, Streptococcus equinus\|Clostridium saccharolyticum, Streptococcus gordonii\|Clostridium saccharolyticum, Streptococcus infantarius\|Clostridium saccharolyticum, Streptococcus infantis\|Clostridium saccharolyticum, Streptococcus mitis\|Clostridium saccharolyticum, Streptococcus mutans\|Clostridium saccharolyticum, Streptococcus oralis\|Clostridium saccharolyticum, Streptococcus parasanguinis\|Clostridium saccharolyticum, Streptococcus peroris\|Clostridium saccharolyticum, Streptococcus pneumoniae\|Clostridium saccharolyticum, Streptococcus salivarius\|Clostridium saccharolyticum, Streptococcus sanguinis\|Clostridium saccharolyticum, Streptococcus thermophilus\|Clostridium saccharolyticum, Streptococcus vestibularis\|Clostridium saccharolyticum, Subdoligranulum variabile\|Clostridium saccharolyticum, Succinatimonas hippei\|Clostridium saccharolyticum, Sutterella wadsworthensis\|Clostridium saccharolyticum, Tropheryma whipplei\|Clostridium saccharolyticum, Veillonella atypica\|Clostridium saccharolyticum, Veillonella dispar\|Clostridium saccharolyticum, Veillonella parvula\|Clostridium saccharolyticum, Victivallis vadensis\|Clostridium scindens, Clostridium scindens\|Clostridium scindens, Clostridium symbiosum, Clostridium scindens, Clostridium tertium\|Clostridium scindens, Collinsella aerofaciens\|Clostridium scindens, Collinsella intestinalis\|Clostridium scindens, Collinsella stercoris\|Clostridium scindens, Coprobacillus sp. D7\|Clostridium scindens, Coprococcus catus\|Clostridium scindens, Coprococcus comes\|Clostridium scindens, Coprococcus eutactus\|Clostridium scindens, Corynebacterium aurimucosum\|Clostridium scindens, Corynebacterium matruchotii\|Clostridium scindens, Cryptobacterium curtum\|Clostridium scindens, Desulfovibrio desulfuricans\|Clostridium scindens, Desulfovibrio piger\|Clostridium scindens, Dialister invisus\|Clostridium scindens, Dialister microaerophilus\|Clostridium scindens, Dorea formicigenerans\|Clostridium scindens, Dorea longicatena\|Clostridium scindens, Eggerthella lenta\|Clostridium scindens, Eikenella corrodens\|Clostridium scindens, Enterobacter cancerogenus\|Clostridium scindens, Enterobacter cloacae\|Clostridium scindens, Enterococcus faecalis\|Clostridium scindens, Enterococcus faecium\|Clostridium scindens, Enterococcus gallinarum\|Clostridium scindens, Erysipelotrichaceae bacterium 3_1_53\|Clostridium scindens, Escherichia coli\|Clostridium scindens, Escherichia fergusonii\|Clostridium scindens, Ethanoligenens harbinense\|Clostridium scindens, Eubacterium cellulosolvens\|Clostridium scindens, Eubacterium eligens\|Clostridium scindens, Eubacterium hallii\|Clostridium scindens, Eubacterium limosum\|Clostridium scindens, Eubacterium rectale\|Clostridium scindens, Eubacterium siraeum\|Clostridium scindens, Eubacterium ventriosum\|Clostridium scindens, Faecalibacterium prausnitzii\|Clostridium scindens, Finegoldia magna\|Clostridium scindens, Fusobacterium gonidiaformans\|Clostridium scindens, Fusobacterium mortiferum\|Clostridium scindens, Fusobacterium nucleatum\|Clostridium scindens, Fusobacterium varium\|Clostridium scindens, Gardnerella vaginalis\|Clostridium scindens, Gemella haemolysans\|Clostridium scindens, Gemella morbillorum\|Clostridium scindens, Gordonibacter pamelaeae\|Clostridium scindens, Granulicatella adiacens\|Clostridium scindens, Granulicatella elegans\|Clostridium scindens, Haemophilus influenzae\|Clostridium scindens, Haemophilus parainfluenzae\|Clostridium scindens, Helicobacter pullorum\|Clostridium scindens, Helicobacter pylori\|Clostridium scindens, Holdemania filiformis\|Clostridium scindens, Kingella oralis\|Clostridium scindens, Klebsiella pneumoniae\|Clostridium scindens, Klebsiella variicola\|Clostridium scindens, Lachnospiraceae bacterium 5_1_57FAA\|Clostridium scindens, Lactobacillus acidophilus\|Clostridium scindens, Lactobacillus amylovorus\|Clostridium scindens, Lactobacillus brevis\|Clostridium scindens, Lactobacillus casei\|Clostridium scindens, Lactobacillus crispatus\|Clostridium scindens, Lactobacillus delbrueckii\|Clostridium scindens, Lactobacillus fermentum\|Clostridium scindens, Lactobacillus gasseri\|Clostridium scindens, Lactobacillus iners\|Clostridium scindens, Lactobacillus jensenii\|Clostridium scindens, Lactobacillus johnsonii\|Clostridium scindens, Lactobacillus paracasei\|Clostridium scindens, Lactobacillus plantarum\|Clostridium scindens, Lactobacillus reuteri\|Clostridium scindens, Lactobacillus rhamnosus\|Clostridium scindens, Lactobacillus ruminis\|Clostridium scindens, Lactobacillus sakei\|Clostridium scindens, Lactobacillus salivarius\|Clostridium scindens, Lactococcus lactis\|Clostridium scindens, Lautropia mirabilis\|Clostridium scindens, Leuconostoc citreum\|Clostridium scindens, Leuconostoc gasicomitatum\|Clostridium scindens, Leuconostoc mesenteroides\|Clostridium scindens, Listeria monocytogenes\|Clostridium scindens, Marvinbryantia formatexigens\|Clostridium scindens, Megamonas hypermegale\|Clostridium scindens, Megasphaera micronuciformis\|Clostridium scindens, Methanobrevibacter smithii\|Clostridium scindens, Methanosphaera stadtmanae\|Clostridium scindens, Methylobacterium radiotolerans\|Clostridium scindens, Mitsuokella multacida\|Clostridium scindens, Mobiluncus curtisii\|Clostridium scindens, Mycoplasma hominis\|Clostridium scindens, Neisseria mucosa\|Clostridium scindens, Odoribacter splanchnicus\|Clostridium scindens, Olsenella uli\|Clostridium scindens, Oribacterium sinus\|Clostridium scindens, Oxalobacter formigenes\|Clostridium scindens, Parabacteroides distasonis\|Clostridium scindens, Parabacteroides johnsonii\|Clostridium scindens, Parabacteroides merdae\|Clostridium scindens, Parvimonas micra\|Clostridium scindens, Pediococcus acidilactici\|Clostridium scindens, Pediococcus pentosaceus\|Clostridium scindens, Peptoniphilus duerdenii\|Clostridium scindens, Peptoniphilus harei\|Clostridium scindens, Peptoniphilus lacrimalis\|Clostridium scindens, Peptostreptococcus anaerobius\|Clostridium scindens, Peptostreptococcus stomatis\|Clostridium scindens, Porphyromonas asaccharolytica\|Clostridium scindens, Porphyromonas uenonis\|Clostridium scindens, Prevotella amnii\|Clostridium scindens, Prevotella bergensis\|Clostridium scindens, Prevotella bivia\|Clostridium scindens, Prevotella buccae\|Clostridium scindens, Prevotella buccalis\|Clostridium scindens, Prevotella copri\|Clostridium scindens, Prevotella disiens\|Clostridium scindens, Prevotella melaninogenica\|Clostridium scindens, Prevotella multiformis\|Clostridium scindens, Prevotella oralis\|Clostridium scindens, Prevotella oris\|Clostridium scindens, Prevotella salivae\|Clostridium scindens, Prevotella timonensis\|Clostridium scindens, Propionibacterium acnes\|Clostridium scindens, Propionibacterium freudenreichii\|Clostridium scindens, Proteus mirabilis\|Clostridium scindens, Proteus penneri\|Clostridium scindens, Pseudoflavonifractor capillosus\|Clostridium scindens, Pseudomonas aeruginosa\|Clostridium scindens, Pseudomonas fluorescens\|Clostridium scindens, Pseudomonas putida\|Clostridium scindens, Pseudoramibacter alactolyticus\|Clostridium scindens, Pyramidobacter piscolens\|Clostridium scindens, Rhodopseudomonas palustris\|Clostridium scindens, Roseburia intestinalis\|Clostridium scindens, Roseburia inulinivorans\|Clostridium scindens, Rothia dentocariosa\|Clostridium scindens, Rothia mucilaginosa\|Clostridium scindens, Ruminococcus albus\|Clostridium scindens, Ruminococcus bromii\|Clostridium scindens, Ruminococcus gnavus\|Clostridium scindens, Ruminococcus lactaris\|Clostridium scindens, Ruminococcus obeum\|Clostridium scindens, Ruminococcus torques\|Clostridium scindens, Selenomonas sputigena\|Clostridium scindens, Shigella boydii\|Clostridium scindens, Shigella dysenteriae\|Clostridium scindens, Shigella sonnei\|Clostridium scindens, Slackia exigua\|Clostridium scindens, Solobacterium moorei\|Clostridium scindens, Staphylococcus aureus\|Clostridium scindens, Staphylococcus epidermidis\|Clostridium scindens, Staphylococcus hominis\|Clostridium scindens, Staphylococcus saprophyticus\|Clostridium scindens, Staphylococcus warneri\|Clostridium scindens, Streptococcus agalactiae\|Clostridium scindens, Streptococcus anginosus\|Clostridium scindens, Streptococcus australis\|Clostridium scindens, Streptococcus bovis\|Clostridium scindens, Streptococcus cristatus\|Clostridium scindens, Streptococcus dysgalactiae\|Clostridium |

TABLE 2-continued

| Table 2. Specific binary combinations of OTUs. Individual pairings are differentiated by "\|" and OTUs within a combination are differentiated by "," |
|---|
| *scindens, Streptococcus equinus\|Clostridium scindens, Streptococcus gordonii\|Clostridium scindens, Streptococcus infantarius\|Clostridium scindens, Streptococcus infantis\|Clostridium scindens, Streptococcus mitis\|Clostridium scindens, Streptococcus mutans\|Clostridium scindens, Streptococcus oralis\|Clostridium scindens, Streptococcus parasanguinis\|Clostridium scindens, Streptococcus peroris\|Clostridium scindens, Streptococcus pneumoniae\|Clostridium scindens, Streptococcus salivarius\|Clostridium scindens, Streptococcus sanguinis\|Clostridium scindens, Streptococcus thermophilus\|Clostridium scindens, Streptococcus vestibularis\|Clostridium scindens, Subdoligranulum variabile\|Clostridium scindens, Succinatimonas hippei\|Clostridium scindens, Sutterella wadsworthensis\|Clostridium scindens, Tropheryma whipplei\|Clostridium scindens, Veillonella atypica\|Clostridium scindens, Veillonella dispar\|Clostridium scindens, Veillonella parvula\|Clostridium scindens, Victivallis vadensis\|Clostridium symbiosum, Clostridium symbiosum\|Clostridium symbiosum, Clostridium tertium\|Clostridium symbiosum, Collinsella aerofaciens\|Clostridium symbiosum, Collinsella intestinalis\|Clostridium symbiosum, Collinsella stercoris\|Clostridium symbiosum, Coprobacillus* sp. D7\|*Clostridium symbiosum, Coprococcus catus\|Clostridium symbiosum, Coprococcus comes\|Clostridium symbiosum, Coprococcus eutactus\|Clostridium symbiosum, Corynebacterium aurimucosum\|Clostridium symbiosum, Corynebacterium matruchotii\|Clostridium symbiosum, Cryptobacterium curtum\|Clostridium symbiosum, Desulfovibrio desulfuricans\|Clostridium symbiosum, Desulfovibrio piger\|Clostridium symbiosum, Dialister invisus\|Clostridium symbiosum, Dialister microaerophilus\|Clostridium symbiosum, Dorea formicigenerans\|Clostridium symbiosum, Dorea longicatena\|Clostridium symbiosum, Eggerthella lenta\|Clostridium symbiosum, Eikenella corrodens\|Clostridium symbiosum, Enterobacter cancerogenus\|Clostridium symbiosum, Enterobacter cloacae\|Clostridium symbiosum, Enterococcus faecalis\|Clostridium symbiosum, Enterococcus faecium\|Clostridium symbiosum, Enterococcus gallinarum\|Clostridium symbiosum, Erysipelotrichaceae bacterium* 3_1_53\|*Clostridium symbiosum, Escherichia coli\|Clostridium symbiosum, Escherichia fergusonii\|Clostridium symbiosum, Ethanoligenens harbinense\|Clostridium symbiosum, Eubacterium cellulosolvens\|Clostridium symbiosum, Eubacterium eligens\|Clostridium symbiosum, Eubacterium hallii\|Clostridium symbiosum, Eubacterium limosum\|Clostridium symbiosum, Eubacterium rectale\|Clostridium symbiosum, Eubacterium siraeum\|Clostridium symbiosum, Eubacterium ventriosum\|Clostridium symbiosum, Faecalibacterium prausnitzii\|Clostridium symbiosum, Finegoldia magna\|Clostridium symbiosum, Fusobacterium gonidiaformans\|Clostridium symbiosum, Fusobacterium mortiferum\|Clostridium symbiosum, Fusobacterium nucleatum\|Clostridium symbiosum, Fusobacterium varium\|Clostridium symbiosum, Gardnerella vaginalis\|Clostridium symbiosum, Gemella haemolysans\|Clostridium symbiosum, Gemella morbillorum\|Clostridium symbiosum, Gordonibacter pamelaeae\|Clostridium symbiosum, Granulicatella adiacens\|Clostridium symbiosum, Granulicatella elegans\|Clostridium symbiosum, Haemophilus influenzae\|Clostridium symbiosum, Haemophilus parainfluenzae\|Clostridium symbiosum, Helicobacter pullorum\|Clostridium symbiosum, Helicobacter pylori\|Clostridium symbiosum, Holdemania filiformis\|Clostridium symbiosum, Kingella oralis\|Clostridium symbiosum, Klebsiella pneumoniae\|Clostridium symbiosum, Klebsiella variicola\|Clostridium symbiosum, Lachnospiraceae bacterium* 5_1_57FAA\|*Clostridium symbiosum, Lactobacillus acidophilus\|Clostridium symbiosum, Lactobacillus amylovorus\|Clostridium symbiosum, Lactobacillus brevis\|Clostridium symbiosum, Lactobacillus casei\|Clostridium symbiosum, Lactobacillus crispatus\|Clostridium symbiosum, Lactobacillus delbrueckii\|Clostridium symbiosum, Lactobacillus fermentum\|Clostridium symbiosum, Lactobacillus gasseri\|Clostridium symbiosum, Lactobacillus iners\|Clostridium symbiosum, Lactobacillus jensenii\|Clostridium symbiosum, Lactobacillus johnsonii\|Clostridium symbiosum, Lactobacillus paracasei\|Clostridium symbiosum, Lactobacillus plantarum\|Clostridium symbiosum, Lactobacillus reuteri\|Clostridium symbiosum, Lactobacillus rhamnosus\|Clostridium symbiosum, Lactobacillus ruminis\|Clostridium symbiosum, Lactobacillus sakei\|Clostridium symbiosum, Lactobacillus salivarius\|Clostridium symbiosum, Lactococcus lactis\|Clostridium symbiosum, Lautropia mirabilis\|Clostridium symbiosum, Leuconostoc citreum\|Clostridium symbiosum, Leuconostoc gasicomitatum\|Clostridium symbiosum, Leuconostoc mesenteroides\|Clostridium symbiosum, Listeria monocytogenes\|Clostridium symbiosum, Marvinbryantia formatexigens\|Clostridium symbiosum, Megamonas hypermegale\|Clostridium symbiosum, Megasphaera micronuciformis\|Clostridium symbiosum, Methanobrevibacter smithii\|Clostridium symbiosum, Methanosphaera stadtmanae\|Clostridium symbiosum, Methylobacterium radiotolerans\|Clostridium symbiosum, Mitsuokella multacida\|Clostridium symbiosum, Mobiluncus curtisii\|Clostridium symbiosum, Mycoplasma hominis\|Clostridium symbiosum, Neisseria mucosa\|Clostridium symbiosum, Odoribacter splanchnicus\|Clostridium symbiosum, Olsenella uli\|Clostridium symbiosum, Oribacterium sinus\|Clostridium symbiosum, Oxalobacter formigenes\|Clostridium symbiosum, Parabacteroides distasonis\|Clostridium symbiosum, Parabacteroides johnsonii\|Clostridium symbiosum, Parabacteroides merdae\|Clostridium symbiosum, Parvimonas micra\|Clostridium symbiosum, Pediococcus acidilactici\|Clostridium symbiosum, Pediococcus pentosaceus\|Clostridium symbiosum, Peptoniphilus duerdenii\|Clostridium symbiosum, Peptoniphilus harei\|Clostridium symbiosum, Peptoniphilus lacrimalis\|Clostridium symbiosum, Peptostreptococcus anaerobius\|Clostridium symbiosum, Peptostreptococcus stomatis\|Clostridium symbiosum, Porphyromonas asaccharolytica\|Clostridium symbiosum, Porphyromonas uenonis\|Clostridium symbiosum, Prevotella amnii\|Clostridium symbiosum, Prevotella bergensis\|Clostridium symbiosum, Prevotella bivia\|Clostridium symbiosum, Prevotella buccae\|Clostridium symbiosum, Prevotella buccalis\|Clostridium symbiosum, Prevotella copri\|Clostridium symbiosum, Prevotella disiens\|Clostridium symbiosum, Prevotella melaninogenica\|Clostridium symbiosum, Prevotella multiformis\|Clostridium symbiosum, Prevotella oralis\|Clostridium symbiosum, Prevotella oris\|Clostridium symbiosum, Prevotella salivae\|Clostridium symbiosum, Prevotella timonensis\|Clostridium symbiosum, Propionibacterium acnes\|Clostridium symbiosum, Propionibacterium freudenreichii\|Clostridium symbiosum, Proteus mirabilis\|Clostridium symbiosum, Proteus penneri\|Clostridium symbiosum, Pseudoflavonifractor capillosus\|Clostridium symbiosum, Pseudomonas aeruginosa\|Clostridium symbiosum, Pseudomonas fluorescens\|Clostridium symbiosum, Pseudomonas putida\|Clostridium symbiosum, Pseudoramibacter alactolyticus\|Clostridium symbiosum, Pyramidobacter piscolens\|Clostridium symbiosum, Rhodopseudomonas palustris\|Clostridium symbiosum, Roseburia intestinalis\|Clostridium symbiosum, Roseburia inulinivorans\|Clostridium symbiosum, Rothia dentocariosa\|Clostridium symbiosum, Rothia mucilaginosa\|Clostridium symbiosum, Ruminococcus albus\|Clostridium symbiosum, Ruminococcus bromii\|Clostridium symbiosum, Ruminococcus gnavus\|Clostridium symbiosum, Ruminococcus lactaris\|Clostridium symbiosum, Ruminococcus obeum\|Clostridium symbiosum, Ruminococcus torques\|Clostridium symbiosum, Selenomonas sputigena\|Clostridium symbiosum, Shigella boydii\|Clostridium symbiosum, Shigella dysenteriae\|Clostridium symbiosum, Shigella sonnei\|Clostridium symbiosum, Slackia exigua\|Clostridium symbiosum, Solobacterium moorei\|Clostridium symbiosum, Staphylococcus aureus\|Clostridium symbiosum, Staphylococcus epidermidis\|Clostridium symbiosum, Staphylococcus hominis\|Clostridium symbiosum, Staphylococcus saprophyticus\|Clostridium symbiosum, Staphylococcus warneri\|Clostridium symbiosum, Streptococcus agalactiae\|Clostridium symbiosum, Streptococcus anginosus\|Clostridium symbiosum, Streptococcus australis\|Clostridium symbiosum, Streptococcus bovis\|Clostridium symbiosum, Streptococcus cristatus\|Clostridium symbiosum, Streptococcus dysgalactiae\|Clostridium symbiosum, Streptococcus equinus\|Clostridium symbiosum, Streptococcus gordonii\|Clostridium symbiosum, Streptococcus infantarius\|Clostridium symbiosum, Streptococcus infantis\|Clostridium symbiosum, Streptococcus mitis\|Clostridium symbiosum, Streptococcus mutans\|Clostridium symbiosum, Streptococcus oralis\|Clostridium symbiosum, Streptococcus parasanguinis\|Clostridium symbiosum, Streptococcus peroris\|Clostridium symbiosum, Streptococcus pneumoniae\|Clostridium symbiosum, Streptococcus salivarius\|Clostridium symbiosum, Streptococcus sanguinis\|Clostridium symbiosum, Streptococcus thermophilus\|Clostridium symbiosum, Streptococcus vestibularis\|Clostridium symbiosum, Subdoligranulum variabile\|Clostridium symbiosum, Succinatimonas hippei\|Clostridium symbiosum, Sutterella wadsworthensis\|Clostridium symbiosum, Tropheryma whipplei\|Clostridium symbiosum, Veillonella atypica\|Clostridium symbiosum, Veillonella dispar\|Clostridium symbiosum, Veillonella parvula\|Clostridium symbiosum, Victivallis vadensis\|Clostridium tertium, Clostridium tertium\|Clostridium tertium, Collinsella aerofaciens\|Clostridium tertium, Collinsella intestinalis\|Clostridium tertium, Collinsella stercoris\|Clostridium tertium, Coprobacillus* sp. D7\|*Clostridium tertium, Coprococcus catus\|Clostridium tertium, Coprococcus comes\|Clostridium tertium, Coprococcus eutactus\|Clostridium* |

TABLE 2-continued

Table 2. Specific binary combinations of OTUs. Individual pairings are differentiated by "|" and OTUs within a combination are differentiated by ","

*tertium, Corynebacterium aurimucosum|Clostridium tertium, Corynebacterium matruchotii|Clostridium tertium, Cryptobacterium curtum|Clostridium tertium, Desulfovibrio desulfuricans|Clostridium tertium, Desulfovibrio piger|Clostridium tertium, Dialister invisus|Clostridium tertium, Dialister microaerophilus|Clostridium tertium, Dorea formicigenerans|Clostridium tertium, Dorea longicatena|Clostridium tertium, Eggerthella lenta|Clostridium tertium, Eikenella corrodens|Clostridium tertium, Enterobacter cancerogenus|Clostridium tertium, Enterobacter cloacae|Clostridium tertium, Enterococcus faecalis|Clostridium tertium, Enterococcus faecium|Clostridium tertium, Enterococcus gallinarum|Clostridium tertium, Erysipelotrichaceae bacterium* 3_1_53|*Clostridium tertium, Escherichia coli|Clostridium tertium, Escherichia fergusonii|Clostridium tertium, Ethanoligenens harbinense|Clostridium tertium, Eubacterium cellulosolvens|Clostridium tertium, Eubacterium eligens|Clostridium tertium, Eubacterium hallii|Clostridium tertium, Eubacterium limosum|Clostridium tertium, Eubacterium rectale|Clostridium tertium, Eubacterium siraeum|Clostridium tertium, Eubacterium ventriosum|Clostridium tertium, Faecalibacterium prausnitzii|Clostridium tertium, Finegoldia magna|Clostridium tertium, Fusobacterium gonidiaformans|Clostridium tertium, Fusobacterium mortiferum|Clostridium tertium, Fusobacterium nucleatum|Clostridium tertium, Fusobacterium varium|Clostridium tertium, Gardnerella vaginalis|Clostridium tertium, Gemella haemolysans|Clostridium tertium, Gemella morbillorum|Clostridium tertium, Gordonibacter pamelaeae|Clostridium tertium, Granulicatella adiacens|Clostridium tertium, Granulicatella elegans|Clostridium tertium, Haemophilus influenzae|Clostridium tertium, Haemophilus parainfluenzae|Clostridium tertium, Helicobacter pullorum|Clostridium tertium, Helicobacter pylori|Clostridium tertium, Holdemania filiformis|Clostridium tertium, Kingella oralis|Clostridium tertium, Klebsiella pneumoniae|Clostridium tertium, Klebsiella variicola|Clostridium tertium, Lachnospiraceae bacterium* 5_1_57FAA|*Clostridium tertium, Lactobacillus acidophilus|Clostridium tertium, Lactobacillus amylovorus|Clostridium tertium, Lactobacillus brevis|Clostridium tertium, Lactobacillus casei|Clostridium tertium, Lactobacillus crispatus|Clostridium tertium, Lactobacillus delbrueckii|Clostridium tertium, Lactobacillus fermentum|Clostridium tertium, Lactobacillus gasseri|Clostridium tertium, Lactobacillus iners|Clostridium tertium, Lactobacillus jensenii|Clostridium tertium, Lactobacillus johnsonii|Clostridium tertium, Lactobacillus paracasei|Clostridium tertium, Lactobacillus plantarum|Clostridium tertium, Lactobacillus reuteri|Clostridium tertium, Lactobacillus rhamnosus|Clostridium tertium, Lactobacillus ruminis|Clostridium tertium, Lactobacillus sakei|Clostridium tertium, Lactobacillus salivarius|Clostridium tertium, Lactococcus lactis|Clostridium tertium, Lautropia mirabilis|Clostridium tertium, Leuconostoc citreum|Clostridium tertium, Leuconostoc gasicomitatum|Clostridium tertium, Leuconostoc mesenteroides|Clostridium tertium, Listeria monocytogenes|Clostridium tertium, Marvinbryantia formatexigens|Clostridium tertium, Megamonas hypermegale|Clostridium tertium, Megasphaera micronuciformis|Clostridium tertium, Methanobrevibacter smithii|Clostridium tertium, Methanosphaera stadtmanae|Clostridium tertium, Methylobacterium radiotolerans|Clostridium tertium, Mitsuokella multacida|Clostridium tertium, Mobiluncus curtisii|Clostridium tertium, Mycoplasma hominis|Clostridium tertium, Neisseria mucosa|Clostridium tertium, Odoribacter splanchnicus|Clostridium tertium, Olsenella uli|Clostridium tertium, Oribacterium sinus|Clostridium tertium, Oxalobacter formigenes|Clostridium tertium, Parabacteroides distasonis|Clostridium tertium, Parabacteroides johnsonii|Clostridium tertium, Parabacteroides merdae|Clostridium tertium, Parvimonas micra|Clostridium tertium, Pediococcus acidilactici|Clostridium tertium, Pediococcus pentosaceus|Clostridium tertium, Peptoniphilus duerdenii|Clostridium tertium, Peptoniphilus harei|Clostridium tertium, Peptoniphilus lacrimalis|Clostridium tertium, Peptostreptococcus anaerobius|Clostridium tertium, Peptostreptococcus stomatis|Clostridium tertium, Porphyromonas asaccharolytica|Clostridium tertium, Porphyromonas uenonis|Clostridium tertium, Prevotella amnii|Clostridium tertium, Prevotella bergensis|Clostridium tertium, Prevotella bivia|Clostridium tertium, Prevotella buccae|Clostridium tertium, Prevotella buccalis|Clostridium tertium, Prevotella copri|Clostridium tertium, Prevotella disiens|Clostridium tertium, Prevotella melaninogenica|Clostridium tertium, Prevotella multiformis|Clostridium tertium, Prevotella oralis|Clostridium tertium, Prevotella oris|Clostridium tertium, Prevotella salivae|Clostridium tertium, Prevotella timonensis|Clostridium tertium, Propionibacterium acnes|Clostridium tertium, Propionibacterium freudenreichii|Clostridium tertium, Proteus mirabilis|Clostridium tertium, Proteus penneri|Clostridium tertium, Pseudoflavonifractor capillosus|Clostridium tertium, Pseudomonas aeruginosa|Clostridium tertium, Pseudomonas fluorescens|Clostridium tertium, Pseudomonas putida|Clostridium tertium, Pseudoramibacter alactolyticus|Clostridium tertium, Pyramidobacter piscolens|Clostridium tertium, Rhodopseudomonas palustris|Clostridium tertium, Roseburia intestinalis|Clostridium tertium, Roseburia inulinivorans|Clostridium tertium, Rothia dentocariosa|Clostridium tertium, Rothia mucilaginosa|Clostridium tertium, Ruminococcus albus|Clostridium tertium, Ruminococcus bromii|Clostridium tertium, Ruminococcus gnavus|Clostridium tertium, Ruminococcus lactaris|Clostridium tertium, Ruminococcus obeum|Clostridium tertium, Ruminococcus torques|Clostridium tertium, Selenomonas sputigena|Clostridium tertium, Shigella boydii|Clostridium tertium, Shigella dysenteriae|Clostridium tertium, Shigella sonnei|Clostridium tertium, Slackia exigua|Clostridium tertium, Solobacterium moorei|Clostridium tertium, Staphylococcus aureus|Clostridium tertium, Staphylococcus epidermidis|Clostridium tertium, Staphylococcus hominis|Clostridium tertium, Staphylococcus saprophyticus|Clostridium tertium, Staphylococcus warneri|Clostridium tertium, Streptococcus agalactiae|Clostridium tertium, Streptococcus anginosus|Clostridium tertium, Streptococcus australis|Clostridium tertium, Streptococcus bovis|Clostridium tertium, Streptococcus cristatus|Clostridium tertium, Streptococcus dysgalactiae|Clostridium tertium, Streptococcus equinus|Clostridium tertium, Streptococcus gordonii|Clostridium tertium, Streptococcus infantarius|Clostridium tertium, Streptococcus infantis|Clostridium tertium, Streptococcus mitis|Clostridium tertium, Streptococcus mutans|Clostridium tertium, Streptococcus oralis|Clostridium tertium, Streptococcus parasanguinis|Clostridium tertium, Streptococcus peroris|Clostridium tertium, Streptococcus pneumoniae|Clostridium tertium, Streptococcus salivarius|Clostridium tertium, Streptococcus sanguinis|Clostridium tertium, Streptococcus thermophilus|Clostridium tertium, Streptococcus vestibularis|Clostridium tertium, Subdoligranulum variabile|Clostridium tertium, Succinatimonas hippei|Clostridium tertium, Sutterella wadsworthensis|Clostridium tertium, Tropheryma whipplei|Clostridium tertium, Veillonella atypica|Clostridium tertium, Veillonella dispar|Clostridium tertium, Veillonella parvula|Clostridium tertium, Victivallis vadensis|Collinsella aerofaciens, Collinsella aerofaciens|Collinsella aerofaciens, Collinsella intestinalis|Collinsella aerofaciens, Collinsella stercoris|Collinsella aerofaciens, Coprobacillus* sp. D7|*Collinsella aerofaciens, Coprococcus catus|Collinsella aerofaciens, Coprococcus comes|Collinsella aerofaciens, Coprococcus eutactus|Collinsella aerofaciens, Corynebacterium aurimucosum|Collinsella aerofaciens, Corynebacterium matruchotii|Collinsella aerofaciens, Cryptobacterium curtum|Collinsella aerofaciens, Desulfovibrio desulfuricans|Collinsella aerofaciens, Desulfovibrio piger|Collinsella aerofaciens, Dialister invisus|Collinsella aerofaciens, Dialister microaerophilus|Collinsella aerofaciens, Dorea formicigenerans|Collinsella aerofaciens, Dorea longicatena|Collinsella aerofaciens, Eggerthella lenta|Collinsella aerofaciens, Eikenella corrodens|Collinsella aerofaciens, Enterobacter cancerogenus|Collinsella aerofaciens, Enterobacter cloacae|Collinsella aerofaciens, Enterococcus faecalis|Collinsella aerofaciens, Enterococcus faecium|Collinsella aerofaciens, Enterococcus gallinarum|Collinsella aerofaciens, Erysipelotrichaceae bacterium* 3_1_53|*Collinsella aerofaciens, Escherichia coli|Collinsella aerofaciens, Escherichia fergusonii|Collinsella aerofaciens, Ethanoligenens harbinense|Collinsella aerofaciens, Eubacterium cellulosolvens|Collinsella aerofaciens, Eubacterium eligens|Collinsella aerofaciens, Eubacterium hallii|Collinsella aerofaciens, Eubacterium limosum|Collinsella aerofaciens, Eubacterium rectale|Collinsella aerofaciens, Eubacterium siraeum|Collinsella aerofaciens, Eubacterium ventriosum|Collinsella aerofaciens, Faecalibacterium prausnitzii|Collinsella aerofaciens, Finegoldia magna|Collinsella aerofaciens, Fusobacterium gonidiaformans|Collinsella aerofaciens, Fusobacterium mortiferum|Collinsella aerofaciens, Fusobacterium nucleatum|Collinsella aerofaciens, Fusobacterium varium|Collinsella aerofaciens, Gardnerella vaginalis|Collinsella aerofaciens, Gemella haemolysans|Collinsella aerofaciens, Gemella morbillorum|Collinsella aerofaciens, Gordonibacter pamelaeae|Collinsella aerofaciens, Granulicatella adiacens|Collinsella aerofaciens, Granulicatella elegans|Collinsella aerofaciens, Haemophilus influenzae|Collinsella aerofaciens, Haemophilus parainfluenzae|Collinsella aerofaciens, Helicobacter pullorum|Collinsella aerofaciens, Helicobacter pylori|Collinsella aerofaciens, Holdemania filiformis|Collinsella aerofaciens, Kingella oralis|Collinsella aerofaciens, Klebsiella pneumoniae|Collinsella aerofaciens, Klebsiella variicola|Collinsella aerofaciens, Lachnospiraceae*

TABLE 2-continued

Table 2. Specific binary combinations of OTUs. Individual pairings are differentiated by "|" and OTUs within a combination are differentiated by ","

bacterium 5_1_57FAA|Collinsella aerofaciens, Lactobacillus acidophilus|Collinsella aerofaciens, Lactobacillus amylovorus|Collinsella aerofaciens, Lactobacillus brevis|Collinsella aerofaciens, Lactobacillus casei|Collinsella aerofaciens, Lactobacillus crispatus|Collinsella aerofaciens, Lactobacillus delbrueckii|Collinsella aerofaciens, Lactobacillus fermentum|Collinsella aerofaciens, Lactobacillus gasseri|Collinsella aerofaciens, Lactobacillus iners|Collinsella aerofaciens, Lactobacillus jensenii|Collinsella aerofaciens, Lactobacillus johnsonii|Collinsella aerofaciens, Lactobacillus paracasei|Collinsella aerofaciens, Lactobacillus plantarum|Collinsella aerofaciens, Lactobacillus reuteri|Collinsella aerofaciens, Lactobacillus rhamnosus|Collinsella aerofaciens, Lactobacillus ruminis|Collinsella aerofaciens, Lactobacillus sakei|Collinsella aerofaciens, Lactobacillus salivarius|Collinsella aerofaciens, Lactococcus lactis|Collinsella aerofaciens, Lautropia mirabilis|Collinsella aerofaciens, Leuconostoc citreum|Collinsella aerofaciens, Leuconostoc gasicomitatum|Collinsella aerofaciens, Leuconostoc mesenteroides|Collinsella aerofaciens, Listeria monocytogenes|Collinsella aerofaciens, Marvinbryantia formatexigens|Collinsella aerofaciens, Megamonas hypermegale|Collinsella aerofaciens, Megasphaera micronuciformis|Collinsella aerofaciens, Methanobrevibacter smithii|Collinsella aerofaciens, Methanosphaera stadtmanae|Collinsella aerofaciens, Methylobacterium radiotolerans|Collinsella aerofaciens, Mitsuokella multacida|Collinsella aerofaciens, Mobiluncus curtisii|Collinsella aerofaciens, Mycoplasma hominis|Collinsella aerofaciens, Neisseria mucosa|Collinsella aerofaciens, Odoribacter splanchnicus|Collinsella aerofaciens, Olsenella uli|Collinsella aerofaciens, Oribacterium sinus|Collinsella aerofaciens, Oxalobacter formigenes|Collinsella aerofaciens, Parabacteroides distasonis|Collinsella aerofaciens, Parabacteroides johnsonii|Collinsella aerofaciens, Parabacteroides merdae|Collinsella aerofaciens, Parvimonas micra|Collinsella aerofaciens, Pediococcus acidilactici|Collinsella aerofaciens, Pediococcus pentosaceus|Collinsella aerofaciens, Peptoniphilus duerdenii|Collinsella aerofaciens, Peptoniphilus harei|Collinsella aerofaciens, Peptoniphilus lacrimalis|Collinsella aerofaciens, Peptostreptococcus anaerobius|Collinsella aerofaciens, Peptostreptococcus stomatis|Collinsella aerofaciens, Porphyromonas asaccharolytica|Collinsella aerofaciens, Porphyromonas uenonis|Collinsella aerofaciens, Prevotella amnii|Collinsella aerofaciens, Prevotella bergensis|Collinsella aerofaciens, Prevotella bivia|Collinsella aerofaciens, Prevotella buccae|Collinsella aerofaciens, Prevotella buccalis|Collinsella aerofaciens, Prevotella copri|Collinsella aerofaciens, Prevotella disiens|Collinsella aerofaciens, Prevotella melaninogenica|Collinsella aerofaciens, Prevotella multiformis|Collinsella aerofaciens, Prevotella oralis|Collinsella aerofaciens, Prevotella oris|Collinsella aerofaciens, Prevotella salivae|Collinsella aerofaciens, Prevotella timonensis|Collinsella aerofaciens, Propionibacterium acnes|Collinsella aerofaciens, Propionibacterium freudenreichii|Collinsella aerofaciens, Proteus mirabilis|Collinsella aerofaciens, Proteus penneri|Collinsella aerofaciens, Pseudoflavonifractor capillosus|Collinsella aerofaciens, Pseudomonas aeruginosa|Collinsella aerofaciens, Pseudomonas fluorescens|Collinsella aerofaciens, Pseudomonas putida|Collinsella aerofaciens, Pseudoramibacter alactolyticus|Collinsella aerofaciens, Pyramidobacter piscolens|Collinsella aerofaciens, Rhodopseudomonas palustris|Collinsella aerofaciens, Roseburia intestinalis|Collinsella aerofaciens, Roseburia inulinivorans|Collinsella aerofaciens, Rothia dentocariosa|Collinsella aerofaciens, Rothia mucilaginosa|Collinsella aerofaciens, Ruminococcus albus|Collinsella aerofaciens, Ruminococcus bromii|Collinsella aerofaciens, Ruminococcus gnavus|Collinsella aerofaciens, Ruminococcus lactaris|Collinsella aerofaciens, Ruminococcus obeum|Collinsella aerofaciens, Ruminococcus torques|Collinsella aerofaciens, Selenomonas sputigena|Collinsella aerofaciens, Shigella boydii|Collinsella aerofaciens, Shigella dysenteriae|Collinsella aerofaciens, Shigella sonnei|Collinsella aerofaciens, Slackia exigua|Collinsella aerofaciens, Solobacterium moorei|Collinsella aerofaciens, Staphylococcus aureus|Collinsella aerofaciens, Staphylococcus epidermidis|Collinsella aerofaciens, Staphylococcus hominis|Collinsella aerofaciens, Staphylococcus saprophyticus|Collinsella aerofaciens, Staphylococcus warneri|Collinsella aerofaciens, Streptococcus agalactiae|Collinsella aerofaciens, Streptococcus anginosus|Collinsella aerofaciens, Streptococcus australis|Collinsella aerofaciens, Streptococcus bovis|Collinsella aerofaciens, Streptococcus cristatus|Collinsella aerofaciens, Streptococcus dysgalactiae|Collinsella aerofaciens, Streptococcus equinus|Collinsella aerofaciens, Streptococcus gordonii|Collinsella aerofaciens, Streptococcus infantarius|Collinsella aerofaciens, Streptococcus infantis|Collinsella aerofaciens, Streptococcus mitis|Collinsella aerofaciens, Streptococcus mutans|Collinsella aerofaciens, Streptococcus oralis|Collinsella aerofaciens, Streptococcus parasanguinis|Collinsella aerofaciens, Streptococcus peroris|Collinsella aerofaciens, Streptococcus pneumoniae|Collinsella aerofaciens, Streptococcus salivarius|Collinsella aerofaciens, Streptococcus sanguinis|Collinsella aerofaciens, Streptococcus thermophilus|Collinsella aerofaciens, Streptococcus vestibularis|Collinsella aerofaciens, Subdoligranulum variabile|Collinsella aerofaciens, Succinatimonas hippei|Collinsella aerofaciens, Sutterella wadsworthensis|Collinsella aerofaciens, Tropheryma whipplei|Collinsella aerofaciens, Veillonella atypica|Collinsella aerofaciens, Veillonella dispar|Collinsella aerofaciens, Veillonella parvula|Collinsella aerofaciens, Victivallis vadensis|Collinsella intestinalis, Collinsella intestinalis|Collinsella intestinalis, Collinsella stercoris|Collinsella intestinalis, Coprobacillus sp. D7|Collinsella intestinalis, Coprococcus catus|Collinsella intestinalis, Coprococcus comes|Collinsella intestinalis, Coprococcus eutactus|Collinsella intestinalis, Corynebacterium aurimucosum|Collinsella intestinalis, Corynebacterium matruchotii|Collinsella intestinalis, Cryptobacterium curtum|Collinsella intestinalis, Desulfovibrio desulfuricans|Collinsella intestinalis, Desulfovibrio piger|Collinsella intestinalis, Dialister invisus|Collinsella intestinalis, Dialister microaerophilus|Collinsella intestinalis, Dorea formicigenerans|Collinsella intestinalis, Dorea longicatena|Collinsella intestinalis, Eggerthella lenta|Collinsella intestinalis, Eikenella corrodens|Collinsella intestinalis, Enterobacter cancerogenus|Collinsella intestinalis, Enterobacter cloacae|Collinsella intestinalis, Enterococcus faecalis|Collinsella intestinalis, Enterococcus faecium|Collinsella intestinalis, Enterococcus gallinarum|Collinsella intestinalis, Erysipelotrichaceae bacterium 3_1_53|Collinsella intestinalis, Escherichia coli|Collinsella intestinalis, Escherichia fergusonii|Collinsella intestinalis, Ethanoligenens harbinense|Collinsella intestinalis, Eubacterium cellulosolvens|Collinsella intestinalis, Eubacterium eligens|Collinsella intestinalis, Eubacterium hallii|Collinsella intestinalis, Eubacterium limosum|Collinsella intestinalis, Eubacterium rectale|Collinsella intestinalis, Eubacterium siraeum|Collinsella intestinalis, Eubacterium ventriosum|Collinsella intestinalis, Faecalibacterium prausnitzii|Collinsella intestinalis, Finegoldia magna|Collinsella intestinalis, Fusobacterium gonidiaformans|Collinsella intestinalis, Fusobacterium mortiferum|Collinsella intestinalis, Fusobacterium nucleatum|Collinsella intestinalis, Fusobacterium varium|Collinsella intestinalis, Gardnerella vaginalis|Collinsella intestinalis, Gemella haemolysans|Collinsella intestinalis, Gemella morbillorum|Collinsella intestinalis, Gordonibacter pamelaeae|Collinsella intestinalis, Granulicatella adiacens|Collinsella intestinalis, Granulicatella elegans|Collinsella intestinalis, Haemophilus influenzae|Collinsella intestinalis, Haemophilus parainfluenzae|Collinsella intestinalis, Helicobacter pullorum|Collinsella intestinalis, Helicobacter pylori|Collinsella intestinalis, Holdemania filiformis|Collinsella intestinalis, Kingella oralis|Collinsella intestinalis, Klebsiella pneumoniae|Collinsella intestinalis, Klebsiella variicola|Collinsella intestinalis, Lachnospiraceae bacterium 5_1_57FAA|Collinsella intestinalis, Lactobacillus acidophilus|Collinsella intestinalis, Lactobacillus amylovorus|Collinsella intestinalis, Lactobacillus brevis|Collinsella intestinalis, Lactobacillus casei|Collinsella intestinalis, Lactobacillus crispatus|Collinsella intestinalis, Lactobacillus delbrueckii|Collinsella intestinalis, Lactobacillus fermentum|Collinsella intestinalis, Lactobacillus gasseri|Collinsella intestinalis, Lactobacillus iners|Collinsella intestinalis, Lactobacillus jensenii|Collinsella intestinalis, Lactobacillus johnsonii|Collinsella intestinalis, Lactobacillus paracasei|Collinsella intestinalis, Lactobacillus plantarum|Collinsella intestinalis, Lactobacillus reuteri|Collinsella intestinalis, Lactobacillus rhamnosus|Collinsella intestinalis, Lactobacillus ruminis|Collinsella intestinalis, Lactobacillus sakei|Collinsella intestinalis, Lactobacillus salivarius|Collinsella intestinalis, Lactococcus lactis|Collinsella intestinalis, Lautropia mirabilis|Collinsella intestinalis, Leuconostoc citreum|Collinsella intestinalis, Leuconostoc gasicomitatum|Collinsella intestinalis, Leuconostoc mesenteroides|Collinsella intestinalis, Listeria monocytogenes|Collinsella intestinalis, Marvinbryantia formatexigens|Collinsella intestinalis, Megamonas hypermegale|Collinsella intestinalis, Megasphaera micronuciformis|Collinsella intestinalis, Methanobrevibacter smithii|Collinsella intestinalis, Methanosphaera stadtmanae|Collinsella intestinalis, Methylobacterium radiotolerans|Collinsella intestinalis, Mitsuokella multacida|Collinsella intestinalis, Mobiluncus curtisii|Collinsella intestinalis, Mycoplasma hominis|Collinsella intestinalis, Neisseria mucosa|Collinsella intestinalis, Odoribacter splanchnicus|Collinsella intestinalis, Olsenella uli|Collinsella intestinalis, Oribacterium sinus|Collinsella intestinalis, Oxalobacter TABLE 2-continued Table 2. Specific binary combinations of OTUs. Individual pairings are differentiated by "|" and OTUs within a combination are differentiated by ","

formigenes|Collinsella intestinalis, Parabacteroides distasonis|Collinsella intestinalis, Parabacteroides johnsonii|Collinsella intestinalis, Parabacteroides merdae|Collinsella intestinalis, Parvimonas micra|Collinsella intestinalis, Pediococcus acidilactici|Collinsella intestinalis, Pediococcus pentosaceus|Collinsella intestinalis, Peptoniphilus duerdenii|Collinsella intestinalis, Peptoniphilus harei|Collinsella intestinalis, Peptoniphilus lacrimalis|Collinsella intestinalis, Peptostreptococcus anaerobius|Collinsella intestinalis, Peptostreptococcus stomatis|Collinsella intestinalis, Porphyromonas asaccharolytica|Collinsella intestinalis, Porphyromonas uenonis|Collinsella intestinalis, Prevotella amnii|Collinsella intestinalis, Prevotella bergensis|Collinsella intestinalis, Prevotella bivia|Collinsella intestinalis, Prevotella buccae|Collinsella intestinalis, Prevotella buccalis|Collinsella intestinalis, Prevotella copri|Collinsella intestinalis, Prevotella disiens|Collinsella intestinalis, Prevotella melaninogenica|Collinsella intestinalis, Prevotella multiformis|Collinsella intestinalis, Prevotella oralis|Collinsella intestinalis, Prevotella oris|Collinsella intestinalis, Prevotella salivae|Collinsella intestinalis, Prevotella timonensis|Collinsella intestinalis, Propionibacterium acnes|Collinsella intestinalis, Propionibacterium freudenreichii|Collinsella intestinalis, Proteus mirabilis|Collinsella intestinalis, Proteus penneri|Collinsella intestinalis, Pseudoflavonifractor capillosus|Collinsella intestinalis, Pseudomonas aeruginosa|Collinsella intestinalis, Pseudomonas fluorescens|Collinsella intestinalis, Pseudomonas putida|Collinsella intestinalis, Pseudoramibacter alactolyticus|Collinsella intestinalis, Pyramidobacter piscolens|Collinsella intestinalis, Rhodopseudomonas palustris|Collinsella intestinalis, Roseburia intestinalis|Collinsella intestinalis, Roseburia inulinivorans|Collinsella intestinalis, Rothia dentocariosa|Collinsella intestinalis, Rothia mucilaginosa|Collinsella intestinalis, Ruminococcus albus|Collinsella intestinalis, Ruminococcus bromii|Collinsella intestinalis, Ruminococcus gnavus|Collinsella intestinalis, Ruminococcus lactaris|Collinsella intestinalis, Ruminococcus obeum|Collinsella intestinalis, Ruminococcus torques|Collinsella intestinalis, Selenomonas sputigena|Collinsella intestinalis, Shigella boydii|Collinsella intestinalis, Shigella dysenteriae|Collinsella intestinalis, Shigella sonnei|Collinsella intestinalis, Slackia exigua|Collinsella intestinalis, Solobacterium moorei|Collinsella intestinalis, Staphylococcus aureus|Collinsella intestinalis, Staphylococcus epidermidis|Collinsella intestinalis, Staphylococcus hominis|Collinsella intestinalis, Staphylococcus saprophyticus|Collinsella intestinalis, Staphylococcus warneri|Collinsella intestinalis, Streptococcus agalactiae|Collinsella intestinalis, Streptococcus anginosus|Collinsella intestinalis, Streptococcus australis|Collinsella intestinalis, Streptococcus bovis|Collinsella intestinalis, Streptococcus cristatus|Collinsella intestinalis, Streptococcus dysgalactiae|Collinsella intestinalis, Streptococcus equinus|Collinsella intestinalis, Streptococcus gordonii|Collinsella intestinalis, Streptococcus infantarius|Collinsella intestinalis, Streptococcus infantis|Collinsella intestinalis, Streptococcus mitis|Collinsella intestinalis, Streptococcus mutans|Collinsella intestinalis, Streptococcus oralis|Collinsella intestinalis, Streptococcus parasanguinis|Collinsella intestinalis, Streptococcus peroris|Collinsella intestinalis, Streptococcus pneumoniae|Collinsella intestinalis, Streptococcus salivarius|Collinsella intestinalis, Streptococcus sanguinis|Collinsella intestinalis, Streptococcus thermophilus|Collinsella intestinalis, Streptococcus vestibularis|Collinsella intestinalis, Subdoligranulum variabile|Collinsella intestinalis, Succinatimonas hippei|Collinsella intestinalis, Sutterella wadsworthensis|Collinsella intestinalis, Tropheryma whipplei|Collinsella intestinalis, Veillonella atypica|Collinsella intestinalis, Veillonella dispar|Collinsella intestinalis, Veillonella parvula|Collinsella intestinalis, Victivallis vadensis|Collinsella stercoris, Collinsella stercoris|Collinsella stercoris, Coprobacillus sp. D7|Collinsella stercoris, Coprococcus catus|Collinsella stercoris, Coprococcus comes|Collinsella stercoris, Coprococcus eutactus|Collinsella stercoris, Corynebacterium aurimucosum|Collinsella stercoris, Corynebacterium matruchotii|Collinsella stercoris, Cryptobacterium curtum|Collinsella stercoris, Desulfovibrio desulfuricans|Collinsella stercoris, Desulfovibrio piger|Collinsella stercoris, Dialister invisus|Collinsella stercoris, Dialister microaerophilus|Collinsella stercoris, Dorea formicigenerans|Collinsella stercoris, Dorea longicatena|Collinsella stercoris, Eggerthella lenta|Collinsella stercoris, Eikenella corrodens|Collinsella stercoris, Enterobacter cancerogenus|Collinsella stercoris, Enterobacter cloacae|Collinsella stercoris, Enterococcus faecalis|Collinsella stercoris, Enterococcus faecium|Collinsella stercoris, Enterococcus gallinarum|Collinsella stercoris, Erysipelotrichaceae bacterium 3_1_53|Collinsella stercoris, Escherichia coli|Collinsella stercoris, Escherichia fergusonii|Collinsella stercoris, Ethanoligenens harbinense|Collinsella stercoris, Eubacterium cellulosolvens|Collinsella stercoris, Eubacterium eligens|Collinsella stercoris, Eubacterium hallii|Collinsella stercoris, Eubacterium limosum|Collinsella stercoris, Eubacterium rectale|Collinsella stercoris, Eubacterium siraeum|Collinsella stercoris, Eubacterium ventriosum|Collinsella stercoris, Faecalibacterium prausnitzii|Collinsella stercoris, Finegoldia magna|Collinsella stercoris, Fusobacterium gonidiaformans|Collinsella stercoris, Fusobacterium mortiferum|Collinsella stercoris, Fusobacterium nucleatum|Collinsella stercoris, Fusobacterium varium|Collinsella stercoris, Gardnerella vaginalis|Collinsella stercoris, Gemella haemolysans|Collinsella stercoris, Gemella morbillorum|Collinsella stercoris, Gordonibacter pamelaeae|Collinsella stercoris, Granulicatella adiacens|Collinsella stercoris, Granulicatella elegans|Collinsella stercoris, Haemophilus influenzae|Collinsella stercoris, Haemophilus parainfluenzae|Collinsella stercoris, Helicobacter pullorum|Collinsella stercoris, Helicobacter pylori|Collinsella stercoris, Holdemania filiformis|Collinsella stercoris, Kingella oralis|Collinsella stercoris, Klebsiella pneumoniae|Collinsella stercoris, Klebsiella variicola|Collinsella stercoris, Lachnospiraceae bacterium 5_57FAA|Collinsella stercoris, Lactobacillus acidophilus|Collinsella stercoris, Lactobacillus amylovorus|Collinsella stercoris, Lactobacillus brevis|Collinsella stercoris, Lactobacillus casei|Collinsella stercoris, Lactobacillus crispatus|Collinsella stercoris, Lactobacillus delbrueckii|Collinsella stercoris, Lactobacillus fermentum|Collinsella stercoris, Lactobacillus gasseri|Collinsella stercoris, Lactobacillus iners|Collinsella stercoris, Lactobacillus jensenii|Collinsella stercoris, Lactobacillus johnsonii|Collinsella stercoris, Lactobacillus paracasei|Collinsella stercoris, Lactobacillus plantarum|Collinsella stercoris, Lactobacillus reuteri|Collinsella stercoris, Lactobacillus rhamnosus|Collinsella stercoris, Lactobacillus ruminis|Collinsella stercoris, Lactobacillus sakei|Collinsella stercoris, Lactobacillus salivarius|Collinsella stercoris, Lactococcus lactis|Collinsella stercoris, Lautropia mirabilis|Collinsella stercoris, Leuconostoc citreum|Collinsella stercoris, Leuconostoc gasicomitatum|Collinsella stercoris, Leuconostoc mesenteroides|Collinsella stercoris, Listeria monocytogenes|Collinsella stercoris, Marvinbryantia formatexigens|Collinsella stercoris, Megamonas hypermegale|Collinsella stercoris, Megasphaera micronuciformis|Collinsella stercoris, Methanobrevibacter smithii|Collinsella stercoris, Methanosphaera stadtmanae|Collinsella stercoris, Methylobacterium radiotolerans|Collinsella stercoris, Mitsuokella multacida|Collinsella stercoris, Mobiluncus curtisii|Collinsella stercoris, Mycoplasma hominis|Collinsella stercoris, Neisseria mucosa|Collinsella stercoris, Odoribacter splanchnicus|Collinsella stercoris, Olsenella uli|Collinsella stercoris, Oribacterium sinus|Collinsella stercoris, Oxalobacter formigenes|Collinsella stercoris, Parabacteroides distasonis|Collinsella stercoris, Parabacteroides johnsonii|Collinsella stercoris, Parabacteroides merdae|Collinsella stercoris, Parvimonas micra|Collinsella stercoris, Pediococcus acidilactici|Collinsella stercoris, Pediococcus pentosaceus|Collinsella stercoris, Peptoniphilus duerdenii|Collinsella stercoris, Peptoniphilus harei|Collinsella stercoris, Peptoniphilus lacrimalis|Collinsella stercoris, Peptostreptococcus anaerobius|Collinsella stercoris, Peptostreptococcus stomatis|Collinsella stercoris, Porphyromonas asaccharolytica|Collinsella stercoris, Porphyromonas uenonis|Collinsella stercoris, Prevotella amnii|Collinsella stercoris, Prevotella bergensis|Collinsella stercoris, Prevotella bivia|Collinsella stercoris, Prevotella buccae|Collinsella stercoris, Prevotella buccalis|Collinsella stercoris, Prevotella copri|Collinsella stercoris, Prevotella disiens|Collinsella stercoris, Prevotella melaninogenica|Collinsella stercoris, Prevotella multiformis|Collinsella stercoris, Prevotella oralis|Collinsella stercoris, Prevotella oris|Collinsella stercoris, Prevotella salivae|Collinsella stercoris, Prevotella timonensis|Collinsella stercoris, Propionibacterium acnes|Collinsella stercoris, Propionibacterium freudenreichii|Collinsella stercoris, Proteus mirabilis|Collinsella stercoris, Proteus penneri|Collinsella stercoris, Pseudoflavonifractor capillosus|Collinsella stercoris, Pseudomonas aeruginosa|Collinsella stercoris, Pseudomonas fluorescens|Collinsella stercoris, Pseudomonas putida|Collinsella stercoris, Pseudoramibacter alactolyticus|Collinsella stercoris, Pyramidobacter piscolens|Collinsella stercoris, Rhodopseudomonas palustris|Collinsella stercoris, Roseburia intestinalis|Collinsella stercoris, Roseburia inulinivorans|Collinsella stercoris, Rothia dentocariosa|Collinsella stercoris, Rothia mucilaginosa|Collinsella stercoris, Ruminococcus albus|Collinsella stercoris, Ruminococcus bromii|Collinsella stercoris, Ruminococcus gnavus|Collinsella stercoris, Ruminococcus lactaris|Collinsella stercoris, Ruminococcus obeum|Collinsella stercoris, Ruminococcus torques|Collinsella TABLE 2-continued

| Table 2. Specific binary combinations of OTUs. Individual pairings are differentiated by "\|" and OTUs within a combination are differentiated by "," |
|---|
| stercoris, Selenomonas sputigena\|Collinsella stercoris, Shigella boydii\|Collinsella stercoris, Shigella dysenteriae\|Collinsella stercoris, Shigella sonnei\|Collinsella stercoris, Slackia exigua\|Collinsella stercoris, Solobacterium moorei\|Collinsella stercoris, Staphylococcus aureus\|Collinsella stercoris, Staphylococcus epidermidis\|Collinsella stercoris, Staphylococcus hominis\|Collinsella stercoris, Staphylococcus saprophyticus\|Collinsella stercoris, Staphylococcus warneri\|Collinsella stercoris, Streptococcus agalactiae\|Collinsella stercoris, Streptococcus anginosus\|Collinsella stercoris, Streptococcus australis\|Collinsella stercoris, Streptococcus bovis\|Collinsella stercoris, Streptococcus cristatus\|Collinsella stercoris, Streptococcus dysgalactiae\|Collinsella stercoris, Streptococcus equinus\|Collinsella stercoris, Streptococcus gordonii\|Collinsella stercoris, Streptococcus infantarius\|Collinsella stercoris, Streptococcus infantis\|Collinsella stercoris, Streptococcus mitis\|Collinsella stercoris, Streptococcus mutans\|Collinsella stercoris, Streptococcus oralis\|Collinsella stercoris, Streptococcus parasanguinis\|Collinsella stercoris, Streptococcus peroris\|Collinsella stercoris, Streptococcus pneumoniae\|Collinsella stercoris, Streptococcus salivarius\|Collinsella stercoris, Streptococcus sanguinis\|Collinsella stercoris, Streptococcus thermophilus\|Collinsella stercoris, Streptococcus vestibularis\|Collinsella stercoris, Subdoligranulum variabile\|Collinsella stercoris, Succinatimonas hippei\|Collinsella stercoris, Sutterella wadsworthensis\|Collinsella stercoris, Tropheryma whipplei\|Collinsella stercoris, Veillonella atypica\|Collinsella stercoris, Veillonella dispar\|Collinsella stercoris, Veillonella parvula\|Collinsella stercoris, Victivallis vadensis\|Coprobacillus sp. D7, Coprobacillus sp. D7\|Coprobacillus sp. D7, Coprococcus catus\|Coprobacillus sp. D7, Coprococcus comes\|Coprobacillus sp. D7, Coprococcus eutactus\|Coprobacillus sp. D7, Corynebacterium aurimucosum\|Coprobacillus sp. D7, Corynebacterium matruchotii\|Coprobacillus sp. D7, Cryptobacterium curtum\|Coprobacillus sp. D7, Desulfovibrio desulfuricans\|Coprobacillus sp. D7, Desulfovibrio piger\|Coprobacillus sp. D7, Dialister invisus\|Coprobacillus sp. D7, Dialister microaerophilus\|Coprobacillus sp. D7, Dorea formicigenerans\|Coprobacillus sp. D7, Dorea longicatena\|Coprobacillus sp. D7, Eggerthella lenta\|Coprobacillus sp. D7, Eikenella corrodens\|Coprobacillus sp. D7, Enterobacter cancerogenus\|Coprobacillus sp. D7, Enterobacter cloacae\|Coprobacillus sp. D7, Enterococcus faecalis\|Coprobacillus sp. D7, Enterococcus faecium\|Coprobacillus sp. D7, Enterococcus gallinarum\|Coprobacillus sp. D7, Erysipelotrichaceae bacterium 3_1_53\|Coprobacillus sp. D7, Escherichia coli\|Coprobacillus sp. D7, Escherichia fergusonii\|Coprobacillus sp. D7, Ethanoligenens harbinense\|Coprobacillus sp. D7, Eubacterium cellulosolvens\|Coprobacillus sp. D7, Eubacterium eligens\|Coprobacillus sp. D7, Eubacterium hallii\|Coprobacillus sp. D7, Eubacterium limosum\|Coprobacillus sp. D7, Eubacterium rectale\|Coprobacillus sp. D7, Eubacterium siraeum\|Coprobacillus sp. D7, Eubacterium ventriosum\|Coprobacillus sp. D7, Faecalibacterium prausnitzii\|Coprobacillus sp. D7, Finegoldia magna\|Coprobacillus sp. D7, Fusobacterium gonidiaformans\|Coprobacillus sp. D7, Fusobacterium mortiferum\|Coprobacillus sp. D7, Fusobacterium nucleatum\|Coprobacillus sp. D7, Fusobacterium varium\|Coprobacillus sp. D7, Gardnerella vaginalis\|Coprobacillus sp. D7, Gemella haemolysans\|Coprobacillus sp. D7, Gemella morbillorum\|Coprobacillus sp. D7, Gordonibacter pamelaeae\|Coprobacillus sp. D7, Granulicatella adiacens\|Coprobacillus sp. D7, Granulicatella elegans\|Coprobacillus sp. D7, Haemophilus influenzae\|Coprobacillus sp. D7, Haemophilus parainfluenzae\|Coprobacillus sp. D7, Helicobacter pullorum\|Coprobacillus sp. D7, Helicobacter pylori\|Coprobacillus sp. D7, Holdemania filiformis\|Coprobacillus sp. D7, Kingella oralis\|Coprobacillus sp. D7, Klebsiella pneumoniae\|Coprobacillus sp. D7, Klebsiella variicola\|Coprobacillus sp. D7, Lachnospiraceae bacterium 5_1_57FAA\|Coprobacillus sp. D7, Lactobacillus acidophilus\|Coprobacillus sp. D7, Lactobacillus amylovorus\|Coprobacillus sp. D7, Lactobacillus brevis\|Coprobacillus sp. D7, Lactobacillus casei\|Coprobacillus sp. D7, Lactobacillus crispatus\|Coprobacillus sp. D7, Lactobacillus delbrueckii\|Coprobacillus sp. D7, Lactobacillus fermentum\|Coprobacillus sp. D7, Lactobacillus gasseri\|Coprobacillus sp. D7, Lactobacillus iners\|Coprobacillus sp. D7, Lactobacillus jensenii\|Coprobacillus sp. D7, Lactobacillus johnsonii\|Coprobacillus sp. D7, Lactobacillus paracasei\|Coprobacillus sp. D7, Lactobacillus plantarum\|Coprobacillus sp. D7, Lactobacillus reuteri\|Coprobacillus sp. D7, Lactobacillus rhamnosus\|Coprobacillus sp. D7, Lactobacillus ruminis\|Coprobacillus sp. D7, Lactobacillus sakei\|Coprobacillus sp. D7, Lactobacillus salivarius\|Coprobacillus sp. D7, Lactococcus lactis\|Coprobacillus sp. D7, Lautropia mirabilis\|Coprobacillus sp. D7, Leuconostoc citreum\|Coprobacillus sp. D7, Leuconostoc gasicomitatum\|Coprobacillus sp. D7, Leuconostoc mesenteroides\|Coprobacillus sp. D7, Listeria monocytogenes\|Coprobacillus sp. D7, Marvinbryantia formatexigens\|Coprobacillus sp. D7, Megamonas hypermegale\|Coprobacillus sp. D7, Megasphaera micronuciformis\|Coprobacillus sp. D7, Methanobrevibacter smithii\|Coprobacillus sp. D7, Methanosphaera stadtmanae\|Coprobacillus sp. D7, Methylobacterium radiotolerans\|Coprobacillus sp. D7, Mitsuokella multacida\|Coprobacillus sp. D7, Mobiluncus curtisii\|Coprobacillus sp. D7, Mycoplasma hominis\|Coprobacillus sp. D7, Neisseria mucosa\|Coprobacillus sp. D7, Odoribacter splanchnicus\|Coprobacillus sp. D7, Olsenella uli\|Coprobacillus sp. D7, Oribacterium sinus\|Coprobacillus sp. D7, Oxalobacter formigenes\|Coprobacillus sp. D7, Parabacteroides distasonis\|Coprobacillus sp. D7, Parabacteroides johnsonii\|Coprobacillus sp. D7, Parabacteroides merdae\|Coprobacillus sp. D7, Parvimonas micra\|Coprobacillus sp. D7, Pediococcus acidilactici\|Coprobacillus sp. D7, Pediococcus pentosaceus\|Coprobacillus sp. D7, Peptoniphilus duerdenii\|Coprobacillus sp. D7, Peptoniphilus harei\|Coprobacillus sp. D7, Peptoniphilus lacrimalis\|Coprobacillus sp. D7, Peptostreptococcus anaerobius\|Coprobacillus sp. D7, Peptostreptococcus stomatis\|Coprobacillus sp. D7, Porphyromonas asaccharolytica\|Coprobacillus sp. D7, Porphyromonas uenonis\|Coprobacillus sp. D7, Prevotella amnii\|Coprobacillus sp. D7, Prevotella bergensis\|Coprobacillus sp. D7, Prevotella bivia\|Coprobacillus sp. D7, Prevotella buccae\|Coprobacillus sp. D7, Prevotella buccalis\|Coprobacillus sp. D7, Prevotella copri\|Coprobacillus sp. D7, Prevotella disiens\|Coprobacillus sp. D7, Prevotella melaninogenica\|Coprobacillus sp. D7, Prevotella multiformis\|Coprobacillus sp. D7, Prevotella oralis\|Coprobacillus sp. D7, Prevotella oris\|Coprobacillus sp. D7, Prevotella salivae\|Coprobacillus sp. D7, Prevotella timonensis\|Coprobacillus sp. D7, Propionibacterium acnes\|Coprobacillus sp. D7, Propionibacterium freudenreichii\|Coprobacillus sp. D7, Proteus mirabilis\|Coprobacillus sp. D7, Proteus penneri\|Coprobacillus sp. D7, Pseudoflavonifractor capillosus\|Coprobacillus sp. D7, Pseudomonas aeruginosa\|Coprobacillus sp. D7, Pseudomonas fluorescens\|Coprobacillus sp. D7, Pseudomonas putida\|Coprobacillus sp. D7, Pseudoramibacter alactolyticus\|Coprobacillus sp. D7, Pyramidobacter piscolens\|Coprobacillus sp. D7, Rhodopseudomonas palustris\|Coprobacillus sp. D7, Roseburia intestinalis\|Coprobacillus sp. D7, Roseburia inulinivorans\|Coprobacillus sp. D7, Rothia dentocariosa\|Coprobacillus sp. D7, Rothia mucilaginosa\|Coprobacillus sp. D7, Ruminococcus albus\|Coprobacillus sp. D7, Ruminococcus bromii\|Coprobacillus sp. D7, Ruminococcus gnavus\|Coprobacillus sp. D7, Ruminococcus lactaris\|Coprobacillus sp. D7, Ruminococcus obeum\|Coprobacillus sp. D7, Ruminococcus torques\|Coprobacillus sp. D7, Selenomonas sputigena\|Coprobacillus sp. D7, Shigella boydii\|Coprobacillus sp. D7, Shigella dysenteriae\|Coprobacillus sp. D7, Shigella sonnei\|Coprobacillus sp. D7, Slackia exigua\|Coprobacillus sp. D7, Solobacterium moorei\|Coprobacillus sp. D7, Staphylococcus aureus\|Coprobacillus sp. D7, Staphylococcus epidermidis\|Coprobacillus sp. D7, Staphylococcus hominis\|Coprobacillus sp. D7, Staphylococcus saprophyticus\|Coprobacillus sp. D7, Staphylococcus warneri\|Coprobacillus sp. D7, Streptococcus agalactiae\|Coprobacillus sp. D7, Streptococcus anginosus\|Coprobacillus sp. D7, Streptococcus australis\|Coprobacillus sp. D7, Streptococcus bovis\|Coprobacillus sp. D7, Streptococcus cristatus\|Coprobacillus sp. D7, Streptococcus dysgalactiae\|Coprobacillus sp. D7, Streptococcus equinus\|Coprobacillus sp. D7, Streptococcus gordonii\|Coprobacillus sp. D7, Streptococcus infantarius\|Coprobacillus sp. D7, Streptococcus infantis\|Coprobacillus sp. D7, Streptococcus mitis\|Coprobacillus sp. D7, Streptococcus mutans\|Coprobacillus sp. D7, Streptococcus oralis\|Coprobacillus sp. D7, Streptococcus parasanguinis\|Coprobacillus sp. D7, Streptococcus peroris\|Coprobacillus sp. D7, Streptococcus pneumoniae\|Coprobacillus sp. D7, Streptococcus salivarius\|Coprobacillus sp. D7, Streptococcus sanguinis\|Coprobacillus sp. D7, Streptococcus thermophilus\|Coprobacillus sp. D7, Streptococcus vestibularis\|Coprobacillus sp. D7, Subdoligranulum variabile\|Coprobacillus sp. D7, Succinatimonas hippei\|Coprobacillus sp. D7, Sutterella wadsworthensis\|Coprobacillus sp. D7, Tropheryma whipplei\|Coprobacillus sp. D7, Veillonella atypica\|Coprobacillus sp. D7, Veillonella dispar\|Coprobacillus sp. D7, Veillonella parvula\|Coprobacillus sp. D7, Victivallis vadensis\|Coprococcus catus, Coprococcus catus\|Coprococcus catus, Coprococcus comes\|Coprococcus catus, Coprococcus eutactus\|Coprococcus catus, Corynebacterium aurimucosum\|Coprococcus catus, Corynebacterium matruchotii\|Coprococcus catus, Cryptobacterium curtum\|Coprococcus catus, Desulfovibrio desulfuricans\|Coprococcus catus, Desulfovibrio piger\|Coprococcus catus, Dialister invisus\|Coprococcus catus, Dialister microaerophilus\|Coprococcus catus, Dorea formicigenerans\|Coprococcus catus, Dorea longicatena\|Coprococcus |

TABLE 2-continued

| Table 2. Specific binary combinations of OTUs. Individual pairings are differentiated by "\|" and OTUs within a combination are differentiated by "," |
|---|
| catus, *Eggerthella lenta*\|*Coprococcus catus*, *Eikenella corrodens*\|*Coprococcus catus*, *Enterobacter cancerogenus*\|*Coprococcus catus*, *Enterobacter cloacae*\|*Coprococcus catus*, *Enterococcus faecalis*\|*Coprococcus catus*, *Enterococcus faecium*\|*Coprococcus catus*, *Enterococcus gallinarum*\|*Coprococcus catus*, *Erysipelotrichaceae bacterium* 3_1_53\|*Coprococcus catus*, *Escherichia coli*\|*Coprococcus catus*, *Escherichia fergusonii*\|*Coprococcus catus*, *Ethanoligenens harbinense*\|*Coprococcus catus*, *Eubacterium cellulosolvens*\|*Coprococcus catus*, *Eubacterium eligens*\|*Coprococcus catus*, *Eubacterium hallii*\|*Coprococcus catus*, *Eubacterium limosum*\|*Coprococcus catus*, *Eubacterium rectale*\|*Coprococcus catus*, *Eubacterium siraeum*\|*Coprococcus catus*, *Eubacterium ventriosum*\|*Coprococcus catus*, *Faecalibacterium prausnitzii*\|*Coprococcus catus*, *Finegoldia magna*\|*Coprococcus catus*, *Fusobacterium gonidiaformans*\|*Coprococcus catus*, *Fusobacterium mortiferum*\|*Coprococcus catus*, *Fusobacterium nucleatum*\|*Coprococcus catus*, *Fusobacterium varium*\|*Coprococcus catus*, *Gardnerella vaginalis*\|*Coprococcus catus*, *Gemella haemolysans*\|*Coprococcus catus*, *Gemella morbillorum*\|*Coprococcus catus*, *Gordonibacter pamelaeae*\|*Coprococcus catus*, *Granulicatella adiacens*\|*Coprococcus catus*, *Granulicatella elegans*\|*Coprococcus catus*, *Haemophilus influenzae*\|*Coprococcus catus*, *Haemophilus parainfluenzae*\|*Coprococcus catus*, *Helicobacter pullorum*\|*Coprococcus catus*, *Helicobacter pylori*\|*Coprococcus catus*, *Holdemania filiformis*\|*Coprococcus catus*, *Kingella oralis*\|*Coprococcus catus*, *Klebsiella pneumoniae*\|*Coprococcus catus*, *Klebsiella variicola*\|*Coprococcus catus*, *Lachnospiraceae bacterium* 5_1_57FAA\|*Coprococcus catus*, *Lactobacillus acidophilus*\|*Coprococcus catus*, *Lactobacillus amylovorus*\|*Coprococcus catus*, *Lactobacillus brevis*\|*Coprococcus catus*, *Lactobacillus casei*\|*Coprococcus catus*, *Lactobacillus crispatus*\|*Coprococcus catus*, *Lactobacillus delbrueckii*\|*Coprococcus catus*, *Lactobacillus fermentum*\|*Coprococcus catus*, *Lactobacillus gasseri*\|*Coprococcus catus*, *Lactobacillus iners*\|*Coprococcus catus*, *Lactobacillus jensenii*\|*Coprococcus catus*, *Lactobacillus johnsonii*\|*Coprococcus catus*, *Lactobacillus paracasei*\|*Coprococcus catus*, *Lactobacillus plantarum*\|*Coprococcus catus*, *Lactobacillus reuteri*\|*Coprococcus catus*, *Lactobacillus rhamnosus*\|*Coprococcus catus*, *Lactobacillus ruminis*\|*Coprococcus catus*, *Lactobacillus sakei*\|*Coprococcus catus*, *Lactobacillus salivarius*\|*Coprococcus catus*, *Lactococcus lactis*\|*Coprococcus catus*, *Lautropia mirabilis*\|*Coprococcus catus*, *Leuconostoc citreum*\|*Coprococcus catus*, *Leuconostoc gasicomitatum*\|*Coprococcus catus*, *Leuconostoc mesenteroides*\|*Coprococcus catus*, *Listeria monocytogenes*\|*Coprococcus catus*, *Marvinbryantia formatexigens*\|*Coprococcus catus*, *Megamonas hypermegale*\|*Coprococcus catus*, *Megasphaera micronuciformis*\|*Coprococcus catus*, *Methanobrevibacter smithii*\|*Coprococcus catus*, *Methanosphaera stadtmanae*\|*Coprococcus catus*, *Methylobacterium radiotolerans*\|*Coprococcus catus*, *Mitsuokella multacida*\|*Coprococcus catus*, *Mobiluncus curtisii*\|*Coprococcus catus*, *Mycoplasma hominis*\|*Coprococcus catus*, *Neisseria mucosa*\|*Coprococcus catus*, *Odoribacter splanchnicus*\|*Coprococcus catus*, *Olsenella uli*\|*Coprococcus catus*, *Oribacterium sinus*\|*Coprococcus catus*, *Oxalobacter formigenes*\|*Coprococcus catus*, *Parabacteroides distasonis*\|*Coprococcus catus*, *Parabacteroides johnsonii*\|*Coprococcus catus*, *Parabacteroides merdae*\|*Coprococcus catus*, *Parvimonas micra*\|*Coprococcus catus*, *Pediococcus acidilactici*\|*Coprococcus catus*, *Pediococcus pentosaceus*\|*Coprococcus catus*, *Peptoniphilus duerdenii*\|*Coprococcus catus*, *Peptoniphilus harei*\|*Coprococcus catus*, *Peptoniphilus lacrimalis*\|*Coprococcus catus*, *Peptostreptococcus anaerobius*\|*Coprococcus catus*, *Peptostreptococcus stomatis*\|*Coprococcus catus*, *Porphyromonas asaccharolytica*\|*Coprococcus catus*, *Porphyromonas uenonis*\|*Coprococcus catus*, *Prevotella amnii*\|*Coprococcus catus*, *Prevotella bergensis*\|*Coprococcus catus*, *Prevotella bivia*\|*Coprococcus catus*, *Prevotella buccae*\|*Coprococcus catus*, *Prevotella buccalis*\|*Coprococcus catus*, *Prevotella copri*\|*Coprococcus catus*, *Prevotella disiens*\|*Coprococcus catus*, *Prevotella melaninogenica*\|*Coprococcus catus*, *Prevotella multiformis*\|*Coprococcus catus*, *Prevotella oralis*\|*Coprococcus catus*, *Prevotella oris*\|*Coprococcus catus*, *Prevotella salivae*\|*Coprococcus catus*, *Prevotella timonensis*\|*Coprococcus catus*, *Propionibacterium acnes*\|*Coprococcus catus*, *Propionibacterium freudenreichii*\|*Coprococcus catus*, *Proteus mirabilis*\|*Coprococcus catus*, *Proteus penneri*\|*Coprococcus catus*, *Pseudoflavonifractor capillosus*\|*Coprococcus catus*, *Pseudomonas aeruginosa*\|*Coprococcus catus*, *Pseudomonas fluorescens*\|*Coprococcus catus*, *Pseudomonas putida*\|*Coprococcus catus*, *Pseudoramibacter alactolyticus*\|*Coprococcus catus*, *Pyramidobacter piscolens*\|*Coprococcus catus*, *Rhodopseudomonas palustris*\|*Coprococcus catus*, *Roseburia intestinalis*\|*Coprococcus catus*, *Roseburia inulinivorans*\|*Coprococcus catus*, *Rothia dentocariosa*\|*Coprococcus catus*, *Rothia mucilaginosa*\|*Coprococcus catus*, *Ruminococcus albus*\|*Coprococcus catus*, *Ruminococcus bromii*\|*Coprococcus catus*, *Ruminococcus gnavus*\|*Coprococcus catus*, *Ruminococcus lactaris*\|*Coprococcus catus*, *Ruminococcus obeum*\|*Coprococcus catus*, *Ruminococcus torques*\|*Coprococcus catus*, *Selenomonas sputigena*\|*Coprococcus catus*, *Shigella boydii*\|*Coprococcus catus*, *Shigella dysenteriae*\|*Coprococcus catus*, *Shigella sonnei*\|*Coprococcus catus*, *Slackia exigua*\|*Coprococcus catus*, *Solobacterium moorei*\|*Coprococcus catus*, *Staphylococcus aureus*\|*Coprococcus catus*, *Staphylococcus epidermidis*\|*Coprococcus catus*, *Staphylococcus hominis*\|*Coprococcus catus*, *Staphylococcus saprophyticus*\|*Coprococcus catus*, *Staphylococcus warneri*\|*Coprococcus catus*, *Streptococcus agalactiae*\|*Coprococcus catus*, *Streptococcus anginosus*\|*Coprococcus catus*, *Streptococcus australis*\|*Coprococcus catus*, *Streptococcus bovis*\|*Coprococcus catus*, *Streptococcus cristatus*\|*Coprococcus catus*, *Streptococcus dysgalactiae*\|*Coprococcus catus*, *Streptococcus equinus*\|*Coprococcus catus*, *Streptococcus gordonii*\|*Coprococcus catus*, *Streptococcus infantarius*\|*Coprococcus catus*, *Streptococcus infantis*\|*Coprococcus catus*, *Streptococcus mitis*\|*Coprococcus catus*, *Streptococcus mutans*\|*Coprococcus catus*, *Streptococcus oralis*\|*Coprococcus catus*, *Streptococcus parasanguinis*\|*Coprococcus catus*, *Streptococcus peroris*\|*Coprococcus catus*, *Streptococcus pneumoniae*\|*Coprococcus catus*, *Streptococcus salivarius*\|*Coprococcus catus*, *Streptococcus sanguinis*\|*Coprococcus catus*, *Streptococcus thermophilus*\|*Coprococcus catus*, *Streptococcus vestibularis*\|*Coprococcus catus*, *Subdoligranulum variabile*\|*Coprococcus catus*, *Succinatimonas hippei*\|*Coprococcus catus*, *Sutterella wadsworthensis*\|*Coprococcus catus*, *Tropheryma whipplei*\|*Coprococcus catus*, *Veillonella atypica*\|*Coprococcus catus*, *Veillonella dispar*\|*Coprococcus catus*, *Veillonella parvula*\|*Coprococcus catus*, *Victivallis vadensis*\|*Coprococcus comes*, *Coprococcus comes*\|*Coprococcus comes*, *Coprococcus eutactus*\|*Coprococcus comes*, *Corynebacterium aurimucosum*\|*Coprococcus comes*, *Corynebacterium matruchotii*\|*Coprococcus comes*, *Cryptobacterium curtum*\|*Coprococcus comes*, *Desulfovibrio desulfuricans*\|*Coprococcus comes*, *Desulfovibrio piger*\|*Coprococcus comes*, *Dialister invisus*\|*Coprococcus comes*, *Dialister microaerophilus*\|*Coprococcus comes*, *Dorea formicigenerans*\|*Coprococcus comes*, *Dorea longicatena*\|*Coprococcus comes*, *Eggerthella lenta*\|*Coprococcus comes*, *Eikenella corrodens*\|*Coprococcus comes*, *Enterobacter cancerogenus*\|*Coprococcus comes*, *Enterobacter cloacae*\|*Coprococcus comes*, *Enterococcus faecalis*\|*Coprococcus comes*, *Enterococcus faecium*\|*Coprococcus comes*, *Enterococcus gallinarum*\|*Coprococcus comes*, *Erysipelotrichaceae bacterium* 3_1_53\|*Coprococcus comes*, *Escherichia coli*\|*Coprococcus comes*, *Escherichia fergusonii*\|*Coprococcus comes*, *Ethanoligenens harbinense*\|*Coprococcus comes*, *Eubacterium cellulosolvens*\|*Coprococcus comes*, *Eubacterium eligens*\|*Coprococcus comes*, *Eubacterium hallii*\|*Coprococcus comes*, *Eubacterium limosum*\|*Coprococcus comes*, *Eubacterium rectale*\|*Coprococcus comes*, *Eubacterium siraeum*\|*Coprococcus comes*, *Eubacterium ventriosum*\|*Coprococcus comes*, *Faecalibacterium prausnitzii*\|*Coprococcus comes*, *Finegoldia magna*\|*Coprococcus comes*, *Fusobacterium gonidiaformans*\|*Coprococcus comes*, *Fusobacterium mortiferum*\|*Coprococcus comes*, *Fusobacterium nucleatum*\|*Coprococcus comes*, *Fusobacterium varium*\|*Coprococcus comes*, *Gardnerella vaginalis*\|*Coprococcus comes*, *Gemella haemolysans*\|*Coprococcus comes*, *Gemella morbillorum*\|*Coprococcus comes*, *Gordonibacter pamelaeae*\|*Coprococcus comes*, *Granulicatella adiacens*\|*Coprococcus comes*, *Granulicatella elegans*\|*Coprococcus comes*, *Haemophilus influenzae*\|*Coprococcus comes*, *Haemophilus parainfluenzae*\|*Coprococcus comes*, *Helicobacter pullorum*\|*Coprococcus comes*, *Helicobacter pylori*\|*Coprococcus comes*, *Holdemania filiformis*\|*Coprococcus comes*, *Kingella oralis*\|*Coprococcus comes*, *Klebsiella pneumoniae*\|*Coprococcus comes*, *Klebsiella variicola*\|*Coprococcus comes*, *Lachnospiraceae bacterium* 5_1_57FAA\|*Coprococcus comes*, *Lactobacillus acidophilus*\|*Coprococcus comes*, *Lactobacillus amylovorus*\|*Coprococcus comes*, *Lactobacillus brevis*\|*Coprococcus comes*, *Lactobacillus casei*\|*Coprococcus comes*, *Lactobacillus crispatus*\|*Coprococcus comes*, *Lactobacillus delbrueckii*\|*Coprococcus comes*, *Lactobacillus fermentum*\|*Coprococcus comes*, *Lactobacillus gasseri*\|*Coprococcus comes*, *Lactobacillus iners*\|*Coprococcus comes*, *Lactobacillus jensenii*\|*Coprococcus comes*, *Lactobacillus johnsonii*\|*Coprococcus comes*, *Lactobacillus paracasei*\|*Coprococcus comes*, *Lactobacillus plantarum*\|*Coprococcus comes*, *Lactobacillus reuteri*\|*Coprococcus comes*, *Lactobacillus rhamnosus*\|*Coprococcus comes*, *Lactobacillus ruminis*\|*Coprococcus comes*, *Lactobacillus sakei*\|*Coprococcus comes*, *Lactobacillus salivarius*\|*Coprococcus comes*, *Lactococcus lactis*\|*Coprococcus comes*, *Lautropia mirabilis*\|*Coprococcus comes*, *Leuconostoc citreum*\|*Coprococcus* |

TABLE 2-continued

| Table 2. Specific binary combinations of OTUs. Individual pairings are differentiated by "\|" and OTUs within a combination are differentiated by "," |
|---|
| comes, Leuconostoc gasicomitatum\|Coprococcus comes, Leuconostoc mesenteroides\|Coprococcus comes, Listeria monocytogenes\|Coprococcus comes, Marvinbryantia formatexigens\|Coprococcus comes, Megamonas hypermegale\|Coprococcus comes, Megasphaera micronuciformis\|Coprococcus comes, Methanobrevibacter smithii\|Coprococcus comes, Methanosphaera stadtmanae\|Coprococcus comes, Methylobacterium radiotolerans\|Coprococcus comes, Mitsuokella multacida\|Coprococcus comes, Mobiluncus curtisii\|Coprococcus comes, Mycoplasma hominis\|Coprococcus comes, Neisseria mucosa\|Coprococcus comes, Odoribacter splanchnicus\|Coprococcus comes, Olsenella uli\|Coprococcus comes, Oribacterium sinus\|Coprococcus comes, Oxalobacter formigenes\|Coprococcus comes, Parabacteroides distasonis\|Coprococcus comes, Parabacteroides johnsonii\|Coprococcus comes, Parabacteroides merdae\|Coprococcus comes, Parvimonas micra\|Coprococcus comes, Pediococcus acidilactici\|Coprococcus comes, Pediococcus pentosaceus\|Coprococcus comes, Peptoniphilus duerdenii\|Coprococcus comes, Peptoniphilus harei\|Coprococcus comes, Peptoniphilus lacrimalis\|Coprococcus comes, Peptostreptococcus anaerobius\|Coprococcus comes, Peptostreptococcus stomatis\|Coprococcus comes, Porphyromonas asaccharolytica\|Coprococcus comes, Porphyromonas uenonis\|Coprococcus comes, Prevotella amnii\|Coprococcus comes, Prevotella bergensis\|Coprococcus comes, Prevotella bivia\|Coprococcus comes, Prevotella buccae\|Coprococcus comes, Prevotella buccalis\|Coprococcus comes, Prevotella copri\|Coprococcus comes, Prevotella disiens\|Coprococcus comes, Prevotella melaninogenica\|Coprococcus comes, Prevotella multiformis\|Coprococcus comes, Prevotella oralis\|Coprococcus comes, Prevotella oris\|Coprococcus comes, Prevotella salivae\|Coprococcus comes, Prevotella timonensis\|Coprococcus comes, Propionibacterium acnes\|Coprococcus comes, Propionibacterium freudenreichii\|Coprococcus comes, Proteus mirabilis\|Coprococcus comes, Proteus penneri\|Coprococcus comes, Pseudoflavonifractor capillosus\|Coprococcus comes, Pseudomonas aeruginosa\|Coprococcus comes, Pseudomonas fluorescens\|Coprococcus comes, Pseudomonas putida\|Coprococcus comes, Pseudoramibacter alactolyticus\|Coprococcus comes, Pyramidobacter piscolens\|Coprococcus comes, Rhodopseudomonas palustris\|Coprococcus comes, Roseburia intestinalis\|Coprococcus comes, Roseburia inulinivorans\|Coprococcus comes, Rothia dentocariosa\|Coprococcus comes, Rothia mucilaginosa\|Coprococcus comes, Ruminococcus albus\|Coprococcus comes, Ruminococcus bromii\|Coprococcus comes, Ruminococcus gnavus\|Coprococcus comes, Ruminococcus lactaris\|Coprococcus comes, Ruminococcus obeum\|Coprococcus comes, Ruminococcus torques\|Coprococcus comes, Selenomonas sputigena\|Coprococcus comes, Shigella boydii\|Coprococcus comes, Shigella dysenteriae\|Coprococcus comes, Shigella sonnei\|Coprococcus comes, Slackia exigua\|Coprococcus comes, Solobacterium moorei\|Coprococcus comes, Staphylococcus aureus\|Coprococcus comes, Staphylococcus epidermidis\|Coprococcus comes, Staphylococcus hominis\|Coprococcus comes, Staphylococcus saprophyticus\|Coprococcus comes, Staphylococcus warneri\|Coprococcus comes, Streptococcus agalactiae\|Coprococcus comes, Streptococcus anginosus\|Coprococcus comes, Streptococcus australis\|Coprococcus comes, Streptococcus bovis\|Coprococcus comes, Streptococcus cristatus\|Coprococcus comes, Streptococcus dysgalactiae\|Coprococcus comes, Streptococcus equinus\|Coprococcus comes, Streptococcus gordonii\|Coprococcus comes, Streptococcus infantarius\|Coprococcus comes, Streptococcus infantis\|Coprococcus comes, Streptococcus mitis\|Coprococcus comes, Streptococcus mutans\|Coprococcus comes, Streptococcus oralis\|Coprococcus comes, Streptococcus parasanguinis\|Coprococcus comes, Streptococcus peroris\|Coprococcus comes, Streptococcus pneumoniae\|Coprococcus comes, Streptococcus salivarius\|Coprococcus comes, Streptococcus sanguinis\|Coprococcus comes, Streptococcus thermophilus\|Coprococcus comes, Streptococcus vestibularis\|Coprococcus comes, Subdoligranulum variabile\|Coprococcus comes, Succinatimonas hippei\|Coprococcus comes, Sutterella wadsworthensis\|Coprococcus comes, Tropheryma whipplei\|Coprococcus comes, Veillonella atypica\|Coprococcus comes, Veillonella dispar\|Coprococcus comes, Veillonella parvula\|Coprococcus comes, Victivallis vadensis\|Coprococcus eutactus, Coprococcus eutactus\|Coprococcus eutactus, Corynebacterium aurimucosum\|Coprococcus eutactus, Corynebacterium matruchotii\|Coprococcus eutactus, Cryptobacterium curtum\|Coprococcus eutactus, Desulfovibrio desulfuricans\|Coprococcus eutactus, Desulfovibrio piger\|Coprococcus eutactus, Dialister invisus\|Coprococcus eutactus, Dialister microaerophilus\|Coprococcus eutactus, Dorea formicigenerans\|Coprococcus eutactus, Dorea longicatena\|Coprococcus eutactus, Eggerthella lenta\|Coprococcus eutactus, Eikenella corrodens\|Coprococcus eutactus, Enterobacter cancerogenus\|Coprococcus eutactus, Enterobacter cloacae\|Coprococcus eutactus, Enterococcus faecalis\|Coprococcus eutactus, Enterococcus faecium\|Coprococcus eutactus, Enterococcus gallinarum\|Coprococcus eutactus, Erysipelotrichaceae bacterium 3_1_53\|Coprococcus eutactus, Escherichia coli\|Coprococcus eutactus, Escherichia fergusonii\|Coprococcus eutactus, Ethanoligenens harbinense\|Coprococcus eutactus, Eubacterium cellulosolvens\|Coprococcus eutactus, Eubacterium eligens\|Coprococcus eutactus, Eubacterium hallii\|Coprococcus eutactus, Eubacterium limosum\|Coprococcus eutactus, Eubacterium rectale\|Coprococcus eutactus, Eubacterium siraeum\|Coprococcus eutactus, Eubacterium ventriosum\|Coprococcus eutactus, Faecalibacterium prausnitzii\|Coprococcus eutactus, Finegoldia magna\|Coprococcus eutactus, Fusobacterium gonidiaformans\|Coprococcus eutactus, Fusobacterium mortiferum\|Coprococcus eutactus, Fusobacterium nucleatum\|Coprococcus eutactus, Fusobacterium varium\|Coprococcus eutactus, Gardnerella vaginalis\|Coprococcus eutactus, Gemella haemolysans\|Coprococcus eutactus, Gemella morbillorum\|Coprococcus eutactus, Gordonibacter pamelaeae\|Coprococcus eutactus, Granulicatella adiacens\|Coprococcus eutactus, Granulicatella elegans\|Coprococcus eutactus, Haemophilus influenzae\|Coprococcus eutactus, Haemophilus parainfluenzae\|Coprococcus eutactus, Helicobacter pullorum\|Coprococcus eutactus, Helicobacter pylori\|Coprococcus eutactus, Holdemania filiformis\|Coprococcus eutactus, Kingella oralis\|Coprococcus eutactus, Klebsiella pneumoniae\|Coprococcus eutactus, Klebsiella variicola\|Coprococcus eutactus, Lachnospiraceae bacterium 5_1_57FAA\|Coprococcus eutactus, Lactobacillus acidophilus\|Coprococcus eutactus, Lactobacillus amylovorus\|Coprococcus eutactus, Lactobacillus brevis\|Coprococcus eutactus, Lactobacillus casei\|Coprococcus eutactus, Lactobacillus crispatus\|Coprococcus eutactus, Lactobacillus delbrueckii\|Coprococcus eutactus, Lactobacillus fermentum\|Coprococcus eutactus, Lactobacillus gasseri\|Coprococcus eutactus, Lactobacillus iners\|Coprococcus eutactus, Lactobacillus jensenii\|Coprococcus eutactus, Lactobacillus johnsonii\|Coprococcus eutactus, Lactobacillus paracasei\|Coprococcus eutactus, Lactobacillus plantarum\|Coprococcus eutactus, Lactobacillus reuteri\|Coprococcus eutactus, Lactobacillus rhamnosus\|Coprococcus eutactus, Lactobacillus ruminis\|Coprococcus eutactus, Lactobacillus sakei\|Coprococcus eutactus, Lactobacillus salivarius\|Coprococcus eutactus, Lactococcus lactis\|Coprococcus eutactus, Lautropia mirabilis\|Coprococcus eutactus, Leuconostoc citreum\|Coprococcus eutactus, Leuconostoc gasicomitatum\|Coprococcus eutactus, Leuconostoc mesenteroides\|Coprococcus eutactus, Listeria monocytogenes\|Coprococcus eutactus, Marvinbryantia formatexigens\|Coprococcus eutactus, Megamonas hypermegale\|Coprococcus eutactus, Megasphaera micronuciformis\|Coprococcus eutactus, Methanobrevibacter smithii\|Coprococcus eutactus, Methanosphaera stadtmanae\|Coprococcus eutactus, Methylobacterium radiotolerans\|Coprococcus eutactus, Mitsuokella multacida\|Coprococcus eutactus, Mobiluncus curtisii\|Coprococcus eutactus, Mycoplasma hominis\|Coprococcus eutactus, Neisseria mucosa\|Coprococcus eutactus, Odoribacter splanchnicus\|Coprococcus eutactus, Olsenella uli\|Coprococcus eutactus, Oribacterium sinus\|Coprococcus eutactus, Oxalobacter formigenes\|Coprococcus eutactus, Parabacteroides distasonis\|Coprococcus eutactus, Parabacteroides johnsonii\|Coprococcus eutactus, Parabacteroides merdae\|Coprococcus eutactus, Parvimonas micra\|Coprococcus eutactus, Pediococcus acidilactici\|Coprococcus eutactus, Pediococcus pentosaceus\|Coprococcus eutactus, Peptoniphilus duerdenii\|Coprococcus eutactus, Peptoniphilus harei\|Coprococcus eutactus, Peptoniphilus lacrimalis\|Coprococcus eutactus, Peptostreptococcus anaerobius\|Coprococcus eutactus, Peptostreptococcus stomatis\|Coprococcus eutactus, Porphyromonas asaccharolytica\|Coprococcus eutactus, Porphyromonas uenonis\|Coprococcus eutactus, Prevotella amnii\|Coprococcus eutactus, Prevotella bergensis\|Coprococcus eutactus, Prevotella bivia\|Coprococcus eutactus, Prevotella buccae\|Coprococcus eutactus, Prevotella buccalis\|Coprococcus eutactus, Prevotella copri\|Coprococcus eutactus, Prevotella disiens\|Coprococcus eutactus, Prevotella melaninogenica\|Coprococcus eutactus, Prevotella multiformis\|Coprococcus eutactus, Prevotella oralis\|Coprococcus eutactus, Prevotella oris\|Coprococcus eutactus, Prevotella salivae\|Coprococcus eutactus, Prevotella timonensis\|Coprococcus eutactus, Propionibacterium acnes\|Coprococcus eutactus, Propionibacterium freudenreichii\|Coprococcus eutactus, Proteus mirabilis\|Coprococcus eutactus, Proteus penneri\|Coprococcus eutactus, Pseudoflavonifractor capillosus\|Coprococcus eutactus, Pseudomonas aeruginosa\|Coprococcus eutactus, Pseudomonas fluorescens\|Coprococcus eutactus, Pseudomonas putida\|Coprococcus eutactus, Pseudoramibacter alactolyticus\|Coprococcus |

TABLE 2-continued

Table 2. Specific binary combinations of OTUs. Individual pairings are differentiated by "|" and OTUs within a combination are differentiated by ","

*eutactus, Pyramidobacter piscolens|Coprococcus eutactus, Rhodopseudomonas palustris|Coprococcus eutactus, Roseburia intestinalis|Coprococcus eutactus, Roseburia inulinivorans|Coprococcus eutactus, Rothia dentocariosa|Coprococcus eutactus, Rothia mucilaginosa|Coprococcus eutactus, Ruminococcus albus|Coprococcus eutactus, Ruminococcus bromii|Coprococcus eutactus, Ruminococcus gnavus|Coprococcus eutactus, Ruminococcus lactaris|Coprococcus eutactus, Ruminococcus obeum|Coprococcus eutactus, Ruminococcus torques|Coprococcus eutactus, Selenomonas sputigena|Coprococcus eutactus, Shigella boydii|Coprococcus eutactus, Shigella dysenteriae|Coprococcus eutactus, Shigella sonnei|Coprococcus eutactus, Slackia exigua|Coprococcus eutactus, Solobacterium moorei|Coprococcus eutactus, Staphylococcus aureus|Coprococcus eutactus, Staphylococcus epidermidis|Coprococcus eutactus, Staphylococcus hominis|Coprococcus eutactus, Staphylococcus saprophyticus|Coprococcus eutactus, Staphylococcus warneri|Coprococcus eutactus, Streptococcus agalactiae|Coprococcus eutactus, Streptococcus anginosus|Coprococcus eutactus, Streptococcus australis|Coprococcus eutactus, Streptococcus bovis|Coprococcus eutactus, Streptococcus cristatus|Coprococcus eutactus, Streptococcus dysgalactiae|Coprococcus eutactus, Streptococcus equinus|Coprococcus eutactus, Streptococcus gordonii|Coprococcus eutactus, Streptococcus infantarius|Coprococcus eutactus, Streptococcus infantis|Coprococcus eutactus, Streptococcus mitis|Coprococcus eutactus, Streptococcus mutans|Coprococcus eutactus, Streptococcus oralis|Coprococcus eutactus, Streptococcus parasanguinis|Coprococcus eutactus, Streptococcus peroris|Coprococcus eutactus, Streptococcus pneumoniae|Coprococcus eutactus, Streptococcus salivarius|Coprococcus eutactus, Streptococcus sanguinis|Coprococcus eutactus, Streptococcus thermophilus|Coprococcus eutactus, Streptococcus vestibularis|Coprococcus eutactus, Subdoligranulum variabile|Coprococcus eutactus, Succinatimonas hippei|Coprococcus eutactus, Sutterella wadsworthensis|Coprococcus eutactus, Tropheryma whipplei|Coprococcus eutactus, Veillonella atypica|Coprococcus eutactus, Veillonella dispar|Coprococcus eutactus, Veillonella parvula|Coprococcus eutactus, Victivallis vadensis|Corynebacterium aurimucosum, Corynebacterium aurimucosum|Corynebacterium aurimucosum, Corynebacterium matruchotii|Corynebacterium aurimucosum, Cryptobacterium curtum|Corynebacterium aurimucosum, Desulfovibrio desulfuricans|Corynebacterium aurimucosum, Desulfovibrio piger|Corynebacterium aurimucosum, Dialister invisus|Corynebacterium aurimucosum, Dialister microaerophilus|Corynebacterium aurimucosum, Dorea formicigenerans|Corynebacterium aurimucosum, Dorea longicatena|Corynebacterium aurimucosum, Eggerthella lenta|Corynebacterium aurimucosum, Eikenella corrodens|Corynebacterium aurimucosum, Enterobacter cancerogenus|Corynebacterium aurimucosum, Enterobacter cloacae|Corynebacterium aurimucosum, Enterococcus faecalis|Corynebacterium aurimucosum, Enterococcus faecium|Corynebacterium aurimucosum, Enterococcus gallinarum|Corynebacterium aurimucosum, Erysipelotrichaceae bacterium* 3_1_53|*Corynebacterium aurimucosum, Escherichia coli|Corynebacterium aurimucosum, Escherichia fergusonii|Corynebacterium aurimucosum, Ethanoligenens harbinense|Corynebacterium aurimucosum, Eubacterium cellulosolvens|Corynebacterium aurimucosum, Eubacterium eligens|Corynebacterium aurimucosum, Eubacterium hallii|Corynebacterium aurimucosum, Eubacterium limosum|Corynebacterium aurimucosum, Eubacterium rectale|Corynebacterium aurimucosum, Eubacterium siraeum|Corynebacterium aurimucosum, Eubacterium ventriosum|Corynebacterium aurimucosum, Faecalibacterium prausnitzii|Corynebacterium aurimucosum, Finegoldia magna|Corynebacterium aurimucosum, Fusobacterium gonidiaformans|Corynebacterium aurimucosum, Fusobacterium mortifenim|Corynebacterium aurimucosum, Fusobacterium nucleatum|Corynebacterium aurimucosum, Fusobacterium varium|Corynebacterium aurimucosum, Gardnerella vaginalis|Corynebacterium aurimucosum, Gemella haemolysans|Corynebacterium aurimucosum, Gemella morbillorum|Corynebacterium aurimucosum, Gordonibacter pamelaeae|Corynebacterium aurimucosum, Granulicatella adiacens|Corynebacterium aurimucosum, Granulicatella elegans|Corynebacterium aurimucosum, Haemophilus influenzae|Corynebacterium aurimucosum, Haemophilus parainfluenzae|Corynebacterium aurimucosum, Helicobacter pullorum|Corynebacterium aurimucosum, Helicobacter pylori|Corynebacterium aurimucosum, Holdemania filiformis|Corynebacterium aurimucosum, Kingella oralis|Corynebacterium aurimucosum, Klebsiella pneumoniae|Corynebacterium aurimucosum, Klebsiella variicola|Corynebacterium aurimucosum, Lachnospiraceae bacterium* 5_1_57FAA|*Corynebacterium aurimucosum, Lactobacillus acidophilus|Corynebacterium aurimucosum, Lactobacillus amylovorus|Corynebacterium aurimucosum, Lactobacillus brevis|Corynebacterium aurimucosum, Lactobacillus casei|Corynebacterium aurimucosum, Lactobacillus crispatus|Corynebacterium aurimucosum, Lactobacillus delbrueckii|Corynebacterium aurimucosum, Lactobacillus fermentum|Corynebacterium aurimucosum, Lactobacillus gasseri|Corynebacterium aurimucosum, Lactobacillus iners|Corynebacterium aurimucosum, Lactobacillus jensenii|Corynebacterium aurimucosum, Lactobacillus johnsonii|Corynebacterium aurimucosum, Lactobacillus paracasei|Corynebacterium aurimucosum, Lactobacillus plantarum|Corynebacterium aurimucosum, Lactobacillus reuteri|Corynebacterium aurimucosum, Lactobacillus rhamnosus|Corynebacterium aurimucosum, Lactobacillus ruminis|Corynebacterium aurimucosum, Lactobacillus sakei|Corynebacterium aurimucosum, Lactobacillus salivarius|Corynebacterium aurimucosum, Lactococcus lactis|Corynebacterium aurimucosum, Lautropia mirabilis|Corynebacterium aurimucosum, Leuconostoc citreum|Corynebacterium aurimucosum, Leuconostoc gasicomitatum|Corynebacterium aurimucosum, Leuconostoc mesenteroides|Corynebacterium aurimucosum, Listeria monocytogenes|Corynebacterium aurimucosum, Marvinbryantia formatexigens|Corynebacterium aurimucosum, Megamonas hypermegale|Corynebacterium aurimucosum, Megasphaera micronuciformis|Corynebacterium aurimucosum, Methanobrevibacter smithii|Corynebacterium aurimucosum, Methanosphaera stadtmanae|Corynebacterium aurimucosum, Methylobacterium radiotolerans|Corynebacterium aurimucosum, Mitsuokella multacida|Corynebacterium aurimucosum, Mobiluncus curtisii|Corynebacterium aurimucosum, Mycoplasma hominis|Corynebacterium aurimucosum, Neisseria mucosa|Corynebacterium aurimucosum, Odoribacter splanchnicus|Corynebacterium aurimucosum, Olsenella uli|Corynebacterium aurimucosum, Oribacterium sinus|Corynebacterium aurimucosum, Oxalobacter formigenes|Corynebacterium aurimucosum, Parabacteroides distasonis|Corynebacterium aurimucosum, Parabacteroides johnsonii|Corynebacterium aurimucosum, Parabacteroides merdae|Corynebacterium aurimucosum, Parvimonas micra|Corynebacterium aurimucosum, Pediococcus acidilactici|Corynebacterium aurimucosum, Pediococcus pentosaceus|Corynebacterium aurimucosum, Peptoniphilus duerdenii|Corynebacterium aurimucosum, Peptoniphilus harei|Corynebacterium aurimucosum, Peptoniphilus lacrimalis|Corynebacterium aurimucosum, Peptostreptococcus anaerobius|Corynebacterium aurimucosum, Peptostreptococcus stomatis|Corynebacterium aurimucosum, Porphyromonas asaccharolytica|Corynebacterium aurimucosum, Porphyromonas uenonis|Corynebacterium aurimucosum, Prevotella amnii|Corynebacterium aurimucosum, Prevotella bergensis|Corynebacterium aurimucosum, Prevotella bivia|Corynebacterium aurimucosum, Prevotella buccae|Corynebacterium aurimucosum, Prevotella buccalis|Corynebacterium aurimucosum, Prevotella copri|Corynebacterium aurimucosum, Prevotella disiens|Corynebacterium aurimucosum, Prevotella melaninogenica|Corynebacterium aurimucosum, Prevotella multiformis|Corynebacterium aurimucosum, Prevotella oralis|Corynebacterium aurimucosum, Prevotella oris|Corynebacterium aurimucosum, Prevotella salivae|Corynebacterium aurimucosum, Prevotella timonensis|Corynebacterium aurimucosum, Propionibacterium acnes|Corynebacterium aurimucosum, Propionibacterium freudenreichii|Corynebacterium aurimucosum, Proteus mirabilis|Corynebacterium aurimucosum, Proteus penneri|Corynebacterium aurimucosum, Pseudoflavonifractor capillosus|Corynebacterium aurimucosum, Pseudomonas aeruginosa|Corynebacterium aurimucosum, Pseudomonas fluorescens|Corynebacterium aurimucosum, Pseudomonas putida|Corynebacterium aurimucosum, Pseudoramibacter alactolyticus|Corynebacterium aurimucosum, Pyramidobacter piscolens|Corynebacterium aurimucosum, Rhodopseudomonas palustris|Corynebacterium aurimucosum, Roseburia intestinalis|Corynebacterium aurimucosum, Roseburia inulinivorans|Corynebacterium aurimucosum, Rothia dentocariosa|Corynebacterium aurimucosum, Rothia mucilaginosa|Corynebacterium aurimucosum, Ruminococcus albus|Corynebacterium aurimucosum, Ruminococcus bromii|Corynebacterium aurimucosum, Ruminococcus gnavus|Corynebacterium aurimucosum, Ruminococcus lactaris|Corynebacterium aurimucosum, Ruminococcus obeum|Corynebacterium aurimucosum, Ruminococcus torques|Corynebacterium aurimucosum, Selenomonas sputigena|Corynebacterium aurimucosum, Shigella boydii|Corynebacterium aurimucosum, Shigella dysenteriae|Corynebacterium aurimucosum, Shigella sonnei|Corynebacterium aurimucosum, Slackia exigua|Corynebacterium aurimucosum, Solobacterium*

TABLE 2-continued

| Table 2. Specific binary combinations of OTUs. Individual pairings are differentiated by "\|" and OTUs within a combination are differentiated by "," |
|---|
| *moorei\|Corynebacterium aurimucosum, Staphylococcus aureus\|Corynebacterium aurimucosum, Staphylococcus epidermidis\|Corynebacterium aurimucosum, Staphylococcus hominis\|Corynebacterium aurimucosum, Staphylococcus saprophyticus\|Corynebacterium aurimucosum, Staphylococcus warneri\|Corynebacterium aurimucosum, Streptococcus agalactiae\|Corynebacterium aurimucosum, Streptococcus anginosus\|Corynebacterium aurimucosum, Streptococcus australis\|Corynebacterium aurimucosum, Streptococcus bovis\|Corynebacterium aurimucosum, Streptococcus cristatus\|Corynebacterium aurimucosum, Streptococcus dysgalactiae\|Corynebacterium aurimucosum, Streptococcus equinus\|Corynebacterium aurimucosum, Streptococcus gordonii\|Corynebacterium aurimucosum, Streptococcus infantarius\|Corynebacterium aurimucosum, Streptococcus infantis\|Corynebacterium aurimucosum, Streptococcus mitis\|Corynebacterium aurimucosum, Streptococcus mutans\|Corynebacterium aurimucosum, Streptococcus oralis\|Corynebacterium aurimucosum, Streptococcus parasanguinis\|Corynebacterium aurimucosum, Streptococcus peroris\|Corynebacterium aurimucosum, Streptococcus pneumoniae\|Corynebacterium aurimucosum, Streptococcus salivarius\|Corynebacterium aurimucosum, Streptococcus sanguinis\|Corynebacterium aurimucosum, Streptococcus thermophilus\|Corynebacterium aurimucosum, Streptococcus vestibularis\|Corynebacterium aurimucosum, Subdoligranulum variabile\|Corynebacterium aurimucosum, Succinatimonas hippei\|Corynebacterium aurimucosum, Sutterella wadsworthensis\|Corynebacterium aurimucosum, Tropheryma whipplei\|Corynebacterium aurimucosum, Veillonella atypica\|Corynebacterium aurimucosum, Veillonella dispar\|Corynebacterium aurimucosum, Veillonella parvula\|Corynebacterium aurimucosum, Victivallis vadensis\|Corynebacterium matruchotii, Corynebacterium matruchotii\|Corynebacterium matruchotii, Cryptobacterium curtum\|Corynebacterium matruchotii, Desulfovibrio desulfuricans\|Corynebacterium matruchotii, Desulfovibrio piger\|Corynebacterium matruchotii, Dialister invisus\|Corynebacterium matruchotii, Dialister microaerophilus\|Corynebacterium matruchotii, Dorea formicigenerans\|Corynebacterium matruchotii, Dorea longicatena\|Corynebacterium matruchotii, Eggerthella lenta\|Corynebacterium matruchotii, Eikenella corrodens\|Corynebacterium matruchotii, Enterobacter cancerogenus\|Corynebacterium matruchotii, Enterobacter cloacae\|Corynebacterium matruchotii, Enterococcus faecalis\|Corynebacterium matruchotii, Enterococcus faecium\|Corynebacterium matruchotii, Enterococcus gallinarum\|Corynebacterium matruchotii, Erysipelotrichaceae bacterium* 3_1_53\|*Corynebacterium matruchotii, Escherichia coli\|Corynebacterium matruchotii, Escherichia fergusonii\|Corynebacterium matruchotii, Ethanoligenens harbinense\|Corynebacterium matruchotii, Eubacterium cellulosolvens\|Corynebacterium matruchotii, Eubacterium eligens\|Corynebacterium matruchotii, Eubacterium hallii\|Corynebacterium matruchotii, Eubacterium limosum\|Corynebacterium matruchotii, Eubacterium rectale\|Corynebacterium matruchotii, Eubacterium siraeum\|Corynebacterium matruchotii, Eubacterium ventriosum\|Corynebacterium matruchotii, Faecalibacterium prausnitzii\|Corynebacterium matruchotii, Finegoldia magna\|Corynebacterium matruchotii, Fusobacterium gonidiaformans\|Corynebacterium matruchotii, Fusobacterium mortiferum\|Corynebacterium matruchotii, Fusobacterium nucleatum\|Corynebacterium matruchotii, Fusobacterium varium\|Corynebacterium matruchotii, Gardnerella vaginalis\|Corynebacterium matruchotii, Gemella haemolysans\|Corynebacterium matruchotii, Gemella morbillorum\|Corynebacterium matruchotii, Gordonibacter pamelaeae\|Corynebacterium matruchotii, Granulicatella adiacens\|Corynebacterium matruchotii, Granulicatella elegans\|Corynebacterium matruchotii, Haemophilus influenzae\|Corynebacterium matruchotii, Haemophilus parainfluenzae\|Corynebacterium matruchotii, Helicobacter pullorum\|Corynebacterium matruchotii, Helicobacter pylori\|Corynebacterium matruchotii, Holdemania filiformis\|Corynebacterium matruchotii, Kingella oralis\|Corynebacterium matruchotii, Klebsiella pneumoniae\|Corynebacterium matruchotii, Klebsiella variicola\|Corynebacterium matruchotii, Lachnospiraceae bacterium* 5_1_57FAA\|*Corynebacterium matruchotii, Lactobacillus acidophilus\|Corynebacterium matruchotii, Lactobacillus amylovorus\|Corynebacterium matruchotii, Lactobacillus brevis\|Corynebacterium matruchotii, Lactobacillus casei\|Corynebacterium matruchotii, Lactobacillus crispatus\|Corynebacterium matruchotii, Lactobacillus delbrueckii\|Corynebacterium matruchotii, Lactobacillus fermentum\|Corynebacterium matruchotii, Lactobacillus gasseri\|Corynebacterium matruchotii, Lactobacillus iners\|Corynebacterium matruchotii, Lactobacillus jensenii\|Corynebacterium matruchotii, Lactobacillus johnsonii\|Corynebacterium matruchotii, Lactobacillus paracasei\|Corynebacterium matruchotii, Lactobacillus plantarum\|Corynebacterium matruchotii, Lactobacillus reuteri\|Corynebacterium matruchotii, Lactobacillus rhamnosus\|Corynebacterium matruchotii, Lactobacillus ruminis\|Corynebacterium matruchotii, Lactobacillus sakei\|Corynebacterium matruchotii, Lactobacillus salivarius\|Corynebacterium matruchotii, Lactococcus lactis\|Corynebacterium matruchotii, Lautropia mirabilis\|Corynebacterium matruchotii, Leuconostoc citreum\|Corynebacterium matruchotii, Leuconostoc gasicomitatum\|Corynebacterium matruchotii, Leuconostoc mesenteroides\|Corynebacterium matruchotii, Listeria monocytogenes\|Corynebacterium matruchotii, Marvinbryantia formatexigens\|Corynebacterium matruchotii, Megamonas hypermegale\|Corynebacterium matruchotii, Megasphaera micronuciformis\|Corynebacterium matruchotii, Methanobrevibacter smithii\|Corynebacterium matruchotii, Methanosphaera stadtmanae\|Corynebacterium matruchotii, Methylobacterium radiotolerans\|Corynebacterium matruchotii, Mitsuokella multacida\|Corynebacterium matruchotii, Mobiluncus curtisii\|Corynebacterium matruchotii, Mycoplasma hominis\|Corynebacterium matruchotii, Neisseria mucosa\|Corynebacterium matruchotii, Odoribacter splanchnicus\|Corynebacterium matruchotii, Olsenella uli\|Corynebacterium matruchotii, Oribacterium sinus\|Corynebacterium matruchotii, Oxalobacter formigenes\|Corynebacterium matruchotii, Parabacteroides distasonis\|Corynebacterium matruchotii, Parabacteroides johnsonii\|Corynebacterium matruchotii, Parabacteroides merdae\|Corynebacterium matruchotii, Parvimonas micra\|Corynebacterium matruchotii, Pediococcus acidilactici\|Corynebacterium matruchotii, Pediococcus pentosaceus\|Corynebacterium matruchotii, Peptoniphilus duerdenii\|Corynebacterium matruchotii, Peptoniphilus harei\|Corynebacterium matruchotii, Peptoniphilus lacrimalis\|Corynebacterium matruchotii, Peptostreptococcus anaerobius\|Corynebacterium matruchotii, Peptostreptococcus stomatis\|Corynebacterium matruchotii, Porphyromonas asaccharolytica\|Corynebacterium matruchotii, Porphyromonas uenonis\|Corynebacterium matruchotii, Prevotella amnii\|Corynebacterium matruchotii, Prevotella bergensis\|Corynebacterium matruchotii, Prevotella bivia\|Corynebacterium matruchotii, Prevotella buccae\|Corynebacterium matruchotii, Prevotella buccalis\|Corynebacterium matruchotii, Prevotella copri\|Corynebacterium matruchotii, Prevotella disiens\|Corynebacterium matruchotii, Prevotella melaninogenica\|Corynebacterium matruchotii, Prevotella multiformis\|Corynebacterium matruchotii, Prevotella oralis\|Corynebacterium matruchotii, Prevotella oris\|Corynebacterium matruchotii, Prevotella salivae\|Corynebacterium matruchotii, Prevotella timonensis\|Corynebacterium matruchotii, Propionibacterium acnes\|Corynebacterium matruchotii, Propionibacterium freudenreichii\|Corynebacterium matruchotii, Proteus mirabilis\|Corynebacterium matruchotii, Proteus penneri\|Corynebacterium matruchotii, Pseudoflavonifractor capillosus\|Corynebacterium matruchotii, Pseudomonas aeruginosa\|Corynebacterium matruchotii, Pseudomonas fluorescens\|Corynebacterium matruchotii, Pseudomonas putida\|Corynebacterium matruchotii, Pseudoramibacter alactolyticus\|Corynebacterium matruchotii, Pyramidobacter piscolens\|Corynebacterium matruchotii, Rhodopseudomonas palustris\|Corynebacterium matruchotii, Roseburia intestinalis\|Corynebacterium matruchotii, Roseburia inulinivorans\|Corynebacterium matruchotii, Rothia dentocariosa\|Corynebacterium matruchotii, Rothia mucilaginosa\|Corynebacterium matruchotii, Ruminococcus albus\|Corynebacterium matruchotii, Ruminococcus bromii\|Corynebacterium matruchotii, Ruminococcus gnavus\|Corynebacterium matruchotii, Ruminococcus lactaris\|Corynebacterium matruchotii, Ruminococcus obeum\|Corynebacterium matruchotii, Ruminococcus torques\|Corynebacterium matruchotii, Selenomonas sputigena\|Corynebacterium matruchotii, Shigella boydii\|Corynebacterium matruchotii, Shigella dysenteriae\|Corynebacterium matruchotii, Shigella sonnei\|Corynebacterium matruchotii, Slackia exigua\|Corynebacterium matruchotii, Solobacterium moorei\|Corynebacterium matruchotii, Staphylococcus aureus\|Corynebacterium matruchotii, Staphylococcus epidermidis\|Corynebacterium matruchotii, Staphylococcus hominis\|Corynebacterium matruchotii, Staphylococcus saprophyticus\|Corynebacterium matruchotii, Staphylococcus warneri\|Corynebacterium matruchotii, Streptococcus agalactiae\|Corynebacterium matruchotii, Streptococcus anginosus\|Corynebacterium matruchotii, Streptococcus australis\|Corynebacterium matruchotii, Streptococcus bovis\|Corynebacterium matruchotii, Streptococcus cristatus\|Corynebacterium matruchotii, Streptococcus dysgalactiae\|Corynebacterium matruchotii, Streptococcus equinus\|Corynebacterium matruchotii, Streptococcus gordonii\|Corynebacterium matruchotii, Streptococcus infantarius\|Corynebacterium matruchotii, Streptococcus* |

TABLE 2-continued

| Table 2. Specific binary combinations of OTUs. Individual pairings are differentiated by "\|" and OTUs within a combination are differentiated by "," |
| --- |
| infantis\|Corynebacterium matruchotii, Streptococcus mitis\|Corynebacterium matruchotii, Streptococcus mutans\|Corynebacterium matruchotii, Streptococcus oralis\|Corynebacterium matruchotii, Streptococcus parasanguinis\|Corynebacterium matruchotii, Streptococcus peroris\|Corynebacterium matruchotii, Streptococcus pneumoniae\|Corynebacterium matruchotii, Streptococcus salivarius\|Corynebacterium matruchotii, Streptococcus sanguinis\|Corynebacterium matruchotii, Streptococcus thermophilus\|Corynebacterium matruchotii, Streptococcus vestibularis\|Corynebacterium matruchotii, Subdoligranulum variabile\|Corynebacterium matruchotii, Succinatimonas hippei\|Corynebacterium matruchotii, Sutterella wadsworthensis\|Corynebacterium matruchotii, Tropheryma whipplei\|Corynebacterium matruchotii, Veillonella atypica\|Corynebacterium matruchotii, Veillonella dispar\|Corynebacterium matruchotii, Veillonella parvula\|Corynebacterium matruchotii, Victivallis vadensis\|Cryptobacterium curtum, Cryptobacterium curtum\|Cryptobacterium curtum, Desulfovibrio desulfuricans\|Cryptobacterium curtum, Desulfovibrio piger\|Cryptobacterium curtum, Dialister invisus\|Cryptobacterium curtum, Dialister microaerophilus\|Cryptobacterium curtum, Dorea formicigenerans\|Cryptobacterium curtum, Dorea longicatena\|Cryptobacterium curtum, Eggerthella lenta\|Cryptobacterium curtum, Eikenella corrodens\|Cryptobacterium curtum, Enterobacter cancerogenus\|Cryptobacterium curtum, Enterobacter cloacae\|Cryptobacterium curtum, Enterococcus faecalis\|Cryptobacterium curtum, Enterococcus faecium\|Cryptobacterium curtum, Enterococcus gallinarum\|Cryptobacterium curtum, Erysipelotrichaceae bacterium 3_1_53\|Cryptobacterium curtum, Escherichia coli\|Cryptobacterium curtum, Escherichia fergusonii\|Cryptobacterium curtum, Ethanoligenens harbinense\|Cryptobacterium curtum, Eubacterium cellulosolvens\|Cryptobacterium curtum, Eubacterium eligens\|Cryptobacterium curtum, Eubacterium hallii\|Cryptobacterium curtum, Eubacterium limosum\|Cryptobacterium curtum, Eubacterium rectale\|Cryptobacterium curtum, Eubacterium siraeum\|Cryptobacterium curtum, Eubacterium ventriosum\|Cryptobacterium curtum, Faecalibacterium prausnitzii\|Cryptobacterium curtum, Finegoldia magna\|Cryptobacterium curtum, Fusobacterium gonidiaformans\|Cryptobacterium curtum, Fusobacterium mortiferum\|Cryptobacterium curtum, Fusobacterium nucleatum\|Cryptobacterium curtum, Fusobacterium varium\|Cryptobacterium curtum, Gardnerella vaginalis\|Cryptobacterium curtum, Gemella haemolysans\|Cryptobacterium curtum, Gemella morbillorum\|Cryptobacterium curtum, Gordonibacter pamelaeae\|Cryptobacterium curtum, Granulicatella adiacens\|Cryptobacterium curtum, Granulicatella elegans\|Cryptobacterium curtum, Haemophilus influenzae\|Cryptobacterium curtum, Haemophilus parainfluenzae\|Cryptobacterium curtum, Helicobacter pullorum\|Cryptobacterium curtum, Helicobacter pylori\|Cryptobacterium curtum, Holdemania filiformis\|Cryptobacterium curtum, Kingella oralis\|Cryptobacterium curtum, Klebsiella pneumoniae\|Cryptobacterium curtum, Klebsiella variicola\|Cryptobacterium curtum, Lachnospiraceae bacterium 5_1_57FAA\|Cryptobacterium curtum, Lactobacillus acidophilus\|Cryptobacterium curtum, Lactobacillus amylovorus\|Cryptobacterium curtum, Lactobacillus brevis\|Cryptobacterium curtum, Lactobacillus casei\|Cryptobacterium curtum, Lactobacillus crispatus\|Cryptobacterium curtum, Lactobacillus delbrueckii\|Cryptobacterium curtum, Lactobacillus fermentum\|Cryptobacterium curtum, Lactobacillus gasseri\|Cryptobacterium curtum, Lactobacillus iners\|Cryptobacterium curtum, Lactobacillus jensenii\|Cryptobacterium curtum, Lactobacillus johnsonii\|Cryptobacterium curtum, Lactobacillus paracasei\|Cryptobacterium curtum, Lactobacillus plantarum\|Cryptobacterium curtum, Lactobacillus reuteri\|Cryptobacterium curtum, Lactobacillus rhamnosus\|Cryptobacterium curtum, Lactobacillus ruminis\|Cryptobacterium curtum, Lactobacillus sakei\|Cryptobacterium curtum, Lactobacillus salivarius\|Cryptobacterium curtum, Lactococcus lactis\|Cryptobacterium curtum, Lautropia mirabilis\|Cryptobacterium curtum, Leuconostoc citreum\|Cryptobacterium curtum, Leuconostoc gasicomitatum\|Cryptobacterium curtum, Leuconostoc mesenteroides\|Cryptobacterium curtum, Listeria monocytogenes\|Cryptobacterium curtum, Marvinbryantia formatexigens\|Cryptobacterium curtum, Megamonas hypermegale\|Cryptobacterium curtum, Megasphaera micronuciformis\|Cryptobacterium curtum, Methanobrevibacter smithii\|Cryptobacterium curtum, Methanosphaera stadtmanae\|Cryptobacterium curtum, Methylobacterium radiotolerans\|Cryptobacterium curtum, Mitsuokella multacida\|Cryptobacterium curtum, Mobiluncus curtisii\|Cryptobacterium curtum, Mycoplasma hominis\|Cryptobacterium curtum, Neisseria mucosa\|Cryptobacterium curtum, Odoribacter splanchnicus\|Cryptobacterium curtum, Olsenella uli\|Cryptobacterium curtum, Oribacterium sinus\|Cryptobacterium curtum, Oxalobacter formigenes\|Cryptobacterium curtum, Parabacteroides distasonis\|Cryptobacterium curtum, Parabacteroides johnsonii\|Cryptobacterium curtum, Parabacteroides merdae\|Cryptobacterium curtum, Parvimonas micra\|Cryptobacterium curtum, Pediococcus acidilactici\|Cryptobacterium curtum, Pediococcus pentosaceus\|Cryptobacterium curtum, Peptoniphilus duerdenii\|Cryptobacterium curtum, Peptoniphilus harei\|Cryptobacterium curtum, Peptoniphilus lacrimalis\|Cryptobacterium curtum, Peptostreptococcus anaerobius\|Cryptobacterium curtum, Peptostreptococcus stomatis\|Cryptobacterium curtum, Porphyromonas asaccharolytica\|Cryptobacterium curtum, Porphyromonas uenonis\|Cryptobacterium curtum, Prevotella amnii\|Cryptobacterium curtum, Prevotella bergensis\|Cryptobacterium curtum, Prevotella bivia\|Cryptobacterium curtum, Prevotella buccae\|Cryptobacterium curtum, Prevotella buccalis\|Cryptobacterium curtum, Prevotella copri\|Cryptobacterium curtum, Prevotella disiens\|Cryptobacterium curtum, Prevotella melaninogenica\|Cryptobacterium curtum, Prevotella multiformis\|Cryptobacterium curtum, Prevotella oralis\|Cryptobacterium curtum, Prevotella oris\|Cryptobacterium curtum, Prevotella salivae\|Cryptobacterium curtum, Prevotella timonensis\|Cryptobacterium curtum, Propionibacterium acnes\|Cryptobacterium curtum, Propionibacterium freudenreichii\|Cryptobacterium curtum, Proteus mirabilis\|Cryptobacterium curtum, Proteus penneri\|Cryptobacterium curtum, Pseudoflavonifractor capillosus\|Cryptobacterium curtum, Pseudomonas aeruginosa\|Cryptobacterium curtum, Pseudomonas fluorescens\|Cryptobacterium curtum, Pseudomonas putida\|Cryptobacterium curtum, Pseudoramibacter alactolyticus\|Cryptobacterium curtum, Pyramidobacter piscolens\|Cryptobacterium curtum, Rhodopseudomonas palustris\|Cryptobacterium curtum, Roseburia intestinalis\|Cryptobacterium curtum, Roseburia inulinivorans\|Cryptobacterium curtum, Rothia dentocariosa\|Cryptobacterium curtum, Rothia mucilaginosa\|Cryptobacterium curtum, Ruminococcus albus\|Cryptobacterium curtum, Ruminococcus bromii\|Cryptobacterium curtum, Ruminococcus gnavus\|Cryptobacterium curtum, Ruminococcus lactaris\|Cryptobacterium curtum, Ruminococcus obeum\|Cryptobacterium curtum, Ruminococcus torques\|Cryptobacterium curtum, Selenomonas sputigena\|Cryptobacterium curtum, Shigella boydii\|Cryptobacterium curtum, Shigella dysenteriae\|Cryptobacterium curtum, Shigella sonnei\|Cryptobacterium curtum, Slackia exigua\|Cryptobacterium curtum, Solobacterium moorei\|Cryptobacterium curtum, Staphylococcus aureus\|Cryptobacterium curtum, Staphylococcus epidermidis\|Cryptobacterium curtum, Staphylococcus hominis\|Cryptobacterium curtum, Staphylococcus saprophyticus\|Cryptobacterium curtum, Staphylococcus warneri\|Cryptobacterium curtum, Streptococcus agalactiae\|Cryptobacterium curtum, Streptococcus anginosus\|Cryptobacterium curtum, Streptococcus australis\|Cryptobacterium curtum, Streptococcus bovis\|Cryptobacterium curtum, Streptococcus cristatus\|Cryptobacterium curtum, Streptococcus dysgalactiae\|Cryptobacterium curtum, Streptococcus equinus\|Cryptobacterium curtum, Streptococcus gordonii\|Cryptobacterium curtum, Streptococcus infantarius\|Cryptobacterium curtum, Streptococcus infantis\|Cryptobacterium curtum, Streptococcus mitis\|Cryptobacterium curtum, Streptococcus mutans\|Cryptobacterium curtum, Streptococcus oralis\|Cryptobacterium curtum, Streptococcus parasanguinis\|Cryptobacterium curtum, Streptococcus peroris\|Cryptobacterium curtum, Streptococcus pneumoniae\|Cryptobacterium curtum, Streptococcus salivarius\|Cryptobacterium curtum, Streptococcus sanguinis\|Cryptobacterium curtum, Streptococcus thermophilus\|Cryptobacterium curtum, Streptococcus vestibularis\|Cryptobacterium curtum, Subdoligranulum variabile\|Cryptobacterium curtum, Succinatimonas hippei\|Cryptobacterium curtum, Sutterella wadsworthensis\|Cryptobacterium curtum, Tropheryma whipplei\|Cryptobacterium curtum, Veillonella atypica\|Cryptobacterium curtum, Veillonella dispar\|Cryptobacterium curtum, Veillonella parvula\|Cryptobacterium curtum, Victivallis vadensis\|Desulfovibrio desulfuricans, Desulfovibrio desulfuricans\|Desulfovibrio desulfuricans, Desulfovibrio piger\|Desulfovibrio desulfuricans, Dialister invisus\|Desulfovibrio desulfuricans, Dialister microaerophilus\|Desulfovibrio desulfuricans, Dorea formicigenerans\|Desulfovibrio desulfuricans, Dorea longicatena\|Desulfovibrio desulfuricans, Eggerthella lenta\|Desulfovibrio desulfuricans, Eikenella corrodens\|Desulfovibrio desulfuricans, Enterobacter cancerogenus\|Desulfovibrio desulfuricans, Enterobacter cloacae\|Desulfovibrio desulfuricans, Enterococcus faecalis\|Desulfovibrio desulfuricans, Enterococcus faecium\|Desulfovibrio desulfuricans, Enterococcus gallinarum\|Desulfovibrio desulfuricans, Erysipelotrichaceae bacterium 3_1_53\|Desulfovibrio |

TABLE 2-continued

| Table 2. Specific binary combinations of OTUs. Individual pairings are differentiated by "\|" and OTUs within a combination are differentiated by "," |
| --- |
| *desulfuricans, Escherichia coli\|Desulfovibrio desulfuricans, Escherichia fergusonii\|Desulfovibrio desulfuricans, Ethanoligenens harbinense\|Desulfovibrio desulfuricans, Eubacterium cellulosolvens\|Desulfovibrio desulfuricans, Eubacterium eligens\|Desulfovibrio desulfuricans, Eubacterium hallii\|Desulfovibrio desulfuricans, Eubacterium limosum\|Desulfovibrio desulfuricans, Eubacterium rectale\|Desulfovibrio desulfuricans, Eubacterium siraeum\|Desulfovibrio desulfuricans, Eubacterium ventriosum\|Desulfovibrio desulfuricans, Faecalibacterium prausnitzii\|Desulfovibrio desulfuricans, Finegoldia magna\|Desulfovibrio desulfuricans, Fusobacterium gonidiaformans\|Desulfovibrio desulfuricans, Fusobacterium mortiferum\|Desulfovibrio desulfuricans, Fusobacterium nucleatum\|Desulfovibrio desulfuricans, Fusobacterium varium\|Desulfovibrio desulfuricans, Gardnerella vaginalis\|Desulfovibrio desulfuricans, Gemella haemolysans\|Desulfovibrio desulfuricans, Gemella morbillorum\|Desulfovibrio desulfuricans, Gordonibacter pamelaeae\|Desulfovibrio desulfuricans, Granulicatella adiacens\|Desulfovibrio desulfuricans, Granulicatella elegans\|Desulfovibrio desulfuricans, Haemophilus influenzae\|Desulfovibrio desulfuricans, Haemophilus parainfluenzae\|Desulfovibrio desulfuricans, Helicobacter pullorum\|Desulfovibrio desulfuricans, Helicobacter pylori\|Desulfovibrio desulfuricans, Holdemania filiformis\|Desulfovibrio desulfuricans, Kingella oralis\|Desulfovibrio desulfuricans, Klebsiella pneumoniae\|Desulfovibrio desulfuricans, Klebsiella variicola\|Desulfovibrio desulfuricans, Lachnospiraceae bacterium* 5_1_57FAA\|*Desulfovibrio desulfuricans, Lactobacillus acidophilus\|Desulfovibrio desulfuricans, Lactobacillus amylovorus\|Desulfovibrio desulfuricans, Lactobacillus brevis\|Desulfovibrio desulfuricans, Lactobacillus casei\|Desulfovibrio desulfuricans, Lactobacillus crispatus\|Desulfovibrio desulfuricans, Lactobacillus delbrueckii\|Desulfovibrio desulfuricans, Lactobacillus fermentum\|Desulfovibrio desulfuricans, Lactobacillus gasseri\|Desulfovibrio desulfuricans, Lactobacillus iners\|Desulfovibrio desulfuricans, Lactobacillus jensenii\|Desulfovibrio desulfuricans, Lactobacillus johnsonii\|Desulfovibrio desulfuricans, Lactobacillus paracasei\|Desulfovibrio desulfuricans, Lactobacillus plantarum\|Desulfovibrio desulfuricans, Lactobacillus reuteri\|Desulfovibrio desulfuricans, Lactobacillus rhamnosus\|Desulfovibrio desulfuricans, Lactobacillus ruminis\|Desulfovibrio desulfuricans, Lactobacillus sakei\|Desulfovibrio desulfuricans, Lactobacillus salivarius\|Desulfovibrio desulfuricans, Lactococcus lactis\|Desulfovibrio desulfuricans, Lautropia mirabilis\|Desulfovibrio desulfuricans, Leuconostoc citreum\|Desulfovibrio desulfuricans, Leuconostoc gasicomitatum\|Desulfovibrio desulfuricans, Leuconostoc mesenteroides\|Desulfovibrio desulfuricans, Listeria monocytogenes\|Desulfovibrio desulfuricans, Marvinbryantia formatexigens\|Desulfovibrio desulfuricans, Megamonas hypermegale\|Desulfovibrio desulfuricans, Megasphaera micronuciformis\|Desulfovibrio desulfuricans, Methanobrevibacter smithii\|Desulfovibrio desulfuricans, Methanosphaera stadtmanae\|Desulfovibrio desulfuricans, Methylobacterium radiotolerans\|Desulfovibrio desulfuricans, Mitsuokella multacida\|Desulfovibrio desulfuricans, Mobiluncus curtisii\|Desulfovibrio desulfuricans, Mycoplasma hominis\|Desulfovibrio desulfuricans, Neisseria mucosa\|Desulfovibrio desulfuricans, Odoribacter splanchnicus\|Desulfovibrio desulfuricans, Olsenella uli\|Desulfovibrio desulfuricans, Oribacterium sinus\|Desulfovibrio desulfuricans, Oxalobacter formigenes\|Desulfovibrio desulfuricans, Parabacteroides distasonis\|Desulfovibrio desulfuricans, Parabacteroides johnsonii\|Desulfovibrio desulfuricans, Parabacteroides merdae\|Desulfovibrio desulfuricans, Parvimonas micra\|Desulfovibrio desulfuricans, Pediococcus acidilactici\|Desulfovibrio desulfuricans, Pediococcus pentosaceus\|Desulfovibrio desulfuricans, Peptoniphilus duerdenii\|Desulfovibrio desulfuricans, Peptoniphilus harei\|Desulfovibrio desulfuricans, Peptoniphilus lacrimalis\|Desulfovibrio desulfuricans, Peptostreptococcus anaerobius\|Desulfovibrio desulfuricans, Peptostreptococcus stomatis\|Desulfovibrio desulfuricans, Porphyromonas asaccharolytica\|Desulfovibrio desulfuricans, Porphyromonas uenonis\|Desulfovibrio desulfuricans, Prevotella amnii\|Desulfovibrio desulfuricans, Prevotella bergensis\|Desulfovibrio desulfuricans, Prevotella bivia\|Desulfovibrio desulfuricans, Prevotella buccae\|Desulfovibrio desulfuricans, Prevotella buccalis\|Desulfovibrio desulfuricans, Prevotella copri\|Desulfovibrio desulfuricans, Prevotella disiens\|Desulfovibrio desulfuricans, Prevotella melaninogenica\|Desulfovibrio desulfuricans, Prevotella multiformis\|Desulfovibrio desulfuricans, Prevotella oralis\|Desulfovibrio desulfuricans, Prevotella oris\|Desulfovibrio desulfuricans, Prevotella salivae\|Desulfovibrio desulfuricans, Prevotella timonensis\|Desulfovibrio desulfuricans, Propionibacterium acnes\|Desulfovibrio desulfuricans, Propionibacterium freudenreichii\|Desulfovibrio desulfuricans, Proteus mirabilis\|Desulfovibrio desulfuricans, Proteus penneri\|Desulfovibrio desulfuricans, Pseudoflavonifractor capillosus\|Desulfovibrio desulfuricans, Pseudomonas aeruginosa\|Desulfovibrio desulfuricans, Pseudomonas fluorescens\|Desulfovibrio desulfuricans, Pseudomonas putida\|Desulfovibrio desulfuricans, Pseudoramibacter alactolyticus\|Desulfovibrio desulfuricans, Pyramidobacter piscolens\|Desulfovibrio desulfuricans, Rhodopseudomonas palustris\|Desulfovibrio desulfuricans, Roseburia intestinalis\|Desulfovibrio desulfuricans, Roseburia inulinivorans\|Desulfovibrio desulfuricans, Rothia dentocariosa\|Desulfovibrio desulfuricans, Rothia mucilaginosa\|Desulfovibrio desulfuricans, Ruminococcus albus\|Desulfovibrio desulfuricans, Ruminococcus bromii\|Desulfovibrio desulfuricans, Ruminococcus gnavus\|Desulfovibrio desulfuricans, Ruminococcus lactaris\|Desulfovibrio desulfuricans, Ruminococcus obeum\|Desulfovibrio desulfuricans, Ruminococcus torques\|Desulfovibrio desulfuricans, Selenomonas sputigena\|Desulfovibrio desulfuricans, Shigella boydii\|Desulfovibrio desulfuricans, Shigella dysenteriae\|Desulfovibrio desulfuricans, Shigella sonnei\|Desulfovibrio desulfuricans, Slackia exigua\|Desulfovibrio desulfuricans, Solobacterium moorei\|Desulfovibrio desulfuricans, Staphylococcus aureus\|Desulfovibrio desulfuricans, Staphylococcus epidermidis\|Desulfovibrio desulfuricans, Staphylococcus hominis\|Desulfovibrio desulfuricans, Staphylococcus saprophyticus\|Desulfovibrio desulfuricans, Staphylococcus warneri\|Desulfovibrio desulfuricans, Streptococcus agalactiae\|Desulfovibrio desulfuricans, Streptococcus anginosus\|Desulfovibrio desulfuricans, Streptococcus australis\|Desulfovibrio desulfuricans, Streptococcus bovis\|Desulfovibrio desulfuricans, Streptococcus cristatus\|Desulfovibrio desulfuricans, Streptococcus dysgalactiae\|Desulfovibrio desulfuricans, Streptococcus equinus\|Desulfovibrio desulfuricans, Streptococcus gordonii\|Desulfovibrio desulfuricans, Streptococcus infantarius\|Desulfovibrio desulfuricans, Streptococcus infantis\|Desulfovibrio desulfuricans, Streptococcus mitis\|Desulfovibrio desulfuricans, Streptococcus mutans\|Desulfovibrio desulfuricans, Streptococcus oralis\|Desulfovibrio desulfuricans, Streptococcus parasanguinis\|Desulfovibrio desulfuricans, Streptococcus peroris\|Desulfovibrio desulfuricans, Streptococcus pneumoniae\|Desulfovibrio desulfuricans, Streptococcus salivarius\|Desulfovibrio desulfuricans, Streptococcus sanguinis\|Desulfovibrio desulfuricans, Streptococcus thermophilus\|Desulfovibrio desulfuricans, Streptococcus vestibularis\|Desulfovibrio desulfuricans, Subdoligranulum variabile\|Desulfovibrio desulfuricans, Succinatimonas hippei\|Desulfovibrio desulfuricans, Sutterella wadsworthensis\|Desulfovibrio desulfuricans, Tropheryma whipplei\|Desulfovibrio desulfuricans, Veillonella atypica\|Desulfovibrio desulfuricans, Veillonella dispar\|Desulfovibrio desulfuricans, Veillonella parvula\|Desulfovibrio desulfuricans, Victivallis vadensis\|Desulfovibrio piger, Desulfovibrio piger\|Desulfovibrio piger, Dialister invisus\|Desulfovibrio piger, Dialister microaerophilus\|Desulfovibrio piger, Dorea formicigenerans\|Desulfovibrio piger, Dorea longicatena\|Desulfovibrio piger, Eggerthella lenta\|Desulfovibrio piger, Eikenella corrodens\|Desulfovibrio piger, Enterobacter cancerogenus\|Desulfovibrio piger, Enterobacter cloacae\|Desulfovibrio piger, Enterococcus faecalis\|Desulfovibrio piger, Enterococcus faecium\|Desulfovibrio piger, Enterococcus gallinarum\|Desulfovibrio piger, Erysipelotrichaceae bacterium* 3_1_53\|*Desulfovibrio piger, Escherichia coli\|Desulfovibrio piger, Escherichia fergusonii\|Desulfovibrio piger, Ethanoligenens harbinense\|Desulfovibrio piger, Eubacterium cellulosolvens\|Desulfovibrio piger, Eubacterium eligens\|Desulfovibrio piger, Eubacterium hallii\|Desulfovibrio piger, Eubacterium limosum\|Desulfovibrio piger, Eubacterium rectale\|Desulfovibrio piger, Eubacterium siraeum\|Desulfovibrio piger, Eubacterium ventriosum\|Desulfovibrio piger, Faecalibacterium prausnitzii\|Desulfovibrio piger, Finegoldia magna\|Desulfovibrio piger, Fusobacterium gonidiaformans\|Desulfovibrio piger, Fusobacterium mortiferum\|Desulfovibrio piger, Fusobacterium nucleatum\|Desulfovibrio piger, Fusobacterium varium\|Desulfovibrio piger, Gardnerella vaginalis\|Desulfovibrio piger, Gemella haemolysans\|Desulfovibrio piger, Gemella morbillorum\|Desulfovibrio piger, Gordonibacter pamelaeae\|Desulfovibrio piger, Granulicatella adiacens\|Desulfovibrio piger, Granulicatella elegans\|Desulfovibrio piger, Haemophilus influenzae\|Desulfovibrio piger, Haemophilus parainfluenzae\|Desulfovibrio piger, Helicobacter pullorum\|Desulfovibrio piger, Helicobacter pylori\|Desulfovibrio piger, Holdemania filiformis\|Desulfovibrio piger, Kingella oralis\|Desulfovibrio piger, Klebsiella pneumoniae\|Desulfovibrio piger, Klebsiella variicola\|Desulfovibrio piger, Lachnospiraceae bacterium* 5_1_57FAA\|*Desulfovibrio piger, Lactobacillus acidophilus\|Desulfovibrio piger, Lactobacillus amylovorus\|Desulfovibrio piger, Lactobacillus brevis\|Desulfovibrio piger, Lactobacillus casei\|Desulfovibrio piger, Lactobacillus crispatus\|Desulfovibrio* |

TABLE 2-continued

| Table 2. Specific binary combinations of OTUs. Individual pairings are differentiated by "\|" and OTUs within a combination are differentiated by "," |
|---|
| piger, Lactobacillus delbrueckii\|Desulfovibrio piger, Lactobacillus fermentum\|Desulfovibrio piger, Lactobacillus gasseri\|Desulfovibrio piger, Lactobacillus iners\|Desulfovibrio piger, Lactobacillus jensenii\|Desulfovibrio piger, Lactobacillus johnsonii\|Desulfovibrio piger, Lactobacillus paracasei\|Desulfovibrio piger, Lactobacillus plantarum\|Desulfovibrio piger, Lactobacillus reuteri\|Desulfovibrio piger, Lactobacillus rhamnosus\|Desulfovibrio piger, Lactobacillus ruminis\|Desulfovibrio piger, Lactobacillus sakei\|Desulfovibrio piger, Lactobacillus salivarius\|Desulfovibrio piger, Lactococcus lactis\|Desulfovibrio piger, Lautropia mirabilis\|Desulfovibrio piger, Leuconostoc citreum\|Desulfovibrio piger, Leuconostoc gasicomitatum\|Desulfovibrio piger, Leuconostoc mesenteroides\|Desulfovibrio piger, Listeria monocytogenes\|Desulfovibrio piger, Marvinbryantia formatexigens\|Desulfovibrio piger, Megamonas hypermegale\|Desulfovibrio piger, Megasphaera micronuciformis\|Desulfovibrio piger, Methanobrevibacter smithii\|Desulfovibrio piger, Methanosphaera stadtmanae\|Desulfovibrio piger, Methylobacterium radiotolerans\|Desulfovibrio piger, Mitsuokella multacida\|Desulfovibrio piger, Mobiluncus curtisii\|Desulfovibrio piger, Mycoplasma hominis\|Desulfovibrio piger, Neisseria mucosa\|Desulfovibrio piger, Odoribacter splanchnicus\|Desulfovibrio piger, Olsenella uli\|Desulfovibrio piger, Oribacterium sinus\|Desulfovibrio piger, Oxalobacter formigenes\|Desulfovibrio piger, Parabacteroides distasonis\|Desulfovibrio piger, Parabacteroides johnsonii\|Desulfovibrio piger, Parabacteroides merdae\|Desulfovibrio piger, Parvimonas micra\|Desulfovibrio piger, Pediococcus acidilactici\|Desulfovibrio piger, Pediococcus pentosaceus\|Desulfovibrio piger, Peptoniphilus duerdenii\|Desulfovibrio piger, Peptoniphilus harei\|Desulfovibrio piger, Peptoniphilus lacrimalis\|Desulfovibrio piger, Peptostreptococcus anaerobius\|Desulfovibrio piger, Peptostreptococcus stomatis\|Desulfovibrio piger, Porphyromonas asaccharolytica\|Desulfovibrio piger, Porphyromonas uenonis\|Desulfovibrio piger, Prevotella amnii\|Desulfovibrio piger, Prevotella bergensis\|Desulfovibrio piger, Prevotella bivia\|Desulfovibrio piger, Prevotella buccae\|Desulfovibrio piger, Prevotella buccalis\|Desulfovibrio piger, Prevotella copri\|Desulfovibrio piger, Prevotella disiens\|Desulfovibrio piger, Prevotella melaninogenica\|Desulfovibrio piger, Prevotella multiformis\|Desulfovibrio piger, Prevotella oralis\|Desulfovibrio piger, Prevotella oris\|Desulfovibrio piger, Prevotella salivae\|Desulfovibrio piger, Prevotella timonensis\|Desulfovibrio piger, Propionibacterium acnes\|Desulfovibrio piger, Propionibacterium freudenreichii\|Desulfovibrio piger, Proteus mirabilis\|Desulfovibrio piger, Proteus penneri\|Desulfovibrio piger, Pseudoflavonifractor capillosus\|Desulfovibrio piger, Pseudomonas aeruginosa\|Desulfovibrio piger, Pseudomonas fluorescens\|Desulfovibrio piger, Pseudomonas putida\|Desulfovibrio piger, Pseudoramibacter alactolyticus\|Desulfovibrio piger, Pyramidobacter piscolens\|Desulfovibrio piger, Rhodopseudomonas palustris\|Desulfovibrio piger, Roseburia intestinalis\|Desulfovibrio piger, Roseburia inulinivorans\|Desulfovibrio piger, Rothia dentocariosa\|Desulfovibrio piger, Rothia mucilaginosa\|Desulfovibrio piger, Ruminococcus albus\|Desulfovibrio piger, Ruminococcus bromii\|Desulfovibrio piger, Ruminococcus gnavus\|Desulfovibrio piger, Ruminococcus lactaris\|Desulfovibrio piger, Ruminococcus obeum\|Desulfovibrio piger, Ruminococcus torques\|Desulfovibrio piger, Selenomonas sputigena\|Desulfovibrio piger, Shigella boydii\|Desulfovibrio piger, Shigella dysenteriae\|Desulfovibrio piger, Shigella sonnei\|Desulfovibrio piger, Slackia exigua\|Desulfovibrio piger, Solobacterium moorei\|Desulfovibrio piger, Staphylococcus aureus\|Desulfovibrio piger, Staphylococcus epidermidis\|Desulfovibrio piger, Staphylococcus hominis\|Desulfovibrio piger, Staphylococcus saprophyticus\|Desulfovibrio piger, Staphylococcus warneri\|Desulfovibrio piger, Streptococcus agalactiae\|Desulfovibrio piger, Streptococcus anginosus\|Desulfovibrio piger, Streptococcus australis\|Desulfovibrio piger, Streptococcus bovis\|Desulfovibrio piger, Streptococcus cristatus\|Desulfovibrio piger, Streptococcus dysgalactiae\|Desulfovibrio piger, Streptococcus equinus\|Desulfovibrio piger, Streptococcus gordonii\|Desulfovibrio piger, Streptococcus infantarius\|Desulfovibrio piger, Streptococcus infantis\|Desulfovibrio piger, Streptococcus mitis\|Desulfovibrio piger, Streptococcus mutans\|Desulfovibrio piger, Streptococcus oralis\|Desulfovibrio piger, Streptococcus parasanguinis\|Desulfovibrio piger, Streptococcus peroris\|Desulfovibrio piger, Streptococcus pneumoniae\|Desulfovibrio piger, Streptococcus salivarius\|Desulfovibrio piger, Streptococcus sanguinis\|Desulfovibrio piger, Streptococcus thermophilus\|Desulfovibrio piger, Streptococcus vestibularis\|Desulfovibrio piger, Subdoligranulum variabile\|Desulfovibrio piger, Succinatimonas hippei\|Desulfovibrio piger, Sutterella wadsworthensis\|Desulfovibrio piger, Tropheryma whipplei\|Desulfovibrio piger, Veillonella atypica\|Desulfovibrio piger, Veillonella dispar\|Desulfovibrio piger, Veillonella parvula\|Desulfovibrio piger, Victivallis vadensis\|Dialister invisus, Dialister invisus\|Dialister invisus, Dialister microaerophilus\|Dialister invisus, Dorea formicigenerans\|Dialister invisus, Dorea longicatena\|Dialister invisus, Eggerthella lenta\|Dialister invisus, Eikenella corrodens\|Dialister invisus, Enterobacter cancerogenus\|Dialister invisus, Enterobacter cloacae\|Dialister invisus, Enterococcus faecalis\|Dialister invisus, Enterococcus faecium\|Dialister invisus, Enterococcus gallinarum\|Dialister invisus, Erysipelotrichaceae bacterium 3_1_53\|Dialister invisus, Escherichia coli\|Dialister invisus, Escherichia fergusonii\|Dialister invisus, Ethanoligenens harbinense\|Dialister invisus, Eubacterium cellulosolvens\|Dialister invisus, Eubacterium eligens\|Dialister invisus, Eubacterium hallii\|Dialister invisus, Eubacterium limosum\|Dialister invisus, Eubacterium rectale\|Dialister invisus, Eubacterium siraeum\|Dialister invisus, Eubacterium ventriosum\|Dialister invisus, Faecalibacterium prausnitzii\|Dialister invisus, Finegoldia magna\|Dialister invisus, Fusobacterium gonidiaformans\|Dialister invisus, Fusobacterium mortiferum\|Dialister invisus, Fusobacterium nucleatum\|Dialister invisus, Fusobacterium varium\|Dialister invisus, Gardnerella vaginalis\|Dialister invisus, Gemella haemolysans\|Dialister invisus, Gemella morbillorum\|Dialister invisus, Gordonibacter pamelaeae\|Dialister invisus, Granulicatella adiacens\|Dialister invisus, Granulicatella elegans\|Dialister invisus, Haemophilus influenzae\|Dialister invisus, Haemophilus parainfluenzae\|Dialister invisus, Helicobacter pullorum\|Dialister invisus, Helicobacter pylori\|Dialister invisus, Holdemania filiformis\|Dialister invisus, Kingella oralis\|Dialister invisus, Klebsiella pneumoniae\|Dialister invisus, Klebsiella variicola\|Dialister invisus, Lachnospiraceae bacterium 5_1_57FAA\|Dialister invisus, Lactobacillus acidophilus\|Dialister invisus, Lactobacillus amylovorus\|Dialister invisus, Lactobacillus brevis\|Dialister invisus, Lactobacillus casei\|Dialister invisus, Lactobacillus crispatus\|Dialister invisus, Lactobacillus delbrueckii\|Dialister invisus, Lactobacillus fermentum\|Dialister invisus, Lactobacillus gasseri\|Dialister invisus, Lactobacillus iners\|Dialister invisus, Lactobacillus jensenii\|Dialister invisus, Lactobacillus johnsonii\|Dialister invisus, Lactobacillus paracasei\|Dialister invisus, Lactobacillus plantarum\|Dialister invisus, Lactobacillus reuteri\|Dialister invisus, Lactobacillus rhamnosus\|Dialister invisus, Lactobacillus ruminis\|Dialister invisus, Lactobacillus sakei\|Dialister invisus, Lactobacillus salivarius\|Dialister invisus, Lactococcus lactis\|Dialister invisus, Lautropia mirabilis\|Dialister invisus, Leuconostoc citreum\|Dialister invisus, Leuconostoc gasicomitatum\|Dialister invisus, Leuconostoc mesenteroides\|Dialister invisus, Listeria monocytogenes\|Dialister invisus, Marvinbryantia formatexigens\|Dialister invisus, Megamonas hypermegale\|Dialister invisus, Megasphaera micronuciformis\|Dialister invisus, Methanobrevibacter smithii\|Dialister invisus, Methanosphaera stadtmanae\|Dialister invisus, Methylobacterium radiotolerans\|Dialister invisus, Mitsuokella multacida\|Dialister invisus, Mobiluncus curtisii\|Dialister invisus, Mycoplasma hominis\|Dialister invisus, Neisseria mucosa\|Dialister invisus, Odoribacter splanchnicus\|Dialister invisus, Olsenella uli\|Dialister invisus, Oribacterium sinus\|Dialister invisus, Oxalobacter formigenes\|Dialister invisus, Parabacteroides distasonis\|Dialister invisus, Parabacteroides johnsonii\|Dialister invisus, Parabacteroides merdae\|Dialister invisus, Parvimonas micra\|Dialister invisus, Pediococcus acidilactici\|Dialister invisus, Pediococcus pentosaceus\|Dialister invisus, Peptoniphilus duerdenii\|Dialister invisus, Peptoniphilus harei\|Dialister invisus, Peptoniphilus lacrimalis\|Dialister invisus, Peptostreptococcus anaerobius\|Dialister invisus, Peptostreptococcus stomatis\|Dialister invisus, Porphyromonas asaccharolytica\|Dialister invisus, Porphyromonas uenonis\|Dialister invisus, Prevotella amnii\|Dialister invisus, Prevotella bergensis\|Dialister invisus, Prevotella bivia\|Dialister invisus, Prevotella buccae\|Dialister invisus, Prevotella buccalis\|Dialister invisus, Prevotella copri\|Dialister invisus, Prevotella disiens\|Dialister invisus, Prevotella melaninogenica\|Dialister invisus, Prevotella multiformis\|Dialister invisus, Prevotella oralis\|Dialister invisus, Prevotella oris\|Dialister invisus, Prevotella salivae\|Dialister invisus, Prevotella timonensis\|Dialister invisus, Propionibacterium acnes\|Dialister invisus, Propionibacterium freudenreichii\|Dialister invisus, Proteus mirabilis\|Dialister invisus, Proteus penneri\|Dialister invisus, Pseudoflavonifractor capillosus\|Dialister invisus, Pseudomonas aeruginosa\|Dialister invisus, Pseudomonas fluorescens\|Dialister invisus, Pseudomonas putida\|Dialister invisus, Pseudoramibacter alactolyticus\|Dialister invisus, Pyramidobacter piscolens\|Dialister invisus, Rhodopseudomonas palustris\|Dialister invisus, Roseburia intestinalis\|Dialister invisus, Roseburia inulinivorans\|Dialister invisus, Rothia dentocariosa\|Dialister invisus, Rothia mucilaginosa\|Dialister invisus, Ruminococcus albus\|Dialister invisus, Ruminococcus bromii\|Dialister |

TABLE 2-continued

| Table 2. Specific binary combinations of OTUs. Individual pairings are differentiated by "\|" and OTUs within a combination are differentiated by "," |
| --- |
| *invisus, Ruminococcus gnavus\|Dialister invisus, Ruminococcus lactaris\|Dialister invisus, Ruminococcus obeum\|Dialister invisus, Ruminococcus torques\|Dialister invisus, Selenomonas sputigena\|Dialister invisus, Shigella boydii\|Dialister invisus, Shigella dysenteriae\|Dialister invisus, Shigella sonnei\|Dialister invisus, Slackia exigua\|Dialister invisus, Solobacterium moorei\|Dialister invisus, Staphylococcus aureus\|Dialister invisus, Staphylococcus epidermidis\|Dialister invisus, Staphylococcus hominis\|Dialister invisus, Staphylococcus saprophyticus\|Dialister invisus, Staphylococcus warneri\|Dialister invisus, Streptococcus agalactiae\|Dialister invisus, Streptococcus anginosus\|Dialister invisus, Streptococcus australis\|Dialister invisus, Streptococcus bovis\|Dialister invisus, Streptococcus cristatus\|Dialister invisus, Streptococcus dysgalactiae\|Dialister invisus, Streptococcus equinus\|Dialister invisus, Streptococcus gordonii\|Dialister invisus, Streptococcus infantarius\|Dialister invisus, Streptococcus infantis\|Dialister invisus, Streptococcus mitis\|Dialister invisus, Streptococcus mutans\|Dialister invisus, Streptococcus oralis\|Dialister invisus, Streptococcus parasanguinis\|Dialister invisus, Streptococcus peroris\|Dialister invisus, Streptococcus pneumoniae\|Dialister invisus, Streptococcus salivarius\|Dialister invisus, Streptococcus sanguinis\|Dialister invisus, Streptococcus thermophilus\|Dialister invisus, Streptococcus vestibularis\|Dialister invisus, Subdoligranulum variabile\|Dialister invisus, Succinatimonas hippei\|Dialister invisus, Sutterella wadsworthensis\|Dialister invisus, Tropheryma whipplei\|Dialister invisus, Veillonella atypica\|Dialister invisus, Veillonella dispar\|Dialister invisus, Veillonella parvula\|Dialister invisus, Victivallis vadensis\|Dialister microaerophilus, Dialister microaerophilus\|Dialister microaerophilus, Dorea formicigenerans\|Dialister microaerophilus, Dorea longicatena\|Dialister microaerophilus, Eggerthella lenta\|Dialister microaerophilus, Eikenella corrodens\|Dialister microaerophilus, Enterobacter cancerogenus\|Dialister microaerophilus, Enterobacter cloacae\|Dialister microaerophilus, Enterococcus faecalis\|Dialister microaerophilus, Enterococcus faecium\|Dialister microaerophilus, Enterococcus gallinarum\|Dialister microaerophilus, Erysipelotrichaceae bacterium* 3_1_53\|*Dialister microaerophilus, Escherichia coli\|Dialister microaerophilus, Escherichia fergusonii\|Dialister microaerophilus, Ethanoligenens harbinense\|Dialister microaerophilus, Eubacterium cellulosolvens\|Dialister microaerophilus, Eubacterium eligens\|Dialister microaerophilus, Eubacterium hallii\|Dialister microaerophilus, Eubacterium limosum\|Dialister microaerophilus, Eubacterium rectale\|Dialister microaerophilus, Eubacterium siraeum\|Dialister microaerophilus, Eubacterium ventriosum\|Dialister microaerophilus, Faecalibacterium prausnitzii\|Dialister microaerophilus, Finegoldia magna\|Dialister microaerophilus, Fusobacterium gonidiaformans\|Dialister microaerophilus, Fusobacterium mortiferum\|Dialister microaerophilus, Fusobacterium nucleatum\|Dialister microaerophilus, Fusobacterium varium\|Dialister microaerophilus, Gardnerella vaginalis\|Dialister microaerophilus, Gemella haemolysans\|Dialister microaerophilus, Gemella morbillorum\|Dialister microaerophilus, Gordonibacter pamelaeae\|Dialister microaerophilus, Granulicatella adiacens\|Dialister microaerophilus, Granulicatella elegans\|Dialister microaerophilus, Haemophilus influenzae\|Dialister microaerophilus, Haemophilus parainfluenzae\|Dialister microaerophilus, Helicobacter pullorum\|Dialister microaerophilus, Helicobacter pylori\|Dialister microaerophilus, Holdemania filiformis\|Dialister microaerophilus, Kingella oralis\|Dialister microaerophilus, Klebsiella pneumoniae\|Dialister microaerophilus, Klebsiella variicola\|Dialister microaerophilus, Lachnospiraceae bacterium* 5_1_57FAA\|*Dialister microaerophilus, Lactobacillus acidophilus\|Dialister microaerophilus, Lactobacillus amylovorus\|Dialister microaerophilus, Lactobacillus brevis\|Dialister microaerophilus, Lactobacillus casei\|Dialister microaerophilus, Lactobacillus crispatus\|Dialister microaerophilus, Lactobacillus delbrueckii\|Dialister microaerophilus, Lactobacillus fermentum\|Dialister microaerophilus, Lactobacillus gasseri\|Dialister microaerophilus, Lactobacillus iners\|Dialister microaerophilus, Lactobacillus jensenii\|Dialister microaerophilus, Lactobacillus johnsonii\|Dialister microaerophilus, Lactobacillus paracasei\|Dialister microaerophilus, Lactobacillus plantarum\|Dialister microaerophilus, Lactobacillus reuteri\|Dialister microaerophilus, Lactobacillus rhamnosus\|Dialister microaerophilus, Lactobacillus ruminis\|Dialister microaerophilus, Lactobacillus sakei\|Dialister microaerophilus, Lactobacillus salivarius\|Dialister microaerophilus, Lactococcus lactis\|Dialister microaerophilus, Lautropia mirabilis\|Dialister microaerophilus, Leuconostoc citreum\|Dialister microaerophilus, Leuconostoc gasicomitatum\|Dialister microaerophilus, Leuconostoc mesenteroides\|Dialister microaerophilus, Listeria monocytogenes\|Dialister microaerophilus, Marvinbryantia formatexigens\|Dialister microaerophilus, Megamonas hypermegale\|Dialister microaerophilus, Megasphaera micronuciformis\|Dialister microaerophilus, Methanobrevibacter smithii\|Dialister microaerophilus, Methanosphaera stadtmanae\|Dialister microaerophilus, Methylobacterium radiotolerans\|Dialister microaerophilus, Mitsuokella multacida\|Dialister microaerophilus, Mobiluncus curtisii\|Dialister microaerophilus, Mycoplasma hominis\|Dialister microaerophilus, Neisseria mucosa\|Dialister microaerophilus, Odoribacter splanchnicus\|Dialister microaerophilus, Olsenella uli\|Dialister microaerophilus, Oribacterium sinus\|Dialister microaerophilus, Oxalobacter formigenes\|Dialister microaerophilus, Parabacteroides distasonis\|Dialister microaerophilus, Parabacteroides johnsonii\|Dialister microaerophilus, Parabacteroides merdae\|Dialister microaerophilus, Parvimonas micra\|Dialister microaerophilus, Pediococcus acidilactici\|Dialister microaerophilus, Pediococcus pentosaceus\|Dialister microaerophilus, Peptoniphilus duerdenii\|Dialister microaerophilus, Peptoniphilus harei\|Dialister microaerophilus, Peptoniphilus lacrimalis\|Dialister microaerophilus, Peptostreptococcus anaerobius\|Dialister microaerophilus, Peptostreptococcus stomatis\|Dialister microaerophilus, Porphyromonas asaccharolytica\|Dialister microaerophilus, Porphyromonas uenonis\|Dialister microaerophilus, Prevotella amnii\|Dialister microaerophilus, Prevotella bergensis\|Dialister microaerophilus, Prevotella bivia\|Dialister microaerophilus, Prevotella buccae\|Dialister microaerophilus, Prevotella buccalis\|Dialister microaerophilus, Prevotella copri\|Dialister microaerophilus, Prevotella disiens\|Dialister microaerophilus, Prevotella melaninogenica\|Dialister microaerophilus, Prevotella multiformis\|Dialister microaerophilus, Prevotella oralis\|Dialister microaerophilus, Prevotella oris\|Dialister microaerophilus, Prevotella salivae\|Dialister microaerophilus, Prevotella timonensis\|Dialister microaerophilus, Propionibacterium acnes\|Dialister microaerophilus, Propionibacterium freudenreichii\|Dialister microaerophilus, Proteus mirabilis\|Dialister microaerophilus, Proteus penneri\|Dialister microaerophilus, Pseudoflavonifractor capillosus\|Dialister microaerophilus, Pseudomonas aeruginosa\|Dialister microaerophilus, Pseudomonas fluorescens\|Dialister microaerophilus, Pseudomonas putida\|Dialister microaerophilus, Pseudoramibacter alactolyticus\|Dialister microaerophilus, Pyramidobacter piscolens\|Dialister microaerophilus, Rhodopseudomonas palustris\|Dialister microaerophilus, Roseburia intestinalis\|Dialister microaerophilus, Roseburia inulinivorans\|Dialister microaerophilus, Rothia dentocariosa\|Dialister microaerophilus, Rothia mucilaginosa\|Dialister microaerophilus, Ruminococcus albus\|Dialister microaerophilus, Ruminococcus bromii\|Dialister microaerophilus, Ruminococcus gnavus\|Dialister microaerophilus, Ruminococcus lactaris\|Dialister microaerophilus, Ruminococcus obeum\|Dialister microaerophilus, Ruminococcus torques\|Dialister microaerophilus, Selenomonas sputigena\|Dialister microaerophilus, Shigella boydii\|Dialister microaerophilus, Shigella dysenteriae\|Dialister microaerophilus, Shigella sonnei\|Dialister microaerophilus, Slackia exigua\|Dialister microaerophilus, Solobacterium moorei\|Dialister microaerophilus, Staphylococcus aureus\|Dialister microaerophilus, Staphylococcus epidermidis\|Dialister microaerophilus, Staphylococcus hominis\|Dialister microaerophilus, Staphylococcus saprophyticus\|Dialister microaerophilus, Staphylococcus warneri\|Dialister microaerophilus, Streptococcus agalactiae\|Dialister microaerophilus, Streptococcus anginosus\|Dialister microaerophilus, Streptococcus australis\|Dialister microaerophilus, Streptococcus bovis\|Dialister microaerophilus, Streptococcus cristatus\|Dialister microaerophilus, Streptococcus dysgalactiae\|Dialister microaerophilus, Streptococcus equinus\|Dialister microaerophilus, Streptococcus gordonii\|Dialister microaerophilus, Streptococcus infantarius\|Dialister microaerophilus, Streptococcus infantis\|Dialister microaerophilus, Streptococcus mitis\|Dialister microaerophilus, Streptococcus mutans\|Dialister microaerophilus, Streptococcus oralis\|Dialister microaerophilus, Streptococcus parasanguinis\|Dialister microaerophilus, Streptococcus peroris\|Dialister microaerophilus, Streptococcus pneumoniae\|Dialister microaerophilus, Streptococcus salivarius\|Dialister microaerophilus, Streptococcus sanguinis\|Dialister microaerophilus, Streptococcus thermophilus\|Dialister microaerophilus, Streptococcus vestibularis\|Dialister microaerophilus, Subdoligranulum variabile\|Dialister microaerophilus, Succinatimonas hippei\|Dialister microaerophilus, Sutterella wadsworthensis\|Dialister microaerophilus, Tropheryma whipplei\|Dialister microaerophilus, Veillonella atypica\|Dialister microaerophilus, Veillonella dispar\|Dialister microaerophilus, Veillonella parvula\|Dialister microaerophilus, Victivallis vadensis\|Dorea formicigenerans, Dorea formicigenerans\|Dorea formicigenerans, Dorea longicatena\|Dorea formicigenerans, Eggerthella lenta\|Dorea formicigenerans, Eikenella corrodens\|Dorea formicigenerans, Enterobacter cancerogenus\|Dorea formicigenerans, Enterobacter cloacae\|Dorea* |

TABLE 2-continued

Table 2. Specific binary combinations of OTUs. Individual pairings are differentiated by "|" and OTUs within a combination are differentiated by ","

*formicigenerans, Enterococcus faecalis|Dorea formicigenerans, Enterococcus faecium|Dorea formicigenerans, Enterococcus gallinarum|Dorea formicigenerans, Erysipelotrichaceae bacterium* 3_1_53|*Dorea formicigenerans, Escherichia coli|Dorea formicigenerans, Escherichia fergusonii|Dorea formicigenerans, Ethanoligenens harbinense|Dorea formicigenerans, Eubacterium cellulosolvens|Dorea formicigenerans, Eubacterium eligens|Dorea formicigenerans, Eubacterium hallii|Dorea formicigenerans, Eubacterium limosum|Dorea formicigenerans, Eubacterium rectale|Dorea formicigenerans, Eubacterium siraeum|Dorea formicigenerans, Eubacterium ventriosum|Dorea formicigenerans, Faecalibacterium prausnitzii|Dorea formicigenerans, Finegoldia magna|Dorea formicigenerans, Fusobacterium gonidiaformans|Dorea formicigenerans, Fusobacterium mortiferum|Dorea formicigenerans, Fusobacterium nucleatum|Dorea formicigenerans, Fusobacterium varium|Dorea formicigenerans, Gardnerella vaginalis|Dorea formicigenerans, Gemella haemolysans|Dorea formicigenerans, Gemella morbillorum|Dorea formicigenerans, Gordonibacter pamelaeae|Dorea formicigenerans, Granulicatella adiacens|Dorea formicigenerans, Granulicatella elegans|Dorea formicigenerans, Haemophilus influenzae|Dorea formicigenerans, Haemophilus parainfluenzae|Dorea formicigenerans, Helicobacter pullorum|Dorea formicigenerans, Helicobacter pylori|Dorea formicigenerans, Holdemania filiformis|Dorea formicigenerans, Kingella oralis|Dorea formicigenerans, Klebsiella pneumoniae|Dorea formicigenerans, Klebsiella variicola|Dorea formicigenerans, Lachnospiraceae bacterium* 5_1_57FAA|*Dorea formicigenerans, Lactobacillus acidophilus|Dorea formicigenerans, Lactobacillus amylovorus|Dorea formicigenerans, Lactobacillus brevis|Dorea formicigenerans, Lactobacillus casei|Dorea formicigenerans, Lactobacillus crispatus|Dorea formicigenerans, Lactobacillus delbrueckii|Dorea formicigenerans, Lactobacillus fermentum|Dorea formicigenerans, Lactobacillus gasseri|Dorea formicigenerans, Lactobacillus iners|Dorea formicigenerans, Lactobacillus jensenii|Dorea formicigenerans, Lactobacillus johnsonii|Dorea formicigenerans, Lactobacillus paracasei|Dorea formicigenerans, Lactobacillus plantarum|Dorea formicigenerans, Lactobacillus reuteri|Dorea formicigenerans, Lactobacillus rhamnosus|Dorea formicigenerans, Lactobacillus ruminis|Dorea formicigenerans, Lactobacillus sakei|Dorea formicigenerans, Lactobacillus salivarius|Dorea formicigenerans, Lactococcus lactis|Dorea formicigenerans, Lautropia mirabilis|Dorea formicigenerans, Leuconostoc citreum|Dorea formicigenerans, Leuconostoc gasicomitatum|Dorea formicigenerans, Leuconostoc mesenteroides|Dorea formicigenerans, Listeria monocytogenes|Dorea formicigenerans, Marvinbryantia formatexigens|Dorea formicigenerans, Megamonas hypermegale|Dorea formicigenerans, Megasphaera micronuciformis|Dorea formicigenerans, Methanobrevibacter smithii|Dorea formicigenerans, Methanosphaera stadtmanae|Dorea formicigenerans, Methylobacterium radiotolerans|Dorea formicigenerans, Mitsuokella multacida|Dorea formicigenerans, Mobiluncus curtisii|Dorea formicigenerans, Mycoplasma hominis|Dorea formicigenerans, Neisseria mucosa|Dorea formicigenerans, Odoribacter splanchnicus|Dorea formicigenerans, Olsenella uli|Dorea formicigenerans, Oribacterium sinus|Dorea formicigenerans, Oxalobacter formigenes|Dorea formicigenerans, Parabacteroides distasonis|Dorea formicigenerans, Parabacteroides johnsonii|Dorea formicigenerans, Parabacteroides merdae|Dorea formicigenerans, Parvimonas micra|Dorea formicigenerans, Pediococcus acidilactici|Dorea formicigenerans, Pediococcus pentosaceus|Dorea formicigenerans, Peptoniphilus duerdenii|Dorea formicigenerans, Peptoniphilus harei|Dorea formicigenerans, Peptoniphilus lacrimalis|Dorea formicigenerans, Peptostreptococcus anaerobius|Dorea formicigenerans, Peptostreptococcus stomatis|Dorea formicigenerans, Porphyromonas asaccharolytica|Dorea formicigenerans, Porphyromonas uenonis|Dorea formicigenerans, Prevotella amnii|Dorea formicigenerans, Prevotella bergensis|Dorea formicigenerans, Prevotella bivia|Dorea formicigenerans, Prevotella buccae|Dorea formicigenerans, Prevotella buccalis|Dorea formicigenerans, Prevotella copri|Dorea formicigenerans, Prevotella disiens|Dorea formicigenerans, Prevotella melaninogenica|Dorea formicigenerans, Prevotella multiformis|Dorea formicigenerans, Prevotella oralis|Dorea formicigenerans, Prevotella oris|Dorea formicigenerans, Prevotella salivae|Dorea formicigenerans, Prevotella timonensis|Dorea formicigenerans, Propionibacterium acnes|Dorea formicigenerans, Propionibacterium freudenreichii|Dorea formicigenerans, Proteus mirabilis|Dorea formicigenerans, Proteus penneri|Dorea formicigenerans, Pseudoflavonifractor capillosus|Dorea formicigenerans, Pseudomonas aeruginosa|Dorea formicigenerans, Pseudomonas fluorescens|Dorea formicigenerans, Pseudomonas putida|Dorea formicigenerans, Pseudoramibacter alactolyticus|Dorea formicigenerans, Pyramidobacter piscolens|Dorea formicigenerans, Rhodopseudomonas palustris|Dorea formicigenerans, Roseburia intestinalis|Dorea formicigenerans, Roseburia inulinivorans|Dorea formicigenerans, Rothia dentocariosa|Dorea formicigenerans, Rothia mucilaginosa|Dorea formicigenerans, Ruminococcus albus|Dorea formicigenerans, Ruminococcus bromii|Dorea formicigenerans, Ruminococcus gnavus|Dorea formicigenerans, Ruminococcus lactaris|Dorea formicigenerans, Ruminococcus obeum|Dorea formicigenerans, Ruminococcus torques|Dorea formicigenerans, Selenomonas sputigena|Dorea formicigenerans, Shigella boydii|Dorea formicigenerans, Shigella dysenteriae|Dorea formicigenerans, Shigella sonnei|Dorea formicigenerans, Slackia exigua|Dorea formicigenerans, Solobacterium moorei|Dorea formicigenerans, Staphylococcus aureus|Dorea formicigenerans, Staphylococcus epidermidis|Dorea formicigenerans, Staphylococcus hominis|Dorea formicigenerans, Staphylococcus saprophyticus|Dorea formicigenerans, Staphylococcus warneri|Dorea formicigenerans, Streptococcus agalactiae|Dorea formicigenerans, Streptococcus anginosus|Dorea formicigenerans, Streptococcus australis|Dorea formicigenerans, Streptococcus bovis|Dorea formicigenerans, Streptococcus cristatus|Dorea formicigenerans, Streptococcus dysgalactiae|Dorea formicigenerans, Streptococcus equinus|Dorea formicigenerans, Streptococcus gordonii|Dorea formicigenerans, Streptococcus infantarius|Dorea formicigenerans, Streptococcus infantis|Dorea formicigenerans, Streptococcus mitis|Dorea formicigenerans, Streptococcus mutans|Dorea formicigenerans, Streptococcus oralis|Dorea formicigenerans, Streptococcus parasanguinis|Dorea formicigenerans, Streptococcus peroris|Dorea formicigenerans, Streptococcus pneumoniae|Dorea formicigenerans, Streptococcus salivarius|Dorea formicigenerans, Streptococcus sanguinis|Dorea formicigenerans, Streptococcus thermophilus|Dorea formicigenerans, Streptococcus vestibularis|Dorea formicigenerans, Subdoligranulum variabile|Dorea formicigenerans, Succinatimonas hippei|Dorea formicigenerans, Sutterella wadsworthensis|Dorea formicigenerans, Tropheryma whipplei|Dorea formicigenerans, Veillonella atypica|Dorea formicigenerans, Veillonella dispar|Dorea formicigenerans, Veillonella parvulai|Dorea formicigenerans, Victivallis vadensis|Dorea longicatena, Dorea longicatena|Dorea longicatena, Eggerthella lenta|Dorea longicatena, Eikenella corrodens|Dorea longicatena, Enterobacter cancerogenus|Dorea longicatena, Enterobacter cloacae|Dorea longicatena, Enterococcus faecalis|Dorea longicatena, Enterococcus faecium|Dorea longicatena, Enterococcus gallinarum|Dorea longicatena, Erysipelotrichaceae bacterium* 3_1_53|*Dorea longicatena, Escherichia coli|Dorea longicatena, Escherichia fergusonii|Dorea longicatena, Ethanoligenens harbinense|Dorea longicatena, Eubacterium cellulosolvens|Dorea longicatena, Eubacterium eligens|Dorea longicatena, Eubacterium hallii|Dorea longicatena, Eubacterium limosum|Dorea longicatena, Eubacterium rectale|Dorea longicatena, Eubacterium siraeum|Dorea longicatena, Eubacterium ventriosum|Dorea longicatena, Faecalibacterium prausnitzii|Dorea longicatena, Finegoldia magna|Dorea longicatena, Fusobacterium gonidiaformans|Dorea longicatena, Fusobacterium mortiferum|Dorea longicatena, Fusobacterium nucleatum|Dorea longicatena, Fusobacterium varium|Dorea longicatena, Gardnerella vaginalis|Dorea longicatena, Gemella haemolysans|Dorea longicatena, Gemella morbillorum|Dorea longicatena, Gordonibacter pamelaeae|Dorea longicatena, Granulicatella adiacens|Dorea longicatena, Granulicatella elegans|Dorea longicatena, Haemophilus influenzae|Dorea longicatena, Haemophilus parainfluenzae|Dorea longicatena, Helicobacter pullorum|Dorea longicatena, Helicobacter pylori|Dorea longicatena, Holdemania filiformis|Dorea longicatena, Kingella oralis|Dorea longicatena, Klebsiella pneumoniae|Dorea longicatena, Klebsiella variicola|Dorea longicatena, Lachnospiraceae bacterium* 5_1_57FAA|*Dorea longicatena, Lactobacillus acidophilus|Dorea longicatena, Lactobacillus amylovorus|Dorea longicatena, Lactobacillus brevis|Dorea longicatena, Lactobacillus casei|Dorea longicatena, Lactobacillus crispatus|Dorea longicatena, Lactobacillus delbrueckii|Dorea longicatena, Lactobacillus fermentum|Dorea longicatena, Lactobacillus gasseri|Dorea longicatena, Lactobacillus iners|Dorea longicatena, Lactobacillus jensenii|Dorea longicatena, Lactobacillus johnsonii|Dorea longicatena, Lactobacillus paracasei|Dorea longicatena, Lactobacillus plantarum|Dorea longicatena, Lactobacillus reuteri|Dorea longicatena, Lactobacillus rhamnosus|Dorea longicatena, Lactobacillus ruminis|Dorea longicatena, Lactobacillus sakei|Dorea longicatena, Lactobacillus salivarius|Dorea*

TABLE 2-continued

Table 2. Specific binary combinations of OTUs. Individual pairings are differentiated by "|" and OTUs within a combination are differentiated by ","

longicatena, Lactococcus lactis|Dorea longicatena, Lautropia mirabilis|Dorea longicatena, Leuconostoc citreum|Dorea longicatena, Leuconostoc gasicomitatum|Dorea longicatena, Leuconostoc mesenteroides|Dorea longicatena, Listeria monocytogenes|Dorea longicatena, Marvinbryantia formatexigens|Dorea longicatena, Megamonas hypermegale|Dorea longicatena, Megasphaera micronuciformis|Dorea longicatena, Methanobrevibacter smithii|Dorea longicatena, Methanosphaera stadtmanae|Dorea longicatena, Methylobacterium radiotolerans|Dorea longicatena, Mitsuokella multacida|Dorea longicatena, Mobiluncus curtisii|Dorea longicatena, Mycoplasma hominis|Dorea longicatena, Neisseria mucosa|Dorea longicatena, Odoribacter splanchnicus|Dorea longicatena, Olsenella uli|Dorea longicatena, Oribacterium sinus|Dorea longicatena, Oxalobacter formigenes|Dorea longicatena, Parabacteroides distasonis|Dorea longicatena, Parabacteroides johnsonii|Dorea longicatena, Parabacteroides merdae|Dorea longicatena, Parvimonas micra|Dorea longicatena, Pediococcus acidilactici|Dorea longicatena, Pediococcus pentosaceus|Dorea longicatena, Peptoniphilus duerdenii|Dorea longicatena, Peptoniphilus harei|Dorea longicatena, Peptoniphilus lacrimalis|Dorea longicatena, Peptostreptococcus anaerobius|Dorea longicatena, Peptostreptococcus stomatis|Dorea longicatena, Porphyromonas asaccharolytica|Dorea longicatena, Porphyromonas uenonis|Dorea longicatena, Prevotella amnii|Dorea longicatena, Prevotella bergensis|Dorea longicatena, Prevotella bivia|Dorea longicatena, Prevotella buccae|Dorea longicatena, Prevotella buccalis|Dorea longicatena, Prevotella copri|Dorea longicatena, Prevotella disiens|Dorea longicatena, Prevotella melaninogenica|Dorea longicatena, Prevotella multiformis|Dorea longicatena, Prevotella oralis|Dorea longicatena, Prevotella oris|Dorea longicatena, Prevotella salivae|Dorea longicatena, Prevotella timonensis|Dorea longicatena, Propionibacterium acnes|Dorea longicatena, Propionibacterium freudenreichii|Dorea longicatena, Proteus mirabilis|Dorea longicatena, Proteus penneri|Dorea longicatena, Pseudoflavonifractor capillosus|Dorea longicatena, Pseudomonas aeruginosa|Dorea longicatena, Pseudomonas fluorescens|Dorea longicatena, Pseudomonas putida|Dorea longicatena, Pseudoramibacter alactolyticus|Dorea longicatena, Pyramidobacter piscolens|Dorea longicatena, Rhodopseudomonas palustris|Dorea longicatena, Roseburia intestinalis|Dorea longicatena, Roseburia inulinivorans|Dorea longicatena, Rothia dentocariosa|Dorea longicatena, Rothia mucilaginosa|Dorea longicatena, Ruminococcus albus|Dorea longicatena, Ruminococcus bromii|Dorea longicatena, Ruminococcus gnavus|Dorea longicatena, Ruminococcus lactaris|Dorea longicatena, Ruminococcus obeum|Dorea longicatena, Ruminococcus torques|Dorea longicatena, Selenomonas sputigena|Dorea longicatena, Shigella boydii|Dorea longicatena, Shigella dysenteriae|Dorea longicatena, Shigella sonnei|Dorea longicatena, Slackia exigua|Dorea longicatena, Solobacterium moorei|Dorea longicatena, Staphylococcus aureus|Dorea longicatena, Staphylococcus epidermidis|Dorea longicatena, Staphylococcus hominis|Dorea longicatena, Staphylococcus saprophyticus|Dorea longicatena, Staphylococcus warneri|Dorea longicatena, Streptococcus agalactiae|Dorea longicatena, Streptococcus anginosus|Dorea longicatena, Streptococcus australis|Dorea longicatena, Streptococcus bovis|Dorea longicatena, Streptococcus cristatus|Dorea longicatena, Streptococcus dysgalactiae|Dorea longicatena, Streptococcus equinus|Dorea longicatena, Streptococcus gordonii|Dorea longicatena, Streptococcus infantarius|Dorea longicatena, Streptococcus infantis|Dorea longicatena, Streptococcus mitis|Dorea longicatena, Streptococcus mutans|Dorea longicatena, Streptococcus oralis|Dorea longicatena, Streptococcus parasanguinis|Dorea longicatena, Streptococcus peroris|Dorea longicatena, Streptococcus pneumoniae|Dorea longicatena, Streptococcus salivarius|Dorea longicatena, Streptococcus sanguinis|Dorea longicatena, Streptococcus thermophilus|Dorea longicatena, Streptococcus vestibularis|Dorea longicatena, Subdoligranulum variabile|Dorea longicatena, Succinatimonas hippei|Dorea longicatena, Sutterella wadsworthensis|Dorea longicatena, Tropheryma whipplei|Dorea longicatena, Veillonella atypica|Dorea longicatena, Veillonella dispar|Dorea longicatena, Veillonella parvula|Dorea longicatena, Victivallis vadensis|Eggerthella lenta, Eggerthella lenta|Eggerthella lenta, Eikenella corrodens|Eggerthella lenta, Enterobacter cancerogenus|Eggerthella lenta, Enterobacter cloacae|Eggerthella lenta, Enterococcus faecalis|Eggerthella lenta, Enterococcus faecium|Eggerthella lenta, Enterococcus gallinarum|Eggerthella lenta, Erysipelotrichaceae bacterium 3_1_53|Eggerthella lenta, Escherichia coli|Eggerthella lenta, Escherichia fergusonii|Eggerthella lenta, Ethanoligenens harbinense|Eggerthella lenta, Eubacterium cellulosolvens|Eggerthella lenta, Eubacterium eligens|Eggerthella lenta, Eubacterium hallii|Eggerthella lenta, Eubacterium limosum|Eggerthella lenta, Eubacterium rectale|Eggerthella lenta, Eubacterium siraeum|Eggerthella lenta, Eubacterium ventriosum|Eggerthella lenta, Faecalibacterium prausnitzii|Eggerthella lenta, Finegoldia magna|Eggerthella lenta, Fusobacterium gonidiaformans|Eggerthella lenta, Fusobacterium mortiferum|Eggerthella lenta, Fusobacterium nucleatum|Eggerthella lenta, Fusobacterium varium|Eggerthella lenta, Gardnerella vaginalis|Eggerthella lenta, Gemella haemolysans|Eggerthella lenta, Gemella morbillorum|Eggerthella lenta, Gordonibacter pamelaeae|Eggerthella lenta, Granulicatella adiacens|Eggerthella lenta, Granulicatella elegans|Eggerthella lenta, Haemophilus influenzae|Eggerthella lenta, Haemophilus parainfluenzae|Eggerthella lenta, Helicobacter pullorum|Eggerthella lenta, Helicobacter pylori|Eggerthella lenta, Holdemania filiformis|Eggerthella lenta, Kingella oralis|Eggerthella lenta, Klebsiella pneumoniae|Eggerthella lenta, Klebsiella variicola|Eggerthella lenta, Lachnospiraceae bacterium 5_1_57FAA|Eggerthella lenta, Lactobacillus acidophilus|Eggerthella lenta, Lactobacillus amylovorus|Eggerthella lenta, Lactobacillus brevis|Eggerthella lenta, Lactobacillus casei|Eggerthella lenta, Lactobacillus crispatus|Eggerthella lenta, Lactobacillus delbrueckii|Eggerthella lenta, Lactobacillus fermentum|Eggerthella lenta, Lactobacillus gasseri|Eggerthella lenta, Lactobacillus iners|Eggerthella lenta, Lactobacillus jensenii|Eggerthella lenta, Lactobacillus johnsonii|Eggerthella lenta, Lactobacillus paracasei|Eggerthella lenta, Lactobacillus plantarum|Eggerthella lenta, Lactobacillus reuteri|Eggerthella lenta, Lactobacillus rhamnosus|Eggerthella lenta, Lactobacillus ruminis|Eggerthella lenta, Lactobacillus sakei|Eggerthella lenta, Lactobacillus salivarius|Eggerthella lenta, Lactococcus lactis|Eggerthella lenta, Lautropia mirabilis|Eggerthella lenta, Leuconostoc citreum|Eggerthella lenta, Leuconostoc gasicomitatum|Eggerthella lenta, Leuconostoc mesenteroides|Eggerthella lenta, Listeria monocytogenes|Eggerthella lenta, Marvinbryantia formatexigens|Eggerthella lenta, Megamonas hypermegale|Eggerthella lenta, Megasphaera micronuciformis|Eggerthella lenta, Methanobrevibacter smithii|Eggerthella lenta, Methanosphaera stadtmanae|Eggerthella lenta, Methylobacterium radiotolerans|Eggerthella lenta, Mitsuokella multacida|Eggerthella lenta, Mobiluncus curtisii|Eggerthella lenta, Mycoplasma hominis|Eggerthella lenta, Neisseria mucosa|Eggerthella lenta, Odoribacter splanchnicus|Eggerthella lenta, Olsenella uli|Eggerthella lenta, Oribacterium sinus|Eggerthella lenta, Oxalobacter formigenes|Eggerthella lenta, Parabacteroides distasonis|Eggerthella lenta, Parabacteroides johnsonii|Eggerthella lenta, Parabacteroides merdae|Eggerthella lenta, Parvimonas micra|Eggerthella lenta, Pediococcus acidilactici|Eggerthella lenta, Pediococcus pentosaceus|Eggerthella lenta, Peptoniphilus duerdenii|Eggerthella lenta, Peptoniphilus harei|Eggerthella lenta, Peptoniphilus lacrimalis|Eggerthella lenta, Peptostreptococcus anaerobius|Eggerthella lenta, Peptostreptococcus stomatis|Eggerthella lenta, Porphyromonas asaccharolytica|Eggerthella lenta, Porphyromonas uenonis|Eggerthella lenta, Prevotella amnii|Eggerthella lenta, Prevotella bergensis|Eggerthella lenta, Prevotella bivia|Eggerthella lenta, Prevotella buccae|Eggerthella lenta, Prevotella buccalis|Eggerthella lenta, Prevotella copri|Eggerthella lenta, Prevotella disiens|Eggerthella lenta, Prevotella melaninogenica|Eggerthella lenta, Prevotella multiformis|Eggerthella lenta, Prevotella oralis|Eggerthella lenta, Prevotella oris|Eggerthella lenta, Prevotella salivae|Eggerthella lenta, Prevotella timonensis|Eggerthella lenta, Propionibacterium acnes|Eggerthella lenta, Propionibacterium freudenreichii|Eggerthella lenta, Proteus mirabilis|Eggerthella lenta, Proteus penneri|Eggerthella lenta, Pseudoflavonifractor capillosus|Eggerthella lenta, Pseudomonas aeruginosa|Eggerthella lenta, Pseudomonas fluorescens|Eggerthella lenta, Pseudomonas putida|Eggerthella lenta, Pseudoramibacter alactolyticus|Eggerthella lenta, Pyramidobacter piscolens|Eggerthella lenta, Rhodopseudomonas palustris|Eggerthella lenta, Roseburia intestinalis|Eggerthella lenta, Roseburia inulinivorans|Eggerthella lenta, Rothia dentocariosa|Eggerthella lenta, Rothia mucilaginosa|Eggerthella lenta, Ruminococcus albus|Eggerthella lenta, Ruminococcus bromii|Eggerthella lenta, Ruminococcus gnavus|Eggerthella lenta, Ruminococcus lactaris|Eggerthella lenta, Ruminococcus obeum|Eggerthella lenta, Ruminococcus torques|Eggerthella lenta, Selenomonas sputigena|Eggerthella lenta, Shigella boydii|Eggerthella lenta, Shigella dysenteriae|Eggerthella lenta, Shigella sonnei|Eggerthella lenta, Slackia exigua|Eggerthella lenta, Solobacterium moorei|Eggerthella lenta, Staphylococcus aureus|Eggerthella lenta, Staphylococcus epidermidis|Eggerthella lenta, Staphylococcus hominis|Eggerthella lenta, Staphylococcus saprophyticus|Eggerthella lenta, Staphylococcus warneri|Eggerthella lenta, Streptococcus agalactiae|Eggerthella lenta, Streptococcus anginosus|Eggerthella lenta, Streptococcus australis|Eggerthella lenta, Streptococcus bovis|Eggerthella lenta, Streptococcus TABLE 2-continued Table 2. Specific binary combinations of OTUs. Individual pairings are differentiated by "|" and OTUs within a combination are differentiated by ","

cristatus|Eggerthella lenta, Streptococcus dysgalactiae|Eggerthella lenta, Streptococcus equinus|Eggerthella lenta, Streptococcus gordonii|Eggerthella lenta, Streptococcus infantarius|Eggerthella lenta, Streptococcus infantis|Eggerthella lenta, Streptococcus mitis|Eggerthella lenta, Streptococcus mutans|Eggerthella lenta, Streptococcus oralis|Eggerthella lenta, Streptococcus parasanguinis|Eggerthella lenta, Streptococcus peroris|Eggerthella lenta, Streptococcus pneumoniae|Eggerthella lenta, Streptococcus salivarius|Eggerthella lenta, Streptococcus sanguinis|Eggerthella lenta, Streptococcus thermophilus|Eggerthella lenta, Streptococcus vestibularis|Eggerthella lenta, Subdoligranulum variabile|Eggerthella lenta, Succinatimonas hippei|Eggerthella lenta, Sutterella wadsworthensis|Eggerthella lenta, Tropheryma whipplei|Eggerthella lenta, Veillonella atypica|Eggerthella lenta, Veillonella dispar|Eggerthella lenta, Veillonella parvula|Eggerthella lenta, Victivallis vadensis|Eikenella corrodens, Eikenella corrodens, Eikenella corrodens, Enterobacter cancerogenus|Eikenella corrodens, Enterobacter cloacae|Eikenella corrodens, Enterococcus faecalis|Eikenella corrodens, Enterococcus faecium|Eikenella corrodens, Enterococcus gallinarum|Eikenella corrodens, Erysipelotrichaceae bacterium 3_1_53|Eikenella corrodens, Escherichia coli|Eikenella corrodens, Escherichia fergusonii|Eikenella corrodens, Ethanoligenens harbinense|Eikenella corrodens, Eubacterium cellulosolvens|Eikenella corrodens, Eubacterium eligens|Eikenella corrodens, Eubacterium hallii|Eikenella corrodens, Eubacterium limosum|Eikenella corrodens, Eubacterium rectale|Eikenella corrodens, Eubacterium siraeum|Eikenella corrodens, Eubacterium ventriosum|Eikenella corrodens, Faecalibacterium prausnitzii|Eikenella corrodens, Finegoldia magna|Eikenella corrodens, Fusobacterium gonidiaformans|Eikenella corrodens, Fusobacterium mortiferum|Eikenella corrodens, Fusobacterium nucleatum|Eikenella corrodens, Fusobacterium varium|Eikenella corrodens, Gardnerella vaginalis|Eikenella corrodens, Gemella haemolysans|Eikenella corrodens, Gemella morbillorum|Eikenella corrodens, Gordonibacter pamelaeae|Eikenella corrodens, Granulicatella adiacens|Eikenella corrodens, Granulicatella elegans|Eikenella corrodens, Haemophilus influenzae|Eikenella corrodens, Haemophilus parainfluenzae|Eikenella corrodens, Helicobacter pullorum|Eikenella corrodens, Helicobacter pylori|Eikenella corrodens, Holdemania filiformis|Eikenella corrodens, Kingella oralis|Eikenella corrodens, Klebsiella pneumoniae|Eikenella corrodens, Klebsiella variicola|Eikenella corrodens, Lachnospiraceae bacterium 5_1_57FAA|Eikenella corrodens, Lactobacillus acidophilus|Eikenella corrodens, Lactobacillus amylovorus|Eikenella corrodens, Lactobacillus brevis|Eikenella corrodens, Lactobacillus casei|Eikenella corrodens, Lactobacillus crispatus|Eikenella corrodens, Lactobacillus delbrueckii|Eikenella corrodens, Lactobacillus fermentum|Eikenella corrodens, Lactobacillus gasseri|Eikenella corrodens, Lactobacillus iners|Eikenella corrodens, Lactobacillus jensenii|Eikenella corrodens, Lactobacillus johnsonii|Eikenella corrodens, Lactobacillus paracasei|Eikenella corrodens, Lactobacillus plantarum|Eikenella corrodens, Lactobacillus reuteri|Eikenella corrodens, Lactobacillus rhamnosus|Eikenella corrodens, Lactobacillus ruminis|Eikenella corrodens, Lactobacillus sakei|Eikenella corrodens, Lactobacillus salivarius|Eikenella corrodens, Lactococcus lactis|Eikenella corrodens, Lautropia mirabilis|Eikenella corrodens, Leuconostoc citreum|Eikenella corrodens, Leuconostoc gasicomitatum|Eikenella corrodens, Leuconostoc mesenteroides|Eikenella corrodens, Listeria monocytogenes|Eikenella corrodens, Marvinbryantia formatexigens|Eikenella corrodens, Megamonas hypermegale|Eikenella corrodens, Megasphaera micronuciformis|Eikenella corrodens, Methanobrevibacter smithii|Eikenella corrodens, Methanosphaera stadtmanae|Eikenella corrodens, Methylobacterium radiotolerans|Eikenella corrodens, Mitsuokella multacida|Eikenella corrodens, Mobiluncus curtisii|Eikenella corrodens, Mycoplasma hominis|Eikenella corrodens, Neisseria mucosa|Eikenella corrodens, Odoribacter splanchnicus|Eikenella corrodens, Olsenella uli|Eikenella corrodens, Oribacterium sinus|Eikenella corrodens, Oxalobacter formigenes|Eikenella corrodens, Parabacteroides distasonis|Eikenella corrodens, Parabacteroides johnsonii|Eikenella corrodens, Parabacteroides merdae|Eikenella corrodens, Parvimonas micra|Eikenella corrodens, Pediococcus acidilactici|Eikenella corrodens, Pediococcus pentosaceus|Eikenella corrodens, Peptoniphilus duerdenii|Eikenella corrodens, Peptoniphilus harei|Eikenella corrodens, Peptoniphilus lacrimalis|Eikenella corrodens, Peptostreptococcus anaerobius|Eikenella corrodens, Peptostreptococcus stomatis|Eikenella corrodens, Porphyromonas asaccharolytica|Eikenella corrodens, Porphyromonas uenonis|Eikenella corrodens, Prevotella amnii|Eikenella corrodens, Prevotella bergensis|Eikenella corrodens, Prevotella bivia|Eikenella corrodens, Prevotella buccae|Eikenella corrodens, Prevotella buccalis|Eikenella corrodens, Prevotella copri|Eikenella corrodens, Prevotella disiens|Eikenella corrodens, Prevotella melaninogenica|Eikenella corrodens, Prevotella multiformis|Eikenella corrodens, Prevotella oralis|Eikenella corrodens, Prevotella oris|Eikenella corrodens, Prevotella salivae|Eikenella corrodens, Prevotella timonensis|Eikenella corrodens, Propionibacterium acnes|Eikenella corrodens, Propionibacterium freudenreichii|Eikenella corrodens, Proteus mirabilis|Eikenella corrodens, Proteus penneri|Eikenella corrodens, Pseudoflavonifractor capillosus|Eikenella corrodens, Pseudomonas aeruginosa|Eikenella corrodens, Pseudomonas fluorescens|Eikenella corrodens, Pseudomonas putida|Eikenella corrodens, Pseudoramibacter alactolyticus|Eikenella corrodens, Pyramidobacter piscolens|Eikenella corrodens, Rhodopseudomonas palustris|Eikenella corrodens, Roseburia intestinalis|Eikenella corrodens, Roseburia inulinivorans|Eikenella corrodens, Rothia dentocariosa|Eikenella corrodens, Rothia mucilaginosa|Eikenella corrodens, Ruminococcus albus|Eikenella corrodens, Ruminococcus bromii|Eikenella corrodens, Ruminococcus gnavus|Eikenella corrodens, Ruminococcus lactaris|Eikenella corrodens, Ruminococcus obeum|Eikenella corrodens, Ruminococcus torques|Eikenella corrodens, Selenomonas sputigena|Eikenella corrodens, Shigella boydii|Eikenella corrodens, Shigella dysenteriae|Eikenella corrodens, Shigella sonnei|Eikenella corrodens, Slackia exigua|Eikenella corrodens, Solobacterium moorei|Eikenella corrodens, Staphylococcus aureus|Eikenella corrodens, Staphylococcus epidermidis|Eikenella corrodens, Staphylococcus hominis|Eikenella corrodens, Staphylococcus saprophyticus|Eikenella corrodens, Staphylococcus warneri|Eikenella corrodens, Streptococcus agalactiae|Eikenella corrodens, Streptococcus anginosus|Eikenella corrodens, Streptococcus australis|Eikenella corrodens, Streptococcus bovis|Eikenella corrodens, Streptococcus cristatus|Eikenella corrodens, Streptococcus dysgalactiae|Eikenella corrodens, Streptococcus equinus|Eikenella corrodens, Streptococcus gordonii|Eikenella corrodens, Streptococcus infantarius|Eikenella corrodens, Streptococcus infantis|Eikenella corrodens, Streptococcus mitis|Eikenella corrodens, Streptococcus mutans|Eikenella corrodens, Streptococcus oralis|Eikenella corrodens, Streptococcus parasanguinis|Eikenella corrodens, Streptococcus peroris|Eikenella corrodens, Streptococcus pneumoniae|Eikenella corrodens, Streptococcus salivarius|Eikenella corrodens, Streptococcus sanguinis|Eikenella corrodens, Streptococcus thermophilus|Eikenella corrodens, Streptococcus vestibularis|Eikenella corrodens, Subdoligranulum variabile|Eikenella corrodens, Succinatimonas hippei|Eikenella corrodens, Sutterella wadsworthensis|Eikenella corrodens, Tropheryma whipplei|Eikenella corrodens, Veillonella atypica|Eikenella corrodens, Veillonella dispar|Eikenella corrodens, Veillonella parvula|Eikenella corrodens, Victivallis vadensis|Enterobacter cancerogenus, Enterobacter cancerogenus|Enterobacter cancerogenus, Enterobacter cloacae|Enterobacter cancerogenus, Enterococcus faecalis|Enterobacter cancerogenus, Enterococcus faecium|Enterobacter cancerogenus, Enterococcus gallinarum|Enterobacter cancerogenus, Erysipelotrichaceae bacterium 3_1_53|Enterobacter cancerogenus, Escherichia coli|Enterobacter cancerogenus, Escherichia fergusonii|Enterobacter cancerogenus, Ethanoligenens harbinense|Enterobacter cancerogenus, Eubacterium cellulosolvens|Enterobacter cancerogenus, Eubacterium eligens|Enterobacter cancerogenus, Eubacterium hallii|Enterobacter cancerogenus, Eubacterium limosum|Enterobacter cancerogenus, Eubacterium rectale|Enterobacter cancerogenus, Eubacterium siraeum|Enterobacter cancerogenus, Eubacterium ventriosum|Enterobacter cancerogenus, Faecalibacterium prausnitzii|Enterobacter cancerogenus, Finegoldia magna|Enterobacter cancerogenus, Fusobacterium gonidiaformans|Enterobacter cancerogenus, Fusobacterium mortiferum|Enterobacter cancerogenus, Fusobacterium nucleatum|Enterobacter cancerogenus, Fusobacterium varium|Enterobacter cancerogenus, Gardnerella vaginalis|Enterobacter cancerogenus, Gemella haemolysans|Enterobacter cancerogenus, Gemella morbillorum|Enterobacter cancerogenus, Gordonibacter pamelaeae|Enterobacter cancerogenus, Granulicatella adiacens|Enterobacter cancerogenus, Granulicatella elegans|Enterobacter cancerogenus, Haemophilus influenzae|Enterobacter cancerogenus, Haemophilus parainfluenzae|Enterobacter cancerogenus, Helicobacter pullorum|Enterobacter cancerogenus, Helicobacter pylori|Enterobacter cancerogenus, Holdemania filiformis|Enterobacter cancerogenus, Kingella oralis|Enterobacter cancerogenus, Klebsiella pneumoniae|Enterobacter cancerogenus, Klebsiella variicola|Enterobacter cancerogenus, Lachnospiraceae bacterium 5_1_57FAA|Enterobacter cancerogenus, Lactobacillus acidophilus|Enterobacter cancerogenus, Lactobacillus TABLE 2-continued Table 2. Specific binary combinations of OTUs. Individual pairings are differentiated by "|" and OTUs within a combination are differentiated by ","

amylovorus|Enterobacter cancerogenus, Lactobacillus brevis|Enterobacter cancerogenus, Lactobacillus casei|Enterobacter cancerogenus, Lactobacillus crispatus|Enterobacter cancerogenus, Lactobacillus delbrueckii|Enterobacter cancerogenus, Lactobacillus fermentum|Enterobacter cancerogenus, Lactobacillus gasseri|Enterobacter cancerogenus, Lactobacillus iners|Enterobacter cancerogenus, Lactobacillus jensenii|Enterobacter cancerogenus, Lactobacillus johnsonii|Enterobacter cancerogenus, Lactobacillus paracasei|Enterobacter cancerogenus, Lactobacillus plantarum|Enterobacter cancerogenus, Lactobacillus reuteri|Enterobacter cancerogenus, Lactobacillus rhamnosus|Enterobacter cancerogenus, Lactobacillus ruminis|Enterobacter cancerogenus, Lactobacillus sakei|Enterobacter cancerogenus, Lactobacillus salivarius|Enterobacter cancerogenus, Lactococcus lactis|Enterobacter cancerogenus, Lautropia mirabilis|Enterobacter cancerogenus, Leuconostoc citreum|Enterobacter cancerogenus, Leuconostoc gasicomitatum|Enterobacter cancerogenus, Leuconostoc mesenteroides|Enterobacter cancerogenus, Listeria monocytogenes|Enterobacter cancerogenus, Marvinbryantia formatexigens|Enterobacter cancerogenus, Megamonas hypermegale|Enterobacter cancerogenus, Megasphaera micronuciformis|Enterobacter cancerogenus, Methanobrevibacter smithii|Enterobacter cancerogenus, Methanosphaera stadtmanae|Enterobacter cancerogenus, Methylobacterium radiotolerans|Enterobacter cancerogenus, Mitsuokella multacida|Enterobacter cancerogenus, Mobiluncus curtisii|Enterobacter cancerogenus, Mycoplasma hominis|Enterobacter cancerogenus, Neisseria mucosa|Enterobacter cancerogenus, Odoribacter splanchnicus|Enterobacter cancerogenus, Olsenella uli|Enterobacter cancerogenus, Oribacterium sinus|Enterobacter cancerogenus, Oxalobacter formigenes|Enterobacter cancerogenus, Parabacteroides distasonis|Enterobacter cancerogenus, Parabacteroides johnsonii|Enterobacter cancerogenus, Parabacteroides merdae|Enterobacter cancerogenus, Parvimonas micra|Enterobacter cancerogenus, Pediococcus acidilactici|Enterobacter cancerogenus, Pediococcus pentosaceus|Enterobacter cancerogenus, Peptoniphilus duerdenii|Enterobacter cancerogenus, Peptoniphilus harei|Enterobacter cancerogenus, Peptoniphilus lacrimalis|Enterobacter cancerogenus, Peptostreptococcus anaerobius|Enterobacter cancerogenus, Peptostreptococcus stomatis|Enterobacter cancerogenus, Porphyromonas asaccharolytica|Enterobacter cancerogenus, Porphyromonas uenonis|Enterobacter cancerogenus, Prevotella amnii|Enterobacter cancerogenus, Prevotella bergensis|Enterobacter cancerogenus, Prevotella bivia|Enterobacter cancerogenus, Prevotella buccae|Enterobacter cancerogenus, Prevotella buccalis|Enterobacter cancerogenus, Prevotella copri|Enterobacter cancerogenus, Prevotella disiens|Enterobacter cancerogenus, Prevotella melaninogenica|Enterobacter cancerogenus, Prevotella multiformis|Enterobacter cancerogenus, Prevotella oralis|Enterobacter cancerogenus, Prevotella oris|Enterobacter cancerogenus, Prevotella salivae|Enterobacter cancerogenus, Prevotella timonensis|Enterobacter cancerogenus, Propionibacterium acnes|Enterobacter cancerogenus, Propionibacterium freudenreichii|Enterobacter cancerogenus, Proteus mirabilis|Enterobacter cancerogenus, Proteus penneri|Enterobacter cancerogenus, Pseudoflavonifractor capillosus|Enterobacter cancerogenus, Pseudomonas aeruginosa|Enterobacter cancerogenus, Pseudomonas fluorescens|Enterobacter cancerogenus, Pseudomonas putida|Enterobacter cancerogenus, Pseudoramibacter alactolyticus|Enterobacter cancerogenus, Pyramidobacter piscolens|Enterobacter cancerogenus, Rhodopseudomonas palustris|Enterobacter cancerogenus, Roseburia intestinalis|Enterobacter cancerogenus, Roseburia inulinivorans|Enterobacter cancerogenus, Rothia dentocariosa|Enterobacter cancerogenus, Rothia mucilaginosa|Enterobacter cancerogenus, Ruminococcus albus|Enterobacter cancerogenus, Ruminococcus bromii|Enterobacter cancerogenus, Ruminococcus gnavus|Enterobacter cancerogenus, Ruminococcus lactaris|Enterobacter cancerogenus, Ruminococcus obeum|Enterobacter cancerogenus, Ruminococcus torques|Enterobacter cancerogenus, Selenomonas sputigena|Enterobacter cancerogenus, Shigella boydii|Enterobacter cancerogenus, Shigella dysenteriae|Enterobacter cancerogenus, Shigella sonnei|Enterobacter cancerogenus, Slackia exigua|Enterobacter cancerogenus, Solobacterium moorei|Enterobacter cancerogenus, Staphylococcus aureus|Enterobacter cancerogenus, Staphylococcus epidermidis|Enterobacter cancerogenus, Staphylococcus hominis|Enterobacter cancerogenus, Staphylococcus saprophyticus|Enterobacter cancerogenus, Staphylococcus warneri|Enterobacter cancerogenus, Streptococcus agalactiae|Enterobacter cancerogenus, Streptococcus anginosus|Enterobacter cancerogenus, Streptococcus australis|Enterobacter cancerogenus, Streptococcus bovis|Enterobacter cancerogenus, Streptococcus cristatus|Enterobacter cancerogenus, Streptococcus dysgalactiae|Enterobacter cancerogenus, Streptococcus equinus|Enterobacter cancerogenus, Streptococcus gordonii|Enterobacter cancerogenus, Streptococcus infantarius|Enterobacter cancerogenus, Streptococcus infantis|Enterobacter cancerogenus, Streptococcus mitis|Enterobacter cancerogenus, Streptococcus mutans|Enterobacter cancerogenus, Streptococcus oralis|Enterobacter cancerogenus, Streptococcus parasanguinis|Enterobacter cancerogenus, Streptococcus peroris|Enterobacter cancerogenus, Streptococcus pneumoniae|Enterobacter cancerogenus, Streptococcus salivarius|Enterobacter cancerogenus, Streptococcus sanguinis|Enterobacter cancerogenus, Streptococcus thermophilus|Enterobacter cancerogenus, Streptococcus vestibularis|Enterobacter cancerogenus, Subdoligranulum variabile|Enterobacter cancerogenus, Succinatimonas hippei|Enterobacter cancerogenus, Sutterella wadsworthensis|Enterobacter cancerogenus, Tropheryma whipplei|Enterobacter cancerogenus, Veillonella atypica|Enterobacter cancerogenus, Veillonella dispar|Enterobacter cancerogenus, Veillonella parvula|Enterobacter cancerogenus, Victivallis vadensis|Enterobacter cloacae, Enterobacter cloacae|Enterobacter cloacae, Enterococcus faecalis|Enterobacter cloacae, Enterococcus faecium|Enterobacter cloacae, Enterococcus gallinarum|Enterobacter cloacae, Erysipelotrichaceae bacterium 3_1_53|Enterobacter cloacae, Escherichia coli|Enterobacter cloacae, Escherichia fergusonii|Enterobacter cloacae, Ethanoligenens harbinense|Enterobacter cloacae, Eubacterium cellulosolvens|Enterobacter cloacae, Eubacterium eligens|Enterobacter cloacae, Eubacterium hallii|Enterobacter cloacae, Eubacterium limosum|Enterobacter cloacae, Eubacterium rectale|Enterobacter cloacae, Eubacterium siraeum|Enterobacter cloacae, Eubacterium ventriosum|Enterobacter cloacae, Faecalibacterium prausnitzii|Enterobacter cloacae, Finegoldia magna|Enterobacter cloacae, Fusobacterium gonidiaformans|Enterobacter cloacae, Fusobacterium mortiferum|Enterobacter cloacae, Fusobacterium nucleatum|Enterobacter cloacae, Fusobacterium varium|Enterobacter cloacae, Gardnerella vaginalis|Enterobacter cloacae, Gemella haemolysans|Enterobacter cloacae, Gemella morbillorum|Enterobacter cloacae, Gordonibacter pamelaeae|Enterobacter cloacae, Granulicatella adiacens|Enterobacter cloacae, Granulicatella elegans|Enterobacter cloacae, Haemophilus influenzae|Enterobacter cloacae, Haemophilus parainfluenzae|Enterobacter cloacae, Helicobacter pullorum|Enterobacter cloacae, Helicobacter pylori|Enterobacter cloacae, Holdemania filiformis|Enterobacter cloacae, Kingella oralis|Enterobacter cloacae, Klebsiella pneumoniae|Enterobacter cloacae, Klebsiella variicola|Enterobacter cloacae, Lachnospiraceae bacterium 5_1_57FAA|Enterobacter cloacae, Lactobacillus acidophilus|Enterobacter cloacae, Lactobacillus amylovorus|Enterobacter cloacae, Lactobacillus brevis|Enterobacter cloacae, Lactobacillus casei|Enterobacter cloacae, Lactobacillus crispatus|Enterobacter cloacae, Lactobacillus delbrueckii|Enterobacter cloacae, Lactobacillus fermentum|Enterobacter cloacae, Lactobacillus gasseri|Enterobacter cloacae, Lactobacillus iners|Enterobacter cloacae, Lactobacillus jensenii|Enterobacter cloacae, Lactobacillus johnsonii|Enterobacter cloacae, Lactobacillus paracasei|Enterobacter cloacae, Lactobacillus plantarum|Enterobacter cloacae, Lactobacillus reuteri|Enterobacter cloacae, Lactobacillus rhamnosus|Enterobacter cloacae, Lactobacillus ruminis|Enterobacter cloacae, Lactobacillus sakei|Enterobacter cloacae, Lactobacillus salivarius|Enterobacter cloacae, Lactococcus lactis|Enterobacter cloacae, Lautropia mirabilis|Enterobacter cloacae, Leuconostoc citreum|Enterobacter cloacae, Leuconostoc gasicomitatum|Enterobacter cloacae, Leuconostoc mesenteroides|Enterobacter cloacae, Listeria monocytogenes|Enterobacter cloacae, Marvinbryantia formatexigens|Enterobacter cloacae, Megamonas hypermegale|Enterobacter cloacae, Megasphaera micronuciformis|Enterobacter cloacae, Methanobrevibacter smithii|Enterobacter cloacae, Methanosphaera stadtmanae|Enterobacter cloacae, Methylobacterium radiotolerans|Enterobacter cloacae, Mitsuokella multacida|Enterobacter cloacae, Mobiluncus curtisii|Enterobacter cloacae, Mycoplasma hominis|Enterobacter cloacae, Neisseria mucosa|Enterobacter cloacae, Odoribacter splanchnicus|Enterobacter cloacae, Olsenella uli|Enterobacter cloacae, Oribacterium sinus|Enterobacter cloacae, Oxalobacter formigenes|Enterobacter cloacae, Parabacteroides distasonis|Enterobacter cloacae, Parabacteroides johnsonii|Enterobacter cloacae, Parabacteroides merdae|Enterobacter cloacae, Parvimonas micra|Enterobacter cloacae, Pediococcus acidilactici|Enterobacter cloacae, Pediococcus pentosaceus|Enterobacter cloacae, Peptoniphilus duerdenii|Enterobacter cloacae, Peptoniphilus harei|Enterobacter cloacae, Peptoniphilus lacrimalis|Enterobacter cloacae, Peptostreptococcus anaerobius|Enterobacter cloacae, Peptostreptococcus stomatis|Enterobacter TABLE 2-continued

| Table 2. Specific binary combinations of OTUs. Individual pairings are differentiated by "\|" and OTUs within a combination are differentiated by "," |
|---|
| *cloacae, Porphyromonas asaccharolytica\|Enterobacter cloacae, Porphyromonas uenonis\|Enterobacter cloacae, Prevotella amnii\|Enterobacter cloacae, Prevotella bergensis\|Enterobacter cloacae, Prevotella bivia\|Enterobacter cloacae, Prevotella buccae\|Enterobacter cloacae, Prevotella buccalis\|Enterobacter cloacae, Prevotella copri\|Enterobacter cloacae, Prevotella disiens\|Enterobacter cloacae, Prevotella melaninogenica\|Enterobacter cloacae, Prevotella multiformis\|Enterobacter cloacae, Prevotella oralis\|Enterobacter cloacae, Prevotella oris\|Enterobacter cloacae, Prevotella salivae\|Enterobacter cloacae, Prevotella timonensis\|Enterobacter cloacae, Propionibacterium acnes\|Enterobacter cloacae, Propionibacterium freudenreichii\|Enterobacter cloacae, Proteus mirabilis\|Enterobacter cloacae, Proteus penneri\|Enterobacter cloacae, Pseudoflavonifractor capillosus\|Enterobacter cloacae, Pseudomonas aeruginosa\|Enterobacter cloacae, Pseudomonas fluorescens\|Enterobacter cloacae, Pseudomonas putida\|Enterobacter cloacae, Pseudoramibacter alactolyticus\|Enterobacter cloacae, Pyramidobacter piscolens\|Enterobacter cloacae, Rhodopseudomonas palustris\|Enterobacter cloacae, Roseburia intestinalis\|Enterobacter cloacae, Roseburia inulinivorans\|Enterobacter cloacae, Rothia dentocariosa\|Enterobacter cloacae, Rothia mucilaginosa\|Enterobacter cloacae, Ruminococcus albus\|Enterobacter cloacae, Ruminococcus bromii\|Enterobacter cloacae, Ruminococcus gnavus\|Enterobacter cloacae, Ruminococcus lactaris\|Enterobacter cloacae, Ruminococcus obeum\|Enterobacter cloacae, Ruminococcus torques\|Enterobacter cloacae, Selenomonas sputigena\|Enterobacter cloacae, Shigella boydii\|Enterobacter cloacae, Shigella dysenteriae\|Enterobacter cloacae, Shigella sonnei\|Enterobacter cloacae, Slackia exigua\|Enterobacter cloacae, Solobacterium moorei\|Enterobacter cloacae, Staphylococcus aureus\|Enterobacter cloacae, Staphylococcus epidermidis\|Enterobacter cloacae, Staphylococcus hominis\|Enterobacter cloacae, Staphylococcus saprophyticus\|Enterobacter cloacae, Staphylococcus warneri\|Enterobacter cloacae, Streptococcus agalactiae\|Enterobacter cloacae, Streptococcus anginosus\|Enterobacter cloacae, Streptococcus australis\|Enterobacter cloacae, Streptococcus bovis\|Enterobacter cloacae, Streptococcus cristatus\|Enterobacter cloacae, Streptococcus dysgalactiae\|Enterobacter cloacae, Streptococcus equinus\|Enterobacter cloacae, Streptococcus gordonii\|Enterobacter cloacae, Streptococcus infantarius\|Enterobacter cloacae, Streptococcus infantis\|Enterobacter cloacae, Streptococcus mitis\|Enterobacter cloacae, Streptococcus mutans\|Enterobacter cloacae, Streptococcus oralis\|Enterobacter cloacae, Streptococcus parasanguinis\|Enterobacter cloacae, Streptococcus peroris\|Enterobacter cloacae, Streptococcus pneumoniae\|Enterobacter cloacae, Streptococcus salivarius\|Enterobacter cloacae, Streptococcus sanguinis\|Enterobacter cloacae, Streptococcus thermophilus\|Enterobacter cloacae, Streptococcus vestibularis\|Enterobacter cloacae, Subdoligranulum variabile\|Enterobacter cloacae, Succinatimonas hippei\|Enterobacter cloacae, Sutterella wadsworthensis\|Enterobacter cloacae, Tropheryma whipplei\|Enterobacter cloacae, Veillonella atypica\|Enterobacter cloacae, Veillonella dispar\|Enterobacter cloacae, Veillonella parvula\|Enterobacter cloacae, Victivallis vadensis\|Enterococcus faecalis, Enterococcus faecalis\|Enterococcus faecalis, Enterococcus faecium\|Enterococcus faecalis, Enterococcus gallinarum\|Enterococcus faecalis, Erysipelotrichaceae bacterium* 3_1_53*\|Enterococcus faecalis, Escherichia coli\|Enterococcus faecalis, Escherichia fergusonii\|Enterococcus faecalis, Ethanoligenens harbinense\|Enterococcus faecalis, Eubacterium cellulosolvens\|Enterococcus faecalis, Eubacterium eligens\|Enterococcus faecalis, Eubacterium hallii\|Enterococcus faecalis, Eubacterium limosum\|Enterococcus faecalis, Eubacterium rectale\|Enterococcus faecalis, Eubacterium siraeum\|Enterococcus faecalis, Eubacterium ventriosum\|Enterococcus faecalis, Faecalibacterium prausnitzii\|Enterococcus faecalis, Finegoldia magna\|Enterococcus faecalis, Fusobacterium gonidiaformans\|Enterococcus faecalis, Fusobacterium mortiferum\|Enterococcus faecalis, Fusobacterium nucleatum\|Enterococcus faecalis, Fusobacterium varium\|Enterococcus faecalis, Gardnerella vaginalis\|Enterococcus faecalis, Gemella haemolysans\|Enterococcus faecalis, Gemella morbillorum\|Enterococcus faecalis, Gordonibacter pamelaeae\|Enterococcus faecalis, Granulicatella adiacens\|Enterococcus faecalis, Granulicatella elegans\|Enterococcus faecalis, Haemophilus influenzae\|Enterococcus faecalis, Haemophilus parainfluenzae\|Enterococcus faecalis, Helicobacter pullorum\|Enterococcus faecalis, Helicobacter pylori\|Enterococcus faecalis, Holdemania filiformis\|Enterococcus faecalis, Kingella oralis\|Enterococcus faecalis, Klebsiella pneumoniae\|Enterococcus faecalis, Klebsiella variicola\|Enterococcus faecalis, Lachnospiraceae bacterium* 5_1_57FAA*\|Enterococcus faecalis, Lactobacillus acidophilus\|Enterococcus faecalis, Lactobacillus amylovorus\|Enterococcus faecalis, Lactobacillus brevis\|Enterococcus faecalis, Lactobacillus casei\|Enterococcus faecalis, Lactobacillus crispatus\|Enterococcus faecalis, Lactobacillus delbrueckii\|Enterococcus faecalis, Lactobacillus fermentum\|Enterococcus faecalis, Lactobacillus gasseri\|Enterococcus faecalis, Lactobacillus finers\|Enterococcus faecalis, Lactobacillus jensenii\|Enterococcus faecalis, Lactobacillus johnsonii\|Enterococcus faecalis, Lactobacillus paracasei\|Enterococcus faecalis, Lactobacillus plantarum\|Enterococcus faecalis, Lactobacillus reuteri\|Enterococcus faecalis, Lactobacillus rhamnosus\|Enterococcus faecalis, Lactobacillus ruminis\|Enterococcus faecalis, Lactobacillus sakei\|Enterococcus faecalis, Lactobacillus salivarius\|Enterococcus faecalis, Lactococcus lactis\|Enterococcus faecalis, Lautropia mirabilis\|Enterococcus faecalis, Leuconostoc citreum\|Enterococcus faecalis, Leuconostoc gasicomitatum\|Enterococcus faecalis, Leuconostoc mesenteroides\|Enterococcus faecalis, Listeria monocytogenes\|Enterococcus faecalis, Marvinbryantia formatexigens\|Enterococcus faecalis, Megamonas hypermegale\|Enterococcus faecalis, Megasphaera micronuciformis\|Enterococcus faecalis, Methanobrevibacter smithii\|Enterococcus faecalis, Methanosphaera stadtmanae\|Enterococcus faecalis, Methylobacterium radiotolerans\|Enterococcus faecalis, Mitsuokella multacida\|Enterococcus faecalis, Mobiluncus curtisii\|Enterococcus faecalis, Mycoplasma hominis\|Enterococcus faecalis, Neisseria mucosa\|Enterococcus faecalis, Odoribacter splanchnicus\|Enterococcus faecalis, Olsenella uli\|Enterococcus faecalis, Oribacterium sinus\|Enterococcus faecalis, Oxalobacter formigenes\|Enterococcus faecalis, Parabacteroides distasonis\|Enterococcus faecalis, Parabacteroides johnsonii\|Enterococcus faecalis, Parabacteroides merdae\|Enterococcus faecalis, Parvimonas micra\|Enterococcus faecalis, Pediococcus acidilactici\|Enterococcus faecalis, Pediococcus pentosaceus\|Enterococcus faecalis, Peptoniphilus duerdenii\|Enterococcus faecalis, Peptoniphilus harei\|Enterococcus faecalis, Peptoniphilus lacrimalis\|Enterococcus faecalis, Peptostreptococcus anaerobius\|Enterococcus faecalis, Peptostreptococcus stomatis\|Enterococcus faecalis, Porphyromonas asaccharolytica\|Enterococcus faecalis, Porphyromonas uenonis\|Enterococcus faecalis, Prevotella amnii\|Enterococcus faecalis, Prevotella bergensis\|Enterococcus faecalis, Prevotella bivia\|Enterococcus faecalis, Prevotella buccae\|Enterococcus faecalis, Prevotella buccalis\|Enterococcus faecalis, Prevotella copri\|Enterococcus faecalis, Prevotella disiens\|Enterococcus faecalis, Prevotella melaninogenica\|Enterococcus faecalis, Prevotella multiformis\|Enterococcus faecalis, Prevotella oralis\|Enterococcus faecalis, Prevotella oris\|Enterococcus faecalis, Prevotella salivae\|Enterococcus faecalis, Prevotella timonensis\|Enterococcus faecalis, Propionibacterium acnes\|Enterococcus faecalis, Propionibacterium freudenreichii\|Enterococcus faecalis, Proteus mirabilis\|Enterococcus faecalis, Proteus penneri\|Enterococcus faecalis, Pseudoflavonifractor capillosus\|Enterococcus faecalis, Pseudomonas aeruginosa\|Enterococcus faecalis, Pseudomonas fluorescens\|Enterococcus faecalis, Pseudomonas putida\|Enterococcus faecalis, Pseudoramibacter alactolyticus\|Enterococcus faecalis, Pyramidobacter piscolens\|Enterococcus faecalis, Rhodopseudomonas palustris\|Enterococcus faecalis, Roseburia intestinalis\|Enterococcus faecalis, Roseburia inulinivorans\|Enterococcus faecalis, Rothia dentocariosa\|Enterococcus faecalis, Rothia mucilaginosa\|Enterococcus faecalis, Ruminococcus albus\|Enterococcus faecalis, Ruminococcus bromii\|Enterococcus faecalis, Ruminococcus gnavus\|Enterococcus faecalis, Ruminococcus lactaris\|Enterococcus faecalis, Ruminococcus obeum\|Enterococcus faecalis, Ruminococcus torques\|Enterococcus faecalis, Selenomonas sputigena\|Enterococcus faecalis, Shigella boydii\|Enterococcus faecalis, Shigella dysenteriae\|Enterococcus faecalis, Shigella sonnei\|Enterococcus faecalis, Slackia exigua\|Enterococcus faecalis, Solobacterium moorei\|Enterococcus faecalis, Staphylococcus aureus\|Enterococcus faecalis, Staphylococcus epidermidis\|Enterococcus faecalis, Staphylococcus hominis\|Enterococcus faecalis, Staphylococcus saprophyticus\|Enterococcus faecalis, Staphylococcus warneri\|Enterococcus faecalis, Streptococcus agalactiae\|Enterococcus faecalis, Streptococcus anginosus\|Enterococcus faecalis, Streptococcus australis\|Enterococcus faecalis, Streptococcus bovis\|Enterococcus faecalis, Streptococcus cristatus\|Enterococcus faecalis, Streptococcus dysgalactiae\|Enterococcus faecalis, Streptococcus equinus\|Enterococcus faecalis, Streptococcus gordonii\|Enterococcus faecalis, Streptococcus infantarius\|Enterococcus faecalis, Streptococcus infantis\|Enterococcus faecalis, Streptococcus mitis\|Enterococcus faecalis, Streptococcus mutans\|Enterococcus faecalis, Streptococcus oralis\|Enterococcus faecalis, Streptococcus parasanguinis\|Enterococcus faecalis, Streptococcus peroris\|Enterococcus faecalis, Streptococcus pneumoniae\|Enterococcus faecalis, Streptococcus salivarius\|Enterococcus faecalis, Streptococcus* |

TABLE 2-continued

Table 2. Specific binary combinations of OTUs. Individual pairings are differentiated by "|" and OTUs within a combination are differentiated by ","

*sanguinis|Enterococcus faecalis, Streptococcus thermophilus|Enterococcus faecalis, Streptococcus vestibularis|Enterococcus faecalis, Subdoligranulum variabile|Enterococcus faecalis, Succinatimonas hippei|Enterococcus faecalis, Sutterella wadsworthensis|Enterococcus faecalis, Tropheryma whipplei|Enterococcus faecalis, Veillonella atypica|Enterococcus faecalis, Veillonella dispar|Enterococcus faecalis, Veillonella parvula|Enterococcus faecalis, Victivallis vadensis|Enterococcus faecium, Enterococcus faecium|Enterococcus faecium, Enterococcus gallinarum|Enterococcus faecium, Erysipelotrichaceae bacterium* 3_1_53|*Enterococcus faecium, Escherichia coli|Enterococcus faecium, Escherichia fergusonii|Enterococcus faecium, Ethanoligenens harbinense|Enterococcus faecium, Eubacterium cellulosolvens|Enterococcus faecium, Eubacterium eligens|Enterococcus faecium, Eubacterium hallii|Enterococcus faecium, Eubacterium limosum|Enterococcus faecium, Eubacterium rectale|Enterococcus faecium, Eubacterium siraeum|Enterococcus faecium, Eubacterium ventriosum|Enterococcus faecium, Faecalibacterium prausnitzii|Enterococcus faecium, Finegoldia magna|Enterococcus faecium, Fusobacterium gonidiaformans|Enterococcus faecium, Fusobacterium mortiferum|Enterococcus faecium, Fusobacterium nucleatum|Enterococcus faecium, Fusobacterium varium|Enterococcus faecium, Gardnerella vaginalis|Enterococcus faecium, Gemella haemolysans|Enterococcus faecium, Gemella morbillorum|Enterococcus faecium, Gordonibacter pamelaeae|Enterococcus faecium, Granulicatella adiacens|Enterococcus faecium, Granulicatella elegans|Enterococcus faecium, Haemophilus influenzae|Enterococcus faecium, Haemophilus parainfluenzae|Enterococcus faecium, Helicobacter pullorum|Enterococcus faecium, Helicobacter pylori|Enterococcus faecium, Holdemania filiformis|Enterococcus faecium, Kingella oralis|Enterococcus faecium, Klebsiella pneumoniae|Enterococcus faecium, Klebsiella variicola|Enterococcus faecium, Lachnospiraceae bacterium* 5_1_57FAA|*Enterococcus faecium, Lactobacillus acidophilus|Enterococcus faecium, Lactobacillus amylovorus|Enterococcus faecium, Lactobacillus brevis|Enterococcus faecium, Lactobacillus casei|Enterococcus faecium, Lactobacillus crispatus|Enterococcus faecium, Lactobacillus delbrueckii|Enterococcus faecium, Lactobacillus fermentum|Enterococcus faecium, Lactobacillus gasseri|Enterococcus faecium, Lactobacillus iners|Enterococcus faecium, Lactobacillus jensenii|Enterococcus faecium, Lactobacillus johnsonii|Enterococcus faecium, Lactobacillus paracasei|Enterococcus faecium, Lactobacillus plantarum|Enterococcus faecium, Lactobacillus reuteri|Enterococcus faecium, Lactobacillus rhamnosus|Enterococcus faecium, Lactobacillus ruminis|Enterococcus faecium, Lactobacillus sakei|Enterococcus faecium, Lactobacillus salivarius|Enterococcus faecium, Lactococcus lactis|Enterococcus faecium, Lautropia mirabilis|Enterococcus faecium, Leuconostoc citreum|Enterococcus faecium, Leuconostoc gasicomitatum|Enterococcus faecium, Leuconostoc mesenteroides|Enterococcus faecium, Listeria monocytogenes|Enterococcus faecium, Marvinbryantia formatexigens|Enterococcus faecium, Megamonas hypermegale|Enterococcus faecium, Megasphaera micronuciformis|Enterococcus faecium, Methanobrevibacter smithii|Enterococcus faecium, Methanosphaera stadtmanae|Enterococcus faecium, Methylobacterium radiotolerans|Enterococcus faecium, Mitsuokella multacida|Enterococcus faecium, Mobiluncus curtisii|Enterococcus faecium, Mycoplasma hominis|Enterococcus faecium, Neisseria mucosa|Enterococcus faecium, Odoribacter splanchnicus|Enterococcus faecium, Olsenella uli|Enterococcus faecium, Oribacterium sinus|Enterococcus faecium, Oxalobacter formigenes|Enterococcus faecium, Parabacteroides distasonis|Enterococcus faecium, Parabacteroides johnsonii|Enterococcus faecium, Parabacteroides merdae|Enterococcus faecium, Parvimonas micra|Enterococcus faecium, Pediococcus acidilactici|Enterococcus faecium, Pediococcus pentosaceus|Enterococcus faecium, Peptoniphilus duerdenii|Enterococcus faecium, Peptoniphilus harei|Enterococcus faecium, Peptoniphilus lacrimalis|Enterococcus faecium, Peptostreptococcus anaerobius|Enterococcus faecium, Peptostreptococcus stomatis|Enterococcus faecium, Porphyromonas asaccharolytica|Enterococcus faecium, Porphyromonas uenonis|Enterococcus faecium, Prevotella amnii|Enterococcus faecium, Prevotella bergensis|Enterococcus faecium, Prevotella bivia|Enterococcus faecium, Prevotella buccae|Enterococcus faecium, Prevotella buccalis|Enterococcus faecium, Prevotella copri|Enterococcus faecium, Prevotella disiens|Enterococcus faecium, Prevotella melaninogenica|Enterococcus faecium, Prevotella multiformis|Enterococcus faecium, Prevotella oralis|Enterococcus faecium, Prevotella oris|Enterococcus faecium, Prevotella salivae|Enterococcus faecium, Prevotella timonensis|Enterococcus faecium, Propionibacterium acnes|Enterococcus faecium, Propionibacterium freudenreichii|Enterococcus faecium, Proteus mirabilis|Enterococcus faecium, Proteus penneri|Enterococcus faecium, Pseudoflavonifractor capillosus|Enterococcus faecium, Pseudomonas aeruginosa|Enterococcus faecium, Pseudomonas fluorescens|Enterococcus faecium, Pseudomonas putida|Enterococcus faecium, Pseudoramibacter alactolyticus|Enterococcus faecium, Pyramidobacter piscolens|Enterococcus faecium, Rhodopseudomonas palustris|Enterococcus faecium, Roseburia intestinalis|Enterococcus faecium, Roseburia inulinivorans|Enterococcus faecium, Rothia dentocariosa|Enterococcus faecium, Rothia mucilaginosa|Enterococcus faecium, Ruminococcus albus|Enterococcus faecium, Ruminococcus bromii|Enterococcus faecium, Ruminococcus gnavus|Enterococcus faecium, Ruminococcus lactaris|Enterococcus faecium, Ruminococcus obeum|Enterococcus faecium, Ruminococcus torques|Enterococcus faecium, Selenomonas sputigena|Enterococcus faecium, Shigella boydii|Enterococcus faecium, Shigella dysenteriae|Enterococcus faecium, Shigella sonnei|Enterococcus faecium, Slackia exigua|Enterococcus faecium, Solobacterium moorei|Enterococcus faecium, Staphylococcus aureus|Enterococcus faecium, Staphylococcus epidermidis|Enterococcus faecium, Staphylococcus hominis|Enterococcus faecium, Staphylococcus saprophyticus|Enterococcus faecium, Staphylococcus warneri|Enterococcus faecium, Streptococcus agalactiae|Enterococcus faecium, Streptococcus anginosus|Enterococcus faecium, Streptococcus australis|Enterococcus faecium, Streptococcus bovis|Enterococcus faecium, Streptococcus cristatus|Enterococcus faecium, Streptococcus dysgalactiae|Enterococcus faecium, Streptococcus equinus|Enterococcus faecium, Streptococcus gordonii|Enterococcus faecium, Streptococcus infantarius|Enterococcus faecium, Streptococcus infantis|Enterococcus faecium, Streptococcus mitis|Enterococcus faecium, Streptococcus mutans|Enterococcus faecium, Streptococcus oralis|Enterococcus faecium, Streptococcus parasanguinis|Enterococcus faecium, Streptococcus peroris|Enterococcus faecium, Streptococcus pneumoniae|Enterococcus faecium, Streptococcus salivarius|Enterococcus faecium, Streptococcus sanguinis|Enterococcus faecium, Streptococcus thermophilus|Enterococcus faecium, Streptococcus vestibularis|Enterococcus faecium, Subdoligranulum variabile|Enterococcus faecium, Succinatimonas hippei|Enterococcus faecium, Sutterella wadsworthensis|Enterococcus faecium, Tropheryma whipplei|Enterococcus faecium, Veillonella atypica|Enterococcus faecium, Veillonella dispar|Enterococcus faecium, Veillonella parvula|Enterococcus faecium, Victivallis vadensis|Enterococcus gallinarum, Enterococcus gallinarum|Enterococcus gallinarum, Erysipelotrichaceae bacterium* 3_1_53|*Enterococcus gallinarum, Escherichia coli|Enterococcus gallinarum, Escherichia fergusonii|Enterococcus gallinarum, Ethanoligenens harbinense|Enterococcus gallinarum, Eubacterium cellulosolvens|Enterococcus gallinarum, Eubacterium eligens|Enterococcus gallinarum, Eubacterium hallii|Enterococcus gallinarum, Eubacterium limosum|Enterococcus gallinarum, Eubacterium rectale|Enterococcus gallinarum, Eubacterium siraeum|Enterococcus gallinarum, Eubacterium ventriosum|Enterococcus gallinarum, Faecalibacterium prausnitzii|Enterococcus gallinarum, Finegoldia magna|Enterococcus gallinarum, Fusobacterium gonidiaformans|Enterococcus gallinarum, Fusobacterium mortiferum|Enterococcus gallinarum, Fusobacterium nucleatum|Enterococcus gallinarum, Fusobacterium varium|Enterococcus gallinarum, Gardnerella vaginalis|Enterococcus gallinarum, Gemella haemolysans|Enterococcus gallinarum, Gemella morbillorum|Enterococcus gallinarum, Gordonibacter pamelaeae|Enterococcus gallinarum, Granulicatella adiacens|Enterococcus gallinarum, Granulicatella elegans|Enterococcus gallinarum, Haemophilus influenzae|Enterococcus gallinarum, Haemophilus parainfluenzae|Enterococcus gallinarum, Helicobacter pullorum|Enterococcus gallinarum, Helicobacter pylori|Enterococcus gallinarum, Holdemania filiformis|Enterococcus gallinarum, Kingella oralis|Enterococcus gallinarum, Klebsiella pneumoniae|Enterococcus gallinarum, Klebsiella variicola|Enterococcus gallinarum, Lachnospiraceae bacterium* 5_1_57FAA|*Enterococcus gallinarum, Lactobacillus acidophilus|Enterococcus gallinarum, Lactobacillus amylovorus|Enterococcus gallinarum, Lactobacillus brevis|Enterococcus gallinarum, Lactobacillus casei|Enterococcus gallinarum, Lactobacillus crispatus|Enterococcus gallinarum, Lactobacillus delbrueckii|Enterococcus gallinarum, Lactobacillus fermentum|Enterococcus gallinarum, Lactobacillus gasseri|Enterococcus gallinarum, Lactobacillus iners|Enterococcus gallinarum, Lactobacillus jensenii|Enterococcus gallinarum, Lactobacillus johnsonii|Enterococcus gallinarum, Lactobacillus paracasei|Enterococcus gallinarum, Lactobacillus plantarum|Enterococcus gallinarum, Lactobacillus reuteri|Enterococcus*

TABLE 2-continued

Table 2. Specific binary combinations of OTUs. Individual pairings are differentiated by "|" and OTUs within a combination are differentiated by ","

gallinarum, Lactobacillus rhamnosus|Enterococcus gallinarum, Lactobacillus ruminis|Enterococcus gallinarum, Lactobacillus sakei|Enterococcus gallinarum, Lactobacillus salivarius|Enterococcus gallinarum, Lactococcus lactis|Enterococcus gallinarum, Lautropia mirabilis|Enterococcus gallinarum, Leuconostoc citreum|Enterococcus gallinarum, Leuconostoc gasicomitatum|Enterococcus gallinarum, Leuconostoc mesenteroides|Enterococcus gallinarum, Listeria monocytogenes|Enterococcus gallinarum, Marvinbryantia formatexigens|Enterococcus gallinarum, Megamonas hypermegale|Enterococcus gallinarum, Megasphaera micronuciformis|Enterococcus gallinarum, Methanobrevibacter smithii|Enterococcus gallinarum, Methanosphaera stadtmanae|Enterococcus gallinarum, Methylobacterium radiotolerans|Enterococcus gallinarum, Mitsuokella multacida|Enterococcus gallinarum, Mobiluncus curtisii|Enterococcus gallinarum, Mycoplasma hominis|Enterococcus gallinarum, Neisseria mucosa|Enterococcus gallinarum, Odoribacter splanchnicus|Enterococcus gallinarum, Olsenella uli|Enterococcus gallinarum, Oribacterium sinus|Enterococcus gallinarum, Oxalobacter formigenes|Enterococcus gallinarum, Parabacteroides distasonis|Enterococcus gallinarum, Parabacteroides johnsonii|Enterococcus gallinarum, Parabacteroides merdae|Enterococcus gallinarum, Parvimonas micra|Enterococcus gallinarum, Pediococcus acidilactici|Enterococcus gallinarum, Pediococcus pentosaceus|Enterococcus gallinarum, Peptoniphilus duerdenii|Enterococcus gallinarum, Peptoniphilus harei|Enterococcus gallinarum, Peptoniphilus lacrimalis|Enterococcus gallinarum, Peptostreptococcus anaerobius|Enterococcus gallinarum, Peptostreptococcus stomatis|Enterococcus gallinarum, Porphyromonas asaccharolytica|Enterococcus gallinarum, Porphyromonas uenonis|Enterococcus gallinarum, Prevotella amnii|Enterococcus gallinarum, Prevotella bergensis|Enterococcus gallinarum, Prevotella bivia|Enterococcus gallinarum, Prevotella buccae|Enterococcus gallinarum, Prevotella buccalis|Enterococcus gallinarum, Prevotella copri|Enterococcus gallinarum, Prevotella disiens|Enterococcus gallinarum, Prevotella melaninogenica|Enterococcus gallinarum, Prevotella multiformis|Enterococcus gallinarum, Prevotella oralis|Enterococcus gallinarum, Prevotella oris|Enterococcus gallinarum, Prevotella salivae|Enterococcus gallinarum, Prevotella timonensis|Enterococcus gallinarum, Propionibacterium acnes|Enterococcus gallinarum, Propionibacterium freudenreichii|Enterococcus gallinarum, Proteus mirabilis|Enterococcus gallinarum, Proteus penneri|Enterococcus gallinarum, Pseudoflavonifractor capillosus|Enterococcus gallinarum, Pseudomonas aeruginosa|Enterococcus gallinarum, Pseudomonas fluorescens|Enterococcus gallinarum, Pseudomonas putida|Enterococcus gallinarum, Pseudoramibacter alactolyticus|Enterococcus gallinarum, Pyramidobacter piscolens|Enterococcus gallinarum, Rhodopseudomonas palustris|Enterococcus gallinarum, Roseburia intestinalis|Enterococcus gallinarum, Roseburia inulinivorans|Enterococcus gallinarum, Rothia dentocariosa|Enterococcus gallinarum, Rothia mucilaginosa|Enterococcus gallinarum, Ruminococcus albus|Enterococcus gallinarum, Ruminococcus bromii|Enterococcus gallinarum, Ruminococcus gnavus|Enterococcus gallinarum, Ruminococcus lactaris|Enterococcus gallinarum, Ruminococcus obeum|Enterococcus gallinarum, Ruminococcus torques|Enterococcus gallinarum, Selenomonas sputigena|Enterococcus gallinarum, Shigella boydii|Enterococcus gallinarum, Shigella dysenteriae|Enterococcus gallinarum, Shigella sonnei|Enterococcus gallinarum, Slackia exigua|Enterococcus gallinarum, Solobacterium moorei|Enterococcus gallinarum, Staphylococcus aureus|Enterococcus gallinarum, Staphylococcus epidermidis|Enterococcus gallinarum, Staphylococcus hominis|Enterococcus gallinarum, Staphylococcus saprophyticus|Enterococcus gallinarum, Staphylococcus warneri|Enterococcus gallinarum, Streptococcus agalactiae|Enterococcus gallinarum, Streptococcus anginosus|Enterococcus gallinarum, Streptococcus australis|Enterococcus gallinarum, Streptococcus bovis|Enterococcus gallinarum, Streptococcus cristatus|Enterococcus gallinarum, Streptococcus dysgalactiae|Enterococcus gallinarum, Streptococcus equinus|Enterococcus gallinarum, Streptococcus gordonii|Enterococcus gallinarum, Streptococcus infantarius|Enterococcus gallinarum, Streptococcus infantis|Enterococcus gallinarum, Streptococcus mitis|Enterococcus gallinarum, Streptococcus mutans|Enterococcus gallinarum, Streptococcus oralis|Enterococcus gallinarum, Streptococcus parasanguinis|Enterococcus gallinarum, Streptococcus peroris|Enterococcus gallinarum, Streptococcus pneumoniae|Enterococcus gallinarum, Streptococcus salivarius|Enterococcus gallinarum, Streptococcus sanguinis|Enterococcus gallinarum, Streptococcus thermophilus|Enterococcus gallinarum, Streptococcus vestibularis|Enterococcus gallinarum, Subdoligranulum variabile|Enterococcus gallinarum, Succinatimonas hippei|Enterococcus gallinarum, Sutterella wadsworthensis|Enterococcus gallinarum, Tropheryma whipplei|Enterococcus gallinarum, Veillonella atypica|Enterococcus gallinarum, Veillonella dispar|Enterococcus gallinarum, Veillonella parvula|Enterococcus gallinarum, Victivallis vadensis|Erysipelotrichaceae bacterium 3_1_53, Erysipelotrichaceae bacterium 3_1_53|Erysipelotrichaceae bacterium 3_1_53, Escherichia coli|Erysipelotrichaceae bacterium 3_1_53, Escherichia fergusonii|Erysipelotrichaceae bacterium 3_1_53, Ethanoligenens harbinense|Erysipelotrichaceae bacterium 3_1_53, Eubacterium cellulosolvens|Erysipelotrichaceae bacterium 3_1_53, Eubacterium eligens|Erysipelotrichaceae bacterium 3_1_53, Eubacterium hallii|Erysipelotrichaceae bacterium 3_1_53, Eubacterium limosum|Erysipelotrichaceae bacterium 3_1_53, Eubacterium rectale|Erysipelotrichaceae bacterium 3_1_53, Eubacterium siraeum|Erysipelotrichaceae bacterium 3_1_53, Eubacterium ventriosum|Erysipelotrichaceae bacterium 3_1_53, Faecalibacterium prausnitzii|Erysipelotrichaceae bacterium 3_1_53, Finegoldia magna|Erysipelotrichaceae bacterium 3_1_53, Fusobacterium gonidiaformans|Erysipelotrichaceae bacterium 3_1_53, Fusobacterium mortiferum|Erysipelotrichaceae bacterium 3_1_53, Fusobacterium nucleatum|Erysipelotrichaceae bacterium 3_1_53, Fusobacterium varium|Erysipelotrichaceae bacterium 3_1_53, Gardnerella vaginalis|Erysipelotrichaceae bacterium 3_1_53, Gemella haemolysans|Erysipelotrichaceae bacterium 3_1_53, Gemella morbillorum|Erysipelotrichaceae bacterium 3_1_53, Gordonibacter pamelaeae|Erysipelotrichaceae bacterium 3_1_53, Granulicatella adiacens|Erysipelotrichaceae bacterium 3_1_53, Granulicatella elegans|Erysipelotrichaceae bacterium 3_1_53, Haemophilus influenzae|Erysipelotrichaceae bacterium 3_1_53, Haemophilus parainfluenzae|Erysipelotrichaceae bacterium 3_1_53, Helicobacter pullorum|Erysipelotrichaceae bacterium 3_1_53, Helicobacter pylori|Erysipelotrichaceae bacterium 3_1_53, Holdemania filiformis|Erysipelotrichaceae bacterium 3_1_53, Kingella oralis|Erysipelotrichaceae bacterium 3_1_53, Klebsiella pneumoniae|Erysipelotrichaceae bacterium 3_1_53, Klebsiella variicola|Erysipelotrichaceae bacterium 3_1_53, Lachnospiraceae bacterium 5_1_57FAA|Erysipelotrichaceae bacterium 3_1_53, Lactobacillus acidophilus|Erysipelotrichaceae bacterium 3_1_53, Lactobacillus amylovorus|Erysipelotrichaceae bacterium 3_1_53, Lactobacillus brevis|Erysipelotrichaceae bacterium 3_1_53, Lactobacillus casei|Erysipelotrichaceae bacterium 3_1_53, Lactobacillus crispatus|Erysipelotrichaceae bacterium 3_1_53, Lactobacillus delbrueckii|Erysipelotrichaceae bacterium 3_1_53, Lactobacillus fermentum|Erysipelotrichaceae bacterium 3_1_53, Lactobacillus gasseri|Erysipelotrichaceae bacterium 3_1_53, Lactobacillus iners|Erysipelotrichaceae bacterium 3_1_53, Lactobacillus jensenii|Erysipelotrichaceae bacterium 3_1_53, Lactobacillus johnsonii|Erysipelotrichaceae bacterium 3_1_53, Lactobacillus paracasei|Erysipelotrichaceae bacterium 3_1_53, Lactobacillus plantarum|Erysipelotrichaceae bacterium 3_1_53, Lactobacillus reuteri|Erysipelotrichaceae bacterium 3_1_53, Lactobacillus rhamnosus|Erysipelotrichaceae bacterium 3_1_53, Lactobacillus ruminis|Erysipelotrichaceae bacterium 3_1_53, Lactobacillus sakei|Erysipelotrichaceae bacterium 3_1_53, Lactobacillus salivarius|Erysipelotrichaceae bacterium 3_1_53, Lactococcus lactis|Erysipelotrichaceae bacterium 3_1_53, Lautropia mirabilis|Erysipelotrichaceae bacterium 3_1_53, Leuconostoc citreum|Erysipelotrichaceae bacterium 3_1_53, Leuconostoc gasicomitatum|Erysipelotrichaceae bacterium 3_1_53, Leuconostoc mesenteroides|Erysipelotrichaceae bacterium 3_1_53, Listeria monocytogenes|Erysipelotrichaceae bacterium 3_1_53, Marvinbryantia formatexigens|Erysipelotrichaceae bacterium 3_1_53, Megamonas hypermegale|Erysipelotrichaceae bacterium 3_1_53, Megasphaera micronuciformis|Erysipelotrichaceae bacterium 3_1_53, Methanobrevibacter smithii|Erysipelotrichaceae bacterium 3_1_53, Methanosphaera stadtmanae|Erysipelotrichaceae bacterium 3_1_53, Methylobacterium radiotolerans|Erysipelotrichaceae bacterium 3_1_53, Mitsuokella multacida|Erysipelotrichaceae bacterium 3_1_53, Mobiluncus curtisii|Erysipelotrichaceae bacterium 3_1_53, Mycoplasma hominis|Erysipelotrichaceae bacterium 3_1_53, Neisseria mucosa|Erysipelotrichaceae bacterium 3_1_53, Odoribacter splanchnicus|Erysipelotrichaceae bacterium 3_1_53, Olsenella uli|Erysipelotrichaceae bacterium 3_1_53, Oribacterium sinus|Erysipelotrichaceae bacterium 3_1_53, Oxalobacter formigenes|Erysipelotrichaceae bacterium 3_1_53, Parabacteroides distasonis|Erysipelotrichaceae bacterium 3_1_53, Parabacteroides johnsonii|Erysipelotrichaceae bacterium 3_1_53, Parabacteroides merdae|Erysipelotrichaceae bacterium 3_1_53, Parvimonas TABLE 2-continued

| Table 2. Specific binary combinations of OTUs. Individual pairings are differentiated by "\|" and OTUs within a combination are differentiated by "," |
|---|
| micra\|Erysipelotrichaceae bacterium 3_1_53, Pediococcus acidilactici\|Erysipelotrichaceae bacterium 3_1_53, Pediococcus pentosaceus\|Erysipelotrichaceae bacterium 3_1_53, Peptoniphilus duerdenii\|Erysipelotrichaceae bacterium 3_1_53, Peptoniphilus harei\|Erysipelotrichaceae bacterium 3_1_53, Peptoniphilus lacrimalis\|Erysipelotrichaceae bacterium 3_1_53, Peptostreptococcus anaerobius\|Erysipelotrichaceae bacterium 3_1_53, Peptostreptococcus stomatis\|Erysipelotrichaceae bacterium 3_1_53, Porphyromonas asaccharolytica\|Erysipelotrichaceae bacterium 3_1_53, Porphyromonas uenonis\|Erysipelotrichaceae bacterium 3_1_53, Prevotella amnii\|Erysipelotrichaceae bacterium 3_1_53, Prevotella bergensis\|Erysipelotrichaceae bacterium 3_1_53, Prevotella bivia\|Erysipelotrichaceae bacterium 3_1_53, Prevotella buccae\|Erysipelotrichaceae bacterium 3_1_53, Prevotella buccalis\|Erysipelotrichaceae bacterium 3_1_53, Prevotella copri\|Erysipelotrichaceae bacterium 3_1_53, Prevotella disiens\|Erysipelotrichaceae bacterium 3_1_53, Prevotella melaninogenica\|Erysipelotrichaceae bacterium 3_1_53, Prevotella multiformis\|Erysipelotrichaceae bacterium 3_1_53, Prevotella oralis\|Erysipelotrichaceae bacterium 3_1_53, Prevotella oris\|Erysipelotrichaceae bacterium 3_1_53, Prevotella salivae\|Erysipelotrichaceae bacterium 3_1_53, Prevotella timonensis\|Erysipelotrichaceae bacterium 3_1_53, Propionibacterium acnes\|Erysipelotrichaceae bacterium 3_1_53, Propionibacterium freudenreichii\|Erysipelotrichaceae bacterium 3_1_53, Proteus mirabilis\|Erysipelotrichaceae bacterium 3_1_53, Proteus penneri\|Erysipelotrichaceae bacterium 3_1_53, Pseudoflavonifractor capillosus\|Erysipelotrichaceae bacterium 3_1_53, Pseudomonas aeruginosa\|Erysipelotrichaceae bacterium 3_1_53, Pseudomonas fluorescens\|Erysipelotrichaceae bacterium 3_1_53, Pseudomonas putida\|Erysipelotrichaceae bacterium 3_1_53, Pseudoramibacter alactolyticus\|Erysipelotrichaceae bacterium 3_1_53, Pyramidobacter piscolens\|Erysipelotrichaceae bacterium 3_1_53, Rhodopseudomonas palustris\|Erysipelotrichaceae bacterium 3_1_53, Roseburia intestinalis\|Erysipelotrichaceae bacterium 3_1_53, Roseburia inulinivorans\|Erysipelotrichaceae bacterium 3_1_53, Rothia dentocariosa\|Erysipelotrichaceae bacterium 3_1_53, Rothia mucilaginosa\|Erysipelotrichaceae bacterium 3_1_53, Ruminococcus albus\|Erysipelotrichaceae bacterium 3_1_53, Ruminococcus bromii\|Erysipelotrichaceae bacterium 3_1_53, Ruminococcus gnavus\|Erysipelotrichaceae bacterium 3_1_53, Ruminococcus lactaris\|Erysipelotrichaceae bacterium 3_1_53, Ruminococcus obeum\|Erysipelotrichaceae bacterium 3_1_53, Ruminococcus torques\|Erysipelotrichaceae bacterium 3_1_53, Selenomonas sputigena\|Erysipelotrichaceae bacterium 3_1_53, Shigella boydii\|Erysipelotrichaceae bacterium 3_1_53, Shigella dysenteriae\|Erysipelotrichaceae bacterium 3_1_53, Shigella sonnei\|Erysipelotrichaceae bacterium 3_1_53, Slackia exigua\|Erysipelotrichaceae bacterium 3_1_53, Solobacterium moorei\|Erysipelotrichaceae bacterium 3_1_53, Staphylococcus aureus\|Erysipelotrichaceae bacterium 3_1_53, Staphylococcus epidermidis\|Erysipelotrichaceae bacterium 3_1_53, Staphylococcus hominis\|Erysipelotrichaceae bacterium 3_1_53, Staphylococcus saprophyticus\|Erysipelotrichaceae bacterium 3_1_53, Staphylococcus warneri\|Erysipelotrichaceae bacterium 3_1_53, Streptococcus agalactiae\|Erysipelotrichaceae bacterium 3_1_53, Streptococcus anginosus\|Erysipelotrichaceae bacterium 3_1_53, Streptococcus australis\|Erysipelotrichaceae bacterium 3_1_53, Streptococcus bovis\|Erysipelotrichaceae bacterium 3_1_53, Streptococcus cristatus\|Erysipelotrichaceae bacterium 3_1_53, Streptococcus dysgalactiae\|Erysipelotrichaceae bacterium 3_1_53, Streptococcus equinus\|Erysipelotrichaceae bacterium 3_1_53, Streptococcus gordonii\|Erysipelotrichaceae bacterium 3_1_53, Streptococcus infantarius\|Erysipelotrichaceae bacterium 3_1_53, Streptococcus infantis\|Erysipelotrichaceae bacterium 3_1_53, Streptococcus mitis\|Erysipelotrichaceae bacterium 3_1_53, Streptococcus mutans\|Erysipelotrichaceae bacterium 3_1_53, Streptococcus oralis\|Erysipelotrichaceae bacterium 3_1_53, Streptococcus parasanguinis\|Frysipelotrichaceae bacterium 3_1_53, Streptococcus peroris\|Erysipelotrichaceae bacterium 3_1_53, Streptococcus pneumoniae\|Erysipelotrichaceae bacterium 3_1_53, Streptococcus salivarius\|Erysipelotrichaceae bacterium 3_1_53, Streptococcus sanguinis\|Erysipelotrichaceae bacterium 3_1_53, Streptococcus thermophilus\|Erysipelotrichaceae bacterium 3_1_53, Streptococcus vestibularis\|Erysipelotrichaceae bacterium 3_1_53, Subdoligranulum variabile\|Erysipelotrichaceae bacterium 3_1_53, Succinatimonas hippei\|Erysipelotrichaceae bacterium 3_1_53, Sutterella wadsworthensis\|Erysipelotrichaceae bacterium 3_1_53, Tropheryma whipplei\|Erysipelotrichaceae bacterium 3_1_53, Veillonella atypica\|Erysipelotrichaceae bacterium 3_1_53, Veillonella dispar\|Erysipelotrichaceae bacterium 3_1_53, Veillonella parvula\|Erysipelotrichaceae bacterium 3_1_53, Victivallis vadensis\|Escherichia coli, Escherichia coli\|Escherichia coli, Escherichia fergusonii\|Escherichia coli, Ethanoligenens harbinense\|Escherichia coli, Eubacterium cellulosolvens\|Escherichia coli, Eubacterium eligens\|Escherichia coli, Eubacterium hallii\|Escherichia coli, Eubacterium limosum\|Escherichia coli, Eubacterium rectale\|Escherichia coli, Eubacterium siraeum\|Escherichia coli, Eubacterium ventriosum\|Escherichia coli, Faecalibacterium prausnitzii\|Escherichia coli, Finegoldia magna\|Escherichia coli, Fusobacterium gonidiaformans\|Escherichia coli, Fusobacterium mortiferum\|Escherichia coli, Fusobacterium nucleatum\|Escherichia coli, Fusobacterium varium\|Escherichia coli, Gardnerella vaginalis\|Escherichia coli, Gemella haemolysans\|Escherichia coli, Gemella morbillorum\|Escherichia coli, Gordonibacter pamelaeae\|Escherichia coli, Granulicatella adiacens\|Escherichia coli, Granulicatella elegans\|Escherichia coli, Haemophilus influenzae\|Escherichia coli, Haemophilus parainfluenzae\|Escherichia coli, Helicobacter pullorum\|Escherichia coli, Helicobacter pylori\|Escherichia coli, Holdemania filiformis\|Escherichia coli, Kingella oralis\|Escherichia coli, Klebsiella pneumoniae\|Escherichia coli, Klebsiella variicola\|Escherichia coli, Lachnospiraceae bacterium 5_1_57FAA\|Escherichia coli, Lactobacillus acidophilus\|Escherichia coli, Lactobacillus amylovorus\|Escherichia coli, Lactobacillus brevis\|Escherichia coli, Lactobacillus casei\|Escherichia coli, Lactobacillus crispatus\|Escherichia coli, Lactobacillus delbrueckii\|Escherichia coli, Lactobacillus fermentum\|Escherichia coli, Lactobacillus gasseri\|Escherichia coli, Lactobacillus iners\|Escherichia coli, Lactobacillus jensenii\|Escherichia coli, Lactobacillus johnsonii\|Escherichia coli, Lactobacillus paracasei\|Escherichia coli, Lactobacillus plantarum\|Escherichia coli, Lactobacillus reuteri\|Escherichia coli, Lactobacillus rhamnosus\|Escherichia coli, Lactobacillus ruminis\|Escherichia coli, Lactobacillus sakei\|Escherichia coli, Lactobacillus salivarius\|Escherichia coli, Lactococcus lactis\|Escherichia coli, Lautropia mirabilis\|Escherichia coli, Leuconostoc citreum\|Escherichia coli, Leuconostoc gasicomitatum\|Escherichia coli, Leuconostoc mesenteroides\|Escherichia coli, Listeria monocytogenes\|Escherichia coli, Marvinbryantia formatexigens\|Escherichia coli, Megamonas hypermegale\|Escherichia coli, Megasphaera micronuciformis\|Escherichia coli, Methanobrevibacter smithii\|Escherichia coli, Methanosphaera stadtmanae\|Escherichia coli, Methylobacterium radiotolerans\|Escherichia coli, Mitsuokella multacida\|Escherichia coli, Mobiluncus curtisii\|Escherichia coli, Mycoplasma hominis\|Escherichia coli, Neisseria mucosa\|Escherichia coli, Odoribacter splanchnicus\|Escherichia coli, Olsenella uli\|Escherichia coli, Oribacterium sinus\|Escherichia coli, Oxalobacter formigenes\|Escherichia coli, Parabacteroides distasonis\|Escherichia coli, Parabacteroides johnsonii\|Escherichia coli, Parabacteroides merdae\|Escherichia coli, Parvimonas micra\|Escherichia coli, Pediococcus acidilactici\|Escherichia coli, Pediococcus pentosaceus\|Escherichia coli, Peptoniphilus duerdenii\|Escherichia coli, Peptoniphilus harei\|Escherichia coli, Peptoniphilus lacrimalis\|Escherichia coli, Peptostreptococcus anaerobius\|Escherichia coli, Peptostreptococcus stomatis\|Escherichia coli, Porphyromonas asaccharolytica\|Escherichia coli, Porphyromonas uenonis\|Escherichia coli, Prevotella amnii\|Escherichia coli, Prevotella bergensis\|Escherichia coli, Prevotella bivia\|Escherichia coli, Prevotella buccae\|Escherichia coli, Prevotella buccalis\|Escherichia coli, Prevotella copri\|Escherichia coli, Prevotella disiens\|Escherichia coli, Prevotella melaninogenica\|Escherichia coli, Prevotella multiformis\|Escherichia coli, Prevotella oralis\|Escherichia coli, Prevotella oris\|Escherichia coli, Prevotella salivae\|Escherichia coli, Prevotella timonensis\|Escherichia coli, Propionibacterium acnes\|Escherichia coli, Propionibacterium freudenreichii\|Escherichia coli, Proteus mirabilis\|Escherichia coli, Proteus penneri\|Escherichia coli, Pseudoflavonifractor capillosus\|Escherichia coli, Pseudomonas aeruginosa\|Escherichia coli, Pseudomonas fluorescens\|Escherichia coli, Pseudomonas putida\|Escherichia coli, Pseudoramibacter alactolyticus\|Escherichia coli, Pyramidobacter piscolens\|Escherichia coli, Rhodopseudomonas palustris\|Escherichia coli, Roseburia intestinalis\|Escherichia coli, Roseburia inulinivorans\|Escherichia coli, Rothia dentocariosa\|Escherichia coli, Rothia mucilaginosa\|Escherichia coli, Ruminococcus albus\|Escherichia coli, Ruminococcus bromii\|Escherichia coli, Ruminococcus gnavus\|Escherichia coli, Ruminococcus lactaris\|Escherichia coli, Ruminococcus obeum\|Escherichia coli, Ruminococcus torques\|Escherichia coli, Selenomonas sputigena\|Escherichia coli, Shigella boydii\|Escherichia coli, Shigella dysenteriae\|Escherichia coli, Shigella sonnei\|Escherichia coli, Slackia exigua\|Escherichia coli, Solobacterium moorei\|Escherichia coli, Staphylococcus aureus\|Escherichia |

TABLE 2-continued

| Table 2. Specific binary combinations of OTUs. Individual pairings are differentiated by "\|" and OTUs within a combination are differentiated by "," |
|---|
| coli, Staphylococcus epidermidis\|Escherichia coli, Staphylococcus hominis\|Escherichia coli, Staphylococcus saprophyticus\|Escherichia coli, Staphylococcus warneri\|Escherichia coli, Streptococcus agalactiae\|Escherichia coli, Streptococcus anginosus\|Escherichia coli, Streptococcus australis\|Escherichia coli, Streptococcus bovis\|Escherichia coli, Streptococcus cristatus\|Escherichia coli, Streptococcus dysgalactiae\|Escherichia coli, Streptococcus equinus\|Escherichia coli, Streptococcus gordonii\|Escherichia coli, Streptococcus infantarius\|Escherichia coli, Streptococcus infantis\|Escherichia coli, Streptococcus mitis\|Escherichia coli, Streptococcus mutans\|Escherichia coli, Streptococcus oralis\|Escherichia coli, Streptococcus parasanguinis\|Escherichia coli, Streptococcus peroris\|Escherichia coli, Streptococcus pneumoniae\|Escherichia coli, Streptococcus salivarius\|Escherichia coli, Streptococcus sanguinis\|Escherichia coli, Streptococcus thermophilus\|Escherichia coli, Streptococcus vestibularis\|Escherichia coli, Subdoligranulum variabile\|Escherichia coli, Succinatimonas hippei\|Escherichia coli, Sutterella wadsworthensis\|Escherichia coli, Tropheryma whipplei\|Escherichia coli, Veillonella atypica\|Escherichia coli, Veillonella dispar\|Escherichia coli, Veillonella parvula\|Escherichia coli, Victivallis vadensis\|Escherichia fergusonii, Escherichia fergusonii\|Escherichia fergusonii, Ethanoligenens harbinense\|Escherichia fergusonii, Eubacterium cellulosolvens\|Escherichia fergusonii, Eubacterium eligens\|Escherichia fergusonii, Eubacterium hallii\|Escherichia fergusonii, Eubacterium limosum\|Escherichia fergusonii, Eubacterium rectale\|Escherichia fergusonii, Eubacterium siraeum\|Escherichia fergusonii, Eubacterium ventriosum\|Escherichia fergusonii, Faecalibacterium prausnitzii\|Escherichia fergusonii, Finegoldia magna\|Escherichia fergusonii, Fusobacterium gonidiaformans\|Escherichia fergusonii, Fusobacterium mortiferum\|Escherichia fergusonii, Fusobacterium nucleatum\|Escherichia fergusonii, Fusobacterium varium\|Escherichia fergusonii, Gardnerella vaginalis\|Escherichia fergusonii, Gemella haemolysans\|Escherichia fergusonii, Gemella morbillorum\|Escherichia fergusonii, Gordonibacter pamelaeae\|Escherichia fergusonii, Granulicatella adiacens\|Escherichia fergusonii, Granulicatella elegans\|Escherichia fergusonii, Haemophilus influenzae\|Escherichia fergusonii, Haemophilus parainfluenzae\|Escherichia fergusonii, Helicobacter pullorum\|Escherichia fergusonii, Helicobacter pylori\|Escherichia fergusonii, Holdemania filiformis\|Escherichia fergusonii, Kingella oralis\|Escherichia fergusonii, Klebsiella pneumoniae\|Escherichia fergusonii, Klebsiella variicola\|Escherichia fergusonii, Lachnospiraceae bacterium 5_1_57FAA\|Escherichia fergusonii, Lactobacillus acidophilus\|Escherichia fergusonii, Lactobacillus amylovorus\|Escherichia fergusonii, Lactobacillus brevis\|Escherichia fergusonii, Lactobacillus casei\|Escherichia fergusonii, Lactobacillus crispatus\|Escherichia fergusonii, Lactobacillus delbrueckii\|Escherichia fergusonii, Lactobacillus fermentum\|Escherichia fergusonii, Lactobacillus gasseri\|Escherichia fergusonii, Lactobacillus iners\|Escherichia fergusonii, Lactobacillus jensenii\|Escherichia fergusonii, Lactobacillus johnsonii\|Escherichia fergusonii, Lactobacillus paracasei\|Escherichia fergusonii, Lactobacillus plantarum\|Escherichia fergusonii, Lactobacillus reuteri\|Escherichia fergusonii, Lactobacillus rhamnosus\|Escherichia fergusonii, Lactobacillus ruminis\|Escherichia fergusonii, Lactobacillus sakei\|Escherichia fergusonii, Lactobacillus salivarius\|Escherichia fergusonii, Lactococcus lactis\|Escherichia fergusonii, Lautropia mirabilis\|Escherichia fergusonii, Leuconostoc citreum\|Escherichia fergusonii, Leuconostoc gasicomitatum\|Escherichia fergusonii, Leuconostoc mesenteroides\|Escherichia fergusonii, Listeria monocytogenes\|Escherichia fergusonii, Marvinbryantia formatexigens\|Escherichia fergusonii, Megamonas hypermegale\|Escherichia fergusonii, Megasphaera micronuciformis\|Escherichia fergusonii, Methanobrevibacter smithii\|Escherichia fergusonii, Methanosphaera stadtmanae\|Escherichia fergusonii, Methylobacterium radiotolerans\|Escherichia fergusonii, Mitsuokella multacida\|Escherichia fergusonii, Mobiluncus curtisii\|Escherichia fergusonii, Mycoplasma hominis\|Escherichia fergusonii, Neisseria mucosa\|Escherichia fergusonii, Odoribacter splanchnicus\|Escherichia fergusonii, Olsenella uli\|Escherichia fergusonii, Oribacterium sinus\|Escherichia fergusonii, Oxalobacter formigenes\|Escherichia fergusonii, Parabacteroides distasonis\|Escherichia fergusonii, Parabacteroides johnsonii\|Escherichia fergusonii, Parabacteroides merdae\|Escherichia fergusonii, Parvimonas micra\|Escherichia fergusonii, Pediococcus acidilactici\|Escherichia fergusonii, Pediococcus pentosaceus\|Escherichia fergusonii, Peptoniphilus duerdenii\|Escherichia fergusonii, Peptoniphilus harei\|Escherichia fergusonii, Peptoniphilus lacrimalis\|Escherichia fergusonii, Peptostreptococcus anaerobius\|Escherichia fergusonii, Peptostreptococcus stomatis\|Escherichia fergusonii, Porphyromonas asaccharolytica\|Escherichia fergusonii, Porphyromonas uenonis\|Escherichia fergusonii, Prevotella amnii\|Escherichia fergusonii, Prevotella bergensis\|Escherichia fergusonii, Prevotella bivia\|Escherichia fergusonii, Prevotella buccae\|Escherichia fergusonii, Prevotella buccalis\|Escherichia fergusonii, Prevotella copri\|Escherichia fergusonii, Prevotella disiens\|Escherichia fergusonii, Prevotella melaninogenica\|Escherichia fergusonii, Prevotella multiformis\|Escherichia fergusonii, Prevotella oralis\|Escherichia fergusonii, Prevotella oris\|Escherichia fergusonii, Prevotella salivae\|Escherichia fergusonii, Prevotella timonensis\|Escherichia fergusonii, Propionibacterium acnes\|Escherichia fergusonii, Propionibacterium freudenreichii\|Escherichia fergusonii, Proteus mirabilis\|Escherichia fergusonii, Proteus penneri\|Escherichia fergusonii, Pseudoflavonifractor capillosus\|Escherichia fergusonii, Pseudomonas aeruginosa\|Escherichia fergusonii, Pseudomonas fluorescens\|Escherichia fergusonii, Pseudomonas putida\|Escherichia fergusonii, Pseudoramibacter alactolyticus\|Escherichia fergusonii, Pyramidobacter piscolens\|Escherichia fergusonii, Rhodopseudomonas palustris\|Escherichia fergusonii, Roseburia intestinalis\|Escherichia fergusonii, Roseburia inulinivorans\|Escherichia fergusonii, Rothia dentocariosa\|Escherichia fergusonii, Rothia mucilaginosa\|Escherichia fergusonii, Ruminococcus albus\|Escherichia fergusonii, Ruminococcus bromii\|Escherichia fergusonii, Ruminococcus gnavus\|Escherichia fergusonii, Ruminococcus lactaris\|Escherichia fergusonii, Ruminococcus obeum\|Escherichia fergusonii, Ruminococcus torques\|Escherichia fergusonii, Selenomonas sputigena\|Escherichia fergusonii, Shigella boydii\|Escherichia fergusonii, Shigella dysenteriae\|Escherichia fergusonii, Shigella sonnei\|Escherichia fergusonii, Slackia exigua\|Escherichia fergusonii, Solobacterium moorei\|Escherichia fergusonii, Staphylococcus aureus\|Escherichia fergusonii, Staphylococcus epidermidis\|Escherichia fergusonii, Staphylococcus hominis\|Escherichia fergusonii, Staphylococcus saprophyticus\|Escherichia fergusonii, Staphylococcus warneri\|Escherichia fergusonii, Streptococcus agalactiae\|Escherichia fergusonii, Streptococcus anginosus\|Escherichia fergusonii, Streptococcus australis\|Escherichia fergusonii, Streptococcus bovis\|Escherichia fergusonii, Streptococcus cristatus\|Escherichia fergusonii, Streptococcus dysgalactiae\|Escherichia fergusonii, Streptococcus equinus\|Escherichia fergusonii, Streptococcus gordonii\|Escherichia fergusonii, Streptococcus infantarius\|Escherichia fergusonii, Streptococcus infantis\|Escherichia fergusonii, Streptococcus mitis\|Escherichia fergusonii, Streptococcus mutans\|Escherichia fergusonii, Streptococcus oralis\|Escherichia fergusonii, Streptococcus parasanguinis\|Escherichia fergusonii, Streptococcus peroris\|Escherichia fergusonii, Streptococcus pneumoniae\|Escherichia fergusonii, Streptococcus salivarius\|Escherichia fergusonii, Streptococcus sanguinis\|Escherichia fergusonii, Streptococcus thennophilus\|Escherichia fergusonii, Streptococcus vestibularis\|Escherichia fergusonii, Subdoligranulum variabile\|Escherichia fergusonii, Succinatimonas hippei\|Escherichia fergusonii, Sutterella wadsworthensis\|Escherichia fergusonii, Tropheryma whipplei\|Escherichia fergusonii, Veillonella atypica\|Escherichia fergusonii, Veillonella dispar\|Escherichia fergusonii, Veillonella parvula\|Escherichia fergusonii, Victivallis vadensis\|Ethanoligenens harbinense, Ethanoligenens harbinense\|Ethanoligenens harbinense, Eubacterium cellulosolvens\|Ethanoligenens harbinense, Eubacterium eligens\|Ethanoligenens harbinense, Eubacterium hallii\|Ethanoligenens harbinense, Eubacterium limosum\|Ethanoligenens harbinense, Eubacterium rectale\|Ethanoligenens harbinense, Eubacterium siraeum\|Ethanoligenens harbinense, Eubacterium ventriosum\|Ethanoligenens harbinense, Faecalibacterium prausnitzii\|Ethanoligenens harbinense, Finegoldia magna\|Ethanoligenens harbinense, Fusobacterium gonidiaformans\|Ethanoligenens harbinense, Fusobacterium mortiferum\|Ethanoligenens harbinense, Fusobacterium nucleatum\|Ethanoligenens harbinense, Fusobacterium varium\|Ethanoligenens harbinense, Gardnerella vaginalis\|Ethanoligenens harbinense, Gemella haemolysans\|Ethanoligenens harbinense, Gemella morbillorum\|Ethanoligenens harbinense, Gordonibacter pamelaeae\|Ethanoligenens harbinense, Granulicatella adiacens\|Ethanoligenens harbinense, Granulicatella elegans\|Ethanoligenens harbinense, Haemophilus influenzae\|Ethanoligenens harbinense, Haemophilus parainfluenzae\|Ethanoligenens harbinense, Helicobacter pullorum\|Ethanoligenens harbinense, Helicobacter pylori\|Ethanoligenens harbinense, Holdemania filiformis\|Ethanoligenens harbinense, Kingella oralis\|Ethanoligenens harbinense, Klebsiella pneumoniae\|Ethanoligenens harbinense, Klebsiella variicola\|Ethanoligenens harbinense, Lachnospiraceae bacterium 5_1_57FAA\|Ethanoligenens harbinense, Lactobacillus acidophilus\|Ethanoligenens harbinense, Lactobacillus amylovorus\|Ethanoligenens harbinense, Lactobacillus brevis\|Ethanoligenens harbinense, Lactobacillus casei\|Ethanoligenens |

TABLE 2-continued

Table 2. Specific binary combinations of OTUs. Individual pairings are differentiated by "|" and OTUs within a combination are differentiated by ","

*harbinense, Lactobacillus crispatus|Ethanoligenens harbinense, Lactobacillus delbrueckii|Ethanoligenens harbinense, Lactobacillus fermentum|Ethanoligenens harbinense, Lactobacillus gasseri|Ethanoligenens harbinense, Lactobacillus iners|Ethanoligenens harbinense, Lactobacillus jensenii|Ethanoligenens harbinense, Lactobacillus johnsonii|Ethanoligenens harbinense, Lactobacillus paracasei|Ethanoligenens harbinense, Lactobacillus plantarum|Ethanoligenens harbinense, Lactobacillus reuteri|Ethanoligenens harbinense, Lactobacillus rhamnosus|Ethanoligenens harbinense, Lactobacillus ruminis|Ethanoligenens harbinense, Lactobacillus sakei|Ethanoligenens harbinense, Lactobacillus salivarius|Ethanoligenens harbinense, Lactococcus lactis|Ethanoligenens harbinense, Lautropia mirabilis|Ethanoligenens harbinense, Leuconostoc citreum|Ethanoligenens harbinense, Leuconostoc gasicomitatum|Ethanoligenens harbinense, Leuconostoc mesenteroides|Ethanoligenens harbinense, Listeria monocytogenes|Ethanoligenens harbinense, Marvinbryantia formatexigens|Ethanoligenens harbinense, Megamonas hypermegale|Ethanoligenens harbinense, Megasphaera micronuciformis|Ethanoligenens harbinense, Methanobrevibacter smithii|Ethanoligenens harbinense, Methanosphaera stadtmanae|Ethanoligenens harbinense, Methylobacterium radiotolerans|Ethanoligenens harbinense, Mitsuokella multacida|Ethanoligenens harbinense, Mobiluncus curtisii|Ethanoligenens harbinense, Mycoplasma hominis|Ethanoligenens harbinense, Neisseria mucosa|Ethanoligenens harbinense, Odoribacter splanchnicus|Ethanoligenens harbinense, Olsenella uli|Ethanoligenens harbinense, Oribacterium sinus|Ethanoligenens harbinense, Oxalobacter formigenes|Ethanoligenens harbinense, Parabacteroides distasonis|Ethanoligenens harbinense, Parabacteroides johnsonii|Ethanoligenens harbinense, Parabacteroides merdae|Ethanoligenens harbinense, Parvimonas micra|Ethanoligenens harbinense, Pediococcus acidilactici|Ethanoligenens harbinense, Pediococcus pentosaceus|Ethanoligenens harbinense, Peptoniphilus duerdenii|Ethanoligenens harbinense, Peptoniphilus harei|Ethanoligenens harbinense, Peptoniphilus lacrimalis|Ethanoligenens harbinense, Peptostreptococcus anaerobius|Ethanoligenens harbinense, Peptostreptococcus stomatis|Ethanoligenens harbinense, Porphyromonas asaccharolytica|Ethanoligenens harbinense, Porphyromonas uenonis|Ethanoligenens harbinense, Prevotella amnii|Ethanoligenens harbinense, Prevotella bergensis|Ethanoligenens harbinense, Prevotella bivia|Ethanoligenens harbinense, Prevotella buccae|Ethanoligenens harbinense, Prevotella buccalis|Ethanoligenens harbinense, Prevotella copri|Ethanoligenens harbinense, Prevotella disiens|Ethanoligenens harbinense, Prevotella melaninogenica|Ethanoligenens harbinense, Prevotella multiformis|Ethanoligenens harbinense, Prevotella oralis|Ethanoligenens harbinense, Prevotella oris|Ethanoligenens harbinense, Prevotella salivae|Ethanoligenens harbinense, Prevotella timonensis|Ethanoligenens harbinense, Propionibacterium acnes|Ethanoligenens harbinense, Propionibacterium freudenreichii|Ethanoligenens harbinense, Proteus mirabilis|Ethanoligenens harbinense, Proteus penneri|Ethanoligenens harbinense, Pseudoflavonifractor capillosus|Ethanoligenens harbinense, Pseudomonas aeruginosa|Ethanoligenens harbinense, Pseudomonas fluorescens|Ethanoligenens harbinense, Pseudomonas putida|Ethanoligenens harbinense, Pseudoramibacter alactolyticus|Ethanoligenens harbinense, Pyramidobacter piscolens|Ethanoligenens harbinense, Rhodopseudomonas palustris|Ethanoligenens harbinense, Roseburia intestinalis|Ethanoligenens harbinense, Roseburia inulinivorans|Ethanoligenens harbinense, Rothia dentocariosa|Ethanoligenens harbinense, Rothia mucilaginosa|Ethanoligenens harbinense, Ruminococcus albus|Ethanoligenens harbinense, Ruminococcus bromii|Ethanoligenens harbinense, Ruminococcus gnavus|Ethanoligenens harbinense, Ruminococcus lactaris|Ethanoligenens harbinense, Ruminococcus obeum|Ethanoligenens harbinense, Ruminococcus torques|Ethanoligenens harbinense, Selenomonas sputigena|Ethanoligenens harbinense, Shigella boydii|Ethanoligenens harbinense, Shigella dysenteriae|Ethanoligenens harbinense, Shigella sonnei|Ethanoligenens harbinense, Slackia exigua|Ethanoligenens harbinense, Solobacterium moorei|Ethanoligenens harbinense, Staphylococcus aureus|Ethanoligenens harbinense, Staphylococcus epidermidis|Ethanoligenens harbinense, Staphylococcus hominis|Ethanoligenens harbinense, Staphylococcus saprophyticus|Ethanoligenens harbinense, Staphylococcus warneri|Ethanoligenens harbinense, Streptococcus agalactiae|Ethanoligenens harbinense, Streptococcus anginosus|Ethanoligenens harbinense, Streptococcus australis|Ethanoligenens harbinense, Streptococcus bovis|Ethanoligenens harbinense, Streptococcus cristatus|Ethanoligenens harbinense, Streptococcus dysgalactiae|Ethanoligenens harbinense, Streptococcus equinus|Ethanoligenens harbinense, Streptococcus gordonii|Ethanoligenens harbinense, Streptococcus infantarius|Ethanoligenens harbinense, Streptococcus infantis|Ethanoligenens harbinense, Streptococcus mitis|Ethanoligenens harbinense, Streptococcus mutans|Ethanoligenens harbinense, Streptococcus oralis|Ethanoligenens harbinense, Streptococcus parasanguinis|Ethanoligenens harbinense, Streptococcus peroris|Ethanoligenens harbinense, Streptococcus pneumoniae|Ethanoligenens harbinense, Streptococcus salivarius|Ethanoligenens harbinense, Streptococcus sanguinis|Ethanoligenens harbinense, Streptococcus thermophilus|Ethanoligenens harbinense, Streptococcus vestibularis|Ethanoligenens harbinense, Subdoligranulum variabile|Ethanoligenens harbinense, Succinatimonas hippei|Ethanoligenens harbinense, Sutterella wadsworthensis|Ethanoligenens harbinense, Tropheryma whipplei|Ethanoligenens harbinense, Veillonella atypica|Ethanoligenens harbinense, Veillonella dispar|Ethanoligenens harbinense, Veillonella parvula|Ethanoligenens harbinense, Victivallis vadensis|Eubacterium cellulosolvens, Eubacterium cellulosolvens|Eubacterium cellulosolvens, Eubacterium eligens|Eubacterium cellulosolvens, Eubacterium hallii|Eubacterium cellulosolvens, Eubacterium limosum|Eubacterium cellulosolvens, Eubacterium rectale|Eubacterium cellulosolvens, Eubacterium siraeum|Eubacterium cellulosolvens, Eubacterium ventriosum|Eubacterium cellulosolvens, Faecalibacterium prausnitzii|Eubacterium cellulosolvens, Finegoldia magna|Eubacterium cellulosolvens, Fusobacterium gonidiaformans|Eubacterium cellulosolvens, Fusobacterium mortiferum|Eubacterium cellulosolvens, Fusobacterium nucleatum|Eubacterium cellulosolvens, Fusobacterium varium|Eubacterium cellulosolvens, Gardnerella vaginalis|Eubacterium cellulosolvens, Gemella haemolysans|Eubacterium cellulosolvens, Gemella morbillorum|Eubacterium cellulosolvens, Gordonibacter pamelaeae|Eubacterium cellulosolvens, Granulicatella adiacens|Eubacterium cellulosolvens, Granulicatella elegans|Eubacterium cellulosolvens, Haemophilus influenzae|Eubacterium cellulosolvens, Haemophilus parainfluenzae|Eubacterium cellulosolvens, Helicobacter pullorum|Eubacterium cellulosolvens, Helicobacter pylori|Eubacterium cellulosolvens, Holdemania filiformis|Eubacterium cellulosolvens, Kingella oralis|Eubacterium cellulosolvens, Klebsiella pneumoniae|Eubacterium cellulosolvens, Klebsiella variicola|Eubacterium cellulosolvens, Lachnospiraceae bacterium* 5_1_57FAA|*Eubacterium cellulosolvens, Lactobacillus acidophilus|Eubacterium cellulosolvens, Lactobacillus amylovorus|Eubacterium cellulosolvens, Lactobacillus brevis|Eubacterium cellulosolvens, Lactobacillus casei|Eubacterium cellulosolvens, Lactobacillus crispatus|Eubacterium cellulosolvens, Lactobacillus delbrueckii|Eubacterium cellulosolvens, Lactobacillus fermentum|Eubacterium cellulosolvens, Lactobacillus gasseri|Eubacterium cellulosolvens, Lactobacillus iners|Eubacterium cellulosolvens, Lactobacillus jensenii|Eubacterium cellulosolvens, Lactobacillus johnsonii|Eubacterium cellulosolvens, Lactobacillus paracasei|Eubacterium cellulosolvens, Lactobacillus plantarum|Eubacterium cellulosolvens, Lactobacillus reuteri|Eubacterium cellulosolvens, Lactobacillus rhamnosus|Eubacterium cellulosolvens, Lactobacillus ruminis|Eubacterium cellulosolvens, Lactobacillus sakei|Eubacterium cellulosolvens, Lactobacillus salivarius|Eubacterium cellulosolvens, Lactococcus lactis|Eubacterium cellulosolvens, Lautropia mirabilis|Eubacterium cellulosolvens, Leuconostoc citreum|Eubacterium cellulosolvens, Leuconostoc gasicomitatum|Eubacterium cellulosolvens, Leuconostoc mesenteroides|Eubacterium cellulosolvens, Listeria monocytogenes|Eubacterium cellulosolvens, Marvinbryantia formatexigens|Eubacterium cellulosolvens, Megamonas hypermegale|Eubacterium cellulosolvens, Megasphaera micronuciformis|Eubacterium cellulosolvens, Methanobrevibacter smithii|Eubacterium cellulosolvens, Methanosphaera stadtmanae|Eubacterium cellulosolvens, Methylobacterium radiotolerans|Eubacterium cellulosolvens, Mitsuokella multacida|Eubacterium cellulosolvens, Mobiluncus curtisii|Eubacterium cellulosolvens, Mycoplasma hominis|Eubacterium cellulosolvens, Neisseria mucosa|Eubacterium cellulosolvens, Odoribacter splanchnicus|Eubacterium cellulosolvens, Olsenella uli|Eubacterium cellulosolvens, Oribacterium sinus|Eubacterium cellulosolvens, Oxalobacter formigenes|Eubacterium cellulosolvens, Parabacteroides distasonis|Eubacterium cellulosolvens, Parabacteroides johnsonii|Eubacterium cellulosolvens, Parabacteroides merdae|Eubacterium cellulosolvens, Parvimonas micra|Eubacterium cellulosolvens, Pediococcus acidilactici|Eubacterium cellulosolvens, Pediococcus pentosaceus|Eubacterium cellulosolvens, Peptoniphilus duerdenii|Eubacterium cellulosolvens, Peptoniphilus harei|Eubacterium cellulosolvens, Peptoniphilus lacrimalis|Eubacterium cellulosolvens, Peptostreptococcus anaerobius|Eubacterium cellulosolvens, Peptostreptococcus*

TABLE 2-continued

| Table 2. Specific binary combinations of OTUs. Individual pairings are differentiated by "\|" and OTUs within a combination are differentiated by "," |
| --- |
| *stomatis\|Eubacterium cellulosolvens, Porphyromonas asaccharolytica\|Eubacterium cellulosolvens, Porphyromonas uenonis\|Eubacterium cellulosolvens, Prevotella amnii\|Eubacterium cellulosolvens, Prevotella bergensis\|Eubacterium cellulosolvens, Prevotella bivia\|Eubacterium cellulosolvens, Prevotella buccae\|Eubacterium cellulosolvens, Prevotella buccalis\|Eubacterium cellulosolvens, Prevotella copri\|Eubacterium cellulosolvens, Prevotella disiens\|Eubacterium cellulosolvens, Prevotella melaninogenica\|Eubacterium cellulosolvens, Prevotella multiformis\|Eubacterium cellulosolvens, Prevotella oralis\|Eubacterium cellulosolvens, Prevotella oris\|Eubacterium cellulosolvens, Prevotella salivae\|Eubacterium cellulosolvens, Prevotella timonensis\|Eubacterium cellulosolvens, Propionibacterium acnes\|Eubacterium cellulosolvens, Propionibacterium freudenreichii\|Eubacterium cellulosolvens, Proteus mirabilis\|Eubacterium cellulosolvens, Proteus penneri\|Eubacterium cellulosolvens, Pseudoflavonifractor capillosus\|Eubacterium cellulosolvens, Pseudomonas aeruginosa\|Eubacterium cellulosolvens, Pseudomonas fluorescens\|Eubacterium cellulosolvens, Pseudomonas putida\|Eubacterium cellulosolvens, Pseudoramibacter alactolyticus\|Eubacterium cellulosolvens, Pyramidobacter piscolens\|Eubacterium cellulosolvens, Rhodopseudomonas palustris\|Eubacterium cellulosolvens, Roseburia intestinalis\|Eubacterium cellulosolvens, Roseburia inulinivorans\|Eubacterium cellulosolvens, Rothia dentocariosa\|Eubacterium cellulosolvens, Rothia mucilaginosa\|Eubacterium cellulosolvens, Ruminococcus albus\|Eubacterium cellulosolvens, Ruminococcus bromii\|Eubacterium cellulosolvens, Ruminococcus gnavus\|Eubacterium cellulosolvens, Ruminococcus lactaris\|Eubacterium cellulosolvens, Ruminococcus obeum\|Eubacterium cellulosolvens, Ruminococcus torques\|Eubacterium cellulosolvens, Selenomonas sputigena\|Eubacterium cellulosolvens, Shigella boydii\|Eubacterium cellulosolvens, Shigella dysenteriae\|Eubacterium cellulosolvens, Shigella sonnei\|Eubacterium cellulosolvens, Slackia exigua\|Eubacterium cellulosolvens, Solobacterium moorei\|Eubacterium cellulosolvens, Staphylococcus aureus\|Eubacterium cellulosolvens, Staphylococcus epidermidis\|Eubacterium cellulosolvens, Staphylococcus hominis\|Eubacterium cellulosolvens, Staphylococcus saprophyticus\|Eubacterium cellulosolvens, Staphylococcus warneri\|Eubacterium cellulosolvens, Streptococcus agalactiae\|Eubacterium cellulosolvens, Streptococcus anginosus\|Eubacterium cellulosolvens, Streptococcus australis\|Eubacterium cellulosolvens, Streptococcus bovis\|Eubacterium cellulosolvens, Streptococcus cristatus\|Eubacterium cellulosolvens, Streptococcus dysgalactiae\|Eubacterium cellulosolvens, Streptococcus equinus\|Eubacterium cellulosolvens, Streptococcus gordonii\|Eubacterium cellulosolvens, Streptococcus infantarius\|Eubacterium cellulosolvens, Streptococcus infantis\|Eubacterium cellulosolvens, Streptococcus mitis\|Eubacterium cellulosolvens, Streptococcus mutans\|Eubacterium cellulosolvens, Streptococcus oralis\|Eubacterium cellulosolvens, Streptococcus parasanguinis\|Eubacterium cellulosolvens, Streptococcus peroris\|Eubacterium cellulosolvens, Streptococcus pneumoniae\|Eubacterium cellulosolvens, Streptococcus salivarius\|Eubacterium cellulosolvens, Streptococcus sanguinis\|Eubacterium cellulosolvens, Streptococcus thermophilus\|Eubacterium cellulosolvens, Streptococcus vestibularis\|Eubacterium cellulosolvens, Subdoligranulum variabile\|Eubacterium cellulosolvens, Succinatimonas hippei\|Eubacterium cellulosolvens, Sutterella wadsworthensis\|Eubacterium cellulosolvens, Tropheryma whipplei\|Eubacterium cellulosolvens, Veillonella atypica\|Eubacterium cellulosolvens, Veillonella dispar\|Eubacterium cellulosolvens, Veillonella parvula\|Eubacterium cellulosolvens, Victivallis vadensis\|Eubacterium eligens, Eubacterium eligens\|Eubacterium eligens, Eubacterium hallii\|Eubacterium eligens, Eubacterium limosum\|Eubacterium eligens, Eubacterium rectale\|Eubacterium eligens, Eubacterium siraeum\|Eubacterium eligens, Eubacterium ventriosum\|Eubacterium eligens, Faecalibacterium prausnitzii\|Eubacterium eligens, Finegoldia magna\|Eubacterium eligens, Fusobacterium gonidiaformans\|Eubacterium eligens, Fusobacterium mortifenim\|Eubacterium eligens, Fusobacterium nucleatum\|Eubacterium eligens, Fusobacterium varium\|Eubacterium eligens, Gardnerella vaginalis\|Eubacterium eligens, Gemella haemolysans\|Eubacterium eligens, Gemella morbillorum\|Eubacterium eligens, Gordonibacter pamelaeae\|Eubacterium eligens, Granulicatella adiacens\|Eubacterium eligens, Granulicatella elegans\|Eubacterium eligens, Haemophilus influenzae\|Eubacterium eligens, Haemophilus parainfluenzae\|Eubacterium eligens, Helicobacter pullorum\|Eubacterium eligens, Helicobacter pylori\|Eubacterium eligens, Holdemania filiformis\|Eubacterium eligens, Kingella oralis\|Eubacterium eligens, Klebsiella pneumoniae\|Eubacterium eligens, Klebsiella variicola\|Eubacterium eligens, Lachnospiraceae bacterium* 5_1_57FAA*\|Eubacterium eligens, Lactobacillus acidophilus\|Eubacterium eligens, Lactobacillus amylovorus\|Eubacterium eligens, Lactobacillus brevis\|Eubacterium eligens, Lactobacillus casei\|Eubacterium eligens, Lactobacillus crispatus\|Eubacterium eligens, Lactobacillus delbrueckii\|Eubacterium eligens, Lactobacillus fermentum\|Eubacterium eligens, Lactobacillus gasseri\|Eubacterium eligens, Lactobacillus iners\|Eubacterium eligens, Lactobacillus jensenii\|Eubacterium eligens, Lactobacillus johnsonii\|Eubacterium eligens, Lactobacillus paracasei\|Eubacterium eligens, Lactobacillus plantarum\|Eubacterium eligens, Lactobacillus reuteri\|Eubacterium eligens, Lactobacillus rhamnosus\|Eubacterium eligens, Lactobacillus ruminis\|Eubacterium eligens, Lactobacillus sakei\|Eubacterium eligens, Lactobacillus salivarius\|Eubacterium eligens, Lactococcus lactis\|Eubacterium eligens, Lautropia mirabilis\|Eubacterium eligens, Leuconostoc citreum\|Eubacterium eligens, Leuconostoc gasicomitatum\|Eubacterium eligens, Leuconostoc mesenteroides\|Eubacterium eligens, Listeria monocytogenes\|Eubacterium eligens, Marvinbryantia formatexigens\|Eubacterium eligens, Megamonas hypermegale\|Eubacterium eligens, Megasphaera micronuciformis\|Eubacterium eligens, Methanobrevibacter smithii\|Eubacterium eligens, Methanosphaera stadtmanae\|Eubacterium eligens, Methylobacterium radiotolerans\|Eubacterium eligens, Mitsuokella multacida\|Eubacterium eligens, Mobiluncus curtisii\|Eubacterium eligens, Mycoplasma hominis\|Eubacterium eligens, Neisseria mucosa\|Eubacterium eligens, Odoribacter splanchnicus\|Eubacterium eligens, Olsenella uli\|Eubacterium eligens, Oribacterium sinus\|Eubacterium eligens, Oxalobacter formigenes\|Eubacterium eligens, Parabacteroides distasonis\|Eubacterium eligens, Parabacteroides johnsonii\|Eubacterium eligens, Parabacteroides merdae\|Eubacterium eligens, Parvimonas micra\|Eubacterium eligens, Pediococcus acidilactici\|Eubacterium eligens, Pediococcus pentosaceus\|Eubacterium eligens, Peptoniphilus duerdenii\|Eubacterium eligens, Peptoniphilus harei\|Eubacterium eligens, Peptoniphilus lacrimalis\|Eubacterium eligens, Peptostreptococcus anaerobius\|Eubacterium eligens, Peptostreptococcus stomatis\|Eubacterium eligens, Porphyromonas asaccharolytica\|Eubacterium eligens, Porphyromonas uenonis\|Eubacterium eligens, Prevotella amnii\|Eubacterium eligens, Prevotella bergensis\|Eubacterium eligens, Prevotella bivia\|Eubacterium eligens, Prevotella buccae\|Eubacterium eligens, Prevotella buccalis\|Eubacterium eligens, Prevotella copri\|Eubacterium eligens, Prevotella disiens\|Eubacterium eligens, Prevotella melaninogenica\|Eubacterium eligens, Prevotella multiformis\|Eubacterium eligens, Prevotella oralis\|Eubacterium eligens, Prevotella oris\|Eubacterium eligens, Prevotella salivae\|Eubacterium eligens, Prevotella timonensis\|Eubacterium eligens, Propionibacterium acnes\|Eubacterium eligens, Propionibacterium freudenreichii\|Eubacterium eligens, Proteus mirabilis\|Eubacterium eligens, Proteus penneri\|Eubacterium eligens, Pseudoflavonifractor capillosus\|Eubacterium eligens, Pseudomonas aeruginosa\|Eubacterium eligens, Pseudomonas fluorescens\|Eubacterium eligens, Pseudomonas putida\|Eubacterium eligens, Pseudoramibacter alactolyticus\|Eubacterium eligens, Pyramidobacter piscolens\|Eubacterium eligens, Rhodopseudomonas palustris\|Eubacterium eligens, Roseburia intestinalis\|Eubacterium eligens, Roseburia inulinivorans\|Eubacterium eligens, Rothia dentocariosa\|Eubacterium eligens, Rothia mucilaginosa\|Eubacterium eligens, Ruminococcus albus\|Eubacterium eligens, Ruminococcus bromii\|Eubacterium eligens, Ruminococcus gnavus\|Eubacterium eligens, Ruminococcus lactaris\|Eubacterium eligens, Ruminococcus obeum\|Eubacterium eligens, Ruminococcus torques\|Eubacterium eligens, Selenomonas sputigena\|Eubacterium eligens, Shigella boydii\|Eubacterium eligens, Shigella dysenteriae\|Eubacterium eligens, Shigella sonnei\|Eubacterium eligens, Slackia exigua\|Eubacterium eligens, Solobacterium moorei\|Eubacterium eligens, Staphylococcus aureus\|Eubacterium eligens, Staphylococcus epidermidis\|Eubacterium eligens, Staphylococcus hominis\|Eubacterium eligens, Staphylococcus saprophyticus\|Eubacterium eligens, Staphylococcus warneri\|Eubacterium eligens, Streptococcus agalactiae\|Eubacterium eligens, Streptococcus anginosus\|Eubacterium eligens, Streptococcus australis\|Eubacterium eligens, Streptococcus bovis\|Eubacterium eligens, Streptococcus cristatus\|Eubacterium eligens, Streptococcus dysgalactiae\|Eubacterium eligens, Streptococcus equinus\|Eubacterium eligens, Streptococcus gordonii\|Eubacterium eligens, Streptococcus infantarius\|Eubacterium eligens, Streptococcus infantis\|Eubacterium eligens, Streptococcus mitis\|Eubacterium eligens, Streptococcus mutans\|Eubacterium eligens, Streptococcus oralis\|Eubacterium eligens, Streptococcus parasanguinis\|Eubacterium eligens, Streptococcus peroris\|Eubacterium eligens, Streptococcus pneumoniae\|Eubacterium eligens, Streptococcus salivarius\|Eubacterium eligens, Streptococcus* |

TABLE 2-continued

Table 2. Specific binary combinations of OTUs. Individual pairings are differentiated by "|" and OTUs within a combination are differentiated by ","

*sanguinis|Eubacterium eligens, Streptococcus thermophilus|Eubacterium eligens, Streptococcus vestibularis|Eubacterium eligens, Subdoligranulum variabile|Eubacterium eligens, Succinatimonas hippei|Eubacterium eligens, Sutterella wadsworthensis|Eubacterium eligens, Tropheryma whipplei|Eubacterium eligens, Veillonella atypica|Eubacterium eligens, Veillonella dispar|Eubacterium eligens, Veillonella parvula|Eubacterium eligens, Victivallis vadensis|Eubacterium hallii, Eubacterium hallii|Eubacterium hallii, Eubacterium limosum|Eubacterium hallii, Eubacterium rectale|Eubacterium hallii, Eubacterium siraeum|Eubacterium hallii, Eubacterium ventriosum|Eubacterium hallii, Faecalibacterium prausnitzii|Eubacterium hallii, Finegoldia magna|Eubacterium hallii, Fusobacterium gonidiaformans|Eubacterium hallii, Fusobacterium mortiferum|Eubacterium hallii, Fusobacterium nucleatum|Eubacterium hallii, Fusobacterium varium|Eubacterium hallii, Gardnerella vaginalis|Eubacterium hallii, Gemella haemolysans|Eubacterium hallii, Gemella morbillorum|Eubacterium hallii, Gordonibacter pamelaeae|Eubacterium hallii, Granulicatella adiacens|Eubacterium hallii, Granulicatella elegans|Eubacterium hallii, Haemophilus influenzae|Eubacterium hallii, Haemophilus parainfluenzae|Eubacterium hallii, Helicobacter pullorum|Eubacterium hallii, Helicobacter pylori|Eubacterium hallii, Holdemania filiformis|Eubacterium hallii, Kingella oralis|Eubacterium hallii, Klebsiella pneumoniae|Eubacterium hallii, Klebsiella variicola|Eubacterium hallii, Lachnospiraceae bacterium* 5_1_57FAA|*Eubacterium hallii, Lactobacillus acidophilus|Eubacterium hallii, Lactobacillus amylovorus|Eubacterium hallii, Lactobacillus brevis|Eubacterium hallii, Lactobacillus casei|Eubacterium hallii, Lactobacillus crispatus|Eubacterium hallii, Lactobacillus delbrueckii|Eubacterium hallii, Lactobacillus fermentum|Eubacterium hallii, Lactobacillus gasseri|Eubacterium hallii, Lactobacillus iners|Eubacterium hallii, Lactobacillus jensenii|Eubacterium hallii, Lactobacillus johnsonii|Eubacterium hallii, Lactobacillus paracasei|Eubacterium hallii, Lactobacillus plantarum|Eubacterium hallii, Lactobacillus reuteri|Eubacterium hallii, Lactobacillus rhamnosus|Eubacterium hallii, Lactobacillus ruminis|Eubacterium hallii, Lactobacillus sakei|Eubacterium hallii, Lactobacillus salivarius|Eubacterium hallii, Lactococcus lactis|Eubacterium hallii, Lautropia mirabilis|Eubacterium hallii, Leuconostoc citreum|Eubacterium hallii, Leuconostoc gasicomitatum|Eubacterium hallii, Leuconostoc mesenteroides|Eubacterium hallii, Listeria monocytogenes|Eubacterium hallii, Marvinbryantia formatexigens|Eubacterium hallii, Megamonas hypermegale|Eubacterium hallii, Megasphaera micronuciformis|Eubacterium hallii, Methanobrevibacter smithii|Eubacterium hallii, Methanosphaera stadtmanae|Eubacterium hallii, Methylobacterium radiotolerans|Eubacterium hallii, Mitsuokella multacida|Eubacterium hallii, Mobiluncus curtisii|Eubacterium hallii, Mycoplasma hominis|Eubacterium hallii, Neisseria mucosa|Eubacterium hallii, Odoribacter splanchnicus|Eubacterium hallii, Olsenella uli|Eubacterium hallii, Oribacterium sinus|Eubacterium hallii, Oxalobacter formigenes|Eubacterium hallii, Parabacteroides distasonis|Eubacterium hallii, Parabacteroides johnsonii|Eubacterium hallii, Parabacteroides merdae|Eubacterium hallii, Parvimonas micra|Eubacterium hallii, Pediococcus acidilactici|Eubacterium hallii, Pediococcus pentosaceus|Eubacterium hallii, Peptoniphilus duerdenii|Eubacterium hallii, Peptoniphilus harei|Eubacterium hallii, Peptoniphilus lacrimalis|Eubacterium hallii, Peptostreptococcus anaerobius|Eubacterium hallii, Peptostreptococcus stomatis|Eubacterium hallii, Porphyromonas asaccharolytica|Eubacterium hallii, Porphyromonas uenonis|Eubacterium hallii, Prevotella amnii|Eubacterium hallii, Prevotella bergensis|Eubacterium hallii, Prevotella bivia|Eubacterium hallii, Prevotella buccae|Eubacterium hallii, Prevotella buccalis|Eubacterium hallii, Prevotella copri|Eubacterium hallii, Prevotella disiens|Eubacterium hallii, Prevotella melaninogenica|Eubacterium hallii, Prevotella multiformis|Eubacterium hallii, Prevotella oralis|Eubacterium hallii, Prevotella oris|Eubacterium hallii, Prevotella salivae|Eubacterium hallii, Prevotella timonensis|Eubacterium hallii, Propionibacterium acnes|Eubacterium hallii, Propionibacterium freudenreichii|Eubacterium hallii, Proteus mirabilis|Eubacterium hallii, Proteus penneri|Eubacterium hallii, Pseudoflavonifractor capillosus|Eubacterium hallii, Pseudomonas aeruginosa|Eubacterium hallii, Pseudomonas fluorescens|Eubacterium hallii, Pseudomonas putida|Eubacterium hallii, Pseudoramibacter alactolyticus|Eubacterium hallii, Pyramidobacter piscolens|Eubacterium hallii, Rhodopseudomonas palustris|Eubacterium hallii, Roseburia intestinalis|Eubacterium hallii, Roseburia inulinivorans|Eubacterium hallii, Rothia dentocariosa|Eubacterium hallii, Rothia mucilaginosa|Eubacterium hallii, Ruminococcus albus|Eubacterium hallii, Ruminococcus bromii|Eubacterium hallii, Ruminococcus gnavus|Eubacterium hallii, Ruminococcus lactaris|Eubacterium hallii, Ruminococcus obeum|Eubacterium hallii, Ruminococcus torques|Eubacterium hallii, Selenomonas sputigena|Eubacterium hallii, Shigella boydii|Eubacterium hallii, Shigella dysenteriae|Eubacterium hallii, Shigella sonnei|Eubacterium hallii, Slackia exigua|Eubacterium hallii, Solobacterium moorei|Eubacterium hallii, Staphylococcus aureus|Eubacterium hallii, Staphylococcus epidermidis|Eubacterium hallii, Staphylococcus hominis|Eubacterium hallii, Staphylococcus saprophyticus|Eubacterium hallii, Staphylococcus warneri|Eubacterium hallii, Streptococcus agalactiae|Eubacterium hallii, Streptococcus anginosus|Eubacterium hallii, Streptococcus australis|Eubacterium hallii, Streptococcus bovis|Eubacterium hallii, Streptococcus cristatus|Eubacterium hallii, Streptococcus dysgalactiae|Eubacterium hallii, Streptococcus equinus|Eubacterium hallii, Streptococcus gordonii|Eubacterium hallii, Streptococcus infantarius|Eubacterium hallii, Streptococcus infantis|Eubacterium hallii, Streptococcus mitis|Eubacterium hallii, Streptococcus mutans|Eubacterium hallii, Streptococcus oralis|Eubacterium hallii, Streptococcus parasanguinis|Eubacterium hallii, Streptococcus peroris|Eubacterium hallii, Streptococcus pneumoniae|Eubacterium hallii, Streptococcus salivarius|Eubacterium hallii, Streptococcus sanguinis|Eubacterium hallii, Streptococcus thermophilus|Eubacterium hallii, Streptococcus vestibularis|Eubacterium hallii, Subdoligranulum variabile|Eubacterium hallii, Succinatimonas hippei|Eubacterium hallii, Sutterella wadsworthensis|Eubacterium hallii, Tropheryma whipplei|Eubacterium hallii, Veillonella atypica|Eubacterium hallii, Veillonella dispar|Eubacterium hallii, Veillonella parvula|Eubacterium hallii, Victivallis vadensis|Eubacterium limosum, Eubacterium limosum|Eubacterium limosum, Eubacterium rectale|Eubacterium limosum, Eubacterium siraeum|Eubacterium limosum, Eubacterium ventriosum|Eubacterium limosum, Faecalibacterium prausnitzii|Eubacterium limosum, Finegoldia magna|Eubacterium limosum, Fusobacterium gonidiaformans|Eubacterium limosum, Fusobacterium mortiferum|Eubacterium limosum, Fusobacterium nucleatum|Eubacterium limosum, Fusobacterium varium|Eubacterium limosum, Gardnerella vaginalis|Eubacterium limosum, Gemella haemolysans|Eubacterium limosum, Gemella morbillorum|Eubacterium limosum, Gordonibacter pamelaeae|Eubacterium limosum, Granulicatella adiacens|Eubacterium limosum, Granulicatella elegans|Eubacterium limosum, Haemophilus influenzae|Eubacterium limosum, Haemophilus parainfluenzae|Eubacterium limosum, Helicobacter pullorum|Eubacterium limosum, Helicobacter pylori|Eubacterium limosum, Holdemania filiformis|Eubacterium limosum, Kingella oralis|Eubacterium limosum, Klebsiella pneumoniae|Eubacterium limosum, Klebsiella variicola|Eubacterium limosum, Lachnospiraceae bacterium* 5_1_57FAA|*Eubacterium limosum, Lactobacillus acidophilus|Eubacterium limosum, Lactobacillus amylovorus|Eubacterium limosum, Lactobacillus brevis|Eubacterium limosum, Lactobacillus casei|Eubacterium limosum, Lactobacillus crispatus|Eubacterium limosum, Lactobacillus delbrueckii|Eubacterium limosum, Lactobacillus fermentum|Eubacterium limosum, Lactobacillus gasseri|Eubacterium limosum, Lactobacillus iners|Eubacterium limosum, Lactobacillus jensenii|Eubacterium limosum, Lactobacillus johnsonii|Eubacterium limosum, Lactobacillus paracasei|Eubacterium limosum, Lactobacillus plantarum|Eubacterium limosum, Lactobacillus reuteri|Eubacterium limosum, Lactobacillus rhamnosus|Eubacterium limosum, Lactobacillus ruminis|Eubacterium limosum, Lactobacillus sakei|Eubacterium limosum, Lactobacillus salivarius|Eubacterium limosum, Lactococcus lactis|Eubacterium limosum, Lautropia mirabilis|Eubacterium limosum, Leuconostoc citreum|Eubacterium limosum, Leuconostoc gasicomitatum|Eubacterium limosum, Leuconostoc mesenteroides|Eubacterium limosum, Listeria monocytogenes|Eubacterium limosum, Marvinbryantia formatexigens|Eubacterium limosum, Megamonas hypermegale|Eubacterium limosum, Megasphaera micronuciformis|Eubacterium limosum, Methanobrevibacter smithii|Eubacterium limosum, Methanosphaera stadtmanae|Eubacterium limosum, Methylobacterium radiotolerans|Eubacterium limosum, Mitsuokella multacida|Eubacterium limosum, Mobiluncus curtisii|Eubacterium limosum, Mycoplasma hominis|Eubacterium limosum, Neisseria mucosa|Eubacterium limosum, Odoribacter splanchnicus|Eubacterium limosum, Olsenella uli|Eubacterium limosum, Oribacterium sinus|Eubacterium limosum, Oxalobacter formigenes|Eubacterium limosum, Parabacteroides distasonis|Eubacterium limosum, Parabacteroides johnsonii|Eubacterium limosum, Parabacteroides merdae|Eubacterium limosum, Parvimonas micra|Eubacterium limosum, Pediococcus acidilactici|Eubacterium limosum, Pediococcus pentosaceus|Eubacterium limosum, Peptoniphilus duerdenii|Eubacterium limosum, Peptoniphilus harei|Eubacterium limosum, Peptoniphilus lacrimalis|Eubacterium*

TABLE 2-continued

| Table 2. Specific binary combinations of OTUs. Individual pairings are differentiated by "\|" and OTUs within a combination are differentiated by "," |
|---|
| *limosum, Peptostreptococcus anaerobius\|Eubacterium limosum, Peptostreptococcus stomatis\|Eubacterium limosum, Porphyromonas asaccharolytica\|Eubacterium limosum, Porphyromonas uenonis\|Eubacterium limosum, Prevotella amnii\|Eubacterium limosum, Prevotella bergensis\|Eubacterium limosum, Prevotella bivia\|Eubacterium limosum, Prevotella buccae\|Eubacterium limosum, Prevotella buccalis\|Eubacterium limosum, Prevotella copri\|Eubacterium limosum, Prevotella disiens\|Eubacterium limosum, Prevotella melaninogenica\|Eubacterium limosum, Prevotella multiformis\|Eubacterium limosum, Prevotella oralis\|Eubacterium limosum, Prevotella oris\|Eubacterium limosum, Prevotella salivae\|Eubacterium limosum, Prevotella timonensis\|Eubacterium limosum, Propionibacterium acnes\|Eubacterium limosum, Propionibacterium freudenreichii\|Eubacterium limosum, Proteus mirabilis\|Eubacterium limosum, Proteus penneri\|Eubacterium limosum, Pseudoflavonifractor capillosus\|Eubacterium limosum, Pseudomonas aeruginosa\|Eubacterium limosum, Pseudomonas fluorescens\|Eubacterium limosum, Pseudomonas putida\|Eubacterium limosum, Pseudoramibacter alactolyticus\|Eubacterium limosum, Pyramidobacter piscolens\|Eubacterium limosum, Rhodopseudomonas palustris\|Eubacterium limosum, Roseburia intestinalis\|Eubacterium limosum, Roseburia inulinivorans\|Eubacterium limosum, Rothia dentocariosa\|Eubacterium limosum, Rothia mucilaginosa\|Eubacterium limosum, Ruminococcus albus\|Eubacterium limosum, Ruminococcus bromii\|Eubacterium limosum, Ruminococcus gnavus\|Eubacterium limosum, Ruminococcus lactaris\|Eubacterium limosum, Ruminococcus obeum\|Eubacterium limosum, Ruminococcus torques\|Eubacterium limosum, Selenomonas sputigena\|Eubacterium limosum, Shigella boydii\|Eubacterium limosum, Shigella dysenteriae\|Eubacterium limosum, Shigella sonnei\|Eubacterium limosum, Slackia exigua\|Eubacterium limosum, Solobacterium moorei\|Eubacterium limosum, Staphylococcus aureus\|Eubacterium limosum, Staphylococcus epidermidis\|Eubacterium limosum, Staphylococcus hominis\|Eubacterium limosum, Staphylococcus saprophyticus\|Eubacterium limosum, Staphylococcus warneri\|Eubacterium limosum, Streptococcus agalactiae\|Eubacterium limosum, Streptococcus anginosus\|Eubacterium limosum, Streptococcus australis\|Eubacterium limosum, Streptococcus bovis\|Eubacterium limosum, Streptococcus cristatus\|Eubacterium limosum, Streptococcus dysgalactiae\|Eubacterium limosum, Streptococcus equinus\|Eubacterium limosum, Streptococcus gordonii\|Eubacterium limosum, Streptococcus infantarius\|Eubacterium limosum, Streptococcus infantis\|Eubacterium limosum, Streptococcus mitis\|Eubacterium limosum, Streptococcus mutans\|Eubacterium limosum, Streptococcus oralis\|Eubacterium limosum, Streptococcus parasanguinis\|Eubacterium limosum, Streptococcus peroris\|Eubacterium limosum, Streptococcus pneumoniae\|Eubacterium limosum, Streptococcus salivarius\|Eubacterium limosum, Streptococcus sanguinis\|Eubacterium limosum, Streptococcus thermophilus\|Eubacterium limosum, Streptococcus vestibularis\|Eubacterium limosum, Subdoligranulum variabile\|Eubacterium limosum, Succinatimonas hippei\|Eubacterium limosum, Sutterella wadsworthensis\|Eubacterium limosum, Tropheryma whipplei\|Eubacterium limosum, Veillonella atypica\|Eubacterium limosum, Veillonella dispar\|Eubacterium limosum, Veillonella parvula\|Eubacterium limosum, Victivallis vadensis\|Eubacterium rectale, Eubacterium rectale\|Eubacterium rectale, Eubacterium siraeum\|Eubacterium rectale, Eubacterium ventriosum\|Eubacterium rectale, Faecalibacterium prausnitzii\|Eubacterium rectale, Finegoldia magna\|Eubacterium rectale, Fusobacterium gonidiaformans\|Eubacterium rectale, Fusobacterium mortiferum\|Eubacterium rectale, Fusobacterium nucleatum\|Eubacterium rectale, Fusobacterium varium\|Eubacterium rectale, Gardnerella vaginalis\|Eubacterium rectale, Gemella haemolysans\|Eubacterium rectale, Gemella morbillorum\|Eubacterium rectale, Gordonibacter pamelaeae\|Eubacterium rectale, Granulicatella adiacens\|Eubacterium rectale, Granulicatella elegans\|Eubacterium rectale, Haemophilus influenzae\|Eubacterium rectale, Haemophilus parainfluenzae\|Eubacterium rectale, Helicobacter pullorum\|Eubacterium rectale, Helicobacter pylori\|Eubacterium rectale, Holdemania filiformis\|Eubacterium rectale, Kingella oralis\|Eubacterium rectale, Klebsiella pneumoniae\|Eubacterium rectale, Klebsiella variicola\|Eubacterium rectale, Lachnospiraceae bacterium* 5_1_57FAA*\|Eubacterium rectale, Lactobacillus acidophilus\|Eubacterium rectale, Lactobacillus amylovorus\|Eubacterium rectale, Lactobacillus brevis\|Eubacterium rectale, Lactobacillus casei\|Eubacterium rectale, Lactobacillus crispatus\|Eubacterium rectale, Lactobacillus delbrueckii\|Eubacterium rectale, Lactobacillus fermentum\|Eubacterium rectale, Lactobacillus gasseri\|Eubacterium rectale, Lactobacillus iners\|Eubacterium rectale, Lactobacillus jensenii\|Eubacterium rectale, Lactobacillus johnsonii\|Eubacterium rectale, Lactobacillus paracasei\|Eubacterium rectale, Lactobacillus plantarum\|Eubacterium rectale, Lactobacillus reuteri\|Eubacterium rectale, Lactobacillus rhamnosus\|Eubacterium rectale, Lactobacillus ruminis\|Eubacterium rectale, Lactobacillus sakei\|Eubacterium rectale, Lactobacillus salivarius\|Eubacterium rectale, Lactococcus lactis\|Eubacterium rectale, Lautropia mirabilis\|Eubacterium rectale, Leuconostoc citreum\|Eubacterium rectale, Leuconostoc gasicomitatum\|Eubacterium rectale, Leuconostoc mesenteroides\|Eubacterium rectale, Listeria monocytogenes\|Eubacterium rectale, Marvinbryantia formatexigens\|Eubacterium rectale, Megamonas hypermegale\|Eubacterium rectale, Megasphaera micronuciformis\|Eubacterium rectale, Methanobrevibacter smithii\|Eubacterium rectale, Methanosphaera stadtmanae\|Eubacterium rectale, Methylobacterium radiotolerans\|Eubacterium rectale, Mitsuokella multacida\|Eubacterium rectale, Mobiluncus curtisii\|Eubacterium rectale, Mycoplasma hominis\|Eubacterium rectale, Neisseria mucosa\|Eubacterium rectale, Odoribacter splanchnicus\|Eubacterium rectale, Olsenella uli\|Eubacterium rectale, Oribacterium sinus\|Eubacterium rectale, Oxalobacter formigenes\|Eubacterium rectale, Parabacteroides distasonis\|Eubacterium rectale, Parabacteroides johnsonii\|Eubacterium rectale, Parabacteroides merdae\|Eubacterium rectale, Parvimonas micra\|Eubacterium rectale, Pediococcus acidilactici\|Eubacterium rectale, Pediococcus pentosaceus\|Eubacterium rectale, Peptoniphilus duerdenii\|Eubacterium rectale, Peptoniphilus harei\|Eubacterium rectale, Peptoniphilus lacrimalis\|Eubacterium rectale, Peptostreptococcus anaerobius\|Eubacterium rectale, Peptostreptococcus stomatis\|Eubacterium rectale, Porphyromonas asaccharolytica\|Eubacterium rectale, Porphyromonas uenonis\|Eubacterium rectale, Prevotella amnii\|Eubacterium rectale, Prevotella bergensis\|Eubacterium rectale, Prevotella bivia\|Eubacterium rectale, Prevotella buccae\|Eubacterium rectale, Prevotella buccalis\|Eubacterium rectale, Prevotella copri\|Eubacterium rectale, Prevotella disiens\|Eubacterium rectale, Prevotella melaninogenica\|Eubacterium rectale, Prevotella multiformis\|Eubacterium rectale, Prevotella oralis\|Eubacterium rectale, Prevotellaoris\|Eubacterium rectale, Prevotella salivae\|Eubacterium rectale, Prevotella timonensis\|Eubacterium rectale, Propionibacterium acnes\|Eubacterium rectale, Propionibacterium freudenreichii\|Eubacterium rectale, Proteus mirabilis\|Eubacterium rectale, Proteus penneri\|Eubacterium rectale, Pseudoflavonifractor capillosus\|Eubacterium rectale, Pseudomonas aeruginosa\|Eubacterium rectale, Pseudomonas fluorescens\|Eubacterium rectale, Pseudomonas putida\|Eubacterium rectale, Pseudoramibacter alactolyticus\|Eubacterium rectale, Pyramidobacter piscolens\|Eubacterium rectale, Rhodopseudomonas palustris\|Eubacterium rectale, Roseburia intestinalis\|Eubacterium rectale, Roseburia inulinivorans\|Eubacterium rectale, Rothia dentocariosa\|Eubacterium rectale, Rothia mucilaginosa\|Eubacterium rectale, Ruminococcus albus\|Eubacterium rectale, Ruminococcus bromii\|Eubacterium rectale, Ruminococcus gnavus\|Eubacterium rectale, Ruminococcus lactaris\|Eubacterium rectale, Ruminococcus obeum\|Eubacterium rectale, Ruminococcus torques\|Eubacterium rectale, Selenomonas sputigena\|Eubacterium rectale, Shigella boydii\|Eubacterium rectale, Shigella dysenteriae\|Eubacterium rectale, Shigella sonnei\|Eubacterium rectale, Slackia exigua\|Eubacterium rectale, Solobacterium moorei\|Eubacterium rectale, Staphylococcus aureus\|Eubacterium rectale, Staphylococcus epidermidis\|Eubacterium rectale, Staphylococcus hominis\|Eubacterium rectale, Staphylococcus saprophyticus\|Eubacterium rectale, Staphylococcus warneri\|Eubacterium rectale, Streptococcus agalactiae\|Eubacterium rectale, Streptococcus anginosus\|Eubacterium rectale, Streptococcus australis\|Eubacterium rectale, Streptococcus bovis\|Eubacterium rectale, Streptococcus cristatus\|Eubacterium rectale, Streptococcus dysgalactiae\|Eubacterium rectale, Streptococcus equinus\|Eubacterium rectale, Streptococcus gordonii\|Eubacterium rectale, Streptococcus infantarius\|Eubacterium rectale, Streptococcus infantis\|Eubacterium rectale, Streptococcus mitis\|Eubacterium rectale, Streptococcus mutans\|Eubacterium rectale, Streptococcus oralis\|Eubacterium rectale, Streptococcus parasanguinis\|Eubacterium rectale, Streptococcus peroris\|Eubacterium rectale, Streptococcus pneumoniae\|Eubacterium rectale, Streptococcus salivarius\|Eubacterium rectale, Streptococcus sanguinis\|Eubacterium rectale, Streptococcus thermophilus\|Eubacterium rectale, Streptococcus vestibularis\|Eubacterium rectale, Subdoligranulum variabile\|Eubacterium rectale, Succinatimonas hippei\|Eubacterium rectale, Sutterella wadsworthensis\|Eubacterium rectale, Tropheryma whipplei\|Eubacterium rectale, Veillonella atypica\|Eubacterium rectale, Veillonella dispar\|Eubacterium rectale, Veillonella parvula\|Eubacterium rectale, Victivallis vadensis\|Eubacterium siraeum, Eubacterium siraeum\|Eubacterium siraeum, Eubacterium* |

TABLE 2-continued

| Table 2. Specific binary combinations of OTUs. Individual pairings are differentiated by "\|" and OTUs within a combination are differentiated by "," |
| --- |
| *ventriosum\|Eubacterium siraeum, Faecalibacterium prausnitzii\|Eubacterium siraeum, Finegoldia magna\|Eubacterium siraeum, Fusobacterium gonidiaformans\|Eubacterium siraeum, Fusobacterium mortiferum\|Eubacterium siraeum, Fusobacterium nucleatum\|Eubacterium siraeum, Fusobacterium varium\|Eubacterium siraeum, Gardnerella vaginalis\|Eubacterium siraeum, Gemella haemolysans\|Eubacterium siraeum, Gemella morbillorum\|Eubacterium siraeum, Gordonibacter pamelaeae\|Eubacterium siraeum, Granulicatella adiacens\|Eubacterium siraeum, Granulicatella elegans\|Eubacterium siraeum, Haemophilus influenzae\|Eubacterium siraeum, Haemophilus parainfluenzae\|Eubacterium siraeum, Helicobacter pullorum\|Eubacterium siraeum, Helicobacter pylori\|Eubacterium siraeum, Holdemania filiformis\|Eubacterium siraeum, Kingella oralis\|Eubacterium siraeum, Klebsiella pneumoniae\|Eubacterium siraeum, Klebsiella variicola\|Eubacterium siraeum, Lachnospiraceae bacterium 5_1_57FAA\|Eubacterium siraeum, Lactobacillus acidophilus\|Eubacterium siraeum, Lactobacillus amylovorus\|Eubacterium siraeum, Lactobacillus brevis\|Eubacterium siraeum, Lactobacillus casei\|Eubacterium siraeum, Lactobacillus crispatus\|Eubacterium siraeum, Lactobacillus delbrueckii\|Eubacterium siraeum, Lactobacillus fermentum\|Eubacterium siraeum, Lactobacillus gasseri\|Eubacterium siraeum, Lactobacillus iners\|Eubacterium siraeum, Lactobacillus jensenii\|Eubacterium siraeum, Lactobacillus johnsonii\|Eubacterium siraeum, Lactobacillus paracasei\|Eubacterium siraeum, Lactobacillus plantarum\|Eubacterium siraeum, Lactobacillus reuteri\|Eubacterium siraeum, Lactobacillus rhamnosus\|Eubacterium siraeum, Lactobacillus ruminis\|Eubacterium siraeum, Lactobacillus sakei\|Eubacterium siraeum, Lactobacillus salivarius\|Eubacterium siraeum, Lactococcus lactis\|Eubacterium siraeum, Lautropia mirabilis\|Eubacterium siraeum, Leuconostoc citreum\|Eubacterium siraeum, Leuconostoc gasicomitatum\|Eubacterium siraeum, Leuconostoc mesenteroides\|Eubacterium siraeum, Listeria monocytogenes\|Eubacterium siraeum, Marvinbryantia formatexigens\|Eubacterium siraeum, Megamonas hypermegale\|Eubacterium siraeum, Megasphaera micronuciformis\|Eubacterium siraeum, Methanobrevibacter smithii\|Eubacterium siraeum, Methanosphaera stadtmanae\|Eubacterium siraeum, Methylobacterium radiotolerans\|Eubacterium siraeum, Mitsuokella multacida\|Eubacterium siraeum, Mobiluncus curtisii\|Eubacterium siraeum, Mycoplasma hominis\|Eubacterium siraeum, Neisseria mucosa\|Eubacterium siraeum, Odoribacter splanchnicus\|Eubacterium siraeum, Olsenella uli\|Eubacterium siraeum, Oribacterium sinus\|Eubacterium siraeum, Oxalobacter formigenes\|Eubacterium siraeum, Parabacteroides distasonis\|Eubacterium siraeum, Parabacteroides johnsonii\|Eubacterium siraeum, Parabacteroides merdae\|Eubacterium siraeum, Parvimonas micra\|Eubacterium siraeum, Pediococcus acidilactici\|Eubacterium siraeum, Pediococcus pentosaceus\|Eubacterium siraeum, Peptoniphilus duerdenii\|Eubacterium siraeum, Peptoniphilus harei\|Eubacterium siraeum, Peptoniphilus lacrimalis\|Eubacterium siraeum, Peptostreptococcus anaerobius\|Eubacterium siraeum, Peptostreptococcus stomatis\|Eubacterium siraeum, Porphyromonas asaccharolytica\|Eubacterium siraeum, Porphyromonas uenonis\|Eubacterium siraeum, Prevotella amnii\|Eubacterium siraeum, Prevotella bergensis\|Eubacterium siraeum, Prevotella bivia\|Eubacterium siraeum, Prevotella buccae\|Eubacterium siraeum, Prevotella buccalis\|Eubacterium siraeum, Prevotella copri\|Eubacterium siraeum, Prevotella disiens\|Eubacterium siraeum, Prevotella melaninogenica\|Eubacterium siraeum, Prevotella multiformis\|Eubacterium siraeum, Prevotella oralis\|Eubacterium siraeum, Prevotella oris\|Eubacterium siraeum, Prevotella salivae\|Eubacterium siraeum, Prevotella timonensis\|Eubacterium siraeum, Propionibacterium acnes\|Eubacterium siraeum, Propionibacterium freudenreichii\|Eubacterium siraeum, Proteus mirabilis\|Eubacterium siraeum, Proteus penneri\|Eubacterium siraeum, Pseudoflavonifractor capillosus\|Eubacterium siraeum, Pseudomonas aeruginosa\|Eubacterium siraeum, Pseudomonas fluorescens\|Eubacterium siraeum, Pseudomonas putida\|Eubacterium siraeum, Pseudoramibacter alactolyticus\|Eubacterium siraeum, Pyramidobacter piscolens\|Eubacterium siraeum, Rhodopseudomonas palustris\|Eubacterium siraeum, Roseburia intestinalis\|Eubacterium siraeum, Roseburia inulinivorans\|Eubacterium siraeum, Rothia dentocariosa\|Eubacterium siraeum, Rothia mucilaginosa\|Eubacterium siraeum, Ruminococcus albus\|Eubacterium siraeum, Ruminococcus bromii\|Eubacterium siraeum, Ruminococcus gnavus\|Eubacterium siraeum, Ruminococcus lactaris\|Eubacterium siraeum, Ruminococcus obeum\|Eubacterium siraeum, Ruminococcus torques\|Eubacterium siraeum, Selenomonas sputigena\|Eubacterium siraeum, Shigella boydii\|Eubacterium siraeum, Shigella dysenteriae\|Eubacterium siraeum, Shigella sonnei\|Eubacterium siraeum, Slackia exigua\|Eubacterium siraeum, Solobacterium moorei\|Eubacterium siraeum, Staphylococcus aureus\|Eubacterium siraeum, Staphylococcus epidermidis\|Eubacterium siraeum, Staphylococcus hominis\|Eubacterium siraeum, Staphylococcus saprophyticus\|Eubacterium siraeum, Staphylococcus warneri\|Eubacterium siraeum, Streptococcus agalactiae\|Eubacterium siraeum, Streptococcus anginosus\|Eubacterium siraeum, Streptococcus australis\|Eubacterium siraeum, Streptococcus bovis\|Eubacterium siraeum, Streptococcus cristatus\|Eubacterium siraeum, Streptococcus dysgalactiae\|Eubacterium siraeum, Streptococcus equinus\|Eubacterium siraeum, Streptococcus gordonii\|Eubacterium siraeum, Streptococcus infantarius\|Eubacterium siraeum, Streptococcus infantis\|Eubacterium siraeum, Streptococcus mitis\|Eubacterium siraeum, Streptococcus mutans\|Eubacterium siraeum, Streptococcus oralis\|Eubacterium siraeum, Streptococcus parasanguinis\|Eubacterium siraeum, Streptococcus peroris\|Eubacterium siraeum, Streptococcus pneumoniae\|Eubacterium siraeum, Streptococcus salivarius\|Eubacterium siraeum, Streptococcus sanguinis\|Eubacterium siraeum, Streptococcus thermophilus\|Eubacterium siraeum, Streptococcus vestibularis\|Eubacterium siraeum, Subdoligranulum variabile\|Eubacterium siraeum, Succinatimonas hippei\|Eubacterium siraeum, Sutterella wadsworthensis\|Eubacterium siraeum, Tropheryma whipplei\|Eubacterium siraeum, Veillonella atypica\|Eubacterium siraeum, Veillonella dispar\|Eubacterium siraeum, Veillonella parvula\|Eubacterium siraeum, Victivallis vadensis\|Eubacterium ventriosum, Eubacterium ventriosum\|Eubacterium ventriosum, Faecalibacterium prausnitzii\|Eubacterium ventriosum, Finegoldia magna\|Eubacterium ventriosum, Fusobacterium gonidiaformans\|Eubacterium ventriosum, Fusobacterium mortiferum\|Eubacterium ventriosum, Fusobacterium nucleatum\|Eubacterium ventriosum, Fusobacterium varium\|Eubacterium ventriosum, Gardnerella vaginalis\|Eubacterium ventriosum, Gemella haemolysans\|Eubacterium ventriosum, Gemella morbillorum\|Eubacterium ventriosum, Gordonibacter pamelaeae\|Eubacterium ventriosum, Granulicatella adiacens\|Eubacterium ventriosum, Granulicatella elegans\|Eubacterium ventriosum, Haemophilus influenzae\|Eubacterium ventriosum, Haemophilus parainfluenzae\|Eubacterium ventriosum, Helicobacter pullorum\|Eubacterium ventriosum, Helicobacter pylori\|Eubacterium ventriosum, Holdemania filiformis\|Eubacterium ventriosum, Kingella oralis\|Eubacterium ventriosum, Klebsiella pneumoniae\|Eubacterium ventriosum, Klebsiella variicola\|Eubacterium ventriosum, Lachnospiraceae bacterium 5_1_57FAA\|Eubacterium ventriosum, Lactobacillus acidophilus\|Eubacterium ventriosum, Lactobacillus amylovorus\|Eubacterium ventriosum, Lactobacillus brevis\|Eubacterium ventriosum, Lactobacillus casei\|Eubacterium ventriosum, Lactobacillus crispatus\|Eubacterium ventriosum, Lactobacillus delbrueckii\|Eubacterium ventriosum, Lactobacillus fermentum\|Eubacterium ventriosum, Lactobacillus gasseri\|Eubacterium ventriosum, Lactobacillus iners\|Eubacterium ventriosum, Lactobacillus jensenii\|Eubacterium ventriosum, Lactobacillus johnsonii\|Eubacterium ventriosum, Lactobacillus paracasei\|Eubacterium ventriosum, Lactobacillus plantarum\|Eubacterium ventriosum, Lactobacillus reuteri\|Eubacterium ventriosum, Lactobacillus rhamnosus\|Eubacterium ventriosum, Lactobacillus ruminis\|Eubacterium ventriosum, Lactobacillus sakei\|Eubacterium ventriosum, Lactobacillus salivarius\|Eubacterium ventriosum, Lactococcus lactis\|Eubacterium ventriosum, Lautropia mirabilis\|Eubacterium ventriosum, Leuconostoc citreum\|Eubacterium ventriosum, Leuconostoc gasicomitatum\|Eubacterium ventriosum, Leuconostoc mesenteroides\|Eubacterium ventriosum, Listeria monocytogenes\|Eubacterium ventriosum, Marvinbryantia formatexigens\|Eubacterium ventriosum, Megamonas hypermegale\|Eubacterium ventriosum, Megasphaera micronuciformis\|Eubacterium ventriosum, Methanobrevibacter smithii\|Eubacterium ventriosum, Methanosphaera stadtmanae\|Eubacterium ventriosum, Methylobacterium radiotolerans\|Eubacterium ventriosum, Mitsuokella multacida\|Eubacterium ventriosum, Mobiluncus curtisii\|Eubacterium ventriosum, Mycoplasma hominis\|Eubacterium ventriosum, Neisseria mucosa\|Eubacterium ventriosum, Odoribacter splanchnicus\|Eubacterium ventriosum, Olsenella uli\|Eubacterium ventriosum, Oribacterium sinus\|Eubacterium ventriosum, Oxalobacter formigenes\|Eubacterium ventriosum, Parabacteroides distasonis\|Eubacterium ventriosum, Parabacteroides johnsonii\|Eubacterium ventriosum, Parabacteroides merdae\|Eubacterium ventriosum, Parvimonas micra\|Eubacterium ventriosum, Pediococcus acidilactici\|Eubacterium ventriosum, Pediococcus pentosaceus\|Eubacterium ventriosum, Peptoniphilus duerdenii\|Eubacterium ventriosum, Peptoniphilus harei\|Eubacterium ventriosum, Peptoniphilus lacrimalis\|Eubacterium ventriosum, Peptostreptococcus anaerobius\|Eubacterium ventriosum, Peptostreptococcus stomatis\|Eubacterium ventriosum, Porphyromonas* |

TABLE 2-continued

Table 2. Specific binary combinations of OTUs. Individual pairings are differentiated by "|" and OTUs within a combination are differentiated by ","

asaccharolytica|Eubacterium ventriosum, Porphyromonas uenonis|Eubacterium ventriosum, Prevotella amnii|Eubacterium ventriosum, Prevotella bergensis|Eubacterium ventriosum, Prevotella bivia|Eubacterium ventriosum, Prevotella buccae|Eubacterium ventriosum, Prevotella buccalis|Eubacterium ventriosum, Prevotella copri|Eubacterium ventriosum, Prevotella disiens|Eubacterium ventriosum, Prevotella melaninogenica|Eubacterium ventriosum, Prevotella multiformis|Eubacterium ventriosum, Prevotella oralis|Eubacterium ventriosum, Prevotella oris|Eubacterium ventriosum, Prevotella salivae|Eubacterium ventriosum, Prevotella timonensis|Eubacterium ventriosum, Propionibacterium acnes|Eubacterium ventriosum, Propionibacterium freudenreichii|Eubacterium ventriosum, Proteus mirabilis|Eubacterium ventriosum, Proteus penneri|Eubacterium ventriosum, Pseudoflavonifractor capillosus|Eubacterium ventriosum, Pseudomonas aeruginosa|Eubacterium ventriosum, Pseudomonas fluorescens|Eubacterium ventriosum, Pseudomonas putida|Eubacterium ventriosum, Pseudoramibacter alactolyticus|Eubacterium ventriosum, Pyramidobacter piscolens|Eubacterium ventriosum, Rhodopseudomonas palustris|Eubacterium ventriosum, Roseburia intestinalis|Eubacterium ventriosum, Roseburia inulinivorans|Eubacterium ventriosum, Rothia dentocariosa|Eubacterium ventriosum, Rothia mucilaginosa|Eubacterium ventriosum, Ruminococcus albus|Eubacterium ventriosum, Ruminococcus bromii|Eubacterium ventriosum, Ruminococcus gnavus|Eubacterium ventriosum, Ruminococcus lactaris|Eubacterium ventriosum, Ruminococcus obeum|Eubacterium ventriosum, Ruminococcus torques|Eubacterium ventriosum, Selenomonas sputigena|Eubacterium ventriosum, Shigella boydii|Eubacterium ventriosum, Shigella dysenteriae|Eubacterium ventriosum, Shigella sonnei|Eubacterium ventriosum, Slackia exigua|Eubacterium ventriosum, Solobacterium moorei|Eubacterium ventriosum, Staphylococcus aureus|Eubacterium ventriosum, Staphylococcus epidermidis|Eubacterium ventriosum, Staphylococcus hominis|Eubacterium ventriosum, Staphylococcus saprophyticus|Eubacterium ventriosum, Staphylococcus warneri|Eubacterium ventriosum, Streptococcus agalactiae|Eubacterium ventriosum, Streptococcus anginosus|Eubacterium ventriosum, Streptococcus australis|Eubacterium ventriosum, Streptococcus bovis|Eubacterium ventriosum, Streptococcus cristatus|Eubacterium ventriosum, Streptococcus dysgalactiae|Eubacterium ventriosum, Streptococcus equinus|Eubacterium ventriosum, Streptococcus gordonii|Eubacterium ventriosum, Streptococcus infantarius|Eubacterium ventriosum, Streptococcus infantis|Eubacterium ventriosum, Streptococcus mitis|Eubacterium ventriosum, Streptococcus mutans|Eubacterium ventriosum, Streptococcus oralis|Eubacterium ventriosum, Streptococcus parasanguinis|Eubacterium ventriosum, Streptococcus peroris|Eubacterium ventriosum, Streptococcus pneumoniae|Eubacterium ventriosum, Streptococcus salivarius|Eubacterium ventriosum, Streptococcus sanguinis|Eubacterium ventriosum, Streptococcus thermophilus|Eubacterium ventriosum, Streptococcus vestibularis|Eubacterium ventriosum, Subdoligranulum variabile|Eubacterium ventriosum, Succinatimonas hippei|Eubacterium ventriosum, Sutterella wadsworthensis|Eubacterium ventriosum, Tropheryma whipplei|Eubacterium ventriosum, Veillonella atypica|Eubacterium ventriosum, Veillonella dispar|Eubacterium ventriosum, Veillonella parvula|Eubacterium ventriosum, Victivallis vadensis|Faecalibacterium prausnitzii, Faecalibacterium prausnitzii|Faecalibacterium prausnitzii, Finegoldia magna|Faecalibacterium prausnitzii, Fusobacterium gonidiaformans|Faecalibacterium prausnitzii, Fusobacterium mortiferum|Faecalibacterium prausnitzii, Fusobacterium nucleatum|Faecalibacterium prausnitzii, Fusobacterium varium|Faecalibacterium prausnitzii, Gardnerella vaginalis|Faecalibacterium prausnitzii, Gemella haemolysans|Faecalibacterium prausnitzii, Gemella morbillorum|Faecalibacterium prausnitzii, Gordonibacter pamelaeae|Faecalibacterium prausnitzii, Granulicatella adiacens|Faecalibacterium prausnitzii, Granulicatella elegans|Faecalibacterium prausnitzii, Haemophilus influenzae|Faecalibacterium prausnitzii, Haemophilus parainfluenzae|Faecalibacterium prausnitzii, Helicobacter pullomru|Faecalibacterium prausnitzii, Helicobacter pylori|Faecalibacterium prausnitzii, Holdemania filiformis|Faecalibacterium prausnitzii, Kingella oralis|Faecalibacterium prausnitzii, Klebsiella pneumoniae|Faecalibacterium prausnitzii, Klebsiella variicola|Faecalibacterium prausnitzii, Lachnospiraceae bacterium 5_1_57FAA|Faecalibacterium prausnitzii, Lactobacillus acidophilus|Faecalibacterium prausnitzii, Lactobacillus amylovorus|Faecalibacterium prausnitzii, Lactobacillus brevis|Faecalibacterium prausnitzii, Lactobacillus casei|Faecalibacterium prausnitzii, Lactobacillus crispatus|Faecalibacterium prausnitzii, Lactobacillus delbrueckii|Faecalibacterium prausnitzii, Lactobacillus fermentum|Faecalibacterium prausnitzii, Lactobacillus gasseri|Faecalibacterium prausnitzii, Lactobacillus iners|Faecalibacterium prausnitzii, Lactobacillus jensenii|Faecalibacterium prausnitzii, Lactobacillus johnsonii|Faecalibacterium prausnitzii, Lactobacillus paracasei|Faecalibacterium prausnitzii, Lactobacillus plantarum|Faecalibacterium prausnitzii, Lactobacillus reuteri|Faecalibacterium prausnitzii, Lactobacillus rhamnosus|Faecalibacterium prausnitzii, Lactobacillus ruminis|Faecalibacterium prausnitzii, Lactobacillus sakei|Faecalibacterium prausnitzii, Lactobacillus salivarius|Faecalibacterium prausnitzii, Lactococcus lactis|Faecalibacterium prausnitzii, Lautropia mirabilis|Faecalibacterium prausnitzii, Leuconostoc citreum|Faecalibacterium prausnitzii, Leuconostoc gasicomitatum|Faecalibacterium prausnitzii, Leuconostoc mesenteroides|Faecalibacterium prausnitzii, Listeria monocytogenes|Faecalibacterium prausnitzii, Marvinbryantia formatexigens|Faecalibacterium prausnitzii, Megamonas hypermegale|Faecalibacterium prausnitzii, Megasphaera micronuciformis|Faecalibacterium prausnitzii, Methanobrevibacter smithii|Faecalibacterium prausnitzii, Methanosphaera stadtmanae|Faecalibacterium prausnitzii, Methylobacterium radiotolerans|Faecalibacterium prausnitzii, Mitsuokella multacida|Faecalibacterium prausnitzii, Mobiluncus curtisii|Faecalibacterium prausnitzii, Mycoplasma hominis|Faecalibacterium prausnitzii, Neisseria mucosa|Faecalibacterium prausnitzii, Odoribacter splanchnicus|Faecalibacterium prausnitzii, Olsenella uli|Faecalibacterium prausnitzii, Oribacterium sinus|Faecalibacterium prausnitzii, Oxalobacter formigenes|Faecalibacterium prausnitzii, Parabacteroides distasonis|Faecalibacterium prausnitzii, Parabacteroides johnsonii|Faecalibacterium prausnitzii, Parabacteroides merdae|Faecalibacterium prausnitzii, Parvimonas micra|Faecalibacterium prausnitzii, Pediococcus acidilactici|Faecalibacterium prausnitzii, Pediococcus pentosaceus|Faecalibacterium prausnitzii, Peptoniphilus duerdenii|Faecalibacterium prausnitzii, Peptoniphilus harei|Faecalibacterium prausnitzii, Peptoniphilus lacrimalis|Faecalibacterium prausnitzii, Peptostreptococcus anaerobius|Faecalibacterium prausnitzii, Peptostreptococcus stomatis|Faecalibacterium prausnitzii, Porphyromonas asaccharolytica|Faecalibacterium prausnitzii, Porphyromonas uenonis|Faecalibacterium prausnitzii, Prevotella amnii|Faecalibacterium prausnitzii, Prevotella bergensis|Faecalibacterium prausnitzii, Prevotella bivia|Faecalibacterium prausnitzii, Prevotella buccae|Faecalibacterium prausnitzii, Prevotella buccalis|Faecalibacterium prausnitzii, Prevotella copri|Faecalibacterium prausnitzii, Prevotella disiens|Faecalibacterium prausnitzii, Prevotella melaninogenica|Faecalibacterium prausnitzii, Prevotella multiformis|Faecalibacterium prausnitzii, Prevotella oralis|Faecalibacterium prausnitzii, Prevotella oris|Faecalibacterium prausnitzii, Prevotella salivae|Faecalibacterium prausnitzii, Prevotella timonensis|Faecalibacterium prausnitzii, Propionibacterium acnes|Faecalibacterium prausnitzii, Propionibacterium freudenreichii|Faecalibacterium prausnitzii, Proteus mirabilis|Faecalibacterium prausnitzii, Proteus penneri|Faecalibacterium prausnitzii, Pseudoflavonifractor capillosus|Faecalibacterium prausnitzii, Pseudomonas aeruginosa|Faecalibacterium prausnitzii, Pseudomonas fluorescens|Faecalibacterium prausnitzii, Pseudomonas putida|Faecalibacterium prausnitzii, Pseudoramibacter alactolyticus|Faecalibacterium prausnitzii, Pyramidobacter piscolens|Faecalibacterium prausnitzii, Rhodopseudomonas palustris|Faecalibacterium prausnitzii, Roseburia intestinalis|Faecalibacterium prausnitzii, Roseburia inulinivorans|Faecalibacterium prausnitzii, Rothia dentocariosa|Faecalibacterium prausnitzii, Rothia mucilaginosal|Faecalibacterium prausnitzii, Ruminococcus albus|Faecalibacterium prausnitzii, Ruminococcus bromii|Faecalibacterium prausnitzii, Ruminococcus gnavus|Faecalibacterium prausnitzii, Ruminococcus lactaris|Faecalibacterium prausnitzii, Ruminococcus obeum|Faecalibacterium prausnitzii, Ruminococcus torques|Faecalibacterium prausnitzii, Selenomonas sputigena|Faecalibacterium prausnitzii, Shigella boydii|Faecalibacterium prausnitzii, Shigella dysenteriae|Faecalibacterium prausnitzii, Shigella sonnei|Faecalibacterium prausnitzii, Slackia exigua|Faecalibacterium prausnitzii, Solobacterium moorei|Faecalibacterium prausnitzii, Staphylococcus aureus|Faecalibacterium prausnitzii, Staphylococcus epidermidis|Faecalibacterium prausnitzii, Staphylococcus hominis|Faecalibacterium prausnitzii, Staphylococcus saprophyticus|Faecalibacterium prausnitzii, Staphylococcus warneri|Faecalibacterium prausnitzii, Streptococcus agalactiae|Faecalibacterium prausnitzii, Streptococcus anginosus|Faecalibacterium prausnitzii, Streptococcus australis|Faecalibacterium prausnitzii, Streptococcus bovis|Faecalibacterium prausnitzii, Streptococcus cristatus|Faecalibacterium prausnitzii, Streptococcus dysgalactiae|Faecalibacterium prausnitzii, Streptococcus equinus|Faecalibacterium prausnitzii, Streptococcus gordonii|Faecalibacterium TABLE 2-continued

| Table 2. Specific binary combinations of OTUs. Individual pairings are differentiated by "\|" and OTUs within a combination are differentiated by "," |
|---|
| *prausnitzii, Streptococcus infantarius\|Faecalibacterium prausnitzii, Streptococcus infantis\|Faecalibacterium prausnitzii, Streptococcus mitis\|Faecalibacterium prausnitzii, Streptococcus mutans\|Faecalibacterium prausnitzii, Streptococcus oralis\|Faecalibacterium prausnitzii, Streptococcus parasanguinis\|Faecalibacterium prausnitzii, Streptococcus peroris\|Faecalibacterium prausnitzii, Streptococcus pneumoniae\|Faecalibacterium prausnitzii, Streptococcus salivarius\|Faecalibacterium prausnitzii, Streptococcus sanguinis\|Faecalibacterium prausnitzii, Streptococcus thermophilus\|Faecalibacterium prausnitzii, Streptococcus vestibularis\|Faecalibacterium prausnitzii, Subdoligranulum variabile\|Faecalibacterium prausnitzii, Succinatimonas hippei\|Faecalibacterium prausnitzii, Sutterella wadsworthensis\|Faecalibacterium prausnitzii, Tropheryma whipplei\|Faecalibacterium prausnitzii, Veillonella atypica\|Faecalibacterium prausnitzii, Veillonella dispar\|Faecalibacterium prausnitzii, Veillonella parvula\|Faecalibacterium prausnitzii, Victivallis vadensis\|Finegoldia magna, Finegoldia magna\|Finegoldia magna, Fusobacterium gonidiaformans\|Finegoldia magna, Fusobacterium mortiferum\|Finegoldia magna, Fusobacterium nucleatum\|Finegoldia magna, Fusobacterium varium\|Finegoldia magna, Gardnerella vaginalis\|Finegoldia magna, Gemella haemolysans\|Finegoldia magna, Gemella morbillorum\|Finegoldia magna, Gordonibacter pamelaeae\|Finegoldia magna, Granulicatella adiacens\|Finegoldia magna, Granulicatella elegans\|Finegoldia magna, Haemophilus influenzae\|Finegoldia magna, Haemophilus parainfluenzae\|Finegoldia magna, Helicobacter pullorum\|Finegoldia magna, Helicobacter pylori\|Finegoldia magna, Holdemania filiformis\|Finegoldia magna, Kingella oralis\|Finegoldia magna, Klebsiella pneumoniae\|Finegoldia magna, Klebsiella variicola\|Finegoldia magna, Lachnospiraceae bacterium* 5_1_57FAA\|*Finegoldia magna, Lactobacillus acidophilus\|Finegoldia magna, Lactobacillus amylovorus\|Finegoldia magna, Lactobacillus brevis\|Finegoldia magna, Lactobacillus casei\|Finegoldia magna, Lactobacillus crispatus\|Finegoldia magna, Lactobacillus delbrueckii\|Finegoldia magna, Lactobacillus fermentum\|Finegoldia magna, Lactobacillus gasseri\|Finegoldia magna, Lactobacillus iners\|Finegoldia magna, Lactobacillus jensenii\|Finegoldia magna, Lactobacillus johnsonii\|Finegoldia magna, Lactobacillus paracasei\|Finegoldia magna, Lactobacillus plantarum\|Finegoldia magna, Lactobacillus reuteri\|Finegoldia magna, Lactobacillus rhamnosus\|Finegoldia magna, Lactobacillus ruminis\|Finegoldia magna, Lactobacillus sakei\|Finegoldia magna, Lactobacillus salivarius\|Finegoldia magna, Lactococcus lactis\|Finegoldia magna, Lautropia mirabilis\|Finegoldia magna, Leuconostoc citreum\|Finegoldia magna, Leuconostoc gasicomitatum\|Finegoldia magna, Leuconostoc mesenteroides\|Finegoldia magna, Listeria monocytogenes\|Finegoldia magna, Marvinbryantia formatexigens\|Finegoldia magna, Megamonas hypermegale\|Finegoldia magna, Megasphaera micronuciformis\|Finegoldia magna, Methanobrevibacter smithii\|Finegoldia magna, Methanosphaera stadtmanae\|Finegoldia magna, Methylobacterium radiotolerans\|Finegoldia magna, Mitsuokella multacida\|Finegoldia magna, Mobiluncus curtisii\|Finegoldia magna, Mycoplasma hominis\|Finegoldia magna, Neisseria mucosa\|Finegoldia magna, Odoribacter splanchnicus\|Finegoldia magna, Olsenella uli\|Finegoldia magna, Oribacterium sinus\|Finegoldia magna, Oxalobacter formigenes\|Finegoldia magna, Parabacteroides distasonis\|Finegoldia magna, Parabacteroides johnsonii\|Finegoldia magna, Parabacteroides merdae\|Finegoldia magna, Parvimonas micra\|Finegoldia magna, Pediococcus acidilactici\|Finegoldia magna, Pediococcus pentosaceus\|Finegoldia magna, Peptoniphilus duerdenii\|Finegoldia magna, Peptoniphilus harei\|Finegoldia magna, Peptoniphilus lacrimalis\|Finegoldia magna, Peptostreptococcus anaerobius\|Finegoldia magna, Peptostreptococcus stomatis\|Finegoldia magna, Porphyromonas asaccharolytica\|Finegoldia magna, Porphyromonas uenonis\|Finegoldia magna, Prevotella amnii\|Finegoldia magna, Prevotella bergensis\|Finegoldia magna, Prevotella bivia\|Finegoldia magna, Prevotella buccae\|Finegoldia magna, Prevotella buccalis\|Finegoldia magna, Prevotella copri\|Finegoldia magna, Prevotella disiens\|Finegoldia magna, Prevotella melaninogenica\|Pinegoldia magna, Prevotella multiformis\|Finegoldia magna, Prevotella oralis\|Finegoldia magna, Prevotella oris\|Finegoldia magna, Prevotella salivae\|Finegoldia magna, Prevotella timonensis\|Finegoldia magna, Propionibacterium acnes\|Finegoldia magna, Propionibacterium freudenreichii\|Finegoldia magna, Proteus mirabilis\|Finegoldia magna, Proteus penneri\|Finegoldia magna, Pseudoflavonifractor capillosus\|Finegoldia magna, Pseudomonas aeruginosa\|Finegoldia magna, Pseudomonas fluorescens\|Finegoldia magna, Pseudomonas putida\|Finegoldia magna, Pseudoramibacter alactolyticus\|Finegoldia magna, Pyramidobacter piscolens\|Finegoldia magna, Rhodopseudomonas palustris\|Finegoldia magna, Roseburia intestinalis\|Finegoldia magna, Roseburia inulinivorans\|Finegoldia magna, Rothia dentocariosa\|Finegoldia magna, Rothia mucilaginosa\|Finegoldia magna, Ruminococcus albus\|Finegoldia magna, Ruminococcus bromii\|Finegoldia magna, Ruminococcus gnavus\|Finegoldia magna, Ruminococcus lactaris\|Finegoldia magna, Ruminococcus obeum\|Finegoldia magna, Ruminococcus torques\|Finegoldia magna, Selenomonas sputigena\|Finegoldia magna, Shigella boydii\|Finegoldia magna, Shigella dysenteriae\|Finegoldia magna, Shigella sonnei\|Finegoldia magna, Slackia exigua\|Finegoldia magna, Solobacterium moorei\|Finegoldia magna, Staphylococcus aureus\|Finegoldia magna, Staphylococcus epidermidis\|Finegoldia magna, Staphylococcus hominis\|Finegoldia magna, Staphylococcus saprophyticus\|Finegoldia magna, Staphylococcus warneri\|Finegoldia magna, Streptococcus agalactiae\|Finegoldia magna, Streptococcus anginosus\|Finegoldia magna, Streptococcus australis\|Finegoldia magna, Streptococcus bovis\|Finegoldia magna, Streptococcus cristatus\|Finegoldia magna, Streptococcus dysgalactiae\|Finegoldia magna, Streptococcus equinus\|Finegoldia magna, Streptococcus gordonii\|Finegoldia magna, Streptococcus infantarius\|Finegoldia magna, Streptococcus infantis\|Finegoldia magna, Streptococcus mitis\|Finegoldia magna, Streptococcus mutans\|Finegoldia magna, Streptococcus oralis\|Finegoldia magna, Streptococcus parasanguinis\|Finegoldia magna, Streptococcus peroris\|Finegoldia magna, Streptococcus pneumoniae\|Finegoldia magna, Streptococcus salivarius\|Finegoldia magna, Streptococcus sanguinis\|Finegoldia magna, Streptococcus thermophilus\|Finegoldia magna, Streptococcus vestibularis\|Finegoldia magna, Subdoligranulum variabile\|Finegoldia magna, Succinatimonas hippei\|Finegoldia magna, Sutterella wadsworthensis\|Finegoldia magna, Tropheryma whipplei\|Finegoldia magna, Veillonella atypica\|Finegoldia magna, Veillonella dispar\|Finegoldia magna, Veillonella parvula\|Finegoldia magna, Victivallis vadensis\|Fusobacterium gonidiaformans, Fusobacterium gonidiaformans\|Fusobacterium gonidiaformans, Fusobacterium mortiferum\|Fusobacterium gonidiaformans, Fusobacterium nucleatum\|Fusobacterium gonidiaformans, Fusobacterium varium\|Fusobacterium gonidiaformans, Gardnerella vaginalis\|Fusobacterium gonidiaformans, Gemella haemolysans\|Fusobacterium gonidiaformans, Gemella morbillorum\|Fusobacterium gonidiaformans, Gordonibacter pamelaeae\|Fusobacterium gonidiaformans, Granulicatella adiacens\|Fusobacterium gonidiaformans, Granulicatella elegans\|Fusobacterium gonidiaformans, Haemophilus influenzae\|Fusobacterium gonidiaformans, Haemophilus parainfluenzae\|Fusobacterium gonidiaformans, Helicobacter pullorum\|Fusobacterium gonidiaformans, Helicobacter pylori\|Fusobacterium gonidiaformans, Holdemania filiformis\|Fusobacterium gonidiaformans, Kingella oralis\|Fusobacterium gonidiaformans, Klebsiella pneumoniae\|Fusobacterium gonidiaformans, Klebsiella variicola\|Fusobacterium gonidiaformans, Lachnospiraceae bacterium* 5_1_57FAA\|*Fusobacterium gonidiaformans, Lactobacillus acidophilus\|Fusobacterium gonidiaformans, Lactobacillus amylovorus\|Fusobacterium gonidiaformans, Lactobacillus brevis\|Fusobacterium gonidiaformans, Lactobacillus casei\|Fusobacterium gonidiaformans, Lactobacillus crispatus\|Fusobacterium gonidiaformans, Lactobacillus delbrueckii\|Fusobacterium gonidiaformans, Lactobacillus fermentum\|Fusobacterium gonidiaformans, Lactobacillus gasseri\|Fusobacterium gonidiaformans, Lactobacillus iners\|Fusobacterium gonidiaformans, Lactobacillus jensenii\|Fusobacterium gonidiaformans, Lactobacillus johnsonii\|Fusobacterium gonidiaformans, Lactobacillus paracasei\|Fusobacterium gonidiaformans, Lactobacillus plantarum\|Fusobacterium gonidiaformans, Lactobacillus reuteri\|Fusobacterium gonidiaformans, Lactobacillus rhamnosus\|Fusobacterium gonidiaformans, Lactobacillus ruminis\|Fusobacterium gonidiaformans, Lactobacillus sakei\|Fusobacterium gonidiaformans, Lactobacillus salivarius\|Fusobacterium gonidiaformans, Lactococcus lactis\|Fusobacterium gonidiaformans, Lautropia mirabilis\|Fusobacterium gonidiaformans, Leuconostoc citreum\|Fusobacterium gonidiaformans, Leuconostoc gasicomitatum\|Fusobacterium gonidiaformans, Leuconostoc mesenteroides\|Fusobacterium gonidiaformans, Listeria monocytogenes\|Fusobacterium gonidiaformans, Marvinbryantia formatexigens\|Fusobacterium gonidiaformans, Megamonas hypermegale\|Fusobacterium gonidiaformans, Megasphaera micronuciformis\|Fusobacterium gonidiaformans, Methanobrevibacter smithii\|Fusobacterium gonidiaformans, Methanosphaera stadtmanae\|Fusobacterium gonidiaformans, Methylobacterium radiotolerans\|Fusobacterium gonidiaformans, Mitsuokella multacida\|Fusobacterium gonidiaformans, Mobiluncus curtisii\|Fusobacterium gonidiaformans, Mycoplasma hominis\|Fusobacterium gonidiaformans, Neisseria mucosa\|Fusobacterium* |

TABLE 2-continued

Table 2. Specific binary combinations of OTUs. Individual pairings are differentiated by "|" and OTUs within a combination are differentiated by ","

*gonidiaformans, Odoribacter splanchnicus|Fusobacterium gonidiaformans, Olsenella uli|Fusobacterium gonidiaformans, Oribacterium sinus|Fusobacterium gonidiaformans, Oxalobacter formigenes|Fusobacterium gonidiaformans, Parabacteroides distasonis|Fusobacterium gonidiaformans, Parabacteroides johnsonii|Fusobacterium gonidiaformans, Parabacteroides merdae|Fusobacterium gonidiaformans, Parvimonas micra|Fusobacterium gonidiaformans, Pediococcus acidilactici|Fusobacterium gonidiaformans, Pediococcus pentosaceus|Fusobacterium gonidiaformans, Peptoniphilus duerdenii|Fusobacterium gonidiaformans, Peptoniphilus harei|Fusobacterium gonidiaformans, Peptoniphilus lacrimalis|Fusobacterium gonidiaformans, Peptostreptococcus anaerobius|Fusobacterium gonidiaformans, Peptostreptococcus stomatis|Fusobacterium gonidiaformans, Porphyromonas asaccharolytica|Fusobacterium gonidiaformans, Porphyromonas uenonis|Fusobacterium gonidiaformans, Prevotella amnii|Fusobacterium gonidiaformans, Prevotella bergensis|Fusobacterium gonidiaformans, Prevotella bivia|Fusobacterium gonidiaformans, Prevotella buccae|Fusobacterium gonidiaformans, Prevotella buccalis|Fusobacterium gonidiaformans, Prevotella copri|Fusobacterium gonidiaformans, Prevotella disiens|Fusobacterium gonidiaformans, Prevotella melaninogenica|Fusobacterium gonidiaformans, Prevotella multiformis|Fusobacterium gonidiaformans, Prevotella oralis|Fusobacterium gonidiaformans, Prevotella oris|Fusobacterium gonidiaformans, Prevotella salivae|Fusobacterium gonidiaformans, Prevotella timonensis|Fusobacterium gonidiaformans, Propionibacterium acnes|Fusobacterium gonidiaformans, Propionibacterium freudenreichii|Fusobacterium gonidiaformans, Proteus mirabilis|Fusobacterium gonidiaformans, Proteus penneri|Fusobacterium gonidiaformans, Pseudoflavonifractor capillosus|Fusobacterium gonidiaformans, Pseudomonas aeruginosa|Fusobacterium gonidiaformans, Pseudomonas fluorescens|Fusobacterium gonidiaformans, Pseudomonas putida|Fusobacterium gonidiaformans, Pseudoramibacter alactolyticus|Fusobacterium gonidiaformans, Pyramidobacter piscolens|Fusobacterium gonidiaformans, Rhodopseudomonas palustris|Fusobacterium gonidiaformans, Roseburia intestinalis|Fusobacterium gonidiaformans, Roseburia inulinivorans|Fusobacterium gonidiaformans, Rothia dentocariosa|Fusobacterium gonidiaformans, Rothia mucilaginosa|Fusobacterium gonidiaformans, Ruminococcus albus|Fusobacterium gonidiaformans, Ruminococcus bromii|Fusobacterium gonidiaformans, Ruminococcus gnavus|Fusobacterium gonidiaformans, Ruminococcus lactaris|Fusobacterium gonidiaformans, Ruminococcus obeum|Fusobacterium gonidiaformans, Ruminococcus torques|Fusobacterium gonidiaformans, Selenomonas sputigena|Fusobacterium gonidiaformans, Shigella boydii|Fusobacterium gonidiaformans, Shigella dysenteriae|Fusobacterium gonidiaformans, Shigella sonnei|Fusobacterium gonidiaformans, Slackia exigua|Fusobacterium gonidiaformans, Solobacterium moorei|Fusobacterium gonidiaformans, Staphylococcus aureus|Fusobacterium gonidiaformans, Staphylococcus epidermidis|Fusobacterium gonidiaformans, Staphylococcus hominis|Fusobacterium gonidiaformans, Staphylococcus saprophyticus|Fusobacterium gonidiaformans, Staphylococcus warneri|Fusobacterium gonidiaformans, Streptococcus agalactiae|Fusobacterium gonidiaformans, Streptococcus anginosus|Fusobacterium gonidiaformans, Streptococcus australis|Fusobacterium gonidiaformans, Streptococcus bovis|Fusobacterium gonidiaformans, Streptococcus cristatus|Fusobacterium gonidiaformans, Streptococcus dysgalactiae|Fusobacterium gonidiaformans, Streptococcus equinus|Fusobacterium gonidiaformans, Streptococcus gordonii|Fusobacterium gonidiaformans, Streptococcus infantarius|Fusobacterium gonidiaformans, Streptococcus infantis|Fusobacterium gonidiaformans, Streptococcus mitis|Fusobacterium gonidiaformans, Streptococcus mutans|Fusobacterium gonidiaformans, Streptococcus oralis|Fusobacterium gonidiaformans, Streptococcus parasanguinis|Fusobacterium gonidiaformans, Streptococcus peroris|Fusobacterium gonidiaformans, Streptococcus pneumoniae|Fusobacterium gonidiaformans, Streptococcus salivarius|Fusobacterium gonidiaformans, Streptococcus sanguinis|Fusobacterium gonidiaformans, Streptococcus thermophilus|Fusobacterium gonidiaformans, Streptococcus vestibularis|Fusobacterium gonidiaformans, Subdoligranulum variabile|Fusobacterium gonidiaformans, Succinatimonas hippei|Fusobacterium gonidiaformans, Sutterella wadsworthensis|Fusobacterium gonidiaformans, Tropheryma whipplei|Fusobacterium gonidiaformans, Veillonella atypica|Fusobacterium gonidiaformans, Veillonella dispar|Fusobacterium gonidiaformans, Veillonella parvula|Fusobacterium gonidiaformans, Victivallis vadensis|Fusobacterium mortiferum, Fusobacterium mortiferum|Fusobacterium mortiferum, Fusobacterium nucleatum|Fusobacterium mortiferum, Fusobacterium varium|Fusobacterium mortiferum, Gardnerella vaginalis|Fusobacterium mortiferum, Gemella haemolysans|Fusobacterium mortiferum, Gemella morbillorum|Fusobacterium mortiferum, Gordonibacter pamelaeae|Fusobacterium mortifentm, Granulicatella adiacens|Fusobacterium mortiferum, Granulicatella elegans|Fusobacterium mortiferum, Haemophilus influenzae|Fusobacterium mortiferum, Haemophilus parainfluenzae|Fusobacterium mortiferum, Helicobacter pullorum|Fusobacterium mortiferum, Helicobacter pylori|Fusobacterium mortiferum, Holdemania filiformis|Fusobacterium mortiferum, Kingella oralis|Fusobacterium mortiferum, Klebsiella pneumoniae|Fusobacterium mortiferum, Klebsiella variicola|Fusobacterium mortiferum, Lachnospiraceae bacterium* 5_1_57FAA|*Fusobacterium mortiferum, Lactobacillus acidophilus|Fusobacterium mortiferum, Lactobacillus amylovorus|Fusobacterium mortiferum, Lactobacillus brevis|Fusobacterium mortiferum, Lactobacillus casei|Fusobacterium mortiferum, Lactobacillus crispatus|Fusobacterium mortiferum, Lactobacillus delbrueckii|Fusobacterium mortiferum, Lactobacillus fermentum|Fusobacterium mortiferum, Lactobacillus gasseri|Fusobacterium mortiferum, Lactobacillus iners|Fusobacterium mortiferum, Lactobacillus jensenii|Fusobacterium mortiferum, Lactobacillus johnsonii|Fusobacterium mortiferum, Lactobacillus paracasei|Fusobacterium mortiferum, Lactobacillus plantarum|Fusobacterium mortiferum, Lactobacillus reuteri|Fusobacterium mortiferum, Lactobacillus rhamnosus|Fusobacterium mortiferum, Lactobacillus ruminis|Fusobacterium mortiferum, Lactobacillus sakei|Fusobacterium mortiferum, Lactobacillus salivarius|Fusobacterium mortiferum, Lactococcus lactis|Fusobacterium mortiferum, Lautropia mirabilis|Fusobacterium mortiferum, Leuconostoc citreum|Fusobacterium mortiferum, Leuconostoc gasicomitatum|Fusobacterium mortiferum, Leuconostoc mesenteroides|Fusobacterium mortiferum, Listeria monocytogenes|Fusobacterium mortiferum, Marvinbryantia formatexigens|Fusobacterium mortiferum, Megamonas hypermegale|Fusobacterium mortiferum, Megasphaera micronuciformis|Fusobacterium mortiferum, Methanobrevibacter smithii|Fusobacterium mortiferum, Methanosphaera stadtmanae|Fusobacterium mortiferum, Methylobacterium radiotolerans|Fusobacterium mortiferum, Mitsuokella multacida|Fusobacterium mortiferum, Mobiluncus curtisii|Fusobacterium mortiferum, Mycoplasma hominis|Fusobacterium mortiferum, Neisseria mucosa|Fusobacterium mortiferum, Odoribacter splanchnicus|Fusobacterium mortiferum, Olsenella uli|Fusobacterium mortiferum, Oribacterium sinus|Fusobacterium mortiferum, Oxalobacter formigenes|Fusobacterium mortiferum, Parabacteroides distasonis|Fusobacterium mortiferum, Parabacteroides johnsonii|Fusobacterium mortiferum, Parabacteroides merdae|Fusobacterium mortiferum, Parvimonas micra|Fusobacterium mortiferum, Pediococcus acidilactici|Fusobacterium mortiferum, Pediococcus pentosaceus|Fusobacterium mortiferum, Peptoniphilus duerdenii|Fusobacterium mortiferum, Peptoniphilus harei|Fusobacterium mortiferum, Peptoniphilus lacrimalis|Fusobacterium mortiferum, Peptostreptococcus anaerobius|Fusobacterium mortiferum, Peptostreptococcus stomatis|Fusobacterium mortiferum, Porphyromonas asaccharolytica|Fusobacterium mortiferum, Porphyromonas uenonis|Fusobacterium mortiferum, Prevotella amnii|Fusobacterium mortiferum, Prevotella bergensis|Fusobacterium mortiferum, Prevotella bivia|Fusobacterium mortiferum, Prevotella buccae|Fusobacterium mortiferum, Prevotella buccalis|Fusobacterium mortiferum, Prevotella copri|Fusobacterium mortiferum, Prevotella disiens|Fusobacterium mortiferum, Prevotella melaninogenica|Fusobacterium mortiferum, Prevotella multiformis|Fusobacterium mortiferum, Prevotella oralis|Fusobacterium mortiferum, Prevotella oris|Fusobacterium mortiferum, Prevotella salivae|Fusobacterium mortiferum, Prevotella timonensis|Fusobacterium mortiferum, Propionibacterium acnes|Fusobacterium mortiferum, Propionibacterium freudenreichii|Fusobacterium mortiferum, Proteus mirabilis|Fusobacterium mortiferum, Proteus penneri|Fusobacterium mortiferum, Pseudoflavonifractor capillosus|Fusobacterium mortiferum, Pseudomonas aeruginosa|Fusobacterium mortiferum, Pseudomonas fluorescens|Fusobacterium mortiferum, Pseudomonas putida|Fusobacterium mortiferum, Pseudoramibacter alactolyticus|Fusobacterium mortiferum, Pyramidobacter piscolens|Fusobacterium mortiferum, Rhodopseudomonas palustris|Fusobacterium mortiferum, Roseburia intestinalis|Fusobacterium mortiferum, Roseburia inulinivorans|Fusobacterium mortiferum, Rothia dentocariosa|Fusobacterium mortiferum, Rothia mucilaginosa|Fusobacterium mortiferum, Ruminococcus albus|Fusobacterium mortiferum, Ruminococcus bromii|Fusobacterium mortiferum, Ruminococcus gnavus|Fusobacterium mortiferum, Ruminococcus*

TABLE 2-continued

Table 2. Specific binary combinations of OTUs. Individual pairings are differentiated by "|" and OTUs within a combination are differentiated by ","

*lactaris|Fusobacterium mortiferum, Ruminococcus obeum|Fusobacterium mortiferum, Ruminococcus torques|Fusobacterium mortiferum, Selenomonas sputigena|Fusobacterium mortiferum, Shigella boydii|Fusobacterium mortiferum, Shigella dysenteriae|Fusobacterium mortiferum, Shigella sonnei|Fusobacterium mortiferum, Slackia exigua|Fusobacterium mortiferum, Solobacterium moorei|Fusobacterium mortiferum, Staphylococcus aureus|Fusobacterium mortiferum, Staphylococcus epidermidis|Fusobacterium mortiferum, Staphylococcus hominis|Fusobacterium mortiferum, Staphylococcus saprophyticus|Fusobacterium mortiferum, Staphylococcus warneri|Fusobacterium mortiferum, Streptococcus agalactiae|Fusobacterium mortiferum, Streptococcus anginosus|Fusobacterium mortiferum, Streptococcus australis|Fusobacterium mortiferum, Streptococcus bovis|Fusobacterium mortiferum, Streptococcus cristatus|Fusobacterium mortiferum, Streptococcus dysgalactiae|Fusobacterium mortiferum, Streptococcus equinus|Fusobacterium mortiferum, Streptococcus gordonii|Fusobacterium mortiferum, Streptococcus infantarius|Fusobacterium mortiferum, Streptococcus infantis|Fusobacterium mortiferum, Streptococcus mitis|Fusobacterium mortiferum, Streptococcus mutans|Fusobacterium mortiferum, Streptococcus oralis|Fusobacterium mortiferum, Streptococcus parasanguinis|Fusobacterium mortiferum, Streptococcus peroris|Fusobacterium mortiferum, Streptococcus pneumoniae|Fusobacterium mortifentm, Streptococcus salivarius|Fusobacterium mortiferum, Streptococcus sanguinis|Fusobacterium mortiferum, Streptococcus thermophilus|Fusobacterium mortiferum, Streptococcus vestibularis|Fusobacterium mortiferum, Subdoligranulum variabile|Fusobacterium mortiferum, Succinatimonas hippei|Fusobacterium mortiferum, Sutterella wadsworthensis|Fusobacterium mortiferum, Tropheryma whipplei|Fusobacterium mortiferum, Veillonella atypica|Fusobacterium mortiferum, Veillonella dispar|Fusobacterium mortiferum, Veillonella parvula|Fusobacterium mortiferum, Victivallis vadensis|Fusobacterium nucleatum, Fusobacterium nucleatum|Fusobacterium nucleatum, Fusobacterium varium|Fusobacterium nucleatum, Gardnerella vaginalis|Fusobacterium nucleatum, Gemella haemolysans|Fusobacterium nucleatum, Gemella morbillorum|Fusobacterium nucleatum, Gordonibacter pamelaeae|Fusobacterium nucleatum, Granulicatella adiacens|Fusobacterium nucleatum, Granulicatella elegans|Fusobacterium nucleatum, Haemophilus influenzae|Fusobacterium nucleatum, Haemophilus parainfluenzae|Fusobacterium nucleatum, Helicobacter pullorum|Fusobacterium nucleatum, Helicobacter pylori|Fusobacterium nucleatum, Holdemania filiformis|Fusobacterium nucleatum, Kingella oralis|Fusobacterium nucleatum, Klebsiella pneumoniae|Fusobacterium nucleatum, Klebsiella variicola|Fusobacterium nucleatum, Lachnospiraceae bacterium* 5_1_57FAA|*Fusobacterium nucleatum, Lactobacillus acidophilus|Fusobacterium nucleatum, Lactobacillus amylovorus|Fusobacterium nucleatum, Lactobacillus brevis|Fusobacterium nucleatum, Lactobacillus casei|Fusobacterium nucleatum, Lactobacillus crispatus|Fusobacterium nucleatum, Lactobacillus delbrueckii|Fusobacterium nucleatum, Lactobacillus fermentum|Fusobacterium nucleatum, Lactobacillus gasseri|Fusobacterium nucleatum, Lactobacillus iners|Fusobacterium nucleatum, Lactobacillus jensenii|Fusobacterium nucleatum, Lactobacillus johnsonii|Fusobacterium nucleatum, Lactobacillus paracasei|Fusobacterium nucleatum, Lactobacillus plantarum|Fusobacterium nucleatum, Lactobacillus reuteri|Fusobacterium nucleatum, Lactobacillus rhamnosus|Fusobacterium nucleatum, Lactobacillus ruminis|Fusobacterium nucleatum, Lactobacillus sakei|Fusobacterium nucleatum, Lactobacillus salivarius|Fusobacterium nucleatum, Lactococcus lactis|Fusobacterium nucleatum, Lautropia mirabilis|Fusobacterium nucleatum, Leuconostoc citreum|Fusobacterium nucleatum, Leuconostoc gasicomitatum|Fusobacterium nucleatum, Leuconostoc mesenteroides|Fusobacterium nucleatum, Listeria monocytogenes|Fusobacterium nucleatum, Marvinbryantia formatexigens|Fusobacterium nucleatum, Megamonas hypermegale|Fusobacterium nucleatum, Megasphaera micronuciformis|Fusobacterium nucleatum, Methanobrevibacter smithii|Fusobacterium nucleatum, Methanosphaera stadtmanae|Fusobacterium nucleatum, Methylobacterium radiotolerans|Fusobacterium nucleatum, Mitsuokella multacida|Fusobacterium nucleatum, Mobiluncus curtisii|Fusobacterium nucleatum, Mycoplasma hominis|Fusobacterium nucleatum, Neisseria mucosa|Fusobacterium nucleatum, Odoribacter splanchnicus|Fusobacterium nucleatum, Olsenella uli|Fusobacterium nucleatum, Oribacterium sinus|Fusobacterium nucleatum, Oxalobacter formigenes|Fusobacterium nucleatum, Parabacteroides distasonis|Fusobacterium nucleatum, Parabacteroides johnsonii|Fusobacterium nucleatum, Parabacteroides merdae|Fusobacterium nucleatum, Parvimonas micra|Fusobacterium nucleatum, Pediococcus acidilactici|Fusobacterium nucleatum, Pediococcus pentosaceus|Fusobacterium nucleatum, Peptoniphilus duerdenii|Fusobacterium nucleatum, Peptoniphilus harei|Fusobacterium nucleatum, Peptoniphilus lacrimalis|Fusobacterium nucleatum, Peptostreptococcus anaerobius|Fusobacterium nucleatum, Peptostreptococcus stomatis|Fusobacterium nucleatum, Porphyromonas asaccharolytica|Fusobacterium nucleatum, Porphyromonas uenonis|Fusobacterium nucleatum, Prevotella amnii|Fusobacterium nucleatum, Prevotella bergensis|Fusobacterium nucleatum, Prevotella bivia|Fusobacterium nucleatum, Prevotella buccae|Fusobacterium nucleatum, Prevotella buccalis|Fusobacterium nucleatum, Prevotella copri|Fusobacterium nucleatum, Prevotella disiens|Fusobacterium nucleatum, Prevotella melaninogenica|Fusobacterium nucleatum, Prevotella multiformis|Fusobacterium nucleatum, Prevotella oralis|Fusobacterium nucleatum, Prevotella oris|Fusobacterium nucleatum, Prevotella salivae|Fusobacterium nucleatum, Prevotella timonensis|Fusobacterium nucleatum, Propionibacterium acnes|Fusobacterium nucleatum, Propionibacterium freudenreichii|Fusobacterium nucleatum, Proteus mirabilis|Fusobacterium nucleatum, Proteus penneri|Fusobacterium nucleatum, Pseudoflavonifractor capillosus|Fusobacterium nucleatum, Pseudomonas aeruginosa|Fusobacterium nucleatum, Pseudomonas fluorescens|Fusobacterium nucleatum, Pseudomonas putida|Fusobacterium nucleatum, Pseudoramibacter alactolyticus|Fusobacterium nucleatum, Pyramidobacter piscolens|Fusobacterium nucleatum, Rhodopseudomonas palustris|Fusobacterium nucleatum, Roseburia intestinalis|Fusobacterium nucleatum, Roseburia inulinivorans|Fusobacterium nucleatum, Rothia dentocariosa|Fusobacterium nucleatum, Rothia mucilaginosa|Fusobacterium nucleatum, Ruminococcus albus|Fusobacterium nucleatum, Ruminococcus bromii|Fusobacterium nucleatum, Ruminococcus gnavus|Fusobacterium nucleatum, Ruminococcus lactaris|Fusobacterium nucleatum, Ruminococcus obeum|Fusobacterium nucleatum, Ruminococcus torques|Fusobacterium nucleatum, Selenomonas sputigena|Fusobacterium nucleatum, Shigella boydii|Fusobacterium nucleatum, Shigella dysenteriae|Fusobacterium nucleatum, Shigella sonnei|Fusobacterium nucleatum, Slackia exigua|Fusobacterium nucleatum, Solobacterium moorei|Fusobacterium nucleatum, Staphylococcus aureus|Fusobacterium nucleatum, Staphylococcus epidermidis|Fusobacterium nucleatum, Staphylococcus hominis|Fusobacterium nucleatum, Staphylococcus saprophyticus|Fusobacterium nucleatum, Staphylococcus warneri|Fusobacterium nucleatum, Streptococcus agalactiae|Fusobacterium nucleatum, Streptococcus anginosus|Fusobacterium nucleatum, Streptococcus australis|Fusobacterium nucleatum, Streptococcus bovis|Fusobacterium nucleatum, Streptococcus cristatus|Fusobacterium nucleatum, Streptococcus dysgalactiae|Fusobacterium nucleatum, Streptococcus equinus|Fusobacterium nucleatum, Streptococcus gordonii|Fusobacterium nucleatum, Streptococcus infantarius|Fusobacterium nucleatum, Streptococcus infantis|Fusobacterium nucleatum, Streptococcus mitis|Fusobacterium nucleatum, Streptococcus mutans|Fusobacterium nucleatum, Streptococcus oralis|Fusobacterium nucleatum, Streptococcus parasanguinis|Fusobacterium nucleatum, Streptococcus peroris|Fusobacterium nucleatum, Streptococcus pneumoniae|Fusobacterium nucleatum, Streptococcus salivarius|Fusobacterium nucleatum, Streptococcus sanguinis|Fusobacterium nucleatum, Streptococcus thermophilus|Fusobacterium nucleatum, Streptococcus vestibularis|Fusobacterium nucleatum, Subdoligranulum variabile|Fusobacterium nucleatum, Succinatimonas hippei|Fusobacterium nucleatum, Sutterella wadsworthensis|Fusobacterium nucleatum, Tropheryma whipplei|Fusobacterium nucleatum, Veillonella atypica|Fusobacterium nucleatum, Veillonella dispar|Fusobacterium nucleatum, Veillonella parvula|Fusobacterium nucleatum, Victivallis vadensis|Fusobacterium varium, Fusobacterium varium|Fusobacterium varium, Gardnerella vaginalis|Fusobacterium varium, Gemella haemolysans|Fusobacterium varium, Gemella morbillorum|Fusobacterium varium, Gordonibacter pamelaeae|Fusobacterium varium, Granulicatella adiacens|Fusobacterium varium, Granulicatella elegans|Fusobacterium varium, Haemophilus influenzae|Fusobacterium varium, Haemophilus parainfluenzae|Fusobacterium varium, Helicobacter pullorum|Fusobacterium varium, Helicobacter pylori|Fusobacterium varium, Holdemania filiformis|Fusobacterium varium, Kingella oralis|Fusobacterium varium, Klebsiella pneumoniae|Fusobacterium varium, Klebsiella variicola|Fusobacterium varium, Lachnospiraceae bacterium* 5_1_57FAA|*Fusobacterium varium, Lactobacillus acidophilus|Fusobacterium varium, Lactobacillus amylovorus|Fusobacterium varium, Lactobacillus brevis|Fusobacterium varium, Lactobacillus casei|Fusobacterium varium, Lactobacillus crispatus|Fusobacterium varium, Lactobacillus delbrueckii|Fusobacterium*

TABLE 2-continued

| Table 2. Specific binary combinations of OTUs. Individual pairings are differentiated by "\|" and OTUs within a combination are differentiated by "," |
| --- |
| *varium, Lactobacillus fermentum\|Fusobacterium varium, Lactobacillus gasseri\|Fusobacterium varium, Lactobacillus iners\|Fusobacterium varium, Lactobacillus jensenii\|Fusobacterium varium, Lactobacillus johnsonii\|Fusobacterium varium, Lactobacillus paracasei\|Fusobacterium varium, Lactobacillus plantarum\|Fusobacterium varium, Lactobacillus reuteri\|Fusobacterium varium, Lactobacillus rhamnosus\|Fusobacterium varium, Lactobacillus ruminis\|Fusobacterium varium, Lactobacillus sakei\|Fusobacterium varium, Lactobacillus salivarius\|Fusobacterium varium, Lactococcus lactis\|Fusobacterium varium, Lautropia mirabilis\|Fusobacterium varium, Leuconostoc citreum\|Fusobacterium varium, Leuconostoc gasicomitatum\|Fusobacterium varium, Leuconostoc mesenteroides\|Fusobacterium varium, Listeria monocytogenes\|Fusobacterium varium, Marvinbryantia formatexigens\|Fusobacterium varium, Megamonas hypermegale\|Fusobacterium varium, Megasphaera micronuciformis\|Fusobacterium varium, Methanobrevibacter smithii\|Fusobacterium varium, Methanosphaera stadtmanae\|Fusobacterium varium, Methylobacterium radiotolerans\|Fusobacterium varium, Mitsuokella multacida\|Fusobacterium varium, Mobiluncus curtisii\|Fusobacterium varium, Mycoplasma hominis\|Fusobacterium varium, Neisseria mucosa\|Fusobacterium varium, Odoribacter splanchnicus\|Fusobacterium varium, Olsenella uli\|Fusobacterium varium, Oribacterium sinus\|Fusobacterium varium, Oxalobacter formigenes\|Fusobacterium varium, Parabacteroides distasonis\|Fusobacterium varium, Parabacteroides johnsonii\|Fusobacterium varium, Parabacteroides merdae\|Fusobacterium varium, Parvimonas micra\|Fusobacterium varium, Pediococcus acidilactici\|Fusobacterium varium, Pediococcus pentosaceus\|Fusobacterium varium, Peptoniphilus duerdenii\|Fusobacterium varium, Peptoniphilus harei\|Fusobacterium varium, Peptoniphilus lacrimalis\|Fusobacterium varium, Peptostreptococcus anaerobius\|Fusobacterium varium, Peptostreptococcus stomatis\|Fusobacterium varium, Porphyromonas asaccharolytica\|Fusobacterium varium, Porphyromonas uenonis\|Fusobacterium varium, Prevotella amnii\|Fusobacterium varium, Prevotella bergensis\|Fusobacterium varium, Prevotella bivia\|Fusobacterium varium, Prevotella buccae\|Fusobacterium varium, Prevotella buccalis\|Fusobacterium varium, Prevotella copri\|Fusobacterium varium, Prevotella disiens\|Fusobacterium varium, Prevotella melaninogenica\|Fusobacterium varium, Prevotella multiformis\|Fusobacterium varium, Prevotella oralis\|Fusobacterium varium, Prevotella oris\|Fusobacterium varium, Prevotella salivae\|Fusobacterium varium, Prevotella timonensis\|Fusobacterium varium, Propionibacterium acnes\|Fusobacterium varium, Propionibacterium freudenreichii\|Fusobacterium varium, Proteus mirabilis\|Fusobacterium varium, Proteus penneri\|Fusobacterium varium, Pseudoflavonifractor capillosus\|Fusobacterium varium, Pseudomonas aeruginosa\|Fusobacterium varium, Pseudomonas fluorescens\|Fusobacterium varium, Pseudomonas putida\|Fusobacterium varium, Pseudoramibacter alactolyticus\|Fusobacterium varium, Pyramidobacter piscolens\|Fusobacterium varium, Rhodopseudomonas palustris\|Fusobacterium varium, Roseburia intestinalis\|Fusobacterium varium, Roseburia inulinivorans\|Fusobacterium varium, Rothia dentocariosa\|Fusobacterium varium, Rothia mucilaginosa\|Fusobacterium varium, Ruminococcus albus\|Fusobacterium varium, Ruminococcus bromii\|Fusobacterium varium, Ruminococcus gnavus\|Fusobacterium varium, Ruminococcus lactaris\|Fusobacterium varium, Ruminococcus obeum\|Fusobacterium varium, Ruminococcus torques\|Fusobacterium varium, Selenomonas sputigena\|Fusobacterium varium, Shigella boydii\|Fusobacterium varium, Shigella dysenteriae\|Fusobacterium varium, Shigella sonnei\|Fusobacterium varium, Slackia exigua\|Fusobacterium varium, Solobacterium moorei\|Fusobacterium varium, Staphylococcus aureus\|Fusobacterium varium, Staphylococcus epidermidis\|Fusobacterium varium, Staphylococcus hominis\|Fusobacterium varium, Staphylococcus saprophyticus\|Fusobacterium varium, Staphylococcus warneri\|Fusobacterium varium, Streptococcus agalactiae\|Fusobacterium varium, Streptococcus anginosus\|Fusobacterium varium, Streptococcus australis\|Fusobacterium varium, Streptococcus bovis\|Fusobacterium varium, Streptococcus cristatus\|Fusobacterium varium, Streptococcus dysgalactiae\|Fusobacterium varium, Streptococcus equinus\|Fusobacterium varium, Streptococcus gordonii\|Fusobacterium varium, Streptococcus infantarius\|Fusobacterium varium, Streptococcus infantis\|Fusobacterium varium, Streptococcus mitis\|Fusobacterium varium, Streptococcus mutans\|Fusobacterium varium, Streptococcus oralis\|Fusobacterium varium, Streptococcus parasanguinis\|Fusobacterium varium, Streptococcus peroris\|Fusobacterium varium, Streptococcus pneumoniae\|Fusobacterium varium, Streptococcus salivarius\|Fusobacterium varium, Streptococcus sanguinis\|Fusobacterium varium, Streptococcus thermophilus\|Fusobacterium varium, Streptococcus vestibularis\|Fusobacterium varium, Subdoligranulum variabile\|Fusobacterium varium, Succinatimonas hippei\|Fusobacterium varium, Sutterella wadsworthensis\|Fusobacterium varium, Tropheryma whipplei\|Fusobacterium varium, Veillonella atypica\|Fusobacterium varium, Veillonella dispar\|Fusobacterium varium, Veillonella parvula\|Fusobacterium varium, Victivallis vadensis\|Gardnerella vaginalis, Gardnerella vaginalis\|Gardnerella vaginalis, Gemella haemolysans\|Gardnerella vaginalis, Gemella morbillorum\|Gardnerella vaginalis, Gordonibacter pamelaeae\|Gardnerella vaginalis, Granulicatella adiacens\|Gardnerella vaginalis, Granulicatella elegans\|Gardnerella vaginalis, Haemophilus influenzae\|Gardnerella vaginalis, Haemophilus parainfluenzae\|Gardnerella vaginalis, Helicobacter pullorum\|Gardnerella vaginalis, Helicobacter pylori\|Gardnerella vaginalis, Holdemania filiformis\|Gardnerella vaginalis, Kingella oralis\|Gardnerella vaginalis, Klebsiella pneumoniae\|Gardnerella vaginalis, Klebsiella variicola\|Gardnerella vaginalis, Lachnospiraceae bacterium 5_1_57FAA\|Gardnerella vaginalis, Lactobacillus acidophilus\|Gardnerella vaginalis, Lactobacillus amylovorus\|Gardnerella vaginalis, Lactobacillus brevis\|Gardnerella vaginalis, Lactobacillus casei\|Gardnerella vaginalis, Lactobacillus crispatus\|Gardnerella vaginalis, Lactobacillus delbrueckii\|Gardnerella vaginalis, Lactobacillus fermentum\|Gardnerella vaginalis, Lactobacillus gasseri\|Gardnerella vaginalis, Lactobacillus iners\|Gardnerella vaginalis, Lactobacillus jensenii\|Gardnerella vaginalis, Lactobacillus johnsonii\|Gardnerella vaginalis, Lactobacillus paracasei\|Gardnerella vaginalis, Lactobacillus plantarum\|Gardnerella vaginalis, Lactobacillus reuteri\|Gardnerella vaginalis, Lactobacillus rhamnosus\|Gardnerella vaginalis, Lactobacillus ruminis\|Gardnerella vaginalis, Lactobacillus sakei\|Gardnerella vaginalis, Lactobacillus salivarius\|Gardnerella vaginalis, Lactococcus lactis\|Gardnerella vaginalis, Lautropia mirabilis\|Gardnerella vaginalis, Leuconostoc citreum\|Gardnerella vaginalis, Leuconostoc gasicomitatum\|Gardnerella vaginalis, Leuconostoc mesenteroides\|Gardnerella vaginalis, Listeria monocytogenes\|Gardnerella vaginalis, Marvinbryantia formatexigens\|Gardnerella vaginalis, Megamonas hypermegale\|Gardnerella vaginalis, Megasphaera micronuciformis\|Gardnerella vaginalis, Methanobrevibacter smithii\|Gardnerella vaginalis, Methanosphaera stadtmanae\|Gardnerella vaginalis, Methylobacterium radiotolerans\|Gardnerella vaginalis, Mitsuokella multacida\|Gardnerella vaginalis, Mobiluncus curtisii\|Gardnerella vaginalis, Mycoplasma hominis\|Gardnerella vaginalis, Neisseria mucosa\|Gardnerella vaginalis, Odoribacter splanchnicus\|Gardnerella vaginalis, Olsenella uli\|Gardnerella vaginalis, Oribacterium sinus\|Gardnerella vaginalis, Oxalobacter formigenes\|Gardnerella vaginalis, Parabacteroides distasonis\|Gardnerella vaginalis, Parabacteroides johnsonii\|Gardnerella vaginalis, Parabacteroides merdae\|Gardnerella vaginalis, Parvimonas micra\|Gardnerella vaginalis, Pediococcus acidilactici\|Gardnerella vaginalis, Pediococcus pentosaceus\|Gardnerella vaginalis, Peptoniphilus duerdenii\|Gardnerella vaginalis, Peptoniphilus harei\|Gardnerella vaginalis, Peptoniphilus lacrimalis\|Gardnerella vaginalis, Peptostreptococcus anaerobius\|Gardnerella vaginalis, Peptostreptococcus stomatis\|Gardnerella vaginalis, Porphyromonas asaccharolytica\|Gardnerella vaginalis, Porphyromonas uenonis\|Gardnerella vaginalis, Prevotella amnii\|Gardnerella vaginalis, Prevotella bergensis\|Gardnerella vaginalis, Prevotella bivia\|Gardnerella vaginalis, Prevotella buccae\|Gardnerella vaginalis, Prevotella buccalis\|Gardnerella vaginalis, Prevotella copri\|Gardnerella vaginalis, Prevotella disiens\|Gardnerella vaginalis, Prevotella melaninogenica\|Gardnerella vaginalis, Prevotella multiformis\|Gardnerella vaginalis, Prevotella oralis\|Gardnerella vaginalis, Prevotella oris\|Gardnerella vaginalis, Prevotella salivae\|Gardnerella vaginalis, Prevotella timonensis\|Gardnerella vaginalis, Propionibacterium acnes\|Gardnerella vaginalis, Propionibacterium freudenreichii\|Gardnerella vaginalis, Proteus mirabilis\|Gardnerella vaginalis, Proteus penneri\|Gardnerella vaginalis, Pseudoflavonifractor capillosus\|Gardnerella vaginalis, Pseudomonas aeruginosa\|Gardnerella vaginalis, Pseudomonas fluorescens\|Gardnerella vaginalis, Pseudomonas putida\|Gardnerella vaginalis, Pseudoramibacter alactolyticus\|Gardnerella vaginalis, Pyramidobacter piscolens\|Gardnerella vaginalis, Rhodopseudomonas palustris\|Gardnerella vaginalis, Roseburia intestinalis\|Gardnerella vaginalis, Roseburia inulinivorans\|Gardnerella vaginalis, Rothia dentocariosa\|Gardnerella vaginalis, Rothia mucilaginosa\|Gardnerella vaginalis, Ruminococcus albus\|Gardnerella vaginalis, Ruminococcus bromii\|Gardnerella vaginalis, Ruminococcus gnavus\|Gardnerella vaginalis, Ruminococcus lactaris\|Gardnerella vaginalis, Ruminococcus obeum\|Gardnerella vaginalis, Ruminococcus torques\|Gardnerella vaginalis, Selenomonas sputigena\|Gardnerella vaginalis, Shigella boydii\|Gardnerella vaginalis, Shigella dysenteriae\|Gardnerella vaginalis, Shigella sonnei\|Gardnerella* |

TABLE 2-continued

| Table 2. Specific binary combinations of OTUs. Individual pairings are differentiated by "\|" and OTUs within a combination are differentiated by "," |
|---|
| *vaginalis, Slackia exigua\|Gardnerella vaginalis, Solobacterium moorei\|Gardnerella vaginalis, Staphylococcus aureus\|Gardnerella vaginalis, Staphylococcus epidermidis\|Gardnerella vaginalis, Staphylococcus hominis\|Gardnerella vaginalis, Staphylococcus saprophyticus\|Gardnerella vaginalis, Staphylococcus warneri\|Gardnerella vaginalis, Streptococcus agalactiae\|Gardnerella vaginalis, Streptococcus anginosus\|Gardnerella vaginalis, Streptococcus australis\|Gardnerella vaginalis, Streptococcus bovis\|Gardnerella vaginalis, Streptococcus cristatus\|Gardnerella vaginalis, Streptococcus dysgalactiae\|Gardnerella vaginalis, Streptococcus equinus\|Gardnerella vaginalis, Streptococcus gordonii\|Gardnerella vaginalis, Streptococcus infantarius\|Gardnerella vaginalis, Streptococcus infantis\|Gardnerella vaginalis, Streptococcus mitis\|Gardnerella vaginalis, Streptococcus mutans\|Gardnerella vaginalis, Streptococcus oralis\|Gardnerella vaginalis, Streptococcus parasanguinis\|Gardnerella vaginalis, Streptococcus peroris\|Gardnerella vaginalis, Streptococcus pneumoniae\|Gardnerella vaginalis, Streptococcus salivarius\|Gardnerella vaginalis, Streptococcus sanguinis\|Gardnerella vaginalis, Streptococcus thermophilus\|Gardnerella vaginalis, Streptococcus vestibularis\|Gardnerella vaginalis, Subdoligranulum variabile\|Gardnerella vaginalis, Succinatimonas hippei\|Gardnerella vaginalis, Sutterella wadsworthensis\|Gardnerella vaginalis, Tropheryma whipplei\|Gardnerella vaginalis, Veillonella atypica\|Gardnerella vaginalis, Veillonella dispar\|Gardnerella vaginalis, Veillonella parvula\|Gardnerella vaginalis, Victivallis vadensis\|Gemella haemolysans, Gemella haemolysans\|Gemella haemolysans, Gemella morbillorum\|Gemella haemolysans, Gordonibacter pamelaeae\|Gemella haemolysans, Granulicatella adiacens\|Gemella haemolysans, Granulicatella elegans\|Gemella haemolysans, Haemophilus influenzae\|Gemella haemolysans, Haemophilus parainfluenzae\|Gemella haemolysans, Helicobacter pullorum\|Gemella haemolysans, Helicobacter pylori\|Gemella haemolysans, Holdemania filiformis\|Gemella haemolysans, Kingella oralis\|Gemella haemolysans, Klebsiella pneumoniae\|Gemella haemolysans, Klebsiella variicola\|Gemella haemolysans, Lachnospiraceae bacterium* 5_1_57FAA\|*Gemella haemolysans, Lactobacillus acidophilus\|Gemella haemolysans, Lactobacillus amylovorus\|Gemella haemolysans, Lactobacillus brevis\|Gemella haemolysans, Lactobacillus casei\|Gemella haemolysans, Lactobacillus crispatus\|Gemella haemolysans, Lactobacillus delbrueckii\|Gemella haemolysans, Lactobacillus fermentum\|Gemella haemolysans, Lactobacillus gasseri\|Gemella haemolysans, Lactobacillus iners\|Gemella haemolysans, Lactobacillus jensenii\|Gemella haemolysans, Lactobacillus johnsonii\|Gemella haemolysans, Lactobacillus paracasei\|Gemella haemolysans, Lactobacillus plantarum\|Gemella haemolysans, Lactobacillus reuteri\|Gemella haemolysans, Lactobacillus rhamnosus\|Gemella haemolysans, Lactobacillus ruminis\|Gemella haemolysans, Lactobacillus sakei\|Gemella haemolysans, Lactobacillus salivarius\|Gemella haemolysans, Lactococcus lactis\|Gemella haemolysans, Lautropia mirabilis\|Gemella haemolysans, Leuconostoc citreum\|Gemella haemolysans, Leuconostoc gasicomitatum\|Gemella haemolysans, Leuconostoc mesenteroides\|Gemella haemolysans, Listeria monocytogenes\|Gemella haemolysans, Marvinbryantia formatexigens\|Gemella haemolysans, Megamonas hypermegale\|Gemella haemolysans, Megasphaera micronuciformis\|Gemella haemolysans, Methanobrevibacter smithii\|Gemella haemolysans, Methanosphaera stadtmanae\|Gemella haemolysans, Methylobacterium radiotolerans\|Gemella haemolysans, Mitsuokella multacida\|Gemella haemolysans, Mobiluncus curtisii\|Gemella haemolysans, Mycoplasma hominis\|Gemella haemolysans, Neisseria mucosa\|Gemella haemolysans, Odoribacter splanchnicus\|Gemella haemolysans, Olsenella uli\|Gemella haemolysans, Oribacterium sinus\|Gemella haemolysans, Oxalobacter formigenes\|Gemella haemolysans, Parabacteroides distasonis\|Gemella haemolysans, Parabacteroides johnsonii\|Gemella haemolysans, Parabacteroides merdae\|Gemella haemolysans, Parvimonas micra\|Gemella haemolysans, Pediococcus acidilactici\|Gemella haemolysans, Pediococcus pentosaceus\|Gemella haemolysans, Peptoniphilus duerdenii\|Gemella haemolysans, Peptoniphilus harei\|Gemella haemolysans, Peptoniphilus lacrimalis\|Gemella haemolysans, Peptostreptococcus anaerobius\|Gemella haemolysans, Peptostreptococcus stomatis\|Gemella haemolysans, Porphyromonas asaccharolytica\|Gemella haemolysans, Porphyromonas uenonis\|Gemella haemolysans, Prevotella amnii\|Gemella haemolysans, Prevotella bergensis\|Gemella haemolysans, Prevotella bivia\|Gemella haemolysans, Prevotella buccae\|Gemella haemolysans, Prevotella buccalis\|Gemella haemolysans, Prevotella copri\|Gemella haemolysans, Prevotella disiens\|Gemella haemolysans, Prevotella melaninogenica\|Gemella haemolysans, Prevotella multiformis\|Gemella haemolysans, Prevotella oralis\|Gemella haemolysans, Prevotella oris\|Gemella haemolysans, Prevotella salivae\|Gemella haemolysans, Prevotella timonensis\|Gemella haemolysans, Propionibacterium acnes\|Gemella haemolysans, Propionibacterium freudenreichii\|Gemella haemolysans, Proteus mirabilis\|Gemella haemolysans, Proteus penneri\|Gemella haemolysans, Pseudoflavonifractor capillosus\|Gemella haemolysans, Pseudomonas aeruginosa\|Gemella haemolysans, Pseudomonas fluorescens\|Gemella haemolysans, Pseudomonas putida\|Gemella haemolysans, Pseudoramibacter alactolyticus\|Gemella haemolysans, Pyramidobacter piscolens\|Gemella haemolysans, Rhodopseudomonas palustris\|Gemella haemolysans, Roseburia intestinalis\|Gemella haemolysans, Roseburia inulinivorans\|Gemella haemolysans, Rothia dentocariosa\|Gemella haemolysans, Rothia mucilaginosa\|Gemella haemolysans, Ruminococcus albus\|Gemella haemolysans, Ruminococcus bromii\|Gemella haemolysans, Ruminococcus gnavus\|Gemella haemolysans, Ruminococcus lactaris\|Gemella haemolysans, Ruminococcus obeum\|Gemella haemolysans, Ruminococcus torques\|Gemella haemolysans, Selenomonas sputigena\|Gemella haemolysans, Shigella boydii\|Gemella haemolysans, Shigella dysenteriae\|Gemella haemolysans, Shigella sonnei\|Gemella haemolysans, Slackia exigua\|Gemella haemolysans, Solobacterium moorei\|Gemella haemolysans, Staphylococcus aureus\|Gemella haemolysans, Staphylococcus epidermidis\|Gemella haemolysans, Staphylococcus hominis\|Gemella haemolysans, Staphylococcus saprophyticus\|Gemella haemolysans, Staphylococcus warneri\|Gemella haemolysans, Streptococcus agalactiae\|Gemella haemolysans, Streptococcus anginosus\|Gemella haemolysans, Streptococcus australis\|Gemella haemolysans, Streptococcus bovis\|Gemella haemolysans, Streptococcus cristatus\|Gemella haemolysans, Streptococcus dysgalactiae\|Gemella haemolysans, Streptococcus equinus\|Gemella haemolysans, Streptococcus gordonii\|Gemella haemolysans, Streptococcus infantarius\|Gemella haemolysans, Streptococcus infantis\|Gemella haemolysans, Streptococcus mitis\|Gemella haemolysans, Streptococcus mutans\|Gemella haemolysans, Streptococcus oralis\|Gemella haemolysans, Streptococcus parasanguinis\|Gemella haemolysans, Streptococcus peroris\|Gemella haemolysans, Streptococcus pneumoniae\|Gemella haemolysans, Streptococcus salivarius\|Gemella haemolysans, Streptococcus sanguinis\|Gemella haemolysans, Streptococcus thermophilus\|Gemella haemolysans, Streptococcus vestibularis\|Gemella haemolysans, Subdoligranulum variabile\|Gemella haemolysans, Succinatimonas hippei\|Gemella haemolysans, Sutterella wadsworthensis\|Gemella haemolysans, Tropheryma whipplei\|Gemella haemolysans, Veillonella atypica\|Gemella haemolysans, Veillonella dispar\|Gemella haemolysans, Veillonella parvula\|Gemella haemolysans, Victivallis vadensis\|Gemella morbillorum, Gemella morbillorum\|Gemella morbillorum, Gordonibacter pamelaeae\|Gemella morbillorum, Granulicatella adiacens\|Gemella morbillorum, Granulicatella elegans\|Gemella morbillorum, Haemophilus influenzae\|Gemella morbillorum, Haemophilus parainfluenzae\|Gemella morbillorum, Helicobacter pullorum\|Gemella morbillorum, Helicobacter pylori\|Gemella morbillorum, Holdemania filiformis\|Gemella morbillorum, Kingella oralis\|Gemella morbillorum, Klebsiella pneumoniae\|Gemella morbillorum, Klebsiella variicola\|Gemella morbillorum, Lachnospiraceae bacterium* 5_1_57FAA\|*Gemella morbillorum, Lactobacillus acidophilus\|Gemella morbillorum, Lactobacillus amylovorus\|Gemella morbillorum, Lactobacillus brevis\|Gemella morbillorum, Lactobacillus casei\|Gemella morbillorum, Lactobacillus crispatus\|Gemella morbillorum, Lactobacillus delbrueckii\|Gemella morbillorum, Lactobacillus fermentum\|Gemella morbillorum, Lactobacillus gasseri\|Gemella morbillorum, Lactobacillus iners\|Gemella morbillorum, Lactobacillus jensenii\|Gemella morbillorum, Lactobacillus johnsonii\|Gemella morbillorum, Lactobacillus paracasei\|Gemella morbillorum, Lactobacillus plantarum\|Gemella morbillorum, Lactobacillus reuteri\|Gemella morbillorum, Lactobacillus rhamnosus\|Gemella morbillorum, Lactobacillus ruminis\|Gemella morbillorum, Lactobacillus sakei\|Gemella morbillorum, Lactobacillus salivarius\|Gemella morbillorum, Lactococcus lactis\|Gemella morbillorum, Lautropia mirabilis\|Gemella morbillorum, Leuconostoc citreum\|Gemella morbillorum, Leuconostoc gasicomitatum\|Gemella morbillorum, Leuconostoc mesenteroides\|Gemella morbillorum, Listeria monocytogenes\|Gemella morbillorum, Marvinbryantia formatexigens\|Gemella morbillorum, Megamonas hypermegale\|Gemella morbillorum, Megasphaera micronuciformis\|Gemella morbillorum, Methanobrevibacter smithii\|Gemella morbillorum, Methanosphaera stadtmanae\|Gemella morbillorum, Methylobacterium radiotolerans\|Gemella morbillorum, Mitsuokella multacida\|Gemella morbillorum, Mobiluncus curtisii\|Gemella morbillorum, Mycoplasma hominis\|Gemella* |

TABLE 2-continued

Table 2. Specific binary combinations of OTUs. Individual pairings are differentiated by "|" and OTUs within a combination are differentiated by ","

*morbillorum, Neisseria mucosa|Gemella morbillorum, Odoribacter splanchnicus|Gemella morbillorum, Olsenella uli|Gemella morbillorum, Oribacterium sinus|Gemella morbillorum, Oxalobacter formigenes|Gemella morbillorum, Parabacteroides distasonis|Gemella morbillorum, Parabacteroides johnsonii|Gemella morbillorum, Parabacteroides merdae|Gemella morbillorum, Parvimonas micra|Gemella morbillorum, Pediococcus acidilactici|Gemella morbillorum, Pediococcus pentosaceus|Gemella morbillorum, Peptoniphilus duerdenii|Gemella morbillorum, Peptoniphilus harei|Gemella morbillorum, Peptoniphilus lacrimalis|Gemella morbillorum, Peptostreptococcus anaerobius|Gemella morbillorum, Peptostreptococcus stomatis|Gemella morbillorum, Porphyromonas asaccharolytica|Gemella morbillorum, Porphyromonas uenonis|Gemella morbillorum, Prevotella amnii|Gemella morbillorum, Prevotella bergensis|Gemella morbillorum, Prevotella bivia|Gemella morbillorum, Prevotella buccae|Gemella morbillorum, Prevotella buccalis|Gemella morbillorum, Prevotella copri|Gemella morbillorum, Prevotella disiens|Gemella morbillorum, Prevotella melaninogenica|Gemella morbillorum, Prevotella multiformis|Gemella morbillorum, Prevotella oralis|Gemella morbillorum, Prevotella oris|Gemella morbillorum, Prevotella salivae|Gemella morbillorum, Prevotella timonensis|Gemella morbillorum, Propionibacterium acnes|Gemella morbillorum, Propionibacterium freudenreichii|Gemella morbillorum, Proteus mirabilis|Gemella morbillorum, Proteus penneri|Gemella morbillorum, Pseudoflavonifractor capillosus|Gemella morbillorum, Pseudomonas aeruginosa|Gemella morbillorum, Pseudomonas fluorescens|Gemella morbillorum, Pseudomonas putida|Gemella morbillorum, Pseudoramibacter alactolyticus|Gemella morbillorum, Pyramidobacter piscolens|Gemella morbillorum, Rhodopseudomonas palustris|Gemella morbillorum, Roseburia intestinalis|Gemella morbillorum, Roseburia inulinivorans|Gemella morbillorum, Rothia dentocariosa|Gemella morbillorum, Rothia mucilaginosa|Gemella morbillorum, Ruminococcus albus|Gemella morbillorum, Ruminococcus bromii|Gemella morbillorum, Ruminococcus gnavus|Gemella morbillorum, Ruminococcus lactaris|Gemella morbillorum, Ruminococcus obeum|Gemella morbillorum, Ruminococcus torques|Gemella morbillorum, Selenomonas sputigena|Gemella morbillorum, Shigella boydii|Gemella morbillorum, Shigella dysenteriae|Gemella morbillorum, Shigella sonnei|Gemella morbillorum, Slackia exigua|Gemella morbillorum, Solobacterium moorei|Gemella morbillorum, Staphylococcus aureus|Gemella morbillorum, Staphylococcus epidermidis|Gemella morbillorum, Staphylococcus hominis|Gemella morbillorum, Staphylococcus saprophyticus|Gemella morbillorum, Staphylococcus warneri|Gemella morbillorum, Streptococcus agalactiae|Gemella morbillorum, Streptococcus anginosus|Gemella morbillorum, Streptococcus australis|Gemella morbillorum, Streptococcus bovis|Gemella morbillorum, Streptococcus cristatus|Gemella morbillorum, Streptococcus dysgalactiae|Gemella morbillorum, Streptococcus equinus|Gemella morbillorum, Streptococcus gordonii|Gemella morbillorum, Streptococcus infantarius|Gemella morbillorum, Streptococcus infantis|Gemella morbillorum, Streptococcus mitis|Gemella morbillorum, Streptococcus mutans|Gemella morbillorum, Streptococcus oralis|Gemella morbillorum, Streptococcus parasanguinis|Gemella morbillorum, Streptococcus peroris|Gemella morbillorum, Streptococcus pneumoniae|Gemella morbillorum, Streptococcus salivarius|Gemella morbillorum, Streptococcus sanguinis|Gemella morbillorum, Streptococcus thermophilus|Gemella morbillorum, Streptococcus vestibularis|Gemella morbillorum, Subdoligranulum variabile|Gemella morbillorum, Succinatimonas hippei|Gemella morbillorum, Sutterella wadsworthensis|Gemella morbillorum, Tropheryma whipplei|Gemella morbillorum, Veillonella atypica|Gemella morbillorum, Veillonella dispar|Gemella morbillorum, Veillonella parvula|Gemella morbillorum, Victivallis vadensis|Gordonibacter pamelaeae, Gordonibacter pamelaeae|Gordonibacter pamelaeae, Granulicatella adiacens|Gordonibacter pamelaeae, Granulicatella elegans|Gordonibacter pamelaeae, Haemophilus influenzae|Gordonibacter pamelaeae, Haemophilus parainfluenzae|Gordonibacter pamelaeae, Helicobacter pullorum|Gordonibacter pamelaeae, Helicobacter pylori|Gordonibacter pamelaeae, Holdemania filiformis|Gordonibacter pamelaeae, Kingella oralis|Gordonibacter pamelaeae, Klebsiella pneumoniae|Gordonibacter pamelaeae, Klebsiella variicola|Gordonibacter pamelaeae, Lachnospiraceae bacterium* 5_1_57FAA|*Gordonibacter pamelaeae, Lactobacillus acidophilus|Gordonibacter pamelaeae, Lactobacillus amylovorus|Gordonibacter pamelaeae, Lactobacillus brevis|Gordonibacter pamelaeae, Lactobacillus casei|Gordonibacter pamelaeae, Lactobacillus crispatus|Gordonibacter pamelaeae, Lactobacillus delbrueckii|Gordonibacter pamelaeae, Lactobacillus fermentum|Gordonibacter pamelaeae, Lactobacillus gasseri|Gordonibacter pamelaeae, Lactobacillus iners|Gordonibacter pamelaeae, Lactobacillus jensenii|Gordonibacter pamelaeae, Lactobacillus johnsonii|Gordonibacter pamelaeae, Lactobacillus paracasei|Gordonibacter pamelaeae, Lactobacillus plantarum|Gordonibacter pamelaeae, Lactobacillus reuteri|Gordonibacter pamelaeae, Lactobacillus rhamnosus|Gordonibacter pamelaeae, Lactobacillus ruminis|Gordonibacter pamelaeae, Lactobacillus sakei|Gordonibacter pamelaeae, Lactobacillus salivarius|Gordonibacter pamelaeae, Lactococcus lactis|Gordonibacter pamelaeae, Lautropia mirabilis|Gordonibacter pamelaeae, Leuconostoc citreum|Gordonibacter pamelaeae, Leuconostoc gasicomitatum|Gordonibacter pamelaeae, Leuconostoc mesenteroides|Gordonibacter pamelaeae, Listeria monocytogenes|Gordonibacter pamelaeae, Marvinbryantia formatexigens|Gordonibacter pamelaeae, Megamonas hypermegale|Gordonibacter pamelaeae, Megasphaera micronuciformis|Gordonibacter pamelaeae, Methanobrevibacter smithii|Gordonibacter pamelaeae, Methanosphaera stadtmanae|Gordonibacter pamelaeae, Methylobacterium radiotolerans|Gordonibacter pamelaeae, Mitsuokella multacida|Gordonibacter pamelaeae, Mobiluncus curtisii|Gordonibacter pamelaeae, Mycoplasma hominis|Gordonibacter pamelaeae, Neisseria mucosa|Gordonibacter pamelaeae, Odoribacter splanchnicus|Gordonibacter pamelaeae, Olsenella uli|Gordonibacter pamelaeae, Oribacterium sinus|Gordonibacter pamelaeae, Oxalobacter formigenes|Gordonibacter pamelaeae, Parabacteroides distasonis|Gordonibacter pamelaeae, Parabacteroides johnsonii|Gordonibacter pamelaeae, Parabacteroides merdae|Gordonibacter pamelaeae, Parvimonas micra|Gordonibacter pamelaeae, Pediococcus acidilactici|Gordonibacter pamelaeae, Pediococcus pentosaceus|Gordonibacter pamelaeae, Peptoniphilus duerdenii|Gordonibacter pamelaeae, Peptoniphilus harei|Gordonibacter pamelaeae, Peptoniphilus lacrimalis|Gordonibacter pamelaeae, Peptostreptococcus anaerobius|Gordonibacter pamelaeae, Peptostreptococcus stomatis|Gordonibacter pamelaeae, Porphyromonas asaccharolytica|Gordonibacter pamelaeae, Porphyromonas uenonis|Gordonibacter pamelaeae, Prevotella amnii|Gordonibacter pamelaeae, Prevotella bergensis|Gordonibacter pamelaeae, Prevotella bivia|Gordonibacter pamelaeae, Prevotella buccae|Gordonibacter pamelaeae, Prevotella buccalis|Gordonibacter pamelaeae, Prevotella copri|Gordonibacter pamelaeae, Prevotella disiens|Gordonibacter pamelaeae, Prevotella melaninogenica|Gordonibacter pamelaeae, Prevotella multiformis|Gordonibacter pamelaeae, Prevotella oralis|Gordonibacter pamelaeae, Prevotella oris|Gordonibacter pamelaeae, Prevotella salivae|Gordonibacter pamelaeae, Prevotella timonensis|Gordonibacter pamelaeae, Propionibacterium acnes|Gordonibacter pamelaeae, Propionibacterium freudenreichii|Gordonibacter pamelaeae, Proteus mirabilis|Gordonibacter pamelaeae, Proteus penneri|Gordonibacter pamelaeae, Pseudoflavonifractor capillosus|Gordonibacter pamelaeae, Pseudomonas aeruginosa|Gordonibacter pamelaeae, Pseudomonas fluorescens|Gordonibacter pamelaeae, Pseudomonas putida|Gordonibacter pamelaeae, Pseudoramibacter alactolyticus|Gordonibacter pamelaeae, Pyramidobacter piscolens|Gordonibacter pamelaeae, Rhodopseudomonas palustris|Gordonibacter pamelaeae, Roseburia intestinalis|Gordonibacter pamelaeae, Roseburia inulinivorans|Gordonibacter pamelaeae, Rothia dentocariosa|Gordonibacter pamelaeae, Rothia mucilaginosa|Gordonibacter pamelaeae, Ruminococcus albus|Gordonibacter pamelaeae, Ruminococcus bromii|Gordonibacter pamelaeae, Ruminococcus gnavus|Gordonibacter pamelaeae, Ruminococcus lactaris|Gordonibacter pamelaeae, Ruminococcus obeum|Gordonibacter pamelaeae, Ruminococcus torques|Gordonibacter pamelaeae, Selenomonas sputigena|Gordonibacter pamelaeae, Shigella boydii|Gordonibacter pamelaeae, Shigella dysenteriae|Gordonibacter pamelaeae, Shigella sonnei|Gordonibacter pamelaeae, Slackia exigua|Gordonibacter pamelaeae, Solobacterium moorei|Gordonibacter pamelaeae, Staphylococcus aureus|Gordonibacter pamelaeae, Staphylococcus epidermidis|Gordonibacter pamelaeae, Staphylococcus hominis|Gordonibacter pamelaeae, Staphylococcus saprophyticus|Gordonibacter pamelaeae, Staphylococcus warneri|Gordonibacter pamelaeae, Streptococcus agalactiae|Gordonibacter pamelaeae, Streptococcus anginosus|Gordonibacter pamelaeae, Streptococcus australis|Gordonibacter pamelaeae, Streptococcus bovis|Gordonibacter pamelaeae, Streptococcus cristatus|Gordonibacter pamelaeae, Streptococcus dysgalactiae|Gordonibacter pamelaeae, Streptococcus equinus|Gordonibacter pamelaeae, Streptococcus gordonii|Gordonibacter pamelaeae, Streptococcus infantarius|Gordonibacter pamelaeae, Streptococcus infantis|Gordonibacter pamelaeae, Streptococcus*

TABLE 2-continued

Table 2. Specific binary combinations of OTUs. Individual pairings are differentiated by "|" and OTUs within a combination are differentiated by ","

mitis|Gordonibacter pamelaeae, Streptococcus mutans|Gordonibacter pamelaeae, Streptococcus oralis|Gordonibacter pamelaeae, Streptococcus parasanguinis|Gordonibacter pamelaeae, Streptococcus peroris|Gordonibacter pamelaeae, Streptococcus pneumoniae|Gordonibacter pamelaeae, Streptococcus salivarius|Gordonibacter pamelaeae, Streptococcus sanguinis|Gordonibacter pamelaeae, Streptococcus thermophilus|Gordonibacter pamelaeae, Streptococcus vestibularis|Gordonibacter pamelaeae, Subdoligranulum variabile|Gordonibacter pamelaeae, Succinatimonas hippei|Gordonibacter pamelaeae, Sutterella wadsworthensis|Gordonibacter pamelaeae, Tropheryma whipplei|Gordonibacter pamelaeae, Veillonella atypica|Gordonibacter pamelaeae, Veillonella dispar|Gordonibacter pamelaeae, Veillonella parvula|Gordonibacter pamelaeae, Victivallis vadensis|Granulicatella adiacens, Granulicatella adiacens|Granulicatella adiacens, Granulicatella elegans|Granulicatella adiacens, Haemophilus influenzae|Granulicatella adiacens, Haemophilus parainfluenzae|Granulicatella adiacens, Helicobacter pullorum|Granulicatella adiacens, Helicobacter pylori|Granulicatella adiacens, Holdemania filiformis|Granulicatella adiacens, Kingella oralis|Granulicatella adiacens, Klebsiella pneumoniae|Granulicatella adiacens, Klebsiella variicola|Granulicatella adiacens, Lachnospiraceae bacterium 5_1_57FAA|Granulicatella adiacens, Lactobacillus acidophilus|Granulicatella adiacens, Lactobacillus amylovorus|Granulicatella adiacens, Lactobacillus brevis|Granulicatella adiacens, Lactobacillus casei|Granulicatella adiacens, Lactobacillus crispatus|Granulicatella adiacens, Lactobacillus delbrueckii|Granulicatella adiacens, Lactobacillus fermentum|Granulicatella adiacens, Lactobacillus gasseri|Granulicatella adiacens, Lactobacillus iners|Granulicatella adiacens, Lactobacillus jensenii|Granulicatella adiacens, Lactobacillus johnsonii|Granulicatella adiacens, Lactobacillus paracasei|Granulicatella adiacens, Lactobacillus plantarum|Granulicatella adiacens, Lactobacillus reuteri|Granulicatella adiacens, Lactobacillus rhamnosus|Granulicatella adiacens, Lactobacillus ruminis|Granulicatella adiacens, Lactobacillus sakei|Granulicatella adiacens, Lactobacillus salivarius|Granulicatella adiacens, Lactococcus lactis|Granulicatella adiacens, Lautropia mirabilis|Granulicatella adiacens, Leuconostoc citreum|Granulicatella adiacens, Leuconostoc gasicomitatum|Granulicatella adiacens, Leuconostoc mesenteroides|Granulicatella adiacens, Listeria monocytogenes|Granulicatella adiacens, Marvinbryantia formatexigens|Granulicatella adiacens, Megamonas hypermegale|Granulicatella adiacens, Megasphaera micronuciformis|Granulicatella adiacens, Methanobrevibacter smithii|Granulicatella adiacens, Methanosphaera stadtmanae|Granulicatella adiacens, Methylobacterium radiotolerans|Granulicatella adiacens, Mitsuokella multacida|Granulicatella adiacens, Mobiluncus curtisii|Granulicatella adiacens, Mycoplasma hominis|Granulicatella adiacens, Neisseria mucosa|Granulicatella adiacens, Odoribacter splanchnicus|Granulicatella adiacens, Olsenella uli|Granulicatella adiacens, Oribacterium sinus|Granulicatella adiacens, Oxalobacter formigenes|Granulicatella adiacens, Parabacteroides distasonis|Granulicatella adiacens, Parabacteroides johnsonii|Granulicatella adiacens, Parabacteroides merdae|Granulicatella adiacens, Parvimonas micra|Granulicatella adiacens, Pediococcus acidilactici|Granulicatella adiacens, Pediococcus pentosaceus|Granulicatella adiacens, Peptoniphilus duerdenii|Granulicatella adiacens, Peptoniphilus harei|Granulicatella adiacens, Peptoniphilus lacrimalis|Granulicatella adiacens, Peptostreptococcus anaerobius|Granulicatella adiacens, Peptostreptococcus stomatis|Granulicatella adiacens, Porphyromonas asaccharolytica|Granulicatella adiacens, Porphyromonas uenonis|Granulicatella adiacens, Prevotella amnii|Granulicatella adiacens, Prevotella bergensis|Granulicatella adiacens, Prevotella bivia|Granulicatella adiacens, Prevotella buccae|Granulicatella adiacens, Prevotella buccalis|Granulicatella adiacens, Prevotella copri|Granulicatella adiacens, Prevotella disiens|Granulicatella adiacens, Prevotella melaninogenica|Granulicatella adiacens, Prevotella multiformis|Granulicatella adiacens, Prevotella oralis|Granulicatella adiacens, Prevotella oris|Granulicatella adiacens, Prevotella salivae|Granulicatella adiacens, Prevotella timonensis|Granulicatella adiacens, Propionibacterium acnes|Granulicatella adiacens, Propionibacterium freudenreichii|Granulicatella adiacens, Proteus mirabilis|Granulicatella adiacens, Proteus penneri|Granulicatella adiacens, Pseudoflavonifractor capillosus|Granulicatella adiacens, Pseudomonas aeruginosa|Granulicatella adiacens, Pseudomonas fluorescens|Granulicatella adiacens, Pseudomonas putida|Granulicatella adiacens, Pseudoramibacter alactolyticus|Granulicatella adiacens, Pyramidobacter piscolens|Granulicatella adiacens, Rhodopseudomonas palustris|Granulicatella adiacens, Roseburia intestinalis|Granulicatella adiacens, Roseburia inulinivorans|Granulicatella adiacens, Rothia dentocariosa|Granulicatella adiacens, Rothia mucilaginosa|Granulicatella adiacens, Ruminococcus albus|Granulicatella adiacens, Ruminococcus bromii|Granulicatella adiacens, Ruminococcus gnavus|Granulicatella adiacens, Ruminococcus lactaris|Granulicatella adiacens, Ruminococcus obeum|Granulicatella adiacens, Ruminococcus torques|Granulicatella adiacens, Selenomonas sputigena|Granulicatella adiacens, Shigella boydii|Granulicatella adiacens, Shigella dysenteriae|Granulicatella adiacens, Shigella sonnei|Granulicatella adiacens, Slackia exigua|Granulicatella adiacens, Solobacterium moorei|Granulicatella adiacens, Staphylococcus aureus|Granulicatella adiacens, Staphylococcus epidermidis|Granulicatella adiacens, Staphylococcus hominis|Granulicatella adiacens, Staphylococcus saprophyticus|Granulicatella adiacens, Staphylococcus warneri|Granulicatella adiacens, Streptococcus agalactiae|Granulicatella adiacens, Streptococcus anginosus|Granulicatella adiacens, Streptococcus australis|Granulicatella adiacens, Streptococcus bovis|Granulicatella adiacens, Streptococcus cristatus|Granulicatella adiacens, Streptococcus dysgalactiae|Granulicatella adiacens, Streptococcus equinus|Granulicatella adiacens, Streptococcus gordonii|Granulicatella adiacens, Streptococcus infantarius|Granulicatella adiacens, Streptococcus infantis|Granulicatella adiacens, Streptococcus mitis|Granulicatella adiacens, Streptococcus mutans|Granulicatella adiacens, Streptococcus oralis|Granulicatella adiacens, Streptococcus parasanguinis|Granulicatella adiacens, Streptococcus peroris|Granulicatella adiacens, Streptococcus pneumoniae|Granulicatella adiacens, Streptococcus salivarius|Granulicatella adiacens, Streptococcus sanguinis|Granulicatella adiacens, Streptococcus thermophilus|Granulicatella adiacens, Streptococcus vestibularis|Granulicatella adiacens, Subdoligranulum variabile|Granulicatella adiacens, Succinatimonas hippei|Granulicatella adiacens, Sutterella wadsworthensis|Granulicatella adiacens, Tropheryma whipplei|Granulicatella adiacens, Veillonella atypica|Granulicatella adiacens, Veillonella dispar|Granulicatella adiacens, Veillonella parvula|Granulicatella adiacens, Victivallis vadensis|Granulicatella elegans, Granulicatella elegans|Granulicatella elegans, Haemophilus influenzae|Granulicatella elegans, Haemophilus parainfluenzae|Granulicatella elegans, Helicobacter pullorum|Granulicatella elegans, Helicobacter pylori|Granulicatella elegans, Holdemania filiformis|Granulicatella elegans, Kingella oralis|Granulicatella elegans, Klebsiella pneumoniae|Granulicatella elegans, Klebsiella variicola|Granulicatella elegans, Lachnospiraceae bacterium 5_1_57FAA|Granulicatella elegans, Lactobacillus acidophilus|Granulicatella elegans, Lactobacillus amylovorus|Granulicatella elegans, Lactobacillus brevis|Granulicatella elegans, Lactobacillus casei|Granulicatella elegans, Lactobacillus crispatus|Granulicatella elegans, Lactobacillus delbrueckii|Granulicatella elegans, Lactobacillus fermentum|Granulicatella elegans, Lactobacillus gasseri|Granulicatella elegans, Lactobacillus iners|Granulicatella elegans, Lactobacillus jensenii|Granulicatella elegans, Lactobacillus johnsonii|Granulicatella elegans, Lactobacillus paracasei|Granulicatella elegans, Lactobacillus plantarum|Granulicatella elegans, Lactobacillus reuteri|Granulicatella elegans, Lactobacillus rhamnosus|Granulicatella elegans, Lactobacillus ruminis|Granulicatella elegans, Lactobacillus sakei|Granulicatella elegans, Lactobacillus salivarius|Granulicatella elegans, Lactococcus lactis|Granulicatella elegans, Lautropia mirabilis|Granulicatella elegans, Leuconostoc citreum|Granulicatella elegans, Leuconostoc gasicomitatum|Granulicatella elegans, Leuconostoc mesenteroides|Granulicatella elegans, Listeria monocytogenes|Granulicatella elegans, Marvinbryantia formatexigens|Granulicatella elegans, Megamonas hypermegale|Granulicatella elegans, Megasphaera micronuciformis|Granulicatella elegans, Methanobrevibacter smithii|Granulicatella elegans, Methanosphaera stadtmanae|Granulicatella elegans, Methylobacterium radiotolerans|Granulicatella elegans, Mitsuokella multacida|Granulicatella elegans, Mobiluncus curtisii|Granulicatella elegans, Mycoplasma hominis|Granulicatella elegans, Neisseria mucosa|Granulicatella elegans, Odoribacter splanchnicus|Granulicatella elegans, Olsenella uli|Granulicatella elegans, Oribacterium sinus|Granulicatella elegans, Oxalobacter formigenes|Granulicatella elegans, Parabacteroides distasonis|Granulicatella elegans, Parabacteroides johnsonii|Granulicatella elegans, Parabacteroides merdae|Granulicatella elegans, Parvimonas micra|Granulicatella elegans, Pediococcus acidilactici|Granulicatella elegans, Pediococcus pentosaceus|Granulicatella elegans, Peptoniphilus duerdenii|Granulicatella elegans, Peptoniphilus harei|Granulicatella elegans, Peptoniphilus lacrimalis|Granulicatella elegans, Peptostreptococcus anaerobius|Granulicatella elegans, Peptostreptococcus TABLE 2-continued Table 2. Specific binary combinations of OTUs. Individual pairings are differentiated by "|" and OTUs within a combination are differentiated by ","

*stomatis|Granulicatella elegans, Porphyromonas asaccharolytica|Granulicatella elegans, Porphyromonas uenonis|Granulicatella elegans, Prevotella amnii|Granulicatella elegans, Prevotella bergensis|Granulicatella elegans, Prevotella bivia|Granulicatella elegans, Prevotella buccae|Granulicatella elegans, Prevotella buccalis|Granulicatella elegans, Prevotella copri|Granulicatella elegans, Prevotella disiens|Granulicatella elegans, Prevotella melaninogenica|Granulicatella elegans, Prevotella multiformis|Granulicatella elegans, Prevotella oralis|Granulicatella elegans, Prevotella oris|Granulicatella elegans, Prevotella salivae|Granulicatella elegans, Prevotella timonensis|Granulicatella elegans, Propionibacterium acnes|Granulicatella elegans, Propionibacterium freudenreichii|Granulicatella elegans, Proteus mirabilis|Granulicatella elegans, Proteus penneri|Granulicatella elegans, Pseudoflavonifractor capillosus|Granulicatella elegans, Pseudomonas aeruginosa|Granulicatella elegans, Pseudomonas fluorescens|Granulicatella elegans, Pseudomonas putida|Granulicatella elegans, Pseudoramibacter alactolyticus|Granulicatella elegans, Pyramidobacter piscolens|Granulicatella elegans, Rhodopseudomonas palustris|Granulicatella elegans, Roseburia intestinalis|Granulicatella elegans, Roseburia inulinivorans|Granulicatella elegans, Rothia dentocariosa|Granulicatella elegans, Rothia mucilaginosa|Granulicatella elegans, Ruminococcus albus|Granulicatella elegans, Ruminococcus bromii|Granulicatella elegans, Ruminococcus gnavus|Granulicatella elegans, Ruminococcus lactaris|Granulicatella elegans, Ruminococcus obeum|Granulicatella elegans, Ruminococcus torques|Granulicatella elegans, Selenomonas sputigena|Granulicatella elegans, Shigella boydii|Granulicatella elegans, Shigella dysenteriae|Granulicatella elegans, Shigella sonnei|Granulicatella elegans, Slackia exigua|Granulicatella elegans, Solobacterium moorei|Granulicatella elegans, Staphylococcus aureus|Granulicatella elegans, Staphylococcus epidermidis|Granulicatella elegans, Staphylococcus hominis|Granulicatella elegans, Staphylococcus saprophyticus|Granulicatella elegans, Staphylococcus warneri|Granulicatella elegans, Streptococcus agalactiae|Granulicatella elegans, Streptococcus anginosus|Granulicatella elegans, Streptococcus australis|Granulicatella elegans, Streptococcus bovis|Granulicatella elegans, Streptococcus cristatus|Granulicatella elegans, Streptococcus dysgalactiae|Granulicatella elegans, Streptococcus equinus|Granulicatella elegans, Streptococcus gordonii|Granulicatella elegans, Streptococcus infantarius|Granulicatella elegans, Streptococcus infantis|Granulicatella elegans, Streptococcus mitis|Granulicatella elegans, Streptococcus mutans|Granulicatella elegans, Streptococcus oralis|Granulicatella elegans, Streptococcus parasanguinis|Granulicatella elegans, Streptococcus peroris|Granulicatella elegans, Streptococcus pneumoniae|Granulicatella elegans, Streptococcus salivarius|Granulicatella elegans, Streptococcus sanguinis|Granulicatella elegans, Streptococcus thermophilus|Granulicatella elegans, Streptococcus vestibularis|Granulicatella elegans, Subdoligranulum variabile|Granulicatella elegans, Succinatimonas hippei|Granulicatella elegans, Sutterella wadsworthensis|Granulicatella elegans, Tropheryma whipplei|Granulicatella elegans, Veillonella atypica|Granulicatella elegans, Veillonella dispar|Granulicatella elegans, Veillonella parvula|Granulicatella elegans, Victivallis vadensis|Haemophilus influenzae, Haemophilus influenzae|Haemophilus influenzae, Haemophilus parainfluenzae|Haemophilus influenzae, Helicobacter pullorum|Haemophilus influenzae, Helicobacter pylori|Haemophilus influenzae, Holdemania filiformis|Haemophilus influenzae, Kingella oralis|Haemophilus influenzae, Klebsiella pneumoniae|Haemophilus influenzae, Klebsiella variicola|Haemophilus influenzae, Lachnospiraceae bacterium* 5_1_57FAA|*Haemophilus influenzae, Lactobacillus acidophilus|Haemophilus influenzae, Lactobacillus amylovorus|Haemophilus influenzae, Lactobacillus brevis|Haemophilus influenzae, Lactobacillus casei|Haemophilus influenzae, Lactobacillus crispatus|Haemophilus influenzae, Lactobacillus delbrueckii|Haemophilus influenzae, Lactobacillus fermentum|Haemophilus influenzae, Lactobacillus gasseri|Haemophilus influenzae, Lactobacillus iners|Haemophilus influenzae, Lactobacillus jensenii|Haemophilus influenzae, Lactobacillus johnsonii|Haemophilus influenzae, Lactobacillus paracasei|Haemophilus influenzae, Lactobacillus plantarum|Haemophilus influenzae, Lactobacillus reuteri|Haemophilus influenzae, Lactobacillus rhamnosus|Haemophilus influenzae, Lactobacillus ruminis|Haemophilus influenzae, Lactobacillus sakei|Haemophilus influenzae, Lactobacillus salivarius|Haemophilus influenzae, Lactococcus lactis|Haemophilus influenzae, Lautropia mirabilis|Haemophilus influenzae, Leuconostoc citreum|Haemophilus influenzae, Leuconostoc gasicomitatum|Haemophilus influenzae, Leuconostoc mesenteroides|Haemophilus influenzae, Listeria monocytogenes|Haemophilus influenzae, Marvinbryantia formatexigens|Haemophilus influenzae, Megamonas hypermegale|Haemophilus influenzae, Megasphaera micronuciformis|Haemophilus influenzae, Methanobrevibacter smithii|Haemophilus influenzae, Methanosphaera stadtmanae|Haemophilus influenzae, Methylobacterium radiotolerans|Haemophilus influenzae, Mitsuokella multacida|Haemophilus influenzae, Mobiluncus curtisii|Haemophilus influenzae, Mycoplasma hominis|Haemophilus influenzae, Neisseria mucosa|Haemophilus influenzae, Odoribacter splanchnicus|Haemophilus influenzae, Olsenella uli|Haemophilus influenzae, Oribacterium sinus|Haemophilus influenzae, Oxalobacter formigenes|Haemophilus influenzae, Parabacteroides distasonis|Haemophilus influenzae, Parabacteroides johnsonii|Haemophilus influenzae, Parabacteroides merdae|Haemophilus influenzae, Parvimonas micra|Haemophilus influenzae, Pediococcus acidilactici|Haemophilus influenzae, Pediococcus pentosaceus|Haemophilus influenzae, Peptoniphilus duerdenii|Haemophilus influenzae, Peptoniphilus harei|Haemophilus influenzae, Peptoniphilus lacrimalis|Haemophilus influenzae, Peptostreptococcus anaerobius|Haemophilus influenzae, Peptostreptococcus stomatis|Haemophilus influenzae, Porphyromonas asaccharolytica|Haemophilus influenzae, Porphyromonas uenonis|Haemophilus influenzae, Prevotella amnii|Haemophilus influenzae, Prevotella bergensis|Haemophilus influenzae, Prevotella bivia|Haemophilus influenzae, Prevotella buccae|Haemophilus influenzae, Prevotella buccalis|Haemophilus influenzae, Prevotella copri|Haemophilus influenzae, Prevotella disiens|Haemophilus influenzae, Prevotella melaninogenica|Haemophilus influenzae, Prevotella multiformis|Haemophilus influenzae, Prevotella oralis|Haemophilus influenzae, Prevotella oris|Haemophilus influenzae, Prevotella salivae|Haemophilus influenzae, Prevotella timonensis|Haemophilus influenzae, Propionibacterium acnes|Haemophilus influenzae, Propionibacterium freudenreichii|Haemophilus influenzae, Proteus mirabilis|Haemophilus influenzae, Proteus penneri|Haemophilus influenzae, Pseudoflavonifractor capillosus|Haemophilus influenzae, Pseudomonas aeruginosa|Haemophilus influenzae, Pseudomonas fluorescens|Haemophilus influenzae, Pseudomonas putida|Haemophilus influenzae, Pseudoramibacter alactolyticus|Haemophilus influenzae, Pyramidobacter piscolens|Haemophilus influenzae, Rhodopseudomonas palustris|Haemophilus influenzae, Roseburia intestinalis|Haemophilus influenzae, Roseburia inulinivorans|Haemophilus influenzae, Rothia dentocariosa|Haemophilus influenzae, Rothia mucilaginosa|Haemophilus influenzae, Ruminococcus albus|Haemophilus influenzae, Ruminococcus bromii|Haemophilus influenzae, Ruminococcus gnavus|Haemophilus influenzae, Ruminococcus lactaris|Haemophilus influenzae, Ruminococcus obeum|Haemophilus influenzae, Ruminococcus torques|Haemophilus influenzae, Selenomonas sputigena|Haemophilus influenzae, Shigella boydii|Haemophilus influenzae, Shigella dysenteriae|Haemophilus influenzae, Shigella sonnei|Haemophilus influenzae, Slackia exigua|Haemophilus influenzae, Solobacterium moorei|Haemophilus influenzae, Staphylococcus aureus|Haemophilus influenzae, Staphylococcus epidermidis|Haemophilus influenzae, Staphylococcus hominis|Haemophilus influenzae, Staphylococcus saprophyticus|Haemophilus influenzae, Staphylococcus warneri|Haemophilus influenzae, Streptococcus agalactiae|Haemophilus influenzae, Streptococcus anginosus|Haemophilus influenzae, Streptococcus australis|Haemophilus influenzae, Streptococcus bovis|Haemophilus influenzae, Streptococcus cristatus|Haemophilus influenzae, Streptococcus dysgalactiae|Haemophilus influenzae, Streptococcus equinus|Haemophilus influenzae, Streptococcus gordonii|Haemophilus influenzae, Streptococcus infantarius|Haemophilus influenzae, Streptococcus infantis|Haemophilus influenzae, Streptococcus mitis|Haemophilus influenzae, Streptococcus mutans|Haemophilus influenzae, Streptococcus oralis|Haemophilus influenzae, Streptococcus parasanguinis|Haemophilus influenzae, Streptococcus peroris|Haemophilus influenzae, Streptococcus pneumoniae|Haemophilus influenzae, Streptococcus salivarius|Haemophilus influenzae, Streptococcus sanguinis|Haemophilus influenzae, Streptococcus thermophilus|Haemophilus influenzae, Streptococcus vestibularis|Haemophilus influenzae, Subdoligranulum variabile|Haemophilus influenzae, Succinatimonas hippei|Haemophilus influenzae, Sutterella wadsworthensis|Haemophilus influenzae, Tropheryma whipplei|Haemophilus influenzae, Veillonella atypica|Haemophilus influenzae, Veillonella dispar|Haemophilus influenzae, Veillonella parvula|Haemophilus influenzae, Victivallis vadensis|Haemophilus parainfluenzae, Haemophilus parainfluenzae|Haemophilus parainfluenzae, Helicobacter pullorum|Haemophilus parainfluenzae, Helicobacter pylori|Haemophilus*

TABLE 2-continued

| Table 2. Specific binary combinations of OTUs. Individual pairings are differentiated by "\|" and OTUs within a combination are differentiated by "," |
|---|
| *parainfluenzae, Holdemania filiformis\|Haemophilus parainfluenzae, Kingella oralis\|Haemophilus parainfluenzae, Klebsiella pneumoniae\|Haemophilus parainfluenzae, Klebsiella variicola\|Haemophilus parainfluenzae, Lachnospiraceae bacterium* 5_1_57FAA*\|Haemophilus parainfluenzae, Lactobacillus acidophilus\|Haemophilus parainfluenzae, Lactobacillus amylovorus\|Haemophilus parainfluenzae, Lactobacillus brevis\|Haemophilus parainfluenzae, Lactobacillus casei\|Haemophilus parainfluenzae, Lactobacillus crispatus\|Haemophilus parainfluenzae, Lactobacillus delbrueckii\|Haemophilus parainfluenzae, Lactobacillus fermentum\|Haemophilus parainfluenzae, Lactobacillus gasseri\|Haemophilus parainfluenzae, Lactobacillus iners\|Haemophilus parainfluenzae, Lactobacillus jensenii\|Haemophilus parainfluenzae, Lactobacillus johnsonii\|Haemophilus parainfluenzae, Lactobacillus paracasei\|Haemophilus parainfluenzae, Lactobacillus plantarum\|Haemophilus parainfluenzae, Lactobacillus reuteri\|Haemophilus parainfluenzae, Lactobacillus rhamnosus\|Haemophilus parainfluenzae, Lactobacillus ruminis\|Haemophilus parainfluenzae, Lactobacillus sakei\|Haemophilus parainfluenzae, Lactobacillus salivarius\|Haemophilus parainfluenzae, Lactococcus lactis\|Haemophilus parainfluenzae, Lautropia mirabilis\|Haemophilus parainfluenzae, Leuconostoc citreum\|Haemophilus parainfluenzae, Leuconostoc gasicomitatum\|Haemophilus parainfluenzae, Leuconostoc mesenteroides\|Haemophilus parainfluenzae, Listeria monocytogenes\|Haemophilus parainfluenzae, Marvinbryantia formatexigens\|Haemophilus parainfluenzae, Megamonas hypermegale\|Haemophilus parainfluenzae, Megasphaera micronuciformis\|Haemophilus parainfluenzae, Methanobrevibacter smithii\|Haemophilus parainfluenzae, Methanosphaera stadtmanae\|Haemophilus parainfluenzae, Methylobacterium radiotolerans\|Haemophilus parainfluenzae, Mitsuokella multacida\|Haemophilus parainfluenzae, Mobiluncus curtisii\|Haemophilus parainfluenzae, Mycoplasma hominis\|Haemophilus parainfluenzae, Neisseria mucosa\|Haemophilus parainfluenzae, Odoribacter splanchnicus\|Haemophilus parainfluenzae, Olsenella uli\|Haemophilus parainfluenzae, Oribacterium sinus\|Haemophilus parainfluenzae, Oxalobacter formigenes\|Haemophilus parainfluenzae, Parabacteroides distasonis\|Haemophilus parainfluenzae, Parabacteroides johnsonii\|Haemophilus parainfluenzae, Parabacteroides merdae\|Haemophilus parainfluenzae, Parvimonas micra\|Haemophilus parainfluenzae, Pediococcus acidilactici\|Haemophilus parainfluenzae, Pediococcus pentosaceus\|Haemophilus parainfluenzae, Peptoniphilus duerdenii\|Haemophilus parainfluenzae, Peptoniphilus harei\|Haemophilus parainfluenzae, Peptoniphilus lacrimalis\|Haemophilus parainfluenzae, Peptostreptococcus anaerobius\|Haemophilus parainfluenzae, Peptostreptococcus stomatis\|Haemophilus parainfluenzae, Porphyromonas asaccharolytica\|Haemophilus parainfluenzae, Porphyromonas uenonis\|Haemophilus parainfluenzae, Prevotella amnii\|Haemophilus parainfluenzae, Prevotella bergensis\|Haemophilus parainfluenzae, Prevotella bivia\|Haemophilus parainfluenzae, Prevotella buccae\|Haemophilus parainfluenzae, Prevotella buccalis\|Haemophilus parainfluenzae, Prevotella copri\|Haemophilus parainfluenzae, Prevotella disiens\|Haemophilus parainfluenzae, Prevotella melaninogenica\|Haemophilus parainfluenzae, Prevotella multiformis\|Haemophilus parainfluenzae, Prevotella oralis\|Haemophilus parainfluenzae, Prevotella oris\|Haemophilus parainfluenzae, Prevotella salivae\|Haemophilus parainfluenzae, Prevotella timonensis\|Haemophilus parainfluenzae, Propionibacterium acnes\|Haemophilus parainfluenzae, Propionibacterium freudenreichii\|Haemophilus parainfluenzae, Proteus mirabilis\|Haemophilus parainfluenzae, Proteus penneri\|Haemophilus parainfluenzae, Pseudoflavonifractor capillosus\|Haemophilus parainfluenzae, Pseudomonas aeruginosa\|Haemophilus parainfluenzae, Pseudomonas fluorescens\|Haemophilus parainfluenzae, Pseudomonas putida\|Haemophilus parainfluenzae, Pseudoramibacter alactolyticus\|Haemophilus parainfluenzae, Pyramidobacter piscolens\|Haemophilus parainfluenzae, Rhodopseudomonas palustris\|Haemophilus parainfluenzae, Roseburia intestinalis\|Haemophilus parainfluenzae, Roseburia inulinivorans\|Haemophilus parainfluenzae, Rothia dentocariosa\|Haemophilus parainfluenzae, Rothia mucilaginosa\|Haemophilus parainfluenzae, Ruminococcus albus\|Haemophilus parainfluenzae, Ruminococcus bromii\|Haemophilus parainfluenzae, Ruminococcus gnavus\|Haemophilus parainfluenzae, Ruminococcus lactaris\|Haemophilus parainfluenzae, Ruminococcus obeum\|Haemophilus parainfluenzae, Ruminococcus torques\|Haemophilus parainfluenzae, Selenomonas sputigena\|Haemophilus parainfluenzae, Shigella boydii\|Haemophilus parainfluenzae, Shigella dysenteriae\|Haemophilus parainfluenzae, Shigella sonnei\|Haemophilus parainfluenzae, Slackia exigua\|Haemophilus parainfluenzae, Solobacterium moorei\|Haemophilus parainfluenzae, Staphylococcus aureus\|Haemophilus parainfluenzae, Staphylococcus epidermidis\|Haemophilus parainfluenzae, Staphylococcus hominis\|Haemophilus parainfluenzae, Staphylococcus saprophyticus\|Haemophilus parainfluenzae, Staphylococcus warneri\|Haemophilus parainfluenzae, Streptococcus agalactiae\|Haemophilus parainfluenzae, Streptococcus anginosus\|Haemophilus parainfluenzae, Streptococcus australis\|Haemophilus parainfluenzae, Streptococcus bovis\|Haemophilus parainfluenzae, Streptococcus cristatus\|Haemophilus parainfluenzae, Streptococcus dysgalactiae\|Haemophilus parainfluenzae, Streptococcus equinus\|Haemophilus parainfluenzae, Streptococcus gordonii\|Haemophilus parainfluenzae, Streptococcus infantarius\|Haemophilus parainfluenzae, Streptococcus infantis\|Haemophilus parainfluenzae, Streptococcus mitis\|Haemophilus parainfluenzae, Streptococcus mutans\|Haemophilus parainfluenzae, Streptococcus oralis\|Haemophilus parainfluenzae, Streptococcus parasanguinis\|Haemophilus parainfluenzae, Streptococcus peroris\|Haemophilus parainfluenzae, Streptococcus pneumoniae\|Haemophilus parainfluenzae, Streptococcus salivarius\|Haemophilus parainfluenzae, Streptococcus sanguinis\|Haemophilus parainfluenzae, Streptococcus thermophilus\|Haemophilus parainfluenzae, Streptococcus vestibularis\|Haemophilus parainfluenzae, Subdoligranulum variabile\|Haemophilus parainfluenzae, Succinatimonas hippei\|Haemophilus parainfluenzae, Sutterella wadsworthensis\|Haemophilus parainfluenzae, Tropheryma whipplei\|Haemophilus parainfluenzae, Veillonella atypica\|Haemophilus parainfluenzae, Veillonella dispar\|Haemophilus parainfluenzae, Veillonella parvula\|Haemophilus parainfluenzae, Victivallis vadensis\|Helicobacter pullorum, Helicobacter pullorum\|Helicobacter pullorum, Helicobacter pylori\|Helicobacter pullorum, Holdemania filiformis\|Helicobacter pullorum, Kingella oralis\|Helicobacter pullorum, Klebsiella pneumoniae\|Helicobacter pullorum, Klebsiella variicola\|Helicobacter pullorum, Lachnospiraceae bacterium* 5_1_57FAA*\|Helicobacter pullorum, Lactobacillus acidophilus\|Helicobacter pullorum, Lactobacillus amylovorus\|Helicobacter pullorum, Lactobacillus brevis\|Helicobacter pullorum, Lactobacillus casei\|Helicobacter pullorum, Lactobacillus crispatus\|Helicobacter pullorum, Lactobacillus delbrueckii\|Helicobacter pullorum, Lactobacillus fermentum\|Helicobacter pullorum, Lactobacillus gasseri\|Helicobacter pullorum, Lactobacillus iners\|Helicobacter pullorum, Lactobacillus jensenii\|Helicobacter pullorum, Lactobacillus johnsonii\|Helicobacter pullorum, Lactobacillus paracasei\|Helicobacter pullorum, Lactobacillus plantarum\|Helicobacter pullorum, Lactobacillus reuteri\|Helicobacter pullorum, Lactobacillus rhamnosus\|Helicobacter pullorum, Lactobacillus ruminis\|Helicobacter pullorum, Lactobacillus sakei\|Helicobacter pullorum, Lactobacillus salivarius\|Helicobacter pullorum, Lactococcus lactis\|Helicobacter pullorum, Lautropia mirabilis\|Helicobacter pullorum, Leuconostoc citreum\|Helicobacter pullorum, Leuconostoc gasicomitatum\|Helicobacter pullorum, Leuconostoc mesenteroides\|Helicobacter pullorum, Listeria monocytogenes\|Helicobacter pullorum, Marvinbryantia formatexigens\|Helicobacter pullorum, Megamonas hypermegale\|Helicobacter pullorum, Megasphaera micronuciformis\|Helicobacter pullorum, Methanobrevibacter smithii\|Helicobacter pullorum, Methanosphaera stadtmanae\|Helicobacter pullorum, Methylobacterium radiotolerans\|Helicobacter pullorum, Mitsuokella multacida\|Helicobacter pullorum, Mobiluncus curtisii\|Helicobacter pullorum, Mycoplasma hominis\|Helicobacter pullorum, Neisseria mucosa\|Helicobacter pullorum, Odoribacter splanchnicus\|Helicobacter pullorum, Olsenella uli\|Helicobacter pullorum, Oribacterium sinus\|Helicobacter pullorum, Oxalobacter formigenes\|Helicobacter pullorum, Parabacteroides distasonis\|Helicobacter pullorum, Parabacteroides johnsonii\|Helicobacter pullorum, Parabacteroides merdae\|Helicobacter pullorum, Parvimonas micra\|Helicobacter pullorum, Pediococcus acidilactici\|Helicobacter pullorum, Pediococcus pentosaceus\|Helicobacter pullorum, Peptoniphilus duerdenii\|Helicobacter pullorum, Peptoniphilus harei\|Helicobacter pullorum, Peptoniphilus lacrimalis\|Helicobacter pullorum, Peptostreptococcus anaerobius\|Helicobacter pullorum, Peptostreptococcus stomatis\|Helicobacter pullorum, Porphyromonas asaccharolytica\|Helicobacter pullorum, Porphyromonas uenonis\|Helicobacter pullorum, Prevotella amnii\|Helicobacter pullorum, Prevotella bergensis\|Helicobacter pullorum, Prevotella bivia\|Helicobacter pullorum, Prevotella buccae\|Helicobacter pullorum, Prevotella buccalis\|Helicobacter pullorum, Prevotella copri\|Helicobacter pullorum, Prevotella disiens\|Helicobacter pullorum, Prevotella melaninogenica\|Helicobacter pullorum, Prevotella multiformis\|Helicobacter pullorum, Prevotella oralis\|Helicobacter pullorum, Prevotella oris\|Helicobacter pullorum, Prevotella salivae\|Helicobacter* |

TABLE 2-continued

| Table 2. Specific binary combinations of OTUs. Individual pairings are differentiated by "\|" and OTUs within a combination are differentiated by "," |
|---|
| *pullorum, Prevotella timonensis\|Helicobacter pullorum, Propionibacterium acnes\|Helicobacter pullorum, Propionibacterium freudenreichii\|Helicobacter pullorum, Proteus mirabilis\|Helicobacter pullorum, Proteus penneri\|Helicobacter pullorum, Pseudoflavonifractor capillosus\|Helicobacter pullorum, Pseudomonas aeruginosa\|Helicobacter pullorum, Pseudomonas fluorescens\|Helicobacter pullorum, Pseudomonas putida\|Helicobacter pullorum, Pseudoramibacter alactolyticus\|Helicobacter pullorum, Pyramidobacter piscolens\|Helicobacter pullorum, Rhodopseudomonas palustris\|Helicobacter pullorum, Roseburia intestinalis\|Helicobacter pullorum, Roseburia inulinivorans\|Helicobacter pullorum, Rothia dentocariosa\|Helicobacter pullorum, Rothia mucilaginosa\|Helicobacter pullorum, Ruminococcus albus\|Helicobacter pullorum, Ruminococcus bromialelicobacter pullorum, Ruminococcus gnavus\|Helicobacter pullorum, Ruminococcus lactaris\|Helicobacter pullorum, Ruminococcus obeum\|Helicobacter pullorum, Ruminococcus torques\|Helicobacter pullorum, Selenomonas sputigena\|Helicobacter pullorum, Shigella boydii\|Helicobacter pullorum, Shigella dysenteriae\|Helicobacter pullorum, Shigella sonnei\|Helicobacter pullorum, Slackia exigua\|Helicobacter pullorum, Solobacterium moorei\|Helicobacter pullorum, Staphylococcus aureus\|Helicobacter pullorum, Staphylococcus epidermidis\|Helicobacter pullorum, Staphylococcus hominis\|Helicobacter pullorum, Staphylococcus saprophyticus\|Helicobacter pullorum, Staphylococcus warneri\|Helicobacter pullorum, Streptococcus agalactiae\|Helicobacter pullorum, Streptococcus anginosus\|Helicobacter pullorum, Streptococcus australis\|Helicobacter pullorum, Streptococcus bovis\|Helicobacter pullorum, Streptococcus cristatus\|Helicobacter pullorum, Streptococcus dysgalactiae\|Helicobacter pullorum, Streptococcus equinus\|Helicobacter pullorum, Streptococcus gordonii\|Helicobacter pullorum, Streptococcus infantarius\|Helicobacter pullorum, Streptococcus infantis\|Helicobacter pullorum, Streptococcus mitis\|Helicobacter pullorum, Streptococcus mutans\|Helicobacter pullorum, Streptococcus oralis\|Helicobacter pullorum, Streptococcus parasanguinis\|Helicobacter pullorum, Streptococcus peroris\|Helicobacter pullorum, Streptococcus pneumoniae\|Helicobacter pullorum, Streptococcus salivarius\|Helicobacter pullorum, Streptococcus sanguinis\|Helicobacter pullorum, Streptococcus thermophilus\|Helicobacter pullorum, Streptococcus vestibularis\|Helicobacter pullorum, Subdoligranulum variabile\|Helicobacter pullorum, Succinatimonas hippei\|Helicobacter pullorum, Sutterella wadsworthensis\|Helicobacter pullorum, Tropheryma whipplei\|Helicobacter pullorum, Veillonella atypica\|Helicobacter pullorum, Veillonella dispar\|Helicobacter pullorum, Veillonella parvula\|Helicobacter pullorum, Victivallis vadensis\|Helicobacter pylori, Helicobacter pylori\|Helicobacter pylori, Holdemania filiformis\|Helicobacter pylori, Kingella oralis\|Helicobacter pylori, Klebsiella pneumoniae\|Helicobacter pylori, Klebsiella variicola\|Helicobacter pylori, Lachnospiraceae bacterium* 5_1_57FAA*\|Helicobacter pylori, Lactobacillus acidophilus\|Helicobacter pylori, Lactobacillus amylovorus\|Helicobacter pylori, Lactobacillus brevis\|Helicobacter pylori, Lactobacillus casei\|Helicobacter pylori, Lactobacillus crispatus\|Helicobacter pylori, Lactobacillus delbrueckii\|Helicobacter pylori, Lactobacillus fermentum\|Helicobacter pylori, Lactobacillus gasseri\|Helicobacter pylori, Lactobacillus iners\|Helicobacter pylori, Lactobacillus jensenii\|Helicobacter pylori, Lactobacillus johnsonii\|Helicobacter pylori, Lactobacillus paracasei\|Helicobacter pylori, Lactobacillus plantarum\|Helicobacter pylori, Lactobacillus reuteri\|Helicobacter pylori, Lactobacillus rhamnosus\|Helicobacter pylori, Lactobacillus ruminis\|Helicobacter pylori, Lactobacillus sakei\|Helicobacter pylori, Lactobacillus salivarius\|Helicobacter pylori, Lactococcus lactis\|Helicobacter pylori, Lautropia mirabilis\|Helicobacter pylori, Leuconostoc citreum\|Helicobacter pylori, Leuconostoc gasicomitatum\|Helicobacter pylori, Leuconostoc mesenteroides\|Helicobacter pylori, Listeria monocytogenes\|Helicobacter pylori, Marvinbryantia formatexigens\|Helicobacter pylori, Megamonas hypermegale\|Helicobacter pylori, Megasphaera micronuciformis\|Helicobacter pylori, Methanobrevibacter smithii\|Helicobacter pylori, Methanosphaera stadtmanae\|Helicobacter pylori, Methylobacterium radiotolerans\|Helicobacter pylori, Mitsuokella multacida\|Helicobacter pylori, Mobiluncus curtisii\|Helicobacter pylori, Mycoplasma hominis\|Helicobacter pylori, Neisseria mucosa\|Helicobacter pylori, Odoribacter splanchnicus\|Helicobacter pylori, Olsenella uli\|Helicobacter pylori, Oribacterium sinus\|Helicobacter pylori, Oxalobacter formigenes\|Helicobacter pylori, Parabacteroides distasonis\|Helicobacter pylori, Parabacteroides johnsonii\|Helicobacter pylori, Parabacteroides merdae\|Helicobacter pylori, Parvimonas micra\|Helicobacter pylori, Pediococcus acidilactici\|Helicobacter pylori, Pediococcus pentosaceus\|Helicobacter pylori, Peptoniphilus duerdenii\|Helicobacter pylori, Peptoniphilus harei\|Helicobacter pylori, Peptoniphilus lacrimalis\|Helicobacter pylori, Peptostreptococcus anaerobius\|Helicobacter pylori, Peptostreptococcus stomatis\|Helicobacter pylori, Porphyromonas asaccharolytica\|Helicobacter pylori, Porphyromonas uenonis\|Helicobacter pylori, Prevotella amnii\|Helicobacter pylori, Prevotella bergensis\|Helicobacter pylori, Prevotella bivia\|Helicobacter pylori, Prevotella buccae\|Helicobacter pylori, Prevotella buccalis\|Helicobacter pylori, Prevotella copri\|Helicobacter pylori, Prevotella disiens\|Helicobacter pylori, Prevotella melaninogenica\|Helicobacter pylori, Prevotella multiformis\|Helicobacter pylori, Prevotella oralis\|Helicobacter pylori, Prevotella oris\|Helicobacter pylori, Prevotella salivae\|Helicobacter pylori, Prevotella timonensis\|Helicobacter pylori, Propionibacterium acnes\|Helicobacter pylori, Propionibacterium freudenreichii\|Helicobacter pylori, Proteus mirabilis\|Helicobacter pylori, Proteus penneri\|Helicobacter pylori, Pseudoflavonifractor capillosus\|Helicobacter pylori, Pseudomonas aeruginosa\|Helicobacter pylori, Pseudomonas fluorescens\|Helicobacter pylori, Pseudomonas putida\|Helicobacter pylori, Pseudoramibacter alactolyticus\|Helicobacter pylori, Pyramidobacter piscolens\|Helicobacter pylori, Rhodopseudomonas palustris\|Helicobacter pylori, Roseburia intestinalis\|Helicobacter pylori, Roseburia inulinivorans\|Helicobacter pylori, Rothia dentocariosa\|Helicobacter pylori, Rothia mucilaginosa\|Helicobacter pylori, Ruminococcus albus\|Helicobacter pylori, Ruminococcus bromii\|Helicobacter pylori, Ruminococcus gnavus\|Helicobacter pylori, Ruminococcus lactaris\|Helicobacter pylori, Ruminococcus obeum\|Helicobacter pylori, Ruminococcus torques\|Helicobacter pylori, Selenomonas sputigena\|Helicobacter pylori, Shigella boydii\|Helicobacter pylori, Shigella dysenteriae\|Helicobacter pylori, Shigella sonnei\|Helicobacter pylori, Slackia exigua\|Helicobacter pylori, Solobacterium moorei\|Helicobacter pylori, Staphylococcus aureus\|Helicobacter pylori, Staphylococcus epidermidis\|Helicobacter pylori, Staphylococcus hominis\|Helicobacter pylori, Staphylococcus saprophyticus\|Helicobacter pylori, Staphylococcus warneri\|Helicobacter pylori, Streptococcus agalactiae\|Helicobacter pylori, Streptococcus anginosus\|Helicobacter pylori, Streptococcus australis\|Helicobacter pylori, Streptococcus bovis\|Helicobacter pylori, Streptococcus cristatus\|Helicobacter pylori, Streptococcus dysgalactiae\|Helicobacter pylori, Streptococcus equinus\|Helicobacter pylori, Streptococcus gordonii\|Helicobacter pylori, Streptococcus infantarius\|Helicobacter pylori, Streptococcus infantis\|Helicobacter pylori, Streptococcus mitis\|Helicobacter pylori, Streptococcus mutans\|Helicobacter pylori, Streptococcus oralis\|Helicobacter pylori, Streptococcus parasanguinis\|Helicobacter pylori, Streptococcus peroris\|Helicobacter pylori, Streptococcus pneumoniae\|Helicobacter pylori, Streptococcus salivarius\|Helicobacter pylori, Streptococcus sanguinis\|Helicobacter pylori, Streptococcus thermophilus\|Helicobacter pylori, Streptococcus vestibularis\|Helicobacter pylori, Subdoligranulum variabile\|Helicobacter pylori, Succinatimonas hippei\|Helicobacter pylori, Sutterella wadsworthensis\|Helicobacter pylori, Tropheryma whipplei\|Helicobacter pylori, Veillonella atypica\|Helicobacter pylori, Veillonella dispar\|Helicobacter pylori, Veillonella parvula\|Helicobacter pylori, Victivallis vadensis\|Holdemania filiformis, Holdemania filiformis\|Holdemania filiformis, Kingella oralis\|Holdemania filiformis, Klebsiella pneumoniae\|Holdemania filiformis, Klebsiella variicola\|Holdemania filiformis, Lachnospiraceae bacterium* 5_1_57FAA*\|Holdemania filiformis, Lactobacillus acidophilus\|Holdemania filiformis, Lactobacillus amylovorus\|Holdemania filiformis, Lactobacillus brevis\|Holdemania filiformis, Lactobacillus casei\|Holdemania filiformis, Lactobacillus crispatus\|Holdemania filiformis, Lactobacillus delbrueckii\|Holdemania filiformis, Lactobacillus fermentum\|Holdemania filiformis, Lactobacillus gasseri\|Holdemania filiformis, Lactobacillus iners\|Holdemania filiformis, Lactobacillus jensenii\|Holdemania filiformis, Lactobacillus johnsonii\|Holdemania filiformis, Lactobacillus paracasei\|Holdemania filiformis, Lactobacillus plantarum\|Holdemania filiformis, Lactobacillus reuteri\|Holdemania filiformis, Lactobacillus rhamnosus\|Holdemania filiformis, Lactobacillus mminis\|Holdemania filiformis, Lactobacillus sakei\|Holdemania filiformis, Lactobacillus salivarius\|Holdemania filiformis, Lactococcus lactis\|Holdemania filiformis, Lautropia mirabilis\|Holdemania filiformis, Leuconostoc citreum\|Holdemania filiformis, Leuconostoc gasicomitatum\|Holdemania filiformis, Leuconostoc mesenteroides\|Holdemania filiformis, Listeria monocytogenes\|Holdemania filiformis, Marvinbryantia formatexigens\|Holdemania filiformis, Megamonas hypermegale\|Holdemania filiformis, Megasphaera micronuciformis\|Holdemania filiformis, Methanobrevibacter smithii\|Holdemania filiformis, Methanosphaera stadtmanae\|Holdemania filiformis, Methylobacterium* |

TABLE 2-continued

Table 2. Specific binary combinations of OTUs. Individual pairings are differentiated by "|" and OTUs within a combination are differentiated by ","

*radiotolerans|Holdemania filiformis, Mitsuokella multacida|Holdemania filiformis, Mobiluncus curtisii|Holdemania filiformis, Mycoplasma hominis|Holdemania filiformis, Neisseria mucosa|Holdemania filiformis, Odoribacter splanchnicus|Holdemania filiformis, Olsenella uli|Holdemania filiformis, Oribacterium sinus|Holdemania filiformis, Oxalobacter formigenes|Holdemania filiformis, Parabacteroides distasonis|Holdemania filiformis, Parabacteroides johnsonii|Holdemania filiformis, Parabacteroides merdae|Holdemania filiformis, Parvimonas micra|Holdemania filiformis, Pediococcus acidilactici|Holdemania filiformis, Pediococcus pentosaceus|Holdemania filiformis, Peptoniphilus duerdenii|Holdemania filiformis, Peptoniphilus harei|Holdemania filiformis, Peptoniphilus lacrimalis|Holdemania filiformis, Peptostreptococcus anaerobius|Holdemania filiformis, Peptostreptococcus stomatis|Holdemania filiformis, Porphyromonas asaccharolytica|Holdemania filiformis, Porphyromonas uenonis|Holdemania filiformis, Prevotella amnii|Holdemania filiformis, Prevotella bergensis|Holdemania filiformis, Prevotella bivia|Holdemania filiformis, Prevotella buccae|Holdemania filiformis, Prevotella buccalis|Holdemania filiformis, Prevotella copri|Holdemania filiformis, Prevotella disiens|Holdemania filiformis, Prevotella melaninogenica|Holdemania filiformis, Prevotella multiformis|Holdemania filiformis, Prevotella oralis|Holdemania filiformis, Prevotella oris|Holdemania filiformis, Prevotella salivae|Holdemania filiformis, Prevotella timonensis|Holdemania filiformis, Propionibacterium acnes|Holdemania filiformis, Propionibacterium freudenreichii|Holdemania filiformis, Proteus mirabilis|Holdemania filiformis, Proteus penneri|Holdemania filiformis, Pseudoflavonifractor capillosus|Holdemania filiformis, Pseudomonas aeruginosa|Holdemania filiformis, Pseudomonas fluorescens|Holdemania filiformis, Pseudomonas putida|Holdemania filiformis, Pseudoramibacter alactolyticus|Holdemania filiformis, Pyramidobacter piscolens|Holdemania filiformis, Rhodopseudomonas palustris|Holdemania filiformis, Roseburia intestinalis|Holdemania filiformis, Roseburia inulinivorans|Holdemania filiformis, Rothia dentocariosa|Holdemania filiformis, Rothia mucilaginosa|Holdemania filiformis, Ruminococcus albus|Holdemania filiformis, Ruminococcus bromii|Holdemania filiformis, Ruminococcus gnavus|Holdemania filiformis, Ruminococcus lactaris|Holdemania filiformis, Ruminococcus obeum|Holdemania filiformis, Ruminococcus torques|Holdemania filiformis, Selenomonas sputigena|Holdemania filiformis, Shigella boydii|Holdemania filiformis, Shigella dysenteriae|Holdemania filiformis, Shigella sonnei|Holdemania filiformis, Slackia exigua|Holdemania filiformis, Solobacterium moorei|Holdemania filiformis, Staphylococcus aureus|Holdemania filiformis, Staphylococcus epidermidis|Holdemania filiformis, Staphylococcus hominis|Holdemania filiformis, Staphylococcus saprophyticus|Holdemania filiformis, Staphylococcus warneri|Holdemania filiformis, Streptococcus agalactiae|Holdemania filiformis, Streptococcus anginosus|Holdemania filiformis, Streptococcus australis|Holdemania filiformis, Streptococcus bovis|Holdemania filiformis, Streptococcus cristatus|Holdemania filiformis, Streptococcus dysgalactiae|Holdemania filiformis, Streptococcus equinus|Holdemania filiformis, Streptococcus gordonii|Holdemania filiformis, Streptococcus infantarius|Holdemania filiformis, Streptococcus infantis|Holdemania filiformis, Streptococcus mitis|Holdemania filiformis, Streptococcus mutans|Holdemania filiformis, Streptococcus oralis|Holdemania filiformis, Streptococcus parasanguinis|Holdemania filiformis, Streptococcus peroris|Holdemania filiformis, Streptococcus pneumoniae|Holdemania filiformis, Streptococcus salivarius|Holdemania filiformis, Streptococcus sanguinis|Holdemania filiformis, Streptococcus thermophilus|Holdemania filiformis, Streptococcus vestibularis|Holdemania filiformis, Subdoligranulum variabile|Holdemania filiformis, Succinatimonas hippei|Holdemania filiformis, Sutterella wadsworthensis|Holdemania filiformis, Tropheryma whipplei|Holdemania filiformis, Veillonella atypica|Holdemania filiformis, Veillonella dispar|Holdemania filiformis, Veillonella parvula|Holdemania filiformis, Victivallis vadensis|Kingella oralis, Kingella oralis|Kingella oralis, Klebsiella pneumoniae|Kingella oralis, Klebsiella variicola|Ningella oralis, Lachnospiraceae bacterium* 5_1_57FAA|*Kingella oralis, Lactobacillus acidophilus|Kingella oralis, Lactobacillus amylovorus|Kingella oralis, Lactobacillus brevis|Kingella oralis, Lactobacillus casei|Kingella oralis, Lactobacillus crispatus|Kingella oralis, Lactobacillus delbrueckii|Kingella oralis, Lactobacillus fermentum|Ningella oralis, Lactobacillus gasseri|Kingella oralis, Lactobacillus iners|Kingella oralis, Lactobacillus jensenii|Kingella oralis, Lactobacillus johnsonii|Kingella oralis, Lactobacillus paracasei|Kingella oralis, Lactobacillus plantarum|Kingella oralis, Lactobacillus reuteri|Kingella oralis, Lactobacillus rhamnosus|Kingella oralis, Lactobacillus ruminis|Kingella oralis, Lactobacillus sakei|Kingella oralis, Lactobacillus salivarius|Kingella oralis, Lactococcus lactis|Kingella oralis, Lautropia mirabilis|Kingella oralis, Leuconostoc citreum|Ningella oralis, Leuconostoc gasicomitatum|Ningella oralis, Leuconostoc mesenteroides|Kingella oralis, Listeria monocytogenes|Kingella oralis, Marvinbryantia formatexigens|Kingella oralis, Megamonas hypermegale|Kingella oralis, Megasphaera micronuciformis|Kingella oralis, Methanobrevibacter smithii|Kingella oralis, Methanosphaera stadtmanae|Kingella oralis, Methylobacterium radiotolerans|Kingella oralis, Mitsuokella multacida|Kingella oralis, Mobiluncus curtisii|Kingella oralis, Mycoplasma hominis|Kingella oralis, Neisseria mucosa|Kingella oralis, Odoribacter splanchnicus|Kingella oralis, Olsenella uli|Kingella oralis, Oribacterium sinus|Kingella oralis, Oxalobacter formigenes|Kingella oralis, Parabacteroides distasonis|Kingella oralis, Parabacteroides johnsonii|Kingella oralis, Parabacteroides merdae|Kingella oralis, Parvimonas micra|Kingella oralis, Pediococcus acidilactici|Kingella oralis, Pediococcus pentosaceus|Kingella oralis, Peptoniphilus duerdenii|Kingella oralis, Peptoniphilus harei|Kingella oralis, Peptoniphilus lacrimalis|Kingella oralis, Peptostreptococcus anaerobius|Kingella oralis, Peptostreptococcus stomatis|Kingella oralis, Porphyromonas asaccharolytica|Kingella oralis, Porphyromonas uenonis|Kingella oralis, Prevotella amnii|Kingella oralis, Prevotella bergensis|Kingella oralis, Prevotella bivia|Kingella oralis, Prevotella buccae|Kingella oralis, Prevotella buccalis|Kingella oralis, Prevotella copri|Kingella oralis, Prevotella disiens|Kingella oralis, Prevotella melaninogenica|Kingella oralis, Prevotella multiformis|Kingella oralis, Prevotella oralis|Kingella oralis, Prevotella oris|Kingella oralis, Prevotella salivae|Kingella oralis, Prevotella timonensis|Kingella oralis, Propionibacterium acnes|Kingella oralis, Propionibacterium freudenreichii|Kingella oralis, Proteus mirabilis|Kingella oralis, Proteus penneri|Kingella oralis, Pseudoflavonifractor capillosus|Kingella oralis, Pseudomonas aeruginosa|Kingella oralis, Pseudomonas fluorescens|Kingella oralis, Pseudomonas putidaj|Kingella oralis, Pseudoramibacter alactolyticus|Kingella oralis, Pyramidobacter piscolens|Kingella oralis, Rhodopseudomonas palustris|Kingella oralis, Roseburia intestinalis|Kingella oralis, Roseburia inulinivorans|Kingella oralis, Rothia dentocariosa|Kingella oralis, Rothia mucilaginosa|Kingella oralis, Ruminococcus albus|Kingella oralis, Ruminococcus bromii|Kingella oralis, Ruminococcus gaavus|Kingella oralis, Ruminococcus lactaris|Kingella oralis, Ruminococcus obeum|Kingella oralis, Ruminococcus torques|Kingella oralis, Selenomonas sputigena|Kingella oralis, Shigella boydii|Kingella oralis, Shigella dysenteriae|Kingella oralis, Shigella sonnei|Kingella oralis, Slackia exigua|Kingella oralis, Solobacterium moorei|Kingella oralis, Staphylococcus aureus|Kingella oralis, Staphylococcus epidermidis|Kingella oralis, Staphylococcus hominis|Kingella oralis, Staphylococcus saprophyticus|Kingella oralis, Staphylococcus warneri|Kingella oralis, Streptococcus agalactiae|Kingella oralis, Streptococcus anginosus|Kingella oralis, Streptococcus australis|Kingella oralis, Streptococcus bovis|Kingella oralis, Streptococcus cristatus|Kingella oralis, Streptococcus dysgalactiae|Kingella oralis, Streptococcus equinus|Kingella oralis, Streptococcus gordonii|Kingella oralis, Streptococcus infantarius|Kingella oralis, Streptococcus infantis|Kingella oralis, Streptococcus mitis|Kingella oralis, Streptococcus mutans|Kingella oralis, Streptococcus oralis|Kingella oralis, Streptococcus parasanguinis|Kingella oralis, Streptococcus peroris|Kingella oralis, Streptococcus pneumoniae|Kingella oralis, Streptococcus salivarius|Kingella oralis, Streptococcus sanguinis|Kingella oralis, Streptococcus thermophilus|Kingella oralis, Streptococcus vestibularis|Kingella oralis, Subdoligranulum variabile|Kingella oralis, Succinatimonas hippei|Kingella oralis, Sutterella wadsworthensis|Kingella oralis, Tropheryma whipplei|Kingella oralis, Veillonella atypica|Kingella oralis, Veillonella dispar|Kingella oralis, Veillonella parvula|Kingella oralis, Victivallis vadensis|Klebsiella pneumoniae, Klebsiella pneumoniae|Klebsiella pneumoniae, Klebsiella variicola|Klebsiella pneumoniae, Lachnospiraceae bacterium* 5_1_57FAA|*Klebsiella pneumoniae, Lactobacillus acidophilus|Klebsiella pneumoniae, Lactobacillus amylovorus|Klebsiella pneumoniae, Lactobacillus brevis|Klebsiella pneumoniae, Lactobacillus casei|Klebsiella pneumoniae, Lactobacillus crispatus|Klebsiella pneumoniae, Lactobacillus delbrueckii|Klebsiella pneumoniae, Lactobacillus fermentum|Klebsiella pneumoniae, Lactobacillus gasseri|Klebsiella pneumoniae, Lactobacillus iners|Klebsiella pneumoniae, Lactobacillus jensenii|Klebsiella pneumoniae, Lactobacillus johnsonii|Klebsiella pneumoniae, Lactobacillus paracasei|Klebsiella pneumoniae, Lactobacillus plantarum|Klebsiella pneumoniae, Lactobacillus reuteri|Klebsiella pneumoniae, Lactobacillus rhamnosus|Klebsiella*

TABLE 2-continued

| Table 2. Specific binary combinations of OTUs. Individual pairings are differentiated by "\|" and OTUs within a combination are differentiated by "," |
|---|
| *pneumoniae, Lactobacillus ruminis\|Klebsiella pneumoniae, Lactobacillus sakei\|Klebsiella pneumoniae, Lactobacillus salivarius\|Klebsiella pneumoniae, Lactococcus lactis\|Klebsiella pneumoniae, Lautropia mirabilis\|Klebsiella pneumoniae, Leuconostoc citreum\|Klebsiella pneumoniae, Leuconostoc gasicomitatum\|Klebsiella pneumoniae, Leuconostoc mesenteroides\|Klebsiella pneumoniae, Listeria monocytogenes\|Klebsiella pneumoniae, Marvinbryantia formatexigens\|Klebsiella pneumoniae, Megamonas hypermegale\|Klebsiella pneumoniae, Megasphaera micronuciformis\|Klebsiella pneumoniae, Methanobrevibacter smithii\|Klebsiella pneumoniae, Methanosphaera stadtmanae\|Klebsiella pneumoniae, Methylobacterium radiotolerans\|Klebsiella pneumoniae, Mitsuokella multacida\|Klebsiella pneumoniae, Mobiluncus curtisii\|Klebsiella pneumoniae, Mycoplasma hominis\|Klebsiella pneumoniae, Neisseria mucosa\|Klebsiella pneumoniae, Odoribacter splanchnicus\|Klebsiella pneumoniae, Olsenella uli\|Klebsiella pneumoniae, Oribacterium sinus\|Klebsiella pneumoniae, Oxalobacter formigenes\|Klebsiella pneumoniae, Parabacteroides distasonis\|Klebsiella pneumoniae, Parabacteroides johnsonii\|Klebsiella pneumoniae, Parabacteroides merdae\|Klebsiella pneumoniae, Parvimonas micra\|Klebsiella pneumoniae, Pediococcus acidilactici\|Klebsiella pneumoniae, Pediococcus pentosaceus\|Klebsiella pneumoniae, Peptoniphilus duerdenii\|Klebsiella pneumoniae, Peptoniphilus harei\|Klebsiella pneumoniae, Peptoniphilus lacrimalis\|Klebsiella pneumoniae, Peptostreptococcus anaerobius\|Klebsiella pneumoniae, Peptostreptococcus stomatis\|Klebsiella pneumoniae, Porphyromonas asaccharolytica\|Klebsiella pneumoniae, Porphyromonas uenonis\|Klebsiella pneumoniae, Prevotella amnii\|Klebsiella pneumoniae, Prevotella bergensis\|Klebsiella pneumoniae, Prevotella bivia\|Klebsiella pneumoniae, Prevotella buccae\|Klebsiella pneumoniae, Prevotella buccalis\|Klebsiella pneumoniae, Prevotella copri\|Klebsiella pneumoniae, Prevotella disiens\|Klebsiella pneumoniae, Prevotella melaninogenica\|Klebsiella pneumoniae, Prevotella multiformis\|Klebsiella pneumoniae, Prevotella oralis\|Klebsiella pneumoniae, Prevotella oris\|Klebsiella pneumoniae, Prevotella salivae\|Klebsiella pneumoniae, Prevotella timonensis\|Klebsiella pneumoniae, Propionibacterium acnes\|Klebsiella pneumoniae, Propionibacterium freudenreichii\|Klebsiella pneumoniae, Proteus mirabilis\|Klebsiella pneumoniae, Proteus penneri\|Klebsiella pneumoniae, Pseudoflavonifractor capillosus\|Klebsiella pneumoniae, Pseudomonas aeruginosa\|Klebsiella pneumoniae, Pseudomonas fluorescens\|Klebsiella pneumoniae, Pseudomonas putida\|Klebsiella pneumoniae, Pseudoramibacter alactolyticus\|Klebsiella pneumoniae, Pyramidobacter piscolens\|Klebsiella pneumoniae, Rhodopseudomonas palustris\|Klebsiella pneumoniae, Roseburia intestinalis\|Klebsiella pneumoniae, Roseburia inulinivorans\|Klebsiella pneumoniae, Rothia dentocariosa\|Klebsiella pneumoniae, Rothia mucilaginosa\|Klebsiella pneumoniae, Ruminococcus albus\|Klebsiella pneumoniae, Ruminococcus bromii\|Klebsiella pneumoniae, Ruminococcus gnavus\|Klebsiella pneumoniae, Ruminococcus lactaris\|Klebsiella pneumoniae, Ruminococcus obeum\|Klebsiella pneumoniae, Ruminococcus torques\|Klebsiella pneumoniae, Selenomonas sputigena\|Klebsiella pneumoniae, Shigella boydii\|Klebsiella pneumoniae, Shigella dysenteriae\|Klebsiella pneumoniae, Shigella sonnei\|Klebsiella pneumoniae, Slackia exigua\|Klebsiella pneumoniae, Solobacterium moorei\|Klebsiella pneumoniae, Staphylococcus aureus\|Klebsiella pneumoniae, Staphylococcus epidermidis\|Klebsiella pneumoniae, Staphylococcus hominis\|Klebsiella pneumoniae, Staphylococcus saprophyticus\|Klebsiella pneumoniae, Staphylococcus warneri\|Klebsiella pneumoniae, Streptococcus agalactiae\|Klebsiella pneumoniae, Streptococcus anginosus\|Klebsiella pneumoniae, Streptococcus australis\|Klebsiella pneumoniae, Streptococcus bovis\|Klebsiella pneumoniae, Streptococcus cristatus\|Klebsiella pneumoniae, Streptococcus dysgalactiae\|Klebsiella pneumoniae, Streptococcus equinus\|Klebsiella pneumoniae, Streptococcus gordonii\|Klebsiella pneumoniae, Streptococcus infantarius\|Klebsiella pneumoniae, Streptococcus infantis\|Klebsiella pneumoniae, Streptococcus mitis\|Klebsiella pneumoniae, Streptococcus mutans\|Klebsiella pneumoniae, Streptococcus oralis\|Klebsiella pneumoniae, Streptococcus parasanguinis\|Klebsiella pneumoniae, Streptococcus peroris\|Klebsiella pneumoniae, Streptococcus pneumoniae\|Klebsiella pneumoniae, Streptococcus salivarius\|Klebsiella pneumoniae, Streptococcus sanguinis\|Klebsiella pneumoniae, Streptococcus thermophilus\|Klebsiella pneumoniae, Streptococcus vestibularis\|Klebsiella pneumoniae, Subdoligranulum variabile\|Klebsiella pneumoniae, Succinatimonas hippei\|Klebsiella pneumoniae, Sutterella wadsworthensis\|Klebsiella pneumoniae, Tropheryma whipplei\|Klebsiella pneumoniae, Veillonella atypica\|Klebsiella pneumoniae, Veillonella dispar\|Klebsiella pneumoniae, Veillonella parvula\|Klebsiella pneumoniae, Victivallis vadensis\|Klebsiella variicola, Klebsiella variicola\|Klebsiella variicola, Lachnospiraceae bacterium 5_1_57FAA\|Klebsiella variicola, Lactobacillus acidophilus\|Klebsiella variicola, Lactobacillus amylovorus\|Klebsiella variicola, Lactobacillus brevis\|Klebsiella variicola, Lactobacillus casei\|Klebsiella variicola, Lactobacillus crispatus\|Klebsiella variicola, Lactobacillus delbrueckii\|Klebsiella variicola, Lactobacillus fermentum\|Klebsiella variicola, Lactobacillus gasseri\|Klebsiella variicola, Lactobacillus iners\|Klebsiella variicola, Lactobacillus jensenii\|Klebsiella variicola, Lactobacillus johnsonii\|Klebsiella variicola, Lactobacillus paracasei\|Klebsiella variicola, Lactobacillus plantarum\|Klebsiella variicola, Lactobacillus reuteri\|Klebsiella variicola, Lactobacillus rhamnosus\|Klebsiella variicola, Lactobacillus ruminis\|Klebsiella variicola, Lactobacillus sakei\|Klebsiella variicola, Lactobacillus salivarius\|Klebsiella variicola, Lactococcus lactis\|Klebsiella variicola, Lautropia mirabilis\|Klebsiella variicola, Leuconostoc citreum\|Klebsiella variicola, Leuconostoc gasicomitatum\|Klebsiella variicola, Leuconostoc mesenteroides\|Klebsiella variicola, Listeria monocytogenes\|Klebsiella variicola, Marvinbryantia formatexigens\|Klebsiella variicola, Megamonas hypermegale\|Klebsiella variicola, Megasphaera micronuciformis\|Klebsiella variicola, Methanobrevibacter smithii\|Klebsiella variicola, Methanosphaera stadtmanae\|Klebsiella variicola, Methylobacterium radiotolerans\|Pebsiella variicola, Mitsuokella multacida\|Klebsiella variicola, Mobiluncus curtisii\|Klebsiella variicola, Mycoplasma hominis\|Klebsiella variicola, Neisseria mucosa\|Klebsiella variicola, Odoribacter splanchnicus\|Klebsiella variicola, Olsenella uli\|Klebsiella variicola, Oribacterium sinus\|Klebsiella variicola, Oxalobacter formigenes\|Klebsiella variicola, Parabacteroides distasonis\|Klebsiella variicola, Parabacteroides johnsonii\|Klebsiella variicola, Parabacteroides merdae\|Klebsiella variicola, Parvimonas micra\|Klebsiella variicola, Pediococcus acidilactici\|Klebsiella variicola, Pediococcus pentosaceus\|Klebsiella variicola, Peptoniphilus duerdenii\|Klebsiella variicola, Peptoniphilus harei\|Klebsiella variicola, Peptoniphilus lacrimalis\|Klebsiella variicola, Peptostreptococcus anaerobius\|Klebsiella variicola, Peptostreptococcus stomatis\|Klebsiella variicola, Porphyromonas asaccharolytica\|Klebsiella variicola, Porphyromonas uenonis\|Klebsiella variicola, Prevotella amnii\|Klebsiella variicola, Prevotella bergensis\|Klebsiella variicola, Prevotella bivia\|Klebsiella variicola, Prevotella buccae\|Klebsiella variicola, Prevotella buccalis\|Klebsiella variicola, Prevotella copri\|Klebsiella variicola, Prevotella disiens\|Klebsiella variicola, Prevotella melaninogenica\|Klebsiella variicola, Prevotella multiformis\|Klebsiella variicola, Prevotella oralis\|Klebsiella variicola, Prevotella oris\|Klebsiella variicola, Prevotella salivae\|Klebsiella variicola, Prevotella timonensis\|Klebsiella variicola, Propionibacterium acnes\|Klebsiella variicola, Propionibacterium freudenreichii\|Klebsiella variicola, Proteus mirabilis\|Klebsiella variicola, Proteus penneri\|Klebsiella variicola, Pseudoflavonifractor capillosus\|Klebsiella variicola, Pseudomonas aeruginosa\|Klebsiella variicola, Pseudomonas fluorescens\|Klebsiella variicola, Pseudomonas putida\|Klebsiella variicola, Pseudoramibacter alactolyticus\|Klebsiella variicola, Pyramidobacter piscolens\|Klebsiella variicola, Rhodopseudomonas palustris\|Klebsiella variicola, Roseburia intestinalis\|Klebsiella variicola, Roseburia inulinivorans\|Klebsiella variicola, Rothia dentocariosa\|Klebsiella variicola, Rothia mucilaginosa\|Klebsiella variicola, Ruminococcus albus\|Klebsiella variicola, Ruminococcus bromii\|Klebsiella variicola, Ruminococcus gnavus\|Klebsiella variicola, Ruminococcus lactaris\|Klebsiella variicola, Ruminococcus obeum\|Klebsiella variicola, Ruminococcus torques\|Klebsiella variicola, Selenomonas sputigena\|Klebsiella variicola, Shigella boydii\|Klebsiella variicola, Shigella dysenteriae\|Klebsiella variicola, Shigella sonnei\|Klebsiella variicola, Slackia exigua\|Klebsiella variicola, Solobacterium moorei\|Klebsiella variicola, Staphylococcus aureus\|Klebsiella variicola, Staphylococcus epidermidis\|Klebsiella variicola, Staphylococcus hominis\|Klebsiella variicola, Staphylococcus saprophyticus\|Klebsiella variicola, Staphylococcus warneri\|Klebsiella variicola, Streptococcus agalactiae\|Klebsiella variicola, Streptococcus anginosus\|Klebsiella variicola, Streptococcus australis\|Klebsiella variicola, Streptococcus bovis\|Klebsiella variicola, Streptococcus cristatus\|Klebsiella variicola, Streptococcus dysgalactiae\|Klebsiella variicola, Streptococcus equinus\|Klebsiella variicola, Streptococcus gordonii\|Klebsiella variicola, Streptococcus infantarius\|Klebsiella variicola, Streptococcus infantis\|Klebsiella variicola, Streptococcus mitis\|Klebsiella variicola, Streptococcus mutans\|Klebsiella variicola, Streptococcus oralis\|Klebsiella variicola, Streptococcus parasanguinis\|Klebsiella variicola, Streptococcus peroris\|Klebsiella* |

TABLE 2-continued

Table 2. Specific binary combinations of OTUs. Individual pairings are differentiated by "|" and OTUs within a combination are differentiated by ","

variicola, Streptococcus pneumoniae|Klebsiella variicola, Streptococcus salivarius|Klebsiella variicola, Streptococcus sanguinis|Klebsiella variicola, Streptococcus thermophilus|Klebsiella variicola, Streptococcus vestibularis|Klebsiella variicola, Subdoligranulum variabile|Klebsiella variicola, Succinatimonas hippei|Klebsiella variicola, Sutterella wadsworthensis|Klebsiella variicola, Tropheryma whipplei|Klebsiella variicola, Veillonella atypica|Klebsiella variicola, Veillonella dispar|Klebsiella variicola, Veillonella parvula|Klebsiella variicola, Victivallis vadensis|Lachnospiraceae bacterium 5_1_57FAA, Lachnospiraceae bacterium 5_1_57FAA|Lachnospiraceae bacterium 5_1_57FAA, Lactobacillus acidophilus|Lachnospiraceae bacterium 5_1_57FAA, Lactobacillus amylovorus|Lachnospiraceae bacterium 5_1_57FAA, Lactobacillus brevis|Lachnospiraceae bacterium 5_1_57FAA, Lactobacillus casei|Lachnospiraceae bacterium 5_1_57FAA, Lactobacillus crispatus|Lachnospiraceae bacterium 5_1_57FAA, Lactobacillus delbrueckii|Lachnospiraceae bacterium 5_1_57FAA, Lactobacillus fermentum|Lachnospiraceae bacterium 5_1_57FAA, Lactobacillus gasseri|Lachnospiraceae bacterium 5_1_57FAA, Lactobacillus iners|Lachnospiraceae bacterium 5_1_57FAA, Lactobacillus jensenii|Lachnospiraceae bacterium 5_1_57FAA, Lactobacillus johnsonii|Lachnospiraceae bacterium 5_1_57FAA, Lactobacillus paracasei|Lachnospiraceae bacterium 5_1_57FAA, Lactobacillus plantarum|Lachnospiraceae bacterium 5_1_57FAA, Lactobacillus reuteri|Lachnospiraceae bacterium 5_1_57FAA, Lactobacillus rhamnosus|Lachnospiraceae bacterium 5_1_57FAA, Lactobacillus ruminis|Lachnospiraceae bacterium 5_1_57FAA, Lactobacillus sakei|Lachnospiraceae bacterium 5_1_57FAA, Lactobacillus salivarius|Lachnospiraceae bacterium 5_1_57FAA, Lactococcus lactis|Lachnospiraceae bacterium 5_1_57FAA, Lautropia mirabilis|Lachnospiraceae bacterium 5_1_57FAA, Leuconostoc citreum|Lachnospiraceae bacterium 5_1_57FAA, Leuconostoc gasicomitatum|Lachnospiraceae bacterium 5_1_57FAA, Leuconostoc mesenteroides|Lachnospiraceae bacterium 5_1_57FAA, Listeria monocytogenes|Lachnospiraceae bacterium 5_1_57FAA, Marvinbryantia formatexigens|Lachnospiraceae bacterium 5_1_57FAA, Megamonas hypermegale|Lachnospiraceae bacterium 5_1_57FAA, Megasphaera micronuciformis|Lachnospiraceae bacterium 5_1_57FAA, Methanobrevibacter smithii|Lachnospiraceae bacterium 5_1_57FAA, Methanosphaera stadtmanae|Lachnospiraceae bacterium 5_1_57FAA, Methylobacterium radiotolerans|Lachnospiraceae bacterium 5_1_57FAA, Mitsuokella multacida|Lachnospiraceae bacterium 5_1_57FAA, Mobiluncus curtisii|Lachnospiraceae bacterium 5_1_57FAA, Mycoplasma hominis|Lachnospiraceae bacterium 5_1_57FAA, Neisseria mucosa|Lachnospiraceae bacterium 5_1_57FAA, Odoribacter splanchnicus|Lachnospiraceae bacterium 5_1_57FAA, Olsenella uli|Lachnospiraceae bacterium 5_1_57FAA, Oribacterium sinus|Lachnospiraceae bacterium 5_1_57FAA, Oxalobacter formigenes|Lachnospiraceae bacterium 5_1_57FAA, Parabacteroides distasonis|Lachnospiraceae bacterium 5_1_57FAA, Parabacteroides johnsonii|Lachnospiraceae bacterium 5_1_57FAA, Parabacteroides merdae|Lachnospiraceae bacterium 5_1_57FAA, Parvimonas micra|Lachnospiraceae bacterium 5_1_57FAA, Pediococcus acidilactici|Lachnospiraceae bacterium 5_1_57FAA, Pediococcus pentosaceus|Lachnospiraceae bacterium 5_1_57FAA, Peptoniphilus duerdenii|Lachnospiraceae bacterium 5_1_57FAA, Peptoniphilus harei|Lachnospiraceae bacterium 5_1_57FAA, Peptoniphilus lacrimalis|Lachnospiraceae bacterium 5_1_57FAA, Peptostreptococcus anaerobius|Lachnospiraceae bacterium 5_1_57FAA, Peptostreptococcus stomatis|Lachnospiraceae bacterium 5_1_57FAA, Porphyromonas asaccharolytica|Lachnospiraceae bacterium 5_1_57FAA, Porphyromonas uenonis|Lachnospiraceae bacterium 5_1_57FAA, Prevotella amnii|Lachnospiraceae bacterium 5_1_57FAA, Prevotella bergensis|Lachnospiraceae bacterium 5_1_57FAA, Prevotella bivia|Lachnospiraceae bacterium 5_1_57FAA, Prevotella buccae|Lachnospiraceae bacterium 5_1_57FAA, Prevotella buccalis|Lachnospiraceae bacterium 5_1_57FAA, Prevotella copri|Lachnospiraceae bacterium 5_1_57FAA, Prevotella disiens|Lachnospiraceae bacterium 5_1_57FAA, Prevotella melaninogenica|Lachnospiraceae bacterium 5_1_57FAA, Prevotella multiformis|Lachnospiraceae bacterium 5_1_57FAA, Prevotella oralis|Lachnospiraceae bacterium 5_1_57FAA, Prevotella oris|Lachnospiraceae bacterium 5_1_57FAA, Prevotella salivae|Lachnospiraceae bacterium 5_1_57FAA, Prevotella timonensis|Lachnospiraceae bacterium 5_1_57FAA, Propionibacterium acnes|Lachnospiraceae bacterium 5_1_57FAA, Propionibacterium freudenreichii|Lachnospiraceae bacterium 5_1_57FAA, Proteus mirabilis|Lachnospiraceae bacterium 5_1_57FAA, Proteus penneri|Lachnospiraceae bacterium 5_1_57FAA, Pseudoflavonifractor capillosus|Lachnospiraceae bacterium 5_1_57FAA, Pseudomonas aeruginosa|Lachnospiraceae bacterium 5_1_57FAA, Pseudomonas fluorescens|Lachnospiraceae bacterium 5_1_57FAA, Pseudomonas putida|Lachnospiraceae bacterium 5_1_57FAA, Pseudoramibacter alactolyticus|Lachnospiraceae bacterium 5_1_57FAA, Pyramidobacter piscolens|Lachnospiraceae bacterium 5_1_57FAA, Rhodopseudomonas palustris|Lachnospiraceae bacterium 5_1_57FAA, Roseburia intestinalis|Lachnospiraceae bacterium 5_1_57FAA, Roseburia inulinivorans|Lachnospiraceae bacterium 5_1_57FAA, Rothia dentocariosa|Lachnospiraceae bacterium 5_1_57FAA, Rothia mucilaginosa|Lachnospiraceae bacterium 5_1_57FAA, Ruminococcus albus|Lachnospiraceae bacterium 5_1_57FAA, Ruminococcus bromii|Lachnospiraceae bacterium 5_1_57FAA, Ruminococcus gnavus|Lachnospiraceae bacterium 5_1_57FAA, Ruminococcus lactaris|Lachnospiraceae bacterium 5_1_57FAA, Ruminococcus obeum|Lachnospiraceae bacterium 5_1_57FAA, Ruminococcus torques|Lachnospiraceae bacterium 5_1_57FAA, Selenomonas sputigena|Lachnospiraceae bacterium 5_1_57FAA, Shigella boydii|Lachnospiraceae bacterium 5_1_57FAA, Shigella dysenteriae|Lachnospiraceae bacterium 5_1_57FAA, Shigella sonnei|Lachnospiraceae bacterium 5_1_57FAA, Slackia exigua|Lachnospiraceae bacterium 5_1_57FAA, Solobacterium moorei|Lachnospiraceae bacterium 5_1_57FAA, Staphylococcus aureus|Lachnospiraceae bacterium 5_1_57FAA, Staphylococcus epidermidis|Lachnospiraceae bacterium 5_1_57FAA, Staphylococcus hominis|Lachnospiraceae bacterium 5_1_57FAA, Staphylococcus saprophyticus|Lachnospiraceae bacterium 5_1_57FAA, Staphylococcus warneri|Lachnospiraceae bacterium 5_1_57FAA, Streptococcus agalactiae|Lachnospiraceae bacterium 5_1_57FAA, Streptococcus anginosus|Lachnospiraceae bacterium 5_1_57FAA, Streptococcus australis|Lachnospiraceae bacterium 5_1_57FAA, Streptococcus bovis|Lachnospiraceae bacterium 5_1_57FAA, Streptococcus cristatus|Lachnospiraceae bacterium 5_1_57FAA, Streptococcus dysgalactiae|Lachnospiraceae bacterium 5_1_57FAA, Streptococcus equinus|Lachnospiraceae bacterium 5_1_57FAA, Streptococcus gordonii|Lachnospiraceae bacterium 5_1_57FAA, Streptococcus infantarius|Lachnospiraceae bacterium 5_1_57FAA, Streptococcus infantis|Lachnospiraceae bacterium 5_1_57FAA, Streptococcus mitis|Lachnospiraceae bacterium 5_1_57FAA, Streptococcus mutans|Lachnospiraceae bacterium 5_1_57FAA, Streptococcus oralis|Lachnospiraceae bacterium 5_1_57FAA, Streptococcus parasanguinis|Lachnospiraceae bacterium 5_1_57FAA, Streptococcus peroris|Lachnospiraceae bacterium 5_1_57FAA, Streptococcus pneumoniae|Lachnospiraceae bacterium 5_1_57FAA, Streptococcus salivarius|Lachnospiraceae bacterium 5_1_57FAA, Streptococcus sanguinis|Lachnospiraceae bacterium 5_1_57FAA, Streptococcus thermophilus|Lachnospiraceae bacterium 5_1_57FAA, Streptococcus vestibularis|Lachnospiraceae bacterium 5_1_57FAA, Subdoligranulum variabile|Lachnospiraceae bacterium 5_1_57FAA, Succinatimonas hippei|Lachnospiraceae bacterium 5_1_57FAA, Sutterella wadsworthensis|Lachnospiraceae bacterium 5_1_57FAA, Tropheryma whipplei|Lachnospiraceae bacterium 5_1_57FAA, Veillonella atypica|Lachnospiraceae bacterium 5_1_57FAA, Veillonella dispar|Lachnospiraceae bacterium 5_1_57FAA, Veillonella parvula|Lachnospiraceae bacterium 5_1_57FAA, Victivallis vadensis|Lactobacillus acidophilus, Lactobacillus acidophilus|Lactobacillus acidophilus, Lactobacillus amylovorus|Lactobacillus acidophilus, Lactobacillus brevis|Lactobacillus acidophilus, Lactobacillus casei|Lactobacillus acidophilus, Lactobacillus crispatus|Lactobacillus acidophilus, Lactobacillus delbrueckii|Lactobacillus acidophilus, Lactobacillus fermentum|Lactobacillus acidophilus, Lactobacillus gasseri|Lactobacillus acidophilus, Lactobacillus iners|Lactobacillus acidophilus, Lactobacillus jensenii|Lactobacillus acidophilus, Lactobacillus johnsonii|Lactobacillus acidophilus, Lactobacillus paracasei|Lactobacillus acidophilus, Lactobacillus plantarum|Lactobacillus acidophilus, Lactobacillus reuteri|Lactobacillus acidophilus, Lactobacillus rhamnosus|Lactobacillus acidophilus, Lactobacillus ruminis|Lactobacillus acidophilus, Lactobacillus sakei|Lactobacillus acidophilus, Lactobacillus salivarius|Lactobacillus acidophilus, Lactococcus lactis|Lactobacillus acidophilus, Lautropia mirabilis|Lactobacillus acidophilus, Leuconostoc citreum|Lactobacillus acidophilus, Leuconostoc gasicomitatum|Lactobacillus acidophilus, Leuconostoc mesenteroides|Lactobacillus acidophilus, Listeria monocytogenes|Lactobacillus acidophilus, Marvinbryantia formatexigens|Lactobacillus acidophilus, Megamonas hypermegale|Lactobacillus acidophilus, Megasphaera micronuciformis|Lactobacillus acidophilus, Methanobrevibacter smithii|Lactobacillus TABLE 2-continued

| Table 2. Specific binary combinations of OTUs. Individual pairings are differentiated by "\|" and OTUs within a combination are differentiated by "," |
|---|
| *acidophilus, Methanosphaera stadtmanae\|Lactobacillus acidophilus, Methylobacterium radiotolerans\|Lactobacillus acidophilus, Mitsuokella multacida\|Lactobacillus acidophilus, Mobiluncus curtisii\|Lactobacillus acidophilus, Mycoplasma hominis\|Lactobacillus acidophilus, Neisseria mucosa\|Lactobacillus acidophilus, Odoribacter splanchnicus\|Lactobacillus acidophilus, Olsenella uli\|Lactobacillus acidophilus, Oribacterium sinus\|Lactobacillus acidophilus, Oxalobacter formigenes\|Lactobacillus acidophilus, Parabacteroides distasonis\|Lactobacillus acidophilus, Parabacteroides johnsonii\|Lactobacillus acidophilus, Parabacteroides merdae\|Lactobacillus acidophilus, Parvimonas micra\|Lactobacillus acidophilus, Pediococcus acidilactici\|Lactobacillus acidophilus, Pediococcus pentosaceus\|Lactobacillus acidophilus, Peptoniphilus duerdenii\|Lactobacillus acidophilus, Peptoniphilus harei\|Lactobacillus acidophilus, Peptoniphilus lacrimalis\|Lactobacillus acidophilus, Peptostreptococcus anaerobius\|Lactobacillus acidophilus, Peptostreptococcus stomatis\|Lactobacillus acidophilus, Porphyromonas asaccharolytica\|Lactobacillus acidophilus, Porphyromonas uenonis\|Lactobacillus acidophilus, Prevotella amnii\|Lactobacillus acidophilus, Prevotella bergensis\|Lactobacillus acidophilus, Prevotella bivia\|Lactobacillus acidophilus, Prevotella buccae\|Lactobacillus acidophilus, Prevotella buccalis\|Lactobacillus acidophilus, Prevotella copri\|Lactobacillus acidophilus, Prevotella disiens\|Lactobacillus acidophilus, Prevotella melaninogenica\|Lactobacillus acidophilus, Prevotella multiformis\|Lactobacillus acidophilus, Prevotella oralis\|Lactobacillus acidophilus, Prevotella oris\|Lactobacillus acidophilus, Prevotella salivae\|Lactobacillus acidophilus, Prevotella timonensis\|Lactobacillus acidophilus, Propionibacterium acnes\|Lactobacillus acidophilus, Propionibacterium freudenreichii\|Lactobacillus acidophilus, Proteus mirabilis\|Lactobacillus acidophilus, Proteus penneri\|Lactobacillus acidophilus, Pseudoflavonifractor capillosus\|Lactobacillus acidophilus, Pseudomonas aeruginosa\|Lactobacillus acidophilus, Pseudomonas fluorescens\|Lactobacillus acidophilus, Pseudomonas putida\|Lactobacillus acidophilus, Pseudoramibacter alactolyticus\|Lactobacillus acidophilus, Pyramidobacter piscolens\|Lactobacillus acidophilus, Rhodopseudomonas palustris\|Lactobacillus acidophilus, Roseburia intestinalis\|Lactobacillus acidophilus, Roseburia inulinivorans\|Lactobacillus acidophilus, Rothia dentocariosa\|Lactobacillus acidophilus, Rothia mucilaginosa\|Lactobacillus acidophilus, Ruminococcus albus\|Lactobacillus acidophilus, Ruminococcus bromii\|Lactobacillus acidophilus, Ruminococcus gnavus\|Lactobacillus acidophilus, Ruminococcus lactaris\|Lactobacillus acidophilus, Ruminococcus obeum\|Lactobacillus acidophilus, Ruminococcus torques\|Lactobacillus acidophilus, Selenomonas sputigena\|Lactobacillus acidophilus, Shigella boydii\|Lactobacillus acidophilus, Shigella dysenteriae\|Lactobacillus acidophilus, Shigella sonnei\|Lactobacillus acidophilus, Slackia exigua\|Lactobacillus acidophilus, Solobacterium moorei\|Lactobacillus acidophilus, Staphylococcus aureus\|Lactobacillus acidophilus, Staphylococcus epidermidis\|Lactobacillus acidophilus, Staphylococcus hominis\|Lactobacillus acidophilus, Staphylococcus saprophyticus\|Lactobacillus acidophilus, Staphylococcus warneri\|Lactobacillus acidophilus, Streptococcus agalactiae\|Lactobacillus acidophilus, Streptococcus anginosus\|Lactobacillus acidophilus, Streptococcus australis\|Lactobacillus acidophilus, Streptococcus bovis\|Lactobacillus acidophilus, Streptococcus cristatus\|Lactobacillus acidophilus, Streptococcus dysgalactiae\|Lactobacillus acidophilus, Streptococcus equinus\|Lactobacillus acidophilus, Streptococcus gordonii\|Lactobacillus acidophilus, Streptococcus infantarius\|Lactobacillus acidophilus, Streptococcus infantis\|Lactobacillus acidophilus, Streptococcus mitis\|Lactobacillus acidophilus, Streptococcus mutans\|Lactobacillus acidophilus, Streptococcus oralis\|Lactobacillus acidophilus, Streptococcus parasanguinis\|Lactobacillus acidophilus, Streptococcus peroris\|Lactobacillus acidophilus, Streptococcus pneumoniae\|Lactobacillus acidophilus, Streptococcus salivarius\|Lactobacillus acidophilus, Streptococcus sanguinis\|Lactobacillus acidophilus, Streptococcus thermophilus\|Lactobacillus acidophilus, Streptococcus vestibularis\|Lactobacillus acidophilus, Subdoligranulum variabile\|Lactobacillus acidophilus, Succinatimonas hippei\|Lactobacillus acidophilus, Sutterella wadsworthensis\|Lactobacillus acidophilus, Tropheryma whipplei\|Lactobacillus acidophilus, Veillonella atypica\|Lactobacillus acidophilus, Veillonella dispar\|Lactobacillus acidophilus, Veillonella parvula\|Lactobacillus acidophilus, Victivallis vadensis\|Lactobacillus amylovorus, Lactobacillus amylovorus\|Lactobacillus amylovorus, Lactobacillus brevis\|Lactobacillus amylovorus, Lactobacillus casei\|Lactobacillus amylovorus, Lactobacillus crispatus\|Lactobacillus amylovorus, Lactobacillus delbrueckii\|Lactobacillus amylovorus, Lactobacillus fermentum\|Lactobacillus amylovorus, Lactobacillus gasseri\|Lactobacillus amylovorus, Lactobacillus iners\|Lactobacillus amylovorus, Lactobacillus jensenii\|Lactobacillus amylovorus, Lactobacillus johnsonii\|Lactobacillus amylovorus, Lactobacillus paracasei\|Lactobacillus amylovorus, Lactobacillus plantarum\|Lactobacillus amylovorus, Lactobacillus reuteri\|Lactobacillus amylovorus, Lactobacillus rhamnosus\|Lactobacillus amylovorus, Lactobacillus ruminis\|Lactobacillus amylovorus, Lactobacillus sakei\|Lactobacillus amylovorus, Lactobacillus salivarius\|Lactobacillus amylovorus, Lactococcus lactis\|Lactobacillus amylovorus, Lautropia mirabilis\|Lactobacillus amylovorus, Leuconostoc citreum\|Lactobacillus amylovorus, Leuconostoc gasicomitatum\|Lactobacillus amylovorus, Leuconostoc mesenteroides\|Lactobacillus amylovorus, Listeria monocytogenes\|Lactobacillus amylovorus, Marvinbryantia formatexigens\|Lactobacillus amylovorus, Megamonas hypermegale\|Lactobacillus amylovorus, Megasphaera micronuciformis\|Lactobacillus amylovorus, Methanobrevibacter smithii\|Lactobacillus amylovorus, Methanosphaera stadtmanae\|Lactobacillus amylovorus, Methylobacterium radiotolerans\|Lactobacillus amylovorus, Mitsuokella multacida\|Lactobacillus amylovorus, Mobiluncus curtisii\|Lactobacillus amylovorus, Mycoplasma hominis\|Lactobacillus amylovorus, Neisseria mucosa\|Lactobacillus amylovorus, Odoribacter splanchnicus\|Lactobacillus amylovorus, Olsenella uli\|Lactobacillus amylovorus, Oribacterium sinus\|Lactobacillus amylovorus, Oxalobacter formigenes\|Lactobacillus amylovorus, Parabacteroides distasonis\|Lactobacillus amylovorus, Parabacteroides johnsonii\|Lactobacillus amylovorus, Parabacteroides merdae\|Lactobacillus amylovorus, Parvimonas micra\|Lactobacillus amylovorus, Pediococcus acidilactici\|Lactobacillus amylovorus, Pediococcus pentosaceus\|Lactobacillus amylovorus, Peptoniphilus duerdenii\|Lactobacillus amylovorus, Peptoniphilus harei\|Lactobacillus amylovorus, Peptoniphilus lacrimalis\|Lactobacillus amylovorus, Peptostreptococcus anaerobius\|Lactobacillus amylovorus, Peptostreptococcus stomatis\|Lactobacillus amylovorus, Porphyromonas asaccharolytica\|Lactobacillus amylovorus, Porphyromonas uenonis\|Lactobacillus amylovorus, Prevotella amnii\|Lactobacillus amylovorus, Prevotella bergensis\|Lactobacillus amylovorus, Prevotella bivia\|Lactobacillus amylovorus, Prevotella buccae\|Lactobacillus amylovorus, Prevotella buccalis\|Lactobacillus amylovorus, Prevotella copri\|Lactobacillus amylovorus, Prevotella disiens\|Lactobacillus amylovorus, Prevotella melaninogenica\|Lactobacillus amylovorus, Prevotella multiformis\|Lactobacillus amylovorus, Prevotella oralis\|Lactobacillus amylovorus, Prevotella oris\|Lactobacillus amylovorus, Prevotella salivae\|Lactobacillus amylovorus, Prevotella timonensis\|Lactobacillus amylovorus, Propionibacterium acnes\|Lactobacillus amylovorus, Propionibacterium freudenreichii\|Lactobacillus amylovorus, Proteus mirabilis\|Lactobacillus amylovorus, Proteus penneri\|Lactobacillus amylovorus, Pseudoflavonifractor capillosus\|Lactobacillus amylovorus, Pseudomonas aeruginosa\|Lactobacillus amylovorus, Pseudomonas fluorescens\|Lactobacillus amylovorus, Pseudomonas putida\|Lactobacillus amylovorus, Pseudoramibacter alactolyticus\|Lactobacillus amylovorus, Pyramidobacter piscolens\|Lactobacillus amylovorus, Rhodopseudomonas palustris\|Lactobacillus amylovorus, Roseburia intestinalis\|Lactobacillus amylovorus, Roseburia inulinivorans\|Lactobacillus amylovorus, Rothia dentocariosa\|Lactobacillus amylovorus, Rothia mucilaginosa\|Lactobacillus amylovorus, Ruminococcus albus\|Lactobacillus amylovorus, Ruminococcus bromii\|Lactobacillus amylovorus, Ruminococcus gnavus\|Lactobacillus amylovorus, Ruminococcus lactaris\|Lactobacillus amylovorus, Ruminococcus obeum\|Lactobacillus amylovorus, Ruminococcus torques\|Lactobacillus amylovorus, Selenomonas sputigena\|Lactobacillus amylovorus, Shigella boydii\|Lactobacillus amylovorus, Shigella dysenteriae\|Lactobacillus amylovorus, Shigella sonnei\|Lactobacillus amylovorus, Slackia exigua\|Lactobacillus amylovorus, Solobacterium moorei\|Lactobacillus amylovorus, Staphylococcus aureus\|Lactobacillus amylovorus, Staphylococcus epidermidis\|Lactobacillus amylovorus, Staphylococcus hominis\|Lactobacillus amylovorus, Staphylococcus saprophyticus\|Lactobacillus amylovorus, Staphylococcus warneri\|Lactobacillus amylovorus, Streptococcus agalactiae\|Lactobacillus amylovorus, Streptococcus anginosus\|Lactobacillus amylovorus, Streptococcus australis\|Lactobacillus amylovorus, Streptococcus bovis\|Lactobacillus amylovorus, Streptococcus cristatus\|Lactobacillus amylovorus, Streptococcus dysgalactiae\|Lactobacillus amylovorus, Streptococcus equinus\|Lactobacillus amylovorus, Streptococcus gordonii\|Lactobacillus amylovorus, Streptococcus infantarius\|Lactobacillus amylovorus, Streptococcus infantis\|Lactobacillus amylovorus, Streptococcus mitis\|Lactobacillus amylovorus, Streptococcus mutans\|Lactobacillus amylovorus, Streptococcus oralis\|Lactobacillus amylovorus, Streptococcus* |

TABLE 2-continued

| Table 2. Specific binary combinations of OTUs. Individual pairings are differentiated by "\|" and OTUs within a combination are differentiated by "," |
|---|
| *parasanguinis\|Lactobacillus amylovorus, Streptococcus peroris\|Lactobacillus amylovorus, Streptococcus pneumoniae\|Lactobacillus amylovorus, Streptococcus salivarius\|Lactobacillus amylovorus, Streptococcus sanguinis\|Lactobacillus amylovorus, Streptococcus thermophilus\|Lactobacillus amylovorus, Streptococcus vestibularis\|Lactobacillus amylovorus, Subdoligranulum variabile\|Lactobacillus amylovorus, Succinatimonas hippei\|Lactobacillus amylovorus, Sutterella wadsworthensis\|Lactobacillus amylovorus, Tropheryma whipplei\|Lactobacillus amylovorus, Veillonella atypica\|Lactobacillus amylovorus, Veillonella dispar\|Lactobacillus amylovorus, Veillonella parvula\|Lactobacillus amylovorus, Victivallis vadensis\|Lactobacillus brevis, Lactobacillus brevis\|Lactobacillus brevis, Lactobacillus casei\|Lactobacillus brevis, Lactobacillus crispatus\|Lactobacillus brevis, Lactobacillus delbrueckii\|Lactobacillus brevis, Lactobacillus fermentum\|Lactobacillus brevis, Lactobacillus gasseri\|Lactobacillus brevis, Lactobacillus iners\|Lactobacillus brevis, Lactobacillus jensenii\|Lactobacillus brevis, Lactobacillus johnsonii\|Lactobacillus brevis, Lactobacillus paracasei\|Lactobacillus brevis, Lactobacillus plantarum\|Lactobacillus brevis, Lactobacillus reuteri\|Lactobacillus brevis, Lactobacillus rhamnosus\|Lactobacillus brevis, Lactobacillus ruminis\|Lactobacillus brevis, Lactobacillus sakei\|Lactobacillus brevis, Lactobacillus salivarius\|Lactobacillus brevis, Lactococcus lactis\|Lactobacillus brevis, Lautropia mirabilis\|Lactobacillus brevis, Leuconostoc citreum\|Lactobacillus brevis, Leuconostoc gasicomitatum\|Lactobacillus brevis, Leuconostoc mesenteroides\|Lactobacillus brevis, Listeria monocytogenes\|Lactobacillus brevis, Marvinbryantia formatexigens\|Lactobacillus brevis, Megamonas hypermegale\|Lactobacillus brevis, Megasphaera micronuciformis\|Lactobacillus brevis, Methanobrevibacter smithii\|Lactobacillus brevis, Methanosphaera stadtmanae\|Lactobacillus brevis, Methylobacterium radiotolerans\|Lactobacillus brevis, Mitsuokella multacida\|Lactobacillus brevis, Mobiluncus curtisii\|Lactobacillus brevis, Mycoplasma hominis\|Lactobacillus brevis, Neisseria mucosa\|Lactobacillus brevis, Odoribacter splanchnicus\|Lactobacillus brevis, Olsenella uli\|Lactobacillus brevis, Oribacterium sinus\|Lactobacillus brevis, Oxalobacter formigenes\|Lactobacillus brevis, Parabacteroides distasonis\|Lactobacillus brevis, Parabacteroides johnsonii\|Lactobacillus brevis, Parabacteroides merdae\|Lactobacillus brevis, Parvimonas micra\|Lactobacillus brevis, Pediococcus acidilactici\|Lactobacillus brevis, Pediococcus pentosaceus\|Lactobacillus brevis, Peptoniphilus duerdenii\|Lactobacillus brevis, Peptoniphilus harei\|Lactobacillus brevis, Peptoniphilus lacrimalis\|Lactobacillus brevis, Peptostreptococcus anaerobius\|Lactobacillus brevis, Peptostreptococcus stomatis\|Lactobacillus brevis, Porphyromonas asaccharolytica\|Lactobacillus brevis, Porphyromonas uenonis\|Lactobacillus brevis, Prevotella amnii\|Lactobacillus brevis, Prevotella bergensis\|Lactobacillus brevis, Prevotella bivia\|Lactobacillus brevis, Prevotella buccae\|Lactobacillus brevis, Prevotella buccalis\|Lactobacillus brevis, Prevotella copri\|Lactobacillus brevis, Prevotella disiens\|Lactobacillus brevis, Prevotella melaninogenica\|Lactobacillus brevis, Prevotella multiformis\|Lactobacillus brevis, Prevotella oralis\|Lactobacillus brevis, Prevotella oris\|Lactobacillus brevis, Prevotella salivae\|Lactobacillus brevis, Prevotella timonensis\|Lactobacillus brevis, Propionibacterium acnes\|Lactobacillus brevis, Propionibacterium freudenreichii\|Lactobacillus brevis, Proteus mirabilis\|Lactobacillus brevis, Proteus penneri\|Lactobacillus brevis, Pseudoflavonifractor capillosus\|Lactobacillus brevis, Pseudomonas aeruginosa\|Lactobacillus brevis, Pseudomonas fluorescens\|Lactobacillus brevis, Pseudomonas putida\|Lactobacillus brevis, Pseudoramibacter alactolyticus\|Lactobacillus brevis, Pyramidobacter piscolens\|Lactobacillus brevis, Rhodopseudomonas palustris\|Lactobacillus brevis, Roseburia intestinalis\|Lactobacillus brevis, Roseburia inulinivorans\|Lactobacillus brevis, Rothia dentocariosa\|Lactobacillus brevis, Rothia mucilaginosa\|Lactobacillus brevis, Ruminococcus albus\|Lactobacillus brevis, Ruminococcus bromii\|Lactobacillus brevis, Ruminococcus gnavus\|Lactobacillus brevis, Ruminococcus lactaris\|Lactobacillus brevis, Ruminococcus obeum\|Lactobacillus brevis, Ruminococcus torques\|Lactobacillus brevis, Selenomonas sputigena\|Lactobacillus brevis, Shigella boydii\|Lactobacillus brevis, Shigella dysenteriae\|Lactobacillus brevis, Shigella sonnei\|Lactobacillus brevis, Slackia exigua\|Lactobacillus brevis, Solobacterium moorei\|Lactobacillus brevis, Staphylococcus aureus\|Lactobacillus brevis, Staphylococcus epidermidis\|Lactobacillus brevis, Staphylococcus hominis\|Lactobacillus brevis, Staphylococcus saprophyticus\|Lactobacillus brevis, Staphylococcus warneri\|Lactobacillus brevis, Streptococcus agalactiae\|Lactobacillus brevis, Streptococcus anginosus\|Lactobacillus brevis, Streptococcus australis\|Lactobacillus brevis, Streptococcus bovis\|Lactobacillus brevis, Streptococcus cristatus\|Lactobacillus brevis, Streptococcus dysgalactiae\|Lactobacillus brevis, Streptococcus equinus\|Lactobacillus brevis, Streptococcus gordonii\|Lactobacillus brevis, Streptococcus infantarius\|Lactobacillus brevis, Streptococcus infantis\|Lactobacillus brevis, Streptococcus mitis\|Lactobacillus brevis, Streptococcus mutans\|Lactobacillus brevis, Streptococcus oralis\|Lactobacillus brevis, Streptococcus parasanguinis\|Lactobacillus brevis, Streptococcus peroris\|Lactobacillus brevis, Streptococcus pneumoniae\|Lactobacillus brevis, Streptococcus salivarius\|Lactobacillus brevis, Streptococcus sanguinis\|Lactobacillus brevis, Streptococcus thermophilus\|Lactobacillus brevis, Streptococcus vestibularis\|Lactobacillus brevis, Subdoligranulum variabile\|Lactobacillus brevis, Succinatimonas hippei\|Lactobacillus brevis, Sutterella wadsworthensis\|Lactobacillus brevis, Tropheryma whipplei\|Lactobacillus brevis, Veillonella atypica\|Lactobacillus brevis, Veillonella dispar\|Lactobacillus brevis, Veillonella parvula\|Lactobacillus brevis, Victivallis vadensis\|Lactobacillus casei, Lactobacillus casei\|Lactobacillus casei, Lactobacillus crispatus\|Lactobacillus casei, Lactobacillus delbrueckii\|Lactobacillus casei, Lactobacillus fermentum\|Lactobacillus casei, Lactobacillus gasseri\|Lactobacillus casei, Lactobacillus iners\|Lactobacillus casei, Lactobacillus jensenii\|Lactobacillus casei, Lactobacillus johnsonii\|Lactobacillus casei, Lactobacillus paracasei\|Lactobacillus casei, Lactobacillus plantarum\|Lactobacillus casei, Lactobacillus reuteri\|Lactobacillus casei, Lactobacillus rhamnosus\|Lactobacillus casei, Lactobacillus ruminis\|Lactobacillus casei, Lactobacillus sakei\|Lactobacillus casei, Lactobacillus salivarius\|Lactobacillus casei, Lactococcus lactis\|Lactobacillus casei, Lautropia mirabilis\|Lactobacillus casei, Leuconostoc citreum\|Lactobacillus casei, Leuconostoc gasicomitatum\|Lactobacillus casei, Leuconostoc mesenteroides\|Lactobacillus casei, Listeria monocytogenes\|Lactobacillus casei, Marvinbryantia formatexigens\|Lactobacillus casei, Megamonas hypermegale\|Lactobacillus casei, Megasphaera micronuciformis\|Lactobacillus casei, Methanobrevibacter smithii\|Lactobacillus casei, Methanosphaera stadtmanae\|Lactobacillus casei, Methylobacterium radiotolerans\|Lactobacillus casei, Mitsuokella multacida\|Lactobacillus casei, Mobiluncus curtisii\|Lactobacillus casei, Mycoplasma hominis\|Lactobacillus casei, Neisseria mucosa\|Lactobacillus casei, Odoribacter splanchnicus\|Lactobacillus casei, Olsenella uli\|Lactobacillus casei, Oribacterium sinus\|Lactobacillus casei, Oxalobacter formigenes\|Lactobacillus casei, Parabacteroides distasonis\|Lactobacillus casei, Parabacteroides johnsonii\|Lactobacillus casei, Parabacteroides merdae\|Lactobacillus casei, Parvimonas micra\|Lactobacillus casei, Pediococcus acidilactici\|Lactobacillus casei, Pediococcus pentosaceus\|Lactobacillus casei, Peptoniphilus duerdenii\|Lactobacillus casei, Peptoniphilus harei\|Lactobacillus casei, Peptoniphilus lacrimalis\|Lactobacillus casei, Peptostreptococcus anaerobius\|Lactobacillus casei, Peptostreptococcus stomatis\|Lactobacillus casei, Porphyromonas asaccharolytica\|Lactobacillus casei, Porphyromonas uenonis\|Lactobacillus casei, Prevotella amnii\|Lactobacillus casei, Prevotella bergensis\|Lactobacillus casei, Prevotella bivia\|Lactobacillus casei, Prevotella buccae\|Lactobacillus casei, Prevotella buccalis\|Lactobacillus casei, Prevotella copri\|Lactobacillus casei, Prevotella disiens\|Lactobacillus casei, Prevotella melaninogenica\|Lactobacillus casei, Prevotella multiformis\|Lactobacillus casei, Prevotella oralis\|Lactobacillus casei, Prevotella oris\|Lactobacillus casei, Prevotella salivae\|Lactobacillus casei, Prevotella timonensis\|Lactobacillus casei, Propionibacterium acnes\|Lactobacillus casei, Propionibacterium freudenreichii\|Lactobacillus casei, Proteus mirabilis\|Lactobacillus casei, Proteus penneri\|Lactobacillus casei, Pseudoflavonifractor capillosus\|Lactobacillus casei, Pseudomonas aeruginosa\|Lactobacillus casei, Pseudomonas fluorescens\|Lactobacillus casei, Pseudomonas putida\|Lactobacillus casei, Pseudoramibacter alactolyticus\|Lactobacillus casei, Pyramidobacter piscolens\|Lactobacillus casei, Rhodopseudomonas palustris\|Lactobacillus casei, Roseburia intestinalis\|Lactobacillus casei, Roseburia inulinivorans\|Lactobacillus casei, Rothia dentocariosa\|Lactobacillus casei, Rothia mucilaginosa\|Lactobacillus casei, Ruminococcus albus\|Lactobacillus casei, Ruminococcus bromii\|Lactobacillus casei, Ruminococcus gnavus\|Lactobacillus casei, Ruminococcus lactaris\|Lactobacillus casei, Ruminococcus obeum\|Lactobacillus casei, Ruminococcus torques\|Lactobacillus casei, Selenomonas sputigena\|Lactobacillus casei, Shigella boydii\|Lactobacillus casei, Shigella dysenteriae\|Lactobacillus casei, Shigella sonnei\|Lactobacillus casei, Slackia exigua\|Lactobacillus casei, Solobacterium moorei\|Lactobacillus casei, Staphylococcus aureus\|Lactobacillus casei, Staphylococcus epidermidis\|Lactobacillus casei, Staphylococcus hominis\|Lactobacillus casei, Staphylococcus saprophyticus\|Lactobacillus casei, Staphylococcus warneri\|Lactobacillus casei, Streptococcus* |

TABLE 2-continued

Table 2. Specific binary combinations of OTUs. Individual pairings are differentiated by "|" and OTUs within a combination are differentiated by ","

*agalactiae|Lactobacillus casei, Streptococcus anginosus|Lactobacillus casei, Streptococcus australis|Lactobacillus casei, Streptococcus bovis|Lactobacillus casei, Streptococcus cristatus|Lactobacillus casei, Streptococcus dysgalactiae|Lactobacillus casei, Streptococcus equinus|Lactobacillus casei, Streptococcus gordonii|Lactobacillus casei, Streptococcus infantarius|Lactobacillus casei, Streptococcus infantis|Lactobacillus casei, Streptococcus mitis|Lactobacillus casei, Streptococcus mutans|Lactobacillus casei, Streptococcus oralis|Lactobacillus casei, Streptococcus parasanguinis|Lactobacillus casei, Streptococcus peroris|Lactobacillus casei, Streptococcus pneumoniae|Lactobacillus casei, Streptococcus salivarius|Lactobacillus casei, Streptococcus sanguinis|Lactobacillus casei, Streptococcus thermophilus|Lactobacillus casei, Streptococcus vestibularis|Lactobacillus casei, Subdoligranulum variabile|Lactobacillus casei, Succinatimonas hippei|Lactobacillus casei, Sutterella wadsworthensis|Lactobacillus casei, Tropheryma whipplei|Lactobacillus casei, Veillonella atypica|Lactobacillus casei, Veillonella dispar|Lactobacillus casei, Veillonella parvula|Lactobacillus casei, Victivallis vadensis|Lactobacillus crispatus, Lactobacillus crispatus|Lactobacillus crispatus, Lactobacillus delbrueckii|Lactobacillus crispatus, Lactobacillus fermentum|Lactobacillus crispatus, Lactobacillus gasseri|Lactobacillus crispatus, Lactobacillus iners|Lactobacillus crispatus, Lactobacillus jensenii|Lactobacillus crispatus, Lactobacillus johnsonii|Lactobacillus crispatus, Lactobacillus paracasei|Lactobacillus crispatus, Lactobacillus plantarum|Lactobacillus crispatus, Lactobacillus reuteri|Lactobacillus crispatus, Lactobacillus rhamnosus|Lactobacillus crispatus, Lactobacillus ruminis|Lactobacillus crispatus, Lactobacillus sakei|Lactobacillus crispatus, Lactobacillus salivarius|Lactobacillus crispatus, Lactococcus lactis|Lactobacillus crispatus, Lautropia mirabilis|Lactobacillus crispatus, Leuconostoc citreum|Lactobacillus crispatus, Leuconostoc gasicomitatum|Lactobacillus crispatus, Leuconostoc mesenteroides|Lactobacillus crispatus, Listeria monocytogenes|Lactobacillus crispatus, Marvinbryantia formatexigens|Lactobacillus crispatus, Megamonas hypermegale|Lactobacillus crispatus, Megasphaera micronuciformis|Lactobacillus crispatus, Methanobrevibacter smithii|Lactobacillus crispatus, Methanosphaera stadtmanae|Lactobacillus crispatus, Methylobacterium radiotolerans|Lactobacillus crispatus, Mitsuokella multacida|Lactobacillus crispatus, Mobiluncus curtisii|Lactobacillus crispatus, Mycoplasma hominis|Lactobacillus crispatus, Neisseria mucosa|Lactobacillus crispatus, Odoribacter splanchnicus|Lactobacillus crispatus, Olsenella uli|Lactobacillus crispatus, Oribacterium sinus|Lactobacillus crispatus, Oxalobacter formigenes|Lactobacillus crispatus, Parabacteroides distasonis|Lactobacillus crispatus, Parabacteroides johnsonii|Lactobacillus crispatus, Parabacteroides merdae|Lactobacillus crispatus, Parvimonas micra|Lactobacillus crispatus, Pediococcus acidilactici|Lactobacillus crispatus, Pediococcus pentosaceus|Lactobacillus crispatus, Peptoniphilus duerdenii|Lactobacillus crispatus, Peptoniphilus harei|Lactobacillus crispatus, Peptoniphilus lacrimalis|Lactobacillus crispatus, Peptostreptococcus anaerobius|Lactobacillus crispatus, Peptostreptococcus stomatis|Lactobacillus crispatus, Porphyromonas asaccharolytica|Lactobacillus crispatus, Porphyromonas uenonis|Lactobacillus crispatus, Prevotella amnii|Lactobacillus crispatus, Prevotella bergensis|Lactobacillus crispatus, Prevotella bivia|Lactobacillus crispatus, Prevotella buccae|Lactobacillus crispatus, Prevotella buccalis|Lactobacillus crispatus, Prevotella copri|Lactobacillus crispatus, Prevotella disiens|Lactobacillus crispatus, Prevotella melaninogenica|Lactobacillus crispatus, Prevotella multiformis|Lactobacillus crispatus, Prevotella oralis|Lactobacillus crispatus, Prevotella oris|Lactobacillus crispatus, Prevotella salivae|Lactobacillus crispatus, Prevotella timonensis|Lactobacillus crispatus, Propionibacterium acnes|Lactobacillus crispatus, Propionibacterium freudenreichii|Lactobacillus crispatus, Proteus mirabilis|Lactobacillus crispatus, Proteus penneri|Lactobacillus crispatus, Pseudoflavonifractor capillosus|Lactobacillus crispatus, Pseudomonas aeruginosa|Lactobacillus crispatus, Pseudomonas fluorescens|Lactobacillus crispatus, Pseudomonas putida|Lactobacillus crispatus, Pseudoramibacter alactolyticus|Lactobacillus crispatus, Pyramidobacter piscolens|Lactobacillus crispatus, Rhodopseudomonas palustris|Lactobacillus crispatus, Roseburia intestinalis|Lactobacillus crispatus, Roseburia inulinivorans|Lactobacillus crispatus, Rothia dentocariosa|Lactobacillus crispatus, Rothia mucilaginosa|Lactobacillus crispatus, Ruminococcus albus|Lactobacillus crispatus, Ruminococcus bromii|Lactobacillus crispatus, Ruminococcus gnavus|Lactobacillus crispatus, Ruminococcus lactaris|Lactobacillus crispatus, Ruminococcus obeum|Lactobacillus crispatus, Ruminococcus torques|Lactobacillus crispatus, Selenomonas sputigena|Lactobacillus crispatus, Shigella boydii|Lactobacillus crispatus, Shigella dysenteriae|Lactobacillus crispatus, Shigella sonnei|Lactobacillus crispatus, Slackia exigua|Lactobacillus crispatus, Solobacterium moorei|Lactobacillus crispatus, Staphylococcus aureus|Lactobacillus crispatus, Staphylococcus epidermidis|Lactobacillus crispatus, Staphylococcus hominis|Lactobacillus crispatus, Staphylococcus saprophyticus|Lactobacillus crispatus, Staphylococcus warneri|Lactobacillus crispatus, Streptococcus agalactiae|Lactobacillus crispatus, Streptococcus anginosus|Lactobacillus crispatus, Streptococcus australis|Lactobacillus crispatus, Streptococcus bovis|Lactobacillus crispatus, Streptococcus cristatus|Lactobacillus crispatus, Streptococcus dysgalactiae|Lactobacillus crispatus, Streptococcus equinus|Lactobacillus crispatus, Streptococcus gordonii|Lactobacillus crispatus, Streptococcus infantarius|Lactobacillus crispatus, Streptococcus infantis|Lactobacillus crispatus, Streptococcus mitis|Lactobacillus crispatus, Streptococcus mutans|Lactobacillus crispatus, Streptococcus oralis|Lactobacillus crispatus, Streptococcus parasanguinis|Lactobacillus crispatus, Streptococcus peroris|Lactobacillus crispatus, Streptococcus pneumoniae|Lactobacillus crispatus, Streptococcus salivarius|Lactobacillus crispatus, Streptococcus sanguinis|Lactobacillus crispatus, Streptococcus thermophilus|Lactobacillus crispatus, Streptococcus vestibularis|Lactobacillus crispatus, Subdoligranulum variabile|Lactobacillus crispatus, Succinatimonas hippei|Lactobacillus crispatus, Sutterella wadsworthensis|Lactobacillus crispatus, Tropheryma whipplei|Lactobacillus crispatus, Veillonella atypica|Lactobacillus crispatus, Veillonella dispar|Lactobacillus crispatus, Veillonella parvula|Lactobacillus crispatus, Victivallis vadensis|Lactobacillus delbrueckii, Lactobacillus delbrueckii|Lactobacillus delbrueckii, Lactobacillus fermentum|Lactobacillus delbrueckii, Lactobacillus gasseri|Lactobacillus delbrueckii, Lactobacillus iners|Lactobacillus delbrueckii, Lactobacillus jensenii|Lactobacillus delbrueckii, Lactobacillus johnsonii|Lactobacillus delbrueckii, Lactobacillus paracasei|Lactobacillus delbrueckii, Lactobacillus plantarum|Lactobacillus delbrueckii, Lactobacillus reuteri|Lactobacillus delbrueckii, Lactobacillus rhamnosus|Lactobacillus delbrueckii, Lactobacillus ruminis|Lactobacillus delbrueckii, Lactobacillus sakei|Lactobacillus delbrueckii, Lactobacillus salivarius|Lactobacillus delbrueckii, Lactococcus lactis|Lactobacillus delbrueckii, Lautropia mirabilis|Lactobacillus delbrueckii, Leuconostoc citreum|Lactobacillus delbrueckii, Leuconostoc gasicomitatum|Lactobacillus delbrueckii, Leuconostoc mesenteroides|Lactobacillus delbrueckii, Listeria monocytogenes|Lactobacillus delbrueckii, Marvinbryantia formatexigens|Lactobacillus delbrueckii, Megamonas hypermegale|Lactobacillus delbrueckii, Megasphaera micronuciformis|Lactobacillus delbrueckii, Methanobrevibacter smithii|Lactobacillus delbrueckii, Methanosphaera stadtmanae|Lactobacillus delbrueckii, Methylobacterium radiotolerans|Lactobacillus delbrueckii, Mitsuokella multacida|Lactobacillus delbrueckii, Mobiluncus curtisii|Lactobacillus delbrueckii, Mycoplasma hominis|Lactobacillus delbrueckii, Neisseria mucosa|Lactobacillus delbrueckii, Odoribacter splanchnicus|Lactobacillus delbrueckii, Olsenella uli|Lactobacillus delbrueckii, Oribacterium sinus|Lactobacillus delbrueckii, Oxalobacter formigenes|Lactobacillus delbrueckii, Parabacteroides distasonis|Lactobacillus delbrueckii, Parabacteroides johnsonii|Lactobacillus delbrueckii, Parabacteroides merdae|Lactobacillus delbrueckii, Parvimonas micra|Lactobacillus delbrueckii, Pediococcus acidilactici|Lactobacillus delbrueckii, Pediococcus pentosaceus|Lactobacillus delbrueckii, Peptoniphilus duerdenii|Lactobacillus delbrueckii, Peptoniphilus harei|Lactobacillus delbrueckii, Peptoniphilus lacrimalis|Lactobacillus delbrueckii, Peptostreptococcus anaerobius|Lactobacillus delbrueckii, Peptostreptococcus stomatis|Lactobacillus delbrueckii, Porphyromonas asaccharolytica|Lactobacillus delbrueckii, Porphyromonas uenonis|Lactobacillus delbrueckii, Prevotella amnii|Lactobacillus delbrueckii, Prevotella bergensis|Lactobacillus delbrueckii, Prevotella bivia|Lactobacillus delbrueckii, Prevotella buccae|Lactobacillus delbrueckii, Prevotella buccalis|Lactobacillus delbrueckii, Prevotella copri|Lactobacillus delbrueckii, Prevotella disiens|Lactobacillus delbrueckii, Prevotella melaninogenica|Lactobacillus delbrueckii, Prevotella multiformis|Lactobacillus delbrueckii, Prevotella oralis|Lactobacillus delbrueckii, Prevotella oris|Lactobacillus delbrueckii, Prevotella salivae|Lactobacillus delbrueckii, Prevotella timonensis|Lactobacillus delbrueckii, Propionibacterium acnes|Lactobacillus delbrueckii, Propionibacterium freudenreichii|Lactobacillus delbrueckii, Proteus mirabilis|Lactobacillus delbrueckii, Proteus penneri|Lactobacillus delbrueckii, Pseudoflavonifractor capillosus|Lactobacillus delbrueckii, Pseudomonas aeruginosa|Lactobacillus delbrueckii, Pseudomonas*

TABLE 2-continued

| Table 2. Specific binary combinations of OTUs. Individual pairings are differentiated by "\|" and OTUs within a combination are differentiated by "," |
|---|
| *fluorescens\|Lactobacillus delbrueckii, Pseudomonas putida\|Lactobacillus delbrueckii, Pseudoramibacter alactolyticus\|Lactobacillus delbrueckii, Pyramidobacter piscolens\|Lactobacillus delbrueckii, Rhodopseudomonas palustris\|Lactobacillus delbrueckii, Roseburia intestinalis\|Lactobacillus delbrueckii, Roseburia inulinivorans\|Lactobacillus delbrueckii, Rothia dentocariosa\|Lactobacillus delbrueckii, Rothia mucilaginosa\|Lactobacillus delbrueckii, Ruminococcus albus\|Lactobacillus delbrueckii, Ruminococcus bromii\|Lactobacillus delbrueckii, Ruminococcus gnavus\|Lactobacillus delbrueckii, Ruminococcus lactaris\|Lactobacillus delbrueckii, Ruminococcus obeum\|Lactobacillus delbrueckii, Ruminococcus torques\|Lactobacillus delbrueckii, Selenomonas sputigena\|Lactobacillus delbrueckii, Shigella boydii\|Lactobacillus delbrueckii, Shigella dysenteriae\|Lactobacillus delbrueckii, Shigella sonnei\|Lactobacillus delbrueckii, Slackia exigua\|Lactobacillus delbrueckii, Solobacterium moorei\|Lactobacillus delbrueckii, Staphylococcus aureus\|Lactobacillus delbrueckii, Staphylococcus epidermidis\|Lactobacillus delbrueckii, Staphylococcus hominis\|Lactobacillus delbrueckii, Staphylococcus saprophyticus\|Lactobacillus delbrueckii, Staphylococcus warneri\|Lactobacillus delbrueckii, Streptococcus agalactiae\|Lactobacillus delbrueckii, Streptococcus anginosus\|Lactobacillus delbrueckii, Streptococcus australis\|Lactobacillus delbrueckii, Streptococcus bovis\|Lactobacillus delbrueckii, Streptococcus cristatus\|Lactobacillus delbrueckii, Streptococcus dysgalactiae\|Lactobacillus delbrueckii, Streptococcus equinus\|Lactobacillus delbrueckii, Streptococcus gordonii\|Lactobacillus delbrueckii, Streptococcus infantarius\|Lactobacillus delbrueckii, Streptococcus infantis\|Lactobacillus delbrueckii, Streptococcus mitis\|Lactobacillus delbrueckii, Streptococcus mutans\|Lactobacillus delbrueckii, Streptococcus oralis\|Lactobacillus delbrueckii, Streptococcus parasanguinis\|Lactobacillus delbrueckii, Streptococcus peroris\|Lactobacillus delbrueckii, Streptococcus pneumoniae\|Lactobacillus delbrueckii, Streptococcus salivarius\|Lactobacillus delbrueckii, Streptococcus sanguinis\|Lactobacillus delbrueckii, Streptococcus thermophilus\|Lactobacillus delbrueckii, Streptococcus vestibularis\|Lactobacillus delbrueckii, Subdoligranulum variabile\|Lactobacillus delbrueckii, Succinatimonas hippei\|Lactobacillus delbrueckii, Sutterella wadsworthensis\|Lactobacillus delbrueckii, Tropheryma whipplei\|Lactobacillus delbrueckii, Veillonella atypica\|Lactobacillus delbrueckii, Veillonella dispar\|Lactobacillus delbrueckii, Veillonella parvula\|Lactobacillus delbrueckii, Victivallis vadensis\|Lactobacillus fermentum, Lactobacillus fermentum, Lactobacillus gasseri\|Lactobacillus fermentum, Lactobacillus iners\|Lactobacillus fermentum, Lactobacillus jensenii\|Lactobacillus fermentum, Lactobacillus johnsonii\|Lactobacillus fermentum, Lactobacillus paracasei\|Lactobacillus fermentum, Lactobacillus plantarum\|Lactobacillus fermentum, Lactobacillus reuteri\|Lactobacillus fermentum, Lactobacillus rhamnosus\|Lactobacillus fermentum, Lactobacillus ruminis\|Lactobacillus fermentum, Lactobacillus sakei\|Lactobacillus fermentum, Lactobacillus salivarius\|Lactobacillus fermentum, Lactococcus lactis\|Lactobacillus fermentum, Lautropia mirabilis\|Lactobacillus fermentum, Leuconostoc citreum\|Lactobacillus fermentum, Leuconostoc gasicomitatum\|Lactobacillus fermentum, Leuconostoc mesenteroides\|Lactobacillus fermentum, Listeria monocytogenes\|Lactobacillus fermentum, Marvinbryantia formatexigens\|Lactobacillus fermentum, Megamonas hypermegale\|Lactobacillus fermentum, Megasphaera micronuciformis\|Lactobacillus fermentum, Methanobrevibacter smithii\|Lactobacillus fermentum, Methanosphaera stadtmanae\|Lactobacillus fermentum, Methylobacterium radiotolerans\|Lactobacillus fermentum, Mitsuokella multacida\|Lactobacillus fermentum, Mobiluncus curtisii\|Lactobacillus fermentum, Mycoplasma hominis\|Lactobacillus fermentum, Neisseria mucosa\|Lactobacillus fermentum, Odoribacter splanchnicus\|Lactobacillus fermentum, Olsenella uli\|Lactobacillus fermentum, Oribacterium sinus\|Lactobacillus fermentum, Oxalobacter formigenes\|Lactobacillus fermentum, Parabacteroides distasonis\|Lactobacillus fermentum, Parabacteroides johnsonii\|Lactobacillus fermentum, Parabacteroides merdae\|Lactobacillus fermentum, Parvimonas micra\|Lactobacillus fermentum, Pediococcus acidilactici\|Lactobacillus fermentum, Pediococcus pentosaceus\|Lactobacillus fermentum, Peptoniphilus duerdenii\|Lactobacillus fermentum, Peptoniphilus harei\|Lactobacillus fermentum, Peptoniphilus lacrimalis\|Lactobacillus fermentum, Peptostreptococcus anaerobius\|Lactobacillus fermentum, Peptostreptococcus stomatis\|Lactobacillus fermentum, Porphyromonas asaccharolytica\|Lactobacillus fermentum, Porphyromonas uenonis\|Lactobacillus fermentum, Prevotella amnii\|Lactobacillus fermentum, Prevotella bergensis\|Lactobacillus fermentum, Prevotella bivia\|Lactobacillus fermentum, Prevotella buccae\|Lactobacillus fermentum, Prevotella buccalis\|Lactobacillus fermentum, Prevotella copri\|Lactobacillus fermentum, Prevotella disiens\|Lactobacillus fermentum, Prevotella melaninogenica\|Lactobacillus fermentum, Prevotella multiformis\|Lactobacillus fermentum, Prevotella oralis\|Lactobacillus fermentum, Prevotella oris\|Lactobacillus fermentum, Prevotella salivae\|Lactobacillus fermentum, Prevotella timonensis\|Lactobacillus fermentum, Propionibacterium acnes\|Lactobacillus fermentum, Propionibacterium freudenreichii\|Lactobacillus fermentum, Proteus mirabilis\|Lactobacillus fermentum, Proteus penneri\|Lactobacillus fermentum, Pseudoflavonifractor capillosus\|Lactobacillus fermentum, Pseudomonas aeruginosa\|Lactobacillus fermentum, Pseudomonas fluorescens\|Lactobacillus fermentum, Pseudomonas putida\|Lactobacillus fermentum, Pseudoramibacter alactolyticus\|Lactobacillus fermentum, Pyramidobacter piscolens\|Lactobacillus fermentum, Rhodopseudomonas palustris\|Lactobacillus fermentum, Roseburia intestinalis\|Lactobacillus fermentum, Roseburia inulinivorans\|Lactobacillus fermentum, Rothia dentocariosa\|Lactobacillus fermentum, Rothia mucilaginosa\|Lactobacillus fermentum, Ruminococcus albus\|Lactobacillus fermentum, Ruminococcus bromii\|Lactobacillus fermentum, Ruminococcus gnavus\|Lactobacillus fermentum, Ruminococcus lactaris\|Lactobacillus fermentum, Ruminococcus obeum\|Lactobacillus fermentum, Ruminococcus torques\|Lactobacillus fermentum, Selenomonas sputigena\|Lactobacillus fermentum, Shigella boydii\|Lactobacillus fermentum, Shigella dysenteriae\|Lactobacillus fermentum, Shigella sonnei\|Lactobacillus fermentum, Slackia exigua\|Lactobacillus fermentum, Solobacterium moorei\|Lactobacillus fermentum, Staphylococcus aureus\|Lactobacillus fermentum, Staphylococcus epidermidis\|Lactobacillus fermentum, Staphylococcus hominis\|Lactobacillus fermentum, Staphylococcus saprophyticus\|Lactobacillus fermentum, Staphylococcus warneri\|Lactobacillus fermentum, Streptococcus agalactiae\|Lactobacillus fermentum, Streptococcus anginosus\|Lactobacillus fermentum, Streptococcus australis\|Lactobacillus fermentum, Streptococcus bovis\|Lactobacillus fermentum, Streptococcus cristatus\|Lactobacillus fermentum, Streptococcus dysgalactiae\|Lactobacillus fermentum, Streptococcus equinus\|Lactobacillus fermentum, Streptococcus gordonii\|Lactobacillus fermentum, Streptococcus infantarius\|Lactobacillus fermentum, Streptococcus infantis\|Lactobacillus fermentum, Streptococcus mitis\|Lactobacillus fermentum, Streptococcus mutans\|Lactobacillus fermentum, Streptococcus oralis\|Lactobacillus fermentum, Streptococcus parasanguinis\|Lactobacillus fermentum, Streptococcus peroris\|Lactobacillus fermentum, Streptococcus pneumoniae\|Lactobacillus fermentum, Streptococcus salivarius\|Lactobacillus fermentum, Streptococcus sanguinis\|Lactobacillus fermentum, Streptococcus thermophilus\|Lactobacillus fermentum, Streptococcus vestibularis\|Lactobacillus fermentum, Subdoligranulum variabile\|Lactobacillus fermentum, Succinatimonas hippei\|Lactobacillus fermentum, Sutterella wadsworthensis\|Lactobacillus fermentum, Tropheryma whipplei\|Lactobacillus fermentum, Veillonella atypica\|Lactobacillus fermentum, Veillonella dispar\|Lactobacillus fermentum, Veillonella parvula\|Lactobacillus fermentum, Victivallis vadensis\|Lactobacillus gasseri, Lactobacillus gasseri\|Lactobacillus gasseri, Lactobacillus iners\|Lactobacillus gasseri, Lactobacillus jensenii\|Lactobacillus gasseri, Lactobacillus johnsonii\|Lactobacillus gasseri, Lactobacillus paracasei\|Lactobacillus gasseri, Lactobacillus plantarum\|Lactobacillus gasseri, Lactobacillus reuteri\|Lactobacillus gasseri, Lactobacillus rhamnosus\|Lactobacillus gasseri, Lactobacillus ruminis\|Lactobacillus gasseri, Lactobacillus sakei\|Lactobacillus gasseri, Lactobacillus salivarius\|Lactobacillus gasseri, Lactococcus lactis\|Lactobacillus gasseri, Lautropia mirabilis\|Lactobacillus gasseri, Leuconostoc citreum\|Lactobacillus gasseri, Leuconostoc gasicomitatum\|Lactobacillus gasseri, Leuconostoc mesenteroides\|Lactobacillus gasseri, Listeria monocytogenes\|Lactobacillus gasseri, Marvinbryantia formatexigens\|Lactobacillus gasseri, Megamonas hypermegale\|Lactobacillus gasseri, Megasphaera micronuciformis\|Lactobacillus gasseri, Methanobrevibacter smithii\|Lactobacillus gasseri, Methanosphaera stadtmanae\|Lactobacillus gasseri, Methylobacterium radiotolerans\|Lactobacillus gasseri, Mitsuokella multacida\|Lactobacillus gasseri, Mobiluncus curtisii\|Lactobacillus gasseri, Mycoplasma hominis\|Lactobacillus gasseri, Neisseria mucosa\|Lactobacillus gasseri, Odoribacter splanchnicus\|Lactobacillus gasseri, Olsenella uli\|Lactobacillus gasseri, Oribacterium sinus\|Lactobacillus gasseri, Oxalobacter formigenes\|Lactobacillus gasseri, Parabacteroides distasonis\|Lactobacillus gasseri, Parabacteroides johnsonii\|Lactobacillus gasseri, Parabacteroides merdae\|Lactobacillus gasseri, Parvimonas micra\|Lactobacillus gasseri, Pediococcus acidilactici\|Lactobacillus gasseri, Pediococcus pentosaceus\|Lactobacillus gasseri, Peptoniphilus duerdenii\|Lactobacillus* |

TABLE 2-continued

| Table 2. Specific binary combinations of OTUs. Individual pairings are differentiated by "\|" and OTUs within a combination are differentiated by "," |
| --- |
| *gasseri, Peptoniphilus harei\|Lactobacillus gasseri, Peptoniphilus lacrimalis\|Lactobacillus gasseri, Peptostreptococcus anaerobius\|Lactobacillus gasseri, Peptostreptococcus stomatis\|Lactobacillus gasseri, Porphyromonas asaccharolytica\|Lactobacillus gasseri, Porphyromonas uenonis\|Lactobacillus gasseri, Prevotella amnii\|Lactobacillus gasseri, Prevotella bergensis\|Lactobacillus gasseri, Prevotella bivia\|Lactobacillus gasseri, Prevotella buccae\|Lactobacillus gasseri, Prevotella buccalis\|Lactobacillus gasseri, Prevotella copri\|Lactobacillus gasseri, Prevotella disiens\|Lactobacillus gasseri, Prevotella melaninogenica\|Lactobacillus gasseri, Prevotella multiformis\|Lactobacillus gasseri, Prevotella oralis\|Lactobacillus gasseri, Prevotella oris\|Lactobacillus gasseri, Prevotella salivae\|Lactobacillus gasseri, Prevotella timonensis\|Lactobacillus gasseri, Propionibacterium acnes\|Lactobacillus gasseri, Propionibacterium freudenreichii\|Lactobacillus gasseri, Proteus mirabilis\|Lactobacillus gasseri, Proteus penneri\|Lactobacillus gasseri, Pseudoflavonifractor capillosus\|Lactobacillus gasseri, Pseudomonas aeruginosa\|Lactobacillus gasseri, Pseudomonas fluorescens\|Lactobacillus gasseri, Pseudomonas putida\|Lactobacillus gasseri, Pseudoramibacter alactolyticus\|Lactobacillus gasseri, Pyramidobacter piscolens\|Lactobacillus gasseri, Rhodopseudomonas palustris\|Lactobacillus gasseri, Roseburia intestinalis\|Lactobacillus gasseri, Roseburia inulinivorans\|Lactobacillus gasseri, Rothia dentocariosa\|Lactobacillus gasseri, Rothia mucilaginosa\|Lactobacillus gasseri, Ruminococcus albus\|Lactobacillus gasseri, Ruminococcus bromii\|Lactobacillus gasseri, Ruminococcus gnavus\|Lactobacillus gasseri, Ruminococcus lactaris\|Lactobacillus gasseri, Ruminococcus obeum\|Lactobacillus gasseri, Ruminococcus torques\|Lactobacillus gasseri, Selenomonas sputigena\|Lactobacillus gasseri, Shigella boydii\|Lactobacillus gasseri, Shigella dysenteriae\|Lactobacillus gasseri, Shigella sonnei\|Lactobacillus gasseri, Slackia exigua\|Lactobacillus gasseri, Solobacterium moorei\|Lactobacillus gasseri, Staphylococcus aureus\|Lactobacillus gasseri, Staphylococcus epidermidis\|Lactobacillus gasseri, Staphylococcus hominis\|Lactobacillus gasseri, Staphylococcus saprophyticus\|Lactobacillus gasseri, Staphylococcus warneri\|Lactobacillus gasseri, Streptococcus agalactiae\|Lactobacillus gasseri, Streptococcus anginosus\|Lactobacillus gasseri, Streptococcus australis\|Lactobacillus gasseri, Streptococcus bovis\|Lactobacillus gasseri, Streptococcus cristatus\|Lactobacillus gasseri, Streptococcus dysgalactiae\|Lactobacillus gasseri, Streptococcus equinus\|Lactobacillus gasseri, Streptococcus gordonii\|Lactobacillus gasseri, Streptococcus infantarius\|Lactobacillus gasseri, Streptococcus infantis\|Lactobacillus gasseri, Streptococcus mitis\|Lactobacillus gasseri, Streptococcus mutans\|Lactobacillus gasseri, Streptococcus oralis\|Lactobacillus gasseri, Streptococcus parasanguinis\|Lactobacillus gasseri, Streptococcus peroris\|Lactobacillus gasseri, Streptococcus pneumoniae\|Lactobacillus gasseri, Streptococcus salivarius\|Lactobacillus gasseri, Streptococcus sanguinis\|Lactobacillus gasseri, Streptococcus thermophilus\|Lactobacillus gasseri, Streptococcus vestibularis\|Lactobacillus gasseri, Subdoligranulum variabile\|Lactobacillus gasseri, Succinatimonas hippei\|Lactobacillus gasseri, Sutterella wadsworthensis\|Lactobacillus gasseri, Tropheryma whipplei\|Lactobacillus gasseri, Veillonella atypica\|Lactobacillus gasseri, Veillonella dispar\|Lactobacillus gasseri, Veillonella parvula\|Lactobacillus gasseri, Victivallis vadensis\|Lactobacillus iners, Lactobacillus iners\|Lactobacillus iners, Lactobacillus jensenii\|Lactobacillus iners, Lactobacillus johnsonii\|Lactobacillus iners, Lactobacillus paracasei\|Lactobacillus iners, Lactobacillus plantarum\|Lactobacillus iners, Lactobacillus reuteri\|Lactobacillus iners, Lactobacillus rhamnosus\|Lactobacillus iners, Lactobacillus ruminis\|Lactobacillus iners, Lactobacillus sakei\|Lactobacillus iners, Lactobacillus salivarius\|Lactobacillus iners, Lactococcus lactis\|Lactobacillus iners, Lautropia mirabilis\|Lactobacillus iners, Leuconostoc citreum\|Lactobacillus iners, Leuconostoc gasicomitatum\|Lactobacillus iners, Leuconostoc mesenteroides\|Lactobacillus iners, Listeria monocytogenes\|Lactobacillus iners, Marvinbryantia formatexigens\|Lactobacillus iners, Megamonas hypermegale\|Lactobacillus iners, Megasphaera micronuciformis\|Lactobacillus iners, Methanobrevibacter smithii\|Lactobacillus iners, Methanosphaera stadtmanae\|Lactobacillus iners, Methylobacterium radiotolerans\|Lactobacillus iners, Mitsuokella multacida\|Lactobacillus iners, Mobiluncus curtisii\|Lactobacillus iners, Mycoplasma hominis\|Lactobacillus iners, Neisseria mucosa\|Lactobacillus iners, Odoribacter splanchnicus\|Lactobacillus iners, Olsenella uli\|Lactobacillus iners, Oribacterium sinus\|Lactobacillus iners, Oxalobacter formigenes\|Lactobacillus iners, Parabacteroides distasonis\|Lactobacillus iners, Parabacteroides johnsonii\|Lactobacillus iners, Parabacteroides merdae\|Lactobacillus iners, Parvimonas micra\|Lactobacillus iners, Pediococcus acidilactici\|Lactobacillus iners, Pediococcus pentosaceus\|Lactobacillus iners, Peptoniphilus duerdenii\|Lactobacillus iners, Peptoniphilus harei\|Lactobacillus iners, Peptoniphilus lacrimalis\|Lactobacillus iners, Peptostreptococcus anaerobius\|Lactobacillus iners, Peptostreptococcus stomatis\|Lactobacillus iners, Porphyromonas asaccharolytica\|Lactobacillus iners, Porphyromonas uenonis\|Lactobacillus iners, Prevotella amnii\|Lactobacillus iners, Prevotella bergensis\|Lactobacillus iners, Prevotella bivia\|Lactobacillus iners, Prevotella buccae\|Lactobacillus iners, Prevotella buccalis\|Lactobacillus iners, Prevotella copri\|Lactobacillus iners, Prevotella disiens\|Lactobacillus iners, Prevotella melaninogenica\|Lactobacillus iners, Prevotella multiformis\|Lactobacillus iners, Prevotella oralis\|Lactobacillus iners, Prevotella oris\|Lactobacillus iners, Prevotella salivae\|Lactobacillus iners, Prevotella timonensis\|Lactobacillus iners, Propionibacterium acnes\|Lactobacillus iners, Propionibacterium freudenreichii\|Lactobacillus iners, Proteus mirabilis\|Lactobacillus iners, Proteus penneri\|Lactobacillus iners, Pseudoflavonifractor capillosus\|Lactobacillus iners, Pseudomonas aeruginosa\|Lactobacillus iners, Pseudomonas fluorescens\|Lactobacillus iners, Pseudomonas putida\|Lactobacillus iners, Pseudoramibacter alactolyticus\|Lactobacillus iners, Pyramidobacter piscolens\|Lactobacillus iners, Rhodopseudomonas palustris\|Lactobacillus iners, Roseburia intestinalis\|Lactobacillus iners, Roseburia inulinivorans\|Lactobacillus iners, Rothia dentocariosa\|Lactobacillus iners, Rothia mucilaginosa\|Lactobacillus iners, Ruminococcus albus\|Lactobacillus iners, Ruminococcus bromii\|Lactobacillus iners, Ruminococcus gnavus\|Lactobacillus iners, Ruminococcus lactaris\|Lactobacillus iners, Ruminococcus obeum\|Lactobacillus iners, Ruminococcus torques\|Lactobacillus iners, Selenomonas sputigena\|Lactobacillus iners, Shigella boydii\|Lactobacillus iners, Shigella dysenteriae\|Lactobacillus iners, Shigella sonnei\|Lactobacillus iners, Slackia exigua\|Lactobacillus iners, Solobacterium moorei\|Lactobacillus iners, Staphylococcus aureus\|Lactobacillus iners, Staphylococcus epidermidis\|Lactobacillus iners, Staphylococcus hominis\|Lactobacillus iners, Staphylococcus saprophyticus\|Lactobacillus iners, Staphylococcus warneri\|Lactobacillus iners, Streptococcus agalactiae\|Lactobacillus iners, Streptococcus anginosus\|Lactobacillus iners, Streptococcus australis\|Lactobacillus iners, Streptococcus bovis\|Lactobacillus iners, Streptococcus cristatus\|Lactobacillus iners, Streptococcus dysgalactiae\|Lactobacillus iners, Streptococcus equinus\|Lactobacillus iners, Streptococcus gordonii\|Lactobacillus iners, Streptococcus infantarius\|Lactobacillus iners, Streptococcus infantis\|Lactobacillus iners, Streptococcus mitis\|Lactobacillus iners, Streptococcus mutans\|Lactobacillus iners, Streptococcus oralis\|Lactobacillus iners, Streptococcus parasanguinis\|Lactobacillus iners, Streptococcus peroris\|Lactobacillus iners, Streptococcus pneumoniae\|Lactobacillus iners, Streptococcus salivarius\|Lactobacillus iners, Streptococcus sanguinis\|Lactobacillus iners, Streptococcus thermophilus\|Lactobacillus iners, Streptococcus vestibularis\|Lactobacillus iners, Subdoligranulum variabile\|Lactobacillus iners, Succinatimonas hippei\|Lactobacillus iners, Sutterella wadsworthensis\|Lactobacillus iners, Tropheryma whipplei\|Lactobacillus iners, Veillonella atypica\|Lactobacillus iners, Veillonella dispar\|Lactobacillus iners, Veillonella parvula\|Lactobacillus iners, Victivallis vadensis\|Lactobacillus jensenii, Lactobacillus jensenii\|Lactobacillus jensenii, Lactobacillus johnsonii\|Lactobacillus jensenii, Lactobacillus paracasei\|Lactobacillus jensenii, Lactobacillus plantarum\|Lactobacillus jensenii, Lactobacillus reuteri\|Lactobacillus jensenii, Lactobacillus rhamnosus\|Lactobacillus jensenii, Lactobacillus ruminis\|Lactobacillus jensenii, Lactobacillus sakei\|Lactobacillus jensenii, Lactobacillus salivarius\|Lactobacillus jensenii, Lactococcus lactis\|Lactobacillus jensenii, Lautropia mirabilis\|Lactobacillus jensenii, Leuconostoc citreum\|Lactobacillus jensenii, Leuconostoc gasicomitatum\|Lactobacillus jensenii, Leuconostoc mesenteroides\|Lactobacillus jensenii, Listeria monocytogenes\|Lactobacillus jensenii, Marvinbryantia formatexigens\|Lactobacillus jensenii, Megamonas hypermegale\|Lactobacillus jensenii, Megasphaera micronuciformis\|Lactobacillus jensenii, Methanobrevibacter smithii\|Lactobacillus jensenii, Methanosphaera stadtmanae\|Lactobacillus jensenii, Methylobacterium radiotolerans\|Lactobacillus jensenii, Mitsuokella multacida\|Lactobacillus jensenii, Mobiluncus curtisii\|Lactobacillus jensenii, Mycoplasma hominis\|Lactobacillus jensenii, Neisseria mucosa\|Lactobacillus jensenii, Odoribacter splanchnicus\|Lactobacillus jensenii, Olsenella uli\|Lactobacillus jensenii, Oribacterium sinus\|Lactobacillus jensenii, Oxalobacter formigenes\|Lactobacillus jensenii, Parabacteroides distasonis\|Lactobacillus jensenii, Parabacteroides johnsonii\|Lactobacillus jensenii, Parabacteroides merdae\|Lactobacillus jensenii, Parvimonas micra\|Lactobacillus jensenii, Pediococcus acidilactici\|Lactobacillus jensenii, Pediococcus pentosaceus\|Lactobacillus jensenii, Peptoniphilus* |

TABLE 2-continued

Table 2. Specific binary combinations of OTUs. Individual pairings are differentiated by "|" and OTUs within a combination are differentiated by ","

duerdenii|Lactobacillus jensenii, Peptoniphilus harei|Lactobacillus jensenii, Peptoniphilus lacrimalis|Lactobacillus jensenii, Peptostreptococcus anaerobius|Lactobacillus jensenii, Peptostreptococcus stomatis|Lactobacillus jensenii, Porphyromonas asaccharolytica|Lactobacillus jensenii, Porphyromonas uenonis|Lactobacillus jensenii, Prevotella amnii|Lactobacillus jensenii, Prevotella bergensis|Lactobacillus jensenii, Prevotella bivia|Lactobacillus jensenii, Prevotella buccae|Lactobacillus jensenii, Prevotella buccalis|Lactobacillus jensenii, Prevotella copri|Lactobacillus jensenii, Prevotella disiens|Lactobacillus jensenii, Prevotella melaninogenica|Lactobacillus jensenii, Prevotella multiformis|Lactobacillus jensenii, Prevotella oralis|Lactobacillus jensenii, Prevotella oris|Lactobacillus jensenii, Prevotella salivae|Lactobacillus jensenii, Prevotella timonensis|Lactobacillus jensenii, Propionibacterium acnes|Lactobacillus jensenii, Propionibacterium freudenreichii|Lactobacillus jensenii, Proteus mirabilis|Lactobacillus jensenii, Proteus penneri|Lactobacillus jensenii, Pseudoflavonifractor capillosus|Lactobacillus jensenii, Pseudomonas aeruginosa|Lactobacillus jensenii, Pseudomonas fluorescens|Lactobacillus jensenii, Pseudomonas putida|Lactobacillus jensenii, Pseudoramibacter alactolyticus|Lactobacillus jensenii, Pyramidobacter piscolens|Lactobacillus jensenii, Rhodopseudomonas palustris|Lactobacillus jensenii, Roseburia intestinalis|Lactobacillus jensenii, Roseburia inulinivorans|Lactobacillus jensenii, Rothia dentocariosa|Lactobacillus jensenii, Rothia mucilaginosa|Lactobacillus jensenii, Ruminococcus albus|Lactobacillus jensenii, Ruminococcus bromii|Lactobacillus jensenii, Ruminococcus gnavus|Lactobacillus jensenii, Ruminococcus lactaris|Lactobacillus jensenii, Ruminococcus obeum|Lactobacillus jensenii, Ruminococcus torques|Lactobacillus jensenii, Selenomonas sputigena|Lactobacillus jensenii, Shigella boydii|Lactobacillus jensenii, Shigella dysenteriae jensenii, Shigella sonnei|Lactobacillus jensenii, Slackia exigua|Lactobacillus jensenii, Solobacterium moorei|Lactobacillus jensenii, Staphylococcus aureus|Lactobacillus jensenii, Staphylococcus epidermidis|Lactobacillus jensenii, Staphylococcus hominis|Lactobacillus jensenii, Staphylococcus saprophyticus|Lactobacillus jensenii, Staphylococcus warneri|Lactobacillus jensenii, Streptococcus agalactiae|Lactobacillus jensenii, Streptococcus anginosus|Lactobacillus jensenii, Streptococcus australis|Lactobacillus jensenii, Streptococcus bovis|Lactobacillus jensenii, Streptococcus cristatus|Lactobacillus jensenii, Streptococcus dysgalactiae|Lactobacillus jensenii, Streptococcus equinus|Lactobacillus jensenii, Streptococcus gordonii|Lactobacillus jensenii, Streptococcus infantarius|Lactobacillus jensenii, Streptococcus infantis|Lactobacillus jensenii, Streptococcus mitis|Lactobacillus jensenii, Streptococcus mutans|Lactobacillus jensenii, Streptococcus oralis|Lactobacillus jensenii, Streptococcus parasanguinis|Lactobacillus jensenii, Streptococcus peroris|Lactobacillus jensenii, Streptococcus pneumoniae|Lactobacillus jensenii, Streptococcus salivarius|Lactobacillus jensenii, Streptococcus sanguinis|Lactobacillus jensenii, Streptococcus thermophilus|Lactobacillus jensenii, Streptococcus vestibularis|Lactobacillus jensenii, Subdoligranulum variabile|Lactobacillus jensenii, Succinatimonas hippei|Lactobacillus jensenii, Sutterella wadsworthensis|Lactobacillus jensenii, Tropheryma whipplei|Lactobacillus jensenii, Veillonella atypica|Lactobacillus jensenii, Veillonella dispar|Lactobacillus jensenii, Veillonella parvula|Lactobacillus jensenii, Victivallis vadensis|Lactobacillus johnsonii, Lactobacillus johnsonii|Lactobacillus johnsonii, Lactobacillus paracasei|Lactobacillus johnsonii, Lactobacillus plantarum|Lactobacillus johnsonii, Lactobacillus reuteri|Lactobacillus johnsonii, Lactobacillus rhamnosus|Lactobacillus johnsonii, Lactobacillus ruminis|Lactobacillus johnsonii, Lactobacillus sakei|Lactobacillus johnsonii, Lactobacillus salivarius|Lactobacillus johnsonii, Lactococcus lactis|Lactobacillus johnsonii, Lautropia mirabilis|Lactobacillus johnsonii, Leuconostoc citreum|Lactobacillus johnsonii, Leuconostoc gasicomitatum|Lactobacillus johnsonii, Leuconostoc mesenteroides|Lactobacillus johnsonii, Listeria monocytogenes|Lactobacillus johnsonii, Marvinbryantia formatexigens|Lactobacillus johnsonii, Megamonas hypermegale|Lactobacillus johnsonii, Megasphaera micronuciformis|Lactobacillus johnsonii, Methanobrevibacter smithii|Lactobacillus johnsonii, Methanosphaera stadtmana|Lactobacillus johnsonii, Methylobacterium radiotolerans|Lactobacillus johnsonii, Mitsuokella multacida|Lactobacillus johnsonii, Mobiluncus curtisii|Lactobacillus johnsonii, Mycoplasma hominis|Lactobacillus johnsonii, Neisseria mucosa|Lactobacillus johnsonii, Odoribacter splanchnicus|Lactobacillus johnsonii, Olsenella uli|Lactobacillus johnsonii, Oribacterium sinus|Lactobacillus johnsonii, Oxalobacter formigenes|Lactobacillus johnsonii, Parabacteroides distasonis|Lactobacillus johnsonii, Parabacteroides johnsonii|Lactobacillus johnsonii, Parabacteroides merdae|Lactobacillus johnsonii, Parvimonas micra|Lactobacillus johnsonii, Pediococcus acidilactici|Lactobacillus johnsonii, Pediococcus pentosaceus|Lactobacillus johnsonii, Peptoniphilus duerdenii|Lactobacillus johnsonii, Peptoniphilus harei|Lactobacillus johnsonii, Peptoniphilus lacrimalis|Lactobacillus johnsonii, Peptostreptococcus anaerobius|Lactobacillus johnsonii, Peptostreptococcus stomatis|Lactobacillus johnsonii, Porphyromonas asaccharolytica|Lactobacillus johnsonii, Porphyromonas uenonis|Lactobacillus johnsonii, Prevotella amnii|Lactobacillus johnsonii, Prevotella bergensis|Lactobacillus johnsonii, Prevotella bivia|Lactobacillus johnsonii, Prevotella buccae|Lactobacillus johnsonii, Prevotella buccalis|Lactobacillus johnsonii, Prevotella copri|Lactobacillus johnsonii, Prevotella disiens|Lactobacillus johnsonii, Prevotella melaninogenica|Lactobacillus johnsonii, Prevotella multiformis|Lactobacillus johnsonii, Prevotella oralis|Lactobacillus johnsonii, Prevotella oris|Lactobacillus johnsonii, Prevotella salivae|Lactobacillus johnsonii, Prevotella timonensis|Lactobacillus johnsonii, Propionibacterium acnes|Lactobacillus johnsonii, Propionibacterium freudenreichii|Lactobacillus johnsonii, Proteus mirabilis|Lactobacillus johnsonii, Proteus penneri|Lactobacillus johnsonii, Pseudoflavonifractor capillosus|Lactobacillus johnsonii, Pseudomonas aeruginosa|Lactobacillus johnsonii, Pseudomonas fluorescens|Lactobacillus johnsonii, Pseudomonas putida|Lactobacillus johnsonii, Pseudoramibacter alactolyticus|Lactobacillus johnsonii, Pyramidobacter piscolens|Lactobacillus johnsonii, Rhodops eudomonas palustris|Lactobacillus johnsonii, Roseburia intestinalis|Lactobacillus johnsonii, Roseburia inulinivorans|Lactobacillus johnsonii, Rothia dentocariosa|Lactobacillus johnsonii, Rothia mucilaginosa|Lactobacillus johnsonii, Ruminococcus albus|Lactobacillus johnsonii, Ruminococcus bromii|Lactobacillus johnsonii, Ruminococcus gnavus|Lactobacillus johnsonii, Ruminococcus lactaris|Lactobacillus johnsonii, Ruminococcus obeum|Lactobacillus johnsonii, Ruminococcus torques|Lactobacillus johnsonii, Selenomonas sputigena|Lactobacillus johnsonii, Shigella boydii|Lactobacillus johnsonii, Shigella dysenteriae|Lactobacillus johnsonii, Shigella sonnei|Lactobacillus johnsonii, Slackia exigua|Lactobacillus johnsonii, Solobacterium moorei|Lactobacillus johnsonii, Staphylococcus aureus|Lactobacillus johnsonii, Staphylococcus epidermidis|Lactobacillus johnsonii, Staphylococcus hominis|Lactobacillus johnsonii, Staphylococcus saprophyticus|Lactobacillus johnsonii, Staphylococcus warneri|Lactobacillus johnsonii, Streptococcus agalactiae|Lactobacillus johnsonii, Streptococcus anginosus|Lactobacillus johnsonii, Streptococcus australis|Lactobacillus johnsonii, Streptococcus bovis|Lactobacillus johnsonii, Streptococcus cristatus|Lactobacillus johnsonii, Streptococcus dysgalactiae|Lactobacillus johnsonii, Streptococcus equinus|Lactobacillus johnsonii, Streptococcus gordonii|Lactobacillus johnsonii, Streptococcus infantarius|Lactobacillus johnsonii, Streptococcus infantis|Lactobacillus johnsonii, Streptococcus mitis|Lactobacillus johnsonii, Streptococcus mutans|Lactobacillus johnsonii, Streptococcus oralis|Lactobacillus johnsonii, Streptococcus parasanguinis|Lactobacillus johnsonii, Streptococcus peroris|Lactobacillus johnsonii, Streptococcus pneumoniae|Lactobacillus johnsonii, Streptococcus salivarius|Lactobacillus johnsonii, Streptococcus sanguinis|Lactobacillus johnsonii, Streptococcus thermophilus|Lactobacillus johnsonii, Streptococcus vestibularis|Lactobacillus johnsonii, Subdoligranulum variabile|Lactobacillus johnsonii, Succinatimonas hippei|Lactobacillus johnsonii, Sutterella wadsworthensis|Lactobacillus johnsonii, Tropheryma whipplei|Lactobacillus johnsonii, Veillonella atypica|Lactobacillus johnsonii, Veillonella dispar|Lactobacillus johnsonii, Veillonella parvula|Lactobacillus johnsonii, Victivallis vadensis|Lactobacillus paracasei, Lactobacillus paracasei|Lactobacillus paracasei, Lactobacillus plantarum|Lactobacillus paracasei, Lactobacillus reuteri|Lactobacillus paracasei, Lactobacillus rhamnosus|Lactobacillus paracasei, Lactobacillus ruminis|Lactobacillus paracasei, Lactobacillus sakei|Lactobacillus paracasei, Lactobacillus salivarius|Lactobacillus paracasei, Lactococcus lactis|Lactobacillus paracasei, Lautropia mirabilis|Lactobacillus paracasei, Leuconostoc citreum|Lactobacillus paracasei, Leuconostoc gasicomitatum|Lactobacillus paracasei, Leuconostoc mesenteroides|Lactobacillus paracasei, Listeria monocytogenes|Lactobacillus paracasei, Marvinbryantia formatexigens|Lactobacillus paracasei, Megamonas hypermegale|Lactobacillus paracasei, Megasphaera micronuciformis|Lactobacillus paracasei, Methanobrevibacter smithii|Lactobacillus paracasei, Methanosphaera stadtmanae|Lactobacillus paracasei, Methylobacterium radiotolerans|Lactobacillus paracasei, Mitsuokella multacida|Lactobacillus paracasei, Mobiluncus curtisii|Lactobacillus paracasei, Mycoplasma hominis|Lactobacillus paracasei, Neisseria mucosa|Lactobacillus paracasei, Odoribacter TABLE 2-continued Table 2. Specific binary combinations of OTUs. Individual pairings are differentiated by "|" and OTUs within a combination are differentiated by ","

*splanchnicus|Lactobacillus paracasei, Olsenella uli|Lactobacillus paracasei, Oribacterium sinus|Lactobacillus paracasei, Oxalobacter formigenes|Lactobacillus paracasei, Parabacteroides distasonis|Lactobacillus paracasei, Parabacteroides johnsonii|Lactobacillus paracasei, Parabacteroides merdae|Lactobacillus paracasei, Parvimonas micra|Lactobacillus paracasei, Pediococcus acidilactici|Lactobacillus paracasei, Pediococcus pentosaceus|Lactobacillus paracasei, Peptoniphilus duerdenii|Lactobacillus paracasei, Peptoniphilus harei|Lactobacillus paracasei, Peptoniphilus lacrimalis|Lactobacillus paracasei, Peptostreptococcus anaerobius|Lactobacillus paracasei, Peptostreptococcus stomatis|Lactobacillus paracasei, Porphyromonas asaccharolytica|Lactobacillus paracasei, Porphyromonas uenonis|Lactobacillus paracasei, Prevotella amnii|Lactobacillus paracasei, Prevotella bergensis|Lactobacillus paracasei, Prevotella bivia|Lactobacillus paracasei, Prevotella buccae|Lactobacillus paracasei, Prevotella buccalis|Lactobacillus paracasei, Prevotella copri|Lactobacillus paracasei, Prevotella disiens|Lactobacillus paracasei, Prevotella melaninogenica|Lactobacillus paracasei, Prevotella multiformis|Lactobacillus paracasei, Prevotella oralis|Lactobacillus paracasei, Prevotella oris|Lactobacillus paracasei, Prevotella salivae|Lactobacillus paracasei, Prevotella timonensis|Lactobacillus paracasei, Propionibacterium acnes|Lactobacillus paracasei, Propionibacterium freudenreichii|Lactobacillus paracasei, Proteus mirabilis|Lactobacillus paracasei, Proteus penneri|Lactobacillus paracasei, Pseudoflavonifractor capillosus|Lactobacillus paracasei, Pseudomonas aeruginosa|Lactobacillus paracasei, Pseudomonas fluorescens|Lactobacillus paracasei, Pseudomonas putida|Lactobacillus paracasei, Pseudoramibacter alactolyticus|Lactobacillus paracasei, Pyramidobacter piscolens|Lactobacillus paracasei, Rhodopseudomonas palustris|Lactobacillus paracasei, Roseburia intestinalis|Lactobacillus paracasei, Roseburia inulinivorans|Lactobacillus paracasei, Rothia dentocariosa|Lactobacillus paracasei, Rothia mucilaginosa|Lactobacillus paracasei, Ruminococcus albus|Lactobacillus paracasei, Ruminococcus bromii|Lactobacillus paracasei, Ruminococcus gnavus|Lactobacillus paracasei, Ruminococcus lactaris|Lactobacillus paracasei, Ruminococcus obeum|Lactobacillus paracasei, Ruminococcus torques|Lactobacillus paracasei, Selenomonas sputigena|Lactobacillus paracasei, Shigella boydii|Lactobacillus paracasei, Shigella dysenteria|Lactobacillus paracasei, Shigella sonnei|Lactobacillus paracasei, Slackia exigua|Lactobacillus paracasei, Solobacterium moorei|Lactobacillus paracasei, Staphylococcus aureus|Lactobacillus paracasei, Staphylococcus epidermidis|Lactobacillus paracasei, Staphylococcus hominis|Lactobacillus paracasei, Staphylococcus saprophyticus|Lactobacillus paracasei, Staphylococcus warneri|Lactobacillus paracasei, Streptococcus agalactiae|Lactobacillus paracasei, Streptococcus anginosus|Lactobacillus paracasei, Streptococcus australis|Lactobacillus paracasei, Streptococcus bovis|Lactobacillus paracasei, Streptococcus cristatus|Lactobacillus paracasei, Streptococcus dysgalactiae|Lactobacillus paracasei, Streptococcus equinus|Lactobacillus paracasei, Streptococcus gordonii|Lactobacillus paracasei, Streptococcus infantarius|Lactobacillus paracasei, Streptococcus infantis|Lactobacillus paracasei, Streptococcus mitis|Lactobacillus paracasei, Streptococcus mutans|Lactobacillus paracasei, Streptococcus oralis|Lactobacillus paracasei, Streptococcus parasanguinis|Lactobacillus paracasei, Streptococcus peroris|Lactobacillus paracasei, Streptococcus pneumoniae|Lactobacillus paracasei, Streptococcus salivarius|Lactobacillus paracasei, Streptococcus sanguinis|Lactobacillus paracasei, Streptococcus thermophilus|Lactobacillus paracasei, Streptococcus vestibularis|Lactobacillus paracasei, Subdoligranulum variabile|Lactobacillus paracasei, Succinatimonas hippei|Lactobacillus paracasei, Sutterella wadsworthensis|Lactobacillus paracasei, Tropheryma whipplei|Lactobacillus paracasei, Veillonella atypica|Lactobacillus paracasei, Veillonella dispar|Lactobacillus paracasei, Veillonella parvula|Lactobacillus paracasei, Victivallis vadensis|Lactobacillus plantarum, Lactobacillus plantarum|Lactobacillus plantarum, Lactobacillus reuteri|Lactobacillus plantarum, Lactobacillus rhamnosus|Lactobacillus plantarum, Lactobacillus ruminis|Lactobacillus plantarum, Lactobacillus sakei|Lactobacillus plantarum, Lactobacillus salivarius|Lactobacillus plantarum, Lactococcus lactis|Lactobacillus plantarum, Lautropia mirabilis|Lactobacillus plantarum, Leuconostoc citreum|Lactobacillus plantarum, Leuconostoc gasicomitatum|Lactobacillus plantarum, Leuconostoc mesenteroides|Lactobacillus plantarum, Listeria monocytogenes|Lactobacillus plantarum, Marvinbryantia formatexigens|Lactobacillus plantarum, Megamonas hypermegale|Lactobacillus plantarum, Megasphaera micronuciformis|Lactobacillus plantarum, Methanobrevibacter smithii|Lactobacillus plantarum, Methanosphaera stadtmanae|Lactobacillus plantarum, Methylobacterium radiotolerans|Lactobacillus plantarum, Mitsuokella multacida|Lactobacillus plantarum, Mobiluncus curtisii|Lactobacillus plantarum, Mycoplasma hominis|Lactobacillus plantarum, Neisseria mucosa|Lactobacillus plantarum, Odoribacter splanchnicus|Lactobacillus plantarum, Olsenella uli|Lactobacillus plantarum, Oribacterium sinus|Lactobacillus plantarum, Oxalobacter formigenes|Lactobacillus plantarum, Parabacteroides distasonis|Lactobacillus plantarum, Parabacteroides johnsonii|Lactobacillus plantarum, Parabacteroides merdae|Lactobacillus plantarum, Parvimonas micra|Lactobacillus plantarum, Pediococcus acidilactici|Lactobacillus plantarum, Pediococcus pentosaceus|Lactobacillus plantarum, Peptoniphilus duerdenii|Lactobacillus plantarum, Peptoniphilus harei|Lactobacillus plantarum, Peptoniphilus lacrimalis|Lactobacillus plantarum, Peptostreptococcus anaerobius|Lactobacillus plantarum, Peptostreptococcus stomatis|Lactobacillus plantarum, Porphyromonas asaccharolytica|Lactobacillus plantarum, Porphyromonas uenonis|Lactobacillus plantarum, Prevotella amnii|Lactobacillus plantarum, Prevotella bergensis|Lactobacillus plantarum, Prevotella bivia|Lactobacillus plantarum, Prevotella buccae|Lactobacillus plantarum, Prevotella buccalis|Lactobacillus plantarum, Prevotella copri|Lactobacillus plantarum, Prevotella disiens|Lactobacillus plantarum, Prevotella melaninogenica|Lactobacillus plantarum, Prevotella multiformis|Lactobacillus plantarum, Prevotella oralis|Lactobacillus plantarum, Prevotella oris|Lactobacillus plantarum, Prevotella salivae|Lactobacillus plantarum, Prevotella timonensis|Lactobacillus plantarum, Propionibacterium acnes|Lactobacillus plantarum, Propionibacterium freudenreichii|Lactobacillus plantarum, Proteus mirabilis|Lactobacillus plantarum, Proteus penneri|Lactobacillus plantarum, Pseudoflavonifractor capillosus|Lactobacillus plantarum, Pseudomonas aeruginosa|Lactobacillus plantarum, Pseudomonas fluorescens|Lactobacillus plantarum, Pseudomonas putida|Lactobacillus plantarum, Pseudoramibacter alactolyticus|Lactobacillus plantarum, Pyramidobacter piscolens|Lactobacillus plantarum, Rhodopseudomonas palustris|Lactobacillus plantarum, Roseburia intestinalis|Lactobacillus plantarum, Roseburia inulinivorans|Lactobacillus plantarum, Rothia dentocariosa|Lactobacillus plantarum, Rothia mucilaginosa|Lactobacillus plantarum, Ruminococcus albus|Lactobacillus plantarum, Ruminococcus bromii|Lactobacillus plantarum, Ruminococcus gnavus|Lactobacillus plantarum, Ruminococcus lactaris|Lactobacillus plantarum, Ruminococcus obeum|Lactobacillus plantarum, Ruminococcus torques|Lactobacillus plantarum, Selenomonas sputigena|Lactobacillus plantarum, Shigella boydii|Lactobacillus plantarum, Shigella dysenteriae|Lactobacillus plantarum, Shigella sonnei|Lactobacillus plantarum, Slackia exigua|Lactobacillus plantarum, Solobacterium moorei|Lactobacillus plantarum, Staphylococcus aureus|Lactobacillus plantarum, Staphylococcus epidermidis|Lactobacillus plantarum, Staphylococcus hominis|Lactobacillus plantarum, Staphylococcus saprophyticus|Lactobacillus plantarum, Staphylococcus warneri|Lactobacillus plantarum, Streptococcus agalactiae|Lactobacillus plantarum, Streptococcus anginosus|Lactobacillus plantarum, Streptococcus australis|Lactobacillus plantarum, Streptococcus bovis|Lactobacillus plantarum, Streptococcus cristatus|Lactobacillus plantarum, Streptococcus dysgalactiae|Lactobacillus plantarum, Streptococcus equinus|Lactobacillus plantarum, Streptococcus gordonii|Lactobacillus plantarum, Streptococcus infantarius|Lactobacillus plantarum, Streptococcus infantis|Lactobacillus plantarum, Streptococcus mitis|Lactobacillus plantarum, Streptococcus mutans|Lactobacillus plantarum, Streptococcus oralis|Lactobacillus plantarum, Streptococcus parasanguinis|Lactobacillus plantarum, Streptococcus peroris|Lactobacillus plantarum, Streptococcus pneumoniae|Lactobacillus plantarum, Streptococcus salivarius|Lactobacillus plantarum, Streptococcus sanguinis|Lactobacillus plantarum, Streptococcus thermophilus|Lactobacillus plantarum, Streptococcus vestibularis|Lactobacillus plantarum, Subdoligranulum variabile|Lactobacillus plantarum, Succinatimonas hippei|Lactobacillus plantarum, Sutterella wadsworthensis|Lactobacillus plantarum, Tropheryma whipplei|Lactobacillus plantarum, Veillonella atypica|Lactobacillus plantarum, Veillonella dispar|Lactobacillus plantarum, Veillonella parvula|Lactobacillus plantarum, Victivallis vadensis|Lactobacillus reuteri, Lactobacillus reuteri|Lactobacillus reuteri, Lactobacillus rhamnosus, Lactobacillus reuteri, Lactobacillus ruminis|Lactobacillus reuteri, Lactobacillus sakei|Lactobacillus reuteri, Lactobacillus salivarius|Lactobacillus reuteri, Lactococcus lactis|Lactobacillus reuteri, Lautropia mirabilis|Lactobacillus reuteri, Leuconostoc citreum|Lactobacillus reuteri, Leuconostoc gasicomitatum|Lactobacillus reuteri, Leuconostoc mesenteroides|Lactobacillus reuteri, Listeria*

TABLE 2-continued

| Table 2. Specific binary combinations of OTUs. Individual pairings are differentiated by "\|" and OTUs within a combination are differentiated by "," |
|---|
| *monocytogenes\|Lactobacillus reuteri, Marvinbryantia formatexigens\|Lactobacillus reuteri, Megamonas hypermegale\|Lactobacillus reuteri, Megasphaera micronuciformis\|Lactobacillus reuteri, Methanobrevibacter smithii\|Lactobacillus reuteri, Methanosphaera stadtmanae\|Lactobacillus reuteri, Methylobacterium radiotolerans\|Lactobacillus reuteri, Mitsuokella multacida\|Lactobacillus reuteri, Mobiluncus curtisii\|Lactobacillus reuteri, Mycoplasma hominis\|Lactobacillus reuteri, Neisseria mucosa\|Lactobacillus reuteri, Odoribacter splanchnicus\|Lactobacillus reuteri, Olsenella uli\|Lactobacillus reuteri, Oribacterium sinus\|Lactobacillus reuteri, Oxalobacter formigenes\|Lactobacillus reuteri, Parabacteroides distasonis\|Lactobacillus reuteri, Parabacteroides johnsonii\|Lactobacillus reuteri, Parabacteroides merdae\|Lactobacillus reuteri, Parvimonas micra\|Lactobacillus reuteri, Pediococcus acidilactici\|Lactobacillus reuteri, Pediococcus pentosaceus\|Lactobacillus reuteri, Peptoniphilus duerdenii\|Lactobacillus reuteri, Peptoniphilus harei\|Lactobacillus reuteri, Peptoniphilus lacrimalis\|Lactobacillus reuteri, Peptostreptococcus anaerobius\|Lactobacillus reuteri, Peptostreptococcus stomatis\|Lactobacillus reuteri, Porphyromonas asaccharolytica\|Lactobacillus reuteri, Porphyromonas uenonis\|Lactobacillus reuteri, Prevotella amnii\|Lactobacillus reuteri, Prevotella bergensis\|Lactobacillus reuteri, Prevotella bivia\|Lactobacillus reuteri, Prevotella buccae\|Lactobacillus reuteri, Prevotella buccalis\|Lactobacillus reuteri, Prevotella copri\|Lactobacillus reuteri, Prevotella disiens\|Lactobacillus reuteri, Prevotella melaninogenica\|Lactobacillus reuteri, Prevotella multiformis\|Lactobacillus reuteri, Prevotella oralis\|Lactobacillus reuteri, Prevotella oris\|Lactobacillus reuteri, Prevotella salivae\|Lactobacillus reuteri, Prevotella timonensis\|Lactobacillus reuteri, Propionibacterium acnes\|Lactobacillus reuteri, Propionibacterium freudenreichii\|Lactobacillus reuteri, Proteus mirabilis\|Lactobacillus reuteri, Proteus penneri\|Lactobacillus reuteri, Pseudoflavonifractor capillosus\|Lactobacillus reuteri, Pseudomonas aeruginosa\|Lactobacillus reuteri, Pseudomonas fluorescens\|Lactobacillus reuteri, Pseudomonas putida\|Lactobacillus reuteri, Pseudoramibacter alactolyticus\|Lactobacillus reuteri, Pyramidobacter piscolens\|Lactobacillus reuteri, Rhodopseudomonas palustris\|Lactobacillus reuteri, Roseburia intestinalis\|Lactobacillus reuteri, Roseburia inulinivorans\|Lactobacillus reuteri, Rothia dentocariosa\|Lactobacillus reuteri, Rothia mucilaginosa\|Lactobacillus reuteri, Ruminococcus albus\|Lactobacillus reuteri, Ruminococcus bromii\|Lactobacillus reuteri, Ruminococcus gnavus\|Lactobacillus reuteri, Ruminococcus lactaris\|Lactobacillus reuteri, Ruminococcus obeum\|Lactobacillus reuteri, Ruminococcus torques\|Lactobacillus reuteri, Selenomonas sputigena\|Lactobacillus reuteri, Shigella boydii\|Lactobacillus reuteri, Shigella dysenteriae\|Lactobacillus reuteri, Shigella sonnei\|Lactobacillus reuteri, Slackia exigua\|Lactobacillus reuteri, Solobacterium moorei\|Lactobacillus reuteri, Staphylococcus aureus\|Lactobacillus reuteri, Staphylococcus epidermidis\|Lactobacillus reuteri, Staphylococcus hominis\|Lactobacillus reuteri, Staphylococcus saprophyticus\|Lactobacillus reuteri, Staphylococcus warneri\|Lactobacillus reuteri, Streptococcus agalactiae\|Lactobacillus reuteri, Streptococcus anginosus\|Lactobacillus reuteri, Streptococcus australis\|Lactobacillus reuteri, Streptococcus bovis\|Lactobacillus reuteri, Streptococcus cristatus\|Lactobacillus reuteri, Streptococcus dysgalactiae\|Lactobacillus reuteri, Streptococcus equinus\|Lactobacillus reuteri, Streptococcus gordonii\|Lactobacillus reuteri, Streptococcus infantarius\|Lactobacillus reuteri, Streptococcus infantis\|Lactobacillus reuteri, Streptococcus mitis\|Lactobacillus reuteri, Streptococcus mutans\|Lactobacillus reuteri, Streptococcus oralis\|Lactobacillus reuteri, Streptococcus parasanguinis\|Lactobacillus reuteri, Streptococcus peroris\|Lactobacillus reuteri, Streptococcus pneumoniae\|Lactobacillus reuteri, Streptococcus salivarius\|Lactobacillus reuteri, Streptococcus sanguinis\|Lactobacillus reuteri, Streptococcus thermophilus\|Lactobacillus reuteri, Streptococcus vestibularis\|Lactobacillus reuteri, Subdoligranulum variabile\|Lactobacillus reuteri, Succinatimonas hippei\|Lactobacillus reuteri, Sutterella wadsworthensis\|Lactobacillus reuteri, Tropheryma whipplei\|Lactobacillus reuteri, Veillonella atypica\|Lactobacillus reuteri, Veillonella dispar\|Lactobacillus reuteri, Veillonella parvula\|Lactobacillus reuteri, Victivallis vadensis\|Lactobacillus rhamnosus, Lactobacillus rhamnosus, Lactobacillus ruminis\|Lactobacillus rhamnosus, Lactobacillus sakei\|Lactobacillus rhamnosus, Lactobacillus salivarius\|Lactobacillus rhamnosus, Lactococcus lactis\|Lactobacillus rhamnosus, Lautropia mirabilis\|Lactobacillus rhamnosus, Leuconostoc citreum\|Lactobacillus rhamnosus, Leuconostoc gasicomitatum\|Lactobacillus rhamnosus, Leuconostoc mesenteroides\|Lactobacillus rhamnosus, Listeria monocytogenes\|Lactobacillus rhamnosus, Marvinbryantia formatexigens\|Lactobacillus rhamnosus, Megamonas hypermegale\|Lactobacillus rhamnosus, Megasphaera micronuciformis\|Lactobacillus rhamnosus, Methanobrevibacter smithii\|Lactobacillus rhamnosus, Methanosphaera stadtmanae\|Lactobacillus rhamnosus, Methylobacterium radiotolerans\|Lactobacillus rhamnosus, Mitsuokella multacida\|Lactobacillus rhamnosus, Mobiluncus curtisii\|Lactobacillus rhamnosus, Mycoplasma hominis\|Lactobacillus rhamnosus, Neisseria mucosa\|Lactobacillus rhamnosus, Odoribacter splanchnicus\|Lactobacillus rhamnosus, Olsenella uli\|Lactobacillus rhamnosus, Oribacterium sinus\|Lactobacillus rhamnosus, Oxalobacter formigenes\|Lactobacillus rhamnosus, Parabacteroides distasonis\|Lactobacillus rhamnosus, Parabacteroides johnsonii\|Lactobacillus rhamnosus, Parabacteroides merdae\|Lactobacillus rhamnosus, Parvimonas micra\|Lactobacillus rhamnosus, Pediococcus acidilactici\|Lactobacillus rhamnosus, Pediococcus pentosaceus\|Lactobacillus rhamnosus, Peptoniphilus duerdenii\|Lactobacillus rhamnosus, Peptoniphilus harei\|Lactobacillus rhamnosus, Peptoniphilus lacrimalis\|Lactobacillus rhamnosus, Peptostreptococcus anaerobius\|Lactobacillus rhamnosus, Peptostreptococcus stomatis\|Lactobacillus rhamnosus, Porphyromonas asaccharolytica\|Lactobacillus rhamnosus, Porphyromonas uenonis\|Lactobacillus rhamnosus, Prevotella amnii\|Lactobacillus rhamnosus, Prevotella bergensis\|Lactobacillus rhamnosus, Prevotella bivia\|Lactobacillus rhamnosus, Prevotella buccae\|Lactobacillus rhamnosus, Prevotella buccalis\|Lactobacillus rhamnosus, Prevotella copri\|Lactobacillus rhamnosus, Prevotella disiens\|Lactobacillus rhamnosus, Prevotella melaninogenica\|Lactobacillus rhamnosus, Prevotella multiformis\|Lactobacillus rhamnosus, Prevotella oralis\|Lactobacillus rhamnosus, Prevotella oris\|Lactobacillus rhamnosus, Prevotella salivae\|Lactobacillus rhamnosus, Prevotella timonensis\|Lactobacillus rhamnosus, Propionibacterium acnes\|Lactobacillus rhamnosus, Propionibacterium freudenreichii\|Lactobacillus rhamnosus, Proteus mirabilis\|Lactobacillus rhamnosus, Proteus penneri\|Lactobacillus rhamnosus, Pseudoflavonifractor capillosus\|Lactobacillus rhamnosus, Pseudomonas aeruginosa\|Lactobacillus rhamnosus, Pseudomonas fluorescens\|Lactobacillus rhamnosus, Pseudomonas putida\|Lactobacillus rhamnosus, Pseudoramibacter alactolyticus\|Lactobacillus rhamnosus, Pyramidobacter piscolens\|Lactobacillus rhamnosus, Rhodopseudomonas palustris\|Lactobacillus rhamnosus, Roseburia intestinalis\|Lactobacillus rhamnosus, Roseburia inulinivorans\|Lactobacillus rhamnosus, Rothia dentocariosa\|Lactobacillus rhamnosus, Rothia mucilaginosa\|Lactobacillus rhamnosus, Ruminococcus albus\|Lactobacillus rhamnosus, Ruminococcus bromii\|Lactobacillus rhamnosus, Ruminococcus gnavus\|Lactobacillus rhamnosus, Ruminococcus lactaris\|Lactobacillus rhamnosus, Ruminococcus obeum\|Lactobacillus rhamnosus, Ruminococcus torques\|Lactobacillus rhamnosus, Selenomonas sputigena\|Lactobacillus rhamnosus, Shigella boydii\|Lactobacillus rhamnosus, Shigella dysenteriae\|Lactobacillus rhamnosus, Shigella sonnei\|Lactobacillus rhamnosus, Slackia exigua\|Lactobacillus rhamnosus, Solobacterium moorei\|Lactobacillus rhamnosus, Staphylococcus aureus\|Lactobacillus rhamnosus, Staphylococcus epidermidis\|Lactobacillus rhamnosus, Staphylococcus hominis\|Lactobacillus rhamnosus, Staphylococcus saprophyticus\|Lactobacillus rhamnosus, Staphylococcus warneri\|Lactobacillus rhamnosus, Streptococcus agalactiae\|Lactobacillus rhamnosus, Streptococcus anginosus\|Lactobacillus rhamnosus, Streptococcus australis\|Lactobacillus rhamnosus, Streptococcus bovis\|Lactobacillus rhamnosus, Streptococcus cristatus\|Lactobacillus rhamnosus, Streptococcus dysgalactiae\|Lactobacillus rhamnosus, Streptococcus equinus\|Lactobacillus rhamnosus, Streptococcus gordonii\|Lactobacillus rhamnosus, Streptococcus infantarius\|Lactobacillus rhamnosus, Streptococcus infantis\|Lactobacillus rhamnosus, Streptococcus mitis\|Lactobacillus rhamnosus, Streptococcus mutans\|Lactobacillus rhamnosus, Streptococcus oralis\|Lactobacillus rhamnosus, Streptococcus parasanguinis\|Lactobacillus rhamnosus, Streptococcus peroris\|Lactobacillus rhamnosus, Streptococcus pneumoniae\|Lactobacillus rhamnosus, Streptococcus salivarius\|Lactobacillus rhamnosus, Streptococcus sanguinis\|Lactobacillus rhamnosus, Streptococcus thermophilus\|Lactobacillus rhamnosus, Streptococcus vestibularis\|Lactobacillus rhamnosus, Subdoligranulum variabile\|Lactobacillus rhamnosus, Succinatimonas hippei\|Lactobacillus rhamnosus, Sutterella wadsworthensis\|Lactobacillus rhamnosus, Tropheryma whipplei\|Lactobacillus rhamnosus, Veillonella atypica\|Lactobacillus rhamnosus, Veillonella dispar\|Lactobacillus rhamnosus, Veillonella parvula\|Lactobacillus rhamnosus, Victivallis vadensis\|Lactobacillus ruminis, Lactobacillus ruminis\|Lactobacillus ruminis, Lactobacillus sakei\|Lactobacillus ruminis, Lactobacillus salivarius\|Lactobacillus ruminis, Lactococcus lactis\|Lactobacillus ruminis, Lautropia mirabilis\|Lactobacillus ruminis, Leuconostoc* |

TABLE 2-continued

Table 2. Specific binary combinations of OTUs. Individual pairings are differentiated by "|" and OTUs within a combination are differentiated by ","

*citreum|Lactobacillus ruminis, Leuconostoc gasicomitatum|Lactobacillus ruminis, Leuconostoc mesenteroides|Lactobacillus ruminis, Listeria monocytogenes|Lactobacillus ruminis, Marvinbryantia formatexigens|Lactobacillus ruminis, Megamonas hypermegale|Lactobacillus ruminis, Megasphaera micronuciformis|Lactobacillus ruminis, Methanobrevibacter smithii|Lactobacillus ruminis, Methanosphaera stadtmanae|Lactobacillus ruminis, Methylobacterium radiotolerans|Lactobacillus ruminis, Mitsuokella multacida|Lactobacillus ruminis, Mobiluncus curtisii|Lactobacillus ruminis, Mycoplasma hominis|Lactobacillus ruminis, Neisseria mucosa|Lactobacillus ruminis, Odoribacter splanchnicus|Lactobacillus ruminis, Olsenella uli|Lactobacillus ruminis, Oribacterium sinus|Lactobacillus ruminis, Oxalobacter formigenes|Lactobacillus ruminis, Parabacteroides distasonis|Lactobacillus ruminis, Parabacteroides johnsonii|Lactobacillus ruminis, Parabacteroides merdae|Lactobacillus ruminis, Parvimonas micra|Lactobacillus ruminis, Pediococcus acidilactici|Lactobacillus ruminis, Pediococcus pentosaceus|Lactobacillus ruminis, Peptoniphilus duerdenii|Lactobacillus ruminis, Peptoniphilus harei|Lactobacillus ruminis, Peptoniphilus lacrimalis|Lactobacillus ruminis, Peptostreptococcus anaerobius|Lactobacillus ruminis, Peptostreptococcus stomatis|Lactobacillus ruminis, Porphyromonas asaccharolytica|Lactobacillus ruminis, Porphyromonas uenonis|Lactobacillus ruminis, Prevotella amnii|Lactobacillus ruminis, Prevotella bergensis|Lactobacillus ruminis, Prevotella bivia|Lactobacillus ruminis, Prevotella buccae|Lactobacillus ruminis, Prevotella buccalis|Lactobacillus ruminis, Prevotella copri|Lactobacillus ruminis, Prevotella disiens|Lactobacillus ruminis, Prevotella melaninogenica|Lactobacillus ruminis, Prevotella multiformis|Lactobacillus ruminis, Prevotella oralis|Lactobacillus ruminis, Prevotella oris|Lactobacillus ruminis, Prevotella salivae|Lactobacillus ruminis, Prevotella timonensis|Lactobacillus ruminis, Propionibacterium acnes|Lactobacillus ruminis, Propionibacterium freudenreichii|Lactobacillus ruminis, Proteus mirabilis|Lactobacillus ruminis, Proteus penneri|Lactobacillus ruminis, Pseudoflavonifractor capillosus|Lactobacillus ruminis, Pseudomonas aeruginosa|Lactobacillus ruminis, Pseudomonas fluorescens|Lactobacillus ruminis, Pseudomonas putida|Lactobacillus ruminis, Pseudoramibacter alactolyticus|Lactobacillus ruminis, Pyramidobacter piscolens|Lactobacillus ruminis, Rhodopseudomonas palustris|Lactobacillus ruminis, Roseburia intestinalis|Lactobacillus ruminis, Roseburia inulinivorans|Lactobacillus ruminis, Rothia dentocariosa|Lactobacillus ruminis, Rothia mucilaginosa|Lactobacillus ruminis, Ruminococcus albus|Lactobacillus ruminis, Ruminococcus bromii|Lactobacillus ruminis, Ruminococcus gnavus|Lactobacillus ruminis, Ruminococcus lactaris|Lactobacillus ruminis, Ruminococcus obeum|Lactobacillus ruminis, Ruminococcus torques|Lactobacillus ruminis, Selenomonas sputigena|Lactobacillus ruminis, Shigella boydii|Lactobacillus ruminis, Shigella dysenteriae|Lactobacillus ruminis, Shigella sonnei|Lactobacillus ruminis, Slackia exigua|Lactobacillus ruminis, Solobacterium moorei|Lactobacillus ruminis, Staphylococcus aureus|Lactobacillus ruminis, Staphylococcus epidermidis|Lactobacillus ruminis, Staphylococcus hominis|Lactobacillus ruminis, Staphylococcus saprophyticus|Lactobacillus ruminis, Staphylococcus warneri|Lactobacillus ruminis, Streptococcus agalactiae|Lactobacillus ruminis, Streptococcus anginosus|Lactobacillus ruminis, Streptococcus australis|Lactobacillus ruminis, Streptococcus bovis|Lactobacillus ruminis, Streptococcus cristatus|Lactobacillus ruminis, Streptococcus dysgalactiae|Lactobacillus ruminis, Streptococcus equinus|Lactobacillus ruminis, Streptococcus gordonii|Lactobacillus ruminis, Streptococcus infantarius|Lactobacillus ruminis, Streptococcus infantis|Lactobacillus ruminis, Streptococcus mitis|Lactobacillus ruminis, Streptococcus mutans|Lactobacillus ruminis, Streptococcus oralis|Lactobacillus ruminis, Streptococcus parasanguinis|Lactobacillus ruminis, Streptococcus peroris|Lactobacillus ruminis, Streptococcus pneumoniae|Lactobacillus ruminis, Streptococcus salivarius|Lactobacillus ruminis, Streptococcus sanguinis|Lactobacillus ruminis, Streptococcus thermophilus|Lactobacillus ruminis, Streptococcus vestibularis|Lactobacillus ruminis, Subdoligranulum variabile|Lactobacillus ruminis, Succinatimonas hippei|Lactobacillus ruminis, Sutterella wadsworthensis|Lactobacillus ruminis, Tropheryma whipplei|Lactobacillus ruminis, Veillonella atypica|Lactobacillus ruminis, Veillonella dispar|Lactobacillus ruminis, Veillonella parvula|Lactobacillus ruminis, Victivallis vadensis|Lactobacillus sakei, Lactobacillus sakei|Lactobacillus sakei, Lactobacillus salivarius|Lactobacillus sakei, Lactococcus lactis|Lactobacillus sakei, Lautropia mirabilis|Lactobacillus sakei, Leuconostoc citreum|Lactobacillus sakei, Leuconostoc gasicomitatum|Lactobacillus sakei, Leuconostoc mesenteroides|Lactobacillus sakei, Listeria monocytogenes|Lactobacillus sakei, Marvinbryantia formatexigens|Lactobacillus sakei, Megamonas hypermegale|Lactobacillus sakei, Megasphaera micronuciformis|Lactobacillus sakei, Methanobrevibacter smithii|Lactobacillus sakei, Methanosphaera stadtmanae|Lactobacillus sakei, Methylobacterium radiotolerans|Lactobacillus sakei, Mitsuokella multacida|Lactobacillus sakei, Mobiluncus curtisii|Lactobacillus sakei, Mycoplasma hominis|Lactobacillus sakei, Neisseria mucosa|Lactobacillus sakei, Odoribacter splanchnicus|Lactobacillus sakei, Olsenella uli|Lactobacillus sakei, Oribacterium sinus|Lactobacillus sakei, Oxalobacter formigenes|Lactobacillus sakei, Parabacteroides distasonis|Lactobacillus sakei, Parabacteroides johnsonii|Lactobacillus sakei, Parabacteroides merdae|Lactobacillus sakei, Parvimonas micra|Lactobacillus sakei, Pediococcus acidilactici|Lactobacillus sakei, Pediococcus pentosaceus|Lactobacillus sakei, Peptoniphilus duerdenii|Lactobacillus sakei, Peptoniphilus harei|Lactobacillus sakei, Peptoniphilus lacrimalis|Lactobacillus sakei, Peptostreptococcus anaerobius|Lactobacillus sakei, Peptostreptococcus stomatis|Lactobacillus sakei, Porphyromonas asaccharolytica|Lactobacillus sakei, Porphyromonas uenonis|Lactobacillus sakei, Prevotella amnii|Lactobacillus sakei, Prevotella bergensis|Lactobacillus sakei, Prevotella bivia|Lactobacillus sakei, Prevotella buccae|Lactobacillus sakei, Prevotella buccalis|Lactobacillus sakei, Prevotella copri|Lactobacillus sakei, Prevotella disiens|Lactobacillus sakei, Prevotella melaninogenica|Lactobacillus sakei, Prevotella multiformis|Lactobacillus sakei, Prevotella oralis|Lactobacillus sakei, Prevotella oris|Lactobacillus sakei, Prevotella salivae|Lactobacillus sakei, Prevotella timonensis|Lactobacillus sakei, Propionibacterium acnes|Lactobacillus sakei, Propionibacterium freudenreichii|Lactobacillus sakei, Proteus mirabilis|Lactobacillus sakei, Proteus penneri|Lactobacillus sakei, Pseudoflavonifractor capillosus|Lactobacillus sakei, Pseudomonas aeruginosa|Lactobacillus sakei, Pseudomonas fluorescens|Lactobacillus sakei, Pseudomonas putida|Lactobacillus sakei, Pseudoramibacter alactolyticus|Lactobacillus sakei, Pyramidobacter piscolens|Lactobacillus sakei, Rhodopseudomonas palustris|Lactobacillus sakei, Roseburia intestinalis|Lactobacillus sakei, Roseburia inulinivorans|Lactobacillus sakei, Rothia dentocariosa|Lactobacillus sakei, Rothia mucilaginosa|Lactobacillus sakei, Ruminococcus albus|Lactobacillus sakei, Ruminococcus bromii|Lactobacillus sakei, Ruminococcus gnavus|Lactobacillus sakei, Ruminococcus lactaris|Lactobacillus sakei, Ruminococcus obeum|Lactobacillus sakei, Ruminococcus torques|Lactobacillus sakei, Selenomonas sputigena|Lactobacillus sakei, Shigella boydii|Lactobacillus sakei, Shigella dysenteriae|Lactobacillus sakei, Shigella sonnei|Lactobacillus sakei, Slackia exigua|Lactobacillus sakei, Solobacterium moorei|Lactobacillus sakei, Staphylococcus aureus|Lactobacillus sakei, Staphylococcus epidermidis|Lactobacillus sakei, Staphylococcus hominis|Lactobacillus sakei, Staphylococcus saprophyticus|Lactobacillus sakei, Staphylococcus warneri|Lactobacillus sakei, Streptococcus agalactiae|Lactobacillus sakei, Streptococcus anginosus|Lactobacillus sakei, Streptococcus australis|Lactobacillus sakei, Streptococcus bovis|Lactobacillus sakei, Streptococcus cristatus|Lactobacillus sakei, Streptococcus dysgalactiae|Lactobacillus sakei, Streptococcus equinus|Lactobacillus sakei, Streptococcus gordonii|Lactobacillus sakei, Streptococcus infantarius|Lactobacillus sakei, Streptococcus infantis|Lactobacillus sakei, Streptococcus mitis|Lactobacillus sakei, Streptococcus mutans|Lactobacillus sakei, Streptococcus oralis|Lactobacillus sakei, Streptococcus parasanguinis|Lactobacillus sakei, Streptococcus peroris|Lactobacillus sakei, Streptococcus pneumoniae|Lactobacillus sakei, Streptococcus salivarius|Lactobacillus sakei, Streptococcus sanguinis|Lactobacillus sakei, Streptococcus thermophilus|Lactobacillus sakei, Streptococcus vestibularis|Lactobacillus sakei, Subdoligranulum variabile|Lactobacillus sakei, Succinatimonas hippei|Lactobacillus sakei, Sutterella wadsworthensis|Lactobacillus sakei, Tropheryma whipplei|Lactobacillus sakei, Veillonella atypica|Lactobacillus sakei, Veillonella dispar|Lactobacillus sakei, Veillonella parvula|Lactobacillus sakei, Victivallis vadensis|Lactobacillus salivarius, Lactobacillus salivarius|Lactobacillus salivarius, Lactococcus lactis|Lactobacillus salivarius, Lautropia mirabilis|Lactobacillus salivarius, Leuconostoc citreum|Lactobacillus salivarius, Leuconostoc gasicomitatum|Lactobacillus salivarius, Leuconostoc mesenteroides|Lactobacillus salivarius, Listeria monocytogenes|Lactobacillus salivarius, Marvinbryantia formatexigens|Lactobacillus salivarius, Megamonas hypermegale|Lactobacillus salivarius, Megasphaera micronuciformis|Lactobacillus salivarius, Methanobrevibacter smithii|Lactobacillus salivarius, Methanosphaera stadtmanae|Lactobacillus salivarius, Methylobacterium radiotolerans|Lactobacillus salivarius, Mitsuokella multacida|Lactobacillus salivarius, Mobiluncus*

TABLE 2-continued

Table 2. Specific binary combinations of OTUs. Individual pairings are differentiated by "|" and OTUs within a combination are differentiated by ","

curtisii|Lactobacillus salivarius, Mycoplasma hominis|Lactobacillus salivarius, Neisseria mucosa|Lactobacillus salivarius, Odoribacter splanchnicus|Lactobacillus salivarius, Olsenella uli|Lactobacillus salivarius, Oribacterium sinus|Lactobacillus salivarius, Oxalobacter formigenes|Lactobacillus salivarius, Parabacteroides distasonis|Lactobacillus salivarius, Parabacteroides johnsonii|Lactobacillus salivarius, Parabacteroides merdae|Lactobacillus salivarius, Parvimonas micra|Lactobacillus salivarius, Pediococcus acidilactici|Lactobacillus salivarius, Pediococcus pentosaceus|Lactobacillus salivarius, Peptoniphilus duerdenii|Lactobacillus salivarius, Peptoniphilus harei|Lactobacillus salivarius, Peptoniphilus lacrimalis|Lactobacillus salivarius, Peptostreptococcus anaerobius|Lactobacillus salivarius, Peptostreptococcus stomatis|Lactobacillus salivarius, Porphyromonas asaccharolytica|Lactobacillus salivarius, Porphyromonas uenonis|Lactobacillus salivarius, Prevotella amnii|Lactobacillus salivarius, Prevotella bergensis|Lactobacillus salivarius, Prevotella bivia|Lactobacillus salivarius, Prevotella buccae|Lactobacillus salivarius, Prevotella buccalis|Lactobacillus salivarius, Prevotella copri|Lactobacillus salivarius, Prevotella disiens|Lactobacillus salivarius, Prevotella melaninogenica|Lactobacillus salivarius, Prevotella multiformis|Lactobacillus salivarius, Prevotella oralis|Lactobacillus salivarius, Prevotella oris|Lactobacillus salivarius, Prevotella salivae|Lactobacillus salivarius, Prevotella timonensis|Lactobacillus salivarius, Propionibacterium acnes|Lactobacillus salivarius, Propionibacterium freudenreichii|Lactobacillus salivarius, Proteus mirabilis|Lactobacillus salivarius, Proteus penneri|Lactobacillus salivarius, Pseudoflavonifractor capillosus|Lactobacillus salivarius, Pseudomonas aeruginosa|Lactobacillus salivarius, Pseudomonas fluorescens|Lactobacillus salivarius, Pseudomonas putida|Lactobacillus salivarius, Pseudoramibacter alactolyticus|Lactobacillus salivarius, Pyramidobacter piscolens|Lactobacillus salivarius, Rhodopseudomonas palustris|Lactobacillus salivarius, Roseburia intestinalis|Lactobacillus salivarius, Roseburia inulinivorans|Lactobacillus salivarius, Rothia dentocariosa|Lactobacillus salivarius, Rothia mucilaginosa|Lactobacillus salivarius, Ruminococcus albus|Lactobacillus salivarius, Ruminococcus bromii|Lactobacillus salivarius, Ruminococcus gnavus|Lactobacillus salivarius, Ruminococcus lactaris|Lactobacillus salivarius, Ruminococcus obeum|Lactobacillus salivarius, Ruminococcus torques|Lactobacillus salivarius, Selenomonas sputigena|Lactobacillus salivarius, Shigella boydii|Lactobacillus salivarius, Shigella dysenteriae|Lactobacillus salivarius, Shigella sonnei|Lactobacillus salivarius, Slackia exigua|Lactobacillus salivarius, Solobacterium moorei|Lactobacillus salivarius, Staphylococcus aureus|Lactobacillus salivarius, Staphylococcus epidermidis|Lactobacillus salivarius, Staphylococcus hominis|Lactobacillus salivarius, Staphylococcus saprophyticus|Lactobacillus salivarius, Staphylococcus warneri|Lactobacillus salivarius, Streptococcus agalactiae|Lactobacillus salivarius, Streptococcus anginosus|Lactobacillus salivarius, Streptococcus australis|Lactobacillus salivarius, Streptococcus bovis|Lactobacillus salivarius, Streptococcus cristatus|Lactobacillus salivarius, Streptococcus dysgalactiae|Lactobacillus salivarius, Streptococcus equinus|Lactobacillus salivarius, Streptococcus gordonii|Lactobacillus salivarius, Streptococcus infantarius|Lactobacillus salivarius, Streptococcus infantis|Lactobacillus salivarius, Streptococcus mitis|Lactobacillus salivarius, Streptococcus mutans|Lactobacillus salivarius, Streptococcus oralis|Lactobacillus salivarius, Streptococcus parasanguinis|Lactobacillus salivarius, Streptococcus peroris|Lactobacillus salivarius, Streptococcus pneumoniae|Lactobacillus salivarius, Streptococcus salivarius|Lactobacillus salivarius, Streptococcus sanguinis|Lactobacillus salivarius, Streptococcus thermophilus|Lactobacillus salivarius, Streptococcus vestibularis|Lactobacillus salivarius, Subdoligranulum variabile|Lactobacillus salivarius, Succinatimonas hippei|Lactobacillus salivarius, Sutterella wadsworthensis|Lactobacillus salivarius, Tropheryma whipplei|Lactobacillus salivarius, Veillonella atypica|Lactobacillus salivarius, Veillonella dispar|Lactobacillus salivarius, Veillonella parvula|Lactobacillus salivarius, Victivallis vadensis|Lactococcus lactis, Lactococcus lactis|Lactococcus lactis, Lautropia mirabilis|Lactococcus lactis, Leuconostoc citreum|Lactococcus lactis, Leuconostoc gasicomitatum|Lactococcus lactis, Leuconostoc mesenteroides|Lactococcus lactis, Listeria monocytogenes|Lactococcus lactis, Marvinbryantia formatexigens|Lactococcus lactis, Megamonas hypermegale|Lactococcus lactis, Megasphaera micronuciformis|Lactococcus lactis, Methanobrevibacter smithii|Lactococcus lactis, Methanosphaera stadtmanae|Lactococcus lactis, Methylobacterium radiotolerans|Lactococcus lactis, Mitsuokella multacida|Lactococcus lactis, Mobiluncus curtisii|Lactococcus lactis, Mycoplasma hominis|Lactococcus lactis, Neisseria mucosa|Lactococcus lactis, Odoribacter splanchnicus|Lactococcus lactis, Olsenella uli|Lactococcus lactis, Oribacterium sinus|Lactococcus lactis, Oxalobacter formigenes|Lactococcus lactis, Parabacteroides distasonis|Lactococcus lactis, Parabacteroides johnsonii|Lactococcus lactis, Parabacteroides merdae|Lactococcus lactis, Parvimonas micra|Lactococcus lactis, Pediococcus acidilactici|Lactococcus lactis, Pediococcus pentosaceus|Lactococcus lactis, Peptoniphilus duerdenii|Lactococcus lactis, Peptoniphilus harei|Lactococcus lactis, Peptoniphilus lacrimalis|Lactococcus lactis, Peptostreptococcus anaerobius|Lactococcus lactis, Peptostreptococcus stomatis|Lactococcus lactis, Porphyromonas asaccharolytica|Lactococcus lactis, Porphyromonas uenonis|Lactococcus lactis, Prevotella amnii|Lactococcus lactis, Prevotella bergensis|Lactococcus lactis, Prevotella bivia|Lactococcus lactis, Prevotella buccae|Lactococcus lactis, Prevotella buccalis|Lactococcus lactis, Prevotella copri|Lactococcus lactis, Prevotella disiens|Lactococcus lactis, Prevotella melaninogenica|Lactococcus lactis, Prevotella multiformis|Lactococcus lactis, Prevotella oralis|Lactococcus lactis, Prevotella oris|Lactococcus lactis, Prevotella salivae|Lactococcus lactis, Prevotella timonensis|Lactococcus lactis, Propionibacterium acnes|Lactococcus lactis, Propionibacterium freudenreichii|Lactococcus lactis, Proteus mirabilis|Lactococcus lactis, Proteus penneri|Lactococcus lactis, Pseudoflavonifractor capillosus|Lactococcus lactis, Pseudomonas aeruginosa|Lactococcus lactis, Pseudomonas fluorescens|Lactococcus lactis, Pseudomonas putida|Lactococcus lactis, Pseudoramibacter alactolyticus|Lactococcus lactis, Pyramidobacter piscolens|Lactococcus lactis, Rhodopseudomonas palustris|Lactococcus lactis, Roseburia intestinalis|Lactococcus lactis, Roseburia inulinivorans|Lactococcus lactis, Rothia dentocariosa|Lactococcus lactis, Rothia mucilaginosa|Lactococcus lactis, Ruminococcus albus|Lactococcus lactis, Ruminococcus bromii|Lactococcus lactis, Ruminococcus gnavus|Lactococcus lactis, Ruminococcus lactaris|Lactococcus lactis, Ruminococcus obeum|Lactococcus lactis, Ruminococcus torques|Lactococcus lactis, Selenomonas sputigena|Lactococcus lactis, Shigella boydii|Lactococcus lactis, Shigella dysenteriae|Lactococcus lactis, Shigella sonnei|Lactococcus lactis, Slackia exigua|Lactococcus lactis, Solobacterium moorei|Lactococcus lactis, Staphylococcus aureus|Lactococcus lactis, Staphylococcus epidermidis|Lactococcus lactis, Staphylococcus hominis|Lactococcus lactis, Staphylococcus saprophyticus|Lactococcus lactis, Staphylococcus warneri|Lactococcus lactis, Streptococcus agalactiae|Lactococcus lactis, Streptococcus anginosus|Lactococcus lactis, Streptococcus australis|Lactococcus lactis, Streptococcus bovis|Lactococcus lactis, Streptococcus cristatus|Lactococcus lactis, Streptococcus dysgalactiae|Lactococcus lactis, Streptococcus equinus|Lactococcus lactis, Streptococcus gordonii|Lactococcus lactis, Streptococcus infantarius|Lactococcus lactis, Streptococcus infantis|Lactococcus lactis, Streptococcus mitis|Lactococcus lactis, Streptococcus mutans|Lactococcus lactis, Streptococcus oralis|Lactococcus lactis, Streptococcus parasanguinis|Lactococcus lactis, Streptococcus peroris|Lactococcus lactis, Streptococcus pneumoniae|Lactococcus lactis, Streptococcus salivarius|Lactococcus lactis, Streptococcus sanguinis|Lactococcus lactis, Streptococcus thermophilus|Lactococcus lactis, Streptococcus vestibularis|Lactococcus lactis, Subdoligranulum variabile|Lactococcus lactis, Succinatimonas hippei|Lactococcus lactis, Sutterella wadsworthensis|Lactococcus lactis, Tropheryma whipplei|Lactococcus lactis, Veillonella atypica|Lactococcus lactis, Veillonella dispar|Lactococcus lactis, Veillonella parvula|Lactococcus lactis, Victivallis vadensis|Lautropia mirabilis, Lautropia mirabilis|Lautropia mirabilis, Leuconostoc citreum|Lautropia mirabilis, Leuconostoc gasicomitatum|Lautropia mirabilis, Leuconostoc mesenteroides|Lautropia mirabilis, Listeria monocytogenes|Lautropia mirabilis, Marvinbryantia formatexigens|Lautropia mirabilis, Megamonas hypermegale|Lautropia mirabilis, Megasphaera micronuciformis|Lautropia mirabilis, Methanobrevibacter smithii|Lautropia mirabilis, Methanosphaera stadtmanae|Lautropia mirabilis, Methylobacterium radiotolerans|Lautropia mirabilis, Mitsuokella multacida|Lautropia mirabilis, Mobiluncus curtisii|Lautropia mirabilis, Mycoplasma hominis|Lautropia mirabilis, Neisseria mucosa|Lautropia mirabilis, Odoribacter splanchnicus|Lautropia mirabilis, Olsenella uli|Lautropia mirabilis, Oribacterium sinus|Lautropia mirabilis, Oxalobacter formigenes|Lautropia mirabilis, Parabacteroides distasonis|Lautropia mirabilis, Parabacteroides johnsonii|Lautropia mirabilis, Parabacteroides merdae|Lautropia mirabilis, Parvimonas micra|Lautropia mirabilis, Pediococcus acidilactici|Lautropia mirabilis, Pediococcus pentosaceus|Lautropia mirabilis, Peptoniphilus duerdenii|Lautropia mirabilis, Peptoniphilus harei|Lautropia mirabilis, Peptoniphilus TABLE 2-continued Table 2. Specific binary combinations of OTUs. Individual pairings are differentiated by "|" and OTUs within a combination are differentiated by ","

*lacrimalis|Lautropia mirabilis, Peptostreptococcus anaerobius|Lautropia mirabilis, Peptostreptococcus stomatis|Lautropia mirabilis, Porphyromonas asaccharolytica|Lautropia mirabilis, Porphyromonas uenonis|Lautropia mirabilis, Prevotella amnii|Lautropia mirabilis, Prevotella bergensis|Lautropia mirabilis, Prevotella bivia|Lautropia mirabilis, Prevotella buccae|Lautropia mirabilis, Prevotella buccalis|Lautropia mirabilis, Prevotella copri|Lautropia mirabilis, Prevotella disiens|Lautropia mirabilis, Prevotella melaninogenica|Lautropia mirabilis, Prevotella multiformis|Lautropia mirabilis, Prevotella oralis|Lautropia mirabilis, Prevotella oris|Lautropia mirabilis, Prevotella salivae|Lautropia mirabilis, Prevotella timonensis|Lautropia mirabilis, Propionibacterium acnes|Lautropia mirabilis, Propionibacterium freudenreichii|Lautropia mirabilis, Proteus mirabilis|Lautropia mirabilis, Proteus penneri|Lautropia mirabilis, Pseudoflavonifractor capillosus|Lautropia mirabilis, Pseudomonas aeruginosa|Lautropia mirabilis, Pseudomonas fluorescens|Lautropia mirabilis, Pseudomonas putida|Lautropia mirabilis, Pseudoramibacter alactolyticus|Lautropia mirabilis, Pyramidobacter piscolens|Lautropia mirabilis, Rhodopseudomonas palustris|Lautropia mirabilis, Roseburia intestinalis|Lautropia mirabilis, Roseburia inulinivorans|Lautropia mirabilis, Rothia dentocariosa|Lautropia mirabilis, Rothia mucilaginosa|Lautropia mirabilis, Ruminococcus albus|Lautropia mirabilis, Ruminococcus bromii|Lautropia mirabilis, Ruminococcus gnavus|Lautropia mirabilis, Ruminococcus lactaris|Lautropia mirabilis, Ruminococcus obeum|Lautropia mirabilis, Ruminococcus torques|Lautropia mirabilis, Selenomonas sputigena|Lautropia mirabilis, Shigella boydii|Lautropia mirabilis, Shigella dysenteriae|Lautropia mirabilis, Shigella sonnei|Lautropia mirabilis, Slackia exigua|Lautropia mirabilis, Solobacterium moorei|Lautropia mirabilis, Staphylococcus aureus|Lautropia mirabilis, Staphylococcus epidermidis|Lautropia mirabilis, Staphylococcus hominis|Lautropia mirabilis, Staphylococcus saprophyticus|Lautropia mirabilis, Staphylococcus warneri|Lautropia mirabilis, Streptococcus agalactiae|Lautropia mirabilis, Streptococcus anginosus|Lautropia mirabilis, Streptococcus australis|Lautropia mirabilis, Streptococcus bovis|Lautropia mirabilis, Streptococcus cristatus|Lautropia mirabilis, Streptococcus dysgalactiae|Lautropia mirabilis, Streptococcus equinus|Lautropia mirabilis, Streptococcus gordonii|Lautropia mirabilis, Streptococcus infantarius|Lautropia mirabilis, Streptococcus infantis|Lautropia mirabilis, Streptococcus mitis|Lautropia mirabilis, Streptococcus mutans|Lautropia mirabilis, Streptococcus oralis|Lautropia mirabilis, Streptococcus parasanguinis|Lautropia mirabilis, Streptococcus peroris|Lautropia mirabilis, Streptococcus pneumoniae|Lautropia mirabilis, Streptococcus salivarius|Lautropia mirabilis, Streptococcus sanguinis|Lautropia mirabilis, Streptococcus thermophilus|Lautropia mirabilis, Streptococcus vestibularis|Lautropia mirabilis, Subdoligranulum variabile|Lautropia mirabilis, Succinatimonas hippei|Lautropia mirabilis, Sutterella wadsworthensis|Lautropia mirabilis, Tropheryma whipplei|Lautropia mirabilis, Veillonella atypica|Lautropia mirabilis, Veillonella dispar|Lautropia mirabilis, Veillonella parvula|Lautropia mirabilis, Victivallis vadensis|Leuconostoc citreum, Leuconostoc citreum|Leuconostoc citreum, Leuconostoc gasicomitatum|Leuconostoc citreum, Leuconostoc mesenteroides|Leuconostoc citreum, Listeria monocytogenes|Leuconostoc citreum, Marvinbryantia formatexigens|Leuconostoc citreum, Megamonas hypermegale|Leuconostoc citreum, Megasphaera micronuciformis|Leuconostoc citreum, Methanobrevibacter smithii|Leuconostoc citreum, Methanosphaera stadtmanae|Leuconostoc citreum, Methylobacterium radiotolerans|Leuconostoc citreum, Mitsuokella multacida|Leuconostoc citreum, Mobiluncus curtisii|Leuconostoc citreum, Mycoplasma hominis|Leuconostoc citreum, Neisseria mucosa|Leuconostoc citreum, Odoribacter splanchnicus|Leuconostoc citreum, Olsenella uli|Leuconostoc citreum, Oribacterium sinus|Leuconostoc citreum, Oxalobacter formigenes|Leuconostoc citreum, Parabacteroides distasonis|Leuconostoc citreum, Parabacteroides johnsonii|Leuconostoc citreum, Parabacteroides merdae|Leuconostoc citreum, Parvimonas micra|Leuconostoc citreum, Pediococcus acidilactici|Leuconostoc citreum, Pediococcus pentosaceus|Leuconostoc citreum, Peptoniphilus duerdenii|Leuconostoc citreum, Peptoniphilus harei|Leuconostoc citreum, Peptoniphilus lacrimalis|Leuconostoc citreum, Peptostreptococcus anaerobius|Leuconostoc citreum, Peptostreptococcus stomatis|Leuconostoc citreum, Porphyromonas asaccharolytica|Leuconostoc citreum, Porphyromonas uenonis|Leuconostoc citreum, Prevotella amnii|Leuconostoc citreum, Prevotella bergensis|Leuconostoc citreum, Prevotella bivia|Leuconostoc citreum, Prevotella buccae|Leuconostoc citreum, Prevotella buccalis|Leuconostoc citreum, Prevotella copri|Leuconostoc citreum, Prevotella disiens|Leuconostoc citreum, Prevotella melaninogenica|Leuconostoc citreum, Prevotella multiformis|Leuconostoc citreum, Prevotella oralis|Leuconostoc citreum, Prevotella oris|Leuconostoc citreum, Prevotella salivae|Leuconostoc citreum, Prevotella timonensis|Leuconostoc citreum, Propionibacterium acnes|Leuconostoc citreum, Propionibacterium freudenreichii|Leuconostoc citreum, Proteus mirabilis|Leuconostoc citreum, Proteus penneri|Leuconostoc citreum, Pseudoflavonifractor capillosus|Leuconostoc citreum, Pseudomonas aeruginosa|Leuconostoc citreum, Pseudomonas fluorescens|Leuconostoc citreum, Pseudomonas putida|Leuconostoc citreum, Pseudoramibacter alactolyticus|Leuconostoc citreum, Pyramidobacter piscolens|Leuconostoc citreum, Rhodopseudomonas palustris|Leuconostoc citreum, Roseburia intestinalis|Leuconostoc citreum, Roseburia inulinivorans|Leuconostoc citreum, Rothia dentocariosa|Leuconostoc citreum, Rothia mucilaginosa|Leuconostoc citreum, Ruminococcus albus|Leuconostoc citreum, Ruminococcus bromii|Leuconostoc citreum, Ruminococcus gnavus|Leuconostoc citreum, Ruminococcus lactaris|Leuconostoc citreum, Ruminococcus obeum|Leuconostoc citreum, Ruminococcus torques|Leuconostoc citreum, Selenomonas sputigena|Leuconostoc citreum, Shigella boydii|Leuconostoc citreum, Shigella dysenteriae|Leuconostoc citreum, Shigella sonnei|Leuconostoc citreum, Slackia exigua|Leuconostoc citreum, Solobacterium moorei|Leuconostoc citreum, Staphylococcus aureus|Leuconostoc citreum, Staphylococcus epidermidis|Leuconostoc citreum, Staphylococcus hominis|Leuconostoc citreum, Staphylococcus saprophyticus|Leuconostoc citreum, Staphylococcus warneri|Leuconostoc citreum, Streptococcus agalactiae|Leuconostoc citreum, Streptococcus anginosus|Leuconostoc citreum, Streptococcus australis|Leuconostoc citreum, Streptococcus bovis|Leuconostoc citreum, Streptococcus cristatus|Leuconostoc citreum, Streptococcus dysgalactiae|Leuconostoc citreum, Streptococcus equinus|Leuconostoc citreum, Streptococcus gordonii|Leuconostoc citreum, Streptococcus infantarius|Leuconostoc citreum, Streptococcus infantis|Leuconostoc citreum, Streptococcus mitis|Leuconostoc citreum, Streptococcus mutans|Leuconostoc citreum, Streptococcus oralis|Leuconostoc citreum, Streptococcus parasanguinis|Leuconostoc citreum, Streptococcus peroris|Leuconostoc citreum, Streptococcus pneumoniae|Leuconostoc citreum, Streptococcus salivarius|Leuconostoc citreum, Streptococcus sanguinis|Leuconostoc citreum, Streptococcus thermophilus|Leuconostoc citreum, Streptococcus vestibularis|Leuconostoc citreum, Subdoligranulum variabile|Leuconostoc citreum, Succinatimonas hippei|Leuconostoc citreum, Sutterella wadsworthensis|Leuconostoc citreum, Tropheryma whipplei|Leuconostoc citreum, Veillonella atypica|Leuconostoc citreum, Veillonella dispar|Leuconostoc citreum, Veillonella parvula|Leuconostoc citreum, Victivallis vadensis|Leuconostoc gasicomitatum, Leuconostoc gasicomitatum|Leuconostoc gasicomitatum, Leuconostoc mesenteroides|Leuconostoc gasicomitatum, Listeria monocytogenes|Leuconostoc gasicomitatum, Marvinbryantia formatexigens|Leuconostoc gasicomitatum, Megamonas hypermegale|Leuconostoc gasicomitatum, Megasphaera micronuciformis|Leuconostoc gasicomitatum, Methanobrevibacter smithii|Leuconostoc gasicomitatum, Methanosphaera stadtmanae|Leuconostoc gasicomitatum, Methylobacterium radiotolerans|Leuconostoc gasicomitatum, Mitsuokella multacida|Leuconostoc gasicomitatum, Mobiluncus curtisii|Leuconostoc gasicomitatum, Mycoplasma hominis|Leuconostoc gasicomitatum, Neisseria mucosa|Leuconostoc gasicomitatum, Odoribacter splanchnicus|Leuconostoc gasicomitatum, Olsenella uli|Leuconostoc gasicomitatum, Oribacterium sinus|Leuconostoc gasicomitatum, Oxalobacter formigenes|Leuconostoc gasicomitatum, Parabacteroides distasonis|Leuconostoc gasicomitatum, Parabacteroides johnsonii|Leuconostoc gasicomitatum, Parabacteroides merdae|Leuconostoc gasicomitatum, Parvimonas micra|Leuconostoc gasicomitatum, Pediococcus acidilactici|Leuconostoc gasicomitatum, Pediococcus pentosaceus|Leuconostoc gasicomitatum, Peptoniphilus duerdenii|Leuconostoc gasicomitatum, Peptoniphilus harei|Leuconostoc gasicomitatum, Peptoniphilus lacrimalis|Leuconostoc gasicomitatum, Peptostreptococcus anaerobius|Leuconostoc gasicomitatum, Peptostreptococcus stomatis|Leuconostoc gasicomitatum, Porphyromonas asaccharolytica|Leuconostoc gasicomitatum, Porphyromonas uenonis|Leuconostoc gasicomitatum, Prevotella amnii|Leuconostoc gasicomitatum, Prevotella bergensis|Leuconostoc gasicomitatum, Prevotella bivia|Leuconostoc gasicomitatum, Prevotella buccae|Leuconostoc gasicomitatum, Prevotella buccalis|Leuconostoc gasicomitatum, Prevotella copri|Leuconostoc gasicomitatum, Prevotella disiens|Leuconostoc gasicomitatum, Prevotella melaninogenica|Leuconostoc gasicomitatum, Prevotella multiformis|Leuconostoc gasicomitatum, Prevotella oralis|Leuconostoc*

TABLE 2-continued

Table 2. Specific binary combinations of OTUs. Individual pairings are differentiated by "|" and OTUs within a combination are differentiated by ","

*gasicomitatum, Prevotella oris|Leuconostoc gasicomitatum, Prevotella salivae|Leuconostoc gasicomitatum, Prevotella timonensis|Leuconostoc gasicomitatum, Propionibacterium acnes|Leuconostoc gasicomitatum, Propionibacterium freudenreichii|Leuconostoc gasicomitatum, Proteus mirabilis|Leuconostoc gasicomitatum, Proteus penneri|Leuconostoc gasicomitatum, Pseudoflavonifractor capillosus|Leuconostoc gasicomitatum, Pseudomonas aeruginosa|Leuconostoc gasicomitatum, Pseudomonas fluorescens|Leuconostoc gasicomitatum, Pseudomonas putida|Leuconostoc gasicomitatum, Pseudoramibacter alactolyticus|Leuconostoc gasicomitatum, Pyramidobacter piscolens|Leuconostoc gasicomitatum, Rhodopseudomonas palustris|Leuconostoc gasicomitatum, Roseburia intestinalis|Leuconostoc gasicomitatum, Roseburia inulinivorans|Leuconostoc gasicomitatum, Rothia dentocariosa|Leuconostoc gasicomitatum, Rothia mucilaginosa|Leuconostoc gasicomitatum, Ruminococcus albus|Leuconostoc gasicomitatum, Ruminococcus bromii|Leuconostoc gasicomitatum, Ruminococcus gnavus|Leuconostoc gasicomitatum, Ruminococcus lactaris|Leuconostoc gasicomitatum, Ruminococcus obeum|Leuconostoc gasicomitatum, Ruminococcus torques|Leuconostoc gasicomitatum, Selenomonas sputigena|Leuconostoc gasicomitatum, Shigella boydii|Leuconostoc gasicomitatum, Shigella dysenteriae|Leuconostoc gasicomitatum, Shigella sonnei|Leuconostoc gasicomitatum, Slackia exigua|Leuconostoc gasicomitatum, Solobacterium moorei|Leuconostoc gasicomitatum, Staphylococcus aureus|Leuconostoc gasicomitatum, Staphylococcus epidermidis|Leuconostoc gasicomitatum, Staphylococcus hominis|Leuconostoc gasicomitatum, Staphylococcus saprophyticus|Leuconostoc gasicomitatum, Staphylococcus warneri|Leuconostoc gasicomitatum, Streptococcus agalactiae|Leuconostoc gasicomitatum, Streptococcus anginosus|Leuconostoc gasicomitatum, Streptococcus australis|Leuconostoc gasicomitatum, Streptococcus bovis|Leuconostoc gasicomitatum, Streptococcus cristatus|Leuconostoc gasicomitatum, Streptococcus dysgalactiae|Leuconostoc gasicomitatum, Streptococcus equinus|Leuconostoc gasicomitatum, Streptococcus gordonii|Leuconostoc gasicomitatum, Streptococcus infantarius|Leuconostoc gasicomitatum, Streptococcus infantis|Leuconostoc gasicomitatum, Streptococcus mitis|Leuconostoc gasicomitatum, Streptococcus mutans|Leuconostoc gasicomitatum, Streptococcus oralis|Leuconostoc gasicomitatum, Streptococcus parasanguinis|Leuconostoc gasicomitatum, Streptococcus peroris|Leuconostoc gasicomitatum, Streptococcus pneumoniae|Leuconostoc gasicomitatum, Streptococcus salivarius|Leuconostoc gasicomitatum, Streptococcus sanguinis|Leuconostoc gasicomitatum, Streptococcus thermophilus|Leuconostoc gasicomitatum, Streptococcus vestibularis|Leuconostoc gasicomitatum, Subdoligranulum variabile|Leuconostoc gasicomitatum, Succinatimonas hippei|Leuconostoc gasicomitatum, Sutterella wadsworthensis|Leuconostoc gasicomitatum, Tropheryma whipplei|Leuconostoc gasicomitatum, Veillonella atypica|Leuconostoc gasicomitatum, Veillonella dispar|Leuconostoc gasicomitatum, Veillonella parvula|Leuconostoc gasicomitatum, Victivallis vadensis|Leuconostoc mesenteroides, Leuconostoc mesenteroides|Leuconostoc mesenteroides, Listeria monocytogenes|Leuconostoc mesenteroides, Marvinbryantia formatexigens|Leuconostoc mesenteroides, Megamonas hypermegale|Leuconostoc mesenteroides, Megasphaera micronuciformis|Leuconostoc mesenteroides, Methanobrevibacter smithii|Leuconostoc mesenteroides, Methanosphaera stadtmanae|Leuconostoc mesenteroides, Methylobacterium radiotolerans|Leuconostoc mesenteroides, Mitsuokella multacida|Leuconostoc mesenteroides, Mobiluncus curtisii|Leuconostoc mesenteroides, Mycoplasma hominis|Leuconostoc mesenteroides, Neisseria mucosa|Leuconostoc mesenteroides, Odoribacter splanchnicus|Leuconostoc mesenteroides, Olsenella uli|Leuconostoc mesenteroides, Oribacterium sinus|Leuconostoc mesenteroides, Oxalobacter formigenes|Leuconostoc mesenteroides, Parabacteroides distasonis|Leuconostoc mesenteroides, Parabacteroides johnsonii|Leuconostoc mesenteroides, Parabacteroides merdae|Leuconostoc mesenteroides, Parvimonas micra|Leuconostoc mesenteroides, Pediococcus acidilactici|Leuconostoc mesenteroides, Pediococcus pentosaceus|Leuconostoc mesenteroides, Peptoniphilus duerdenii|Leuconostoc mesenteroides, Peptoniphilus harei|Leuconostoc mesenteroides, Peptoniphilus lacrimalis|Leuconostoc mesenteroides, Peptostreptococcus anaerobius|Leuconostoc mesenteroides, Peptostreptococcus stomatis|Leuconostoc mesenteroides, Porphyromonas asaccharolytica|Leuconostoc mesenteroides, Porphyromonas uenonis|Leuconostoc mesenteroides, Prevotella amnii|Leuconostoc mesenteroides, Prevotella bergensis|Leuconostoc mesenteroides, Prevotella bivia|Leuconostoc mesenteroides, Prevotella buccae|Leuconostoc mesenteroides, Prevotella buccalis|Leuconostoc mesenteroides, Prevotella copri|Leuconostoc mesenteroides, Prevotella disiens|Leuconostoc mesenteroides, Prevotella melaninogenica|Leuconostoc mesenteroides, Prevotella multiformis|Leuconostoc mesenteroides, Prevotella oralis|Leuconostoc mesenteroides, Prevotella oris|Leuconostoc mesenteroides, Prevotella salivae|Leuconostoc mesenteroides, Prevotella timonensis|Leuconostoc mesenteroides, Propionibacterium acnes|Leuconostoc mesenteroides, Propionibacterium freudenreichii|Leuconostoc mesenteroides, Proteus mirabilis|Leuconostoc mesenteroides, Proteus penneri|Leuconostoc mesenteroides, Pseudoflavonifractor capillosus|Leuconostoc mesenteroides, Pseudomonas aeruginosa|Leuconostoc mesenteroides, Pseudomonas fluorescens|Leuconostoc mesenteroides, Pseudomonas putida|Leuconostoc mesenteroides, Pseudoramibacter alactolyticus|Leuconostoc mesenteroides, Pyramidobacter piscolens|Leuconostoc mesenteroides, Rhodopseudomonas palustris|Leuconostoc mesenteroides, Roseburia intestinalis|Leuconostoc mesenteroides, Roseburia inulinivorans|Leuconostoc mesenteroides, Rothia dentocariosa|Leuconostoc mesenteroides, Rothia mucilaginosa|Leuconostoc mesenteroides, Ruminococcus albus|Leuconostoc mesenteroides, Ruminococcus bromii|Leuconostoc mesenteroides, Ruminococcus gnavus|Leuconostoc mesenteroides, Ruminococcus lactaris|Leuconostoc mesenteroides, Ruminococcus obeum|Leuconostoc mesenteroides, Ruminococcus torques|Leuconostoc mesenteroides, Selenomonas sputigena|Leuconostoc mesenteroides, Shigella boydii|Leuconostoc mesenteroides, Shigella dysenteriae|Leuconostoc mesenteroides, Shigella sonnei|Leuconostoc mesenteroides, Slackia exigua|Leuconostoc mesenteroides, Solobacterium moorei|Leuconostoc mesenteroides, Staphylococcus aureus|Leuconostoc mesenteroides, Staphylococcus epidermidis|Leuconostoc mesenteroides, Staphylococcus hominis|Leuconostoc mesenteroides, Staphylococcus saprophyticus|Leuconostoc mesenteroides, Staphylococcus warneri|Leuconostoc mesenteroides, Streptococcus agalactiae|Leuconostoc mesenteroides, Streptococcus anginosus|Leuconostoc mesenteroides, Streptococcus australis|Leuconostoc mesenteroides, Streptococcus bovis|Leuconostoc mesenteroides, Streptococcus cristatus|Leuconostoc mesenteroides, Streptococcus dysgalactiae|Leuconostoc mesenteroides, Streptococcus equinus|Leuconostoc mesenteroides, Streptococcus gordonii|Leuconostoc mesenteroides, Streptococcus infantarius|Leuconostoc mesenteroides, Streptococcus infantis|Leuconostoc mesenteroides, Streptococcus mitis|Leuconostoc mesenteroides, Streptococcus mutans|Leuconostoc mesenteroides, Streptococcus oralis|Leuconostoc mesenteroides, Streptococcus parasanguinis|Leuconostoc mesenteroides, Streptococcus peroris|Leuconostoc mesenteroides, Streptococcus pneumoniae|Leuconostoc mesenteroides, Streptococcus salivarius|Leuconostoc mesenteroides, Streptococcus sanguinis|Leuconostoc mesenteroides, Streptococcus thermophilus|Leuconostoc mesenteroides, Streptococcus vestibularis|Leuconostoc mesenteroides, Subdoligranulum variabile|Leuconostoc mesenteroides, Succinatimonas hippei|Leuconostoc mesenteroides, Sutterella wadsworthensis|Leuconostoc mesenteroides, Tropheryma whipplei|Leuconostoc mesenteroides, Veillonella atypica|Leuconostoc mesenteroides, Veillonella dispar|Leuconostoc mesenteroides, Veillonella parvula|Leuconostoc mesenteroides, Victivallis vadensis|Listeria monocytogenes, Listeria monocytogenes|Listeria monocytogenes, Marvinbryantia formatexigens|Listeria monocytogenes, Megamonas hypermegale|Listeria monocytogenes, Megasphaera micronuciformis|Listeria monocytogenes, Methanobrevibacter smithii|Listeria monocytogenes, Methanosphaera stadtmanae|Listeria monocytogenes, Methylobacterium radiotolerans|Listeria monocytogenes, Mitsuokella multacida|Listeria monocytogenes, Mobiluncus curtisii|Listeria monocytogenes, Mycoplasma hominis|Listeria monocytogenes, Neisseria mucosa|Listeria monocytogenes, Odoribacter splanchnicus|Listeria monocytogenes, Olsenella uli|Listeria monocytogenes, Oribacterium sinus|Listeria monocytogenes, Oxalobacter formigenes|Listeria monocytogenes, Parabacteroides distasonis|Listeria monocytogenes, Parabacteroides johnsonii|Listeria monocytogenes, Parabacteroides merdae|Listeria monocytogenes, Parvimonas micra|Listeria monocytogenes, Pediococcus acidilactici|Listeria monocytogenes, Pediococcus pentosaceus|Listeria monocytogenes, Peptoniphilus duerdenii|Listeria monocytogenes, Peptoniphilus harei|Listeria monocytogenes, Peptoniphilus lacrimalis|Listeria monocytogenes, Peptostreptococcus anaerobius|Listeria monocytogenes, Peptostreptococcus stomatis|Listeria monocytogenes, Porphyromonas asaccharolytica|Listeria monocytogenes, Porphyromonas uenonis|Listeria monocytogenes, Prevotella amnii|Listeria monocytogenes, Prevotella bergensis|Listeria monocytogenes, Prevotella bivia|Listeria*

TABLE 2-continued

| Table 2. Specific binary combinations of OTUs. Individual pairings are differentiated by "\|" and OTUs within a combination are differentiated by "," |
| --- |
| *monocytogenes, Prevotella buccae\|Listeria monocytogenes, Prevotella buccalis\|Listeria monocytogenes, Prevotella copri\|Listeria monocytogenes, Prevotella disiens\|Listeria monocytogenes, Prevotella melaninogenica\|Listeria monocytogenes, Prevotella multiformis\|Listeria monocytogenes, Prevotella oralis\|Listeria monocytogenes, Prevotella oris\|Listeria monocytogenes, Prevotella salivae\|Listeria monocytogenes, Prevotella timonensis\|Listeria monocytogenes, Propionibacterium acnes\|Listeria monocytogenes, Propionibacterium freudenreichii\|Listeria monocytogenes, Proteus mirabilis\|Listeria monocytogenes, Proteus penneri\|Listeria monocytogenes, Pseudoflavonifractor capillosus\|Listeria monocytogenes, Pseudomonas aeruginosa\|Listeria monocytogenes, Pseudomonas fluorescens\|Listeria monocytogenes, Pseudomonas putida\|Listeria monocytogenes, Pseudoramibacter alactolyticus\|Listeria monocytogenes, Pyramidobacter piscolens\|Listeria monocytogenes, Rhodopseudomonas palustris\|Listeria monocytogenes, Roseburia intestinalis\|Listeria monocytogenes, Roseburia inulinivorans\|Listeria monocytogenes, Rothia dentocariosa\|Listeria monocytogenes, Rothia mucilaginosa\|Listeria monocytogenes, Ruminococcus albus\|Listeria monocytogenes, Ruminococcus bromii\|Listeria monocytogenes, Ruminococcus gnavus\|Listeria monocytogenes, Ruminococcus lactaris\|Listeria monocytogenes, Ruminococcus obeum\|Listeria monocytogenes, Ruminococcus torques\|Listeria monocytogenes, Selenomonas sputigena\|Listeria monocytogenes, Shigella boydii\|Listeria monocytogenes, Shigella dysenteriae\|Listeria monocytogenes, Shigella sonnei\|Listeria monocytogenes, Slackia exigua\|Listeria monocytogenes, Solobacterium moorei\|Listeria monocytogenes, Staphylococcus aureus\|Listeria monocytogenes, Staphylococcus epidermidis\|Listeria monocytogenes, Staphylococcus hominis\|Listeria monocytogenes, Staphylococcus saprophyticus\|Listeria monocytogenes, Staphylococcus warneri\|Listeria monocytogenes, Streptococcus agalactiae\|Listeria monocytogenes, Streptococcus anginosus\|Listeria monocytogenes, Streptococcus australis\|Listeria monocytogenes, Streptococcus bovis\|Listeria monocytogenes, Streptococcus cristatus\|Listeria monocytogenes, Streptococcus dysgalactiae\|Listeria monocytogenes, Streptococcus equinus\|Listeria monocytogenes, Streptococcus gordonii\|Listeria monocytogenes, Streptococcus infantarius\|Listeria monocytogenes, Streptococcus infantis\|Listeria monocytogenes, Streptococcus mitis\|Listeria monocytogenes, Streptococcus mutans\|Listeria monocytogenes, Streptococcus oralis\|Listeria monocytogenes, Streptococcus parasanguinis\|Listeria monocytogenes, Streptococcus peroris\|Listeria monocytogenes, Streptococcus pneumoniae\|Listeria monocytogenes, Streptococcus salivarius\|Listeria monocytogenes, Streptococcus sanguinis\|Listeria monocytogenes, Streptococcus thermophilus\|Listeria monocytogenes, Streptococcus vestibularis\|Listeria monocytogenes, Subdoligranulum variabile\|Listeria monocytogenes, Succinatimonas hippei\|Listeria monocytogenes, Sutterella wadsworthensis\|Listeria monocytogenes, Tropheryma whipplei\|Listeria monocytogenes, Veillonella atypica\|Listeria monocytogenes, Veillonella dispar\|Listeria monocytogenes, Veillonella parvula\|Listeria monocytogenes, Victivallis vadensis\|Marvinbryantia formatexigens, Marvinbryantia formatexigens\|Marvinbryantia formatexigens, Megamonas hypermegale\|Marvinbryantia formatexigens, Megasphaera micronuciformis\|Marvinbryantia formatexigens, Methanobrevibacter smithii\|Marvinbryantia formatexigens, Methanosphaera stadtmanae\|Marvinbryantia formatexigens, Methylobacterium radiotolerans\|Marvinbryantia formatexigens, Mitsuokella multacida\|Marvinbryantia formatexigens, Mobiluncus curtisii\|Marvinbryantia formatexigens, Mycoplasma hominis\|Marvinbryantia formatexigens, Neisseria mucosa\|Marvinbryantia formatexigens, Odoribacter splanchnicus\|Marvinbryantia formatexigens, Olsenella uli\|Marvinbryantia formatexigens, Oribacterium sinus\|Marvinbryantia formatexigens, Oxalobacter formigenes\|Marvinbryantia formatexigens, Parabacteroides distasonis\|Marvinbryantia formatexigens, Parabacteroides johnsonii\|Marvinbryantia formatexigens, Parabacteroides merdae\|Marvinbryantia formatexigens, Parvimonas micra\|Marvinbryantia formatexigens, Pediococcus acidilactici\|Marvinbryantia formatexigens, Pediococcus pentosaceus\|Marvinbryantia formatexigens, Peptoniphilus duerdenii\|Marvinbryantia formatexigens, Peptoniphilus harei\|Marvinbryantia formatexigens, Peptoniphilus lacrimalis\|Marvinbryantia formatexigens, Peptostreptococcus anaerobius\|Marvinbryantia formatexigens, Peptostreptococcus stomatis\|Marvinbryantia formatexigens, Porphyromonas asaccharolytica\|Marvinbryantia formatexigens, Porphyromonas uenonis\|Marvinbryantia formatexigens, Prevotella amnii\|Marvinbryantia formatexigens, Prevotella bergensis\|Marvinbryantia formatexigens, Prevotella bivia\|Marvinbryantia formatexigens, Prevotella buccae\|Marvinbryantia formatexigens, Prevotella buccalis\|Marvinbryantia formatexigens, Prevotella copri\|Marvinbryantia formatexigens, Prevotella disiens\|Marvinbryantia formatexigens, Prevotella melaninogenica\|Marvinbryantia formatexigens, Prevotella multiformis\|Marvinbryantia formatexigens, Prevotella oralis\|Marvinbryantia formatexigens, Prevotella oris\|Marvinbryantia formatexigens, Prevotella salivae\|Marvinbryantia formatexigens, Prevotella timonensis\|Marvinbryantia formatexigens, Propionibacterium acnes\|Marvinbryantia formatexigens, Propionibacterium freudenreichii\|Marvinbryantia formatexigens, Proteus mirabilis\|Marvinbryantia formatexigens, Proteus penneri\|Marvinbryantia formatexigens, Pseudoflavonifractor capillosus\|Marvinbryantia formatexigens, Pseudomonas aeruginosa\|Marvinbryantia formatexigens, Pseudomonas fluorescens\|Marvinbryantia formatexigens, Pseudomonas putida\|Marvinbryantia formatexigens, Pseudoramibacter alactolyticus\|Marvinbryantia formatexigens, Pyramidobacter piscolens\|Marvinbryantia formatexigens, Rhodopseudomonas palustris\|Marvinbryantia formatexigens, Roseburia intestinalis\|Marvinbryantia formatexigens, Roseburia inulinivorans\|Marvinbryantia formatexigens, Rothia dentocariosa\|Marvinbryantia formatexigens, Rothia mucilaginosa\|Marvinbryantia formatexigens, Ruminococcus albus\|Marvinbryantia formatexigens, Ruminococcus bromii\|Marvinbryantia formatexigens, Ruminococcus gnavus\|Marvinbryantia formatexigens, Ruminococcus lactaris\|Marvinbryantia formatexigens, Ruminococcus obeum\|Marvinbryantia formatexigens, Ruminococcus torques\|Marvinbryantia formatexigens, Selenomonas sputigena\|Marvinbryantia formatexigens, Shigella boydii\|Marvinbryantia formatexigens, Shigella dysenteriae\|Marvinbryantia formatexigens, Shigella sonnei\|Marvinbryantia formatexigens, Slackia exigua\|Marvinbryantia formatexigens, Solobacterium moorei\|Marvinbryantia formatexigens, Staphylococcus aureus\|Marvinbryantia formatexigens, Staphylococcus epidermidis\|Marvinbryantia formatexigens, Staphylococcus hominis\|Marvinbryantia formatexigens, Staphylococcus saprophyticus\|Marvinbryantia formatexigens, Staphylococcus warneri\|Marvinbryantia formatexigens, Streptococcus agalactiae\|Marvinbryantia formatexigens, Streptococcus anginosus\|Marvinbryantia formatexigens, Streptococcus australis\|Marvinbryantia formatexigens, Streptococcus bovis\|Marvinbryantia formatexigens, Streptococcus cristatus\|Marvinbryantia formatexigens, Streptococcus dysgalactiae\|Marvinbryantia formatexigens, Streptococcus equinus\|Marvinbryantia formatexigens, Streptococcus gordonii\|Marvinbryantia formatexigens, Streptococcus infantarius\|Marvinbryantia formatexigens, Streptococcus infantis\|Marvinbryantia formatexigens, Streptococcus mitis\|Marvinbryantia formatexigens, Streptococcus mutans\|Marvinbryantia formatexigens, Streptococcus oralis\|Marvinbryantia formatexigens, Streptococcus parasanguinis\|Marvinbryantia formatexigens, Streptococcus peroris\|Marvinbryantia formatexigens, Streptococcus pneumoniae\|Marvinbryantia formatexigens, Streptococcus salivarius\|Marvinbryantia formatexigens, Streptococcus sanguinis\|Marvinbryantia formatexigens, Streptococcus thermophilus\|Marvinbryantia formatexigens, Streptococcus vestibularis\|Marvinbryantia formatexigens, Subdoligranulum variabile\|Marvinbryantia formatexigens, Succinatimonas hippei\|Marvinbryantia formatexigens, Sutterella wadsworthensis\|Marvinbryantia formatexigens, Tropheryma whipplei\|Marvinbryantia formatexigens, Veillonella atypica\|Marvinbryantia formatexigens, Veillonella dispar\|Marvinbryantia formatexigens, Veillonella parvula\|Marvinbryantia formatexigens, Victivallis vadensis\|Megamonas hypermegale, Megamonas hypermegale\|Megamonas hypermegale, Megasphaera micronuciformis\|Megamonas hypermegale, Methanobrevibacter smithii\|Megamonas hypermegale, Methanosphaera stadtmanae\|Megamonas hypermegale, Methylobacterium radiotolerans\|Megamonas hypermegale, Mitsuokella multacida\|Megamonas hypermegale, Mobiluncus curtisii\|Megamonas hypermegale, Mycoplasma hominis\|Megamonas hypermegale, Neisseria mucosa\|Megamonas hypermegale, Odoribacter splanchnicus\|Megamonas hypermegale, Olsenella uli\|Megamonas hypermegale, Oribacterium sinus\|Megamonas hypermegale, Oxalobacter formigenes\|Megamonas hypermegale, Parabacteroides distasonis\|Megamonas hypermegale, Parabacteroides johnsonii\|Megamonas hypermegale, Parabacteroides merdae\|Megamonas hypermegale, Parvimonas micra\|Megamonas hypermegale, Pediococcus acidilactici\|Megamonas hypermegale, Pediococcus pentosaceus\|Megamonas hypermegale, Peptoniphilus duerdenii\|Megamonas hypermegale, Peptoniphilus harei\|Megamonas hypermegale, Peptoniphilus lacrimalis\|Megamonas hypermegale, Peptostreptococcus anaerobius\|Megamonas hypermegale, Peptostreptococcus stomatis\|Megamonas hypermegale, Porphyromonas* |

TABLE 2-continued

Table 2. Specific binary combinations of OTUs. Individual pairings are differentiated by "|" and OTUs within a combination are differentiated by ","

*asaccharolytica|Megamonas hypermegale, Porphyromonas uenonis|Megamonas hypermegale, Prevotella amnii|Megamonas hypermegale, Prevotella bergensis|Megamonas hypermegale, Prevotella bivia|Megamonas hypermegale, Prevotella buccae|Megamonas hypermegale, Prevotella buccalis|Megamonas hypermegale, Prevotella copri|Megamonas hypermegale, Prevotella disiens|Megamonas hypermegale, Prevotella melaninogenica|Megamonas hypermegale, Prevotella multiformis|Megamonas hypermegale, Prevotella oralis|Megamonas hypermegale, Prevotella oris|Megamonas hypermegale, Prevotella salivae|Megamonas hypermegale, Prevotella timonensis|Megamonas hypermegale, Propionibacterium acnes|Megamonas hypermegale, Propionibacterium freudenreichii|Megamonas hypermegale, Proteus mirabilis|Megamonas hypermegale, Proteus penneri|Megamonas hypermegale, Pseudoflavonifractor capillosus|Megamonas hypermegale, Pseudomonas aeruginosa|Megamonas hypermegale, Pseudomonas fluorescens|Megamonas hypermegale, Pseudomonas putida|Megamonas hypermegale, Pseudoramibacter alactolyticus|Megamonas hypermegale, Pyramidobacter piscolens|Megamonas hypermegale, Rhodopseudomonas palustris|Megamonas hypermegale, Roseburia intestinalis|Megamonas hypermegale, Roseburia inulinivorans|Megamonas hypermegale, Rothia dentocariosa|Megamonas hypermegale, Rothia mucilaginosa|Megamonas hypermegale, Ruminococcus albus|Megamonas hypermegale, Ruminococcus bromii|Megamonas hypermegale, Ruminococcus gnavus|Megamonas hypermegale, Ruminococcus lactaris|Megamonas hypermegale, Ruminococcus obeum|Megamonas hypermegale, Ruminococcus torques|Megamonas hypermegale, Selenomonas sputigena|Megamonas hypermegale, Shigella boydii|Megamonas hypermegale, Shigella dysenteriae|Megamonas hypermegale, Shigella sonnei|Megamonas hypermegale, Slackia exigua|Megamonas hypermegale, Solobacterium moorei|Megamonas hypermegale, Staphylococcus aureus|Megamonas hypermegale, Staphylococcus epidermidis|Megamonas hypermegale, Staphylococcus hominis|Megamonas hypermegale, Staphylococcus saprophyticus|Megamonas hypermegale, Staphylococcus warneri|Megamonas hypermegale, Streptococcus agalactiae|Megamonas hypermegale, Streptococcus anginosus|Megamonas hypermegale, Streptococcus australis|Megamonas hypermegale, Streptococcus bovis|Megamonas hypermegale, Streptococcus cristatus|Megamonas hypermegale, Streptococcus dysgalactiae|Megamonas hypermegale, Streptococcus equinus|Megamonas hypermegale, Streptococcus gordonii|Megamonas hypermegale, Streptococcus infantarius|Megamonas hypermegale, Streptococcus infantis|Megamonas hypermegale, Streptococcus mitis|Megamonas hypermegale, Streptococcus mutans|Megamonas hypermegale, Streptococcus oralis|Megamonas hypermegale, Streptococcus parasanguinis|Megamonas hypermegale, Streptococcus peroris|Megamonas hypermegale, Streptococcus pneumoniae|Megamonas hypermegale, Streptococcus salivarius|Megamonas hypermegale, Streptococcus sanguinis|Megamonas hypermegale, Streptococcus thermophilus|Megamonas hypermegale, Streptococcus vestibularis|Megamonas hypermegale, Subdoligranulum variabile|Megamonas hypermegale, Succinatimonas hippei|Megamonas hypermegale, Sutterella wadsworthensis|Megamonas hypermegale, Tropheryma whipplei|Megamonas hypermegale, Veillonella atypica|Megamonas hypermegale, Veillonella dispar|Megamonas hypermegale, Veillonella parvula|Megamonas hypermegale, Victivallis vadensis|Megasphaera micronuciformis, Megasphaera micronuciformis|Megasphaera micronuciformis, Methanobrevibacter smithii|Megasphaera micronuciformis, Methanosphaera stadtmanae|Megasphaera micronuciformis, Methylobacterium radiotolerans|Megasphaera micronuciformis, Mitsuokella multacida|Megasphaera micronuciformis, Mobiluncus curtisii|Megasphaera micronuciformis, Mycoplasma hominis|Megasphaera micronuciformis, Neisseria mucosa|Megasphaera micronuciformis, Odoribacter splanchnicus|Megasphaera micronuciformis, Olsenella uli|Megasphaera micronuciformis, Oribacterium sinus|Megasphaera micronuciformis, Oxalobacter formigenes|Megasphaera micronuciformis, Parabacteroides distasonis|Megasphaera micronuciformis, Parabacteroides johnsonii|Megasphaera micronuciformis, Parabacteroides merdae|Megasphaera micronuciformis, Parvimonas micra|Megasphaera micronuciformis, Pediococcus acidilactici|Megasphaera micronuciformis, Pediococcus pentosaceus|Megasphaera micronuciformis, Peptoniphilus duerdenii|Megasphaera micronuciformis, Peptoniphilus harei|Megasphaera micronuciformis, Peptoniphilus lacrimalis|Megasphaera micronuciformis, Peptostreptococcus anaerobius|Megasphaera micronuciformis, Peptostreptococcus stomatis|Megasphaera micronuciformis, Porphyromonas asaccharolytica|Megasphaera micronuciformis, Porphyromonas uenonis|Megasphaera micronuciformis, Prevotella amnii|Megasphaera micronuciformis, Prevotella bergensis|Megasphaera micronuciformis, Prevotella bivia|Megasphaera micronuciformis, Prevotella buccae|Megasphaera micronuciformis, Prevotella buccalis|Megasphaera micronuciformis, Prevotella copri|Megasphaera micronuciformis, Prevotella disiens|Megasphaera micronuciformis, Prevotella melaninogenica|Megasphaera micronuciformis, Prevotella multiformis|Megasphaera micronuciformis, Prevotella oralis|Megasphaera micronuciformis, Prevotella oris|Megasphaera micronuciformis, Prevotella salivae|Megasphaera micronuciformis, Prevotella timonensis|Megasphaera micronuciformis, Propionibacterium acnes|Megasphaera micronuciformis, Propionibacterium freudenreichii|Megasphaera micronuciformis, Proteus mirabilis|Megasphaera micronuciformis, Proteus penneri|Megasphaera micronuciformis, Pseudoflavonifractor capillosus|Megasphaera micronuciformis, Pseudomonas aeruginosa|Megasphaera micronuciformis, Pseudomonas fluorescens|Megasphaera micronuciformis, Pseudomonas putida|Megasphaera micronuciformis, Pseudoramibacter alactolyticus|Megasphaera micronuciformis, Pyramidobacter piscolens|Megasphaera micronuciformis, Rhodopseudomonas palustris|Megasphaera micronuciformis, Roseburia intestinalis|Megasphaera micronuciformis, Roseburia inulinivorans|Megasphaera micronuciformis, Rothia dentocariosa|Megasphaera micronuciformis, Rothia mucilaginosa|Megasphaera micronuciformis, Ruminococcus albus|Megasphaera micronuciformis, Ruminococcus bromii|Megasphaera micronuciformis, Ruminococcus gnavus|Megasphaera micronuciformis, Ruminococcus lactaris|Megasphaera micronuciformis, Ruminococcus obeum|Megasphaera micronuciformis, Ruminococcus torques|Megasphaera micronuciformis, Selenomonas sputigena|Megasphaera micronuciformis, Shigella boydii|Megasphaera micronuciformis, Shigella dysenteriae|Megasphaera micronuciformis, Shigella sonnei|Megasphaera micronuciformis, Slackia exigua|Megasphaera micronuciformis, Solobacterium moorei|Megasphaera micronuciformis, Staphylococcus aureus|Megasphaera micronuciformis, Staphylococcus epidermidis|Megasphaera micronuciformis, Staphylococcus hominis|Megasphaera micronuciformis, Staphylococcus saprophyticus|Megasphaera micronuciformis, Staphylococcus warneri|Megasphaera micronuciformis, Streptococcus agalactiae|Megasphaera micronuciformis, Streptococcus anginosus|Megasphaera micronuciformis, Streptococcus australis|Megasphaera micronuciformis, Streptococcus bovis|Megasphaera micronuciformis, Streptococcus cristatus|Megasphaera micronuciformis, Streptococcus dysgalactiae|Megasphaera micronuciformis, Streptococcus equinus|Megasphaera micronuciformis, Streptococcus gordonii|Megasphaera micronuciformis, Streptococcus infantarius|Megasphaera micronuciformis, Streptococcus infantis|Megasphaera micronuciformis, Streptococcus mitis|Megasphaera micronuciformis, Streptococcus mutans|Megasphaera micronuciformis, Streptococcus oralis|Megasphaera micronuciformis, Streptococcus parasanguinis|Megasphaera micronuciformis, Streptococcus peroris|Megasphaera micronuciformis, Streptococcus pneumoniae|Megasphaera micronuciformis, Streptococcus salivarius|Megasphaera micronuciformis, Streptococcus sanguinis|Megasphaera micronuciformis, Streptococcus thermophilus|Megasphaera micronuciformis, Streptococcus vestibularis|Megasphaera micronuciformis, Subdoligranulum variabile|Megasphaera micronuciformis, Succinatimonas hippei|Megasphaera micronuciformis, Sutterella wadsworthensis|Megasphaera micronuciformis, Tropheryma whipplei|Megasphaera micronuciformis, Veillonella atypica|Megasphaera micronuciformis, Veillonella dispar|Megasphaera micronuciformis, Veillonella parvula|Megasphaera micronuciformis, Victivallis vadensis|Methanobrevibacter smithii, Methanobrevibacter smithii|Methanobrevibacter smithii, Methanosphaera stadtmanae|Methanobrevibacter smithii, Methylobacterium radiotolerans|Methanobrevibacter smithii, Mitsuokella multacida|Methanobrevibacter smithii, Mobiluncus curtisii|Methanobrevibacter smithii, Mycoplasma hominis|Methanobrevibacter smithii, Neisseria mucosa|Methanobrevibacter smithii, Odoribacter splanchnicus|Methanobrevibacter smithii, Olsenella uli|Methanobrevibacter smithii, Oribacterium sinus|Methanobrevibacter smithii, Oxalobacter formigenes|Methanobrevibacter smithii, Parabacteroides distasonis|Methanobrevibacter smithii, Parabacteroides johnsonii|Methanobrevibacter smithii, Parabacteroides merdae|Methanobrevibacter smithii, Parvimonas micra|Methanobrevibacter smithii, Pediococcus acidilactici|Methanobrevibacter smithii, Pediococcus pentosaceus|Methanobrevibacter smithii, Peptoniphilus duerdenii|Methanobrevibacter smithii, Peptoniphilus harei|Methanobrevibacter smithii, Peptoniphilus lacrimalis|Methanobrevibacter*

TABLE 2-continued

| Table 2. Specific binary combinations of OTUs. Individual pairings are differentiated by "\|" and OTUs within a combination are differentiated by "," |
|---|
| *smithii, Peptostreptococcus anaerobius\|Methanobrevibacter smithii, Peptostreptococcus stomatis\|Methanobrevibacter smithii, Porphyromonas asaccharolytica\|Methanobrevibacter smithii, Porphyromonas uenonis\|Methanobrevibacter smithii, Prevotella amnii\|Methanobrevibacter smithii, Prevotella bergensis\|Methanobrevibacter smithii, Prevotella bivia\|Methanobrevibacter smithii, Prevotella buccae\|Methanobrevibacter smithii, Prevotella buccalis\|Methanobrevibacter smithii, Prevotella copri\|Methanobrevibacter smithii, Prevotella disiens\|Methanobrevibacter smithii, Prevotella melaninogenica\|Methanobrevibacter smithii, Prevotella multiformis\|Methanobrevibacter smithii, Prevotella oralis\|Methanobrevibacter smithii, Prevotella oris\|Methanobrevibacter smithii, Prevotella salivae\|Methanobrevibacter smithii, Prevotella timonensis\|Methanobrevibacter smithii, Propionibacterium acnes\|Methanobrevibacter smithii, Propionibacterium freudenreichi\|Methanobrevibacter smithii, Proteus mirabilis\|Methanobrevibacter smithii, Proteus penneri\|Methanobrevibacter smithii, Pseudoflavonifractor capillosus\|Methanobrevibacter smithii, Pseudomonas aeruginosa\|Methanobrevibacter smithii, Pseudomonas fluorescens\|Methanobrevibacter smithii, Pseudomonas putida\|Methanobrevibacter smithii, Pseudoramibacter alactolyticus\|Methanobrevibacter smithii, Pyramidobacter piscolens\|Methanobrevibacter smithii, Rhodopseudomonas palustris\|Methanobrevibacter smithii, Roseburia intestinalis\|Methanobrevibacter smithii, Roseburia inulinivorans\|Methanobrevibacter smithii, Rothia dentocariosa\|Methanobrevibacter smithii, Rothia mucilaginosa\|Methanobrevibacter smithii, Ruminococcus albus\|Methanobrevibacter smithii, Ruminococcus bromii\|Methanobrevibacter smithii, Ruminococcus gnavus\|Methanobrevibacter smithii, Ruminococcus lactaris\|Methanobrevibacter smithii, Ruminococcus obeum\|Methanobrevibacter smithii, Ruminococcus torques\|Methanobrevibacter smithii, Selenomonas sputigena\|Methanobrevibacter smithii, Shigella boydii\|Methanobrevibacter smithii, Shigella dysenteriae\|Methanobrevibacter smithii, Shigella sonnei\|Methanobrevibacter smithii, Slackia exigua\|Methanobrevibacter smithii, Solobacterium moorei\|Methanobrevibacter smithii, Staphylococcus aureus\|Methanobrevibacter smithii, Staphylococcus epidermidis\|Methanobrevibacter smithii, Staphylococcus hominis\|Methanobrevibacter smithii, Staphylococcus saprophyticus\|Methanobrevibacter smithii, Staphylococcus warneri\|Methanobrevibacter smithii, Streptococcus agalactiae\|Methanobrevibacter smithii, Streptococcus anginosus\|Methanobrevibacter smithii, Streptococcus australis\|Methanobrevibacter smithii, Streptococcus bovis\|Methanobrevibacter smithii, Streptococcus cristatus\|Methanobrevibacter smithii, Streptococcus dysgalactiae\|Methanobrevibacter smithii, Streptococcus equinus\|Methanobrevibacter smithii, Streptococcus gordonii\|Methanobrevibacter smithii, Streptococcus infantarius\|Methanobrevibacter smithii, Streptococcus infantis\|Methanobrevibacter smithii, Streptococcus mitis\|Methanobrevibacter smithii, Streptococcus mutans\|Methanobrevibacter smithii, Streptococcus oralis\|Methanobrevibacter smithii, Streptococcus parasanguinis\|Methanobrevibacter smithii, Streptococcus peroris\|Methanobrevibacter smithii, Streptococcus pneumoniae\|Methanobrevibacter smithii, Streptococcus salivarius\|Methanobrevibacter smithii, Streptococcus sanguinis\|Methanobrevibacter smithii, Streptococcus thermophflus\|Methanobrevibacter smithii, Streptococcus vestibularis\|Methanobrevibacter smithii, Subdoligranulum variabile\|Methanobrevibacter smithii, Succinatimonas hippei\|Methanobrevibacter smithii, Sutterella wadsworthensis\|Methanobrevibacter smithii, Tropheryma whipplei\|Methanobrevibacter smithii, Veillonella atypica\|Methanobrevibacter smithii, Veillonella dispar\|Methanobrevibacter smithii, Veillonella parvula\|Methanobrevibacter smithii, Victivallis vadensis\|Methanosphaera stadtmanae, Methanosphaera stadtmanae\|Methanosphaera stadtmanae, Methylobacterium radiotolerans\|Methanosphaera stadtmanae, Mitsuokella multacida\|Methanosphaera stadtmanae, Mobiluncus curtisii\|Methanosphaera stadtmanae, Mycoplasma hominis\|Methanosphaera stadtmanae, Neisseria mucosa\|Methanosphaera stadtmanae, Odoribacter splanchnicus\|Methanosphaera stadtmanae, Olsenella uli\|Methanosphaera stadtmanae, Oribacterium sinus\|Methanosphaera stadtmanae, Oxalobacter formigenes\|Methanosphaera stadtmanae, Parabacteroides distasonis\|Methanosphaera stadtmanae, Parabacteroides johnsonii\|Methanosphaera stadtmanae, Parabacteroides merdae\|Methanosphaera stadtmanae, Parvimonas micra\|Methanosphaera stadtmanae, Pediococcus acidilactici\|Methanosphaera stadtmanae, Pediococcus pentosaceus\|Methanosphaera stadtmanae, Peptoniphilus duerdenii\|Methanosphaera stadtmanae, Peptoniphilus harei\|Methanosphaera stadtmanae, Peptoniphilus lacrimalis\|Methanosphaera stadtmanae, Peptostreptococcus anaerobius\|Methanosphaera stadtmanae, Peptostreptococcus stomatis\|Methanosphaera stadtmanae, Porphyromonas asaccharolytica\|Methanosphaera stadtmanae, Porphyromonas uenonis\|Methanosphaera stadtmanae, Prevotella amnii\|Methanosphaera stadtmanae, Prevotella bergensis\|Methanosphaera stadtmanae, Prevotella bivia\|Methanosphaera stadtmanae, Prevotella buccae\|Methanosphaera stadtmanae, Prevotella buccalis\|Methanosphaera stadtmanae, Prevotella copri\|Methanosphaera stadtmanae, Prevotella disiens\|Methanosphaera stadtmanae, Prevotella melaninogenica\|Methanosphaera stadtmanae, Prevotella multiformis\|Methanosphaera stadtmanae, Prevotella oralis\|Methanosphaera stadtmanae, Prevotella oris\|Methanosphaera stadtmanae, Prevotella salivae\|Methanosphaera stadtmanae, Prevotella timonensis\|Methanosphaera stadtmanae, Propionibacterium acnes\|Methanosphaera stadtmanae, Propionibacterium freudenreichii\|Methanosphaera stadtmanae, Proteus mirabilis\|Methanosphaera stadtmanae, Proteus penneri\|Methanosphaera stadtmanae, Pseudoflavonifractor capillosus\|Methanosphaera stadtmanae, Pseudomonas aeruginosa\|Methanosphaera stadtmanae, Pseudomonas fluorescens\|Methanosphaera stadtmanae, Pseudomonas putida\|Methanosphaera stadtmanae, Pseudoramibacter alactolyticus\|Methanosphaera stadtmanae, Pyramidobacter piscolens\|Methanosphaera stadtmanae, Rhodopseudomonas palustris\|Methanosphaera stadtmanae, Roseburia intestinalis\|Methanosphaera stadtmanae, Roseburia inulinivorans\|Methanosphaera stadtmanae, Rothia dentocariosa\|Methanosphaera stadtmanae, Rothia mucilaginosa\|Methanosphaera stadtmanae, Ruminococcus albus\|Methanosphaera stadtmanae, Ruminococcus bromii\|Methanosphaera stadtmanae, Ruminococcus gnavus\|Methanosphaera stadtmanae, Ruminococcus lactaris\|Methanosphaera stadtmanae, Ruminococcus obeum\|Methanosphaera stadtmanae, Ruminococcus torques\|Methanosphaera stadtmanae, Selenomonas sputigena\|Methanosphaera stadtmanae, Shigella boydii\|Methanosphaera stadtmanae, Shigella dysenteriae\|Methanosphaera stadtmanae, Shigella sonnei\|Methanosphaera stadtmanae, Slackia exigua\|Methanosphaera stadtmanae, Solobacterium moorei\|Methanosphaera stadtmanae, Staphylococcus aureus\|Methanosphaera stadtmanae, Staphylococcus epidermidis\|Methanosphaera stadtmanae, Staphylococcus hominis\|Methanosphaera stadtmanae, Staphylococcus saprophyticus\|Methanosphaera stadtmanae, Staphylococcus warneri\|Methanosphaera stadtmanae, Streptococcus agalactiae\|Methanosphaera stadtmanae, Streptococcus anginosus\|Methanosphaera stadtmanae, Streptococcus australis\|Methanosphaera stadtmanae, Streptococcus bovis\|Methanosphaera stadtmanae, Streptococcus cristatus\|Methanosphaera stadtmanae, Streptococcus dysgalactiae\|Methanosphaera stadtmanae, Streptococcus equinus\|Methanosphaera stadtmanae, Streptococcus gordonii\|Methanosphaera stadtmanae, Streptococcus infantarius\|Methanosphaera stadtmanae, Streptococcus infantis\|Methanosphaera stadtmanae, Streptococcus mitis\|Methanosphaera stadtmanae, Streptococcus mutans\|Methanosphaera stadtmanae, Streptococcus oralis\|Methanosphaera stadtmanae, Streptococcus parasanguinis\|Methanosphaera stadtmanae, Streptococcus peroris\|Methanosphaera stadtmanae, Streptococcus pneumoniae\|Methanosphaera stadtmanae, Streptococcus salivarius\|Methanosphaera stadtmanae, Streptococcus sanguinis\|Methanosphaera stadtmanae, Streptococcus thermophilus\|Methanosphaera stadtmanae, Streptococcus vestibularis\|Methanosphaera stadtmanae, Subdoligranulum variabile\|Methanosphaera stadtmanae, Succinatimonas hippei\|Methanosphaera stadtmanae, Sutterella wadsworthensis\|Methanosphaera stadtmanae, Tropheryma whipplei\|Methanosphaera stadtmanae, Veillonella atypica\|Methanosphaera stadtmanae, Veillonella dispar\|Methanosphaera stadtmanae, Veillonella parvula\|Methanosphaera stadtmanae, Victivallis vadensis\|Methylobacterium radiotolerans, Methylobacterium radiotolerans\|Methylobacterium radiotolerans, Mitsuokella multacida\|Methylobacterium radiotolerans, Mobiluncus curtisii\|Methylobacterium radiotolerans, Mycoplasma hominis\|Methylobacterium radiotolerans, Neisseria mucosa\|Methylobacterium radiotolerans, Odoribacter splanchnicus\|Methylobacterium radiotolerans, Olsenella uli\|Methylobacterium radiotolerans, Oribacterium sinus\|Methylobacterium radiotolerans, Oxalobacter formigenes\|Methylobacterium radiotolerans, Parabacteroides distasonis\|Methylobacterium radiotolerans, Parabacteroides johnsonii\|Methylobacterium radiotolerans, Parabacteroides merdae\|Methylobacterium radiotolerans, Parvimonas micra\|Methylobacterium radiotolerans, Pediococcus acidilactici\|Methylobacterium radiotolerans, Pediococcus pentosaceus\|Methylobacterium radiotolerans, Peptoniphilus duerdenii\|Methylobacterium radiotolerans, Peptoniphilus harei\|Methylobacterium radiotolerans, Peptoniphilus* |

TABLE 2-continued

| Table 2. Specific binary combinations of OTUs. Individual pairings are differentiated by "\|" and OTUs within a combination are differentiated by "," |
| --- |
| *lacrimalis\|Methylobacterium radiotolerans, Peptostreptococcus anaerobius\|Methylobacterium radiotolerans, Peptostreptococcus stomatis\|Methylobacterium radiotolerans, Porphyromonas asaccharolytica\|Methylobacterium radiotolerans, Porphyromonas uenonis\|Methylobacterium radiotolerans, Prevotella amnii\|Methylobacterium radiotolerans, Prevotella bergensis\|Methylobacterium radiotolerans, Prevotella bivia\|Methylobacterium radiotolerans, Prevotella buccae\|Methylobacterium radiotolerans, Prevotella buccalis\|Methylobacterium radiotolerans, Prevotella copri\|Methylobacterium radiotolerans, Prevotella disiens\|Methylobacterium radiotolerans, Prevotella melaninogenica\|Methylobacterium radiotolerans, Prevotella multiformis\|Methylobacterium radiotolerans, Prevotella oralis\|Methylobacterium radiotolerans, Prevotella oris\|Methylobacterium radiotolerans, Prevotella salivae\|Methylobacterium radiotolerans, Prevotella timonensis\|Methylobacterium radiotolerans, Propionibacterium acnes\|Methylobacterium radiotolerans, Propionibacterium freudenreichii\|Methylobacterium radiotolerans, Proteus mirabilis\|Methylobacterium radiotolerans, Proteus penneri\|Methylobacterium radiotolerans, Pseudoflavonifractor capillosus\|Methylobacterium radiotolerans, Pseudomonas aeruginosa\|Methylobacterium radiotolerans, Pseudomonas fluorescens\|Methylobacterium radiotolerans, Pseudomonas putida\|Methylobacterium radiotolerans, Pseudoramibacter alactolyticus\|Methylobacterium radiotolerans, Pyramidobacter piscolens\|Methylobacterium radiotolerans, Rhodopseudomonas palustris\|Methylobacterium radiotolerans, Roseburia intestinalis\|Methylobacterium radiotolerans, Roseburia inulinivorans\|Methylobacterium radiotolerans, Rothia dentocariosa\|Methylobacterium radiotolerans, Rothia mucilaginosa\|Methylobacterium radiotolerans, Ruminococcus albus\|Methylobacterium radiotolerans, Ruminococcus bromii\|Methylobacterium radiotolerans, Ruminococcus gnavus\|Methylobacterium radiotolerans, Ruminococcus lactaris\|Methylobacterium radiotolerans, Ruminococcus obeum\|Methylobacterium radiotolerans, Ruminococcus torques\|Methylobacterium radiotolerans, Selenomonas sputigena\|Methylobacterium radiotolerans, Shigella boydii\|Methylobacterium radiotolerans, Shigella dysenteriae\|Methylobacterium radiotolerans, Shigella sonnei\|Methylobacterium radiotolerans, Slackia exigua\|Methylobacterium radiotolerans, Solobacterium moorei\|Methylobacterium radiotolerans, Staphylococcus aureus\|Methylobacterium radiotolerans, Staphylococcus epidermidis\|Methylobacterium radiotolerans, Staphylococcus hominis\|Methylobacterium radiotolerans, Staphylococcus saprophyticus\|Methylobacterium radiotolerans, Staphylococcus warneri\|Methylobacterium radiotolerans, Streptococcus agalactiae\|Methylobacterium radiotolerans, Streptococcus anginosus\|Methylobacterium radiotolerans, Streptococcus australis\|Methylobacterium radiotolerans, Streptococcus bovis\|Methylobacterium radiotolerans, Streptococcus cristatus\|Methylobacterium radiotolerans, Streptococcus dysgalactiae\|Methylobacterium radiotolerans, Streptococcus equinus\|Methylobacterium radiotolerans, Streptococcus gordonii\|Methylobacterium radiotolerans, Streptococcus infantarius\|Methylobacterium radiotolerans, Streptococcus infantis\|Methylobacterium radiotolerans, Streptococcus mitis\|Methylobacterium radiotolerans, Streptococcus mutans\|Methylobacterium radiotolerans, Streptococcus oralis\|Methylobacterium radiotolerans, Streptococcus parasanguinis\|Methylobacterium radiotolerans, Streptococcus peroris\|Methylobacterium radiotolerans, Streptococcus pneumoniae\|Methylobacterium radiotolerans, Streptococcus salivarius\|Methylobacterium radiotolerans, Streptococcus sanguinis\|Methylobacterium radiotolerans, Streptococcus thermophilus\|Methylobacterium radiotolerans, Streptococcus vestibularis\|Methylobacterium radiotolerans, Subdoligranulum variabile\|Methylobacterium radiotolerans, Succinatimonas hippei\|Methylobacterium radiotolerans, Sutterella wadsworthensis\|Methylobacterium radiotolerans, Tropheryma whipplei\|Methylobacterium radiotolerans, Veillonella atypica\|Methylobacterium radiotolerans, Veillonella dispar\|Methylobacterium radiotolerans, Veillonella parvula\|Methylobacterium radiotolerans, Victivallis vadensis\|Mitsuokella multacida, Mitsuokella multacida\|Mitsuokella multacida, Mobiluncus curtisii\|Mitsuokella multacida, Mycoplasma hominis\|Mitsuokella multacida, Neisseria mucosa\|Mitsuokella multacida, Odoribacter splanchnicus\|Mitsuokella multacida, Olsenella uli\|Mitsuokella multacida, Oribacterium sinus\|Mitsuokella multacida, Oxalobacter formigenes\|Mitsuokella multacida, Parabacteroides distasonis\|Mitsuokella multacida, Parabacteroides johnsonii\|Mitsuokella multacida, Parabacteroides merdae\|Mitsuokella multacida, Parvimonas micra\|Mitsuokella multacida, Pediococcus acidilactici\|Mitsuokella multacida, Pediococcus pentosaceus\|Mitsuokella multacida, Peptoniphilus duerdenii\|Mitsuokella multacida, Peptoniphilus harei\|Mitsuokella multacida, Peptoniphilus lacrimalis\|Mitsuokella multacida, Peptostreptococcus anaerobius\|Mitsuokella multacida, Peptostreptococcus stomatis\|Mitsuokella multacida, Porphyromonas asaccharolytica\|Mitsuokella multacida, Porphyromonas uenonis\|Mitsuokella multacida, Prevotella amnii\|Mitsuokella multacida, Prevotella bergensis\|Mitsuokella multacida, Prevotella bivia\|Mitsuokella multacida, Prevotella buccae\|Mitsuokella multacida, Prevotella buccalis\|Mitsuokella multacida, Prevotella copri\|Mitsuokella multacida, Prevotella disiens\|Mitsuokella multacida, Prevotella melaninogenica\|Mitsuokella multacida, Prevotella multiformis\|Mitsuokella multacida, Prevotella oralis\|Mitsuokella multacida, Prevotella oris\|Mitsuokella multacida, Prevotella salivae\|Mitsuokella multacida, Prevotella timonensis\|Mitsuokella multacida, Propionibacterium acnes\|Mitsuokella multacida, Propionibacterium freudenreichi\|Mitsuokella multacida, Proteus mirabilis\|Mitsuokella multacida, Proteus penneri\|Mitsuokella multacida, Pseudoflavonifractor capillosus\|Mitsuokella multacida, Pseudomonas aeruginosa\|Mitsuokella multacida, Pseudomonas fluorescens\|Mitsuokella multacida, Pseudomonas putida\|Mitsuokella multacida, Pseudoramibacter alactolyticus\|Mitsuokella multacida, Pyramidobacter piscolens\|Mitsuokella multacida, Rhodopseudomonas palustris\|Mitsuokella multacida, Roseburia intestinalis\|Mitsuokella multacida, Roseburia inulinivorans\|Mitsuokella multacida, Rothia dentocariosa\|Mitsuokella multacida, Rothia mucilaginosa\|Mitsuokella multacida, Ruminococcus albus\|Mitsuokella multacida, Ruminococcus bromii\|Mitsuokella multacida, Ruminococcus gnavus\|Mitsuokella multacida, Ruminococcus lactaris\|Mitsuokella multacida, Ruminococcus obeum\|Mitsuokella multacida, Ruminococcus torques\|Mitsuokella multacida, Selenomonas sputigena\|Mitsuokella multacida, Shigella boydii\|Mitsuokella multacida, Shigella dysenteriae\|Mitsuokella multacida, Shigella sonnei\|Mitsuokella multacida, Slackia exigua\|Mitsuokella multacida, Solobacterium moorei\|Mitsuokella multacida, Staphylococcus aureus\|Mitsuokella multacida, Staphylococcus epidermidis\|Mitsuokella multacida, Staphylococcus hominis\|Mitsuokella multacida, Staphylococcus saprophyticus\|Mitsuokella multacida, Staphylococcus warneri\|Mitsuokella multacida, Streptococcus agalactiae\|Mitsuokella multacida, Streptococcus anginosus\|Mitsuokella multacida, Streptococcus australis\|Mitsuokella multacida, Streptococcus bovis\|Mitsuokella multacida, Streptococcus cristatus\|Mitsuokella multacida, Streptococcus dysgalactiae\|Mitsuokella multacida, Streptococcus equinus\|Mitsuokella multacida, Streptococcus gordonii\|Mitsuokella multacida, Streptococcus infantarius\|Mitsuokella multacida, Streptococcus infantis\|Mitsuokella multacida, Streptococcus mitis\|Mitsuokella multacida, Streptococcus mutans\|Mitsuokella multacida, Streptococcus oralis\|Mitsuokella multacida, Streptococcus parasanguinis\|Mitsuokella multacida, Streptococcus peroris\|Mitsuokella multacida, Streptococcus pneumoniae\|Mitsuokella multacida, Streptococcus salivarius\|Mitsuokella multacida, Streptococcus sanguinis\|Mitsuokella multacida, Streptococcus thermophilus\|Mitsuokella multacida, Streptococcus vestibularis\|Mitsuokella multacida, Subdoligranulum variabile\|Mitsuokella multacida, Succinatimonas hippei\|Mitsuokella multacida, Sutterella wadsworthensis\|Mitsuokella multacida, Tropheryma whipplei\|Mitsuokella multacida, Veillonella atypica\|Mitsuokella multacida, Veillonella dispar\|Mitsuokella multacida, Veillonella parvula\|Mitsuokella multacida, Victivallis vadensis\|Mobiluncus curtisii, Mobiluncus curtisii\|Mobiluncus curtisii, Mycoplasma hominis\|Mobiluncus curtisii, Neisseria mucosa\|Mobiluncus curtisii, Odoribacter splanchnicus\|Mobiluncus curtisii, Olsenella uli\|Mobiluncus curtisii, Oribacterium sinus\|Mobiluncus curtisii, Oxalobacter formigenes\|Mobiluncus curtisii, Parabacteroides distasonis\|Mobiluncus curtisii, Parabacteroides johnsonii\|Mobiluncus curtisii, Parabacteroides merdae\|Mobiluncus curtisii, Parvimonas micra\|Mobiluncus curtisii, Pediococcus acidilactici\|Mobiluncus curtisii, Pediococcus pentosaceus\|Mobiluncus curtisii, Peptoniphilus duerdenii\|Mobiluncus curtisii, Peptoniphilus harei\|Mobiluncus curtisii, Peptoniphilus lacrimalis\|Mobiluncus curtisii, Peptostreptococcus anaerobius\|Mobiluncus curtisii, Peptostreptococcus stomatis\|Mobiluncus curtisii, Porphyromonas asaccharolytica\|Mobiluncus curtisii, Porphyromonas uenonis\|Mobiluncus curtisii, Prevotella amnii\|Mobiluncus curtisii, Prevotella bergensis\|Mobiluncus curtisii, Prevotella bivia\|Mobiluncus curtisii, Prevotella buccae\|Mobiluncus curtisii, Prevotella buccalis\|Mobiluncus curtisii, Prevotella copri\|Mobiluncus curtisii, Prevotella disiens\|Mobiluncus curtisii, Prevotella melaninogenica\|Mobiluncus curtisii, Prevotella multiformis\|Mobiluncus curtisii, Prevotella oralis\|Mobiluncus curtisii, Prevotella oris\|Mobiluncus curtisii, Prevotella salivae\|Mobiluncus curtisii, Prevotella timonensis\|Mobiluncus curtisii, Propionibacterium* |

TABLE 2-continued

| Table 2. Specific binary combinations of OTUs. Individual pairings are differentiated by "\|" and OTUs within a combination are differentiated by "," |
|---|
| acnes\|Mobiluncus curtisii, Propionibacterium freudenreichii\|Mobiluncus curtisii, Proteus mirabilis\|Mobiluncus curtisii, Proteus penneri\|Mobiluncus curtisii, Pseudoflavonifractor capillosus\|Mobiluncus curtisii, Pseudomonas aeruginosa\|Mobiluncus curtisii, Pseudomonas fluorescens\|Mobiluncus curtisii, Pseudomonas putida\|Mobiluncus curtisii, Pseudoramibacter alactolyticus\|Mobiluncus curtisii, Pyramidobacter piscolens\|Mobiluncus curtisii, Rhodopseudomonas palustris\|Mobiluncus curtisii, Roseburia intestinalis\|Mobiluncus curtisii, Roseburia inulinivorans\|Mobiluncus curtisii, Rothia dentocariosa\|Mobiluncus curtisii, Rothia mucilaginosa\|Mobiluncus curtisii, Ruminococcus albus\|Mobiluncus curtisii, Ruminococcus bromii\|Mobiluncus curtisii, Ruminococcus gnavus\|Mobiluncus curtisii, Ruminococcus lactaris\|Mobiluncus curtisii, Ruminococcus obeum\|Mobiluncus curtisii, Ruminococcus torques\|Mobiluncus curtisii, Selenomonas sputigena\|Mobiluncus curtisii, Shigella boydii\|Mobiluncus curtisii, Shigella dysenteriae\|Mobiluncus curtisii, Shigella sonnei\|Mobiluncus curtisii, Slackia exigua\|Mobiluncus curtisii, Solobacterium moorei\|Mobiluncus curtisii, Staphylococcus aureus\|Mobiluncus curtisii, Staphylococcus epidermidis\|Mobiluncus curtisii, Staphylococcus hominis\|Mobiluncus curtisii, Staphylococcus saprophyticus\|Mobiluncus curtisii, Staphylococcus warneri\|Mobiluncus curtisii, Streptococcus agalactiae\|Mobiluncus curtisii, Streptococcus anginosus\|Mobiluncus curtisii, Streptococcus australis\|Mobiluncus curtisii, Streptococcus bovis\|Mobiluncus curtisii, Streptococcus cristatus\|Mobiluncus curtisii, Streptococcus dysgalactiae\|Mobiluncus curtisii, Streptococcus equinus\|Mobiluncus curtisii, Streptococcus gordonii\|Mobiluncus curtisii, Streptococcus infantarius\|Mobiluncus curtisii, Streptococcus infantis\|Mobiluncus curtisii, Streptococcus mitis\|Mobiluncus curtisii, Streptococcus mutans\|Mobiluncus curtisii, Streptococcus oralis\|Mobiluncus curtisii, Streptococcus parasanguinis\|Mobiluncus curtisii, Streptococcus peroris\|Mobiluncus curtisii, Streptococcus pneumoniae\|Mobiluncus curtisii, Streptococcus salivarius\|Mobiluncus curtisii, Streptococcus sanguinis\|Mobiluncus curtisii, Streptococcus thermophilus\|Mobiluncus curtisii, Streptococcus vestibularis\|Mobiluncus curtisii, Subdoligranulum variabile\|Mobiluncus curtisii, Succinatimonas hippei\|Mobiluncus curtisii, Sutterella wadsworthensis\|Mobiluncus curtisii, Tropheryma whipplei\|Mobiluncus curtisii, Veillonella atypica\|Mobiluncus curtisii, Veillonella dispar\|Mobiluncus curtisii, Veillonella parvula\|Mobiluncus curtisii, Victivallis vadensis\|Mycoplasma hominis, Mycoplasma hominis\|Mycoplasma hominis, Neisseria mucosa\|Mycoplasma hominis, Odoribacter splanchnicus\|Mycoplasma hominis, Olsenella uli\|Mycoplasma hominis, Oribacterium sinus\|Mycoplasma hominis, Oxalobacter formigenes\|Mycoplasma hominis, Parabacteroides distasonis\|Mycoplasma hominis, Parabacteroides johnsonii\|Mycoplasma hominis, Parabacteroides merdae\|Mycoplasma hominis, Parvimonas micra\|Mycoplasma hominis, Pediococcus acidilactici\|Mycoplasma hominis, Pediococcus pentosaceus\|Mycoplasma hominis, Peptoniphilus duerdenii\|Mycoplasma hominis, Peptoniphilus harei\|Mycoplasma hominis, Peptoniphilus lacrimalis\|Mycoplasma hominis, Peptostreptococcus anaerobius\|Mycoplasma hominis, Peptostreptococcus stomatis\|Mycoplasma hominis, Porphyromonas asaccharolytica\|Mycoplasma hominis, Porphyromonas uenonis\|Mycoplasma hominis, Prevotella amnii\|Mycoplasma hominis, Prevotella bergensis\|Mycoplasma hominis, Prevotella bivia\|Mycoplasma hominis, Prevotella buccae\|Mycoplasma hominis, Prevotella buccalis\|Mycoplasma hominis, Prevotella copri\|Mycoplasma hominis, Prevotella disiens\|Mycoplasma hominis, Prevotella melaninogenica\|Mycoplasma hominis, Prevotella multiformis\|Mycoplasma hominis, Prevotella oralis\|Mycoplasma hominis, Prevotella oris\|Mycoplasma hominis, Prevotella salivae\|Mycoplasma hominis, Prevotella timonensis\|Mycoplasma hominis, Propionibacterium acnes\|Mycoplasma hominis, Propionibacterium freudenreichii\|Mycoplasma hominis, Proteus mirabilis\|Mycoplasma hominis, Proteus penneri\|Mycoplasma hominis, Pseudoflavonifractor capillosus\|Mycoplasma hominis, Pseudomonas aeruginosa\|Mycoplasma hominis, Pseudomonas fluorescens\|Mycoplasma hominis, Pseudomonas putida\|Mycoplasma hominis, Pseudoramibacter alactolyticus\|Mycoplasma hominis, Pyramidobacter piscolens\|Mycoplasma hominis, Rhodopseudomonas palustris\|Mycoplasma hominis, Roseburia intestinalis\|Mycoplasma hominis, Roseburia inulinivorans\|Mycoplasma hominis, Rothia dentocariosa\|Mycoplasma hominis, Rothia mucilaginosa\|Mycoplasma hominis, Ruminococcus albus\|Mycoplasma hominis, Ruminococcus bromii\|Mycoplasma hominis, Ruminococcus gnavus\|Mycoplasma hominis, Ruminococcus lactaris\|Mycoplasma hominis, Ruminococcus obeum\|Mycoplasma hominis, Ruminococcus torques\|Mycoplasma hominis, Selenomonas sputigena\|Mycoplasma hominis, Shigella boydii\|Mycoplasma hominis, Shigella dysenteriae\|Mycoplasma hominis, Shigella sonnei\|Mycoplasma hominis, Slackia exigua\|Mycoplasma hominis, Solobacterium moorei\|Mycoplasma hominis, Staphylococcus aureus\|Mycoplasma hominis, Staphylococcus epidermidis\|Mycoplasma hominis, Staphylococcus hominis\|Mycoplasma hominis, Staphylococcus saprophyticus\|Mycoplasma hominis, Staphylococcus warneri\|Mycoplasma hominis, Streptococcus agalactiae\|Mycoplasma hominis, Streptococcus anginosus\|Mycoplasma hominis, Streptococcus australis\|Mycoplasma hominis, Streptococcus bovis\|Mycoplasma hominis, Streptococcus cristatus\|Mycoplasma hominis, Streptococcus dysgalactiae\|Mycoplasma hominis, Streptococcus equinus\|Mycoplasma hominis, Streptococcus gordonii\|Mycoplasma hominis, Streptococcus infantarius\|Mycoplasma hominis, Streptococcus infantis\|Mycoplasma hominis, Streptococcus mitis\|Mycoplasma hominis, Streptococcus mutans\|Mycoplasma hominis, Streptococcus oralis\|Mycoplasma hominis, Streptococcus parasanguinis\|Mycoplasma hominis, Streptococcus peroris\|Mycoplasma hominis, Streptococcus pneumoniae\|Mycoplasma hominis, Streptococcus salivarius\|Mycoplasma hominis, Streptococcus sanguinis\|Mycoplasma hominis, Streptococcus thermophilus\|Mycoplasma hominis, Streptococcus vestibularis\|Mycoplasma hominis, Subdoligranulum variabile\|Mycoplasma hominis, Succinatimonas hippei\|Mycoplasma hominis, Sutterella wadsworthensis\|Mycoplasma hominis, Tropheryma whipplei\|Mycoplasma hominis, Veillonella atypica\|Mycoplasma hominis, Veillonella dispar\|Mycoplasma hominis, Veillonella parvula\|Mycoplasma hominis, Victivallis vadensis\|Neisseria mucosa, Neisseria mucosa\|Neisseria mucosa, Odoribacter splanchnicus\|Neisseria mucosa, Olsenella uli\|Neisseria mucosa, Oribacterium sinus\|Neisseria mucosa, Oxalobacter formigenes\|Neisseria mucosa, Parabacteroides distasonis\|Neisseria mucosa, Parabacteroides johnsonii\|Neisseria mucosa, Parabacteroides merdae\|Neisseria mucosa, Parvimonas micra\|Neisseria mucosa, Pediococcus acidilactici\|Neisseria mucosa, Pediococcus pentosaceus\|Neisseria mucosa, Peptoniphilus duerdenii\|Neisseria mucosa, Peptoniphilus harei\|Neisseria mucosa, Peptoniphilus lacrimalis\|Neisseria mucosa, Peptostreptococcus anaerobius\|Neisseria mucosa, Peptostreptococcus stomatis\|Neisseria mucosa, Porphyromonas asaccharolytica\|Neisseria mucosa, Porphyromonas uenonis\|Neisseria mucosa, Prevotella amnii\|Neisseria mucosa, Prevotella bergensis\|Neisseria mucosa, Prevotella bivia\|Neisseria mucosa, Prevotella buccae\|Neisseria mucosa, Prevotella buccalis\|Neisseria mucosa, Prevotella copri\|Neisseria mucosa, Prevotella disiens\|Neisseria mucosa, Prevotella melaninogenica\|Neisseria mucosa, Prevotella multiformis\|Neisseria mucosa, Prevotella oralis\|Neisseria mucosa, Prevotella oris\|Neisseria mucosa, Prevotella salivae\|Neisseria mucosa, Prevotella timonensis\|Neisseria mucosa, Propionibacterium acnes\|Neisseria mucosa, Propionibacterium freudenreichii\|Neisseria mucosa, Proteus mirabilis\|Neisseria mucosa, Proteus penneri\|Neisseria mucosa, Pseudoflavonifractor capillosus\|Neisseria mucosa, Pseudomonas aeruginosa\|Neisseria mucosa, Pseudomonas fluorescens\|Neisseria mucosa, Pseudomonas putida\|Neisseria mucosa, Pseudoramibacter alactolyticus\|Neisseria mucosa, Pyramidobacter piscolens\|Neisseria mucosa, Rhodopseudomonas palustris\|Neisseria mucosa, Roseburia intestinalis\|Neisseria mucosa, Roseburia inulinivorans\|Neisseria mucosa, Rothia dentocariosa\|Neisseria mucosa, Rothia mucilaginosa\|Neisseria mucosa, Ruminococcus albus\|Neisseria mucosa, Ruminococcus bromii\|Neisseria mucosa, Ruminococcus gnavus\|Neisseria mucosa, Ruminococcus lactaris\|Neisseria mucosa, Ruminococcus obeum\|Neisseria mucosa, Ruminococcus torques\|Neisseria mucosa, Selenomonas sputigena\|Neisseria mucosa, Shigella boydii\|Neisseria mucosa, Shigella dysenteriae\|Neisseria mucosa, Shigella sonnei\|Neisseria mucosa, Slackia exigua\|Neisseria mucosa, Solobacterium moorei\|Neisseria mucosa, Staphylococcus aureus\|Neisseria mucosa, Staphylococcus epidermidis\|Neisseria mucosa, Staphylococcus hominis\|Neisseria mucosa, Staphylococcus saprophyticus\|Neisseria mucosa, Staphylococcus warneri\|Neisseria mucosa, Streptococcus agalactiae\|Neisseria mucosa, Streptococcus anginosus\|Neisseria mucosa, Streptococcus australis\|Neisseria mucosa, Streptococcus bovis\|Neisseria mucosa, Streptococcus cristatus\|Neisseria mucosa, Streptococcus dysgalactiae\|Neisseria mucosa, Streptococcus equinus\|Neisseria mucosa, Streptococcus gordonii\|Neisseria mucosa, Streptococcus infantarius\|Neisseria mucosa, Streptococcus infantis\|Neisseria mucosa, Streptococcus mitis\|Neisseria mucosa, Streptococcus mutans\|Neisseria mucosa, Streptococcus oralis\|Neisseria mucosa, Streptococcus parasanguinis\|Neisseria mucosa, Streptococcus peroris\|Neisseria mucosa, Streptococcus pneumoniae\|Neisseria mucosa, Streptococcus salivarius\|Neisseria mucosa, Streptococcus sanguinis\|Neisseria mucosa, Streptococcus thermophilus\|Neisseria mucosa, Streptococcus vestibularis\|Neisseria mucosa, Subdoligranulum variabile\|Neisseria mucosa, Succinatimonas hippei\|Neisseria |

TABLE 2-continued

| Table 2. Specific binary combinations of OTUs. Individual pairings are differentiated by "\|" and OTUs within a combination are differentiated by "," |
|---|
| *mucosa, Sutterella wadsworthensis\|Neisseria mucosa, Tropheryma whipplei\|Neisseria mucosa, Veillonella atypica\|Neisseria mucosa, Veillonella dispar\|Neisseria mucosa, Veillonella parvula\|Neisseria mucosa, Victivallis vadensis\|Odoribacter splanchnicus, Odoribacter splanchnicus\|Odoribacter splanchnicus, Olsenella uli\|Odoribacter splanchnicus, Oribacterium sinus\|Odoribacter splanchnicus, Oxalobacter formigenes\|Odoribacter splanchnicus, Parabacteroides distasonis\|Odoribacter splanchnicus, Parabacteroides johnsonii\|Odoribacter splanchnicus, Parabacteroides merdae\|Odoribacter splanchnicus, Parvimonas micra\|Odoribacter splanchnicus, Pediococcus acidilactici\|Odoribacter splanchnicus, Pediococcus pentosaceus\|Odoribacter splanchnicus, Peptoniphilus duerdenii\|Odoribacter splanchnicus, Peptoniphilus harei\|Odoribacter splanchnicus, Peptoniphilus lacrimalis\|Odoribacter splanchnicus, Peptostreptococcus anaerobius\|Odoribacter splanchnicus, Peptostreptococcus stomatis\|Odoribacter splanchnicus, Porphyromonas asaccharolytica\|Odoribacter splanchnicus, Porphyromonas uenonis\|Odoribacter splanchnicus, Prevotella amnii\|Odoribacter splanchnicus, Prevotella bergensis\|Odoribacter splanchnicus, Prevotella bivia\|Odoribacter splanchnicus, Prevotella buccae\|Odoribacter splanchnicus, Prevotella buccalis\|Odoribacter splanchnicus, Prevotella copri\|Odoribacter splanchnicus, Prevotella disiens\|Odoribacter splanchnicus, Prevotella melaninogenica\|Odoribacter splanchnicus, Prevotella multiformis\|Odoribacter splanchnicus, Prevotella oralis\|Odoribacter splanchnicus, Prevotella oris\|Odoribacter splanchnicus, Prevotella salivae\|Odoribacter splanchnicus, Prevotella timonensis\|Odoribacter splanchnicus, Propionibacterium acnes\|Odoribacter splanchnicus, Propionibacterium freudenreichii\|Odoribacter splanchnicus, Proteus mirabilis\|Odoribacter splanchnicus, Proteus penneri\|Odoribacter splanchnicus, Pseudoflavonifractor capillosus\|Odoribacter splanchnicus, Pseudomonas aeruginosa\|Odoribacter splanchnicus, Pseudomonas fluorescens\|Odoribacter splanchnicus, Pseudomonas putida\|Odoribacter splanchnicus, Pseudoramibacter alactolyticus\|Odoribacter splanchnicus, Pyramidobacter piscolens\|Odoribacter splanchnicus, Rhodopseudomonas palustris\|Odoribacter splanchnicus, Roseburia intestinalis\|Odoribacter splanchnicus, Roseburia inulinivorans\|Odoribacter splanchnicus, Rothia dentocariosa\|Odoribacter splanchnicus, Rothia mucilaginosa\|Odoribacter splanchnicus, Ruminococcus albus\|Odoribacter splanchnicus, Ruminococcus bromii\|Odoribacter splanchnicus, Ruminococcus gnavus\|Odoribacter splanchnicus, Ruminococcus lactaris\|Odoribacter splanchnicus, Ruminococcus obeum\|Odoribacter splanchnicus, Ruminococcus torques\|Odoribacter splanchnicus, Selenomonas sputigena\|Odoribacter splanchnicus, Shigella boydii\|Odoribacter splanchnicus, Shigella dysenteriae\|Odoribacter splanchnicus, Shigella sonnei\|Odoribacter splanchnicus, Slackia exigua\|Odoribacter splanchnicus, Solobacterium moorei\|Odoribacter splanchnicus, Staphylococcus aureus\|Odoribacter splanchnicus, Staphylococcus epidermidis\|Odoribacter splanchnicus, Staphylococcus hominis\|Odoribacter splanchnicus, Staphylococcus saprophyticus\|Odoribacter splanchnicus, Staphylococcus warneri\|Odoribacter splanchnicus, Streptococcus agalactiae\|Odoribacter splanchnicus, Streptococcus anginosus\|Odoribacter splanchnicus, Streptococcus australis\|Odoribacter splanchnicus, Streptococcus bovis\|Odoribacter splanchnicus, Streptococcus cristatus\|Odoribacter splanchnicus, Streptococcus dysgalactiae\|Odoribacter splanchnicus, Streptococcus equinus\|Odoribacter splanchnicus, Streptococcus gordonii\|Odoribacter splanchnicus, Streptococcus infantarius\|Odoribacter splanchnicus, Streptococcus infantis\|Odoribacter splanchnicus, Streptococcus mitis\|Odoribacter splanchnicus, Streptococcus mutans\|Odoribacter splanchnicus, Streptococcus oralis\|Odoribacter splanchnicus, Streptococcus parasanguinis\|Odoribacter splanchnicus, Streptococcus peroris\|Odoribacter splanchnicus, Streptococcus pneumoniae\|Odoribacter splanchnicus, Streptococcus salivarius\|Odoribacter splanchnicus, Streptococcus sanguinis\|Odoribacter splanchnicus, Streptococcus thermophilus\|Odoribacter splanchnicus, Streptococcus vestibularis\|Odoribacter splanchnicus, Subdoligranulum variabile\|Odoribacter splanchnicus, Succinatimonas hippei\|Odoribacter splanchnicus, Sutterella wadsworthensis\|Odoribacter splanchnicus, Tropheryma whipplei\|Odoribacter splanchnicus, Veillonella atypica\|Odoribacter splanchnicus, Veillonella dispar\|Odoribacter splanchnicus, Veillonella parvula\|Pdoribacter splanchnicus, Victivallis vadensis\|Olsenella uli, Olsenella uli\|Olsenella uli, Oribacterium sinus\|Olsenella uli, Oxalobacter formigenes\|Olsenella uli, Parabacteroides distasonis\|Olsenella uli, Parabacteroides johnsonii\|Olsenella uli, Parabacteroides merdae\|Olsenella uli, Parvimonas micra\|Olsenella uli, Pediococcus acidilactici\|Olsenella uli, Pediococcus pentosaceus\|Olsenella uli, Peptoniphilus duerdenii\|Olsenella uli, Peptoniphilus harei\|Olsenella uli, Peptoniphilus lacrimalis\|Olsenella uli, Peptostreptococcus anaerobius\|Olsenella uli, Peptostreptococcus stomatis\|Olsenella uli, Porphyromonas asaccharolytica\|Olsenella uli, Porphyromonas uenonis\|Olsenella uli, Prevotella amnii\|Olsenella uli, Prevotella bergensis\|Olsenella uli, Prevotella bivia\|Olsenella uli, Prevotella buccae\|Olsenella uli, Prevotella buccalis\|Olsenella uli, Prevotella copri\|Olsenella uli, Prevotella disiens\|Olsenella uli, Prevotella melaninogenica\|Olsenella uli, Prevotella multiformis\|Olsenella uli, Prevotella oralis\|Olsenella uli, Prevotella oris\|Olsenella uli, Prevotella salivae\|Olsenella uli, Prevotella timonensis\|Olsenella uli, Propionibacterium acnes\|Olsenella uli, Propionibacterium freudenreichii\|Olsenella uli, Proteus mirabilis\|Olsenella uli, Proteus penneri\|Olsenella uli, Pseudoflavonifractor capillosus\|Olsenella uli, Pseudomonas aeruginosa\|Olsenella uli, Pseudomonas fluorescens\|Olsenella uli, Pseudomonas putida\|Olsenella uli, Pseudoramibacter alactolyticus\|Olsenella uli, Pyramidobacter piscolens\|Olsenella uli, Rhodopseudomonas palustris\|Olsenella uli, Roseburia intestinalis\|Olsenella uli, Roseburia inulinivorans\|Olsenella uli, Rothia dentocariosa\|Olsenella uli, Rothia mucilaginosa\|Olsenella uli, Ruminococcus albus\|Olsenella uli, Ruminococcus bromii\|Olsenella uli, Ruminococcus gnavus\|Olsenella uli, Ruminococcus lactaris\|Olsenella uli, Ruminococcus obeum\|Olsenella uli, Ruminococcus torques\|Olsenella uli, Selenomonas sputigena\|Olsenella uli, Shigella boydii\|Olsenella uli, Shigella dysenteriae\|Olsenella uli, Shigella sonnei\|Olsenella uli, Slackia exigua\|Olsenella uli, Solobacterium moorei\|Olsenella uli, Staphylococcus aureus\|Olsenella uli, Staphylococcus epidermidis\|Olsenella uli, Staphylococcus hominis\|Olsenella uli, Staphylococcus saprophyticus\|Olsenella uli, Staphylococcus warneri\|Olsenella uli, Streptococcus agalactiae\|Olsenella uli, Streptococcus anginosus\|Olsenella uli, Streptococcus australis\|Olsenella uli, Streptococcus bovis\|Olsenella uli, Streptococcus cristatus\|Olsenella uli, Streptococcus dysgalactiae\|Olsenella uli, Streptococcus equinus\|Olsenella uli, Streptococcus gordonii\|Olsenella uli, Streptococcus infantarius\|Olsenella uli, Streptococcus infantis\|Olsenella uli, Streptococcus mitis\|Olsenella uli, Streptococcus mutans\|Olsenella uli, Streptococcus oralis\|Olsenella uli, Streptococcus parasanguinis\|Olsenella uli, Streptococcus peroris\|Olsenella uli, Streptococcus pneumoniae\|Olsenella uli, Streptococcus salivarius\|Olsenella uli, Streptococcus sanguinis\|Olsenella uli, Streptococcus thermophilus\|Olsenella uli, Streptococcus vestibularis\|Olsenella uli, Subdoligranulum variabile\|Olsenella uli, Succinatimonas hippei\|Olsenella uli, Sutterella wadsworthensis\|Olsenella uli, Tropheryma whipplei\|Olsenella uli, Veillonella atypica\|Olsenella uli, Veillonella dispar\|Olsenella uli, Veillonella parvula\|Olsenella uli, Victivallis vadensis\|Oribacterium sinus, Oribacterium sinus\|Oribacterium sinus, Oxalobacter formigenes\|Oribacterium sinus, Parabacteroides distasonis\|Oribacterium sinus, Parabacteroides johnsonii\|Oribacterium sinus, Parabacteroides merdae\|Oribacterium sinus, Parvimonas micra\|Oribacterium sinus, Pediococcus acidilactici\|Oribacterium sinus, Pediococcus pentosaceus\|Oribacterium sinus, Peptoniphilus duerdenii\|Oribacterium sinus, Peptoniphilus harei\|Oribacterium sinus, Peptoniphilus lacrimalis\|Oribacterium sinus, Peptostreptococcus anaerobius\|Oribacterium sinus, Peptostreptococcus stomatis\|Oribacterium sinus, Porphyromonas asaccharolytica\|Oribacterium sinus, Porphyromonas uenonis\|Oribacterium sinus, Prevotella amnii\|Oribacterium sinus, Prevotella bergensis\|Oribacterium sinus, Prevotella bivia\|Oribacterium sinus, Prevotella buccae\|Oribacterium sinus, Prevotella buccalis\|Oribacterium sinus, Prevotella copri\|Oribacterium sinus, Prevotella disiens\|Oribacterium sinus, Prevotella melaninogenica\|Oribacterium sinus, Prevotella multiformis\|Oribacterium sinus, Prevotella oralis\|Oribacterium sinus, Prevotella oris\|Oribacterium sinus, Prevotella salivae\|Oribacterium sinus, Prevotella timonensis\|Oribacterium sinus, Propionibacterium acnes\|Oribacterium sinus, Propionibacterium freudenreichii\|Oribacterium sinus, Proteus mirabilis\|Oribacterium sinus, Proteus penneri\|Oribacterium sinus, Pseudoflavonifractor capillosus\|Oribacterium sinus, Pseudomonas aeruginosa\|Oribacterium sinus, Pseudomonas fluorescens\|Oribacterium sinus, Pseudomonas putida\|Oribacterium sinus, Pseudoramibacter alactolyticus\|Oribacterium sinus, Pyramidobacter piscolens\|Oribacterium sinus, Rhodopseudomonas palustris\|Oribacterium sinus, Roseburia intestinalis\|Oribacterium sinus, Roseburia inulinivorans\|Oribacterium sinus, Rothia dentocariosa\|Oribacterium sinus, Rothia mucilaginosa\|Oribacterium sinus, Ruminococcus albus\|Oribacterium sinus, Ruminococcus bromii\|Oribacterium sinus, Ruminococcus gnavus\|Oribacterium sinus, Ruminococcus lactaris\|Oribacterium sinus, Ruminococcus obeum\|Oribacterium sinus, Ruminococcus torques\|Oribacterium sinus, Selenomonas sputigena\|Oribacterium sinus, Shigella boydii\|Oribacterium sinus, Shigella dysenteriae\|Oribacterium sinus, Shigella sonnei\|Oribacterium sinus, Slackia exigua\|Oribacterium sinus, Solobacterium* |

TABLE 2-continued

| Table 2. Specific binary combinations of OTUs. Individual pairings are differentiated by "\|" and OTUs within a combination are differentiated by "," |
|---|
| *moorei\|Oribacterium sinus, Staphylococcus aureus\|Oribacterium sinus, Staphylococcus epidermidis\|Oribacterium sinus, Staphylococcus hominis\|Oribacterium sinus, Staphylococcus saprophyticus\|Oribacterium sinus, Staphylococcus warneri\|Oribacterium sinus, Streptococcus agalactiae\|Oribacterium sinus, Streptococcus anginosus\|Oribacterium sinus, Streptococcus australis\|Oribacterium sinus, Streptococcus bovis\|Oribacterium sinus, Streptococcus cristatus\|Oribacterium sinus, Streptococcus dysgalactiae\|Oribacterium sinus, Streptococcus equinus\|Oribacterium sinus, Streptococcus gordonii\|Oribacterium sinus, Streptococcus infantarius\|Oribacterium sinus, Streptococcus infantis\|Oribacterium sinus, Streptococcus mitis\|Oribacterium sinus, Streptococcus mutans\|Oribacterium sinus, Streptococcus oralis\|Oribacterium sinus, Streptococcus parasanguinis\|Oribacterium sinus, Streptococcus peroris\|Oribacterium sinus, Streptococcus pneumoniae\|Oribacterium sinus, Streptococcus salivarius\|Oribacterium sinus, Streptococcus sanguinis\|Oribacterium sinus, Streptococcus thermophilus\|Oribacterium sinus, Streptococcus vestibularis\|Oribacterium sinus, Subdoligranulum variabile\|Oribacterium sinus, Succinatimonas hippei\|Oribacterium sinus, Sutterella wadsworthensis\|Oribacterium sinus, Tropheryma whipplei\|Oribacterium sinus, Veillonella atypica\|Oribacterium sinus, Veillonella dispar\|Oribacterium sinus, Veillonella parvula\|Oribacterium sinus, Victivallis vadensis\|Oxalobacter formigenes, Oxalobacter formigenes\|Oxalobacter formigenes, Parabacteroides distasonis\|Oxalobacter formigenes, Parabacteroides johnsonii\|Oxalobacter formigenes, Parabacteroides merdae\|Oxalobacter formigenes, Parvimonas micra\|Oxalobacter formigenes, Pediococcus acidilactici\|Oxalobacter formigenes, Pediococcus pentosaceus\|Oxalobacter formigenes, Peptoniphilus duerdenii\|Oxalobacter formigenes, Peptoniphilus harei\|Oxalobacter formigenes, Peptoniphilus lacrimalis\|Oxalobacter formigenes, Peptostreptococcus anaerobius\|Oxalobacter formigenes, Peptostreptococcus stomatis\|Oxalobacter formigenes, Porphyromonas asaccharolytica\|Oxalobacter formigenes, Porphyromonas uenonis\|Oxalobacter formigenes, Prevotella amnii\|Oxalobacter formigenes, Prevotella bergensis\|Oxalobacter formigenes, Prevotella bivia\|Oxalobacter formigenes, Prevotella buccae\|Oxalobacter formigenes, Prevotella buccalis\|Oxalobacter formigenes, Prevotella copri\|Oxalobacter formigenes, Prevotella disiens\|Oxalobacter formigenes, Prevotella melaninogenica\|Oxalobacter formigenes, Prevotella multiformis\|Oxalobacter formigenes, Prevotella oralis\|Oxalobacter formigenes, Prevotella oris\|Oxalobacter formigenes, Prevotella salivae\|Oxalobacter formigenes, Prevotella timonensis\|Oxalobacter formigenes, Propionibacterium acnes\|Oxalobacter formigenes, Propionibacterium freudenreichii\|Oxalobacter formigenes, Proteus mirabilis\|Oxalobacter formigenes, Proteus penneri\|Oxalobacter formigenes, Pseudoflavonifractor capillosus\|Oxalobacter formigenes, Pseudomonas aeruginosa\|Oxalobacter formigenes, Pseudomonas fluorescens\|Oxalobacter formigenes, Pseudomonas putida\|Oxalobacter formigenes, Pseudoramibacter alactolyticus\|Oxalobacter formigenes, Pyramidobacter piscolens\|Oxalobacter formigenes, Rhodopseudomonas palustris\|Oxalobacter formigenes, Roseburia intestinalis\|Oxalobacter formigenes, Roseburia inulinivorans\|Oxalobacter formigenes, Rothia dentocariosa\|Oxalobacter formigenes, Rothia mucilaginosa\|Oxalobacter formigenes, Ruminococcus albus\|Oxalobacter formigenes, Ruminococcus bromii\|Oxalobacter formigenes, Ruminococcus gnavus\|Oxalobacter formigenes, Ruminococcus lactaris\|Oxalobacter formigenes, Ruminococcus obeum\|Oxalobacter formigenes, Ruminococcus torques\|Oxalobacter formigenes, Selenomonas sputigena\|Oxalobacter formigenes, Shigella boydii\|Oxalobacter formigenes, Shigella dysenteriae\|Oxalobacter formigenes, Shigella sonnei\|Oxalobacter formigenes, Slackia exigua\|Oxalobacter formigenes, Solobacterium moorei\|Oxalobacter formigenes, Staphylococcus aureus\|Oxalobacter formigenes, Staphylococcus epidermidis\|Oxalobacter formigenes, Staphylococcus hominis\|Oxalobacter formigenes, Staphylococcus saprophyticus\|Oxalobacter formigenes, Staphylococcus warneri\|Oxalobacter formigenes, Streptococcus agalactiae\|Oxalobacter formigenes, Streptococcus anginosus\|Oxalobacter formigenes, Streptococcus australis\|Oxalobacter formigenes, Streptococcus bovis\|Oxalobacter formigenes, Streptococcus cristatus\|Oxalobacter formigenes, Streptococcus dysgalactiae\|Oxalobacter formigenes, Streptococcus equinus\|Oxalobacter formigenes, Streptococcus gordonii\|Oxalobacter formigenes, Streptococcus infantarius\|Oxalobacter formigenes, Streptococcus infantis\|Oxalobacter formigenes, Streptococcus mitis\|Oxalobacter formigenes, Streptococcus mutans\|Oxalobacter formigenes, Streptococcus oralis\|Oxalobacter formigenes, Streptococcus parasanguinis\|Oxalobacter formigenes, Streptococcus peroris\|Oxalobacter formigenes, Streptococcus pneumoniae\|Oxalobacter formigenes, Streptococcus salivarius\|Oxalobacter formigenes, Streptococcus sanguinis\|Oxalobacter formigenes, Streptococcus thermophilus\|Oxalobacter formigenes, Streptococcus vestibularis\|Oxalobacter formigenes, Subdoligranulum variabile\|Oxalobacter formigenes, Succinatimonas hippei\|Oxalobacter formigenes, Sutterella wadsworthensis\|Oxalobacter formigenes, Tropheryma whipplei\|Oxalobacter formigenes, Veillonella atypica\|Oxalobacter formigenes, Veillonella dispar\|Oxalobacter formigenes, Veillonella parvula\|Oxalobacter formigenes, Victivallis vadensis\|Parabacteroides distasonis, Parabacteroides distasonis\|Parabacteroides distasonis, Parabacteroides johnsonii\|Parabacteroides distasonis, Parabacteroides merdae, Parabacteroides distasonis, Parvimonas micra\|Parabacteroides distasonis, Pediococcus acidilactici\|Parabacteroides distasonis, Pediococcus pentosaceus\|Parabacteroides distasonis, Peptoniphilus duerdenii\|Parabacteroides distasonis, Peptoniphilus harei\|Parabacteroides distasonis, Peptoniphilus lacrimalis\|Parabacteroides distasonis, Peptostreptococcus anaerobius\|Parabacteroides distasonis, Peptostreptococcus stomatis\|Parabacteroides distasonis, Porphyromonas asaccharolytica\|Parabacteroides distasonis, Porphyromonas uenonis\|Parabacteroides distasonis, Prevotella amnii\|Parabacteroides distasonis, Prevotella bergensis\|Parabacteroides distasonis, Prevotella bivia\|Parabacteroides distasonis, Prevotella buccae\|Parabacteroides distasonis, Prevotella buccalis\|Parabacteroides distasonis, Prevotella copri\|Parabacteroides distasonis, Prevotella disiens\|Parabacteroides distasonis, Prevotella melaninogenica\|Parabacteroides distasonis, Prevotella multiformis\|Parabacteroides distasonis, Prevotella oralis\|Parabacteroides distasonis, Prevotella oris\|Parabacteroides distasonis, Prevotella salivae\|Parabacteroides distasonis, Prevotella timonensis\|Parabacteroides distasonis, Propionibacterium acnes\|Parabacteroides distasonis, Propionibacterium freudenreichii\|Parabacteroides distasonis, Proteus mirabilis\|Parabacteroides distasonis, Proteus penneri\|Parabacteroides distasonis, Pseudoflavonifractor capillosus\|Parabacteroides distasonis, Pseudomonas aeruginosa\|Parabacteroides distasonis, Pseudomonas fluorescens\|Parabacteroides distasonis, Pseudomonas putida\|Parabacteroides distasonis, Pseudoramibacter alactolyticus\|Parabacteroides distasonis, Pyramidobacter piscolens\|Parabacteroides distasonis, Rhodopseudomonas palustris\|Parabacteroides distasonis, Roseburia intestinalis\|Parabacteroides distasonis, Roseburia inulinivorans\|Parabacteroides distasonis, Rothia dentocariosa\|Parabacteroides distasonis, Rothia mucilaginosa\|Parabacteroides distasonis, Ruminococcus albus\|Parabacteroides distasonis, Ruminococcus bromii\|Parabacteroides distasonis, Ruminococcus gnavus\|Parabacteroides distasonis, Ruminococcus lactaris\|Parabacteroides distasonis, Ruminococcus obeum\|Parabacteroides distasonis, Ruminococcus torques\|Parabacteroides distasonis, Selenomonas sputigena\|Parabacteroides distasonis, Shigella boydii\|Parabacteroides distasonis, Shigella dysenteriae\|Parabacteroides distasonis, Shigella sonnei\|Parabacteroides distasonis, Slackia exigua\|Parabacteroides distasonis, Solobacterium moorei\|Parabacteroides distasonis, Staphylococcus aureus\|Parabacteroides distasonis, Staphylococcus epidermidis\|Parabacteroides distasonis, Staphylococcus hominis\|Parabacteroides distasonis, Staphylococcus saprophyticus\|Parabacteroides distasonis, Staphylococcus warneri\|Parabacteroides distasonis, Streptococcus agalactiae\|Parabacteroides distasonis, Streptococcus anginosus\|Parabacteroides distasonis, Streptococcus australis\|Parabacteroides distasonis, Streptococcus bovis\|Parabacteroides distasonis, Streptococcus cristatus\|Parabacteroides distasonis, Streptococcus dysgalactiae\|Parabacteroides distasonis, Streptococcus equinus\|Parabacteroides distasonis, Streptococcus gordonii\|Parabacteroides distasonis, Streptococcus infantarius\|Parabacteroides distasonis, Streptococcus infantis\|Parabacteroides distasonis, Streptococcus mitis\|Parabacteroides distasonis, Streptococcus mutans\|Parabacteroides distasonis, Streptococcus oralis\|Parabacteroides distasonis, Streptococcus parasanguinis\|Parabacteroides distasonis, Streptococcus peroris\|Parabacteroides distasonis, Streptococcus pneumoniae\|Parabacteroides distasonis, Streptococcus salivarius\|Parabacteroides distasonis, Streptococcus sanguinis\|Parabacteroides distasonis, Streptococcus thermophilus\|Parabacteroides distasonis, Streptococcus vestibularis\|Parabacteroides distasonis, Subdoligranulum variabile\|Parabacteroides distasonis, Succinatimonas hippei\|Parabacteroides distasonis, Sutterella wadsworthensis\|Parabacteroides distasonis, Tropheryma whipplei\|Parabacteroides distasonis, Veillonella atypica\|Parabacteroides distasonis, Veillonella dispar\|Parabacteroides distasonis, Veillonella parvula\|Parabacteroides distasonis, Victivallis vadensis\|Parabacteroides johnsonii, Parabacteroides johnsonii\|Parabacteroides johnsonii, Parabacteroides merdae\|Parabacteroides johnsonii, Parvimonas micra\|Parabacteroides johnsonii, Pediococcus acidilactici\|Parabacteroides* |

TABLE 2-continued

| Table 2. Specific binary combinations of OTUs. Individual pairings are differentiated by "\|" and OTUs within a combination are differentiated by "," |
| --- |
| *johnsonii, Pediococcus pentosaceus\|Parabacteroides johnsonii, Peptoniphilus duerdenii\|Parabacteroides johnsonii, Peptoniphilus harei\|Parabacteroides johnsonii, Peptoniphilus lacrimalis\|Parabacteroides johnsonii, Peptostreptococcus anaerobius\|Parabacteroides johnsonii, Peptostreptococcus stomatis\|Parabacteroides johnsonii, Porphyromonas asaccharolytica\|Parabacteroides johnsonii, Porphyromonas uenonis\|Parabacteroides johnsonii, Prevotella amnii\|Parabacteroides johnsonii, Prevotella bergensis\|Parabacteroides johnsonii, Prevotella bivia\|Parabacteroides johnsonii, Prevotella buccae\|Parabacteroides johnsonii, Prevotella buccalis\|Parabacteroides johnsonii, Prevotella copri\|Parabacteroides johnsonii, Prevotella disiens\|Parabacteroides johnsonii, Prevotella melaninogenica\|Parabacteroides johnsonii, Prevotella multiformis\|Parabacteroides johnsonii, Prevotella oralis\|Parabacteroides johnsonii, Prevotella oris\|Parabacteroides johnsonii, Prevotella salivae\|Parabacteroides johnsonii, Prevotella timonensis\|Parabacteroides johnsonii, Propionibacterium acnes\|Parabacteroides johnsonii, Propionibacterium freudenreichii\|Parabacteroides johnsonii, Proteus mirabilis\|Parabacteroides johnsonii, Proteus penneri\|Parabacteroides johnsonii, Pseudoflavonifractor capillosus\|Parabacteroides johnsonii, Pseudomonas aeruginosa\|Parabacteroides johnsonii, Pseudomonas fluorescens\|Parabacteroides johnsonii, Pseudomonas putida\|Parabacteroides johnsonii, Pseudoramibacter alactolyticus\|Parabacteroides johnsonii, Pyramidobacter piscolens\|Parabacteroides johnsonii, Rhodopseudomonas palustris\|Parabacteroides johnsonii, Roseburia intestinalis\|Parabacteroides johnsonii, Roseburia inulinivorans\|Parabacteroides johnsonii, Rothia dentocariosa\|Parabacteroides johnsonii, Rothia mucilaginosa\|Parabacteroides johnsonii, Ruminococcus albus\|Parabacteroides johnsonii, Ruminococcus bromii\|Parabacteroides johnsonii, Ruminococcus gnavus\|Parabacteroides johnsonii, Ruminococcus lactaris\|Parabacteroides johnsonii, Ruminococcus obeum\|Parabacteroides johnsonii, Ruminococcus torques\|Parabacteroides johnsonii, Selenomonas sputigena\|Parabacteroides johnsonii, Shigella boydii\|Parabacteroides johnsonii, Shigella dysenteriae\|Parabacteroides johnsonii, Shigella sonnei\|Parabacteroides johnsonii, Slackia exigua\|Parabacteroides johnsonii, Solobacterium moorei\|Parabacteroides johnsonii, Staphylococcus aureus\|Parabacteroides johnsonii, Staphylococcus epidermidis\|Parabacteroides johnsonii, Staphylococcus hominis\|Parabacteroides johnsonii, Staphylococcus saprophyticus\|Parabacteroides johnsonii, Staphylococcus warneri\|Parabacteroides johnsonii, Streptococcus agalactiae\|Parabacteroides johnsonii, Streptococcus anginosus\|Parabacteroides johnsonii, Streptococcus australis\|Parabacteroides johnsonii, Streptococcus bovis\|Parabacteroides johnsonii, Streptococcus cristatus\|Parabacteroides johnsonii, Streptococcus dysgalactiae\|Parabacteroides johnsonii, Streptococcus equinus\|Parabacteroides johnsonii, Streptococcus gordonii\|Parabacteroides johnsonii, Streptococcus infantarius\|Parabacteroides johnsonii, Streptococcus infantis\|Parabacteroides johnsonii, Streptococcus mitis\|Parabacteroides johnsonii, Streptococcus mutans\|Parabacteroides johnsonii, Streptococcus oralis\|Parabacteroides johnsonii, Streptococcus parasanguinis\|Parabacteroides johnsonii, Streptococcus peroris\|Parabacteroides johnsonii, Streptococcus pneumoniae\|Parabacteroides johnsonii, Streptococcus salivarius\|Parabacteroides johnsonii, Streptococcus sanguinis\|Parabacteroides johnsonii, Streptococcus thermophilus\|Parabacteroides johnsonii, Streptococcus vestibularis\|Parabacteroides johnsonii, Subdoligranulum variabile\|Parabacteroides johnsonii, Succinatimonas hippei\|Parabacteroides johnsonii, Sutterella wadsworthensis\|Parabacteroides johnsonii, Tropheryma whipplei\|Parabacteroides johnsonii, Veillonella atypica\|Parabacteroides johnsonii, Veillonella dispar\|Parabacteroides johnsonii, Veillonella parvula\|Parabacteroides johnsonii, Victivallis vadensis\|Parabacteroides merdae, Parabacteroides merdae\|Parabacteroides merdae, Parvimonas micra\|Parabacteroides merdae, Pediococcus acidilactici\|Parabacteroides merdae, Pediococcus pentosaceus\|Parabacteroides merdae, Peptoniphilus duerdenii\|Parabacteroides merdae, Peptoniphilus harei\|Parabacteroides merdae, Peptoniphilus lacrimalis\|Parabacteroides merdae, Peptostreptococcus anaerobius\|Parabacteroides merdae, Peptostreptococcus stomatis\|Parabacteroides merdae, Porphyromonas asaccharolytica\|Parabacteroides merdae, Porphyromonas uenonis\|Parabacteroides merdae, Prevotella amnii\|Parabacteroides merdae, Prevotella bergensis\|Parabacteroides merdae, Prevotella bivia\|Parabacteroides merdae, Prevotella buccae\|Parabacteroides merdae, Prevotella buccalis\|Parabacteroides merdae, Prevotella copri\|Parabacteroides merdae, Prevotella disiens\|Parabacteroides merdae, Prevotella melaninogenica\|Parabacteroides merdae, Prevotella multiformis\|Parabacteroides merdae, Prevotella oralis\|Parabacteroides merdae, Prevotella oris\|Parabacteroides merdae, Prevotella salivae\|Parabacteroides merdae, Prevotella timonensis\|Parabacteroides merdae, Propionibacterium acnes\|Parabacteroides merdae, Propionibacterium freudenreichii\|Parabacteroides merdae, Proteus mirabilis\|Parabacteroides merdae, Proteus penneri\|Parabacteroides merdae, Pseudoflavonifractor capillosus\|Parabacteroides merdae, Pseudomonas aeruginosa\|Parabacteroides merdae, Pseudomonas fluorescens\|Parabacteroides merdae, Pseudomonas putida\|Parabacteroides merdae, Pseudoramibacter alactolyticus\|Parabacteroides merdae, Pyramidobacter piscolens\|Parabacteroides merdae, Rhodopseudomonas palustris\|Parabacteroides merdae, Roseburia intestinalis\|Parabacteroides merdae, Roseburia inulinivorans\|Parabacteroides merdae, Rothia dentocariosa\|Parabacteroides merdae, Rothia mucilaginosa\|Parabacteroides merdae, Ruminococcus albus\|Parabacteroides merdae, Ruminococcus bromii\|Parabacteroides merdae, Ruminococcus gnavus\|Parabacteroides merdae, Ruminococcus lactaris\|Parabacteroides merdae, Ruminococcus obeum\|Parabacteroides merdae, Ruminococcus torques\|Parabacteroides merdae, Selenomonas sputigena\|Parabacteroides merdae, Shigella boydii\|Parabacteroides merdae, Shigella dysenteriae\|Parabacteroides merdae, Shigella sonnei\|Parabacteroides merdae, Slackia exigua\|Parabacteroides merdae, Solobacterium moorei\|Parabacteroides merdae, Staphylococcus aureus\|Parabacteroides merdae, Staphylococcus epidermidis\|Parabacteroides merdae, Staphylococcus hominis\|Parabacteroides merdae, Staphylococcus saprophyticus\|Parabacteroides merdae, Staphylococcus warneri\|Parabacteroides merdae, Streptococcus agalactiae\|Parabacteroides merdae, Streptococcus anginosus\|Parabacteroides merdae, Streptococcus australis\|Parabacteroides merdae, Streptococcus bovis\|Parabacteroides merdae, Streptococcus cristatus\|Parabacteroides merdae, Streptococcus dysgalactiae\|Parabacteroides merdae, Streptococcus equinus\|Parabacteroides merdae, Streptococcus gordonii\|Parabacteroides merdae, Streptococcus infantarius\|Parabacteroides merdae, Streptococcus infantis\|Parabacteroides merdae, Streptococcus mitis\|Parabacteroides merdae, Streptococcus mutans\|Parabacteroides merdae, Streptococcus oralis\|Parabacteroides merdae, Streptococcus parasanguinis\|Parabacteroides merdae, Streptococcus peroris\|Parabacteroides merdae, Streptococcus pneumoniae\|Parabacteroides merdae, Streptococcus salivarius\|Parabacteroides merdae, Streptococcus sanguinis\|Parabacteroides merdae, Streptococcus thermophilus\|Parabacteroides merdae, Streptococcus vestibularis\|Parabacteroides merdae, Subdoligranulum variabile\|Parabacteroides merdae, Succinatimonas hippei\|Parabacteroides merdae, Sutterella wadsworthensis\|Parabacteroides merdae, Tropheryma whipplei\|Parabacteroides merdae, Veillonella atypica\|Parabacteroides merdae, Veillonella dispar\|Parabacteroides merdae, Veillonella parvula\|Parabacteroides merdae, Victivallis vadensis\|Parvimonas micra, Parvimonas micra\|Parvimonas micra, Pediococcus acidilactici\|Parvimonas micra, Pediococcus pentosaceus\|Parvimonas micra, Peptoniphilus duerdenii\|Parvimonas micra, Peptoniphilus harei\|Parvimonas micra, Peptoniphilus lacrimalis\|Parvimonas micra, Peptostreptococcus anaerobius\|Parvimonas micra, Peptostreptococcus stomatis\|Parvimonas micra, Porphyromonas asaccharolytica\|Parvimonas micra, Porphyromonas uenonis\|Parvimonas micra, Prevotella amnii\|Parvimonas micra, Prevotella bergensis\|Parvimonas micra, Prevotella bivia\|Parvimonas micra, Prevotella buccae\|Parvimonas micra, Prevotella buccalis\|Parvimonas micra, Prevotella copri\|Parvimonas micra, Prevotella disiens\|Parvimonas micra, Prevotella melaninogenica\|Parvimonas micra, Prevotella multiformis\|Parvimonas micra, Prevotella oralis\|Parvimonas micra, Prevotella oris\|Parvimonas micra, Prevotella salivae\|Parvimonas micra, Prevotella timonensis\|Parvimonas micra, Propionibacterium acnes\|Parvimonas micra, Propionibacterium freudenreichii\|Parvimonas micra, Proteus mirabilis\|Parvimonas micra, Proteus penneri\|Parvimonas micra, Pseudoflavonifractor capillosus\|Parvimonas micra, Pseudomonas aeruginosa\|Parvimonas micra, Pseudomonas fluorescens\|Parvimonas micra, Pseudomonas putida\|Parvimonas micra, Pseudoramibacter alactolyticus\|Parvimonas micra, Pyramidobacter piscolens\|Parvimonas micra, Rhodopseudomonas palustris\|Parvimonas micra, Roseburia intestinalis\|Parvimonas micra, Roseburia inulinivorans\|Parvimonas micra, Rothia dentocariosa\|Parvimonas micra, Rothia mucilaginosa\|Parvimonas micra, Ruminococcus albus\|Parvimonas micra, Ruminococcus bromii\|Parvimonas micra, Ruminococcus gnavus\|Parvimonas micra, Ruminococcus lactaris\|Parvimonas micra, Ruminococcus obeum\|Parvimonas micra, Ruminococcus torques\|Parvimonas micra, Selenomonas sputigena\|Parvimonas micra, Shigella boydii\|Parvimonas micra, Shigella dysenteriae\|Parvimonas micra, Shigella sonnei\|Parvimonas micra, Slackia exigua\|Parvimonas micra, Solobacterium moorei\|Parvimonas micra, Staphylococcus aureus\|Parvimonas* |

TABLE 2-continued

Table 2. Specific binary combinations of OTUs. Individual pairings are differentiated by "|" and OTUs within a combination are differentiated by ","

*micra, Staphylococcus epidermidis|Parvimonas micra, Staphylococcus hominis|Parvimonas micra, Staphylococcus saprophyticus|Parvimonas micra, Staphylococcus warneri|Parvimonas micra, Streptococcus agalactiae|Parvimonas micra, Streptococcus anginosus|Parvimonas micra, Streptococcus australis|Parvimonas micra, Streptococcus bovis|Parvimonas micra, Streptococcus cristatus|Parvimonas micra, Streptococcus dysgalactiae|Parvimonas micra, Streptococcus equinus|Parvimonas micra, Streptococcus gordonii|Parvimonas micra, Streptococcus infantarius|Parvimonas micra, Streptococcus infantis|Parvimonas micra, Streptococcus mitis|Parvimonas micra, Streptococcus mutans|Parvimonas micra, Streptococcus oralis|Parvimonas micra, Streptococcus parasanguinis|Parvimonas micra, Streptococcus peroris|Parvimonas micra, Streptococcus pneumoniae|Parvimonas micra, Streptococcus salivarius|Parvimonas micra, Streptococcus sanguinis|Parvimonas micra, Streptococcus thermophilus|Parvimonas micra, Streptococcus vestibularis|Parvimonas micra, Subdoligranulum variabile|Parvimonas micra, Succinatimonas hippei|Parvimonas micra, Sutterella wadsworthensis|Parvimonas micra, Tropheryma whipplei|Parvimonas micra, Veillonella atypica|Parvimonas micra, Veillonella dispar|Parvimonas micra, Veillonella parvula|Parvimonas micra, Victivallis vadensis|Pediococcus acidilactici, Pediococcus acidilactici|Pediococcus acidilactici, Pediococcus pentosaceus|Pediococcus acidilactici, Peptoniphilus duerdenii|Pediococcus acidilactici, Peptoniphilus harei|Pediococcus acidilactici, Peptoniphilus lacrimalis|Pediococcus acidilactici, Peptostreptococcus anaerobius|Pediococcus acidilactici, Peptostreptococcus stomatis|Pediococcus acidilactici, Porphyromonas asaccharolytica|Pediococcus acidilactici, Porphyromonas uenonis|Pediococcus acidilactici, Prevotella amnii|Pediococcus acidilactici, Prevotella bergensis|Pediococcus acidilactici, Prevotella bivia|Pediococcus acidilactici, Prevotella buccae|Pediococcus acidilactici, Prevotella buccalis|Pediococcus acidilactici, Prevotella copri|Pediococcus acidilactici, Prevotella disiens|Pediococcus acidilactici, Prevotella melaninogenica|Pediococcus acidilactici, Prevotella multiformis|Pediococcus acidilactici, Prevotella oralis|Pediococcus acidilactici, Prevotella oris|Pediococcus acidilactici, Prevotella salivae|Pediococcus acidilactici, Prevotella timonensis|Pediococcus acidilactici, Propionibacterium acnes|Pediococcus acidilactici, Propionibacterium freudenreichii|Pediococcus acidilactici, Proteus mirabilis|Pediococcus acidilactici, Proteus penneri|Pediococcus acidilactici, Pseudoflavonifractor capillosus|Pediococcus acidilactici, Pseudomonas aeruginosa|Pediococcus acidilactici, Pseudomonas fluorescens|Pediococcus acidilactici, Pseudomonas putida|Pediococcus acidilactici, Pseudoramibacter alactolyticus|Pediococcus acidilactici, Pyramidobacter piscolens|Pediococcus acidilactici, Rhodopseudomonas palustris|Pediococcus acidilactici, Roseburia intestinalis|Pediococcus acidilactici, Roseburia inulinivorans|Pediococcus acidilactici, Rothia dentocariosa|Pediococcus acidilactici, Rothia mucilaginosa|Pediococcus acidilactici, Ruminococcus albus|Pediococcus acidilactici, Ruminococcus bromii|Pediococcus acidilactici, Ruminococcus gnavus|Pediococcus acidilactici, Ruminococcus lactaris|Pediococcus acidilactici, Ruminococcus obeum|Pediococcus acidilactici, Ruminococcus torques|Pediococcus acidilactici, Selenomonas sputigena|Pediococcus acidilactici, Shigella boydii|Pediococcus acidilactici, Shigella dysenteriae|Pediococcus acidilactici, Shigella sonnei|Pediococcus acidilactici, Slackia exigua|Pediococcus acidilactici, Solobacterium moorei|Pediococcus acidilactici, Staphylococcus aureus|Pediococcus acidilactici, Staphylococcus epidermidis|Pediococcus acidilactici, Staphylococcus hominis|Pediococcus acidilactici, Staphylococcus saprophyticus|Pediococcus acidilactici, Staphylococcus warneri|Pediococcus acidilactici, Streptococcus agalactiae|Pediococcus acidilactici, Streptococcus anginosus|Pediococcus acidilactici, Streptococcus australis|Pediococcus acidilactici, Streptococcus bovis|Pediococcus acidilactici, Streptococcus cristatus|Pediococcus acidilactici, Streptococcus dysgalactiae|Pediococcus acidilactici, Streptococcus equinus|Pediococcus acidilactici, Streptococcus gordonii|Pediococcus acidilactici, Streptococcus infantarius|Pediococcus acidilactici, Streptococcus infantis|Pediococcus acidilactici, Streptococcus mitis|Pediococcus acidilactici, Streptococcus mutans|Pediococcus acidilactici, Streptococcus oralis|Pediococcus acidilactici, Streptococcus parasanguinis|Pediococcus acidilactici, Streptococcus peroris|Pediococcus acidilactici, Streptococcus pneumoniae|Pediococcus acidilactici, Streptococcus salivarius|Pediococcus acidilactici, Streptococcus sanguinis|Pediococcus acidilactici, Streptococcus thermophilus|Pediococcus acidilactici, Streptococcus vestibularis|Pediococcus acidilactici, Subdoligranulum variabile|Pediococcus acidilactici, Succinatimonas hippei|Pediococcus acidilactici, Sutterella wadsworthensis|Pediococcus acidilactici, Tropheryma whipplei|Pediococcus acidilactici, Veillonella atypica|Pediococcus acidilactici, Veillonella dispar|Pediococcus acidilactici, Veillonella parvula|Pediococcus acidilactici, Victivallis vadensis|Pediococcus pentosaceus, Pediococcus pentosaceus|Pediococcus pentosaceus, Peptoniphilus duerdenii|Pediococcus pentosaceus, Peptoniphilus harei|Pediococcus pentosaceus, Peptoniphilus lacrimalis|Pediococcus pentosaceus, Peptostreptococcus anaerobius|Pediococcus pentosaceus, Peptostreptococcus stomatis|Pediococcus pentosaceus, Porphyromonas asaccharolytica|Pediococcus pentosaceus, Porphyromonas uenonis|Pediococcus pentosaceus, Prevotella amnii|Pediococcus pentosaceus, Prevotella bergensis|Pediococcus pentosaceus, Prevotella bivia|Pediococcus pentosaceus, Prevotella buccae|Pediococcus pentosaceus, Prevotella buccalis|Pediococcus pentosaceus, Prevotella copri|Pediococcus pentosaceus, Prevotella disiens|Pediococcus pentosaceus, Prevotella melaninogenica|Pediococcus pentosaceus, Prevotella multiformis|Pediococcus pentosaceus, Prevotella oralis|Pediococcus pentosaceus, Prevotella oris|Pediococcus pentosaceus, Prevotella salivae|Pediococcus pentosaceus, Prevotella timonensis|Pediococcus pentosaceus, Propionibacterium acnes|Pediococcus pentosaceus, Propionibacterium freudenreichii|Pediococcus pentosaceus, Proteus mirabilis|Pediococcus pentosaceus, Proteus penneri|Pediococcus pentosaceus, Pseudoflavonifractor capillosus|Pediococcus pentosaceus, Pseudomonas aeruginosa|Pediococcus pentosaceus, Pseudomonas fluorescens|Pediococcus pentosaceus, Pseudomonas putida|Pediococcus pentosaceus, Pseudoramibacter alactolyticus|Pediococcus pentosaceus, Pyramidobacter piscolens|Pediococcus pentosaceus, Rhodopseudomonas palustris|Pediococcus pentosaceus, Roseburia intestinalis|Pediococcus pentosaceus, Roseburia inulinivorans|Pediococcus pentosaceus, Rothia dentocariosa|Pediococcus pentosaceus, Rothia mucilaginosa|Pediococcus pentosaceus, Ruminococcus albus|Pediococcus pentosaceus, Ruminococcus bromii|Pediococcus pentosaceus, Ruminococcus gnavus|Pediococcus pentosaceus, Ruminococcus lactaris|Pediococcus pentosaceus, Ruminococcus obeum|Pediococcus pentosaceus, Ruminococcus torques|Pediococcus pentosaceus, Selenomonas sputigena|Pediococcus pentosaceus, Shigella boydii|Pediococcus pentosaceus, Shigella dysenteriae|Pediococcus pentosaceus, Shigella sonnei|Pediococcus pentosaceus, Slackia exigua|Pediococcus pentosaceus, Solobacterium moorei|Pediococcus pentosaceus, Staphylococcus aureus|Pediococcus pentosaceus, Staphylococcus epidermidis|Pediococcus pentosaceus, Staphylococcus hominis|Pediococcus pentosaceus, Staphylococcus saprophyticus|Pediococcus pentosaceus, Staphylococcus warneri|Pediococcus pentosaceus, Streptococcus agalactiae|Pediococcus pentosaceus, Streptococcus anginosus|Pediococcus pentosaceus, Streptococcus australis|Pediococcus pentosaceus, Streptococcus bovis|Pediococcus pentosaceus, Streptococcus cristatus|Pediococcus pentosaceus, Streptococcus dysgalactiae|Pediococcus pentosaceus, Streptococcus equinus|Pediococcus pentosaceus, Streptococcus gordonii|Pediococcus pentosaceus, Streptococcus infantarius|Pediococcus pentosaceus, Streptococcus infantis|Pediococcus pentosaceus, Streptococcus mitis|Pediococcus pentosaceus, Streptococcus mutans|Pediococcus pentosaceus, Streptococcus oralis|Pediococcus pentosaceus, Streptococcus parasanguinis|Pediococcus pentosaceus, Streptococcus peroris|Pediococcus pentosaceus, Streptococcus pneumoniae|Pediococcus pentosaceus, Streptococcus salivarius|Pediococcus pentosaceus, Streptococcus sanguinis|Pediococcus pentosaceus, Streptococcus thermophilus|Pediococcus pentosaceus, Streptococcus vestibularis|Pediococcus pentosaceus, Subdoligranulum variabile|Pediococcus pentosaceus, Succinatimonas hippei|Pediococcus pentosaceus, Sutterella wadsworthensis|Pediococcus pentosaceus, Tropheryma whipplei|Pediococcus pentosaceus, Veillonella atypica|Pediococcus pentosaceus, Veillonella dispar|Pediococcus pentosaceus, Veillonella parvula|Pediococcus pentosaceus, Victivallis vadensis|Peptoniphilus duerdenii, Peptoniphilus duerdenii|Peptoniphilus duerdenii, Peptoniphilus harei|Peptoniphilus duerdenii, Peptoniphilus lacrimalis|Peptoniphilus duerdenii, Peptostreptococcus anaerobius|Peptoniphilus duerdenii, Peptostreptococcus stomatis|Peptoniphilus duerdenii, Porphyromonas asaccharolytica|Peptoniphilus duerdenii, Porphyromonas uenonis|Peptoniphilus duerdenii, Prevotella amnii|Peptoniphilus duerdenii, Prevotella bergensis|Peptoniphilus duerdenii, Prevotella bivia|Peptoniphilus duerdenii, Prevotella buccae|Peptoniphilus duerdenii, Prevotella buccalis|Peptoniphilus duerdenii, Prevotella copri|Peptoniphilus duerdenii, Prevotella disiens|Peptoniphilus duerdenii, Prevotella melaninogenica|Peptoniphilus duerdenii, Prevotella multiformis|Peptoniphilus duerdenii, Prevotella oralis|Peptoniphilus duerdenii, Prevotella oris|Peptoniphilus duerdenii, Prevotella salivae|Peptoniphilus*

TABLE 2-continued

| Table 2. Specific binary combinations of OTUs. Individual pairings are differentiated by "\|" and OTUs within a combination are differentiated by "," |
|---|
| *duerdenii, Prevotella timonensis\|Peptoniphilus duerdenii, Propionibacterium acnes\|Peptoniphilus duerdenii, Propionibacterium freudenreichii\|Peptoniphilus duerdenii, Proteus mirabilis\|Peptoniphilus duerdenii, Proteus penneri\|Peptoniphilus duerdenii, Pseudoflavonifractor capillosus\|Peptoniphilus duerdenii, Pseudomonas aeruginosa\|Peptoniphilus duerdenii, Pseudomonas fluorescens\|Peptoniphilus duerdenii, Pseudomonas putida\|Peptoniphilus duerdenii, Pseudoramibacter alactolyticus\|Peptoniphilus duerdenii, Pyramidobacter piscolens\|Peptoniphilus duerdenii, Rhodopseudomonas palustris\|Peptoniphilus duerdenii, Roseburia intestinalis\|Peptoniphilus duerdenii, Roseburia inulinivorans\|Peptoniphilus duerdenii, Rothia dentocariosa\|Peptoniphilus duerdenii, Rothia mucilaginosa\|Peptoniphilus duerdenii, Ruminococcus albus\|Peptoniphilus duerdenii, Ruminococcus bromii\|Peptoniphilus duerdenii, Ruminococcus gnavus\|Peptoniphilus duerdenii, Ruminococcus lactaris\|Peptoniphilus duerdenii, Ruminococcus obeum\|Peptoniphilus duerdenii, Ruminococcus torques\|Peptoniphilus duerdenii, Selenomonas sputigena\|Peptoniphilus duerdenii, Shigella boydii\|Peptoniphilus duerdenii, Shigella dysenteriae\|Peptoniphilus duerdenii, Shigella sonnei\|Peptoniphilus duerdenii, Slackia exigua\|Peptoniphilus duerdenii, Solobacterium moorei\|Peptoniphilus duerdenii, Staphylococcus aureus\|Peptoniphilus duerdenii, Staphylococcus epidermidis\|Peptoniphilus duerdenii, Staphylococcus hominis\|Peptoniphilus duerdenii, Staphylococcus saprophyticus\|Peptoniphilus duerdenii, Staphylococcus warneri\|Peptoniphilus duerdenii, Streptococcus agalactiae\|Peptoniphilus duerdenii, Streptococcus anginosus\|Peptoniphilus duerdenii, Streptococcus australis\|Peptoniphilus duerdenii, Streptococcus bovis\|Peptoniphilus duerdenii, Streptococcus cristatus\|Peptoniphilus duerdenii, Streptococcus dysgalactiae\|Peptoniphilus duerdenii, Streptococcus equinus\|Peptoniphilus duerdenii, Streptococcus gordonii\|Peptoniphilus duerdenii, Streptococcus infantarius\|Peptoniphilus duerdenii, Streptococcus infantis\|Peptoniphilus duerdenii, Streptococcus mitis\|Peptoniphilus duerdenii, Streptococcus mutans\|Peptoniphilus duerdenii, Streptococcus oralis\|Peptoniphilus duerdenii, Streptococcus parasanguinis\|Peptoniphilus duerdenii, Streptococcus peroris\|Peptoniphilus duerdenii, Streptococcus pneumoniae\|Peptoniphilus duerdenii, Streptococcus salivarius\|Peptoniphilus duerdenii, Streptococcus sanguinis\|Peptoniphilus duerdenii, Streptococcus thermophilus\|Peptoniphilus duerdenii, Streptococcus vestibularis\|Peptoniphilus duerdenii, Subdoligranulum variabile\|Peptoniphilus duerdenii, Succinatimonas hippei\|Peptoniphilus duerdenii, Sutterella wadsworthensis\|Peptoniphilus duerdenii, Tropheryma whipplei\|Peptoniphilus duerdenii, Veillonella atypica\|Peptoniphilus duerdenii, Veillonella dispar\|Peptoniphilus duerdenii, Veillonella parvula\|Peptoniphilus duerdenii, Victivallis vadensis\|Peptoniphilus harei, Peptoniphilus harei\|Peptoniphilus harei, Peptoniphilus lacrimalis\|Peptoniphilus harei, Peptostreptococcus anaerobius\|Peptoniphilus harei, Peptostreptococcus stomatis\|Peptoniphilus harei, Porphyromonas asaccharolytica\|Peptoniphilus harei, Porphyromonas uenonis\|Peptoniphilus harei, Prevotella amnii\|Peptoniphilus harei, Prevotella bergensis\|Peptoniphilus harei, Prevotella bivia\|Peptoniphilus harei, Prevotella buccae\|Peptoniphilus harei, Prevotella buccalis\|Peptoniphilus harei, Prevotella copri\|Peptoniphilus harei, Prevotella disiens\|Peptoniphilus harei, Prevotella melaninogenica\|Peptoniphilus harei, Prevotella multiformis\|Peptoniphilus harei, Prevotella oralis\|Peptoniphilus harei, Prevotella oris\|Peptoniphilus harei, Prevotella salivae\|Peptoniphilus harei, Prevotella timonensis\|Peptoniphilus harei, Propionibacterium acnes\|Peptoniphilus harei, Propionibacterium freudenreichi\|Peptoniphilus harei, Proteus mirabilis\|Peptoniphilus harei, Proteus penneri\|Peptoniphilus harei, Pseudoflavonifractor capillosus\|Peptoniphilus harei, Pseudomonas aeruginosaj\|Peptoniphilus harei, Pseudomonas fluorescens\|Peptoniphilus harei, Pseudomonas putida\|Peptoniphilus harei, Pseudoramibacter alactolyticus\|Peptoniphilus harei, Pyramidobacter piscolens\|Peptoniphilus harei, Rhodopseudomonas palustris\|Peptoniphilus harei, Roseburia intestinalis\|Peptoniphilus harei, Roseburia inulinivorans\|Peptoniphilus harei, Rothia dentocariosa\|Peptoniphilus harei, Rothia mucilaginosa\|Peptoniphilus harei, Ruminococcus albus\|Peptoniphilus harei, Ruminococcus bromii\|Peptoniphilus harei, Ruminococcus gnavus\|Peptoniphilus harei, Ruminococcus lactaris\|Peptoniphilus harei, Ruminococcus obeum\|Peptoniphilus harei, Ruminococcus torques\|Peptoniphilus harei, Selenomonas sputigena\|Peptoniphilus harei, Shigella boydii\|Peptoniphilus harei, Shigella dysenteriae\|Peptoniphilus harei, Shigella sonnei\|Peptoniphilus harei, Slackia exigua\|Peptoniphilus harei, Solobacterium moorei\|Peptoniphilus harei, Staphylococcus aureus\|Peptoniphilus harei, Staphylococcus epidermidis\|Peptoniphilus harei, Staphylococcus hominis\|Peptoniphilus harei, Staphylococcus saprophyticus\|Peptoniphilus harei, Staphylococcus warneri\|Peptoniphilus harei, Streptococcus agalactiae\|Peptoniphilus harei, Streptococcus anginosus\|Peptoniphilus harei, Streptococcus australis\|Peptoniphilus harei, Streptococcus bovis\|Peptoniphilus harei, Streptococcus cristatus\|Peptoniphilus harei, Streptococcus dysgalactiae\|Peptoniphilus harei, Streptococcus equinus\|Peptoniphilus harei, Streptococcus gordonii\|Peptoniphilus harei, Streptococcus infantarius\|Peptoniphilus harei, Streptococcus infantis\|Peptoniphilus harei, Streptococcus mitis\|Peptoniphilus harei, Streptococcus mutans\|Peptoniphilus harei, Streptococcus oralis\|Peptoniphilus harei, Streptococcus parasanguinis\|Peptoniphilus harei, Streptococcus peroris\|Peptoniphilus harei, Streptococcus pneumoniae\|Peptoniphilus harei, Streptococcus salivarius\|Peptoniphilus harei, Streptococcus sanguinis\|Peptoniphilus harei, Streptococcus thermophilus\|Peptoniphilus harei, Streptococcus vestibularis\|Peptoniphilus harei, Subdoligranulum variabile\|Peptoniphilus harei, Succinatimonas hippei\|Peptoniphilus harei, Sutterella wadsworthensis\|Peptoniphilus harei, Tropheryma whipplei\|Peptoniphilus harei, Veillonella atypica\|Peptoniphilus harei, Veillonella dispar\|Peptoniphilus harei, Veillonella parvula\|Peptoniphilus harei, Victivallis vadensis\|Peptoniphilus lacrimalis, Peptoniphilus lacrimalis\|Peptoniphilus lacrimalis, Peptostreptococcus anaerobius\|Peptoniphilus lacrimalis, Peptostreptococcus stomatis\|Peptoniphilus lacrimalis, Porphyromonas asaccharolytica\|Peptoniphilus lacrimalis, Porphyromonas uenonis\|Peptoniphilus lacrimalis, Prevotella amnii\|Peptoniphilus lacrimalis, Prevotella bergensis\|Peptoniphilus lacrimalis, Prevotella bivia\|Peptoniphilus lacrimalis, Prevotella buccae\|Peptoniphilus lacrimalis, Prevotella buccalis\|Peptoniphilus lacrimalis, Prevotella copri\|Peptoniphilus lacrimalis, Prevotella disiens\|Peptoniphilus lacrimalis, Prevotella melaninogenica\|Peptoniphilus lacrimalis, Prevotella multiformis\|Peptoniphilus lacrimalis, Prevotella oralis\|Peptoniphilus lacrimalis, Prevotella oris\|Peptoniphilus lacrimalis, Prevotella salivae\|Peptoniphilus lacrimalis, Prevotella timonensis\|Peptoniphilus lacrimalis, Propionibacterium acnes\|Peptoniphilus lacrimalis, Propionibacterium freudenreichi\|Peptoniphilus lacrimalis, Proteus mirabilis\|Peptoniphilus lacrimalis, Proteus penneri\|Peptoniphilus lacrimalis, Pseudoflavonifractor capillosus\|Peptoniphilus lacrimalis, Pseudomonas aeruginosa\|Peptoniphilus lacrimalis, Pseudomonas fluorescens\|Peptoniphilus lacrimalis, Pseudomonas putida\|Peptoniphilus lacrimalis, Pseudoramibacter alactolyticus\|Peptoniphilus lacrimalis, Pyramidobacter piscolens\|Peptoniphilus lacrimalis, Rhodopseudomonas palustris\|Peptoniphilus lacrimalis, Roseburia intestinalis\|Peptoniphilus lacrimalis, Roseburia inulinivorans\|Peptoniphilus lacrimalis, Rothia dentocariosa\|Peptoniphilus lacrimalis, Rothia mucflaginosa\|Peptoniphilus lacrimalis, Ruminococcus albus\|Peptoniphilus lacrimalis, Ruminococcus bromii\|Peptoniphilus lacrimalis, Ruminococcus gnavus\|Peptoniphilus lacrimalis, Ruminococcus lactaris\|Peptoniphilus lacrimalis, Ruminococcus obeum\|Peptoniphilus lacrimalis, Ruminococcus torques\|Peptoniphilus lacrimalis, Selenomonas sputigena\|Peptoniphilus lacrimalis, Shigella boydii\|Peptoniphilus lacrimalis, Shigella dysenteriae\|Peptoniphilus lacrimalis, Shigella sonnei\|Peptoniphilus lacrimalis, Slackia exigua\|Peptoniphilus lacrimalis, Solobacterium moorei\|Peptoniphilus lacrimalis, Staphylococcus aureus\|Peptoniphilus lacrimalis, Staphylococcus epidermidis\|Peptoniphilus lacrimalis, Staphylococcus hominis\|Peptoniphilus lacrimalis, Staphylococcus saprophyticus\|Peptoniphilus lacrimalis, Staphylococcus warneri\|Peptoniphilus lacrimalis, Streptococcus agalactiae\|Peptoniphilus lacrimalis, Streptococcus anginosus\|Peptoniphilus lacrimalis, Streptococcus australis\|Peptoniphilus lacrimalis, Streptococcus bovis\|Peptoniphilus lacrimalis, Streptococcus cristatus\|Peptoniphilus lacrimalis, Streptococcus dysgalactiae\|Peptoniphilus lacrimalis, Streptococcus equinus\|Peptoniphilus lacrimalis, Streptococcus gordonii\|Peptoniphilus lacrimalis, Streptococcus infantarius\|Peptoniphilus lacrimalis, Streptococcus infantis\|Peptoniphilus lacrimalis, Streptococcus mitis\|Peptoniphilus lacrimalis, Streptococcus mutans\|Peptoniphilus lacrimalis, Streptococcus oralis\|Peptoniphilus lacrimalis, Streptococcus parasanguinis\|Peptoniphilus lacrimalis, Streptococcus peroris\|Peptoniphilus lacrimalis, Streptococcus pneumoniae\|Peptoniphilus lacrimalis, Streptococcus salivarius\|Peptoniphilus lacrimalis, Streptococcus sanguinis\|Peptoniphilus lacrimalis, Streptococcus thermophilus\|Peptoniphilus lacrimalis, Streptococcus vestibularis\|Peptoniphilus lacrimalis, Subdoligranulum variabile\|Peptoniphilus lacrimalis, Succinatimonas hippei\|Peptoniphilus lacrimalis, Sutterella wadsworthensis\|Peptoniphilus lacrimalis, Tropheryma whipplei\|Peptoniphilus lacrimalis, Veillonella atypica\|Peptoniphilus lacrimalis, Veillonella dispar\|Peptoniphilus lacrimalis, Veillonella parvula\|Peptoniphilus lacrimalis, Victivallis vadensis\|Peptostreptococcus* |

TABLE 2-continued

| Table 2. Specific binary combinations of OTUs. Individual pairings are differentiated by "\|" and OTUs within a combination are differentiated by "," |
| --- |
| *anaerobius, Peptostreptococcus anaerobius\|Peptostreptococcus anaerobius, Peptostreptococcus stomatis\|Peptostreptococcus anaerobius, Porphyromonas asaccharolytica\|Peptostreptococcus anaerobius, Porphyromonas uenonis\|Peptostreptococcus anaerobius, Prevotella amnii\|Peptostreptococcus anaerobius, Prevotella bergensis\|Peptostreptococcus anaerobius, Prevotella bivia\|Peptostreptococcus anaerobius, Prevotella buccae\|Peptostreptococcus anaerobius, Prevotella buccalis\|Peptostreptococcus anaerobius, Prevotella copri\|Peptostreptococcus anaerobius, Prevotella disiens\|Peptostreptococcus anaerobius, Prevotella melaninogenica\|Peptostreptococcus anaerobius, Prevotella multiformis\|Peptostreptococcus anaerobius, Prevotella oralis\|Peptostreptococcus anaerobius, Prevotella oris\|Peptostreptococcus anaerobius, Prevotella salivae\|Peptostreptococcus anaerobius, Prevotella timonensis\|Peptostreptococcus anaerobius, Propionibacterium acnes\|Peptostreptococcus anaerobius, Propionibacterium freudenreichii\|Peptostreptococcus anaerobius, Proteus mirabilis\|Peptostreptococcus anaerobius, Proteus penneri\|Peptostreptococcus anaerobius, Pseudoflavonifractor capillosus\|Peptostreptococcus anaerobius, Pseudomonas aeruginosa\|Peptostreptococcus anaerobius, Pseudomonas fluorescens\|Peptostreptococcus anaerobius, Pseudomonas putida\|Peptostreptococcus anaerobius, Pseudoramibacter alactolyticus\|Peptostreptococcus anaerobius, Pyramidobacter piscolens\|Peptostreptococcus anaerobius, Rhodopseudomonas palustris\|Peptostreptococcus anaerobius, Roseburia intestinalis\|Peptostreptococcus anaerobius, Roseburia inulinivorans\|Peptostreptococcus anaerobius, Rothia dentocariosa\|Peptostreptococcus anaerobius, Rothia mucilaginosa\|Peptostreptococcus anaerobius, Ruminococcus albus\|Peptostreptococcus anaerobius, Ruminococcus bromii\|Peptostreptococcus anaerobius, Ruminococcus gnavus\|Peptostreptococcus anaerobius, Ruminococcus lactaris\|Peptostreptococcus anaerobius, Ruminococcus obeum\|Peptostreptococcus anaerobius, Ruminococcus torques\|Peptostreptococcus anaerobius, Selenomonas sputigena\|Peptostreptococcus anaerobius, Shigella boydii\|Peptostreptococcus anaerobius, Shigella dysenteriae\|Peptostreptococcus anaerobius, Shigella sonne\|Peptostreptococcus anaerobius, Slackia exigua\|Peptostreptococcus anaerobius, Solobacterium moorei\|Peptostreptococcus anaerobius, Staphylococcus aureus\|Peptostreptococcus anaerobius, Staphylococcus epidermidis\|Peptostreptococcus anaerobius, Staphylococcus hominis\|Peptostreptococcus anaerobius, Staphylococcus saprophyticus\|Peptostreptococcus anaerobius, Staphylococcus warneri\|Peptostreptococcus anaerobius, Streptococcus agalactiae\|Peptostreptococcus anaerobius, Streptococcus anginosus\|Peptostreptococcus anaerobius, Streptococcus australis\|Peptostreptococcus anaerobius, Streptococcus bovis\|Peptostreptococcus anaerobius, Streptococcus cristatus\|Peptostreptococcus anaerobius, Streptococcus dysgalactiae\|Peptostreptococcus anaerobius, Streptococcus equinus\|Peptostreptococcus anaerobius, Streptococcus gordonii\|Peptostreptococcus anaerobius, Streptococcus infantarius\|Peptostreptococcus anaerobius, Streptococcus infantis\|Peptostreptococcus anaerobius, Streptococcus mitis\|Peptostreptococcus anaerobius, Streptococcus mutans\|Peptostreptococcus anaerobius, Streptococcus oralis\|Peptostreptococcus anaerobius, Streptococcus parasanguinis\|Peptostreptococcus anaerobius, Streptococcus peroris\|Peptostreptococcus anaerobius, Streptococcus pneumoniae\|Peptostreptococcus anaerobius, Streptococcus salivarius\|Peptostreptococcus anaerobius, Streptococcus sanguinis\|Peptostreptococcus anaerobius, Streptococcus thermophilus\|Peptostreptococcus anaerobius, Streptococcus vestibularis\|Peptostreptococcus anaerobius, Subdoligranulum variabile\|Peptostreptococcus anaerobius, Succinatimonas hippei\|Peptostreptococcus anaerobius, Sutterella wadsworthensis\|Peptostreptococcus anaerobius, Tropheryma whipplei\|Peptostreptococcus anaerobius, Veillonella atypica\|Peptostreptococcus anaerobius, Veillonella dispar\|Peptostreptococcus anaerobius, Veillonella parvula\|Peptostreptococcus anaerobius, Victivallis vadensis\|Peptostreptococcus stomatis, Peptostreptococcus stomatis\|Peptostreptococcus stomatis, Porphyromonas asaccharolytica\|Peptostreptococcus stomatis, Porphyromonas uenonis\|Peptostreptococcus stomatis, Prevotella amnii\|Peptostreptococcus stomatis, Prevotella bergensis\|Peptostreptococcus stomatis, Prevotella bivia\|Peptostreptococcus stomatis, Prevotella buccae\|Peptostreptococcus stomatis, Prevotella buccalis\|Peptostreptococcus stomatis, Prevotella copri\|Peptostreptococcus stomatis, Prevotella disiens\|Peptostreptococcus stomatis, Prevotella melaninogenica\|Peptostreptococcus stomatis, Prevotella multiformis\|Peptostreptococcus stomatis, Prevotella oralis\|Peptostreptococcus stomatis, Prevotella oris\|Peptostreptococcus stomatis, Prevotella salivae\|Peptostreptococcus stomatis, Prevotella timonensis\|Peptostreptococcus stomatis, Propionibacterium acnes\|Peptostreptococcus stomatis, Propionibacterium freudenreichii\|Peptostreptococcus stomatis, Proteus mirabilis\|Peptostreptococcus stomatis, Proteus penneri\|Peptostreptococcus stomatis, Pseudoflavonifractor capillosus\|Peptostreptococcus stomatis, Pseudomonas aeruginosa\|Peptostreptococcus stomatis, Pseudomonas fluorescens\|Peptostreptococcus stomatis, Pseudomonas putida\|Peptostreptococcus stomatis, Pseudoramibacter alactolyticus\|Peptostreptococcus stomatis, Pyramidobacter piscolens\|Peptostreptococcus stomatis, Rhodopseudomonas palustris\|Peptostreptococcus stomatis, Roseburia intestinalis\|Peptostreptococcus stomatis, Roseburia inulinivorans\|Peptostreptococcus stomatis, Rothia dentocariosa\|Peptostreptococcus stomatis, Rothia mucilaginosa\|Peptostreptococcus stomatis, Ruminococcus albus\|Peptostreptococcus stomatis, Ruminococcus bromii\|Peptostreptococcus stomatis, Ruminococcus gnavus\|Peptostreptococcus stomatis, Ruminococcus lactaris\|Peptostreptococcus stomatis, Ruminococcus obeum\|Peptostreptococcus stomatis, Ruminococcus torques\|Peptostreptococcus stomatis, Selenomonas sputigena\|Peptostreptococcus stomatis, Shigella boydii\|Peptostreptococcus stomatis, Shigella dysenteriae\|Peptostreptococcus stomatis, Shigella sonnei\|Peptostreptococcus stomatis, Slackia exigua\|Peptostreptococcus stomatis, Solobacterium moorei\|Peptostreptococcus stomatis, Staphylococcus aureus\|Peptostreptococcus stomatis, Staphylococcus epidermidis\|Peptostreptococcus stomatis, Staphylococcus hominis\|Peptostreptococcus stomatis, Staphylococcus saprophyticus\|Peptostreptococcus stomatis, Staphylococcus warneri\|Peptostreptococcus stomatis, Streptococcus agalactiae\|Peptostreptococcus stomatis, Streptococcus anginosus\|Peptostreptococcus stomatis, Streptococcus australis\|Peptostreptococcus stomatis, Streptococcus bovis\|Peptostreptococcus stomatis, Streptococcus cristatus\|Peptostreptococcus stomatis, Streptococcus dysgalactiae\|Peptostreptococcus stomatis, Streptococcus equinus\|Peptostreptococcus stomatis, Streptococcus gordonii\|Peptostreptococcus stomatis, Streptococcus infantarius\|Peptostreptococcus stomatis, Streptococcus infantis\|Peptostreptococcus stomatis, Streptococcus mitis\|Peptostreptococcus stomatis, Streptococcus mutans\|Peptostreptococcus stomatis, Streptococcus oralis\|Peptostreptococcus stomatis, Streptococcus parasanguinis\|Peptostreptococcus stomatis, Streptococcus peroris\|Peptostreptococcus stomatis, Streptococcus pneumoniae\|Peptostreptococcus stomatis, Streptococcus salivarius\|Peptostreptococcus stomatis, Streptococcus sanguinis\|Peptostreptococcus stomatis, Streptococcus thermophilus\|Peptostreptococcus stomatis, Streptococcus vestibularis\|Peptostreptococcus stomatis, Subdoligranulum variabile\|Peptostreptococcus stomatis, Succinatimonas hippei\|Peptostreptococcus stomatis, Sutterella wadsworthensis\|Peptostreptococcus stomatis, Tropheryma whipplei\|Peptostreptococcus stomatis, Veillonella atypica\|Peptostreptococcus stomatis, Veillonella dispar\|Peptostreptococcus stomatis, Veillonella parvula\|Peptostreptococcus stomatis, Victivallis vadensis\|Porphyromonas asaccharolytica, Porphyromonas asaccharolytica\|Porphyromonas asaccharolytica, Porphyromonas uenonis\|Porphyromonas asaccharolytica, Prevotella amnii\|Porphyromonas asaccharolytica, Prevotella bergensis\|Porphyromonas asaccharolytica, Prevotella bivia\|Porphyromonas asaccharolytica, Prevotella buccae\|Porphyromonas asaccharolytica, Prevotella buccalis\|Porphyromonas asaccharolytica, Prevotella copri\|Porphyromonas asaccharolytica, Prevotella disiens\|Porphyromonas asaccharolytica, Prevotella melaninogenica\|Porphyromonas asaccharolytica, Prevotella multiformis\|Porphyromonas asaccharolytica, Prevotella oralis\|Porphyromonas asaccharolytica, Prevotella oris\|Porphyromonas asaccharolytica, Prevotella salivae\|Porphyromonas asaccharolytica, Prevotella timonensis\|Porphyromonas asaccharolytica, Propionibacterium acnes\|Porphyromonas asaccharolytica, Propionibacterium freudenreichii\|Porphyromonas asaccharolytica, Proteus mirabilis\|Porphyromonas asaccharolytica, Proteus penneri\|Porphyromonas asaccharolytica, Pseudoflavonifractor capillosus\|Porphyromonas asaccharolytica, Pseudomonas aeruginosa\|Porphyromonas asaccharolytica, Pseudomonas fluorescens\|Porphyromonas asaccharolytica, Pseudomonas putida\|Porphyromonas asaccharolytica, Pseudoramibacter alactolyticus\|Porphyromonas asaccharolytica, Pyramidobacter piscolens\|Porphyromonas asaccharolytica, Rhodopseudomonas palustris\|Porphyromonas asaccharolytica, Roseburia intestinalis\|Porphyromonas asaccharolytica, Roseburia inulinivorans\|Porphyromonas asaccharolytica, Rothia dentocariosa\|Porphyromonas asaccharolytica, Rothia mucilaginosa\|Porphyromonas asaccharolytica, Ruminococcus albus\|Porphyromonas asaccharolytica, Ruminococcus bromii\|Porphyromonas asaccharolytica, Ruminococcus gnavus\|Porphyromonas asaccharolytica, Ruminococcus lactaris\|Porphyromonas* |

TABLE 2-continued

| Table 2. Specific binary combinations of OTUs. Individual pairings are differentiated by "\|" and OTUs within a combination are differentiated by "," |
|---|
| asaccharolytica, Ruminococcus obeum\|Porphyromonas asaccharolytica, Ruminococcus torques\|Porphyromonas asaccharolytica, Selenomonas sputigena\|Porphyromonas asaccharolytica, Shigella boydii\|Porphyromonas asaccharolytica, Shigella dysenteriae\|Porphyromonas asaccharolytica, Shigella sonne\|Porphyromonas asaccharolytica, Slackia exigua\|Porphyromonas asaccharolytica, Solobacterium moorei\|Porphyromonas asaccharolytica, Staphylococcus aureus\|Porphyromonas asaccharolytica, Staphylococcus epidermidis\|Porphyromonas asaccharolytica, Staphylococcus hominis\|Porphyromonas asaccharolytica, Staphylococcus saprophyticus\|Porphyromonas asaccharolytica, Staphylococcus warneri\|Porphyromonas asaccharolytica, Streptococcus agalactiae\|Porphyromonas asaccharolytica, Streptococcus anginosus\|Porphyromonas asaccharolytica, Streptococcus australis\|Porphyromonas asaccharolytica, Streptococcus bovis\|Porphyromonas asaccharolytica, Streptococcus cristatus\|Porphyromonas asaccharolytica, Streptococcus dysgalactiae\|Porphyromonas asaccharolytica, Streptococcus equinus\|Porphyromonas asaccharolytica, Streptococcus gordonii\|Porphyromonas asaccharolytica, Streptococcus infantarius\|Porphyromonas asaccharolytica, Streptococcus infantis\|Porphyromonas asaccharolytica, Streptococcus mitis\|Porphyromonas asaccharolytica, Streptococcus mutans\|Porphyromonas asaccharolytica, Streptococcus oralis\|Porphyromonas asaccharolytica, Streptococcus parasanguinis\|Porphyromonas asaccharolytica, Streptococcus peroris\|Porphyromonas asaccharolytica, Streptococcus pneumoniae\|Porphyromonas asaccharolytica, Streptococcus salivarius\|Porphyromonas asaccharolytica, Streptococcus sanguinis\|Porphyromonas asaccharolytica, Streptococcus thermophilus\|Porphyromonas asaccharolytica, Streptococcus vestibularis\|Porphyromonas asaccharolytica, Subdoligranulum variabile\|Porphyromonas asaccharolytica, Succinatimonas hippei\|Porphyromonas asaccharolytica, Sutterella wadsworthensis\|Porphyromonas asaccharolytica, Tropheryma whipplei\|Porphyromonas asaccharolytica, Veillonella atypica\|Porphyromonas asaccharolytica, Veillonella dispar\|Porphyromonas asaccharolytica, Veillonella parvula\|Porphyromonas asaccharolytica, Victivallis vadensis\|Porphyromonas uenonis, Porphyromonas uenonis\|Porphyromonas uenonis, Prevotella amnii\|Porphyromonas uenonis, Prevotella bergensis\|Porphyromonas uenonis, Prevotella bivia\|Porphyromonas uenonis, Prevotella buccae\|Porphyromonas uenonis, Prevotella buccalis\|Porphyromonas uenonis, Prevotella copri\|Porphyromonas uenonis, Prevotella disiens\|Porphyromonas uenonis, Prevotella melaninogenica\|Porphyromonas uenonis, Prevotella multiformis\|Porphyromonas uenonis, Prevotella oralis\|Porphyromonas uenonis, Prevotella oris\|Porphyromonas uenonis, Prevotella salivae\|Porphyromonas uenonis, Prevotella timonensis\|Porphyromonas uenonis, Propionibacterium acnes\|Porphyromonas uenonis, Propionibacterium freudenreichii\|Porphyromonas uenonis, Proteus mirabilis\|Porphyromonas uenonis, Proteus penneri\|Porphyromonas uenonis, Pseudoflavonifractor capillosus\|Porphyromonas uenonis, Pseudomonas aeruginosa\|Porphyromonas uenonis, Pseudomonas fluorescens\|Porphyromonas uenonis, Pseudomonas putida\|Porphyromonas uenonis, Pseudoramibacter alactolyticus\|Porphyromonas uenonis, Pyramidobacter piscolens\|Porphyromonas uenonis, Rhodopseudomonas palustris\|Porphyromonas uenonis, Roseburia intestinalis\|Polphyromonas uenonis, Roseburia inulinivorans\|Porphyromonas uenonis, Rothia dentocariosa\|Porphyromonas uenonis, Rothia mucilaginosa\|Porphyromonas uenonis, Ruminococcus albus\|Porphyromonas uenonis, Ruminococcus bromii\|Porphyromonas uenonis, Ruminococcus gnavus\|Porphyromonas uenonis, Ruminococcus lactaris\|Porphyromonas uenonis, Ruminococcus obeum\|Porphyromonas uenonis, Ruminococcus torques\|Porphyromonas uenonis, Selenomonas sputigena\|Porphyromonas uenonis, Shigella boydii\|Porphyromonas uenonis, Shigella dysenteriae\|Porphyromonas uenonis, Shigella sonnei\|Porphyromonas uenonis, Slackia exigua\|Porphyromonas uenonis, Solobacterium moorei\|Porphyromonas uenonis, Staphylococcus aureus\|Porphyromonas uenonis, Staphylococcus epidermidis\|Porphyromonas uenonis, Staphylococcus hominis\|Porphyromonas uenonis, Staphylococcus saprophyticus\|Porphyromonas uenonis, Staphylococcus warneri\|Porphyromonas uenonis, Streptococcus agalactiae\|Porphyromonas uenonis, Streptococcus anginosus\|Porphyromonas uenonis, Streptococcus australis\|Porphyromonas uenonis, Streptococcus bovis\|Porphyromonas uenonis, Streptococcus cristatus\|Porphyromonas uenonis, Streptococcus dysgalactiae\|Porphyromonas uenonis, Streptococcus equinus\|Porphyromonas uenonis, Streptococcus gordonii\|Porphyromonas uenonis, Streptococcus infantarius\|Porphyromonas uenonis, Streptococcus infantis\|Porphyromonas uenonis, Streptococcus mitis\|Porphyromonas uenonis, Streptococcus mutans\|Porphyromonas uenonis, Streptococcus oralis\|Porphyromonas uenonis, Streptococcus parasanguinis\|Porphyromonas uenonis, Streptococcus peroris\|Porphyromonas uenonis, Streptococcus pneumoniae\|Porphyromonas uenonis, Streptococcus salivarius\|Porphyromonas uenonis, Streptococcus sanguinis\|Porphyromonas uenonis, Streptococcus thermophilus\|Porphyromonas uenonis, Streptococcus vestibularis\|Porphyromonas uenonis, Subdoligranulum variabile\|Porphyromonas uenonis, Succinatimonas hippei\|Porphyromonas uenonis, Sutterella wadsworthensis\|Porphyromonas uenonis, Tropheryma whipplei\|Porphyromonas uenonis, Veillonella atypica\|Porphyromonas uenonis, Veillonella dispar\|Porphyromonas uenonis, Veillonella parvula\|Porphyromonas uenonis, Victivallis vadensis\|Prevotella amnii, Prevotella amnii\|Prevotella amnii, Prevotella bergensis\|Prevotella amnii, Prevotella bivia\|Prevotella amnii, Prevotella buccae\|Prevotella amnii, Prevotella buccalis\|Prevotella amnii, Prevotella copri\|Prevotella amnii, Prevotella disiens\|Prevotella amnii, Prevotella melaninogenica\|Prevotella amnii, Prevotella multiformis\|Prevotella amnii, Prevotella oralis\|Prevotella amnii, Prevotella oris\|Prevotella amnii, Prevotella salivae\|Prevotella amnii, Prevotella timonensis\|Prevotella amnii, Propionibacterium acnes\|Prevotella amnii, Propionibacterium freudenreichii\|Prevotella amnii, Proteus mirabilis\|Prevotella amnii, Proteus penneri\|Prevotella amnii, Pseudoflavonifractor capillosus\|Prevotella amnii, Pseudomonas aeruginosa\|Prevotella amnii, Pseudomonas fluorescens\|Prevotella amnii, Pseudomonas putida\|Prevotella amnii, Pseudoramibacter alactolyticus\|Prevotella amnii, Pyramidobacter piscolens\|Prevotella amnii, Rhodopseudomonas palustris\|Prevotella amnii, Roseburia intestinalis\|Prevotella amnii, Roseburia inulinivorans\|Prevotella amnii, Rothia dentocariosa\|Prevotella amnii, Rothia mucilaginosa\|Prevotella amnii, Ruminococcus albus\|Prevotella amnii, Ruminococcus bromii\|Prevotella amnii, Ruminococcus gnavus\|Prevotella amnii, Ruminococcus lactaris\|Prevotella amnii, Ruminococcus obeum\|Prevotella amnii, Ruminococcus torques\|Prevotella amnii, Selenomonas sputigena\|Prevotella amnii, Shigella boydii\|Prevotella amnii, Shigella dysenteriae\|Prevotella amnii, Shigella sonnei\|Prevotella amnii, Slackia exigua\|Prevotella amnii, Solobacterium moorei\|Prevotella amnii, Staphylococcus aureus\|Prevotella amnii, Staphylococcus epidermidis\|Prevotella amnii, Staphylococcus hominis\|Prevotella amnii, Staphylococcus saprophyticus\|Prevotella amnii, Staphylococcus warneri\|Prevotella amnii, Streptococcus agalactiae\|Prevotella amnii, Streptococcus anginosus\|Prevotella amnii, Streptococcus australis\|Prevotella amnii, Streptococcus bovis\|Prevotella amnii, Streptococcus cristatus\|Prevotella amnii, Streptococcus dysgalactiae\|Prevotella amnii, Streptococcus equinus\|Prevotella amnii, Streptococcus gordonii\|Prevotella amnii, Streptococcus infantarius\|Prevotella amnii, Streptococcus infantis\|Prevotella amnii, Streptococcus mitis\|Prevotella amnii, Streptococcus mutans\|Prevotella amnii, Streptococcus oralis\|Prevotella amnii, Streptococcus parasanguinis\|Prevotella amnii, Streptococcus peroris\|Prevotella amnii, Streptococcus pneumoniae\|Prevotella amnii, Streptococcus salivarius\|Prevotella amnii, Streptococcus sanguinis\|Prevotella amnii, Streptococcus thermophilus\|Prevotella amnii, Streptococcus vestibularis\|Prevotella amnii, Subdoligranulum variabile\|Prevotella amnii, Succinatimonas hippei\|Prevotella amnii, Sutterella wadsworthensis\|Prevotella amnii, Tropheryma whipplei\|Prevotella amnii, Veillonella atypica\|Prevotella amnii, Veillonella dispar\|Prevotella amnii, Veillonella parvula\|Prevotella amnii, Victivallis vadensis\|Prevotella bergensis, Prevotella bergensis\|Prevotella bergensis, Prevotella bivia\|Prevotella bergensis, Prevotella buccae\|Prevotella bergensis, Prevotella buccalis\|Prevotella bergensis, Prevotella copri\|Prevotella bergensis, Prevotella disiens\|Prevotella bergensis, Prevotella melaninogenica\|Prevotella bergensis, Prevotella multiformis\|Prevotella bergensis, Prevotella oralis\|Prevotella bergensis, Prevotella oris\|Prevotella bergensis, Prevotella salivae\|Prevotella bergensis, Prevotella timonensis\|Prevotella bergensis, Propionibacterium acnes\|Prevotella bergensis, Propionibacterium freudenreichii\|Prevotella bergensis, Proteus mirabilis\|Prevotella bergensis, Proteus penneri\|Prevotella bergensis, Pseudoflavonifractor capillosus\|Prevotella bergensis, Pseudomonas aeruginosa\|Prevotella bergensis, Pseudomonas fluorescens\|Prevotella bergensis, Pseudomonas putida\|Prevotella bergensis, Pseudoramibacter alactolyticus\|Prevotella bergensis, Pyramidobacter piscolens\|Prevotella bergensis, Rhodopseudomonas palustris\|Prevotella bergensis, Roseburia intestinalis\|Prevotella bergensis, Roseburia inulinivorans\|Prevotella bergensis, Rothia dentocariosa\|Prevotella bergensis, Rothia mucilaginosa\|Prevotella bergensis, Ruminococcus albus\|Prevotella bergensis, Ruminococcus bromii\|Prevotella bergensis, Ruminococcus gnavus\|Prevotella bergensis, Ruminococcus lactaris\|Prevotella bergensis, Ruminococcus obeum\|Prevotella bergensis, Ruminococcus |

TABLE 2-continued

| Table 2. Specific binary combinations of OTUs. Individual pairings are differentiated by "\|" and OTUs within a combination are differentiated by "," |
|---|
| *torques\|Prevotella bergensis, Selenomonas sputigena\|Prevotella bergensis, Shigella boydii\|Prevotella bergensis, Shigella dysenteriae\|Prevotella bergensis, Shigella sonnei\|Prevotella bergensis, Slackia exigua\|Prevotella bergensis, Solobacterium moorei\|Prevotella bergensis, Staphylococcus aureus\|Prevotella bergensis, Staphylococcus epidermidis\|Prevotella bergensis, Staphylococcus hominis\|Prevotella bergensis, Staphylococcus saprophyticus\|Prevotella bergensis, Staphylococcus warneri\|Prevotella bergensis, Streptococcus agalactiae\|Prevotella bergensis, Streptococcus anginosus\|Prevotella bergensis, Streptococcus australis\|Prevotella bergensis, Streptococcus bovis\|Prevotella bergensis, Streptococcus cristatus\|Prevotella bergensis, Streptococcus dysgalactiae\|Prevotella bergensis, Streptococcus equinus\|Prevotella bergensis, Streptococcus gordonii\|Prevotella bergensis, Streptococcus infantarius\|Prevotella bergensis, Streptococcus infantis\|Prevotella bergensis, Streptococcus mitis\|Prevotella bergensis, Streptococcus mutans\|Prevotella bergensis, Streptococcus oralis\|Prevotella bergensis, Streptococcus parasanguinis\|Prevotella bergensis, Streptococcus peroris\|Prevotella bergensis, Streptococcus pneumoniae\|Prevotella bergensis, Streptococcus salivarius\|Prevotella bergensis, Streptococcus sanguinis\|Prevotella bergensis, Streptococcus thermophilus\|Prevotella bergensis, Streptococcus vestibularis\|Prevotella bergensis, Subdoligranulum variabile\|Prevotella bergensis, Succinatimonas hippei\|Prevotella bergensis, Sutterella wadsworthensis\|Prevotella bergensis, Tropheryma whipplei\|Prevotella bergensis, Veillonella atypica\|Prevotella bergensis, Veillonella dispar\|Prevotella bergensis, Veillonella parvula\|Prevotella bergensis, Victivallis vadensis\|Prevotella bivia, Prevotella bivia\|Prevotella bivia, Prevotella buccae, Prevotella bivia, Prevotella buccalis\|Prevotella bivia, Prevotella copri\|Prevotella bivia, Prevotella disiens\|Prevotella bivia, Prevotella melaninogenica\|Prevotella bivia, Prevotella multiformis\|Prevotella bivia, Prevotella oralis\|Prevotella bivia, Prevotella oris\|Prevotella bivia, Prevotella salivae\|Prevotella bivia, Prevotella timonensis\|Prevotella bivia, Propionibacterium acnes\|Prevotella bivia, Propionibacterium freudenreichii\|Prevotella bivia, Proteus mirabilis\|Prevotella bivia, Proteus penneri\|Prevotella bivia, Pseudoflavonifractor capillosus\|Prevotella bivia, Pseudomonas aeruginosa\|Prevotella bivia, Pseudomonas fluorescens\|Prevotella bivia, Pseudomonas putida\|Prevotella bivia, Pseudoramibacter alactolyticus\|Prevotella bivia, Pyramidobacter piscolens\|Prevotella bivia, Rhodopseudomonas palustris\|Prevotella bivia, Roseburia intestinalis\|Prevotella bivia, Roseburia inulinivorans\|Prevotella bivia, Rothia dentocariosa\|Prevotella bivia, Rothia mucilaginosa\|Prevotella bivia, Ruminococcus albus\|Prevotella bivia, Ruminococcus bromii\|Prevotella bivia, Ruminococcus gnavus\|Prevotella bivia, Ruminococcus lactaris\|Prevotella bivia, Ruminococcus obeum\|Prevotella bivia, Ruminococcus torques\|Prevotella bivia, Selenomonas sputigena\|Prevotella bivia, Shigella boydii\|Prevotella bivia, Shigella dysenteriae\|Prevotella bivia, Shigella sonnei\|Prevotella bivia, Slackia exigua\|Prevotella bivia, Solobacterium moorei\|Prevotella bivia, Staphylococcus aureus\|Prevotella bivia, Staphylococcus epidermidis\|Prevotella bivia, Staphylococcus hominis\|Prevotella bivia, Staphylococcus saprophyticus\|Prevotella bivia, Staphylococcus warneri\|Prevotella bivia, Streptococcus agalactiae\|Prevotella bivia, Streptococcus anginosus\|Prevotella bivia, Streptococcus australis\|Prevotella bivia, Streptococcus bovis\|Prevotella bivia, Streptococcus cristatus\|Prevotella bivia, Streptococcus dysgalactiae\|Prevotella bivia, Streptococcus equinus\|Prevotella bivia, Streptococcus gordonii\|Prevotella bivia, Streptococcus infantarius\|Prevotella bivia, Streptococcus infantis\|Prevotella bivia, Streptococcus mitis\|Prevotella bivia, Streptococcus mutans\|Prevotella bivia, Streptococcus oralis\|Prevotella bivia, Streptococcus parasanguinis\|Prevotella bivia, Streptococcus peroris\|Prevotella bivia, Streptococcus pneumoniae\|Prevotella bivia, Streptococcus salivarius\|Prevotella bivia, Streptococcus sanguinis\|Prevotella bivia, Streptococcus thermophilus\|Prevotella bivia, Streptococcus vestibularis\|Prevotella bivia, Subdoligranulum variabile\|Prevotella bivia, Succinatimonas hippei\|Prevotella bivia, Sutterella wadsworthensis\|Prevotella bivia, Tropheryma whipplei\|Prevotella bivia, Veillonella atypica\|Prevotella bivia, Veillonella dispar\|Prevotella bivia, Veillonella parvula\|Prevotella bivia, Victivallis vadensis\|Prevotella buccae, Prevotella buccae\|Prevotella buccae, Prevotella buccalis\|Prevotella buccae, Prevotella copri\|Prevotella buccae, Prevotella disiens\|Prevotella buccae, Prevotella melaninogenica\|Prevotella buccae, Prevotella multiformis\|Prevotella buccae, Prevotella oralis\|Prevotella buccae, Prevotella oris\|Prevotella buccae, Prevotella salivae\|Prevotella buccae, Prevotella timonensis\|Prevotella buccae, Propionibacterium acnes\|Prevotella buccae, Propionibacterium freudenreichii\|Prevotella buccae, Proteus mirabilis\|Prevotella buccae, Proteus penneri\|Prevotella buccae, Pseudoflavonifractor capillosus\|Prevotella buccae, Pseudomonas aeruginosa\|Prevotella buccae, Pseudomonas fluorescens\|Prevotella buccae, Pseudomonas putida\|Prevotella buccae, Pseudoramibacter alactolyticus\|Prevotella buccae, Pyramidobacter piscolens\|Prevotella buccae, Rhodopseudomonas palustris\|Prevotella buccae, Roseburia intestinalis\|Prevotella buccae, Roseburia inulinivorans\|Prevotella buccae, Rothia dentocariosa\|Prevotella buccae, Rothia mucilaginosa\|Prevotella buccae, Ruminococcus albus\|Prevotella buccae, Ruminococcus bromii\|Prevotella buccae, Ruminococcus gnavus\|Prevotella buccae, Ruminococcus lactaris\|Prevotella buccae, Ruminococcus obeum\|Prevotella buccae, Ruminococcus torques\|Prevotella buccae, Selenomonas sputigena\|Prevotella buccae, Shigella boydii\|Prevotella buccae, Shigella dysenteriae\|Prevotella buccae, Shigella sonnei\|Prevotella buccae, Slackia exigua\|Prevotella buccae, Solobacterium moorei\|Prevotella buccae, Staphylococcus aureus\|Prevotella buccae, Staphylococcus epidermidis\|Prevotella buccae, Staphylococcus hominis\|Prevotella buccae, Staphylococcus saprophyticus\|Prevotella buccae, Staphylococcus warneri\|Prevotella buccae, Streptococcus agalactiae\|Prevotella buccae, Streptococcus anginosus\|Prevotella buccae, Streptococcus australis\|Prevotella buccae, Streptococcus bovis\|Prevotella buccae, Streptococcus cristatus\|Prevotella buccae, Streptococcus dysgalactiae\|Prevotella buccae, Streptococcus equinus\|Prevotella buccae, Streptococcus gordonii\|Prevotella buccae, Streptococcus infantarius\|Prevotella buccae, Streptococcus infantis\|Prevotella buccae, Streptococcus mitis\|Prevotella buccae, Streptococcus mutans\|Prevotella buccae, Streptococcus oralis\|Prevotella buccae, Streptococcus parasanguinis\|Prevotella buccae, Streptococcus peroris\|Prevotella buccae, Streptococcus pneumoniae\|Prevotella buccae, Streptococcus salivarius\|Prevotella buccae, Streptococcus sanguinis\|Prevotella buccae, Streptococcus thermophilus\|Prevotella buccae, Streptococcus vestibularis\|Prevotella buccae, Subdoligranulum variabile\|Prevotella buccae, Succinatimonas hippei\|Prevotella buccae, Sutterella wadsworthensis\|Prevotella buccae, Tropheryma whipplei\|Prevotella buccae, Veillonella atypica\|Prevotella buccae, Veillonella dispar\|Prevotella buccae, Veillonella parvula\|Prevotella buccae, Victivallis vadensis\|Prevotella buccalis, Prevotella buccalis\|Prevotella buccalis, Prevotella copri\|Prevotella buccalis, Prevotella disiens\|Prevotella buccalis, Prevotella melaninogenica\|Prevotella buccalis, Prevotella multiformis\|Prevotella buccalis, Prevotella oralis\|Prevotella buccalis, Prevotella oris\|Prevotella buccalis, Prevotella salivae\|Prevotella buccalis, Prevotella timonensis\|Prevotella buccalis, Propionibacterium acnes\|Prevotella buccalis, Propionibacterium freudenreichii\|Prevotella buccalis, Proteus mirabilis\|Prevotella buccalis, Proteus penneri\|Prevotella buccalis, Pseudoflavonifractor capillosus\|Prevotella buccalis, Pseudomonas aeruginosa\|Prevotella buccalis, Pseudomonas fluorescens\|Prevotella buccalis, Pseudomonas putida\|Prevotella buccalis, Pseudoramibacter alactolyticus\|Prevotella buccalis, Pyramidobacter piscolens\|Prevotella buccalis, Rhodopseudomonas palustris\|Prevotella buccalis, Roseburia intestinalis\|Prevotella buccalis, Roseburia inulinivorans\|Prevotella buccalis, Rothia dentocariosa\|Prevotella buccalis, Rothia mucilaginosa\|Prevotella buccalis, Ruminococcus albus\|Prevotella buccalis, Ruminococcus bromii\|Prevotella buccalis, Ruminococcus gnavus\|Prevotella buccalis, Ruminococcus lactaris\|Prevotella buccalis, Ruminococcus obeum\|Prevotella buccalis, Ruminococcus torques\|Prevotella buccalis, Selenomonas sputigena\|Prevotella buccalis, Shigella boydii\|Prevotella buccalis, Shigella dysenteriae\|Prevotella buccalis, Shigella sonnei\|Prevotella buccalis, Slackia exigua\|Prevotella buccalis, Solobacterium moorei\|Prevotella buccalis, Staphylococcus aureus\|Prevotella buccalis, Staphylococcus epidermidis\|Prevotella buccalis, Staphylococcus hominis\|Prevotella buccalis, Staphylococcus saprophyticus\|Prevotella buccalis, Staphylococcus warneri\|Prevotella buccalis, Streptococcus agalactiae\|Prevotella buccalis, Streptococcus anginosus\|Prevotella buccalis, Streptococcus australis\|Prevotella buccalis, Streptococcus bovis\|Prevotella buccalis, Streptococcus cristatus\|Prevotella buccalis, Streptococcus dysgalactiae\|Prevotella buccalis, Streptococcus equinus\|Prevotella buccalis, Streptococcus gordonii\|Prevotella buccalis, Streptococcus infantarius\|Prevotella buccalis, Streptococcus infantis\|Prevotella buccalis, Streptococcus mitis\|Prevotella buccalis, Streptococcus mutans\|Prevotella buccalis, Streptococcus oralis\|Prevotella buccalis, Streptococcus parasanguinis\|Prevotella buccalis, Streptococcus peroris\|Prevotella buccalis, Streptococcus pneumoniae\|Prevotella buccalis, Streptococcus salivarius\|Prevotella buccalis, Streptococcus sanguinis\|Prevotella buccalis, Streptococcus thermophilus\|Prevotella buccalis, Streptococcus vestibularis\|Prevotella buccalis, Subdoligranulum variabile\|Prevotella buccalis, Succinatimonas hippei\|Prevotella buccalis, Sutterella wadsworthensis\|Prevotella* |

TABLE 2-continued

Table 2. Specific binary combinations of OTUs. Individual pairings are differentiated by "|" and OTUs within a combination are differentiated by ","

buccalis, Tropheryma whipplei|Prevotella buccalis, Veillonella atypica|Prevotella buccalis, Veillonella dispar|Prevotella buccalis, Veillonella parvula|Prevotella buccalis, Victivallis vadensis|Prevotella copri, Prevotella copri|Prevotella copri, Prevotella disiens|Prevotella copri, Prevotella melaninogenica|Prevotella copri, Prevotella multiformis|Prevotella copri, Prevotella oralis|Prevotella copri, Prevotella oris|Prevotella copri, Prevotella salivae|Prevotella copri, Prevotella timonensis|Prevotella copri, Propionibacterium acnes|Prevotella copri, Propionibacterium freudenreichii|Prevotella copri, Proteus mirabilis|Prevotella copri, Proteus penneri|Prevotella copri, Pseudoflavonifractor capillosus|Prevotella copri, Pseudomonas aeruginosa|Prevotella copri, Pseudomonas fluorescens|Prevotella copri, Pseudomonas putida|Prevotella copri, Pseudoramibacter alactolyticus|Prevotella copri, Pyramidobacter piscolens|Prevotella copri, Rhodopseudomonas palustris|Prevotella copri, Roseburia intestinalis|Prevotella copri, Roseburia inulinivorans|Prevotella copri, Rothia dentocariosa|Prevotella copri, Rothia mucilaginosa|Prevotella copri, Ruminococcus albus|Prevotella copri, Ruminococcus bromii|Prevotella copri, Ruminococcus gnavus|Prevotella copri, Ruminococcus lactaris|Prevotella copri, Ruminococcus obeum|Prevotella copri, Ruminococcus torques|Prevotella copri, Selenomonas sputigena|Prevotella copri, Shigella boydii|Prevotella copri, Shigella dysenteriae|Prevotella copri, Shigella sonnei|Prevotella copri, Slackia exigua|Prevotella copri, Solobacterium moorei|Prevotella copri, Staphylococcus aureus|Prevotella copri, Staphylococcus epidermidis|Prevotella copri, Staphylococcus hominis|Prevotella copri, Staphylococcus saprophyticus|Prevotella copri, Staphylococcus warneri|Prevotella copri, Streptococcus agalactiae|Prevotella copri, Streptococcus anginosus|Prevotella copri, Streptococcus australis|Prevotella copri, Streptococcus bovis|Prevotella copri, Streptococcus cristatus|Prevotella copri, Streptococcus dysgalactiae|Prevotella copri, Streptococcus equinus|Prevotella copri, Streptococcus gordonii|Prevotella copri, Streptococcus infantarius|Prevotella copri, Streptococcus infantis|Prevotella copri, Streptococcus mitis|Prevotella copri, Streptococcus mutans|Prevotella copri, Streptococcus oralis|Prevotella copri, Streptococcus parasanguinis|Prevotella copri, Streptococcus peroris|Prevotella copri, Streptococcus pneumoniae|Prevotella copri, Streptococcus salivarius|Prevotella copri, Streptococcus sanguinis|Prevotella copri, Streptococcus thermophilus|Prevotella copri, Streptococcus vestibularis|Prevotella copri, Subdoligranulum variabile|Prevotella copri, Succinatimonas hippei|Prevotella copri, Sutterella wadsworthensis|Prevotella copri, Tropheryma whipplei|Prevotella copri, Veillonella atypica|Prevotella copri, Veillonella dispar|Prevotella copri, Veillonella parvula|Prevotella copri, Victivallis vadensis|Prevotella disiens, Prevotella disiens|Prevotella disiens, Prevotella melaninogenica|Prevotella disiens, Prevotella multiformis|Prevotella disiens, Prevotella oralis|Prevotella disiens, Prevotella oris|Prevotella disiens, Prevotella salivae|Prevotella disiens, Prevotella timonensis|Prevotella disiens, Propionibacterium acnes|Prevotella disiens, Propionibacterium freudenreichii|Prevotella disiens, Proteus mirabilis|Prevotella disiens, Proteus penneri|Prevotella disiens, Pseudoflavonifractor capillosus|Prevotella disiens, Pseudomonas aeruginosa|Prevotella disiens, Pseudomonas fluorescens|Prevotella disiens, Pseudomonas putida|Prevotella disiens, Pseudoramibacter alactolyticus|Prevotella disiens, Pyramidobacter piscolens|Prevotella disiens, Rhodopseudomonas palustris|Prevotella disiens, Roseburia intestinalis|Prevotella disiens, Roseburia inulinivorans|Prevotella disiens, Rothia dentocariosa|Prevotella disiens, Rothia mucilaginosa|Prevotella disiens, Ruminococcus albus|Prevotella disiens, Ruminococcus bromii|Prevotella disiens, Ruminococcus gnavus|Prevotella disiens, Ruminococcus lactaris|Prevotella disiens, Ruminococcus obeum|Prevotella disiens, Ruminococcus torques|Prevotella disiens, Selenomonas sputigena|Prevotella disiens, Shigella boydii|Prevotella disiens, Shigella dysenteriae|Prevotella disiens, Shigella sonnei|Prevotella disiens, Slackia exigua|Prevotella disiens, Solobacterium moorei|Prevotella disiens, Staphylococcus aureus|Prevotella disiens, Staphylococcus epidermidis|Prevotella disiens, Staphylococcus hominis|Prevotella disiens, Staphylococcus saprophyticus|Prevotella disiens, Staphylococcus warneri|Prevotella disiens, Streptococcus agalactiae|Prevotella disiens, Streptococcus anginosus|Prevotella disiens, Streptococcus australis|Prevotella disiens, Streptococcus bovis|Prevotella disiens, Streptococcus cristatus|Prevotella disiens, Streptococcus dysgalactiae|Prevotella disiens, Streptococcus equinus|Prevotella disiens, Streptococcus gordonii|Prevotella disiens, Streptococcus infantarius|Prevotella disiens, Streptococcus infantis|Prevotella disiens, Streptococcus mitis|Prevotella disiens, Streptococcus mutans|Prevotella disiens, Streptococcus oralis|Prevotella disiens, Streptococcus parasanguinis|Prevotella disiens, Streptococcus peroris|Prevotella disiens, Streptococcus pneumoniae|Prevotella disiens, Streptococcus salivarius|Prevotella disiens, Streptococcus sanguinis|Prevotella disiens, Streptococcus thermophilus|Prevotella disiens, Streptococcus vestibularis|Prevotella disiens, Subdoligranulum variabile|Prevotella disiens, Succinatimonas hippei|Prevotella disiens, Sutterella wadsworthensis|Prevotella disiens, Tropheryma whipplei|Prevotella disiens, Veillonella atypica|Prevotella disiens, Veillonella dispar|Prevotella disiens, Veillonella parvula|Prevotella disiens, Victivallis vadensis|Prevotella melaninogenica, Prevotella melaninogenica|Prevotella melaninogenica, Prevotella multiformis|Prevotella melaninogenica, Prevotella oralis|Prevotella melaninogenica, Prevotella oris|Prevotella melaninogenica, Prevotella salivae|Prevotella melaninogenica, Prevotella timonensis|Prevotella melaninogenica, Propionibacterium acnes|Prevotella melaninogenica, Propionibacterium freudenreichii|Prevotella melaninogenica, Proteus mirabilis|Prevotella melaninogenica, Proteus penneri|Prevotella melaninogenica, Pseudoflavonifractor capillosus|Prevotella melaninogenica, Pseudomonas aeruginosa|Prevotella melaninogenica, Pseudomonas fluorescens|Prevotella melaninogenica, Pseudomonas putida|Prevotella melaninogenica, Pseudoramibacter alactolyticus|Prevotella melaninogenica, Pyramidobacter piscolens|Prevotella melaninogenica, Rhodopseudomonas palustris|Prevotella melaninogenica, Roseburia intestinalis|Prevotella melaninogenica, Roseburia inulinivorans|Prevotella melaninogenica, Rothia dentocariosa|Prevotella melaninogenica, Rothia mucilaginosa|Prevotella melaninogenica, Ruminococcus albus|Prevotella melaninogenica, Ruminococcus bromii|Prevotella melaninogenica, Ruminococcus gnavus|Prevotella melaninogenica, Ruminococcus lactaris|Prevotella melaninogenica, Ruminococcus obeum|Prevotella melaninogenica, Ruminococcus torques|Prevotella melaninogenica, Selenomonas sputigena|Prevotella melaninogenica, Shigella boydii|Prevotella melaninogenica, Shigella dysenteriae|Prevotella melaninogenica, Shigella sonnei|Prevotella melaninogenica, Slackia exigua|Prevotella melaninogenica, Solobacterium moorei|Prevotella melaninogenica, Staphylococcus aureus|Prevotella melaninogenica, Staphylococcus epidermidis|Prevotella melaninogenica, Staphylococcus hominis|Prevotella melaninogenica, Staphylococcus saprophyticus|Prevotella melaninogenica, Staphylococcus warneri|Prevotella melaninogenica, Streptococcus agalactiae|Prevotella melaninogenica, Streptococcus anginosus|Prevotella melaninogenica, Streptococcus australis|Prevotella melaninogenica, Streptococcus bovis|Prevotella melaninogenica, Streptococcus cristatus|Prevotella melaninogenica, Streptococcus dysgalactiae|Prevotella melaninogenica, Streptococcus equinus|Prevotella melaninogenica, Streptococcus gordonii|Prevotella melaninogenica, Streptococcus infantarius|Prevotella melaninogenica, Streptococcus infantis|Prevotella melaninogenica, Streptococcus mitis|Prevotella melaninogenica, Streptococcus mutans|Prevotella melaninogenica, Streptococcus oralis|Prevotella melaninogenica, Streptococcus parasanguinis|Prevotella melaninogenica, Streptococcus peroris|Prevotella melaninogenica, Streptococcus pneumoniae|Prevotella melaninogenica, Streptococcus salivarius|Prevotella melaninogenica, Streptococcus sanguinis|Prevotella melaninogenica, Streptococcus thermophilus|Prevotella melaninogenica, Streptococcus vestibularis|Prevotella melaninogenica, Subdoligranulum variabile|Prevotella melaninogenica, Succinatimonas hippei|Prevotella melaninogenica, Sutterella wadsworthensis|Prevotella melaninogenica, Tropheryma whipplei|Prevotella melaninogenica, Veillonella atypica|Prevotella melaninogenica, Veillonella dispar|Prevotella melaninogenica, Veillonella parvula|Prevotella melaninogenica, Victivallis vadensis|Prevotella multiformis, Prevotella multiformis|Prevotella multiformis, Prevotella oralis|Prevotella multiformis, Prevotella oris|Prevotella multiformis, Prevotella salivae|Prevotella multiformis, Prevotella timonensis|Prevotella multiformis, Propionibacterium acnes|Prevotella multiformis, Propionibacterium freudenreichii|Prevotella multiformis, Proteus mirabilis|Prevotella multiformis, Proteus penneri|Prevotella multiformis, Pseudoflavonifractor capillosus|Prevotella multiformis, Pseudomonas aeruginosa|Prevotella multiformis, Pseudomonas fluorescens|Prevotella multiformis, Pseudomonas putida|Prevotella multiformis, Pseudoramibacter alactolyticus|Prevotella multiformis, Pyramidobacter piscolens|Prevotella multiformis, Rhodopseudomonas palustris|Prevotella multiformis, Roseburia intestinalis|Prevotella multiformis, Roseburia inulinivorans|Prevotella multiformis, Rothia dentocariosa|Prevotella multiformis, Rothia mucilaginosa|Prevotella multiformis, Ruminococcus albus|Prevotella multiformis, Ruminococcus bromii|Prevotella multiformis, Ruminococcus gnavus|Prevotella multiformis, Ruminococcus lactaris|Prevotella TABLE 2-continued Table 2. Specific binary combinations of OTUs. Individual pairings are differentiated by "|" and OTUs within a combination are differentiated by ","

*multiformis, Ruminococcus obeum|Prevotella multiformis, Ruminococcus torques|Prevotella multiformis, Selenomonas sputigena|Prevotella multiformis, Shigella boydii|Prevotella multiformis, Shigella dysenteriae|Prevotella multiformis, Shigella sonnei|Prevotella multiformis, Slackia exigua|Prevotella multiformis, Solobacterium moorei|Prevotella multiformis, Staphylococcus aureus|Prevotella multiformis, Staphylococcus epidermidis|Prevotella multiformis, Staphylococcus hominis|Prevotella multiformis, Staphylococcus saprophyticus|Prevotella multiformis, Staphylococcus warneri|Prevotella multiformis, Streptococcus agalactiae|Prevotella multiformis, Streptococcus anginosus|Prevotella multiformis, Streptococcus australis|Prevotella multiformis, Streptococcus bovis|Prevotella multiformis, Streptococcus cristatus|Prevotella multiformis, Streptococcus dysgalactiae|Prevotella multiformis, Streptococcus equinus|Prevotella multiformis, Streptococcus gordonii|Prevotella multiformis, Streptococcus infantarius|Prevotella multiformis, Streptococcus infantis|Prevotella multiformis, Streptococcus mitis|Prevotella multiformis, Streptococcus mutans|Prevotella multiformis, Streptococcus oralis|Prevotella multiformis, Streptococcus parasanguinis|Prevotella multiformis, Streptococcus peroris|Prevotella multiformis, Streptococcus pneumoniae|Prevotella multiformis, Streptococcus salivarius|Prevotella multiformis, Streptococcus sanguinis|Prevotella multiformis, Streptococcus thermophilus|Prevotella multiformis, Streptococcus vestibularis|Prevotella multiformis, Subdoligranulum variabile|Prevotella multiformis, Succinatimonas hippei|Prevotella multiformis, Sutterella wadsworthensis|Prevotella multiformis, Tropheryma whipplei|Prevotella multiformis, Veillonella atypica|Prevotella multiformis, Veillonella dispar|Prevotella multiformis, Veillonella parvula|Prevotella multiformis, Victivallis vadensis|Prevotella oralis, Prevotella oralis|Prevotella oralis, Prevotella oris|Prevotella oralis, Prevotella salivae|Prevotella oralis, Prevotella timonensis|Prevotella oralis, Propionibacterium acnes|Prevotella oralis, Propionibacterium freudenreichii|Prevotella oralis, Proteus mirabilis|Prevotella oralis, Proteus penneri|Prevotella oralis, Pseudoflavonifractor capillosus|Prevotella oralis, Pseudomonas aeruginosa|Prevotella oralis, Pseudomonas fluorescens|Prevotella oralis, Pseudomonas putida|Prevotella oralis, Pseudoramibacter alactolyticus|Prevotella oralis, Pyramidobacter piscolens|Prevotella oralis, Rhodopseudomonas palustris|Prevotella oralis, Roseburia intestinalis|Prevotella oralis, Roseburia inulinivorans|Prevotella oralis, Rothia dentocariosa|Prevotella oralis, Rothia mucilaginosa|Prevotella oralis, Ruminococcus albus|Prevotella oralis, Ruminococcus bromii|Prevotella oralis, Ruminococcus gnavus|Prevotella oralis, Ruminococcus lactaris|Prevotella oralis, Ruminococcus obeum|Prevotella oralis, Ruminococcus torques|Prevotella oralis, Selenomonas sputigena|Prevotella oralis, Shigella boydii|Prevotella oralis, Shigella dysenteriae|Prevotella oralis, Shigella sonnei|Prevotella oralis, Slackia exigua|Prevotella oralis, Solobacterium moorei|Prevotella oralis, Staphylococcus aureus|Prevotella oralis, Staphylococcus epidermidis|Prevotella oralis, Staphylococcus hominis|Prevotella oralis, Staphylococcus saprophyticus|Prevotella oralis, Staphylococcus warneri|Prevotella oralis, Streptococcus agalactiae|Prevotella oralis, Streptococcus anginosus|Prevotella oralis, Streptococcus australis|Prevotella oralis, Streptococcus bovis|Prevotella oralis, Streptococcus cristatus|Prevotella oralis, Streptococcus dysgalactiae|Prevotella oralis, Streptococcus equinus|Prevotella oralis, Streptococcus gordonii|Prevotella oralis, Streptococcus infantarius|Prevotella oralis, Streptococcus infantis|Prevotella oralis, Streptococcus mitis|Prevotella oralis, Streptococcus mutans|Prevotella oralis, Streptococcus oralis|Prevotella oralis, Streptococcus parasanguinis|Prevotella oralis, Streptococcus peroris|Prevotella oralis, Streptococcus pneumoniae|Prevotella oralis, Streptococcus salivarius|Prevotella oralis, Streptococcus sanguinis|Prevotella oralis, Streptococcus thermophilus|Prevotella oralis, Streptococcus vestibularis|Prevotella oralis, Subdoligranulum variabile|Prevotella oralis, Succinatimonas hippei|Prevotella oralis, Sutterella wadsworthensis|Prevotella oralis, Tropheryma whipplei|Prevotella oralis, Veillonella atypica|Prevotella oralis, Veillonella dispar|Prevotella oralis, Veillonella parvula|Prevotella oralis, Victivallis vadensis|Prevotella oris, Prevotella oris|Prevotella oris, Prevotella salivae|Prevotella oris, Prevotella timonensis|Prevotella oris, Propionibacterium acnes|Prevotella oris, Propionibacterium freudenreichii|Prevotella oris, Proteus mirabilis|Prevotella oris, Proteus penneri|Prevotella oris, Pseudoflavonifractor capillosus|Prevotella oris, Pseudomonas aeruginosa|Prevotella oris, Pseudomonas fluorescens|Prevotella oris, Pseudomonas putida|Prevotella oris, Pseudoramibacter alactolyticus|Prevotella oris, Pyramidobacter piscolens|Prevotella oris, Rhodopseudomonas palustris|Prevotella oris, Roseburia intestinalis|Prevotella oris, Roseburia inulinivorans|Prevotella oris, Rothia dentocariosa|Prevotella oris, Rothia mucilaginosa|Prevotella oris, Ruminococcus albus|Prevotella oris, Ruminococcus bromii|Prevotella oris, Ruminococcus gnavus|Prevotella oris, Ruminococcus lactaris|Prevotella oris, Ruminococcus obeum|Prevotella oris, Ruminococcus torques|Prevotella oris, Selenomonas sputigena|Prevotella oris, Shigella boydii|Prevotella oris, Shigella dysenteriae|Prevotella oris, Shigella sonnei|Prevotella oris, Slackia exigua|Prevotella oris, Solobacterium moorei|Prevotella oris, Staphylococcus aureus|Prevotella oris, Staphylococcus epidermidis|Prevotella oris, Staphylococcus hominis|Prevotella oris, Staphylococcus saprophyticus|Prevotella oris, Staphylococcus warneri|Prevotella oris, Streptococcus agalactiae|Prevotella oris, Streptococcus anginosus|Prevotella oris, Streptococcus australis|Prevotella oris, Streptococcus bovis|Prevotella oris, Streptococcus cristatus|Prevotella oris, Streptococcus dysgalactiae|Prevotella oris, Streptococcus equinus|Prevotella oris, Streptococcus gordonii|Prevotella oris, Streptococcus infantarius|Prevotella oris, Streptococcus infantis|Prevotella oris, Streptococcus mitis|Prevotella oris, Streptococcus mutans|Prevotella oris, Streptococcus oralis|Prevotella oris, Streptococcus parasanguinis|Prevotella oris, Streptococcus peroris|Prevotella oris, Streptococcus pneumoniae|Prevotella oris, Streptococcus salivarius|Prevotella oris, Streptococcus sanguinis|Prevotella oris, Streptococcus thermophilus|Prevotella oris, Streptococcus vestibularis|Prevotella oris, Subdoligranulum variabile|Prevotella oris, Succinatimonas hippei|Prevotella oris, Sutterella wadsworthensis|Prevotella oris, Tropheryma whipplei|Prevotella oris, Veillonella atypica|Prevotella oris, Veillonella dispar|Prevotella oris, Veillonella parvula|Prevotella oris, Victivallis vadensis|Prevotella salivae, Prevotella salivae|Prevotella salivae, Prevotella timonensis|Prevotella salivae, Propionibacterium acnes|Prevotella salivae, Propionibacterium freudenreichii|Prevotella salivae, Proteus mirabilis|Prevotella salivae, Proteus penneri|Prevotella salivae, Pseudoflavonifractor capillosus|Prevotella salivae, Pseudomonas aeruginosa|Prevotella salivae, Pseudomonas fluorescens|Prevotella salivae, Pseudomonas putida|Prevotella salivae, Pseudoramibacter alactolyticus|Prevotella salivae, Pyramidobacter piscolens|Prevotella salivae, Rhodopseudomonas palustris|Prevotella salivae, Roseburia intestinalis|Prevotella salivae, Roseburia inulinivorans|Prevotella salivae, Rothia dentocariosa|Prevotella salivae, Rothia mucilaginosa|Prevotella salivae, Ruminococcus albus|Prevotella salivae, Ruminococcus bromii|Prevotella salivae, Ruminococcus gnavus|Prevotella salivae, Ruminococcus lactaris|Prevotella salivae, Ruminococcus obeum|Prevotella salivae, Ruminococcus torques|Prevotella salivae, Selenomonas sputigena|Prevotella salivae, Shigella boydii|Prevotella salivae, Shigella dysenteriae|Prevotella salivae, Shigella sonnei|Prevotella salivae, Slackia exigua|Prevotella salivae, Solobacterium moorei|Prevotella salivae, Staphylococcus aureus|Prevotella salivae, Staphylococcus epidermidis|Prevotella salivae, Staphylococcus hominis|Prevotella salivae, Staphylococcus saprophyticus|Prevotella salivae, Staphylococcus warneri|Prevotella salivae, Streptococcus agalactiae|Prevotella salivae, Streptococcus anginosus|Prevotella salivae, Streptococcus australis|Prevotella salivae, Streptococcus bovis|Prevotella salivae, Streptococcus cristatus|Prevotella salivae, Streptococcus dysgalactiae|Prevotella salivae, Streptococcus equinus|Prevotella salivae, Streptococcus gordonii|Prevotella salivae, Streptococcus infantarius|Prevotella salivae, Streptococcus infantis|Prevotella salivae, Streptococcus mitis|Prevotella salivae, Streptococcus mutans|Prevotella salivae, Streptococcus oralis|Prevotella salivae, Streptococcus parasanguinis|Prevotella salivae, Streptococcus peroris|Prevotella salivae, Streptococcus pneumoniae|Prevotella salivae, Streptococcus salivarius|Prevotella salivae, Streptococcus sanguinis|Prevotella salivae, Streptococcus thermophilus|Prevotella salivae, Streptococcus vestibularis|Prevotella salivae, Subdoligranulum variabile|Prevotella salivae, Succinatimonas hippei|Prevotella salivae, Sutterella wadsworthensis|Prevotella salivae, Tropheryma whipplei|Prevotella salivae, Veillonella atypica|Prevotella salivae, Veillonella dispar|Prevotella salivae, Veillonella parvula|Prevotella salivae, Victivallis vadensis|Prevotella timonensis, Prevotella timonensis|Prevotella timonensis, Propionibacterium acnes|Prevotella timonensis, Propionibacterium freudenreichii|Prevotella timonensis, Proteus mirabilis|Prevotella timonensis, Proteus penneri|Prevotella timonensis, Pseudoflavonifractor capillosus|Prevotella timonensis, Pseudomonas aeruginosa|Prevotella timonensis, Pseudomonas fluorescens|Prevotella timonensis, Pseudomonas putida|Prevotella timonensis, Pseudoramibacter alactolyticus|Prevotella timonensis, Pyramidobacter piscolens|Prevotella timonensis, Rhodopseudomonas palustris|Prevotella timonensis, Roseburia intestinalis|Prevotella*

TABLE 2-continued

| Table 2. Specific binary combinations of OTUs. Individual pairings are differentiated by "\|" and OTUs within a combination are differentiated by "," |
|---|
| *timonensis, Roseburia inulinivorans\|Prevotella timonensis, Rothia dentocariosa\|Prevotella timonensis, Rothia mucilaginosa\|Prevotella timonensis, Ruminococcus albus\|Prevotella timonensis, Ruminococcus bromii\|Prevotella timonensis, Ruminococcus gnavus\|Prevotella timonensis, Ruminococcus lactaris\|Prevotella timonensis, Ruminococcus obeum\|Prevotella timonensis, Ruminococcus torques\|Prevotella timonensis, Selenomonas sputigena\|Prevotella timonensis, Shigella boydii\|Prevotella timonensis, Shigella dysenteriae\|Prevotella timonensis, Shigella sonnei\|Prevotella timonensis, Slackia exigua\|Prevotella timonensis, Solobacterium moorei\|Prevotella timonensis, Staphylococcus aureus\|Prevotella timonensis, Staphylococcus epidermidis\|Prevotella timonensis, Staphylococcus hominis\|Prevotella timonensis, Staphylococcus saprophyticus\|Prevotella timonensis, Staphylococcus warneri\|Prevotella timonensis, Streptococcus agalactiae\|Prevotella timonensis, Streptococcus anginosus\|Prevotella timonensis, Streptococcus australis\|Prevotella timonensis, Streptococcus bovis\|Prevotella timonensis, Streptococcus cristatus\|Prevotella timonensis, Streptococcus dysgalactiae\|Prevotella timonensis, Streptococcus equinus\|Prevotella timonensis, Streptococcus gordonii\|Prevotella timonensis, Streptococcus infantarius\|Prevotella timonensis, Streptococcus infantis\|Prevotella timonensis, Streptococcus mitis\|Prevotella timonensis, Streptococcus mutans\|Prevotella timonensis, Streptococcus oralis\|Prevotella timonensis, Streptococcus parasanguinis\|Prevotella timonensis, Streptococcus peroris\|Prevotella timonensis, Streptococcus pneumoniae\|Prevotella timonensis, Streptococcus salivarius\|Prevotella timonensis, Streptococcus sanguinis\|Prevotella timonensis, Streptococcus thermophilus\|Prevotella timonensis, Streptococcus vestibularis\|Prevotella timonensis, Subdoligranulum variabile\|Prevotella timonensis, Succinatimonas hippei\|Prevotella timonensis, Sutterella wadsworthensis\|Prevotella timonensis, Tropheryma whipplei\|Prevotella timonensis, Veillonella atypica\|Prevotella timonensis, Veillonella dispar\|Prevotella timonensis, Veillonella parvula\|Prevotella timonensis, Victivallis vadensis\|Propionibacterium acnes, Propionibacterium acnes\|Propionibacterium acnes, Propionibacterium freudenreichii\|Propionibacterium acnes, Proteus mirabilis\|Propionibacterium acnes, Proteus penneri\|Propionibacterium acnes, Pseudoflavonifractor capillosus\|Propionibacterium acnes, Pseudomonas aeruginosa\|Propionibacterium acnes, Pseudomonas fluorescens\|Propionibacterium acnes, Pseudomonas putida\|Propionibacterium acnes, Pseudoramibacter alactolyticus\|Propionibacterium acnes, Pyramidobacter piscolens\|Propionibacterium acnes, Rhodopseudomonas palustris\|Propionibacterium acnes, Roseburia intestinalis\|Propionibacterium acnes, Roseburia inulinivorans\|Propionibacterium acnes, Rothia dentocariosa\|Propionibacterium acnes, Rothia mucflaginosa\|Propionibacterium acnes, Ruminococcus albus\|Propionibacterium acnes, Ruminococcus bromii\|Propionibacterium acnes, Ruminococcus gnavus\|Propionibacterium acnes, Ruminococcus lactaris\|Propionibacterium acnes, Ruminococcus obeum\|Propionibacterium acnes, Ruminococcus torques\|Propionibacterium acnes, Selenomonas sputigena\|Propionibacterium acnes, Shigella boydii\|Propionibacterium acnes, Shigella dysenteriae\|Propionibacterium acnes, Shigella sonnei\|Propionibacterium acnes, Slackia exigua\|Propionibacterium acnes, Solobacterium moorei\|Propionibacterium acnes, Staphylococcus aureus\|Propionibacterium acnes, Staphylococcus epidermidis\|Propionibacterium acnes, Staphylococcus hominis\|Propionibacterium acnes, Staphylococcus saprophyticus\|Propionibacterium acnes, Staphylococcus warneri\|Propionibacterium acnes, Streptococcus agalactiae\|Propionibacterium acnes, Streptococcus anginosus\|Propionibacterium acnes, Streptococcus australis\|Propionibacterium acnes, Streptococcus bovis\|Propionibacterium acnes, Streptococcus cristatus\|Propionibacterium acnes, Streptococcus dysgalactiae\|Propionibacterium acnes, Streptococcus equinus\|Propionibacterium acnes, Streptococcus gordonii\|Propionibacterium acnes, Streptococcus infantarius\|Propionibacterium acnes, Streptococcus infantis\|Propionibacterium acnes, Streptococcus mitis\|Propionibacterium acnes, Streptococcus mutans\|Propionibacterium acnes, Streptococcus oralis\|Propionibacterium acnes, Streptococcus parasanguinis\|Propionibacterium acnes, Streptococcus peroris\|Propionibacterium acnes, Streptococcus pneumoniae\|Propionibacterium acnes, Streptococcus salivarius\|Propionibacterium acnes, Streptococcus sanguinis\|Propionibacterium acnes, Streptococcus thermophilus\|Propionibacterium acnes, Streptococcus vestibularis\|Propionibacterium acnes, Subdoligranulum variabile\|Propionibacterium acnes, Succinatimonas hippei\|Propionibacterium acnes, Sutterella wadsworthensis\|Propionibacterium acnes, Tropheryma whipplei\|Propionibacterium acnes, Veillonella atypica\|Propionibacterium acnes, Veillonella dispar\|Propionibacterium acnes, Veillonella parvula\|Propionibacterium acnes, Victivallis vadensis\|Propionibacterium freudenreichii, Propionibacterium freudenreichii\|Propionibacterium freudenreichii, Proteus mirabilis\|Propionibacterium freudenreichii, Proteus penneri\|Propionibacterium freudenreichii, Pseudoflavonifractor capillosus\|Propionibacterium freudenreichii, Pseudomonas aeruginosa\|Propionibacterium freudenreichii, Pseudomonas fluorescens\|Propionibacterium freudenreichii, Pseudomonas putida\|Propionibacterium freudenreichii, Pseudoramibacter alactolyticus\|Propionibacterium freudenreichii, Pyramidobacter piscolens\|Propionibacterium freudenreichii, Rhodopseudomonas palustris\|Propionibacterium freudenreichii, Roseburia intestinalis\|Propionibacterium freudenreichii, Roseburia inulinivorans\|Propionibacterium freudenreichii, Rothia dentocariosa\|Propionibacterium freudenreichii, Rothia mucilaginosa\|Propionibacterium freudenreichii, Ruminococcus albus\|Propionibacterium freudenreichii, Ruminococcus bromii\|Propionibacterium freudenreichii, Ruminococcus gnavus\|Propionibacterium freudenreichii, Ruminococcus lactaris\|Propionibacterium freudenreichii, Ruminococcus obeum\|Propionibacterium freudenreichii, Ruminococcus torques\|Propionibacterium freudenreichii, Selenomonas sputigena\|Propionibacterium freudenreichii, Shigella boydii\|Propionibacterium freudenreichii, Shigella dysenteriae\|Propionibacterium freudenreichii, Shigella sonnei\|Propionibacterium freudenreichii, Slackia exigua\|Propionibacterium freudenreichii, Solobacterium moore\|Propionibacterium freudenreichii, Staphylococcus aureus\|Propionibacterium freudenreichii, Staphylococcus epidermidis\|Propionibacterium freudenreichii, Staphylococcus hominis\|Propionibacterium freudenreichii, Staphylococcus saprophyticus\|Propionibacterium freudenreichii, Staphylococcus warneri\|Propionibacterium freudenreichii, Streptococcus agalactiae\|Propionibacterium freudenreichii, Streptococcus anginosus\|Propionibacterium freudenreichii, Streptococcus australis\|Propionibacterium freudenreichii, Streptococcus bovis\|Propionibacterium freudenreichii, Streptococcus cristatus\|Propionibacterium freudenreichii, Streptococcus dysgalactiae\|Propionibacterium freudenreichii, Streptococcus equinus\|Propionibacterium freudenreichii, Streptococcus gordonii\|Propionibacterium freudenreichii, Streptococcus infantarius\|Propionibacterium freudenreichii, Streptococcus infantis\|Propionibacterium freudenreichii, Streptococcus mitis\|Propionibacterium freudenreichii, Streptococcus mutans\|Propionibacterium freudenreichii, Streptococcus oralis\|Propionibacterium freudenreichii, Streptococcus parasanguinis\|Propionibacterium freudenreichii, Streptococcus peroris\|Propionibacterium freudenreichii, Streptococcus pneumoniae\|Propionibacterium freudenreichii, Streptococcus salivarius\|Propionibacterium freudenreichii, Streptococcus sanguinis\|Propionibacterium freudenreichii, Streptococcus thermophilus\|Propionibacterium freudenreichii, Streptococcus vestibularis\|Propionibacterium freudenreichii, Subdoligranulum variabile\|Propionibacterium freudenreichii, Succinatimonas hippei\|Propionibacterium freudenreichii, Sutterella wadsworthensis\|Propionibacterium freudenreichii, Tropheryma whipplei\|Propionibacterium freudenreichii, Veillonella atypica\|Propionibacterium freudenreichii, Veillonella dispar\|Propionibacterium freudenreichii, Veillonella parvula\|Propionibacterium freudenreichii, Victivallis vadensis\|Proteus mirabilis, Proteus mirabilis\|Proteus mirabilis, Proteus penneri\|Proteus mirabilis, Pseudoflavonifractor capillosus\|Proteus mirabilis, Pseudomonas aeruginosa\|Proteus mirabilis, Pseudomonas fluorescens\|Proteus mirabilis, Pseudomonas putida\|Proteus mirabilis, Pseudoramibacter alactolyticus\|Proteus mirabilis, Pyramidobacter piscolens\|Proteus mirabilis, Rhodopseudomonas palustris\|Proteus mirabilis, Roseburia intestinalis\|Proteus mirabilis, Roseburia inulinivorans\|Proteus mirabilis, Rothia dentocariosa\|Proteus mirabilis, Rothia mucilaginosa\|Proteus mirabilis, Ruminococcus albus\|Proteus mirabilis, Ruminococcus bromii\|Proteus mirabilis, Ruminococcus gnavus\|Proteus mirabilis, Ruminococcus lactaris\|Proteus mirabilis, Ruminococcus obeum\|Proteus mirabilis, Ruminococcus torques\|Proteus mirabilis, Selenomonas sputigena\|Proteus mirabilis, Shigella boydii\|Proteus mirabilis, Shigella dysenteriae\|Proteus mirabilis, Shigella sonnei\|Proteus mirabilis, Slackia exigua\|Proteus mirabilis, Solobacterium moorei\|Proteus mirabilis, Staphylococcus aureus\|Proteus mirabilis, Staphylococcus epidermidis\|Proteus mirabilis, Staphylococcus hominis\|Proteus mirabilis, Staphylococcus saprophyticus\|Proteus mirabilis, Staphylococcus warneri\|Proteus mirabilis, Streptococcus agalactiae\|Proteus mirabilis, Streptococcus anginosus\|Proteus mirabilis, Streptococcus australis\|Proteus mirabilis, Streptococcus bovis\|Proteus mirabilis, Streptococcus cristatus\|Proteus mirabilis, Streptococcus dysgalactiae\|Proteus mirabilis, Streptococcus equinus\|Proteus mirabilis, Streptococcus gordonii\|Proteus mirabilis, Streptococcus infantarius\|Proteus* |

TABLE 2-continued

| Table 2. Specific binary combinations of OTUs. Individual pairings are differentiated by "\|" and OTUs within a combination are differentiated by "," |
|---|
| mirabilis, Streptococcus infantis\|Proteus mirabilis, Streptococcus mitis\|Proteus mirabilis, Streptococcus mutans\|Proteus mirabilis, Streptococcus oralis\|Proteus mirabilis, Streptococcus parasanguinis\|Proteus mirabilis, Streptococcus peroris\|Proteus mirabilis, Streptococcus pneumoniae\|Proteus mirabilis, Streptococcus salivarius\|Proteus mirabilis, Streptococcus sanguinis\|Proteus mirabilis, Streptococcus thermophilus\|Proteus mirabilis, Streptococcus vestibularis\|Proteus mirabilis, Subdoligranulum variabile\|Proteus mirabilis, Succinatimonas hippei\|Proteus mirabilis, Sutterella wadsworthensis\|Proteus mirabilis, Tropheryma whipplei\|Proteus mirabilis, Veillonella atypica\|Proteus mirabilis, Veillonella dispar\|Proteus mirabilis, Veillonella parvula\|Proteus mirabilis, Victivallis vadensis\|Proteus penneri, Proteus penneri\|Proteus penneri, Pseudoflavonifractor capillosus\|Proteus penneri, Pseudomonas aeruginosa\|Proteus penneri, Pseudomonas fluorescens\|Proteus penneri, Pseudomonas putida\|Proteus penneri, Pseudoramibacter alactolyticus\|Proteus penneri, Pyramidobacter piscolens\|Proteus penneri, Rhodopseudomonas palustris\|Proteus penneri, Roseburia intestinalis\|Proteus penneri, Roseburia inulinivorans\|Proteus penneri, Rothia dentocariosa\|Proteus penneri, Rothia mucilaginosa\|Proteus penneri, Ruminococcus albus\|Proteus penneri, Ruminococcus bromii\|Proteus penneri, Ruminococcus gnavus\|Proteus penneri, Ruminococcus lactaris\|Proteus penneri, Ruminococcus obeum\|Proteus penneri, Ruminococcus torques\|Proteus penneri, Selenomonas sputigena\|Proteus penneri, Shigella boydii\|Proteus penneri, Shigella dysenteriae\|Proteus penneri, Shigella sonnei\|Proteus penneri, Slackia exigua\|Proteus penneri, Solobacterium moorei\|Proteus penneri, Staphylococcus aureus\|Proteus penneri, Staphylococcus epidermidis\|Proteus penneri, Staphylococcus hominis\|Proteus penneri, Staphylococcus saprophyticus\|Proteus penneri, Staphylococcus warneri\|Proteus penneri, Streptococcus agalactiae\|Proteus penneri, Streptococcus anginosus\|Proteus penneri, Streptococcus australis\|Proteus penneri, Streptococcus bovis\|Proteus penneri, Streptococcus cristatus\|Proteus penneri, Streptococcus dysgalactiae\|Proteus penneri, Streptococcus equinus\|Proteus penneri, Streptococcus gordonii\|Proteus penneri, Streptococcus infantarius\|Proteus penneri, Streptococcus infantis\|Proteus penneri, Streptococcus mitis\|Proteus penneri, Streptococcus mutans\|Proteus penneri, Streptococcus oralis\|Proteus penneri, Streptococcus parasanguinis\|Proteus penneri, Streptococcus peroris\|Proteus penneri, Streptococcus pneumoniae\|Proteus penneri, Streptococcus salivarius\|Proteus penneri, Streptococcus sanguinis\|Proteus penneri, Streptococcus thermophilus\|Proteus penneri, Streptococcus vestibularis\|Proteus penneri, Subdoligranulum variabile\|Proteus penneri, Succinatimonas hippei\|Proteus penneri, Sutterella wadsworthensis\|Proteus penneri, Tropheryma whipplei\|Proteus penneri, Veillonella atypica\|Proteus penneri, Veillonella dispar\|Proteus penneri, Veillonella parvula\|Proteus penneri, Victivallis vadensis\|Pseudoflavonifractor capillosus, Pseudoflavonifractor capillosus\|Pseudoflavonifractor capillosus, Pseudomonas aeruginosa\|Pseudoflavonifractor capillosus, Pseudomonas fluorescens\|Pseudoflavonifractor capillosus, Pseudomonas putida\|Pseudoflavonifractor capillosus, Pseudoramibacter alactolyticus\|Pseudoflavonifractor capillosus, Pyramidobacter piscolens\|Pseudoflavonifractor capillosus, Rhodopseudomonas palustris\|Pseudoflavonifractor capillosus, Roseburia intestinalis\|Pseudoflavonifractor capillosus, Roseburia inulinivorans\|Pseudoflavonifractor capillosus, Rothia dentocariosa\|Pseudoflavonifractor capillosus, Rothia mucilaginosa\|Pseudoflavonifractor capillosus, Ruminococcus albus\|Pseudoflavonifractor capillosus, Ruminococcus bromii\|Pseudoflavonifractor capillosus, Ruminococcus gnavus\|Pseudoflavonifractor capillosus, Ruminococcus lactaris\|Pseudoflavonifractor capillosus, Ruminococcus obeum\|Pseudoflavonifractor capillosus, Ruminococcus torques\|Pseudoflavonifractor capillosus, Selenomonas sputigena\|Pseudoflavonifractor capillosus, Shigella boydii\|Pseudoflavonifractor capillosus, Shigella dysenteriae\|Pseudoflavonifractor capillosus, Shigella sonnei\|Pseudoflavonifractor capillosus, Slackia exigua\|Pseudoflavonifractor capillosus, Solobacterium moorei\|Pseudoflavonifractor capillosus, Staphylococcus aureus\|Pseudoflavonifractor capillosus, Staphylococcus epidermidis\|Pseudoflavonifractor capillosus, Staphylococcus hominis\|Pseudoflavonifractor capillosus, Staphylococcus saprophyticus\|Pseudoflavonifractor capillosus, Staphylococcus warneri\|Pseudoflavonifractor capillosus, Streptococcus agalactiae\|Pseudoflavonifractor capillosus, Streptococcus anginosus\|Pseudoflavonifractor capillosus, Streptococcus australis\|Pseudoflavonifractor capillosus, Streptococcus bovis\|Pseudoflavonifractor capillosus, Streptococcus cristatus\|Pseudoflavonifractor capillosus, Streptococcus dysgalactiae\|Pseudoflavonifractor capillosus, Streptococcus equinus\|Pseudoflavonifractor capillosus, Streptococcus gordonii\|Pseudoflavonifractor capillosus, Streptococcus infantarius\|Pseudoflavonifractor capillosus, Streptococcus infantis\|Pseudoflavonifractor capillosus, Streptococcus mitis\|Pseudoflavonifractor capillosus, Streptococcus mutans\|Pseudoflavonifractor capillosus, Streptococcus oralis\|Pseudoflavonifractor capillosus, Streptococcus parasanguinis\|Pseudoflavonifractor capillosus, Streptococcus peroris\|Pseudoflavonifractor capillosus, Streptococcus pneumoniae\|Pseudoflavonifractor capillosus, Streptococcus salivarius\|Pseudoflavonifractor capillosus, Streptococcus sanguinis\|Pseudoflavonifractor capillosus, Streptococcus thermophilus\|Pseudoflavonifractor capillosus, Streptococcus vestibularis\|Pseudoflavonifractor capillosus, Subdoligranulum variabile\|Pseudoflavonifractor capillosus, Succinatimonas hippei\|Pseudoflavonifractor capillosus, Sutterella wadsworthensis\|Pseudoflavonifractor capillosus, Tropheryma whipplei\|Pseudoflavonifractor capillosus, Veillonella atypica\|Pseudoflavonifractor capillosus, Veillonella dispar\|Pseudoflavonifractor capillosus, Veillonella parvula\|Pseudoflavonifractor capillosus, Victivallis vadensis\|Pseudomonas aeruginosa, Pseudomonas aeruginosa\|Pseudomonas aeruginosa, Pseudomonas fluorescens\|Pseudomonas aeruginosa, Pseudomonas putida\|Pseudomonas aeruginosa, Pseudoramibacter alactolyticus\|Pseudomonas aeruginosa, Pyramidobacter piscolens\|Pseudomonas aeruginosa, Rhodopseudomonas palustris\|Pseudomonas aeruginosa, Roseburia intestinalis\|Pseudomonas aeruginosa, Roseburia inulinivorans\|Pseudomonas aeruginosa, Rothia dentocariosa\|Pseudomonas aeruginosa, Rothia mucilaginosa\|Pseudomonas aeruginosa, Ruminococcus albus\|Pseudomonas aeruginosa, Ruminococcus bromii\|Pseudomonas aeruginosa, Ruminococcus gnavus\|Pseudomonas aeruginosa, Ruminococcus lactaris\|Pseudomonas aeruginosa, Ruminococcus obeum\|Pseudomonas aeruginosa, Ruminococcus torques\|Pseudomonas aeruginosa, Selenomonas sputigena\|Pseudomonas aeruginosa, Shigella boydii\|Pseudomonas aeruginosa, Shigella dysenteriae\|Pseudomonas aeruginosa, Shigella sonnei\|Pseudomonas aeruginosa, Slackia exigua\|Pseudomonas aeruginosa, Solobacterium moorei\|Pseudomonas aeruginosa, Staphylococcus aureus\|Pseudomonas aeruginosa, Staphylococcus epidermidis\|Pseudomonas aeruginosa, Staphylococcus hominis\|Pseudomonas aeruginosa, Staphylococcus saprophyticus\|Pseudomonas aeruginosa, Staphylococcus warneri\|Pseudomonas aeruginosa, Streptococcus agalactiae\|Pseudomonas aeruginosa, Streptococcus anginosus\|Pseudomonas aeruginosa, Streptococcus australis\|Pseudomonas aeruginosa, Streptococcus bovis\|Pseudomonas aeruginosa, Streptococcus cristatus\|Pseudomonas aeruginosa, Streptococcus dysgalactiae\|Pseudomonas aeruginosa, Streptococcus equinus\|Pseudomonas aeruginosa, Streptococcus gordonii\|Pseudomonas aeruginosa, Streptococcus infantarius\|Pseudomonas aeruginosa, Streptococcus infantis\|Pseudomonas aeruginosa, Streptococcus mitis\|Pseudomonas aeruginosa, Streptococcus mutans\|Pseudomonas aeruginosa, Streptococcus oralis\|Pseudomonas aeruginosa, Streptococcus parasanguinis\|Pseudomonas aeruginosa, Streptococcus peroris\|Pseudomonas aeruginosa, Streptococcus pneumoniae\|Pseudomonas aeruginosa, Streptococcus salivarius\|Pseudomonas aeruginosa, Streptococcus sanguinis\|Pseudomonas aeruginosa, Streptococcus thermophilus\|Pseudomonas aeruginosa, Streptococcus vestibularis\|Pseudomonas aeruginosa, Subdoligranulum variabile\|Pseudomonas aeruginosa, Succinatimonas hippei\|Pseudomonas aeruginosa, Sutterella wadsworthensis\|Pseudomonas aeruginosa, Tropheryma whipplei\|Pseudomonas aeruginosa, Veillonella atypica\|Pseudomonas aeruginosa, Veillonella dispar\|Pseudomonas aeruginosa, Veillonella parvula\|Pseudomonas aeruginosa, Victivallis vadensis\|Pseudomonas fluorescens, Pseudomonas fluorescens\|Pseudomonas fluorescens, Pseudomonas putida\|Pseudomonas fluorescens, Pseudoramibacter alactolyticus\|Pseudomonas fluorescens, Pyramidobacter piscolens\|Pseudomonas fluorescens, Rhodopseudomonas palustris\|Pseudomonas fluorescens, Roseburia intestinalis\|Pseudomonas fluorescens, Roseburia inulinivorans\|Pseudomonas fluorescens, Rothia dentocariosa\|Pseudomonas fluorescens, Rothia mucilaginosa\|Pseudomonas fluorescens, Ruminococcus albus\|Pseudomonas fluorescens, Ruminococcus bromii\|Pseudomonas fluorescens, Ruminococcus gnavus\|Pseudomonas fluorescens, Ruminococcus lactaris\|Pseudomonas fluorescens, Ruminococcus obeum\|Pseudomonas fluorescens, Ruminococcus torques\|Pseudomonas fluorescens, Selenomonas sputigena\|Pseudomonas fluorescens, Shigella boydii\|Pseudomonas fluorescens, Shigella dysenteriae\|Pseudomonas fluorescens, Shigella sonnei\|Pseudomonas fluorescens, Slackia exigua\|Pseudomonas fluorescens, Solobacterium moorei\|Pseudomonas fluorescens, Staphylococcus aureus\|Pseudomonas fluorescens, Staphylococcus epidermidis\|Pseudomonas fluorescens, Staphylococcus hominis\|Pseudomonas fluorescens, Staphylococcus |

TABLE 2-continued

| Table 2. Specific binary combinations of OTUs. Individual pairings are differentiated by "\|" and OTUs within a combination are differentiated by "," |
|---|
| *saprophyticus\|Pseudomonas fluorescens, Staphylococcus warneri\|Pseudomonas fluorescens, Streptococcus agalactiae\|Pseudomonas fluorescens, Streptococcus anginosus\|Pseudomonas fluorescens, Streptococcus australis\|Pseudomonas fluorescens, Streptococcus bovis\|Pseudomonas fluorescens, Streptococcus cristatus\|Pseudomonas fluorescens, Streptococcus dysgalactiae\|Pseudomonas fluorescens, Streptococcus equinus\|Pseudomonas fluorescens, Streptococcus gordonii\|Pseudomonas fluorescens, Streptococcus infantarius\|Pseudomonas fluorescens, Streptococcus infantis\|Pseudomonas fluorescens, Streptococcus mitis\|Pseudomonas fluorescens, Streptococcus mutans\|Pseudomonas fluorescens, Streptococcus oralis\|Pseudomonas fluorescens, Streptococcus parasanguinis\|Pseudomonas fluorescens, Streptococcus peroris\|Pseudomonas fluorescens, Streptococcus pneumoniae\|Pseudomonas fluorescens, Streptococcus salivarius\|Pseudomonas fluorescens, Streptococcus sanguinis\|Pseudomonas fluorescens, Streptococcus thermophilus\|Pseudomonas fluorescens, Streptococcus vestibularis\|Pseudomonas fluorescens, Subdoligranulum variabile\|Pseudomonas fluorescens, Succinatimonas hippei\|Pseudomonas fluorescens, Sutterella wadsworthensis\|Pseudomonas fluorescens, Tropheryma whipplei\|Pseudomonas fluorescens, Veillonella atypica\|Pseudomonas fluorescens, Veillonella dispar\|Pseudomonas fluorescens, Veillonella parvula\|Pseudomonas fluorescens, Victivallis vadensis\|Pseudomonas putida, Pseudomonas putida\|Pseudomonas putida, Pseudoramibacter alactolyticus\|Pseudomonas putida, Pyramidobacter piscolens\|Pseudomonas putida, Rhodopseudomonas palustris\|Pseudomonas putida, Roseburia intestinalis\|Pseudomonas putida, Roseburia inulinivorans\|Pseudomonas putida, Rothia dentocariosa\|Pseudomonas putida, Rothia mucilaginosa\|Pseudomonas putida, Ruminococcus albus\|Pseudomonas putida, Ruminococcus bromii\|Pseudomonas putida, Ruminococcus gnavus\|Pseudomonas putida, Ruminococcus lactaris\|Pseudomonas putida, Ruminococcus obeum\|Pseudomonas putida, Ruminococcus torques\|Pseudomonas putida, Selenomonas sputigena\|Pseudomonas putida, Shigella boydii\|Pseudomonas putida, Shigella dysenteriae\|Pseudomonas putida, Shigella sonnei\|Pseudomonas putida, Slackia exigua\|Pseudomonas putida, Solobacterium moorei\|Pseudomonas putida, Staphylococcus aureus\|Pseudomonas putida, Staphylococcus epidermidis\|Pseudomonas putida, Staphylococcus hominis\|Pseudomonas putida, Staphylococcus saprophyticus\|Pseudomonas putida, Staphylococcus warneri\|Pseudomonas putida, Streptococcus agalactiae\|Pseudomonas putida, Streptococcus anginosus\|Pseudomonas putida, Streptococcus australis\|Pseudomonas putida, Streptococcus bovis\|Pseudomonas putida, Streptococcus cristatus\|Pseudomonas putida, Streptococcus dysgalactiae\|Pseudomonas putida, Streptococcus equinus\|Pseudomonas putida, Streptococcus gordonii\|Pseudomonas putida, Streptococcus infantarius\|Pseudomonas putida, Streptococcus infantis\|Pseudomonas putida, Streptococcus mitis\|Pseudomonas putida, Streptococcus mutans\|Pseudomonas putida, Streptococcus oralis\|Pseudomonas putida, Streptococcus parasanguinis\|Pseudomonas putida, Streptococcus peroris\|Pseudomonas putida, Streptococcus pneumoniae\|Pseudomonas putida, Streptococcus salivarius\|Pseudomonas putida, Streptococcus sanguinis\|Pseudomonas putida, Streptococcus thermophilus\|Pseudomonas putida, Streptococcus vestibularis\|Pseudomonas putida, Subdoligranulum variabile\|Pseudomonas putida, Succinatimonas hippei\|Pseudomonas putida, Sutterella wadsworthensis\|Pseudomonas putida, Tropheryma whipplei\|Pseudomonas putida, Veillonella atypica\|Pseudomonas putida, Veillonella dispar\|Pseudomonas putida, Veillonella parvula\|Pseudomonas putida, Victivallis vadensis\|Pseudoramibacter alactolyticus, Pseudoramibacter alactolyticus\|Pseudoramibacter alactolyticus, Pyramidobacter piscolens\|Pseudoramibacter alactolyticus, Rhodopseudomonas palustris\|Pseudoramibacter alactolyticus, Roseburia intestinalis\|Pseudoramibacter alactolyticus, Roseburia inulinivorans\|Pseudoramibacter alactolyticus, Rothia dentocariosa\|Pseudoramibacter alactolyticus, Rothia mucilaginosa\|Pseudoramibacter alactolyticus, Ruminococcus albus\|Pseudoramibacter alactolyticus, Ruminococcus bromii\|Pseudoramibacter alactolyticus, Ruminococcus gnavus\|Pseudoramibacter alactolyticus, Ruminococcus lactaris\|Pseudoramibacter alactolyticus, Ruminococcus obeum\|Pseudoramibacter alactolyticus, Ruminococcus torques\|Pseudoramibacter alactolyticus, Selenomonas sputigena\|Pseudoramibacter alactolyticus, Shigella boydii\|Pseudoramibacter alactolyticus, Shigella dysenteriae\|Pseudoramibacter alactolyticus, Shigella sonnei\|Pseudoramibacter alactolyticus, Slackia exigua\|Pseudoramibacter alactolyticus, Solobacterium moorei\|Pseudoramibacter alactolyticus, Staphylococcus aureus\|Pseudoramibacter alactolyticus, Staphylococcus epidermidis\|Pseudoramibacter alactolyticus, Staphylococcus hominis\|Pseudoramibacter alactolyticus, Staphylococcus saprophyticus\|Pseudoramibacter alactolyticus, Staphylococcus warneri\|Pseudoramibacter alactolyticus, Streptococcus agalactiae\|Pseudoramibacter alactolyticus, Streptococcus anginosus\|Pseudoramibacter alactolyticus, Streptococcus australis\|Pseudoramibacter alactolyticus, Streptococcus bovis\|Pseudoramibacter alactolyticus, Streptococcus cristatus\|Pseudoramibacter alactolyticus, Streptococcus dysgalactiae\|Pseudoramibacter alactolyticus, Streptococcus equinus\|Pseudoramibacter alactolyticus, Streptococcus gordonii\|Pseudoramibacter alactolyticus, Streptococcus infantarius\|Pseudoramibacter alactolyticus, Streptococcus infantis\|Pseudoramibacter alactolyticus, Streptococcus mitis\|Pseudoramibacter alactolyticus, Streptococcus mutans\|Pseudoramibacter alactolyticus, Streptococcus oralis\|Pseudoramibacter alactolyticus, Streptococcus parasanguinis\|Pseudoramibacter alactolyticus, Streptococcus peroris\|Pseudoramibacter alactolyticus, Streptococcus pneumoniae\|Pseudoramibacter alactolyticus, Streptococcus salivarius\|Pseudoramibacter alactolyticus, Streptococcus sanguinis\|Pseudoramibacter alactolyticus, Streptococcus thermophilus\|Pseudoramibacter alactolyticus, Streptococcus vestibularis\|Pseudoramibacter alactolyticus, Subdoligranulum variabile\|Pseudoramibacter alactolyticus, Succinatimonas hippei\|Pseudoramibacter alactolyticus, Sutterella wadsworthensis\|Pseudoramibacter alactolyticus, Tropheryma whipplei\|Pseudoramibacter alactolyticus, Veillonella atypica\|Pseudoramibacter alactolyticus, Veillonella dispar\|Pseudoramibacter alactolyticus, Veillonella parvula\|Pseudoramibacter alactolyticus, Victivallis vadensis\|Pyramidobacter piscolens, Pyramidobacter piscolens\|Pyramidobacter piscolens, Rhodopseudomonas palustris\|Pyramidobacter piscolens, Roseburia intestinalis\|Pyramidobacter piscolens, Roseburia inulinivorans\|Pyramidobacter piscolens, Rothia dentocariosa\|Pyramidobacter piscolens, Rothia mucilaginosa\|Pyramidobacter piscolens, Ruminococcus albus\|Pyramidobacter piscolens, Ruminococcus bromii\|Pyramidobacter piscolens, Ruminococcus gnavus\|Pyramidobacter piscolens, Ruminococcus lactaris\|Pyramidobacter piscolens, Ruminococcus obeum\|Pyramidobacter piscolens, Ruminococcus torques\|Pyramidobacter piscolens, Selenomonas sputigena\|Pyramidobacter piscolens, Shigella boydii\|Pyramidobacter piscolens, Shigella dysenteriae\|Pyramidobacter piscolens, Shigella sonnei\|Pyramidobacter piscolens, Slackia exigua\|Pyramidobacter piscolens, Solobacterium moorei\|Pyramidobacter piscolens, Staphylococcus aureus\|Pyramidobacter piscolens, Staphylococcus epidermidis\|Pyramidobacter piscolens, Staphylococcus hominis\|Pyramidobacter piscolens, Staphylococcus saprophyticus\|Pyramidobacter piscolens, Staphylococcus warneri\|Pyramidobacter piscolens, Streptococcus agalactiae\|Pyramidobacter piscolens, Streptococcus anginosus\|Pyramidobacter piscolens, Streptococcus australis\|Pyramidobacter piscolens, Streptococcus bovis\|Pyramidobacter piscolens, Streptococcus cristatus\|Pyramidobacter piscolens, Streptococcus dysgalactiae\|Pyramidobacter piscolens, Streptococcus equinus\|Pyramidobacter piscolens, Streptococcus gordonii\|Pyramidobacter piscolens, Streptococcus infantarius\|Pyramidobacter piscolens, Streptococcus infantis\|Pyramidobacter piscolens, Streptococcus mitis\|Pyramidobacter piscolens, Streptococcus mutans\|Pyramidobacter piscolens, Streptococcus oralis\|Pyramidobacter piscolens, Streptococcus parasanguinis\|Pyramidobacter piscolens, Streptococcus peroris\|Pyramidobacter piscolens, Streptococcus pneumoniae\|Pyramidobacter piscolens, Streptococcus salivarius\|Pyramidobacter piscolens, Streptococcus sanguinis\|Pyramidobacter piscolens, Streptococcus thermophilus\|Pyramidobacter piscolens, Streptococcus vestibularis\|Pyramidobacter piscolens, Subdoligranulum variabile\|Pyramidobacter piscolens, Succinatimonas hippei\|Pyramidobacter piscolens, Sutterella wadsworthensis\|Pyramidobacter piscolens, Tropheryma whipplei\|Pyramidobacter piscolens, Veillonella atypica\|Pyramidobacter piscolens, Veillonella dispar\|Pyramidobacter piscolens, Veillonella parvula\|Pyramidobacter piscolens, Victivallis vadensis\|Rhodopseudomonas palustris, Rhodopseudomonas palustris\|Rhodopseudomonas palustris, Roseburia intestinalis\|Rhodopseudomonas palustris, Roseburia inulinivorans\|Rhodopseudomonas palustris, Rothia dentocariosa\|Rhodopseudomonas palustris, Rothia mucilaginosa\|Rhodopseudomonas palustris, Ruminococcus albus\|Rhodopseudomonas palustris, Ruminococcus bromii\|Rhodopseudomonas palustris, Ruminococcus gnavus\|Rhodopseudomonas palustris, Ruminococcus lactaris\|Rhodopseudomonas palustris, Ruminococcus obeum\|Rhodopseudomonas palustris, Ruminococcus torques\|Rhodopseudomonas palustris, Selenomonas sputigena\|Rhodopseudomonas palustris, Shigella boydii\|Rhodopseudomonas palustris, Shigella dysenteriae\|Rhodopseudomonas palustris, Shigella sonnei\|Rhodopseudomonas palustris, Slackia exigua\|Rhodopseudomonas palustris, Solobacterium moorei\|Rhodopseudomonas* |

TABLE 2-continued

Table 2. Specific binary combinations of OTUs. Individual pairings are differentiated by "|" and OTUs within a combination are differentiated by ","

*palustris, Staphylococcus aureus|Rhodopseudomonas palustris, Staphylococcus epidermidis|Rhodopseudomonas palustris, Staphylococcus hominis|Rhodopseudomonas palustris, Staphylococcus saprophyticus|Rhodopseudomonas palustris, Staphylococcus warneri|Rhodopseudomonas palustris, Streptococcus agalactiae|Rhodopseudomonas palustris, Streptococcus anginosus|Rhodopseudomonas palustris, Streptococcus australis|Rhodopseudomonas palustris, Streptococcus bovis|Rhodopseudomonas palustris, Streptococcus cristatus|Rhodopseudomonas palustris, Streptococcus dysgalactiae|Rhodopseudomonas palustris, Streptococcus equinus|Rhodopseudomonas palustris, Streptococcus gordonii|Rhodopseudomonas palustris, Streptococcus infantarius|Rhodopseudomonas palustris, Streptococcus infantis|Rhodopseudomonas palustris, Streptococcus mitis|Rhodopseudomonas palustris, Streptococcus mutans|Rhodopseudomonas palustris, Streptococcus oralis|Rhodopseudomonas palustris, Streptococcus parasanguinis|Rhodopseudomonas palustris, Streptococcus peroris|Rhodopseudomonas palustris, Streptococcus pneumoniae|Rhodopseudomonas palustris, Streptococcus salivarius|Rhodopseudomonas palustris, Streptococcus sanguinis|Rhodopseudomonas palustris, Streptococcus thermophilus|Rhodopseudomonas palustris, Streptococcus vestibularis|Rhodopseudomonas palustris, Subdoligranulum variabile|Rhodopseudomonas palustris, Succinatimonas hippei|Rhodopseudomonas palustris, Sutterella wadsworthensis|Rhodopseudomonas palustris, Tropheryma whipplei|Rhodopseudomonas palustris, Veillonella atypica|Rhodopseudomonas palustris, Veillonella dispar|Rhodopseudomonas palustris, Veillonella parvula|Rhodopseudomonas palustris, Victivallis vadensis|Roseburia intestinalis, Roseburia intestinalis|Roseburia intestinalis, Roseburia inulinivorans|Roseburia intestinalis, Rothia dentocariosa|Roseburia intestinalis, Rothia mucilaginosa|Roseburia intestinalis, Ruminococcus albus|Roseburia intestinalis, Ruminococcus bromii|Roseburia intestinalis, Ruminococcus gnavus|Roseburia intestinalis, Ruminococcus lactaris|Roseburia intestinalis, Ruminococcus obeum|Roseburia intestinalis, Ruminococcus torques|Roseburia intestinalis, Selenomonas sputigena|Roseburia intestinalis, Shigella boydii|Roseburia intestinalis, Shigella dysenteriae|Roseburia intestinalis, Shigella sonnei|Roseburia intestinalis, Slackia exigua|Roseburia intestinalis, Solobacterium moorei|Roseburia intestinalis, Staphylococcus aureus|Roseburia intestinalis, Staphylococcus epidermidis|Roseburia intestinalis, Staphylococcus hominis|Roseburia intestinalis, Staphylococcus saprophyticus|Roseburia intestinalis, Staphylococcus warneri|Roseburia intestinalis, Streptococcus agalactiae|Roseburia intestinalis, Streptococcus anginosus|Roseburia intestinalis, Streptococcus australis|Roseburia intestinalis, Streptococcus bovis|Roseburia intestinalis, Streptococcus cristatus|Roseburia intestinalis, Streptococcus dysgalactiae|Roseburia intestinalis, Streptococcus equinus|Roseburia intestinalis, Streptococcus gordonii|Roseburia intestinalis, Streptococcus infantarius|Roseburia intestinalis, Streptococcus infantis|Roseburia intestinalis, Streptococcus mitis|Roseburia intestinalis, Streptococcus mutans|Roseburia intestinalis, Streptococcus oralis|Roseburia intestinalis, Streptococcus parasanguinis|Roseburia intestinalis, Streptococcus peroris|Roseburia intestinalis, Streptococcus pneumoniae|Roseburia intestinalis, Streptococcus salivarius|Roseburia intestinalis, Streptococcus sanguinis|Roseburia intestinalis, Streptococcus thermophilus|Roseburia intestinalis, Streptococcus vestibularis|Roseburia intestinalis, Subdoligranulum variabile|Roseburia intestinalis, Succinatimonas hippei|Roseburia intestinalis, Sutterella wadsworthensis|Roseburia intestinalis, Tropheryma whipplei|Roseburia intestinalis, Veillonella atypica|Roseburia intestinalis, Veillonella dispar|Roseburia intestinalis, Veillonella parvula|Roseburia intestinalis, Victivallis vadensis|Roseburia inulinivorans, Roseburia inulinivorans|Roseburia inulinivorans, Rothia dentocariosa|Roseburia inulinivorans, Rothia mucilaginosa|Roseburia inulinivorans, Ruminococcus albus|Roseburia inulinivorans, Ruminococcus bromii|Roseburia inulinivorans, Ruminococcus gnavus|Roseburia inulinivorans, Ruminococcus lactaris|Roseburia inulinivorans, Ruminococcus obeum|Roseburia inulinivorans, Ruminococcus torques|Roseburia inulinivorans, Selenomonas sputigena|Roseburia inulinivorans, Shigella boydii|Roseburia inulinivorans, Shigella dysenteriae|Roseburia inulinivorans, Shigella sonnei|Roseburia inulinivorans, Slackia exigua|Roseburia inulinivorans, Solobacterium moorei|Roseburia inulinivorans, Staphylococcus aureus|Roseburia inulinivorans, Staphylococcus epidermidis|Roseburia inulinivorans, Staphylococcus hominis|Roseburia inulinivorans, Staphylococcus saprophyticus|Roseburia inulinivorans, Staphylococcus warneri|Roseburia inulinivorans, Streptococcus agalactiae|Roseburia inulinivorans, Streptococcus anginosus|Roseburia inulinivorans, Streptococcus australis|Roseburia inulinivorans, Streptococcus bovis|Roseburia inulinivorans, Streptococcus cristatus|Roseburia inulinivorans, Streptococcus dysgalactiae|Roseburia inulinivorans, Streptococcus equinus|Roseburia inulinivorans, Streptococcus gordonii|Roseburia inulinivorans, Streptococcus infantarius|Roseburia inulinivorans, Streptococcus infantis|Roseburia inulinivorans, Streptococcus mitis|Roseburia inulinivorans, Streptococcus mutans|Roseburia inulinivorans, Streptococcus oralis|Roseburia inulinivorans, Streptococcus parasanguinis|Roseburia inulinivorans, Streptococcus peroris|Roseburia inulinivorans, Streptococcus pneumoniae|Roseburia inulinivorans, Streptococcus salivarius|Roseburia inulinivorans, Streptococcus sanguinis|Roseburia inulinivorans, Streptococcus thermophilus|Roseburia inulinivorans, Streptococcus vestibularis|Roseburia inulinivorans, Subdoligranulum variabile|Roseburia inulinivorans, Succinatimonas hippei|Roseburia inulinivorans, Sutterella wadsworthensis|Roseburia inulinivorans, Tropheryma whipplei|Roseburia inulinivorans, Veillonella atypica|Roseburia inulinivorans, Veillonella dispar|Roseburia inulinivorans, Veillonella parvula|Roseburia inulinivorans, Victivallis vadensis|Rothia dentocariosa, Rothia dentocariosa|Rothia dentocariosa, Rothia mucilaginosa|Rothia dentocariosa, Ruminococcus albus|Rothia dentocariosa, Ruminococcus bromii|Rothia dentocariosa, Ruminococcus gnavus|Rothia dentocariosa, Ruminococcus lactaris|Rothia dentocariosa, Ruminococcus obeum|Rothia dentocariosa, Ruminococcus torques|Rothia dentocariosa, Selenomonas sputigena|Rothia dentocariosa, Shigella boydii|Rothia dentocariosa, Shigella dysenteriae|Rothia dentocariosa, Shigella sonnei|Rothia dentocariosa, Slackia exigua|Rothia dentocariosa, Solobacterium moorei|Rothia dentocariosa, Staphylococcus aureus|Rothia dentocariosa, Staphylococcus epidermidis|Rothia dentocariosa, Staphylococcus hominis|Rothia dentocariosa, Staphylococcus saprophyticus|Rothia dentocariosa, Staphylococcus warneri|Rothia dentocariosa, Streptococcus agalactiae|Rothia dentocariosa, Streptococcus anginosus|Rothia dentocariosa, Streptococcus australis|Rothia dentocariosa, Streptococcus bovis|Rothia dentocariosa, Streptococcus cristatus|Rothia dentocariosa, Streptococcus dysgalactiae|Rothia dentocariosa, Streptococcus equinus|Rothia dentocariosa, Streptococcus gordonii|Rothia dentocariosa, Streptococcus infantarius|Rothia dentocariosa, Streptococcus infantis|Rothia dentocariosa, Streptococcus mitis|Rothia dentocariosa, Streptococcus mutans|Rothia dentocariosa, Streptococcus oralis|Rothia dentocariosa, Streptococcus parasanguinis|Rothia dentocariosa, Streptococcus peroris|Rothia dentocariosa, Streptococcus pneumoniae|Rothia dentocariosa, Streptococcus salivarius|Rothia dentocariosa, Streptococcus sanguinis|Rothia dentocariosa, Streptococcus thermophilus|Rothia dentocariosa, Streptococcus vestibularis|Rothia dentocariosa, Subdoligranulum variabile|Rothia dentocariosa, Succinatimonas hippei|Rothia dentocariosa, Sutterella wadsworthensis|Rothia dentocariosa, Tropheryma whipplei|Rothia dentocariosa, Veillonella atypica|Rothia dentocariosa, Veillonella dispar|Rothia dentocariosa, Veillonella parvula|Rothia dentocariosa, Victivallis vadensis|Rothia mucilaginosa, Rothia mucilaginosa|Rothia mucilaginosa, Ruminococcus albus|Rothia mucilaginosa, Ruminococcus bromii|Rothia mucilaginosa, Ruminococcus gnavus|Rothia mucilaginosa, Ruminococcus lactaris|Rothia mucilaginosa, Ruminococcus obeum|Rothia mucilaginosa, Ruminococcus torques|Rothia mucilaginosa, Selenomonas sputigena|Rothia mucilaginosa, Shigella boydii|Rothia mucilaginosa, Shigella dysenteriae|Rothia mucilaginosa, Shigella sonnei|Rothia mucilaginosa, Slackia exigua|Rothia mucilaginosa, Solobacterium moorei|Rothia mucilaginosa, Staphylococcus aureus|Rothia mucilaginosa, Staphylococcus epidermidis|Rothia mucilaginosa, Staphylococcus hominis|Rothia mucilaginosa, Staphylococcus saprophyticus|Rothia mucilaginosa, Staphylococcus warneri|Rothia mucilaginosa, Streptococcus agalactiae|Rothia mucilaginosa, Streptococcus anginosus|Rothia mucilaginosa, Streptococcus australis|Rothia mucilaginosa, Streptococcus bovis|Rothia mucilaginosa, Streptococcus cristatus|Rothia mucilaginosa, Streptococcus dysgalactiae|Rothia mucilaginosa, Streptococcus equinus|Rothia mucilaginosa, Streptococcus gordonii|Rothia mucilaginosa, Streptococcus infantarius|Rothia mucilaginosa, Streptococcus infantis|Rothia mucilaginosa, Streptococcus mitis|Rothia mucilaginosa, Streptococcus mutans|Rothia mucilaginosa, Streptococcus oralis|Rothia mucilaginosa, Streptococcus parasanguinis|Rothia mucilaginosa, Streptococcus peroris|Rothia mucilaginosa, Streptococcus pneumoniae|Rothia mucilaginosa, Streptococcus salivarius|Rothia mucilaginosa, Streptococcus sanguinis|Rothia mucilaginosa, Streptococcus thermophilus|Rothia mucilaginosa, Streptococcus vestibularis|Rothia*

TABLE 2-continued

Table 2. Specific binary combinations of OTUs. Individual pairings are differentiated by "|" and OTUs within a combination are differentiated by ","

*mucilaginosa, Subdoligranulum variabile|Rothia mucilaginosa, Succinatimonas hippei|Rothia mucilaginosa, Sutterella wadsworthensis|Rothia mucilaginosa, Tropheryma whipplei|Rothia mucilaginosa, Veillonella atypica|Rothia mucilaginosa, Veillonella dispar|Rothia mucilaginosa, Veillonella parvula|Rothia mucilaginosa, Victivallis vadensis|Ruminococcus albus, Ruminococcus albus|Ruminococcus albus, Ruminococcus bromii|Ruminococcus albus, Ruminococcus gnavus|Ruminococcus albus, Ruminococcus lactaris|Ruminococcus albus, Ruminococcus obeum|Ruminococcus albus, Ruminococcus torques|Ruminococcus albus, Selenomonas sputigena|Ruminococcus albus, Shigella boydii|Ruminococcus albus, Shigella dysenteriae|Ruminococcus albus, Shigella sonnei|Ruminococcus albus, Slackia exigua|Ruminococcus albus, Solobacterium moorei|Ruminococcus albus, Staphylococcus aureus|Ruminococcus albus, Staphylococcus epidermidis|Ruminococcus albus, Staphylococcus hominis|Ruminococcus albus, Staphylococcus saprophyticus|Ruminococcus albus, Staphylococcus warneri|Ruminococcus albus, Streptococcus agalactiae|Ruminococcus albus, Streptococcus anginosus|Ruminococcus albus, Streptococcus australis|Ruminococcus albus, Streptococcus bovis|Ruminococcus albus, Streptococcus cristatus|Ruminococcus albus, Streptococcus dysgalactiae|Ruminococcus albus, Streptococcus equinus|Ruminococcus albus, Streptococcus gordonii|Ruminococcus albus, Streptococcus infantarius|Ruminococcus albus, Streptococcus infantis|Ruminococcus albus, Streptococcus mitis|Ruminococcus albus, Streptococcus mutans|Ruminococcus albus, Streptococcus oralis|Ruminococcus albus, Streptococcus parasanguinis|Ruminococcus albus, Streptococcus peroris|Ruminococcus albus, Streptococcus pneumoniae|Ruminococcus albus, Streptococcus salivarius|Ruminococcus albus, Streptococcus sanguinis|Ruminococcus albus, Streptococcus thermophilus|Ruminococcus albus, Streptococcus vestibularis|Ruminococcus albus, Subdoligranulum variabile|Ruminococcus albus, Succinatimonas hippei|Ruminococcus albus, Sutterella wadsworthensis|Ruminococcus albus, Tropheryma whipplei|Ruminococcus albus, Veillonella atypica|Ruminococcus albus, Veillonella dispar|Ruminococcus albus, Veillonella parvula|Ruminococcus albus, Victivallis vadensis|Ruminococcus bromii, Ruminococcus bromii|Ruminococcus bromii, Ruminococcus gnavus|Ruminococcus bromii, Ruminococcus lactaris|Ruminococcus bromii, Ruminococcus obeum|Ruminococcus bromii, Ruminococcus torques|Ruminococcus bromii, Selenomonas sputigena|Ruminococcus bromii, Shigella boydii|Ruminococcus bromii, Shigella dysenteriae|Ruminococcus bromii, Shigella sonnei|Ruminococcus bromii, Slackia exigua|Ruminococcus bromii, Solobacterium moorei|Ruminococcus bromii, Staphylococcus aureus|Ruminococcus bromii, Staphylococcus epidermidis|Ruminococcus bromii, Staphylococcus hominis|Ruminococcus bromii, Staphylococcus saprophyticus|Ruminococcus bromii, Staphylococcus warneri|Ruminococcus bromii, Streptococcus agalactiae|Ruminococcus bromii, Streptococcus anginosus|Ruminococcus bromii, Streptococcus australis|Ruminococcus bromii, Streptococcus bovis|Ruminococcus bromii, Streptococcus cristatus|Ruminococcus bromii, Streptococcus dysgalactiae|Ruminococcus bromii, Streptococcus equinus|Ruminococcus bromii, Streptococcus gordonii|Ruminococcus bromii, Streptococcus infantarius|Ruminococcus bromii, Streptococcus infantis|Ruminococcus bromii, Streptococcus mitis|Ruminococcus bromii, Streptococcus mutans|Ruminococcus bromii, Streptococcus oralis|Ruminococcus bromii, Streptococcus parasanguinis|Ruminococcus bromii, Streptococcus peroris|Ruminococcus bromii, Streptococcus pneumoniae|Ruminococcus bromii, Streptococcus salivarius|Ruminococcus bromii, Streptococcus sanguinis|Ruminococcus bromii, Streptococcus thermophilus|Ruminococcus bromii, Streptococcus vestibularis|Ruminococcus bromii, Subdoligranulum variabile|Ruminococcus bromii, Succinatimonas hippei|Ruminococcus bromii, Sutterella wadsworthensis|Ruminococcus bromii, Tropheryma whipplei|Ruminococcus bromii, Veillonella atypica|Ruminococcus bromii, Veillonella dispar|Ruminococcus bromii, Veillonella parvula|Ruminococcus bromii, Victivallis vadensis|Ruminococcus gnavus, Ruminococcus gnavus|Ruminococcus gnavus, Ruminococcus lactaris|Ruminococcus gnavus, Ruminococcus obeum|Ruminococcus gnavus, Ruminococcus torques|Ruminococcus gnavus, Selenomonas sputigena|Ruminococcus gnavus, Shigella boydii|Ruminococcus gnavus, Shigella dysenteriae|Ruminococcus gnavus, Shigella sonnei|Ruminococcus gnavus, Slackia exigua|Ruminococcus gnavus, Solobacterium moorei|Ruminococcus gnavus, Staphylococcus aureus|Ruminococcus gnavus, Staphylococcus epidermidis|Ruminococcus gnavus, Staphylococcus hominis|Ruminococcus gnavus, Staphylococcus saprophyticus|Ruminococcus gnavus, Staphylococcus warneri|Ruminococcus gnavus, Streptococcus agalactiae|Ruminococcus gnavus, Streptococcus anginosus|Ruminococcus gnavus, Streptococcus australis|Ruminococcus gnavus, Streptococcus bovis|Ruminococcus gnavus, Streptococcus cristatus|Ruminococcus gnavus, Streptococcus dysgalactiae|Ruminococcus gnavus, Streptococcus equinus|Ruminococcus gnavus, Streptococcus gordonii|Ruminococcus gnavus, Streptococcus infantarius|Ruminococcus gnavus, Streptococcus infantis|Ruminococcus gnavus, Streptococcus mitis|Ruminococcus gnavus, Streptococcus mutans|Ruminococcus gnavus, Streptococcus oralis|Ruminococcus gnavus, Streptococcus parasanguinis|Ruminococcus gnavus, Streptococcus peroris|Ruminococcus gnavus, Streptococcus pneumoniae|Ruminococcus gnavus, Streptococcus salivarius|Ruminococcus gnavus, Streptococcus sanguinis|Ruminococcus gnavus, Streptococcus thermophilus|Ruminococcus gnavus, Streptococcus vestibularis|Ruminococcus gnavus, Subdoligranulum variabile|Ruminococcus gnavus, Succinatimonas hippei|Ruminococcus gnavus, Sutterella wadsworthensis|Ruminococcus gnavus, Tropheryma whipplei|Ruminococcus gnavus, Veillonella atypica|Ruminococcus gnavus, Veillonella dispar|Ruminococcus gnavus, Veillonella parvula|Ruminococcus gnavus, Victivallis vadensis|Ruminococcus lactaris, Ruminococcus lactaris|Ruminococcus lactaris, Ruminococcus obeum|Ruminococcus lactaris, Ruminococcus torques|Ruminococcus lactaris, Selenomonas sputigena|Ruminococcus lactaris, Shigella boydii|Ruminococcus lactaris, Shigella dysenteriae|Ruminococcus lactaris, Shigella sonnei|Ruminococcus lactaris, Slackia exigua|Ruminococcus lactaris, Solobacterium moorei|Ruminococcus lactaris, Staphylococcus aureus|Ruminococcus lactaris, Staphylococcus epidermidis|Ruminococcus lactaris, Staphylococcus hominis|Ruminococcus lactaris, Staphylococcus saprophyticus|Ruminococcus lactaris, Staphylococcus warneri|Ruminococcus lactaris, Streptococcus agalactiae|Ruminococcus lactaris, Streptococcus anginosus|Ruminococcus lactaris, Streptococcus australis|Ruminococcus lactaris, Streptococcus bovis|Ruminococcus lactaris, Streptococcus cristatus|Ruminococcus lactaris, Streptococcus dysgalactiae|Ruminococcus lactaris, Streptococcus equinus|Ruminococcus lactaris, Streptococcus gordonii|Ruminococcus lactaris, Streptococcus infantarius|Ruminococcus lactaris, Streptococcus infantis|Ruminococcus lactaris, Streptococcus mitis|Ruminococcus lactaris, Streptococcus mutans|Ruminococcus lactaris, Streptococcus oralis|Ruminococcus lactaris, Streptococcus parasanguinis|Ruminococcus lactaris, Streptococcus peroris|Ruminococcus lactaris, Streptococcus pneumoniae|Ruminococcus lactaris, Streptococcus salivarius|Ruminococcus lactaris, Streptococcus sanguinis|Ruminococcus lactaris, Streptococcus thermophilus|Ruminococcus lactaris, Streptococcus vestibularis|Ruminococcus lactaris, Subdoligranulum variabile|Ruminococcus lactaris, Succinatimonas hippei|Ruminococcus lactaris, Sutterella wadsworthensis|Ruminococcus lactaris, Tropheryma whipplei|Ruminococcus lactaris, Veillonella atypica|Ruminococcus lactaris, Veillonella dispar|Ruminococcus lactaris, Veillonella parvula|Ruminococcus lactaris, Victivallis vadensis|Ruminococcus obeum, Ruminococcus obeum|Ruminococcus obeum, Ruminococcus torques|Ruminococcus obeum, Selenomonas sputigena|Ruminococcus obeum, Shigella boydii|Ruminococcus obeum, Shigella dysenteriae|Ruminococcus obeum, Shigella sonnei|Ruminococcus obeum, Slackia exigua|Ruminococcus obeum, Solobacterium moorei|Ruminococcus obeum, Staphylococcus aureus|Ruminococcus obeum, Staphylococcus epidermidis|Ruminococcus obeum, Staphylococcus hominis|Ruminococcus obeum, Staphylococcus saprophyticus|Ruminococcus obeum, Staphylococcus warneri|Ruminococcus obeum, Streptococcus agalactiae|Ruminococcus obeum, Streptococcus anginosus|Ruminococcus obeum, Streptococcus australis|Ruminococcus obeum, Streptococcus bovis|Ruminococcus obeum, Streptococcus cristatus|Ruminococcus obeum, Streptococcus dysgalactiae|Ruminococcus obeum, Streptococcus equinus|Ruminococcus obeum, Streptococcus gordonii|Ruminococcus obeum, Streptococcus infantarius|Ruminococcus obeum, Streptococcus infantis|Ruminococcus obeum, Streptococcus mitis|Ruminococcus obeum, Streptococcus mutans|Ruminococcus obeum, Streptococcus oralis|Ruminococcus obeum, Streptococcus parasanguinis|Ruminococcus obeum, Streptococcus peroris|Ruminococcus obeum, Streptococcus pneumoniae|Ruminococcus obeum, Streptococcus salivarius|Ruminococcus obeum, Streptococcus sanguinis|Ruminococcus obeum, Streptococcus thermophilus|Ruminococcus obeum, Streptococcus vestibularis|Ruminococcus obeum, Subdoligranulum variabile|Ruminococcus obeum, Succinatimonas hippei|Ruminococcus obeum, Sutterella wadsworthensis|Ruminococcus obeum, Tropheryma whipplei|Ruminococcus obeum, Veillonella atypica|Ruminococcus obeum, Veillonella dispar|Ruminococcus*

TABLE 2-continued

Table 2. Specific binary combinations of OTUs. Individual pairings are differentiated by "|" and OTUs within a combination are differentiated by ","

*obeum, Veillonella parvula|Ruminococcus obeum, Victivallis vadensis|Ruminococcus torques, Ruminococcus torques|Ruminococcus torques, Selenomonas sputigena|Ruminococcus torques, Shigella boydii|Ruminococcus torques, Shigella dysenteriae|Ruminococcus torques, Shigella sonnei|Ruminococcus torques, Slackia exigua|Ruminococcus torques, Solobacterium moorei|Ruminococcus torques, Staphylococcus aureus|Ruminococcus torques, Staphylococcus epidermidis|Ruminococcus torques, Staphylococcus hominis|Ruminococcus torques, Staphylococcus saprophyticus|Ruminococcus torques, Staphylococcus warneri|Ruminococcus torques, Streptococcus agalactiae|Ruminococcus torques, Streptococcus anginosus|Ruminococcus torques, Streptococcus australis|Ruminococcus torques, Streptococcus bovis|Ruminococcus torques, Streptococcus cristatus|Ruminococcus torques, Streptococcus dysgalactiae|Ruminococcus torques, Streptococcus equinus|Ruminococcus torques, Streptococcus gordonii|Ruminococcus torques, Streptococcus infantarius|Ruminococcus torques, Streptococcus infantis|Ruminococcus torques, Streptococcus mitis|Ruminococcus torques, Streptococcus mutans|Ruminococcus torques, Streptococcus oralis|Ruminococcus torques, Streptococcus parasanguinis|Ruminococcus torques, Streptococcus peroris|Ruminococcus torques, Streptococcus pneumoniae|Ruminococcus torques, Streptococcus salivarius|Ruminococcus torques, Streptococcus sanguinis|Ruminococcus torques, Streptococcus thermophilus|Ruminococcus torques, Streptococcus vestibularis|Ruminococcus torques, Subdoligranulum variabile|Ruminococcus torques, Succinatimonas hippei|Ruminococcus torques, Sutterella wadsworthensis|Ruminococcus torques, Tropheryma whipplei|Ruminococcus torques, Veillonella atypica|Ruminococcus torques, Veillonella dispar|Ruminococcus torques, Veillonella parvula|Ruminococcus torques, Victivallis vadensis|Selenomonas sputigena, Selenomonas sputigena|Selenomonas sputigena, Shigella boydii|Selenomonas sputigena, Shigella dysenteriae|Selenomonas sputigena, Shigella sonnei|Selenomonas sputigena, Slackia exigua|Selenomonas sputigena, Solobacterium moorei|Selenomonas sputigena, Staphylococcus aureus|Selenomonas sputigena, Staphylococcus epidermidis|Selenomonas sputigena, Staphylococcus hominis|Selenomonas sputigena, Staphylococcus saprophyticus|Selenomonas sputigena, Staphylococcus warneri|Selenomonas sputigena, Streptococcus agalactiae|Selenomonas sputigena, Streptococcus anginosus|Selenomonas sputigena, Streptococcus australis|Selenomonas sputigena, Streptococcus bovis|Selenomonas sputigena, Streptococcus cristatus|Selenomonas sputigena, Streptococcus dysgalactiae|Selenomonas sputigena, Streptococcus equinus|Selenomonas sputigena, Streptococcus gordonii|Selenomonas sputigena, Streptococcus infantarius|Selenomonas sputigena, Streptococcus infantis|Selenomonas sputigena, Streptococcus mitis|Selenomonas sputigena, Streptococcus mutans|Selenomonas sputigena, Streptococcus oralis|Selenomonas sputigena, Streptococcus parasanguinis|Selenomonas sputigena, Streptococcus peroris|Selenomonas sputigena, Streptococcus pneumoniae|Selenomonas sputigena, Streptococcus salivarius|Selenomonas sputigena, Streptococcus sanguinis|Selenomonas sputigena, Streptococcus thermophilus|Selenomonas sputigena, Streptococcus vestibularis|Selenomonas sputigena, Subdoligranulum variabile|Selenomonas sputigena, Succinatimonas hippei|Selenomonas sputigena, Sutterella wadsworthensis|Selenomonas sputigena, Tropheryma whipplei|Selenomonas sputigena, Veillonella atypica|Selenomonas sputigena, Veillonella dispar|Selenomonas sputigena, Veillonella parvula|Selenomonas sputigena, Victivallis vadensis|Shigella boydii, Shigella boydii|Shigella boydii, Shigella dysenteriae|Shigella boydii, Shigella sonnei|Shigella boydii, Slackia exigua|Shigella boydii, Solobacterium moorei|Shigella boydii, Staphylococcus aureus|Shigella boydii, Staphylococcus epidermidis|Shigella boydii, Staphylococcus hominis|Shigella boydii, Staphylococcus saprophyticus|Shigella boydii, Staphylococcus warneri|Shigella boydii, Streptococcus agalactiae|Shigella boydii, Streptococcus anginosus|Shigella boydii, Streptococcus australis|Shigella boydii, Streptococcus bovis|Shigella boydii, Streptococcus cristatus|Shigella boydii, Streptococcus dysgalactiae|Shigella boydii, Streptococcus equinus|Shigella boydii, Streptococcus gordonii|Shigella boydii, Streptococcus infantarius|Shigella boydii, Streptococcus infantis|Shigella boydii, Streptococcus mitis|Shigella boydii, Streptococcus mutans|Shigella boydii, Streptococcus oralis|Shigella boydii, Streptococcus parasanguinis|Shigella boydii, Streptococcus peroris|Shigella boydii, Streptococcus pneumoniae|Shigella boydii, Streptococcus salivarius|Shigella boydii, Streptococcus sanguinis|Shigella boydii, Streptococcus thermophilus|Shigella boydii, Streptococcus vestibularis|Shigella boydii, Subdoligranulum variabile|Shigella boydii, Succinatimonas hippei|Shigella boydii, Sutterella wadsworthensis|Shigella boydii, Tropheryma whipplei|Shigella boydii, Veillonella atypica|Shigella boydii, Veillonella dispar|Shigella boydii, Veillonella parvula|Shigella boydii, Victivallis vadensis|Shigella dysenteriae, Shigella dysenteriae|Shigella dysenteriae, Shigella sonnei|Shigella dysenteriae, Slackia exigua|Shigella dysenteriae, Solobacterium moorei|Shigella dysenteriae, Staphylococcus aureus|Shigella dysenteriae, Staphylococcus epidermidis|Shigella dysenteriae, Staphylococcus hominis|Shigella dysenteriae, Staphylococcus saprophyticus|Shigella dysenteriae, Staphylococcus warneri|Shigella dysenteriae, Streptococcus agalactiae|Shigella dysenteriae, Streptococcus anginosus|Shigella dysenteriae, Streptococcus australis|Shigella dysenteriae, Streptococcus bovis|Shigella dysenteriae, Streptococcus cristatus|Shigella dysenteriae, Streptococcus dysgalactiae|Shigella dysenteriae, Streptococcus equinus|Shigella dysenteriae, Streptococcus gordonii|Shigella dysenteriae, Streptococcus infantarius|Shigella dysenteriae, Streptococcus infantis|Shigella dysenteriae, Streptococcus mitis|Shigella dysenteriae, Streptococcus mutans|Shigella dysenteriae, Streptococcus oralis|Shigella dysenteriae, Streptococcus parasanguinis|Shigella dysenteriae, Streptococcus peroris|Shigella dysenteriae, Streptococcus pneumoniae|Shigella dysenteriae, Streptococcus salivarius|Shigella dysenteriae, Streptococcus sanguinis|Shigella dysenteriae, Streptococcus thermophilus|Shigella dysenteriae, Streptococcus vestibularis|Shigella dysenteriae, Subdoligranulum variabile|Shigella dysenteriae, Succinatimonas hippei|Shigella dysenteriae, Sutterella wadsworthensis|Shigella dysenteriae, Tropheryma whipplei|Shigella dysenteriae, Veillonella atypica|Shigella dysenteriae, Veillonella dispar|Shigella dysenteriae, Veillonella parvula|Shigella dysenteriae, Victivallis vadensis|Shigella sonnei, Shigella sonnei|Shigella sonnei, Slackia exigua|Shigella sonnei, Solobacterium moorei|Shigella sonnei, Staphylococcus aureus|Shigella sonnei, Staphylococcus epidermidis|Shigella sonnei, Staphylococcus hominis|Shigella sonnei, Staphylococcus saprophyticus|Shigella sonnei, Staphylococcus warneri|Shigella sonnei, Streptococcus agalactiae|Shigella sonnei, Streptococcus anginosus|Shigella sonnei, Streptococcus australis|Shigella sonnei, Streptococcus bovis|Shigella sonnei, Streptococcus cristatus|Shigella sonnei, Streptococcus dysgalactiae|Shigella sonnei, Streptococcus equinus|Shigella sonnei, Streptococcus gordonii|Shigella sonnei, Streptococcus infantarius|Shigella sonnei, Streptococcus infantis|Shigella sonnei, Streptococcus mitis|Shigella sonnei, Streptococcus mutans|Shigella sonnei, Streptococcus oralis|Shigella sonnei, Streptococcus parasanguinis|Shigella sonnei, Streptococcus peroris|Shigella sonnei, Streptococcus pneumoniae|Shigella sonnei, Streptococcus salivarius|Shigella sonnei, Streptococcus sanguinis|Shigella sonnei, Streptococcus thermophilus|Shigella sonnei, Streptococcus vestibularis|Shigella sonnei, Subdoligranulum variabile|Shigella sonnei, Succinatimonas hippei|Shigella sonnei, Sutterella wadsworthensis|Shigella sonnei, Tropheryma whipplei|Shigella sonnei, Veillonella atypica|Shigella sonnei, Veillonella dispar|Shigella sonnei, Veillonella parvula|Shigella sonnei, Victivallis vadensis|Slackia exigua, Slackia exigua|Slackia exigua, Solobacterium moorei|Slackia exigua, Staphylococcus aureus|Slackia exigua, Staphylococcus epidermidis|Slackia exigua, Staphylococcus hominis|Slackia exigua, Staphylococcus saprophyticus|Slackia exigua, Staphylococcus warneri|Slackia exigua, Streptococcus agalactiae|Slackia exigua, Streptococcus anginosus|Slackia exigua, Streptococcus australis|Slackia exigua, Streptococcus bovis|Slackia exigua, Streptococcus cristatus|Slackia exigua, Streptococcus dysgalactiae|Slackia exigua, Streptococcus equinus|Slackia exigua, Streptococcus gordonii|Slackia exigua, Streptococcus infantarius|Slackia exigua, Streptococcus infantis|Slackia exigua, Streptococcus mitis|Slackia exigua, Streptococcus mutans|Slackia exigua, Streptococcus oralis|Slackia exigua, Streptococcus*

TABLE 2-continued

Table 2. Specific binary combinations of OTUs. Individual pairings are differentiated by "|" and OTUs within a combination are differentiated by ","

parasanguinis|Slackia exigua, Streptococcus peroris|Slackia exigua, Streptococcus pneumoniae|Slackia exigua, Streptococcus salivarius|Slackia exigua, Streptococcus sanguinis|Slackia exigua, Streptococcus thermophilus|Slackia exigua, Streptococcus vestibularis|Slackia exigua, Subdoligranulum variabile|Slackia exigua, Succinatimonas hippei|Slackia exigua, Sutterella wadsworthensis|Slackia exigua, Tropheryma whipplei|Slackia exigua, Veillonella atypica|Slackia exigua, Veillonella dispar|Slackia exigua, Veillonella parvula|Slackia exigua, Victivallis vadensis|Solobacterium moorei, Solobacterium moorei|Solobacterium moorei, Staphylococcus aureus|Solobacterium moorei, Staphylococcus epidermidis|Solobacterium moorei, Staphylococcus hominis|Solobacterium moorei, Staphylococcus saprophyticus|Solobacterium moorei, Staphylococcus warneri|Solobacterium moorei, Streptococcus agalactiae|Solobacterium moorei, Streptococcus anginosus|Solobacterium moorei, Streptococcus australis|Solobacterium moorei, Streptococcus bovis|Solobacterium moorei, Streptococcus cristatus|Solobacterium moorei, Streptococcus dysgalactiae|Solobacterium moorei, Streptococcus equinus|Solobacterium moorei, Streptococcus gordonii|Solobacterium moorei, Streptococcus infantarius|Solobacterium moorei, Streptococcus infantis|Solobacterium moorei, Streptococcus mitis|Solobacterium moorei, Streptococcus mutans|Solobacterium moorei, Streptococcus oralis|Solobacterium moorei, Streptococcus parasanguinis|Solobacterium moorei, Streptococcus peroris|Solobacterium moorei, Streptococcus pneumoniae|Solobacterium moorei, Streptococcus salivarius|Solobacterium moorei, Streptococcus sanguinis|Solobacterium moorei, Streptococcus thermophilus|Solobacterium moorei, Streptococcus vestibularis|Solobacterium moorei, Subdoligranulum variabile|Solobacterium moorei, Succinatimonas hippei|Solobacterium moorei, Sutterella wadsworthensis|Solobacterium moorei, Tropheryma whipplei|Solobacterium moorei, Veillonella atypica|Solobacterium moorei, Veillonella dispar|Solobacterium moorei, Veillonella parvula|Solobacterium moorei, Victivallis vadensis|Staphylococcus aureus, Staphylococcus aureus|Staphylococcus aureus, Staphylococcus epidermidis|Staphylococcus aureus, Staphylococcus hominis|Staphylococcus aureus, Staphylococcus saprophyticus|Staphylococcus aureus, Staphylococcus warneri|Staphylococcus aureus, Streptococcus agalactiae|Staphylococcus aureus, Streptococcus anginosus|Staphylococcus aureus, Streptococcus australis|Staphylococcus aureus, Streptococcus bovis|Staphylococcus aureus, Streptococcus cristatus|Staphylococcus aureus, Streptococcus dysgalactiae|Staphylococcus aureus, Streptococcus equinus|Staphylococcus aureus, Streptococcus gordonii|Staphylococcus aureus, Streptococcus infantarius|Staphylococcus aureus, Streptococcus infantis|Staphylococcus aureus, Streptococcus mitis|Staphylococcus aureus, Streptococcus mutans|Staphylococcus aureus, Streptococcus oralis|Staphylococcus aureus, Streptococcus parasanguinis|Staphylococcus aureus, Streptococcus peroris|Staphylococcus aureus, Streptococcus pneumoniae|Staphylococcus aureus, Streptococcus salivarius|Staphylococcus aureus, Streptococcus sanguinis|Staphylococcus aureus, Streptococcus thermophilus|Staphylococcus aureus, Streptococcus vestibularis|Staphylococcus aureus, Subdoligranulum variabile|Staphylococcus aureus, Succinatimonas hippei|Staphylococcus aureus, Sutterella wadsworthensis|Staphylococcus aureus, Tropheryma whipplei|Staphylococcus aureus, Veillonella atypica|Staphylococcus aureus, Veillonella dispar|Staphylococcus aureus, Veillonella parvula|Staphylococcus aureus, Victivallis vadensis|Staphylococcus epidermidis, Staphylococcus epidermidis|Staphylococcus epidermidis, Staphylococcus hominis|Staphylococcus epidermidis, Staphylococcus saprophyticus|Staphylococcus epidermidis, Staphylococcus warneri|Staphylococcus epidermidis, Streptococcus agalactiae|Staphylococcus epidermidis, Streptococcus anginosus|Staphylococcus epidermidis, Streptococcus australis|Staphylococcus epidermidis, Streptococcus bovis|Staphylococcus epidermidis, Streptococcus cristatus|Staphylococcus epidermidis, Streptococcus dysgalactiae|Staphylococcus epidermidis, Streptococcus equinus|Staphylococcus epidermidis, Streptococcus gordonii|Staphylococcus epidermidis, Streptococcus infantarius|Staphylococcus epidermidis, Streptococcus infantis|Staphylococcus epidermidis, Streptococcus mitis|Staphylococcus epidermidis, Streptococcus mutans|Staphylococcus epidermidis, Streptococcus oralis|Staphylococcus epidermidis, Streptococcus parasanguinis|Staphylococcus epidermidis, Streptococcus peroris|Staphylococcus epidermidis, Streptococcus pneumoniae|Staphylococcus epidermidis, Streptococcus salivarius|Staphylococcus epidermidis, Streptococcus sanguinis|Staphylococcus epidermidis, Streptococcus thermophilus|Staphylococcus epidermidis, Streptococcus vestibularis|Staphylococcus epidermidis, Subdoligranulum variabile|Staphylococcus epidermidis, Succinatimonas hippei|Staphylococcus epidermidis, Sutterella wadsworthensis|Staphylococcus epidermidis, Tropheryma whipplei|Staphylococcus epidermidis, Veillonella atypica|Staphylococcus epidermidis, Veillonella dispar|Staphylococcus epidermidis, Veillonella parvula|Staphylococcus epidermidis, Victivallis vadensis|Staphylococcus hominis, Staphylococcus hominis|Staphylococcus hominis, Staphylococcus saprophyticus|Staphylococcus hominis, Staphylococcus warneri|Staphylococcus hominis, Streptococcus agalactiae|Staphylococcus hominis, Streptococcus anginosus|Staphylococcus hominis, Streptococcus australis|Staphylococcus hominis, Streptococcus bovis|Staphylococcus hominis, Streptococcus cristatus|Staphylococcus hominis, Streptococcus dysgalactiae|Staphylococcus hominis, Streptococcus equinus|Staphylococcus hominis, Streptococcus gordonii|Staphylococcus hominis, Streptococcus infantarius|Staphylococcus hominis, Streptococcus infantis|Staphylococcus hominis, Streptococcus mitis|Staphylococcus hominis, Streptococcus mutans|Staphylococcus hominis, Streptococcus oralis|Staphylococcus hominis, Streptococcus parasanguinis|Staphylococcus hominis, Streptococcus peroris|Staphylococcus hominis, Streptococcus pneumoniae|Staphylococcus hominis, Streptococcus salivarius|Staphylococcus hominis, Streptococcus sanguinis|Staphylococcus hominis, Streptococcus thermophilus|Staphylococcus hominis, Streptococcus vestibularis|Staphylococcus hominis, Subdoligranulum variabile|Staphylococcus hominis, Succinatimonas hippei|Staphylococcus hominis, Sutterella wadsworthensis|Staphylococcus hominis, Tropheryma whipplei|Staphylococcus hominis, Veillonella atypica|Staphylococcus hominis, Veillonella dispar|Staphylococcus hominis, Veillonella parvula|Staphylococcus hominis, Victivallis vadensis|Staphylococcus saprophyticus, Staphylococcus saprophyticus|Staphylococcus saprophyticus, Staphylococcus warneri|Staphylococcus saprophyticus, Streptococcus agalactiae|Staphylococcus saprophyticus, Streptococcus anginosus|Staphylococcus saprophyticus, Streptococcus australis|Staphylococcus saprophyticus, Streptococcus bovis|Staphylococcus saprophyticus, Streptococcus cristatus|Staphylococcus saprophyticus, Streptococcus dysgalactiae|Staphylococcus saprophyticus, Streptococcus equinus|Staphylococcus saprophyticus, Streptococcus gordonii|Staphylococcus saprophyticus, Streptococcus infantarius|Staphylococcus saprophyticus, Streptococcus infantis|Staphylococcus saprophyticus, Streptococcus mitis|Staphylococcus saprophyticus, Streptococcus mutans|Staphylococcus saprophyticus, Streptococcus oralis|Staphylococcus saprophyticus, Streptococcus parasanguinis|Staphylococcus saprophyticus, Streptococcus peroris|Staphylococcus saprophyticus, Streptococcus pneumoniae|Staphylococcus saprophyticus, Streptococcus salivarius|Staphylococcus saprophyticus, Streptococcus sanguinis|Staphylococcus saprophyticus, Streptococcus thermophilus|Staphylococcus saprophyticus, Streptococcus vestibularis|Staphylococcus saprophyticus, Subdoligranulum variabile|Staphylococcus saprophyticus, Succinatimonas hippei|Staphylococcus saprophyticus, Sutterella wadsworthensis|Staphylococcus saprophyticus, Tropheryma whipplei|Staphylococcus saprophyticus, Veillonella atypica|Staphylococcus saprophyticus, Veillonella dispar|Staphylococcus saprophyticus, Veillonella parvula|Staphylococcus saprophyticus, Victivallis vadensis|Staphylococcus warneri, Staphylococcus warneri|Staphylococcus warneri, Streptococcus agalactiae|Staphylococcus warneri, Streptococcus anginosus|Staphylococcus warneri, Streptococcus australis|Staphylococcus warneri, Streptococcus bovis|Staphylococcus warneri, Streptococcus cristatus|Staphylococcus warneri, Streptococcus dysgalactiae|Staphylococcus warneri, Streptococcus equinus|Staphylococcus warneri, Streptococcus gordonii|Staphylococcus warneri, Streptococcus infantarius|Staphylococcus warneri, Streptococcus infantis|Staphylococcus warneri, Streptococcus mitis|Staphylococcus warneri, Streptococcus mutans|Staphylococcus warneri, Streptococcus oralis|Staphylococcus warneri, Streptococcus parasanguinis|Staphylococcus warneri, Streptococcus TABLE 2-continued Table 2. Specific binary combinations of OTUs. Individual pairings are differentiated by "|" and OTUs within a combination are differentiated by ","

*peroris|Staphylococcus warneri, Streptococcus pneumoniae|Staphylococcus warneri, Streptococcus salivarius|Staphylococcus warneri, Streptococcus sanguinis|Staphylococcus warneri, Streptococcus thermophilus|Staphylococcus warneri, Streptococcus vestibularis|Staphylococcus warneri, Subdoligranulum variabile|Staphylococcus warneri, Succinatimonas hippei|Staphylococcus warneri, Sutterella wadsworthensis|Staphylococcus warneri, Tropheryma whipplei|Staphylococcus warneri, Veillonella atypica|Staphylococcus warneri, Veillonella dispar|Staphylococcus warneri, Veillonella parvula|Staphylococcus warneri, Victivallis vadensis|Streptococcus agalactiae, Streptococcus agalactiae|Streptococcus agalactiae, Streptococcus anginosus|Streptococcus agalactiae, Streptococcus australis|Streptococcus agalactiae, Streptococcus bovis|Streptococcus agalactiae, Streptococcus cristatus|Streptococcus agalactiae, Streptococcus dysgalactiae|Streptococcus agalactiae, Streptococcus equinus|Streptococcus agalactiae, Streptococcus gordonii|Streptococcus agalactiae, Streptococcus infantarius|Streptococcus agalactiae, Streptococcus infantis|Streptococcus agalactiae, Streptococcus mitis|Streptococcus agalactiae, Streptococcus mutans|Streptococcus agalactiae, Streptococcus oralis|Streptococcus agalactiae, Streptococcus parasanguinis|Streptococcus agalactiae, Streptococcus peroris|Streptococcus agalactiae, Streptococcus pneumoniae|Streptococcus agalactiae, Streptococcus salivarius|Streptococcus agalactiae, Streptococcus sanguinis|Streptococcus agalactiae, Streptococcus thermophilus|Streptococcus agalactiae, Streptococcus vestibularis|Streptococcus agalactiae, Subdoligranulum variabile|Streptococcus agalactiae, Succinatimonas hippei|Streptococcus agalactiae, Sutterella wadsworthensis|Streptococcus agalactiae, Tropheryma whipplei|Streptococcus agalactiae, Veillonella atypica|Streptococcus agalactiae, Veillonella dispar|Streptococcus agalactiae, Veillonella parvula|Streptococcus agalactiae, Victivallis vadensis|Streptococcus anginosus, Streptococcus anginosus|Streptococcus anginosus, Streptococcus australis|Streptococcus anginosus, Streptococcus bovis|Streptococcus anginosus, Streptococcus cristatus|Streptococcus anginosus, Streptococcus dysgalactiae|Streptococcus anginosus, Streptococcus equinus|Streptococcus anginosus, Streptococcus gordonii|Streptococcus anginosus, Streptococcus infantarius|Streptococcus anginosus, Streptococcus infantis|Streptococcus anginosus, Streptococcus mitis|Streptococcus anginosus, Streptococcus mutans|Streptococcus anginosus, Streptococcus oralis|Streptococcus anginosus, Streptococcus parasanguinis|Streptococcus anginosus, Streptococcus peroris|Streptococcus anginosus, Streptococcus pneumoniae|Streptococcus anginosus, Streptococcus salivarius|Streptococcus anginosus, Streptococcus sanguinis|Streptococcus anginosus, Streptococcus thermophilus|Streptococcus anginosus, Streptococcus vestibularis|Streptococcus anginosus, Subdoligranulum variabile|Streptococcus anginosus, Succinatimonas hippei|Streptococcus anginosus, Sutterella wadsworthensis|Streptococcus anginosus, Tropheryma whipplei|Streptococcus anginosus, Veillonella atypica|Streptococcus anginosus, Veillonella dispar|Streptococcus anginosus, Veillonella parvula|Streptococcus anginosus, Victivallis vadensis|Streptococcus australis, Streptococcus australis|Streptococcus australis, Streptococcus bovis|Streptococcus australis, Streptococcus cristatus|Streptococcus australis, Streptococcus dysgalactiae|Streptococcus australis, Streptococcus equinus|Streptococcus australis, Streptococcus gordonii|Streptococcus australis, Streptococcus infantarius|Streptococcus australis, Streptococcus infantis|Streptococcus australis, Streptococcus mitis|Streptococcus australis, Streptococcus mutans|Streptococcus australis, Streptococcus oralis|Streptococcus australis, Streptococcus parasanguinis|Streptococcus australis, Streptococcus peroris|Streptococcus australis, Streptococcus pneumoniae|Streptococcus australis, Streptococcus salivarius|Streptococcus australis, Streptococcus sanguinis|Streptococcus australis, Streptococcus thermophilus|Streptococcus australis, Streptococcus vestibularis|Streptococcus australis, Subdoligranulum variabile|Streptococcus australis, Succinatimonas hippei|Streptococcus australis, Sutterella wadsworthensis|Streptococcus australis, Tropheryma whipplei|Streptococcus australis, Veillonella atypica|Streptococcus australis, Veillonella dispar|Streptococcus australis, Veillonella parvula|Streptococcus australis, Victivallis vadensis|Streptococcus bovis, Streptococcus bovis|Streptococcus bovis, Streptococcus cristatus|Streptococcus bovis, Streptococcus dysgalactiae|Streptococcus bovis, Streptococcus equinus|Streptococcus bovis, Streptococcus gordonii|Streptococcus bovis, Streptococcus infantarius|Streptococcus bovis, Streptococcus infantis|Streptococcus bovis, Streptococcus mitis|Streptococcus bovis, Streptococcus mutans|Streptococcus bovis, Streptococcus oralis|Streptococcus bovis, Streptococcus parasanguinis|Streptococcus bovis, Streptococcus peroris|Streptococcus bovis, Streptococcus pneumoniae|Streptococcus bovis, Streptococcus salivarius|Streptococcus bovis, Streptococcus sanguinis|Streptococcus bovis, Streptococcus thermophilus|Streptococcus bovis, Streptococcus vestibularis|Streptococcus bovis, Subdoligranulum variabile|Streptococcus bovis, Succinatimonas hippei|Streptococcus bovis, Sutterella wadsworthensis|Streptococcus bovis, Tropheryma whipplei|Streptococcus bovis, Veillonella atypica|Streptococcus bovis, Veillonella dispar|Streptococcus bovis, Veillonella parvula|Streptococcus bovis, Victivallis vadensis|Streptococcus cristatus, Streptococcus cristatus|Streptococcus cristatus, Streptococcus dysgalactiae|Streptococcus cristatus, Streptococcus equinus|Streptococcus cristatus, Streptococcus gordonii|Streptococcus cristatus, Streptococcus infantarius|Streptococcus cristatus, Streptococcus infantis|Streptococcus cristatus, Streptococcus mitis|Streptococcus cristatus, Streptococcus mutans|Streptococcus cristatus, Streptococcus oralis|Streptococcus cristatus, Streptococcus parasanguinis|Streptococcus cristatus, Streptococcus peroris|Streptococcus cristatus, Streptococcus pneumoniae|Streptococcus cristatus, Streptococcus salivarius|Streptococcus cristatus, Streptococcus sanguinis|Streptococcus cristatus, Streptococcus thermophilus|Streptococcus cristatus, Streptococcus vestibularis|Streptococcus cristatus, Subdoligranulum variabile|Streptococcus cristatus, Succinatimonas hippei|Streptococcus cristatus, Sutterella wadsworthensis|Streptococcus cristatus, Tropheryma whipplei|Streptococcus cristatus, Veillonella atypica|Streptococcus cristatus, Veillonella dispar|Streptococcus cristatus, Veillonella parvula|Streptococcus cristatus, Victivallis vadensis|Streptococcus dysgalactiae, Streptococcus dysgalactiae|Streptococcus dysgalactiae, Streptococcus equinus|Streptococcus dysgalactiae, Streptococcus gordonii|Streptococcus dysgalactiae, Streptococcus infantarius|Streptococcus dysgalactiae, Streptococcus infantis|Streptococcus dysgalactiae, Streptococcus mitis|Streptococcus dysgalactiae, Streptococcus mutans|Streptococcus dysgalactiae, Streptococcus oralis|Streptococcus dysgalactiae, Streptococcus parasanguinis|Streptococcus dysgalactiae, Streptococcus peroris|Streptococcus dysgalactiae, Streptococcus pneumoniae|Streptococcus dysgalactiae, Streptococcus salivarius, Streptococcus dysgalactiae, Streptococcus sanguinis|Streptococcus dysgalactiae, Streptococcus thermophilus|Streptococcus dysgalactiae, Streptococcus vestibularis|Streptococcus dysgalactiae, Subdoligranulum variabile|Streptococcus dysgalactiae, Succinatimonas hippei|Streptococcus dysgalactiae, Sutterella wadsworthensis|Streptococcus dysgalactiae, Tropheryma whipplei|Streptococcus dysgalactiae, Veillonella atypica|Streptococcus dysgalactiae, Veillonella dispar|Streptococcus dysgalactiae, Veillonella parvula|Streptococcus dysgalactiae, Victivallis vadensis|Streptococcus equinus, Streptococcus equinus|Streptococcus equinus, Streptococcus gordonii|Streptococcus equinus, Streptococcus infantarius|Streptococcus equinus, Streptococcus infantis|Streptococcus equinus, Streptococcus mitis|Streptococcus equinus, Streptococcus mutans|Streptococcus equinus, Streptococcus oralis|Streptococcus equinus, Streptococcus parasanguinis|Streptococcus equinus, Streptococcus peroris|Streptococcus equinus, Streptococcus pneumoniae|Streptococcus equinus, Streptococcus salivarius|Streptococcus equinus, Streptococcus sanguinis|Streptococcus equinus, Streptococcus thermophilus|Streptococcus equinus, Streptococcus vestibularis|Streptococcus equinus, Subdoligranulum variabile|Streptococcus equinus, Succinatimonas hippei|Streptococcus equinus, Sutterella wadsworthensis|Streptococcus equinus, Tropheryma whipplei|Streptococcus equinus, Veillonella atypica|Streptococcus equinus, Veillonella dispar|Streptococcus equinus, Veillonella parvula|Streptococcus equinus, Victivallis vadensis|Streptococcus gordonii, Streptococcus gordonii|Streptococcus gordonii, Streptococcus infantarius|Streptococcus gordonii, Streptococcus infantis|Streptococcus gordonii, Streptococcus mitis|Streptococcus gordonii, Streptococcus mutans|Streptococcus gordonii, Streptococcus oralis, Streptococcus gordonii, Streptococcus parasanguinis|Streptococcus gordonii, Streptococcus peroris|Streptococcus gordonii, Streptococcus pneumoniae|Streptococcus gordonii, Streptococcus salivarius|Streptococcus gordonii, Streptococcus sanguinis|Streptococcus gordonii, Streptococcus thermophilus|Streptococcus gordonii, Streptococcus vestibularis|Streptococcus gordonii, Subdoligranulum variabile|Streptococcus gordonii, Succinatimonas hippei|Streptococcus gordonii, Sutterella wadsworthensis|Streptococcus gordonii, Tropheryma whipplei|Streptococcus gordonii, Veillonella atypica|Streptococcus gordonii, Veillonella dispar|Streptococcus gordonii, Veillonella parvula|Streptococcus gordonii, Victivallis vadensis|Streptococcus infantarius, Streptococcus infantarius|Streptococcus infantarius, Streptococcus infantis|Streptococcus*

TABLE 2-continued

Table 2. Specific binary combinations of OTUs. Individual pairings are differentiated by “|” and OTUs within a combination are differentiated by “,”

*infantarius, Streptococcus mitis|Streptococcus infantarius, Streptococcus mutans|Streptococcus infantarius, Streptococcus oralis|Streptococcus infantarius, Streptococcus parasanguinis|Streptococcus infantarius, Streptococcus peroris|Streptococcus infantarius, Streptococcus pneumoniae|Streptococcus infantarius, Streptococcus salivarius|Streptococcus infantarius, Streptococcus sanguinis|Streptococcus infantarius, Streptococcus thermophilus|Streptococcus infantarius, Streptococcus vestibularis|Streptococcus infantarius, Subdoligranulum variabile|Streptococcus infantarius, Succinatimonas hippei|Streptococcus infantarius, Sutterella wadsworthensis|Streptococcus infantarius, Tropheryma whipplei|Streptococcus infantarius, Veillonella atypica|Streptococcus infantarius, Veillonella dispar|Streptococcus infantarius, Veillonella parvula|Streptococcus infantarius, Victivallis vadensis|Streptococcus infantis, Streptococcus infantis|Streptococcus infantis, Streptococcus mitis|Streptococcus infantis, Streptococcus mutans|Streptococcus infantis, Streptococcus oralis, Streptococcus infantis, Streptococcus parasanguinis|Streptococcus infantis, Streptococcus peroris|Streptococcus infantis, Streptococcus pneumoniae|Streptococcus infantis, Streptococcus salivarius, Streptococcus infantis, Streptococcus sanguinis|Streptococcus infantis, Streptococcus thermophilus|Streptococcus infantis, Streptococcus vestibularis|Streptococcus infantis, Subdoligranulum variabile|Streptococcus infantis, Succinatimonas hippei|Streptococcus infantis, Sutterella wadsworthensis|Streptococcus infantis, Tropheryma whipplei|Streptococcus infantis, Veillonella atypica|Streptococcus infantis, Veillonella dispar|Streptococcus infantis, Veillonella parvula|Streptococcus infantis, Victivallis vadensis|Streptococcus mitis, Streptococcus mitis|Streptococcus mitis, Streptococcus mutans|Streptococcus mitis, Streptococcus oralis|Streptococcus mitis, Streptococcus parasanguinis|Streptococcus mitis, Streptococcus peroris|Streptococcus mitis, Streptococcus pneumoniae|Streptococcus mitis, Streptococcus salivarius|Streptococcus mitis, Streptococcus sanguinis|Streptococcus mitis, Streptococcus thermophilus|Streptococcus mitis, Streptococcus vestibularis|Streptococcus mitis, Subdoligranulum variabile|Streptococcus mitis, Succinatimonas hippei|Streptococcus mitis, Sutterella wadsworthensis|Streptococcus mitis, Tropheryma whipplei|Streptococcus mitis, Veillonella atypica|Streptococcus mitis, Veillonella dispar|Streptococcus mitis, Veillonella parvula|Streptococcus mitis, Victivallis vadensis|Streptococcus mutans, Streptococcus mutans|Streptococcus mutans, Streptococcus oralis|Streptococcus mutans, Streptococcus parasanguinis|Streptococcus mutans, Streptococcus peroris|Streptococcus mutans, Streptococcus pneumoniae|Streptococcus mutans, Streptococcus salivarius|Streptococcus mutans, Streptococcus sanguinis|Streptococcus mutans, Streptococcus thermophilus|Streptococcus mutans, Streptococcus vestibularis|Streptococcus mutans, Subdoligranulum variabile|Streptococcus mutans, Succinatimonas hippei|Streptococcus mutans, Sutterella wadsworthensis|Streptococcus mutans, Tropheryma whipplei|Streptococcus mutans, Veillonella atypica|Streptococcus mutans, Veillonella dispar|Streptococcus mutans, Veillonella parvula|Streptococcus mutans, Victivallis vadensis|Streptococcus oralis, Streptococcus oralis|Streptococcus oralis, Streptococcus parasanguinis|Streptococcus oralis, Streptococcus peroris|Streptococcus oralis, Streptococcus pneumoniae|Streptococcus oralis, Streptococcus salivarius|Streptococcus oralis, Streptococcus sanguinis|Streptococcus oralis, Streptococcus thermophilus|Streptococcus oralis, Streptococcus vestibularis|Streptococcus oralis, Subdoligranulum variabile|Streptococcus oralis, Succinatimonas hippei|Streptococcus oralis, Sutterella wadsworthensis|Streptococcus oralis, Tropheryma whipplei|Streptococcus oralis, Veillonella atypica|Streptococcus oralis, Veillonella dispar|Streptococcus oralis, Veillonella parvula|Streptococcus oralis, Victivallis vadensis|Streptococcus parasanguinis, Streptococcus parasanguinis|Streptococcus parasanguinis, Streptococcus peroris|Streptococcus parasanguinis, Streptococcus pneumoniae|Streptococcus parasanguinis, Streptococcus salivarius|Streptococcus parasanguinis, Streptococcus sanguinis|Streptococcus parasanguinis, Streptococcus thermophilus|Streptococcus parasanguinis, Streptococcus vestibularis|Streptococcus parasanguinis, Subdoligranulum variabile|Streptococcus parasanguinis, Succinatimonas hippei|Streptococcus parasanguinis, Sutterella wadsworthensis|Streptococcus parasanguinis, Tropheryma whipplei|Streptococcus parasanguinis, Veillonella atypica|Streptococcus parasanguinis, Veillonella dispar|Streptococcus parasanguinis, Veillonella parvula|Streptococcus parasanguinis, Victivallis vadensis|Streptococcus peroris, Streptococcus peroris|Streptococcus peroris, Streptococcus pneumoniae|Streptococcus peroris, Streptococcus salivarius|Streptococcus peroris, Streptococcus sanguinis|Streptococcus peroris, Streptococcus thermophilus|Streptococcus peroris, Streptococcus vestibularis|Streptococcus peroris, Subdoligranulum variabile|Streptococcus peroris, Succinatimonas hippei|Streptococcus peroris, Sutterella wadsworthensis|Streptococcus peroris, Tropheryma whipplei|Streptococcus peroris, Veillonella atypica|Streptococcus peroris, Veillonella dispar|Streptococcus peroris, Veillonella parvula|Streptococcus peroris, Victivallis vadensis|Streptococcus pneumoniae, Streptococcus pneumoniae|Streptococcus pneumoniae, Streptococcus salivarius|Streptococcus pneumoniae, Streptococcus sanguinis|Streptococcus pneumoniae, Streptococcus thermophilus|Streptococcus pneumoniae, Streptococcus vestibularis|Streptococcus pneumoniae, Subdoligranulum variabile|Streptococcus pneumoniae, Succinatimonas hippei|Streptococcus pneumoniae, Sutterella wadsworthensis|Streptococcus pneumoniae, Tropheryma whipplei|Streptococcus pneumoniae, Veillonella atypica|Streptococcus pneumoniae, Veillonella dispar|Streptococcus pneumoniae, Veillonella parvula|Streptococcus pneumoniae, Victivallis vadensis|Streptococcus salivarius, Streptococcus salivarius|Streptococcus salivarius, Streptococcus sanguinis|Streptococcus salivarius, Streptococcus thermophilus|Streptococcus salivarius, Streptococcus vestibularis|Streptococcus salivarius, Subdoligranulum variabile|Streptococcus salivarius, Succinatimonas hippei|Streptococcus salivarius, Sutterella wadsworthensis|Streptococcus salivarius, Tropheryma whipplei|Streptococcus salivarius, Veillonella atypica|Streptococcus salivarius, Veillonella dispar|Streptococcus salivarius, Veillonella parvula|Streptococcus salivarius, Victivallis vadensis|Streptococcus sanguinis, Streptococcus sanguinis|Streptococcus sanguinis, Streptococcus thermophilus|Streptococcus sanguinis, Streptococcus vestibularis|Streptococcus sanguinis, Subdoligranulum variabile|Streptococcus sanguinis, Succinatimonas hippei|Streptococcus sanguinis, Sutterella wadsworthensis|Streptococcus sanguinis, Tropheryma whipplei|Streptococcus sanguinis, Veillonella atypica|Streptococcus sanguinis, Veillonella dispar|Streptococcus sanguinis, Veillonella parvula|Streptococcus sanguinis, Victivallis vadensis|Streptococcus thermophilus, Streptococcus thermophilus|Streptococcus thermophilus, Streptococcus vestibularis|Streptococcus thermophilus, Subdoligranulum variabile|Streptococcus thermophilus, Succinatimonas hippei|Streptococcus thermophilus, Sutterella wadsworthensis|Streptococcus thermophilus, Tropheryma whipplei|Streptococcus thermophilus, Veillonella atypica|Streptococcus thermophilus, Veillonella dispar|Streptococcus thermophilus, Veillonella parvula|Streptococcus thermophilus, Victivallis vadensis|Streptococcus vestibularis, Streptococcus vestibularis|Streptococcus vestibularis, Subdoligranulum variabile|Streptococcus vestibularis, Succinatimonas hippei|Streptococcus vestibularis, Sutterella wadsworthensis|Streptococcus vestibularis, Tropheryma whipplei|Streptococcus vestibularis, Veillonella atypica|Streptococcus vestibularis, Veillonella dispar|Streptococcus vestibularis, Veillonella parvula|Streptococcus vestibularis, Victivallis vadensis|Subdoligranulum variabile, Subdoligranulum variabile|Subdoligranulum variabile, Succinatimonas hippei|Subdoligranulum variabile, Sutterella wadsworthensis|Subdoligranulum variabile, Tropheryma whipplei|Subdoligranulum variabile, Veillonella atypica|Subdoligranulum variabile, Veillonella dispar|Subdoligranulum variabile, Veillonella parvula|Subdoligranulum variabile, Victivallis vadensis|Succinatimonas hippei, Succinatimonas hippei|Succinatimonas hippei, Sutterella wadsworthensis|Succinatimonas hippei, Tropheryma whipplei|Succinatimonas hippei, Veillonella atypica|Succinatimonas hippei, Veillonella dispar|Succinatimonas hippei, Veillonella parvula|Succinatimonas hippei, Victivallis vadensis|Sutterella wadsworthensis, Sutterella wadsworthensis|Sutterella wadsworthensis, Tropheryma whipplei|Sutterella wadsworthensis, Veillonella atypica|Sutterella wadsworthensis, Veillonella dispar|Sutterella wadsworthensis, Veillonella parvula|Sutterella wadsworthensis, Victivallis vadensis|Tropheryma whipplei, Tropheryma whipplei|Tropheryma whipplei, Veillonella atypica|Tropheryma whipplei, Veillonella dispar|Tropheryma whipplei, Veillonella parvula|Tropheryma whipplei, Victivallis vadensis|Veillonella atypica, Veillonella atypica|Veillonella atypica, Veillonella dispar|Veillonella atypica, Veillonella parvula|Veillonella atypica, Victivallis vadensis|Veillonella dispar, Veillonella dispar|Veillonella dispar, Veillonella parvula|Veillonella dispar, Victivallis vadensis|Veillonella parvula, Veillonella parvula|Veillonella parvula, Victivallis vadensis|Victivallis vadensis, Victivallis vadensis*

TABLE 3

| SPC1 | SPC2 | OTU1 | OTU2 | Result |
|---|---|---|---|---|
| SPC10414 | SPC10414 | Alistipes_shahii | Alistipes_shahii | |
| SPC10211 | SPC10414 | Bacteroides_caccae | Alistipes_shahii | |
| SPC10213 | SPC10414 | Bacteroides_eggerthii | Alistipes_shahii | −− |
| SPC10030 | SPC10414 | Bacteroides_ovatus | Alistipes_shahii | |
| SPC00006 | SPC10414 | Bacteroides_sp_1_1_6 | Alistipes_shahii | ++++ |
| SPC00007 | SPC10414 | Bacteroides_sp_3_1_23 | Alistipes_shahii | + |
| SPC10019 | SPC10414 | Bacteroides_sp_D20 | Alistipes_shahii | − |
| SPC00005 | SPC10414 | Bacteroides_vulgatus | Alistipes_shahii | +++ |
| SPC10081 | SPC10414 | Bacteroides_vulgatus | Alistipes_shahii | + |
| SPC10301 | SPC10414 | Bifidobacterium_adolescentis | Alistipes_shahii | ++++ |
| SPC10298 | SPC10414 | Bifidobacterium_pseudocatenulatum | Alistipes_shahii | |
| SPC00021 | SPC10414 | Blautia_producta | Alistipes_shahii | ++++ |
| SPC10403 | SPC10414 | Blautia_schinkii | Alistipes_shahii | |
| SPC10243 | SPC10414 | Clostridium_hathewayi | Alistipes_shahii | ++++ |
| SPC00026 | SPC10414 | Clostridium_nexile | Alistipes_shahii | |
| SPC00027 | SPC10414 | Clostridium_sp_HGF2 | Alistipes_shahii | |
| SPC10355 | SPC10414 | Clostridium_symbiosum | Alistipes_shahii | |
| SPC10097 | SPC10414 | Collinsella_aerofaciens | Alistipes_shahii | ++++ |
| SPC00009 | SPC10414 | Coprobacillus_sp_D7 | Alistipes_shahii | ++++ |
| SPC00080 | SPC10414 | Coprococcus_catus | Alistipes_shahii | − |
| SPC10304 | SPC10414 | Coprococcus_comes | Alistipes_shahii | |
| SPC00018 | SPC10414 | Dorea_formicigenerans | Alistipes_shahii | −−−− |
| SPC00057 | SPC10414 | Dorea_longicatena | Alistipes_shahii | ++++ |
| SPC00008 | SPC10414 | Enterococcus_faecalis | Alistipes_shahii | ++++ |
| SPC10001 | SPC10414 | Erysipelotrichaceae_bacterium | Alistipes_shahii | −−− |
| SPC00001 | SPC10414 | Escherichia_coli | Alistipes_shahii | ++++ |
| SPC10110 | SPC10414 | Escherichia_coli | Alistipes_shahii | ++++ |
| SPC00022 | SPC10414 | Eubacterium_eligens | Alistipes_shahii | −− |
| SPC10363 | SPC10414 | Eubacterium_rectale | Alistipes_shahii | |
| SPC00054 | SPC10414 | Faecalibacterium_prausnitzii | Alistipes_shahii | |
| SPC10386 | SPC10414 | Faecalibacterium_prausnitzii | Alistipes_shahii | |
| SPC10390 | SPC10414 | Lachnospiraceae_bacterium_5_1_57FAA | Alistipes_shahii | + |
| SPC00056 | SPC10414 | Odoribacter_splanchnicus | Alistipes_shahii | |
| SPC10388 | SPC10414 | Odoribacter_splanchnicus | Alistipes_shahii | |
| SPC10048 | SPC10414 | Parabacteroides_merdae | Alistipes_shahii | |
| SPC00061 | SPC10414 | Roseburia_intestinalis | Alistipes_shahii | − |
| SPC10197 | SPC10414 | Ruminococcus_obeum | Alistipes_shahii | |
| SPC10233 | SPC10414 | Ruminococcus_torques | Alistipes_shahii | |
| SPC00015 | SPC10414 | Streptococcus_thermophilus | Alistipes_shahii | |
| SPC10211 | SPC10211 | Bacteroides_caccae | Bacteroides_caccae | ++++ |
| SPC10030 | SPC10211 | Bacteroides_ovatus | Bacteroides_caccae | |
| SPC00006 | SPC10211 | Bacteroides_sp_1_1_6 | Bacteroides_caccae | ++++ |
| SPC00007 | SPC10211 | Bacteroides_sp_3_1_23 | Bacteroides_caccae | +++ |
| SPC10019 | SPC10211 | Bacteroides_sp_D20 | Bacteroides_caccae | +++ |
| SPC00005 | SPC10211 | Bacteroides_vulgatus | Bacteroides_caccae | ++++ |
| SPC10081 | SPC10211 | Bacteroides_vulgatus | Bacteroides_caccae | + |
| SPC00021 | SPC10211 | Blautia_producta | Bacteroides_caccae | ++++ |
| SPC00026 | SPC10211 | Clostridium_nexile | Bacteroides_caccae | |
| SPC00027 | SPC10211 | Clostridium_sp_HGF2 | Bacteroides_caccae | |
| SPC10097 | SPC10211 | Collinsella_aerofaciens | Bacteroides_caccae | ++++ |
| SPC00009 | SPC10211 | Coprobacillus_sp_D7 | Bacteroides_caccae | +++ |
| SPC00080 | SPC10211 | Coprococcus_catus | Bacteroides_caccae | ++++ |
| SPC00018 | SPC10211 | Dorea_formicigenerans | Bacteroides_caccae | +++ |
| SPC00057 | SPC10211 | Dorea_longicatena | Bacteroides_caccae | |
| SPC00008 | SPC10211 | Enterococcus_faecalis | Bacteroides_caccae | ++++ |
| SPC10001 | SPC10211 | Erysipelotrichaceae_bacterium | Bacteroides_caccae | ++ |
| SPC00001 | SPC10211 | Escherichia_coli | Bacteroides_caccae | ++++ |
| SPC10110 | SPC10211 | Escherichia_coli | Bacteroides_caccae | ++++ |
| SPC00022 | SPC10211 | Eubacterium_eligens | Bacteroides_caccae | ++ |
| SPC00054 | SPC10211 | Faecalibacterium_prausnitzii | Bacteroides_caccae | − |
| SPC00056 | SPC10211 | Odoribacter_splanchnicus | Bacteroides_caccae | |
| SPC10048 | SPC10211 | Parabacteroides_merdae | Bacteroides_caccae | + |
| SPC00061 | SPC10211 | Roseburia_intestinalis | Bacteroides_caccae | + |
| SPC10197 | SPC10211 | Ruminococcus_obeum | Bacteroides_caccae | ++++ |
| SPC00015 | SPC10211 | Streptococcus_thermophilus | Bacteroides_caccae | ++ |
| SPC10211 | SPC10213 | Bacteroides_caccae | Bacteroides_eggerthii | ++++ |
| SPC10213 | SPC10213 | Bacteroides_eggerthii | Bacteroides_eggerthii | ++++ |
| SPC10030 | SPC10213 | Bacteroides_ovatus | Bacteroides_eggerthii | |
| SPC00006 | SPC10213 | Bacteroides_sp_1_1_6 | Bacteroides_eggerthii | +++ |
| SPC00007 | SPC10213 | Bacteroides_sp_3_1_23 | Bacteroides_eggerthii | ++ |
| SPC10019 | SPC10213 | Bacteroides_sp_D20 | Bacteroides_eggerthii | |
| SPC00005 | SPC10213 | Bacteroides_vulgatus | Bacteroides_eggerthii | ++++ |
| SPC10081 | SPC10213 | Bacteroides_vulgatus | Bacteroides_eggerthii | + |
| SPC00021 | SPC10213 | Blautia_producta | Bacteroides_eggerthii | ++++ |
| SPC00026 | SPC10213 | Clostridium_nexile | Bacteroides_eggerthii | |
| SPC00027 | SPC10213 | Clostridium_sp_HGF2 | Bacteroides_eggerthii | − |
| SPC10097 | SPC10213 | Collinsella_aerofaciens | Bacteroides_eggerthii | ++++ |
| SPC00009 | SPC10213 | Coprobacillus_sp_D7 | Bacteroides_eggerthii | |

TABLE 3-continued

| SPC1 | SPC2 | OTU1 | OTU2 | Result |
|---|---|---|---|---|
| SPC00080 | SPC10213 | Coprococcus_catus | Bacteroides_eggerthii | + |
| SPC00018 | SPC10213 | Dorea_formicigenerans | Bacteroides_eggerthii | |
| SPC00057 | SPC10213 | Dorea_longicatena | Bacteroides_eggerthii | − |
| SPC00008 | SPC10213 | Enterococcus_faecalis | Bacteroides_eggerthii | ++++ |
| SPC10001 | SPC10213 | Erysipelotrichaceae_bacterium | Bacteroides_eggerthii | |
| SPC00001 | SPC10213 | Escherichia_coli | Bacteroides_eggerthii | ++++ |
| SPC10110 | SPC10213 | Escherichia_coli | Bacteroides_eggerthii | ++++ |
| SPC00022 | SPC10213 | Eubacterium_eligens | Bacteroides_eggerthii | |
| SPC00054 | SPC10213 | Faecalibacterium_prausnitzii | Bacteroides_eggerthii | |
| SPC00056 | SPC10213 | Odoribacter_splanchnicus | Bacteroides_eggerthii | |
| SPC10048 | SPC10213 | Parabacteroides_merdae | Bacteroides_eggerthii | |
| SPC00061 | SPC10213 | Roseburia_intestinalis | Bacteroides_eggerthii | |
| SPC10197 | SPC10213 | Ruminococcus_obeum | Bacteroides_eggerthii | ++++ |
| SPC00015 | SPC10213 | Streptococcus_thermophilus | Bacteroides_eggerthii | |
| SPC10030 | SPC10030 | Bacteroides_ovatus | Bacteroides_ovatus | +++ |
| SPC00006 | SPC10030 | Bacteroides_sp_1_1_6 | Bacteroides_ovatus | ++++ |
| SPC00007 | SPC10030 | Bacteroides_sp_3_1_23 | Bacteroides_ovatus | |
| SPC10019 | SPC10030 | Bacteroides_sp_D20 | Bacteroides_ovatus | − |
| SPC00005 | SPC10030 | Bacteroides_vulgatus | Bacteroides_ovatus | + |
| SPC00021 | SPC10030 | Blautia_producta | Bacteroides_ovatus | ++++ |
| SPC00026 | SPC10030 | Clostridium_nexile | Bacteroides_ovatus | |
| SPC00027 | SPC10030 | Clostridium_sp_HGF2 | Bacteroides_ovatus | |
| SPC00009 | SPC10030 | Coprobacillus_sp_D7 | Bacteroides_ovatus | |
| SPC00080 | SPC10030 | Coprococcus_catus | Bacteroides_ovatus | |
| SPC00018 | SPC10030 | Dorea_formicigenerans | Bacteroides_ovatus | |
| SPC00057 | SPC10030 | Dorea_longicatena | Bacteroides_ovatus | − |
| SPC00008 | SPC10030 | Enterococcus_faecalis | Bacteroides_ovatus | ++++ |
| SPC10001 | SPC10030 | Erysipelotrichaceae_bacterium | Bacteroides_ovatus | |
| SPC00001 | SPC10030 | Escherichia_coli | Bacteroides_ovatus | ++++ |
| SPC00022 | SPC10030 | Eubacterium_eligens | Bacteroides_ovatus | − |
| SPC00054 | SPC10030 | Faecalibacterium_prausnitzii | Bacteroides_ovatus | |
| SPC00056 | SPC10030 | Odoribacter_splanchnicus | Bacteroides_ovatus | |
| SPC00061 | SPC10030 | Roseburia_intestinalis | Bacteroides_ovatus | |
| SPC00015 | SPC10030 | Streptococcus_thermophilus | Bacteroides_ovatus | ++ |
| SPC00006 | SPC00006 | Bacteroides_sp_1_1_6 | Bacteroides_sp_1_1_6 | ++++ |
| SPC00005 | SPC00006 | Bacteroides_vulgatus | Bacteroides_sp_1_1_6 | ++++ |
| SPC00001 | SPC00006 | Escherichia_coli | Bacteroides_sp_1_1_6 | ++++ |
| SPC00006 | SPC00007 | Bacteroides_sp_1_1_6 | Bacteroides_sp_3_1_23 | ++++ |
| SPC00007 | SPC00007 | Bacteroides_sp_3_1_23 | Bacteroides_sp_3_1_23 | |
| SPC00005 | SPC00007 | Bacteroides_vulgatus | Bacteroides_sp_3_1_23 | +++ |
| SPC00001 | SPC00007 | Escherichia_coli | Bacteroides_sp_3_1_23 | ++++ |
| SPC00006 | SPC10019 | Bacteroides_sp_1_1_6 | Bacteroides_sp_D20 | ++++ |
| SPC00007 | SPC10019 | Bacteroides_sp_3_1_23 | Bacteroides_sp_D20 | ++++ |
| SPC10019 | SPC10019 | Bacteroides_sp_D20 | Bacteroides_sp_D20 | |
| SPC00005 | SPC10019 | Bacteroides_vulgatus | Bacteroides_sp_D20 | + |
| SPC00021 | SPC10019 | Blautia_producta | Bacteroides_sp_D20 | ++++ |
| SPC00026 | SPC10019 | Clostridium_nexile | Bacteroides_sp_D20 | − |
| SPC00027 | SPC10019 | Clostridium_sp_HGF2 | Bacteroides_sp_D20 | |
| SPC00009 | SPC10019 | Coprobacillus_sp_D7 | Bacteroides_sp_D20 | |
| SPC00080 | SPC10019 | Coprococcus_catus | Bacteroides_sp_D20 | |
| SPC00018 | SPC10019 | Dorea_formicigenerans | Bacteroides_sp_D20 | − |
| SPC00057 | SPC10019 | Dorea_longicatena | Bacteroides_sp_D20 | |
| SPC00008 | SPC10019 | Enterococcus_faecalis | Bacteroides_sp_D20 | ++++ |
| SPC10001 | SPC10019 | Erysipelotrichaceae_bacterium | Bacteroides_sp_D20 | |
| SPC00001 | SPC10019 | Escherichia_coli | Bacteroides_sp_D20 | ++++ |
| SPC00022 | SPC10019 | Eubacterium_eligens | Bacteroides_sp_D20 | − |
| SPC00054 | SPC10019 | Faecalibacterium_prausnitzii | Bacteroides_sp_D20 | |
| SPC00056 | SPC10019 | Odoribacter_splanchnicus | Bacteroides_sp_D20 | |
| SPC00061 | SPC10019 | Roseburia_intestinalis | Bacteroides_sp_D20 | − |
| SPC00015 | SPC10019 | Streptococcus_thermophilus | Bacteroides_sp_D20 | + |
| SPC10030 | SPC10081 | Bacteroides_ovatus | Bacteroides_vulgatus | |
| SPC00006 | SPC10081 | Bacteroides_sp_1_1_6 | Bacteroides_vulgatus | |
| SPC00007 | SPC10081 | Bacteroides_sp_3_1_23 | Bacteroides_vulgatus | − |
| SPC10019 | SPC10081 | Bacteroides_sp_D20 | Bacteroides_vulgatus | |
| SPC00005 | SPC00005 | Bacteroides_vulgatus | Bacteroides_vulgatus | + |
| SPC00005 | SPC10081 | Bacteroides_vulgatus | Bacteroides_vulgatus | ++ |
| SPC10081 | SPC10081 | Bacteroides_vulgatus | Bacteroides_vulgatus | |
| SPC00021 | SPC10081 | Blautia_producta | Bacteroides_vulgatus | ++++ |
| SPC00026 | SPC10081 | Clostridium_nexile | Bacteroides_vulgatus | |
| SPC00027 | SPC10081 | Clostridium_sp_HGF2 | Bacteroides_vulgatus | +++ |
| SPC00009 | SPC10081 | Coprobacillus_sp_D7 | Bacteroides_vulgatus | − |
| SPC00080 | SPC10081 | Coprococcus_catus | Bacteroides_vulgatus | ++ |
| SPC00018 | SPC10081 | Dorea_formicigenerans | Bacteroides_vulgatus | |
| SPC00057 | SPC10081 | Dorea_longicatena | Bacteroides_vulgatus | |
| SPC00008 | SPC10081 | Enterococcus_faecalis | Bacteroides_vulgatus | ++++ |
| SPC10001 | SPC10081 | Erysipelotrichaceae_bacterium | Bacteroides_vulgatus | |
| SPC00001 | SPC00005 | Escherichia_coli | Bacteroides_vulgatus | ++++ |
| SPC00001 | SPC10081 | Escherichia_coli | Bacteroides_vulgatus | ++++ |

TABLE 3-continued

| SPC1 | SPC2 | OTU1 | OTU2 | Result |
|---|---|---|---|---|
| SPC00022 | SPC10081 | Eubacterium_eligens | Bacteroides_vulgatus | |
| SPC00054 | SPC10081 | Faecalibacterium_prausnitzii | Bacteroides_vulgatus | |
| SPC00056 | SPC10081 | Odoribacter_splanchnicus | Bacteroides_vulgatus | |
| SPC10048 | SPC10081 | Parabacteroides_merdae | Bacteroides_vulgatus | + |
| SPC00061 | SPC10081 | Roseburia_intestinalis | Bacteroides_vulgatus | |
| SPC00015 | SPC10081 | Streptococcus_thermophilus | Bacteroides_vulgatus | −− |
| SPC10211 | SPC10301 | Bacteroides_caccae | Bifidobacterium_adolescentis | ++++ |
| SPC10213 | SPC10301 | Bacteroides_eggerthii | Bifidobacterium_adolescentis | ++++ |
| SPC10030 | SPC10301 | Bacteroides_ovatus | Bifidobacterium_adolescentis | ++++ |
| SPC00006 | SPC10301 | Bacteroides_sp_1_1_6 | Bifidobacterium_adolescentis | ++++ |
| SPC00007 | SPC10301 | Bacteroides_sp_3_1_23 | Bifidobacterium_adolescentis | ++++ |
| SPC10019 | SPC10301 | Bacteroides_sp_D20 | Bifidobacterium_adolescentis | ++++ |
| SPC00005 | SPC10301 | Bacteroides_vulgatus | Bifidobacterium_adolescentis | ++++ |
| SPC10081 | SPC10301 | Bacteroides_vulgatus | Bifidobacterium_adolescentis | ++++ |
| SPC10301 | SPC10301 | Bifidobacterium_adolescentis | Bifidobacterium_adolescentis | ++++ |
| SPC10298 | SPC10301 | Bifidobacterium_pseudocatenulatum | Bifidobacterium_adolescentis | ++++ |
| SPC00021 | SPC10301 | Blautia_producta | Bifidobacterium_adolescentis | ++++ |
| SPC10243 | SPC10301 | Clostridium_hathewayi | Bifidobacterium_adolescentis | ++++ |
| SPC00026 | SPC10301 | Clostridium_nexile | Bifidobacterium_adolescentis | ++++ |
| SPC00027 | SPC10301 | Clostridium_sp_HGF2 | Bifidobacterium_adolescentis | ++++ |
| SPC10097 | SPC10301 | Collinsella_aerofaciens | Bifidobacterium_adolescentis | ++++ |
| SPC00009 | SPC10301 | Coprobacillus_sp_D7 | Bifidobacterium_adolescentis | ++++ |
| SPC00080 | SPC10301 | Coprococcus_catus | Bifidobacterium_adolescentis | |
| SPC00018 | SPC10301 | Dorea_formicigenerans | Bifidobacterium_adolescentis | ++++ |
| SPC00057 | SPC10301 | Dorea_longicatena | Bifidobacterium_adolescentis | ++++ |
| SPC00008 | SPC10301 | Enterococcus_faecalis | Bifidobacterium_adolescentis | ++++ |
| SPC10001 | SPC10301 | Erysipelotrichaceae_bacterium | Bifidobacterium_adolescentis | ++++ |
| SPC00001 | SPC10301 | Escherichia_coli | Bifidobacterium_adolescentis | ++++ |
| SPC10110 | SPC10301 | Escherichia_coli | Bifidobacterium_adolescentis | ++++ |
| SPC00022 | SPC10301 | Eubacterium_eligens | Bifidobacterium_adolescentis | ++++ |
| SPC00054 | SPC10301 | Faecalibacterium_prausnitzii | Bifidobacterium_adolescentis | + |
| SPC00056 | SPC10301 | Odoribacter_splanchnicus | Bifidobacterium_adolescentis | +++ |
| SPC10048 | SPC10301 | Parabacteroides_merdae | Bifidobacterium_adolescentis | ++++ |
| SPC00061 | SPC10301 | Roseburia_intestinalis | Bifidobacterium_adolescentis | +++ |
| SPC10197 | SPC10301 | Ruminococcus_obeum | Bifidobacterium_adolescentis | ++++ |
| SPC10233 | SPC10301 | Ruminococcus_torques | Bifidobacterium_adolescentis | ++++ |
| SPC00015 | SPC10301 | Streptococcus_thermophilus | Bifidobacterium_adolescentis | ++++ |
| SPC10211 | SPC10298 | Bacteroides_caccae | Bifidobacterium_pseudocatenulatum | ++++ |
| SPC10213 | SPC10298 | Bacteroides_eggerthii | Bifidobacterium_pseudocatenulatum | ++++ |
| SPC10030 | SPC10298 | Bacteroides_ovatus | Bifidobacterium_pseudocatenulatum | ++++ |
| SPC00006 | SPC10298 | Bacteroides_sp_1_1_6 | Bifidobacterium_pseudocatenulatum | ++++ |
| SPC00007 | SPC10298 | Bacteroides_sp_3_1_23 | Bifidobacterium_pseudocatenulatum | ++++ |
| SPC10019 | SPC10298 | Bacteroides_sp_D20 | Bifidobacterium_pseudocatenulatum | −− |
| SPC00005 | SPC10298 | Bacteroides_vulgatus | Bifidobacterium_pseudocatenulatum | ++++ |
| SPC10081 | SPC10298 | Bacteroides_vulgatus | Bifidobacterium_pseudocatenulatum | ++++ |
| SPC10298 | SPC10298 | Bifidobacterium_pseudocatenulatum | Bifidobacterium_pseudocatenulatum | ++++ |
| SPC00021 | SPC10298 | Blautia_producta | Bifidobacterium_pseudocatenulatum | + |
| SPC10243 | SPC10298 | Clostridium_hathewayi | Bifidobacterium_pseudocatenulatum | ++++ |
| SPC00026 | SPC10298 | Clostridium_nexile | Bifidobacterium_pseudocatenulatum | ++++ |
| SPC00027 | SPC10298 | Clostridium_sp_HGF2 | Bifidobacterium_pseudocatenulatum | +++ |
| SPC10097 | SPC10298 | Collinsella_aerofaciens | Bifidobacterium_pseudocatenulatum | ++++ |
| SPC00009 | SPC10298 | Coprobacillus_sp_D7 | Bifidobacterium_pseudocatenulatum | +++ |
| SPC00080 | SPC10298 | Coprococcus_catus | Bifidobacterium_pseudocatenulatum | |
| SPC00018 | SPC10298 | Dorea_formicigenerans | Bifidobacterium_pseudocatenulatum | +++ |
| SPC00057 | SPC10298 | Dorea_longicatena | Bifidobacterium_pseudocatenulatum | ++++ |
| SPC00008 | SPC10298 | Enterococcus_faecalis | Bifidobacterium_pseudocatenulatum | ++++ |
| SPC10001 | SPC10298 | Erysipelotrichaceae_bacterium | Bifidobacterium_pseudocatenulatum | |
| SPC00001 | SPC10298 | Escherichia_coli | Bifidobacterium_pseudocatenulatum | ++++ |
| SPC10110 | SPC10298 | Escherichia_coli | Bifidobacterium_pseudocatenulatum | ++++ |
| SPC00022 | SPC10298 | Eubacterium_eligens | Bifidobacterium_pseudocatenulatum | ++++ |
| SPC00054 | SPC10298 | Faecalibacterium_prausnitzii | Bifidobacterium_pseudocatenulatum | ++ |
| SPC00056 | SPC10298 | Odoribacter_splanchnicus | Bifidobacterium_pseudocatenulatum | + |
| SPC10048 | SPC10298 | Parabacteroides_merdae | Bifidobacterium_pseudocatenulatum | ++++ |
| SPC00061 | SPC10298 | Roseburia_intestinalis | Bifidobacterium_pseudocatenulatum | +++ |
| SPC10197 | SPC10298 | Ruminococcus_obeum | Bifidobacterium_pseudocatenulatum | ++++ |
| SPC10233 | SPC10298 | Ruminococcus_torques | Bifidobacterium_pseudocatenulatum | ++++ |
| SPC00015 | SPC10298 | Streptococcus_thermophilus | Bifidobacterium_pseudocatenulatum | ++++ |
| SPC10414 | SPC10415 | Alistipes_shahii | Blautia_producta | |
| SPC10211 | SPC10415 | Bacteroides_caccae | Blautia_producta | + |
| SPC10213 | SPC10415 | Bacteroides_eggerthii | Blautia_producta | |
| SPC10030 | SPC10415 | Bacteroides_ovatus | Blautia_producta | − |
| SPC00006 | SPC00021 | Bacteroides_sp_1_1_6 | Blautia_producta | ++++ |
| SPC00006 | SPC10415 | Bacteroides_sp_1_1_6 | Blautia_producta | ++++ |
| SPC00007 | SPC00021 | Bacteroides_sp_3_1_23 | Blautia_producta | ++++ |
| SPC00007 | SPC10415 | Bacteroides_sp_3_1_23 | Blautia_producta | ++ |
| SPC10019 | SPC10415 | Bacteroides_sp_D20 | Blautia_producta | |
| SPC00005 | SPC00021 | Bacteroides_vulgatus | Blautia_producta | ++++ |
| SPC00005 | SPC10415 | Bacteroides_vulgatus | Blautia_producta | ++++ |

TABLE 3-continued

| SPC1 | SPC2 | OTU1 | OTU2 | Result |
|---|---|---|---|---|
| SPC10081 | SPC10415 | Bacteroides_vulgatus | Blautia_producta | ++++ |
| SPC10301 | SPC10415 | Bifidobacterium_adolescentis | Blautia_producta | ++++ |
| SPC10298 | SPC10415 | Bifidobacterium_pseudocatenulatum | Blautia_producta | |
| SPC00021 | SPC00021 | Blautia_producta | Blautia_producta | ++++ |
| SPC00021 | SPC10415 | Blautia_producta | Blautia_producta | ++++ |
| SPC10415 | SPC10415 | Blautia_producta | Blautia_producta | + |
| SPC10415 | SPC10415 | Blautia_producta | Blautia_producta | ++++ |
| SPC10403 | SPC10415 | Blautia_schinkii | Blautia_producta | |
| SPC10256 | SPC10415 | Clostridium_butyricum | Blautia_producta | ++++ |
| SPC10358 | SPC10415 | Clostridium_orbiscindens | Blautia_producta | ++++ |
| SPC10325 | SPC10415 | Clostridium_bolteae | Blautia_producta | ++++ |
| SPC10167 | SPC10415 | Clostridium_disporicum | Blautia_producta | ++++ |
| SPC10243 | SPC10415 | Clostridium_hathewayi | Blautia_producta | +++ |
| SPC10313 | SPC10415 | Clostridium_hylemonae | Blautia_producta | ++++ |
| SPC10202 | SPC10415 | Clostridium_innocuum | Blautia_producta | ++++ |
| SPC10238 | SPC10415 | Clostridium_mayombei | Blautia_producta | ++++ |
| SPC00026 | SPC10415 | Clostridium_nexile | Blautia_producta | − |
| SPC00027 | SPC10415 | Clostridium_sp_HGF2 | Blautia_producta | |
| SPC10355 | SPC10415 | Clostridium_symbiosum | Blautia_producta | |
| SPC10355 | SPC10415 | Clostridium_symbiosum | Blautia_producta | ++++ |
| SPC10155 | SPC10415 | Clostridium_tertium | Blautia_producta | ++++ |
| SPC10097 | SPC10415 | Collinsella_aerofaciens | Blautia_producta | ++++ |
| SPC10097 | SPC10415 | Collinsella_aerofaciens | Blautia_producta | ++++ |
| SPC00009 | SPC00021 | Coprobacillus_sp_D7 | Blautia_producta | ++++ |
| SPC00009 | SPC10415 | Coprobacillus_sp_D7 | Blautia_producta | ++++ |
| SPC00080 | SPC10415 | Coprococcus_catus | Blautia_producta | −−−− |
| SPC10304 | SPC10415 | Coprococcus_comes | Blautia_producta | |
| SPC10304 | SPC10415 | Coprococcus_comes | Blautia_producta | ++++ |
| SPC00018 | SPC00021 | Dorea_formicigenerans | Blautia_producta | ++++ |
| SPC00018 | SPC10415 | Dorea_formicigenerans | Blautia_producta | −− |
| SPC00057 | SPC10415 | Dorea_longicatena | Blautia_producta | +++ |
| SPC00008 | SPC00021 | Enterococcus_faecalis | Blautia_producta | ++++ |
| SPC00008 | SPC10415 | Enterococcus_faecalis | Blautia_producta | ++++ |
| SPC10001 | SPC10415 | Erysipelotrichaceae_bacterium | Blautia_producta | −−− |
| SPC00001 | SPC00021 | Escherichia_coli | Blautia_producta | ++++ |
| SPC00001 | SPC10415 | Escherichia_coli | Blautia_producta | ++++ |
| SPC10110 | SPC10415 | Escherichia_coli | Blautia_producta | ++++ |
| SPC00022 | SPC10415 | Eubacterium_eligens | Blautia_producta | −−− |
| SPC10363 | SPC10415 | Eubacterium_rectale | Blautia_producta | + |
| SPC00054 | SPC10415 | Faecalibacterium_prausnitzii | Blautia_producta | |
| SPC10386 | SPC10415 | Faecalibacterium_prausnitzii | Blautia_producta | + |
| SPC10386 | SPC10415 | Faecalibacterium_prausnitzii | Blautia_producta | ++++ |
| SPC10390 | SPC10415 | Lachnospiraceae_bacterium_5_1_57FAA | Blautia_producta | + |
| SPC10390 | SPC10415 | Lachnospiraceae_bacterium_5_1_57FAA | Blautia_producta | ++++ |
| SPC00056 | SPC10415 | Odoribacter_splanchnicus | Blautia_producta | − |
| SPC10388 | SPC10415 | Odoribacter_splanchnicus | Blautia_producta | + |
| SPC10048 | SPC10415 | Parabacteroides_merdae | Blautia_producta | +++ |
| SPC00061 | SPC10415 | Roseburia_intestinalis | Blautia_producta | − |
| SPC10468 | SPC10415 | Ruminococcus_gnavus | Blautia_producta | ++++ |
| SPC10197 | SPC10415 | Ruminococcus_obeum | Blautia_producta | |
| SPC10233 | SPC10415 | Ruminococcus_torques | Blautia_producta | |
| SPC00015 | SPC00021 | Streptococcus_thermophilus | Blautia_producta | ++++ |
| SPC00015 | SPC10415 | Streptococcus_thermophilus | Blautia_producta | |
| SPC10211 | SPC10403 | Bacteroides_caccae | Blautia_schinkii | |
| SPC10213 | SPC10403 | Bacteroides_eggerthii | Blautia_schinkii | −− |
| SPC10030 | SPC10403 | Bacteroides_ovatus | Blautia_schinkii | − |
| SPC00006 | SPC10403 | Bacteroides_sp_1_1_6 | Blautia_schinkii | +++ |
| SPC00007 | SPC10403 | Bacteroides_sp_3_1_23 | Blautia_schinkii | + |
| SPC10019 | SPC10403 | Bacteroides_sp_D20 | Blautia_schinkii | −− |
| SPC00005 | SPC10403 | Bacteroides_vulgatus | Blautia_schinkii | ++ |
| SPC10081 | SPC10403 | Bacteroides_vulgatus | Blautia_schinkii | |
| SPC10301 | SPC10403 | Bifidobacterium_adolescentis | Blautia_schinkii | ++ |
| SPC10298 | SPC10403 | Bifidobacterium_pseudocatenulatum | Blautia_schinkii | − |
| SPC00021 | SPC10403 | Blautia_producta | Blautia_schinkii | ++++ |
| SPC10403 | SPC10403 | Blautia_schinkii | Blautia_schinkii | |
| SPC10243 | SPC10403 | Clostridium_hathewayi | Blautia_schinkii | ++++ |
| SPC00026 | SPC10403 | Clostridium_nexile | Blautia_schinkii | −− |
| SPC00027 | SPC10403 | Clostridium_sp_HGF2 | Blautia_schinkii | |
| SPC10355 | SPC10403 | Clostridium_symbiosum | Blautia_schinkii | |
| SPC10097 | SPC10403 | Collinsella_aerofaciens | Blautia_schinkii | ++++ |
| SPC00009 | SPC10403 | Coprobacillus_sp_D7 | Blautia_schinkii | ++++ |
| SPC00080 | SPC10403 | Coprococcus_catus | Blautia_schinkii | −−− |
| SPC10304 | SPC10403 | Coprococcus_comes | Blautia_schinkii | + |
| SPC00018 | SPC10403 | Dorea_formicigenerans | Blautia_schinkii | |
| SPC00057 | SPC10403 | Dorea_longicatena | Blautia_schinkii | +++ |
| SPC00008 | SPC10403 | Enterococcus_faecalis | Blautia_schinkii | ++++ |
| SPC10001 | SPC10403 | Erysipelotrichaceae_bacterium | Blautia_schinkii | −−− |
| SPC00001 | SPC10403 | Escherichia_coli | Blautia_schinkii | ++++ |

TABLE 3-continued

| SPC1 | SPC2 | OTU1 | OTU2 | Result |
|---|---|---|---|---|
| SPC10110 | SPC10403 | Escherichia_coli | Blautia_schinkii | ++++ |
| SPC00022 | SPC10403 | Eubacterium_eligens | Blautia_schinkii | − |
| SPC10363 | SPC10403 | Eubacterium_rectale | Blautia_schinkii | + |
| SPC00054 | SPC10403 | Faecalibacterium_prausnitzii | Blautia_schinkii | |
| SPC10386 | SPC10403 | Faecalibacterium_prausnitzii | Blautia_schinkii | |
| SPC10390 | SPC10403 | Lachnospiraceae_bacterium_5_1_57FAA | Blautia_schinkii | |
| SPC00056 | SPC10403 | Odoribacter_splanchnicus | Blautia_schinkii | |
| SPC10388 | SPC10403 | Odoribacter_splanchnicus | Blautia_schinkii | − |
| SPC10048 | SPC10403 | Parabacteroides_merdae | Blautia_schinkii | |
| SPC00061 | SPC10403 | Roseburia_intestinalis | Blautia_schinkii | − |
| SPC10197 | SPC10403 | Ruminococcus_obeum | Blautia_schinkii | |
| SPC10233 | SPC10403 | Ruminococcus_torques | Blautia_schinkii | |
| SPC00015 | SPC10403 | Streptococcus_thermophilus | Blautia_schinkii | |
| SPC10256 | SPC10256 | *Clostridium butyricum* | *Clostridium butyricum* | ++++ |
| SPC10167 | SPC10256 | Clostridium_disporicum | *Clostridium butyricum* | ++++ |
| SPC10202 | SPC10256 | Clostridium_innocuum | *Clostridium butyricum* | ++++ |
| SPC10238 | SPC10256 | Clostridium_mayombei | *Clostridium butyricum* | ++++ |
| SPC10155 | SPC10256 | Clostridium_tertium | *Clostridium butyricum* | ++++ |
| SPC10097 | SPC10256 | Collinsella_aerofaciens | *Clostridium butyricum* | ++++ |
| SPC10304 | SPC10256 | Coprococcus_comes | *Clostridium butyricum* | ++++ |
| SPC10256 | SPC10358 | *Clostridium butyricum* | *Clostridium orbiscindens* | ++++ |
| SPC10358 | SPC10358 | *Clostridium orbiscindens* | *Clostridium orbiscindens* | + |
| SPC10325 | SPC10358 | Clostridium_bolteae | *Clostridium orbiscindens* | ++++ |
| SPC10167 | SPC10358 | Clostridium_disporicum | *Clostridium orbiscindens* | ++++ |
| SPC10313 | SPC10358 | Clostridium_hylemonae | *Clostridium orbiscindens* | |
| SPC10202 | SPC10358 | Clostridium_innocuum | *Clostridium orbiscindens* | ++++ |
| SPC10238 | SPC10358 | Clostridium_mayombei | *Clostridium orbiscindens* | ++++ |
| SPC10355 | SPC10358 | Clostridium_symbiosum | *Clostridium orbiscindens* | ++++ |
| SPC10155 | SPC10358 | Clostridium_tertium | *Clostridium orbiscindens* | ++++ |
| SPC10097 | SPC10358 | Collinsella_aerofaciens | *Clostridium orbiscindens* | ++++ |
| SPC10304 | SPC10358 | Coprococcus_comes | *Clostridium orbiscindens* | ++++ |
| SPC10386 | SPC10358 | Faecalibacterium_prausnitzii | *Clostridium orbiscindens* | |
| SPC10256 | SPC10325 | *Clostridium butyricum* | Clostridium_bolteae | ++++ |
| SPC10325 | SPC10325 | Clostridium_bolteae | Clostridium_bolteae | ++++ |
| SPC10167 | SPC10325 | Clostridium_disporicum | Clostridium_bolteae | ++++ |
| SPC10313 | SPC10325 | Clostridium_hylemonae | Clostridium_bolteae | |
| SPC10202 | SPC10325 | Clostridium_innocuum | Clostridium_bolteae | ++++ |
| SPC10238 | SPC10325 | Clostridium_mayombei | Clostridium_bolteae | ++++ |
| SPC10355 | SPC10325 | Clostridium_symbiosum | Clostridium_bolteae | ++++ |
| SPC10155 | SPC10325 | Clostridium_tertium | Clostridium_bolteae | ++++ |
| SPC10097 | SPC10325 | Collinsella_aerofaciens | Clostridium_bolteae | ++++ |
| SPC10304 | SPC10325 | Coprococcus_comes | Clostridium_bolteae | ++++ |
| SPC10167 | SPC10167 | Clostridium_disporicum | Clostridium_disporicum | +++ |
| SPC10202 | SPC10167 | Clostridium_innocuum | Clostridium_disporicum | +++ |
| SPC10155 | SPC10167 | Clostridium_tertium | Clostridium_disporicum | ++++ |
| SPC10097 | SPC10167 | Collinsella_aerofaciens | Clostridium_disporicum | − |
| SPC10211 | SPC10243 | Bacteroides_caccae | Clostridium_hathewayi | ++++ |
| SPC10213 | SPC10243 | Bacteroides_eggerthii | Clostridium_hathewayi | ++++ |
| SPC10030 | SPC10243 | Bacteroides_ovatus | Clostridium_hathewayi | ++++ |
| SPC00006 | SPC10243 | Bacteroides_sp_1_1_6 | Clostridium_hathewayi | ++++ |
| SPC00007 | SPC10243 | Bacteroides_sp_3_1_23 | Clostridium_hathewayi | ++++ |
| SPC10019 | SPC10243 | Bacteroides_sp_D20 | Clostridium_hathewayi | ++++ |
| SPC00005 | SPC10243 | Bacteroides_vulgatus | Clostridium_hathewayi | ++++ |
| SPC10081 | SPC10243 | Bacteroides_vulgatus | Clostridium_hathewayi | ++++ |
| SPC00021 | SPC10243 | Blautia_producta | Clostridium_hathewayi | ++++ |
| SPC10243 | SPC10243 | Clostridium_hathewayi | Clostridium_hathewayi | ++++ |
| SPC00026 | SPC10243 | Clostridium_nexile | Clostridium_hathewayi | |
| SPC00027 | SPC10243 | Clostridium_sp_HGF2 | Clostridium_hathewayi | |
| SPC10097 | SPC10243 | Collinsella_aerofaciens | Clostridium_hathewayi | ++++ |
| SPC00009 | SPC10243 | Coprobacillus_sp_D7 | Clostridium_hathewayi | ++++ |
| SPC00080 | SPC10243 | Coprococcus_catus | Clostridium_hathewayi | +++ |
| SPC00018 | SPC10243 | Dorea_formicigenerans | Clostridium_hathewayi | ++++ |
| SPC00057 | SPC10243 | Dorea_longicatena | Clostridium_hathewayi | |
| SPC00008 | SPC10243 | Enterococcus_faecalis | Clostridium_hathewayi | ++++ |
| SPC10001 | SPC10243 | Erysipelotrichaceae_bacterium | Clostridium_hathewayi | ++++ |
| SPC00001 | SPC10243 | Escherichia_coli | Clostridium_hathewayi | ++++ |
| SPC10110 | SPC10243 | Escherichia_coli | Clostridium_hathewayi | ++++ |
| SPC00022 | SPC10243 | Eubacterium_eligens | Clostridium_hathewayi | + |
| SPC00054 | SPC10243 | Faecalibacterium_prausnitzii | Clostridium_hathewayi | |
| SPC00056 | SPC10243 | Odoribacter_splanchnicus | Clostridium_hathewayi | |
| SPC10048 | SPC10243 | Parabacteroides_merdae | Clostridium_hathewayi | + |
| SPC00061 | SPC10243 | Roseburia_intestinalis | Clostridium_hathewayi | +++ |
| SPC10197 | SPC10243 | Ruminococcus_obeum | Clostridium_hathewayi | ++++ |
| SPC10233 | SPC10243 | Ruminococcus_torques | Clostridium_hathewayi | ++++ |
| SPC00015 | SPC10243 | Streptococcus_thermophilus | Clostridium_hathewayi | ++ |
| SPC10256 | SPC10313 | *Clostridium butyricum* | Clostridium_hylemonae | ++++ |
| SPC10325 | SPC10313 | Clostridium_bolteae | Clostridium_hylemonae | |
| SPC10167 | SPC10313 | Clostridium_disporicum | Clostridium_hylemonae | |

TABLE 3-continued

| SPC1 | SPC2 | OTU1 | OTU2 | Result |
|---|---|---|---|---|
| SPC10313 | SPC10313 | Clostridium_hylemonae | Clostridium_hylemonae | |
| SPC10202 | SPC10313 | Clostridium_innocuum | Clostridium_hylemonae | ++++ |
| SPC10238 | SPC10313 | Clostridium_mayombei | Clostridium_hylemonae | ++++ |
| SPC10155 | SPC10313 | Clostridium_tertium | Clostridium_hylemonae | ++++ |
| SPC10097 | SPC10313 | Collinsella_aerofaciens | Clostridium_hylemonae | +++ |
| SPC10304 | SPC10313 | Coprococcus_comes | Clostridium_hylemonae | + |
| SPC10167 | SPC10202 | Clostridium_disporicum | Clostridium_innocuum | +++ |
| SPC10202 | SPC10202 | Clostridium_innocuum | Clostridium_innocuum | ++++ |
| SPC10238 | SPC10202 | Clostridium_mayombei | Clostridium_innocuum | ++++ |
| SPC10155 | SPC10202 | Clostridium_tertium | Clostridium_innocuum | ++++ |
| SPC10097 | SPC10202 | Collinsella_aerofaciens | Clostridium_innocuum | +++ |
| SPC10256 | SPC10238 | *Clostridium butyricum* | Clostridium_mayombei | ++++ |
| SPC10167 | SPC10238 | Clostridium_disporicum | Clostridium_mayombei | ++++ |
| SPC10202 | SPC10238 | Clostridium_innocuum | Clostridium_mayombei | ++++ |
| SPC10238 | SPC10238 | Clostridium_mayombei | Clostridium_mayombei | ++++ |
| SPC10155 | SPC10238 | Clostridium_tertium | Clostridium_mayombei | ++++ |
| SPC10097 | SPC10238 | Collinsella_aerofaciens | Clostridium_mayombei | ++++ |
| SPC00006 | SPC00026 | Bacteroides_sp_1_1_6 | Clostridium_nexile | ++++ |
| SPC00007 | SPC00026 | Bacteroides_sp_3_1_23 | Clostridium_nexile | ++++ |
| SPC00005 | SPC00026 | Bacteroides_vulgatus | Clostridium_nexile | ++++ |
| SPC00021 | SPC00026 | Blautia_producta | Clostridium_nexile | ++++ |
| SPC00026 | SPC00026 | Clostridium_nexile | Clostridium_nexile | ++ |
| SPC00009 | SPC00026 | Coprobacillus_sp_D7 | Clostridium_nexile | |
| SPC00018 | SPC00026 | Dorea_formicigenerans | Clostridium_nexile | |
| SPC00008 | SPC00026 | Enterococcus_faecalis | Clostridium_nexile | ++++ |
| SPC00001 | SPC00026 | Escherichia_coli | Clostridium_nexile | ++++ |
| SPC00022 | SPC00026 | Eubacterium_eligens | Clostridium_nexile | + |
| SPC00015 | SPC00026 | Streptococcus_thermophilus | Clostridium_nexile | + |
| SPC00006 | SPC00027 | Bacteroides_sp_1_1_6 | Clostridium_sp_HGF2 | ++++ |
| SPC00007 | SPC00027 | Bacteroides_sp_3_1_23 | Clostridium_sp_HGF2 | ++++ |
| SPC00005 | SPC00027 | Bacteroides_vulgatus | Clostridium_sp_HGF2 | ++ |
| SPC00021 | SPC00027 | Blautia_producta | Clostridium_sp_HGF2 | ++++ |
| SPC00026 | SPC00027 | Clostridium_nexile | Clostridium_sp_HGF2 | ++++ |
| SPC00027 | SPC00027 | Clostridium_sp_HGF2 | Clostridium_sp_HGF2 | ++++ |
| SPC00009 | SPC00027 | Coprobacillus_sp_D7 | Clostridium_sp_HGF2 | – |
| SPC00018 | SPC00027 | Dorea_formicigenerans | Clostridium_sp_HGF2 | |
| SPC00008 | SPC00027 | Enterococcus_faecalis | Clostridium_sp_HGF2 | ++++ |
| SPC00001 | SPC00027 | Escherichia_coli | Clostridium_sp_HGF2 | ++++ |
| SPC00022 | SPC00027 | Eubacterium_eligens | Clostridium_sp_HGF2 | |
| SPC00015 | SPC00027 | Streptococcus_thermophilus | Clostridium_sp_HGF2 | + |
| SPC10211 | SPC10355 | Bacteroides_caccae | Clostridium_symbiosum | +++ |
| SPC10213 | SPC10355 | Bacteroides_eggerthii | Clostridium_symbiosum | ++++ |
| SPC10030 | SPC10355 | Bacteroides_ovatus | Clostridium_symbiosum | |
| SPC00006 | SPC10355 | Bacteroides_sp_1_1_6 | Clostridium_symbiosum | ++++ |
| SPC00007 | SPC10355 | Bacteroides_sp_3_1_23 | Clostridium_symbiosum | ++++ |
| SPC10019 | SPC10355 | Bacteroides_sp_D20 | Clostridium_symbiosum | |
| SPC00005 | SPC10355 | Bacteroides_vulgatus | Clostridium_symbiosum | +++ |
| SPC10081 | SPC10355 | Bacteroides_vulgatus | Clostridium_symbiosum | |
| SPC10301 | SPC10355 | Bifidobacterium_adolescentis | Clostridium_symbiosum | ++++ |
| SPC10298 | SPC10355 | Bifidobacterium_pseudocatenulatum | Clostridium_symbiosum | + |
| SPC00021 | SPC10355 | Blautia_producta | Clostridium_symbiosum | ++++ |
| SPC10256 | SPC10355 | *Clostridium butyricum* | Clostridium_symbiosum | ++++ |
| SPC10358 | SPC10355 | *Clostridium orbiscindens* | Clostridium_symbiosum | ++++ |
| SPC10325 | SPC10355 | Clostridium_bolteae | Clostridium_symbiosum | ++++ |
| SPC10167 | SPC10355 | Clostridium_disporicum | Clostridium_symbiosum | ++++ |
| SPC10243 | SPC10355 | Clostridium_hathewayi | Clostridium_symbiosum | ++++ |
| SPC10313 | SPC10355 | Clostridium_hylemonae | Clostridium_symbiosum | +++ |
| SPC10202 | SPC10355 | Clostridium_innocuum | Clostridium_symbiosum | ++++ |
| SPC10238 | SPC10355 | Clostridium_mayombei | Clostridium_symbiosum | ++++ |
| SPC00026 | SPC10355 | Clostridium_nexile | Clostridium_symbiosum | + |
| SPC00027 | SPC10355 | Clostridium_sp_HGF2 | Clostridium_symbiosum | |
| SPC10355 | SPC10355 | Clostridium_symbiosum | Clostridium_symbiosum | + |
| SPC10355 | SPC10355 | Clostridium_symbiosum | Clostridium_symbiosum | ++++ |
| SPC10155 | SPC10355 | Clostridium_tertium | Clostridium_symbiosum | + |
| SPC10097 | SPC10355 | Collinsella_aerofaciens | Clostridium_symbiosum | +++ |
| SPC10097 | SPC10355 | Collinsella_aerofaciens | Clostridium_symbiosum | ++++ |
| SPC00009 | SPC10355 | Coprobacillus_sp_D7 | Clostridium_symbiosum | |
| SPC00080 | SPC10355 | Coprococcus_catus | Clostridium_symbiosum | – |
| SPC10304 | SPC10355 | Coprococcus_comes | Clostridium_symbiosum | |
| SPC10304 | SPC10355 | Coprococcus_comes | Clostridium_symbiosum | ++++ |
| SPC00018 | SPC10355 | Dorea_formicigenerans | Clostridium_symbiosum | |
| SPC00057 | SPC10355 | Dorea_longicatena | Clostridium_symbiosum | ++++ |
| SPC00008 | SPC10355 | Enterococcus_faecalis | Clostridium_symbiosum | ++++ |
| SPC10001 | SPC10355 | Erysipelotrichaceae_bacterium | Clostridium_symbiosum | |
| SPC00001 | SPC10355 | Escherichia_coli | Clostridium_symbiosum | ++++ |
| SPC10110 | SPC10355 | Escherichia_coli | Clostridium_symbiosum | ++++ |
| SPC00022 | SPC10355 | Eubacterium_eligens | Clostridium_symbiosum | + |
| SPC00054 | SPC10355 | Faecalibacterium_prausnitzii | Clostridium_symbiosum | |

TABLE 3-continued

| SPC1 | SPC2 | OTU1 | OTU2 | Result |
|---|---|---|---|---|
| SPC00056 | SPC10355 | Odoribacter_splanchnicus | Clostridium_symbiosum | |
| SPC10048 | SPC10355 | Parabacteroides_merdae | Clostridium_symbiosum | – |
| SPC00061 | SPC10355 | Roseburia_intestinalis | Clostridium_symbiosum | –– |
| SPC10197 | SPC10355 | Ruminococcus_obeum | Clostridium_symbiosum | ++++ |
| SPC10233 | SPC10355 | Ruminococcus_torques | Clostridium_symbiosum | ++ |
| SPC00015 | SPC10355 | Streptococcus_thermophilus | Clostridium_symbiosum | |
| SPC10167 | SPC10155 | Clostridium_disporicum | Clostridium_tertium | ++++ |
| SPC10155 | SPC10155 | Clostridium_tertium | Clostridium_tertium | ++++ |
| SPC10097 | SPC10155 | Collinsella_aerofaciens | Clostridium_tertium | |
| SPC10030 | SPC10097 | Bacteroides_oyatus | Collinsella_aerofaciens | ++++ |
| SPC00006 | SPC10097 | Bacteroides_sp_1_1_6 | Collinsella_aerofaciens | ++++ |
| SPC00007 | SPC10097 | Bacteroides_sp_3_1_23 | Collinsella_aerofaciens | ++++ |
| SPC10019 | SPC10097 | Bacteroides_sp_D20 | Collinsella_aerofaciens | ++++ |
| SPC00005 | SPC10097 | Bacteroides_vulgatus | Collinsella_aerofaciens | ++++ |
| SPC10081 | SPC10097 | Bacteroides_vulgatus | Collinsella_aerofaciens | ++++ |
| SPC00021 | SPC10097 | Blautia_producta | Collinsella_aerofaciens | ++++ |
| SPC00026 | SPC10097 | Clostridium_nexile | Collinsella_aerofaciens | + |
| SPC00027 | SPC10097 | Clostridium_sp_HGF2 | Collinsella_aerofaciens | ++++ |
| SPC10155 | SPC10097 | Clostridium_tertium | Collinsella_aerofaciens | |
| SPC10097 | SPC10097 | Collinsella_aerofaciens | Collinsella_aerofaciens | ++++ |
| SPC10097 | SPC10097 | Collinsella_aerofaciens | Collinsella_aerofaciens | |
| SPC00009 | SPC10097 | Coprobacillus_sp_D7 | Collinsella_aerofaciens | +++ |
| SPC00080 | SPC10097 | Coprococcus_catus | Collinsella_aerofaciens | ++++ |
| SPC00018 | SPC10097 | Dorea_formicigenerans | Collinsella_aerofaciens | ++ |
| SPC00057 | SPC10097 | Dorea_longicatena | Collinsella_aerofaciens | ++++ |
| SPC00008 | SPC10097 | Enterococcus_faecalis | Collinsella_aerofaciens | ++++ |
| SPC10001 | SPC10097 | Erysipelotrichaceae_bacterium | Collinsella_aerofaciens | ++++ |
| SPC00001 | SPC10097 | Escherichia_coli | Collinsella_aerofaciens | ++++ |
| SPC00022 | SPC10097 | Eubacterium_eligens | Collinsella_aerofaciens | +++ |
| SPC00054 | SPC10097 | Faecalibacterium_prausnitzii | Collinsella_aerofaciens | +++ |
| SPC00056 | SPC10097 | Odoribacter_splanchnicus | Collinsella_aerofaciens | +++ |
| SPC10048 | SPC10097 | Parabacteroides_merdae | Collinsella_aerofaciens | ++++ |
| SPC00061 | SPC10097 | Roseburia_intestinalis | Collinsella_aerofaciens | ++ |
| SPC00015 | SPC10097 | Streptococcus_thermophilus | Collinsella_aerofaciens | + |
| SPC00006 | SPC00009 | Bacteroides_sp_1_1_6 | Coprobacillus_sp_D7 | +++ |
| SPC00007 | SPC00009 | Bacteroides_sp_3_1_23 | Coprobacillus_sp_D7 | |
| SPC00005 | SPC00009 | Bacteroides_vulgatus | Coprobacillus_sp_D7 | + |
| SPC00009 | SPC00009 | Coprobacillus_sp_D7 | Coprobacillus_sp_D7 | – |
| SPC00008 | SPC00009 | Enterococcus_faecalis | Coprobacillus_sp_D7 | ++++ |
| SPC00001 | SPC00009 | Escherichia_coli | Coprobacillus_sp_D7 | ++ |
| SPC00006 | SPC00080 | Bacteroides_sp_1_1_6 | Coprococcus_catus | ++++ |
| SPC00007 | SPC00080 | Bacteroides_sp_3_1_23 | Coprococcus_catus | |
| SPC00005 | SPC00080 | Bacteroides_vulgatus | Coprococcus_catus | + |
| SPC00021 | SPC00080 | Blautia_producta | Coprococcus_catus | ++++ |
| SPC00026 | SPC00080 | Clostridium_nexile | Coprococcus_catus | |
| SPC00027 | SPC00080 | Clostridium_sp_HGF2 | Coprococcus_catus | ––– |
| SPC00009 | SPC00080 | Coprobacillus_sp_D7 | Coprococcus_catus | ––– |
| SPC00080 | SPC00080 | Coprococcus_catus | Coprococcus_catus | |
| SPC00018 | SPC00080 | Dorea_formicigenerans | Coprococcus_catus | |
| SPC00057 | SPC00080 | Dorea_longicatena | Coprococcus_catus | |
| SPC00008 | SPC00080 | Enterococcus_faecalis | Coprococcus_catus | ++++ |
| SPC00001 | SPC00080 | Escherichia_coli | Coprococcus_catus | ++++ |
| SPC00022 | SPC00080 | Eubacterium_eligens | Coprococcus_catus | |
| SPC00054 | SPC00080 | Faecalibacterium_prausnitzii | Coprococcus_catus | |
| SPC00056 | SPC00080 | Odoribacter_splanchnicus | Coprococcus_catus | |
| SPC00061 | SPC00080 | Roseburia_intestinalis | Coprococcus_catus | |
| SPC00015 | SPC00080 | Streptococcus_thermophilus | Coprococcus_catus | |
| SPC10211 | SPC10304 | Bacteroides_caccae | Coprococcus_comes | +++ |
| SPC10213 | SPC10304 | Bacteroides_eggerthii | Coprococcus_comes | +++ |
| SPC10030 | SPC10304 | Bacteroides_ovatus | Coprococcus_comes | |
| SPC00006 | SPC10304 | Bacteroides_sp_1_1_6 | Coprococcus_comes | +++ |
| SPC00007 | SPC10304 | Bacteroides_sp_3_1_23 | Coprococcus_comes | ++++ |
| SPC10019 | SPC10304 | Bacteroides_sp_D20 | Coprococcus_comes | |
| SPC00005 | SPC10304 | Bacteroides_vulgatus | Coprococcus_comes | ++++ |
| SPC10081 | SPC10304 | Bacteroides_vulgatus | Coprococcus_comes | |
| SPC10301 | SPC10304 | Bifidobacterium_adolescentis | Coprococcus_comes | ++++ |
| SPC10298 | SPC10304 | Bifidobacterium_pseudocatenulatum | Coprococcus_comes | ++++ |
| SPC00021 | SPC10304 | Blautia_producta | Coprococcus_comes | ++++ |
| SPC10256 | SPC10304 | *Clostridium butyricum* | Coprococcus_comes | ++++ |
| SPC10167 | SPC10304 | Clostridium_disporicum | Coprococcus_comes | ++++ |
| SPC10243 | SPC10304 | Clostridium_hathewayi | Coprococcus_comes | ++++ |
| SPC10313 | SPC10304 | Clostridium_hylemonae | Coprococcus_comes | + |
| SPC10202 | SPC10304 | Clostridium_innocuum | Coprococcus_comes | ++++ |
| SPC10238 | SPC10304 | Clostridium_mayombei | Coprococcus_comes | ++++ |
| SPC00026 | SPC10304 | Clostridium_nexile | Coprococcus_comes | |
| SPC00027 | SPC10304 | Clostridium_sp_HGF2 | Coprococcus_comes | |
| SPC10155 | SPC10304 | Clostridium_tertium | Coprococcus_comes | ++++ |
| SPC10097 | SPC10304 | Collinsella_aerofaciens | Coprococcus_comes | ++++ |

TABLE 3-continued

| SPC1 | SPC2 | OTU1 | OTU2 | Result |
|---|---|---|---|---|
| SPC10097 | SPC10304 | Collinsella_aerofaciens | Coprococcus_comes | +++ |
| SPC00009 | SPC10304 | Coprobacillus_sp_D7 | Coprococcus_comes | +++ |
| SPC00080 | SPC10304 | Coprococcus_catus | Coprococcus_comes | −− |
| SPC10304 | SPC10304 | Coprococcus_comes | Coprococcus_comes | |
| SPC10304 | SPC10304 | Coprococcus_comes | Coprococcus_comes | ++ |
| SPC00018 | SPC10304 | Dorea_formicigenerans | Coprococcus_comes | |
| SPC00057 | SPC10304 | Dorea_longicatena | Coprococcus_comes | |
| SPC00008 | SPC10304 | Enterococcus_faecalis | Coprococcus_comes | ++++ |
| SPC10001 | SPC10304 | Erysipelotrichaceae_bacterium | Coprococcus_comes | − |
| SPC00001 | SPC10304 | Escherichia_coli | Coprococcus_comes | ++++ |
| SPC10110 | SPC10304 | Escherichia_coli | Coprococcus_comes | ++++ |
| SPC00022 | SPC10304 | Eubacterium_eligens | Coprococcus_comes | ++ |
| SPC00054 | SPC10304 | Faecalibacterium_prausnitzii | Coprococcus_comes | |
| SPC00056 | SPC10304 | Odoribacter_splanchnicus | Coprococcus_comes | |
| SPC10048 | SPC10304 | Parabacteroides_merdae | Coprococcus_comes | − |
| SPC00061 | SPC10304 | Roseburia_intestinalis | Coprococcus_comes | − |
| SPC10197 | SPC10304 | Ruminococcus_obeum | Coprococcus_comes | ++++ |
| SPC10233 | SPC10304 | Ruminococcus_torques | Coprococcus_comes | ++++ |
| SPC00015 | SPC10304 | Streptococcus_thermophilus | Coprococcus_comes | ++ |
| SPC00006 | SPC00018 | Bacteroides_sp_1_1_6 | Dorea_formicigenerans | +++ |
| SPC00007 | SPC00018 | Bacteroides_sp_3_1_23 | Dorea_formicigenerans | |
| SPC00005 | SPC00018 | Bacteroides_vulgatus | Dorea_formicigenerans | ++ |
| SPC00009 | SPC00018 | Coprobacillus_sp_D7 | Dorea_formicigenerans | − |
| SPC00018 | SPC00018 | Dorea_formicigenerans | Dorea_formicigenerans | −− |
| SPC00008 | SPC00018 | Enterococcus_faecalis | Dorea_formicigenerans | ++++ |
| SPC00001 | SPC00018 | Escherichia_coli | Dorea_formicigenerans | ++ |
| SPC00015 | SPC00018 | Streptococcus_thermophilus | Dorea_formicigenerans | |
| SPC00006 | SPC00057 | Bacteroides_sp_1_1_6 | Dorea_longicatena | ++++ |
| SPC00007 | SPC00057 | Bacteroides_sp_3_1_23 | Dorea_longicatena | +++ |
| SPC00005 | SPC00057 | Bacteroides_vulgatus | Dorea_longicatena | ++++ |
| SPC00021 | SPC00057 | Blautia_producta | Dorea_longicatena | ++++ |
| SPC00026 | SPC00057 | Clostridium_nexile | Dorea_longicatena | |
| SPC00027 | SPC00057 | Clostridium_sp_HGF2 | Dorea_longicatena | −− |
| SPC00009 | SPC00057 | Coprobacillus_sp_D7 | Dorea_longicatena | |
| SPC00018 | SPC00057 | Dorea_formicigenerans | Dorea_longicatena | ++ |
| SPC00057 | SPC00057 | Dorea_longicatena | Dorea_longicatena | − |
| SPC00008 | SPC00057 | Enterococcus_faecalis | Dorea_longicatena | ++++ |
| SPC00001 | SPC00057 | Escherichia_coli | Dorea_longicatena | ++++ |
| SPC00022 | SPC00057 | Eubacterium_eligens | Dorea_longicatena | ++ |
| SPC00054 | SPC00057 | Faecalibacterium_prausnitzii | Dorea_longicatena | − |
| SPC00056 | SPC00057 | Odoribacter_splanchnicus | Dorea_longicatena | |
| SPC00015 | SPC00057 | Streptococcus_thermophilus | Dorea_longicatena | + |
| SPC00006 | SPC00008 | Bacteroides_sp_1_1_6 | Enterococcus_faecalis | ++++ |
| SPC00007 | SPC00008 | Bacteroides_sp_3_1_23 | Enterococcus_faecalis | ++++ |
| SPC00005 | SPC00008 | Bacteroides_vulgatus | Enterococcus_faecalis | ++++ |
| SPC00008 | SPC00008 | Enterococcus_faecalis | Enterococcus_faecalis | ++++ |
| SPC00001 | SPC00008 | Escherichia_coli | Enterococcus_faecalis | ++++ |
| SPC00006 | SPC10001 | Bacteroides_sp_1_1_6 | Erysipelotrichaceae_bacterium | ++++ |
| SPC00007 | SPC10001 | Bacteroides_sp_3_1_23 | Erysipelotrichaceae_bacterium | |
| SPC00005 | SPC10001 | Bacteroides_vulgatus | Erysipelotrichaceae_bacterium | + |
| SPC00021 | SPC10001 | Blautia_producta | Erysipelotrichaceae_bacterium | ++++ |
| SPC00026 | SPC10001 | Clostridium_nexile | Erysipelotrichaceae_bacterium | |
| SPC00027 | SPC10001 | Clostridium_sp_HGF2 | Erysipelotrichaceae_bacterium | −− |
| SPC00009 | SPC10001 | Coprobacillus_sp_D7 | Erysipelotrichaceae_bacterium | − |
| SPC00080 | SPC10001 | Coprococcus_catus | Erysipelotrichaceae_bacterium | |
| SPC00018 | SPC10001 | Dorea_formicigenerans | Erysipelotrichaceae_bacterium | −− |
| SPC00057 | SPC10001 | Dorea_longicatena | Erysipelotrichaceae_bacterium | |
| SPC00008 | SPC10001 | Enterococcus_faecalis | Erysipelotrichaceae_bacterium | ++++ |
| SPC10001 | SPC10001 | Erysipelotrichaceae_bacterium | Erysipelotrichaceae_bacterium | − |
| SPC00001 | SPC10001 | Escherichia_coli | Erysipelotrichaceae_bacterium | ++++ |
| SPC00022 | SPC10001 | Eubacterium_eligens | Erysipelotrichaceae_bacterium | − |
| SPC00054 | SPC10001 | Faecalibacterium_prausnitzii | Erysipelotrichaceae_bacterium | − |
| SPC00056 | SPC10001 | Odoribacter_splanchnicus | Erysipelotrichaceae_bacterium | |
| SPC00061 | SPC10001 | Roseburia_intestinalis | Erysipelotrichaceae_bacterium | − |
| SPC00015 | SPC10001 | Streptococcus_thermophilus | Erysipelotrichaceae_bacterium | |
| SPC10030 | SPC10110 | Bacteroides_ovatus | Escherichia_coli | ++++ |
| SPC00006 | SPC10110 | Bacteroides_sp_1_1_6 | Escherichia_coli | ++++ |
| SPC00007 | SPC10110 | Bacteroides_sp_3_1_23 | Escherichia_coli | ++++ |
| SPC10019 | SPC10110 | Bacteroides_sp_D20 | Escherichia_coli | ++++ |
| SPC00005 | SPC10110 | Bacteroides_vulgatus | Escherichia_coli | ++++ |
| SPC10081 | SPC10110 | Bacteroides_vulgatus | Escherichia_coli | ++++ |
| SPC00021 | SPC10110 | Blautia_producta | Escherichia_coli | ++++ |
| SPC00026 | SPC10110 | Clostridium_nexile | Escherichia_coli | ++++ |
| SPC00027 | SPC10110 | Clostridium_sp_HGF2 | Escherichia_coli | ++++ |
| SPC10097 | SPC10110 | Collinsella_aerofaciens | Escherichia_coli | ++++ |
| SPC00009 | SPC10110 | Coprobacillus_sp_D7 | Escherichia_coli | ++ |
| SPC00080 | SPC10110 | Coprococcus_catus | Escherichia_coli | ++++ |
| SPC00018 | SPC10110 | Dorea_formicigenerans | Escherichia_coli | ++++ |

TABLE 3-continued

| SPC1 | SPC2 | OTU1 | OTU2 | Result |
|---|---|---|---|---|
| SPC00057 | SPC10110 | Dorea_longicatena | Escherichia_coli | ++++ |
| SPC00008 | SPC10110 | Enterococcus_faecalis | Escherichia_coli | ++++ |
| SPC10001 | SPC10110 | Erysipelotrichaceae_bacterium | Escherichia_coli | ++++ |
| SPC00001 | SPC00001 | Escherichia_coli | Escherichia_coli | ++++ |
| SPC00001 | SPC10110 | Escherichia_coli | Escherichia_coli | ++++ |
| SPC10110 | SPC10110 | Escherichia_coli | Escherichia_coli | ++++ |
| SPC00022 | SPC10110 | Eubacterium_eligens | Escherichia_coli | ++++ |
| SPC00054 | SPC10110 | Faecalibacterium_prausnitzii | Escherichia_coli | +++ |
| SPC00056 | SPC10110 | Odoribacter_splanchnicus | Escherichia_coli | +++ |
| SPC10048 | SPC10110 | Parabacteroides_merdae | Escherichia_coli | ++++ |
| SPC00061 | SPC10110 | Roseburia_intestinalis | Escherichia_coli | +++ |
| SPC00015 | SPC10110 | Streptococcus_thermophilus | Escherichia_coli | +++ |
| SPC00006 | SPC00022 | Bacteroides_sp_1_1_6 | Eubacterium_eligens | ++++ |
| SPC00007 | SPC00022 | Bacteroides_sp_3_1_23 | Eubacterium_eligens | |
| SPC00005 | SPC00022 | Bacteroides_vulgatus | Eubacterium_eligens | +++ |
| SPC00021 | SPC00022 | Blautia_producta | Eubacterium_eligens | ++++ |
| SPC00009 | SPC00022 | Coprobacillus_sp_D7 | Eubacterium_eligens | |
| SPC00018 | SPC00022 | Dorea_formicigenerans | Eubacterium_eligens | −− |
| SPC00008 | SPC00022 | Enterococcus_faecalis | Eubacterium_eligens | ++++ |
| SPC00001 | SPC00022 | Escherichia_coli | Eubacterium_eligens | ++ |
| SPC00022 | SPC00022 | Eubacterium_eligens | Eubacterium_eligens | |
| SPC00015 | SPC00022 | Streptococcus_thermophilus | Eubacterium_eligens | |
| SPC10211 | SPC10363 | Bacteroides_caccae | Eubacterium_rectale | |
| SPC10213 | SPC10363 | Bacteroides_eggerthii | Eubacterium_rectale | |
| SPC10030 | SPC10363 | Bacteroides_ovatus | Eubacterium_rectale | |
| SPC00006 | SPC10363 | Bacteroides_sp_1_1_6 | Eubacterium_rectale | ++++ |
| SPC00007 | SPC10363 | Bacteroides_sp_3_1_23 | Eubacterium_rectale | +++ |
| SPC10019 | SPC10363 | Bacteroides_sp_D20 | Eubacterium_rectale | −− |
| SPC00005 | SPC10363 | Bacteroides_vulgatus | Eubacterium_rectale | ++++ |
| SPC10081 | SPC10363 | Bacteroides_vulgatus | Eubacterium_rectale | |
| SPC10301 | SPC10363 | Bifidobacterium_adolescentis | Eubacterium_rectale | ++++ |
| SPC10298 | SPC10363 | Bifidobacterium_pseudocatenulatum | Eubacterium_rectale | |
| SPC00021 | SPC10363 | Blautia_producta | Eubacterium_rectale | ++++ |
| SPC10415 | SPC10567 | Blautia_producta | Eubacterium_rectale | ++++ |
| SPC10256 | SPC10567 | *Clostridium butyricum* | Eubacterium_rectale | ++++ |
| SPC10358 | SPC10567 | Clostridium orbiscindens | Eubacterium_rectale | + |
| SPC10325 | SPC10567 | Clostridium_bolteae | Eubacterium_rectale | ++ |
| SPC10167 | SPC10567 | Clostridium_disporicum | Eubacterium_rectale | ++++ |
| SPC10243 | SPC10363 | Clostridium_hathewayi | Eubacterium_rectale | ++++ |
| SPC10313 | SPC10567 | Clostridium_hylemonae | Eubacterium_rectale | |
| SPC10202 | SPC10567 | Clostridium_innocuum | Eubacterium_rectale | ++++ |
| SPC10238 | SPC10567 | Clostridium_mayombei | Eubacterium_rectale | ++++ |
| SPC00026 | SPC10363 | Clostridium_nexile | Eubacterium_rectale | − |
| SPC00027 | SPC10363 | Clostridium_sp_HGF2 | Eubacterium_rectale | −− |
| SPC10355 | SPC10363 | Clostridium_symbiosum | Eubacterium_rectale | ++ |
| SPC10355 | SPC10567 | Clostridium_symbiosum | Eubacterium_rectale | + |
| SPC10155 | SPC10567 | Clostridium_tertium | Eubacterium_rectale | ++++ |
| SPC10097 | SPC10363 | Collinsella_aerofaciens | Eubacterium_rectale | ++++ |
| SPC10097 | SPC10567 | Collinsella_aerofaciens | Eubacterium_rectale | ++++ |
| SPC00009 | SPC10363 | Coprobacillus_sp_D7 | Eubacterium_rectale | +++ |
| SPC00080 | SPC10363 | Coprococcus_catus | Eubacterium_rectale | −−− |
| SPC10304 | SPC10363 | Coprococcus_comes | Eubacterium_rectale | + |
| SPC10304 | SPC10567 | Coprococcus_comes | Eubacterium_rectale | ++++ |
| SPC00018 | SPC10363 | Dorea_formicigenerans | Eubacterium_rectale | − |
| SPC00057 | SPC10363 | Dorea_longicatena | Eubacterium_rectale | ++++ |
| SPC00008 | SPC10363 | Enterococcus_faecalis | Eubacterium_rectale | ++++ |
| SPC10001 | SPC10363 | Erysipelotrichaceae_bacterium | Eubacterium_rectale | − |
| SPC00001 | SPC10363 | Escherichia_coli | Eubacterium_rectale | ++++ |
| SPC10110 | SPC10363 | Escherichia_coli | Eubacterium_rectale | ++++ |
| SPC00022 | SPC10363 | Eubacterium_eligens | Eubacterium_rectale | |
| SPC10363 | SPC10363 | Eubacterium_rectale | Eubacterium_rectale | +++ |
| SPC10567 | SPC10567 | Eubacterium_rectale | Eubacterium_rectale | |
| SPC00054 | SPC10363 | Faecalibacterium_prausnitzii | Eubacterium_rectale | −− |
| SPC10386 | SPC10567 | Faecalibacterium_prausnitzii | Eubacterium_rectale | |
| SPC10390 | SPC10567 | Lachnospiraceae_bacterium_5_1_57FAA | Eubacterium_rectale | +++ |
| SPC00056 | SPC10363 | Odoribacter_splanchnicus | Eubacterium_rectale | − |
| SPC10048 | SPC10363 | Parabacteroides_merdae | Eubacterium_rectale | − |
| SPC00061 | SPC10363 | Roseburia_intestinalis | Eubacterium_rectale | −−−− |
| SPC10470 | SPC10567 | Ruminococcus_bromii | Eubacterium_rectale | + |
| SPC10468 | SPC10567 | Ruminococcus_gnavus | Eubacterium_rectale | ++++ |
| SPC10197 | SPC10363 | Ruminococcus_obeum | Eubacterium_rectale | ++ |
| SPC10233 | SPC10363 | Ruminococcus_torques | Eubacterium_rectale | + |
| SPC00015 | SPC10363 | Streptococcus_thermophilus | Eubacterium_rectale | |
| SPC10211 | SPC10386 | Bacteroides_caccae | Faecalibacterium_prausnitzii | |
| SPC10213 | SPC10386 | Bacteroides_eggerthii | Faecalibacterium_prausnitzii | − |
| SPC10030 | SPC10386 | Bacteroides_ovatus | Faecalibacterium_prausnitzii | − |
| SPC00006 | SPC00054 | Bacteroides_sp_1_1_6 | Faecalibacterium_prausnitzii | ++++ |
| SPC00006 | SPC10386 | Bacteroides_sp_1_1_6 | Faecalibacterium_prausnitzii | +++ |

TABLE 3-continued

| SPC1 | SPC2 | OTU1 | OTU2 | Result |
|---|---|---|---|---|
| SPC00007 | SPC00054 | Bacteroides_sp_3_1_23 | Faecalibacterium_prausnitzii | ++ |
| SPC00007 | SPC10386 | Bacteroides_sp_3_1_23 | Faecalibacterium_prausnitzii | |
| SPC10019 | SPC10386 | Bacteroides_sp_D20 | Faecalibacterium_prausnitzii | −− |
| SPC00005 | SPC00054 | Bacteroides_vulgatus | Faecalibacterium_prausnitzii | ++++ |
| SPC00005 | SPC10386 | Bacteroides_vulgatus | Faecalibacterium_prausnitzii | +++ |
| SPC10081 | SPC10386 | Bacteroides_vulgatus | Faecalibacterium_prausnitzii | −−− |
| SPC10301 | SPC10386 | Bifidobacterium_adolescentis | Faecalibacterium_prausnitzii | + |
| SPC10298 | SPC10386 | Bifidobacterium_pseudocatenulatum | Faecalibacterium_prausnitzii | |
| SPC00021 | SPC00054 | Blautia_producta | Faecalibacterium_prausnitzii | ++++ |
| SPC00021 | SPC10386 | Blautia_producta | Faecalibacterium_prausnitzii | ++++ |
| SPC10256 | SPC10386 | *Clostridium butyricum* | Faecalibacterium_prausnitzii | ++++ |
| SPC10358 | SPC10386 | *Clostridium orbiscindens* | Faecalibacterium_prausnitzii | |
| SPC10325 | SPC10386 | Clostridium_bolteae | Faecalibacterium_prausnitzii | ++ |
| SPC10167 | SPC10386 | Clostridium_disporicum | Faecalibacterium_prausnitzii | |
| SPC10243 | SPC10386 | Clostridium_hathewayi | Faecalibacterium_prausnitzii | +++ |
| SPC10313 | SPC10386 | Clostridium_hylemonae | Faecalibacterium_prausnitzii | |
| SPC10202 | SPC10386 | Clostridium_innocuum | Faecalibacterium_prausnitzii | ++++ |
| SPC10238 | SPC10386 | Clostridium_mayombei | Faecalibacterium_prausnitzii | ++++ |
| SPC00026 | SPC00054 | Clostridium_nexile | Faecalibacterium_prausnitzii | |
| SPC00026 | SPC10386 | Clostridium_nexile | Faecalibacterium_prausnitzii | − |
| SPC00027 | SPC00054 | Clostridium_sp_HGF2 | Faecalibacterium_prausnitzii | ++ |
| SPC00027 | SPC10386 | Clostridium_sp_HGF2 | Faecalibacterium_prausnitzii | −− |
| SPC10355 | SPC10386 | Clostridium_symbiosum | Faecalibacterium_prausnitzii | +++ |
| SPC10355 | SPC10386 | Clostridium_symbiosum | Faecalibacterium_prausnitzii | ++++ |
| SPC10155 | SPC10386 | Clostridium_tertium | Faecalibacterium_prausnitzii | ++++ |
| SPC10097 | SPC10386 | Collinsella_aerofaciens | Faecalibacterium_prausnitzii | ++++ |
| SPC10097 | SPC10386 | Collinsella_aerofaciens | Faecalibacterium_prausnitzii | ++++ |
| SPC00009 | SPC00054 | Coprobacillus_sp_D7 | Faecalibacterium_prausnitzii | −−− |
| SPC00009 | SPC10386 | Coprobacillus_sp_D7 | Faecalibacterium_prausnitzii | |
| SPC00080 | SPC10386 | Coprococcus_catus | Faecalibacterium_prausnitzii | −−− |
| SPC10304 | SPC10386 | Coprococcus_comes | Faecalibacterium_prausnitzii | |
| SPC10304 | SPC10386 | Coprococcus_comes | Faecalibacterium_prausnitzii | +++ |
| SPC00018 | SPC00054 | Dorea_formicigenerans | Faecalibacterium_prausnitzii | |
| SPC00018 | SPC10386 | Dorea_formicigenerans | Faecalibacterium_prausnitzii | −−− |
| SPC00057 | SPC10386 | Dorea_longicatena | Faecalibacterium_prausnitzii | +++ |
| SPC00008 | SPC00054 | Enterococcus_faecalis | Faecalibacterium_prausnitzii | ++++ |
| SPC00008 | SPC10386 | Enterococcus_faecalis | Faecalibacterium_prausnitzii | ++++ |
| SPC10001 | SPC10386 | Erysipelotrichaceae_bacterium | Faecalibacterium_prausnitzii | −− |
| SPC00001 | SPC00054 | Escherichia_coli | Faecalibacterium_prausnitzii | ++++ |
| SPC00001 | SPC10386 | Escherichia_coli | Faecalibacterium_prausnitzii | ++++ |
| SPC10110 | SPC10386 | Escherichia_coli | Faecalibacterium_prausnitzii | ++ |
| SPC00022 | SPC00054 | Eubacterium_eligens | Faecalibacterium_prausnitzii | |
| SPC00022 | SPC10386 | Eubacterium_eligens | Faecalibacterium_prausnitzii | |
| SPC10363 | SPC10386 | Eubacterium_rectale | Faecalibacterium_prausnitzii | + |
| SPC00054 | SPC00054 | Faecalibacterium_prausnitzii | Faecalibacterium_prausnitzii | + |
| SPC00054 | SPC10386 | Faecalibacterium_prausnitzii | Faecalibacterium_prausnitzii | |
| SPC10386 | SPC10386 | Faecalibacterium_prausnitzii | Faecalibacterium_prausnitzii | + |
| SPC10386 | SPC10386 | Faecalibacterium_prausnitzii | Faecalibacterium_prausnitzii | |
| SPC10390 | SPC10386 | Lachnospiraceae_bacterium_5_1_57FAA | Faecalibacterium_prausnitzii | ++++ |
| SPC00056 | SPC10386 | Odoribacter_splanchnicus | Faecalibacterium_prausnitzii | −− |
| SPC10048 | SPC10386 | Parabacteroides_merdae | Faecalibacterium_prausnitzii | |
| SPC00061 | SPC10386 | Roseburia_intestinalis | Faecalibacterium_prausnitzii | |
| SPC10197 | SPC10386 | Ruminococcus_obeum | Faecalibacterium_prausnitzii | |
| SPC10233 | SPC10386 | Ruminococcus_torques | Faecalibacterium_prausnitzii | |
| SPC00015 | SPC00054 | Streptococcus_thermophilus | Faecalibacterium_prausnitzii | |
| SPC00015 | SPC10386 | Streptococcus_thermophilus | Faecalibacterium_prausnitzii | |
| SPC10211 | SPC10390 | Bacteroides_caccae | Lachnospiraceae_bacterium_5_1_57FAA | |
| SPC10213 | SPC10390 | Bacteroides_eggerthii | Lachnospiraceae_bacterium_5_1_57FAA | |
| SPC10030 | SPC10390 | Bacteroides_ovatus | Lachnospiraceae_bacterium_5_1_57FAA | − |
| SPC00006 | SPC10390 | Bacteroides_sp_1_1_6 | Lachnospiraceae_bacterium_5_1_57FAA | +++ |
| SPC00007 | SPC10390 | Bacteroides_sp_3_1_23 | Lachnospiraceae_bacterium_5_1_57FAA | |
| SPC10019 | SPC10390 | Bacteroides_sp_D20 | Lachnospiraceae_bacterium_5_1_57FAA | −−− |
| SPC00005 | SPC10390 | Bacteroides_vulgatus | Lachnospiraceae_bacterium_5_1_57FAA | +++ |
| SPC10081 | SPC10390 | Bacteroides_vulgatus | Lachnospiraceae_bacterium_5_1_57FAA | −− |
| SPC10301 | SPC10390 | Bifidobacterium_adolescentis | Lachnospiraceae_bacterium_5_1_57FAA | ++++ |
| SPC10298 | SPC10390 | Bifidobacterium_pseudocatenulatum | Lachnospiraceae_bacterium_5_1_57FAA | |
| SPC00021 | SPC10390 | Blautia_producta | Lachnospiraceae_bacterium_5_1_57FAA | ++++ |
| SPC10415 | SPC10390 | Blautia_producta | Lachnospiraceae_bacterium_5_1_57FAA | ++++ |
| SPC10256 | SPC10390 | *Clostridium butyricum* | Lachnospiraceae_bacterium_5_1_57FAA | ++++ |
| SPC10358 | SPC10390 | *Clostridium orbiscindens* | Lachnospiraceae_bacterium_5_1_57FAA | ++++ |
| SPC10325 | SPC10390 | Clostridium_bolteae | Lachnospiraceae_bacterium_5_1_57FAA | ++++ |
| SPC10167 | SPC10390 | Clostridium_disporicum | Lachnospiraceae_bacterium_5_1_57FAA | ++++ |
| SPC10243 | SPC10390 | Clostridium_hathewayi | Lachnospiraceae_bacterium_5_1_57FAA | ++++ |
| SPC10313 | SPC10390 | Clostridium_hylemonae | Lachnospiraceae_bacterium_5_1_57FAA | ++++ |
| SPC10202 | SPC10390 | Clostridium_innocuum | Lachnospiraceae_bacterium_5_1_57FAA | ++++ |
| SPC10238 | SPC10390 | Clostridium_mayombei | Lachnospiraceae_bacterium_5_1_57FAA | ++++ |
| SPC00026 | SPC10390 | Clostridium_nexile | Lachnospiraceae_bacterium_5_1_57FAA | − |
| SPC00027 | SPC10390 | Clostridium_sp_HGF2 | Lachnospiraceae_bacterium_5_1_57FAA | − |

TABLE 3-continued

| SPC1 | SPC2 | OTU1 | OTU2 | Result |
|---|---|---|---|---|
| SPC10355 | SPC10390 | Clostridium_symbiosum | Lachnospiraceae_bacterium_5_1_57FAA | + |
| SPC10355 | SPC10390 | Clostridium_symbiosum | Lachnospiraceae_bacterium_5_1_57FAA | ++++ |
| SPC10155 | SPC10390 | Clostridium_tertium | Lachnospiraceae_bacterium_5_1_57FAA | ++++ |
| SPC10097 | SPC10390 | Collinsella_aerofaciens | Lachnospiraceae_bacterium_5_1_57FAA | ++++ |
| SPC10097 | SPC10390 | Collinsella_aerofaciens | Lachnospiraceae_bacterium_5_1_57FAA | ++++ |
| SPC00009 | SPC10390 | Coprobacillus_sp_D7 | Lachnospiraceae_bacterium_5_1_57FAA | ++++ |
| SPC00080 | SPC10390 | Coprococcus_catus | Lachnospiraceae_bacterium_5_1_57FAA | |
| SPC10304 | SPC10390 | Coprococcus_comes | Lachnospiraceae_bacterium_5_1_57FAA | |
| SPC10304 | SPC10390 | Coprococcus_comes | Lachnospiraceae_bacterium_5_1_57FAA | ++++ |
| SPC00018 | SPC10390 | Dorea_formicigenerans | Lachnospiraceae_bacterium_5_1_57FAA | −− |
| SPC00057 | SPC10390 | Dorea_longicatena | Lachnospiraceae_bacterium_5_1_57FAA | ++++ |
| SPC00008 | SPC10390 | Enterococcus_faecalis | Lachnospiraceae_bacterium_5_1_57FAA | ++++ |
| SPC10001 | SPC10390 | Erysipelotrichaceae_bacterium | Lachnospiraceae_bacterium_5_1_57FAA | −−− |
| SPC00001 | SPC10390 | Escherichia_coli | Lachnospiraceae_bacterium_5_1_57FAA | ++++ |
| SPC10110 | SPC10390 | Escherichia_coli | Lachnospiraceae_bacterium_5_1_57FAA | ++++ |
| SPC00022 | SPC10390 | Eubacterium_eligens | Lachnospiraceae_bacterium_5_1_57FAA | |
| SPC10363 | SPC10390 | Eubacterium_rectale | Lachnospiraceae_bacterium_5_1_57FAA | |
| SPC00054 | SPC10390 | Faecalibacterium_prausnitzii | Lachnospiraceae_bacterium_5_1_57FAA | |
| SPC10386 | SPC10390 | Faecalibacterium_prausnitzii | Lachnospiraceae_bacterium_5_1_57FAA | |
| SPC10386 | SPC10390 | Faecalibacterium_prausnitzii | Lachnospiraceae_bacterium_5_1_57FAA | ++++ |
| SPC10390 | SPC10390 | Lachnospiraceae_bacterium_5_1_57FAA | Lachnospiraceae_bacterium_5_1_57FAA | |
| SPC10390 | SPC10390 | Lachnospiraceae_bacterium_5_1_57FAA | Lachnospiraceae_bacterium_5_1_57FAA | ++++ |
| SPC00056 | SPC10390 | Odoribacter_splanchnicus | Lachnospiraceae_bacterium_5_1_57FAA | −− |
| SPC10388 | SPC10390 | Odoribacter_splanchnicus | Lachnospiraceae_bacterium_5_1_57FAA | |
| SPC10048 | SPC10390 | Parabacteroides_merdae | Lachnospiraceae_bacterium_5_1_57FAA | − |
| SPC00061 | SPC10390 | Roseburia_intestinalis | Lachnospiraceae_bacterium_5_1_57FAA | |
| SPC10197 | SPC10390 | Ruminococcus_obeum | Lachnospiraceae_bactenum_5_1_57FAA | |
| SPC10233 | SPC10390 | Ruminococcus_torques | Lachnospiraceae_bactenum_5_1_57FAA | |
| SPC00015 | SPC10390 | Streptococcus_thermophilus | Lachnospiraceae_bactenum_5_1_57FAA | |
| SPC10211 | SPC10388 | Bacteroides_caccae | Odoribacter_splanchnicus | |
| SPC10213 | SPC10388 | Bacteroides_eggerthii | Odoribacter_splanchnicus | − |
| SPC10030 | SPC10388 | Bacteroides_ovatus | Odoribacter_splanchnicus | −− |
| SPC00006 | SPC00056 | Bacteroides_sp_1_1_6 | Odoribacter_splanchnicus | ++++ |
| SPC00006 | SPC10388 | Bacteroides_sp_1_1_6 | Odoribacter_splanchnicus | + |
| SPC00007 | SPC00056 | Bacteroides_sp_3_1_23 | Odoribacter_splanchnicus | + |
| SPC00007 | SPC10388 | Bacteroides_sp_3_1_23 | Odoribacter_splanchnicus | |
| SPC10019 | SPC10388 | Bacteroides_sp_D20 | Odoribacter_splanchnicus | −−− |
| SPC00005 | SPC00056 | Bacteroides_vulgatus | Odoribacter_splanchnicus | +++ |
| SPC00005 | SPC10388 | Bacteroides_vulgatus | Odoribacter_splanchnicus | +++ |
| SPC10081 | SPC10388 | Bacteroides_vulgatus | Odoribacter_splanchnicus | − |
| SPC10301 | SPC10388 | Bifidobacterium_adolescentis | Odoribacter_splanchnicus | ++++ |
| SPC10298 | SPC10388 | Bifidobacterium_pseudocatenulatum | Odoribacter_splanchnicus | +++ |
| SPC00021 | SPC00056 | Blautia_producta | Odoribacter_splanchnicus | ++++ |
| SPC00021 | SPC10388 | Blautia_producta | Odoribacter_splanchnicus | ++++ |
| SPC10243 | SPC10388 | Clostridium_hathewayi | Odoribacter_splanchnicus | ++++ |
| SPC00026 | SPC00056 | Clostridium_nexile | Odoribacter_splanchnicus | |
| SPC00026 | SPC10388 | Clostridium_nexile | Odoribacter_splanchnicus | −−− |
| SPC00027 | SPC00056 | Clostridium_sp_HGF2 | Odoribacter_splanchnicus | |
| SPC00027 | SPC10388 | Clostridium_sp_HGF2 | Odoribacter_splanchnicus | −−− |
| SPC10355 | SPC10388 | Clostridium_symbiosum | Odoribacter_splanchnicus | ++ |
| SPC10097 | SPC10388 | Collinsella_aerofaciens | Odoribacter_splanchnicus | ++++ |
| SPC00009 | SPC00056 | Coprobacillus_sp_D7 | Odoribacter_splanchnicus | − |
| SPC00009 | SPC10388 | Coprobacillus_sp_D7 | Odoribacter_splanchnicus | +++ |
| SPC00080 | SPC10388 | Coprococcus_catus | Odoribacter_splanchnicus | −− |
| SPC10304 | SPC10388 | Coprococcus_comes | Odoribacter_splanchnicus | |
| SPC00018 | SPC00056 | Dorea_formicigenerans | Odoribacter_splanchnicus | |
| SPC00018 | SPC10388 | Dorea_formicigenerans | Odoribacter_splanchnicus | − |
| SPC00057 | SPC10388 | Dorea_longicatena | Odoribacter_splanchnicus | ++++ |
| SPC00008 | SPC00056 | Enterococcus_faecalis | Odoribacter_splanchnicus | ++++ |
| SPC00008 | SPC10388 | Enterococcus_faecalis | Odoribacter_splanchnicus | ++++ |
| SPC10001 | SPC10388 | Erysipelotrichaceae_bacterium | Odoribacter_splanchnicus | −− |
| SPC00001 | SPC00056 | Escherichia_coli | Odoribacter_splanchnicus | ++++ |
| SPC00001 | SPC10388 | Escherichia_coli | Odoribacter_splanchnicus | ++++ |
| SPC10110 | SPC10388 | Escherichia_coli | Odoribacter_splanchnicus | ++++ |
| SPC00022 | SPC00056 | Eubacterium_eligens | Odoribacter_splanchnicus | |
| SPC00022 | SPC10388 | Eubacterium_eligens | Odoribacter_splanchnicus | |
| SPC10363 | SPC10388 | Eubacterium_rectale | Odoribacter_splanchnicus | + |
| SPC00054 | SPC00056 | Faecalibacterium_prausnitzii | Odoribacter_splanchnicus | |
| SPC00054 | SPC10388 | Faecalibacterium_prausnitzii | Odoribacter_splanchnicus | − |
| SPC10386 | SPC10388 | Faecalibacterium_prausnitzii | Odoribacter_splanchnicus | + |
| SPC00056 | SPC00056 | Odoribacter_splanchnicus | Odoribacter_splanchnicus | |
| SPC00056 | SPC10388 | Odoribacter_splanchnicus | Odoribacter_splanchnicus | −−− |
| SPC10388 | SPC10388 | Odoribacter_splanchnicus | Odoribacter_splanchnicus | + |
| SPC10048 | SPC10388 | Parabacteroides_merdae | Odoribacter_splanchnicus | |
| SPC00061 | SPC10388 | Roseburia_intestinalis | Odoribacter_splanchnicus | |
| SPC10197 | SPC10388 | Ruminococcus_obeum | Odoribacter_splanchnicus | + |
| SPC10233 | SPC10388 | Ruminococcus_torques | Odoribacter_splanchnicus | |
| SPC00015 | SPC00056 | Streptococcus_thermophilus | Odoribacter_splanchnicus | |

TABLE 3-continued

| SPC1 | SPC2 | OTU1 | OTU2 | Result |
|---|---|---|---|---|
| SPC00015 | SPC10388 | Streptococcus_thermophilus | Odoribacter_splanchnicus | + |
| SPC10030 | SPC10048 | Bacteroides_ovatus | Parabacteroides_merdae | |
| SPC00006 | SPC10048 | Bacteroides_sp_1_1_6 | Parabacteroides_merdae | ++++ |
| SPC00007 | SPC10048 | Bacteroides_sp_3_1_23 | Parabacteroides_merdae | +++ |
| SPC10019 | SPC10048 | Bacteroides_sp_D20 | Parabacteroides_merdae | |
| SPC00005 | SPC10048 | Bacteroides_vulgatus | Parabacteroides_merdae | ++++ |
| SPC00021 | SPC10048 | Blautia_producta | Parabacteroides_merdae | ++++ |
| SPC00026 | SPC10048 | Clostridium_nexile | Parabacteroides_merdae | ++ |
| SPC00027 | SPC10048 | Clostridium_sp_HGF2 | Parabacteroides_merdae | +++ |
| SPC00009 | SPC10048 | Coprobacillus_sp_D7 | Parabacteroides_merdae | − |
| SPC00080 | SPC10048 | Coprococcus_catus | Parabacteroides_merdae | +++ |
| SPC00018 | SPC10048 | Dorea_formicigenerans | Parabacteroides_merdae | |
| SPC00057 | SPC10048 | Dorea_longicatena | Parabacteroides_merdae | |
| SPC00008 | SPC10048 | Enterococcus_faecalis | Parabacteroides_merdae | ++++ |
| SPC10001 | SPC10048 | Erysipelotrichaceae_bacterium | Parabacteroides_merdae | |
| SPC00001 | SPC10048 | Escherichia_coli | Parabacteroides_merdae | ++++ |
| SPC00022 | SPC10048 | Eubacterium_eligens | Parabacteroides_merdae | |
| SPC00054 | SPC10048 | Faecalibacterium_prausnitzii | Parabacteroides_merdae | + |
| SPC00056 | SPC10045 | Odoribacter_splanchnicus | Parabacteroides_merdae | |
| SPC10048 | SPC10048 | Parabacteroides_merdae | Parabacteroides_merdae | +++ |
| SPC00061 | SPC10048 | Roseburia_intestinalis | Parabacteroides_merdae | |
| SPC00015 | SPC10048 | Streptococcus_thermophilus | Parabacteroides_merdae | |
| SPC00006 | SPC00061 | Bacteroides_sp_1_1_6 | Roseburia_intestinalis | ++++ |
| SPC00007 | SPC00061 | Bacteroides_sp_3_1_23 | Roseburia_intestinalis | + |
| SPC00005 | SPC00061 | Bacteroides_vulgatus | Roseburia_intestinalis | + |
| SPC00021 | SPC00061 | Blautia_producta | Roseburia_intestinalis | ++++ |
| SPC00026 | SPC00061 | Clostridium_nexile | Roseburia_intestinalis | − |
| SPC00027 | SPC00061 | Clostridium_sp_HGF2 | Roseburia_intestinalis | −−− |
| SPC00009 | SPC00061 | Coprobacillus_sp_D7 | Roseburia_intestinalis | − |
| SPC00018 | SPC00061 | Dorea_formicigenerans | Roseburia_intestinalis | |
| SPC00057 | SPC00061 | Dorea_longicatena | Roseburia_intestinalis | − |
| SPC00008 | SPC00061 | Enterococcus_faecalis | Roseburia_intestinalis | ++++ |
| SPC00001 | SPC00061 | Escherichia_coli | Roseburia_intestinalis | ++++ |
| SPC00022 | SPC00061 | Eubacterium_eligens | Roseburia_intestinalis | |
| SPC00054 | SPC00061 | Faecalibacterium_prausnitzii | Roseburia_intestinalis | |
| SPC00056 | SPC00061 | Odoribacter_splanchnicus | Roseburia_intestinalis | − |
| SPC00061 | SPC00061 | Roseburia_intestinalis | Roseburia_intestinalis | |
| SPC00015 | SPC00061 | Streptococcus_thermophilus | Roseburia_intestinalis | |
| SPC10415 | SPC10470 | Blautia_producta | Ruminococcus_bromii | ++++ |
| SPC10256 | SPC10470 | *Clostridium butyricum* | Ruminococcus_bromii | ++++ |
| SPC10358 | SPC10470 | *Clostridium orbiscindens* | Ruminococcus_bromii | |
| SPC10325 | SPC10470 | Clostridium_bolteae | Ruminococcus_bromii | +++ |
| SPC10167 | SPC10470 | Clostridium_disporicum | Ruminococcus_bromii | |
| SPC10313 | SPC10470 | Clostridium_hylemonae | Ruminococcus_bromii | |
| SPC10202 | SPC10470 | Clostridium_innocuum | Ruminococcus_bromii | ++++ |
| SPC10238 | SPC10470 | Clostridium_mayombei | Ruminococcus_bromii | ++++ |
| SPC10355 | SPC10470 | Clostridium_symbiosum | Ruminococcus_bromii | ++++ |
| SPC10155 | SPC10470 | Clostridium_tertium | Ruminococcus_bromii | ++++ |
| SPC10097 | SPC10470 | Collinsella_aerofaciens | Ruminococcus_bromii | ++++ |
| SPC10304 | SPC10470 | Coprococcus_comes | Ruminococcus_bromii | ++++ |
| SPC10567 | SPC10470 | Eubacterium_rectale | Ruminococcus_bromii | + |
| SPC10386 | SPC10470 | Faecalibacterium_prausnitzii | Ruminococcus_bromii | |
| SPC10390 | SPC10470 | Lachnospiraceae_bacterium_5_1_57FAA | Ruminococcus_bromii | ++++ |
| SPC10470 | SPC10470 | Ruminococcus_bromii | Ruminococcus_bromii | − |
| SPC10468 | SPC10470 | Ruminococcus_gnavus | Ruminococcus_bromii | ++++ |
| SPC10415 | SPC10468 | Blautia_producta | Ruminococcus_gnavus | ++++ |
| SPC10256 | SPC10468 | *Clostridium butyricum* | Ruminococcus_gnavus | ++++ |
| SPC10358 | SPC10468 | *Clostridium orbiscindens* | Ruminococcus_gnavus | ++++ |
| SPC10325 | SPC10468 | Clostridium_bolteae | Ruminococcus_gnavus | ++++ |
| SPC10167 | SPC10468 | Clostridium_disporicum | Ruminococcus_gnavus | ++++ |
| SPC10313 | SPC10468 | Clostridium_hylemonae | Ruminococcus_gnavus | +++ |
| SPC10202 | SPC10468 | Clostridium_innocuum | Ruminococcus_gnavus | ++++ |
| SPC10238 | SPC10468 | Clostridium_mayombei | Ruminococcus_gnavus | ++++ |
| SPC10355 | SPC10468 | Clostridium_symbiosum | Ruminococcus_gnavus | ++++ |
| SPC10155 | SPC10468 | Clostridium_tertium | Ruminococcus_gnavus | ++++ |
| SPC10097 | SPC10468 | Collinsella_aerofaciens | Ruminococcus_gnavus | ++++ |
| SPC10304 | SPC10468 | Coprococcus_comes | Ruminococcus_gnavus | ++++ |
| SPC10386 | SPC10468 | Faecalibacterium_prausnitzii | Ruminococcus_gnavus | ++++ |
| SPC10390 | SPC10468 | Lachnospiraceae_bacterium_5_1_57FAA | Ruminococcus_gnavus | ++++ |
| SPC10470 | SPC10468 | Ruminococcus_bromii | Ruminococcus_gnavus | ++++ |
| SPC10468 | SPC10468 | Ruminococcus_gnavus | Ruminococcus_gnavus | +++ |
| SPC10030 | SPC10197 | Bacteroides_ovatus | Ruminococcus_obeum | |
| SPC00006 | SPC10197 | Bacteroides_sp_1_1_6 | Ruminococcus_obeum | +++ |
| SPC00007 | SPC10197 | Bacteroides_sp_3_1_23 | Ruminococcus_obeum | +++ |
| SPC10019 | SPC10197 | Bacteroides_sp_D20 | Ruminococcus_obeum | |
| SPC00005 | SPC10197 | Bacteroides_vulgatus | Ruminococcus_obeum | ++++ |
| SPC10081 | SPC10197 | Bacteroides_vulgatus | Ruminococcus_obeum | |
| SPC00021 | SPC10197 | Blautia_producta | Ruminococcus_obeum | ++++ |

TABLE 3-continued

| SPC1 | SPC2 | OTU1 | OTU2 | Result |
|---|---|---|---|---|
| SPC00026 | SPC10197 | Clostridium_nexile | Ruminococcus_obeum | – |
| SPC00027 | SPC10197 | Clostridium_sp_HGF2 | Ruminococcus_obeum | –– |
| SPC10097 | SPC10197 | Collinsella_aerofaciens | Ruminococcus_obeum | ++++ |
| SPC00009 | SPC10197 | Coprobacillus_sp_D7 | Ruminococcus_obeum | + |
| SPC00080 | SPC10197 | Coprococcus_catus | Ruminococcus_obeum | |
| SPC00018 | SPC10197 | Dorea_formicigenerans | Ruminococcus_obeum | ++++ |
| SPC00057 | SPC10197 | Dorea_longicatena | Ruminococcus_obeum | – |
| SPC00008 | SPC10197 | Enterococcus_faecalis | Ruminococcus_obeum | ++++ |
| SPC10001 | SPC10197 | Erysipelotrichaceae_bacterium | Ruminococcus_obeum | |
| SPC00001 | SPC10197 | Escherichia_coli | Ruminococcus_obeum | +++ |
| SPC10110 | SPC10197 | Escherichia_coli | Ruminococcus_obeum | ++++ |
| SPC00022 | SPC10197 | Eubacterium_eligens | Ruminococcus_obeum | + |
| SPC00054 | SPC10197 | Faecalibacterium_prausnitzii | Ruminococcus_obeum | |
| SPC00056 | SPC10197 | Odoribacter_splanchnicus | Ruminococcus_obeum | – |
| SPC10048 | SPC10197 | Parabacteroides_merdae | Ruminococcus_obeum | |
| SPC00061 | SPC10197 | Roseburia_intestinalis | Ruminococcus_obeum | |
| SPC10197 | SPC10197 | Ruminococcus_obeum | Ruminococcus_obeum | ++++ |
| SPC00015 | SPC10197 | Streptococcus_thermophilus | Ruminococcus_obeum | +++ |
| SPC10211 | SPC10233 | Bacteroides_caccae | Ruminococcus_torques | ++++ |
| SPC10213 | SPC10233 | Bacteroides_eggerthii | Ruminococcus_torques | ++++ |
| SPC10030 | SPC10233 | Bacteroides_ovatus | Ruminococcus_torques | ++++ |
| SPC00006 | SPC10233 | Bacteroides_sp_1_1_6 | Ruminococcus_torques | ++++ |
| SPC00007 | SPC10233 | Bacteroides_sp_3_1_23 | Ruminococcus_torques | ++++ |
| SPC10019 | SPC10233 | Bacteroides_sp_D20 | Ruminococcus_torques | ++ |
| SPC00005 | SPC10233 | Bacteroides_vulgatus | Ruminococcus_torques | ++++ |
| SPC10081 | SPC10233 | Bacteroides_vulgatus | Ruminococcus_torques | ++++ |
| SPC00021 | SPC10233 | Blautia_producta | Ruminococcus_torques | ++++ |
| SPC00026 | SPC10233 | Clostridium_nexile | Ruminococcus_torques | + |
| SPC00027 | SPC10233 | Clostridium_sp_HGF2 | Ruminococcus_torques | |
| SPC10097 | SPC10233 | Collinsella_aerofaciens | Ruminococcus_torques | ++++ |
| SPC00009 | SPC10233 | Coprobacillus_sp_D7 | Ruminococcus_torques | ++++ |
| SPC00080 | SPC10233 | Coprococcus_catus | Ruminococcus_torques | + |
| SPC00018 | SPC10233 | Dorea_formicigenerans | Ruminococcus_torques | ++++ |
| SPC00057 | SPC10233 | Dorea_longicatena | Ruminococcus_torques | |
| SPC00008 | SPC10233 | Enterococcus_faecalis | Ruminococcus_torques | ++++ |
| SPC10001 | SPC10233 | Erysipelotrichaceae_bacterium | Ruminococcus_torques | + |
| SPC00001 | SPC10233 | Escherichia_coli | Ruminococcus_torques | ++++ |
| SPC10110 | SPC10233 | Escherichia_coli | Ruminococcus_torques | ++++ |
| SPC00022 | SPC10233 | Eubacterium_eligens | Ruminococcus_torques | ++ |
| SPC00054 | SPC10233 | Faecalibacterium_prausnitzii | Ruminococcus_torques | |
| SPC00056 | SPC10233 | Odoribacter_splanchnicus | Ruminococcus_torques | |
| SPC10048 | SPC10233 | Parabacteroides_merdae | Ruminococcus_torques | + |
| SPC00061 | SPC10233 | Roseburia_intestinalis | Ruminococcus_torques | + |
| SPC10197 | SPC10233 | Ruminococcus_obeum | Ruminococcus_torques | ++++ |
| SPC10233 | SPC10233 | Ruminococcus_torques | Ruminococcus_torques | ++++ |
| SPC00015 | SPC10233 | Streptococcus_thermophilus | Ruminococcus_torques | + |
| SPC00006 | SPC00015 | Bacteroides_sp_1_1_6 | Streptococcus_thermophilus | +++ |
| SPC00007 | SPC00015 | Bacteroides_sp_3_1_23 | Streptococcus_thermophilus | +++ |
| SPC00005 | SPC00015 | Bacteroides_vulgatus | Streptococcus_thermophilus | + |
| SPC00009 | SPC00015 | Coprobacillus_sp_D7 | Streptococcus_thermophilus | + |
| SPC00008 | SPC00015 | Enterococcus_faecalis | Streptococcus_thermophilus | ++++ |
| SPC00001 | SPC00015 | Escherichia_coli | Streptococcus_thermophilus | + |
| SPC00015 | SPC00015 | Streptococcus_thermophilus | Streptococcus_thermophilus | |

TABLE 4

| SPC1 | SPC2 | SPC3 | OTU1 | OTU2 | OTU3 | Results |
|---|---|---|---|---|---|---|
| SPC10325 | SPC10415 | SPC10567 | Clostridium_bolteae | *Blautia producta* | Eubacterium_rectale | ++++ |
| SPC10325 | SPC10355 | SPC10415 | Clostridium_bolteae | Clostridium_symbiosum | *Blautia producta* | ++++ |
| SPC10325 | SPC10355 | SPC10567 | Clostridium_bolteae | Clostridium_symbiosum | Eubacterium_rectale | – |
| SPC10325 | SPC10355 | SPC10386 | Clostridium_bolteae | Clostridium_symbiosum | Faecalibacterium_prausnitzii | – |
| SPC10325 | SPC10355 | SPC10390 | Clostridium_bolteae | Clostridium_symbiosum | Lachnospiraceae_bacterium__5_1_57FAA | |
| SPC10325 | SPC10386 | SPC10415 | Clostridium_bolteae | Faecalibacterium_prausnitzii | *Blautia producta* | ++++ |
| SPC10325 | SPC10386 | SPC10567 | Clostridium_bolteae | Faecalibacterium_prausnitzii | Eubacterium_rectale | |
| SPC10325 | SPC10386 | SPC10390 | Clostridium_bolteae | Faecalibacterium_prausnitzii | Lachnospiraceae_bacterium__5_1_57FAA | ++++ |
| SPC10325 | SPC10390 | SPC10415 | Clostridium_bolteae | Lachnospiraceae_bacterium__5_1_57FAA | *Blautia producta* | ++++ |
| SPC10325 | SPC10390 | SPC10567 | Clostridium_bolteae | Lachnospiraceae_bacterium__5_1_57FAA | Eubacterium_rectale | + |
| SPC10355 | SPC10415 | SPC10567 | Clostridium_symbiosum | *Blautia producta* | Eubacterium_rectale | ++++ |
| SPC10355 | SPC10386 | SPC10415 | Clostridium_symbiosum | Faecalibacterium_prausnitzii | *Blautia producta* | ++++ |
| SPC10355 | SPC10386 | SPC10567 | Clostridium_symbiosum | Faecalibacterium_prausnitzii | Eubacterium_rectale | |

TABLE 4-continued

| SPC1 | SPC2 | SPC3 | OTU1 | OTU2 | OTU3 | Results |
|---|---|---|---|---|---|---|
| SPC10355 | SPC10386 | SPC10390 | Clostridium_symbiosum | Faecalibacterium_prausnitzii | Lachnospiraceae_bacterium_5_1_57FAA | + |
| SPC10355 | SPC10390 | SPC10415 | Clostridium_symbiosum | Lachnospiraceae_bacterium_5_1_57FAA | *Blautia producta* | ++++ |
| SPC10355 | SPC10390 | SPC10567 | Clostridium_symbiosum | Lachnospiraceae_bacterium_5_1_57FAA | Eubacterium_rectale | |
| SPC10097 | SPC10415 | SPC10567 | Collinsella_aerofaciens | *Blautia producta* | Eubacterium_rectale | ++++ |
| SPC10097 | SPC10325 | SPC10415 | Collinsella_aerofaciens | Clostridium_bolteae | *Blautia producta* | ++++ |
| SPC10097 | SPC10325 | SPC10355 | Collinsella_aerofaciens | Clostridium_bolteae | Clostridium_symbiosum | ++++ |
| SPC10097 | SPC10325 | SPC10567 | Collinsella_aerofaciens | Clostridium_bolteae | Eubacterium_rectale | ++++ |
| SPC10097 | SPC10325 | SPC10386 | Collinsella_aerofaciens | Clostridium_bolteae | Faecalibacterium_prausnitzii | ++++ |
| SPC10097 | SPC10325 | SPC10390 | Collinsella_aerofaciens | Clostridium_bolteae | Lachnospiraceae_bacterium_5_1_57FAA | ++++ |
| SPC10097 | SPC10355 | SPC10415 | Collinsella_aerofaciens | Clostridium_symbiosum | *Blautia producta* | ++++ |
| SPC10097 | SPC10355 | SPC10567 | Collinsella_aerofaciens | Clostridium_symbiosum | Eubacterium_rectale | |
| SPC10097 | SPC10355 | SPC10386 | Collinsella_aerofaciens | Clostridium_symbiosum | Faecalibacterium_prausnitzii | |
| SPC10097 | SPC10355 | SPC10390 | Collinsella_aerofaciens | Clostridium_symbiosum | Lachnospiraceae_bacterium_5_1_57FAA | + |
| SPC10097 | SPC10304 | SPC10415 | Collinsella_aerofaciens | Coprococcus_comes | *Blautia producta* | ++++ |
| SPC10097 | SPC10304 | SPC10325 | Collinsella_aerofaciens | Coprococcus_comes | Clostridium_bolteae | ++++ |
| SPC10097 | SPC10304 | SPC10355 | Collinsella_aerofaciens | Coprococcus_comes | Clostridium_symbiosum | +++ |
| SPC10097 | SPC10304 | SPC10567 | Collinsella_aerofaciens | Coprococcus_comes | Eubacterium_rectale | +++ |
| SPC10097 | SPC10304 | SPC10386 | Collinsella_aerofaciens | Coprococcus_comes | Faecalibacterium_prausnitzii | ++++ |
| SPC10097 | SPC10304 | SPC10390 | Collinsella_aerofaciens | Coprococcus_comes | Lachnospiraceae_bacterium_5_1_57FAA | +++ |
| SPC10097 | SPC10386 | SPC10415 | Collinsella_aerofaciens | Faecalibacterium_prausnitzii | *Blautia producta* | ++++ |
| SPC10097 | SPC10386 | SPC10567 | Collinsella_aerofaciens | Faecalibacterium_prausnitzii | Eubacterium_rectale | +++ |
| SPC10097 | SPC10386 | SPC10390 | Collinsella_aerofaciens | Faecalibacterium_prausnitzii | Lachnospiraceae_bacterium_5_1_57FAA | +++ |
| SPC10097 | SPC10390 | SPC10415 | Collinsella_aerofaciens | Lachnospiraceae_bacterium_5_1_57FAA | *Blautia producta* | ++++ |
| SPC10097 | SPC10390 | SPC10567 | Collinsella_aerofaciens | Lachnospiraceae_bacterium_5_1_57FAA | Eubacterium_rectale | ++++ |
| SPC10304 | SPC10415 | SPC10567 | Coprococcus_comes | *Blautia producta* | Eubacterium_rectale | ++++ |
| SPC10304 | SPC10325 | SPC10415 | Coprococcus_comes | Clostridium_bolteae | *Blautia producta* | ++++ |
| SPC10304 | SPC10325 | SPC10355 | Coprococcus_comes | Clostridium_bolteae | Clostridium_symbiosum | |
| SPC10304 | SPC10325 | SPC10567 | Coprococcus_comes | Clostridium_bolteae | Eubacterium_rectale | −− |
| SPC10304 | SPC10325 | SPC10386 | Coprococcus_comes | Clostridium_bolteae | Faecalibacterium_prausnitzii | +++ |
| SPC10304 | SPC10325 | SPC10390 | Coprococcus_comes | Clostridium_bolteae | Lachnospiraceae_bacterium_5_1_57FAA | +++ |
| SPC10304 | SPC10355 | SPC10415 | Coprococcus_comes | Clostridium_symbiosum | *Blautia producta* | ++++ |
| SPC10304 | SPC10355 | SPC10567 | Coprococcus_comes | Clostridium_symbiosum | Eubacterium_rectale | −−− |
| SPC10304 | SPC10355 | SPC10386 | Coprococcus_comes | Clostridium_symbiosum | Faecalibacterium_prausnitzii | |
| SPC10304 | SPC10355 | SPC10390 | Coprococcus_comes | Clostridium_symbiosum | Lachnospiraceae_bacterium_5_1_57FAA | |
| SPC10304 | SPC10386 | SPC10415 | Coprococcus_comes | Faecalibacterium_prausnitzii | *Blautia producta* | ++++ |
| SPC10304 | SPC10386 | SPC10567 | Coprococcus_comes | Faecalibacterium_prausnitzii | Eubacterium_rectale | − |
| SPC10304 | SPC10386 | SPC10390 | Coprococcus_comes | Faecalibacterium_prausnitzii | Lachnospiraceae_bacterium_5_1_57FAA | |
| SPC10304 | SPC10390 | SPC10415 | Coprococcus_comes | Lachnospiraceae_bacterium_5_1_57FAA | *Blautia producta* | ++++ |
| SPC10304 | SPC10390 | SPC10567 | Coprococcus_comes | Lachnospiraceae_bacterium_5_1_57FAA | Eubacterium_rectale | |
| SPC10386 | SPC10415 | SPC10567 | Faecalibacterium_prausnitzii | *Blautia producta* | Eubacterium_rectale | ++++ |
| SPC10386 | SPC10390 | SPC10415 | Faecalibacterium_prausnitzii | Lachnospiraceae_bacterium_5_1_57FAA | *Blautia producta* | ++++ |
| SPC10386 | SPC10390 | SPC10567 | Faecalibacterium_prausnitzii | Lachnospiraceae_bacterium_5_1_57FAA | Eubacterium_rectale | |
| SPC10390 | SPC10415 | SPC10567 | Lachnospiraceae_bacterium_5_1_57FAA | *Blautia producta* | Eubacterium_rectale | ++++ |

TABLE 5

| Species | Domain | Phylum | Class | Order | Family | Genus | NIAID Category A, B, C Pathogen |
|---|---|---|---|---|---|---|---|
| *Bacillus anthracis* | Bacteria | Firmicutes | Bacilli | Bacillales | Bacillaceae | *Bacillus* | Category-A |
| *Bifidobacterium dentium* | Bacteria | Actinobacteria | Actinobacteria | Bifidobacteriales | Bifidobacteriaceae | *Bifidobacterium* | No |
| *Bordetella bronchiseptica* | Bacteria | Proteobacteria | Betaproteobacteria | Burkholderiales | Alcaligenaceae | *Bordetella* | No |

TABLE 5-continued

| Species | Domain | Phylum | Class | Order | Family | Genus | NIAID Cateogry A, B, C Pathogen |
|---|---|---|---|---|---|---|---|
| *Bordetella holmesii* | Bacteria | Proteobacteria | Beta-proteobacteria | Burkholderiales | Alcaligenaceae | *Bordetella* | No |
| *Bordetella parapertussis* | Bacteria | Proteobacteria | Beta-proteobacteria | Burkholderiales | Alcaligenaceae | *Bordetella* | No |
| *Bordetella pertussis* | Bacteria | Proteobacteria | Beta-proteobacteria | Burkholderiales | Alcaligenaceae | *Bordetella* | No |
| *Borrelia afzelii* | Bacteria | Spirochaetes | Spirochaetia | Spirochaetales | Spirochaetaceae | *Borrelia* | No |
| *Borrelia burgdorferi* | Bacteria | Spirochaetes | Spirochaetia | Spirochaetales | Spirochaetaceae | *Borrelia* | No |
| *Borrelia crocidurae* | Bacteria | Spirochaetes | Spirochaetia | Spirochaetales | Spirochaetaceae | *Borrelia* | No |
| *Borrelia duttonii* | Bacteria | Spirochaetes | Spirochaetia | Spirochaetales | Spirochaetaceae | *Borrelia* | No |
| *Borrelia garinii* | Bacteria | Spirochaetes | Spirochaetia | Spirochaetales | Spirochaetaceae | *Borrelia* | No |
| *Borrelia hermsii* | Bacteria | Spirochaetes | Spirochaetia | Spirochaetales | Spirochaetaceae | *Borrelia* | No |
| *Borrelia hispanica* | Bacteria | Spirochaetes | Spirochaetia | Spirochaetales | Spirochaetaceae | *Borrelia* | No |
| *Borrelia persica* | Bacteria | Spirochaetes | Spirochaetia | Spirochaetales | Spirochaetaceae | *Borrelia* | No |
| *Borrelia recurrentis* | Bacteria | Spirochaetes | Spirochaetia | Spirochaetales | Spirochaetaceae | *Borrelia* | No |
| *Borrelia* sp. NE49 | Bacteria | Spirochaetes | Spirochaetia | Spirochaetales | Spirochaetaceae | *Borrelia* | No |
| *Borrelia spielmanii* | Bacteria | Spirochaetes | Spirochaetia | Spirochaetales | Spirochaetaceae | *Borrelia* | No |
| *Borrelia turicatae* | Bacteria | Spirochaetes | Spirochaetia | Spirochaetales | Spirochaetaceae | *Borrelia* | No |
| *Borrelia valaisiana* | Bacteria | Spirochaetes | Spirochaetia | Spirochaetales | Spirochaetaceae | *Borrelia* | No |
| *Brucella abortus* | Bacteria | Proteobacteria | Alpha-proteobacteria | Rhizobiales | Brucellaceae | *Brucella* | Cate-gory-B |
| *Brucella canis* | Bacteria | Proteobacteria | Alpha-proteobacteria | Rhizobiales | Brucellaceae | *Brucella* | Cate-gory-B |
| *Brucella ceti* | Bacteria | Proteobacteria | Alpha-proteobacteria | Rhizobiales | Brucellaceae | *Brucella* | Cate-gory-B |
| *Brucella melitensis* | Bacteria | Proteobacteria | Alpha-proteobacteria | Rhizobiales | Brucellaceae | *Brucella* | Cate-gory-B |
| *Brucella microti* | Bacteria | Proteobacteria | Alpha-proteobacteria | Rhizobiales | Brucellaceae | *Brucella* | Cate-gory-B |
| *Brucella ovis* | Bacteria | Proteobacteria | Alpha-proteobacteria | Rhizobiales | Brucellaceae | *Brucella* | Cate-gory-B |
| *Brucella* sp. 83/13 | Bacteria | Proteobacteria | Alpha-proteobacteria | Rhizobiales | Brucellaceae | *Brucella* | Cate-gory-B |
| *Brucella* sp. BO1 | Bacteria | Proteobacteria | Alpha-proteobacteria | Rhizobiales | Brucellaceae | *Brucella* | Cate-gory-B |
| *Brucella suis* | Bacteria | Proteobacteria | Alpha-proteobacteria | Rhizobiales | Brucellaceae | *Brucella* | Cate-gory-B |
| *Burkholderia ambifaria* | Bacteria | Proteobacteria | Beta-proteobacteria | Burkholderiales | Burkholderiaceae | *Burkholderia* | No |
| *Burkholderia cenocepacia* | Bacteria | Proteobacteria | Beta-proteobacteria | Burkholderiales | Burkholderiaceae | *Burkholderia* | No |
| *Burkholderia cepacia* | Bacteria | Proteobacteria | Beta-proteobacteria | Burkholderiales | Burkholderiaceae | *Burkholderia* | No |
| *Burkholderia mallei* | Bacteria | Proteobacteria | Beta-proteobacteria | Burkholderiales | Burkholderiaceae | *Burkholderia* | Cate-gory-B |
| *Burkholderia multivorans* | Bacteria | Proteobacteria | Beta-proteobacteria | Burkholderiales | Burkholderiaceae | *Burkholderia* | No |
| *Burkholderia oklahomensis* | Bacteria | Proteobacteria | Beta-proteobacteria | Burkholderiales | Burkholderiaceae | *Burkholderia* | No |
| *Burkholderia pseudomallei* | Bacteria | Proteobacteria | Beta-proteobacteria | Burkholderiales | Burkholderiaceae | *Burkholderia* | Cate-gory-B |
| *Burkholderia rhizoxinica* | Bacteria | Proteobacteria | Beta-proteobacteria | Burkholderiales | Burkholderiaceae | *Burkholderia* | No |
| *Burkholderia* sp. 383 | Bacteria | Proteobacteria | Beta-proteobacteria | Burkholderiales | Burkholderiaceae | *Burkholderia* | No |
| *Burkholderia xenovorans* | Bacteria | Proteobacteria | Beta-proteobacteria | Burkholderiales | Burkholderiaceae | *Burkholderia* | No |
| *Burkholderiales bacterium* 1_1_47 | Bacteria | Proteobacteria | Beta-proteobacteria | Burkholderiales | | | No |
| *Campylobacter coli* | Bacteria | Proteobacteria | Epsilon-proteobacteria | Campylo-bacterales | Campylo-bacteraceae | *Campylobacter* | No |
| *Campylobacter concisus* | Bacteria | Proteobacteria | Epsilon-proteobacteria | Campylo-bacterales | Campylo-bacteraceae | *Campylobacter* | No |
| *Campylobacter curvus* | Bacteria | Proteobacteria | Epsilon-proteobacteria | Campylo-bacterales | Campylo-bacteraceae | *Campylobacter* | No |
| *Campylobacter fetus* | Bacteria | Proteobacteria | Epsilon-proteobacteria | Campylo-bacterales | Campylo-bacteraceae | *Campylobacter* | No |
| *Campylobacter gracilis* | Bacteria | Proteobacteria | Epsilon-proteobacteria | Campylo-bacterales | Campylo-bacteraceae | *Campylobacter* | No |
| *Campylobacter hominis* | Bacteria | Proteobacteria | Epsilon-proteobacteria | Campylo-bacterales | Campylo-bacteraceae | *Campylobacter* | No |
| *Campylobacter jejuni* | Bacteria | Proteobacteria | Epsilon-proteobacteria | Campylo-bacterales | Campylo-bacteraceae | *Campylobacter* | Cate-gory-B |
| *Campylobacter lari* | Bacteria | Proteobacteria | Epsilon-proteobacteria | Campylo-bacterales | Campylo-bacteraceae | *Campylobacter* | No |

TABLE 5-continued

| Species | Domain | Phylum | Class | Order | Family | Genus | NIAID Cateogry A, B, C Pathogen |
|---|---|---|---|---|---|---|---|
| *Campylobacter rectus* | Bacteria | Proteobacteria | Epsilon-proteobacteria | Campylo-bacterales | Campylo-bacteraceae | *Campylobacter* | No |
| *Campylobacter showae* | Bacteria | Proteobacteria | Epsilon-proteobacteria | Campylo-bacterales | Campylo-bacteraceae | *Campylobacter* | No |
| *Campylobacter* sp. FOBRC14 | Bacteria | Proteobacteria | Epsilon-proteobacteria | Campylo-bacterales | Campylo-bacteraceae | *Campylobacter* | No |
| *Campylobacter* sp. FOBRC15 | Bacteria | Proteobacteria | Epsilon-proteobacteria | Campylo-bacterales | Campylo-bacteraceae | *Campylobacter* | No |
| *Campylobacter* sp. oral clone BB120 | Bacteria | Proteobacteria | Epsilon-proteobacteria | Campylo-bacterales | Campylo-bacteraceae | *Campylobacter* | No |
| *Campylobacter sputorum* | Bacteria | Proteobacteria | Epsilon-proteobacteria | Campylo-bacterales | Campylo-bacteraceae | *Campylobacter* | No |
| *Campylobacter upsaliensis* | Bacteria | Proteobacteria | Epsilon-proteobacteria | Campylo-bacterales | Campylo-bacteraceae | *Campylobacter* | No |
| *Chlamydia muridarum* | Bacteria | Chlamydiae | Chlamydiia | Chlamydiales | Chlamydiaceae | *Chlamydia* | No |
| *Chlamydia psittaci* | Bacteria | Chlamydiae | Chlamydiia | Chlamydiales | Chlamydiaceae | *Chlamydia* | Cate-gory-B |
| Chlamydia trachomatis | Bacteria | Chlamydiae | Chlamydiia | Chlamydiales | Chlamydiaceae | *Chlamydia* | No |
| *Chlamydophila pecorum* | Bacteria | Chlamydiae | Chlamydiia | Chlamydiales | Chlamydiaceae | *Chlamydia* | No |
| *Chlamydophila pneumoniae* | Bacteria | Chlamydiae | Chlamydiia | Chlamydiales | Chlamydiaceae | *Chlamydia* | No |
| *Chlamydophila psittaci* | Bacteria | Chlamydiae | Chlamydiia | Chlamydiales | Chlamydiaceae | *Chlamydia* | No |
| *Clostridium botulinum* | Bacteria | Firmicutes | Clostridia | Clostridiales | Clostridiaceae | *Clostridium* | Cate-gory-A |
| *Clostridium difficile* | Bacteria | Firmicutes | Clostridia | Clostridiales | Peptostrep-tococcaceae | | No |
| *Clostridium perfringens* | Bacteria | Firmicutes | Clostridia | Clostridiales | Clostridiaceae | *Clostridium* | Cate-gory-B |
| *Corynebacterium amycolatum* | Bacteria | Actino-bacteria | Actino-bacteria | Actinomycetales | Corynebacteriaceae | *Corynebacterium* | No |
| *Corynebacterium diphtheriae* | Bacteria | Actino-bacteria | Actino-bacteria | Actinomycetales | Corynebacteriaceae | *Corynebacterium* | No |
| *Corynebacterium jeikeium* | Bacteria | Actino-bacteria | Actino-bacteria | Actinomycetales | Corynebacteriaceae | *Corynebacterium* | No |
| *Corynebacterium striatum* | Bacteria | Actino-bacteria | Actino-bacteria | Actinomycetales | Corynebacteriaceae | *Corynebacterium* | No |
| *Corynebacterium urealyticum* | Bacteria | Actino-bacteria | Actino-bacteria | Actinomycetales | Corynebacteriaceae | *Corynebacterium* | No |
| *Corynebacterium xerosis* | Bacteria | Actino-bacteria | Actino-bacteria | Actinomycetales | Corynebacteriaceae | *Corynebacterium* | No |
| *Coxiella burnetii* | Bacteria | Proteobacteria | Gamma-proteobacteria | Legionellales | Coxiellaceae | *Coxiella* | Cate-gory-B |
| *Ehrlichia chaffeensis* | Bacteria | Proteobacteria | Alpha-proteobacteria | Rickettsiales | Anaplasmataceae | *Ehrlichia* | No |
| *Escherichia coli* | Bacteria | Proteobacteria | Gamma-proteobacteria | Enterobacteriales | Enterobacteriaceae | *Escherichia* | Cate-gory-B |
| *Francisella tularensis* | Bacteria | Proteobacteria | Gamma-proteobacteria | Thiotrichales | Francisellaceae | *Francisella* | Cate-gory-A |
| *Haemophilus ducreyi* | Bacteria | Proteobacteria | Gamma-proteobacteria | Pasteurellales | Pasteurellaceae | *Haemophilus* | No |
| *Haemophilus influenzae* | Bacteria | Proteobacteria | Gamma-proteobacteria | Pasteurellales | Pasteurellaceae | *Haemophilus* | No |
| *Helicobacter pylori* | Bacteria | Proteobacteria | Epsilon-proteobacteria | Campylo-bacterales | Helicobacteraceae | *Helicobacter* | No |
| *Klebsiella oxytoca* | Bacteria | Proteobacteria | Gamma-proteobacteria | Enterobacteriales | Enterobacteriaceae | *Klebsiella* | No |
| *Klebsiella pneumoniae* | Bacteria | Proteobacteria | Gamma-proteobacteria | Enterobacteriales | Enterobacteriaceae | *Klebsiella* | No |
| *Legionella hackeliae* | Bacteria | Proteobacteria | Gamma-proteobacteria | Legionellales | Legionellaceae | *Legionella* | No |
| *Legionella longbeachae* | Bacteria | Proteobacteria | Gamma-proteobacteria | Legionellales | Legionellaceae | *Legionella* | No |
| *Legionella pneumophila* | Bacteria | Proteobacteria | Gamma-proteobacteria | Legionellales | Legionellaceae | *Legionella* | No |
| *Legionella* sp. D3923 | Bacteria | Proteobacteria | Gamma-proteobacteria | Legionellales | Legionellaceae | *Legionella* | No |
| *Legionella* sp. D4088 | Bacteria | Proteobacteria | Gamma-proteobacteria | Legionellales | Legionellaceae | *Legionella* | No |
| *Legionella* sp. H63 | Bacteria | Proteobacteria | Gamma-proteobacteria | Legionellales | Legionellaceae | *Legionella* | No |
| *Legionella* sp. NML 93L054 | Bacteria | Proteobacteria | Gamma-proteobacteria | Legionellales | Legionellaceae | *Legionella* | No |
| *Legionella steelei* | Bacteria | Proteobacteria | Gamma-proteobacteria | Legionellales | Legionellaceae | *Legionella* | No |
| *Leptospira borgpetersenii* | Bacteria | Spirochaetes | Spirochaetia | Spirochaetales | Leptospiraceae | *Leptospira* | No |
| *Leptospira broomii* | Bacteria | Spirochaetes | Spirochaetia | Spirochaetales | Leptospiraceae | *Leptospira* | No |

TABLE 5-continued

| Species | Domain | Phylum | Class | Order | Family | Genus | NIAID Cateogry A, B, C Pathogen |
|---|---|---|---|---|---|---|---|
| Leptospira interrogans | Bacteria | Spirochaetes | Spirochaetia | Spirochaetales | Leptospiraceae | Leptospira | No |
| Leptospira licerasiae | Bacteria | Spirochaetes | Spirochaetia | Spirochaetales | Leptospiraceae | Leptospira | No |
| Listeria grayi | Bacteria | Firmicutes | Bacilli | Bacillales | Listeriaceae | Listeria | No |
| Listeria monocytogenes | Bacteria | Firmicutes | Bacilli | Bacillales | Listeriaceae | Listeria | Category-B |
| Listeria welshimeri | Bacteria | Firmicutes | Bacilli | Bacillales | Listeriaceae | Listeria | No |
| Mycobacterium abscessus | Bacteria | Actinobacteria | Actinobacteria | Actinomycetales | Mycobacteriaceae | Mycobacterium | No |
| Mycobacterium africanum | Bacteria | Actinobacteria | Actinobacteria | Actinomycetales | Mycobacteriaceae | Mycobacterium | No |
| Mycobacterium alsiensis | Bacteria | Actinobacteria | Actinobacteria | Actinomycetales | Mycobacteriaceae | Mycobacterium | No |
| Mycobacterium avium | Bacteria | Actinobacteria | Actinobacteria | Actinomycetales | Mycobacteriaceae | Mycobacterium | No |
| Mycobacterium chelonae | Bacteria | Actinobacteria | Actinobacteria | Actinomycetales | Mycobacteriaceae | Mycobacterium | No |
| Mycobacterium colombiense | Bacteria | Actinobacteria | Actinobacteria | Actinomycetales | Mycobacteriaceae | Mycobacterium | No |
| Mycobacterium elephantis | Bacteria | Actinobacteria | Actinobacteria | Actinomycetales | Mycobacteriaceae | Mycobacterium | No |
| Mycobacterium gordonae | Bacteria | Actinobacteria | Actinobacteria | Actinomycetales | Mycobacteriaceae | Mycobacterium | No |
| Mycobacterium intracellulare | Bacteria | Actinobacteria | Actinobacteria | Actinomycetales | Mycobacteriaceae | Mycobacterium | No |
| Mycobacterium kansasii | Bacteria | Actinobacteria | Actinobacteria | Actinomycetales | Mycobacteriaceae | Mycobacterium | No |
| Mycobacterium lacus | Bacteria | Actinobacteria | Actinobacteria | Actinomycetales | Mycobacteriaceae | Mycobacterium | No |
| Mycobacterium leprae | Bacteria | Actinobacteria | Actinobacteria | Actinomycetales | Mycobacteriaceae | Mycobacterium | No |
| Mycobacterium lepromatosis | Bacteria | Actinobacteria | Actinobacteria | Actinomycetales | Mycobacteriaceae | Mycobacterium | No |
| Mycobacterium mageritense | Bacteria | Actinobacteria | Actinobacteria | Actinomycetales | Mycobacteriaceae | Mycobacterium | No |
| Mycobacterium mantenii | Bacteria | Actinobacteria | Actinobacteria | Actinomycetales | Mycobacteriaceae | Mycobacterium | No |
| Mycobacterium marinum | Bacteria | Actinobacteria | Actinobacteria | Actinomycetales | Mycobacteriaceae | Mycobacterium | No |
| Mycobacterium microti | Bacteria | Actinobacteria | Actinobacteria | Actinomycetales | Mycobacteriaceae | Mycobacterium | No |
| Mycobacterium neoaurum | Bacteria | Actinobacteria | Actinobacteria | Actinomycetales | Mycobacteriaceae | Mycobacterium | No |
| Mycobacterium parascrofulaceum | Bacteria | Actinobacteria | Actinobacteria | Actinomycetales | Mycobacteriaceae | Mycobacterium | No |
| Mycobacterium paraterrae | Bacteria | Actinobacteria | Actinobacteria | Actinomycetales | Mycobacteriaceae | Mycobacterium | No |
| Mycobacterium phlei | Bacteria | Actinobacteria | Actinobacteria | Actinomycetales | Mycobacteriaceae | Mycobacterium | No |
| Mycobacterium seoulense | Bacteria | Actinobacteria | Actinobacteria | Actinomycetales | Mycobacteriaceae | Mycobacterium | No |
| Mycobacterium smegmatis | Bacteria | Actinobacteria | Actinobacteria | Actinomycetales | Mycobacteriaceae | Mycobacterium | No |
| Mycobacterium tuberculosis | Bacteria | Actinobacteria | Actinobacteria | Actinomycetales | Mycobacteriaceae | Mycobacterium | Category-C |
| Mycobacterium ulcerans | Bacteria | Actinobacteria | Actinobacteria | Actinomycetales | Mycobacteriaceae | Mycobacterium | No |
| Mycobacterium vulneris | Bacteria | Actinobacteria | Actinobacteria | Actinomycetales | Mycobacteriaceae | Mycobacterium | No |
| Neisseria gonorrhoeae | Bacteria | Proteobacteria | Betaproteobacteria | Neisseriales | Neisseriaceae | Neisseria | No |
| Neisseria meningitidis | Bacteria | Proteobacteria | Betaproteobacteria | Neisseriales | Neisseriaceae | Neisseria | No |
| Orientia tsutsugamushi | Bacteria | Proteobacteria | Alphaproteobacteria | Rickettsiales | Rickettsiaceae | Orientia | No |
| Rickettsia akari | Bacteria | Proteobacteria | Alphaproteobacteria | Rickettsiales | Rickettsiaceae | Rickettsia | No |
| Rickettsia conorii | Bacteria | Proteobacteria | Alphaproteobacteria | Rickettsiales | Rickettsiaceae | Rickettsia | No |
| Rickettsia prowazekii | Bacteria | Proteobacteria | Alphaproteobacteria | Rickettsiales | Rickettsiaceae | Rickettsia | Category-B |
| Rickettsia rickettsii | Bacteria | Proteobacteria | Alphaproteobacteria | Rickettsiales | Rickettsiaceae | Rickettsia | No |
| Rickettsia slovaca | Bacteria | Proteobacteria | Alphaproteobacteria | Rickettsiales | Rickettsiaceae | Rickettsia | No |

TABLE 5-continued

| Species | Domain | Phylum | Class | Order | Family | Genus | NIAID Cateogry A, B, C Pathogen |
|---|---|---|---|---|---|---|---|
| *Rickettsia typhi* | Bacteria | Proteobacteria | Alpha-proteobacteria | Rickettsiales | Rickettsiaceae | *Rickettsia* | No |
| *Salmonella bongori* | Bacteria | Proteobacteria | Gamma-proteobacteria | Enterobacteriales | Enterobacteriaceae | *Salmonella* | Category-B |
| *Salmonella enterica* | Bacteria | Proteobacteria | Gamma-proteobacteria | Enterobacteriales | Enterobacteriaceae | *Salmonella* | Category-B |
| *Salmonella typhimurium* | Bacteria | Proteobacteria | Gamma-proteobacteria | Enterobacteriales | Enterobacteriaceae | *Salmonella* | Category-B |
| *Shigella boydii* | Bacteria | Proteobacteria | Gamma-proteobacteria | Enterobacteriales | Enterobacteriaceae | *Shigella* | Category-B |
| *Shigella dysenteriae* | Bacteria | Proteobacteria | Gamma-proteobacteria | Enterobacteriales | Enterobacteriaceae | *Shigella* | Category-B |
| *Shigella flexneri* | Bacteria | Proteobacteria | Gamma-proteobacteria | Enterobacteriales | Enterobacteriaceae | *Shigella* | Category-B |
| *Shigella sonnei* | Bacteria | Proteobacteria | Gamma-proteobacteria | Enterobacteriales | Enterobacteriaceae | *Shigella* | Category-B |
| *Shigella* sp. D9 | Bacteria | Proteobacteria | Gamma-proteobacteria | Enterobacteriales | Enterobacteriaceae | *Shigella* | Category-B |
| *Staphylococcus aureus* | Bacteria | Firmicutes | Bacilli | Bacillales | Staphylococcaceae | *Staphylococcus* | Category-B |
| *Streptococcus pyogenes* | Bacteria | Firmicutes | Bacilli | Lactobacillales | Streptococcaceae | *Streptococcus* | No |
| *Treponema denticola* | Bacteria | Spirochaetes | Spirochaetia | Spirochaetales | Spirochaetaceae | *Treponema* | No |
| *Treponema lecithinolyticum* | Bacteria | Spirochaetes | Spirochaetia | Spirochaetales | Spirochaetaceae | *Treponema* | No |
| *Treponema pallidum* | Bacteria | Spirochaetes | Spirochaetia | Spirochaetales | Spirochaetaceae | *Treponema* | No |
| *Treponema parvum* | Bacteria | Spirochaetes | Spirochaetia | Spirochaetales | Spirochaetaceae | *Treponema* | No |
| *Treponema putidum* | Bacteria | Spirochaetes | Spirochaetia | Spirochaetales | Spirochaetaceae | *Treponema* | No |
| *Treponema refringens* | Bacteria | Spirochaetes | Spirochaetia | Spirochaetales | Spirochaetaceae | *Treponema* | No |
| *Treponema socranskii* | Bacteria | Spirochaetes | Spirochaetia | Spirochaetales | Spirochaetaceae | *Treponema* | No |
| *Treponema vincentii* | Bacteria | Spirochaetes | Spirochaetia | Spirochaetales | Spirochaetaceae | *Treponema* | No |
| *Vibrio cholerae* | Bacteria | Proteobacteria | Gamma-proteobacteria | Vibrionales | Vibrionaceae | *Vibrio* | Category-B |
| *Vibrio fluvialis* | Bacteria | Proteobacteria | Gamma-proteobacteria | Vibrionales | Vibrionaceae | *Vibrio* | Category-B |
| *Vibrio furnissii* | Bacteria | Proteobacteria | Gamma-proteobacteria | Vibrionales | Vibrionaceae | *Vibrio* | Category-B |
| *Vibrio mimicus* | Bacteria | Proteobacteria | Gamma-proteobacteria | Vibrionales | Vibrionaceae | *Vibrio* | Category-B |
| *Vibrio parahaemolyticus* | Bacteria | Proteobacteria | Gamma-proteobacteria | Vibrionales | Vibrionaceae | *Vibrio* | Category-B |
| *Vibrio* sp. RC341 | Bacteria | Proteobacteria | Gamma-proteobacteria | Vibrionales | Vibrionaceae | *Vibrio* | Category-B |
| *Vibrio vulnificus* | Bacteria | Proteobacteria | Gamma-proteobacteria | Vibrionales | Vibrionaceae | *Vibrio* | Category-B |
| *Yersinia aldovae* | Bacteria | Proteobacteria | Gamma-proteobacteria | Enterobacteriales | Enterobacteriaceae | *Yersinia* | No |
| *Yersinia aleksiciae* | Bacteria | Proteobacteria | Gamma-proteobacteria | Enterobacteriales | Enterobacteriaceae | *Yersinia* | No |
| *Yersinia bercovieri* | Bacteria | Proteobacteria | Gamma-proteobacteria | Enterobacteriales | Enterobacteriaceae | *Yersinia* | No |
| *Yersinia enterocolitica* | Bacteria | Proteobacteria | Gamma-proteobacteria | Enterobacteriales | Enterobacteriaceae | *Yersinia* | Category-B |
| *Yersinia frederiksenii* | Bacteria | Proteobacteria | Gamma-proteobacteria | Enterobacteriales | Enterobacteriaceae | *Yersinia* | No |
| *Yersinia intermedia* | Bacteria | Proteobacteria | Gamma-proteobacteria | Enterobacteriales | Enterobacteriaceae | *Yersinia* | No |
| *Yersinia kristensenii* | Bacteria | Proteobacteria | Gamma-proteobacteria | Enterobacteriales | Enterobacteriaceae | *Yersinia* | No |
| *Yersinia mollaretii* | Bacteria | Proteobacteria | Gamma-proteobacteria | Enterobacteriales | Enterobacteriaceae | *Yersinia* | No |
| *Yersinia pestis* | Bacteria | Proteobacteria | Gamma-proteobacteria | Enterobacteriales | Enterobacteriaceae | *Yersinia* | Category-A |
| *Yersinia pseudotuberculosis* | Bacteria | Proteobacteria | Gamma-proteobacteria | Enterobacteriales | Enterobacteriaceae | *Yersinia* | No |
| *Yersinia rohdei* | Bacteria | Proteobacteria | Gamma-proteobacteria | Enterobacteriales | Enterobacteriaceae | *Yersinia* | No |
| Multi-Drug Resistant bacteria | Bacteria | multiple | multiple | multiple | multiple | multiple | Category-C |
| Carbapenem-Resistent Enterobacteriaceae (CRE) | Bacteria | multiple | multiple | multiple | multiple | multiple | Category-C |
| Extended Spectrum Beta-Lactam Resistant Enterococci (ESBL) | Bacteria | multiple | multiple | multiple | multiple | multiple | Category-C |
| Vancomycin-Resistant Enterococci (VRE) | Bacteria | multiple | multiple | multiple | multiple | multiple | Category-C |

TABLE 6

| List |
|---|
| Abdominal abscess |
| Abdominal cavity inflammation |
| Abscess |
| *Absidia* infection |
| Achromatopsia |
| Acidemia |
| *Acinetobacter baumanii* infection |
| *Acinetobacter* infection |
| *Acinetobacter lwoffii* infection |
| Acne |
| Acne vulgaris |
| Acoustic neuroma |
| Acromegaly |
| *Actinomyces israelii* infection |
| Acute bronchitis |
| Acute chest syndrome |
| Acute coronary syndrome |
| Acute decompensated heart failure |
| Acute external otitis |
| Acute lung injury |
| Acute lymphoblastic leukemia |
| Acute myelogenous leukemia |
| Acute promyelocytic leukemia |
| Acute sinusitis |
| Addison's disease |
| Adenocarcinoma |
| Adenoid hypertrophy |
| Adenoma |
| Adenomyosis |
| Adenosine deaminase deficiency |
| Adenovirus infection |
| Adhesive capsulitis |
| Adrenal cortical carcinoma |
| Adrenal gland hypofunction |
| Adrenomyeloneuropathy |
| Adult respiratory distress syndrome |
| Adult T-cell lymphoma |
| Adult varicella zoster virus infection |
| Advanced solid tumor |
| Agammaglobulinemia |
| Age related macular degeneration |
| Aggression |
| Aggressive fibromatosis |
| Aging |
| Agitation |
| AL amyloidosis |
| Albuminuria |
| Alcoholism (and effects) |
| Alkaptonuria |
| Allergic conjunctivitis |
| Allergic rhinitis |
| Allergy |
| Alopecia |
| Alopecia areata |
| Alpha mannosidosis |
| Alpha-1 antitrypsin deficiency |
| ALS |
| Alzheimers disease |
| Amenorrhea |
| Amnesia |
| *Amoeba* infection |
| Amoebic liver abscess |
| Amphetamine dependence |
| Amyloidosis |
| Anal cancer |
| Anal fissure |
| Anal fistula |
| Anal tumor |
| Anaplastic astrocytoma |
| Anaplastic large cell lymphoma |
| Anemia |
| Anesthesia |
| Angina |
| Angioedema |
| Angiomyolipoma |
| Angiosarcoma |
| Angle closure glaucoma |
| Ankylosing spondylitis |

TABLE 6-continued

| List |
|---|
| Anorexia nervosa |
| Anovulation |
| Antibiotic treatment |
| Antiphospholipid syndrome |
| Antitbiotic associated diarrhea |
| Anus pain |
| Anxiety disorder |
| Aortic aneurysm |
| Aortic stenosis |
| Aplastic anemia |
| Apnea |
| Appendicitis |
| Appetite loss |
| Arterial occlusive disease |
| Arterial thrombosis |
| Arteriosclerosis |
| Arteriovenous malformation |
| Artery disease |
| Arthralgia |
| Arthritis |
| Ascites |
| Asperger syndrome |
| *Aspergillus fumigatus* infection |
| *Aspergillus* infection |
| Asthma |
| Astrocytoma |
| Ataxia telangiectasia |
| Atherosclerosis |
| Atopic dermatitis |
| Atopy/Allergic Sensitivity |
| Atrial fibrillation |
| Atrial flutter |
| Atrophic vaginitis |
| Atrophy |
| Attention deficit hyperactivity disorder |
| Autism |
| Autoimmune disease |
| Autoimmune hemolytic anemia |
| Autosomal dominant polycystic kidney disease |
| B-cell acute lymphoblastic leukemia |
| B-cell lymphoma |
| *Bacillus anthracis* infection |
| *Bacillus* infection |
| Back pain |
| Bacteremia |
| Bacterial endocarditis |
| Bacterial eye infection |
| Bacterial infection |
| Bacterial meningitis |
| Bacterial pneumonia |
| Bacterial respiratory tract infection |
| Bacterial skin infection |
| Bacterial susceptibility |
| Bacterial urinary tract infection |
| Bacterial vaginosis |
| *Bacteroides caccae* infection |
| *Bacteroides fragilis* infection |
| *Bacteroides* infection |
| *Bacteroides thetaiotaomicron* infection |
| *Bacteroides uniformis* infection |
| *Bacteroides vulgatus* infection |
| Balanitis |
| Bariatric surgery |
| Bartholinitis |
| *Bartonella bacilliformis* infection |
| *Bartonella* infection |
| Basal cell carcinoma |
| Becker muscular dystrophy |
| Behcets disease |
| Beta thalassemia |
| *Bifidobacterium* infection |
| Biliary cancer |
| Biliary cirrhosis |
| Biliary tract disease |
| Biliary tract infection |
| Biliary tumor |
| Binge eating disorder |
| Bipolar disorder |

TABLE 6-continued

| List |
| --- |
| Bipolar I disorder |
| Birth complication |
| BK virus infection |
| Bladder cancer |
| Bladder tumor |
| *Blastomyces* infection |
| Bleeding |
| Blepharitis |
| Blepharospasm |
| Blood clotting disorder |
| Blood clotting factor deficiency |
| Blood transfusion |
| Bone and joint infection |
| Bone disease |
| Bone infection |
| Bone injury |
| Bone marrow disease |
| Bone marrow failure |
| Bone marrow transplantation |
| Bone metastases |
| Bone resorption |
| Bone tumor |
| *Bordetella pertussis* infection |
| *Borrelia burgdorferi* infection |
| *Borrelia recurrentis* infection |
| Brain disease |
| Brain hemorrhage |
| Brain infarction |
| Brain injury |
| Brain ischemia |
| Brain tumor |
| Breast cancer |
| Breast disease |
| Breast tumor |
| Bronchiectasis |
| Bronchiolitis |
| Bronchitis |
| Bronchospasm |
| *Brucella* infection |
| Budd Chiari syndrome |
| Bulimia nervosa |
| *Burkholderia* infection |
| Burkitts lymphoma |
| Bursitis |
| Cachexia |
| *Campylobacter fetus* infection |
| *Campylobacter* infection |
| *Campylobacter jejuni* infection |
| Cancer |
| Cancer pain |
| *Candida albicans* infection |
| *Candida* infection |
| *Candida krusei* infection |
| Capillary leak syndrome |
| Carbamoyl phosphate synthase I deficiency |
| Carcinoid syndrome |
| Carcinoid tumor |
| Carcinoma |
| Cardiac edema |
| Cardiac failure |
| Cardiac hypertrophy |
| Cardiac reperfusion injury |
| Cardiotoxicity drug-induced |
| Cardiovascular disease |
| Carnitine palmitoyltransferase deficiency |
| Cartilage disease |
| Castlemans disease |
| Cataplexy |
| Cataract |
| Celiac Disease |
| Cellulitis |
| Central nervous system disease |
| Central nervous system injury |
| Central nervous system tumor |
| Cerebral edema |
| Cerebral hemorrhage |
| Cerebral hypoxia |
| Cerebral infarction |

TABLE 6-continued

| List |
| --- |
| Cerebral palsy |
| Cerebrotendinous xanthomatosis |
| Cerebrovascular disease |
| Cerebrovascular ischemia |
| Cervical dysplasia |
| Cervical dystonia |
| Cervicitis |
| Cervix disease |
| Cervix infection |
| Cervix injury |
| Chemotherapy induced nausea and vomiting |
| Chemotherapy-induced diarrhea |
| Chemotherapy-induced emesis |
| *Chlamydia* infection |
| *Chlamydia pneumoniae* infection |
| *Chlamydia trachomatis* infection |
| Chlamydiae infection |
| Cholangiocarcinoma |
| Cholangitis |
| Cholecystitis |
| Cholelithiasis |
| Cholesteryl ester storage disease |
| Chondrosarcoma |
| Chorioretinitis |
| Choroidal neovascularization |
| Choroiditis |
| Chromoblastomycosis |
| Chronic bronchitis |
| Chronic fatigue syndrome |
| Chronic granulomatous disease |
| Chronic infection |
| Chronic inflammatory demyelinating polyneuropathy |
| Chronic lymphocytic leukemia |
| Chronic myelocytic leukemia |
| Chronic obstructive airway disease |
| Chronic obstructive pulmonary disease |
| Chronic Polio Shedders |
| Chronic thromboembolic pulmonary hypertension |
| Churg-Strauss syndrome |
| CINCA syndrome |
| Circadian rhythm sleep disorder |
| Cirrhosis |
| *Citrobacter* infection |
| Citrullinuria |
| *Cladophialophora* infection |
| Clostridiaceae infection |
| *Clostridium botulinum* infection |
| *Clostridium difficile* infection |
| *Clostridium* infection |
| *Clostridium tetani* infection |
| Cluster headache |
| CMV retinitis |
| Coats disease |
| Cocaine addiction |
| *Coccidioides* infection |
| Cognitive disorder |
| Cold agglutinin disease |
| Colitis |
| Colon cancer |
| Colon polyps |
| Colon tumor |
| Colorectal cancer |
| Colorectal tumor |
| Common cold |
| Compensated liver cirrhosis |
| Complement diseases |
| Complex partial seizure |
| Complex regional pain syndrome |
| Complicated skin and skin structure infection |
| Complicated urinary tract infection |
| Compulsive gambling |
| Condyloma |
| Congenital adrenal hyperplasia |
| Congenital heart defect |
| Congenital hemophilia |
| Congestive heart failure |
| Conjunctiva disease |
| Conjunctival neoplasm |

TABLE 6-continued

| List |
|---|
| Conjunctivitis |
| Connective tissue disease |
| Constipation |
| Constipation predominant irritable bowel syndrome |
| Contact dermatitis |
| Contraception |
| Copper metabolism disorder |
| Corneal disease |
| Corneal injury |
| Corneal transplant rejection |
| Corneal transplantation |
| Corneal ulcer |
| Coronary artery disease |
| Coronary thrombosis |
| *Corynebacterium diphtheriae* infection |
| *Corynebacterium* infection |
| Cough |
| *Coxiella* infection |
| CRE infection |
| Crohns disease |
| Cryopyrin associated periodic syndrome |
| *Cryptococcus* infection |
| *Cryptococcus neoformans* infection |
| *Cryptococcus neoformans* meningitis |
| *Cryptosporidium* infection |
| Cushings disease |
| Cutaneous lupus erythematosus |
| Cutaneous T-cell lymphoma |
| Cystic fibrosis |
| Cystic hygroma |
| Cystinosis |
| Cystinuria |
| Cystitis |
| Cytomegalovirus infection |
| Dacryocystitis |
| Deafness |
| Decubitus ulcer |
| Deep vein thrombosis |
| Degenerative disc disease |
| Dementia |
| Dengue virus infection |
| Depression |
| Dermatitis |
| Dermatofibrosarcoma |
| Dermatological disease |
| Dermatomycosis |
| Dermatomyositis |
| Dermatophytosis |
| Diabetes insipidus |
| Diabetes mellitus |
| Diabetic complication |
| Diabetic foot ulcer |
| Diabetic ketoacidosis |
| Diabetic macular edema |
| Diabetic nephropathy |
| Diabetic neuropathy |
| Diabetic retinopathy |
| Diarrhea |
| Diarrhea predominant irritable bowel syndrome |
| Diastolic heart failure |
| Diffuse large B-cell lymphoma |
| Digoxin overdose |
| Discoid lupus erythematosus |
| Disseminated intravascular coagulation |
| Diverticulitis |
| Diverticulosis |
| DNA virus infection |
| Drug withdrawal syndrome |
| Dry age related macular degeneration |
| Duchenne dystrophy |
| Dumping syndrome |
| Duodenal ulcer |
| Dupuytren contracture |
| Dysgeusia |
| Dysmenorrhea |
| Dyspareunia |
| Dyspepsia |
| Dystonia |

TABLE 6-continued

| List |
|---|
| Dysuria |
| Ebola virus infection |
| Eczema |
| Edema |
| Eisenmenger syndrome |
| Embolism |
| Emesis |
| Emotional lability |
| Emphysema |
| Empyema |
| End stage renal disease |
| Endocarditis |
| Endocrine disease |
| Endocrine tumor |
| Endometrioid carcinoma |
| Endometriosis |
| Endophthalmitis |
| *Entamoeba histolytica* infection |
| Enteritis |
| *Enterobacter aerogenes* infection |
| *Enterobacter cloacae* infection |
| *Enterobacter* infection |
| Enterobacteriaceae infection |
| *Enterococcus faecalis* infection |
| *Enterococcus faecium* infection |
| *Enterococcus* infection |
| Enterocolitis |
| Enterotoxigenic *Escherichia coli* (ETEC) |
| Enterovirus 71 infection |
| Enuresis |
| Eosinophilic esophagitis |
| Ependymoma |
| Epidermolysis bullosa |
| *Epidermophyton* infection |
| Epididymitis |
| Epididymo-orchitis |
| Epilepsy |
| Epstein Barr virus infection |
| Erectile dysfunction |
| Erysipelas |
| Erythema |
| Erythema multiforme |
| Erythema nodosum leprae |
| Erythropoietic protoporphyria |
| ESBL (Extended Spectrum Beta Lactamase) Producing Bacterial Infection |
| *Escherichia coli* infection |
| Esophageal cancer |
| Esophageal varices |
| Esophagitis |
| Esophagus tumor |
| Essential hypertension |
| Estrogen deficiency |
| Ewing sarcoma |
| Exocrine pancreatic insufficiency |
| *Exophiala* infection |
| Extrinsic allergic alveolitis |
| Fabry disease |
| Factor I deficiency |
| Factor II deficiency |
| Factor IX deficiency |
| Factor VII deficiency |
| Factor VIII deficiency |
| Factor XIII deficiency |
| Fallopian tube cancer |
| Fallopian tube tumor |
| Familial adenomatous polyposis |
| Familial amyloid neuropathy |
| Familial cold autoinflammatory syndrome |
| Familial hypercholesterolemia |
| Familial mediterranean fever |
| *Fasciola hepatica* infection |
| Fatigue |
| Febrile neutropenia |
| Fecal incontinence |
| Female contraception |
| Female genital tract infection |
| Female genital tract tumor |
| Female infertility |

TABLE 6-continued

| List |
|---|
| Female sexual dysfunction |
| Fever |
| Fibromyalgia |
| Fibrosis |
| Fistula |
| Flavivirus infection |
| Folic acid deficiency |
| Follicle center lymphoma |
| Folliculitis |
| Food Allergy |
| Food poisoning |
| Fragile X syndrome |
| *Francisella tularensis* infection |
| Friedreich ataxia |
| Frontotemporal dementia |
| Functional bowel disorder |
| Fungal infection |
| Fungal meningitis |
| Fungal respiratory tract infection |
| Fungal urinary tract infection |
| *Fusarium* infection |
| *Fusobacterium* infection |
| Galactorrhea |
| Gallbladder tumor |
| GALT |
| Gastric injury |
| Gastric motility disorder |
| Gastric ulcers |
| Gastritis |
| Gastroesophageal reflux |
| Gastrointestinal disease |
| Gastrointestinal infection |
| Gastrointestinal pain |
| Gastrointestinal stromal tumor |
| Gastrointestinal tumor |
| Gastrointestinal ulcer |
| Gastroparesis |
| Gaucher disease |
| Gauchers disease type I |
| Gauchers disease type III |
| General anesthesia |
| Generalized anxiety disorder |
| Genetic disorder |
| Genital herpes |
| Genital system disease |
| Genital tract infection |
| Genital ulcer |
| Genitourinary disease |
| Genitourinary tract tumor |
| Germ cell and embryonic cancer |
| Gestational diabetes |
| Giant bone cell tumor |
| *Giardia lamblia* infection |
| Gigantism |
| Gingivitis |
| Glaucoma |
| Glaucoma surgical procedure |
| Glioblastoma |
| Glioma |
| Gliosarcoma |
| Glomerulonephritis |
| Glossitis |
| Glucose intolerance |
| Goiter |
| Gout |
| Graft versus host disease |
| Gram negative bacterium infection |
| Gram positive bacterium infection |
| Granulomatosis |
| Growth disorder |
| Growth hormone deficiency |
| Guillain Barre syndrome |
| Gynecological disorder |
| Gynecomastia |
| *Haemophilus aegyptus* infection |
| *Haemophilus ducreyi* infection |
| *Haemophilus* infection |
| *Haemophilus influenzae* infection |

TABLE 6-continued

| List |
|---|
| *Haemophilus parainfluenzae* infection |
| Hairy cell leukemia |
| Hallervorden-Spatz syndrome |
| Hantavirus infection |
| Head and neck tumor |
| Headache |
| Hearing loss |
| Heart arrhythmia |
| Heart disease |
| Heart transplant rejection |
| *Helicobacter pylori* infection |
| Helminth infection |
| Hemangioma |
| Hematological disease |
| Hematological neoplasm |
| Hematoma |
| Hematopoietic stem cell transplantation |
| Hemiplegia |
| Hemochromatosis |
| Hemoglobinopathy |
| Hemolytic anemia |
| Hemolytic uremic syndrome |
| Hemophilia |
| Hemorrhagic shock |
| Hemorrhoids |
| Heparin induced thrombocytopenia |
| Hepatic edema |
| Hepatic encephalopathy |
| Hepatic porphyria |
| Hepatitis |
| Hepatitis A virus infection |
| Hepatitis B virus infection |
| Hepatitis C virus infection |
| Hepatitis D virus infection |
| Hepatitis E virus infection |
| Hepatitis virus infection |
| Hepatobiliary disease |
| Hepatobiliary system tumor |
| Hepatocellular carcinoma |
| Hepatorenal syndrome |
| Hereditary angioedema |
| Herpes simplex virus infection |
| Herpesvirus infection |
| Herpetic keratitis |
| Hidradenitis |
| Hidradenitis suppurativa |
| Hippel Lindau syndrome |
| Histoplasma infection |
| HIV infection |
| HIV-1 infection |
| HIV-2 infection |
| HIV-associated lipodystrophy |
| Hodgkins disease |
| Homocystinuria |
| Hormone deficiency |
| Hormone dependent prostate cancer |
| Hormone refractory prostate cancer |
| Hot flashes |
| HSV-1 infection |
| HSV-2 infection |
| Human T cell leukemia virus 1 infection |
| Hunter syndrome |
| Huntingtons chorea |
| Hydrocephalus |
| Hyperactivity |
| Hyperammonemia |
| Hyperandrogenism |
| Hyperbilirubinemia |
| Hypercalcemia |
| Hypercholesterolemia |
| Hypereosinophilic syndrome |
| Hyperglycemia |
| Hyperhidrosis |
| Hyperkalemia |
| Hyperlipidemia |
| Hyperlipoproteinemia type I |
| Hypernatremia |
| Hyperoxaluria |

TABLE 6-continued

| List |
|---|
| Hyperparathyroidism |
| Hyperphosphatemia |
| Hyperpigmentation |
| Hyperprolactinemia |
| Hypersensitivity |
| Hypersomnia |
| Hypertension |
| Hyperthyroidism |
| Hypertriglyceridemia |
| Hypertrophic cardiomyopathy |
| Hyperuricemia |
| Hypoalbuminemia |
| Hypocalcemia |
| Hypogammaglobulinemia |
| Hypoglycemia |
| Hypogonadism |
| Hyponatremia |
| Hypoparathyroidism |
| Hypophosphatasia |
| Hypophosphatemia |
| Hypotension |
| Hypothyroidism |
| Hypovolemia |
| Ichthyosis vulgaris |
| Idiopathic pulmonary fibrosis |
| IgA nephropathy |
| Ileus |
| Immediate type hypersensitivity |
| Immune complex disease |
| Immune deficiency |
| Immune disorder |
| Immune thrombocytopenic purpura |
| Immunocompromised |
| Immunoglobulin G deficiency |
| Impetigo |
| Inappropriate ADH syndrome |
| Inborn error of metabolism |
| Inclusion body myositis |
| Indigestion |
| Infantile spasms |
| Infectious arthritis |
| Infectious disease |
| Infectious endocarditis |
| Infertility |
| Inflammatory bowel disease |
| Inflammatory disease |
| Influenza virus A infection |
| Influenza virus B infection |
| Influenza virus infection |
| Injury |
| Insomnia |
| Insulin dependent diabetes |
| Intermittent claudication |
| Interstitial cystitis |
| Interstitial lung disease |
| Intervertebral disc disease |
| Intestine disease |
| Intestine infection |
| Intoxication |
| Iritis |
| Iron deficiency anemia |
| Iron metabolism disorder |
| Iron overload |
| Irritable bowel syndrome |
| Ischemia |
| Ischemic heart disease |
| Ischemic stroke |
| Islet cell transplant rejection |
| Japanese encephalitis virus infection |
| Jaundice |
| Jaw disease |
| Joint disease |
| Joint infection |
| Juvenile myoclonic epilepsy |
| Juvenile rheumatoid arthritis |
| Kaposis sarcoma |
| Kawasaki disease |
| Keratitis |

TABLE 6-continued

| List |
|---|
| Keratoconjunctivitis |
| Keratosis |
| Kidney dialysis |
| Kidney transplant rejection |
| *Klebsiella granulomatis* infection |
| *Klebsiella* infection |
| *Klebsiella pneumoniae* infection |
| Labor complication |
| Lacrimal gland disease |
| Lactation disorder |
| Lambert-Eaton syndrome |
| Large intestine tumor |
| Laron syndrome |
| Laryngitis |
| Laryngopharyngitis |
| Lebers hereditary optic atrophy |
| Left heart disease pulmonary hypertension |
| Leg ulcer |
| *Legionella* infection |
| *Legionella pneumophila* infection |
| Leigh disease |
| *Leishmania braziliensis* infection |
| *Leishmania donovani* infection |
| *Leishmania* infection |
| *Leishmania tropica* infection |
| Lennox Gastaut syndrome |
| Leprosy |
| Leptospiraceae infection |
| Lesch Nyhan syndrome |
| Leukemia |
| Leukopenia |
| Leukopenia drug induced |
| Leukoplakia |
| Lewy body dementia |
| Lichen |
| Lipid metabolism disorder |
| Lipodystrophy |
| Lipoma |
| Lipoprotein lipase deficiency |
| Liposarcoma |
| *Listeria monocytogenes* infection |
| Listerosis |
| Liver abscess |
| Liver cancer |
| Liver cirrhosis |
| Liver disease |
| Liver fibrosis |
| Liver injury |
| Liver transplant rejection |
| Liver tumor |
| Lower back pain |
| Lower limb fracture |
| Lower respiratory tract infection |
| Lung abscess |
| Lung cancer |
| Lung disease |
| Lung disease pulmonary hypertension |
| Lung embolism |
| Lung infection |
| Lung inflammation |
| Lung malformation |
| Lung transplant rejection |
| Lung tumor |
| Lupus erythematosus panniculitis |
| Lupus nephritis |
| Lyme disease |
| Lymphadenitis |
| Lymphadenopathy |
| Lymphangioleiomyomatosis |
| Lymphangitis |
| Lymphatic system disease |
| Lymphedema |
| Lymphoblastic leukemia |
| Lymphoid leukemia |
| Lymphoma |
| Lysosomal acid lipase deficiency |
| Macroglobulinemia |
| Macular disease |

TABLE 6-continued

| List |
|---|
| Macular edema |
| Macular telangiectasia 2 |
| Major depressive disorder |
| Male contraception |
| Male hypogonadism |
| Male infertility |
| Male osteoporosis |
| Male sexual dysfunction |
| Mania |
| Mantle cell lymphoma |
| Marburg virus infection |
| Marginal zone B-cell lymphoma |
| Maroteaux-Lamy syndrome |
| Mastalgia |
| Mastitis |
| Mastocytosis |
| Mastoiditis |
| Measles virus infection |
| Meconium aspiration syndrome |
| Medullary thyroid cancer |
| Medulloblastoma |
| Melanoma |
| Membranoproliferative glomerulonephritis |
| Membranous glomerulonephritis |
| MEN1 |
| MEN2 |
| Meningioma |
| Meningitis |
| Menopause |
| Menorrhagia |
| Menstruation disorder |
| Mental deficiency |
| Merkel cell carcinoma |
| Mesothelioma |
| Metabolic bone disease |
| Metabolic disorder |
| Metabolic Syndrome |
| Metabolic syndrome X |
| Metal intoxication |
| Metastasis |
| Metastatic brain cancer |
| Metastatic breast cancer |
| Metastatic colon cancer |
| Metastatic colorectal cancer |
| Metastatic esophageal cancer |
| Metastatic gastrointestinal cancer |
| Metastatic head and neck cancer |
| Metastatic liver cancer |
| Metastatic lung cancer |
| Metastatic non small cell lung cancer |
| Metastatic ovary cancer |
| Metastatic pancreas cancer |
| Metastatic prostate cancer |
| Metastatic renal cancer |
| Metastatic stomach cancer |
| Methyl malonic acidemia |
| Metrorrhagia |
| Micrococcaceae infection |
| *Micrococcus* infection |
| Microsporidial infection |
| *Microsporum* infection |
| Migraine |
| Mild cognitive impairment |
| Mitochondrial disease |
| Molluscum contagiosum infection |
| Monkeypox virus infection |
| *Moraxella catarrhalis* infection |
| *Moraxella* infection |
| *Morganella* infection |
| *Morganella morganii* infection |
| Morning sickness |
| Morquio syndrome |
| Motion sickness |
| Motor neurone disease |
| Mouth tumor |
| Mouth ulcer |
| Movement disorder |
| MRSA infection |

TABLE 6-continued

| List |
|---|
| Muckle Wells syndrome |
| Mucopolysaccharidosis type I |
| Mucor infection |
| Mucositis |
| Multidrug resistant infection |
| Multiple myeloma |
| Multiple sclerosis |
| Mumps virus infection |
| Muscle hypertonia |
| Muscle injury |
| Muscle spasm |
| Muscle weakness |
| Muscular dystrophy |
| Musculoskeletal disease |
| Musculoskeletal pain |
| Musculoskeletal system inflammation |
| Myalgia |
| Myasthenia gravis |
| *Mycobacterium* infection |
| *Mycobacterium leprae* infection |
| *Mycobacterium tuberculosis* infection |
| *Mycoplasma* infection |
| *Mycoplasma pneumoniae* infection |
| Mycosis fungoides |
| Mydriasis |
| Myelitis |
| Myelodysplastic syndrome |
| Myelofibrosis |
| Myeloid leukemia |
| Myeloproliferative disorder |
| Myocardial disease |
| Myocardial infarction |
| N-acetylglutamate synthase deficiency |
| Nail disease |
| Narcolepsy |
| Nasal polyps |
| Nasopharyngeal carcinoma |
| Nausea |
| Nausea drug-induced |
| Necrotizing enterocolitis |
| Necrotizing Pancreatitis |
| *Neisseria gonorrhoeae* infection |
| *Neisseria* infection |
| *Neisseria meningitidis* infection |
| *Neisseria meningitidis* meningitis |
| Nelson syndrome |
| Nematode infection |
| Neonatal respiratory distress syndrome |
| Neoplasm |
| Neoplastic meningitis |
| Nephritis |
| Nephroblastoma |
| Nephropathic cystinosis |
| Nephrotic syndrome |
| Nerve injury |
| Nerve tumor |
| Neuroblastoma |
| Neurodegenerative disease |
| Neuroendocrine tumor |
| Neurofibromatosis |
| Neurofibromatosis type I |
| Neurological disease |
| Neuromuscular blockade |
| Neuromuscular disease |
| Neuromyelitis optica |
| Neuropathic pain |
| Neuropathy |
| Neutropenia |
| Nicotine dependence |
| Niemann Pick disease type C |
| Nocturia |
| Non alcoholic fatty liver disease |
| Non segmental vitiligo |
| Non small cell lung cancer |
| Non-alcoholic steatohepatitis |
| Non-Hodgkin lymphoma |
| Non-insulin dependent diabetes |
| Non-small-cell lung cancer |

TABLE 6-continued

| List |
|---|
| Obesity |
| Obsessive compulsive disorder |
| Obstructive sleep apnea |
| Occlusive coronary artery disease |
| Ocular cystinosis |
| Ocular disease |
| Ocular hypertension |
| Ocular infection |
| Ocular inflammation |
| Ocular melanoma |
| Ocular pain |
| Ocular surgical procedure |
| Onychomycosis |
| Open angle glaucoma |
| Opiate dependence |
| Optic neuritis |
| Oral mucositis |
| Orbital inflammatory disease |
| Organ transplant rejection |
| Organ transplantation |
| Ornithine transcarbamylase deficiency |
| Orthostatic hypotension |
| Ostealgia |
| Osteoarthritis |
| Osteogenesis imperfecta |
| Osteolysis |
| Osteomalacia |
| Osteomyelitis |
| Osteonecrosis |
| Osteopenia |
| Osteopetrosis |
| Osteoporosis |
| Osteosarcoma |
| Otitis |
| Otitis externa |
| Otitis media |
| Otorhinolaryngological disease |
| Otorhinolaryngological infection |
| Ovarian hyperstimulation syndrome |
| Ovary cancer |
| Ovary tumor |
| Overactive bladder |
| Overgrowth syndrome |
| Pagets bone disease |
| Pain |
| Pancreas disease |
| Pancreas transplant rejection |
| Pancreas tumor |
| Pancreatic ductal adenocarcinoma |
| Pancreatic endocrine tumor |
| Pancreatic ulcers |
| Pancreatitis |
| Panic disorder |
| Panophthalmitis |
| Papillary thyroid tumor |
| Papillomavirus infection |
| Papular skin disease |
| Papulosis |
| Paracetamol overdose |
| Paralysis |
| Paraproteinemia |
| Parasitic infection |
| Parkinsons disease |
| Paroxysmal nocturnal hemoglobinuria |
| Partial seizure |
| Parturition |
| Patent ductus arteriosus |
| Pediatric varicella zoster virus infection |
| Pediculosis capitis infestation |
| Pelvic inflammatory disease |
| Pemphigoid |
| Pemphigus |
| Penile induration |
| Penis tumor |
| Peptic ulcer |
| *Peptostreptococcus* infection |
| Perennial allergic rhinitis |
| Perianal fistula |

TABLE 6-continued

| List |
|---|
| Periarthritis |
| Pericoronitis |
| Periodontal disease |
| Periodontitis |
| Peripheral arterial occlusive disease |
| Peripheral neuropathy |
| Peripheral T-cell lymphoma |
| Peripheral vascular disease |
| Peritoneal tumor |
| Peritonitis |
| Peritonsillitis |
| Pervasive child developmental disorder |
| Pharyngitis |
| Phenylketonuria |
| Phlebothrombosis |
| Pink eye infection |
| Pituitary tumor |
| Pityriasis |
| Planned abortion |
| *Plasmodium falciparum* infection |
| *Plasmodium* infection |
| *Plasmodium malariae* infection |
| *Plasmodium vivax* infection |
| Pleural disease |
| Pneumocystis carinii infection |
| Pneumonia |
| POEMS syndrome |
| Poison intoxication |
| Poliovirus infection |
| Polyarteritis nodosa |
| Polychondritis |
| Polycystic kidney disease |
| Polycystic ovary syndrome |
| Polycythemia |
| Polycythemia vera |
| Polymorphus light eruption |
| Polymyalgia rheumatica |
| Polymyositis |
| Polyomavirus infection |
| Pompes disease |
| Port wine stain |
| Portal hypertension |
| Post traumatic stress disorder |
| Post-surgical bacterial leakage |
| Postherpetic neuralgia |
| Postmenopausal osteoporosis |
| Postnatal depression |
| Pouchitis |
| Pre-eclampsia |
| Precocious puberty |
| Premature ejaculation |
| Premature labor |
| Premature ovarian failure |
| Premenstrual syndrome |
| *Prevotella* infection |
| Priapism |
| Primary biliary cirrhosis |
| Primary sclerosing cholangitis |
| Proctitis |
| Progestogen deficiency |
| Progressive supranuclear palsy |
| Proliferative diabetic retinopathy |
| Prolymphocytic leukemia |
| Prophylaxis |
| *Propionibacterium acnes* infection |
| *Propionibacterium* infection |
| Prostate cancer |
| Prostate hyperplasia |
| Prostate tumor |
| Prostatitis |
| Protein C deficiency |
| Proteinuria |
| Proteus infection |
| *Proteus mirabilis* infection |
| Protozoal infection |
| *Providencia* infection |
| Prurigo |
| Pruritus |

TABLE 6-continued

| List |
|---|
| Pseudomembranous colitis |
| *Pseudomonas aeruginosa* infection |
| *Pseudomonas* infection |
| Psoriasis |
| Psoriatic arthritis |
| Psychiatric disorder |
| Psychotic disorder |
| Pterygium |
| Pulmonary artery hypertension |
| Pulmonary fibrosis |
| Pulmonary heart disease |
| Pulmonary hypertension |
| Purpura |
| Pyelonephritis |
| Pyoderma gangrenosum |
| Rabies virus infection |
| Radiation sickness |
| Radiotherapy induced emesis |
| Raynauds disease |
| Rectal cancer |
| Rectal tumor |
| Rectosigmoiditis |
| Renal cell carcinoma |
| Renal disease |
| Renal failure |
| Renal injury |
| Renal osteodystrophy |
| Renal tubule disease |
| Renal tumor |
| Renovascular hypertension |
| Reperfusion injury |
| Reproductive disorder |
| Respiratory congestion |
| Respiratory disease |
| Respiratory disorder |
| Respiratory distress syndrome |
| Respiratory insufficiency |
| Respiratory syncytial virus infection |
| Respiratory tract infection |
| Respiratory tract inflammation |
| Restenosis |
| Restless legs syndrome |
| Retinal dystrophy |
| Retinal venous occlusion |
| Retinitis pigmentosa |
| Retinoblastoma |
| Retinopathy |
| Retinopathy of prematurity |
| Rett syndrome |
| Rheumatoid arthritis |
| Rhinitis |
| Rhinopharyngitis |
| *Rhizomucor* infection |
| *Rhizopus* infection |
| Rickets |
| *Rickettsia* infection |
| Rocky mountain spotted fever |
| Rosacea |
| Ross River virus infection |
| Rotavirus infection |
| Rotavirus Vaccine Adjunct |
| Rubella virus infection |
| *Salmonella* infection |
| *Salmonella typhi* infection |
| Salpingitis |
| Sandhoff disease |
| Sarcoidosis |
| Sarcoma |
| Sarcopenia |
| SARS coronavirus infection |
| Scabies infection |
| Scar tissue |
| *Scedosporium* infection |
| Schistosomiasis |
| Schizoaffective disorder |
| Schizophrenia |
| Scleritis |
| Scleroderma |

TABLE 6-continued

| List |
|---|
| Seasonal affective disorder |
| Seasonal allergic rhinitis |
| Sebaceous gland disease |
| Seborrheic dermatitis |
| Secondary hyperparathyroidism |
| Seizure disorder |
| Seminoma |
| Sepsis |
| Septic shock |
| *Serratia* infection |
| *Serratia marcescens* infection |
| Serum sickness |
| Severe combined immunodeficiency syndrome |
| Sexual deviation |
| Sexual dysfunction |
| Sezary syndrome |
| *Shigella boydii* infection |
| *Shigella dysenteriae* infection |
| *Shigella flexneri* infection |
| *Shigella* infection |
| *Shigella sonnei* infection |
| Shock |
| Short bowel syndrome |
| Sialadenitis |
| Sialorrhea |
| Sickle beta 0 thalassemia |
| Sickle cell anemia |
| Sickle cell crisis |
| Sinusitis |
| Sitosterolemia |
| Sjoegrens syndrome |
| Skin allergy |
| Skin burns |
| Skin cancer |
| Skin infection |
| Skin Inflammatory disease |
| Skin lymphoma |
| Skin tumor |
| Skin ulcer |
| Sleep apnea |
| Sleep disorder |
| Small-cell lung cancer |
| Social phobia |
| Soft tissue sarcoma |
| Solid tumor |
| Spinal cord disease |
| Spinal cord injury |
| Spinal cord tumor |
| Spinal muscular atrophy |
| Spinal stenosis |
| Spinocerebellar ataxia |
| Spinocerebellar degenerations |
| Splenomegaly |
| Spondylarthritis |
| Spondylosyndesis |
| Spontaneous abortion |
| Squamous cell carcinoma |
| Stage III melanoma |
| Stage IV melanoma |
| *Staphylococcus aureus* infection |
| *Staphylococcus epidermidis* infection |
| *Staphylococcus* infection |
| *Staphylococcus saprophyticus* infection |
| Stem cell transplantation |
| *Stenotrophomonas maltophilia* infection |
| Stevens Johnson syndrome |
| Stomach cancer |
| Stomach disease |
| Stomach infection |
| Stomach tumor |
| Stomach ulcer |
| Stomatitis |
| Strabismus |
| *Streptococcus agalactiae* infection |
| *Streptococcus constellatus* infection |
| *Streptococcus* infection |
| *Streptococcus intermedius* infection |
| *Streptococcus mitis* infection |

TABLE 6-continued

| List |
|---|
| *Streptococcus oralis* infection |
| *Streptococcus pneumoniae* infection |
| *Streptococcus pyogenes* infection |
| Stress urinary incontinence |
| Stroke |
| Stutter |
| Subcortical vascular dementia |
| Sucrase isomaltase deficiency |
| Sunburn |
| Surgery |
| Surgical procedure |
| Synovitis |
| Systemic lupus erythematosus |
| Systemic mastocytosis |
| Systolic heart failure |
| T-cell acute lymphoblastic leukemia |
| T-cell lymphoma |
| Tachycardia |
| Tardive dyskinesia |
| Tay Sachs disease |
| Temporal arteritis |
| Tendon injury |
| Tenosynovitis |
| Testis tumor |
| Testosterone deficiency |
| Thalassemia major |
| Thrombasthenia |
| Thromboangiitis obliterans |
| Thrombocyte disorder |
| Thrombocythemia |
| Thrombocytopenia |
| Thrombocytopenic purpura |
| Thrombocytosis |
| Thromboembolism |
| Thrombosis |
| Thymoma |
| Thyroid associated ophthalmopathy |
| Thyroid tumor |
| Tinea |
| Tinea capitis |
| Tinea corporis |
| Tinea cruris |
| Tinea pedis |
| Tinnitus |
| Tonic clonic epilepsy |
| Tonsillitis |
| Tooth disease |
| Topical anesthesia |
| Torticollis |
| Tourette syndrome |
| Toxic epidermal necrolysis |
| Toxicity |
| Transitional cell carcinoma |
| Transplant rejection |
| Transplantation |
| Traumatic brain injury |
| Traveler's diarrhea |
| Trench mouth |
| *Treponema* infection |
| *Treponema pallidum* infection |
| *Trichomonas* infection |
| *Trichophyton* infection |
| Trigeminal neuralgia |
| *Trypanosoma brucei* infection |
| *Trypanosoma cruzi* infection |
| Trypanosomiasis |
| Tuberous sclerosis |
| Tumor lysis syndrome |
| Turners syndrome |
| Type 1 Diabetes |
| Type 2 Diabetes |
| Type I tyrosinemia |
| Ulcer |
| Ulcerative colitis |
| Ulcerative proctitis |
| Umbilical cord stem cell transplantation |
| Unidentified indication |
| Unstable angina |

TABLE 6-continued

| List |
|---|
| Upper respiratory tract infection |
| *Ureaplasma urealyticum* infection |
| Uremia |
| Urethritis |
| Urinary dysfunction |
| Urinary incontinence |
| Urinary retention |
| Urinary tract disease |
| Urinary tract infection |
| Urinary tract tumor |
| Urogenital tract infection |
| Urolithiasis |
| Urticaria |
| Uterine cervix tumor |
| Uterine fibroids |
| Uterus infection |
| Uterus tumor |
| Uveal melanoma |
| Uveitis |
| Vaccination |
| Vaccinia virus infection |
| Vaginal infection |
| Vaginitis |
| Variant angina pectoris |
| Varicella zoster virus infection |
| Varices |
| Varicosis ulcer |
| Variola virus infection |
| Vascular dementia |
| Vascular disease |
| Vascular neoplasm |
| Vascular occlusive disease |
| Vasculitis |
| Venous occlusive disease |
| Ventricular arrhythmia |
| Ventricular fibrillation |
| Ventricular tachycardia |
| Verruca vulgaris |
| Vertigo |
| *Vibrio cholerae* infection |
| Viral encephalitis |
| Viral eye infection |
| Viral hemorrhagic fever |
| Viral infection |
| Viral respiratory tract infection |
| Viral susceptibility |
| *Viridans* group *Streptococcus* infection |
| Vitamin B12 deficiency |
| Vitamin D deficiency |
| Vitamin E deficiency |
| Vitamin K deficiency |
| Vitiligo |
| Vitreous hemorrhage |
| Von Willebrands disease |
| Vancomycin-Resistant *Enterococcus* Infection |
| Vulva disease |
| Vulvovaginitis |
| Wasting disease |
| Wasting Syndrome |
| Wegener granulomatosis |
| Weight loss |
| West Nile virus infection |
| Wet age related macular degeneration |
| Whipple's disease |
| Wilson disease |
| Wound healing |
| X linked dominant hypophosphatemic rickets |
| Xenobiotic metabolism |
| Xerophthalmia |
| Xerostomia |
| Yellow fever virus infection |
| *Yersinia pestis* infection |
| Zollinger-Ellison syndrome |
| Flatulence |
| Gastrointestinal Disorder |
| General Inflammation |

TABLE 7

| List |
| --- |
| Abdominal cavity inflammation |
| *Absidia* infection |
| *Acinetobacter baumanii* infection |
| *Acinetobacter* infection |
| *Acinetobacter lwoffii* infection |
| Acne |
| *Actinomyces israelii* infection |
| Adenovirus infection |
| Adult varicella zoster virus infection |
| Aging |
| Alcoholism (and effects) |
| Allergic conjunctivitis |
| Allergic rhinitis |
| Allergy |
| ALS |
| Alzheimers disease |
| *Amoeba* infection |
| Anal cancer |
| Antibiotic treatment |
| Antitbiotic associated diarrhea |
| Arteriosclerosis |
| Arthritis |
| *Aspergillus fumigatus* infection |
| *Aspergillus* infection |
| Asthma |
| Atherosclerosis |
| Atopic dermatitis |
| Atopy/Allergic Sensitivity |
| Autism |
| Autoimmune disease |
| *Bacillus anthracis* infection |
| *Bacillus* infection |
| Bacterial endocarditis |
| Bacterial eye infection |
| Bacterial infection |
| Bacterial meningitis |
| Bacterial pneumonia |
| Bacterial respiratory tract infection |
| Bacterial skin infection |
| Bacterial susceptibility |
| Bacterial urinary tract infection |
| Bacterial vaginosis |
| *Bacteroides caccae* infection |
| *Bacteroides fragilis* infection |
| *Bacteroides* infection |
| *Bacteroides thetaiotaomicron* infection |
| *Bacteroides uniformis* infection |
| *Bacteroides vulgatus* infection |
| *Bartonella bacilliformis* infection |
| *Bartonella* infection |
| *Bifidobacterium* infection |
| Biliary cancer |
| Biliary cirrhosis |
| Biliary tract disease |
| Biliary tract infection |
| Biliary tumor |
| BK virus infection |
| *Blastomyces* infection |
| Bone and joint infection |
| Bone infection |
| *Bordetella pertussis* infection |
| *Borrelia burgdorferi* infection |
| *Borrelia recurrentis* infection |
| *Brucella* infection |
| *Burkholderia* infection |
| Cachexia |
| *Campylobacter fetus* infection |
| *Campylobacter* infection |
| *Campylobacter jejuni* infection |
| Cancer |
| *Candida albicans* infection |
| *Candida* infection |
| *Candida krusei* infection |
| Celiac Disease |
| Cervix infection |
| Chemotherapy-induced diarrhea |
| *Chlamydia* infection |
| *Chlamydia pneumoniae* infection |

TABLE 7-continued

| List |
| --- |
| *Chlamydia trachomatis* infection |
| Chlamydiae infection |
| Chronic fatigue syndrome |
| Chronic infection |
| Chronic inflammatory demyelinating polyneuropathy |
| Chronic Polio Shedders |
| Circadian rhythm sleep disorder |
| Cirrhosis |
| *Citrobacter* infection |
| *Cladophialophora* infection |
| Clostridiaceae infection |
| *Clostridium botulinum* infection |
| *Clostridium difficile* infection |
| *Clostridium* infection |
| *Clostridium tetani* infection |
| *Coccidioides* infection |
| Colitis |
| Colon cancer |
| Colorectal cancer |
| Common cold |
| Compensated liver cirrhosis |
| Complicated skin and skin structure infection |
| Complicated urinary tract infection |
| Constipation |
| Constipation predominant irritable bowel syndrome |
| *Corynebacterium diphtheriae* infection |
| *Corynebacterium* infection |
| *Coxiella* infection |
| CRE infection |
| Crohns disease |
| *Cryptococcus* infection |
| *Cryptococcus neoformans* infection |
| *Cryptosporidium* infection |
| Cutaneous lupus erythematosus |
| Cystic fibrosis |
| Cystitis |
| Cytomegalovirus infection |
| Dementia |
| Dengue virus infection |
| Depression |
| Dermatitis |
| Diabetes mellitus |
| Diabetic complication |
| Diabetic foot ulcer |
| Diarrhea |
| Diarrhea predominant irritable bowel syndrome |
| Discoid lupus erythematosus |
| Diverticulitis |
| DNA virus infection |
| Duodenal ulcer |
| Ebola virus infection |
| *Entamoeba histolytica* infection |
| *Enterobacter aerogenes* infection |
| *Enterobacter cloacae* infection |
| *Enterobacter* infection |
| Enterobacteriaceae infection |
| *Enterococcus faecalis* infection |
| *Enterococcus faecium* infection |
| *Enterococcus* infection |
| Enterocolitis |
| Enterovirus 71 infection |
| *Epidermophyton* infection |
| Epstein Barr virus infection |
| ESBL (Extended Spectrum Beta Lactamase) Producing Bacterial Infection |
| *Escherichia coli* infection |
| Esophageal cancer |
| *Exophiala* infection |
| Familial cold autoinflammatory syndrome |
| *Fasciola hepatica* infection |
| Female genital tract infection |
| Female genital tract tumor |
| Female infertility |
| Fibrosis |
| Flavivirus infection |
| Food Allergy |
| *Francisella tularensis* infection |
| Functional bowel disorder |
| Fungal infection |

TABLE 7-continued

| List |
| --- |
| Fungal respiratory tract infection |
| Fungal urinary tract infection |
| *Fusarium* infection |
| *Fusobacterium* infection |
| Gastric ulcers |
| Gastrointestinal infection |
| Gastrointestinal pain |
| Gastrointestinal ulcer |
| Genital tract infection |
| Genitourinary disease |
| Genitourinary tract tumor |
| Gestational diabetes |
| *Giardia lamblia* infection |
| Gingivitis |
| Gram negative bacterium infection |
| Gram positive bacterium infection |
| *Haemophilus aegyptus* infection |
| *Haemophilus ducreyi* infection |
| *Haemophilus* infection |
| *Haemophilus influenzae* infection |
| *Haemophilus parainfluenzae* infection |
| Hantavirus infection |
| *Helicobacter pylori* infection |
| Helminth infection |
| Hepatitis A virus infection |
| Hepatitis B virus infection |
| Hepatitis C virus infection |
| Hepatitis D virus infection |
| Hepatitis E virus infection |
| Hepatitis virus infection |
| Herpes simplex virus infection |
| Herpesvirus infection |
| Histoplasma infection |
| HIV infection |
| HIV-1 infection |
| HIV-2 infection |
| HSV-1 infection |
| HSV-2 infection |
| Human T cell leukemia virus 1 infection |
| Hypercholesterolemia |
| Hyperoxaluria |
| Hypertension |
| Infectious arthritis |
| Infectious disease |
| Infectious endocarditis |
| Infertility |
| Inflammatory bowel disease |
| Inflammatory disease |
| Influenza virus A infection |
| Influenza virus B infection |
| Influenza virus infection |
| Insomnia |
| Insulin dependent diabetes |
| Intestine infection |
| Irritable bowel syndrome |
| Japanese encephalitis virus infection |
| Joint infection |
| Juvenile rheumatoid arthritis |
| *Klebsiella granulomatis* infection |
| *Klebsiella* infection |
| *Klebsiella pneumoniae* infection |
| *Legionella* infection |
| *Legionella pneumophila* infection |
| *Leishmania braziliensis* infection |
| *Leishmania donovani* infection |
| *Leishmania* infection |
| *Leishmania tropica* infection |
| Leptospiraceae infection |
| *Listeria monocytogenes* infection |
| Listerosis |
| Liver cirrhosis |
| Liver fibrosis |
| Lower respiratory tract infection |
| Lung infection |
| Lung inflammation |
| Lupus erythematosus panniculitis |
| Lupus nephritis |
| Lyme disease |

TABLE 7-continued

| List |
| --- |
| Male infertility |
| Marburg virus infection |
| Measles virus infection |
| Metabolic disorder |
| Metabolic Syndrome |
| Metastatic colon cancer |
| Metastatic colorectal cancer |
| Metastatic esophageal cancer |
| Metastatic gastrointestinal cancer |
| Metastatic stomach cancer |
| Micrococcaceae infection |
| *Micrococcus* infection |
| Microsporidial infection |
| *Microsporum* infection |
| Molluscum contagiosum infection |
| Monkeypox virus infection |
| *Moraxella catarrhalis* infection |
| *Moraxella* infection |
| *Morganella* infection |
| *Morganella morganii* infection |
| MRSA infection |
| Mucor infection |
| Multidrug resistant infection |
| Multiple sclerosis |
| Mumps virus infection |
| Musculoskeletal system inflammation |
| *Mycobacterium* infection |
| *Mycobacterium leprae* infection |
| *Mycobacterium tuberculosis* infection |
| *Mycoplasma* infection |
| *Mycoplasma pneumoniae* infection |
| Necrotizing enterocolitis |
| Necrotizing Pancreatitis |
| *Neisseria gonorrhoeae* infection |
| *Neisseria* infection |
| *Neisseria meningitidis* infection |
| Nematode infection |
| Non alcoholic fatty liver disease |
| Non-alcoholic steatohepatitis |
| Non-insulin dependent diabetes |
| Obesity |
| Ocular infection |
| Ocular inflammation |
| Orbital inflammatory disease |
| Osteoarthritis |
| Otorhinolaryngological infection |
| Pain |
| Papillomavirus infection |
| Parasitic infection |
| Parkinsons disease |
| Pediatric varicella zoster virus infection |
| Pelvic inflammatory disease |
| *Peptostreptococcus* infection |
| Perennial allergic rhinitis |
| Periarthritis |
| Pink eye infection |
| *Plasmodium falciparum* infection |
| *Plasmodium* infection |
| *Plasmodium malariae* infection |
| *Plasmodium vivax* infection |
| *Pneumocystis carinii* infection |
| Poliovirus infection |
| Polyomavirus infection |
| Post-surgical bacterial leakage |
| Pouchitis |
| *Prevotella* infection |
| Primary biliary cirrhosis |
| Primary sclerosing cholangitis |
| *Propionibacterium acnes* infection |
| *Propionibacterium* infection |
| Prostate cancer |
| *Proteus* infection |
| *Proteus mirabilis* infection |
| Protozoal infection |
| *Providencia* infection |
| *Pseudomonas aeruginosa* infection |
| *Pseudomonas* infection |
| Psoriasis |

TABLE 7-continued

| List |
| --- |
| Psoriatic arthritis |
| Pulmonary fibrosis |
| Rabies virus infection |
| Rectal cancer |
| Respiratory syncytial virus infection |
| Respiratory tract infection |
| Respiratory tract inflammation |
| Rheumatoid arthritis |
| Rhinitis |
| *Rhizomucor* infection |
| *Rhizopus* infection |
| *Rickettsia* infection |
| Ross River virus infection |
| Rotavirus infection |
| Rubella virus infection |
| *Salmonella* infection |
| *Salmonella typhi* infection |
| Sarcopenia |
| SARS coronavirus infection |
| Scabies infection |
| *Scedosporium* infection |
| Scleroderma |
| Seasonal allergic rhinitis |
| *Serratia* infection |
| *Serratia marcescens* infection |
| *Shigella boydii* infection |
| *Shigella dysenteriae* infection |
| *Shigella flexneri* infection |
| *Shigella* infection |
| *Shigella sonnei* infection |
| Short bowel syndrome |
| Skin allergy |
| Skin cancer |
| Skin infection |
| Skin Inflammatory disease |
| Sleep disorder |
| Spondylarthritis |
| *Staphylococcus aureus* infection |
| *Staphylococcus epidermidis* infection |
| *Staphylococcus* infection |
| *Staphylococcus saprophyticus* infection |
| *Stenotrophomonas maltophilia* infection |
| Stomach cancer |
| Stomach infection |
| Stomach ulcer |
| *Streptococcus agalactiae* infection |
| *Streptococcus constellatus* infection |
| *Streptococcus* infection |
| *Streptococcus intermedius* infection |
| *Streptococcus mitis* infection |
| *Streptococcus oralis* infection |
| *Streptococcus pneumoniae* infection |
| *Streptococcus pyogenes* infection |
| Systemic lupus erythematosus |
| Traveler's diarrhea |
| Trench mouth |
| *Treponema* infection |
| *Treponema pallidum* infection |
| *Trichomonas* infection |
| *Trichophyton* infection |
| *Trypanosoma brucei* infection |
| *Trypanosoma cruzi* infection |
| Type 1 Diabetes |
| Type 2 Diabetes |
| Ulcerative colitis |
| Upper respiratory tract infection |
| *Ureaplasma urealyticum* infection |
| Urinary tract disease |
| Urinary tract infection |
| Urinary tract tumor |
| Urogenital tract infection |
| Uterus infection |
| Vaccinia virus infection |
| Vaginal infection |
| Varicella zoster virus infection |
| Variola virus infection |
| *Vibrio cholerae* infection |
| Viral eye infection |
| Viral infection |
| Viral respiratory tract infection |
| *Viridans* group *Streptococcus* infection |
| Vancomycin-Resistant *Enterococcus* Infection |
| Wasting Syndrome |
| Weight loss |
| West Nile virus infection |
| Whipple's disease |
| Xenobiotic metabolism |
| Yellow fever virus infection |
| *Yersinia pestis* infection |
| Flatulence |
| Gastrointestinal Disorder |
| General Inflammation |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09028841B2). An electronic copy of the "Sequence Listing" will also be available from the USPTO upon request and payment of the fee set forth in 37 CFR 1.19(b)(3).

What is claimed is:

1. A method of treating or preventing an occurrence or a recurrence of a *Clostridium difficile* infection, comprising administering to a human subject in need thereof an effective amount of a therapeutic composition comprising a first purified bacterial population consisting of bacteria comprising 16S rDNA sequence at least about 97% identical to a 16S rDNA sequence present in a reference *Collinsella aerofaciens* OTU, and a second purified bacterial population consisting of bacteria comprising 16S rDNA sequence at least about 97% identical to a 16S rDNA sequence present in a reference bacterium of the family Clostridiaceae listed in Table 1, wherein a synergistic combination of the first purified bacterial population and the second purified bacterial population is cytotoxic or cytostatic to a pathogenic bacterium, wherein the therapeutic composition is administered under conditions such that the first purified bacterial population and the second purified bacterial population exert an inhibitory effect on a pathogenic bacterium present in or entering into the gastrointestinal tract of the human subject, such that the number of *Clostridium difficile* bacteria present in the gastrointestinal tract is not detectably increased or is detectably decreased over a period of time.

2. The method of claim 1, wherein the number of *Clostridium difficile* bacteria present in or excreted from the gastrointestinal tract of the human subject is detectably reduced within one month of administration of the bacterial composition.

3. The method of claim 1, wherein the first purified bacterial population and the second purified bacterial population synergistically interact to be cytotoxic and/or cytostatic to the *Clostridium difficile* bacteria as demonstrated by a CivSim assay.

4. The method of claim 1, wherein the therapeutic composition is orally administered.

5. The method of claim 1, wherein the therapeutic composition comprises a medical food.

6. The method of claim 1, wherein the composition is capable of inhibiting proliferation of the pathogenic bacterium when the bacterial population of the composition is present at a concentration at least equal to the concentration of the pathogenic bacterium.

7. The method of claim 1, wherein the first purified bacterial population and the second purified bacterial population are capable of functionally populating the gastrointestinal tract of a human subject to whom the composition is administered.

8. The method of claim 7, wherein the functional populating of the gastrointestinal tract comprises preventing, treating, reducing the severity of or reducing a symptom of a dysbiosis of the gastrointestinal tract.

9. The method of claim 7, wherein the functional populating of the gastrointestinal tract comprises i) reducing the number of one or more types of pathogenic bacteria in the gastrointestinal tract; or ii) increasing the number of one or more non-athogenic bacteria in the gastrointestinal tract.

* * * * *

UNITED STATES PATENT AND TRADEMARK OFFICE

CERTIFICATE OF CORRECTION

PATENT NO. : 9,028,841 B2
APPLICATION NO. : 14/221190
DATED : May 12, 2015
INVENTOR(S) : Matthew R. Henn et al.

It is certified that error appears in the above-identified patent and that said Letters Patent is hereby corrected as shown below:

Title page, item (72), Inventors:
On line 1, replace "Someville, MA" with -- Somerville, MA --.

In the Claims:
Column 528, line 17, replace "more non-athogenic bacteria in the gastrointestinal tract." with -- more non-pathogenic bacteria in the gastrointestinal tract. --.

Signed and Sealed this
Tenth Day of May, 2016

Michelle K. Lee
*Director of the United States Patent and Trademark Office*